US012637503B2

(12) United States Patent
Nara et al.

(10) Patent No.: US 12,637,503 B2
(45) Date of Patent: May 26, 2026

(54) **ANTIGEN-BINDING MOLECULES THAT BIND TO *PORPHYROMONAS GINGIVALIS***

(71) Applicant: K-Bio Investment, LLC, Austin, TX (US)

(72) Inventors: Peter L. Nara, Senecaville, OH (US); Daniel L. Sindelar, St. Louis, MO (US)

(73) Assignee: K-Bio Investment, LLC, Austin, TX (US)

( * ) Notice: Subject to any disclaimer, the term of this patent is extended or adjusted under 35 U.S.C. 154(b) by 702 days.

(21) Appl. No.: 18/051,456

(22) Filed: Oct. 31, 2022

(65) Prior Publication Data

US 2023/0365662 A1     Nov. 16, 2023

Related U.S. Application Data

(63) Continuation-in-part of application No. PCT/US2021/057758, filed on Nov. 2, 2021.

(60) Provisional application No. 63/364,592, filed on May 12, 2022, provisional application No. 63/364,182, filed on May 4, 2022, provisional application No. 63/231,964, filed on Aug. 11, 2021, provisional application No. 63/225,295, filed on Jul. 23, 2021, provisional application No. 63/221,405, filed on Jul. 13, 2021, provisional application No. 63/208,873, filed on Jun. 9, 2021, provisional application No. 63/135,878, filed on Jan. 11, 2021, provisional application No. 63/109,286, filed on Nov. 3, 2020.

(51) Int. Cl.
| | |
|---|---|
| *C07K 16/00* | (2006.01) |
| *A61K 39/395* | (2006.01) |
| *C07K 16/1203* | (2026.01) |

(52) U.S. Cl.
CPC ...... *C07K 16/1203* (2013.01); *C07K 2317/21* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,881,175 A | 11/1989 | Ladner |
| 4,946,778 A | 8/1990 | Ladner et al. |
| 5,260,203 A | 11/1993 | Ladner et al. |
| 5,304,489 A | 4/1994 | Rosen |
| 5,741,957 A | 4/1998 | Deboer et al. |
| 5,849,992 A | 12/1998 | Meade et al. |
| 6,017,532 A | 1/2000 | Travis |
| 6,080,560 A | 6/2000 | Russell et al. |
| 6,129,917 A | 10/2000 | Potempa |
| 6,274,718 B1 | 8/2001 | Travis |
| 6,512,162 B2 | 1/2003 | McBride et al. |

| | | |
|---|---|---|
| 6,627,193 B1 | 9/2003 | Travis |
| 7,419,671 B2 | 9/2008 | Reynolds et al. |
| 8,871,213 B2 | 10/2014 | Reynolds et al. |
| 9,366,673 B2 | 6/2016 | McCluskey et al. |
| 9,518,109 B2 | 12/2016 | Reynolds et al. |
| 10,676,470 B2 | 6/2020 | Konradi et al. |
| 2002/0192206 A1 | 12/2002 | Kozarov et al. |
| 2003/0167531 A1 | 9/2003 | Russell et al. |
| 2003/0232022 A1 | 12/2003 | Reynolds et al. |
| 2006/0270045 A1 | 11/2006 | Cregg et al. |
| 2007/0036734 A1 | 2/2007 | Tahara et al. |
| 2011/0280880 A1 | 11/2011 | Reynolds et al. |
| 2012/0156211 A1 | 6/2012 | McCluskey et al. |
| 2015/0023983 A1 | 1/2015 | Stephenson |
| 2017/0014468 A1* | 1/2017 | Dominy ................. A61K 38/05 |
| 2018/0334440 A1 | 11/2018 | Konradi et al. |
| 2019/0000971 A1 | 1/2019 | Bakaletz et al. |
| 2019/0192645 A1 | 6/2019 | Fairman |
| 2019/0194263 A1 | 6/2019 | Reynolds et al. |
| 2019/0322659 A1 | 10/2019 | Konradi et al. |
| 2020/0088724 A1 | 3/2020 | Zhan et al. |
| 2021/0188996 A1 | 6/2021 | Huille et al. |
| 2022/0226454 A1 | 7/2022 | Nara et al. |
| 2023/0365662 A1 | 11/2023 | Nara et al. |
| 2024/0400654 A1 | 12/2024 | Nara et al. |
| 2025/0289872 A1 | 9/2025 | Nara et al. |
| 2025/0334585 A1 | 10/2025 | Nara et al. |

FOREIGN PATENT DOCUMENTS

| | | |
|---|---|---|
| CN | 105418758 | 3/2016 |
| JP | 2012-500633 | 1/2012 |
| JP | 2015-178533 | 10/2015 |
| WO | WO 97/34629 | 9/1997 |
| WO | WO 01/029242 | 4/2001 |
| WO | WO 08/000028 | 1/2008 |

(Continued)

OTHER PUBLICATIONS

Adams et al., Aug. 27, 2019, Parkinson's Disease A Systemic Inflammatory Disease Accompanied by Bacterial Inflammagens, Frontiers in Aging Neuroscience, 11(Article 210), 17 pp.

Adhikari et al., 2018, Estimation of Transmission of Porphyromonas Gingivalis from Mother to Child through Saliva, J Nepal Med Assoc, 56(212):781-786.

Ahmad et al., 2022, Neuroinflammation: A Potential Risk for Dementia, International Journal of Molecular Sciences, 23:616, 18 pp.

Alexsijevic et al., 2022, Porphyromonas gingivalis Virulence Factors and Clinical Significance in Periodontal Disease and Coronary Artery Diseases, Pathogens, 11:1173, 19 pp.

Almaghlouth et al., Jan. 2014, Effect of periodontal treatment on peak serum levels inflammatory markers, Clin Oral Invest, DOI 10.1007/s00784-014-1187-4, 9 pp.

(Continued)

*Primary Examiner* — Meera Natarajan
(74) *Attorney, Agent, or Firm* — Fish & Richardson P.C.

(57) ABSTRACT

Antigen-binding molecules (ABMs) that bind to *Porphyromonas gingivalis* are described. The ABMs may be human or humanized ABMs. The ABMs find use in treating infections involving *P. gingivalis*, such as periodontal disease. Also provided are methods of treating or preventing a disorder or disease by administering the ABM.

35 Claims, 173 Drawing Sheets

Specification includes a Sequence Listing.

(56)         References Cited

FOREIGN PATENT DOCUMENTS

| WO | WO 13/119966 | 8/2013 |
| WO | WO 2016/061264 A1 | 4/2016 |
| WO | WO 2019/019426 | 1/2019 |
| WO | WO 20/027617 | 2/2020 |
| WO | WO 21/105669 | 6/2021 |
| WO | WO 22/081516 | 4/2022 |
| WO | WO 22/098661 | 5/2022 |
| WO | WO 2022/150719 A2 | 7/2022 |
| WO | WO 23/288204 | 1/2023 |
| WO | WO 2023/079442 A2 | 5/2023 |
| WO | WO 23/212526 | 11/2023 |

OTHER PUBLICATIONS

Almarhoumi et al., 2023, Microglial cell response to experimental periodontal disease, Journal of Neuroinflammation, 20: 142, 18 pp.
Altschul et al., 1990, Basic Local Alignment Search Tool, J. Mol. Biol., 215:403-410.
Altschul et al., 1997, Gapped BLAST and PSI-BLAST: a new generation of protein database search programs, Nucl. Acids Res., 25(17):3389-3402.
Alzheimer's Drug Discovery Foundation, Mar. 13, 2023, Gingipain Inhibitors (COR338/Atuzaginstat, COR588/LHP588), 13 pp.
Alzheimers.gov, GAIN Trial: COR388 for Alzheimer's Disease, https://www.alzheimers.gov/clinical-trials/gain-trial-cor388-alzheimers-disease, downloaded Sep. 30, 2022, 4 pp.
Ausubel et al., 1987-1994, Current Protocols in Molecular Biology, John Wiley & Sons,. Inc. (TOC).
Benedyk et al., 2019, Type IX secretion system is pivotal for expression of gingipain-associated virulence of Porphyromonas gingivalis, Molecular Oral Microbiology, 34:237-244.
Bennett et al., Mar. 28, 2019, RNA Sequencing Reveals Small and Variable Contributions of Infectious Agents to Transcriptomes of Postmortem Nervous Tissues From Amyotrophic Lateral Sclerosis, Alzheimer's Disease and Parkinson's Disease Subjects, and Increased Expression of Genes From Disease-Activated Microglia, Frontiers in Neuroscience, 13(Article 235), 10 pp.
Bird et al., Oct. 21, 1988, Single-Chain Antigen-Binding Proteins, Science, 242:423-426.
Blasco-Baque et al., 2017, eriodontitis induced by Porphyromonas gingivalis drives periodontal microbiota dysbiosis and insulin resistance via an impaired adaptive immune response, Gut, 66:872-885.
Booth et al., 1997, Characterization of the Porphyromonas gingivalis antigen recognized by a monoclonal antibody which prevents colonization by the organism, J. Periodont., 32:54-60.
Booth et al., Feb. 1996, Passive Immunization with Monoclonal Antibodies against Porphyromonas gingivalis in Patients with Periodontitis, Infection and Immunity, 64(2):422-427.
Brown et al., 2024, The endotoxin hypothesis of Alzheimer's disease, Molecular Neurodegeneration, 19:30, 14 pp.
Cabanillas et al., Jan.-Feb. 2024, Periodontitis and Neuropathic Diseases: A Literature Review, Journal of International Society of Preventive and Community Dentistry, 14(1):10-15.
Canettieri et al., 2006, Production of monoclonal antibodies against *Streptococcus mutans* antigens, Braz Oral Res, 20(4):297-302.
Chen et al., Age- and sex-related differences of periodontal bone resorption, cognitive function, and immune state in APP/PS1 murine model of Alzheimer's disease, Journal of Neuroinflammation, 20:153, 14 pp.
Cheng et al., 2023, Exogenous monocyte myeloid-derived suppressor cells ameliorate immune imbalance, neuroinflammation and cognitive impairment in 5xFAD mice infected with Porphyromonas gingivalis, Journal of Neuroinflammation, 20:55, 18 pp.
Chothia et al., 1987, Canonical Structures for the Hypervariable Regions of Immunoglobulins, J. Mol. Biol. 196:901-917.
Chu et al., Jun. 1991, Hemolytic Activity in the Periodontopathogen Porphyromonas gingivalis: Kinetics of Enzyme Release and Localization, Infect. Immun., 59(6): 1932-1940.

Cichonska et al., 2024, Recent Aspects of Periodontitis and Alzheimer's Disease—A Narrative Review, International Journal of Molecular Sciences, 25:2612, 1-26.
ClinicalTrials.gov, Apr. 10, 2014, NCT02109705, Porphyromonas gingivalis and Alzheimer's Disease (PGNEURO), 3 pp.
ClinicalTrials.gov, Feb. 1, 2018, NCT03418688, A multiple ascending dose study of COR388, 4 pp.
ClinicalTrials.gov, Jan. 30, 2019, NCT03823404, Gain Trial; Phase 2/3 study of COR388 in subjects with Alzheimer's disease, 4 pp.
ClinicalTrials.gov, Jul. 2, 2010, NCT01156155, Periodontal disease and P. Gingivalis in rheumatoid arthritis, 1 p.
ClinicalTrials.gov, Mar. 11, 2016, NCT02705885, IgY Efficacy on periodontitis patients, 3 pp.
ClinicalTrials.gov, Nov. 6, 2017, NCT03331900, Study of COR388 HCI in healthy subjects, 3 pp.
Co et al., Feb. 15, 1992, Chimeric and Humanized Antibodies with Specificity for the CD33 Antigen, J Immunol 148(4):1149-1154.
Colligan et al., eds., 1992-1996, Current Protocols in Immunology, John Wiley & Sons, Inc., (TOC).
Corpet et al., 1988, Multiple sequence alignment with hierarchical clustering, Nucl. Acids Res., 16(22):10881-10890.
Critchley, Jun. 1, 2017, Brush your teeth! It could save your life, https://pursuit.unimelb.edu.au/topics/porphyromonas-gingivalis, downloaded Sep. 13, 2022, 6 pp.
Dall'Acqua et al., 2002, Increasing the affinity of a human IgG1 for the neonatal Fc receptor: biological consequences, The Journal of Immunology, 169:5171-5180.
De Wildt et al., 1996, Characterization of human variable domain antibody fragments against the UI RNA-associated A protein, selected from a synthetic and a patient-derived combinatorial V gene library, Eur J. Immunol., 26(3):629-639.
Dong et al., Apr. 7, 2022, Correlation Analysis of Gut Microbiota and Serum Metabolome With Porphyromonas gingivalis-Induced Metabolic Disorders, Froeingers in Cellular and Infection Microbiology, 12(Article 858902), 13 pp.
Emery et al., Dec. 9, 2022, High resolution 16S rRNA gene Next Generation Sequencing study of brain areas associated with Alzheimer's and Parkinson's disease, Frontiers in Aging Neuroscience, 14:1026260, 25 pp.
Endo et al., 2003, High-throughput, genome-scale protein production method based on the wheat germ cell-free expression system, Biotechnol. Adv., 21:695-713.
Ermini et al., 2024, Ultrastructural localization of Porphyromonas gingivalis gingipains in the substantia nigra of Parkinson's disease brains, NPJ Parkinson's Disease, 10:90, 16 pp.
Fitzpatrick et al., Jun. 18, 2009, The gingipains: scissors and glue of the periodontal pathogen, Porphyromonas gingivalis, Future Microbiology, 4(4):471-487.
Franciotti et al., 2021, Exploring the Connection between Porphyromonas gingivalis and neurodegenative Diseases: A Pilot Quantitative Study on the Bacterium Abundance in Oral Cavity and the Amount of Antibodies in Serum, Biomoleculres, 11:845, 12 pp.
Franciotti et al., 2023, The Immune System Response to Porphyromonas gingivalis in Neurological Diseases, Microorganisms, 11:2555.
Fu et al., 2022, Oral microbiome and serological analyses on association of Alzheimer's disease and periodontitis, Oral Diseases, 00:1-11.
Fu et al., 2023, Oral porphyromonas gingivalis infections increase the risk of Alzheimer's disease: a review, Oral Health Prev Dent, 21:2-16.
Fulop et al., Sep. 10, 2018, Role of Microbes in the Development of Alzheimer's Disease: State of the Art—An International Symposium Presented at the 2017 IAGG Congress in San Francisco, Frontiers in Genetics, 9(Article 362), 16 pp.
Ge et al., May 25, 2022, Fast, Simple, and Highly Specific Molecular Detection of Porphyromonas gingivalis Using Isothermal Amplification and Lateral Flow Strip Methods, Frontiers in C=ellular and Infection Microbiology, 12(Article 895261), 10 pp.
Genco et al., Sep. 1998, A peptide domain on gingipain R which confers immunity against porphyromonas gingivalis infection in mice, Infect Immun, 66(9):4108-4114.
Gerits et al., 2017, New approaches to combat Porphyromonas gingivalis biofilms, Journal of Oral Micobiology, 9:1300366, 11 pp.

(56)         References Cited

OTHER PUBLICATIONS

Ghosh et al., 2021, Cellular and molecular influencers of neuroinflammation in Alzheimer's disease: Recent concepts & roles, Neurochemistry International, 151:105212.

Gong et al., Aug. 9, 2022, Outer membrane vesicles of Porphyromonas gingivalis trigger NLRP3 inflammasome and induce neuroinflammation, tau phosphorylation, and memory dysfunction in mice, Frontiers in Cellular and Infection Microbiology, 12:925435, 18 pp.

Gonzalez-Sanchez et al., 2020, Decreased salivary lactoferrin levels are specific to Alzheimer's disease , EBioMedicine, 57:102834, 10 pp.

Gorman et al., Nov. 1982, The Rous sarcoma virus long terminal repeat is a strong promoter when introduced into a variety of eukaryotic cells by DNA-mediated transfection, PNAS 79:6777-6781.

Grabrucker et al., 2023, Microbiota from Alzheimer's patients induce deficits in cognition and hippocampal neurogenesis, Brain, 00:1-19, https://doi.org/10.1093/brain/awad303.

Grenier et al., Aug. 2003, Effect of Inactivation of the Arg- and/or Lys-Gingipain Gene on Selected Virulence and Physiological Properties of Porphyromonas gingivalis, Infection and Immunity, 71(8):4742-4748.

Grosschedl et al., Jul. 1985, Cell-Type Specificity of Immunoglobulin Gene Expression is Regulated by at Least Three DNA Sequence Elements, Cell 41:885-897.

Ha et al., 2021, Anti-atherosclerotic vaccination against Porphyromonas gingivalis as a potential comparator of statin in mice, PeerJ, 9:e11293, 10 pp.

Ha et al., Nov. 24, 2020, Delivery of Periodontopathogenic Extracellular Vesicles to Brain Monocytes and Microglial IL-6 Promotion by RNA Cargo, Frontiers in Molecular Biosciences, 7(Article 596366), 11 pp.

Ha et al., Oct. 23, 2023, Periodontitis promotes bacterial extracellular vesicle-induced neuroinflammation in the brain and trigeminal ganglion, PLOS Pathog, 19(10):e1011743, 26 pp.

Haditsch et al., 2020, Alzheimer's Disease-Like Neurodegeneration in Porphyromonas gingivalis Infected Neurons with Persistent Expression of Active Gingipains, Journal of Alzheimer's Disease, 75:1361-1376.

Hamamoto et al., 2020, Effect of Porphyromonas gingivalis infection on gut dysbiosis and resultant arthritis exacerbation in mouse model, Arthritis Research & Therapy, 22;249, 15 pp.

Han et al., Dec. 2019, Extracellular RNAs in periodontopathogenic outer membrane vesicles promote TNF-a production in human macrophages and cross the blood-brain barrier in mice, The FASEB Journal, 33:13412-13422.

Han et al., Oct. 1996, The Hemagglutinin Gene A (hagA) of Porphyromonas gingivalis 381 Contains Four Large, Contiguous, Direct Repeats, Infection and Immunity, 64(10):4000-4007.

Haque, 2022, Advances in novel therapeutic approaches for periodontal diseases, BMC Oral Health, 22:492, 23 pp.

Hayashi et al., Mar. 2011, Porphyromonas gingivalis Accelerates Inflammatory Atherosclerosis in the Innominate Artery of ApoE Deficient Mice, Atherosclerosis, 215(1):52-59.

Higgins et al., 1988, CLUSTAL: a package for performing multiple sequence alignment on a microcomputer, Gene, 73:237-244.

Higgins et al., 1989, Fast and sensitive multiple sequence alignments on a microcomputer CABIOS, 5(2):151-153.

How et al., Feb. 9, 2016, Porphyromonas gingivalis: An Overview of Periodontopathic Pathogen below the Gum Line, Frontiers in Microbiology, 7(Article 53):1-14.

Howard et al., 2021, Porphyromonas gingivalis: where do we stand in our battle against this oral pathogen? RSC Medicinal Chemistry, 12:666-704.

Huang et al., 1992, Parallelization of a local similarity algorithm, CABIOS, 8(2):155-165.

Huang et al., 2019, Immunization with cell-free-generated vaccine protects from Porphyromonas gingivalis-induced alveolar bone loss, Journal of Clinical Periodontology, 46:197-205.

Huang et al., 2022, Novel regimens of phytopolyphenols with cisplatin or memantine and ZnSO4 for synergistic inhibition of growth and gingipains of the cultured Porphyromonas gingivalis, Journal of Dental Sciences, 17:1796-1801.

Huston et al., Aug. 1988, Protein engineering of antibody binding sites: Recovery of specific activity in an anti-digoxin single-chain Fv analogue produced in *Escherichia coli*, Proc. Natl. Acad. Sci. USA 85:5879-5883.

Ilievski et al., 2018, Chronic oral application of a periodontal pathogen reults in brain inflammation, neurodegeneration and amyloid beta production in wild type mice, PLoS One, 13(10):e0204941, 24 pp.

Ilievski et al., 2020, Identification of a periodontal pathogen in pancreatic islets of humans and a mouse model of periodontitis, Nature Research: Scientific Reports, 10:9976, 14 pp.

Imai et al., 2020, Porphyromonas gingivalis gingipains potentially affect MUC5AC gene expression and protein levels in respiratory epithelial cells, FEBS Open Bio, 26 pp.

Jackson et al., 2000, A consensus Porphyromonas gingivalis promoter sequence, FEMS Microbiology Letters, 186:133-138.

Jain et al., Jul. 2018, KB001-A, a novel anti-inflammatory, found to be safe and well-tolerated in cystic fibrosis patients infected with Pseudomonas aeruginosa, Journal of Cystic Fibrosis, 17(4):484-491.

Jeong et al., 2023, Effective microbial molecular diagnosis of periodontitis-related pathogen Porphyromonas gingivalis from salivary samples using rgpA gene, Genomics & Informatics, 21(1):e13, 8 pp.

Johnston et al., Jun. 10, 1988, Mitochondrial Transformation in Yeast by Bombardment with Microprojectiles, Science, 240:1538-1541.

Kabat et al., 1991, Sequences of Proteins of Immunological Interest, Fifth Edition, U.S. Department of Health and Human Services, NIH Publication No. 91-3242 (TOC).

Kamer et al., Feb. 2015, Periodontal disease associates with higher brain amyloid load in normal elderly, Neurobiol Aging, 36(2):627-633.

Kang et al., Jul. 1, 2022, Interaction Between Autophagy and Porphyromonas gingivalis-Induced Inflammation, Frontiers in Cellular and Infection Microbiology, 12(Article 892610), 15 pp.

Kapoor et al., 2018, Malaria Derived Glycosylphosphatidylinositol Anchor Enhances Anti- Pfs25 Functional Antibodies That Block Malaria Transmission, Biochemistry, 57:516-519.

Karlin et al., 1990, Methods for assessing the statistical significance of molecular sequence features by using general scoring schemes, Proc. Natl. Acad. Sci. USA, 87:2264-2668.

Kato et al., Sep./Oct. 2018, Oral Administration of Porphyromonas gingivalis Alters the Gut Microbiome and Serum Metabolome, mSphere, 3(5):300460-18.

Kawamoto et al., Oct. 11, 2021, Oral Dysbiosis in Severe Forms of Periodontitis Is Associated With Gut Dysbiosis and Correlated With Salivary Inflammatory Mediators: A Preliminary Study, Frontiers in Oral Health, 2(article 211495), 15 pp.

Kelly et al., 1997, The relationship between colonization and haemagglutination inhibiting and B cell epitopes of porphyromonas gingivalis, Clin Exp Immunol, 110:285-291.

Kendrew et al. (eds.), 1994, The Encyclopedia of Molecular Biology, published by Blackwell Science Ltd. (TOC).

Kinney et al., 2018, Inflammation as a central mechanism in Alzheimer's disease, Alzheimer's & Dementia: Translational Research & Clinical Interventions, 4:575-590.

Koizumi et al., Jul. 2008, Nasal Immunization with Porphyromonas gingivalis Outer Membrane Protein Decreases P. gingivalis-Induced Atherosclerosis and Inflammation in Spontaneously Hyperlipidemic Mice, Infection and Immunity, 76(7):2958-2965.

Kozarov et al., Feb. 2000, Expression and Immunogenicity of Hemagglutinin A from Porphyromonas gingivalis in an Avirulent Salmonella enterica Serovar Typhimurium Vaccine Strain, Infection and Immunity, 68(2):732-739.

Krebs et al., 2009, Lewin's Genes X, Jones & Bartlett Publishing (TOC).

(56) References Cited

OTHER PUBLICATIONS

Kuboniwa et al., May 2001, Specific antibodies to porphyomonas gingivalis Lys-ginigpain by DNA vaccination inhibit bacterial binding to hemoglobin and protect mice from infection, Infect Immun, 69(5):2972-2979.

Lefkovits et al., eds., 1979 and 1981, Immunological Methods, vols. I and II, Acad. Press, NY (TOC).

Lehmann, 2020, Oral Porphyromonas gingivalis Infection Induces Epigenetic Changes that Promote Persistence of Cardiovascular Disease, Master of Science Thesis, University of Alberta, 91 pp.

Li et al., 2010, Targeted Antimicrobial Therapy Against *Streptococcus mutans* Establishes Protective Non-cariogenic Oral Biofilms and Reduces Subsequent Infection, Int J Oral Sci, 2(2):66-73.

Li et al., 2011, Gingipains from porphyromonas gingivalis—complex domain structures confer diverse functions, Eur. J. Microbiol. Immunol., 1:41-58.

Liu et al., 2017, Infection of microglia with Porphyromonas gingivalis promotes cell migration and an inflammatory response through the gingipainmediated activation of proteaseactivated receptor-2 in mice, Scientific Reposrts, 7:11759, 13 pp.

Lonn et al., 2018, Lipoprotein modifications by gingipains of Porphyromonas, J Periodont Res., 53:403-513.

Ma et al., 1989, Specificity of monoclonal antibodies in local passive immunization against Streptococcus mutans, Clin. Exp. Immunol., 77:331-337.

Ma et al., 2020, Antibody stability A key to performance—Analysis, influences and improvement, Biochimie, 177:213-225.

Ma et al., 2023, Extracellular vesicles derived from Porphyromonas gingivalis induce trigeminal nerve-mediated cognitive impairment, Journal of Advanced Research, 54:293-303.

Makiura et al., 2008, Diabetes Relationship of Porphyromonas gingivalis with glycemic level in patients with type 2 diabetes following periodontal treatment, Oral Microbiology Immunology, 23:348-351.

Maniatis et al., 1982, Molecular Cloning, Lab. Manual, Cold Spring Harbor Laboratory (TOC).

Martinez-Guzman et al., Jan. 15, 2012, Detection of IgG, IgA and IgM antibodies against porphyromonas gingivalis in gingival crevicular fluid and saliva in patients with chronic periodontitis, Journal of Infectious Diseases and Immunity, 4(1):10-15.

Matto et al., Jan. 1998, Detection of Porphyromonas gingivalis from Saliva by PCR by Using a Simple Sample-Processing Method, Journal of Clinical Microbiology, 36(1):157-160.

McPherson et al. eds., 1991, PCR, A Practical Approach, IRL Press Oxford, UK, (TOC).

Mei et al., 2020, Porphyromonas gingivalis and its systemic impact: current status, Pathogens, 9:944, 23 pp.

Meyers, ed., 1995, Molecular Biology and Biotechnology: a Comprehensive Desk Reference, Wiley-VCH Publishers, Inc. (TOC).

Miklossy, 2011, Alzheimer's disease—a neurospirochetosis. Analysis of the evidence following Koch's and Hill's criteria, Journal of Neuroinflammation, 8:90, 16 pp.

Miller et al., Jul. 1989, Cloning and expression of a yeast ubiquitin-protein cleaving activity in escherichia coli, Bio/Technology, 7:698-704.

Morikawa et al., 2023, Systemic Administration of Lipopolysaccharide from Porphyromonas gingivalis Decreases Neprilysin Expression in the Mouse Hippocampus, in vivo, 37:163-172.

Muhall et al., 2020, Porphyromonas gingivalis, a Long-Range Pathogen: Systemic Impact and Therapeutic Implications, Microorganisms, 8:869, 15 pp.

Myers et al., 1988, Optimal alignments in linear space, CABIOS, 4(1):11-17.

Nadkarni et al., Oct. 2009, Lysine Gingipain (kgp) Biovars of Porphyromonas gingivalis Exhibit Differential Distribution on Oral Mucosal Sites, Journal of Clinical Micobiology, 47(10):3350-3352.

Nakajima et al., 2015, Oral Administration of P. gingivalis Induces Dysbiosis of Gut Microbiota and Impaired Barrier Function Leading to Dissemination of Enterobacteria to the Liver, Plos One, 10(7):e0134234, 15 pp.

Nara et al., 2021, Porphyromonas gingivalis Outer Membrane vesicles as the major driver of and Explanation for Neuropathogenesis, the Cholinergic Hypothesis, Iron Dyshomeostasis, and Salivary Lactoferrin in Alzheimer's Disease, Journal of Alzheimer's Disease, Journal of Alzheimer's Disease, 82:1417-1450.

Nara et al., 2021, Porphyromonas gingivalis outer membrane vesicles as the major drivers of and source for the toxic insult and iron accumulation/deposition in Alzheimer's disease, Alzheimer's & Dementia, 17(Suppl. 3):e056458.

Nara, 2002, Further preclinical development of a clinically effective bio-therapeutic against Porphyromonas gingivalis, Alzheimer's & Dementia, 17(Suppl. 9):e056482.

Needleman et al., 1970, A General Method Applicable to the Search for Similarities in the Amino Acid Sequence of Two Proteins, J. Mol. Biol., 48:443-453.

Nielsen et al., 2017, Orally absorbed cyclic peptides, Chemical Reviews, 117:8094-8128.

O'Brien-Simpson et al., 2016, A therapeutic Porphyromonas gingivalis gingipain vaccine induces neutralising IgG1 antibodies that protect against experimental periodontitis, NPJ Vaccines, 1:16022, 11 pp.

O'Brien-Simpson et al., Mar. 2009, Porphyromonas gingivalis RgpA-Kgp Proteinase-Adhesin Complexes Penetrate Gingival Tissue and Induce Proinflammatory Cytokines or Apoptosis in a Concentration-Dependent Manner, Infection and Immunity, 77:1246-1261.

O'Brien-Simpson et al., Sep. 2015, Development and evaluation of a saliva-based chair-side diagnostic for the detection of Porphyromonas gingivalis, Journal of Oral Microbiology, 7:29129.

Oh et al., Dec. 7, 2023, Organ aging signatures in the plasma proteome track health and disease, Nature, 624:164-172.

Okamura et al., 2021, Outer membrane vesicles of Porphyromonas gingivalis: Novel communication tool and strategy, Japanese Dental Science Review, 57:138-146.

Okayama et al., Feb. 1983, A cDNA Cloning Vector That Permits Expression of cDNA Inserts in Mammalian Cells, Mol. Cell. Biol. 3(2):280-289.

Olczak et al., 2005, Iron and heme utilization in Porphyromonas gingivalis, FEMS Microbiology Reviews, 29:119-144.

Park et al., 2022, Leaky Gum The Revisited Origin of Systemic Diseases, Cells, 11:1079-, 17 pp.

Patel et al. 2020, In Vivo Delivery of Nucleic Acid-Encoded Monoclonal Antibodies, BioDrugs, 34:273-293.

Patil et al., Mar.-Apr. 2013, Effect of Periodontal Therapy on Serum C-Reactive Protein Levels in Patients with Gingivitis and Chronic Periodontitis: A Clinicobiochemical Study, The Journal of Contemporary Dental Practice, 14(2):233-237.

Pearson et al., 1994, Using the FASTA Program to Search Protein and DNA Sequence Databases, Meth. Mol. Biol., 24:307:331.

Pearson et al., Apr. 1988, Improved tools for biological sequence comparison, Proc. Natl. Acad. Sci. USA, 85:2444-2448.

Peng et al., 2022, Oral microbiota in human systematic diseases, International Journal of Oral Science, 14:14, 11 pp.

Peng et al., May 2020, Targeting a cysteine protease from a pathobiont alleviates experimental arthritis, Arthritis Res Ther., 22(1):114-.

Pezzotti et al., 2023, In Situ Raman Study of Neurodegenerated Human Neuroblastoma Cells Exposed to Outer-Membrane Vesicles Isolated from Porphyromonas gingivalis, International Journal of Molecular Sciences, 24:13351, 31 pp.

Pisa et al., 2017, Polymicrobial Infections In Brain Tissue From Alzheimer's Disease Patients, Scientific Reports, 7:5559, 14 pp.

Porter et al., 2006, The Merck Manual of Diagnosis and Therapy, 19th Edition, Merck Research Laboratories (TOC).

Qiu et al., 2024, Profiles of subgingival microbiomes and gingival crevicular metabolic signatures in patients with amnestic mild cognitive impairment and Alzheimer's disease, Alzheimer's Research & Therapy, 16:41, 17 pp.

Queen et al., 1986, Cell-type Specific Regulation of a Kappa Immunoglobulin Gene by Promoter and Enhancer Elements, Immunol Rev 89:49-68.

(56) References Cited

OTHER PUBLICATIONS

Queiroz de Andrade et al., 2019, Immunological Pathways Triggered by Porphyromonas gingivalis and fusobacterium nucleatum: Therapeutic Possibilities? Mediators of Inflammation, 2019(Article ID 7241312), 20 pp.

Rams et al., 2023, Emergence of Antibiotic-Resistant Porphyromonas gingivalis in United States Periodontitis Patients, Antibiotics, 12:1584, 12 pp.

Reynolds, Characterisation of novel P. gingivalis cell surface proteinase/adhesins, https://dental.unimelb.edu.au/research/research-groups/oral-biologyresearch-group/characterisation-of-novel-p.-gingivalis-cell-surface-proteinaseadhesins, downloaded Sep. 29, 2022, 2 pp.

Robinette et al., Aug. 26, 2011, A therapeutic anti-*Streptococcus mutans* monoclonal antibody used in human passive protection trials influences the adaptive immune response, Vaccine, 29(37):6292-6300.

Rocco et al., May 9, 2018, Targeting the HUβeta protein prevents porphyromonas gingivalis from entering into preexisting biofilms, Journal of Bacteriology, 200(11):e00790-17, 11 pp.

Rocha et al., Jul. 5, 2021, A Porphyromonas gingivalis Capsule-Conjugate Vaccine Protects From Experimental Oral Bone Loss, Frontiers in Oral Health, 2(Article 686402), 11 pp.

Roslund et al., 2022, Antibiotic treatment and supplemental hemin availability affect the volatile organic compounds produced by P. gingivalis in vitro, Nature: Scientific Reports, https://doi.org/10.1038/s41598-022-26497-0, 11 p.

Rubinstein et al., 2024, Periodontitis and brain magnetic resonance imaging markers of Alzheimer's disease and cognitive aging, Alzheimer's Dement., https://doi.org/10.1002/alz.13683, pp. 1-18.

Ryder, 2020, Porphyromonas gingivalis and Alzheimer disease: Recent findings and potential therapies, J Periodontol, 91(Suppl. 1):S45-S49.

Sabbagh et al., 2022, COR388 (atuzaginstat): an investigational gingipain inhibitor for the treatment of Alzheimer disease, Expert Opinion on Investigational Drugs, 31(10):987-993.

Sabin et al., 1989, High-level expression and in vivo processing of chimeric ubiquitin fusion proteins in saccharomyces cerevisiae, Bio/Technology, 7:705-709.

Said-Sadier et al., 2023, Association between Periodontal Disease and Cognitive Impairment in Adults, Int. J. Environ. Res. Public Health, 20:4707, 16 pp.

Sambroook et al., 2001, Molecular Cloning: A Laboratory Manual, Third Edition, Cold Spring Harbor Press (TOC).

Sansores-Espana et al., Dec. 10, 2021, Oral-Gut-Brain Axis in Experimental Models of Periodontitis: Associating Gut Dysbiosis With Neurodegenerative Diseases, Frontiers in Aging, 2(Article 781582), 21 pp.

Sasaki et al., Oct. 24, 2018, Endotoxemia by Porphyromonas gingivalis Injection Aggravates Non-alcoholic Fatty Liver Disease Disrupts GlucoseLipid Metabolism, and Alters Gut Microbiota in Mice, Frontiers in Microbiology, 9(Article 2470), 16 pp.

Schwahn et al., 2021, Effect of periodontal treatment on preclinical Alzheimer's disease—Results of a trial emulation approach, Alzheimer's & Dementia, 18:127-141.

Scopes, 1982, Protein Purification: Principles and Practice, Springer-Verlag, NY (TOC).

Seo et al., Jan. 4, 2024, Current understanding of the Alzheimer's disease-associated microbiome and therapeutic strategies, Experimental & Molecular Medicine, 56:86-94.

Seyama et al., Feb. 20, 2020, Outer membrane vesicles of Porphyromonas gingivalis attenuate insulin sensitivity by delivering gingipains to the liver, BBA—Molecular Basis of Disease, 1866(6):165731, 12 pp.

Shaker et al., Feb. 18, 2022, Computational Design of a Multi-Epitope Vaccine Against Porphyromonas gingivalis, Frontiers in Immunology, 13(Article 806825), 15 p.

Sitaraman et al., 2009, High-Throughput Protein Expression Using Cell-Free System, Methods Mol. Biol., 498:229-244.

Smith et al., 1981, Comparison of biosequences, Adv. Appl. Math., 2:482-489.

Sochalska et al., May 23, 2017, Manipulation of Neutrophils by Porphyromonas gingivalis in the Development of Periodontitis, Frontiers in Cellular and Infection Microbiology, 7(Article 197), 15 pp.

Spirin, Oct. 2004, High-throughput cell-free systems for synthesis of functionally active proteins, Trends Biotechnol., 22(10):538-545.

Suh et al., 2019, Periodontitis-induced systemic inflammation exacerbates atherosclerosis partly via endothelial-mesenchymal transition in mice, International Journal of Oral Science, 11:21, 12 pp.

Tang et al., 2022, Treponema denticola Induces Alzheimer Like Tau Hyperphosphorylation by Activating Hippocampal Neuroinflammation in Mice, Journal of Dental Research 101(8):992-1001.

Tang et al., 2023, Advances in the Study of the Pathology and Treatment of Alzheimer's Disease and Its Association with Periodontitis, Life, 13:2203, 22 pp.

Tatusova et al., 1999, BLAST 2 Sequences, a new tool for comparing protein and nucleotide sequences, FEMS Microbiol. Lett, 174:247-250.

Thapa et al., Sep. 1, 2023, Translocation of gut commensal bacteria to the brain, bioRxiv preprint doi: https://doi.org/10.1101/2023.08.30.555630 , 27 pp.

The University of Melbourne, 2019, World first discovery at the Melbourne Dental School: porphyromonas gingivalis and Alzheimer's Disease, Dent-AL Alumni Newsletter, Issue 29/2019, p. 4.

The University of Melbourne, Development of a define porphyromonas gingivalis vaccine, downloaded Sep. 21, 2022, https://findanexpert.unimelb.edu.au/project/10602-development-of-a-defined-porphyromonas-gingivalis-vaccine, 2 pp.

The University of Melbourne, Melbourne Dental School, Annual Research Report, 2020/21. 58 pp.

Tsien, 1998, The Green Fluorescent Protein, Annual Reviews of Biochemistry, 67:509-544.

Turunen et al., 2012, Recognition of porphyromonas gingivalis gingipain epitopes by natural IgM binding to malondialdehyde modified low-density lipoprotein, PLoS One, 7(4):e34910.

University Library, Systematic reviews for the health sciences: grey literature, downloaded Sep. 28, 2022, https://researchguides.uic.edu/systematicreviews/greyliterature, 2 pp.

University of Melbourne, Dec. 5, 2016, World-first therapeutic dental vaccine, ScienceDaily, 3 pp.

Veith et al., 2018, Outer Membrane Vesicle Proteome of Porphyromonas gingivalis Is Differentially Modulated Relative to the Outer Membrane in Response to Heme Availability, Journal Proteome Research, 17(7):2377-2389.

Verkhusha et al., 2004, The Molecular Properties and Applications of Anthoza Fluorescent Proteins and Chromophores, Nature Biotechnology, 22(3):289-296.

Verma et al., 2023, P. gingivalis-LPS Induces Mitochondrial Dysfunction Mediated by|Neuroinflammation through Oxidative Stress, International Journal of Molecular Sciences, 24:950, 14 pp.

Vincents et al., Oct. 2011, Cleavage of IgG1 and IgG3 by gingipain K from Porphyromonas gingivalis may compromise host defense in progressive periodontitis, The FASEB Journal, 25:3741-3750.

Vojtechova et al., Nov. 2022, Infectious origin of Alzheimer's disease: Amyloid beta as a component of brain antimicrobial immunity, PLoS Pathogens, 18(11):e1010929, 26 pp.

Walchli et al., 2020, Accelerated Aggregation Studies of Monoclonal Antibodies: Considerations for Storage Stability, Journal of Pharmaceutical Sciences, 109:595-602.

Walker et al., Oct. 2023, Oh my gut! Is the microbial origin of neurodegenerative diseases real? Infection and Immunity, 91(10), 10 pp.

Wang et al., 2023, IL-1β and TNF-α play an important role in modulating the risk of periodontitis and Alzheimer's disease, Journal of Neuroinflammation, 20:71, 30 pp.

Wang et al., Mar. 2, 2022, Oral and Gut Microbial Dysbiosis and Non-alcoholic Fatty Liver Disease The Central Role of Porphyromonas gingivalis, Frontiers in Medicine, 9(Article 822190), 16 pp.

Ward et al., Oct. 12, 1989, Binding activities of a repertoire of single immunoglobulin variable domains secreted from *Escherichia coli*, Nature, 341:544-546.

(56) References Cited

OTHER PUBLICATIONS

Watanabe et al., Aug. 2011, Complete Genome Sequence of the Bacterium Porphyromonas gingivalis TDC60, Which Causes Periodontal Disease, Journal of Bacteriology, 193(16):4259-4260.

Weber et al., Jun. 2, 2023, The role of microbiome-host interactions in the development of Alzheimer's disease, Frontiers in Cellular and Infection Microbiology, 13:1151021, 20 pp.

Weidle et al., 1987, Reconstitution of functionally active antibody directed against creatine kinase from separately expressed heavy and light chains in non-lymphoid cells, Gene 51:21-29.

Whitson et al., 2022, Infection and inflammation: New perspectives on Alzheimer's disease, Brain, Behavior, & Immunity—Health, 22:100462, 9 pp.

Whittle et al., 1987, Expression in COS cells of a mouse-human chimaeric B72.3 Antibody, Protein Engin., 1(6):499-505.

Winnacker, 1987, From Genes to Clones: Introduction to Gene Technology, VCH Publishers, NY (TOC).

Xu et al., Jan./Feb. 2015, Production of bispecific antibodies in "knobs-into-holes" using a cell-free expressions system, mAbs 7(1):231-242.

Yang et al., 2016, Porphyromonas gingivalis-derived outer membrane vesicles promote calcification of vascular smooth muscle cells through ERK1/2-RUNX2, FEBS Open Bio, 6:1310-1319.

Yoshida et al., 2022, Porphyromonas gingivalis outer membrane vesicles in cerebral ventricles activate microglia in mice, Oral Diseases, 00:1-10.

Zawada et al., Jul. 2011, Microscale to Manufacturing Scale-up of Cell-Free Cytokine Production-A New Approach for Shortening Protein Production Development Timelines, Biotechnology and Bioengineering, 108(7):1570-1578.

Zhang et al., 2018, Porphyromonas gingivalis lipopolysaccharide induces cognitive dysfunction, mediated by neuronal inflammation via activation of the TLR4 signaling pathway in C57BL/6 mice, Journal of Neuroinflammation, 15:37, 14 pp.

Zhang et al., 2020, Stability enhancement in a mAb and Fab coformulation, Nature Research: Scientific Reports, 10:21129, 11 pp.

Zhang et al., Dec. 13, 2023, Advances in the prevention and treatment of Alzheimer's disease based on oral bacteria, Frontiers in Psychiatry, 14:1291455, 10 pp.

Zhou et al., 2023, Neuroinflammation in Alzheimer's Disease: A Potential Role of Nose-Picking in Pathogen Entry via the Olfactory System? Biomolecules, 13:1568, 22 pp.

International search report and written opinion dated Oct. 3, 2023 in application No. PCT/US23/66125.

Boisvert et al., "Clathrin-dependent entry of a gingipain adhesin peptide and Porphyromonas gingivalis into host cells," Cellular Microbiology, Nov. 6, 2008, 10(12):2538-2552.

Boisvert et al., "Translocation of Porphyromonas gingivalis Gingipain Adhesin Peptide A44 to Host Mitochondria Prevents Apoptosis," Infection and Immunity, Aug. 1, 2010, 78(8):3616-3624.

Dominy et al., "Porphyromonas gingivalis in Alzheimer's disease brains: Evidence for disease causation and treatment with small-molecule inhibitors," Science Advances, Jan. 2019, 5(1):1-21.

Extended European Search Report in European Appln. No. 22737262. 0, mailed on Feb. 25, 2025, 29 pages.

Extended European Search Report in European Appln. No. 22843013. 8, mailed on Mar. 18, 2025, 7 pages.

Extended European Search Report in European Appln. No. 22889542. 1, mailed on Sep. 5, 2025, 11 pages.

Gibson et al., "Gingipain-Specific IgG in the Sera of Patients With Periodontal Disease Is Necessary for Opsonophagocytosis of Porphyromonas gingivalis," Journal of Periodontology, Oct. 2005, 76(10):1629-1636.

Hitzeman et al., "Expression, Processing, And Secretion of Heterologous Gene Products By Yeast," Paper, Presented at Proceedings of the Eleventh International Conference on Yeast Genetics and Molecular Biology, Montpellier, France, Sep. 13-17, 1982; Recent Advances in Yeast Molecular Biology, Sep. 1982, pp. 173-190.

Inagaki et al., "Antibody Responses of Periodontitis Patients to Gingipains of Porphyromonas gingivalis," Journal of Periodontology, Oct. 2003, 74(10):1432-1439.

International Preliminary Report on Patentability in International Appln. No. PCT/IB2022/060535, mailed on Jul. 14, 2023, 5 pages.

International Preliminary Report on Patentability in International Appln. No. PCT/US2021/57758, mailed on May 19, 2023, 7 pages.

International Preliminary Report on Patentability in International Appln. No. PCT/US2022/011853, mailed on Jul. 20, 2023, 11 pages.

International Search Report and Written Opinion in International Appln. No. PCT/US2021/57758, mailed on Mar. 1, 2022, 9 pages.

International Search Report and Written Opinion in International Appln. No. PCT/US2022/073614, mailed Nov. 30, 2022, 21 pages.

International Search Report and Written Opinion in International Appln. No. PCT/US2022/11853, mailed on Jun. 21, 2022, 15 pages.

Karlin et al., "Applications and statistics for multiple high-scoring segments in molecular sequences," Proceedings of the National Academy of Sciences, Jun. 15, 1993, 90(12):5873-5877.

Marcotte et al., "Expression of single-chain antibody against RgpA protease of Porphyromonas gingivalis in Lactobacillus," Journal of Applied Microbiology, Feb. 1, 2006, 100(2):256-263.

Milla et al., "Anti-PcrV antibody in cystic fibrosis: A novel approach targeting Pseudomonas aeruginosa airway infection," Pediatric Pulmonology, Jul. 2014, 49(7):650-658.

Nguyen et al., "Humoral Responses to Porphyromonas gingivalis Gingipain Adhesin Domains in Subjects with Chronic Periodontitis," Infection and Immunity, Mar. 2004, 72(3):1374-1382.

Partial Supplementary European Search Report in European Appln. No 22737262.0, mailed Nov. 10, 2024, 23 pages.

Kaizuka et al., "Human Monoclonal Antibody Inhibits Porphyromonas gingivalis Hemagglutinin Activity," Paper, Journal of Periodontology, Jan. 1, 2003 American Academy of Periodontology, US, Jan. 2003, 74(1):38-43.

Shibata et al., "Construction of novel human monoclonal antibodies neutralizing Porphyromonas gingivalis hemagglutination activity using transgenic mice expressing human Ig loci," Paper, Vaccine, May 31, 2005 Elsevier, Amsterdam, NL, May 2005, 23(29):3850-3856.

Cavaco et al., "Peptibodies: An elegant solution for a long-standing problem," Peptide science, 2017, 1-13.

Chung et al., "Effects of Periodontal Treatment in Patents with Periodontitis and Kidney Failure: A Pilot Study," International Journal of Environmental Research and Public Health, 2022, 19, 1533.

Li et al., "Association between Porphyromonas Gingivalis and systemic diseases: Focus on T cells-mediated adaptive immunity," Frontiers in Cellular and Infection Microbiology, 2022, 20 pages.

Quinn et al., "How do you diagnose rheumatoid arthritis early?," Best Practice & Research Clinical Rheumatology, 2001, 15(1):49-66.

* cited by examiner

FIG. 1A

Heavy chain amino acid sequence of KB001

```
20     EVQLKQSGPGLVAPSQSLSITCTVSGFSLSIYSVHWVROPPGKGLEWLGMIWGGGSSDYN     79
       |->VH                     HCDR1                      HCDR2
80     SALKSRLSISKDNSKSQVFLKMNSLQTDDTAMYYCARNGNFYAMDYWGQGTSVTVSSA       137
                                         HCDR3              |->CH1
138    KTTPPSVYPLAPGSAAQTNSMVTLGCLVKGYFPEPVTVTWNSGSLSSGVHTFPAVLQSDL    197

198    YTLSSSVTVPSSTWPSETVTCNVAHPASSTKVDKKIVPRDCGCKPCICTVPEVSSVFIFP    257
                                         |->CH2
258    PKPKDVLTITLTPKVTCVVVDISKDDPEVQFSWFVDDVEVHTAQTQPREEQFNSTFRSVS    317
                                             |->CH3
318    ELPIMHQDWLNGKEFKCRVNSAAFPAPIEKTISKTKGRPKAPQVYTIPPPKEQMAKDKVS    377

378    LTCMITDFFPEDITVEWQWNGQPAENYKNTQPIMNTNGSYFVYSKLNVQKSNWEAGNTFT    437

438    CSVLHEGLHNHHTEKSLSHSPGK          (SEQ ID NO:1)
```

FIG. 1B

Light chain amino acid sequence of KB001

```
-22    MDFQVQIFSFLLISASVIMSRG

1      QIVLTQSPAIMSASLGERVTMTCTASSSVSSSFLHWYQQKPGSSPQLWIYSTSNLASGVP
       |->VL                     LCDR1                 LCDR2
61     ARFSGSGSGTSYSLTISSMEAEDAATYYCHQYHHSPYIYTFGGGTKLEIKRADAAPTVSI
                                         LCDR3              |-CL
121    FPPSSEQLTSGGASVVCFLNNFYPKDINVKWKIDGSERQNGVLNSWTDQDSKDSTYSMSS

181    TLTLTKDEYERHNSYTCEATHKTSTSPIVKSFNRNEC (SEQ ID NO:2)
```

FIG. 2A

Full length RgpA from *P. gingivalis* W50; Accession CAA57997

```
1      mknlnkfvsi alcssllggm afaqqtelgr npnvrllest qqsvtkvqfr mdnlkftevq 61     tpkgmaqvpt ytegvnlsek gmptlpilsr slavsdtrem kvevvsskfi ekknvliaps 121    kgmimrnedp kkipyvygks ysqnkffpge iatlddpfil rdvrgqvvnf aplqynpvtk 181    tlriyteitv avsetseqgk nilnkkgtfa qfedtykrmf mnyepgrytp veekqngrmi 241    vivakkyegd ikdfvdwknq rglrtevkva ediaspvtan aiqqfvkqey ekegndlryv 301    lligdhkdip akitpgiksd qvygqivgnd hynevfigrf sceskedlkt qidrtihyer 361    nittedkwlg qalciasaeg gpsadngesd iqhenvianl ltqygytkii kcydpgvtpk 421    niidafnggi slanytghgs etawgtshfg tthvkqltns nqlpfifdva cvngdflfsm 481    pcfaealmra qkdgkptgtv aiiastinqs waspmrgqde mneilcekhp nnikrtfggv 541    tmngmfamve kykkdgekml dtwtvfgdps llvrtlvptk mqvtapaqin ltdasvnvsc 601    dyngaiatis angkmfgsav vengtatinl tgltnestlt ltvvgynket viktintnge 661    pnpyqpvsnl tattqgqkvt lkwdapstkt nattntarsv dgirelvlls vsdapellrs 721    gqaeivleah dvwndgsgyq illdadhdqy gqvipsdtht lwpncsvpan lfapfeytvp 781    enadpscspt nmimdgtasv nip̲a̲g̲t̲y̲d̲f̲a̲ ̲i̲a̲a̲p̲q̲a̲n̲a̲k̲i̲ ̲w̲i̲a̲g̲q̲q̲p̲t̲k̲e̲ ̲d̲d̲y̲v̲f̲e̲a̲g̲k̲k̲

841    y̲h̲f̲l̲m̲k̲k̲m̲g̲s̲ ̲g̲d̲g̲t̲e̲l̲t̲i̲s̲e̲ ̲g̲g̲g̲s̲d̲y̲t̲v̲t̲v̲ ̲y̲r̲d̲g̲t̲k̲i̲k̲e̲g̲ ̲l̲t̲a̲t̲t̲f̲e̲e̲d̲g̲ ̲v̲a̲a̲g̲n̲h̲e̲y̲c̲v̲

901    e̲v̲k̲y̲t̲a̲g̲v̲s̲p̲ ̲k̲v̲c̲k̲d̲v̲t̲v̲e̲q̲ ̲s̲n̲e̲f̲a̲p̲v̲q̲n̲l̲ ̲t̲gsavggkvt lkwdapngtp npnpnpnpnp 961    npgtttlses fengipaswk tidadgdghg wkpgnapgia gynsngcvys esfglggigv 1021   ltpdnylitp aldlpnggkl tfwvcaqdan yasehyavya sstgndasnf tnalleetit 1081   akgvrspeai rgriqstwrq ktvdlpagtk yvafrhfqst dmfyidldev eikangkrad 1141   fretfessth geataewtti dadgdfqgwl clssgqldwl tahggtnvvs sfswngmaln 1201   pdnyliskdv tgatkvkyyy avndgfpgdh yavmisktgt nagdftvvfe etpnginkgg 1261   arfglstead gakpqsqwie rtvdlpagtk yvafrhyncs dlnyillddi qftmggsptp 1321   tdytytvyrd gtkikeglte ttfeedgvat gnheycvevk ytagvspkkc vnvtvnstqf 1381   npvknlkaqp dggdvvlkwe apsakktegs revkrigdgl fvtiepandv raneakvvla 1441   adnvwgdntg yqflldadhn tfgsvipatg plftgtassd lysanfeyli panadpvvtt 1501   qniivtgqge vvipggvydy citnpepasg kmwiagdggn qparyddftf eagkkytftm
```

FIG. 2A (continued)

```
1561   rragmgdgtd meveddspas ytytvyrdgt kikegltett yrdagmsaqs heycvevkyt 1621   agvspkvcvd yipdgvadvt aqkpytltvv qktitvtcqg eamiydmngr rlaagrntvv 1681   ytaqggyyav mvvvdgksyv kklaik   (SEQ ID NO:21)
```

FIG. 2B

RgpA from *P. gingivalis* HG66; Accession P28784

```
          10         20         30         40         50
MKNLNKFVSI ALCSSLLGGM AFAQQTELGR NPNVRLLEST QQSVTKVQFR
          60         70         80         90        100
MDNLKFTEVQ TPKGMAQVPT YTEGVNLSEK GMPTLPILSR SLAVSDTREM
         110        120        130        140        150
KVEVVSSKFI EKKNVLIAPS KGMIMRNEDP KKIPYVYGKS YSQNKFFPGE
         160        170        180        190        200
IATLDDPFIL RDVRGQVVNF APLQYNPVTK TLRIYTEITV AVSETSEQGK
         210        220        230        240        250
NILNKKGTFA GFEDTYKRMF MNYEPGRYTP VEEKQNGRMI VIVAKKYEGD
         260        270        280        290        300
IKDFVDWKNQ RGLRTEVKVA EDIASPVTAN AIQQFVKQEY EKEGNDLRYV
         310        320        330        340        350
LLIGDHKDIP AKITPGIKSD QVYGQIVGND HYNEVFIGRF SCESKEDLKT
         360        370        380        390        400
QIDRTIHYER NITTEDKWLG QALCIASAEG GPSADNGESD IQHENVIANL
         410        420        430        440        450
LTQYGYTKII KCYDPGVTPK NIIDAFNGGI SLANYTGHGS ETAWGTSHFG
         460        470        480        490        500
TTHVKQLTNS NQLPFIFDVA CVNGDFLFSM PCFAEALMRA QKDGKPTGTV
         510        520        530        540        550
AIIASTINQS WASPMRGQDE MNEILCEKHP NNIKRTFGGV TMNGMFAMVE
         560        570        580        590        600
KYKKDGEKML DTWTVFGDPS LLVRTLVPTK MQVTAPAQIN LTDASVNVSC
         610        620        630        640        650
DYNGAIATIS ANGKMFGSAV VENGTATINL TGLTNESTLT LTVVGYNKET
         660        670        680        690        700
VIKTINTNGE PNPYQPVSNL TATTQGQKVT LKWDAPSTKT NATTNTARSV
         710        720        730        740        750
DGIRELVLLS VSDAPELLRS GQAEIVLEAH DVWNDGSGYQ ILLDADHDQY
         760        770        780        790        800
GQVIPSDTHT LWPNCSVPAN LFAPFEYTVP ENADPSCSPT NMIMDGTASV
         810        820        830        840        850
NIPAGTYDFA IAAPQANAKI WIAGQGPTKE DDYVFEAGKK YHFLMKKMGS
         860        870        880        890        900
GDGTELTISE GGGSDYTYTV YRDGTKIKEG LTETTYRDAG MSAQSHEYCV
         910        920        930        940        950
EVKYAAGVSP KVCVDYIPDG VADVTAQKPY TLTVVGKTIT VTCQGEAMIY
         960        970        980        990
DMNGRRLAAG RNTVVYTAQG GYYAVMVVVD GKSYVEKLAV K    (SEQ ID NO:25)
```

FIG. 3A

Full length RgpB from *P. gingivalis* W50; Accession WP 058019183

```
1     mkknfsrivs ivafssllgg mafaqoaerg rnoqvrllsa eqsmskvqfr mdnlqftdvq
61    tskgvaqvpt ftegvnisek gtpilpilsr slavsetram kvevvsskfi ekkdvliaps
121   kgvisraenp dqipyvygqs ynedkffpge iatlsdpfil rdvrgqvvnf aplqynpvtk
181   tlriyteivv avsetaeagq ntislvknst ftgfediyks vfmnyeatry tpveekengr
241   mivivpkkye ediedfvdwk nqrglrtevk vaediaspvt anaiqqfvkq eyekegndlt
301   yvllvgdhkd ipakitpgik sdqvygqivg ndhynevfig rfsceskedl ktqidrtihy
361   ernittedkw lgqalciasa eggpsadnge sdighenvia dlltqygytk iikcydpgvt
421   pkniidafng gislvnytgh gsetawgtsh fgtthvkqlt nsnqlpfifd vacvngdfly
481   nvpcfaealm raqkdgkptg tvaiiastin qywappmrgq demneilcek hpnnikrtfg
541   gvtmngmfam vekykkdgen mldtwtvfgd psllvrtlvp temqvtapan isasaqtfev
601   acdyngaiat lsddgdmvgt aivkdgkaii klnesiadet nltltvvgyn kvtvikdvkv
661   egtsiadvan dkpytvavsg ktitvespaa gltifdmngr rvataknrmv feaqngvyav
721   riategktyt ekvivk          (SEQ ID NO:22)
```

FIG. 3B

RgpB from *P. gingivalis* W83; Accession P95493

```
10         20         30         40         50
MKKNFSRIVS IVAFSSLLGG MAFAQPAERG RNPQVRLLSA EQSMSKVQFR
      60         70         80         90        100
MDNLKFTGVQ TSKGVAQVPT FTEGVNISEK GTPILPILSR SLAVSETRAM
     110        120        130        140        150
KVEVVSSKFI EKKDVLIAPS KGVISRAENP DQIPYVYGQS YNEDKFFPGE
     160        170        180        190        200
IATLSDPFIL RDVRGQVVNF APLQYNPVTK TLRIYTEIVV AVSETAEAGQ
     210        220        230        240        250
NTISLVKNST FTGFEDIYKS VFMNYEATRY TPVEEKENGR MIVIVPKKYE
     260        270        280        290        300
EDIEDFVDWK NQRGLRTEVK VAEDIASPVT ANAIQQFVKQ EKEKEGNDLT
     310        320        330        340        350
YVLLVGDHKD IPAKITPGIK SDQVYGQIVG NDHYNEVFIG RFSCESKEDL
     360        370        380        390        400
KTQIDRTIHY ERNITTEDKW LGQALCIASA EGGPSADNGE SDIQHENIIA
     410        420        430        440        450
NLLTQYGYTK IIKCYDPGVT PKNIIDAFNG GISLANYTGH GSETAWGTSH
     460        470        480        490        500
FGTTHVKQLT NSNQLPFIFD VACVNGDFLY NVPCFAEALM RAQKDGKPTG
     510        520        530        540        550
TVAIIASTIN QSWASPMRGQ DEMNEILCEK HPNNIKRTFG GVTMNGMFAM
     560        570        580        590        600
VEKYKKDGEK MLDTWTVFGD PSLLVRTLVP TKMQVTAPAN ISASAQTFEV
     610        620        630        640        650
ACDYNGAIAT LSDDGDMVGT AIVKDGKAII KLNESIADET NLTLTVVGYN
     660        670        680        690        700
KVTVIKDVKV EGTSIADVAN DKPYTVAVSG KTITVESPAA GLTIFDMNGR
     710        720        730
RVATAKNRMV FEAQNGVYAV RIATEGKTYT EKVIVK       (SEQ ID NO:26)
```

FIG. 4A

Full length Kgp from *P. gingivalis* W83; Accession AAC26523

```
1     mrkllllliaa  sllgvglyag  sakikldapt  trttctnnsf  kqfdasfsfn  eveltkvetk
61    ggtfasvsip  gafptgevgs  pevpavrkli  avpvgatpvv  rvksfteqvy  slngyqsekl
121   mphqpsmsks  ddpekvpfvy  naaayarkgf  vgqqeltqvem  lgtmrgvria  altinpvqyd
181   vvanqlkvrn  nieievsfqg  adevatqrly  dasfspyfet  aykqlfnrdv  ytdhgdlynt
241   pvrmlvvaga  kfkealkpwl  twkaqkgfyl  dvhytdeaev  gttnasikaf  ihkkyndgla
301   asaapvflal  vgdtdvisge  kgkktkkvtd  lyysavdgdy  fpemytfrms  asspeeltni
361   idkvlmyeka  tmpdksylek  vlliagadys  wnsqvgqpti  kygmqyyynq  ehgytdvyny
421   lkapytgcys  hlntgvsfan  ytahgsetaw  adpllttsql  kaltnkdkyf  laignccita
481   qfdyvqpcfg  evitrvkekg  ayayigsspn  sywgedyyws  vganavfgvq  ptfegtsmgs
541   ydatfledsy  ntvnsimwag  nlaathagni  gnithigahy  yweayhvlgd  gsvmpyramp
601   ktntytlpas  lpqnqasysi  qasagsyvai  skdgvlygtg  vanasgvatv  smtkqiteng
661   nydvvitrsn  ylpvikqiqv  gepspyqpvs  nltattqgqk  vtlkweapsa  kkaegsrevk
721   rigdglfvti  epandvrane  akvvlaadnv  wgdntgyqfl  ldadhntfgs  vipatgplft
781   gtassnlysa  nfeylvpana  dpvvttqnii  vtgqgevvip  ggvydycitn  pepasgkmwi
841   agdggnqpar  yddftfeagk  kytftmrrag  mgdgtdmeve  ddspasytyt  vyrdgtkike
901   gltattfeed  gvaagnheyc  vevkyta|gvs  pkvckdvtve  qsnefapvqn  lt|gssvqqkv
961   tlkwdapngt  pnpnpnpnpn  pgttlsesfe  ngipaswkti  dadgdghgwk  pgnapgiagy
1021  nsngcvyses  fglggigvlt  pdnylitpal  dlpnggkltf  wvcaqdanya  sehyavyass
1081  tgndasnftn  alleetitak  gvrspkairg  riqgtwrqkt  vdlpagtkyv  afrhfqstdm
1141  fyidldevei  kangkradft  etfessthge  apaewttida  dgdqggwlcl  ssgqldwlta
1201  hggsnvvssf  swngmalnpd  nyliskdvtg  atkvkyyyav  ndgfpgdhya  vmisktgtna
1261  gdftvvfeet  pnginkggar  fglsteanga  kpqsvwiert  vdlpagtkyv  afrhyncsdl
1321  nyilllddiqf  tmggsptptd  ytytvyrdgt  kikegltett  feedgvatgn  heycvevkyt
1381  agvspkkcvd  vtvnstqfnp  vqnltaeqap  nsmdailkwn  apaskraevl  nedfengipa
1441  swktidadgd  gnnwttttppp  ggssfaghns  aicvssashi  nfegpqnpdn  ylvtpelslp
1501  gggtltfwvc  aqdanyaseh  yavyasstgn  dasnfanall  eevltaktvv  tapeairgtr
1561  aqgtwyqktv  qlpagtkyva  frhfqctdff  winlddvvit  sgnapsytyt  iyrnntqias
1621  gvtettyrdp  dlatgfytyg  vkvvypnges  aietatlnit  sladvtaqkp  ytltvvgkti
1681  tvtcqgeami  ydmngrrlaa  grntvvytaq  gghyavmvvv  dgksyvekla  vk
(SEQ ID NO:23)
```

FIG. 4B

Kgp from *P. gingivalis*, ATCC 33277; Accession WP_012458488

```
       10         20         30         40         50
MRKLLLLIAA SLLGVGLYAQ SAKIKLDAPT TRTTCTNNSF KQFDASFSFN
       60         70         80         90        100
EVELTKVETK GGTFASVSIP GAFPTGEVGS PEVPAVRKLI AVPVGATPVV
      110        120        130        140        150
RVKSFTEQVY SLNQYGSEKL MPHQPSMSKS DDPEKVPFVY NAAAYARKGF
      160        170        180        190        200
VGQELTQVEM LGTMRGVRIA ALTINPVQYD VVANQLKVRN NIEIEVSFQG
      210        220        230        240        250
ADEVATQRLY DASFSPYFET AYKQLFNRDV YTDHGDLYNT PVRMLVVAGA
      260        270        280        290        300
KFKEALKPWL TWKAQKGFYL DVHYTDEAEV GTTNASIKAF IHKKYNDGLA
      310        320        330        340        350
ASAAPVFLAL VGDTDVISGE KGKKTKKVTD LYYSAVDGDY FPEMYTFRMS
      360        370        380        390        400
ASSPEELTNI IDKVLMYEKA TMPDKSYLEK ALLIAGADSY WNPKIGQQTI
      410        420        430        440        450
KYAVQYYYNQ DHGYTDVYSY PKAPYTGCYS HLNTGVGFAN YTAHGSETSW
      460        470        480        490        500
ADPSLTATQN KALTNKDKYF LAIGNCCVTA QFDYPQPCFG EVMTRVKEKG
      510        520        530        540        550
AYAYIGSSPN SYWGEDYYWS VGANAVFGVQ PTFEGTSMGS YDATFLEDSY
      560        570        580        590        600
NTVNSIMWAG NLAATHAGNI GNITHIGAHY YWEAYHVLGD GSVMPYRAMP
      610        620        630        640        650
KTNTYTLPAS LPQNQASYSI QASAGSYVAI SKDGVLYGTG VANASGVATV
      660        670        680        690        700
NMTKQITENG NYDVVITRSN YLPVIKQIQA GEPSPYQPVS NLTATTQGQK
      710        720        730        740        750
VTLKWDAPSA KKAEASREVK RIGDGLFVTI EPANDVRANE AKVVLAADNV
      760        770        780        790        800
WGDNTGYQFL LDADHNTFGS VIPATGPLFT GTASSNLYSA NFEYLIPANA
      810        820        830        840        850
DPVVTTQNII VTGQGEVVIP GGVYDYCITN PEPASGKMWI AGDGGNQPAR
      860        870        880        890        900
YDDFTFEAGK KYTFTMRRAG MGDGTDMEVE DDSPASYTYT VYRDGTKIQE
      910        920        930        940        950
GLTATTFEED GVAAGNHEYC VEVKYTA[GVS PKVCKDVTVE GSNEFAPVQN]
      960        970        980        990       1000
[LI]GSAVGQKV TLKWDAPNGT PNPNPNPNPG TTTLSESFEN GIPASWKTID
     1010       1020       1030       1040       1050
ADGDGHGWKP GNAPGIAGYN SNGCVYSESF GLGGIGVLTP DNYLITPALD
     1060       1070       1080       1090       1100
LPNGGKLTFW VCAQDANYAS EHYAVYASST GNDASNFTNA LLEETITAKG
     1010       1020       1030       1040       1050
VRSPEAIRGR IQGTWRQKTV DLPAGTKYVA FRHFQSTDMF YIDLDEVEIK
     1060       1070       1080       1090       1200
ANGKRADFTE TFESSTHGEA PAEWTTIDAD GDGQDWLCLS SGQLDWLTAH
```

FIG. 4B (continued)

```
      1210        1220        1230        1240        1250
GGTNVVASFS  WNGMALNPDN  YLISKDVTGA  TKVKYYYAVN  DGFPGDHYAV
      1260        1270        1280        1290        1300
MISKTGTNAG  DFTVVFEETP  NGINKGGARF  GLSTEANGAK  PQSVWIERTV
      1310        1320        1330        1340        1350
DLPAGTKYVA  FRHYNCSDLN  YILLDDIQFT  MGGSPTPTDY  TYTVYRDGTK
      1360        1370        1380        1390        1400
IKEGLTETTE  EEDGVATGNH  EYCVEVKYTA  GVSPKVCVNV  TINPTQFNPV
      1410        1420        1430        1440        1450
KNLKAQPDGG  DVVLKWEAPS  GKRGELLNED  FEGDAIPTGW  TALDADGDGN
      1460        1470        1480        1490        1500
NWDITLNEFT  RGERHVLSPL  RASNVAISYS  SLLQGQEYLP  LTPNNFLITP
      1510        1520        1530        1540        1550
KVEGAKKITY  KVGSPGLPQW  SHDHYALCIS  KSGTAAADFE  VIFEETMTYT
      1560        1570        1580        1590        1600
QGGANLTREK  DLPAGTKYVA  FRHYNCTDVL  GIMIDDVVIT  GEGEGPSYTY
      1610        1620        1630        1640        1650
TVYRDGTKIQ  EGLTETTYRD  AGMSAQSHEY  CVEVKYAAGV  SPKVCVDYIP
      1660        1670        1680        1690        1700
DGVADVTAQK  PYTLTVVGKT  ITVTCQGEAM  IYDMNGRRLA  AGRNTVVYTA
      1710        1720
QGGYYAVMVV  VDGKSYVEKL  AIK        (SEQ ID NO:27)
```

FIG. 5A

Full length HagA from *P. gingivalis* W83; Accession AAQ66831

```
1      mariileahd  vwedgtgyqm  lwdadhnqyg  asipeesfwf  angtipagly  dgfeykvpvn
61     adasfsptnf  vldgtasadi  pagtydyvii  npnpgiiyiv  gegvskgndy  vveagktyhf
121    tvqrqgpgda  asvvvtgegg  nefaovqnlq  wsvsgqtvtl  twqapasdkr  tyvlnesfdt
181    qtlpngwtmi  dadgdghnwl  stinvyntat  htgdgamfsk  swtassgaki  dlspdnylvt
241    pkftvpengk  lsywnssqep  wtnehygvfl  sttgneaanf  tiklleetlg  sgkpapmnlv
301    ksegvkapap  yqertidlsa  yagqqvylaf  rhfgctgifr  lylddvavsg  egssndytyt
361    vyrdnvviaq  nltattfnqe  nvapgqynyc  vevkyta[gvs  pkvckdvtve  gsnefapvqn]
421    [lt]gsavgqkv  tlkwdapngt  pnpnpgtttl  sesfengipa  swktidadgd  gnnwtttppp
481    ggssfaghns  aicvssasyi  nfegpqnpdn  ylvtpelslp  nggtltfwvc  aqdanyaseh
541    yavyasstgn  dasnfanall  eevltaktvv  tapeairgtr  vqgtwyqktv  qlpagtkyva
601    frhfgctdff  winlddveik  angkradfte  tfessthgea  paewttidad  gdgqgwlcls
661    sgqlgwltah  ggtnvvasfs  wngmalnpdn  yliskdvtga  tkvkyyyavn  dgfpgdhyav
721    misktgtnag  dftvvfeetp  nginkggarf  glsteangak  pqsvwiertv  dlpagtkyva
781    frhyncsdln  yillddiqft  mggsptptdy  tytvyrdgtk  ikegltettf  eedgvatgnh
841    eycvevkyta  gvspkecvnv  tvdpvqfnpv  qnltqsavgq  kvtlkwdapn  gtpnpnpgtt
901    tlsesfengi  paswktidad  gdgnnwtttp  ppggtsfagh  nsaicvssas  yinfegpqnp
961    dnylvtpels  lpnggtltfw  vcaqdanyas  ehyavyasst  gndasnfana  lleevltakt
1021   vvtapeairg  trvqgtwyqk  tvqlpagtky  vafrhfgctd  ffwinlddve  ikangkradf
1081   tetfessthg  eapaewttid  adgdgqgwlc  lssgqldwlt  ahggtnvvas  fswngmalnp
1141   dnyliskdvt  gatkvkyyya  vndgfpgdhy  avmisktgtn  agdftvvfee  tpnginkgga
1201   rfglsteang  akpqsvwier  tvdlpagtky  vafrhyncsd  lnyillddiq  ftmggsptpt
1261   dytytvyrdg  tkikegltet  tfeedgvatg  nheycvevky  tagvspkecv  nvtvdpvqfn
1321   pvqnltqsav  gqkvtlkwda  pngtpnpnpg  tttlsesfen  gipaswktid  adgdgnnwtt
1381   tpppggtsfa  ghnsaicvss  asyinfegpq  npdnylvtpe  lslpnggtlt  fwvcaqdany
1441   asehyavyas  stgndasnfa  nalleevlta  ktvvtapeai  rgtrvqgtwy  qktvqlpagt
1501   kyvafrhfgc  tdffwinldd  veikangkra  dftetfesst  hgeapaewtt  idadgdgqgw
1561   lclssgqlgw  ltahggtnvv  asfswngmal  npdnyliskd  vtgatkvkyy  yavndgfpgd
1621   hyavmisktg  tnagdftvvf  eetpnginkg  garfglstea  ngakpqsvwi  ertvdlpagt
1681   kyvafrhync  sdlnyilldd  iqftmggspt  ptdytytvyr  dgtkikeglt  ettfeedgva
1741   tgnheycvev  kytagvspke  cvnvtinptq  fnpvqnltae  qapnsmdail  kwnapaskra
1801   evlnedfeng  ipaswktida  dgdgnnwttt  pppggssfag  hnsaicvssa  syinfegpqn
1861   pdnylvtpel  slpgggtltf  wvcaqdanya  sehyavyass  tgndasnfan  alleevltak
1921   tvvtapeair  gtrvqgtwyq  ktvqlpagtk  yvafrhfgct  dffwinlddv  vitsgnapsy
1981   tytiyrnntq  iasgvtetty  rdpdlatgfy  tygvkvvypn  gesaietatl  nitsladvta
2041   qkpytltvvg  ktitvtcqge  amiydmngrr  laagrntvvy  taqgghyavm  vvvdgksyve
2101   klavk       (SEQ ID NO:24)
```

FIG. 5B

HagA from *P. gingivalis* 381; Accession Q51845

```
         10         20         30         40         50
MRKLNSLFSL AVLLSLLCWG QTAAAQGGPK TAPSVTHQAV QKGIRTSKVK
         60         70         80         90        100
DLRDPIPAGM ARIILEAHDV WEDGTGYQML WDADHNQYGA SIPEESFWFA
        110        120        130        140        150
NGTIPAGLYD PFEYKVPVNA DASFSPTNFV LDGTASADIP AGTYDYVIIN
        160        170        180        190        200
PNPGIIYIVG EGVSKGNDYV VEAGKTYHFT VQRQGPGDAA SVVVTGEGGN
        210        220        230        240        250
EFAPVQNLQW SVSGQTVTLT WQAPASDKRT YVLNESFDTQ TLPNGWTMID
        260        270        280        290        300
ADGDGHNWLS TINVYNTATH TGDGAMFSKS WTASGGAKID LSPDNYLVTP
        310        320        330        340        350
KVTVPENGKL SYWVSSQVPW TNEHYGVFLS TTGNEAANFT IKLLEETLGS
        360        370        380        390        400
DKPAPMNLVK SEGVKLPAPY QERTIDLSAY AGQQVYLAFR HFNSTGIFRL
        410        420        430        440        450
YLDDVAVSGE GSSNDYTYTV YRDNVVIAQN LAATTFNQEN VAPGQNNYCV
        460        470        480        490        500
EVKYTAGVSP KVCKDVTVEG SNEFAHVQNL TGSAVGQKVT LKWDAPNGTP
        510        520        530        540        550
NPNPGTTTLS ESFENGIPAS WKTIDADGDG NNWTTTPPPG GTSFAGHNSA
        560        570        580        590        600
ICASSASYIN FEGPQNPDNY LVTPELSLPN GGTLTFWVCA QDANYASEHY
        610        620        630        640        650
AVYASSTGND ASNFANALLE EVLTAKTVVT APEAIRGTRV QGTWYQKTVQ
        660        670        680        690        700
LPAGTKYVAF RHFGCTDFFW INLDDVEIKA NGKRADFTET FESSTHGEAP
        710        720        730        740        750
AEWTTIDADG DGQGWLCLSS GQLDWLTAHG GTNVVASFSW NGMALNPDNY
        760        770        780        790        800
LISKDVTGAT KVKYYYAVND GFPGDHYAVM ISKTGTNAGD FTVVFEETPN
        810        820        830        840        850
GINKGGARFG LSTEADGAKP QSVWIERTVD LPAGTKYVAF RHYNCSDLNY
        860        870        880        890        900
ILLDDIQFTM GGSPTPTDYT YTVYRDGTKI KEGLTETTFE EDGVATGNHE
        910        920        930        940        950
YCVEVKYTAG VSPKECVNVT VDPVQFNPVQ NLTGSAVGQK VTLKWDAPNG
        960        970        980        990       1000
TPNPNPNPNP GTTTLSESFE NGIPASWKTI DADGDGNNWT TTPPPGGTSF
       1010       1020       1030       1040       1050
AGHNSAICAS SASYINFEGP QNPDNYLVTP ELSLPNGGTL TFWVCAQDAN
       1060       1070       1080       1090       1100
YASEHYAVYA SSTGNDASNF ANALLEEVLT AKTVVTAPEA IRGTRVQGTW
```

FIG. 5B (cont)

```
         1110       1120       1130       1140       1150
    YQKTVQLPAG TKYVAFRHFG CTDFFWINLD DVEIKANGKR ADFTETFESS
         1160       1170       1180       1190       1200
    THGEAPAEWT TIDADGDGQG WLCLSSGQLG WLTAHGGTNV VASFSWNGMA
         1210       1220       1230       1240       1250
    LNPDNYLISK DVTGATKVKY YYAVNDGFPG DHYAVMISKT GTNAGDFTVV
         1260       1270       1280       1290       1300
    FEETPNGINK GGARFGLSTE ADGAKPQSVW IERTVDLPAG TKYVAFRHYN
         1310       1320       1330       1340       1350
    CSDLNYILLD DIQFTMGGSP TPTDYTYTYY RDGTKIKEGL TETTFEEDGV
         1360       1370       1380       1390       1400
    ATGNHEYCVE VKYTAGVSPK ECVNVTVDPV QFNPVQNLTG SAVGQKVTLK
         1410       1420       1430       1440       1450
    WDAPNGTPNP NPNPNPGTTT LSESFENGIP ASWKTIDADG DGNNWTTTPP
         1460       1470       1480       1490       1500
    PGGTSFAGHN SAICASSASY INFEGPQNPD NYLVTPELSL PNGGTLTFWV
         1510       1520       1530       1540       1550
    CAQDANYASE HYAVYASSTG NDASNFANAL LEEVLTAKTV VTAPEAIRGT
         1560       1570       1580       1590       1600
    RVQGTWYQKT VQLPAGTKYV AFRHFGCTDF FWINLDDVEI KANGKRADFT
         1610       1620       1630       1640       1650
    ETFESSTHGE APAEWTTIDA DGDGQGWLCL SSGQLGWLTA HGGTNVVASF
         1660       1670       1680       1690       1700
    SWNGMALNPD NYLISKDVTG ATKVKYYYAV NDGFPGDHYA VMISKTGTNA
         1710       1720       1730       1740       1750
    GDFTVVFEET PNGINKGGAR FGLSTEADGA KPQSVWIERT VDLPAGTKYV
         1760       1770       1780       1790       1800
    AFRHYNCSDL NYILLDDIQF TMGGSPTPTD YTYTVYRDGT KIKEGLTETT
         1810       1820       1830       1840       1850
    FEEDGVATGN HEYCVEVKYT AGVSPKECVN VTVDPVQFNP VQNLTGSAVG
         1860       1870       1880       1890       1900
    QKVTLKWDAP NGTPNPNPNP NPGTTTLSES FENGIPASWK TIDADGDGNN
         1910       1920       1930       1940       1950
    WTTTPPPGGT SFAGHNSAIC VSSASYINFE GPQNPDNYLV TPELSLPGGG
         1960       1970       1980       1990       2000
    TLTFWVCAQD ANYASEHYAV YASSTGNDAS NFANALLEEV LTAKTVVTAP
         2010       2020       2030       2040       2050
    EAIRGTRVQG TWYQKTVQLP AGTKYVAFRH FGCTDFFWIN LDEVEIKANG
         2060       2070       2080       2090       2100
    KRADFTETFE SSTHGEAPAE WTTIDADGDG QGWLCLSSGQ LDWLTAHGGT
         2110       2120       2130       2140       2150
    NVVASFSWNG MALNPDNYLI SKDVTGATKV KYYYAVNDGF PGDHYAVMIS
         2160       2170       2180       2190       2200
    KTGTNAGDFT VVFEETPNGI NKGGARFGLS TEADGAKPQS VWIERTVDLP
         2210       2220       2230       2240       2250
    AGTKYVAFRH YNCSDLNYIL LDDIQFTMGG SPTPTDYTYT VYRDGTKIKE
```

FIG. 5B (cont)

```
       2260       2270       2280       2290       2300
  GLTETTFEED GVATGNHEYC VEVKYTAGVS PKVCVNVTIN PTQFNPVQNL
       2310       2320       2330       2340       2350
  TAEQAPNSMD AILKWNAPAS KRAEVLNEDF ENGIPSSWKT IDADGDGNNW
       2360       2370       2380       2390       2400
  TTTPPPGGSS FAGHNSAICV SSASYINFEG PQNPDNYLVT PELSLPGGGT
       2410       2420       2430       2440       2450
  LTFWVCAQDA NYASEHYAVY ASSTGNDASN FANALLEEVL TAKTVVTAPE
       2460       2470       2480       2490       2500
  AIRGTRVQGT WYQKTVQLPA GTKYVAFRHF GCTDFFWINL DDVVITSGNA
       2510       2520       2530       2540       2550
  PSYTYTIYRN NTQIASGVTE TTYRDPDLAT GFYTYGVKVV YPNGESAIET
       2560       2570       2580       2590       2600
  ATLNITSLAD VTAQKPYTLT VVGKTITVTC QGEAMIYDMN GRRLAAGRNT
       2610       2620
  VVYTAQGGHY AVMVVVDGKS YVEKLAVK        (SEQ ID NO:28)
```

Grouped graph

| Lane 1 | Precision Plus protein STD |
| Lane 2 | OMV W83 5ug |
| Lane 3 | OMV W83 1ug |
| Lane 4 | OMV W83 0.2ug |
| Lane 5 | OMV W83 0.04ug |
| Lane 6 | OMV ΔPPAD W83 5ug |
| Lane 7 | OMV ΔPPAD W83 1ug |
| Lane 8 | OMV ΔPPAD W83 0.2ug |
| Lane 9 | OMV ΔPPAD W83 0.04ug |
| Lane 10 | |

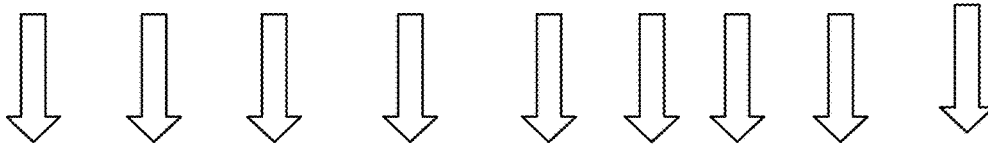
FIG. 10
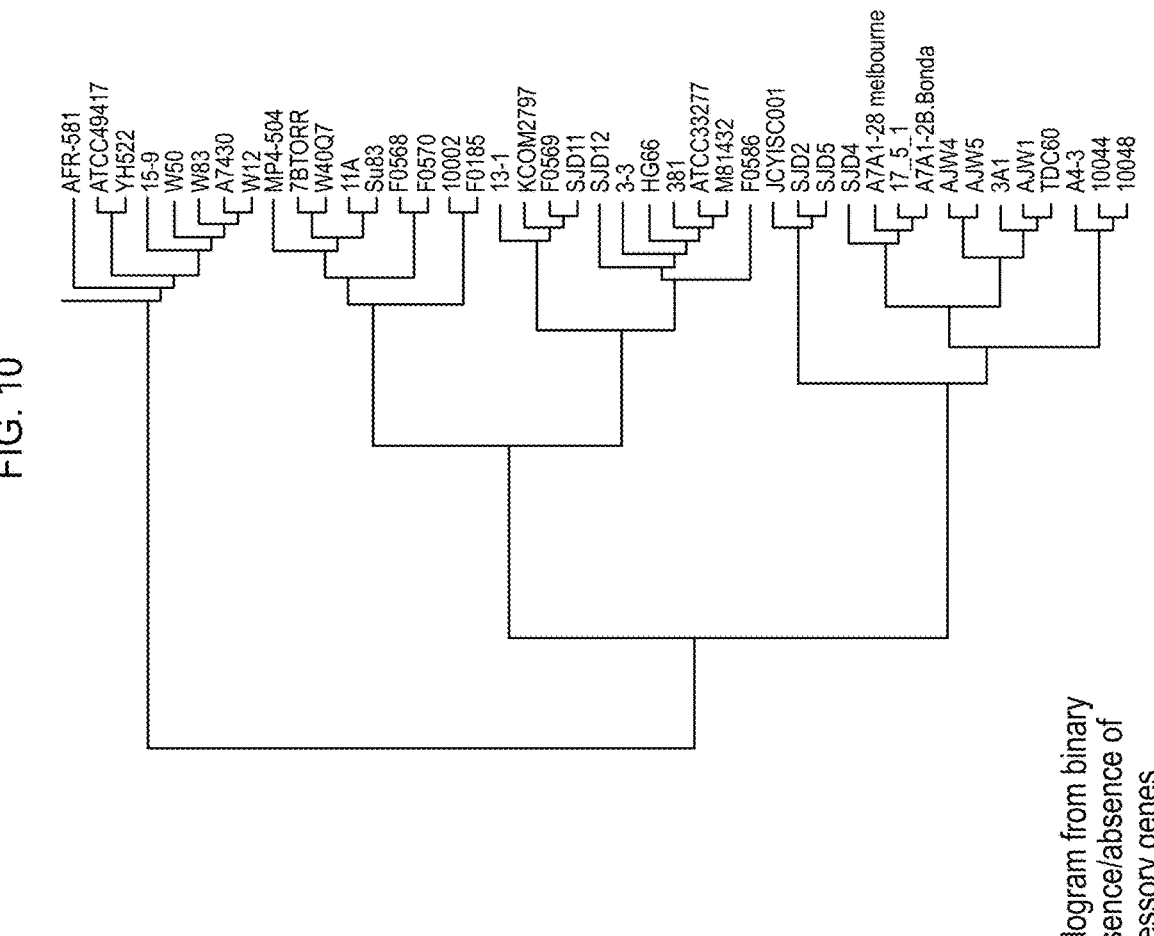
Phylogram from binary presence/absence of accessory genes

_P. gingivalis_ DNA 2 fg   20 fg   100 fg   0.5 pg

Figures 16, 17:
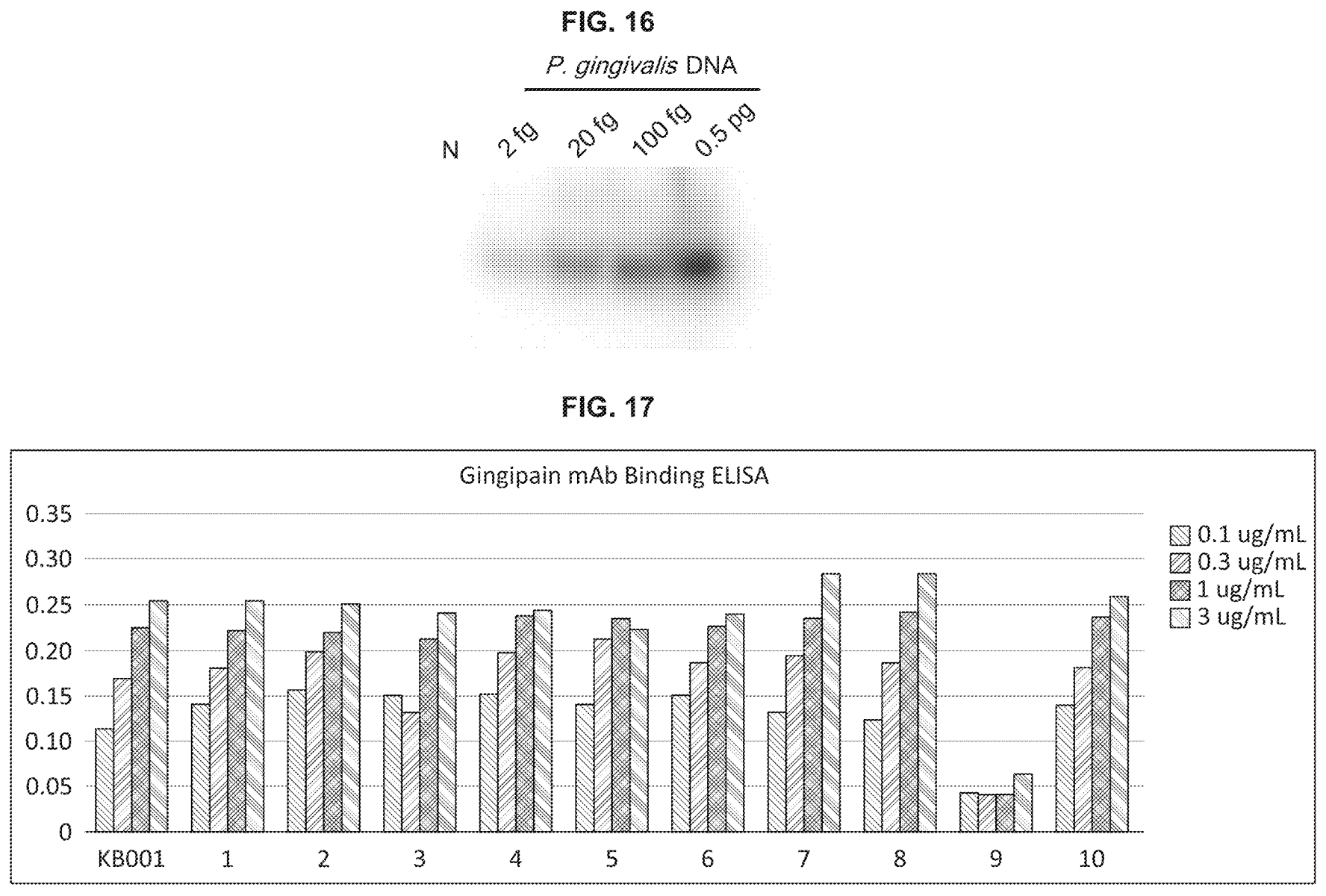

Gingipain mAb Binding ELISA

Legend: 0.1 ug/mL, 0.3 ug/mL, 1 ug/mL, 3 ug/mL

X-axis: KB001, 1, 2, 3, 4, 5, 6, 7, 8, 9, 10

Y-axis: 0, 0.05, 0.10, 0.15, 0.20, 0.25, 0.30, 0.35

FIG. 18

Samples for tryptic digest / MS analysis
are in duplicates just in the case analysis
needs to be repeated.

HG66 RgpA 1    = HG66 Kgp 1
HG66 RgpA 2a  = HG66 Kgp 2A
HG66 RgpA 2b  = HG66 Kgp 2b
etc.

CTD is a unique sample.

FIG. 22A

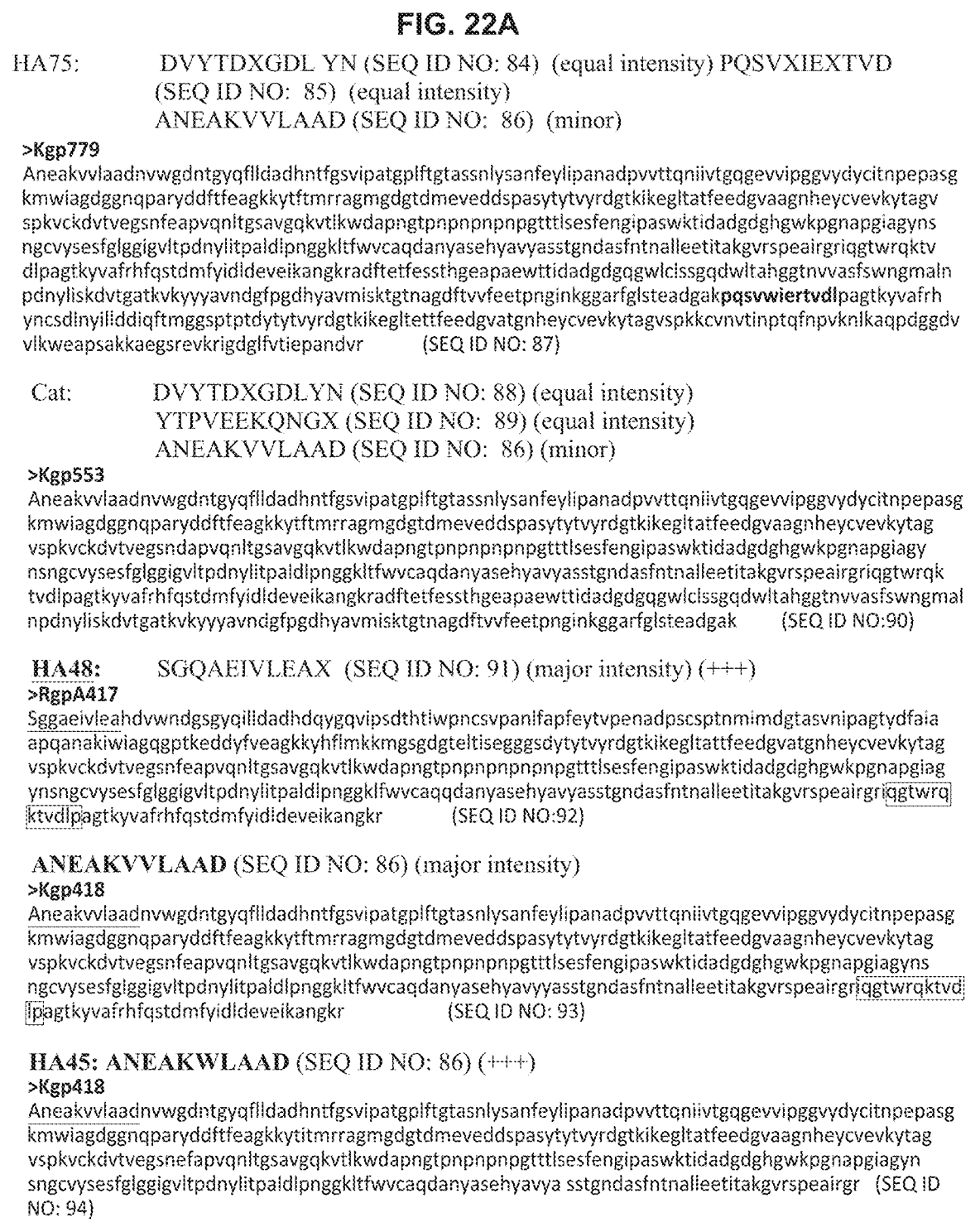

HA75:    DVYTDXGDL YN (SEQ ID NO: 84)  (equal intensity) PQSVXIEXTVD
(SEQ ID NO: 85)  (equal intensity)
ANEAKVVLAAD (SEQ ID NO: 86)  (minor)

>Kgp779
Aneakvvlaadnvwgdntgyqflldadhntfgsvipatgplftgtassnlysanfeylipanadpvvttqniivtgqgevvipggvydycitnpepasg
kmwiagdggnqparyddftfeagkkytftmrragmgdgtdmeveddspasytytvyrdgtkikegltatfeedgvaagnheycvevkytagv
spkvckdvtvegsnfeapvqnltgsavgqkvtlkwdapngtpnpnpnpnpgtttlsesfengipaswktidadgdghgwkpgnapgiagyns
ngcvysesfglggigvltpdnylitpaldipnggkltfwvcaqdanyasehyavyasstgndasfntnalleetitakgvrspeairgriqgtwrqktv
dlpagtkyvafrhfqstdmfyidldeveikangkradftetfessthgeapaewttidadgdgqgwlclssgqdwltahggtnvvasfswngmaln
pdnyliskdvtgatkvkyyyavndgfpgdhyavmisktgtnagdftvvfeetpnginkggarfglsteadgakpqsvwiertvdlpagtkyvafrh
yncsdlnyiliddiqftmggsptptdytytvyrdgtkikegltettfeedgvatgnheycvevkytagvspkkcvnvtinptqfnpvknlkaqpdgggdv
vlkweapsakkaegsrevkrigdglfvtiepandvr        (SEQ ID NO: 87)

Cat:    DVYTDXGDLYN (SEQ ID NO: 88) (equal intensity)
YTPVEEKQNGX (SEQ ID NO: 89) (equal intensity)
ANEAKVVLAAD (SEQ ID NO: 86) (minor)

>Kgp553
Aneakvvlaadnvwgdntgyqflldadhntfgsvipatgplftgtassnlysanfeylipanadpvvttqniivtgqgevvipggvydycitnpepasg
kmwiagdggnqparyddftfeagkkytftmrragmgdgtdmeveddspasytytvyrdgtkikegltatfeedgvaagnheycvevkytag
vspkvckdvtvegsndapvqnltgsavgqkvtlkwdapngtpnpnpnpnpgtttlsesfengipaswktidadgdghgwkpgnapgiagy
nsngcvysesfglggigvltpdnylitpaldipnggkltfwvcaqdanyasehyavyasstgndasfntnalleetitakgvrspeairgriqgtwrqk
tvdlpagtkyvafrhfqstdmfyidldeveikangkradftetfessthgeapaewttidadgdgqgwlclssgqdwltahggtnvvasfswngmal
npdnyliskdvtgatkvkyyyavndgfpgdhyavmisktgtnagdftvvfeetpnginkggarfglsteadgak        (SEQ ID NO:90)

HA48:    SGQAEIVLEAX  (SEQ ID NO: 91) (major intensity) (+++)
>RgpA417
Sggaeivleahdvwndgsgyqilldadhdqygqvipsdthtlwpncsvpanlfapfeytvpenadpscsptnmimdgtasvnipagtydfaia
apqanakiwiagqgptkeddyfveagkkyhflmkkmgsgdgteltiiseggsdytytvyrdgtkikegltattfeedgvatgnheycvevkytag
vspkvckdvtvegsnfeapvqnltgsavgqkvtlkwdapngtpnpnpnpnpgtttlsesfengipaswktidadgdghgwkpgnapgiag
ynsngcvysesfglggigvltpdnylitpaldipnggklfwvcaqqdanyasehyavyasstgndasfntnalleetitakgvrspeairgri⎡qgtwrq⎤
⎣ktvdlp⎦agtkyvafrhfqstdmfyidldeveikangkr        (SEQ ID NO:92)

ANEAKVVLAAD (SEQ ID NO: 86) (major intensity)
>Kgp418
Aneakvvlaadnvwgdntgyqflldadhntfgsvipatgplftgtasnlysanfeylipanadpvvttqniivtgqgevvipggvydycitnpepasg
kmwiagdggnqparyddftfeagkkytftmrragmgdgtdmeveddspasytytvyrdgtkikegltatfeedgvaagnheycvevkytag
vspkvckdvtvegsnfeapvqnltgsavgqkvtlkwdapngtpnpnpnpgtttlsesfengipaswktidadgdghgwkpgnapgiagyns
ngcvysesfglggigvltpdnylitpaldipnggkltfwvcaqdanyasehyavyyasstgndasfntnalleetitakgvrspeairgri⎡qgtwrqktvd⎤
⎣lp⎦agtkyvafrhfqstdmfyidldeveikangkr        (SEQ ID NO: 93)

HA45: ANEAKVVLAAD (SEQ ID NO: 86) (+++)
>Kgp418
Aneakvvlaadnvwgdntgyqflldadhntfgsvipatgplftgtasnlysanfeylipanadpvvttqniivtgqgevvipggvydycitnpepasg
kmwiagdggnqparyddftfeagkkytitmrragmgdgtdmeveddspasytytvyrdgtkikegltatfeedgvaagnheycvevkytag
vspkvckdvtvegsnefapvqnltgsavgqkvtlkwdapngtpnpnpnpgtttlsesfengipaswktidadgdghgwkpgnapgiagyn
sngcvysesfglggigvltpdnylitpaldipnggkltfwvcaqdanyasehyavya sstgndasfntnalleetitakgvrspeairgr   (SEQ ID
NO: 94)

FIG. 22B

HA35: ANEAKVVLAAD (SEQ ID NO: 86) (equal intensity) (+)
>Kgp375
Aneakvvlaadnvwgdntgyqflldadhntfgsvipatgplftgtassnlysanfeylipanadpvvttqniivtgqgevvipggvydycitnpepasg
kmwiagdggnqparyddftfeagkkytftmrragmgdgtdmeveddspasytytvyrdgtkikegltatfeedgvaagnheycvevkytagv
spkvckdvtvegsnfeapvqnltgsavgqkvtlkwdapngtpnpnpnpnpgtttlsesfengipaswktidadgdghgwkpgnapgiagyns
ngcvysesfglggigvltpdnylitpaldlpnggkltfwvcaqdanyasehyavyasstgndasfntnalleetitakgvrspeairgr (SEQ ID
NO: 95)

PQSVXIEXTVD (SEQ ID NO: 85) (equal intensity)
>RgpA361
Pqsvwiertvdlpagtkyvafrhyncsdlnyillddiqftmggsptptdytytvyrdgtkikegltettfeedgvatgnheycvevkytagvspkecv
nvtinptqfnpvknlkaqpdggdvvlkweapsakktegsrevkrigdglfvtiepandvraneakvvlaadnvwgdntgyqflldadhntfgsvipat
gplftgtassnlysanfeylipanadpvvttqnivtgqgevvipggvydycitnpepasgkmwiagdggnqparyddftfeagkkytftmrragm
gdgtdmeveddspasy tytvyrdgtkikegltettyrdagmsaqsheycvevkyaagvspkvcvdyipd (SEQ ID NO:96)

*LPAPYQXNDIX (SEQ ID NO:98) (equal intensity)*
>KgpA361
Pqsvwiertvdlpagtkyvafrhyncsdlnyillddiqftmggsptptdytytvyrdgtkikegltettfeedgvatgnheycvevkytagvspkecvn
vtinptqfnpvknlkaqpdggdvvlkweapsakktegsrevkrigdglfvtiepandvraneakvvlaadnvwgdntgyqflldadhntfgsvipatg
plftgtassnlysanfeylipanadpvvttqnivtgqgevvipggvydycitnpepasgkmwiagdggnqparyddftfeagkkytftmrragmd
gtdmeveddspasy tytvyrdgtkikegltettyrdagmsaqsheycvevkyaagvspkvcvdyipd (SEQ ID NO:97)

HA30: ANEAKVVLAAD (SEQ ID NO: 86) (++)
>Kgp203
Aneakvvlaadnvwgdntgyqflldadhntfgsvipatgplftgtasnlysanfeylipanadpvvttqniivtgqgevvipggvydycitnpepasg
kmwiagdggnqparyddftfeagkkytftmrragmgdgtdmeveddspasytytvyrdgtkikegltatfeedgvaagnheycvevkytag
spkvcvdyipd (SEQ ID NO:99)
>RgpA203
Aneakvvlaadnvwgdntgyqflldadhntfgsvipatgplftgtassnlysanfeylipanadpvvttqniivtgqgevvipggvydycitnpepasg
kmwiagdggnqparyddftfeagkkytftmrragrmgdgtdmeveddspasytytvyrdgtkikegltettyrdagmsaqsheycvevkyaa
gvspkvcvdyipd (SEQ ID NO:100)
>KGP373
Aneakvvlaadnvwgdntgyqflldadhntfgsvipatgplftgtassnlysanfeylipanadpvvttqniivtgqgevvipggvydycitnpepasg
kmwiagdggnqparyddftfeagkkytftmrragmgdgtdmeveddspasytytvyrdgtkikegltatfeedgvgvaagnheycvevkytag
vspkvckdvtvegsnfeapvqnltgsavgqkvtlkwdapngtpnpnpnpnpgtttlsesfengipaswktidadgdghgwkpgnapgiagyns
ngcvysesf glggigvltpdnyli tpaldlpnggkltfwvcaqdanyasehyavyasstgndasfntnalleetitakgvrspeairgr (SEQ ID
NO: 101)

HA17: ADFTETFESS (SEQ ID NO: 102) (+)
>RgpA135
Adftetfesssthgeapaewttidadgdgdqgwlclssgqidwltahggtnvvafsswngmalnpdnyliskdvtgatkvkyyyavndgfpgdhy
avmisktgtnagdftvvfeetpnginkgga rfglsteangak (SEQ ID NO:103)

HA9: IQGTWYQKTVDLP (SEQ ID NO: 104)
>Kgp45
Iqgtwrqktvdlpagtkyvafrhfqstdmfyidldeveikangkr (SEQ ID NO:105)

FIG. 22C

>AAA99810(HG66_Kgp)

*mrklilliaasllgvglyaqnakikldapttrltctnnsfkqfdasfsineveltkvetkggtfasvsipgafptgevgspevpavrkliavpvgatpvvrvksfte qvysinqygseklmphqpsmsksddpekvpfaynaaayarkgfvgqeltqvemlgtmrgvriaaltinpvqydvvanqlkvmnieievsfqgadev atqrlydasfspyfetaykqlfnr*dvytdhgdlyntpvrmlvvagakfkealkpwltwkaqkgfyldvhytdeaevgttnasikafihkkyndglaasaa pvflalvgdtdvisgekgkktkkvtdlyysavdgdyfpemytrfmsasspeeltniidkvlmyekatmpdksylekalliagadsywnpkigqqtikyavq yyynqdhgytdvysypkapytgcyshlntgvgfanytahgsetswadpsvtatqvkaltnknkyflaignccvtaqfdypqpcfgevmtrvkekgaya yigsspnsywgedyywsvganavfgvqptfegtsmgsydatfledsyntvnsimwagnlaathaenignvthigahyyweayhvlgdgsvmpyra mpktntyllpaslpqnqasysiqasagsyvaiskdgvlygtgvanasgvatvnmtkqitengnydvvitrsnylpvikqiqagepspyqpvsnltattqg qkvtlkwdapsakkaegrsevkrigdglfvtiepandvraneakvvlaadnvwgdntgyqflldadhntfgsvipatgplftgtassnlysanfeylipan adpvvttqniivtgqgevvipggvydycitnpepasgkmwiagdggnqparyddftfeagkkytftmrragmgdgtdmeveddspas*ytytvvrda tkikeqltattffeedgvaagnheycvevkvtagvspkvckdvtvegsnefapvgnltgsavgak*vtlkwdapngtpnpnpnpnpgtttlsesfengip aswktidadgdghgwkpgnapgiagynsngcvysesfglggig*M*pdnylitpaldlpnggkltfwvcaqdanyasehyavyasstgndasnft nalleetitakgvrspeairgriqgtwrqktvdlpagtkyvafrhqstdmfyidldeveikangkrpqsvwiertvdlpagtkyvafrhyncsdlnyilld diqftmggsptptd*ytytvyrdgtkikeqltettffeedgvatgnheycvevkvtagvspkkcvnvtinptgfnpvknl*kaqpdggdvvlkweapsakkae gsrevkrigdglfvtiepandvraneakvvlaadnvwgdntgyqflldadhntfgsvipatgplftgtassnlysanfeylipanadpvvttqniivtgqgev vipggvydycitnpepasgkmwiagdggnqparyddftfeagkkytftmrragmgdgtdmeveddspas*tytvvrdgtkikeqltettyrdagmsags heycvevkyaagvspkvcvdyipd*gvadvtaqkpytltvvgktitvtcqgeamiydmngrrlaagrntvvytaqggyyavmvvvdgksyveklavk*

(SEQ ID NO:106)

>AAA69539(HG66_RgpA)

*mknlnkfvsialcssliggmafaqqtelgrnpnvrllestqqsvtkvqfrmdnlkftevqtpkgigqvptytegvnlsekgmptlpilsrslavsdtremkvevv sskfiekknvliapskgmimrnedpkkipyvygksysqnkffpgeiatlddpfilrdvrgqvvnfaplqynpvtktlriyteitvavsetseqgkniInkkgtfagf edtykrmfmnyepg*rytpveekqngrmi*vivakkyegdikdfvdwknqrglrtevkvaediaspvtanaiqqfvkqeyekegndltyvllvgdhkdipa kitpgiksdqvygqivgndhynevfigrfsceskedlktqidrtihyernittedkwlgqalciasaeggpsadngesdiqhenvianlltqygytkiikcydpgv tpkniidafnggislvnytghgsetawgtshigtthvkqltnsnqlpfifdvacvngdflfsmpciaeaImraqkdgkptgtvaiiastinqswasprmgqde mneilcekhpnnikrtfggvtmngmfamvekykkdgekmldtwtvfgdpsilvrtlvptkmqvtapaqinltdasvnvscdyngaiatisangkmfgsav vengtatinltgltnesliiltvvgynketvtktlntngepnpyqpvsnltattqgqkvtlkwdapstktnattntarsvdgirelvilsvsdapeIl*rsggaeivleah dvwndgsgyqilldadhdqyqgvipsdthtlwpncsvpanlfapfeytvpenadpscsptnmimdglasvnipagtydfaiaapqanakiwiagqgptk eddyvfeagkkyhflmkkmgsgdgteltiseggysd*ytytvyrdgtkikeqltattffeedgvatgnheycvevkytagvspkvckdvtvegsnefapvgnlt gsavgqkvtlkw*dapngtpnpnpnpnpgtttlsesfengipaswktidadgdghgwkpgnapgiagynsngcvysesfglggigvltpdnylitpald Ipnggkltfwvcaqdanyasehyavyasstgndasnftnalleetitakgvrspeairgriqgtwrqktvdlpagtkyvafrhqstdmfyidldeveikang kradftetfessthgeapaewttidadgdgqgwlcissgq ldwltahggtnvvasfswngmalnpdnyliskdvtgatkvkyyyavndgfpgdhyavm isktgtnagdftvvfeetpnginkggarfglsteangakpqsvwiertvdlpagtkyvafrhyncsdlnyilddiqftmggsptptd*ytytvyrdgtkikeqltet tffeedgvatgnheycvevkytagvspkecvnvtinptgfnpvknlkagpdggdvvlkw*eapsakkl*egsrevkrigdglfvtiepandvraneakvvlaa dnvwgdntgyqflldadhntfgsvipatgplftgtassnlysanfeylipanadpvvttqniivtgqgevvipggvydycitnpepasgkmwiagdggnqpa ryddflfeagkkytftmrragmgdgtdmeveddspas*tytvyrdgtkikeqltettyrdagmsagsheycvevkyaagvspkvcvdyipd*gvadvtaq kpytltvvgktitvtcqgeamiydmngrrlaagrntvvytaqggyyavmvvvdgksyveklavk*

(SEQ ID NO:107)

FIG. 22D

>KgpHG66_877
YTYTVYRDGTKIKEGLTATTFEEDGVAAGNHEYCVEVKYTAGVSPKVCKDVTVEGSNEFAPVQNLTGSAVGQ
KVTLKW      (SEQ ID NO: 108 )
>KgpHG66_ 1205
YTYTVYRDGTKIKEGLTETTFEEDGVATGNHEYCVEVKYTAGVSPKKCVNVTINPTQFNPVKNLKAQPDGGDV
VLKW  ( SEQ ID NO: 109 )
>KgpHG66_ 1463
YTYTVYRDGTKIKEGLTETTYRDAGMSAQSHEYCVEVKYAAGVSPKVCVDYIPD        (SE ID NO: 110)

>RgpAHG66_866
YTYTVYRDGTKIKEGLTATTFEEDGVATGNHEYCVEVKYTAGVSPKVCKDVTVEGSNEFAPVQNLTGSAVGQ
KVTLKW      (SEQ ID NO: 111)
>RgpAHG66_1321
YTYTVYRDGTKIKEGLTETTFEEDGVATGNHEYCVEVKYTAGVSPKECVNVTINPTQFNPVKNLKAQPDGGDV
VLKW  (SEQ ID NO: 112)
>RgpAHG66_1579
YTYTVYRDGTKIKEGLTETTYRDAGMSAQSHEYCVEVKYAAGVSPKVCVDYIPD        (SEQ ID NO: 110)

>KgpATCC_877
YTYTVYRDGTKIQEGLTATTFEEDGVAAGNHEYCVEVKYTAGVSPKVCKDVTVEGSNEFAPVQNLTGSAVGQ
KVTLKW      (SEQ ID NO: 113)
>KgpATCC_1340
YTYTVYRDGTKIKEGLTETTFEEDGVATGNHEYCVEVKYTAGVSPKVCVNVTINPTQFNPVKNLKAQPDGGDV
VLKW      (SEQ ID NO: 114)
>KgpATCC_ 1598
YTYTVYRDGTKIQEGLTETTYRDAGMSAQSHEYCVEVKYAAGVSPKVCVDYIPDG      (SEQ ID NO: 115)

>KgpW83_887
YTYTVYRDGTKIKEGLTATTFEEDGVAAGNHEYCVEVKYTAGVSPKVCKDVTVEGSNEFAPVQNLTGSAVGQ
KVTLKW      (SEQ ID NO: 108)
>KgpW83_1341
YTYTVYRDGTKIKEGLTETTFEEDGVATGNHEYCVEVKYTAGVSPKKCVNVTINPTQFNPVKNLKAQPDGGDV
VLKW      (SEQ ID NO: 109)
>KgpW83_1607
YTYTIYRNNTQIASGVTETTYRDPDLATGFYTYGVKVVYPNGESAIETATLNI      ( SEQ ID NO: 116)

>Kgp381_887
YTYTVYRDGTKIQEGLTATTFEEDGVAAGNHEYCVEVKYTAGVSPKVCKDVTVEGSNEFAPVQNLTGSAVGQ
KVTLKW      (SEQ ID NO: 113)
>Kgp381_1340
YTYTVYRDGTKIKEGLTETTFEEDGVATGNHEYCVEVKYTAGVSPKVCVNVTINPTQFNPVKNLKAQPDGGDV
VLKW      (SEQ ID NO: 114)
>Kgp381_1598
YTYTVYRDGTKIQEGLTETTYRDAGMSAQSHEYCVEVKYAAGVSPKVCVDYIPDG      (SEQ ID NO: 115)

FIG. 22E

>RgpATCC_863
YTYTVYRDGTKIKEGLTATTFEEDGVATGNHEYCVEVKYTAGVSPKVCKDVTVEGSNEFAPVQNLTGSAVGQ
KVTLKW      (SEQ ID NO: 111)
>RgpATCC_1320
YTYTVYRDGTKIKEGLTETTFEEDGVATGNHEYCVEVKYTAGVSPKECVNVTINPTQFNPVKNLKAQPDGGDV
VLKW      (SEQ ID NO: 112)
>RgpATCC_1578
YTYTVYRDGTKIKEGLTETTYRDAGMSAQSHEYCVEVKYAAGVSPKVCVDYIPDG      (SEQ ID NO: 117)

>RgpAW83_866
YTYTVYRDGTKIKEGLTATTFEEDGVAAGNHEYCVEVKYTAGVSPKVCKDVTVEGSNEFAPVQNLTGSAVGQ
KVTLKW      (SEQ ID NO: 108)
>RgpAW83_1323
YTYTVYRDGTKIKEGLTETTFEEDGVATGNHEYCVEVKYTAGVSPKKCVNVTVNSTQFNPVKNLKAQPDGGD
VVLKW      (SEQ ID NO: 118)
>RgpAW83_1581
YTYTVYRDGTKIKEGLTETTYRDAGMSAQSHEYCVEVKYTAGVSPKVCVDYIPD      (SEQ ID NO: 119)

FIG. 22F

```
                         YTYTIYRNNTQIASGVTETTYRDPD LATGFYTYGVKVVYPNGESAIET ATLNI   53
                         (SEQ ID NO:114)
KgpW83_1607
RgpAW83_1323             YTYTVYRDGTKIKEG LTETTFEEDGVATGNHEYCVEVKYTAGVSPKKCVNVTVN-STQFN        59
KgpHG66_1205             YTYTVYRDGTKIKEG LTETTFEEDGVATGNHEYCVEVKYTAGVSPKKCVNVTIN-PTQFN        59
KgpW83_1341              YTYTVYRDGTKIKEG LTETTFEEDGVATGNHEYCVEVKYTAGVSPKKCVNVTIN-PTQFN        59
RgpAHG66_1321            YTYTVYRDGTKIKEG LTETTFEEDGVATGNHEYCVEVKYTAGVSPKECVNVTIN-PTQFN        59
RgpATCC_1320             YTYTVYRDGTKIKEG LTETTFEEDGVATGNHEYCVEVKYTAGVSPKECVNVTIN-PTQFN        59
KgpATCC_1340             YTYTVYRDGTKIKEG LTETTFEEDGVATGNHEYCVEVKYTAGVSPKVCVNVTIN-PTQFN        59
Kgp381_1340              YTYTVYRDGTKIKEG LTETTFEEDGVATGNHEYCVEVKYTAGVSPKVCVNVTIN-STQFN        59
KgpATCC_877              YTYTVYRDGTKIQEG LTATTFEEDGVAAGNHEYCVEVKYTAGVSPKVCKDVTVEGSNEFA        60
Kgp381_887               YTYTVYRDGTKIQEG LTATTFEEDGVAAGNHEYCVEVKYTAGVSPKVCKDVTVEGSNEFA        60
KgpHG66_877              YTYTVYRDGTKIKEG LTATTFEEDGVAAGNHEYCVEVKYTAGVSPKVCKDVTVEGSNEFA        60
KgpW83_887               YTYTVYRDGTKIKEG LTATTFEEDGVAAGNHEYCVEVKYTAGVSPKVCKDVTVEGSNEFA        60
RgpAW83_866              YTYTVYRDGTKIKEG LTATTFEEDGVAAGNHEYCVEVKYTAGVSPKVCKDVTVEGSNEFA        60
RgpAHG66_866             YTYTVYRDGTKIKEG LTATTFEEDGVATGNHEYCVEVKYTAGVSPKVCKDVTVEGSNEFA        60
RgpATCC_863              YTYTVYRDGTKIKEG LTATTFEEDGVATGNHEYCVEVKYTAGVSPKVCKDVTVEGSNEFA        60
RgpAW83_1581             YTYTVYRDGTKIKEG LTETTYRDAGMSAQSHEYCVEVKYTAGVSPKVCVDYIPD-------        54
KgpHG66_1463             YTYTVYRDGTKIKEG LTETTYRDAGMSAQSHEYCVEVKYAAGVSPKVCVDYIPD-------        54
RgpAHG66_1579            YTYTVYRDGTKIKEG LTETTYRDAGMSAQSHEYCVEVKYAAGVSPKVCVDYIPD------        54
RgpATCC_1578             YTYTVYRDGTKIKEG LTETTYRDAGMSAQSHEYCVEVKYAAGVSPKVCVDYIPDG------        55
KgpATCC_1598             YTYTVYRDGTKIQEG LTETTYRDAGMSAQSHEYCVEVKYAAGVSPKVCVDYIPDG-----        55
Kgp381_1598              YTYTVYRDGTKIQEG LTETTYRDAGMSAQSHEYCVEVKYAAGVSPKVCVDYIPDG-----        55

***********:**** **.,: *.::   *********:***** *

RgpAW83_1323             PVKNLKAQPDGGDVVLKW      77     (SEQ ID NO:116)
KgpHG66_1205             PVKNLKAQPDGGDVVLKW      77     (SEQ ID NO:109)
KgpW83_1341              PVKNLKAQPDGGDVVLKW      77     (SEQ ID NO:109)
RgpAHG66_1321            PVKNLKAQPDGGDVVLKW      77     (SEQ ID NO:112)
RgpATCC_1320             PVKNLKAQPDGGDVVLKW      77     (SEQ ID NO:112)
KgpATCC_1340             PVKNLKAQPDGGDVVLKW      77     (SEQ ID NO:114)
Kgp381_1340             PVKNLKAQPDGGDVVLKW      77     (SEQ ID NO:114)
KgpATCC_877             PVQNLTGSAVGQKVTLKW      78     (SEQ ID NO:113)
Kgp381_887              PVQNLTGSAVGQKVTLKW      78     (SEQ ID NO:113)
KgpHG66_877             PVQNLTGSAVGQKVTLKW      78     (SEQ ID NO:108)
KgpW83_887              PVQNLTGSAVGQKVTLKW      78     (SEQ ID NO:108)
RgpAW83_866             PVQNLTGSAVGQKVTLKW      78     (SEQ ID NO:108)
RgpAHG66_866            PVQNLTGSAVGQKVTLKW      78     (SEQ ID NO:111)
RgpATCC_863             PVQNLTGSAVGQKVTLKW      78     (SEQ ID NO:111)
RgpAW83_1581            ------------------      54     (SEQ ID NO:119)
KgpHG66_1463            ------------------      54     (SEQ ID NO:120)
RgpAHG66_1579           ------------------      54     (SEQ ID NO:120)
RgpATCC_1578            ------------------      55     (SEQ ID NO:117)
KgpATCC_1598            ------------------      55     (SEQ ID NO:115)
Kgp381_1598            ------------------      55     (SEQ ID NO:115)
```

FIG. 22G hemagglutinin protein HagA [Porphyromonas gingivalis W83]
GenBank: AAQ66831.1

>AAQ66831.1 hemagglutinin protein HagA [Porphyromonas gingivalis W83]
MARIILEAHDVWEDGTGYQMLWDADHNQYGASIPEESFWFANGTIPAGLYDPFEYKVPVNADASFSPTNFVL
DGTASADIPAGTYDYVIINPNPGIIYIVGEGVSKGNDYWEAGKTYHFTVQRQGPGDAASVWTGEGGNEFAPVQ
NLQWSVSGQTVTLTWQAPASDKRTYVLNESFDTQTLPNGWTMIDADGDGHNWLSTINVYNTATHTGDGAMF
SKSWTASSGAKIDLEPDNYLVTPKFTVPENGKLSYWVSSQEPWTNEHYGVFLSTTGNEAANFTIKLLEETLGS
GKPAPMNLVKSEGVKAPAPYQERTIDLSAYAGQQVYLAFRHFGCTGIFRLYLDDVAVSGEGSSND<u>YTYTVYR
DNVVIAQNLTATTFNQENVAPGQYNYCVEVKYTAGVSPKVCKDVTVE</u>GSNEFAPVQNLTGSAVGQKVTLKW
DAPNGTPNPNPGTTTLSESFENGIPASWKTIDADGDGNNWTTTPPPGGSSFAGHNSAICVSSASYINFEGPQ
NPDNYLVTPELSLPNGGTLTFWVCAQDANYASEHYAVYASSTGNDASNFANALLEEVLTAKTWTAPEAIRGT
RVQGTWYQKTVQLPAGTKYVAFRHFGCTDFFWINLDDVEIKANGKRADFTETFESSTHGEAPAEWTTIDADG
DGQGWLCLSSGQLGWLTAHGGTNWASFSWNGMALNPDNYLISKDVTGATKVKYYYAVNDGFPGDHYAVMI
SKTGTNAGDFTVVFEETPNGINKGGARFGLSTEANGAKPQSVWIERTVDLPAGTKYVAFRHYNCSDLNYILLD
DIQFTMGGSPTPTD<u>YTYTVYRDGTKIKEGLTETTFEEDGVATGNHEYCVEVKYTAGVSPKECVNVTVDPVQFN</u>
PVQNLTGSAVGQKVTLKWDAPNGTPNPNPGTTTLSESFENGIPASWKTIDADGDGNNWTTTPPPGGTSFAG
HNSAICVSSASYINFEGPQNPDNYLVTPELSLPNGGTLTFWVCAQDANYASEHYAVYASSTGNDASNFANALL
EEVLTAKTWTAPEAIRGTRVQGTWYQKTVQLPAGTKYVAFRHFGCTDFFWINLDDVEIKANGKRADFTETFES
STHGEAPAEWTTIDADGDGQGWLCLSSGQLDWLTAHGGTNWASFSWNGMALNPDNYLISKDVTGATKVKY
YYAVNDGFPGDHYAVMISKTGTNAGDFTVVFEETPNGINKGGARFGLSTEANGAKPQSVWIERTVDLPAGTK
YVAFRHYNCSDLNYILLDDIQFTMGGSPTPTD<u>YTYTVYRDGTKIKEGLTETTFEEDGVATGNHEYCVEVKYTA
GVSPKECVNVTVDPVQFNPVQNLTGSAVGQKVTLKWDAPNGTPNPNPGTTTLSESFENGIPASWKTIDADGD</u>
GNNWTTTPPPGGTSFAGHNSAICVSSASYINFEGPQNPDNYLVTPELSLPNGGTLTFWVCAQDANYASEHYA
VYASSTGNDASNFANALLEEVLTAKTVVTAPEAIRGTRVQGTWYQKTVQLPAGTKYVAFRHFGCTDFFWINLD
DVEIKANGKRADFTETFESSTHGEAPAEWTTIDADGDGQGWLCLSSGQLGWLTAHGGTNVVASFSWNGMAL
NPDNYLISKDVTGATKVKYYYAVNDGFPGDHYAVMISKTGTNAGDFTVVFEETPNGINKGGARFGLSTEANGA
KPQSVWIERTVDLPAGTKYVAFRHYNCSDLNYILLDDIQFTMGGSPTPTD<u>YTYTVYRDGTKIKEGLTETTFEED
GVATGNHEYCVEVKYTAGVSPKECVNVTIN</u>PTQFNPVQNLTAEQAPNSMDAILKWNAPASKRAEVLNEDFEN
GIPASWKTIDADGDGNNWTTTPPPGGSSFAGHNSAICVSSASYINFEGPQNPDNYLVTPELSLPGGGTLTFW
VCAQDANYASEHYAVYASSTGNDASNFANALLEEVLTAKTVVTAPEAIRGTRVQGTWYQKTVQLPAGTKYVA
FRHFGCTDFFWINLDDWITSGNAP<u>SYTYTIYRNNTQIASGVTETTYRDPDLATGFYTYGVKVVYPNGESAIETA
TLNITS</u>LADVTAQKPYTLTWGKTITVTCQGEAMIYDMNGRRLAAGRNTWYTAQGGHYAVMVWDGKSYVEKLA
VK      (SEQ ID NO: 24)

>HagAW83_357
YTYTVYRDNVVIAQNLTATTFNQENVAPGQYNYCVEVKYTAGVSPKVCKDVTVE (SEQ ID NO: 121)
>HagAW83_810
YTYTVYRDGTKIKEGLTETTFEEDGVATGNHEYCVEVKYTAGVSPKECVNVTVD (SEQ ID NO: 122)
>HagAW83_12621
YTYTVYRDGTKIKEGLTETTFEEDGVATGNHEYCVEVKYTAGVSPKECVNVTVD (SEQ ID NO: 122)
>HagAW83_1714
YTYTVYRDGTKIKEGLTETTFEEDGVATGNHEYCVEVKYTAGVSPKECVNVTIN (SEQ ID NO: 123)
>HagAW83_1980
YTYTIYRNNTQIASGVTETTYRDPDLATGFYTYGVKVVYPNGESAIETATLNIT (SEQ ID NO: 124)

FIG. 22H

HagA [Porphyromonas gingivalis ATCC 33277]
GenBank: BAG34252.1
>BAG34252.1 hemagglutinin protein HagA [Porphyromonas gingivalis ATCC 33277]
MRKLNSLFSLAVLLSLLCWGQTAAAQGGPKTAPSVTHQAVQKGIRTSKVKDLRDPIPAGMARIILEAHDVWED
GTGYQMLWDADHNQYGASIPEESFWFANGTIPAGLYDPFEYKVPVNADASFSPTNFVLDGTASADIPAGTYD
YVIINPNPGIIYIVGEGVSKGNDYVVEAGKTYHFTVQRQGPGDAASWVTGEGGNEFAPVQNLQWSVSGQTVT
LTWQAPASDKRTYVLNESFDTQTLPNGWTMIDADGDGHNWLSTINVYNTATHTGDGAFMSKSWTASGGAKI
DLSPDNYLVTPKVTVPENGKLSYWVSSQVPWTNEHYGVFLSTTGNEAANFTIKLLEETLGSDKPAPMNLVKSE
GVKLPAPYQERTIDLSAYAGQQVYLAFRHFNSTGIFRLYLDDVAVSGEGSSND<u>YTYTVYRDNWIAQNLAATTF
NQENVAPGQYNYCVEVKYTAGVSPKVCKDVTVE</u>GSNEFAPVQNLTGSAVGQKVTLKWDAPNGTPNPNPGT
TTLSEFSENGIPASWKTIDADGDGNNWTTTPPPGGTSFAGHNSAICASSASYINFEGPQNPDNYLVTPELSLP
NGGTLTFWVCAQDANYASEHYAVYASSTGNDASNFANALLEEVLTAKTVVTAPEAIRGTRVQGTWYQKTVQL
PAGTKYVFARHFGCTDFFWINLDDVEIKANGKRADFTETFESSTHGEAPAEWTTIDADGDGQGWLCLSSGQL
GWLTAHGGTNVVASFSWNGMALNPDNYLISKDVTGATKVKYYYAVNDGFPGDHYAVMISKTGTNAGDFTVV
FEETPNGINKGGARFGLSTEADGAKPQSVVWIERTVDLPAGTKYVAFRHYNCSDLNYILLDDIQFTMGGSPTPT
D<u>YTYTVYRDGTKIKEGLTETFTEEDGVATGNHEYCVEVKYTAGVSPKECVNVTVD</u>PVQFNPVQNLTGSAVGQ
KVTLKWDAPNGTPNPNPNPNPGTTTLSESFENGIPASWKTIDADGDGNNWTTTPPPGGTSFAGHNSAICASS
ASYINFEGPQNPDNYLVTPELSLPNGGTLTFWVCAQDANYASEHYAVYASSTGNDASNFANALLEEVLTAKTV
VTAPEAIRGTRVQGTWYQKTVQLPAGTKYVFARHFGCTDFFWINLDDVEIKANGKRADFTETFESSTHGEAPA
EWTTIDADGDGQGWLCLSSGQLGWLTAHGGTNVVASFSWNGMALNPDNYLISKDVTGATKVKYYYAVNDG
FPGDHYAVMISKTGTNAGDFTWEETPNGINKGGARFGLSTEADGAKPQSVVWIERTVDLPAGTKYVAFRHYNC
SDLNYILLDDIQFTMGGSPTPTD<u>YTYTVYRDGTKIKEGLTETFTEEDGVATGNHEYCVEVKYTAGVSPKECVNV
TVD</u>PVFQNPVQNLTGSAVGQKVTLKWDAPNGTPNPNPNPNPGTTTLSESFENGIPASWKTIDADGDGNNWT
TTPPPGGTSFAGHNSAICVSSASYINFEGPQNPDNYLVTPELSLPGGGTLTFWVCAQDANYASEHYAVYASST
GNDASNFANALLEEVLTAKTVVTAPEAIRGTRVQGTWYQKTVQLPAGTKYVAFRHFGCTDFFWINLDDVEIKA
NGKRADFTETFESSTHGEAPAEWTTIDADGDGQGWLCLSSGQLGWLTAHGGTNVVASFSWNGMALNPDNY
LISKDVTGATKVKYYYAVNDGFPGDHYAVMISKTGTNAGDFTWFEETPNGINKGGARFGLSTEADGAKPQSV
WIERTVDLPAGTKYVAFRHYNCSDLNYILLDDIQFTMGGSPTPTD<u>YTYTVYRDGTKIKEGLTETTFEEDGVATG
NHEYCVEVKYTAGVSPKECVNVTVD</u>PVFQNPVQNLTGSAVGQKVTLKWDAPNGTPNPNPNPNPGTTTLSES
FENGIPASWKTIDADGDGNNWTTTPPPGGTSFAGHNSAICVSSASYINFEGPQNPDNYLVTPELSLPGGGTLT
FWVCAQDANYASEHYAVYASSTGNDASNFANALLEEVLTAKTWTAPEAIRGTRVQGTWYQKTVQLPAGTKY
VAFRHFGCTDFFWINLDEVEIKANGKRADFTETFESSTHGEAPAEWTTIDADGDGQGWLCLSSGQLDWLTAH
GGTNVVASFSWNGMALNPDNYLISKDVTGATKVKYYYAVNDGFPGDHYAVMISKTGTNAGDFTWFEETPNGI
NKGGARFGLSTEADGAKPQSVVWIERTVDLPAGTKYVAFRHYNCSDLNYILLDDIQFTMGGSPTPTD<u>YTYTVYR
DGTKIKEGLTETTFEEDGVATGNHEYCVEVKYTAGVSPKVCVNVITNPTQFNPVQNLTAEQAPNSMDAILKWN</u>
APASKRAEVLNEDFENGIPSSWKTIDADGDGNNWTTTPPPGGSSFAGHNSAICVSSASYINFEGPQNPDNYL
VTPELSLPGGGTLTFWVCAQDANYASEHYAVYASSTGNDASNFANALLEEVLTAKTVVTAPEAIRGTRVQGT
WYQKTVQLPAGTKYVAFRHFGCTDFFWINLDDVVITSGNAPS<u>YTYTIYRNNTQIASGVTETTYRDPDLATGFYT
YGVKWPNGESAIETATLNITS</u>LADVTAQKPYTLTWGKTITVTCQGEAMIYDMNGRRLAAGRNTVVYTAQGGHY
AVMVVVDGKSYVEKLAVK          (SEQ ID NO:125)

>HagAATCC_416
YTYTVYRDNVVIAQNLAATTFNQENVAPGQYNYCVEVKYTAGVSPKVCKDVTVE          (SEQ ID NO: 126)
>HagAATCC_868
YTYTVYRDGTKIKEGLTETTFEEDGVATGNHEYCVEVKYTAGVSPKECVNVTVD          (SEQ ID NO: 122)
>HagAATCC_I325
YTYTVYRDGTKIKEGLTETTFEEDGVATGNHEYCVEVKYTAGVSPKECVNVTVD          (SEQ ID NO: 122)
>HagAATCC_I781
YTYTVYRDGTKIKEGLTETTFEEDGVATGNHEYCVEVKYTAGVSPKECVNVTVD          (SEQ ID NO: 122)
>HagAATCC_2237
YTYTVYRDGTKIKEGLTETTFEEDGVATGNHEYCVEVKYTAGVSPKVCVNVT IN          (SEQ ID NO: 127)
>HagAATCC_2005
YTYTIYRNNTQIASGVTETTYRDPDLATG FYTYGVKVVYPNGESAIETATLNIT          (SEQ ID NO: 124)

FIG. 22I

>KgpATCC_877
YTYTVYRDGTKIQEGLTATTFEEDGVAAGNHEYCVEVKYTAGVSPKVCKDVTVEG    (SEQ ID NO: 128)
>KgpATCC_1340
YTYTVYRDGTKIKEGLTETTFEEDGVATGNHEYCVEVKYTAGVSPKVCVNVTINP    (SEQ ID NO: 129)
>KgpATCC_1598
YTYTVYRDGTKIQEGLTETTYRDAGMSAQSHEYCVEVKYAAGVSPKVCVDYIPDG    (SEQ ID NO: 115)

>KgpW 83_887
YTYTVYRDGTKIKEGLTATTFEEDGVAAGNHEYCVEVKYTAGVSPKVCKDVTVEG    (SEQ ID NO: 130)
>KgpW83_1341
YTYTVYRDGTKIKEGLTETTFEEDGVATGNHEYCVEVKYTAGVSPKKCVNVTINP    (SEQ ID NO: 131)
>KgpW83_1607
YTYTIYRNNTQIASGVTETTYRDPDLATGFYTYGVKVVYPNGESAIETATLNI    (SEQ ID NO: 114)

>RgpATCC_863
YTYTVYRDGTKIKEGLTATTFEEDGVATGNHEYCVEVKYTAGVSPKVCKDVTVEG    (SEQ ID NO: 132)
>RgpATCC_1320
YTYTVYRDGTKIKEGLTETTFEEDGVATGNHEYCVEVKYTAGVSPKECVNVTINP    (SEQ ID NO: 133)
>RgpATCC_1578
YTYTVYRDGTKIKEGLTETTYRDAGMSAQSHEYCVEVKYAAGVSPKVCVDYIPDG    (SEQ ID NO: 117)

>RgpAW83_866
YTYTVYRDGTKIKEGLTATTFEEDGVAAGNHEYCVEVKYTAGVSPKVCKDVTVEG    (SEQ ID NO: 130)
>RgpAW83_1323
YTYTVYRDGTKIKEG LTETTFEEDGVATGNHEYCVEVKYTAGVSPKKCVNVTVNS    (SEQ ID NO: 134)
>RgpAW83_1581
YTYTVYRDGTKIKEGLTETTYRDAGMSAQSHEYCVEVKYTAGVSPKVCVDYIPD    (SEQ ID NO: 119)

>HagAW83_357
YTYTVYRDNWIAQNLTATTFNQENVAPGQYNYCVEVKYTAGVSPKVCKDVTVE    (SEQ ID NO: 121)
>HagAW83_810
YTYTVYRDGTKIKEGLTETTFEEDGVATGN HEYCVEVKYT AGVSPKECVNVTVD    (SEQ ID NO: 122)
>HagAW83_12621
YTYTVYRDGTKIKEGLTETTFEEDGVATGN HEYCVEVKYT AGVSPKECVNVTVD    (SEQ ID NO: 122)
>HagAW83_1714
YTYTVYRDGTKIKEGLTETTFEEDGVATGNHEYCVEVKYTAGVSPKECVNVTIN    (SEQ ID NO: 123)
>HagAW83_1980
YTYTIYRNNTQIASGVTETTYRDPDLATGFYTYGVKVVYPNGESAIETATLNIT    (SEQ ID NO: 124)

>HagAATCC_416
YTYTVYRDNWIAQNLAATTFNQENVAPGOYNYCVEVKYTAGVSPKVCKDVTVE    (SEQ ID NO: 126)
>HagAATCC_868
YTYTVYRDGTKIKEGLTETTFEEDGVATGNHEYCVEVKYTAGVSPKECVNVTVD    (SEQ ID NO: 122)
>HagAATCC_1325
YTYTVYRDGTKIKEGLTETTFEEDGVATGN HEYCVEVKYT AGVSPKECVNVTVD    (SEQ ID NO: 122)
>HagAATCC_1781
YTYTVYRDGTKIKEGLTETTFEEDGVATGN HEYCVEVKYT AGVSPKECVNVTVD    (SEQ ID NO: 122)
>HagAATCC_2237
YTYTVYRDGTKIKEGLTETTFEEDGVATGNHEYCVEVKYTAGVSPKVCVNVTIN    (SEQ ID NO: 127)
>HagAATCC_2503
YTYTIYRNNTQIASGVTETTYRDPDLATGFYTYGVKVVYPNGESAIETATLNIT    ((SEQ ID NO: 124)

FIG. 22J

```
KgpW83_1607     YTYTIYRNNTQIASGVTfTTYRDPDLATGFYTYGVKVVYPNGESAIETATLNI---      53   (SEQ ID NO:114)
HagAW83_1980    YTYTIYRNNTQIASGVTrTTYRDPDLATGFYTYGVKVVYPNGESAIETATLNIT-      54   (SEQ ID NO:124)
HagAATCC_2505   YTYTIYRNNTQIASGVTETTYRDPDLATGFYTYGVKVVYPNGESAIETATLNIT-      54   (SEQ ID NO:124)

RgpAW83_1581    YTYTVYRDGTKIKEGLT TTYRDAGMSAQSHEYCVEVKYTAGVSPKVCVDYIPD-      54   (SEQ ID NO:119)
KgpATCC_1598    YTYTVYRDGTKIQEGLTrTTYRDAGMSAQSHEYCVEVKYAAGVSPKVCVDYIPDG     55   (SEQ ID NO:115)
RgpATCC_1578    YTYTVYRDGTKIKEGLT TTYRDAGMSAQSHEYCVEVKYAAGVSPKVCVDYIPDG     55   (SEQ ID NO:117)
HagAW83_357     YTYTVYRDNWIAQNLTATTFNQENVAPGQYNYCVEVKYTAGVSPKVCVCKDVTVE-    54   (SEQ ID NO:121)
HagAATCC_416    YTYTVYRDNWIAQNLAATTFNQENVAPGQYNYCVEVKYTAGVSPKVCVCKDVTVE-    54   (SEQ ID NO:126)
RgpATCC_863     YTYTVYRDGTKIKEGLTATTFEEDGVATGNHEYCVEVKYTAGVSPKVCKDVTVEG     55   (SEQ ID NO:132)
KgpATCC_877     YTYTVYRDGTKIQEGLTATTFEEDGVAAGNHEYCVEVKYTAGVSPKVCKDVTVEG     55   (SEQ ID NO:128)
KgpW83_887      YTYTVYRDGTKIKEGLTATTFEEDGVAAGNHEYCVEVKYTAGVSPKVCKDVTVEG     55   (SEQ ID NO:130)
RgpAW83_866     YTYTVYRDGTKIKEGLTATTFEEDGVAAGNHEYCVEVKYTAGVSPKVCKDVTVEG     55   (SEQ ID NO:130)
HagAW83_810     YTYTVYRDGTKIKEGLTETTFEEDGVATGNHEYCVEVKYTAGVSPKECVNVTVD-    54   (SEQ ID NO:122)
HagAW83_12621   YTYTVYRDGTKIKEGLTETTFEEDGVATGNHEYCVEVKYTAGVSPKECVNVTVD-    54   (SEQ ID NO:122)
HagAATCC_868    YTYTVYRDGTKIKEGLTETTFEEDGVATGNHEYCVEVKYTAGVSPKECVNVTVD-    54   (SEQ ID NO:122)
HagAATCC_1325   YTYTVYRDGTKIKEGLTETTFEEDGVATGNHEYCVEVKYTAGVSPKECVNVTVD-    54   (SEQ ID NO:122)
HagAATCC_1781   YTYTVYRDGTKIKEGLTETTFEEDGVATGNHEYCVEVKYTAGVSPKECVNVTVD-    54   (SEQ ID NO:122)
RgpAWS3_1323    YTYTVYRDGTKIKEGLTETTFEEDGVATGNHEYCVEVKYTAGVSPKKCVNVTVNS    55   (SEQ ID NO:134)
RgpATCC_1320    YTYTVYRDGTKIKEGLTETTFEEDGVATGNHEYCVEVKYTAGVSPKECVNVTINP    55   (SEQ ID NO:133)
HagAW83_1714    YTYTVYRDGTKIKEGLTETTFEEDGVATGNHEYCVEVKYTAGVSPKECVNVTIN-    54   (SEQ ID NO:123)
KgpW83_1341     YTYTVYRDGTKIKEGLTETTFEEDGVATGNHEYCVEVKYTAGVSPKKCVNVTINP    55   (SEQ ID NO:131)
KgpATCC_1340    YTYTVYRDGTKIKEGLTETTFEEDGVATGNHEYCVEVKYTAGVSPKVCVNVTINP    55   (SEQ ID NO:129)
HagAATCC_2237   YTYTVYRDGTKIKEGLTETTFEEDGVATGNHEYCVEVKYTAGVSPKVCVNVTIN-    54   (SEQ ID NO:127)

********    *    * **:        :  *** ***** ;:*** ***  *
```

Linear analysis indicates the AP to include: YCVEVKYTAGVSPK (SEQ ID NO: 59)

FIG. 23A

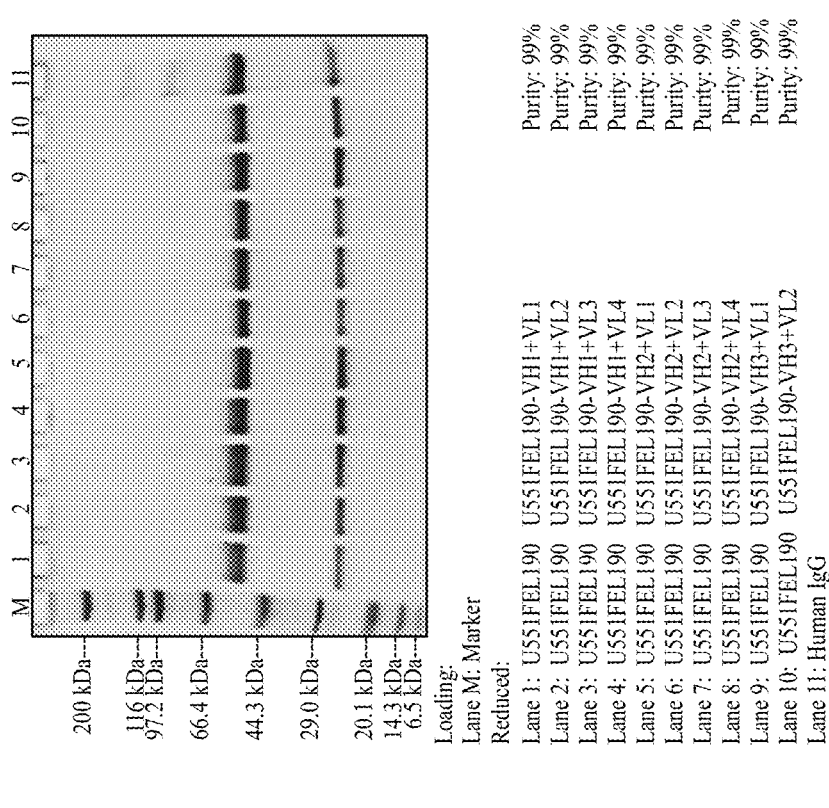

Loading:
Lane M: Marker
Reduced:
Lane 1: US51FEL190    US51FEL190-VH1+VL1      Purity: 99%
Lane 2: US51FEL190    US51FEL190-VH1+VL2      Purity: 99%
Lane 3: US51FEL190    US51FEL190-VH1+VL3      Purity: 99%
Lane 4: US51FEL190    US51FEL190-VH1+VL4      Purity: 99%
Lane 5: US51FEL190    US51FEL190-VH1+VL4      Purity: 99%
Lane 6: US51FEL190    US51FEL190-VH2+VL1      Purity: 99%
Lane 7: US51FEL190    US51FEL190-VH2+VL2      Purity: 99%
Lane 8: US51FEL190    US51FEL190-VH2+VL3      Purity: 99%
Lane 9: US51FEL190    US51FEL190-VH2+VL4      Purity: 99%
Lane 10: US51FEL190    US51FEL190-VH3+VL1      Purity: 99%
Lane 10: US51FEL190-VH3+VL2      Purity: 99%
Lane 11: Human IgG

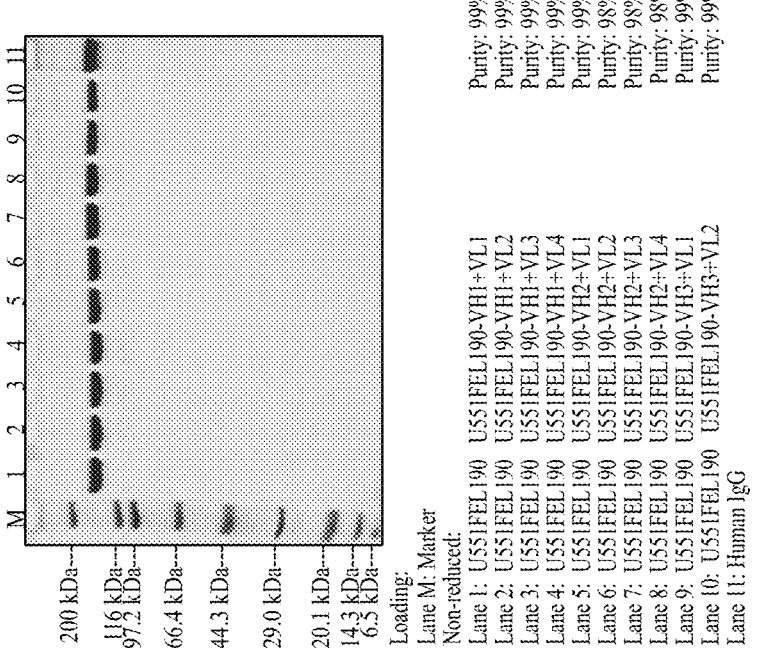

Loading:
Lane M: Marker
Non-reduced:
Lane 1: US51FEL190    US51FEL190-VH1+VL1      Purity: 99%
Lane 2: US51FEL190    US51FEL190-VH1+VL2      Purity: 99%
Lane 3: US51FEL190    US51FEL190-VH1+VL3      Purity: 99%
Lane 4: US51FEL190    US51FEL190-VH1+VL4      Purity: 99%
Lane 5: US51FEL190    US51FEL190-VH2+VL1      Purity: 98%
Lane 6: US51FEL190    US51FEL190-VH2+VL2      Purity: 98%
Lane 7: US51FEL190    US51FEL190-VH2+VL3      Purity: 98%
Lane 8: US51FEL190    US51FEL190-VH2+VL4      Purity: 99%
Lane 9: US51FEL190    US51FEL190-VH3+VL1      Purity: 99%
Lane 10: US51FEL190    US51FEL190-VH3+VL2      Purity: 99%
Lane 11: Human IgG

FIG. 23B

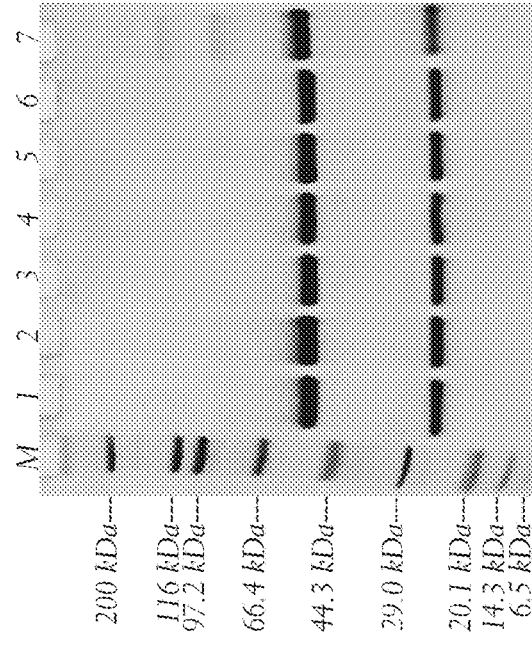

200 kDa---

116 kDa---
97.2 kDa---

66.4 kDa---

44.3 kDa---

29.0 kDa---

20.1 kDa---
14.3 kDa---
6.5 kDa---

Loading:
Reduced:
Lane M: Marker
Lane1: U551FEL190 U551FEL190-VH3+VL3
Purity: 99%
Lane 2: U551FEL190 U551FEL190-VH3+VL4
Purity: 99%
Lane 3: U551FEL190 U551FEL190-VH4+VL1
Purity: 99%
Lane 4: U551FEL190 U551FEL190-VH4+VL2
Purity: 99%
Lane 5: U551FEL190 U551FEL190-VH4+VL3
Purity: 99%
Lane 6: U551FEL190 U551FEL190-VH4+VL4
Purity: 99%
Lane 7: Human IgG

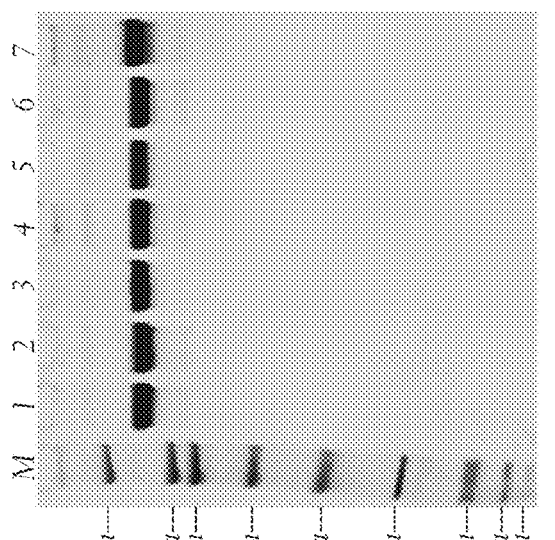

200 kDa---

116 kDa---
97.2 kDa---

66.4 kDa---

44.3 kDa---

29.0 kDa---

20.1 kDa---
14.3 kDa---
6.5 kDa---

Loading:
Non-reduced:
Lane M: Marker
Lane1: U551FEL190 U551FEL190-VH3+VL3
Purity: 99%
Lane 2: U551FEL190 U551FEL190-VH3+VL4
Purity: 98%
Lane 3: U551FEL190 U551FEL190-VH4+VL1
Purity: 99%
Lane 4: U551FEL190 U551FEL190-VH4+VL2
Purity: 98%
Lane 5: U551FEL190 U551FEL190-VH4+VL3
Purity: 99%
Lane 6: U551FEL190 U551FEL190-VH4+VL4
Purity: 98%
Lane 7: Human IgG FIG. 24
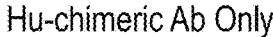
Hu-chimeric Ab Only
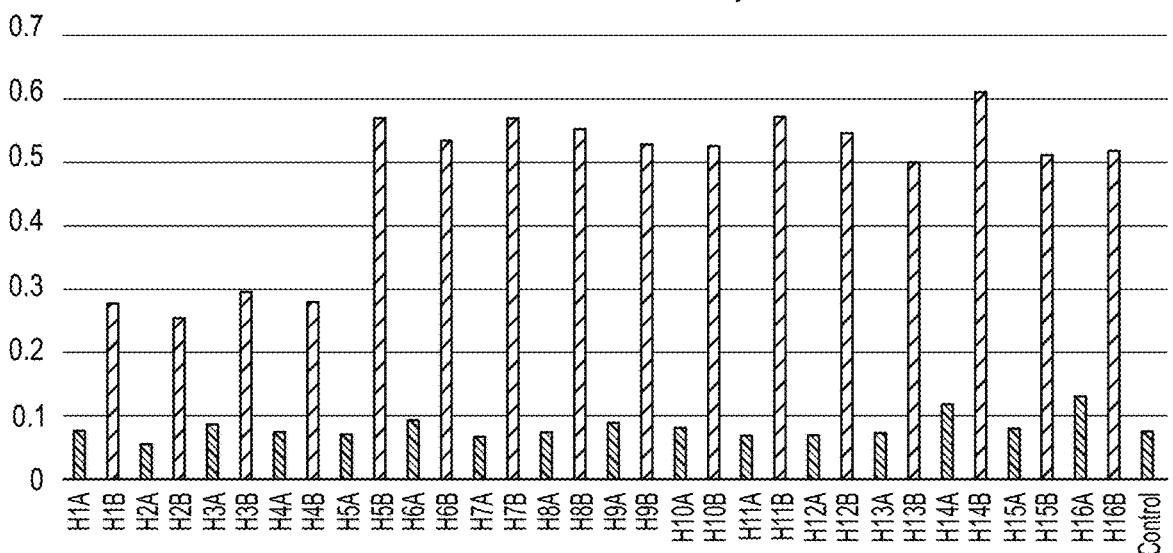
Hu-chimeric Ab + KB001
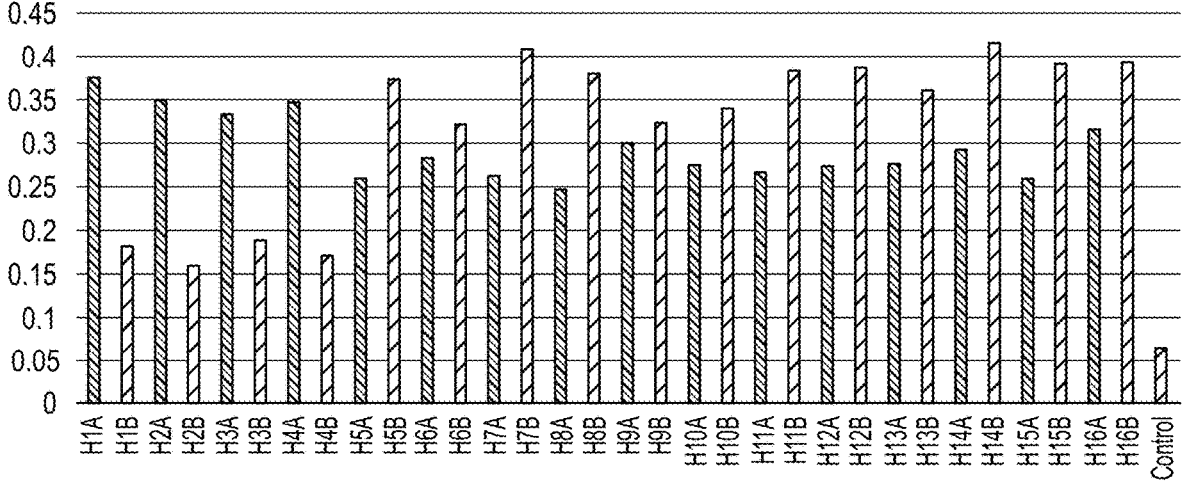

FIG. 26A

Sequence of KB001 antibody (CDR and Hypervariable loop (kabat) are shown underlined)

Grafted antibodies:
VH

> KB001-VH-GRAFTED

QVQLQESGPGLVKPSETLSLTCTVSG FSLSIYSVHWIRQPPGKGLEWIGMIWGGGSSD

YNSALKSRVTISVDTSKNQFSLKLSSVTAADTAVYYCARNGNFYAMDYWGQGTLVTVS

S    (SEQ ID NO:29)

VL

> KB001-VL-GRAFTED

EIVLTQSPGTLSLSPGERATLSCTASSSVSSSFLHWYQQKPGQAPRLLIYSTSNLASGI
PDRFSGSGSGTDFTLTISRLEPEDFAVYYCHQYHHSPYIYTFGGGTKLEIK   (SEQ ID
NO:33)

EVQLKQSGPGLVAPSQSLSITCTVSGFSLSIYSVHWVRQPPGKGLEWLGMIWGGGSSDYNSA

LKSRLSISKDNSKSQVFLKMNSLQTDDTAMYYCARNGNFYAMDYWGQGTSVTVSS    (SEQ

ID NO:9)

> KB001-VL

QIVLTQSPAIMSASLGERVTMTCTASSSVSSSFLHWYQQKPGSSPQLWIYSTSNLASGVPARF

SGSGSGTSYSLTISSMEAEDAATYYCHQYHHSPYIYTFGGGTKLEIK    (SEQ ID NO:10)

FIG. 26C

```
KB001    EVQLKQSGPGLVAPSQSLSITCTVSGFSLSIYSVHWVRQPPGKGLEWLGMIWGGGSSDYN    60
1DVF     QVQLQESGPGLVAPSQSLSITCTVSGFSLTGYGVNWVRQPPGKGLEWLGMIWGDGNTDYN    60
         :***::****************************:  *.*:******************.*.:***

KB001    SALKSRLSLSKDNSKSQVFLKMNSLQTDDTAMYYCARNGNFYAMDYWGQGTSVTVSSQIV    120
1DVF     SALKSRLSISKDNSKSQVFLKMNSLHTDDTARYYCARERD-YRLDYWGQGTTLTVSSDIQ    119
         ********:****************:***** *****:  : *  :*******::****:*

KB001    LTQSPATMSASLGERVTMTCTASSSVSSSFLHWYQQKPGSSPQLWIYSTSNLASGVPARF    180
1DVF     LTQSPSSLSASLGDRVTISCRASQDI-SNYLNWYQQKPDGTVKLLIYYTSRLHSGVPSRF    178
         *****: :*****:***::****,.: *.:*:******..: :* *****,*******:**

KB001    SGSGSGTSYSLTISSMEAEDAATYYCHQYHHSPYIYTFGGGTKLEIK    227    (SEQ ID NO:9)
1DVF     SGSGSGTDYSLTISNLEQEDIATYFCQQGNTLP--WTFGGGTKLEIK    223    (SEQ ID NO:135)
         *******,******,:*  **  ***:*:*  :   *   :***********
```

EVQLKQSGPGLVAPSQLSITCTVSGFSLSIYSVHWVRQPPGKGLEWLGMIWGGGSSDYNSA

LKSRLSISKDNSKSQVFLKMNSLQTDDTAMYYCARNGNFYAMDYWGQGTSVTVSS    (SEQ

ID NO:9)

>KB001-VL

QIVLTQSPAIMSASLGERVTMTCTASSSVSSSFLHWYQQKPGSS*PQL*WIYSTSNLASGVPARF

SGSGSGTSYSLTISSMEAEDAATYYCHQYHHSPYIYTFGGGTKLEIK    (SEQ ID NO:10)

FIG. 26E

The sequences of KB001 antibody and the grafted antibodies were aligned as follows:

Residues in inner core alignment

VH

KB001-VH          EVQLKQSGPGLVAPSQSLSITCTVSGFSLSIYSVHWVRQPPGKGLEWLGMIWGGGSSDYN

KB001-VH-Grafted  QVQLQESGPGLVKPSETLSLTCTVSGFSLSIYSVHWIRQPPGKGLEWICMIWGGGSSDYN

KB001-VH          SALKSRLSISKDNSKSQVFLKMNSLQTDDTAMYYCARNGNFYAMDYWGQGTSVTVSS          (SEQ
ID NO:9)

KB001-VH-Grafted  SALKSRVTISVDTSKNQFSLKLSSVTAADTAVYYCARNGNFYAMDYWGQGTLVTVSS          (SEQ
ID NO:29)

VL

KB001-VL          QIVLTQSPAIMSASLGERVTMTCTASSSVSSSELHWYQQKPGSSPQLWIYSTSNLASGVPAR

KB001-VL-Grafted  EIVLTQSPGTLSLSPGERATLSCTASSSVSSSFLHWYQQKPGQAPRLLIYSTSNLASGIPDR KB001-VL          FSGSGSGTSYSLTISSMEAEDAATYYCHQYHHSPYIYTFGGGTKLEIK          (SEQ ID
NO:10)

KB001-VL-Grafted  FSGSGSGTDFTLTISRLEPEDFAVYYCHQYHHSPYIYTFGGGTKLEIK          (SEQ ID
NO:33)

FIG. 27A

QVQLQESGPGLVKPSETLSLTCTVSGFSLSIYSVHWIRQPPGKGLEWIGMIWGGGSSDYNSALKSRVTISVDTSKNQ
                             HCDR1                                  HCDR2
FSLKLSSVTAADTAVYYCARNGNFYAMDYWGQGTLVTVSS  (SEQ ID NO:29)
             HCDR3

FIG. 27B

Grafted with BM-VH2

QVQLQESGPGLVKPSETLSLTCTVSGFSLSIYSVHWIRQPPGKGLEWIGMIWGGGSSDYNSALKSRLTISKDTSKNQ

VSLKLSSVTAADTAVYYCARNGNFYAMDYWGQGTLVTVSS  (SEQ ID NO:30)

FIG. 27C

Grafted with BM-VH3

QVQLQESGPGLVKPSETLSLTCTVSGFSLSIYSVHWIRQPPGKGLEWLGMIWGGGSSDYNSALKSRLTISVDTSKNQ

VSLKLSSVTAADTAMYYCARNGNFYAMDYWGQGTLVTVSS  (SEQ ID NO:31)

FIG. 27D

Grafted with BM-VH4

QVQLQESGPGLVKPSETLSLTCTVSGFSLSIYSVHWIRQPPGKGLEWLGMIWGGGSSDYNSALKSRLTISKDTSKNQ

VSLKLSSVTAADTAMYYCARNGNFYAMDYWGQGTLVTVSS  (SEQ ID NO:32)

FIG. 28A

Grafted-VL1

EIVLTQSPGTLSLSPGERATLSCTASSSVSSSFLHWYQQKPGQAPRLLIYSTSNLASGIPDRFSGSGSGTDFTLTIS
                        LCDR1                              LCDR2
RLEPEDFAVYYCHQYHHSPYIYTFGGGTKLEIK    (SEQ ID NO:33)
            LCDR3

FIG. 28B

Grafted with BM-VL2

EIVLTQSPGTLSLSPGERATLSCTASSSVSSSFLHWYQQKPGQAPQLWIYSTSNLASGIPDRFSGSGSGTDYTLTIS

RLEPEDFAVYYCHQYHHSPYIYTFGGGTKLEIK    (SEQ ID NO:34)

FIG. 28C

Grafted with BM-VL3

EIVLTQSPGTLSLSPGERATLSCTASSSVSSSFLHWYQQKPGQAPQLWIYSTSNLASGIPDRFSGSGSGTDYTLTIS

RLEPEDFATYYCHQYHHSPYIYTFGGGTKLEIK    (SEQ ID NO:35)

FIG. 28D

Grafted with BM-VL4

EIVLTQSPGTLSLSPGERATLSCTASSSVSSSFLHWYQQKPGQAPQLWIYSTSNLASGIPARFSGSGSGTDYTLTIS

RLEPEDFATYYCHQYHHSPYIYTFGGGTKLEIK    (SEQ ID NO:36)

FIG. 29

Human Constant Region hIgG1CH

ASTKGPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSPGK** (SEQ
ID NO:136)

>hIgkCL
RTVAAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC** (SEQ ID NO:137)

FIG. 30

Humanized VH

>GRAFTED-VH1
QVQLQESGPGLVKPSETLSLTCTVSGFSLSIYSVHWIRQPPGKGLEWIGMIWGGGSSDYNSALKSRVTIS
VDTSKNQFSLKLSSVTAADTAVYYCARNGNFYAMDYWGQGTLVTVSS                    (SEQ ID NO:29)

>GRAFTED-VH2
QVQLQESGPGLVKPSETLSLTCTVSGFSLSIYSVHWIRQPPGKGLEWIGMIWGGGSSDYNSALKSRLTIS
KDTSKNQVSLKLSSVTAADTAVYYCARNGNFYAMDYWGQGTLVTVSS                    (SEQ ID NO:30)

>GRAFTED-VH3
QVQLQESGPGLVKPSETLSLTCTVSGFSLSIYSVHWIRQPPGKGLEWLGMIWGGGSSDYNSALKSRLTIS
VDTSKNQVSLKLSSVTAADTAMYYCARNGNFYAMDYWGQGTLVTVSS                    (SEQ ID NO:31)

>GRAFTED-VH4
QVQLQESGPGLVKPSETLSLTCTVSGFSLSIYSVHWIRQPPGKGLEWLGMIWGGGSSDYNSALKSRLTIS
KDTSKNQVSLKLSSVTAADTAMYYCARNGNFYAMDYWGQGTLVTVSS                    (SEQ ID NO:32)

Humanized VH

>GRAFTED-VH1
EIVLTQSPGTLSLSPGERATLSCTASSSVSSSFLHWYQQKPGQAPRLLIYSTSNLASGIPDRFSGSGSGTD
FTLTISRLEPEDFAVYYCHQYHHSPYIYTFGGGTKLEIK                    (SEQ ID NO:33)

>GRAFTED-VH2
EIVLTQSPGTLSLSPGERATLSCTASSSVSSSFLHWYQQKPGQAPQLWIYSTSNLASGIPDRFSGSGSGT
DYTLTISRLEPEDFAVYYCHQYHHSPYIYTFGGGTKLEIK                    (SEQ ID NO:34)

>GRAFTED-VH3
EIVLTQSPGTLSLSPGERATLSCTASSSVSSSFLHWYQQKPGQAPQLWIYSTSNLASGIPDRFSGSGSGT
DYTLTISRLEPEDFATYYCHQYHHSPYIYTFGGGTKLEIK                    (SEQ ID NO:35)

>GRAFTED-VH4
EIVLTQSPGTLSLSPGERATLSCTASSSVSSSFLHWYQQKPGQAPQLWIYSTSNLASGIPARFSGSGSGT
DYTLTISRLEPEDFATYYCHQYHHSPYIYTFGGGTKLEIK                    (SEQ ID NO:36)

Note: The underlined sequences are CDR regions. The back mutations residues are in bold.

Mouse sequences

> KB001-VH

EVQLKQSGPGLVAPSQSLSITCTVSGFSLSIYSVHWVRQPPGKGLEWLGMIWGGGSSDYNSA
LKSRLSISKDNSKSQVFLKMNSLQTDDTAMYYCARNGNFYAMDYWGQGTSVTVSS    (SEQ
ID NO:9)

>KB001-VL

QIVLTQSPAIMSASLGERVTMTCTASSSVSSSFLHWYQQKPGSSPQLWIYSTSNLASGVPARF
SGSGSGTSYSLTISSMEAEDAATYYCHQYHHSPYIYTFGGGTKLEIK    (SEQ ID NO:10)

FIG. 31

Alignments

KB001-VH      1 EVQLKQSGPGLVAPSQSLSITCTVSGFSLSIYSVHWVRQPPGKGLEWLGMIWGGGSSDYNSALKSRLSISKDNSKSQVFLKMNSLQTDTAMYYCARNGNFYAMDYWGQGTSVTVSS    SEQ ID NO: 9
GRAFTED-VH1   1 QVQLQESGPGLVKPSEHLSLTCTVSGFSLSIYSVHWIRQPPGKGLEWIGMIWGGGSSDYNSALKSRLSISKENGKSQVFLKKNSLQTDTAMYYCARNGNFYAMDYWGQGTLVTVSS    SEQ ID NO: 61
GRAFTED-VH2   1 QVQLQESGPGLVKPSETLSLTCTVSGFSLSIYSVHWIRQPPGKGLEWIGMIWGGGSSDYNSALKSRVTISVDTSKNQVFLKLSSVTAADTAVYYCARNGNFYAMDYWGQGTLVTVSS    SEQ ID NO: 62
GRAFTED-VH3   1 QVQLQESGPGLVKPSFTLSLTCTVSGFSLSIYSVHWIRQPPGKGLEWIGMIWGGGSSDYNSALKSRLTISKDTSKNQVSLKLSSVTAADTAMYYCARNGNFYAMDYWGQGTLVTVSS    SEQ ID NO: 63
GRAFTED-VH4   1 QVQLQESGPGLVKPSEHLSLTCTVSGFSLSIYSVHWIRQPPGKGLEWIGMIWGGGSSDYNSALKSRLTISKDTSKNQVSLKLSSVTAADTAMYYCARNGNFYAMDYWGQGTLVTVSS    SEQ ID NO: 64

KB001-VL      1 QIVLTQSPAIMSASLGERVTMTCTASSSVSSSFLHWYQQKPGSSPQLWIYSTSNLASGVPARFSGSGSGTSYSLTISSMEAEDAATYYCHQYHHSPYIYTFGGGTKLEIK    SEQ ID NO: 10
GRAFTED-VL1   1 EIVLTQSPGTLSLSPGERATLSCTASSSVSSSFLHWYQQKPGQAPRLWIYSTSNLASGIPARFSGSGSGTDYTLTISSLEPEDFATYYCHQYHHSPYIYTFGGGTKLEIK    SEQ ID NO: 65
GRAFTED-VL2   1 EIVLTQSPGTLSLSPGERATLSCTASSSVSSSFLHWYQQKPGQAPQLWIYSTSNLASGIPARFSGSGSGTDYTLTISSLEPEDFATYYCHQYHHSPYIYTFGGGTKLEIK    SEQ ID NO: 66
GRAFTED-VL3   1 EIVLTQSPGTLSLSPGERATLSCTASSSVSSSFLHWYQQKPGQAPQLWIYSTSNLASGIPARFSGSGSGTDYTLTISRLEPEDFATYYCHQYHHSPYIYTFGGGTKLEIK    SEQ ID NO: 67
GRAFTED-VL4   1 EIVLTQSPGTLSLSPGERATLSCTASSSVSSSFLHWYQQKPGQAPQLWIYSTSNLASGIPARFSGSGSGTDYTLTISRLEPEDFATYYCHQYHHSPYIYTFGGGTKLEIK    SEQ ID NO: 68

Grafted-VH1
CAGGTGCAGCTGCAAGAGTCCGGCCCTGGACTCGTGAAGCCCTCCGAGACACTGTCTCTGACCTGTACCGTGTCTGG
CTTTAGCCTGTCCATCTACTCCGTGCACTGGATCCGGCAGCCTCCTGGCAAGGGCCTGGAATGGATCGGCATGATCT
GGGGAGGCGGCTCTAGCGACTACAACTCCGCCCTGAAATCTAGAGTGACCATCTCCGTGGACACCTCCAAGAACCAG
TTCTCCCTGAAGCTGAGCTCTGTGACCGCTGCTGATACCGCCGTGTACTACTGCGCCAGAAATGGCAACTTCTACGC
CATGGACTATTGGGGCCAGGGCACCCTGGTCACAGTGTCCTCT (SEQ ID NO:61)

FIG. 33B

Grafted-VH2
CAGGTGCAGCTGCAAGAGTCCGGCCCTGGACTCGTGAAGCCCTCCGAGACACTGTCTCTGACATGTACCGTGTCTGG
CTTCTCCCTGTCCATCTACTCCGTGCACTGGATCAGACAGCCTCCTGGCAAGGGCCTGGAATGGATCGGCATGATCT
GGGGAGGCGGCTCTTCCGACTACAACTCCGCCCTGAAATCTCGGCTGACCATCTCCAAGGACACCTCTAAGAACCAG
GTCAGCCTGAAGCTGAGCTCTGTGACCGCTGCTGATACCGCCGTGTACTACTGCGCCAGAAATGGCAACTTCTACGC
CATGGACTATTGGGGCCAGGGCACCCTGGTGACCGTGTCCAGC (SEQ ID NO:62)

FIG. 33C

Grafted-VH3
CAGGTGCAGCTGCAAGAGTCCGGCCCTGGACTCGTGAAGCCCTCCGAGACACTGTCTCTGACCTGTACCGTGTCTGG
CTTCTCCCTGTCCATCTACTCCGTGCACTGGATCCGGCAGCCTCCTGGCAAGGGCCTGGAATGGCTGGGCATGATCT
GGGGCGGAGGCTCTAGCGACTACAACTCCGCCCTGAAATCTAGACTGACCATCTCCGTGGACACCTCCAAGAACCAG
GTCAGCCTGAAGCTGAGCTCTGTGACCGCCGCTGATACAGCTATGTACTACTGCGCCAGAAATGGCAACTTCTACGC
CATGGACTATTGGGGCCAGGGCACCCTGGTGACCGTGTCCTCT (SEQ ID NO:63)

FIG. 33D

Grafted-VH4
CAGGTGCAGCTGCAAGAGTCCGGACCCGGCCTCGTGAAGCCTTCCGAGACACTGTCTCTGACCTGTACCGTGTCTGG
CTTCTCCCTGTCCATCTACTCCGTGCACTGGATCCGGCAGCCTCCTGGCAAGGGCCTGGAATGGCTGGGCATGATCT
GGGGCGGCGGAAGCTCCGACTACAACTCCGCCCTGAAATCTAGACTGACCATCTCCAAGGACACCTCTAAGAACCAG
GTCAGCCTGAAGCTGAGCTCTGTGACCGCCGCTGATACCGCTATGTACTACTGCGCCAGAAATGGCAACTTCTACGC
CATGGACTATTGGGGCCAGGGCACCCTGGTGACAGTGTCCTCT (SEQ ID NO:64)

FIG. 34A

```
Grafted-VL1
GAGATCGTGCTGACCCAATCTCCAGGCACCCTGTCTCTCAGCCCTGGCGAGAGAGCCACCCTGTCCTGCACCGCTTC
TAGCTCCGTGTCCTCCAGCTTCCTGCACTGGTACCAGCAGAAACCCGGCCAGGCTCCTAGACTGCTGATCTATTCCA
CCTCCAACCTGGCCTCTGGCATCCCTGACCGGTTCTCCGGCTCTGGCTCCGGAACAGATTTTACACTGACCATCTCC
CGGCTGGAACCTGAGGACTTCGCCGTGTACTACTGTCACCAGTACCACCATTCTCCTTACATCTACACCTTCGGCGG
CGGAACCAAGCTGGAAATCAAG  (SEQ ID NO:65)
```

FIG. 34B

```
Grafted-VL2
GAGATCGTGCTGACACAATCTCCCGGCACCCTCAGCCTGTCTCCAGGCGAGAGAGCCACACTGTCCTGCACCGCTTC
TAGCTCCGTGTCCTCCAGCTTCTGCACTGGTACCAGCAGAAACCTGGCCAGGCTCCTCAGCTGTGGATCTACTCCA
CCTCCAACCTGGCCTCTGGCATCCCTGATCGGTTCTCCGGCTCCGGCTCTGGCACCGACTACACCCTGACCATCTCC
AGACTGGAACCTGAGGACTTCGCCGTGTACTACTGTCACCAGTACCACCATTCTCCTTACATCTATACCTTCGGCGG
AGGAACCAAGCTGGAAATCAAG  (SEQ ID NO:66)
```

FIG. 34C

```
Grafted-VL3
GAGATCGTGCTGACCCAGTCTCCAGGCACACTCAGCCTGTCTCCTGGCGAGCGGGCTACCCTGTCCTGCACCGCCAG
CAGCTCCGTGTCCTCTTCTTTTCTGCACTGGTACCAGCAGAAACCTGGACAAGCTCCTCAGCTGTGGATCTACTCCA
CCTCCAACCTGGCCTCTGGCATCCCCGATAGATTCTCCGGCTCTGGCTCCGGCACCGACTACACACTGACCATCTCC
AGACTGGAACCTGAGGACTTCGCCCACCTACTACTGTCATCAGTACCACCACTCCCCTTACATCTATACCTTCGGCGG
AGGCACCAAGCTGGAAATCAAG  (SEQ ID NO:67)
```

FIG. 34D

```
Grafted-VL4
GAGATCGTGCTGACCCAATCTCCTGGCACCCTGTCTCTGAGCCCAGGCGAGAGAGCCACACTCTCCTGCACCGCTTC
TTCCTCCGTGTCCTCTAGCTTTCTGCACTGGTACCAGCAGAAACCCGGCCAGGCTCCTCAGCTGTGGATCTACTCCA
CCTCCAACCTGGCCTCTGGCATCCCTGCCAGATTCTCCGGATCCGGCTCTGGCACCGATTATACACTGACCATCTCC
CGGCTGGAACCTGAGGACTTCGCCCACCTACTACTGTCACCAGTACCACCATAGCCCTTACATCTACACCTTCGGCGG
CGGAACCAAGCTGGAAATCAAG  (SEQ ID NO:68)
```

FIG. 35A

```
KB001 - VH
GAGGTGCAGCTGAAGCAAAGCGGTCCGGGTCTGGTTGCGCCGAGCCAAAGCCTGAGCATCACCTGCACCGTGAGCGG
CTTCAGCCTGAGCATCTACAGCGTGCACTGGGTTCGTCAGCCGCCGGGCAAGGGTCTGGAATGGCTGGGTATGATCT
GGGGTGGCGGTAGCAGCGACTATAACAGCGCGCTGAAGAGCCGTCTGAGCATTAGCAAGGATAACAGCAAAAGCCAG
GTTTTCCTGAAAATGAACAGCCTGCAAACCGACGATACCGCGATGTACTATTGCGCGCGTAACGGCAACTTTTACGC
GATGGACTATTGGGGCCAAGGTACCAGCGTGACCGTTAGCAGC       (SEQ ID NO:69)
```

FIG. 35B

```
KB001 - VL
CAGATCGTGCTGACCCAAAGCCCGGTTACCATGACCTGCACCGCGAGCAGCAGCGTGAGCAGCAGCTTCCTGCACTG
GTACCAGCAAAAGCCGGGTAGCAGCCCGCAGCTGTGGATCTATAGCACCAGCAACCTGGCGAGCGGTGTTCCGGGCGC
GTTTTAGCGGTAGCGGTAGCGGCACCAGCTACAGCCTGACCATTAGCAGCATGGAGGCGGAAGACGCGGCGACCTAC
TATTGCCACCAATATCACCACAGCCCGTACATCTATACCTTCGGTGGCGGTACCAAGCTGGAGATCAAG     (SEQ
ID NO:70)
```

FIG. 36A

```
>hIgG1CH
GCCAGCACCAAGGGCCCTTCCGTGTTTCCACTGGCCCCCTCCTCTAAATCCACATCTGGCGGCACCGCCGCCCTGGG
CTGTCTGGTGAAGGACTACTTCCCAGAGCCTGTGACAGTGTCCTGGAACTCTGGCGCCCTGACATCCGGCGTGCACA
CATTTCCAGCCGTGCTGCAGAGCTCCGGCCTGTACAGCCTGTCTAGCGTGGTGACAGTGCCCTCCTCTAGCCTGGGC
ACACAGACCTATATCTGCAACGTGAATCACAAGCCAAGCAATACCAAGGTGGACAAGAAGGTGGAGCCCAAGTCCTG
TGATAAGACACACACCTGCCCCCCTTGTCCTGCTCCCGAGCTGCTGGGCGGCCCTAGCGTGTTCCTGTTCCACCCA
AGCCTAAGGACACCCTGATGATCTCCCGGACACCCGAGGTGACCTGCGTGGTGGTGGACGTGTCTCACGAGGATCCT
GAGGTGAAGTTCAACTGGTATGTGGATGGCGTGGAGGTGCACAATGCCAAGACCAAGCCCAGAGAGGAGCAGTACAA
CTCTACATATAGGGTGGTGAGCGTGCTGACCGTGCTGCACCAGGACTGGCTGAACGGCAAGGAGTATAAGTGCAAGG
TGTCCAATAAGGCCCTGCCCGCCCCCATCGAGAAGACAATCAGCAAGGCCAAGGGCCAGCCTCGGGAGCCACAGGTG
TACACCCTGCCTCCATCCAGAGACGAGCTGACCAAGAACCAGGTGTCTCTGACATGTCTGGTGAAGGGCTTCTATCC
TAGCGATATCGCCGTGGAGTGGGAGTCCAATGGCCAGCCAGAGAACAATTACAAGACCACACCCCCTGTGCTGGACT
CCGATGGCTCCTTCTTTCTGTATTCCAAGCTGACCGTGGATAAGTCTCGGTGGCAGCAGGGCAACGTGTTCAGCTGT
TCCGTGATGCACGAAGCCCTGCATAATCACTATACTCAGAAATCCCTGTCCCTGTCACCTGGAAAGTGATAA
        (SEQ ID NO:71)
```

FIG. 36B

```
>hIgkCL
AGGACAGTGGCCGCCCCAAGCGTGTTCATCTTTCCCCCTTCCGACGAGCAGCTGAAGTCTGGCACCGCCAGCGTGGT
GTGCCTGCTGAACAACTTCTACCCTCGGGAGGCCAAGGTCCAGTGGAAGGTGGATAACGCCCTGCAGTCTGGCAATA
GCCAGGAGTCCGTGACCGAGCAGGACTCTAAGGATAGCACATATTCCCTGTCTAGCACCCTGACACTGAGCAAGGCC
GATTACGAGAAGCACAAGGTGTATGCCTGTGAAGTCACCCATCAGGGCCTGTCATCACCCGTCACTAAGTCATTCAA
TCGCGGAGAATGCTGATAA (SEQ ID NO:72)
```

FIG. 37A

Heavy Chain
ATGGGATGGAGCTGGATCTTTCTCTTTCTCCTGTCAGGAACTGCAGGTGTCCTCTCTGAGGTCCAGCTGC
AACAATCAGGACCTGGCCTGGTGGCACCCTCACAGAGCCTGTCCATCACATGCACTGTCTCTGGGTTCTC
ATTATCCATATATAGTGTACACTGGGTTCGCCAGCCTCCAGGAAAGGGTCTGGAGTGGCTGGGAATGATA
TGGGGTGGTGGAAGCTCAGACTATAATTCAGCTCTCAAATCCAGACTGAGCATCAGCAAGGACAACTCCA
AGAGCCAAGTTTTCTTAAAAATGAACAGTCTGCAAACTGATGACACAGCCATGTACTACTGTGCCAGAAA
CGGTAACTTCTATGCTATGGACTACTGGGGTCAAGGAACCTCAGTCACCGTCTCCTCAGCCAAAACGACA
CCCCCATCTGTCTATCCACTGGCCCCTGGATCTGCTGCCCAAACTAACTCCATGGTGACCCTGGGATGCC
TGGTCAAGGGCTATTTCCCTGAGCCAGTGACAGTGACCTGGAACTCTGGATCCCTGTCCAGCGGTGTGCA
CACCTTCCCAGCTGTCCTGCAGTCTGACCTCTACACTCTGAGCAGCTCAGTGACTGTCCCCTCCAGCACC
TGGCCCAGCGAGACCGTCACCTGCAACGTTGCCCACCCGGCCAGCAGCACCAAGGTGGACAAGAAAATTG
TGCCCAGGGATTGTGGTTGTAAGCCTTGCATATGTACAGTCCCAGAAGTATCATCTGTCTTCATCTTCCC
CCCAAAGCCCAAGGATGTGCTCACCATTACTCTGACTCCTAAGGTCACGTGTGTTGTGGTAGACATCAGC
AAGGATGATCCCGAGGTCCAGTTCAGCTGGTTTGTAGATGATGTGGAGGTGCACACAGCTCAGACGCAAC
CCCGGGAGGAGCAGTTCAACAGCACTTTCCGCTCAGTCAGTGAACTTCCCATCATGCACCAGGACTGGCT
CAATGGCAAGGAGTTCAAATGCAGGGTCAACAGTGCAGCTTTCCCTGCCCCCATCGAGAAAACCATCTCC
AAAACCAAAGGCAGACCGAAGGCTCCACAGGTGTACACCATTCCACCTCCCAAGGAGCAGATGGCCAAGG
ATAAAGTCAGTCTGACCTGCATGATAACAGACTTCTTCCCTGAAGACATTACTGTGGAGTGGCAGTGGAA
TGGGCAGCCAGCGGAGAACTACAAGAACACTCAGCCCATCATGAACACGAATGGCTCTTACTTCGTCTAC
AGCAAGCTCAATGTGCAGAAGAGCAACTGGGAGGCAGGAAATACTTCACCTGCTCTGTGTTACATGAGG
GCCTGCACAACCACCATACTGAGAAGAGCCTCTCCCACTCTCCTGGTAAATGA    (SEQ ID NO: 73)

FIG. 37B

```
          10        20        30        40        50        60        70        80        90        100
          *    *    *    *    *    *    *    *    *    *    *    *    *    *    *    *    *    *    *    *
  1 atgggatggagctggatctttctcttctcctgtcaggaactgcaggtgtcctctgagtccgagtcccagtgcaactcagccaTCAGGAGGACTTGGCCTGGTGGCACCCT 100
    M  G  W  S  W  I  F  L  F  L  L  S  G  T  A  G  V  L  S  E  V  Q  L  Q  Q  S  G  P  G  L  V  A  P  S 110       120       130       140       150       160       170       180       190       200
          *    *    *    *    *    *    *    *    *    *    *    *    *    *    *    *    *    *    *    *
103 CACAGAGCCCTGTCCATCACACTGCACTGTCCTGGGTTCCATTATCATTATAGTAGTCCATTATCACTCACTGGGTTCGCCAGCCTCCAGGAAAGGGTCTGGAGTGGCT 200
    Q  S  L  S  I  T  C  T  V  S  G  F  S  L  S  I  I  Y  S  V  H  W  V  R  Q  P  P  G  K  G  L  E  W  L 210       220       230       240       250       260       270       280       290       300
          *    *    *    *    *    *    *    *    *    *    *    *    *    *    *    *    *    *    *    *
201 GGGAATGATATGGGTGGTGGAAGCTCAGACTATAATCAGGCTCAAATCCAGACTGAGCATCAGCAAGGCACACTCCAGGAGCCAAGTTTCTTAAAA 300
    G  M  I  W  G  G  G  S  S  D  Y  N  S  A  L  K  S  R  L  S  I  S  K  D  N  S  K  S  Q  V  F  L  K 310       320       330       340       350       360       370       380       390       400
          *    *    *    *    *    *    *    *    *    *    *    *    *    *    *    *    *    *    *    *
301 ATGAACAGTCTGCAAACTGATGACACAGCCATGTACTACTGTGCCAGAAACGTAACTTCTATGCTATGGACATATGGGGTCAAGGAACCTCAGTCACCG 400
    M  N  S  L  Q  T  D  D  T  A  M  Y  Y  C  A  R  N  G  N  F  Y  A  M  D  I  W  G  Q  G  T  S  V  T  V 410       420       430       440       450       460       470       480       490       500
          *    *    *    *    *    *    *    *    *    *    *    *    *    *    *    *    *    *    *    *
401 TCTCCTCAGCCAAAACGACACCCCATCTGTCTATCCACTGGCCCCTGGATCTGCTGCCAAACTAACTGCCATGGTGTGACCTGGATGCCTGGTCAAGGG 500
    S  S  A  K  T  T  P  P  S  V  Y  P  L  A  P  G  S  A  A  Q  T  N  S  M  V  T  L  G  C  L  V  K  G 510       520       530       540       550       560       570       580       590       600
          *    *    *    *    *    *    *    *    *    *    *    *    *    *    *    *    *    *    *    *
501 CTATTTCCCTGAGCCAGTGACCAGTGACCTGGAACTCTGGATCCCTGTGCCAGCGGTGTGCACACCTTCCCAGCTGTCCTGCAGTCTGACTCCTACACTCTG 600
    Y  F  P  E  P  V  T  V  T  W  N  S  G  S  L  S  S  G  V  H  T  F  P  A  V  L  Q  S  D  L  Y  T  L 610       620       630       640       650       660       670       680       690       700
          *    *    *    *    *    *    *    *    *    *    *    *    *    *    *    *    *    *    *    *
601 AGCCAGCTCAGTGACTGTCCCCTCCAGCAACTGGCCAGCACCTGGCCCCTCCACTGTGCCCCACCGGCCAGCAGGACCACCAAGGtggacaagaaaattg 700
    S  S  S  V  T  V  P  S  S  T  W  P  S  E  T  V  T  C  N  V  A  H  P  A  S  S  T  K  V  D  K  K  I  V 710       720       730       740       750       760       770       780       790       800
          *    *    *    *    *    *    *    *    *    *    *    *    *    *    *    *    *    *    *    *
701 tgccaggaggattgtggttgtaagccttgcatatgtacagtcccagaagtatcatcttcccccaaagcccaaggatgtgctcaccattac 800
    P  R  D  C  G  C  K  P  C  I  C  T  V  P  E  V  S  S  V  F  I  F  P  P  K  P  K  D  V  L  T  I  T
```

FIG. 37B (Cont.)

```
         810       820       830       840       850       860       870       880       890       900
          *         *         *         *         *         *         *         *         *         *
801: tctgactcctaagtcacgtgttgtggtagacatcagcaaggatgatgatatccagtccagttcagctgattgtgtgtttgtagtgatgatgtcgaggtgcacacagct 900
       L  T  P  K  V  T  C  V  V  V  D  I  S  K  D  D  P  E  V  Q  F  S  W  F  V  D  D  V  E  V  H  T  A 910       920       930       940       950       960       970       980       990      1000
          *         *         *         *         *         *         *         *         *         *
901: cagacgcaaccccgggggagagcagtcaacagcacttctccgtctcagtgaattccatcaatgcaccagggactggctcaatggcaaggagttcaaat 1000
       Q  P  R  E  E  Q  F  N  S  T  F  R  S  V  S  B  L  P  I  M  H  Q  D  W  L  N  G  K  E  F  K  C 1010      1020      1030      1040      1050      1060      1070      1080      1090      1100
          *         *         *         *         *         *         *         *         *         *
1001: gcaaggtcaacagtgcagcttccctgccacctgagaaaaccatctccaaaaccaaagccaagggctcacaggtgtacacaccacctcc 1100
        R  V  N  S  A  A  F  P  A  P  I  E  K  K  T  I  S  K  R  G  R  P  P  K  A  P  Q  V  T  I  P  P  P 1110      1120      1130      1140      1150      1160      1170      1180      1190      1200
          *         *         *         *         *         *         *         *         *         *
1101: caaggagcagatggccaagtataaagtcagtctgacctgcatgataacagacttcttccctgaagatcattactgtggagtggaatgggcagcca 1200
        K  E  Q  M  A  K  D  K  V  S  L  T  C  M  I  T  D  F  F  P  E  D  I  T  V  E  W  Q  W  N  G  Q  P 1210      1220      1230      1240      1250      1260      1270      1280      1290      1300
          *         *         *         *         *         *         *         *         *         *
1201: gcggagaactacaagaacactcagcccatcatgaacaacgatggctcttacttcgtctacagcaagctcaatgtgcagaagagcaactgggaggcaggaa 1300
        A  E  N  Y  K  N  T  Q  P  I  M  N  N  D  G  S  Y  F  V  Y  S  K  L  N  V  Q  K  S  N  W  E  A  G  N 1310      1320      1330      1340      1350      1360      1370      1380
          *         *         *         *         *         *         *         *
1301: atactttcacctgctctgtgttacatgagggcctgcacaaccaccatgtcacagaagagctctccccactccctggtaaatga 1383
        T  F  T  C  S  V  L  H  E  G  L  H  N  H  H  T  E  K  S  L  S  H  S  P  G  K   *

(SEQ ID NO:73)
                                                                        (SEQ ID NO:74)
```

FIG. 37C

Light Chain
ATGGATTTTCAGGTGCAGATTTTCAGCTTCCTGCTAATCAGTGCCTCAGTCATAATGTCCAGAGGACAAATTGTTCTCA
CCCAGTCTCCAGCAATCATGTCTGCATC
TCTAGGGGAACGGGTCACCATGACCTGCACTGCCAGCTCAAGTGTAAGTTCCAGTTACTTGCACTGGTACCAGCAGAAG
CCAGGATCCTCCCCCAAACTCTGGATTT
ATAGCACATCCAACCTGGCTTCTGGAGTCCCAGCTCGCTTCAGTGGCAGTGGGTCTGGGACCTCTTACTCTCTCACAAT
CAGCAGCATGGAGGCTGAAGATGCTGCC
ACTTATTACTGCCACCAGTATCATCGTTTCCCACACACGTTCGGAGGGGGGACCAAGCTGGAAATAAAACGGGCTGATG
CTGCACCAACTGTATCCATCTTCCCACC
ATCCAGTGAGCAGTTAACATCTGGAGGTGCCTCAGTCGTGTGCTTCTTGAACAACTTCTACCCCAAAGACATCAATGTC
AAGTGGAAGATTGATGGCAGTGAACGAC
AAAATGGCGTCCTGAACAGTTGGACTGATCAGGACAGCAAAGACAGCACCTACAGCATGAGCAGCACCCTCACGTTGAC
CAAGGACGAGTATGAACGACATAACAGC
TATACCTGTGAGGCCACTCACAAGACATCAACTTCACCCATTGTCAAGAGCTTCAACAGGAATGAGTGTTAG (SEQ ID NO:75)

FIG. 37D

```
1   ATGGATTTTCAGGTGCAGATTTTCAGCTTCCTGCTAATCAGTGCCTCAGCAGTCATCATGT   100
     M  D  F  Q  V  Q  I  F  S  F  L  L  I  S  A  S  V  I  M  S  R  G  Q  I  V  L  T  Q  S  P  A  I  M  S

101 CTGCCATCTCTGGGGGACGGGTCACCATGACCTGCACTGCCAGCTCAAGTGTAAGTTACTTG   200
     A  S  L  G  E  R  V  T  M  T  C  T  A  S  S  S  V  S  S  Y  L  H  W  Y  Q  Q  K  P  G  S  S  E

201 CAAACTCTGGATTTATACGCACATCCAACCTGGCTTCTGGAGTCCCAGCTCGCTTCTCTGGA   300
     K  L  W  I  Y  S  T  S  N  L  A  S  G  V  P  A  R  F  S  G  S  G  S  G  T  S  Y  S  L  T  I  S  S

301 ATGGAGGCTGAAGATGCTGCCACTTATTACTGCCACCAGTATCGTCGTTTCCCACACACGTT   400
     M  E  A  E  D  A  A  T  Y  Y  C  H  Q  Y  R  R  F  P  H  T  F  G  G  G  T  K  L  E  I  K  R  A  D  A

401 CTGCACCAACTGTATCCATCTTCCCACCATCCAGTGAGCAGTTAACATCTGGAGGTGCCTCAG   500
     A  P  T  V  S  I  F  P  P  S  S  E  Q  L  T  S  G  G  A  S  V  V  C  F  L  N  N  F  Y  P  K  D  I

501 CAATGTCAGTGGAAGATTGATGGCAGTGAGCGCCTGAACGGTGACTGATCAGGACAGACAGGC   600
     N  V  K  W  K  I  D  G  S  E  R  Q  N  G  V  L  N  S  W  T  D  Q  D  S  K  D  S  T  Y  S  M  S  S

601 ACCCTCACGTTGACCAAGGACGAGTATGAACGACATAACCAGCTATACCTGTGAGGCCACTC   700
     T  L  T  L  T  K  D  E  Y  E  R  H  N  S  Y  T  C  E  A  T  H  K  T  S  T  S  P  I  V  K  S  F  N  R

701 GGAATGAGTGTTAG   714   (SEQ ID NO:75)
     N  E  C  *                (SEQ ID NO:76)
```

FIG. 40A

>BAG34252.1 hemagglutinin protein HagA [Porphyrononas gingivalis ATCC 33277]

mrklnslfslavllsllcwgqtaaaQGGPKTAPSVTHQAVQKGIRTSKVKDLRDPIPAGMARIILEAHDVWEDGTGYQMLWD
ADHNQYGASIPEESFWFANGTIPAGLYDPFEYKVPVNADASFSPTNFVLDGTASADIPAGTYDYVIINPNPGIIYIV
GEGVSKGNDYWEAGKTYHFTVQRQGPGDAASVWTGEGGNEFAPVQNLQWSVSGQTVTLTWQAPASDKRTY
VLNESFDTQTLPNGWTMIDADGDGHNWLSTINVYNTATHTGDGAMFSKSWTASGGAKIDLSPDNYLVTPKVTV
PENGKLSYWVSSQVPWTNEHYGVFLSTTGNEAANFTIKLLEETLGSDKPAPMNLVKSEGVKLPAPYQERTIDLS
AYAGQQVYLAFRHFNSTGIFRLYLDDVAVSGEGSSNDYTYTVYRDNWIAQNLAATTFNQENVAPGQYNYCVEV
KYTAGVSPKVCKDVTVEGSNEFAPVQNLTGSAVGQKVTLKWDAPNGTPNPNPGTTTLSESFENGIPASWKTID
ADGDGNNWTTTPPPGGTSFAGHNSAICASSASYINFEGPQNPDNYLVTPELSLPNGGTLTFWVCAQDANYASE
HYAVYASSTGNDASNFANALLEEVLTAKTVVTAPEAIRGTRVQGTWYQKTVQLPAGTKYVAFRHFGCTDFFWIN
LDDVEKIANGKRADFTETFESSTHGEAPAEWTTIDADGDGQGWLCLSSGQLGWLTAHGGTNWASFSWNGMAL
NPDNYLISKDVTGATKVKYYYAVNDGFPGDHYAVMISKTGTNAGDFTVVFEETPNGINKGGARFGLSTEADGAK
PQSVWIERTVDLPAGTKYVAFRHYNCSDLNYILLDDIQFTMGGSPTPTDYTYTVYRDGTKIKEGLTETTFEEDGV
ATGNHEYCVEVKYTAGVSPKECVNVTVDPVQFNPVQNLTGSAVGQKVTLKWDAPNGTPNPNPNPNPGTTTLS
ESFENGIPASWKTIDADGDGNNWTTTPPPGGTSFAGHNSAICASSASYINFEGPQNPDNYLVTPELSLPNGGTL
TFWVCAQDANYASEHYAVYASSTGNDASNFANALLEEVLTAKTWTAPEAIRGTRVQGTWYQKTVQLPAGTKYV
AFRHFGCTDFFWINLDDVEIKANGKRADFTETFESSTHGEAPAEWTTIDADGDGQGWLCLSSGQLGWLTAHGG
TNVVASFSWNGMALNPDNYLISKDVTGATKVKYYYAVNDGFPGDHYAVMISKTGTNAGDFTWFEETPNGINK
GGARFGLSTEADGAKPQSVWIERTVDLPAGTKYVAFRHYNCSDLNYILLDDIQFTMGGSPTPTDYTYTVYRDGT
KIKEGLTETTFEEDGVATGNHEYCVEVKYTAGVSPKECVNVTVDPVQFNPVQNLTGSAVGQKVTLKWDAPNGT
PNPNPNPNPGTTTLSESFENGIPASWKTIDADGDGNNWTTTPPPGGTSFAGHNSAICVSSASYINFEGPQNPDN
YLVTPELSLPGGGTLTFWVCAQDANYASEHYAVYASSTGNDASNFANALLEEVLTAKTVVTAPEAIRGTRVQGT
WYQKTVQLPAGTKYVAFRHFGCTDFFWINLDDVEKIANGKRADFTETFESSTHGEAPAEWTTIDADGDGQGWL
CLSSGQLGWLTAHGGTNWASFSWNGMALNPDNYLISKDVTGATKVKYYYAVNDGFPGDHYAVMISKTGTNAG
DFTVVFEETPNGINKGGARFGLSTEADGAKPQSVWIERTVDLPAGTKYVAFRHYNCSDLNYILLDDIQFTMGGSP
TPTDYTYTVYRDGTKIKEGLTETTFEEDGVATGNHEYCVEVKYTAGVSPKECVNVTVDPVQFNPVQNLTGSAVG
QKVTLKWDAPNGTPNPNPNPNPGTTTLSESFENGIPASWKTIDADGDGNNWTTTPPPGGTSFAGHNSAICVSS
ASYINFEGPQNPDNYLVTPELSLPGGGTLTFWVCAQDANYASEHYAVYASSTGNDASNFANALLEEVLTAKTWT
APEAIRGTRVQGTWYQKTVQLPAGTKYVAFRHFGCTDFFWINLDEVEIKANGKRADFTETFESSTHGEAPAEWT
TIDADGDGQGWLCLSSGQLDWLTAHGGTNVVASFSWNGMALNPDNYLISKDVTGATKVKYYYAVNDGFPGDH
YAVMISKTGTNAGDFTWFEETPNGINKGGARFGLSTEADGAKPQSVWIERTVDLPAGTKYVAFRHYNCSDLNYI
LLDDIQFTMGGSPTPTDYTYTVYRDGTKIKEGLTETTFEEDGVATGNHEYCVEVKYTAGVSPKVCVNVTINPTQF
NPVQNLTAEQAPNSMDAILKWNAPASKRAEVLNEDFENGIPSSWKTIDADGDGNNWTTTPPPGGSSFAGHNSA
ICVSSASYINFEGPQNPDNYLVTPELSLPGGGTLTFWVCAQDANYASEHYAVYASSTGNDASNFANALLEEVLT
AKTWTAPEAIRGTRVQGTWYQKTVQLPAGTKYVAFRHFGCTDFFWINLDDWITSGNAPSYTYTIYRNNTQIASG
VTETTYRDPDLATGFYTYGVKWYPNGESAIETATLNITSLADVTAQKPYTLTWGKTITVTCQGEAMIYDMNGRRL
AAGRNTWYTAQGGHYAVMWVDGKSYVEKLAVK        (SEQ ID NO: 125)

FIG. 40B

>HagA ATCC R1 (SEQ ID NO:138)

$R^{684}$ADFTETFESSTHGEAPAEWTTIDADGDGQGWLCLSSGQLGWLTAHGGTNVVASFSWNGMALNPDNYLISKDVTG
ATKVKYYYAVNDGFPGDHYAVMISKTGTNAGDFTVVFEETPNGINKGGARFGLSTEADGAKPQSVWIERTVDLPAGT
KYVAFRHYNCSDLNYILLDDIQFTMGGSPTPTDYTYTVYRDGTKIKEGLTETTFEEDGVATGNHEYCVEVKYTAGVS
PKECVNVTVDPVQFNPVQNLTGSAVGQKVTLKWDAPNGTPNPNPNPNPGTTTLSESFENGIPASWKTIDADGDGNNW
TTTPPPGGTSFAGHNSAICASSASYINFEGPQNPDNYLVTPELSLPNGGTLTFWVCAQDANYASEHYAVYASSTGND
ASNFANALLEEVLTAKTVVTAPEAIRGTRVQGTWYQKTVQLPAGTKYVAFRHFGCTDFFWINLDDVEIKANGK$R^{1140}$A

>HagA ATCC R2 (SEQ ID NO:139)

$R^{1140}$ADFTETFESSTHGEAPAEWTTIDADGDGQGWLCLSSGQLGWLTAHGGTNVVASFSWNGMALNPDNYLISKDVTG
ATKVKYYYAVNDGFPGDHYAVMISKTGTNAGDFTVVFEETPNGINKGGARFGLSTEADGAKPQSVWIERTVDLPAGT
KYVAFRHYNCSDLNYILLDDIQFTMGGSPTPTDYTYTVYRDGTKIKEGLTETTFEEDGVATGNHEYCVEVKYTAGVS
PKECVNVTVDPVQFNPVQNLTGSAVGQKVTLKWDAPNGTPNPNPNPNPGTTTLSESFENGIPASWKTIDADGDGNNW
TTTPPPGGTSFAGHNSAICVSSASYINFEGPQNPDNYLVTPELSLPGGGTLTFWVCAQDANYASEHYAVYASSTGND
ASNFANALLEEVLTAKTVVTAPEAIRGTRVQGTWYQKTVQLPAGTKYVAFRHFGCTDFFWINLDDVEIKANGK$R^{1568}$A

>HagA ATCC R3 (SEQ ID NO:140)

$R^{1596}$ADFTETFESSTHGEAPAEWTTIDADGDGQGWLCLSSGQLGWLTAHGGTNVVASFSWNGMALNPDNYLISKDVTG
ATKVKYYYAVNDGFPGDHYAVMISKTGTNAGDFTVVFEETPNGINKGGARFGLSTEADGAKPQSVWIERTVDLPAGT
KYVAFRHYNCSDLNYILLDDIQFTMGGSPTPTDYTYTVYRDGTKIKEGLTETTFEEDGVATGNHEYCVEVKYTAGVS
PKECVNVTVDPVQFNPVQNLTGSAVGQKVTLKWDAPNGTPNPNPNPNPGTTTLSESFENGIPASWKTIDADGDGNNW
TTTPPPGGTSFAGHNSAICVSSASYINFEGPQNPDNYLVTPELSLPGGGTLTFWVCAQDANYASEHYAVYASSTGND
ASNFANALLEEVLTAKTVVTAPEAIRGTRVQGTWYQKTVQLPAGTKYVAFRHFGCTDFFWINLDDVEIKANGK$R^{2652}$A

>HagA ATCC R4 (SEQ ID NO:141)

$R^{2652}$ADFTETFESSTHGEAPAEWTTIDADGDGQGWLCLSSGQLDWLTAHGGTNVVASFSWNGMALNPDNYLISKDVTG
ATKVKYYYAVNDGFPGDHYAVMISKTGTNAGDFTVVFEETPNGINKGGARFGLSTEADGAKPQSVWIERTVDLPAGT
KYVAFRHYNCSDLNYILLDDIQFTMGGSPTPTDYTYTVYRDGTKIKEGLTETTFEEDGVATGNHEYCVEVKYTAGVS
PKECVNVTVDPVQFNPVQNLTAEQAPNSMDAILKWNAPASKRAEVLNEDFENGIPSSWKTIDADGDGNNWTTTPPPG
GSSFAGHNSAICVSSASYINFEGPQNPDNYLVTPELSLPGGGTLTFWVCAQDANYASEHYAVYASSTGNDASNFANA
LLEEVLTAKTVVTAPEATRGTRVQGTWYQKTVQLPAGTKYVAFRHFGCTDFFWINLDDVVITSGNAPSYTYTIYRNN
TQIASGVTETTYRDPDLATGFYTYGVKVVYPNGESAIETATLNI$T^{2556}$S

>HagA W83 R1 (SEQ ID NO:142)

ADFTETFESSTHGEAPAEWTTIDADGDGQGWLCLSSGQLGWLTAHGGTNVVASFSWNGMALNPDNYLISKDVTGATK
VKYYYAVNDGFPGDHYAVMISKTGTNAGDFTVVFEETPNGINKGGARFGLSTEANGAKPQSVWIERTVDLPAGTKYV
AFRHYNCSDLNYILLDDIQFTMGGSPTPTDYTYTVYRDGTKIKEGLTETTFEEDGVATGNHEYCVEVKYTAGVSPKE
CVNVTVDPVQFNPVQNLTGSAVGQKVTLKWDAPNGTPNPNPGTTTLSESFENGIPASWKTIDADGDGNNWTTTPPPG
GTSFAGHNSAICVSSASYINFEGPQNPDNYLVTPELSLPNGGTLTFWVCAQDANYASEHYAVYASSTGNDASNFANA
LLEEVLTAKTVVTAPEAIRGTRVQGTWYQKTVQLPAGTKYVAFRHFGCTDFFWINLDDVEIKANGKR

>HagA W83 R2 (SEQ ID NO:143)

ADFTETFESSTHGEAPAEWTTIDADGDGQGWLCLSSGQLGWLTAHGGTNVVASFSWNGMALNPDNYLISKDVTGATK
VKYYYAVNDGFPGDHYAVMISKTGTNAGDFTVVFEETPNGINKGGARFGLSTEANGAKPQSVWIERTVDLPAGTKYV
AFRHYNCSDLNYILLDDIQFTMGGSPTPTDYTYTVYRDGTKIKEGLTETTFEEDGVATGNHEYCVEVKYTAGVSPKE
CVNVTVDPVQFNPVQNLTGSAVGQKVTLKWDAPNGTPNPNPGTTTLSESFENGIPASWKTIDADGDGNNWTTTPPPG
GTSFAGHNSAICVSSASYINFEGPQNPDNYLVTPELSLPNGGTLTFWVCAQDANYASEHYAVYASSTGNDASNFANA
LLEEVLTAKTVVTAPEAIRGTRVQGTWYQKTVQLPAGTKYVAFRHFGCTDFFWINLDDVEIKANGKR

>HagA W83 R3 (SEQ ID NO:144)

ADFTETFESSTHGEAPAEWTTIDADGDGQGWLCLSSGQLGWLTAHGGTNVVASFSWNGMALNPDNYLISKDVTGATK
VKYYYAVNDGFPGDHYAVMISKTGTNAGDFTVVFEETPNGINKGGARFGLSTEANGAKPQSVWIERTVDLPAGTKYV
AFRHYNCSDLNYILLDDIQFTMGGSPTPTDYTYTVYRDGTKIKEGLTETTFEEDGVATGNHEYCVEVKYTAGVSPKE
CVNVTINPTQFNPVQNLTAEQAPNSMDAILKWNAPASKRAEVLNEDFENGIPASWKTIDADGDGNNWTTTPPPGGSS
FAGHNSAICVSSASYINFEGPQNPDNYLVTPELSLPGDGTLTFWVCAQDANYASEHYAVYASSTGNDASNFENALLE
EVLTAKTVVTAPEAIRGTRVQGTWYQKTVQLPAGTKYVAFRHFGCTDFFWINLDDVVITSGNAPSYTYTIYRNNTQI
ASGVTETTYRDPDLATGFYTYGVKVVYPNGESAIETATLNIT

FIG. 40B (cont.)

>Kgp W83 N-term (SEQ ID NO:145)
R<sup>737</sup>ANEAKVVLAADNVWGDNTGYQFLLDADHNTFGSVIPATGPLFTGTASSNLYSANFEYLVPANADPVVTTQNIIVT
GQGEVVIPGGVYDYCITNPEPASGKMWIAGDGGNQPARYDDFTFEAGKKYTFTMRRAGMFDGTDMEVEDDSPASYTY
TVYRDGTKIKEGLTATTFEEDGVAAGNHEYCVEVKYTAGVSPKVCKDVTVEGSNEFAPVQNLTGSSVGQKVTLKWDA
PNGTPNPNPNPNPNPGTTLSESFENGIPASWKTIDAPGDGHGWKPGNAPGIAGYNSNGCVYSESFGLGGIGVLTPDN
YLITPALDLPNGGKLTFWVCAQDANYASEHYAVYASSTGNDASNFTNALLEETITAKGVRSPKAIRGRIQGTWRQKT
VDLPAGTKYVAFRHFQSTDMFYIDLDEVEIKANGKR >Kgp W83 C-term (SEQ ID NO:146)
ADFTETFESSTHGEAPAEWTTIDADGDGQGWLCLSSGQLDWLTAHGGSNVVSSFSWNGMALNPDNYLISKDVTGATK
VKYYYAVNDGFPGDHYAVMISKTGTNAGDFTVVFEETPNGINKGGARFGLSTEANGAKPQSVWIERTVDLPAGTKYV
AFRHYNCSDLNYILLDDTQFTMGGSPTPTDYTYTVYRDGTKIKEGLTETTFEEDGVATGNHEYCVEVKYTAGVSPKK
CVDVTVNSTQFNPVQNLTAEQAPNSMDAILKWNAPASKRAEVLNEDFENGIPASWKTIDADGDGNNWTTTPPPGGSS
FAGHNSAICVSSASHINFEGPQNPDNYLVTPELSLPGGGTLTFWVCAQDANYASEHYAVYASSTGNDASNFANALLE
EVLTAKTVVTAPEAIRGTRAQGTWYQKTVQLPAGTKYVAFRHFGCTDFFWINLDDVVITSGNAPSYTYTIYRNNTQI
ASGVTETTYRDPDLATGFYTYGVKVVYPNGESAIETATLNITS >RgpA W83 N-term (SEQ ID NO:147)
R<sup>737</sup>AGQAEIVLEAHDVWNDGSGYQILLDADHDQYGQVIPSDTHTLWPNCSVPANLFAPFEYTVPENADPSCSPTNMIM
DGTASVNIPAGTYDFAIAAFQANAKIWIAGQGPTKEDDYVFEAGKKYHFLMKKMGSGDGTELTISEGGGSDYTYTVY
RDGTKIKEGLTATTFEEDGVATGNHEYCVEVKYTAGVSPKVCKDVTVEGSNEFAPVQNLTGSAVGQKVTLKWDAPNG
TPNPNPNPNPNPGTTTLSESFENGIPASWKTIDADGDGHGWKPGNAPGIAGYNSNGCVYSESFGLGGIGVLTPDN
YLITPALDLPNGGKLTFWVCAQDANYASEHYAVYASSTGNDASNFTNALLEETITAKGVRSPEAMRGRIQGTWRQKT
VDLPAGTKYVAFRHFQSTDMFYIDLDEVEIKANGKR >RgpA W83 C-term (SEQ ID NO:148)
ADFTETFESSTHGEAPAEWTTIDADGDGQGWLCLSSGQLDWLTAHGGTNVVSSFSWNGMALNPDNYLISKDVTGATK
VKYYYAVNDGFPGDHYAVMISKTGTNAGDFTVVFEETPNGINKGGARFGLSTEANGAKPQSVWIERTVDLPAGTKYV
AFRHYNCSDLNYILLDDTQFTMGGSPTPTDYTYTVYRDGTKIKEGLTETTFEEDGVATGNHEYCVEVKYTAGVSPKK
CVNVTVNSTQFNPVKNLKAQPDGGDVVLKWEAPSAKKTEGSREVKRIGDGLFVTIEPANDVRANEAKVVLAADNVWG
DNTGYQFLLDADHNTFGSVIPATGPLFTGTASSDLYSANFESLIPANADPVVTTQNIIVTGQGEVVIPGGVYDYCIT
NPEPASGKMWIAGDGGNQPARYDDFTFEAGKKYTFTMRRAGMGDGTDMEVEDDSPASYTYTVYRDGTKIKEGLTETT
YRDAGMSAQSHEYCVEVKYTAGVSPKVCVDYIPD >Kgp W83 (SEQ ID NO:149)
*R<sup>737</sup>ANEAKVVLAADNVWGDNTGYOFLLDADHNTFGSVIPATGPLFTGTASSNLYSANFEYLVPANADPVVTTONIIVT*
*GOGEVVIPGGVYDYCITNPEPASGKMWIAGDGGNQPARYDDFTFEAGKKYTFTMRRAGMGDGTDMEVEDDSPASYTY*
*TVYRDGTKIKEGLTATTFEEDGVAAGNHEYCVEVKYTAGVSPKVCKDVTVEGSNEFAPVQNLTGSSVGQKVTLKWDA*
*PNGTPNPNPNPNPNPGTTLSESFENGIPASWKTIDADGDGHGWKPGNAPGIAGYNSNGCVYSESFGLGGIGVLTPDN*
*YLITPALDLPNGGKLTFWVCAQDANYASENYAVYASSTGNDASNFTNALLEETITAKgvrspkairgrigqtwrgkt*
*vdlpagtkyvafrhfqstdmfyidldeveikangkrADFTETFESSTHGEAPAEWTTIDADGDGQGWLCLSSGQLDW*
*LTAHGGSNVVSSFSWNGMALNPDNYLISKDVTGATKVKYYYAVNDGFPGDHYAVMISKTGTNAGDFTVVFEETPNGI*
*NKggarfglsteangakPQSVWIERTVDLPAGTKYVAFRHYNCSDLNYILLDDIQFTMGGSPTPTDYTYTVYRDGTK*
*IKEGLTETTFEEDGVATGNHEYCVEVKYTAGVSPKKCVDVTVNSTQFNPVQNLTAEQAPNSMDAILKWNAPASKRAE*
*VLNEDFENGIPASWKTIDADGDGNNWTTTPPPGGSSFAGHNSAICVSSASHINFEGPQNPDNYLVTPELSLPGGGTL*
*TFWVCAQDANYASEHYAVYASSTGNDASNFANALLEEVLTAKTVVTAPEAIRGTRAQGTWYQKTVQLPAGTKYVAFR*
*HFGCTDFEWINLDDVVITSGNAPSYTYTIYRNNTQIASGVTETTYRDPDLATGFYTYGVKVVYPNGESAIETATLNI*
*TS<sup>1661</sup>*

FIG. 40B (cont.)

>RgpA_W83 (SEQ ID NO:150)
R$^{719}$SGQAEIVILEAHDVWNDGSGYQILLDADHDQYGQVIPSDTHTLWPNCSVPANLFAPFEYTVPENADPSCSPT
NMIMDGTASVNIPAGTYDFAIAAPQANAKIWIAGQGPTKEDDYVFEAGKKYHFLMKKMGSGDGTELTISEGGGS
DYTYTVYRDGTKIKEGLTATTFEEDGVATGNHEYCVEVKYTAGVSPKVCKDVTVEGSNEFAPVQNLTGSAVGQK
VTLKWDAPNGTPNPNPNPNPNPNPGTTTLSESFENGIPASWKTIDADGDGHGWKPGNAPGIAGYNSNGCVYSES
FGLGGIGVLTPDNYLITPALDLPNGGKLTFWVCAQDANYASEHYAVYASSTGNDASNFTNALLEETITAKgvrs
peamrqrigqtwrqktvdlpaqtkyvafrhfqstdmfyidldeveikanqkrADFTETFESSTHGEAPAEWTTI
DADGDGQGWLCLSSGQLDWLTAHGGTNVVSSFSWNGMALNPDNYLISKDVTGATKVKYYYAVNDGFPGDHYAVM
ISKTGTNAGDFTVVFEETPNGINKgqarfqlsteadgakPQSVWIERTVDLPAGTKYVAFRHYNCSDLNYILLD
DIQFTMGGSPTPTDYTYTVYRDGTKIKEGLTETTFEEDGVATGNHEYCVEVKYTAGVSPKKCVNVTVNSTQFNP
VKNLKAQPDGGDVVLKWEAPSAKktegsrevkrigdglfvtiepandvrANEAKVVLAADNVWGDNTGYQFLLD
ADHNTFGSVIPATGPLFTGTASSDLYSANFESLIPANADPVVTTQNIIVTGQGEVVIPGGVYDYCITNPEPASG
KMWIAGDGGNQPARYDDFTFEAGKKYTFTMRRAGMGDGTDMEVEDDSPASYTYTVYRDGTKIKEGLTETTYRDA
GMSAQSHEYCVEVKYTAGVSPKVCVDYIPD$^{1634}$

FIG. 40C

CLUSTAL O(1.2.4) multiple sequence alignment

```
HagA_ATCC_R4    ADFTETFESSTHGEAPAEWTTIDADGDGQGWLCLSSGQLDWLTAHGGTNVVASFSWNGMA    60
HagA_W83_R3     ADFTETFESSTHGEAPAEWTTIDADGDGQGWLCLSSGQLGWLTAHGGTNVVASFSWNGMA    60
HagA_W83_R1     ADFTETFESSTHGEAPAEWTTIDADGDGQGWLCLSSGQLGWLTAHGGTNVVASFSWNGMA    60
HagA_W83_R2     ADFTETFESSTHGEAPAEWTTIDADGDGQGWLCLSSGQLDWLTAHGGTNVVASFSWNGMA    60
HagA_ATCC_R1    ADFTETFESSTHGEAPAEWTTIDADGDGQGWLCLSSGQLGWLTAHGGTNVVASFSWNGMA    60
HagA_ATCC_R2    ADFTETFESSTHGEAPAEWTTIDADGDGQGWLCLSSGQLGWLTAHGGTNVVASFSWNGMA    60
HagA_ATCC_R3    ADFTETFESSTHGEAPAEWTTIDADGDGQGWLCLSSGQLGWLTAHGGTNVVASFSWNGMA    60
                ****************************************:********************

HagA_ATCC_R4    LNPDNYLISKDVTGATKVKYYYAVNDGFPGDHYAVMISKTGTNAGDFTVVFEETPNGINK   120
HagA_W83_R3     LNPDNYLISKDVTGATKVKYYYAVNDGFPGDHYAVMISKTGTNAGDFTVVFEETPNGINK   120
HagA_W83_R1     LNPDNYLISKDVTGATKVKYYYAVNDGFPGDHYAVMISKTGTNAGDFTVVFEETPNGINK   120
HagA_W83_R2     LNPDNYLISKDVTGATKVKYYYAVNDGFPGDHYAVMISKTGTNAGDFTVVFEETPNGINK   120
HagA_ATCC_R1    LNPDNYLISKDVTGATKVKYYYAVNDGFPGDHYAVMISKTGTNAGDFTVVFEETPNGINK   120
HagA_ATCC_R2    LNPDNYLISKDVTGATKVKYYYAVNDGFPGDHYAVMISKTGTNAGDFTVVFEETPNGINK   120
HagA_ATCC_R3    LNPDNYLISKDVTGATKVKYYYAVNDGFPGDHYAVMISKTGTNAGDFTVVFEETPNGINK   120
                ************************************************************

HagA_ATCC_R4    GGARFGLSTEADGAKPQSVWIERTVDLPAGTKYVAFRHYNCSDLNYILLDDIQFTMGGSP   180
HagA_W83_R3     GGARFGLSTEANGAKPQSVWIERTVDLPAGTKYVAFRHYNCSDLNYILLDDIQFTMGGSP   180
HagA_W83_R1     GGARFGLSTEANGAKPQSVWIERTVDLPAGTKYVAFRHYNCSDLNYILLDDIQFTMGGSP   180
HagA_W83_R2     GGARFGLSTEANGAKPQSVWIERTVDLPAGTKYVAFRHYNCSDLNYILLDDIQFTMGGSP   180
HagA_ATCC_R1    GGARFGLSTEADGAKPQSVWIERTVDLPAGTKYVAFRHYNCSDLNYILLDDIQFTMGGSP   180
HagA_ATCC_R2    GGARFGLSTEADGAKPQSVWIERTVDLPAGTKYVAFRHYNCSDLNYILLDDIQFTMGGSP   180
HagA_ATCC_R3    GGARFGLSTEADGAKPQSVWIERTVDLPAGTKYVAFRHYNCSDLNYILLDDIQFTMGGSP   180
                ***********:************************************************

HagA_ATCC_R4    TPTDYTYTVYRDGTKIKEGLTETTFEEDGVATGNHEYCVEVKYTAGVSPKVCVNVTINPT   240
HagA_W83_R3     TPTDYTYTVYRDGTKIKEGLTETTFEEDGVATGNHEYCVEVKYTAGVSPKECVNVTINPT   240
HagA_W83_R1     TPTDYTYTVYRDGTKIKEGLTETTFEEDGVATGNHEYCVEVKYTAGVSPKECVNVTVDPV   240
HagA_W83_R2     TPTDYTYTVYRDGTKIKEGLTETTFEEDGVATGNHEYCVEVKYTAGVSPKECVNVTVDPV   240
HagA_ATCC_R1    TPTDYTYTVYRDGTKIKEGLTETTFEEDGVATGNHEYCVEVKYTAGVSPKECVNVTVDPV   240
HagA_ATCC_R2    TPTDYTYTVYRDGTKIKEGLTETTFEEDGVATGNHEYCVEVKYTAGVSPKECVNVTVDPV   240
HagA_ATCC_R3    TPTDYTYTVYRDGTKIKEGLTETTFEEDGVATGNHEYCVEVKYTAGVSPKECVNVTVDPV   240
                ************************************************    ****:;:*

HagA_ATCC_R4    QFNPVQNLTAEQAPNSMDAILKWNAPASK---------RAEVLNEDFENGIPSSWKTIDA   291
HagA_W83_R3     QFNPVQNLTAEQAPNSMDAILKWNAPASK---------RAEVLNEDFENGIPASWKTIDA   291
HagA_W83_R1     QFNPVQNLTGSAVG--QKVTLKWDAPNGTPN-----PNPGTTTLSESFENGIPASWKTIDA   294
HagA_W83_R2     QFNPVQNLTGSAVG--QKVTLKWDAPNGTPN----PNPGTTTLSESFENGIPASWKTIDA   294
HagA_ATCC_R1    QFNPVQNLTGSAVG--QKVTLKWDAPNGTPNPNPNPNPGTTTLSESFENGIPASWKTIDA   298
HagA_ATCC_R2    QFNPVQNLTGSAVG--QKVTLKWDAPNGTPNPNPNPNPGTTTLSESFENGIPASWKTIDA   298
HagA_ATCC_R3    QFNPVQNLTGSAVG--QKVTLKWDAPNGTPNPNPNPNPGTTTLSESFENGIPASWKTIDA   298
                ********        ***:**        . .*.*.******:*:******

HagA_ATCC_R4    DGDGNNWTTTPPPGGSSFAGHNSAICVSSASYINFEGPQNPDNYLVTPELSLPGGGTLTF   351
HagA_W83_R3     DGDGNNWTTTPPPGGSSFAGHNSAICVSSASYINFEGPQNPDNYLVTPELSLPGGGTLTF   351
HagA_W83_R1     DGDGNNWTTTPPPGGTSFAGHNSAICVSSASYINFEGPQNPDNYLVTPELSLPNGGTLTF   354
HagA_W83_R2     DGDGNNWTTTPPPGGTSFAGHNSAICVSSASYINFEGPQNPDNYLVTPELSLPNGGTLTF   354
HagA_ATCC_R1    DGDGNNWTTTPPPGGTSFAGHNSAICASSASYINFEGPQNPDNYLVTPELSLPNGGTLTF   358
HagA_ATCC_R2    DGDGNNWTTTPPPGGTSFAGHNSAICVSSASYINFEGPQNPDNYLVTPELSLPGGGTLTF   358
HagA_ATCC_R3    DGDGNNWTTTPPPGGTSFAGHNSAICVSSASYINFEGPQNPDNYLVTPELSLPGGGTLTF   358
                **************:*.********:.*******,*****************:****

HagA_ATCC_R4    WVCAQDANYASEHYAVYASSTGNDASNFANALLEEVLTAKTVVTAPEAIRGTRVQGTWYQ   411
HagA_W83_R3     WVCAQDANYASEHYAVYASSTGNDASNFANALLEEVLTAKTVVTAPEAIPGTRVQGTWYQ   411
HagA_W83_R1     WVCAQDANYASEHYAVYASSTGNDASNFANALLEEVLTAKTVVTAPEAIPGTRVQGTWYQ   414
HagA_W83_R2     WVCAQDANYASEHYAVYASSTGNDASNFANALLEEVLTAKTVVTAPEAIPGTRVQGTWYQ   414
HagA_ATCC_R1    WVCAQDANYASEHYAVYASSTGNDASNFANALLEEVLTAKTVVTAPEAIPGTRVQGTWYQ   418
HagA_ATCC_R2    WVCAQDANYASEHYAVYASSTGNDASNFANALLEEVLTAKTVVTAPEAIPGTRVQGTWYQ   418
HagA_ATCC_R3    WVCAQDANYASEHYAVYASSTGNDASNFANALLEEVLTAKTVVTAPEAIPGTRVQGTWYQ   418
                ************:*****************************************:******
```

FIG.40C(continued)

```
HagA_ATCC_R4  KTVQLPAGTKYVAFRHFGCTDFFWINLDDWEITSGNAPSYTYTIYRNNTQIASGVTETTY  471
HagA_W83_R3   KTVQLPAGTKYVAFRHFGCTDFFWINLDDWEITSGNAPSYTYTIYRNNTQIASGVTETTY  471
HagA_W83_R1   KTVQLPAGTKYVAFRHFGCTDFFWINLDDVEIKANGKR----------------------  452
HagA_W83_P2   KTVQLPAGTKYVAFRHFGCTDFFWINLDDVEIKANGKR----------------------  452
HagA_ATCC_R1  KTVQLPAGTKYVAFRHFGCTDFFWINLDDVEIKANGKR----------------------  456
HagA_ATCC_R2  KTVQLPAGTKYVAFRHFGCTDFFWINLDDVEIKANGKR----------------------  456
HagA_ATCC_R3  KTVQLPAGTKYVAFRHFGCTDFFWINLDEVEIKANGKR----------------------  456
              ************************* :*  *.:..

HagA_ATCC_R4  RDPDLATGFYTYGVKW YPNGESAIETATLNIT  504  (SEQ ID NO:151)
HagA_W83_R3   RDPDLATGFYTYGVKW YPNGESAIETATLNIT  504  (SEQ ID NO:144)
HagA_W83_R1                                     452  (SEQ ID NO:142)
HagA_W83_P2                                     452  (SEQ ID NO:143)
HagA_ATCC_R1                                    456  (SEQ ID NO:152)
HagA_ATCC_R2                                    456  (SEQ ID NO:153)
HagA_ATCC_R3                                    456  (SEQ ID NO:154)
```

FIG.40D

```
RgpA_C-term   ADFTETFESSTHGEAPAEWTTIDADGDGQGWLCLSSGQLDWLTAHGGTNVVSSFSWNGMA  60
Kgp_C-term    ADFTETFESSTHGEAPAEWTTIDADGDGQGWLCLSSGQLDWLTAHGGSNVVSSFSWNGMA  60
HagA_ATCC_R4  ADFTETFESSTHGEAPAEWTTIDADGDGQGWLCLSSGQLDWLTAHGGTNVVASFSWNGMA  60
HagA_W83_R3   ADFTETFESSTHGEAPAEWTTIDADGDGQGWLCLSSGQLGWLTAHGGTNVVASFSWNGMA  60
              *************************************** :****** :*** :*******

RgpA_C-term   LNPDNYLISKDVTGATKVKYYYAVNDGFPGDHYAVMISKTGTNAGDFTVVFEETPNGINK  120
Kgp_C-term    LNPDNYLISKDVTGATKVKYYYAVNDGFPGDHYAVMISKTGTNAGDFTVVFEETPNGINK  120
HagA_ATCC_R4  LNPDNYLISKDVTGATKVKYYYAVNDGFPGDHYAVMISKTGTNAGDFTVVFEETPNGINK  120
HagA_W83_R3   LNPDNYLISKDVTGATKVKYYYAVNDGFPGDHYAVMISKTGTNAGDFTVVFEETPNGINK  120
              ************************************************************

RgpA_C-term   GGARFGLSTEADGAKPQSVWIERTVDLPAGTKYVAFRHYNCSDLNYILLDDIQFTMGGSP  180
Kgp_C-term    GGARFGLSTEANGAKPQSVWIERTVDLPAGTKYVAFRHYNCSDLNYILLDDIQFTMGGSP  180
HagA_ATCC_R4  GGARFGLSTEADGAKPQSVWIERTVDLPAGTKYVAFRHYNCSDLNYILLDDIQFTMGGSP  180
HagA_W83_R3   GGARFGLSTEANGAKPQSVWIERTVDLPAGTKYVAFRHYNCSDLNYILLDDIQFTMGGSP  180
              **********:* ************************************************

RgpA_C-term   TPTDYTYTVYRDGTKIKEGLTETTFEEDGVATGNHEYCVEVKYTAGVSPKKCVNVTVNST  240
Kgp_C-term    TPTDYTYTVYRDGTKIKEGLTETTFEEDGVATGNHEYCVEVKYTAGVSPKKCVDVTVMST  240
HagA_ATCC_R4  TPTDYTYTVYRDGTKIKEGLTETTFEEDGVATGNHEYCVEVKYTAGVSPKVCVNVTINPT  240
HagA_W83_R3   TPTDYTYTVYRDGTKIKEGLTETTFEEDGVATGNHEYCVEVKYTAGVSPKECVNVTINPT  240
              ************************************************* **:**:* *

RgpA_C-term   QFNPVKNLKAQ--PDGGDWILKWEAPSAKKTEGSREVKRIGDG-LFVTIEPANDVRANEA  297
Kgp_C-term    QFNPVQNLTAEQAPNSMDAILKWNAPASKRAEVLNEDFENGIPASWKTIDA---------  291
HagA_ATCC_R4  QFNPVQNLTAEQAPNSMDAILKWNAPASKRAEVLNEDFENGIPASWKTIDA---------  291
HagA_W83_R3   QFNPVQNLTAEQAPNSMDAILKWNAPASKRAEVLNEDFENGIPASWKTIDA---------  291
              *****:**.*:  *:.  *.:**:**:**:*:* *      *        :**:

RgpA_C-term   KWLAADNVWGDNTGYQFLLDADHNTFGSVIPATGPLFTGTASSDLYS-----ANFESLIP  353
Kgp_C-term    -------------------DGDGNNWTTTPPGSSFAGHNSAICVSSASHINFE--GP     329
HagA_ATCC_R4  -------------------DGDGNNWTTTPPGSSFAGHNSAICVSSASYINFE--GP     329
HagA_W83_R3   -------------------DGDGNNWTTTPPGSSFAGHNSAICVSSASYINFE---GP    329
                                 *.* *.: :. *  *  * *;* *:  *    *** *

RgpA_C-term   ANADPWTTQNIIVTGQGEWI----------------------------PGGVYD----  381
Kgp_C-term    QNPDNYLVTPELSLPGGGTLTFWVCAQDANYASEHYAVYASSTGNDASNFANALLEEVLT  389
HagA_ATCC_R4  QNPDNYLVTPELSLPGGGTLTFWVCAQDANYASEHYAVYASSTGNDASNFANALLEEVLT  389
HagA_W83_R3   QNPDNYLVTPELSLPGGGTLTFWVCAQDANYASEHYAVYASSTGMDASNFANALLEEVLT  389
              * *  :.*       * *
```

FIG.40D(cont)

```
RgpA_C-term    ---YCITNPEPASG-------KMWIAGDGGNQPARYDDFTFEAGKKYTFTMRRAGMC-------CG          430
Kgp_C-term     AKTVVTAPEAIRGTRAQGTWYQ----------KTVQLPAGTKYVA-FFHFGCTDFFWINL               438
HagA_ATCC_R4   AKTVVTAPEAIRGTRVQGTWYQ-----------KTVQLPAGTKYVA-FRHFGCTDFFWINL              438
HagA_W83_R3    AKTVVTAPEAIRGTRVQGTWYQ-----------KTVQLPAGTKYVA-FRHFGCTDFFWINL              438
                 :* **    *         *                  . . :** .** *  :*:* *

RgpA_C-term    TDMEVEDDSPASYTYTVYRDGTKIKEGLTETTYRDAGMSAQSHEYCVEVKYTAGVSPKVC               490
Kgp_C-term     DDVVITSGNAPSYTYTIYRNNTQIASGVTETTYRDPDLATGFYTYGVKVVYPNGESAIET               498
HagA_ATCC_R4   DDVVITSGNAPSYTYTIYRNNTQIASGVTETTYRDFDLATGFYTYGVKVVYPNGESAIET               498
HagA_W83_R3    DDVVITSGNAPSYTYTIYRNNTQIASGVTETTYRDPDLATGFYTYGVKVVYPNGESAIET               498
                *: :  ...  *****:**:.*:*   *:*******     * *:* *  **

RgpA_C-term    VDYIPD-  496 (SEQ  ID  NO:148)
Kgp_C-term     ATLNITS  505 (SEQ  ID  NO:146)
HagA_ATCC_R4   ATLNIT-  504 (SEQ  ID  NO:155)
HagA_W83_R3    ATLNIT-  504 (SEQ  ID  NO:144)
```

FIG.40E

```
Kgp_N-term     -------------------ANEAKWVLAADNVWGDNTGYQFLLDADHNTFGSVIPATGPTLFTGTASS        48
RgpA_N-term     ---------------SGQAEIVLEAHDVWNDGSGYQILLDADHDQYGQVIPSDTHTLWPNCSVP        49
RgpA_C-term     ADFTETFESSTHGEAPAEWTTIDADGDGQGWLCLSS---------------GQLGWLTAHGG        47
HagA_W83_R1     ADFTETFESSTHGEAPAEWTTIDADGDGQGWLCLSS---------------GQLGWLTAHGG        47
HagA_W83_R2     ADFTETFESSTHGEAPAEWTTIDADGDGQGWLCLSS---------------GQLGWLTAHGG        47
HagA_ATCC_R1    ADFTETFESSTHGEAPAEWTTIDADGDGQGWLCLSS---------------GQLGWLTAHGG        47
HagA_ATCC_R2    ADFTETFESSTHGEAPAEWTTIDADGDGQGWLCLSS---------------GQLGWLTAHGG        47
HagA_ATCC_R3    ADFTETFESSTHGEAPAEWTTIDADGDGQGWLCLSS---------------GQLGWLTAHGG        47
Kgp_C-term      ADFTETFESSTHGEAPAEWTTIDADGDGQGWLCLSS---------------GQLGWLTAHGG        47
HagA_ATCC_R4    ADFTETFESSTHGEAPAEWTTIDADGDGQGWLCLSS---------------GQLGWLTAHGG        47
HagA_W83_R3     ADFTETFESSTHGEAPAEWTTIDADGDGQGWLCLSS---------------GQLGWLTAHGG        47
                   .*        _  _  _  _*. .*      *

Kgp_N-term     NLYSA---------------NFEYLVPANADPV--------------------VTTQNII-------------        73
RgpA_N-term     ANLFA-------------PFEYTVPENADPS----------------------CSPTNMI-------------        74
RgpA_C-term     TNWSASFSWNGMALNPDNYLISKDVTGATKVKYYYAVNDGFPGDHYAVMISKTGTNAGDF       107
HagA_W83_R1     TNWSASFSWNGMALNPDNYLISKDVTGATKVKYYYAVNDGFPGDHYAVMISKTGTNAGDF       107
HagA_W83_R2     TNWSASFSWNGMALNPDNYLISKDVTGATKVKYYYAVNDGFPGDHYAVMISKTGTNAGDF       107
HagA_ATCC_R1    TNWSASFSWNGMALNPDNYLISKDVTGATKVKYYYAVNDGFPGDHYAVMISKTGTNAGDF       107
HagA_ATCC_R2    TNWSASFSWNGMALNPDNYLISKDVTGATKVKYYYAVNDGFPGDHYAVMISKTGTNAGDF       107
HagA_ATCC_R3    TNWSASFSWNGMALNPDNYLISKDVTGATKVKYYYAVNDGFPGDHYAVMISKTGTNAGDF       107
Kgp_C-term      SNWSASFSWNGMALNPDNYLISKDVTGATKVKYYYAVNDGFPGDHYAVMISKTGTNAGDF       107
HagA_ATCC_R4    TNWSASFSWNGMALNPDNYLISKDVTGATKVKYYYAVNDGFPGDHYAVMISKTGTNAGDF       107
HagA_W83_R3     TNWSASFSWNGMALNPDNYLISKDVTGATKVKYYYAVNDGFPGDHYAVMISKTGTNAGDF       107
                   .* .                                                   .*

Kgp_N-term     ---V-TGQGEWIPGGVYDYCITNPEPASGKMWIAGDGGNQPARYEDDFTFEAGKKYTFTM       129
RgpA_N-term     ----M-DGTASVNIPAGTYDFAIAAPQ-ANAKIWIAGQG----PTKEDDYVFEAGKKYHFLM      126
RgpA_C-term     TVVFEETPNGINKggarfglsteadgakPQSVWIERTV----------DLPAGTKYVAFR       157
HagA_W83_R1     TVVFEETPNGINKggarfglsteangakPQSVWIERTV----------DLPAGTKYVAFR       157
HagA_W83_R2     TVVFEETPNGINKggarfglsteangakPQSVWIERTV----------DLPAGTKYVAFR       157
HagA_ATCC_R1    TVVFEETPNGINKggarfglsteadgakPQSVWIERTV----------DLPAGTKYVAFR       157
HagA_ATCC_R2    TVVFEETPNGINKggarfglsteadgakPQSVWIERTV----------DLPAGTKYVAFR       157
HagA_ATCC_R3    TVVFEETPNGINKggarfglsteadgakPQSVWIERTV----------DLPAGTKYVAFR       157
Kgp_C-term      TVVFEETPNGINKggarfglsteangakPQSVWIERTV----------DLPAGTKYVAFR       157
HagA_ATCC_R4    TVVFEETPNGINKggarfglsteadgakPQSVWIERTV----------DLPAGTKYVAFR       157
HagA_W83_R3     TVVFEETPNGINKggarfglsteangakPQSVWIERTV----------DLPAGTKYVAFR       157
                .  .  **                      **  **
```

FIG.40E(cont)

```
Kgp_N-term    RR------AGMGDGTDME-VEDDSPASYTYTVYRDGTKIKEGLTATTFEEDGVAAGNHEY   182
RgpA_N-term   KK------MGSGDGTELT-ISEGGGSDYTYTVYRDGTKIKEGLTATTFEEDGVATGNHEY   179
RgpA_C-term   HYNCSDLNYILLDDIQFTMGGSPTPTDYTYTVYRDGTKIKEGLTETTFEEDGVATGNHEY   217
HagA_W83_R1   HYNCSDLNYILLDDIQFTMGGSPTPTDYTYTVYRDGTKIKEGLTETTFEEDGVATGNHEY   217
HagA_W83_R2   HYNCSDLNYILLDDIQFTMGGSPTPTDYTYTVYRDGTKIKEGLTETTFEEDGVATGNHEY   217
HagA_ATCC_R1  HYNCSDLNYILLDDIQFTMGGSPTPTDYTYTVYRDGTKIKEGLTETTFEEDGVATGNHEY   217
HagA_ATCC_R2  HYNCSDLNYILLDDIQFTMGGSPTPTDYTYTVYRDGTKIKEGLTETTFEEDGVATGNHEY   217
HagA_ATCC_R3  HYNCSDLNYILLDDIQFTMGGSPTPTDYTYTVYRDGTKIKEGLTETTFEEDGVATGNHEY   217
Kgp_C-term    HYNCSDLNYILLDDIQFTMGGSPTPTDYTYTVYRDGTKIKEGLTETTFEEDGVATGNHEY   217
HagA_ATCC_R4  HYNCSDLNYILLDDIQFTMGGSPTPTDYTYTVYRDGTKIKEGLTETTFEEDGVATGNHEY   217
HagA_W83_R3   HYNCSDLNYILLDDIQFTMGGSPTPTDYTYTVYRDGTKIKEGLTETTFEEDGVATGNHEY   217
                     *      . ****************** ********.*****

Kgp_N-term    CVEVKYTAGVSPKVCKDVTVEGSNEFAPVQNLTGSS--VGQKVTLKWDAPNGTPNPNPNP   240
RgpA_N-term   CVEVKYTAGVSPKVCKDVTVEGSNEFAPVQNLTGSA--VGQKVTLKWDAPNGTPNPNPNP   237
RgpA_C-term   CVEVKYTAGVSPKKCVNVTVN-STQFNPVKNLKAQP--DGGDW LKWEAPSAKKTEGSRE   274
HagA_W83_R1   CVEVKYTAGVSPKECVNVTVD-PVQFNPVQNLTGSAVG--QKVTLKWDAPNGTPN-----P   270
HagA_W83_R2   CVEVKYTAGVSPKECVNVTVD-PVQFNPVQNLTGSAVG--QKVTLKWDAPNGTPN-----P   270
HagA_ATCC_R1  CVEVKYTAGVSPKECVNVTVD-PVQFNPVQNLTGSAVG--QKVTLKWDAPNGTPNPNPNP   274
HagA_ATCC_R2  CVEVKYTAGVSPKECVNVTVD-PVQFNPVQNLTGSAVG--QKVTLKWDAPNGTPNPNPNP   274
HagA_ATCC_R3  CVEVKYTAGVSPKECVNVTVD-PVQFNPVQNLTGSAVG--QKVTLKWDAPNGTPNPNPNP   274
Kgp_C-term    CVEVKYTAGVSPKKCVDVTVN-STQFNPVQNLTAEQAPNSMDAILKWNAPASK-------   269
HagA_ATCC_R4  CVEVKYTAGVSPKVCVNVTIN-PTQFNPVQNLTAEQAPNSMDAILKWNAPASK-------   269
HagA_W83_R3   CVEVKYTAGVSPKECVNVTIN-PTQFNPVQNLTAEQAPNSMDAILKWNAPASK-------   269
              ****** **** *** *.**..   .* **.**            ***.**

Kgp_N-term    NPN----------PG---TTLSESFENGIPASWKT-----IDADGDGHGWKPGN---APG   279
RgpA_N-term   NPN----------PNFGTTTLSESFENGIPASWKT-----IDADGDGHGWKPGN---APG   279
RgpA_C-term    krigdglfvtiepandvraneakWLAADNVWGDNTGYQFLLDADHNTFGSVIPATGPL   334
HagA_W83_R1   NPGTT-TLSESF---ENG-----------IPASWKT------IDADGDGNNWTTTPPPGGTS   311
HagA_W83_R2   NPGTT-TLSESF--ENG-----------IPASWKT------IDADGDGNNWTTTPPPGGTS   311
HagA_ATCC_R1  NPGTT-TLSESF--ENG-----------IPASWKT-----IDADGDGNNWTTTPPPGGTS   315
HagA_ATCC_R2  NPGTT-TLSESF--ENG-----------IPASWKT-----IDADGDGNNWTTTPPPGGTS   315
HagA_ATCC_R3  NPGTT-TLSESF---ENG-----------IPASWKT------IDADGDGNNWTTTPPPGGTS   315
Kgp_C-term    --RAE-VLNEDF--ENG-----------IPASWKT-----IDADGDGNNWTTTPPPGGSS   308
HagA_ATCC_R4  --RAE-VLNEDF--ENG-----------IPSSWKT------IDADGDGNNWTTTPPPGGSS   308
HagA_W83_R3   ---RAE-VLNEDF--ENG-----------IPASWKT------IDADGDGNNWTTTPPPGGSS   308
                               *              **..

Kgp_N-term    IAGYNSNGCVYSES-FGLGGIGVLTPDNYLITPALDLPNGGKLTFWVCAQDANYASEHYA   338
RgpA_N-term   IAGYNSNGCVYSES-FGLGGIGVLTPDNYLITPALDLPNGGRLTFWVCAQDANYASEHYA   338
RgpA_C-term   FTGTASSDLYS----ANFESLIPANADPWXTTQNIIVTGQGEWI----------------   375
HagA_W83_R1   FAGHNSAICVSSASYINFE--GPQNPDNYLVTPELSLPNGGTLTFWVCAQDANYASEHYA   369
HagA_W83_R2   FAGHNSAICVSSASYINFE--GPQNPDNYLVTPELSLPNGGTLTFWVCAQDANYASEHYA   369
HagA_ATCC_R1  FAGHNSAICVSSASYINFE--GPQNPDNYLVTPELSLPNGGTLTFWVCAQDANYASEHYA   373
HagA_ATCC_R2  FAGHNSAICVSSASYINFE--GPQNPDNYLVTPELSLPGGGTLTFWVCAQDANYASEHYA   373
HagA_ATCC_R3  FAGHNSAICVSSASYINFE--GPQNPDNYLVTPELSLPGGGTLTFWVCAQDANYASEHYA   373
Kgp_C-term    FAGHNSAICVSSASYINFE--GPQNPDNYLVTPELSLPGGGTLTFWVCAQDANYASEHYA   366
HagA_ATCC_R4  FAGHNSAICVSSASYINFE--GPQNPDNYLVTPELSLPGGGTLTFWVCAQDANYASEHYA   366
HagA_W83_R3   FAGHNSAICVSSASYINFE--GPQNPDNYLVTPELSLPGGGTLTFWVCAQDANYASEHYA   366
              ..*   *                  *      *        *
```

FIG.40E(cont)

```
Kgp_N-term     VYASSTGNDASNFTNALLEETITAKGV-RSPKAIRG-RIQGTWRQ------------KTVDL   386
RgpA_N-term    VYASSTGNDASNFTNALLEETITAKGV-RSPEAMRG-RIQGTWRQ------------KTVDL   386
RgpA_C-term    -----------------PGGVYD-------YCITNPEPASG-----KMWIAGDGGNQPARYDDFTF   412
HagA_W83_R1    VYASSTGNDASNFANALLEEVLTAKTWTAPEAIRGTRVQGTWYQ-----------KTVQL   419
HagA_W83_R2    VYASSTGNDASNFANALLEEVLTAKTWTAPEAIRGTRVQGTWYQ-----------KTVQL   419
HagA_ATCC_R1   VYASSTGNDASNFANALLEEVLTAKTWTAPEAIRGTRVQGTWYQ-----------KTVQL   423
HagA_ATCC_R2   VYASSTGNDASNFANALLEEVLTAKTWTAPEAIRGTRVQGTWYQ-----------KTVQL   423
HagA_ATCC_R3   VYASSTGNDASNFANALLEEVLTAKTWTAPEAIRGTRVQGTWYQ-----------KTVQL   423
Kgp_C-term     VYASSTGNDASNFANALLEEVLTAKTWTAPEAIRGTRAQGTWYQ-----------KTVQL   416
HagA_ATCC_R4   VYASSTGNDASNFANALLEEVLTAKTWTAPEAIRGTRVQGTWYQ-----------KTVQL   416
HagA_W83_R3    VYASSTGNDASNFANALLEEVLTAKTWTAPEAIRGTRVQGTWYQ-----------KTVQL   416
                                  *.       *         *

YTYTVYRDGTKIKEGLTETTFEEDGVATGNHEY
Kgp_N-term     PAGTKYVA-FRHFQSTDMFYIDLDEVEIKANGKR-----------------------------   419
RgpA_N-term    PAGTKYVA-FRHFQSTDMFYIDLDEVEIKANGKR-----------------------------   419
RgpA_C-term    EAGKKYTFTMRRAGM-----GDGTDMEVEDDSPASYTYTVYRDGTKIKEGLTETTYRDAG   467
HagA_W83_R1    PAGTKYVA-FRHFGCTDFFWINLDDVEIKANGKR-----------------------------   452
HagA_W83_R2    PAGTKYVA-FRHFGCTDFFWINLDDVEIKANGKR-----------------------------   452
HagA_ATCC_R1   PAGTKYVA-FRHFGCTDFFWINLDDVEIKANGKR-----------------------------   456
HagA_ATCC_R2   PAGTKYVA-FRHFGCTDFFWINLDDVEIKANGKR-----------------------------   456
HagA_ATCC_R3   PAGTKYVA-FRHFGCTDFFWINLDDVEIKANGKR-----------------------------   456
Kgp_C-term     PAGTKYVA-FRHFGCTDFFWINLDDWEITSGNAPSYTYTIYRNNTQIASGVTETTYRDPD   475
HagA_ATCC_R4   PAGTKYVA-FRHFGCTDFFWINLDDWEITSGNAPSYTYTIYRNNTQIASGVTETTYRDPD   475
HagA_W83_R3    PAGTKYVA-FRHFGCTDFFWINLDDWEITSGNAPSYTYTIYRNNTQIASGVTETTYRDPD   475
               ** **    .*.

Kgp_N-term     --------------------------------  419  (SEQ ID NO:156)
RgpA_N-term    --------------------------------  419  (SEQ ID NO:157)
RgpA_C-term    MSAQSHEYCVEVKYTAGVSPKVCVDYIPD-    496  (SEQ ID NO:148)
HagA_W83_R1    --------------------------------  452  (SEQ ID NO:142)
HagA_W83_R2    --------------------------------  452  (SEQ ID NO:143)
HagA_ATCC_R1   --------------------------------  456  (SEQ ID NO:158)
HagA_ATCC_R2   --------------------------------  456  (SEQ ID NO:159)
HagA_ATCC_R3   --------------------------------  456  (SEQ ID NO:160)
Kgp_C-term     LATGFYTYGVKVVYPNGESAIETATLNITS   505  (SEQ ID NO:146)
HagA_ATCC_R4   LATGFYTYGVKVVYPNGESAIETATLNIT-   504  (SEQ ID NO:161)
HagA_W83_R3    LATGFYTYGVKVVYPNGESAIETATLNIT-   504  (SEQ ID NO:144)
```

FIG. 40F

Putative sequence motif in HagA (from W83 and ATCC 33277 strains) and RgpA and Kgp (from W83) encompassing an AP.

```
Kgp_N-term      PASYTYTVYRDGTKIKEGLTATTFEEDGVAAGNHEYCVEVKYTAGVSPKVC       (SEQ ID NO:77)
RgpA_N-term     GSDYTYTVYRDGTKIKEGLTATTFEEDGVATGNHEYCVEVKYTAGVSPKVC       (SEQ ID NO:78)
RgpA_C-term     PTDYTYTVYRDGTKIKEGLTETTFEEDGVATGNHEYCVEVKYTAGVSPKKC       (SEQ ID NO:79)
HagA_W83_R1     PTDYTYTVYRDGTKIKEGLTETTFEEDGVATGNHEYCVEVKYTAGVSPKEC       (SEQ ID NO:80)
HagA_W83_R2     PTDYTYTVYRDGTKIKEGLTETTFEEDGVATGNHEYCVEVKYTAGVSPKEC       (SEQ ID NO:80)
HagA_ATCC_R1    PTDYTYTVYRDGTKIKEGLTETTFEEDGVATGNHEYCVEVKYTAGVSPKEC       (SEQ ID NO:80)
HagA_ATCC_R2    PTDYTYTVYRDGTKIKEGLTETTFEEDGVATGNHEYCVEVKYTAGVSPKEC       (SEQ ID NO:80)
HagA_ATCC_R3    PTDYTYTVYRDGTKIKEGLTETTFEEDGVATGNHEYCVEVKYTAGVSPKEC       (SEQ ID NO:80)
Kgp_C-term      PTDYTYTVYRDGTKIKEGLTETTFEEDGVATGNHEYCVEVKYTAGVSPKKC       (SEQ ID NO:79)
HagA_ATCC_R4    PTDYTYTVYRDGTKIKEGLTETTFEEDGVATGNHEYCVEVKYTAGVSPKVC       (SEQ ID NO:81)
HagA_W83_R3     PTDYTYTVYRDGTKIKEGLTETTFEEDGVATGNHEYCVEVKYTAGVSPKEC       (SEQ ID NO:80)
                *******************************          *
```

```
RgpA_C-term2    PASYTYTVYRDGTKIKEGLTETTYRDAGMSAQS  HEYCVEVKYTAGVSPKVC       (SEQ ID NO:82)
Kgp_C-term2     APS YTYTIYRNNTQIASGVTETTYRDPD LATGFYTYGVKVVYPNGESALET      (SEQ ID NO:83)
```

FIG. 41

Start of GST fusion partner→
MSPILGYWKIKGLVQPTRLLLEYLEEKYEEHLYERDEGDKWRNKKFELGLEFPNLPYYIDGDVKLTQSMA
IIRYIADKHNMLGGCPKERAEISMLEGAVLDIRYGVSRIAYSKDFETLKVDFLSKLPEMLKMFEDRLCHK
TYLNGDHVTHPDFMLYDALDVVLYMDPMCLDAFPKLVCFKKRIEAIPQIDKYLKSSKYIAWPLQGWQATF
GGGDHPPKSDRARYLANASRCGSAENLYFQGADPSCSPTNMIMDGTASVNIPAGTYDFAIAAPQANAKIW
IAGQGPTKEDDYVFEAGKKYHFLMKKMGSGDGTELTISEGGGSDYTYTVYRDGTKIKEGLTATTFEEDGV
AAGNHEYCVEVKYTAGVSPKVCKDVTVEGSNEFAPVQNLTGSAVGQKVTLKWDAPNGHHHHHH (SEQ ID NO: 162)

ATG
TCCCCTATAC TAGGTTATTG GAAAATTAAG GGCCTTGTGC AACCCACTCG ACTTCTTTTG GAATATCTTG
AAGAAAAATA TGAAGAGCAT TTGTATGAGC GCGATGAAGG TGATAAATGG CGAAACAAAA AGTTTGAATT
GGGTTTGGAG TTTCCCAATC TTCCTTATTA TATTGATGGT GATGTTAAAT TAACACAGTC TATGGCCATC
ATACGTTATA TAGCTGACAA GCACAACATG TTGGGTGGTT GTCCAAAAGA GCGTGCAGAG ATTTCAATGC
TTGAAGGAGC GGTTTTGGAT ATTAGATACG GTGTTTCGAG AATTGCATAT AGTAAAGACT TTGAAACTCT
CAAAGTTGAT TTTCTTAGCA AGCTACCTGA AATGCTGAAA ATGTTCGAAG ATCGTTTATG TCATAAAACA
TATTTAAATG GTGATCATGT AACCCATCCT GACTTCATGT TGTATGACGC TCTTGATGTT GTTTTATACA
TGGACCCAAT GTGCCTGGAT GCGTTCCCAA AATTAGTTTG TTTTAAAAAA CGTATTGAAG CTATCCCACA
AATTGATAAG TACTTGAAAT CCAGCAAGTA TATAGCATGG CCTTTGCAGG GCTGGCAAGC CACGTTTGGT
GGTGGCGACC ATCCTCCAAA ATCGGATCTG GTTCCGCGTG GATCCCCGGA ATTCCCGGGT CGACTCGAGC
GGCCGCATCG TGACTGA
     (SEQ ID NO: 163)

FIG. 41 (cont)

```
CGAGCTCGGT  ACCTCGCGAA  TGCATCTAGA  TGCGGATCCG  CAGAGAATCT  GTACTTTCAA
GGAGCAGATC  CGAGCTGTAG  TCCAACGAAT  ATGATTATGG  ATGGCACCGC  ATCTGTCAAC
ATTCCAGCCG  GAACCTACGA  TTTTGCTATT  GCCGCACCAC  AAGCAAATGC  AAAAATTTGG
ATCGCAGGAC  AAGGACCAAC  CAAAGAAGAT  GATTATGTGT  TTGAAGCGGG  GAAGAAATAT
CACTTTCTGA  TGAAAAAAAT  GGGCAGTGGG  GATGGAACCG  AATTGACGAT  TAGCGAAGGG
GGAGGCTCAG  ATTATACATA  CACCGTATAC  CGGGATGGTA  CTAAAATTAA  AGAAGGTTTA
ACAGCAACAA  CGTTTGAAGA  GGATGGCGTA  GCAGCGGGTA  ATCACGAATA  TTGTGTAGAA
GTAAAGTATA  CTGCCGGAGT  GTCACCTAAA  GTGTGTAAAG  ATGTAACAGT  TGAAGGTAGT
AACGAATTTG  CGCCGGTACA  AAATTTAACG  GGTAGTGCAG  TGGGCCAGAA  AGTAACTTTG
AAATGGGATG  CGCCAAATGG  TCACCACCAT  CATCATCATTAATAG
(SEQ ID NO: 164)
```

FIG. 42A rGP-2HagA 3x recombinant epitope protein:     SEQ ID NO: 280

YTPVEEKQNGRMIVIVAKKYEGDIKDFVDWKNQRGLRTEVKVAEDIASPVTANAIQQFVKQEYEKEGNDLTYVLLIGDBKDIPAKITPGIKSDQVYGQIVGN
DHYNEVFIGRFSCESKEDLKTQIDRTIHYERNITFEDKWLGQALCIASAE
GGPSADNGESDIQHENVIANLLTQYGYTKIIKCYDPGVTPKNIIDAFNGGISLANYTGHGSETAWGTSHFGTHVKQLTNSNQLPFIFDVACVNGDELFSMP
CFAEALMRAQKDGKPTGTVAIIASTINQSWASPMRGQDEMNEILCEKHPN
NIKRTFGGVTMNGMFAMVEKYKKDGEKMLDTWTVFGDPSLLVRTLVPFKMQVTAPAQINLTDASVNVSCDYNGAIATISANGKMFGSAVVENGTATINLTGL
TNESTLFLTVVGYNKETVIRTINTNGEPNPYQPVSNLTATFQGQKVTLKW
DAPSTKtnattntaisvdgirelvllsvsdapellrSGQAEIVLEAHDVWNDGSGYQLLDADHDQYGQVIPSDTHTLWPNCSVPANLFAPFEYTVPENA**
*DPSCSPTNMIMDGTASVNIPAGTYDFAIAAPQANAKIWIAGQGPTKEDDYVF
EAGKKYHFLMKKMGSGDGTELTISEGGGS□YTYTVYRDGTKIKEGLT□TTFEED□GVATGNHEYCVEVKYTAGVSPFM□C□DVTV□EGSNEFAPVQNL□TGSAVGQ
KVTLKWDAPNGT□PNPNPNPNPNPGTTTLSESFENGIPASWKTIDADGD
GHGWKPGNAPGIAGYNSNGCVYSESFGLGGIGVLIFPDNYLITPALDLPNGGKLTEWCAQDANYASEHYAVYASSTGNDASNFTNALLEETITAKgvrspea
mrgriggtwrqktvdlpagtkyvafrhfqstdmfyidldeveikangkrAD
FTETFESSTHGEAPAEWTTTDADGDGGWLCLSSGQLDWLTAHGGTNVVSSFSWNGMALNPDNYLIISKDVT□GATKVKYYYAVNDGFPGDHYAVMISKTGTNA
GDFTVVFEETPNGINKggarlglsteadgakPQSVNIERTVDLPAGTKYVA
FRHYNCSDLNYILLDDIQFTMGGSPTPTD□YTYTVYRDGTKIKEGLTETTFEED□GVATGNHEYCVEVKYTAGVSPKK□C□NVTI□NSTQFNPVKNLKAQPDGGDV
VLKWEAPSAKKtegsrevkrigdglfvtiepandvrANEAKVVLAADNVWGD
NTGYQFLLDADHNTFGSVIPAFGPLETGTASSDLYSANFESLIPANADPVVTTQNIIVTGQGEVVIPGGVYDYCITNPEPASGKMWIAGDGGNQPARYDDFT
FEAGKKYFTTMRRAGMGDGTDMEVEDDSPAS□YTYTVYRDGTKIKEGLTET□YRDA□MSAQS□HEYCVEVKYTAGVSPKV□C□DY□HHHHHHH

FIG. 42B

LWPNCSVPANLFAPFEYTVPENADPSCSPTNMIMDGTASVNIPAGTYDFAIAAPQANAKIWIAGQGPTKEDDYVF
                                 DPSCSPTNMIMDGTASVNIPAGTYDFAIAAPQANAKIWIAGQGPTKEDDYVF

EAGKKYHFLMKKMGSGDGTELTISEGGGS□YTYTVYRDGTKIKEGLT□ATTEED□GVATGNHEYCVEVKYTAGVSPKV
EAGKKYHFLMKKMGSGDGTELTISEGGGSDYTYTVYRDGTKIKEGLTATTFEED□GVAAGNHEYCVEVKYTAGVSPKV

□C□DVTV□EGSNEFAPVQNL□TGSAVGQKVTLKWDAPNGTFPNPNPNPNPNPGTTTLSESFENGIPASWKTIDADGD
CKDVTVEGSNEFAPVQNL□TGSAVGQKVTLKWDAPNGHHHHHHH

SEQ ID NO: 281
SEQ ID NO: 282

YTYTVYRDGTKIKEGLTATTFEEDGVATGNHEYCVEVKYTAGVSPKVCKDVTV    SEQ ID NO: 283

ProtScale outsource for user_sequence

FIG. 43

Kgp-8HSLA_domains N-term sequence

>PG_1844 (W83 Kgp) DM024 / Kgp-8HSLA    SEQ ID NO: 284
mrklffliaasllgvglyaQSAKIKLDAPTTRTTCTNNSFKQFDASFSFNEVELTKVETKGGTFASVSIPGAFPTGEVGSPEVPAVRKLI
AVPVGATPVVRVKSFTEQVYSLNQYGSEKLMPHQPSMSKSDDPEKVPFVYNAAAYARKGFVGGQELTQVEMLGTMRGVR
IAALTINPVQYDVVANQLKVRNNIEIEVSFQGADEVATQRLYDASFSPYFETAYKQLFNFDVYTDHGDLYNTPVRMLVVA
GAKFKEALKPWLTWKAQKGFYLDVHYTDEAEVGTTNASIKAFIHKKYNDGLAASAAPVFLALVGDTDVISGEKGKKTK
KVTDLYYSAVDGDYFPEMYTFRMSASSPEELTNIIDKVLMYEKATMPDKSYLEKVLLIAGADYSWNSQVGQPTIKYGMQ
YYYNQEHGYTDVYNYLKAPYTGCYSHLNTGVSFANYTAHGSETAWADPLLTTSQLKALTNKDKYFLAIGNCCITAQFDY
VQPCFGEVITRVKEKGAYAYIGSSPNSYWGEDYYWSVGANAVFGVQPTFEGTSMGSYDATFLEDSYNTVNSIMWAGNLA
ATHAGNIGNITHIGAHYYWEAYHVLGDGSVMPYRAMPKTNTYTLPASLPQNQASYSIQASAGSYVAISKDGVLYGTGVA
NASGVATVSMTKQITENGNYDVVITRSNYLPVIKQIQVGEPSPYQPVSNLTATTQGQKVTLKWEAPSAKKAEGSREVKRIG
DGLFVTIEPANDVRANEAKVVLAADNVWGDNTGYQFLLDADHNTFGSVIPATGPLFTGTASSNLYSANFEYLIPANADPV
VTTQNIIVTGQQEVVIPGGVYDYCITNPEPASGKMWIAGDGGNQPARYDDFTFEAGKKYTFTMRRAGMGDGTDMEVED
DSPAS<u>YTYTVYRDGTKIKEGLT</u>ATTFEEDGVAAGNHEYCVEVKYTAGVSPKVCKDVTVEGSNEFAPVQNLTGSSVGQKV
TLKWDAPNGTPNPNPNPNPNPGTTLSESFENGIPASWKTIDADGDGHGWKPGNAPGIAGYNSNGCVYSESFGLGGIGVLT
PDNYLITPALDLPNGGKLTFWVCAQDANYASEHYAVYASSTGNDASNFTNALLEETITAKGVRSPKAIRGRIQGTW**RQKT
VDLPAGTKYVAFRHFQSTDMFYIDLDEVEIKANGKRADFTETFESSTHGEAPAEWTTIDADGDGQGWLCLSSGQLDW
LTAHGGSNVVSSFSWNGMALNPDNYLISKDVTGATKVKYYYAVNDGFPGDHYAVMISKTGTNAGDFTVVFEETPN
GINKGGARFGLSTEANGAKPQSVWIERTVDLPAGTKYVAFRHYNCSDLNYILLDDIQFTM** GGSPTPTDY |YTVYRDGTK
IKEGLTETTFEEDGVATGNHEYCVEVKYTAGVSPKKCVNVTVNSTQFNPVQNLTAEQAPNSMDAILKWNAPASKR AEVL
NEDFE NGIPASWKTIDADGDGNNWTTTPPPGGSSFAGHNSAICVSSASYINFEGPQNDNYLVTPELSLPGGGTLTFWVCAQ
DANYASEHYAVYASSTGNDASNFANALLEEVLTAKTVVTAPEAIRGTRAQGTWYQKTVQLPAGTKYVAFRHFGCTDFFWI
NLDDVVIT SGNAPSYTYTI YRNNTQIASGVTETTYRDPDLATGFYTYGVKVVYPNGESAIETATLNIT*HHHHHHHH*sladvta
qkpytltvvgktitvtcqgeamiydmngrrlaagmtvvytaqgghyavmvvvdgksyveklavk

| | | | |
|---|---|---|---|
| K0 | R#DVYTDHGDLYNTPV | (reactive both with anti-His tag & KB001) | SEQ ID NO: 285 |
| K0a: | R#DVYTDHGDLYNTPV | | SEQ ID NO: 285 |
| K1 | R#ANEAKVVLAAD | (reactive with KB001) | SEQ ID NO: 286 |
| K2 | R#ANEAKVVLAAD (circa 35 kDa) | | SEQ ID NO: 286 |
| | MAVVINXFF (not derived from Kgp) | | SEQ ID NO: 287 |
| K3 | R#ANEAKVVLAAD (circa 30 kDa) | (reactive with KB001) | SEQ ID NO: 286 |
| K4 | R#AEVLNEDFE (circa 16 kDa) | | SEQ ID NO: 288 |
| K5 | M#GGSPTPTDY (circa 14 kDa) | (weakly reactive with KB001) | SEQ ID NO: 289 |
| | R#AQGTWYQKT 12kDa with C-terminal His-Tag | | SEQ ID NO: 290 |
| K6 | T#SGNAPSYTYTI (>10 kDa) / 7.6 kDa with C-terminal His-Tag | | SEQ ID NO: 291 |

FIG. 44

HRgpA-6H_domains_N-terminal sequence    SEQ ID NO: 292 mknlnkfvsialcssllggmafa*QQTELGRNPNVRLLESTQQSVTKVQFRMDNLKFTEVQTPKGIGQVPTYTEGVNLSEKGMPTLPILSRSLAVSDT REMKVEVVSSKFIEKKNVLIAPSKGMIMRNEDPKKIPYVYGKTYSQNKFFPGEIATLDDPFILRDVRGQVVNFAPLQYNPVTKTLRIYTEIT VAVSETSEQGKNILNKKGTFAGFEDTYKRMFMNYEPGRYT*PVEEKQNGRMIVIVAKKYEGDIKDFVDWKNQRGLRTEVKVAEDIAS PVTANAIQQFVKQEYEKEGNDLTYVLLIGDHKDIPAKITPGIKSDQVYGQIVGNDHYNEVFIGRFSCESKEDLKTQIDRTIHYERNI TTEDKWLGQALCIASAEGGPSADNGESDIQHENVIANLLTQYGYTKIIKCYDPGVTPKNIIDAFNGGISLANYTGHGSETAWGTSH FGTTHVKQLTNSNQLPFIFDVACVNGDFLFSMPCFAEALMRAQKDGKPTGTVAIIASTINQSWASPMRGQDEMNEILCEKHPNNIK RTFGGVTMNGMFAMVEKYKKDGEKMLDTWTVFGDPSLLVRTLVPTKMQVTAPAQINLTDASVNVSCDYNGAIATISANGKMFG SAVVENGTATINLTGLTNESTLTLTVVGYNKETVIKTINTNGEPNPYQPVSNLTATTQGQKVTLKWDAPSTK*tnattntarsvdgirelvllsvsd apellr*SGQAEIVLEAHDVWNDGSGYQILLDADHDQYGQVIPSDTHTLWPNCSVPANLFAPFEYTVPENADPSCSPTNMIMDGTASV NIPAGTYDFAIAAPQANAKIWIAGQGPTKEDDYVFEAGKKYHFLMKKMGSGDGTELTISEGGGSD*YTYTVYRDGTKIKEGLT*ATT FEEDGVATGNHEYCVEVKYTAGVSPKVCKDVTVEGSNEFAPVQNLTGSAVGQKVTLKWDAPNGTPNPNPNPNPNPNPGTTTLSE SFENGIPASWKTIDADGDGHGWKPGNAPGIAGYNSNGCVYSESFGLGGIGVLTPDNYLITPALDLPNGGKLTFWVCAQDANYAS EHYAVYASSTGNDASNFTNALLEETITAK*gvrspeamrgr*qgiwrqklvd*pagtkyvafrhfqstdmfyidldeveikangkrADFTETFESSTHGEAPAE WTTIDADGDGQGWLCLSSGQLDWLTAHGGTNVVSSFSWNGMALNPDNYLISKDVTGATKVKYYYAVNDGFPGDHYAVM ISKTGTNAGDFTVVFEETPNGINKggarfglsteadgak*PQSVWIERTVDLPAGTKYVAFRHYNCSDLNYILLDDIQFTMGGSPTPTDY TYTVYRDGTKIKEGLTETTFEEDGVATGNHEYCVEVKYTAGVSPKKCVNVTVNSTQFNPVKNLKAQPDGGDVVLKWEAPSAKk tegsrevkrigdglfvtiepandv*ANEAKVVLAAD*NVWGDNTGYQFLLDADHNTFGSVIPATGPLFTGTASSDLYSANFESLIPANADPVVTT QNIIVTGQGEVVIPGGVYDYCITNPEPASGKMWIAGDGGNQPARYDDFTFEAGKKYTFTMRRAGMGDGTDMEVEDDSPAS*YTY TVYRDGTKIKEGLT*ETTYRDAGMSAQSHEYCVEVKYTAGVSPK VCVDYIPD*HHHHHH*gvadvtaqkpytltvvgktitvtcqgeamiydmng rrlaagrntvvytaqggyyavmvvvdgksyveklaik

| R0 | R#YTPVEEKQNGRMIV | Reactive with KB001 and weakly with anti-His-tag | SEQ ID NO: 293 |
| R1 | R#SGQAEIVLEAH | Reactive with KB001 | SEQ ID NO: 294 |
| R2 | R#SGQAEIVLEAH (circa 30 kDa) | Reactive with KB001 | SEQ ID NO: 294 |
| R3 | R#ANEAKVVLAAD | Reactive with KB001 and weakly with anti-His-tag | SEQ ID NO: 295 |
| R4 | R#DFTETFESS (16 kDa) | | SEQ ID NO: 296 |
| | K#PQSVWIERTVD | Reactive with KB001 | SEQ ID NO: 297 |
| R5 | K#YVAFRHYNCSD (circa 14kDa) | Weakly reactive with KB001 | SEQ ID NO: 298 |
| R5 | A/X - Q/D - S/P - T/P - T/Y/E - D/Y - Q/D - K/D - Y/V/G - T/I - Q/V/G | | SEQ ID NO: 299 |
| R6 | R#iqgtwrqktvd (circa 8 kDa) | | SEQ ID NO: 300 |

Red font: catalytic (CD)/Ig-like domains. Sequence in low case is presumably absent in the mature RgpA (the non-covalent complex of CDIg with hemagglutinin/adhesion (HA)domains) due to proteolytic processing by Kgp

Highlighted K indicates putative cleavage site by Kgo during proRgpA maturation

Blue font: HA1 domain. Again, low case indicates segment which may be absent in the mature RgpA.
Purple font/underlined: HA2 / HbR domain (low case, see above)
*Green font (italics)*: HA3 (low case, see above)
Black font: HA4
Highlighted blue and green the conserved sequence repeated in HA1, HA3 and HA4

FIG. 45

>U551FEL190-VH2

QVQLQESGPGLVKPSETLSLTCTVSGFSLSIYSVHWIRQPPGKGLEWIGMIWGGGSSDYNSALKSRLTISKDTSK

NQVSLKLSSVTAADTAVYYCARNGNFYAMDYWGQGTLVTVSS     (SEQ ID NO: 165)

>U551FEL190-VH4

QVQLQESGPGLVKPSETLSLTCTVSGFSLSIYSVHWIRQPPGKGLEWLGMIWGGGSSDYNSALKSRLTISKDTSK

NQVSLKLSSVTAADTAMYYCARNGNFYAMDYWGQGTLVTVSS     (SEQ ID NO: 166)

>U551FEL190-VL1

EIVLTQSPGTLSLSPGERATLSCTASSSVSSSFLHWYQQKPGQAPRLLIYSTSNLASGIPDRFSGSGSGTDFTLT
ISRLEPEDFAVYYCHQYHHSPYIYTFGGGTKLEIK          (SEQ ID NO: 167)

>U551FEL190-VL2

EIVLTQSPGTLSLSPGERATLSCTASSSVSSSFLHWYQQKPGQAPQLWIYSTSNLASGIPDRFSGSGSGTDYTLT
ISRLEPEDFAVYYCHQYHHSPYIYTFGGGTKLEIK          (SEQ ID NO: 168)

>U551FEL190-VL3

EIVLTQSPGTLSLSPGERATLSCTASSSVSSSFLHWYQQKPGQAPQLWIYSTSNLASGIPDRFSGSGSGTDYTLT
ISRLEPEDFATYYCHQYHHSPYIYTFGGGTKLEIK          (SEQ ID NO: 169)

>U551FEL190-VL4

EIVLTQSPGTLSLSPGERATLSCTASSSVSSSFLHWYQQKPGQAPQLWIYSTSNLASGIPARFSGSGSGTDYTLT
ISRLEPEDFATYYCHQYHHSPYIYTFGGGTKLEIK      (SEQ ID NO: 170)

>hIgG1CH-pcDNA3.4
ASTKGPSVFPLAPSSKSTSGGTAALGCLVKDYFPEPVTVSWNSGALTSGVHTFPAVLQSSGLYSLSSVVTVPSSSLGT
QTYICNVNHKPSNTKVDKKVEPKSCDXTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYSKLTVDKSRWQQGNVFSCSVMH
EALHNHYTQKSLSLSPGK**     (SEQ ID NO: 171)

>hIgG1CH-pcDNA3.4 (K222A mutation--shown in bold and grey)

ASTKGPSVFPLAPSSKSTSGGTAALGCLVKDYFPEPVTVSWNSGALTSGVHTFPAVLQSSGLYSLSSVVTVPSSSLGT
QTYICNVNHKPSNTKVDKKVEPKSCDXTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYSKLTVDKSRWQQGNVFSCSVMH
EALHNHYTQKSLSLSPGK**     (SEQ ID NO: 172)

>hIgkCL-pcDNA3.4
RTVAAPSVFIFPPSDEQLKSGTASVVCLLNNFYPREAKVQWKVDNALQSGNSQESVTEQDSKDSTYSLSSTLTLSKAD
YEKHKVYACEVTHQGLSSPVTKSFNRGEC**     (SEQ ID NO: 173)

FIG. 46

```
>U551FEL190--VH2
CAGGTGCAGCTGCAAGAGTCCGGCCCTGGACTCGTGAAGCCCTCCGAGACACTGTCTCTGACATGTACCGTGTCT
GGCTTCTCCCTGTCCATCTACTCCGTGCACTGGATCAGACAGCCTCCTGGCAAGGGCCTGGAATGGATCGGCATG
ATCTGGGGAGGCGGCTCTTCCGACTACAACTCCGCCCTGAAATCTCGGCTGACCATCTCCAAGGACACCTCTAAG
AACCAGGTCAGCCTGAAGCTGAGCTCTGTGACCGCTGCTGATACCGCCGTGTACTACTGCGCCAGAAATGGCAAC
TTCTACGCCATGGACTATTGGGGCCAGGGCACCCTGGTGACCGTGTCCAGC     (SEQ ID NO: 174)

>U551FEL190-VH4
CAGGTGCAGCTGCAAGAGTCCGGACCCGGCCTCGTGAAGCCTTCCGAGACACTGTCTCTGACCTGTACCGTGTCT
GGCTTCTCCCTGTCCATCTACTCCGTGCACTGGATCCGGCAGCCTCCTGGCAAGGGCCTGGAATGGCTGGGCATG
ATCTGGGGGCGGCGGAAGCTCCGACTACAACTCCGCCCTGAAATCTAGACTGACCATCTCCAAGGACACCTCTAAG
AACCAGGTCAGCCTGAAGCTGAGCTCTGTGACCGCCGCTGATACCGCTATGTACTACTGCGCCAGAAATGGCAAC
TTCTACGCCATGGACTATTGGGGCCAGGGCACCCTGGTGACAGTGTCCTCT     (SEQ ID NO: 175)

>U551FEL190-VL1
GAGATCGTGCTGACCCAATCTCCAGGCACCCTGTCTCTCAGCCCTGGCGAGAGAGCCACCCTGTCCTGCACCGCT
TCTAGCTCCGTGTCCTCCAGCTTCCTGCACTGGTACCAGCAGAAACCCGGCCAGGCTCCTAGACTGCTGATCTAT
TCCACCTCCAACCTGGCCTCTGGCATCCCTGACCGGTTCTCCGGCTCTGGCTCCGGAACAGATTTTACACTGACC
ATCTCCCGGCTGGAACCTGAGGACTTCGCCGTGTACTACTGTCACCAGTACCACCATTCTCCTTACATCTACACC
TTCGGCGGCGGAACCAAGCTGGAAATCAAG     (SEQ ID NO: 176)

>U551FEL190-VL2
GAGATCGTGCTGACACAATCTCCCGGCACCCTCAGCCTGTCTCCAGGCGAGAGAGCCACACTGTCCTGCACCGCT
TCTAGCTCCGTGTCCTCCAGCTTTCTGCACTGGTACCAGCAGAAACCTGGCCAGGCTCCTCAGCTGTGGATCTAC
TCCACCTCCAACCTGGCCTCTGGCATCCCTGATCGGTTCTCCGGCTCCGGCTCTGGCACCGACTACACCCTGACC
ATCTCCAGACTGGAACCTGAGGACTTCGCCGTGTACTACTGTCACCAGTACCACCATTCTCCTTACATCTATACC
TTCGGCGGAGGAACCAAGCTGGAAATCAAG     (SEQ ID NO: 177)

>U551FEL190-VL3
GAGATCGTGCTGACCCAGTCTCCAGGCACACTCAGCCTGTCTCCTGGCGAGCGGGCTACCCTGTCCTGCACCGCC
AGCAGCTCCGTGTCCTCTTCTTTTCTGCACTGGTACCAGCAGAAACCTGGACAAGCTCCTCAGCTGTGGATCTAC
TCCACCTCCAACCTGGCCTCTGGCATCCCCGATAGATTCTCCGGCTCTGGCTCCGGCACCGACTACACACTGACC
ATCTCCAGACTGGAACCTGAGGACTTCGCCACCTACTACTGTCATCAGTACCACCACTCCCCTTACATCTATACC
TTCGGCGGAGGCACCAAGCTGGAAATCAAG     (SEQ ID NO: 178)

>U551FEL190-VL4
GAGATCGTGCTGACCCAATCTCCTGGCACCCTGTCTCTGAGCCCAGGCGAGAGAGCCACACTCTCCTGCACCGCT
TCTTCCTCCGTGTCCTCTAGCTTTCTGCACTGGTACCAGCAGAAACCCGGCCAGGCTCCTCAGCTGTGGATCTAC
TCCACCTCCAACCTGGCCTCTGGCATCCCTGCCAGATTCTCCGGATCCGGCTCTGGCACCGATTATACACTGACC
ATCTCCCGGCTGGAACCTGAGGACTTCGCCACCTACTACTGTCACCAGTACCACCATAGCCCTTACATCTACACC
TTCGGCGGCGGAACCAAGCTGGAAATCAAG     (SEQ ID NO: 179)

>hIgG1CH-pcDNA3.4
GCCAGCACCAAGGGCCCTTCCGTGTTTCCACTGGCCCCCTCCTCTAAATCCACATCTGGCGGCACCGCCGCCCTGGGC
TGTCTGGTGAAGGACTACTTCCCAGAGCCTGTGACAGTGTCCTGGAACTCTGGCGCCCTGACATCCGGCGTGCACACA
TTTCCAGCCGTGCTGCAGAGCTCCGGCCTGTACAGCCTGTCTAGCGTGGTGACAGTGCCCTCCTCTAGCCTGGGCACA
CAGACCTATATCTGCAACGTGAATCACAAGCCAAGCAATACCAAGGTGGACAAGAAGGTGGAGCCCAAGTCCTGTGAT
AAGACACACACCTGCCCCCCTTGTCCTGCTCCCGAGCTGCTGGGCGGCCCTAGCGTGTTCCTGTTTCCACCCAAGCCT
AAGGACACCCTGATGATCTCCCGGACACCCGAGGTGACCTGCGTGGTGGTGGACGTGTCTCACGAGGATCCTGAGGTG
AAGTTCAACTGGTATGTGGATGGCGTGGAGGTGCACAATGCCAAGACCAAGCCCAGAGAGGAGCAGTACAACTCTACA
```

FIG. 46 (continued)

```
TATAGGGTGGTGAGCGTGCTGACCGTGCTGCACCAGGACTGGCTGAACGGCAAGGAGTATAAGTGCAAGGTGTCCAAT
AAGGCCCTGCCCGCCCCCATCGAGAAGACAATCAGCAAGGCCAAGGGCCAGCCTCGGGAGCCACAGGTGTACACCCTG
CCTCCATCCAGAGACGAGCTGACAAAGAACCAGGTGTCTCTGACATGTCTGGTGAAGGGCTTCTATCCTAGCGATATC
GCCGTGGAGTGGGAGTCCAATGGCCAGCCAGAGAACAATTACAAGACCACACCCCCTGTGCTGGACTCCGATGGCTCC
TTCTTTCTGTATTCCAAGCTGACCGTGGATAAGTCTCGGTGGCAGCAGGGCAACGTGTTCAGCTGTTCCGTGATGCAC
GAAGCCCTGCATAATCACTATACTCAGAAATCCCTGTCCCTGTCACCTGGAAAGTGATAA    (SEQ ID NO: 180)
```

```
>hIgkCL-pcDNA3.4
AGGACAGTGGCCGCCCCAAGCGTGTTCATCTTTCCCCCTTCCGACGAGCAGCTGAAGTCTGGCACCGCCAGCGTGGTG
TGCCTGCTGAACAACTTCTACCCTCGGGAGGCCAAGGTCCAGTGGAAGGTGGATAACGCCCTGCAGTCTGGCAATAGC
CAGGAGTCCGTGACCGAGCAGGACTCTAAGGATAGCACATATTCCCTGTCTAGCACCCTGACACTGAGCAAGGCCGAT
TACGAGAAGCACAAGGTGTATGCCTGTGAAGTCACCCATCAGGGGCTGTCATCACCCGTCACTAAGTCATTCAATCGC
GGAGAATGCTGATAA    (SEQ ID NO: 181)
```

```
>5_U551FEL190--VH2_hIgG1CH-pCDNA3.4
gttaggcgttttgcgctgcttcgcgatgtacgggccagatatacgcgttgacattgattattgactagttattaatag
taatcaattacggggtcattagttcatagcccatatatggagttccgcgttacataacttacggtaaatggcccgcct
ggctgaccgcccaacgacccccgcccattgacgtcaataatgacgtatgttcccatagtaacgccaataagggacttc
cattgacgtcaatgggtggagtatttacggtaaactgcccacttggcagtacatcaagtgtatcatatgccaagtacg
cccctattgacgtcaatgacggtaaatggcccgcctggcattatgcccagtacatgaccttatgggactttcctact
tggcagtacatctacgtattagtcatcgctattaccatggtgatgcggttttggcagtacatcaatgggcgtggatag
cggtttgactcacggggatttccaagtctccacccattgacgtcaatgggagtttgttttggcaccaaaatcaacgg
gactttccaaaatgtcgtaacaactccgccccattgacgcaaatgggcggtaggcgtgtacggtgggaggtctatata
agcagagctcgtttagtgaaccgtcagatcgcctggagacgccatccacgctgttttgacctccatagaagacaccgg
gaccgatccagcctccggactctagaggatcgaaccctTgaattcccgcgccaccatgggctggtcatgcattatttc
tgtttctggtcgcaactgctacaggcgtgcatagtCAGGTGCAGCTGCAAGAGTCCGGCCCTGGACTCGTGAAGCCCT
CCGAGACACTGTCTCTGACATGTACCGTGTCTGGCTTCTCCCTGTCCATCTACTCCGTGCACTGGATCAGACAGCCTC
CTGGCAAGGGCCTGGAATGGATCGGCATGATCTGGGGAGGCGGCTCTTCCGACTACAACTCCGCCCTGAAATCTCGGC
TGACCATCTCCAAGGACACCTCTAAGAACCAGGTCAGCCTGAAGCTGAGCTCTGTGACCGCTGCTGATACCGCCGTGT
ACTACTGCGCCAGAAATGGCAACTTCTACGCCATGGACTATTGGGGCCAGGGCACCCTGGTGACCGTGTCCAGCgcca
gcaccaagggcccttccgtgtttccactggcccctcctctaaatccacatctggcggcaccgccgccctgggctgtc
tggtgaaggactacttccagagcctgtgacagtgtcctggaactctggcgccctgacatccggcgtgcacacatttc
cagccgtgctgcagagctccggcctgtacagcctgtctagcgtggtgacagtgccctcctctagcctgggcacacaga
cctatatctgcaacgtgaatcacaagccaagcaataccaaggtggacaagaaggtggagcccaagtcctgtgataaga
cacacacctgcccccttgtcctgctccgagctgctgggcggccctagcgtgttcctgtttccacccaagcctaagg
acacctgatgatctcccggacacccgaggtgacctgcgtggtggtggacgtgtctcacgaggatcctgaggtgaagt
tcaactggtatgtggatggcgtggaggtgcacaatgccaagaccaagccagagaggagcagtacaactctacatata
gggtggtgagcgtgctgaccgtgctgcaccaggactggctgaacggcaaggagtataagtgcaaggtgtccaataagg
ccctgcccgcccccatcgagaagacaatcagcaaggccaagggccagcctcgggagccacaggtgtacaccctgcctc
catccagagacgagctgacaaagaaccaggtgtctctgacatgtctggtgaagggcttctatcctagcgatatcgccg
tggagtgggagtccaatggccagccagagaacaattacaagaccacacccctgtgctggactccgatggctccttct
ttctgtattccaagctgaccgtggataagtctcggtggcagcagggcaacgtgttcagctgttccgtgatgcacgaag
ccctgcataatcactatactcagaaatccctgtccctgtcacctggaaagtgataagcttaaggttcgatcctacc
ggttagtaatgagtttgatatctcgacaatcaacctctggattacaaaatttgtgaaagattgactggtattcttaac
tatgttgctccttttacgctatgtggatacgctgctttaatgcctttgtatcatgctattgcttcccgtatggctttc
attttctcctccttgtataaatcctggttgctgtctctttatgaggagttgtggcccgttgtcaggcaacgtggcgtg
gtgtgcactgtgtttgctgacgcaacccccactggttggggcattgccaccacctgtcagctcctttccgggactttc
gctttccccctccctattgccacggcggaactcatcgccgcctgccttgcccgctgctgacagggctggctgttg
ggcactgacaattccgtggtgttgtcggggaagctgacgtccttccatggctgctcgcctgtgttgccacctggatt
ctgcgcgggacgtccttctgctacgtcccttcggccctcaatccagcggaccttccttccgcggcctgctgccggct
ctgcggcctcttccgcgtcttcgccttcgccctcagacgagtcggatctcccttTgggccgcctccccgcctggaaac
ggggggaggctaactgaaacacggaaggagacaataccggaaggaacccgcgctatgacggcaataaaaagacagaata
aaacgcacgggtgttgggtcgtttgttcataaacgcggggttcggtcccagggctggcactctgtcgatacccacg
agacccattggggccaatacgcccgcgtttcttccttttcccaccccaccccccaagttcgggtgaaggccaggg
```

FIG. 46 (continued)

```
ctcgcagccaacgtcggggcggcaggccctgccatagcagatctgcgcagctggggctctagggggtatcccacgcg
ccctgtagcggcgcattaagcgcggcgggtgtggtggttacgcgcagcgtgaccgctacacttgccagcgccctagcg
cccgctcctttcgctttcttcccttcctttctcgccacgttcgccggctttccccgtcaagctctaaatcggggcatc
cctttagggttccgatttagtgctttacggcacctcgaccccaaaaaacttgattagggtgatggttcacgtagtggg
ccatcgccctgatagacggttttttcgcccctttgacgttggagtccacgttctttaatagtggactcttgttccaaact
ggaacaacactcaaccctatctcggtctattctttttgatttataagggattttgggggatttcggcctattggttaaaa
aatgagctgatttaacaaaaatttaacgcgaattaattctgtggaatgtgtgtcagttagggtgtggaaagtccccag
gctccccagcaggcagaagtatgcaaagcatgcatctcaattagtcagcaaccaggtgtggaaagtccccaggctccc
cagcaggcagaagtatgcaaagcatgcatctcaattagtcagcaaccatagtccgcccctaactccgcccatccngc
ccctaactccgcccagttccgcccattctccgccccatggctgactaattttttttatttatgcagaggccgaggccg
cctctgcctctgagctattccagaagtagtgaggaggcttttttggaggcctaggcttttgcaaaaagctcccgggag
cttgtatatccattttcggatctgatcaagagacaggatgaggatcgtttcgcatgattgaacaagatggattgcacg
caggttctccggccgcttgggtggagaggctattcggctatgactgggcacaacagacaatcggctgctctgatgccg
ccgtgttccggctgtcagcgcaggggcgcccggttcttttttgtcaagaccgacctgtccggtgccctgaatgaactgc
aggacgaggcagcgcggctatcgtggctggccacgacgggcgttccttgcgcagctgtgctcgacgttgtcactgaag
cgggaagggactggctgctattgggcgaagtgccggggcaggatctcctgtcatctcaccttgctcctgccgagaaag
tatccatcatggctgatgcaatgcggcggctgcatacgcttgatccggctacctgcccattcgaccaccaagcgaaac
atcgcatcgagcgagcacgtactcggatggaagccggtcttgtcgatcaggatgatctggacgaagagcatcaggggc
tcgcgccagccgaactgttcgccaggctcaaggcgcgcatgcccgacggcgaggatctcgtcgtgacccatggcgatg
cctgcttgccgaatatcatggtggaaaatggccgcttttctggattcatcgactgtggccggctggtgtggcggacc
gctatcaggacatagcgttggctacccgtgatattgctgaagagcttggcggcgaatggctgaccgcttcctcgtgc
tttacggtatcgccgctcccgattcgcagcgcatcgccttctatcgccttcttgacgagttcttctgagcgggactct
ggggttcgcgaaatgaccgaccaagcgacgcccaacctgccatcacgagatttcgattccaccgccgccttctatgaa
aggttgggcttcggaatcgttttccgggacgccggctggatgatcctccagcgcggggatctcatgctggagttcttc
gcccacccccaacttgtttattgcagcttataatggttacaaataaagcaatagcatcacaaatttcacaaataaagca
tttttttcactgcattctagttgtggtttgtccaaactcatcaatgtatcttatcatgtctgtataccgtcgacctct
agctagagcttggcgtaatcatggtcatagctgtttcctgtgtgaaattgttatccgctcacaattccacacaacata
cgagccggaagcataaagtgtaaagcctggggtgcctaatgagtgagctaactcacattaattgcgttgcgctcactg
cccgctttccagtcgggaaacctgtcgtgccagctgcattaatgaatcggccaacgcgcggggagaggcggtttgcgt
attgggcgctcttccgcttcctcgctcactgactcgctgcgctcggtcgttcggctgcggcgagcggtatcagctcac
tcaaaggcggtaatacggttatccacagaatcagggggataacgcaggaaagaacatgtgagcaaaaggccagcaaaag
gccaggaaccgtaaaaaggccgcgttgctggcgtttttccataggctccgcccccctgacgagcatcacaaaaatcga
cgctcaagtcagaggtggcgaaacccgacaggactataaagataccaggcgtttccccctggaagctccctcgtgcgc
tctcctgttccgaccctgccgcttaccggatacctgtccgcctttctcccttcgggaagcgtggcgctttctcaatgc
tcacgctgtaggtatctcagttcggtgtaggtcgttcgctccaagctgggctgtgtgcacgaaccccccgttcagccc
gaccgctgcgccttatccggtaactatcgtcttgagtccaacccggtaagacacgacttatcgccactggcagcagcc
actggtaacaggattagcagagcgaggtatgtaggcggtgctacagagttcttgaagtggtggcctaactacggctac
actagaaggacagtatttggtatctgcgctctgctgaagccagttaccttcggaaaaagagttggtagctcttgatcc
ggcaaacaaaccaccgctggtagcggtggtttttttgtttgcaagcagcagattacgcgcagaaaaaaaggatctcaa
gaagatcctttgatcttttctacggggtctgacgctcagtggaacgaaaactcacgttaagggattttggtcatgaga
ttatcaaaaaggatcttcacctagatccttttaaattaaaaatgaagttttaaatcaatctaaagtatatatgagtaa
acttggtctgacagttaccaatgcttaatcagtgaggcacctatctcagcgatctgtctatttcgttcatccatagtt
gcctgactccccgtcgtgtagataactacgatacgggagggcttaccatctggccccagtgctgcaatgataccgcga
gacccacgctcaccggctccagatttatcagcaataaaccagccagccggaagggccgagcgcagaagtggtcctgca
actttatccgcctccatccagtctattaattgttgccgggaagctagagtaagtagttcgccagttaatagtttgcgc
aacgttgttgccattgctacaggcatcgtggtgtcacgctcgtcgtttggtatggcttcattcagctccggttcccaa
cgatcaaggcgagttacatgatcccccatgttgtgcaaaaaagcggttagctccttcggtcctccgatcgttgtcaga
agtaagttggccgcagtgttatcactcatggttatggcagcactgcataattctcttactgtcatgccatccgtaaga
tgcttttctgtgactggtgagtactcaaccaagtcattctgagaatagtgtatgcggcgaccgagttgctcttgcccg
gcgtcaatacgggataataccgcgccacatagcagaactttaaaagtgctcatcattggaaaacgttcttcggggcga
aaactctcaaggatcttaccgctgttgagatccagttcgatgtaacccactcgtgcacccaactgatcttcagcatct
tttactttcaccagcgtttctgggtgagcaaaaacaggaaggcaaaatgccgcaaaaaagggaataagggcgacacgg
aaatgttgaatactcatactcttcctttttcaatattattgaagcatttatcagggttattgtctcatgagcggatac
atatttgaatgtatttagaaaaataaacaaataggggttccgcgcacatttccccgaaaagtgccacctgacgtcgac
```

FIG. 46 (continued)

ggatcgggagatctcccgatcccctatggtcgactctcagtacaatctgctctgatgccgcatagttaagccagtatc
tgctccctgcttgtgtgttggaggtcgctgagtagtgcgcgagcaaaatttaagctacaacaaggcaaggcttgaccg
acaattgcatgaagaatctgcttagg    (SEQ ID NO: 182)

>11_U551FEL190-VH4_hIgG1CH-pCDNA3.4
gttaggcgttttgcgctgcttcgcgatgtacgggccagatatacgcgttgacattgattattgactagttattaatag
taatcaattacgggggtcattagttcatagccccatatatggagttccgcgttacataacttacggtaaatggcccgcct
ggctgaccgcccaacgacccccgcccattgacgtcaataatgacgtatgttcccatagtaacgccaatagggactttc
cattgacgtcaatgggtggagtatttacggtaaactgcccacttggcagtacatcaagtgtatcatatgccaagtacg
cccctattgacgtcaatgacggtaaatggcccgcctggcattatgcccagtacatgaccttatgggactttcctact
tggcagtacatctacgtattagtcatcgctattaccatggtgatgcggttttggcagtacatcaatgggcgtggatag
cggtttgactcacggggatttccaagtctccaccccattgacgtcaatgggagtttgttttggcaccaaaatcaacgg
gactttccaaaatgtcgtaacaactccgccccattgacgcaaatggcgcggtaggcgtgtacggtgggaggtctatata
agcagagctcgtttagtgaaccgtcagatcgcctggagacgccatccacgctgttttgacctccatagaagacaccgg
gaccgatccagcctccggactctagaggatcgaaccctgaattcccgcgcaccatgggctggtcatgcattattc
tgtttctggtcgcaactgctacaggcgtgcatagtCAGGTGCAGCTGCAAGAGTCCGGACCCGGCCTCGTGAAGCCTT
CCGAGACACTGTCTCTGACCTGTACCGTGTCTGGCTTCTCCCTGTCCATCTACTCCGTGCACTGGATCCGGCAGCCTC
CTGGCAAGGGCCTGGAATGGCTGGGCATGATCTGGGGCGGCGGAAGCTCCGACTACAACTCCGCCCTGAAATCTAGAC
TGACCATCTCCAAGGACACCTCTAAGAACCAGGTCAGCCTGAAGCTGAGCTCTGTGACCGCCGCTGATACCGCTATGT
ACTACTGCGCCAGAAATGGCAACTTCTACGCCATGGACTATTGGGGCCAGGGCACCCTGGTGACAGTGTCCTCTgcca
gcaccaagggcccttccgtgtttccactggcccctcctctaaatccacatctggcggcaccgccgccctgggctgtc
tggtgaaggactacttcccagagcctgtgacagtgtcctggaactctggcgccctgacatccggcgtgcacacattc
cagccgtgctgcagagctccggcctgtacagcctgtctagcgtggtgacagtgccctcctctagcctgggcacacaga
cctatatctgcaacgtgaatcacaagccaagcaatccaaggtggacaagaaggtggagcccaagtcctgtgataaga
cacacacctgcccccttgtcctgtcccgagctgctggggcggcccagcgtgttcctgttccacccaagcctaagg
acaccctgatgatctcccggacaccgaggtgacctgcgtggtggtggtggacgtgtctcacgaggatcctgaggtgaagt
tcaactggtatgtggatggcgtggaggtgcacaatgccaagaccaagccagagaggagcagtacaactctacatata
gggtggtgagcgtgctgaccgtgctgcaccaggactggctgaacggcaaggagtataagtgcaaggtgtccaataagg
cctgcccgccccatcgagaagacaatcagcaaggccaaggcagcctcgggagccacaggtgtacaccctgcctc
catccagagacgagctgacaaagaaccaggtgtctctgacatgtctggtgaaggcttctatcctagcgatatcgccg
tggagtgggagtccaatggccagccagagaacaattacaagaccacacccctgtgctggactccgatggctccttct
ttctgtattccaagctgaccgtggataagtctcggtggcagcagggcaacgtgttcagctgttccgtgatgcacgaag
cctgcataatcactatactcagaaatccctgtcctgtcacctggaaagtgataagcttaaggttcgatccctacc
ggttagtaatgagtttgatatctcgacaatcaacctctggattacaaaatttgtgaaagattgactggtattcttaac
tatgttgctccttttacgctatgtggatacgctgctttaatgcctttgtatcatgctattgcttcccgtatggctttc
attttctcctccttgtataaatcctggttgctgtctctttatgaggagttgtggcccgttgtcaggcaacgtggcgtg
gtgtgcactgtgtttgctgacgcaacccccactggttggggcattgccaccacctgtcagctcctttccgggactttc
gctttccccctccctattgccacggcggaactcatcgccgcctgccttgcccgctgctggacagggctcggctgttg
ggcactgacaattccgtggtgttgtcggggaagctgacgtcctttccatggctgctcgcctgtgttgccacctggatt
ctgcgcgggacgtccttctgtacgtccttcggccctcaatccagcggaccttcttcccgcggcctgctgccggct
ctgcggcctcttccgcgtcttcgccttcgccctcagacgagtcggatctccctttgggccgcctccccgcctggaaac
gggggaggctaactgaaacacggaaggagacaataccggaaggaacccgcgctatgacggcaataaaaagacagaata
aaacgcacgggtgttgggtcgtttgttcataaacgcggggttcggtcccaggctggcactctgtcgataccccacg
agacccattgggccaatacgcccgcgtttcttccttttcccaccccaccccccaagtcgggtgaaggcccaggg
ctcgcagcaacgtcgggcggcaggcctgccatagcagatctgcgcagctgggggctctaggggtatccccacgg
ccctgtagcggcgcattaagcgcggcggggtgtggtggttacgcgcagcgtgaccgctacacttgccagcgccctagcg
cccgctcctttcgctttcttcccttcctttctcgccacgttcgccggctttccccgtcaagctctaaatcggggcatc
cctttaggggttccgatttagtgctttacggcacctcgacccaaaaaacttgattagggtgatggttcacgtagtggg
ccatcgccctgatagacggtttttcgccctttgacgttggagtccacgttctttaatagtggactcttgttccaaact
ggaacaacactcaaccctatctcggtctattcttttgatttataagggattttggggatttcggcctattggttaaaa
aatgagctgatttaacaaaaatttaacgcgaattaattctgtggaatgtgtgtcagttagggtgtggaaagtccccag
gctccccagcaggcagaagtatgcaaagcatgcatctcaattagtcagcaaccaggtgtggaaagtccccaggctccc
cagcaggcagaagtatgcaaagcatgcatctcaattagtcagcaaccatagtcccgcccctaactccgcccatcccgc
ccctaactccgcccagttccgcccattctccgccccatggctgactaattttttttatttatgcagaggccgaggccg

FIG. 46 (continued)

```
cctctgcctctgagctattccagaagtagtgaggaggcttttttggaggcctaggcttttgcaaaaagctcccgggag
cttgtatatccattttcggatctgatcaagagacaggatgaggatcgtttcgcatgattgaacaagatggattgcacg
caggttctccggccgcttgggtggagaggctattcggctatgactgggcacaacagacaatcggctgctctgatgccg
ccgtgttccggctgtcagcgcaggggcgcccggttcttttttgtcaagaccgacctgtccggtgccctgaatgaactgc
aggacgaggcagcgcggctatcgtggctggccacgacgggcgttccttgcgcagctgtgctcgacgttgtcactgaag
cgggaagggactggctgctattgggcgaagtgccggggcaggatctcctgtcatctcaccttgctcctgccgagaaag
tatccatcatggctgatgcaatgcggcggctgcatacgcttgatccggctacctgcccattcgaccaccaagcgaaac
atcgcatcgagcgagcacgtactcggatggaagccggtcttgtcgatcaggatgatctggacgaagagcatcaggggc
tcgcgccagccgaactgttcgccaggctcaaggcgcgcatgcccgacggcgaggatctcgtcgtgacccatggcgatg
cctgcttgccgaatatcatggtggaaaatggccgcttttctggattcatcgactgtggccggctgggtgtggcggacc
gctatcaggacatagcgttggctacccgtgatattgctgaagagcttggcggcgaatgggctgaccgcttcctcgtgc
tttacggtatcgccgctcccgattcgcagcgcatcgccttctatcgccttcttgacgagttcttctgagcgggactct
ggggttcgcgaaatgaccgaccaagcgacgcccaacctgccatcacgagatttcgattccacacgccgccttctatgaa
aggttgggcttcggaatcgtttccgggacgccggctggatgatcctccagcgcggggatctcatgctggagttcttc
gcccaccccaacttgtttattgcagcttataatggttacaaataaagcaatagcatcacaaatttcacaaataaagca
ttttttcactgcattctagttgtggtttgtccaaactcatcaatgtatcttatcatgtctgtataccgtcgacctct
agctagagcttggcgtaatcatggtcatagctgtttcctgtgtgaaattgttatccgctcacaattccacacaacata
cgagccggaagcataaagtgtaaagcctggggtgcctaatgagtgagctaactcacattaattgcgttgcgctcactg
cccgctttccagtcgggaaacctgtcgtgccagctgcattaatgaatcggccaacgcgcggggagaggcggtttgcgt
attgggcgctcttccgcttcctcgctcactgactcgctgcgctcggtcgttcggctgcggcgagcggtatcagctcac
tcaaaggcggtaatacggttatccacagaatcaggggataacgcaggaaagaacatgtgagcaaaaggccagcaaaag
gccaggaaccgtaaaaaggccgcgttgctggcgtttttccataggctccgcccccctgacgagcatcacaaaaatcga
cgctcaagtcagaggtggcgaaacccgacaggactataaagataccaggcgtttccccctggaagctccctcgtgcgc
tctcctgttccgaccctgccgcttaccggatacctgtccgcctttctcccttcgggaagcgtggcgctttctcaatgc
tcacgctgtaggtatctcagttcggtgtaggtcgttcgctccaagctgggctgtgtgcacgaaccccccgttcagccc
gaccgctgcgccttatccggtaactatcgtcttgagtccaacccggtaagacacgacttatcgccactggcagcagcc
actggtaacaggattagcagagcgaggtatgtaggcggtgctacagagttcttgaagtggtggcctaactacggctac
actagaaggacagtatttggtatctgcgctctgctgaagccagttaccttcggaaaaagagttggtagctcttgatcc
ggcaaacaaaccaccgctggtagcggtggtttttttgtttgcaagcagcagattacgcgcagaaaaaaaggatctcaa
gaagatcctttgatcttttctacggggtctgacgctcagtggaacgaaaactcacgttaagggattttggtcatgaga
ttatcaaaaaggatcttcacctagatccttttaaattaaaaatgaagttttaaatcaatctaaagtatatatgagtaa
acttggtctgacagttaccaatgcttaatcagtgaggcacctatctcagcgatctgtctatttcgttcatccatagtt
gcctgactccccgtcgtgtagataactacgatacgggagggcttaccatctggccccagtgctgcaatgataccgcga
gacccacgctcaccggctccagatttatcagcaataaaccagccagccggaagggccgagcgcagaagtggtcctgca
actttatccgcctccatccagtctattaattgttgccgggaagctagagtaagtagttcgccagttaatagtttgcgc
aacgttgttgccattgctacaggcatcgtggtgtcacgctcgtcgtttggtatggcttcattcagctccggttcccaa
cgatcaaggcgagttacatgatcccccatgttgtgcaaaaaagcggttagctccttcggtcctccgatcgttgtcaga
agtaagttggccgcagtgttatcactcatggttatggcagcactgcataattctcttactgtcatgccatccgtaaga
tgcttttctgtgactggtgagtactcaaccaagtcattctgagaatagtgtatgcggcgaccgagttgctcttgcccg
gcgtcaatacgggataataccgcgccacatagcagaactttaaaagtgctcatcattggaaaacgttcttcggggcga
aaactctcaaggatcttaccgctgttgagatccagttcgatgtaacccactcgtgcacccaactgatcttcagcatct
tttactttcaccagcgtttctgggtgagcaaaaacaggaaggcaaaatgccgcaaaaaagggaataagggcgacacgg
aaatgttgaatactcatactcttcctttttcaatattattgaagcatttatcagggttattgtctcatgagcggatac
atatttgaatgtatttagaaaaataaacaaataggggttccgcgcacatttccccgaaaagtgccacctgacgtcgac
ggatcgggagatctcccgatcccctatggtcgactctcagtacaatctgctctgatgccgcatagttaagccagtatc
tgctccctgcttgtgtgttggaggtcgctgagtagtgcgcgagcaaaatttaagctacaacaaggcaaggcttgaccg
acaattgcatgaagaatctgcttagg    (SEQ ID NO: 183)

>14_U551FEL190-VL1_hIgkCL-pcDNA3.4
gttaggcgtttttgcgctgcttcgcgatgtacgggccagatatacgcgttgacattgattattgactagttattaatag
taatcaattacggggtcattagttcatagcccatatatggagttccgcgttacataacttacggtaaatggcccgcct
ggctgaccgcccaacgacccccgcccattgacgtcaataatgacgtatgttcccatagtaacgccaatagggactttc
cattgacgtcaatgggtggagtatttacggtaaactgcccacttggcagtacatcaagtgtatcatatgccaagtacg
ccccctattgacgtcaatgacggtaaatggcccgcctggcattatgcccagtacatgaccttatgggactttcctact
```

FIG. 46 (continued)

```
tggcagtacatctacgtattagtcatcgctattaccatggtgatgcggtttttggcagtacatcaatgggcgtggatag
cggtttgactcacgggattttccaagtctccacccattgacgtcaatgggagtttgttttggcaccaaaatcaacgg
gactttccaaaatgtcgtaacaactccgccccattgacgcaaatgggcggtaggcgtgtacggtgggaggtctatata
agcagagctcgtttagtgaaccgtcagatcgcctggagacgccatccacgctgttttgacctccatagaagacaccgg
gaccgatccagcctccggactctagaggatcgaacccttgaattccogccgccaccatgggctggtcatgtattattc
tgtttctggtcgcaactgctacaggggtccatagtGAGATCGTGCTGACCCAATCTCCAGGCACCCTGTCTCTCAGCC
CTGGCGAGAGAGCCACCCTGTCCTGCACCGGCTTCTAGCTCCGTGTCCTCCAGCTTCCTGCACTGGTACCAGCAGAAAC
CCGGCCAGGCTCCTAGACTGCTGATCTATTCCACCTCCAACCTGGCCTCTGGCATCCCTGACCGGTTCTCCGGCTCTG
GCTCCGGAACAGATTTTACACTGACCATCTCCCGGCTGGAACCTGAGGACTTCGCCGTGTACTACTGTCACCAGTACC
ACCATTCTCCTTACATCTACACCTTCGGCGGCGGAACCAAGCTGGAAATCAAGaggacagtggccgccccaagcgtgt
tcatcttccccctccgacgagcagctgaagtctggcaccgccagcgtggtgtgcctgctgaacaacttctaccctc
gggaggccaaggtccagtggaaggtggataacgcoctgcagtctggcaatagccaggagtccgtgaccgagcaggact
ctaaggatagcacatattccctgtctagcacctgacactgagcaaggccgattacgagaagcacaaggtgtatgcct
gtgaagtcacccatcaggggctgtcatcaccgtcactaagtcattcaatcgcggagaatgctgataagcttaagggt
tcgatccctaccggttagtaatgagtttgatatctcgacaatcaacctctggattacaaaatttgtgaaagattgact
ggtattcttaactatgttgctccttttacgctatgtggatacgctgctttaatgcctttgtatcatgctattgcttcc
cgtatggctttcattttctcctccttgtataaatcctggttgctgtctctttatgaggagttgtggcccgttgtcagg
caacgtggcgtggtgtgcactgtgtttgctgacgcaacccccactggttgggcattgccaccacctgtcagctcctt
tccgggactttcgctttccccctccctattgccacggcggaactcatcgccgctgccttgcccgctgctggacaggg
gctcggctgttgggcactgacaattccgtggtgttgtcggggaagctgacgtcctttccatggctgctcgcctgtgtt
gccacctggattctgcgcgggacgtccttctgctacgtcccttcggccctcaatccagcggaccttccttccgcggc
ctgctgccggctctgcggcctcttccgcgtcttcgccttcgccctcagacgagtcggatctccctttgggccgcctcc
ccgcctggaaacgggggaggctaactgaaacacggaaggagacaataccggaaggaaccgcgctatgacggcaataa
aaagacagaataaaacgcacgggtgttgggtcgtttgttcataaacgcggggttcggtcccagggctggcactctgtc
gataccccaccgagacccattgggccaatacgcccgcgtttcttccttttcccacccccaccccccaagttcgggt
gaaggcccagggctcgcagccaacgtcgggggcggcaggccctgccatagcagatctgcgcagctgggggctctaggggg
tatcccacgcgccctgtagcggcgcattaagcgcggcgggtgtggtggttacgcgcagcgtgaccgctacacttgcc
agcgccctagcgcccgctccttcgctttcttcccttccttctcgccacgttcgccggctttccccgtcaagctcta
aatcggggcatccctttagggttccgatttagtgctttacggcacctcgacccaaaaaaacttgattagggtgatggt
tcacgtagtgggccatcgccctgatagacggtttttcgcccttgacgttggagtccacgttctttaatagtggactc
ttgttccaaactggaacaacactcaaccctatctcggtctattcttttgatttataagggattttggggatttcggcc
tattggttaaaaaatgagctgatttaacaaaaatttaacgcgaattaattctgtggaatgtgtgtcagttagggtgtg
gaaagtccccaggctccccagcaggcagaagtatgcaaagcatgcatctcaattagtcagcaaccaggtgtggaaagt
ccccaggctccccagcaggcagaagtatgcaaagcatgcatctcaattagtcagcaaccatagtcccgcccctaactc
cgcccatcccgcccctaactccgcccagttccgcccattctccgccccatggctgactaattttttttatttatgcag
aggccgaggccgcctctgcctctgagctattccagaagtagtgaggaggcttttttggaggcctaggcttttgcaaaa
agctcccgggagcttgtatatccattttcggatctgatcaagagacaggatgaggatcgtttcgcatgattgaacaag
atggattgcacgcaggttctccggccgcttgggtggagaggctattcggctatgactgggcacaacagacaatcggct
gctctgatgccgccgtgttccggctgtcagcgcaggggcgcccggttcttttttgtcaagaccgacctgtccggtgccc
tgaatgaactgcaggacgaggcagcgcggctatcgtggctggccacgacgggcgttccttgcgcagctgtgctcgacg
ttgtcactgaagcgggaagggactggctgctattgggcgaagtgccggggcaggatctcctgtcatctcaccttgctc
ctgccgagaaagtatccatcatggctgatgcaatgcggcggctgcatacgcttgatccggctacctgcccattcgacc
accaagcgaaacatcgcatcgagcgagcacgtactcggatggaagccggtcttgtcgatcaggatgatctggacgaag
agcatcaggggctcgcgccagccgaactgttcgccaggctcaaggcgcgcatgcccgacggcgaggatctcgtcgtga
cccatggcgatgcctgcttgccgaatatcatggtggaaaatggccgcttttctggattcatcgactgtggccggctggg
tgtggcggaccgctatcaggacatagcgttggctacccgtgatattgctgaagagcttggcggcgaatgggctgacc
gcttcctcgtgctttacggtatcgccgctcccgattcgcagcgcatcgccttctatcgccttcttgacgagttcttct
gagcgggactctggggttcgcgaaatgaccgaccaagcgacgcccaacctgccatcacgagatttcgattccaccgcc
gccttctatgaaaggttgggcttcggaatcgttttccgggacgccggctggatgatcctccagcgcggggatctcatg
ctggagttcttcgcccaccccaacttgtttattgcagcttataatggttacaaataaagcaatagcatcacaaatttc
acaaataaagcatttttttcactgcattctagttgtggtttgtccaaactcatcaatgtatcttatcatgtctgtata
ccgtcgacctctagctagagcttggcgtaatcatggtcatagctgtttcctgtgtgaaattgttatccgctcacaatt
ccacacaacatacgagccggaagcataaagtgtaaagcctggggtgcctaatgagtgagctaactcacattaattgcg
ttgcgctcactgcccgctttccagtcgggaaacctgtcgtgccagctgcattaatgaatcggccaacgcgcggggaga
```

FIG. 46 (continued)

```
ggcggttttgcgtattgggcgcgtcttccgcttcctcgctcactgactcgctgcgctcggtcgttcggctgcggcgagcg
gtatcagctcactcaaaggcggtaatacggttatccacagaatcaggggataacgcaggaaagaacatgtgagcaaaa
ggccagcaaaaggccaggaaccgtaaaaaggccgcgttgctggcgtttttccataggctccgcccccctgacgagcat
cacaaaaatcgacgctcaagtcagaggtggcgaaacccgacaggactataaagataccaggcgtttccccctggaagc
tccctcgtgcgctctcctgttccgaccctgccgcttaccggatacctgtccgcctttctcccttcgggaagcgtggcg
ctttctcaatgctcacgctgtaggtatctcagttcggtgtaggtcgttcgctccaagctgggctgtgtgcacgaaccc
cccgttcagcccgaccgctgcgccttatccggtaactatcgtcttgagtccaacccggtaagacacgacttatcgcca
ctggcagcagccactggtaacaggattagcagagcgaggtatgtaggcggtgctacagagttcttgaagtggtggcct
aactacggctacactagaaggacagtatttggtatctgcgctctgctgaagccagttaccttcggaaaaagagttggt
agctcttgatccggcaaacaaaccaccgctggtagcggtggtttttttgtttgcaagcagcagattacgcgcagaaaa
aaaggatctcaagaagatcctttgatcttttctacggggtctgacgctcagtggaacgaaaactcacgttaagggatt
ttggtcatgagattatcaaaaaggatcttcacctagatccttttaaattaaaaatgaagttttaaatcaatctaaagt
atatatgagtaaacttggtctgacagttaccaatgcttaatcagtgaggcacctatctcagcgatctgtctatttcgt
tcatccatagttgcctgactccccgtcgtgtagataactacgatacgggagggcttaccatctggccccagtgctgca
atgataccgcgagacccacgctcaccggctccagatttatcagcaataaaccagccagccggaagggccgagcgcaga
agtggtcctgcaactttatccgcctccatccagtctattaattgttgccgggaagctagagtaagtagttcgccagtt
aatagtttgcgcaacgttgttgccattgctacaggcatcgtggtgtcacgctcgtcgtttggtatggcttcattcagc
tccggttcccaacgatcaaggcgagttacatgatcccccatgttgtgcaaaaaagcggttagctccttcggtcctccg
atcgttgtcagaagtaagttggccgcagtgttatcactcatggttatggcagcactgcataattctcttactgtcatg
ccatccgtaagatgcttttctgtgactggtgagtactcaaccaagtcattctgagaatagtgtatgcggcgaccgagt
tgctcttgcccggcgtcaatacgggataataccgcgccacatagcagaactttaaaagtgctcatcattggaaaacgt
tcttcggggcgaaaactctcaaggatcttaccgctgttgagatccagttcgatgtaacccactcgtgcacccaactga
tcttcagcatcttttactttcaccagcgtttctgggtgagcaaaaacaggaaggcaaaatgccgcaaaaaagggaata
agggcgacacggaaatgttgaatactcatactcttcctttttcaatattattgaagcatttatcagggttattgtctc
atgagcggatacatatttgaatgtatttagaaaaataaacaaataggggttccgcgcacatttccccgaaaagtgcca
cctgacgtcgacggatcgggagatctcccgatcccctatggtcgactctcagtacaatctgctctgatgccgcatagt
taagccagtatctgctccctgcttgtgtgttggaggtcgctgagtagtgcgcgagcaaaatttaagctacaacaaggc
aaggcttgaccgacaattgcatgaagaatctgcttagg   (SEQ ID NO: 184)
```

```
>17_U551FEL190-VL2_hIgkCL-pcDNA3.4
gttaggcgttttgcgctgcttcgcgatgtacgggccagatatacgcgttgacattgattattgactagttattaatag
taatcaattacggggtcattagttcatagcccatatatggagttccgcgttacataacttacggtaaatggcccgcct
ggctgaccgcccaacgacccccgcccattgacgtcaataatgacgtatgttcccatagtaacgccaatagggactttc
cattgacgtcaatgggtggagtatttacggtaaactgcccacttggcagtacatcaagtgtatcatatgccaagtacg
cccctattgacgtcaatgacggtaaatggcccgcctggcattatgcccagtacatgaccttatgggactttcctact
tggcagtacatctacgtattagtcatcgctattaccatggtgatgcggttttggcagtacatcaatgggcgtggatag
cggtttgactcacggggatttccaagtctccaccccattgacgtcaatgggagtttgttttggcaccaaaatcaacgg
gactttccaaaatgtcgtaacaactccgccccattgacgcaaatgggcggtaggcgtgtacggtgggaggtctatata
agcagagctcgtttagtgaaccgtcagatcgcctggagacgccatccacgctgttttgacctccatagaagacaccgg
gaccgatccagcctccggactctagaggatcgaaccttgaattccgcgcgccaccatgggctggtcatgtattattc
tgtttctggtcgcaactgctacaggggtccatagtGAGATCGTGCTGACACAATCTCCCGGCACCCTCAGCCTGTCTC
CAGGCGAGAGAGCCACACTGTCCTGCACCGCTTCTAGCTCCGTGTCCTCCAGCTTCTGCACTGGTACCAGCAGAAAC
CTGGCCAGGCTCCTCAGCTGTGGATCTACTCCACCTCCAACCTGGCCTCTGGCATCCCTGATCGGTTCTCCGGCTCCG
GCTCTGGCACCGACTACACCCTGACCATCTCCAGACTGGAACCTGAGGACTTCGCCGTGTACTACTGTCACCAGTACC
ACCATTCTCCTTACATCTATACCTTCGGCGGAGGAACCAAGCTGGAAATCAAGAggacagtggccgccccaagcgtgt
tcatctttcccccttccgacgagcagctgaagtctggcaccgccagcgtggtgtgcctgctgaacaacttctaccctc
gggaggccaaggtccagtggaaggtggataacgccctgcagtctggcaatagccaggagtccgtgaccgagcaggact
ctaaggatagcacatattccctgtctagcaccctgacactgagcaaggccgattacgagaagcacaaggtgtatgcct
gtgaagtcacccatcagggcctgtctcatcccgtcactaagtcattcaatcgcggagaatgctgataagcttaagggt
tcgatccctaccggttagtaatgagtttgatatctcgacaatcaacctctggattacaaaatttgtgaaagattgact
ggtattcttaactatgttgctccttttacgctatgtggatacgctgctttaatgcctttgtatcatgctattgcttcc
cgtatggctttcattttctcctccttgtataaatcctggttgctgtctctttatgaggagttgtggcccgttgtcagg
caacgtggcgtggtgtgcactgtgtttgctgacgcaaccccactggttggggcattgccaccacctgtcagctcctt
tccgggactttcgctttccccctccctattgccacggcggaactcatcgccgcctgccttgcccgctgctggacaggg
```

FIG. 46 (continued)

```
gctcggctgttgggcactgacaattccgtggtgttgtcggggaagctgacgtccttccatggctgctcgcctgtgtt
gccacctggattctgcgcgggacgtccttctgctacgtcccttcggccctcaatccagcggaccttccttcccgcggc
ctgctgccggctctgcggcctcttccgcgtcttcgccttcgccctcagacgagtcggatctccctttgggccgcctcc
ccgcctggaaacgggggaggctaactgaaacacggaaggagacaatacggaaggaacccgcgctatgacggcaataa
aaagacagaataaaaacgcacgggtgttgggtcgtttgttcataaacgcggggttcggtcccagggctggcactctgtc
gataccccaccgagacccccattggggccaatacgcccgcgtttcttccttttccccaccccacccccaagttcgggt
gaaggccagggctcgcagccaacgtcggggcggcaggccctgccatagcagatctgcgcagctggggctctaggggg
tatcccacgcgccctgtagcggcgcattaagcgcggcgggtgtggtggttacgcgcagcgtgaccgctacacttgcc
agcgccctagcgccgctcctttcgctttcttccttccttctcgccacgttcgccggcttccccgtcaagctcta
aatcggggcatccctttagggttccgatttagtgctttacggcacctcgaccccaaaaaacttgattagggtgatggt
tcacgtagtgggccatcgccctgatagacggttttcgccctttgacgttggagtccacgttctttaatagtggactc
ttgttccaaactggaacaacactcaacctatctcggtctattcttttgatttataagggattttggggatttcggcc
tattggttaaaaaatgagctgatttaacaaaaatttaacgcgaattaattctgtggaatgtgtgtcagttagggtgtg
gaagtccccaggctcccagcaggcagaagtatgcaaagcatgcatctcaattagtcagcaaccaggtgtggaaagt
cccaggctcccagcaggcagaagtatgcaaagcatgcatctcaattagtcagcaaccatagtcccgcccctaactc
cgcccatcccgccctaactccgcccagttccgcccattctccgccccatggctgactaatttttttttatttatgcag
aggccgaggccgcctctgcctctgagctattccagaagtagtgaggaggcttttttggaggcctaggcttttgcaaaa
agctcccgggagcttgtatatccattttcggatctgatcaagagacaggatgaggatcgtttcgcatgattgaacaag
atggattgcacgcaggttctccggccgcttgggtggagaggctattcggctatgactgggcacaacagacaatcggct
gctctgatgccgccgtgttccggctgtcagcgcaggggcgcccggttcttttgtcaagaccgacctgtccggtgccc
tgaatgaactgcaggacgaggcagcgcggctatcgtggctggccacgacgggcgttccttgcgcagctgtgctcgacg
ttgtcactgaagcgggaagggactggctgctattgggcgaagtgccggggcaggatctcctgtcatctcaccttgctc
ctgccgagaaagtatccatcatggctgatgcaatgcggcggctgcatacgcttgatccggctacctgcccattcgacc
accaagcgaaacatcgcatcgagcgagcacgtactcggatggaagccggtcttgtcgatcaggatgatctggacgaag
agcatcaggggctcgcgccagccgaactgttcgccaggctcaaggcgcgcatgcccgacgggcgaggatctcgtcgtga
cccatggcgatgcctgcttgccgaatatcatcgtggaaaatgccgcgcttttctcgattcatcgactgtggccggctgg
gtgtggcggaccgctatcaggacatagcgttggctacccgtgatattgctgaagagcttggcggcgaatgggctgacc
gcttcctcgtgctttacggtatcgccgctcccgattcgcagcgcatcgccttctatcgccttcttgacgagttcttct
gagcgggactctggggttcgcgaaatgaccgaccaagcgacgcccaacctgccatcacgagatttcgattccaccgcc
gccttctatgaaaggttgggcttcggaatcgttttccgggacgccggctggatgatcctccagcgcggggatctcatg
ctggagttcttcgcccacccaacttgtttattgcagcttataatggttacaaataaagcaatagcatcacaaatttc
acaaataaagcattttttttcactgcattctagttgtggtttgtccaaactcatcaatgtatcttatcatgtctgtata
ccgtcgacctctagctagagcttggcgtaatcatggtcatagctgtttcctgtgtgaaattgttatccgctcacaatt
ccacacaacatacgagccggaagcataaagtgtaaagcctggggtgcctaatgagtgagctaactcacattaattgcg
ttgcgctcactgcccgctttccagtcgggaaacctgtcgtgccagctgcattaatgaatcggccaacgcgcggggaga
ggcggtttgcgtattgggcgctcttccgcttcctcgctcactgactcgctgcgctcggtcgttcggctgcggcgagcg
gtatcagctcactcaaaggcggtaatacggttatccacagaatcaggggataacgcaggaaagaacatgtgagcaaaa
ggccagcaaaaggccaggaaccgtaaaaaggccgcgttgctggcgtttttccataggctccgcccccctgacgagcat
cacaaaaatcgacgctcaagtcagaggtggcgaaacccgacaggactataaagataccaggcgtttccccctggaagc
tccctcgtgcgctctcctgttccgaccctgccgcttaccggatacctgtccgcctttctcccttcgggaagcgtggcg
ctttctcaatgctcacgctgtaggtatctcagttcggtgtaggtcgttcgctccaagctgggctgtgtgcacgaaccc
cccgttcagcccgaccgctgcgccttatccggtaactatcgtcttgagtccaacccggtaagacacgacttatcgcca
ctggcagcagccactggtaacaggattagcagagcgaggtatgtaggcggtgctacagagttcttgaagtggtggcct
aactacggctacactagaaggacagtatttggtatctgcgctctgctgaagccagttaccttcggaaaaagagttggt
agctcttgatccggcaaacaaaccaccgctggtagcggtggtttttttgtttgcaagcagcagattacgcgcagaaaa
aaaggatctcaagaagatcctttgatcttttctacggggtctgacgctcagtggaacgaaaactcacgttaagggatt
ttggtcatgagattatcaaaaaggatcttcacctagatccttttaaattaaaaatgaagttttaaatcaatctaaagt
atatatgagtaaacttggtctgacagttaccaatgcttaatcagtgaggcacctatctcagcgatctgtctatttcgt
tcatccatagttgcctgactccccgtcgtgtagataactacgatacgggagggcttaccatctggccccagtgctgca
atgataccgcgagacccacgctcaccggctccagatttatcagcaataaaccagccagccggaagggccgagcgcaga
agtggtcctgcaactttatccgcctccatccagtctattaattgttgccgggaagctagagtaagtagttcgccagtt
aatagtttgcgcaacgttgttgccattgctacaggcatcgtggtgtcacgctcgtcgtttggtatggcttcattcagc
tccggttcccaacgatcaaggcgagttacatgatcccccatgttgtgcaaaaaagcggttagctccttcggtcctccg
atcgttgtcagaagtaagttggccgcagtgttatcactcatggttatggcagcactgcataattctcttactgtcatg
```

FIG. 46 (continued)

```
ccatccgtaagatgcttttctgtgactggtgagtactcaaccaagtcattctgagaatagtgtatgcggcgaccgagt
tgctcttgcccggcgtcaatacgggataataccgcgccacatagcagaactttaaaagtgctcatcattggaaaacgt
tcttcggggcgaaaactctcaaggatcttaccgctgttgagatccagttcgatgtaacccactcgtgcacccaactga
tcttcagcatcttttactttcaccagcgtttctgggtgagcaaaaacaggaaggcaaaatgccgcaaaaaagggaata
agggcgacacggaaatgttgaatactcatactcttcctttttcaatattattgaagcatttatcagggttattgtctc
atgagcggatacatatttgaatgtatttagaaaaataaacaaataggggttccgcgcacatttccccgaaaagtgcca
cctgacgtcgacggatcgggagatctcccgatcccctatggtctcagtacaatctgctctgatgccgcatagt
taagccagtatctgctccctgcttgtgtgttggaggtcgctgagtagtgcgcgagcaaaatttaagctacaacaaggc
aaggcttgaccgacaattgcatgaagaatctgcttagg   (SEQ ID NO: 185)

>20_U551FEL190-VL3_hIgkCL-pcDNA3.4
gttaggcgtttttgcgctgcttcgcgatgtacgggccagatatacgcgttgacattgattattgactagttattaatag
taatcaattacggggtcattagttcatagcccatatatggagttccgcgttacataacttacggtaaatggcccgcct
ggctgaccgcccaacgacccccgcccattgacgtcaataatgacgtatgttcccatagtaacgccaatagggactttc
cattgacgtcaatgggtggagtatttacggtaaactgcccacttggcagtacatcaagtgtatcatatgccaagtacg
cccctattgacgtcaatgacggtaaatggcccgcctggcattatgcccagtacatgacctttatgggactttcctact
tggcagtacatctacgtattagtcatcgctattaccatggtgatgcggttttggcagtacatcaatgggcgtggatag
cggtttgactcacggggatttccaagtctccaccccattgacgtcaatgggagtttgttttggcaccaaaatcaacgg
gactttccaaaatgtcgtaacaactccgccccattgacgcaaatgggcggtaggcgtgtacggtgggaggtctatata
agcagagctcgtttagtgaaccgtcagatcgcctggagacgccatccacgctgttttgacctccatagaagacaccgg
gaccgatccagcctccggactctagaggatcgaacccttgaattccgcgccaccatggctggtcatgtattattc
tgtttctggtcgcaactgctacaggggtccatagtGAGATCGTGCTGACCCAGTCTCCAGGCACACTCAGCCTGTCTC
CTGGCGAGCGGGCTACCCTGTCCTGCACCGCCAGCAGCTCCGTGTCCTCTTCTTTTCTGCACTGGTACCAGCAGAAAC
CTGGACAAGCTCCTCAGCTGCTGGATCTACTCCACCTCCAACCTGGCCTCTGGCATCCCCGATAGATTCTCCGGCTCTG
GCTCCGGCACCGACTACACACTGACCATCTCCAGACTGGAACCTGAGGACTTCGCCACCTACTACTGTCATCAGTACC
ACCACTCCCCTTACATCTATACCTTCGGCGGAGGCACCAAGCTGGAAATCAAGaggacagtggccgcccccaagcgtgt
tcatcttttcccccttccgacgagcagctgaagtctggcaccgccagcgtggtgtgcctgctgaacaacttctaccctc
gggaggccaaggtccagtggaaggtggataacgccctgcagtctggcaatagccaggagtccgtgaccgagcaggact
ctaaggatagcacatattccctgtctagcaccctgacactgagcaaggccgattacgagaagcacaaggtgtatgcct
gtgaagtcacccatcaggggctgtcatcaccgtcactaagtcattcaatcgcggagaatgctgataagcttaagggt
tcgatccctaccggttagtaatgagtttgatatctcgacaatcaacctctggattacaaaatttgtgaaagattgact
ggtattcttaactatgttgctccttttacgctatgtggatacgctgctttaatgcctttgtatcatgctattgcttcc
cgtatggctttcattttctcctccttgtataaatcctggttgctgtctctttatgaggagttgtggcccgttgtcagg
caacgtggcgtggtgtgcactgtgtttgctgacgcaacccccactggttgggcattgccaccacctgtcagctcctt
tccgggactttcgctttccccctccctattgccacggcggaactcatcgccgcctgccttgcccgctgctggacaggg
gctcggctgttgggcactgacaattccgtggtgttgtcggggaagctgacgtcctttccatggctgctcgcctgtgtt
gccacctggattctgcgcgggacgtccttctgctacgtccttcggccctcaatccagcggaccttccttcccgcggc
ctgctgccggctctgcggcctcttccgcgtcttcgccttcgccctcagacgagtcggatctccctttgggccgcctcc
ccgcctggaaacggggaggctaactgaaacacggaaggagacaataccggaaggaacccgcgctatgacggcaataa
aaagacagaataaaacgcacgggtgttgggtcgtttgttcataaacgcggggttcggtcccaggctggcactctgtc
gataccccaccgagacccattggggccaatacgcccgcgtttcttccttttcccaccccaccccccaagttcgggt
gaaggcccagggctcgcagccaacgtcgggcggcaggccctgccatagcagatctgcgcagctggggctctaggggg
tatccccacgcgccctgtagcggcgcattaagcgcggcgggtgtggtggttacgcgcagcgtgaccgctacacttgcc
agcgccctagcgcccgctcctttcgctttcttcccttcctttctcgccacgttcgccggcttccccgtcaagctcta
aatcgggcatccctttagggttccgatttagtgctttacggcacctcgaccccaaaaaacttgattagggtgatggt
tcacgtagtgggccatcgccctgatagacggtttttcgccctttgacgttggagtccacgttctttaatagtggactc
ttgttccaaactggaacaacactcaaccctatctcggtctattcttttgatttataagggattttggggatttcggcc
tattggttaaaaaatgagctgatttaacaaaaatttaacgcgaattaattctgtggaatgtgtgtcagttagggtgtg
gaaagtccccaggctccccagcaggcagaagtatgcaaagcatgcatctcaattagtcagcaaccaggtgtggaaagt
ccccaggctccccagcaggcagaagtatgcaaagcatgcatctcaattagtcagcaaccatagtcccgcccctaactc
cgcccatcccgcccctaactccgcccagttccgcccattctccgccccatggctgactaatttttttttatttatgcag
aggccgaggccgcctctgcctctgagctattccagaagtagtgaggaggcttttttggaggcctaggcttttgcaaaa
agctccccgggagcttgtatatccattttcggatctgatcaagagacaggatgaggatcgtttcgcatgattgaacaag
atggattgcacgcaggttctccggccgcttgggtggagaggctattcggctatgactgggcacaacagacaatcggct
```

FIG. 46 (continued)

```
gctctgatgccgccgtgttccggctgtcagcgcaggggcgcccggttcttttttgtcaagaccgacctgtccggtgccc
tgaatgaactgcaggacgaggcagcgcggctatcgtggctggccacgacgggcgttccttgcgcagctgtgctcgacg
ttgtcactgaagcgggaagggactggctgctattgggcgaagtgccggggcaggatctcctgtcatctcaccttgctc
ctgccgagaaagtatccatcatggctgatgcaatgcggcggctgcatacgcttgatccggctacctgccattcgacc
accaagcgaaacatcgcatcgagcgagcacgtactcggatggaagccggtcttgtcgatcaggatgatctggacgaag
agcatcaggggctcgcgccgacgaactgttcgccaggctcaaggcgcgcatgcccgacggcgaggatctcgtcgtga
cccatggcgatgcctgcttgccgaatatcatggtggaaaatggccgctttttctggattcatcgactgtggccggctgg
gtgtggcggaccgctatcaggacatagcgttggctaccgtgatattgctgaagagcttggcggcgaatgggctgacc
gcttcctcgtgctttacggtatcgccgctcccgattcgcagcgcatcgccttctatcgccttcttgacgagttcttct
gagcgggactctggggttcgcgaaatgaccgaccaagcgacgcccaacctgccatcacgagatttcgattccaccgcc
gccttctatgaaaggttgggcttcggaatcgtttcgggacgccggctggatgatcctccagcgcggggatctcatg
ctggagttcttcgcccaccccaacttgtttattgcagcttataatggttacaaataaagcaatagcatcacaaatttc
acaaataaagcattttttcactgcattctagttgtggtttgtccaaactcatcaatgtatcttatcatgtctgtata
ccgtcgacctctagctagagcttggcgtaatcatggtcatagctgtttcctgtgtgaaattgttatccgctcacaatt
ccacacaacatacgagccggaagcataaagtgtaaagcctggggtgcctaatgagtgagctaactcacattaattgcg
ttgcgctcactgcccgctttccagtcgggaaacctgtcgtgccagctgcattaatgaatcggccaacgcgcggggaga
ggcggtttgcgtattgggcgctcttccgcttcctcgctcactgactcgctgcgctcggtcgttcggctgcggcgagcg
gtatcagctcactcaaaggcggtaatacggttatccacagaatcaggggataacgcaggaaagaacatgtgagcaaaa
ggccagcaaaaggccaggaaccgtaaaaaggccgcgttgctggcgtttttccataggctccgcccccctgacgagcat
cacaaaaatcgacgctcaagtcagaggtggcgaaacccgacaggactataaagataccaggcgtttccccctggaagc
tccctcgtgcgctctcctgttccgaccctgccgcttaccggatacctgtccgcctttctcccttcgggaagcgtggcg
ctttctcaatgctcacgctgtaggtatctcagttcggtgtaggtcgttcgctccaagctgggctgtgtgcacgaaccc
cccgttcagcccgaccgctgcgccttatccggtaactatcgtcttgagtccaacccggtaagacacgacttatcgcca
ctggcagcagccactggtaacaggattagcagagcgaggtatgtaggcggtgctacagagttcttgaagtggtggcct
aactacggctacactagaaggacagtatttggtatctgcgctctgctgaagccagttaccttcggaaaaagagttggt
agctcttgatccggcaaacaaaccaccgctggtagcggtggtttttttgtttgcaagcagcagattacgcgcagaaaa
aaaggatctcaagaagatcctttgatcttttctacggggtctgacgctcagtggaacgaaaactcacgttaagggatt
ttggtcatgagattatcaaaaaggatcttcacctagatccttttaaattaaaaatgaagttttaaatcaatctaaagt
atatatgagtaaacttggtctgacagttaccaatgcttaatcagtgaggcacctatctcagcgatctgtctatttcgt
tcatccatagttgcctgactccccgtcgtgtagataactacgatacgggagggcttaccatctggccccagtgctgca
atgataccgcgagacccacgctcaccggctccagatttatcagcaataaaccagccagccggaagggccgagcgcaga
agtggtcctgcaactttatccgcctccatccagtctattaattgttgccgggaagctagagtaagtagttcgccagtt
aatagtttgcgcaacgttgttgccattgctacaggcatcgtggtgtcacgctcgtcgtttggtatggcttcattcagc
tccggttcccaacgatcaaggcgagttacatgatcccccatgttgtgcaaaaaagcggttagctccttcggtcctccg
atcgttgtcagaagtaagttggccgcagtgttatcactcatggttatggcagcactgcataattctcttactgtcatg
ccatccgtaagatgcttttctgtgactggtgagtactcaaccaagtcattctgagaatagtgtatgcggcgaccgagt
tgctcttgcccggcgtcaatacgggataataccgcgccacatagcagaactttaaaagtgctcatcattggaaaacgt
tcttcggggcgaaaactctcaaggatcttaccgctgttgagatccagttcgatgtaacccactcgtgcacccaactga
tcttcagcatcttttactttcaccagcgtttctgggtgagcaaaaacaggaaggcaaaatgccgcaaaaaagggaata
agggcgacacggaaatgttgaatactcatactcttcctttttcaatattattgaagcatttatcagggttattgtctc
atgagcggatacatatttgaatgtatttagaaaaataaacaaataggggttccgcgcacatttccccgaaaagtgcca
cctgacgtcgacggatcgggagatctcccgatcccctatggtcgactctcagtacaatctgctctgatgccgcatagt
taagccagtatctgctccctgcttgtgtgttggaggtcgctgagtagtgcgcgagcaaaattaagctacaacaaggc
aaggcttgaccgacaattgcatgaagaatctgcttagg    (SEQ ID NO: 186)

>23_U551FEL190-VL4_hIgkCL-pcDNA3.4
gttaggcgttttgcgctgcttcgcgatgtacgggccagatatacgcgttgacattgattattgactagttattaatag
taatcaattacggggtcattagttcatagcccatatatggagttccgcgttacataacttacggtaaatggcccgcct
ggctgaccgcccaacgacccccgcccattgacgtcaataatgacgtatgttcccatagtaacgccaatagggactttc
cattgacgtcaatgggtggagtatttacggtaaactgcccacttggcagtacatcaagtgtatcatatgccaagtacg
ccccctattgacgtcaatgacggtaaatggcccgcctggcattatgcccagtacatgaccttatgggactttcctact
tggcagtacatctacgtattagtcatcgctattaccatggtgatgcggttttggcagtacatcaatgggcgtggatag
cggtttgactcacggggatttccaagtctccaccccattgacgtcaatgggagtttgttttggcaccaaaatcaacgg
gactttccaaaatgtcgtaacaactccgccccattgacgcaaatgggcggtaggcgtgtacggtgggaggtctatata
```

FIG. 46 (continued)

```
agcagagctcgtttagtgaaccgtcagatcgcctggagacgccatccacgctgttttgacctccatagaagacaccgg
gaccgatccagcctccggactctagaggatcgaaccttgaattccccgccgccaccatgggctggtcatgtattattc
tgtttctggtcgcaactgctacaggggtccatagtGAGATCGTGCTGACCCAATCTCCTGGCACCCTGTCTCTGAGCC
CAGGCGAGAGAGCCACACTCTCCTGCACCGCTTCTTCCTCCGTGTCCTCTAGCTTTCTGCACTGGTACCAGCAGAAAC
CCGGCCAGGCTCCTCAGCTGTGGATCTACTCCACCTCCAACCTGGCCTCTGGCATCCCTGCCAGATTCTCCGGATCCG
GCTCTGGCACCGATTATACACTGACCATCTCCCGGCTGGAACCTGAGGACTTCGCCACCTACTACTGTCACCAGTACC
ACCATAGCCCTTACATCTACACCTTCGGCGGCGGAACCAAGCTGGAAATCAAGaggacagtggccgcccaagcgtgt
tcatctttcccccttccgacgagcagctgaagtctggcacgccagcgtggtgtgcctgctgaacaacttctacccctc
gggaggccaaggtccagtggaaggtggataacgccctgcagtctggcaatagccaggagtccgtgaccgagcaggact
ctaaggatagcacatattccctgtctagcaccctgacactgagcaaggccgattacgagaagcacaaggtgtatgcct
gtgaagtcacccatcaggggctgtcatcaccgtcactaagtcattcaatcgcggagaatgctgataagcttaagggt
tcgatccctaccggttagtaatgagtttgatatctcgacaatcaacctctggattacaaaatttgtgaaagattgact
ggtattcttaactatgttgctccttttacgctatgtggatacgctgctttaatgcctttgtatcatgctattgcttcc
cgtatggctttcattttctcctccttgtataaatcctggttgctgtgtctctttatgaggagttgtggcccgttgtcagg
caacgtggcgtggtgtgcactgtgtttgctgacgcaacccccactggttgggggcattgccaccacctgtcagctcctt
tccgggactttcgctttccccctccctattgccacggcggaactcatcgcgcctgccttgcccgctgctggacaggg
gctcggctgttgggcactgacaattccgtggtgttgtcggggaagctgacgtcctttccatggctgctcgcctgtgtt
gccacctggattctgcgcgggacgtccttctgctacgtcccttcggccctcaatccagcggaccttccttccgcggc
ctgctgccggctctgcggcctcttccgcgtcttcgccttcgccctcagacgagtcggatctcccctttgggccgcctcc
ccgcctggaaacggggggaggctaactgaaacacggaaggagacaatacggaaggaacccgcgctatgacggcaataa
aaagacagaataaaacgcacgggtgttgggtcgtttgttcataaacgcggggttcggtcccagggctggcactctgtc
gataccccaccgagacccattggggccaatacgcccgcgttcttccttttccccacccccaccccccaagttcgggt
gaaggcccaggggctcgcagccaacgtcggggcggcaggccctgccatagcagatctgcgcagctggggctctaggggg
tatccccacgcgccctgtagcggcgcattaagcgcggcgggtgtggtggttacgcgcagcgtgaccgctacacttgcc
agcgccctagcgcccgctccttcgctttcttccctctccctttcctcgccacgttcgccggctttccccgtcaagctcta
aatcgggcatccctttagggttccgatttagtgctttacggcacctcgaccccaaaaaacttgattaggtgatggt
tcacgtagtgggccatcgccctgatagacggtttttcgcccttgacgttggagtccacgttctttaatagtggactc
ttgttccaaactggaacaacactcaacctatatctcggtctattcttttgatttataaggattttgggatttcggcc
tattggttaaaaaatgagctgatttaacaaaaatttaacgcgaattaattctgtggaatgtgtgtcagttaggtgtg
gaaagtccccaggctccccagcaggcagaagtatgcaaagcatgcatctcaattagtcagcaaccaggtgtggaaagt
ccccaggctccccagcaggcagaagtatgcaaagcatgcatctcaattagtcagcaaccatagtcccgcccctaactc
cgcccatcccgcccctaactccgcccagttccgcccattctccgccccatggctgactaatttttttttatttatgcag
aggccgaggccgcctctgcctctgagctattccagaagtagtgaggaggcttttttggaggcctaggcttttgcaaaa
agctcccgggagcttgtatatccattttcggatctgatcaagagacaggatgaggatcgtttcgcatgattgaacaag
atggattgcacgcaggttctccggccgcttgggtggagaggctattcggctatgactgggcacaacagacaatcggct
gctctgatgccgccgtgttccggctgtcagcgcaggggcgcccggttcttttttgtcaagaccgacctgtccggtgccc
tgaatgaactgcaggacgaggcagcgcggctatcgtggctggccacgacgggcgttccttgcgcagctgtgctcgacg
ttgtcactgaagcgggaagggactggctgctattgggcgaagtgccggggcaggatctcctgtcatctcaccttgctc
ctgccgagaaagtatccatcatggctgatgcaatgcggcggctgcatacgcttgatccggctacctgcccattcgacc
accaagcgaaacatcgcatcgagcgagcacgtactcggatggaagccggtcttgtcgatcaggatgatctggacgaag
agcatcaggggctcgcgccagccgaactgttcgccaggctcaaggcgcgcatgcccgacggcgaggatctcgtcgtga
cccatggcgatgcctgcttgccgaatatcatggtggaaaatggccgcttttctggattcatcgactgtggccggctgg
gtgtggcggaccgctatcaggacatagcgttggctaccgtgatattgctgaagagcttggcggcgaatgggctgacc
gcttcctcgtgctttacggtatcgccgctcccgattcgcagcgcatcgccttctatcgccttcttgacgagttcttct
gagcgggactctggggttcgcgaaatgaccgaccaagcgacgcccaacctgccatcacgagatttcgattccaccgcc
gccttctatgaaaggttgggcttcggaatcgttttccgggacgccggctggatgatcctccagcgcggggatctcatg
ctggagttcttcgcccaccccaacttgtttattgcagcttataatggttacaaataaagcaatagcatcacaaatttc
acaaataaagcatttttttcactgcattctagttgtggtttgtccaaactcatcaatgtatcttatcatgtctgtata
ccgtcgacctctagctagagcttggcgtaatcatggtcatagctgtttcctgtgtgaaattgttatccgctcacaatt
ccacacaacatacgagccggaagcataaagtgtaaagcctggggtgcctaatgagtgagctaactcacattaattgcg
ttgcgctcactgcccgctttccagtcgggaaacctgtcgtgccagctgcattaatgaatcggccaacgcgcggggaga
ggcggtttgcgtattgggcgctcttccgcttcctcgctcactgactcgctgcgctcggtcgttcggctgcggcgagcg
gtatcagctcactcaaaggcggtaatacggttatccacagaatcaggggataacgcaggaaagaacatgtgagcaaaa
ggccagcaaaaggccaggaaccgtaaaaaggccgcgttgctggcgtttttccataggctccgcccccctgacgagcat
```

FIG. 46 (continued)

```
cacaaaaatcgacgctcaagtcagaggtggcgaaacccgacaggactataaagataccaggcgtttcccctggaagc
tccctcgtgcgctctcctgttccgacctgccgcttaccggatacctgtccgcctttctccttcgggaagcgtggcg
ctttctcaatgctcacgctgtaggtatctcagttcggtgtaggtcgttcgctccaagctgggctgtgtgcacgaacc
ccgttcagccgaccgctgcgccttatccggtaactatcgtcttgagtccaaccggtaagacacgacttatcgcca
ctggcagcagccactggtaacaggattagcagagcgaggtatgtaggcggtgctacagagttcttgaagtggtggcct
aactacggctacactagaaggacagtatttggtatctgcgctctgctgaagccagttaccttcggaaaaagagttggt
agctcttgatccggcaaacaaaccaccgctggtagcggtggttttttttgtttgcaagcagcagattacgcgcagaaaa
aaaggatctcaagaagatcctttgatcttttctacggggtctgacgctcagtggaacgaaaactcacgttaagggatt
ttggtcatgagattatcaaaaaggatcttcacctagatccttttaaattaaaaatgaagttttaaatcaatctaaagt
atatatgagtaaacttggtctgacagttaccaatgcttaatcagtgaggcacctatctcagcgatctgtctatttcgt
tcatccatagttgcctgactccccgtcgtgtagataactacgatacgggagggcttaccatctggccccagtgctgca
atgatacgcgagacccacgctcaccggctccagatttatcagcaataaaccagccagccggaagggccgagcgcaga
agtggtcctgcaactttatccgcctccatccagtctattaattgttgccgggaagctagagtaagtagttcgccagtt
aatagtttgcgcaacgttgttgccattgctacaggcatcgtggtgtcacgctcgtcgtttggtatggcttcattcagc
tccggttcccaacgatcaaggcgagttacatgatccccccatgttgtgcaaaaaagcggttagctccttcggtcctccg
atcgttgtcagaagtaagttggccgcagtgttatcactcatggttatggcagcactgcataattctcttactgtcatg
ccatccgtaagatgcttttctgtgactggtgagtactcaaccaagtcattctgagaatagtgtatgcggcgaccgagt
tgctcttgcccggcgtcaatacgggataataccgcgccacatagcagaactttaaaagtgctcatcattggaaaacgt
tcttcggggcgaaaactctcaaggatcttaccgctgttgagatccagttcgatgtaacccactcgtgcacccaactga
tcttcagcatcttttactttcaccagcgtttctgggtgagcaaaaacaggaaggcaaaatgccgcaaaaaagggaata
agggcgacacggaaatgttgaatactcatactcttcctttttcaatattattgaagcatttatcagggttattgtctc
atgagcggatacatatttgaatgtatttagaaaaataaacaaataggggttccgcgcacatttccccgaaaagtgcca
cctgacgtcgacggatcgggagatctcccgatcccctatggtcgactctcagtacaatctgctctgatgccgcatagt
taagccagtatctgctccctgcttgtgtgttggaggtcgctgagtagtgcgcgagcaaaatttaagctacaacaaggc
aaggcttgaccgacaattgcatgaagaatctgcttagg    (SEQ ID NO: 187)

>2_U551FEL190-VH2-hIgG1CH(K222A)-pcDNA3.4
gttaggcgttttgcgctgcttcgcgatgtacgggccagatatacgcgttgacattgattattgactagttattaatag
taatcaattacggggtcattagttcatagcccatatatggagttccgcgttacataacttacggtaaatggcccgcct
ggctgaccgcccaacgacccccgcccattgacgtcaataatgacgtatgttcccatagtaacgccaatagggactttc
cattgacgtcaatgggtggagtatttacggtaaactgcccacttggcagtacatcaagtgtatcatatgccaagtacg
ccccctattgacgtcaatgacggtaaatggcccgcctggcattatgcccagtacatgaccttatgggactttcctact
tggcagtacatctacgtattagtcatcgctattaccatggtgatgcggttttggcagtacatcaatgggcgtggatag
cggtttgactcacggggatttccaagtctccaccccattgacgtcaatgggagtttgttttggcaccaaaatcaacgg
gactttccaaaatgtcgtaacaactccgccccattgacgcaaatgggcggtaggcgtgtacggtgggaggtctatata
agcagagctcgtttagtgaaccgtcagatcgcctggagacgccatccacgctgttttgacctccatagaagacaccgg
gaccgatccagcctccggactctagaggatcgaacccttgaattcccgccgccaccatgggctggtcatgcattattc
tgtttctggtcgcaactgctacaggcgtgcatagtcaggtgcagctgcaagagtccggccctggactcgtgaagcct
ccgagacactgtctctgacatgtaccgtgtctggcttctccctgtccatctactccgtgcactggatcagacagcctc
ctggcaagggctggaatggatcggcatgatctggggaggcggctcttccgactacaactccgccctgaaatctcggc
tgaccatctccaaggacacctctaagaaccaggtcagcctgaagctgagctctgtgaccgctgctgataccgccgtgt
actactgcgcagaaatggcaacttctacgccatggactattggggccagggcaccctggtgaccgtgtccagcgcca
gcaccaagggcccttccgtgtttccactggcccctctctaaatccacatctggcggcaccgccgccctgggctgtc
tggtgaaggactacttcccagagcctgtgacagtgtcctggaactctggcgccctgacatccggcgtgcacacattc
cagccgtgctgcagagcctccggctctgtacaaccgtgtctagcgtggtgacagtgccctctagcctggcacacaga
cctatatctgcaacgtgaatcacaagccaagcaataccaaggtgacaagaaggtggagcccaagtcctgtgatgcca
cacacacctgcccccttgtcctgctccccgagctgctgggcggccctagcgtgttcctgtttccacccaagcctaagg
acaccctgatgatctcccggacacccgaggtgacctgcgtggtggtggacgtgtctcacgaggatcctgaggtgaagt
tcaactggtatgtggatggcgtggaggtgcacaatgccaagaccaagccagagaggagcagtacaactctacatata
gggtggtgagcgtgctgaccgtgctgcaccaggactggctgaacggcaaggagtataagtgcaaggtgtccaataagg
ccctgcccgcccccatcgagaagacaatcagcaaggccaagggccagcctcgggagccacaggtgtacacccctgcctc
catccagagacgagctgaccaagaaccaggtgtctctgacatgtctggtgaaggcttctatcctagcgatatcgcg
tggagtgggagtccaatggccagccagagaacaattacaagaccacacccctgtgctggactccgatggctccttct
ttctgtattccaagctgaccgtggataagtctcggtggcagcagggcaacgtgttcagctgttccgtgatgcacgaag
```

FIG. 46 (continued)

```
ccctgcataatcactatactcagaaatccctgtccctgtcacctggaaagtgataagcttaagggttcgatccctacc
ggttagtaatgagtttgatatctcgacaatcaacctctggattacaaaatttgtgaaagattgactggtattcttaac
tatgttgctccttttacgctatgtggatacgctgctttaatgcctttgtatcatgctattgcttcccgtatggctttc
attttctcctccttgtataaatcctggttgctgtctctttatgaggagttgtggcccgttgtcaggcaacgtggcgtg
gtgtgcactgtgtttgctgacgcaaccccactggttggggcattgccaccacctgtcagctcctttccgggactttc
gctttccccctccctattgccacggcgggaactcatcgccgcctgccttgcccgctgctggacagggggctcggctgttg
ggcactgacaattccgtggtgttgtcgggggaagctgacgtcctttccatggctgctcgcctgtgttgccacctggatt
ctgcgcgggacgtccttctgctacgtcccttcggccctcaatccagcggaccttccttcccgcggcctgctgccggct
ctgcggcctcttccgcgtcttcgccttcgccctcagacgagtcggatctcccctttgggccgcctccccgcctgaaac
gggggaggctaactgaaacacggaaggagacaatacggaaggaacccgcgctatgacggcaataaaaagacagaata
aaacgcacgggtgttgggtcgtttgttcataaacgcggggttcggtcccagggctggcactctgtcgataccccaccg
agacccattggggccaatacgccgcgcgttcttccttttcccacccaccccccaagttcgggtgaaggcccaggg
ctcgcagccaacgtcggggcggcaggccctgccatagcagatctgcgcagctggggctctaggggggtatcccacgcg
ccctgtagcggcgcattaagcgcggcgggtgtggtggttacgcgcagcgtgaccgctacacttgccagcgccctagcg
ccgctcctttcgcttcttcccttcctttctcgccacgttcgcggcctttccccgtcaagctctaaatcggggcatc
cctttaggggttccgatttagtgctttacggcacctcgaccccaaaaaacttgattagggtgatggttcacgtagtggg
ccatcgccctgatagacggtttttcgcccttttgacgttggagtccacgttctttaatagtggactcttgttccaaact
ggaacaacactcaaccctatctcggtctattcttttgatttataagggattttgggggatttcggcctattggttaaaa
aatgagctgatttaacaaaaatttaacgcgaattaattctgtggaatgtgtgtcagttagggtgtggaaagtccccag
gctcccagcaggcagaagtatgcaaagcatgcatctcaattagtcagcaaccaggtgtggaaagtccccaggctccc
cagcaggcagaagtatgcaaagcatgcatctcaattagtcagcaaccatagtccgccctaactccgcccatcccgc
ccctaactccgcccagttccgcccattctccgccccatggctgactaattttttttatttatgcagaggccgaggccg
cctctgcctctgagctattccagaagtagtgaggaggcttttttggaggcctaggcttttgcaaaaagctcccgggag
cttgtatatccatttcggatctgatcaagagacaggatgaggatcgtttcgcatgattgaacaagatggattgcacg
caggttctccggccgcttgggtggagaggctattcggctatgactgggcacaacagacaatcggctgctctgatgccg
ccgtgttccggctgtcagcgcaggggcgcccggttctttttgtcaagaccgacctgtccggtgccctgaatgaactgc
aggacgaggcagcgcggctatcgtggctggccacgacggcgttccttgcgcagctgtgctcgacgttgtcactgaag
cgggaagggactggctgctattgggcgaagtgccggggcaggatctcctgtcatctcaccttgctcctgccgagaaag
tatccatcatggctgatgcaatgcggcggctgcatacgcttgatccggctacctgcccattcgaccaccaagcgaaac
atcgcatcgagcgagcacgtactcggatggaagccggtcttgtcgatcaggatgatctggacgaagagcatcaggggc
tcgcgccagccgaactgttcgccaggctcaaggcgcgcatgcccgacggcgaggatctcgtcgtgacccatggcgatg
cctgcttgccgaatatcatggtggaaaatggccgcttttctggattcatcgactgtggccggctggtgtggcggacc
gctatcaggacatagcgttggctacccgtgatattgctgaagagcttggcggcgaatgggctgaccgcttcctcgtgc
tttacggtatcgccgctcccgattcgcagcgcatcgccttctatcgccttcttgacgagttcttctgagcgggactct
ggggttcgcgaaatgaccgaccaagcgacgcccaacctgccatcacgagatttcgattccaccgcgccttctatgaa
aggttgggcttcggaatcgttttccgggacgccggctggatgatcctccagcgcggggatctcatgctggagttcttc
gcccaccccaacttgtttattgcagcttataatggttacaaataaagcaatagcatcacaaatttcacaaataaagca
ttttttttcactgcattctagttgtggtttgtccaaactcatcaatgtatcttatcatgtctgtataccgtcgacctct
agctagagcttggcgtaatcatggtcatagctgtttcctgtgtgaaattgttatccgctcacaattccacacaacata
cgagccggaagcataaagtgtaaagcctggggtgcctaatgagtgagctaactcacattaattgcgttgcgctcactg
cccgctttccagtcgggaaacctgtcgtgccagctgcattaatgaatcggccaacgcgcggggagaggcggtttgcgt
attgggcgctcttccgcttcctcgctcactgactcgctgcgctcggtcgttcggctgcggcgagcggtatcagctcac
tcaaaggcggtaatacggttatccacagaatcaggggataacgcaggaaagaacatgtgagcaaaaggccagcaaaag
gccaggaaccgtaaaaaggccgcgttgctggcgtttttccataggctccgcccccctgacgagcatcacaaaaatcga
cgctcaagtcagaggtggcgaaacccgacaggactataaagataccaggcgtttccccctggaagctccctcgtgcgc
tctcctgttccgaccctgccgcttaccggatacctgtccgcctttctcccttcgggaagcgtggcgctttctcaatgc
tcacgctgtaggtatctcagttcggtgtaggtcgttcgctccaagctgggctgtgtgcacgaaccccccgttcagccc
gaccgctgcgccttatccggtaactatcgtcttgagtccaacccggtaagacacgacttatcgccactggcagcagcc
actggtaacaggattagcagagcgaggtatgtaggcggtgctacagagttcttgaagtggtggcctaactacggctac
actagaaggacagtatttggtatctgcgctctgctgaagccagttaccttcggaaaaagagttggtagctcttgatcc
ggcaaacaaaccaccgctggtagcggtggtttttttgtttgcaagcagcagattacgcgcagaaaaaaaggatctcaa
gaagatcctttgatcttttctacggggtctgacgctcagtggaacgaaaactcacgttaagggattttggtcatgaga
ttatcaaaaaggatcttcacctagatccttttaaattaaaaatgaagttttaaatcaatctaaagtatatatgagtaa
acttggtctgacagttaccaatgcttaatcagtgaggcacctatctcagcgatctgtctatttcgttcatccatagtt
```

FIG. 46 (continued)

```
gcctgactcccgtcgtgtagataactacgatacgggagggcttaccatctggcccagtgctgcaatgatacogcga
gacccacgctcaccggctccagatttatcagcaataaaccagccagccggaagggccgagcgcagaagtggtcctgca
actttatccgcctccatccagtctattaattgttgccgggaagctagagtaagtagttcgccagttaatagtttgcgc
aacgttgttgccattgctacaggcatcgtggtgtcacgctcgtcgtttggtatggcttcattcagctccggttcccaa
cgatcaaggcgagttacatgatccccatgttgtgcaaaaaagcggttagctccttcggtcctccgatcgttgtcaga
agtaagttggccgcagtgttatcactcatcggttatggcagcactgcataattctcttactgtcatgccatccgtaaga
tgcttttctgtgactggtgagtactcaaccaagtcattctgagaatagtgtatgcggcgaccgagttgctcttgcccg
gcgtcaatacgggataatacogcgccacatagcagaacttttaaaagtgctcatcattggaaaacgttcttcggggcga
aaactctcaaggatcttaccgctgttgagatccagttcgatgtaacccactcgtgcacccaactgatcttcagcatct
tttactttcaccagcgtttctgggtgagcaaaaacaggaaggcaaaatgccgcaaaaaaggaataagggcgacacgg
aaatgttgaatactcatactcttcctttttcaatattattgaagcatttatcagggttattgtctcatgagcggatac
atatttgaatgtatttagaaaaataaacaaataggggttccgcgcacatttccccgaaaagtgccacctgacgtcgac
ggatcgggagatctcccgatccctatggtcgactctcagtacaatctgctctgatgcgcatagttaagccagtatc
tgctccctgcttgtgtgttggaggtcgctgagtagtgcgcgagcaaaatttaagctacaacaaggcaaggcttgaccg
acaattgcatgaagaatctgcttagg     (SEQ ID NO: 188)

>4_U551FEL190-VH4-hIgG1CH(K222A)-pcDNA3.4
gttaggcgttttgcgctgcttcgcgatgtacgggccagatatacgcgttgacattgattattgactagttattaatag
taatcaattacggggtcattagttcatagcccatatatggagttccgcgttacataacttacggtaaatggcccgcct
ggctgaccgcccaacgacccccgcccattgacgtcaataatgacgtatgttcccatagtaacgccaatagggactttc
cattgacgtcaatgggtggagtatttacggtaaactgcccacttggcagtacatcaagtgtatcatatgccaagtacg
ccccctattgacgtcaatgacggtaaatggcccgcctggcattatgcccagtacatgaccttatgggactttcctact
tggcagtacatctacgtattagtcatcgctattaccatggtgatgcggttttggcagtacatcaatgggcgtggatag
cggtttgactcacggggatttccaagtctccaccccattgacgtcaatgggagtttgttttggcaccaaaatcaacgg
gactttccaaaatgtcgtaacaactccgccccattgacgcaaatgggcggtaggcgtgtacggtgggaggtctatata
agcagagctcgtttagtgaaccgtcagatcgcctggagacgccatccacgctgttttgacctccatagaagacaccgg
gaccgatccagcctccggactctagaggatcgaaccccttgaattccgccgccaccatgggctggtcatgcattattc
tgtttctggtcgcaactgctacaggcgtgcatagtcaggtgcagctgcaagagtccggaccggcctcgtgaagcctt
ccgagacactgtctctgacctgtaccgtgtctggcttctccctgtccatctactccgtgcactggatccggcagcctc
ctggcaagggcctggaatggctgggcatgatctggggcggcggaagctccgactacaactccgcctgaaatctagac
tgaccatctccaaggacacctctaagaaccaggtcagcctgaagctgagctctgtgaccgccgctgataccgctatgt
actactgcgccagaaatggcaacttctacgccatggactattggggccagggcacctggtgacagtgtcctctgcca
gcaccaagggcccttccgtgtttccactggcccccctcctctaaatccacatctggcggcaccgcgccctgggctgtc
tggtgaaggactacttcccagagcctgtgacagtgtcctggaactctggcgccctgacatccggcgtgcacacattc
cagccgtgctgcagagctccggcctgtacagcctgtctagcgtggtgacagtgccctcctctagcctgggcacacaga
cctatatctgcaacgtgaatcacaagccaagcaataccaaggtggacaagaaggtggagcccaagtcctgtgatgcca
cacacacctgcccccttgtcctgctcccgagctgctgggcggccctagcgtgttcctgtttccacccaagcctaagg
acaccctgatgatctcccggacaccgaggtgacctgcgtggtggtggacgtgtctcacgaggatcctgaggtgaagt
tcaactggtatgtggatggcgtggaggtgcacaatgccaagaccaagccagagaggagcagtacaactctacatata
gggtggtgagcgtgctgacogtgctgcaccaggactggctgaacggcaaggagtataagtgcaaggtgtccaataagg
ccctgccgccccatcgagaagacaatcagcaaggccaagggccagcctcgggagccacaggtgtacacoctgcctc
catccagagacgagctgaccaagaaccaggtgtctctgacatgtctggtgaaggcttctatcctagcgatatcgcg
tggagtgggagtccaatggccagccagagaacaattacaagaccacacccctgtgctggactccgatggctccttct
ttctgtattccaagctgaccgtggataagtctcggtggcagcaggggcaacgttccagctgttccgtgatgcacgaag
ccctgcataatcactactaccagaaatccctgcctctgtccgtgaaagtgatagcttaagggttcgatcctacc
ggttagtaatgagtttgatatctcgacaatcaacctctggattacaaaatttgtgaaagattgactggtattcttaac
tatgttgctccttttacgctatgtggatacgctgctttaatgcctttgtatcatgctattgcttcccgtatggcttc
attttctcctccttgtataaatcctggttgctgtctctttatgaggagttgtggcccgttgtcaggcaacgtggcgtg
gtgtgcactgtgtttgctgacgcaaccccoactggttggggcattgccaccacctgtcagctcctttccgggactttc
gctttccccctccctattgccacggcggaactcatcgccgcctgccttgccogctgctggacagggggctcggctgttg
ggcactgacaattccgtggtgttgtcggggaagctgacgtcctttccatggctgctcgcctgtgttgccacctggatt
ctgcgcgggacgtcttctgctacgtcccttcggccctcaatccagcggaccttccttcccgcggcctgctgccggct
ctgcggcctcttccgcgtcttcgccttcgccctcagacgagtcggatctccctttgggccgcctccccgcctggaaac
ggggaggctaactgaaacacggaaggagacaatacoggaaggaacccgcgctatgacggcaataaaaagacagaata
```

FIG. 46 (continued)

```
aaacgcacgggtgttgggtcgtttgttcataaacgcggggttcggtcccagggctggcactctgtcgataccccaccg
agacccattggggccaatacgccgcgtttcttccttttccccaccccaccccccaagttcgggtgaaggcccaggg
ctcgcagccaacgtcggggcggcaggccctgccatagcagatctgcgcagctggggctctagggggtatcccacgcg
ccctgtagcggcgcattaagcgcggcgggtgtggtggttacgcgcagcgtgaccgctacacttgccagcgccctagcg
cccgctcctttcgctttcttccttccttccttctcgccacgttgccgccgctttcccccgtcaagctctaaatcggggcatc
cctttaggttccgatttagtgcttacggcacctcgaccccaaaaaacttgattagggtgatggttcacgtagtggg
ccatcgccctgatagacggttttcgccctttgacgttggagtccacgttctttaatagtggactcttgttccaaact
ggaacaacactcaaccctatctcggtctattcttttgatttataagggattttggggattcggcctattggttaaaa
aatgagctgatttaacaaaaatttaacgcgaattaattctgtggaatgtgtgtcagttaggtgtgtggaaagtccccag
gctccccagcaggcagaagtatgcaaagcatgcatctcaattagtcagcaaccaggtgtggaaagtccccaggctccc
cagcaggcagaagtatgcaaagcatgcatctcaattagtcagcaaccatagtcccgcccctaactccgcccatcccgc
ccctaactccgcccagttccgcccattctccgccccatggctgactaatttttttttatttatgcagaggccgaggccg
cctctgctctgagctattccagaagtagtgaggaggcttttttggaggcctaggcttttgcaaaaagctccgggag
cttgtatatccattttcggatctgatcaagagacaggatgaggatcgtttcgcatgattgaacaagatggattgcacg
caggttctccggccgcttgggtggagaggctattcggctatgactgggcacaacagacaatcggctgctctgatgccg
ccgtgttccggctgtcagcgcaggggcgcccggttcttttttgtcaagaccgacctgtccggtgccctgaatgaactgc
aggacgaggcagcgcggctatcgtggctggccacgacgggcgttccttgcgcagctgtgctcgacgttgtcactgaag
cgggaagggactggctgctattgggcgaagtgccggggcaggatctcctgtcatctcaccttgctcctgccgagaaag
tatccatcatggctgatgcaatgcggcggctgcatacgcttgatccggctacctgcccattcgaccaccaagcgaaac
atcgcatcgagcgagcacgtactcggatggaagccggtcttgtcgatcaggatgatctggacgaagagcatcaggggc
tcgcgccagccgaactgttcgccaggctcaaggcgcgcatgcccgacggcgaggatctcgtcgtgacccatggcgatg
cctgcttgccgaatatcatggtggaaaatggccgcttttctggattcatcgactgtggccggctgggtgtggcggacc
gctatcaggacatagcgttggctacccgtgatattgctgaagagcttggcggcgaatgggctgaccgcttcctcgtgc
tttacggtatcgccgctcccgattcgcagcgcatcgccttctatcgccttcttgacgagttcttctgagcgggactct
ggggttcgcgcgaaatgaccgaccaagcgacgcccaacctgccatcacgagatttcgattccaccgccgccttctatgaa
aggttgggcttcggaatcgttttccgggacgccggctggatgatcctccagcgcggggatctcatgctggagttcttc
gcccaccccaacttgtttattgcagcttataatggttacaaataaagcaatagcatcacaaatttcacaaataaagca
ttttttttcactgcattctagttgtggtttgtccaaactcatcaatgtatcttatcatgtctgtataccgtcgacctct
agctagagcttggcgtaatcatggtcatagctgtttcctgtgtgaaattgttatccgctcacaattccacacaacata
cgagccggaagcataaagtgtaaagcctggggtgcctaatgagtgagctaactcacattaattgcgttgcgctcactg
cccgctttccagtcgggaaacctgtcgtgccagctgcattaatgaatcggccaacgcgcggggagaggcggtttgcgt
attgggcgctcttccgcttcctcgctcactgactcgctgcgctcggtcgttcggctgcggcgagcggtatcagctcac
tcaaaggcggtaatacggttatccacagaatcaggggataacgcaggaaagaacatgtgagcaaaaggccagcaaaag
gccaggaaccgtaaaaaggccgcgttgctggcgtttttccataggctccgcccccctgacgagcatcacaaaaatcga
cgctcaagtcagaggtggcgaaacccgacaggactataaagataccaggcgtttccccctggaagctccctcgtgcgc
tctcctgttccgaccctgccgcttaccggatacctgtccgcctttctcccttcgggaagcgtggcgctttctcaatgc
tcacgctgtaggtatctcagttcggtgtaggtcgttcgctccaagctgggctgtgtgcacgaacccccgttcagccc
gaccgctgcgccttatccggtaactatcgtcttgagtccaacccggtaagacacgacttatcgccactggcagcagcc
actggtaacaggattagcagagcgaggtatgtaggcggtgctacagagttcttgaagtggtggcctaactacggctac
actagaaggacagtatttggtatctgcgctctgctgaagccagttaccttcggaaaaagagttggtagctcttgatcc
ggcaaacaaaccaccgctggtagcggtggtttttttgtttgcaagcagcagattacgcgcagaaaaaaaggatctcaa
gaagatcctttgatcttttctacggggtctgacgctcagtggaacgaaaactcacgttaagggattttggtcatgaga
ttatcaaaaaggatcttcacctagatccttttaaattaaaaatgaagttttaaatcaatctaaagtatatatgagtaa
acttggtctgacagttaccaatgcttaatcagtgaggcacctatctcagcgatctgtctatttcgttcatccatagtt
gcctgactccccgtcgtgtagataactacgatacgggagggcttaccatctggccccagtgctgcaatgataccgcga
gacccacgctcaccggctccagatttatcagcaataaaccagccagccggaagggccgagcgcagaagtggtcctgca
actttatccgcctccatccagtctattaattgttgccgggaagctagagtaagtagttcgccagttaatagtttgcgc
aacgttgttgccattgctacaggcatcgtggtgtcacgctcgtcgtttggtatggcttcattcagctccggttcccaa
cgatcaaggcgagttacatgatcccccatgttgtgcaaaaaagcggttagctccttcggtcctccgatcgttgtcaga
agtaagttggccgcagtgttatcactcatggttatggcagcactgcataattctcttactgtcatgccatccgtaaga
tgcttttctgtgactggtgagtactcaaccaagtcattctgagaatagtgtatgcggcgaccgagttgctcttgcccg
gcgtcaatacgggataataccgcgccacatagcagaactttaaaagtgctcatcattggaaaacgttcttcggggcga
aaactctcaaggatcttaccgctgttgagatccagttcgatgtaacccactcgtgcacccaactgatcttcagcatct
tttactttcaccagcgtttctgggtgagcaaaaacaggaaggcaaaatgccgcaaaaaagggaataagggcgacacgg
```

FIG. 46 (continued)

```
aaatgttgaatactcatactcttccttttttcaatattattgaagcatttatcagggttattgtctcatgagcggatac
atatttgaatgtatttagaaaaataaacaaatagggggttccgcgcacatttccccgaaaagtgccacctgacgtcgac
ggatcgggagatctcccgatcccctatggtcgactctcagtacaatctgctctgatgccgcatagttaagccagtatc
tgctccctgcttgtgtgttggaggtcgctgagtagtgcgcgagcaaaatttaagctacaacaaggcaaggcttgaccg
acaattgcatgaagaatctgcttagg   (SEQ ID NO: 189)
```

FIG. 47

| ID | sequence |
|----|----------|
| H5 | U551FEL190-VH2+VL1 |
| H7 | U551FEL190-VH2+VL3 |
| H8 | U551FEL190-VH2+VL4 |
| H14 | U551FEL190-VH4+VL2 |

U8085FJ218-VL          SEQ ID NO: 1

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| E | V | Q | L | K | Q | S | G | P | G | L | V | A | P | S | Q | S | L | S | I |
| 21 | 22 | 23 | 24 | 25 | 26 | 27 | 28 | 29 | 30 | 31 | 32 | 33 | 34 | 35 | 36 | 37 | 38 | 39 | 40 |
| T | C | T | V | S | G | F | S | L | S | I | Y | S | V | H | W | V | R | Q | P |
| 41 | 42 | 43 | 44 | 45 | 46 | 47 | 48 | 49 | 50 | 51 | 52 | 53 | 54 | 55 | 56 | 57 | 58 | 59 | 60 |
| P | G | K | G | L | E | W | L | G | M | I | W | G | G | G | S | S | D | Y | N |
| 61 | 62 | 63 | 64 | 65 | 66 | 67 | 68 | 69 | 70 | 71 | 72 | 73 | 74 | 75 | 76 | 77 | 78 | 79 | 80 |
| S | A | L | K | S | R | L | S | I | S | K | D | N | S | K | S | Q | V | F | L |
| 81 | 82 | 83 | 84 | 85 | 86 | 87 | 88 | 89 | 90 | 91 | 92 | 93 | 94 | 95 | 96 | 97 | 98 | 99 | 100 |
| K | M | N | S | L | Q | T | D | D | T | A | M | Y | Y | C | A | R | N | G | N |
| 101 | 102 | 103 | 104 | 105 | 106 | 107 | 108 | 109 | 110 | 111 | 112 | 113 | 114 | 115 | 116 | 117 | | | |
| F | Y | A | M | D | Y | W | G | Q | G | T | S | V | T | V | S | S | | | |

FIG. 52B

U8085F J210-VL      SEQ ID NO: 2

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| Q | I | V | L | T | Q | S | P | A | I | M | S | A | S | L | G | E | R | V | T |

| 21 | 22 | 23 | 24 | 25 | 26 | 27 | 28 | 29 | 30 | 31 | 32 | 33 | 34 | 35 | 36 | 37 | 38 | 39 | 40 |
|----|----|----|----|----|----|----|----|----|----|----|----|----|----|----|----|----|----|----|----|
| M | T | C | T | A | S | S | S | V | S | S | S | F | L | H | W | Y | Q | Q | K |

| 41 | 42 | 43 | 44 | 45 | 46 | 47 | 48 | 49 | 50 | 51 | 52 | 53 | 54 | 55 | 56 | 57 | 58 | 59 | 60 |
|----|----|----|----|----|----|----|----|----|----|----|----|----|----|----|----|----|----|----|----|
| P | G | S | S | P | S | L | W | I | S | S | T | S | N | L | A | S | G | S | P |

| 61 | 62 | 63 | 64 | 65 | 66 | 67 | 68 | 69 | 70 | 71 | 72 | 73 | 74 | 75 | 76 | 77 | 78 | 79 | 80 |
|----|----|----|----|----|----|----|----|----|----|----|----|----|----|----|----|----|----|----|----|
| P | G | S | S | G | S | G | S | I | Y | S | Y | S | L | T | I | S | S | M | E |

| 81 | 82 | 83 | 84 | 85 | 86 | 87 | 88 | 89 | 90 | 91 | 92 | 93 | 94 | 95 | 96 | 97 | 98 | 99 | 100 |
|----|----|----|----|----|----|----|----|----|----|----|----|----|----|----|----|----|----|----|----|
| A | E | D | A | A | T | Y | Y | C | H | Q | Y | H | H | S | P | Y | I | Y | T |

| 101 | 102 | 103 | 104 | 105 | 106 | 107 | 108 | 109 | 110 |
|-----|-----|-----|-----|-----|-----|-----|-----|-----|-----|
| F | G | G | G | T | K | L | E | I | K |

FIG. 55

>2_U551FEL190-VH2-hIgG1CH(K222A)-pcDNA3.4 (SEQ ID NO: 191)
gttaggcgttttgcgctgcttcgcgatgtacgggccagatatacgcgttgacattgattattgactagttattaatagtaatcaattacggggtcattagttcatagcc
catatatggagttccgcgttacataacttacggtaaatggcccgcctggctgaccgcccaacgaccccgcccattgacgtcaataatgacgtatgttcccata
gtaacgccaatagggactttccattgacgtcaatgggtggagtattacggtaaactgcccacttggcagtacatcaagtgtatcatatgccaagtacgcccct
attgacgtcaatgacggtaaatggcccgcctggcattatgcccagtacatgaccttatgggactttcctacttggcagtacatctacgtattagtcatcgctattacc
atggtgatgcggttttggcagtacatcaatgggcgtggatagcggtttgactcacggggatttccaagtctccaccccattgacgtcaatggggagtttgttttggca
ccaaaatcaacgggactttccaaaatgtcgtaacaactccgccccattgacgcaaatgggcggtaggcgtgtacggtgggaggtctatataagcagagctc
gtttagtgaaccgtcagatcgcctggagacgccatccacgctgttttgacctccatagaagacaccgggaccgatccagcctccggactctagaggatcgaa
cccttgaattcccgccgccaccatgggctggtcatgcattattctgtttctggtcgcaactgctacaggcgtgcatagtcaggtgcagctgcaagagtccggccct
ggactcgtgaagccctccgagacactgtctgacatgtaccgtgtctggcttccctgtccatctactccgtgcactggatcagacagcctcctggcaagggc
ctggaatggatcggcatgatctggggaggcggctcttccgactacaactccgccctgaaatctcggctgaccatctccaaggacacctcaagaaccaggtc
agcctgaagctgagctctgtgaccgctgctgataccgccgtgtactactgcgcagaaatggcaactctacgccatggactattggggccagggcaccctgg
tgaccgtgtccagcgccagcaccaagggcccttccgtgttccactggccccctcctcaaatccacatctggcggcaccgccgccctgggctgtctggtgaag
gactacttcccagagcctgtgacagtgtcctggaactctggcgccctgacatccggcgtgcacacattccagccgtgctgcagagctccggcctgtacagcct
gtctagcgtggtgacagtgccctcctctagcctgggcacacagacctatatctgcaacgtgaatcacaagccaagcaataccaaggtggacaagaaggtgg
agcccaagtcctgtgatgccacacacacctgccccccttgtcctgctcccgagctgctgggcggccctagcgtgttcctgtttccacccaagcctaaggacacc
ctgatgatctcccggacaccgaggtgacctgcgtggtggtggacgtgtctcacgaggatcctgaggtgaagttcaactggtatgtggatggcgtggaggtgc
acaatgccaagaccaagcccagagaggagcagtacaactctacatataggtggtgagcgtgctgaccgtgctgcaccaggactggctgaacggcaag
gagtataagtgcaaggtgtccaataaggccctgcccgcccccatcgagaagacaatcagcaaggccaaggccagcctcgggaggccacaggtgtacac
cctgcctccatccagagacgagctgaccaagaaccaggtgtctctgacatgtctggtgaaggcttctatcctagcgatatcgccgtggagtgggagtccaat
ggccagccagagaacaattacaagaccacaccccctgtgctggacccgatggctccttcttctctgtattccaagctgaccgtggataagtctcggtggcagca
gggcaacgtgttcagctgttccgtgatgcacgaagccctgcataatcactatactcagaaatccctgtccctgtcacctggaaagtgataagcttaagggttcga
tccctaccggttagtaatgagtttgatatctcgacaatcaacctctggattacaaaatttgtgaaagattgactggtattcttaactatgttgctccttttacgctatgtgg
atacgctgctttaatgcctttgtatcatgctattgcttccgtatggctttcattttctcctccttgtataaatcctggttgctgtctctttatgaggagttgtggcccgttgtca
ggcaacgtggcgtggtgtgcactgtgtttgctgacgcaaccccactggttggggcattgccaccacctgtcagctcctttccgggactttcgctttccccctccct
attgccacggcggaactcatcgccgcctgccttgcccgctgctggacaggggctcggctgttgggcactgacaattccgtggtgttgtcggggaagctgacgtc
cttccatggctgctcgcctgtgttgccacctggattctgcgcgggacgtccttctgctacgtcccttcggccctcaatccagcggaccttccttcccgcggcctgct
gccggctctgcggcctcttccgcgtcttcgccttcgcctcagacgagtcggatctcccttgggccgcctccccgcctggaaacggggggaggctaactgaaa
cacggaaggagacaataccggaaggaacccgcgctatgacggcaataaaaagacagaataaaacgcacgggtgttgggtcgtttgttcataaacgcgg
ggttcggtcccagggctggcactctgtcgataccccaccgagaccccattggggccaatacgcccgcgtttcttcctttccccaccccaccccccaagttcgg
gtgaaggcccagggctcgcagccaacgtcggggcggcaggccctgccatagcagatctgcgcagctggggctctagggggtatcccacgcgccctgta
gcggcgcattaagcgcggcgggtgtggtggttacgcgcagcgtgaccgctacacttgccagcgccctagcgcccgctcctttcgctttcttcccttccttctcgc
cacgttcgccggctttccccgtcaagctctaaatcggggcatccctttagggttccgatttagtgctttacggcacctcgaccccaaaaaacttgattagggtgatg
gttcacgtagtgggccatcgccctgatagacggttttcgcccttgacgttggagtccacgttctttaatagtggactcttgttccaaactggaacaacactcaacc
ctatctcggtctattcttttgatttataaagggattttgggggatttcggcctattggttaaaaaatgagctgatttaacaaaaatttaacgcgaattaattctgtggaatgtg
tgtcagttagggtgtggaaagtccccaggctccccagcaggcagaagtatgcaaagcatgcatctcaattagtcagcaaccaggtgtggaaagtccccagg
ctccccagcaggcagaagtatgcaaagcatgcatctcaattagtcagcaaccatagtccgcccctaactccgcccatcccgcccctaactccgcccagtc
cgcccattctccgccccatggctgactaattttttttatttatgcagaggccgaggccgcctctgcctctgagctattccagaagtagtgaggaggcttttttggagg
cctaggcttttgcaaaaagctcccgggagcttgtatatccattttcggatctgatcaagagacaggatgaggatcgtttcgcatgattgaacaagatggattgca
cgcaggttctccggccgcttgggtggagaggctattcggctatgactgggcacaacagacaatcggctgctctgatgccgccgtgttccggctgtcagcgcag
gggcgcccggttctttttgtcaagaccgacctgtccggtgccctgaatgaactgcaggacgaggcagcgcggctatcgtggctggccacgacggcgttcctt
gcgcagctgtgctcgacgttgtcactgaagcgggaagggactggctgctattgggcgaagtgccggggcaggatctcctgtcatctcaccttgctcctgccga
gaaagtatccatcatggctgatgcaatgcggcggctgcatacgcttgatccggctacctgcccattcgaccaccaagcgaaacatcgcatcgagcgagcac
gtactcggatggaagccggtcttgtcgatcaggatgatctggacgaagagcatcaggggctcgcgccagccgaactgttcgccaggctcaaggcgcgcatg
cccgacggcgaggatctcgtcgtgacccatggcgatgcctgcttgccgaatatcatggtggaaaatggccgcttttctggattcatcgactgtggccggctgggt
gtggcggaccgctatcaggacatagcgttggctacccgtgatattgctgaagagcttggcggcgaatgggctgaccgcttcctcgtgctttacggtatcgccgct
cccgattcgcagcgcatcgccttctatcgccttcttgacgagttcttctgagcgggactctggggttcgcgaaatgaccgaccaagcgacgcccaacctgccat
cacgagattcgattccaccgccgccttctatgaaaggttgggcttcggaatcgttttccgggacgccggctggatgatcctccagcgcggggatctcatgctgg
agttcttcgcccaccccaacttgttattgcagcttataatggttacaaataaagcaatagcatcacaaatttcacaaataaagcatttttttcactgcattctagttgt
ggtttgtccaaactcatcaatgtatcttatcatgtctgtataccgtcgacctctagctagagcttggcgtaatcatggtcatagctgtttcctgtgtgaaattgttatccg
ctcacaattccacacaacatacgagccggaagcataaagtgtaaagcctggggtgcctaatgagtgagctaactcacattaattgcgttgcgctcactgcccg
ctttccagtcgggaaacctgtcgtgccagctgcattaatgaatcggccaacgcgcggggagaggcggtttgcgtattgggcgctcttccgcttcctcgctcactg
actcgctgcgctcggtcgttcggctgcggcgagcggtatcagctcactcaaaggcggtaatacggttatccacagaatcaggggataacgcaggaaagaa

FIG. 55 (continued)

catgtgagcaaaaggccagcaaaaggccaggaaccgtaaaaaggccgcgttgctggcgtttttccataggctccgcccccctgacgagcatcacaaaaat
cgacgctcaagtcagaggtggcgaaacccgacaggactataaagataccaggcgtttccccctggaagctccctcgtgcgctctcctgttccgaccctgccg
cttaccggatacctgtccgcctttctcccttcgggaagcgtggcgctttctcaatgctcacgctgtaggtatctcagttcggtgtaggtcgttcgctccaagctgggct
gtgtgcacgaaccccccgttcagcccgaccgctgcgccttatccggtaactatcgtcttgagtccaacccggtaagacacgacttatcgccactggcagcagc
cactggtaacaggattagcagagcgaggtatgtaggcggtgctacagagttcttgaagtggtggcctaactacggctacactagaaggacagtatttggtatct
gcgctctgctgaagccagttaccttcggaaaaagagttggtagctcttgatccggcaaacaaaccaccgctggtagcggtggtttttttgtttgcaagcagcaga
ttacgcgcagaaaaaaaggatctcaagaagatcctttgatcttttctacggggtctgacgctcagtggaacgaaaactcacgttaaggggattttggtcatgagat
tatcaaaaaggatcttcacctagatccttttaaattaaaaatgaagttttaaatcaatctaaagtatatatgagtaaacttggtctgacagttaccaatgcttaatca
gtgaggcacctatctcagcgatctgtctatttcgttcatccatagttgcctgactccccgtcgtgtagataactacgatacgggagggcttaccatctggccccagt
gctgcaatgataccgcgagacccacgctcaccggctccagatttatcagcaataaaccagccagccggaagggccgagcgcagaagtggtcctgcaactt
tatccgcctccatccagtctattaattgttgccgggaagctagagtaagtagttcgccagttaatagtttgcgcaacgttgttgccattgctacaggcatcgtggtgt
cacgctcgtcgtttggtatggcttcattcagctccggttcccaacgatcaaggcgagttacatgatcccccatgttgtgcaaaaaagcggttagctccttcggtcct
ccgatcgttgtcagaagtaagttggccgcagtgttatcactcatggttatggcagcactgcataattctcttactgtcatgccatccgtaagatgcttttctgtgactg
gtgagtactcaaccaagtcattctgagaatagtgtatgcggcgaccgagttgctcttgcccggcgtcaatacgggataataccgcgccacatagcagaacttt
aaaagtgctcatcattggaaaacgttcttcggggcgaaaactctcaaggatcttaccgctgttgagatccagttcgatgtaacccactcgtgcacccaactgatc
ttcagcatcttttactttcaccagcgtttctgggtgagcaaaaacaggaaggcaaaatgccgcaaaaaagggaataagggcgacacggaaatgttgaatact
catactcttcctttttcaatattattgaagcatttatcagggttattgtctcatgagcggatacatatttgaatgtatttagaaaaataaacaaataggggttccgcgca
catttccccgaaaagtgccacctgacgtcgacggatcgggagatctcccgatcccctatggtcgactctcagtacaatctgctctgatgccgcatagttaagcc
agtatctgctccctgcttgtgtgttggaggtcgctgagtagtgcgcgagcaaaatttaagctacaacaaggcaaggcttgaccgacaattgcatgaagaatctg
cttagg >4_U551FEL190-VH4-hIgG1CH(K222A)-pcDNA3.4        (SEQ ID NO: 192)
gttaggcgtttgcgctgcttcgcgatgtacgggccagatatacgcgttgacattgattattgactagttattaatagtaatcaattacggggtcattagttcatagcc
catatatggagttccgcgttacataacttacggtaaatggcccgcctggctgaccgcccaacgacccccgcccattgacgtcaataatgacgtatgttcccata
gtaacgccaatagggactttccattgacgtcaatgggtggagtatttacggtaaactgcccacttggcagtacatcaagtgtatcatatgccaagtacgcccct
attgacgtcaatgacggtaaatggcccgcctggcattatgcccagtacatgaccttatgggactttcctacttggcagtacatctacgtattagtcatcgctattacc
atggtgatgcggttttggcagtacatcaatgggcgtggatagcggtttgactcacggggatttccaagtctccaccccattgacgtcaatgggagtttgttttggca
ccaaaatcaacgggactttccaaaatgtcgtaacaactccgccccattgacgcaaatgggcggtaggcgtgtacggtgggaggtctatataagcagagctc
gtttagtgaaccgtcagatcgcctggagacgccatccacgctgttttgacctccatagaagacaccgggaccgatccagcctccggactctagaggatcgaa
cccttgaattcccgccgccaccatgggctggtcatgcattattctgtttctggtcgcaactgctacaggcgtgcatagtcaggtgcagctgcaagagtccggacc
cggcctcgtgaagccttccgagacactgtctctgacctgtaccgtgtctggcttctccctgtccatctactccgtgcactggatccggcagcctcctggcaagggc
ctggaatggctgggcatgatctggggcggcggaagctccgactacaaccgccctgaaatctagactgaccatctccaaggacacctcaagaaccaggt
cagcctgaagctgagctctgtgaccgccgctgataccgctatgtactactgcgccagaaatggcaacttctacgccatggactattggggccagggcaccctg
gtgacagtgtcctctgccagcaccaagggcccttccgtgttccactggcccccctctctaaatccacatctggcggcaccgccgccctgggctgtctggtgaa
ggactacttcccagagcctgtgacagtgtcctggaactctggcgccctgacatccggcgtgcacacattccagccgtgctgcagagctccggcctgtacagc
ctgtctagcgtggtgacagtgccctcctctagcctgggcacacagacctatatctgcaacgtgaatcacaagccaagcaataccaaggtggacaagaaggt
ggagcccaagtcctgtgatgccacacacacccgccccctgtcctgctcccgagctgctgggcggccctagcgtgttcctgttccacccaagcctaaggaca
ccctgatgatctcccggacacccgaggtgacctgcgtggtggtggacgtgtctcacgaggatcctgaggtgaagttcaactggtatgtggatggcgtggaggt
gcacaatgccaagaccaagccagagaggagcagtacaactacatataggtggtgagcgtgctgaccgtgctgcaccaggactggctgaacggca
aggagtataagtgcaaggtgtccaataaggccctgcccgcccccatcgagaagacaatcagcaaggccaagggccagcctcgggagccacaggtgtac
accctgcctccatccagagacgagctgacaaagaaccaggtgtctctgacatgtctggtgaagggcttctatcctagcgatatcgccgtggagtgggagtcca
atggccagccagagaacaattacaagaccacacccctgtgctggactccgatggctccttcttctgtattccaagctgaccgtggataagtctcggtggcag
caggggaacgtgttcagctgttccgtgatgcacgaagccctgcataatcactactctgagaaatccctgtccctgtcaccggaaagtgataagcttaagggttc
gatccctaccggtagtaatgagtttgatatctcgacaatcaacctctggattacaaaatttgtgaaagattgactggtattcttaactatgttgctccttttacgctatgt
ggatacgctgctttaatgcctttgtatcatgctattgcttcccgtatggctttcattttctcctccttgtataaatcctggttgctgtctctttatgaggagttgtggcccgttgt
caggcaacgtggcgtggtgtgcactgtgtttgctgacgcaacccccactggttggggcattgccaccacctgtcagctcctttccgggactttcgctttccccctcc
ctattgccacggcggaactcatcgccgcctgccttgcccgctgctggacaggggctcggctgttgggcactgacaattccgtggtgttgtcggggaagctgacg
tcctttccatggctgctcgcctgtgttgccacctggattctgcgcgggacgtccttctgctacgtcccttcggccctcaatccagcggaccttccttcccgcggcctg
ctgccggctctgcggcctcttccgcgtcttcgccttcgccctcagacgagtcggatctccctttgggccgcctccccgcctggaaacggggaggctaactgaa
acacggaaggagacaataccggaaggaacccgcgctatgacggcaataaaaagacagaataaaacgcacgggtgttgggtcgtttgttcataaacgcg
gggttcggtcccagggctggcactctgtcgataccccaccgagacccattgggggccaatacgcccgcgtttcttccttttccccaccccaccccccaagttcg
ggtgaaggcccagggctcgcagccaacgtcggggcggcaggccctgccatcagagatctgcgcagctggggctctaggggtatcccacgcgccctgt
agcggcgcattaagcgcggcgggtgtggtggttacgcgcagcgtgaccgctacacttgccagcgccctagcgcccgctcctttcgctttcttcccttccttctcg

FIG. 55 (continued)

ccacgttcgccggctttccccgtcaagctctaaatcggggcatcccttagggttccgatttagtgctttacggcacctcgaccccaaaaaacttgattagggtgat
ggttcacgtagtgggccatcgccctgatagacggttttcgcccttcgacgttggagtccacgttcttcaatagtggactcttgttccaaactggaacaacactcaac
cctatctcggtctattcttttgatttataaggggatttggggggattcggcctattggttaaaaaatgagctgatttaacaaaaatttaacgcgaattaattctgtggaatgt
gtgtcagttagggtgtggaaaagtccccaggctccccagcaggcagaagtatgcaaagcatgcatctcaattagtcagcaaccaggtgtggaaagtccccag
gctccccagcaggcagaagtatgcaaagcatgcatctcaattagtcagcaaccatagtcccgcccctaactccgcccatcccgcccctaactccgcccagtt
ccgcccattctccgcccccatggctgactaattttttttatttatgcagaggccgaggccgcctctgcctctgagctattccagaagtagtgaggaggctttttttggag
gcctaggctttgcaaaaagctcccgggagcttgtatatccattttcggatctgatcaagagacaggatgaggatcgtttcgcatgattgaacaagatggattgc
acgcaggttctccggccgcttgggtggagaggctattcggctatgactgggcacaacagacaatcggctgctctgatgccgccgtgttccggctgtcagcgca
ggggcgcccggttctttttgtcaagaccgacctgtccggtgccctgaatgaactgcaggacgaggcagcgcggctatcgtggctggccacgacgggcgttcct
tgcgcagctgtgctcgacgttgtcactgaagcgggaagggactggctgctattgggcgaagtgccggggcaggatctcctgtcatctcaccttgctcctgccga
gaaagtatccatcatggctgatgcaatgcggcggctgcatacgcttgatccggctacctgcccattcgaccaccaagcgaaacatcgcatcgagcgagcac
gtactcggatggaagccggtcttgtcgatcaggatgatctggacgaagagcatcaggggctcgcgccagccgaactgttcgccaggctcaaggcgcgcatg
cccgacggcgaggatctcgtcgtgacccatggcgatgcctgcttgccgaatatcatggtggaaaatggccgcttttctggattcatcgactgtggccggctgggt
gtggcggaccgctatcaggacatagcgttggctacccgtgatattgctgaagagcttggcggcgaatgggctgaccgcttcctcgtgctttacggtatcgccgct
cccgattcgcagcgcatcgccttctatcgccttcttgacgagttcttctgagcgggactctggggttcgcgaaatgaccgaccaagcgacgcccaacctgccat
cacgagattcgattccaccgccgccttctatgaaaggttgggcttcggaatcgttttccgggacgccggctggatgatcctccagcgcggggatctcatgctgg
agttcttcgcccaccccaacttgtttattgcagcttataatggttacaaataaagcaatagcatcacaaatttcacaaataaagcatttttttcactgcattctagttgt
ggtttgtccaaactcatcaatgtatcttatcatgtctgtataccgtcgacctctagctagagctcggctaatcatggtcatagctgtttcctgtgtgaaattgttatccg
ctcacaattccacacaacatacgagccggaagcataaagtgtaaagcctggggtgcctaatgagtgagctaactcacattaattgcgttgcgctcactgcccg
ctttccagtcgggaaacctgtcgtgccagctgcattaatgaatcggccaacgcgcggggagaggcggtttgcgtattgggcgctcttccgcttcctcgctcactg
actcgctgcgctcggtcgttcggctgcggcgagcggtatcagctcactcaaaggcggtaatacggttatccacagaatcaggggataacgcaggaaagaa
catgtgagcaaaaggccagcaaaaggccaggaaccgtaaaaaggccgcgttgctggcgtttttccataggctccgcccccctgacgagcatcacaaaaat
cgacgctcaagtcagaggtggcgaaacccgacaggactataaagataccaggcgtttccccctggaagctccctcgtgcgctctcctgttccgaccctgccg
cttaccggatacctgtccgcctttctcccttcgggaagcgtggcgctttctcaatgctcacgctgtaggtatctcagttcggtgtaggtcgttcgctccaagctgggct
gtgtgcacgaaccccccgttcagcccgaccgctgcgccttatccggtaactatcgtcttgagtccaacccggtaagacacgacttatcgccactggcagcagc
cactggtaacaggattagcagagcgaggtatgtaggcggtgctacagagttcttgaagtggtggcctaactacggctacactagaaggacagtatttggtatct
gcgctctgctgaagccagttaccttcggaaaaagagttggtagctcttgatccggcaaacaaaccaccgctggtagcggtggtttttttgtttgcaagcagcaga
ttacgcgcagaaaaaaaggatctcaagaagatcctttgatcttttctacggggtctgacgctcagtggaacgaaaactcacgttaagggattttggtcatgagat
tatcaaaaaggatcttcacctagatccttttaaattaaaaatgaagttttaaatcaatctaaagtatatatgagtaaacttggtctgacagttaccaatgcttaatca
gtgaggcacctatctcagcgatctgtctatttcgttcatccatagttgcctgactccccgtcgtgtagataactacgatacgggagggcttaccatctggccccagt
gctgcaatgataccgcgagacccacgctcaccggctccagatttatcagcaataaaccagccagccggaagggccgagcgcagaagtggtcctgcaactt
tatccgcctccatccagtctattaattgttgccgggaagctagagtaagtagttcgccagttaatagtttgcgcaacgttgttgccattgctacaggcatcgtggtgt
cacgctcgtcgtttggtatggcttcattcagctccggttcccaacgatcaaggcgagttacatgatcccccatgttgtgcaaaaaagcggttagctccttcggtcct
ccgatcgttgtcagaagtaagttggccgcagtgttatcactcatggttatggcagcactgcataattctcttactgtcatgccatccgtaagatgcttttctgtgactg
gtgagtactcaaccaagtcattctgagaatagtgtatgcggcgaccgagttgctcttgcccggcgtcaatacgggataataccgcgccacatagcagaacttt
aaaagtgctcatcattggaaaacgttcttcggggcgaaaactctcaaggatcttaccgctgttgagatccagttcgatgtaacccactcgtgcacccaactgatc
ttcagcatcttttactttcaccagcgtttctgggtgagcaaaaacaggaaggcaaaatgccgcaaaaaagggaataagggcgacacggaaatgttgaatact
catactcttcctttttcaatattattgaagcatttatcagggttattgtctcatgagcggatacatatttgaatgtatttagaaaaataaacaaataggggttccgcgca
catttccccgaaaagtgccacctgacgtcgacggatcgggagatctcccgatcccctatggtcgactctcagtacaatctgctctgatgccgcatagttaagcc
agtatctgctccctgcttgtgtgttggaggtcgctgagtagtgcgcgagcaaaatttaagctacaacaaggcaaggcttgaccgacaattgcatgaagaatctg
cttagg >14_U551FEL190-VL1_hIgkCL-pcDNA3.4              (SEQ ID NO: 193)
Gttaggcgtttgcgctgcttcgcgatgtacgggccagatatacgcgttgacattgattattgactagttattaatagtaatcaattacggggtcattagttcatagcc
catatatggagttccgcgttacataacttacggtaaatggcccgcctggctgaccgcccaacgacccccgcccattgacgtcaataatgacgtatgttcccata
gtaacgccaatagggactttccattgacgtcaatgggtggagtatttacggtaaactgcccacttggcagtacatcaagtgtatcatatgccaagtacgcccct
attgacgtcaatgacggtaaatggcccgcctggcattatgcccagtacatgaccttatgggactttcctacttggcagtacatctacgtattagtcatcgctattacc
atggtgatgcggttttggcagtacatcaatgggcgtggatagcggtttgactcacggggatttccaagtctccaccccattgacgtcaatgggagtttgttttggca
ccaaaatcaacgggactttccaaaatgtcgtaacaactccgccccattgacgcaaatgggcggtaggcgtgtacggtgggaggtctatataagcagagctc
gtttagtgaaccgtcagatcgcctggagacgccatccacgctgtttttgacctccatagaagacaccgggaccgatccagcctccggactctagaggatcgaa
cccttgaattcccgccgccaccatgggctggtcatgtattattctgtttctggtcgcaactgctacaggggtccatagtGAGATCGTGCTGACCCAAT
CTCCAGGCACCCTGTCTCTCAGCCCTGGCGAGAGAGCCACCCTGTCCTGCACCGCTTCTAGCTCCGTGTC
CTCCAGCTTCCTGCACTGGTACCAGCAGAAACCCGGCCAGGCTCCTAGACTGCTGATCTATTCCACCTCCA

FIG. 55 (continued)

ACCTGGCCTCTGGCATCCCTGACCGGTTCTCCGGCTCTGGCTCCGGAACAGATTTTACACTGACCATCTCC
CGGCTGGAACCTGAGGACTTCGCCGTGTACTACTGTCACCAGTACCACCATTCTCCTTACATCTACACCTT
CGGCGGCGGAACCAAGCTGGAAATCAAGaggacagtggccgcccaagcgtgttcatcttccccttccgacgagcagctgaagtctg
gcaccgccagcgtggtgtgcctgctgaacaacttctacctcgggaggccaaggtccagtggaaggtggataacgccctgcagtctggcaatagccagga
gtccgtgaccgagcaggactctaaggatagcacatattccctgtctagcaccctgacactgagcaaggccgattacgagaagcacaaggtgtatgcctgtga
agtcacccatcaggggctgtcatcacccgtcactaagtcattcaatcgcggagaatgctgataagcttaagggttcgatccctaccggttagtaatgagtttgat
atctcgacaatcaacctctggattacaaaaatttgtgaaagattgactggtattcttaactatgttgctccttttacgctatgtggatacgctgctttaatgcctttgtatcat
gctattgcttccgtatggctttcatttctcctccttgtataaatcctggttgctgtctctttatgaggagttgtggcccgttgtcaggcaacgtggcgtggtgtgcactgt
gtttgctgacgcaaccccactggttggggcattgccaccacctgtcagctcctttccgggactttcgctttccccctccctattgccacggcggaactcatcgccg
cctgccttgcccgctgctggacaggggctcggctgttgggcactgacaattccgtggtgttgtcggggaagctgacgtccttccatggctgctcgcctgtgttgcc
acctggattctgcgcggacgtccttctgctacgtcccttcggccctcaatccagcggaccttccttcccgcgggcctgctgccggctctgctgcggcctcttccgcgtct
tcgccttcgccctcagacgagtcggatctccctttgggccgcctcccgcctggaaacggggggaggctaactgaaacacggaaggagacaataccggaag
gaacccgcgctatgacggcaataaaaagacagaataaaacgcacgggtgttgggtcgtttgttcataaacgcggggtcggtcccagggctggcactctgtc
gataccccaccgagaccccattggggccaatacgcccgcgtttcttccttttcccacccaccccccaagttcgggtgaaggcccagggctcgcagccaac
gtcggggcggcaggccctgccatagcagatctgcgcagctggggctctaggggtatcccacgcgccctgtagcggcgcattaagcgcggcgggtgtgg
tggttacgcgcagcgtgaccgctacacttgccagcgccctagcgcccgctccttcgctttctctccttccttctcgccacgttcgccggcttcccgtcaagctct
aaatcggggcatcccttaggggttccgatttagtgctttacggcacctcgaccccaaaaaacttgattagggtgatggttcacgtagtgggccatcgccctgatag
acggtttttcgcccttgacgttggagtccacgttctttaatagtggactcttgttccaaactggaacaacactcaaccctatctcggtctattctttgatttataaggga
ttttggggatttcggcctattggttaaaaaatgagctgatttaacaaaaatttaacgcgaattaattctgtggaatgtgtgtcagttagggtgtggaaagtccccagg
ctccccagcaggcagaagtatgcaaagcatgcatctcaattagtcagcaaccaggtgtggaaagtccccaggctccccagcaggcagaagtatgcaaag
catgcatctcaattagtcagcaaccatagtcccgcccctaactccgcccatcccgcccctaactccgcccagttccgcccattctccgcccccatggctgactaat
tttttttatttatgcagaggccgaggccgcctctgcctctgagctattccagaagtagtgaggaggcttttttggaggcctaggcttttgcaaaaagctcccgggag
cttgtatatccattttcggatctgatcaagagacaggatgaggatcgtttcgcatgattgaacaagatggattgcacgcaggttctccggccgcttgggtggaga
ggctattcggctatgactgggcacaacagacaatcggctgctctgatgccgccgtgttccggctgtcagcgcaggggcgcccggttcttttttgtcaagaccgac
ctgtccggtgccctgaatgaactgcaggacgaggcagcgcggctatcgtggctggccacgacgggcgttccttgcgcagctgtgctcgacgttgtcactgaa
gcgggaagggactggctgctattgggcgaagtgccggggcaggatctcctgtcatctcaccttgctcctgccgagaaagtatccatcatggctgatgcaatgc
ggcggctgcatacgcttgatccggctacctgcccattcgaccaccaagcgaaacatcgcatcgagcgagcacgtactcggatggaagccggtcttgtcgatc
aggatgatctggacgaagagcatcaggggctcgcgccagccgaactgttcgccaggctcaaggcgcgcatgcccgacggcgaggatctcgtcgtgaccc
atggcgatgcctgcttgccgaatatcatggtggaaaatggccgctttctcggattcatcgactgtggccggctgggtgtggcggaccgctatcaggacatagcgt
tggctaccgtgatattgctgaagagcttggcggcgaatgggctgaccgcttcctcgtgctttacggtatcgccgctcccgattcgcagcgcatcgccttctatcg
ccttcttgacgagttcttctgagcgggactctggggttcgcgaaatgaccgaccaagcgacgcccaacctgccatcacgagatttcgattccaccgccgccttct
atgaaaggttgggcttcggaatcgttttccgggacgccggctggatgatcctccagcgcggggatctcatgctggagtcttcgcccacccccaacttgtttattgc
agcttataatggttacaaataaagcaatagcatcacaaatttcacaaataaagcattttttttcactgcattctagttgtggtttgtccaaactcatcaatgtatcttatc
atgtctgtataccgtcgacctctagctagagcttggcgtaatcatggtcatagctgtttcctgtgtgaaattgttatccgctcacaattccacacaacatacgagccg
gaagcatasagtgtaaagcctggggtgcctaatgagtgagctaactcacattaattgcgttgcgctcactgcccgctttccagtcgggaaacctgtcgtgccag
ctgcattaatgaatcggccaacgcgcggggagaggcggtttgcgtattgggcgctcttccgcttcctcgctcactgactcgctgcgctcggtcgttcggctgcgg
cgagcggtatcagctcactcaaaggcggtaatacggttatccacagaatcaggggataacgcaggaaagaacatgtgagcaaaaggccagcaaaagg
ccaggaaccgtaaaaaggccgcgttgctggcgtttttccataggctccgcccccctgacgagcatcacaaaaatcgacgctcaagtcagaggtggcgaaac
ccgacaggactataaagataccaggcgtttccccctggaagctccctcgtgcgctctcctgttccgaccctgccgcttaccggataccgtccgcctttctcccttc
gggaagcgtggcgctttctcaatgctcacgctgtaggtatctcagttcggtgtaggtcgttcgctccaagctgggctgtgtgcacgaaccccccgttcagcccga
ccgctgcgccttatccggtaactatcgtcttgagtccaacccggtaagacacgacttatcgccactggcagcagccactggtaacaggattagcagagcgag
gtatgtaggcggtgctacagagttcttgaagtggtggcctaactacggctacactagaaggacagtattggtatctgcgctctgctgaagccagttaccttcgga
aaaagagttggtagctcttgatccggcaaacaaaccaccgctggtagcggtggtttttttgtttgcaagcagcagattacgcgcagaaaaaaaggatctcaag
aagatcctttgatcttttctacggggtctgacgctcagtggaacgaaaactcacgttaagggattttggtcatgagattatcaaaaaggatcttcacctagatccttt
taaattaaaaatgaagttttaaatcaatctaaagtatatatgagtaaacttggtctgacagttaccaatgcttaatcagtgaggcacctatctcagcgatctgtctatt
tcgttcatccatagttgcctgactccccgtcgtgtagataactacgatacgggagggcttaccatctggccccagtgctgcaatgataccgcgagacccacgct
caccggctccagatttatcagcaataaaccagccagccggaagggccgagcgcagaagtggtcctgcaactttatccgcctccatccagtctattaattgttgc
cgggaagctagagtaagtagttcgccagttaatagtttgcgcaacgttgttgccattgctacaggcatcgtggtgtcacgctcgtcgtttggtatggcttcatcagc
tccggttcccaacgatcaaggcgagttacatgatcccccatgttgtgcaaaaaagcggttagctccttcggtcctccgatcgttgtcagaagtaagttggccgca
gtgttatcactcatggttatggcagcactgcataattctcttactgtcatgccatccgtaagatgcttttctgtgactggtgagtactcaaccaagtcattctgagaata
gtgtatgcggcgaccgagttgctcttgcccggcgtcaatacgggataataccgcgccacatagcagaactttaaaagtgctcatcattggaaaacgttcttcgg
ggcgaaaactctcaaggatcttaccgctgttgagatccagttcgatgtaacccactcgtgcacccaactgatcttcagcatcttttactttcaccagcgtttctgggt
gagcaaaaacaggaaggcaaaatgccgcaaaaaagggaataagggcgacacggaaatgttgaatactcatactcttcctttttcaatattattgaagcattta

FIG. 55 (continued)

tcagggttattgtctcatgagcggatacatatttgaatgtatttagaaaaataaacaaatagggggttccgcgcacatttccccgaaaagtgccacctgacgtcga
cggatcgggagatctcccgatcccctatggtcgactctcagtacaaatctgctctgatgccgcatagttaagccagtatctgctccctgcttgtgtgttggaggtcgct
gagtagtgcgcgagcaaaatttaagctacaacaaggcaaggcttgaccgacaattgcatgaagaatctgcttagg >17_U551FEL190-VL2_hIgkCL-pcDNA3.4                (SEQ ID NO: 194)
gttaggcgtttgcgctgcttcgcgatgtacgggccagatatacgcgttgacattgattattgactagttattaaatagtaatcaattacggggtcattagttcatagcc
catatatggagttccgcgttacataacttacggtaaatggcccgcctggctgaccgcccaacgacccccgcccattgacgtcaataatgacgtatgttcccata
gtaacgccaatagggactttccattgacgtcaatgggtggagtattttacggtaaactgcccacttggcagtacatcaagtgtatcatatgccaagtacgccccct
attgacgtcaatgacggtaaatggcccgcctggcattatgcccagtacatgaccttatgggactttcctacttggcagtacatctacgtattagtcatcgctattacc
atggtgatgcggttttggcagtacatcaatgggcgtggatagcggtttgactcacggggatttccaagtctccacccattgacgtcaatgggagtttgttttggca
ccaaaatcaacgggactttccaaaatgtcgtaacaactccgccccattgacgcaaatgggcggtaggcgtgtacggtgggaggtctatataagcagagctc
gtttagtgaaccgtcagatcgcctggagacgccatccacgctgtttttgacctccatagaagacaccgggaccgatccagcctccggactctagaggatcgaa
cccttgaattcccgccgccaccatgggctggtcatgtattattctgttctggtcgcaactgctacaggggtccatagtGAGATCGTGCTGACACAAT
CTCCCGGCACCCTCAGCCTGTCTCCAGGCGAGAGAGCCACACTGTCCTGCACCGCTTCTAGCTCCGTGTC
CTCCAGCTTTCTGCACTGGTACCAGCAGAAACCTGGCCAGGCTCCTCAGCTGTGGATCTACTCCACCTCCA
ACCTGGCCTCTGGCATCCCTGATCGGTTCTCCGGCTCCGGCTCTGGCACCGACTACACCCTGACCATCTC
CAGACTGGAACCTGAGGACTTCGCCGTGTACTACTGTCACCAGTACCACCATTCTCCTTACATCTATACCTT
CGGCGGAGGAACCAAGCTGGAAATCAAGaggacagtggccgcccaagcgtgttcatcttccccttccgacgagcagctgaagtctgg
caccgccagcgtggtgtgcctgctgaacaacttctaccctcgggaggccaaggtccagtggaaggtggataacgccctgcagtctggcaatagccaggagt
ccgtgaccgagcaggactctaaggatagcacatattccctgtctagcaccctgacactgagcaaggccgattacgagaagcacaaggtgtatgcctgtgaa
gtcacccatcaggggctgtcatcacccgtcactaagtcatcaatcgcggagaatgctgataagcttaagggttcgatccctaccggttagtaatgagtttgatat
ctcgacaatcaacctctggattacaaaatttgtgaaagattgactggtattcttaactatgttgctccttttacgctatgtggatacgctgctttaatgcctttgtatcatg
ctattgcttcccgtatggctttcatttctcctccttgtataaatcctggttgctgtctctttatgaggagttgtggcccgttgtcaggcaacgtggcgtggtgtgcactgtgt
ttgctgacgcaacccccactggttggggcattgccaccacctgtcagctcctttccgggactttcgctttccccctccctattgccacggcggaactcatcgccgc
ctgccttgcccgctgctggacaggggctcggctgttgggcactgacaattccgtggtgttgtcggggaagctgacgtccttccatggctgctcgcctgtgttgcca
cctggattctgcgcgggacgtcctttctgctacgtcccttcggccctcaatccagcggaccttccttcccgcggcctgctgccggctctgcggcctcttccgcgtcttc
gccttcgcccctcagacgagtcggatctcccttgggccgcctccccgcctggaaacggggggaggctaactgaaacacggaaggagacaataccggaagg
aacccgcgctatgacggcaataaaaagacagaataaaacgcacgggtgttgggtcgtttgttcataaacgcggggttcggtcccagggctggcactctgtcg
ataccccaccgagaccccattggggccaatacgcccgcgtttcttccttttcccaccccaccccccaagttcgggtgaaggcccagggctcgcagccaacg
tcggggcggcaggccctgccatagcagatctgcgcagctggggctctaggggggtatccccacgcgccctgtagcggcgcattaagcgcggcgggtgtggt
ggttacgcgcagcgtgaccgctacacttgccagcgccctagcgcccgctcctttcgctttcttcccttcctttctcgccacgttcgccggctttccccgtcaagctcta
aatcggggcatcccttagggttccgatttagtgctttacggcacctcgaccccaaaaaacttgattagggtgatggttcacgtagtgggccatcgccctgataga
cggttttcgcccttttgacgttggagtccacgttctttaatagtggactcttgttccaaactggaacaacactcaaccctatctcggtctattctttttgatttataagggatt
ttggggatttcggcctattggttaaaaaatgagctgatttaacaaaaatttaacgcgaattaattctgtggaatgtgtgtcagttagggtgtggaaagtccccaggc
tccccagcaggcagaagtatgcaaagcatgcatctcaattagtcagcaaccaggtgtggaaagtccccaggctccccagcaggcagaagtatgcaaagc
atgcatctcaattagtcagcaaccatagtcccgcccctaactccgcccatcccgcccctaactccgcccagttccgcccattctccgccccatggctgactaattt
ttttatttatgcagaggccgaggccgcctctgcctctgagctattccagaagtagtgaggaggcttttttggaggcctaggcttttgcaaaaagctcccgggagct
tgtatatccattttcggatctgatcaagagacaggatgaggatcgtttcgcatgattgaacaagatggattgcacgcaggttctccggccgcttgggtggagagg
ctattcggctatgactgggcacaacagacaatcggctgctctgatgccgccgtgttccggctgtcagcgcaggggcgcccggttctttttgtcaagaccgacctg
tccggtgccctgaatgaactgcaggacgaggcagcgcggctatcgtggctggccacgacgggcgttccttgcgcagctgtgctcgacgttgtcactgaagcg
ggaagggactggctgctattgggcgaagtgccggggcaggatctcctgtcatctcaccttgctcctgccgagaaagtatccatcatggctgatgcaatgcggc
ggctgcatacgcttgatccggctacctgcccattcgaccaccaagcgaaacatcgcatcgagcgagcacgtactcggatggaagccggtcttgtcgatcagg
atgatctggacgaagagcatcaggggctcgcgccagccgaactgttcgccaggctcaaggcgcgcatgcccgacggcgaggatctcgtcgtgacccatgg
cgatgcctgcttgccgaatatcatggtggaaaatggccgcttttctggattcatcgactgtggccggctgggtgtggcggaccgctatcaggacatagcgttggc
tacccgtgatattgctgaagagcttggcggcgaatgggctgaccgcttcctcgtgctttacggtatcgccgctcccgattcgcagcgcatcgccttctatcgccttc
ttgacgagttcttctgagcgggactctggggttcgcgaaatgaccgaccaagcgacgcccaacctgccatcacgagatttcgattccaccgccgccttctatga
aaggttgggcttcggaatcgttttccgggacgccgctggatgatcctccagcgcggggatctcatgctggagttcttcgcccaccccaacttgtttattgcagctt
ataatggttacaaataaagcaatagcatcacaaatttcacaaataaagcatttttttcactgcattctagttgtggtttgtccaaactcatcaatgtatcttatcatgtct
gtataccgtcgacctctagctagagcttggcgtaatcatggtcatagctgtttcctgtgtgaaattgttatccgctcacaattccacacaacatacgagccggaag
cataaagtgtaaagcctggggtgcctaatgagtgagctaactcacattaattgcgttgcgctcactgcccgctttccagtcgggaaacctgtcgtgccagctgca
ttaatgaatcggccaacgcgcggggagaggcggtttgcgtattgggcgctcttccgcttcctcgctcactgactcgctgcgctcggtcgttcggctgcggcgagc
ggtatcagctcactcaaaggcggtaatacggttatccacagaatcaggggataacgcaggaaagaacatgtgagcaaaaggccagcaaaaggccagg
aaccgtaaaaaggccgcgttgctggcgtttttccataggctccgcccccctgacgagcatcacaaaaatcgacgctcaagtcagaggtggcgaaacccgac

FIG. 55 (continued)

aggactataaagataccaggcgtttccccctggaagctccctcgtgcgctctcctgttccgaccctgccgcttaccggatacctgtccgccttctcccttcggga
agcgtggcgctttctcaatgctcacgctgtaggtatctcagttcggtgtaggtcgttcgctccaagctgggctgtgtgcacgaacccccgttcagcccgaccgct
gcgccttatccggtaactatcgtcttgagtccaacccggtaagacacgacttatcgccactggcagcagccactggtaacaggattagcagagcgaggtatgt
aggcggtgctacagagttcttgaagtggtggcctaactacggctacactagaaggacagtatttggtatctgcgctctgctgaagccagttaccttcggaaaaa
gagttggtagctcttgatccggcaaacaaaccaccgctggtagcggtggtttttttgtttgcaagcagcagattacgcgcagaaaaaaaggatctcaagaaga
tccttgatctttctacggggtctgacgctcagtggaacgaaaactcacgttaagggattttggtcatgagattatcaaaaaggatcttcacctagatccttttaaatt
aaaaatgaagttttaaatcaatctaaagtatatatgagtaaacttggtctgacagttaccaatgcttaatcagtgaggcacctatctcagcgatcgtctatttcgttc
atccatagttgcctgactccccgtcgtgtagataactacgatacgggagggcttaccatctggccccagtgctgcaatgataccgcgagacccacgctcaccg
gctccagatttatcagcaataaaccagccagccgccgaagggccgagcgcagaagtggtcctgcaactttatccgcctccagtctattaattgttgccgggg
aagctagagtaagtagttcgccagttaatagtttgcgcaacgttgttgccattgctacaggcatcgtggtgtcacgctcgtcgtttggtatggcttcattcagctccg
gttcccaacgatcaaggcgagttacatgatcccccatgttgtgcaaaaaagcggttagctccttcggtcctccgatcgttgtcagaagtaagttggccgcagtgtt
atcactcatggttatggcagcactgcataattctcttactgtcatgccatccgtaagatgcttttctgtgactggtgagtactcaaccaagtcattctgagaatagtgt
atgcggcgaccgagttgctcttgcccggcgtcaatacgggataataccgcgccacatagcagaactttaaaagtgctcatcattggaaaacgttcttcggggc
gaaaactctcaaggatcttaccgctgttgagatccagttcgatgtaacccactcgtgcacccaactgatcttcagcatcttttactttcaccagcgtttctgggtgag
caaaaacaggaaggcaaaatgccgcaaaaaagggaataagggcgacacgaaatgttgaatactcatactcttcctttttcaatattattgaagcatttatca
gggttattgtctcatgagcggatacatatttgaatgtatttagaaaaataaacaaataggggttccgcgcacatttccccgaaaagtgccacctgacgtcgacg
gatcgggagatctcccgatcccctatggtcgactctcagtacaatctgctctgatgccgcatagttaagccagtatctgctccctgcttgtgtgttggaggtcgctg
agtagtgcgcgagcaaaaattaagctacaacaaggcaaggcttgaccgacaattgcatgaagaatctgcttagg >20_U551FEL190-VL3_hIgkCL-pcDNA3.4          (SEQ ID NO: 195)
gttaggcgtttgcgctgcttcgcgatgtacgggccagatatacgcgttgacattgattattgactagttattaatagtaatcaattacggggtcattagttcatagcc
catatatggagttccgcgttacataacttacggtaaatggcccgcctggctgaccgcccaacgacccccgcccattgacgtcaataatgacgtatgttcccata
gtaacgccaatagggactttccattgacgtcaatgggtggagtatttacggtaaactgcccacttggcagtacatcaagtgtatcatatgccaagtacgccccct
attgacgtcaatgacggtaaatggcccgcctggcattatgcccagtacatgaccttatgggactttcctacttggcagtacatctacgtattagtcatcgctattacc
atggtgatgcggttttggcagtacatcaatgggcgtggatagcggtttgactcacggggatttccaagtctccacccattgacgtcaatgggagtttgttttggca
ccaaaatcaacgggactttccaaaatgtcgtaacaactccgccccattgacgcaaatgggcggtaggcgtgtacggtgggaggtctatataagcagagctc
gtttagtgaaccgtcagatcgcctggagacgccatccacgctgttttgacctccatagaagacaccgggaccgatccagcctccggactctagaggatcgaa
cccttgaattcccgccgccaccatgggctggtcatgtattattctgtttctggtcgcaactgctacaggggtccatagtGAGATCGTGCTGACCCAGT
CTCCAGGCACACTCAGCCTGTCTCCTGGCGAGCGGGCTACCCTGTCCTGCACCGCCAGCAGCTCCGTGTC
CTCTTCTTTTCTGCACTGGTACCAGCAGAAACCTGGACAAGCTCCTCAGCTGTGGATCTACTCCACCTCCAA
CCTGGCCTCTGGCATCCCCGATAGATTCTCCGGCTCTGGCTCCGGCACCGACTACACACTGACCATCTCC
AGACTGGAACCTGAGGACTTCGCCACCTACTACTGTCATCAGTACCACCACTCCCCTTACATCTATACCTTC
GGCGGAGGCACCAAGCTGGAAATCAAGaggacagtggccgcccccaagcgtgttcatcttccccccttccgacgagcagctgaagtctggc
accgccagcgtggtgtgcctgctgaacaacttctacctcggaggccaaggtccagtggaaggtggataacgccctgcagtctggcaatagccaggagtc
cgtgaccgagcaggactctaaggatagcacatattcccgtctagcaccctgacactgagcaaggccgattacgagaagcacaaggtgtatgcctgtgaag
tcacccatcaggggctgtcatcaccgtcactaagtcattcaatcgcggagaatgctgataagcttaagggttcgatccctaccggttagtaatgagtttgatatct
cgacaatcaacctctggattacaaaatttgtgaaagattgactggtattcttaactatgttgctccttttacgctatgtggatacgctgctttaatgcctttgtatcatgct
attgcttcccgtatggctttcattttctcctccttgtataaatcctggttgctgtctctttatgaggagttgtggcccgttgtcaggcaacgtggcgtggtgtgcactgtgttt
gctgacgcaacccccactggttggggcattgccaccacctgtcagctcctttccgggactttcgctttccccctccctattgccacggcggaactcatcgccgcct
gccttgcccgctgctggacaggggctcggctgttgggcactgacaattccgtggtgttgtcggggaagctgacgtcctttccatggctgctcgcctgtgttgccac
ctggattctgcgcgggacgtccttctgctacgtcccttcggccctcaatccagcggaccttccttcccgcggcctgctgccggctctgcggcctcttccgcgtcttc
gccttcgccctcagacgagtcggatctccctttgggccgcctccccgcctggaacggggggaggctaactgaaacacggaaggagacaataccggaagg
aacccgcgctatgacggcaataaaaagacagaataaaacgcacgggtgttgggtcgtttgttcataaacgcggggttcggtcccagggctggcactctgtcg
ataccccaccgagaccccattggggccaatacgcccgcgtttcttccttttccccaccccaccccccaagttcgggtgaaggcccagggctcgcagccaacg
tcggggcggcaggccctgccatagcagatctgggggcgctagggacctggggctctaggggtatcccccacgcgccctgtagcggcgcattaagcgcgggtgtggt
ggttacgcgcagcgtgaccgctacacttgccagcgccctagcgcccgctcctttcgctttcttcccttcctttctcgccacgttcgccggctttccccgtcaagctcta
aatcggggcatccctttagggttccgatttagtgctttacggcacctcgaccccaaaaaacttgattagggtgatggttcacgtagtgggccatcgccctgataga
cggtttttcgccctttgacgttggagtccacgttctttaatagtggactcttgttccaaactggaacaacactcaacctatctcggtctattctttgatttataagggatt
ttggggatttcggcctattggttaaaaaatgagctgatttaacaaaaatttaacgcgaattaattctgtggaatgtgtgtcagttagggtgtggaaagtccccaggc
tccccagcaggcagaagtatgcaaagcatgcatctcaattagtcagcaaccaggtgtggaaagtcccaggctccccagcaggcagaagtatgcaaagc
atgcatctcaattagtcagcaaccatagtcccgcccctaactccgcccatcccgcccctaactccgcccagttccgcccattctccgccccatggctgactaattt
tttttatttatgcagaggccgaggccgcctctgcctctgagctattccagaagtagtgaggaggcttttttggaggcctaggcttttgcaaaaagctcccgggagct
tgtatatccattttcggatctgatcaagagacaggatgaggatcgtttcgcatgattgaacaagatggattgcacgcaggttctccggccgcttgggtggagagg

FIG. 55 (continued)

ctattcggctatgactgggcacaacagacaatcggctgctctgatgccgccgtgttccggctgtcagcgcaggggcgcccggttcttttgtcaagaccgacctg
tccggtgccctgaatgaactgcaggacgaggcagcgcgcggctatcgtggctggccacgacgggcgttccttgcgcagctgtgctcgacgttgtcactgaagcg
ggaagggactggctgctatgggcgaagtgccgggggcaggatctcctgtcatctcaccttgctcctgccgagaaagtatccatcatggctgatgcaatgcggc
ggctgcatacgcttgatccggctacctgcccattcgaccaccaagcgaaacatcgcatcgagcgagcacgtactcggatggaagccggtcttgtcgatcagg
atgatctggacgaagagcatcaggggctcgcgccagccgaactgttcgccaggctcaaggcgcgcatgcccgacggcgaggatctcgtcgtgacccatgg
cgatgcctgcttgccgaatatcatggtggaaaatggccgcttttctggattcatcgactgtggccggctgggtgtggcggaccgctatcaggacatagccgttggc
tacccgtgatattgctgaagagcttggcggcgaatgggctgaccgcttcctcgtgctttacggtatcgccgctcccgatcgcagcgcatcgccttctatcgccttc
ttgacgagttcttctgagcgggactctggggttcgcgaaatgaccgaccaagcgacgcccaacctgccatcacgagattcgattccaccgccgccttctatga
aaggttgggcttcggaatcgtttccgggacgccggctggatgatcctccagcgcggggatctcatgctggagttcttcgcccaccccaacttgtttattgcagctt
ataalggttacaaataaagcaatagcatcacaaattcacaaataaagcattttttcactgcattctagttgtgttgtccaaactcatcaatgtatctiatcatgtct
gtataccgtcgacctctagctagagcttggcgtaatcatggtcatagctgtttcctgtgtgaaattgttatccgctcacaattccacacaacatacgagccggaag
cataaagtgtaaagcctggggtgcctaatgagtgagctaactcacattaattgcgttgcgctcactgcccgctttccagtcgggaaacctgtcgtgccagctgca
ttaatgaatcggccaacgcgcggggagaggcggtttgcgtattgggcgctcttccgcttcctcgctcactgactcgctgcgctcggtcgttcggctgcggcgagc
ggtatcagctcactcaaaggcggtaatacggttatccacagaatcaggggataacgcaggaaagaacatgtgagcaaaaggccagcaaaaggccagg
aaccgtaaaaaggccgcgttgctggcgtttttccataggctccgcccccctgacgagcatcacaaaaatcgacgctcaagtcagaggtggcgaaacccgac
aggactataaagataccaggcgtttccccctggaagctccctcgtgcgctctcctgttccgaccctgccgcttaccggataccgtccgcctttctcccttcggga
agcgtggcgctttctcaatgctcacgctgtaggtatctcagttcggtgtaggtcgttcgctccaagctgggctgtgtgcacgaaccccccgttcagcccgaccgct
gcgccttatccggtaactatcgtcttgagtccaacccggtaagacacgacttatcgccactggcagcagccactggtaacaggattagcagagcgaggtatgt
aggcggtgctacagagttcttgaagtggtggcctaactacggctacactagaaggacagtatttggtatctgcgctctgctgaagccagttaccttcggaaaaa
gagttggtagctcttgatccggcaaacaaaccaccgctggtagcggtggtttttttgtttgcaagcagcagattacgcgcagaaaaaaaggatctcaagaaga
tcctttgatcttttctacggggtctgacgctcagtggaacgaaaactcacgttaagggattttggtcatgagattatcaaaaaggatcttcacctagatcctttaaatt
aaaaatgaagttttaaatcaatctaaagtatatatgagtaaacttggtctgacagttaccaatgcttaatcagtgaggcacctatctcagcgatctgtctatttcgttc
atccatagttgcctgactccccgtcgtgtagataactacgatacgggagggcttaccatctggccccagtgctgcaatgataccgcgagacccacgctcaccg
gctccagatttatcagcaataaaccagccagccggaagggccgagcgcagaagtggtcctgcaactttatccgcctccatccagtctattaattgttgccggg
aagctagagtaagtagttcgccagttaatagtttgcgcaacgttgttgccattgctacaggcatcgtggtgtcacgctcgtcgtttggtatggcttcattcagctccg
gttcccaacgatcaaggcgagttacatgatcccccatgttgtgcaaaaaagcggttagctccttcggtcctccgatcgttgtcagaagtaagttggccgcagtgtt
atcactcatggttatggcagcactgcataattctcttactgtcatgccatccgtaagatgcttttctgtgactggtgagtactcaaccaagtcattctgagaatagtgt
atgcggcgaccgagttgctcttgcccggcgtcaatacgggataataccgcgccacatagcagaactttaaaagtgctcatcattggaaaacgttcttcggggc
gaaaactctcaaggatcttaccgctgttgagatccagttcgatgtaacccactcgtgcacccaactgatcttcagcatctttactttcaccagcgtttctgggtgag
caaaaacaggaaggcaaaatgccgcaaaaaagggaataagggcgacacggaaatgttgaatactcatactcttcctttttcaatattattgaagcatttatca
gggttattgtctcatgagcggatacatatttgaatgtatttagaaaaataaacaaataggggttccgcgcacatttccccgaaaagtgccacctgacgtcgacg
gatcgggagatctcccgatcccctatggtcgactctcagtacaatctgctctgatgccgcatagttaagccagtatctgctccctgcttgtgtgttggaggtcgctg
agtagtgcgcgagcaaaatttaagctacaacaaggcaaggcttgaccgacaattgcatgaagaatctgcttagg >23_U551FEL190-VL4_hIgkCL-pcDNA3.4          (SEQ ID NO: 196)
gttaggcgtttgcgctgcttcgcgatgtacgggccagatatacgcgttgacattgattattgactagttattaatagtaatcaattacggggtcattagttcatagcc
catatatggagttccgcgttacataacttacggtaaatggcccgcctggctgaccgcccaacgacccccgcccattgacgtcaataatgacgtatgttcccata
gtaacgccaatagggactttccattgacgtcaatgggtggagtatttacggtaaactgcccacttggcagtacatcaagtgtatcatatgccaagtacgcccct
attgacgtcaatgacggtaaatggcccgcctggcattatgcccagtacatgaccttatgggactttcctacttggcagtacatctacgtattagtcatcgctattacc
atggtgatgcggttttggcagtacatcaatgggcgtggatagcggtttgactcacggggatttccaagtctccaccccattgacgtcaatgggagtttgttttggca
ccaaaatcaacgggactttccaaaatgtcgtaacaactccgccccattgacgcaaatgggcggtaggcgtgtacggtgggaggtctatataagcagagctc
gtttagtgaaccgtcagatcgcctggagacgccatccacgctgttttgacctccatagaagacaccgggaccgatccagcctccggactctagaggatccaa
cccttgaattccgccgccaccatgggctggtcatgtattatctgttcttctggtcgcaactgcacagggggcatagtGAGATCGTGCTGACCCAAT
CTCCTGGCACCCTGTCTCTGAGCCCAGGCGAGAGACCCACCTCTCCTGCACCGCTTCTTCCTCCGTGTC
CTCTAGCTTTCTGCACTGGTACCAGCAGAAACCCGGCCAGGCTCCTCAGCTGTGGATCTACTCCACCTCCA
ACCTGGCCTCTGGCATCCCTGCCCAGATTCTCCGGATCCGGCTCTGGCACCGATTATACACTGACCATCTCC
CGGCTGGAACCTGAGGACTTCGCCACCTACTACTGTCACCAGTACCACCATAGCCCTTACATCTACACCTT
CGGCGGCGGAACCAAGCTGGAAATCAAGaggacagtggccgcccccaagcgtgttcatcttccccttccgacgagcagctgaagtctg
gcaccgccagcgtggtgtgcctgctgaacaacttctaccctcgggaggccaaggtccagtggaaggtggataacgccctgcagtctggcaatagccagga
gtccgtgaccgagcaggactctaaggatagcacatattccctgtctagcaccctgacactgagcaaggccgattacgagaagcacaaggtgtatgcctgtga
agtcacccatcaggggctcgtcatcacccgtcactaagtcattcaatcgcggagaatgctgataagcttaagggttcgatccctaccggttagtaatgagtttgat
atctcgacaatcaacctctggattacaaaatttgtgaaagattgactggtattcttaactatgttgctccttttacgctatgtggatacgctgctttaatgcctttgtatcat
gctattgcttcccgtatggctttcatttctcctccttgtataaatcctggttgctgtgtctctttatgaggagttgtggcccgttgtcaggcaacgtggcgtggtgtgcactgt

FIG. 55 (continued)

gtttgctgacgcaaccccactggttggggcattgccaccacctgtcagctcctttccgggactttcgctttcccctccctattgccacggcggaactcatcgccg
cctgccttgcccgctgctggacaggggctcggctgttgggcactgacaattccgtggtgttgtcggggaagctgacgtccttccatggctgctcgcctgtgttgcc
acctggattctgcgcgggacgtccttctgctacgtcccttcggccctcaatccagcggaccttccttcccgcggcctgctgccggctctgcggcctcttccgcgtct
tcgccttcgccctcagacgagtcggatctcccttgggccgcctccccgcctggaaacggggggaggctaactgaaacacggaaggagacaataccggaag
gaaccccgcgctatgacggcaataaaaagacagaataaaaacgcacgggtgttgggtcgttgttcataaacgcggggttcggtcccaggggctggcactctgtc
gataccccaccgagacccattggggccaatacgcccgcgttcttccttttccccaccccaccccccaagttcgggtgaaggcccagggctcgcagccaac
gtcggggcggcaggccctgccatagcagatctgcgcagctggggctctaggggggtatccccacgcgccctgtagcggcgcattaagcgcggcgggtgtgg
tggttacgcgcagcgtgaccgctacacttgccagcgcccagcgccggctccttcgcttcttccttcctttctcgccacgtcgccggctttccccgtcaagctct
aaatcggggcatccctttagggttccgatttagtgctttacggcacctcgacccaaaaaacttgattagggtgatggttcacgtagtgggccatcgccctgatag
acggtttctcgcccttgacgttggagtccacgttcttaatagtggactcttgttccaaactggaacaacactcaaccctatctcggtctattctttgattataaggga
ttttgggggatttcggcctattggttaaaaaatgagctgatttaacaaaaaatttaacgcgaattaattctgtggaatgtgtgtcagttagggtgtggaaagtccccagg
ctccccagcaggcagaagtatgcaaagcatgcatctcaattagtcagcaaccaggtgtggaaagtccccaggctccccagcaggcagaagtatgcaaag
catgcatctcaattagtcagcaaccatagtcccgccctaactccgcccatcccgcccctaactccgcccagttccgcccattctccgccccatggctgactaat
tttttttatttatgcagaggccgaggccgcctctgcctctgagctattccagaagtagtgaggaggctttttttggaggcctaggcttttgcaaaaagctcccgggag
cttgtatatccattttcggatctgatcaagagacaggatgaggatccgttcgcatgattgaacaagatggattgcacgcaggttctccggccgcttgggtggaga
ggctattcggctatgactgggcacaacagacaatcggctgctctgatgccgccgtgttccggctgtcagcgcaggggcgcccggttcttttgtcaagaccgac
ctgtccggtgccctgaatgaactgcaggacgaggcagcgcggctatcgtggctggccacgacgggcgttccttgcgcagctgtgctcgacgttgtcactgaa
gcgggaagggactggctgctattgggcgaagtgccggggcaggatctcctgtcatctcaccttgctcctgccgagaaagtatccatcatggctgatgcaatgc
ggcggctgcatacgcttgatccggctacctgcccatcgaccaccaagcgaaacatcgcatcgagcgagcacgtactcggatggaagccggtcttgtcgatc
aggatgatctggacgaagagcatcaggggctcgcgccagccgaactgttcgccaggctcaaggcgcgcatgcccgacggcgaggatctcgtcgtgaccc
atggcgatgcctgcttgccgaatatcatggtggaaaatggccgcttttctggattcatcgactgtggccggctgggtgtggcggaccgctatcaggacatagcgt
tggctaccgtgatattgctgaagagcttggcggcgaatgggctgaccgcttcctcgtgctttacggtatcgccgctcccgattcgcagcgcatcgccttctatcg
ccttcttgacgagttcttctgagcgggactctggggttcgcgaaatgaccgaccaagcgacgcccaacctgccatcacgagattcgattccaccgccgccttct
atgaaaggttgggcttcggaatcgtttccgggacgccggctggatgatcctccagcgcggggatctcatgctggagttcttcgcccacccccaacttgtttattgc
agcttataatggttacaaataaagcaatagcatcacaaatttcacaaataaagcatttttttcactgcattctagttgtggtttgtccaaactcatcaatgtatcttatc
atgtctgtataccgtcgacctctagctagagcttggcgtaatcatggtcatagctgtttcctgtgtgaaattgttatccgctcacaattccacacaacatacgagccg
gaagcataaagtgtaaagcctggggtgcctaatgagtgagctaactcacattaattgcgttgcgctcactgcccgctttccagtcgggaaacctgtcgtgccag
ctgcattaatgaatcggccaacgcgcggggagaggcggtttgcgtattgggcgctcttccgcttcctcgctcactgactcgctgcgctcggtcgttcggctgcgg
cgagcggtatcagctcactcaaaggcggtaatacggttatccacagaatcaggggataacgcaggaaagaacatgtgagcaaaaggccagcaaaagg
ccaggaaccgtaaaaaggccgcgttgctggcgtttttccataggctccgcccccctgacgagcatcacaaaaatcgacgctcaagtcagaggtggcgaaac
ccgacaggactataaagataccaggcgtttccccctggaagctccctcgtgcgctctcctgttccgaccctgccgcttaccggatacctgtccgcctttctccctc
gggaagcgtggcgctttctcaatgctcacgctgtaggtatctcagttcggtgtaggtcgttcgctccaagctgggctgtgtgcacgaaccccccgttcagcccga
ccgctgcgccttatccggtaactatcgtcttgagtccaacccggtaagacacgacttatcgccactggcagcagccactggtaacaggattagcagagcgag
gtatgtaggcggtgctacagagttcttgaagtggtggcctaactacggctacactagaaggacagtatttggtatctgcgctctgctgaagccagttaccttcgga
aaaagagttggtagctcttgatccggcaaacaaaccaccgctggtagcggtggtttttttgtttgcaagcagcagattacgcgcagaaaaaaaggatctcaag
aagatcctttgatcttttctacggggtctgacgctcagtggaacgaaaactcacgttaagggattttggtcatgagattatcaaaaaggatctcacctagatccttt
taaattaaaaatgaagttttaaatcaatctaaagtatatatgagtaaacttggtctgacagttaccaatgcttaatcagtgaggcacctatctcagcgatctgtctatt
tcgttcatccatagttgcctgactccccgtcgtgtagataactacgatacgggagggcttaccatctggccccagtgctgcaatgataccgcgagacccacgct
caccggctccagatttatcagcaataaaccagccagccggaagggccgagcgcagaagtggtcctgcaactttatccgcctccatccagtctattaattgttgc
cgggaagctagagtaagtagttcgccagttaatagtttgcgcaacgttgttgccattgctacaggcatcgtggtgtcacgctcgtcgtttggtatggcttcattcagc
tccggttcccaacgatcaaggcgagttacatgatcccccatgttgtgcaaaaaagcggttagctccttcggtcctccgatcgttgtcagaagtaagttggccgca
gtgttatcactcatggttatggcagcactgcataattctcttactgtcatgccatccgtaagatgcttttctgtgactggtgagtactcaaccaagtcattctgagaata
gtgtatgcggcgaccgagttgctcttgcccggcgtcaatacgggataataccgcgccacatagcagaactttaaaagtgctcatcattggaaaacgttcttcgg
ggcgaaaactctcaaggatcttaccgctgttgagatccagttcgatgtaacccactcgtgcacccaactgatcttcagcatcttttactttcaccagcgtttctgggt
gagcaaaaacaggaaggcaaaatgccgcaaaaaagggaataagggcgacacggaaatgttgaatactcatactcttcctttttcaatattattgaagcattta
tcagggttattgtctcatgagcggatacatatttgaatgtatttagaaaaataaacaaataggggttccgcgcacatttccccgaaaagtgccacctgacgtcga
cggatcgggagatctcccgatcccctatggtcgactctcagtacaatctgctctgatgccgcatagttaagccagtatctgctccctgcttgtgtgttggaggtcgct
gagtagtgcgcgagcaaaatttaagctacaacaaggcaaggcttgaccgacaattgcatgaagaatctgcttagg >5_U551FEL190--VH2_hIgG1CH-pCDNA3.4 (SEQ ID NO: 197)
Gttaggcgttttgcgctgcttcgcgatgtacgggccagatatacgcgttgacattgattattgactagttattaatagtaatcaattacggggtcattagttcatagcc
catatatggagttccgcgttacataacttacggtaaatggcccgcctggctgaccgcccaacgacccccgcccattgacgtcaataatgacgtatgttcccata
gtaacgccaatagggactttccattgacgtcaatgggtggagtatttacggtaaactgcccacttggcagtacatcaagtgtatcatatgccaagtacgccccct

FIG. 55 (continued)

attgacgtcaatgacggtaaatggcccgcctggcattatgcccagtacatgaccttatgggactttcctacttggcagtacatctacgtattagtcatcgctattacc
atggtgatgcggttttggcagtacatcaatgggcgtggatagcggtttgactcacggggatttccaagtctccaccccatugacgtcaatgggagttgtttggca
ccaaaatcaacgggactttccaaaatgtcgtaacaactccgccccattgacgcaaatgggcggtaggcgtgtacggtgggaggtctatataagcagagctc
gtttagtgaaccgtcagatcgcctggagacgccatccacgctgttttgacctccatagaagacaccgggaccgatccagcctccggactctagaggatcgaa
cccttgaattccgccgccaccatgggctggtcatgcattattctgtttctggtcgcaactgctacaggcgtgcatagtCAGGTGCAGCTGCAAGAGT
CCGGCCCTGGACTCGTGAAGCCCTCCGAGACACTGTCTCTGACATGTACCGTGTCTGGCTTCTCCCTGTC
CATCTACTCCGTGCACTGGATCAGACAGCCTCCTGGCAAGGGCCTGGAATGGATCGGCATGATCTGGGGA
GGCGGCTCTTCCGACTACAACTCCGCCCTGAAATCTCGGCTGACCATCTCCAAGGACACCTCTAAGAACCA
GGTCAGCCTGAAGCTGAGCTCTGTGACCGCTGCTGATACCGCCGTGTACTACTGCGCCAGAAATGGCAAC
TTCTACGCCATGGACTATTGGGGCCAGGGCACCCTGGTGACCGTGTCCAGCgccagcaccaagggcccttccgtgtttc
cactggcccctcctctaaatccacatctggcggcaccgccgccctgggctgtctggtgaaggactacttcccagagcctgtgacagtgtcctggaactctggc
gccctgacatccggcgtgcacacatttccagccgtgctgcagagctccggcctgtacagcctgtctagcgtggtgacagtgccctcctctagcctgggcacac
agacctatatctgcaacgtgaatcacaagccaagcaataccaaggtggacaagaaggtggagcccaagtcctgtgataagacacacacctgcccccctg
tcctgctcccgagctgctgggcggcccctagcgtgttcctgtttccacccaagcctaaggacacct gatgatctcccggacacccgaggtgacctgcgtggtgg
tggacgtgtctcacgaggatcctgaggtgaagttcaactggtatgtggatggcgtggaggtgcacaatgccaagaccaagcccagagaggagcagtacaa
ctctacatataggatggtgagcgtgctgaccgtgctgcaccaggactggctgaacggcaaggagtataagtgcaaggtgtccaataaggccctgcccgccc
ccatcgagaagacaatcagcaaggccaagggccagcctcgggagccacaggtgtacaccctgcctccatcagagacgagctgacaaagaaccaggt
gtctctgacatgtctggtgaagggcttctatcctagcgatatcgccgtggagtgggagtccaatggccagccagagaacaattacaagaccacacccctgtg
ctggactccgatggctccttctttctgtattccaagctgaccgtggataagtctcggtggcagcagggcaacgtgttcagctgttccgtgatgcacgaagccctgc
ataatcactatactcagaaatccctgtccctgtcacctggaaagtgataagcttaagggttcgatccctaccggttagtaatgagtttgatatctcgacaatcaacc
tctggattacaaaatttgtgaaagattgactggtattcttaactatgttgctccttttacgctatgtggatacgctgctttaatgcctttgtatcatgctattgcttcccgtatg
gctttcattttctcctccttgtataaatcctggttgctgtctctttatgaggagttgtggcccgttgtcaggcaacgtggcgtggtgtgcactgtgtttgctgacgcaaccc
ccactggttggggcattgccaccacctgtcagctcctttccgggactttcgctttccccctccctattgccacggcggaactcatcgccgcctgccttgcccgctgc
tggacaggggctcggctgttgggcactgacaattccgtggtgttgtcggggaagctgacgtcctttccatggctgctcgcctgtgttgccacctggattctgcgcg
ggacgtccttctgctacgtcccttcggccctcaatccagcggaccttccttcccgcgcctgctgccggctctgcggcctcttccgcgtcttcgccttcgccctcag
acgagtcggatctcccttgggccgcctccccgcctggaaacggggggaggctaactgaaacacggaaggagacaataccggaaggaacccgcgctatg
acggcaataaaaagacagaataaaacgcacgggtgttgggtcgttgttcataaacgcggggtcggtcccagggctggcactctgtcgataccccaccga
gacccattggggccaatacgcccgcgtttcttccttttccccacccccaccccccaagttcgggtgaaggcccagggctcgcagccaacgtcggggcggcag
gccctgccatagcagatctgcgcagctggggctctaggggggtatccccacgcgccctgtagcggcgcattaagcgcggcgggtgtggtggttacgcgcagc
gtgaccgctacacttgccagcgccctagcgcccgctccttcgctttcttcccttccttctcgccacgttcgccggctttccccgtcaagctctaaatcggggcatcc
ctttaggggttccgatttagtgctttacggcacctcgaccccaaaaaacttgattagggtgatggttcacgtagtgggccatcgccctgatagacggttttcgccctt
gacgttggagtccacgttctttaatagtggactcttgttccaaactggaacaacactcaaccctatctcggtctattctttgatttataagggattttggggattcggc
ctattggttaaaaaatgagctgatttaacaaaaatttaacgcgaattaattctgtggaatgtgtgtcagttagggtgtggaaagtccccaggctccccagcaggc
agaagtatgcaaagcatgcatctcaattagtcagcaaccaggtgtggaaagtccccaggctccccagcaggcagaagtatgcaaagcatgcatctcaatta
gtcagcaaccatagtcccgcccctaactccgcccatcccgcccctaactccgcccagttccgcccattctccgccccatggctgactaatttttttatttatgcag
aggccgaggccgcctctgcctctgagctattccagaagtagtgaggaggcttttttggaggcctaggcttttgcaaaaagctcccgggagcttgtatatccatttc
ggatctgatcaagagacaggatgaggatcgtttcgcatgattgaacaagatggattgcacgcaggttctccggccgcttgggtggagaggctattcggctatg
actgggcacaacagacaatcggctgctctgatgccgccgtgttccggctgtcagcgcaggggcgcccggttcttttgtcaagaccgacctgtccggtgccctg
aatgaactgcaggacgaggcagcgcggctatcgtggctggccacgacgggcgttccttgcgcagctgtgctcgacgttgtcactgaagcgggaagggact
ggctgctattgggcgaagtgccggggcaggatctcctgtcatctcaccttgctcctgccgagaaagtatccatcatggctgatgcaatgcggcggctgcatacg
cttgatccggctacctgcccattcgaccaccaagcgaaacatcgcatcgagcgagcacgtactcggatggaagccggtcttgtcgatcaggatgatctggac
gaagagcatcaggggctcgcgccagccgaactgttcgccaggctcaaggcgcgcatgcccgacggcgaggatctcgtcgtgacccatggcgatgcctgct
tgccgaatatcatggtggaaaatggccgcttttctggattcatcgactgtggccggctgggtgtggcggaccgctatcaggacatagcgttggctacccgtgata
ttgctgaagagcttggcggcgaatgggctgaccgcttcctcgtgctttacggtatcgccgctcccgattcgcagcgcatcgccttctatcgccttcttgacgagttct
tctgagcgggactctggggttcgcgaaatgaccgaccaagcgacgcccaacctgccatcacgagatttcgattccaccgccgccttctatgaaaggttgggct
tcggaatcgttttccgggacgccggctggatgatcctccagcgcggggatctcatgctggagttcttcgcccaccccaacctgtttattgcagcttataatggttac
aaataaagcaatagcatcacaaatttcacaaataaagcatttttttcactgcattctagttgtggtttgtccaaactcatcaaagtatcttatcatgtctgtataccgtcg
acctctagctagagcttggcgtaatcatggtcatagctgtttcctgtgtgaaattgttatccgctcacaattccacacaacatacgagccggaagcataaagtgta
aagcctggggtgcctaatgagtgagctaactcacattaattgcgttgcgctcactgcccgctttccagtcgggaaacctgtcgtgccagctgcattaatgaatcg
gccaacgcgcggggagaggcggtttgcgtattgggcgctcttccgcttcctcgctcactgactcgctgcgctcggtcgttcggctgcggcgagcggtatcagct
cactcaaaggcggtaatacggttatccacagaatcaggggataacgcaggaaagaacatgtgagcaaaaggccagcaaaaggccaggaaccgtaaa
aaggccgcgttgctggcgtttttccataggctccgcccccctgacgagcatcacaaaaatcgacgctcaagtcagaggtggcgaaacccgacaggactata
aagataccaggcgtttccccctggaagctccctcgtgcgctctcctgttccgaccctgccgcttaccggatacctgtccgcctttctcccttcgggaagcgtggcg

FIG. 55 (continued)

ctttctcaatgctcacgctgtaggtatctcagttcggtgtaggtcgttcgctccaagctgggctgtgtgcacgaaccccccgttcagcccgaccgctgcgccttatc
cggtaactatcgtcttgagtccaacccggtaagacacgacttatcgccactggcagcagccactggtaacaggattagcagagcgaggtatgtaggcggtg
ctacagagttcttgaagtggtggcctaactacggctacactagaaggacagtatttggtatctgcgctctgctgaagccagttaccttcggaaaaagagttggta
gctcttgatccggcaaacaaaccaccgctggtagcggtggtttttttgtttgcaagcagcagattacgcgcagaaaaaaaggatctcaagaagatcctttgatct
tttctacgggggtctgacgctcagtggaacgaaaactcacgttaagggattttggtcatgagattatcaaaaaggatcttcacctagatccttttaaattaaaaatga
agttttaaatcaatctaaagtatatatgagtaaacttggtctgacagttaccaatgcttaatcagtgaggcacctatctcagcgatctgtctatttcgttcatccatagtt
gcctgactccccgtcgtgtagataactacgatacgggagggcttaccatctggccccagtgctgcaatgataccgcgagacccacgctcaccggctccagat
ttatcagcaataaaccagccagccggaagggccgagcgcagaagtggtcctgcaactttatccgcctccatccagtctattaattgttgccgggaagctagag
taagtagttcgccagttaatagtttgcgcaacgttgttgccattgctacaggcatcgtggtgtcacgctcgtcgtttggtatggcttcattcagctccggttcccaacg
atcaaggcgagttacatgatcccccatgttgtgcaaaaaagcggttagctccttcggtcctccgatcgttgtcagaagtaagttggccgcagtgttatcactcatg
gttatggcagcactgcataattctcttactgtcatgccatccgtaagatgcttttctgtgactggtgagtactcaaccaagtcattctgagaatagtgtatgcggcga
ccgagttgctcttgcccggcgtcaatacgggataataccgcgccacatagcagaactttaaaagtgctcatcattggaaaacgttcttcggggcgaaaactctc
aaggatcttaccgctgttgagatccagttcgatgtaacccactcgtgcacccaactgatcttcagcatcttttactttcaccagcgtttctgggtgagcaaaaacag
gaaggcaaaatgccgcaaaaaagggaataagggcgacacggaaatgttgaatactcatactcttcctttttcaatattattgaagcatttatcagggttattgtct
catgagcggatacatatttgaatgtatttagaaaaataaacaaataggggttccgcgcacatttccccgaaaagtgccacctgacgtcgacggatcgggaga
tctcccgatcccctggtcgactctcagtacaatctgctctgatgccgcatagttaagccagtatcgctccctgcttgtgtgttggaggtcgctgagtagtgcgcg
agcaaaatttaagctacaacaaggcaaggcttgaccgacaattgcatgaagaatctgcttagg >11_U551FEL190-VH4_hIgG1CH-pCDNA3.4     (SEQ ID NO: 198)
gttaggcgtttgcgctgcttcgcgatgtacgggccagatatacgcgttgacattgattattgactagttattaatagtaatcaattacggggtcattagttcatagcc
catatatggagttccgcgttacataacttacggtaaatggcccgcctggctgaccgcccaacgacccccgcccattgacgtcaataatgacgtatgttcccata
gtaacgccaatagggactttccattgacgtcaatgggtggagtatttacggtaaactgcccacttggcagtacatcaagtgtatcatatgccaagtacgcccct
attgacgtcaatgacggtaaatggcccgcctggcattatgcccagtacatgaccttatgggactttcctacttggcagtacatctacgtattagtcatcgctattacc
atggtgatgcggttttggcagtacatcaatgggcgtggatagcggtttgactcacggggatttccaagtctccaccccattgacgtcaatgggagtttgttttggca
ccaaaatcaacgggactttccaaaatgtcgtaacaactccgccccattgacgcaaatgggcggtaggcgtgtacggtgggaggtctatataagcagagctc
gtttagtgaaccgtcagatcgcctggagacgccatccacgctgttttgacctccatagaagacaccgggaccgatccagcctccggactctagaggatcgaa
cccttgaattcccgccgccaccatgggctggtcatgcattattctgtttctggtcgcaactgctacaggcgtgcatagtCAGGTGCAGCTGCAAGAGT
CCGGACCCGGCCTCGTGAAGCCTTCCGAGACACTGTCTCTGACCTGTACCGTGTCTGGCTTCTCCCTGTC
CATCTACTCCGTGCACTGGATCCGGCAGCCTCCTGGCAAGGGCCTGGAATGGCTGGGCATGATCTGGGG
CGGCGGAAGCTCCGACTACAACTCCGCCCTGAAATCTAGACTGACCATCTCCAAGGACACCTCTAAGAACC
AGGTCAGCCTGAAGCTGAGCTCTGTGACCGCCGCTGATACCGCTATGTACTACTGCGCCAGAAATGGCAA
CTTCTACGCCATGGACTATTGGGGCCAGGGCACCCTGGTGACAGTGCCTCTgccagcaccaagggcccttccgtgttt
ccactggcccctcctctaaatccacatctggcggcaccgcgccctgggctgtctggtgaaggactacttcccagagcctgtgacagtgtcctggaactctgg
cgccctgacatccggcgtgcacacattccagccgtgctgcagagctccggcctgtacagcctgtctagcgtggtgacagtgccctcctctagcctgggcaca
cagacctatatctgcaacgtgaatcacaagccagcaataccaaggtggacaagaaggtggagcccaagtctgtgataagacacacacctgcccccctt
gtcctgctcccgagctgctgggcggccctagcgtgttcctgttccacccaagcctaaggacaccctgatgatctcccggacaccgaggtgacctgcgtggtg
gtggacgtgtctcacgaggatcctgaggtgaagttcaactggtatgtggatggcgtggaggtgcacaatgccaagaccaagcccagagaggagcagtaca
actacatataggtggtgagcgtgctgaccgtgctgcaccaggactggctgaacggcaaggagtataagtgcaaggtgtccaataaggccctgcccgcc
cccatcgagaagacaatcagcaaggccaagggccagcctcgggagccacaggtgtacaccctgcctccatccagagacgagctgacaaagaaccagg
tgtctctgacatgtctggtgaagggcttctatcctagcgatatcgccgtggagtgggagtccaatggccagccagaacaattacaagaccacacccctgt
gctggactccgatggctccttcttctgtattccaagctgaccgtggataagtctcggtggcagcaggcaacgtgttcagctgttccgtgatgcacgaagccctg
cataatcactactctcagaaatccctgtccctgtcacctggaaagtgataagcttaagggtcgatccctaccggtagtaatgagtttgatatctcgacaatcaac
ctctggattacaaaattgtgaaagattgactggtattcttaactatgttgctccttttacgctatgtggatacgctgctttaatgcctttgtatcatgctattgcttcccgtat
ggctttcattttctcctccttgtataaaatcctggttgctgtctctttatgaggagttgtggcccgttgtcaggcaacgtggcgtggtgtgcactgtgtttgctgacgcaacc
cccactggttggggcattgccaccacctgtcagctcctttccgggactttcgctttccccctccctattgccacggcggaactcatcgccgcctgccttgcccgctg
ctggacaggggctcggctgttgggcactgacaattccggtggtgttgtcggggaagctgacgtcctttccatggctgctcgcctgtgttgccacctggattctgcgc
gggacgtccttctgctacgtcccttcggccctcaatccagcggaccttccttcccgcggcctgctgccggctctgcggcctcttccgcgtcttcgccttcgccctca
gacgagtcggatctcccttgggccgcctccccgcctggaacgggggaggctaactgaaacacggaaggagacaataccggaaggaacccgcgctat
gacggcaataaaaagacagaataaaacgcacgggtgttgggtcgtttgttcataaacgcggggttcggtcccagggctggcactctgtcgataccccaccg
agacccattggggccaatacgcccgcgtttcttccttttccccacccacccccaagttcgggtgaaggcccagggctcgcagccaacgtcggggcggca
ggccctgccatagcagatctgcgcagctggggctctaggggggtatccccacgcgccctgtagcggcgcattaagcgcggcgggtgtggtggttacgcgcag
cgtgaccgctacacttgccagcgccctagcgcccgctcctttcgctttcttcccttcctttctcgccacgttcgccggctttccccgtcaagctctaaatcggggcatc
cctttagggttccgatttagtgctttacggcacctcgacccccaaaaaacttgattagggtgatggttcacgtagtgggccatcgccctgatagacggtttttcgccct

FIG. 55 (continued)

ttgacgttggagtccacgttctttaatagtggactcttgttccaaactggaacaacactcaaccctatctcggtctattcttttgatttataagggattttgggggatttcgg
cctattggttaaaaaatgagctgatttaacaaaaatttaacgcgaattaattctgtggaatgtgtgtcagttagggtgtggaaagtccccaggctccccagcagg
cagaagtatgcaaagcatgcatctcaattagtcagcaaccaggtgtggaaagtccccaggctccccagcaggcaggcagaagtatgcaaagcatgcatctcaatt
agtcagcaaccatagtcccgcccctaactccgcccatcccgcccctaactccgcccagttccgcccattctccgccccatggctgactaattttttttatttatgca
gaggccgaggccgcctctgcctctgagctattccagaagtagtgaggaggctttttggaggcctaggcttttgcaaaaagctccgggagcttgtatatccattt
tcggatctgatcaagagacaggatgaggatcgtttcgcatgattgaacaagatggattgcacgcaggttctccggccgcttgggtggagaggctattcggctat
gactgggcacaacagacaatcggctgctctgatgccgccgtgttccggctgtcagcgcaggggcgcccggttcttttttgtcaagaccgacctgtccggtgccct
gaatgaactgcaggacgaggcagcgcggctatcgtggctggccacgacgggcgttccttgcgcagctgtgctcgacgttgtcactgaagcgggaagggac
tggctgctattgggcgaagtgccggggcaggatctcctgtcatctcaccttgctcctgccgagaaagtatccatcatggctgatgcaatgcggcggctgcatac
gcttgatccggctacctgcccattcgaccaccaagcgaaacatcgcatcgagcgagcacgtactcggatggaagccggtcttgtcgatcaggatgatctgga
cgaagagcatcaggggctcgcgccagccgaactgttcgccaggctcaaggcgcgcatgcccgacggcgaggatctcgtcgtgacccatggcgatgcctg
cttgccgaatatcatggtggaaaatggccgcttttctggattcatcgactgtggccggctgggtgtggcggaccgctatcaggacatagcgttggctacccgtga
tattgctgaagagcttggcggcgaatgggctgaccgcttcctcgtgctttacggtatcgccgctcccgattcgcagcgcatcgccttctatcgccttcttgacgagtt
cttctgagcgggactctggggttcgcgaaatgaccgaccaagcgacgcccaacctgccatcacgagatttcgattccaccgccgccttctatgaaaggttggg
cttcggaatcgtttccgggacgccggctggatgatcctccagcgcggggatctcatgctggagttcttcgcccaccccaacttgtttattgcagcttataatggtta
caaataaagcaatagcatcacaaatttcacaaataaagcatttttttcactgcattctagttgtggtttgtccaaactcatcaatgtatcttatcatgtctgtataccgtc
gacctctagctagagcttggcgtaatcatggtcatagctgtttcctgtgtgaaatgttatccgctcacaattccacacaacatacgagccggaagcataaagtgt
aaagcctggggtgcctaatgagtgagctaactcacattaattgcgttgcgctcactgcccgctttccagtcgggaaacctgtcgtgccagctgcattaatgaatc
ggccaacgcgcggggagaggcggtttgcgtattgggcgctcttccgcttcctcgctcactgactcgctgcgctcggtcgttcggctgcggcgagcggtatcagc
tcactcaaaggcggtaatacggttatccacagaatcaggggataacgcaggaaagaacatgtgagcaaaaggccagcaaaaggccaggaaccgtaaa
aaggccgcgttgctggcgtttttccataggctccgcccccctgacgagcatcacaaaaatcgacgctcaagtcagaggtggcgaaacccgacaggactata
aagataccaggcgtttccccctggaagctccctcgtgcgctctcctgttccgaccctgccgcttaccggatacctgtccgcctttctcccttcgggaagcgtggcg
ctttctcaatgctcacgctgtaggtatctcagttcggtgtaggtcgttcgctccaagctgggctgtgtgcacgaaccccccgttcagcccgaccgctgcgccttatc
cggtaactatcgtcttgagtccaacccggtaagacacgacttatcgccactggcagcagccactggtaacaggattagcagagcgaggtatgtaggcggtg
ctacagagttcttgaagtggtggcctaactacggctacactagaaggacagtatttggtatctgcgctctgctgaagccagttaccttcggaaaaagagttggta
gctcttgatccggcaaacaaaccaccgctggtagcggtggtttttttgtttgcaagcagcagattacgcgcagaaaaaaaggatctcaagaagatcctttgatct
tttctacggggtctgacgctcagtggaacgaaaactcacgttaagggattttggtcatgagattatcaaaaaggatcttcacctagatcctttaaattaaaaatga
agttttaaatcaatctaaagtatatatgagtaaacttggtctgacagttaccaatgcttaatcagtgaggcacctatctcagcgatctgtctatttcgttcatccatagtt
gcctgactccccgtcgtgtagataactacgatacgggagggcttaccatctggccccagtgctgcaatgataccgcgagacccacgctcaccggctccagat
ttatcagcaataaaccagccagccggaagggccgagcgcagaagtggtcctgcaactttatccgcctccatccagtctattaattgttgccgggaagctagag
taagtagttcgccagttaatagtttgcgcaacgttgttgccattgctacaggcatcgtggtgtcacgctcgtcgtttggtatggcttcattcagctccggttcccaacg
atcaaggcgagttacatgatcccccatgttgtgcaaaaaagcggttagctccttcggtcctccgatcgttgtcagaagtaagttggccgcagtgttatcactcatg
gttatggcagcactgcataattctcttactgtcatgccatccgtaagatgcttttctgtgactggtgagtactcaaccaagtcattctgagaatagtgtatgcggcga
ccgagttgctcttgcccggcgtcaatacgggataataccgcgccacatagcagaactttaaaagtgctcatcattggaaaacgttcttcggggcgaaaactctc
aaggatcttaccgctgttgagatccagttcgatgtaacccactcgtgcacccaactgatcttcagcatcttttactttcaccagcgtttctgggtgagcaaaaacag
gaaggcaaaatgccgcaaaaaagggaataagggcgacacgaaatgttgaatactcatactcttcctttttcaatattattgaagcatttatcaggggtattgtct
catgagcggatacatatttgaatgtatttagaaaaataaacaaataggggttccgcgcacatttccccgaaaagtgccacctgacgtcgacggatcggggaga
tctcccgatcccctatggtcgactctcagtacaatctgctctgatgccgcatagttaagccagtatctgctccctgcttgtgtgttggaggtcgctgagtagtgcgcg
agcaaaatttaagctacaacaaggcaaggcttgaccgacaattgcatgaagaatctgcttagg

FIG. 56A

Range 1: 1 to 117 Graphics                    ▼ NextMatch △ PreviousMatch

| Score | Expect | Method | Identities | Positives | Gaps |
|---|---|---|---|---|---|
| 206 bits(525) | 6e-71 | Compositional matrix adjust. | 96/117(82%) | 109/117(93%) | 0/117(0%) |

```
Query    1    EVQLRQSGPGLVAPSWSLSITCTVSGFSLSIYSVHWVRQPPGKGLEWLGMIWGGGSSDYN    60
              +VQL++SGPGLV PS +LS+TCTVSGFSLSIYSVHW+RQPPGKGLEW+GMIWGGGSSDYN
Sbjct    1    QVQLQESGPGLVKPSETLSLTCTVSGFSLSIYSVHWIRQPPGKGLEWIGMIWGGGSSDYN    60

Query   61    SALKSRLSISKDNSKSQVFLKMNSLQTDDTAMYYCARNGNFYAMDYWGQGTSVTVSS    117
              SALKSRL+ISKD SK+QV LK++S+    DTA+YYCARNGNFYAMDYWGQGT VTVSS
Sbjct   61    SALKSRLTISKDTSKNQVSLKLSSVTAADTAVYYCARNGNFYAMDYWGQGTLVTVSS    117
```

Range 2: 16 to 36 Graphics          ▽ NextMatch ▲ PreviousMatch ▲ FirstMatch

| Score | Expect | Method | Identities | Positives | Gaps |
|---|---|---|---|---|---|
| 20.0 bits(40) | 0.028 | Compositional matrix adjust. | 11/33(33%) | 12/21(57%) | 03/21(0%) |

```
Query  355    DKVSLTCMITDFFPEDITVEW    375    (SEQ ID NO: 9)
              + +SLTC ++ F    +V W
Sbjct   16    ETLSLTCTVSGFSLSIYSVHW     36    (SEQ ID NO: 247)
```

FIG. 56B

Range 1: 1 to 110 Graphics                    ▼ NextMatch △ PreviousMatch

| Score | Expect | Method | Identities | Positives | Gaps |
|---|---|---|---|---|---|
| 174 bits(441) | 2e-61 | Compositional matrix adjust. | 87/110(79%) | 97/110(88%) | 0/110(0%) |

```
Query    1    QIVLTQSPAIMSASLGERVTMTCTASSSVSSSFLHWYQQKPGSSPQLWIYSTSNLASGVP    60
              +IVLTQSP +S S GER T++CTASSSVSSSFLHWYQQKPG +P+L IYSTSNLASG+P
Sbjct    1    EIVLTQSPGTLSLSPGERATLSCTASSSVSSSFLHWYQQKPGQAPRLLIYSTSNLASGIP    60

Query   61    ARFSGSGSGTSYSLTISSMEAEDAATYYCHQYHHSPYIYTFGGGTKLEIK    110
               RFSGSGSGT ++LTIS +E ED A YYCHQYHHSPYIYTFGGGTKLEIK
Sbjct   61    DRFSGSGSGTDFTLTISRLEPEDFAVYYCHQYHHSPYIYTFGGGTKLEIK    110
```

Range 2: 73 to 102 Graphics          ▽ NextMatch ▲ PreviousMatch ▲ FirstMatch

| Score | Expect | Method | Identities | Positives | Gaps |
|---|---|---|---|---|---|
| 20.0 bits(40) | 0.012 | Compositional matrix adjust. | 11/33(33%) | 16/33(48%) | 3/33(9%) |

```
Query  181    TLTLTKDEYERHNSYTCEATHKTSTSPIVKSFN    213    (SEQ ID NO: 10)
              TLT+++ E E    Y C   H    SP + +F
Sbjct   73    TLTISRLEPEDFAVYYCHQYHH---SPYIYTFG    102    (SEQ ID NO: 253)
```

FIG. 57

| SEQ ID NO: | | |
|---|---|---|
| 09 | 61BG1.3-VH | |
| 29 | GRAFTED-VH1 | |
| 30 | GRAFTED-VH2 | |
| 31 | GRAFTED-VH3 | |
| 32 | GRAFTED-VH4 | |

FIG. 58

| SEQ ID NO: | | |
|---|---|---|
| 10 | 61BG1.3 | |
| 33 | GRAFTED-VL1 | |
| 34 | GRAFTED-VL2 | |
| 35 | GRAFTED-VL3 | |
| 36 | GRAFTED-VL4 | |

FIG. 59

Human Constant Region
>hIgG1CH                    (SEQ ID NO: 199)
ASTKGPSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDSDGSFFLYSKLTVDK
SRWQQGNVFSCSVMHEALHNHYTQKSLSLSPGK**

>hIgG1CH                    (SEQ ID NO: 200)
GCCAGCACCAAGGGCCCTTCCGTGTTTCCACTGGCCCCCTCCTCTAAATCCACATCTGGCGGCACCGCCG
CCCTGGGCTGTCTGGTGAAGGACTACTTCCCAGAGCCTGTGACAGTGTCCTGGAACTCTGGCGCCCTGAC
ATCCGGCGTGCACACATTTCCAGCCGTGCTGCAGAGCTCCGGCCTGTACAGCCTGTCTAGCGTGGTGACA
GTGCCCTCCTCTAGCCTGGGCACACAGACCTATATCTGCAACGTGAATCACAAGCCAAGCAATACCAAGGT
GGACAAGAAGGTGGAGCCCAAGTCCTGTGATAAGACACACACCTGCCCCCCTTGTCCTGCTCCCGAGCTG
CTGGGCGGCCCTAGCGTGTTCCTGTTTCCACCCAAGCCTAAGGACACCCTGATGATCTCCCGGACACCCG
AGGTGACCTGCGTGGTGGTGGACGTGTCTCACGAGGATCCTGAGGTGAAGTTCAACTGGTATGTGGATGG
CGTGGAGGTGCACAATGCCAAGACCAAGCCCAGAGAGGAGCAGTACAACTCTACATATAGGGTGGTGAGC
GTGCTGACCGTGCTGCACCAGGACTGGCTGAACGGCAAGGAGTATAAGTGCAAGGTGTCCAATAAGGCCC
TGCCCGCCCCCATCGAGAAGACAATCAGCAAGGCCAAGGGCCAGCCTCGGGAGCCACAGGTGTACACCC
TGCCTCCATCCAGAGACGAGCTGACAAAGAACCAGGTGTCTCTGACATGTCTGGTGAAGGGCTTCTATCCT
AGCGATATCGCCGTGGAGTGGGAGTCCAATGGCCAGCCAGAGAACAATTACAAGACCACACCCCCTGTGC
TGGACTCCGATGGCTCCTTCTTTCTGTATTCCAAGCTGACCGTGGATAAGTCTCGGTGGCAGCAGGGCAAC
GTGTTCAGCTGTTCCGTGATGCACGAAGCCCTGCATAATCACTATACTCAGAAATCCCTGTCCCTGTCACCT
GGAAAG<u>TGATAA</u>

>hIgkCL                    (SEQ ID NO: 201)
RTVAAPSVFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC**

>hIgkCL                    (SEQ ID NO: 202)
AGGACAGTGGCCGCCCCAAGCGTGTTCATCTTTCCCCCTTCCGACGAGCAGCTGAAGTCTGGCACCGCCA
GCGTGGTGTGCCTGCTGAACAACTTCTACCCTCGGGAGGCCAAGGTCCAGTGGAAGGTGGATAACGCCCT
GCAGTCTGGCAATAGCCAGGAGTCCGTGACCGAGCAGGACTCTAAGGATAGCACATATTCCCTGTCTAGC
ACCCTGACACTGAGCAAGGCCGATTACGAGAAGCACAAGGTGTATGCCTGTGAAGTCACCCATCAGGGGC
TGTCATCACCCGTCACTAAGTCATTCAATCGCGGAGAATGC<u>TGATAA</u>

FIG. 60

>U551FEL190-VH2-hIgG1CH(K222A)-pcDNA3.4 SEQ ID NO: 203

AFCAASRCTGQIYALTLIIDLLIVINYGVISSPIYGVPRYITYGKWPAWLTAQRPPPIDVNNDVCSHSNANRDFP
LTSMGGVFTVNCPLGSTSSVSYAKYAPYRQRMARLALCPVHDLMGLSYLAVHLRISHRYYHGDAVLAVHQ
WAWIAVLTGISKSPPHRQWEFVLAPKSTGLSKMSQLRPIDANGRACTVGGLYKQSSFSEPSDRLETPSTLF
PPKTPGPIQPPDSRGSNPIPAATMGWSCIILFLVATATGVHS
▶ [QVQLQESGPGLVKPSETLSLTCTVSGFSLSIYSVHWIRQPPGKGLEWIGMIWGGGSSDYNSALKSRLTISK
DTSKNQVSLKLSSVTAADTAVYYCARNGNFYAMDYWGQGTLVTVSS]
ASTKGPSVFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDÄTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGKAGFDPYRLVMSLISRQSTSGLQNL
KIDWYSLCCSFYAMWIRCFNAFVSCYCFPYGFHFLLLVILVAVSLGVVARCQATWRGVHCVRNPHWLGH
CHHLSAPFRDFRFPPPYCHGGTHRRLPCPLLDRGSAVGHQFRGVVGEADVLSMAARLCCHLDSARDVLLL
RPFGPQSSGPSFPRPAAGSAASSASSPSPSDESDLPLGRLPAWKRGRLTETRKETIPEGTRAMTAIKRQNK
THGCWVVCSTRGSVPGLALCRYPTETPLGPIRPRFFLFPTPPPKFGRPRARSQRRGGRPCHSRSAQLGLG
VSPRALRRIKRGGCGGYAQRDRYTCQRPSARSFRFLPFLSRHVRRLSPSSSKSGHPFRVPICFTAPRPQKT
LGWFTWAIALIDGFSPFDVGVHVLWTLVPNWNNTQPYLGLFFFIRDFGDFGLLVKKADLTKIRELILWNVCQL
GCGKSPGSPAGRSMQSMHLNSATRCGKSPGSPAGRSMQSMHLNSATIVPPLTPPIPPLTPPSSAHSPPHG
LIFFIYAEAEAASASELFQKGGFFGGLGFCKKLPGACISIFGSDQETGGSFRMIEQDGLHAGSPAAWVERLF
GYDWAQQTIGCSDAAVFRLSAQGRPVLFVKTDLSGALNELQDEAARLSWLATTGVPCAAVLDVVTEAGRD
WLLLGEVPGQDLLSSHLAPAEKVSIMADAMRRLHTLDPATCPFDHQAKHRIERARTRMEAGLVDQDDLDEE
HQGLAPAELFARLKARMPDGEDLVVTHGDACLPNIMVENGRFSGFIDCGRLGVADRYQDIALATRDIAEELG
GEWADRFLVLYGIAAPDSQRIAFYRLLDEFFAGLWGSRNDRPSDAQPAITRFRFHRRLLKVGLRNRFPGRR
LDDPPARGSHAGVLRPPQLVYCSLWLQIKQHHKFHKSIFFTAFLWFVQTHQCILSCLYTVDLLELGVIMVIAV
SCVKLLSAHNSTQHTSRKHKVSLGCLMSELTHINCVALTARFPVGKPVVPAALMNRPTRGERRFAYWALFR
FLAHLAALGRSAAASGISSLKGGNTVIHRIRGRRKEHVSKRPAKGQEPKGRVAGVFPAPPPRASQKSTLKSE
VAKPDRTIKIPGVSPWKLPRALSCSDPAAYRIPVRLSPFGKRGAFSMLTLVSQFGVGRSLQAGLCARTPRSA
RPLRLIRLSSVQPGKTRLIATGSSHWQDQSEVCRRCYRVLEVVALRLHKDSIWYLRSAEASYLRKKSWLLIR
QTNHRWRWFFCLQAADYAQKKRISRRSFDLFYGVRSVERKLTLRDFGHEIIKKDLHLDPFKLKMKFINLKYIV
NLVQLPMLNQGTYLSDLSISFIHSCLTPRRVDNYDTGGLTIWPQCCNDTARPTLTGSRFISNKPASRKGRAQ
KWSCNFIRLHPVYLLPGSSKFASFAQRCCHCYRHRGVTLVVWYGFIQLRFPTIKASYMIPHVVQKSGLLRSS
DRCQKVGRSVITHGYGSTAFSYCHAIRKMLFCDWVLNQVILRIVYAATELLLPGVNTGYRATQNFKSAHHWK
TFFGAKTLKDLTAVEIQFDVTHSCTQLIFSIFYFHQRFWVSKNRKAKCRKKGNKGDTEMLNTHTLPFSILLKH
LSGLLSHERIHIMYLEKTNRGSAHISPKSATRRRIGRSPDPLWSTLSTICSDAALSQYLLPACVLEVAECASKI
ATTRQGLTDNCMKNLLR

FIG. 61

>U551FEL190-VH4-hIgG1CH(K222A)-pcDNA3.4 SEQ ID NO: 204

AFCAASRCTGQIYALTLIIDLLIVINYGVISSPIYGVPRYITYGKWPAWLTAQRPPPIDVNNDVCSHSNANRDFP
LTSMGGVFTVNCPLGSTSSVSYAKYAPYRQRMARLALCPVHDLMGLSYLAVHLRISHRYYHGDAVLAVHQ
WAWIAVLTGISKSPPHRQWEFVLAPKSTGLSKMSQLRPIDANGRACTVGGLYKQSSFSEPSDRLETPSTLF
PPKTPGPIQPPDSRGSNPIPAATMGWSCIILFLVATATGVHS
▶ |QVQLQESGPGLVKPSETLSLTCTVSG<u>FSLSIY</u>SVHWIRQPPGKGLEWLGMI<u>WGGGSS</u>DYNSALKSRLTISK
DTSKNQVSLKLSSVTAADTAMYYCA<u>RNGNFYAMDY</u>WGQGTLVTVSS]
ASTKGPSVFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDẠTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGKAGFDPYRLVMSLISRQSTSGLQNL
KIDWYSLCCSFYAMWIRCFNAFVSCYCFPYGFHFLLLVILVAVSLGVVARCQATWRGVHCVCRNPHWLGH
CHHLSAPFRDFRFPPPYCHGGTHRRLPCPLLDRGSAVGHQFRGVVGEADVLSMAARLCCHLDSARDVLLL
RPFGPQSSGPSFPRPAAGSAASSASSPSPSDESDLPLGRLPAWKRGRLTETRKETIPEGTRAMTAIKRQNK
THGCWVVCSTRGSVPGLALCRYPTETPLGPIRPRFFLFPTPPPKFGRPRARSQRRGGRPCHSRSAQLGLG
VSPRALRRIKRGGCGGYAQRDRYTCQRPSARSFRFLPFLSRHVRRLSPSSSKSGHPFRVPICFTAPRPQKT
LGWFTWAIALIDGFSPFDVGVHVLWTLVPNWNNTQPYLGLFFFIRDFGDFGLLVKKADLTKIRELILWNVCQL
GCGKSPGSPAGRSMQSMHLNSATRCGKSPGSPAGRSMQSMHLNSATIVPPLTPPIPPLTPPSSAHSPPHG
LIFFIYAEAEAASASELFQKGGFFGGLGFCKKLPGACISIFGSDQETGGSFRMIEQDGLHAGSPAAWVERLF
GYDWAQQTIGCSDAAVFRLSAQGRPVLFVKTDLSGALNELQDEAARLSWLATTGVPCAAVLDVVTEAGRD
WLLLGEVPGQDLLSSHLAPAEKVSIMADAMRRLHTLDPATCPFDHQAKHRIERARTRMEAGLVDQDDLDEE
HQGLAPAELFARLKARMPDGEDLVVTHGDACLPNIMVENGRFSGFIDCGRLGVADRYQDIALATRDIAEELG
GEWADRFLVLYGIAAPDSQRIAFYRLLDEFFAGLWGSRNDRPSDAQPAITRFRFHRRLLKVGLRNRFPGRR
LDDPPARGSHAGVLRPPQLVYCSLWLQIKQHHKFHKSIFFTAFLWFVQTHQCILSCLYTVDLLELGVIMVIAV
SCVKLLSAHNSTQHTSRKHKVSLGCLMSELTHINCVALTARFPVGKPVVPAALMNRPTRGERRFAYWALFR
FLAHLAALGRSAAASGISSLKGGNTVIHRIRGRRKEHVSKRPAKGQEPKGRVAGVFPAPPPRASQKSTLKSE
VAKPDRTIKIPGVSPWKLPRALSCSDPAAYRIPVRLSPFGKRGAFSMLTLVSQFGVGRSLQAGLCARTPRSA
RPLRLIRLSSVQPGKTRLIATGSSHWQDQSEVCRRCYRVLEVVALRLHKDSIWYLRSAEASYLRKKSWLLIR
QTNHRWRWFFCLQAADYAQKKRISRRSFDLFYGVRSVERKLTLRDFGHEIIKKDLHLDPFKLKMKFINLKYIV
NLVQLPMLNQGTYLSDLSISFIHSCLTPRRVDNYDTGGLTIWPQCCNDTARPTLTGSRFISNKPASRKGRAQ
KWSCNFIRLHPVYLLPGSSKFASFAQRCCHCYRHRGVTLVVWYGFIQLRFPTIKASYMIPHVVQKSGLLRSS
DRCQKVGRSVITHGYGSTAFSYCHAIRKMLFCDWVLNQVILRIVYAATELLLPGVNTGYRATQNFKSAHHWK
TFFGAKTLKDLTAVEIQFDVTHSCTQLIFSIFYFHQRFWVSKNRKAKCRKKGNKGDTEMLNTHTLPFSILLKH
LSGLLSHERIHIMYLEKTNRGSAHISPKSATRRRIGRSPDPLWSTLSTICSDAALSQYLLPACVLEVAECASKI
ATTRQGLTDNCMKNLLR

FIG. 62

>U551FEL190-VL1-hIgkCLpc-DNA3.4        SEQ ID NO: 205

AFCAASRCTGQIYALTLIIDLLIVINYGVISSPIYGVPRYITYGKWPAWLTAQRPPPIDVNNDVCSHSNANRDFP
LTSMGGVFTVNCPLGSTSSVSYAKYAPYRQRMARLALCPVHDLMGLSYLAVHLRISHRYYHGDAVLAVHQ
WAWIAVLTGISKSPPHRQWEFVLAPKSTGLSKMSQLRPIDANGRACTVGGLYKQSSFSEPSDRLETPSTLF
PPKTPGPIQPPDSRGSNPIPAATMGWSCIILFLVATATGVHS
▶ [EIVLTQSPGTLSLSPGERATLSCTAS<u>SSVSSSF</u>LHWYQQKPGQAPRLLIY<u>STSN</u>LASGIPDRFSGSGSGTDF
TLTISRLEPEDFAVYYC<u>HQYHHSPYIYTF</u>GGGTKLEIK]
RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGECAGFDPYRLVMSLISRQSTSGLQNLKIDWYSLCCSF
YAMWIRCFNAFVSCYCFPYGFHFLLLVILVAVSLGVVARCQATWRGVHCVCRNPHWLGHCHHLSAPFRDF
RFPPPYCHGGTHRRLPCPLLDRGSAVGHQFRGVVGEADVLSMAARLCCHLDSARDVLLLRPFGPQSSGPS
FPRPAAGSAASSASSPSPSDESDLPLGRLPAWKRGRLTETRKETIPEGTRAMTAIKRQNKTHGCWVVCSTR
GSVPGLALCRYPTETPLGPIRPRFFLFPTPPPKFGRPRARSQRRGGRPCHSRSAQLGLGVSPRALRRIKRG
GCGGYAQRDRYTCQRPSARSFRFLPFLSRHVRRLSPSSSKSGHPFRVPICFTAPRPQKTLGWFTWAIALID
GFSPFDVGVHVLWTLVPNWNNTQPYLGLFFFIRDFGDFGLLVKKADLTKIRELILWNVCQLGCGKSPGSPA
GRSMQSMHLNSATRCGKSPGSPAGRSMQSMHLNSATIVPPLTPPIPPLTPPSSAHSPPHGLIFFIYAEAEAA
SASELFQKGGFFGGLGFCKKLPGACISIFGSDQETGGSFRMIEQDGLHAGSPAAWVERLFGYDWAQQTIG
CSDAAVFRLSAQGRPVLFVKTDLSGALNELQDEAARLSWLATTGVPCAAVLDVVTEAGRDWLLLGEVPGQ
DLLSSHLAPAEKVSIMADAMRRLHTLDPATCPFDHQAKHRIERARTRMEAGLVDQDDLDEEHQGLAPAELF
ARLKARMPDGEDLVVTHGDACLPNIMVENGRFSGFIDCGRLGVADRYQDIALATRDIAEELGGEWADRFLV
LYGIAAPDSQRIAFYRLLDEFFAGLWGSRNDRPSDAQPAITRFRFHRRLLKVGLRNRFPGRRLDDPPARGS
HAGVLRPPQLVYCSLWLQIKQHHKFHKSIFFTAFLWFVQTHQCILSCLYTVDLLELGVIMVIAVSCVKLLSAHN
STQHTSRKHKVSLGCLMSELTHINCVALTARFPVGKPVVPAALMNRPTRGERRFAYWALFRFLAHLAALGR
SAAASGISSLKGGNTVIHRIRGRRKEHVSKRPAKGQEPKGRVAGVFPAPPPRASQKSTLKSEVAKPDRTIKI
PGVSPWKLPRALSCSDPAAYRIPVRLSPFGKRGAFSMLTLVSQFGVGRSLQAGLCARTPRSARPLRLIRLS
SVQPGKTRLIATGSSHWQDQSEVCRRCYRVLEVVALRLHKDSIWYLRSAEASYLRKKSWLLIRQTNHRWR
WFFCLQAADYAQKKRISRRSFDLFYGVRSVERKLTLRDFGHEIIKKDLHLDPFKLKMKFINLKYIVNLVQLPML
NQGTYLSDLSISFIHSCLTPRRVDNYDTGGLTIWPQCCNDTARPTLTGSRFISNKPASRKGRAQKWSCNFIR
LHPVYLLPGSSKFASFAQRCCHCYRHRGVTLVVWYGFIQLRFPTIKASYMIPHVVQKSGLLRSSDRCQKVG
RSVITHGYGSTAFSYCHAIRKMLFCDWVLNQVILRIVYAATELLLPGVNTGYRATQNFKSAHHWKTFFGAKT
LKDLTAVEIQFDVTHSCTQLIFSIFYFHQRFWVSKNRKAKCRKKGNKGDTEMLNTHTLPFSILLKHLSGLLSH
ERIHIMYLEKTNRGSAHISPKSATRRRIGRSPDPLWSTLSTICSDAALSQYLLPACVLEVAECASKIATTRQGL
TDNCMKNLLR

FIG. 63

>U551FEL190-VL2-hIgkCLpc-DNA3.4          SEQ ID NO: 206

AFCAASRCTGQIYALTLIIDLLIVINYGVISSPIYGVPRYITYGKWPAWLTAQRPPPIDVNNDVCSHSNANRDFP
LTSMGGVFTVNCPLGSTSSVSYAKYAPYRQRMARLALCPVHDLMGLSYLAVHLRISHRYYHGDAVLAVHQ
WAWIAVLTGISKSPPHRQWEFVLAPKSTGLSKMSQLRPIDANGRACTVGGLYKQSSFSEPSDRLETPSTLF
PPKTPGPIQPPDSRGSNPIPAATMGWSCIILFLVATATGVHS

▶ [EIVLTQSPGTLSLSPGERATLSCTAS<u>SSVSSSF</u>LHWYQQKPGQAPQLWIY<u>STSN</u>LASGIPDRFSGSGSGTD
YTLTISRLEPEDFAVYYC<u>HQYHHSPYIYT</u>FGGGTKLEIK]
RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGECAGFDPYRLVMSLISRQSTSGLQNLKIDWYSLCCSF
YAMWIRCFNAFVSCYCFPYGFHFLLLVILVAVSLGVVARCQATWRGVHCVCRNPHWLGHCHHLSAPFRDF
RFPPPYCHGGTHRRLPCPLLDRGSAVGHQFRGVVGEADVLSMAARLCCHLDSARDVLLLRPFGPQSSGPS
FPRPAAGSAASSASSPSPSDESDLPLGRLPAWKRGRLTETRKETIPEGTRAMTAIKRQNKTHGCWVVCSTR
GSVPGLALCRYPTETPLGPIRPRFFLFPTPPPKFGRPRARSQRRGGRPCHSRSAQLGLGVSPRALRRIKRG
GCGGYAQRDRYTCQRPSARSFRFLPFLSRHVRRLSPSSSKSGHPFRVPICFTAPRPQKTLGWFTWAIALID
GFSPFDVGVHVLWTLVPNWNNTQPYLGLFFFIRDFGDFGLLVKKADLTKIRELILWNVCQLGCGKSPGSPA
GRSMQSMHLNSATRCGKSPGSPAGRSMQSMHLNSATIVPPLTPPIPPLTPPSSAHSPPHGLIFFIYAEAEAA
SASELFQKGGFFGGLGFCKKLPGACISIFGSDQETGGSFRMIEQDGLHAGSPAAWVERLFGYDWAQQTIG
CSDAAVFRLSAQGRPVLFVKTDLSGALNELQDEAARLSWLATTGVPCAAVLDVVTEAGRDWLLLGEVPGQ
DLLSSHLAPAEKVSIMADAMRRLHTLDPATCPFDHQAKHRIERARTRMEAGLVDQDDLDEEHQGLAPAELF
ARLKARMPDGEDLVVTHGDACLPNIMVENGRFSGFIDCGRLGVADRYQDIALATRDIAEELGGEWADRFLV
LYGIAAPDSQRIAFYRLLDEFFAGLWGSRNDRPSDAQPAITRFRFHRRLLKVGLRNRFPGRRLDDPPARGS
HAGVLRPPQLVYCSLWLQIKQHHKFHKSIFFTAFLWFVQTHQCILSCLYTVDLLELGVIMVIAVSCVKLLSAHN
STQHTSRKHKVSLGCLMSELTHINCVALTARFPVGKPVVPAALMNRPTRGERRFAYWALFRFLAHLAALGR
SAAASGISSLKGGNTVIHRIRGRRKEHVSKRPAKGQEPKGRVAGVFPAPPPRASQKSTLKSEVAKPDRTIKI
PGVSPWKLPRALSCSDPAAYRIPVRLSPFGKRGAFSMLTLVSQFGVGRSLQAGLCARTPRSARPLRLIRLS
SVQPGKTRLIATGSSHWQDQSEVCRRCYRVLEVVALRLHKDSIWYLRSAEASYLRKKSWLLIRQTNHRWR
WFFCLQAADYAQKKRISRRSFDLFYGVRSVERKLTLRDFGHEIIKKDLHLDPFKLKMKFINLKYIVNLVQLPML
NQGTYLSDLSISFIHSCLTPRRVDNYDTGGLTIWPQCCNDTARPTLTGSRFISNKPASRKGRAQKWSCNFIR
LHPVYLLPGSSKFASFAQRCCHCYRHGVTLVVWYGFIQLRFPTIKASYMIPHVVQKSGLLRSSDRCQKVG
RSVITHGYGSTAFSYCHAIRKMLFCDWVLNQVILRIVYAATELLLPGVNTGYRATQNFKSAHHWKTFFGAKT
LKDLTAVEIQFDVTHSCTQLIFSIFYFHQRFWVSKNRKAKCRKKGNKGDTEMLNTHTLPFSILLKHLSGLLSH
ERIHIMYLEKTNRGSAHISPKSATRRRIGRSPDPLWSTLSTICSDAALSQYLLPACVLEVAECASKIATTRQGL
TDNCMKNLLR

FIG. 64

>U551FEL190-VL3-hIgkCLpc-DNA3.4          SEQ ID NO: 207

AFCAASRCTGQIYALTLIIDLLIVINYGVISSPIYGVPRYITYGKWPAWLTAQRPPPIDVNNDVCSHSNANRDFP
LTSMGGVFTVNCPLGSTSSVSYAKYAPYRQRMARLALCPVHDLMGLSYLAVHLRISHRYYHGDAVLAVHQ
WAWIAVLTGISKSPPHRQWEFVLAPKSTGLSKMSQLRPIDANGRACTVGGLYKQSSFSEPSDRLETPSTLF
PPKTPGPIQPPDSRGSNPIPAATMGWSCIILFLVATATGVHS
► [EIVLTQSPGTLSLSPGERATLSCTAS<u>SSVSSSF</u>LHWYQQKPGQAPQLWIY<u>STSN</u>LASGIPDRFSGSGSGTD
YTLTISRLEPEDFATYYC<u>HQYHHSPYIYT</u>FGGGTKLEIK]
RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGECAGFDPYRLVMSLISRQSTSGLQNLKIDWYSLCCSF
YAMWIRCFNAFVSCYCFPYGFHFLLLVILVAVSLGVVARCQATWRGVHCVCRNPHWLGHCHHLSAPFRDF
RFPPPYCHGGTHRRLPCPLLDRGSAVGHQFRGVVGEADVLSMAARLCCHLDSARDVLLLRPFGPQSSGPS
FPRPAAGSAASSASSPSPSDESDLPLGRLPAWKRGRLTETRKETIPEGTRAMTAIKRQNKTHGCWVVCSTR
GSVPGLALCRYPTETPLGPIRPRFFLFPTPPPKFGRPRARSQRRGGRPCHSRSAQLGLGVSPRALRRIKRG
GCGGYAQRDRYTCQRPSARSFRFLPFLSRHVRRLSPSSSKSGHPFRVPICFTAPRPQKTLGWFTWAIALID
GFSPFDVGVHVLWTLVPNWNNTQPYLGLFFFIRDFGDFGLLVKKADLTKIRELILWNVCQLGCGKSPGSPA
GRSMQSMHLNSATRCGKSPGSPAGRSMQSMHLNSATIVPPLTPPIPPLTPPSSAHSPPHGLIFFIYAEAEAA
SASELFQKGGFFGGLGFCKKLPGACISIFGSDQETGGSFRMIEQDGLHAGSPAAWVERLFGYDWAQQTIG
CSDAAVFRLSAQGRPVLFVKTDLSGALNELQDEAARLSWLATTGVPCAAVLDVVTEAGRDWLLLGEVPGQ
DLLSSHLAPAEKVSIMADAMRRLHTLDPATCPFDHQAKHRIERARTRMEAGLVDQDDLDEEHQGLAPAELF
ARLKARMPDGEDLVVTHGDACLPNIMVENGRFSGFIDCGRLGVADRYQDIALATRDIAEELGGEWADRFLV
LYGIAAPDSQRIAFYRLLDEFFAGLWGSRNDRPSDAQPAITRFRFHRRLLKVGLRNRFPGRRLDDPPARGS
HAGVLRPPQLVYCSLWLQIKQHHKFHKSIFFTAFLWFVQTHQCILSCLYTVDLLELGVIMVIAVSCVKLLSAHN
STQHTSRKHKVSLGCLMSELTHINCVALTARFPVGKPVVPAALMNRPTRGERRFAYWALFRFLAHLAALGR
SAAASGISSLKGGNTVIHRIRGRRKEHVSKRPAKGQEPKGRVAGVFPAPPPRASQKSTLKSEVAKPDRTIKI
PGVSPWKLPRALSCSDPAAYRIPVRLSPFGKRGAFSMLTLVSQFGVGRSLQAGLCARTPRSARPLRLIRLS
SVQPGKTRLIATGSSHWQDQSEVCRRCYRVLEVVALRLHKDSIWYLRSAEASYLRKKSWLLIRQTNHRWR
WFFCLQAADYAQKKRISRRSFDLFYGVRSVERKLTLRDFGHEIIKKDLHLDPFKLKMKFINLKYIVNLVQLPML
NQGTYLSDLSISFIHSCLTPRRVDNYDTGGLTIWPQCCNDTARPTLTGSRFISNKPASRKGRAQKWSCNFIR
LHPVYLLPGSSKFASFAQRCCHCYRHGVTLVVWYGFIQLRFPTIKASYMIPHVVQKSGLLRSSDRCQKVG
RSVITHGYGSTAFSYCHAIRKMLFCDWVLNQVILRIVYAATELLLPGVNTGYRATQNFKSAHHWKTFFGAKT
LKDLTAVEIQFDVTHSCTQLIFSIFYFHQRFWVSKNRKAKCRKKGNKGDTEMLNTHTLPFSILLKHLSGLLSH
ERIHIMYLEKTNRGSAHISPKSATRRRIGRSPDPLWSTLSTICSDAALSQYLLPACVLEVAECASKIATTRQGL
TDNCMKNLLR

FIG. 65

>U551FEL190-VL4-hIgkCLpc-DNA3.4          SEQ ID NO: 208

AFCAASRCTGQIYALTLIIDLLIVINYGVISSPIYGVPRYITYGKWPAWLTAQRPPPIDVNNDVCSHSNANRDFP
LTSMGGVFTVNCPLGSTSSVSYAKYAPYRQRMARLALCPVHDLMGLSYLAVHLRISHRYYHGDAVLAVHQ
WAWIAVLTGISKSPPHRQWEFVLAPKSTGLSKMSQLRPIDANGRACTVGGLYKQSSFSEPSDRLETPSTLF
PPKTPGPIQPPDSRGSNPIPAATMGWSCIILFLVATATGVHS

▶ [EIVLTQSPGTLSLSPGERATLSCTASSSVSSSFLHWYQQKPGQAPQLWIYSTSNLASGIPARFSGSGSGTD
YTLTISRLEPEDFATYYCHQYHHSPYIYTFGGGTKLEIK]
RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGECAGFDPYRLVMSLISRQSTSGLQNLKIDWYSLCCSF
YAMWIRCFNAFVSCYCFPYGFHFLLLVILVAVSLGVVARCQATWRGVHCVCRNPHWLGHCHHLSAPFRDF
RFPPPYCHGGTHRRLPCPLLDRGSAVGHQFRGVVGEADVLSMAARLCCHLDSARDVLLLRPFGPQSSGPS
FPRPAAGSAASSASSPSPSDESDLPLGRLPAWKRGRLTETRKETIPEGTRAMTAIKRQNKTHGCWVVCSTR
GSVPGLALCRYPTETPLGPIRPRFFLFPTPPPKFGRPRARSQRRGGRPCHSRSAQLGLGVSPRALRRIKRG
GCGGYAQRDRYTCQRPSARSFRFLPFLSRHVRRLSPSSSKSGHPFRVPICFTAPRPQKTLGWFTWAIALID
GFSPFDVGVHVLWTLVPNWNNTQPYLGLFFFIRDFGDFGLLVKKADLTKIRELILWNVCQLGCGKSPGSPA
GRSMQSMHLNSATRCGKSPGSPAGRSMQSMHLNSATIVPPLTPPIPPLTPPSSAHSPPHGLIFFIYAEAEAA
SASELFQKGGFFGGLGFCKKLPGACISIFGSDQETGGSFRMIEQDGLHAGSPAAWVERLFGYDWAQQTIG
CSDAAVFRLSAQGRPVLFVKTDLSGALNELQDEAARLSWLATTGVPCAAVLDVVTEAGRDWLLLGEVPGQ
DLLSSHLAPAEKVSIMADAMRRLHTLDPATCPFDHQAKHRIERARTRMEAGLVDQDDLDEEHQGLAPAELF
ARLKARMPDGEDLVVTHGDACLPNIMVENGRFSGFIDCGRLGVADRYQDIALATRDIAEELGGEWADRFLV
LYGIAAPDSQRIAFYRLLDEFFAGLWGSRNDRPSDAQPAITRFRFHRRLLKVGLRNRFPGRRLDDPPARGS
HAGVLRPPQLVYCSLWLQIKQHHKFHKSIFFTAFLWFVQTHQCILSCLYTVDLLELGVIMVIAVSCVKLLSAHN
STQHTSRKHKVSLGCLMSELTHINCVALTARFPVGKPVVPAALMNRPTRGERRFAYWALFRFLAHLAALGR
SAAASGISSLKGGNTVIHRIRGRRKEHVSKRPAKGQEPKGRVAGVFPAPPPRASQKSTLKSEVAKPDRTIKI
PGVSPWKLPRALSCSDPAAYRIPVRLSPFGKRGAFSMLTLVSQFGVGRSLQAGLCARTPRSARPLRLIRLS
SVQPGKTRLIATGSSHWQDQSEVCRRCYRVLEVVALRLHKDSIWYLRSAEASYLRKKSWLLIRQTNHRWR
WFFCLQAADYAQKKRISRRSFDLFYGVRSVERKLTLRDFGHEIIKKDLHLDPFKLKMKFINLKYIVNLVQLPML
NQGTYLSDLSISFIHSCLTPRRVDNYDTGGLTIWPQCCNDTARPTLTGSRFISNKPASRKGRAQKWSCNFIR
LHPVYLLPGSSKFASFAQRCCHCYRHGVTLVVWYGFIQLRFPTIKASYMIPHVVQKSGLLRSSDRCQKVG
RSVITHGYGSTAFSYCHAIRKMLFCDWVLNQVILRIVYAATELLLPGVNTGYRATQNFKSAHHWKTFFGAKT
LKDLTAVEIQFDVTHSCTQLIFSIFYFHQRFWVSKNRKAKCRKKGNKGDTEMLNTHTLPFSILLKHLSGLLSH
ERIHIMYLEKTNRGSAHISPKSATRRRIGRSPDPLWSTLSTICSDAALSQYLLPACVLEVAECASKIATTRQGL
TDNCMKNLLR

SEQ ID NO: 222
SEQ ID NO: 223

FIG. 67

```
>U551FEL190-VH4-hIgG1CH(K222A)-pcDNA3.4

<-------------------Leader Sequence-------------------><--------------
tgaattcccgccgccaccatgggctggtcatgcattattctgtttctggtcgcaactgctacaggcgtgcatagtcaggtgcagctgcaa
  .  I  F  A  A  T  M  G  W  S  C  I  I  L  F  L  V  A  T  A  T  G  V  H  S  Q  V  Q  L  Q ------------------------FR1-IMGT-------------------------------------><-----CDR1-IMGT-----><-----
gagtccggacccggcctcgtgaagccttccgagacactgtctctgacctgtaccgtgtctggcttctccctgtccatctactccgtgcac
  E  S  G  P  G  L  V  K  P  S  E  T  L  S  L  T  C  T  V  S  G  F  S  L  S  I  Y  S  V  H ----------------FR2-IMGT-----------------------><------CDR2-IMGT------><----------------------
tggatccggcagcctcctggcaagggcctggaatggctgggcatgatctggggcggcggaagctccgactacaactccgccctgaaatct
  W  I  R  Q  P  P  G  K  G  L  E  W  L  G  M  I  W  G  G  G  S  S  D  Y  N  S  A  L  K  S -----------------FR3-IMGT----------------------------------------------------------------->
agactgaccatctccaaggacacctctaagaaccaggtcagcctgaagctgagctctgtgaccgccgctgataccgctatgtactactgc
  R  L  T  I  S  K  D  T  S  K  N  Q  V  S  L  K  L  S  S  V  T  A  A  D  T  A  M  Y  Y  C <----------CDR3-IMGT-----------><-----------FR4-IMGT------------><------------------------
gccagaaatggcaacttctacgccatggactattggggccagggcaccctggtgaccgtgtctctgccagcaccaaggccctttccgtg
  A  R  N  G  N  F  Y  A  M  D  Y  W  G  Q  G  T  L  V  T  V  S  S  A  S  T  K  G  P  S  V -----------------------------------------------CH1------------------------------------------
tttccactggcccctcctcaaatccacatctggcggcaccgccgccctgggctgtctggtgaaggactacttccctgagcctgtgaca
  F  P  L  A  P  S  S  K  S  T  S  G  G  T  A  A  L  G  C  L  V  K  D  Y  F  P  E  P  V  T ----------------------------------------------CH1----------------------------------------
gtgtcctggaactctggcgccctgacatctggcgtgcacacattccagcgtgtgctgcagagctccggcctgtacagcctgtctagcgtg
  V  S  W  N  S  G  A  L  T  S  G  V  H  T  F  P  A  V  L  Q  S  S  G  L  Y  S  L  S  S  V -----------------------------------------------CH1----------------------------------------->
gtgaccgtgccctcctctagcctgggcacacagacctatatctgcaacgtgaatcacaagccaagcaataccaaggtggacaagaaggtg
  V  T  V  P  S  S  S  L  G  T  Q  T  Y  I  C  N  V  N  H  K  P  S  N  T  K  V  D  K  K  V <--------------------------Hinge Region--------------------------><-------------------------
gagcccaagtcctgtgatgccacacacacctgccccccttgtcctgctcccgagctgctgggcggccctagcgtgttcctgtttccaccc
  E  P  K  S  C  D  A  T  H  T  C  P  P  C  P  A  P  E  L  L  G  G  P  S  V  F  L  F  P  P ----------------------------------------------CH2------------------------------------------
aagcctaaggataccctgatgatctcccggacacccgaggtgacctgcgtggtggtggacgtgtctcacgaggatcctgaggtgaagttc
  K  P  K  D  T  L  M  I  S  R  T  P  E  V  T  C  V  V  V  D  V  S  H  E  D  P  E  V  K  F ----------------------------------------------CH2------------------------------------------
aactggtatgtggatggcgtggaggtgcacaatgccaagaccaagccaagagaggagcagtacaactctacatacagggtggtgagcgtg
  N  W  Y  V  D  G  V  E  V  H  N  A  K  T  K  P  R  E  E  Q  Y  N  S  T  Y  R  V  V  S  V ---------------------------------------------CH2------------------------------------------
ctgaccgtgctgcaccaggactggctgaacggcaaggagtataagtgcaaggtgtccaataaggccctgccagcccccatcgagaaaaca
  L  T  V  L  H  Q  D  W  L  N  G  K  E  Y  K  C  K  V  S  N  K  A  L  P  A  P  I  E  K  T ----------------------><-------------------------------------CH3-------------------------
atcagcaaggccaaggggcagcctcgggagccacaggtgtacaccctgcctccatccagagacgagctgaccaagaaccaggtgtctctg
  I  S  K  A  K  G  Q  P  R  E  P  Q  V  Y  T  L  P  P  S  R  D  E  L  T  K  N  Q  V  S  L ---------------------------------------------CH3-------------------------------------------
acatgtctggtgaagggcttctatcctagcgatatcgccgtggagtgggagtccaatggccagccagagaacaattacaagaccacaccc
  T  C  L  V  K  G  F  Y  P  S  D  I  A  V  E  W  E  S  N  G  Q  P  E  N  N  Y  K  T  T  P ---------------------------------------------CH3-------------------------------------------
cctgtgctggactccgatggctccttcttcctgtattccaagctgaccgtggataagtctcggtggcagcagggcaacgtgttcagctgt
  P  V  L  D  S  D  G  S  F  F  L  Y  S  K  L  T  V  D  K  S  R  W  Q  Q  G  N  V  F  S  C ---------------------------------------------CH3---------------------->
tccgtgatgcacgaagccctgcataatcactatactcagaaatccctgtccctgtcacctggaaagtgataagctta
  S  V  M  H  E  A  L  H  N  H  Y  T  Q  K  S  L  S  L  S  P  G  K  .  .  A
```

SEQ ID NO: 226
SEQ ID NO: 227

\>U551FEL190-VL1- hIgkCL-pcDNA3.4

SEQ ID NO: 228
SEQ ID NO: 229

FIG. 69

>U551FEL190-VL2- hIgkCL-pcDNA3.4

```
                        <----------------------Leader Sequence----------------------><-----------------
tgaattccgcgccaccatgggctggtcatgtattattctgtttctggtcgcaactgctacaggggtccatagtgagatcgtgctgaca
    .  I  P  A  A  T  M  G  W  S  C  I  I  L  F  L  V  A  T  A  T  G  V  H  S  E  I  V  L  T --------------------FR1-IMGT----------------------------------------><----CR1-IMGT----><---------
caatctcccggcaccctcagcctgtctccaggcgagagagccacactgtcctgcaccgcttctagctccgtgtcctccagctttctgcac
 Q  S  P  G  T  L  S  L  S  P  G  E  R  A  T  L  S  C  T  A  S  S  S  V  S  S  S  F  L  H -----------FR2-IMGT----------------------><CDR2-IMGT><------------------------------------
tggtaccagcagaaacctggccaggctcctcagctgtggatctactccaactccaacctggctctggcatccctgatcggttctccggc
 W  Y  Q  Q  K  P  G  Q  A  P  Q  L  W  I  Y  S  T  S  N  L  A  S  G  I  P  D  R  F  S  G ----------FR3-IMGT----------------------------------------------><--------CR3-IMGT--
tccggctctggcaccgactacaccctgaccatctccagactggaacctgaggacttcgccgtgtactactgtcaccagtaccaccattct
 S  G  S  G  T  D  Y  T  L  T  I  S  R  L  E  P  E  D  F  A  V  Y  Y  C  H  Q  Y  H  H  S ------------------><----------FR4-IMGT--------><-----------------------CL-------------------
ccttacatctataccttcggcggagggaccaagctggaaatcaagaggacagtggccgccccaagcgtgttcatctttcccccttccgac
 P  Y  I  Y  T  F  G  G  G  T  K  L  E  I  K  R  T  V  A  A  P  S  V  F  I  F  P  P  S  D -------------------------------------------------CL-----------------------------------------
gagcagctgaagtctggcaccgccagcgtggtgtgcctgctgaacaacttctaccctcgggaggccaaggtccagtggaaggtggataac
 E  Q  L  K  S  G  T  A  S  V  V  C  L  L  N  N  F  Y  P  R  E  A  K  V  Q  W  K  V  D  N -------------------------------------------------CL-----------------------------------------
gccctgcagtctggcaatagccaggagtccgtgaccgagcaggactctaaggatagcacatattccctgtctagcaccctgacactgagc
 A  L  Q  S  G  N  S  Q  E  S  V  T  E  Q  D  S  K  D  S  T  Y  S  L  S  S  T  L  T  L  S -------------------------------------------------CL-----------------------------------------
aagggcgattacgagaagcacaaggtgtatgcctgtgaagtcacccatcagggcctgtcatcaccgtcactaagtcattcaatcgcgga
 K  A  D  Y  E  K  H  K  V  Y  A  C  E  V  T  H  Q  G  L  S  S  P  V  T  K  S  F  N  R  G ------->
gaatgctgataagctta    SEQ ID NO: 230
 E  C  .  .  A        SEQ ID NO: 231
```

>U551FEL190-VL3- hIgkCL-pcDNA3.4

SEQ ID NO: 232
SEQ ID NO: 233

>U551FEL190-VL4-hIgkCL-pcDNA3.4

SEQ ID NO: 234
SEQ ID NO: 235

FIG. 74

>Human IgG1 (P01857)

ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSC          (SEQ ID NO: 216)

DKTHTCPPCPAPELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQGNVFSCSV
MHEALHNHYTQKSLSLSPGK          (SEQ ID NO: 217)

>Human Ig Kappa (P01834)

RTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC          (SEQ ID NO: 218)

>Human Ig Lambda (P0DOY2)

GQPKAAPSVTLFPPSSEELQANKATLVCLISDFYPGAVTVAWKADSSPVKAGVETTTPSKQSNNKYAASS
YLSLTPEQWKSHRSYSCQVTHEGSTVEKTVAPTECS          (SEQ ID NO: 219)

FIG. 75

| Construct ID | Sequence |
|---|---|
| H1 | U551FEL190-VH1+VL1 |
| H2 | U551FEL190-VH1+VL2 |
| H3 | U551FEL190-VH1+VL3 |
| H4 | U551FEL190-VH1+VL4 |
| H5 | U551FEL190-VH2+VL1 |
| H6 | U551FEL190-VH2+VL2 |
| H7 | U551FEL190-VH2+VL3 |
| H8 | U551FEL190-VH2+VL4 |
| H9 | U551FEL190-VH3+VL1 |
| H10 | U551FEL190-VH3+VL2 |
| H11 | U551FEL190-VH3+VL3 |
| H12 | U551FEL190-VH3+VL4 |
| H13 | U551FEL190-VH4+VL1 |
| H14 | U551FEL190-VH4+VL2 |
| H15 | U551FEL190-VH4+VL3 |
| H16 | U551FEL190-VH4+VL4 |

FIG. 76

| Construct ID | Heavy Chain Sequence | Light Chain Sequence |
|---|---|---|
| H5 | U551FEL190--VH2_hIgG1CH-pCDNA3.4 (SEQ ID NO: 223) | U551FEL190-VL1_hIgkCL-pcDNA3.4   (SEQ ID NO: 229) |
| H7 | U551FEL190--VH2_hIgG1CH-pCDNA3.4 (SEQ ID NO: 223) | U551FEL190-VL3_hIgkCL-pcDNA3.4   (SEQ ID NO: 233) |
| H8 | U551FEL190--VH2_hIgG1CH-pCDNA3.4 (SEQ ID NO: 223) | U551FEL190-VL4_hIgkCL-pcDNA3.4   (SE ID NO: 235) |
| H14 | U551FEL190--VH4_hIgG1CH-pCDNA3.4 (SEQ ID NO: 227) | U551FEL190-VL2_hIgkCL-pcDNA3.4   (SEQ ID NO: 231) |
|  |  |  |
| H5 K222A | U551FEL190-VH2-hIgG1CH(K222A)-pcDNA3.4    (SEQ ID NO: 239) | U551FEL190-VL1_hIgkCL-pcDNA3.4   (SEQ ID NO: 229) |
| H7 K222A | U551FEL190-VH2-hIgG1CH(K222A)-pcDNA3.4    (SEQ ID NO: 239) | U551FEL190-VL3_hIgkCL-pcDNA3.4   (SEQ ID NO: 233) |
| H8 K222A | U551FEL190-VH2-hIgG1CH(K222A)-pcDNA3.4    (SEQ ID NO: 239) | U551FEL190-VL4_hIgkCL-pcDNA3.4   (SE ID NO: 235) |
| H14 K222A | U551FEL190-VH4-hIgG1CH(K222A)-pcDNA3.4    (SEQ ID NO: 243) | U551FEL190-VL2_hIgkCL-pcDNA3.4   (SEQ ID NO: 231) |

FIG. 77A (1) U551FEL190-VH1_hIgG1CH-pCDNA3.4

```
atgggctggtcatgcattattctgtttctggtcgcaactgctacaggcgtgcatagtcaggtgc
agctgcaagagtccggccctggactcgtgaagccctccgagacactgtctctgacctgtaccgt
gtctggctttagcctgtccatctactccgtgcactggatccggcagcctcctggcaagggcctg
gaatggatcggcatgatctggggaggcggctctagcgactacaactccgccctgaaatctagag
tgaccatctccgtggacacctccaagaaccagttctccctgaagctgagctctgtgaccgctgc
tgataccgccgtgtactactgcgccagaaatggcaacttctacgccatggactattggggccag
ggcaccctggtcacagtgtcctctgccagcaccaagggcccttccgtgtttccactggcccccct
cctctaaatccacatctggcggcaccgcgccctgggctgtctggtgaaggactacttcccaga
gcctgtgacagtgtcctggaactctggcgccctgacatccggcgtgcacatttccagccgtg
ctgcagagctccggcctgtacagcctgtctagcgtggtgacagtgccctcctctagcctgggca
cacagacctatatctgcaacgtgaatcacaagccaagcaataccaaggtggacaagaaggtgga
gcccaagtcctgtgataagacacacacctgcccccttgtcctgctcccgagctgctgggcggc
cctagcgtgttcctgtttccaccaagcctaaggacaccctgatgatctcccggacacccgagg
tgacctgcgtggtggtggacgtgtctcacgaggatcctgaggtgaagttcaactggtatgtgga
tggcgtggaggtgcacaatgccaagaccaagcccagagaggagcagtacaactctacatatagg
gtggtgagcgtgctgaccgtgctgcaccaggactggctgaacggcaaggagtataagtgcaagg
tgtccaataaggccctgccgcccccatcgagaagacaatcagcaaggccaaggccagcctcg
ggagccacaggtgtacaccctgcctccatccagagacgagctgacaagaaccaggtgtctctg
acatgtctggtgaagggcttctatcctagcgatatcgccgtggagtgggagtccaatggccagc
cagagaacaattacaagaccacacccctgtgctggactccgatggctccttctttctgtattc
caagctgaccgtggataagtctcggtggcagcagggcaacgtgttcagctgttccgtgatgcac
gaagccctgcataatcactatactcagaaatccctgtccctgtcacctggaaagtga
(SEQ ID NO: 220)
```

```
MGWSCIILFLVATATGVHSQVQLQESGPGLVKPSETLSLTCTVSGFSLSIYSVHWIRQPPGKGL
EWIGMIWGGGSSDYNSALKSRVTISVDTSKNQFSLKLSSVTAADTAVYYCARNGNFYAMDYWGQ
GTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMH
EALHNHYTQKSLSLSPGK
(SEQ ID NO: 221)
```

FIG. 77B (2) U551FEL190--VH2_hIgG1CH-pCDNA3.4 atgggctggtcatgcattattctgtttctggtcgcaactgctacaggcgtgcatagtcaggtgc
agctgcaagagtccggccctggactcgtgaagccctccgagacactgtctctgacatgtaccgt
gtctggcttctcctgtccatctactccgtgcactggatcagacagcctcctggcaagggcctg
gaatggatcggcatgatctggggaggcggctcttccgactacaactccgccctgaaatctcggc
tgaccatctccaaggacacctctaagaaccaggtcagcctgaagctgagctctgtgaccgctgc
tgataccgccgtgtactactgcgccagaaatggcaacttctacgccatggactattggggccag
ggcaccctggtaccgtgtccagcgccagcaccaagggcccttccgtgttccactggccccct
cctctaaatccacatctggcggcacgcgccctgggctgtctggtgaaggactacttcccaga
gcctgtgacagtgtcctggaactctggcgccctgacatccggcgtgcacacatttccagccgtg
ctgcagagctccggcctgtacagcctgtctagcgtggtgacagtgccctcctctagcctgggca
cacagacctatatctgcaacgtgaatcacaagccaagcaataccaaggtggacaagaaggtgga
gcccaagtcctgtgataagacacacacctgccccccttgtcctgctcccgagctgctgggcggc
cctagcgtgttcctgtttccacccaagcctaaggacaccctgatgatctcccggacacccgagg
tgacctgcgtggtggtggacgtgtctcacgaggatcctgaggtgaagttcaactggtatgtgga
tggcgtggaggtgcacaatgccaagaccaagccagagaggagcagtacaactctacatatagg
gtggtgagcgtgctgaccgtgctgcaccaggactggctgaacggcaaggagtataagtgcaagg
tgtccaataaggccctgcccgcccccatcgagaagacaatcagcaaggccaaggccagcctcg
ggagccacaggtgtacaccctgcctccatccagagacgagctgacaaagaaccaggtgtctctg
acatgtctggtgaaggcttctatcctagcgatatcgccgtggagtgggagtccaatggccagc
cagagaacaattacaagaccacacccctgtgctggactccgatggctccttctttctgtattc
caagctgaccgtggataagtctcggtggcagcagggcaacgtgttcagctgttccgtgatgcac
gaagccctgcataatcactatactcagaaatccctgtccctgtcacctggaaagtga
(SEQ ID NO: 222)

MGWSCIILFLVATATGVHSQVQLQESGPGLVKPSETLSLTCTVSGFSLSIYSVHWIRQPPGKGL
EWIGMIWGGGSSDYNSALKSRLTISKDTSKNQVSLKLSSVTAADTAVYYCARNGNFYAMDYWGQ
GTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMH
EALHNHYTQKSLSLSPGK
(SEQ ID NO: 223)

FIG. 77C (3)    U551FEL190--VH3_hIgG1CH-pCDNA3.4

```
atgggctggtcatgcattattctgtttctggtcgcaactgctacaggcgtgcatagtcaggtgc
agctgcaagagtccggccctggactcgtgaagccctccgagacactgtctctgacctgtaccgt
gtctggcttctccctgtccatctactccgtgcactggatccggcagcctcctggcaagggcctg
gaatggctgggcatgatctggggcggaggctctagcgactacaactccgccctgaaatctagac
tgaccatctccgtggacacctccaagaaccaggtcagcctgaagctgagctctgtgaccgccgc
tgatacagctatgtactactgcgccagaaatggcaacttctacgccatggactattggggccag
ggcaccctggtgaccgtgtcctctgccagcaccaagggcccttccgtgtttccactggccccct
cctctaaatccacatctggcggcacgcgccctgggctgtctggtgaaggactacttcccaga
gcctgtgacagtgtcctggaactctggcgccctgacatccggcgtgcacacatttccagccgtg
ctgcagagctccggcctgtacagcctgtctagcgtggtgacagtgccctcctctagcctgggca
cacagacctatatctgcaacgtgaatcacaagccaagcaataccaaggtggacaagaaggtgga
gcccaagtcctgtgataagacacacacctgcccccttgtcctgctcccgagctgctgggcggc
cctagcgtgttcctgtttccacccaagcctaaggacaccctgatgatctcccggacacccgagg
tgacctgcgtggtggtggacgtgtctcacgaggatcctgaggtgaagttcaactggtatgtgga
tggcgtggaggtgcacaatgccaagaccaagcccagagaggagcagtacaactctacatatagg
gtggtgagcgtgctgaccgtgctgcaccaggactggctgaacggcaaggagtataagtgcaagg
tgtccaataaggccctgccgcccccatcgagaagacaatcagcaaggccaaggccagcctcg
ggagccacaggtgtacaccctgcctccatccagagacgagctgacaaagaaccaggtgtctctg
acatgtctggtgaagggcttctatcctagcgatatcgccgtggagtgggagtccaatggccagc
cagagaacaattacaagaccacacccctgtgctggactccgatggctccttctttctgtattc
caagctgaccgtggataagtctcggtggcagcagggcaacgtgttcagctgttccgtgatgcac
gaagccctgcataatcactatactcagaaatccctgtccctgtcacctggaaagtga
```
(SEQ ID NO: 224)

```
MGWSCIILFLVATATGVHSQVQLQESGPGLVKPSETLSLTCTVSGFSLSIYSVHWIRQPPGKGL
EWLGMIWGGGSSDYNSALKSRLTISVDTSKNQVSLKLSSVTAADTAMYYCARNGNFYAMDYWGQ
GTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMH
EALHNHYTQKSLSLSPGK
```
(SEQ ID NO: 225)

FIG. 77D (4)  U551FEL190-VH4_hIgG1CH-pCDNA3.4 atgggctggtcatgcattattctgtttctggtcgcaactgctacaggcgtgcatagtcaggtgc
agctgcaagagtccggacccggcctcgtgaagccttccgagacactgtctctgacctgtaccgt
gtctggcttctccctgtccatctactccgtgcactggatccggcagcctcctggcaagggcctg
gaatggctgggcatgatctggggcggcggaagctccgactacaactccgccctgaaatctagac
tgaccatctccaaggacacctctaagaaccaggtcagcctgaagctgagctctgtgaccgccgc
tgataccgctatgtactactgcgccagaaatggcaacttctacgccatggactattggggccag
ggcaccctggtgacagtgtcctctgccagcaccaagggcccttccgtgtttccactggccccct
cctctaaatccacatctggcggcacgcgccctgggctgtctggtgaaggactacttcccaga
gcctgtgacagtgtcctggaactctggcgccctgacatccggcgtgcacatttccagccgtg
ctgcagagctccggcctgtacagcctgtctagcgtggtgacagtgccctcctctagcctgggca
cacagacctatatctgcaacgtgaatcacaagccaagcaataccaaggtggacaagaaggtgga
gcccaagtcctgtgataagacacacacctgccccccttgtcctgctcccgagctgctgggcggc
cctagcgtgttcctgtttccaccaagcctaaggacaccctgatgatctcccggacacccgagg
tgacctgcgtggtggtggacgtgtctcacgaggatcctgaggtgaagttcaactggtatgtgga
tggcgtggaggtgcacaatgccaagaccaagccagagaggagcagtacaactctacatatagg
gtggtgagcgtgctgaccgtgctgcaccaggactggctgaacggcaaggagtataagtgcaagg
tgtccaataaggccctgccgcccccatcgagaagacaatcagcaaggccaaggccagcctcg
ggagccacaggtgtacaccctgcctccatccagagacgagctgacaaagaaccaggtgtctctg
acatgtctggtgaagggcttctatcctagcgatatcgccgtggagtgggagtccaatggccagc
cagagaacaattacaagaccacacccctgtgctggactccgatggctccttctttctgtattc
caagctgaccgtggataagtctcggtggcagcagggcaacgtgttcagctgttccgtgatgcac
gaagccctgcataatcactatactcagaaatccctgtccctgtcacctggaaagtga
(SEQ ID NO: 226)

MGWSCIILFLVATATGVHSQVQLQESGPGLVKPSETLSLTCTVSGFSLSIYSVHWIRQPPGKGL
EWLGMIWGGGSSDYNSALKSRLTISKDTSKNQVSLKLSSVTAADTAMYYCARNGNFYAMDYWGQ
GTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMH
EALHNHYTQKSLSLSPGK
(SEQ ID NO: 227)

FIG. 77E (5) U551FEL190-VL1_hIgkCL-pcDNA3.4

Atgggctggtcatgtattattctgtttctggtcgcaactgctacagggggtccatagtgagatcg
tgctgacccaatctccaggcaccctgtctctcagccctggcgagagagccaccctgtcctgcac
cgcttctagctccgtgtcctccagcttcctgcactggtaccagcagaaacccggccaggctcct
agactgctgatctattccacctccaacctggcctctggcatccctgaccggttctccggctctg
gctccggaacagattttacactgaccatctcccggctggaacctgaggacttcgccgtgtacta
ctgtcaccagtaccaccattctccttacatctacaccttcggcggcggaaccaagctggaaatc
aagaggacagtggccgcccaagcgtgttcatctttcccccttccgacgagcagctgaagtctg
gcaccgccagcgtggtgtgcctgctgaacaacttctacctcgggaggccaaggtccagtggaa
ggtggataacgccctgcagtctggcaatagccaggagtccgtgaccgagcaggactctaaggat
agcacatattccctgtctagcaccctgacactgagcaaggccgattacgagaagcacaaggtgt
atgcctgtgaagtcacccatcaggggctgtcatcacccgtcactaagtcattcaatcgcggaga
atgctga (SEQ ID NO: 228)

MGWSCIILFLVATATGVHSEIVLTQSPGTLSLSPGERATLSCTASSSVSSSFLHWYQQKPGQAP
RLLIYSTSNLASGIPDRFSGSGSGTDFTLTISRLEPEDFAVYYCHQYHHSPYIYTFGGGTKLEI
KRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC (SEQ ID NO: 229)

FIG. 77F (6) U551FEL190-VL2_hIgkCL-pcDNA3.4

Atgggctggtcatgtattattctgtttctggtcgcaactgctacaggggtccatagtgagatcg
tgctgacacaatctcccggcaccctcagcctgtctccaggcgagagagccacactgtcctgcac
cgcttctagctccgtgtcctccagctttctgcactggtaccagcagaaacctggccaggctcct
cagctgtggatctactccacctccaacctggcctctggcatcctgatcggttctccggctccg
gctctggcaccgactacaccctgaccatctccagactggaacctgaggacttcgccgtgtacta
ctgtcaccagtaccaccattctccttacatctataccttcggcggaggaaccaagctggaaatc
aagaggacagtggccgcccaagcgtgttcatctttcccccttccgacgagcagctgaagtctg
gcaccgccagcgtggtgtgcctgctgaacaacttctaccctcgggaggccaaggtccagtggaa
ggtggataacgccctgcagtctggcaatagccaggagtccgtgaccgagcaggactctaaggat
agcacatattccctgtctagcaccctgacactgagcaaggccgattacgagaagcacaaggtgt
atgcctgtgaagtcacccatcagggctgtcatcacccgtcactaagtcattcaatcgcggaga
atgctga (SEQ ID NO: 230)

MGWSCIILFLVATATGVHSEIVLTQSPGTLSLSPGERATLSCTASSSVSSSFLHWYQQKPGQAP
QLWIYSTSNLASGIPDRFSGSGSGTDYTLTISRLEPEDFAVYYCHQYHHSPYIYTFGGGTKLEI
KRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC (SEQ ID NO: 231)

FIG. 77G (7) U551FEL190-VL3_hIgkCL-pcDNA3.4

Atgggctggtcatgtattattctgtttctggtcgcaactgctacaggggtccatagtgagatcg
tgctgacccagtctccaggcacactcagcctgtctcctggcgagcgggctaccctgtcctgcac
cgccagcagctccgtgtcctcttcttttctgcactggtaccagcagaaacctggacaagctcct
cagctgtggatctactccacctccaacctggcctctggcatccccgatagattctccggctctg
gctccggcaccgactacacactgaccatctccagactggaacctgaggacttcgccacctacta
ctgtcatcagtaccaccactcccttacatctataccttcggcggaggcaccaagctggaaatc
aagaggacagtggccgcccccaagcgtgttcatctttcccccttccgacgagcagctgaagtctg
gcaccgccagcgtggtgtgcctgctgaacaacttctacctcgggaggccaaggtccagtggaa
ggtggataacgccctgcagtctggcaatagccaggagtccgtgaccgagcaggactctaaggat
agcacatattccctgtctagcaccctgacactgagcaaggccgattacgagaagcacaaggtgt
atgcctgtgaagtcacccatcagggggctgtcatcacccgtcactaagtcattcaatcgcggaga
atgctga (SEQ ID NO: 232)

MGWSCIILFLVATATGVHSEIVLTQSPGTLSLSPGERATLSCTASSSVSSSFLHWYQQKPGQAP
QLWIYSTSNLASGIPDRFSGSGSGTDYTLTISRLEPEDFATYYCHQYHHSPYIYTFGGGTKLEI
KRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC (SEQ ID NO: 233)

FIG. 77H (8)  U551FEL190-VL4_hIgkCL-pcDNA3.4

Atgggctggtcatgtattattctgtttctggtcgcaactgctacaggggtccatagtgagatcg
tgctgacccaatctcctggcaccctgtctctgagcccaggcgagagagccacactctcctgcac
cgcttcttcctccgtgtcctctagctttctgcactggtaccagcagaaacccggccaggctcct
cagctgtggatctactccacctccaacctggcctctggcatcctgccagattctccggatccg
gctctggcaccgattatacactgaccatctcccggctggaacctgaggacttcgccacctacta
ctgtcaccagtaccaccatagcccttacatctacaccttcggcggcggaaccaagctggaaatc
aagaggacagtggccgccccaagcgtgttcatctttcccccttccgacgagcagctgaagtctg
gcaccgccagcgtggtgtgcctgctgaacaacttctaccctcgggaggccaaggtccagtggaa
ggtggataacgccctgcagtctggcaatagccaggagtccgtgaccgagcaggactctaaggat
agcacatattccctgtctagcaccctgacactgagcaaggccgattacgagaagcacaaggtgt
atgcctgtgaagtcacccatcagggctgtcatcacccgtcactaagtcattcaatcgcggaga
atgctga    (SEQ ID NO: 234)

MGWSCIILFLVATATGVHSEIVLTQSPGTLSLSPGERATLSCTASSSVSSSFLHWYQQKPGQAP
QLWIYSTSNLASGIPARFSGSGSGTDYTLTISRLEPEDFATYYCHQYHHSPYIYTFGGGTKLEI
KRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC        (SEQ ID NO:
235)

FIG. 77I (9)    U551FEL190-VH1_hIgG1CH(K222A)-pCDNA3.4 atgggctggtcatgcattattctgtttctggtcgcaactgctacaggcgtgcatagtcaggtgc
agctgcaagagtccggccctggactcgtgaagccctccgagacactgtctctgacctgtaccgt
gtctggctttagcctgtccatctactccgtgcactggatccggcagcctcctggcaagggcctg
gaatggatcggcatgatctggggaggcggctctagcgactacaactccgccctgaaatctagag
tgaccatctccgtggacacctccaagaaccagttctccctgaagctgagctctgtgaccgctgc
tgataccgccgtgtactactgcgccagaaatggcaacttctacgccatggactattggggccag
ggcaccctggtcacagtgtcctctgccagcaccaagggcccttccgtgtttccactggcccccct
cctctaaatccacatctggcggcaccgcgccctgggctgtctggtgaaggactacttcccaga
gcctgtgacagtgtcctggaactctggcgccctgacatccggcgtgcacacatttccagccgtg
ctgcagagctccggcctgtacagcctgtctagcgtggtgacagtgccctcctctagcctgggca
cacagacctatatctgcaacgtgaatcacaagccaagcaataccaaggtggacaagaaggtgga
gcccaagtcctgtgat<u>GCC</u>acacacacctgccccccttgtcctgctcccgagctgctgggcggc
cctagcgtgttcctgtttccaccaagcctaaggacaccctgatgatctcccggacacccgagg
tgacctgcgtggtggtggacgtgtctcacgaggatcctgaggtgaagttcaactggtatgtgga
tggcgtggaggtgcacaatgccaagaccaagccagagaggagcagtacaactctacatatagg
gtggtgagcgtgctgaccgtgctgcaccaggactggctgaacggcaaggagtataagtgcaagg
tgtccaataaggccctgccgccccatcgagaagacaatcagcaaggccaaggccagcctcg
ggagccacaggtgtacaccctgcctccatccagagacgagctgacaaagaaccaggtgtctctg
acatgtctggtgaagggcttctatcctagcgatatcgccgtggagtgggagtccaatggccagc
cagagaacaattacaagaccacacccctgtgctggactccgatggctccttctttctgtattc
caagctgaccgtggataagtctcggtggcagcagggcaacgtgttcagctgttccgtgatgcac
gaagccctgcataatcactatactcagaaatccctgtccctgtcacctggaaagtga
(SEQ ID NO: 236)

MGWSCIILFLVATATGVHSQVQLQESGPGLVKPSETLSLTCTVSGFSLSIYSVHWIRQPPGKGL
EWIGMIWGGGSSDYNSALKSRVTISVDTSKNQFSLKLSSVTAADTAVYYCARNGNFYAMDYWGQ
GTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCD<u>A</u>THTCPPCPAPELLGG
PSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMH
EALHNHYTQKSLSLSPGK
(SEQ ID NO: 237)

FIG. 77J

(10) U551FEL190-VH2-hIgG1CH(K222A)-pcDNA3.4 atgggctggtcatgcattattctgtttctggtcgcaactgctacaggcgtgcatagtcaggtgc
agctgcaagagtccggccctggactcgtgaagccctccgagacactgtctctgacatgtaccgt
gtctggcttctccctgtccatctactccgtgcactggatcagacagcctcctggcaagggcctg
gaatggatcggcatgatctggggaggcggctcttccgactacaactccgccctgaaatctcggc
tgaccatctccaaggacacctctaagaaccaggtcagcctgaagctgagctctgtgaccgctgc
tgataccgccgtgtactactgcgccagaaatggcaacttctacgccatggactattggggccag
ggcaccctggtgaccgtgtccagcgccagcaccaagggcccttccgtgtttccactggccccct
cctctaaatccacatctggcggcaccgcgccctgggctgtctggtgaaggactacttcccaga
gcctgtgacagtgtcctggaactctggcgccctgacatccggcgtgcacacatttccagccgtg
ctgcagagctccggcctgtacagcctgtctagcgtggtgacagtgccctcctctagcctgggca
cacagacctatatctgcaacgtgaatcacaagccaagcaataccaaggtggacaagaaggtgga
gcccaagtcctgtgat<u>GCC</u>acacacacctgcccccttgtcctgctcccgagctgctgggcggc
cctagcgtgttcctgtttccacccaagcctaaggacaccctgatgatctcccggacacccgagg
tgacctgcgtggtggtggacgtgtctcacgaggatcctgaggtgaagttcaactggtatgtgga
tggcgtggaggtgcacaatgccaagaccaagccagagaggagcagtacaactctacatatagg
gtggtgagcgtgctgaccgtgctgcaccaggactggctgaacggcaaggagtataagtgcaagg
tgtccaataaggccctgccgcccccatcgagaagacaatcagcaaggccaaggccagcctcg
ggagccacaggtgtacaccctgcctccatccagagacgagctgacaaagaaccaggtgtctctg
acatgtctggtgaagggcttctatcctagcgatatcgccgtggagtgggagtccaatggccagc
cagagaacaattacaagaccacacccctgtgctggactccgatggctccttctttctgtattc
caagctgaccgtggataagtctcggtggcagcagggcaacgtgttcagctgttccgtgatgcac
gaagccctgcataatcactatactcagaaatccctgtccctgtcacctggaaagtga
(SEQ ID NO: 238)

MGWSCIILFLVATATGVHSQVQLQESGPGLVKPSETLSLTCTVSGFSLSIYSVHWIRQPPGKGL
EWIGMIWGGGSSDYNSALKSRLTISKDTSKNQVSLKLSSVTAADTAVYYCARNGNFYAMDYWGQ
GTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCD<u>A</u>THTCPPCPAPELLGG
PSVFLFPPKPKDTLMISRTPEVTCVVVDVSHEDPEVKFNWYVDGVEVH<u>N</u>AKTKPREEQYNSTYR
VVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMH
EALHNHYTQKSLSLSPGK        (SEQ ID NO: 239)

FIG. 77K (5)    U551FEL190--VH3_hIgG1CH(K222A)-pCDNA3.4 atgggctggtcatgcattattctgtttctggtcgcaactgctacaggcgtgcatagtcaggtgc
agctgcaagagtccggccctggactcgtgaagccctccgagacactgtctctgacctgtaccgt
gtctggcttctccctgtccatctactccgtgcactggatccggcagcctcctggcaagggcctg
gaatggctgggcatgatctggggcggaggctctagcgactacaactccgccctgaaatctagac
tgaccatctccgtggacacctccaagaaccaggtcagcctgaagctgagctctgtgaccgccgc
tgatacagctatgtactactgcgccagaaatggcaacttctacgccatggactattggggccag
ggcaccctggtgaccgtgtcctctgccagcaccaagggcccttccgtgtttccactggcccct
cctctaaatccacatctggcggcaccgcgccctgggctgtctggtgaaggactacttcccaga
gcctgtgacagtgtcctggaactctggcgccctgacatccggcgtgcacacatttccagccgtg
ctgcagagctccggcctgtacagcctgtctagcgtggtgacagtgccctcctctagcctgggca
cacagacctatatctgcaacgtgaatcacaagccaagcaataccaaggtggacaagaaggtgga
gcccaagtcctgtgatGCCacacacacctgcccccttgtcctgctcccgagctgctgggcggc
cctagcgtgttcctgtttccacccaagcctaaggacaccctgatgatctcccggacacccgagg
tgacctgcgtggtggtggacgtgtctcacgaggatcctgaggtgaagttcaactggtatgtgga
tggcgtggaggtgcacaatgccaagaccaagcccagagaggagcagtacaactctacatatagg
gtggtgagcgtgctgaccgtgctgcaccaggactggctgaacggcaaggagtataagtgcaagg
tgtccaataaggccctgcccgcccccatcgagaagacaatcagcaaggccaaggccagcctcg
ggagccacaggtgtacaccctgcctccatccagagacgagctgacaaagaaccaggtgtctctg
acatgtctggtgaagggcttctatcctagcgatatcgccgtggagtgggagtccaatggccagc
cagagaacaattacaagaccacacccctgtgctggactccgatggctccttctttctgtattc
caagctgaccgtggataagtctcggtggcagcagggcaacgtgttcagctgttccgtgatgcac
gaagccctgcataatcactatactcagaaatccctgtccctgtcacctggaaagtga
(SEQ ID NO: 240)

MGWSCIILFLVATATGVHSQVQLQESGPGLVKPSETLSLTCTVSGFSLSIYSVHWIRQPPGKGL
EWLGMIWGGGSSDYNSALKSRLTISVDTSKNQVSLKLSSVTAADTAMYYCARNGNFYAMDYWGQ
GTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDATHTCPPCPAPELLGG
PSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMH
EALHNHYTQKSLSLSPGK
(SEQ ID NO: 241)

FIG. 77L

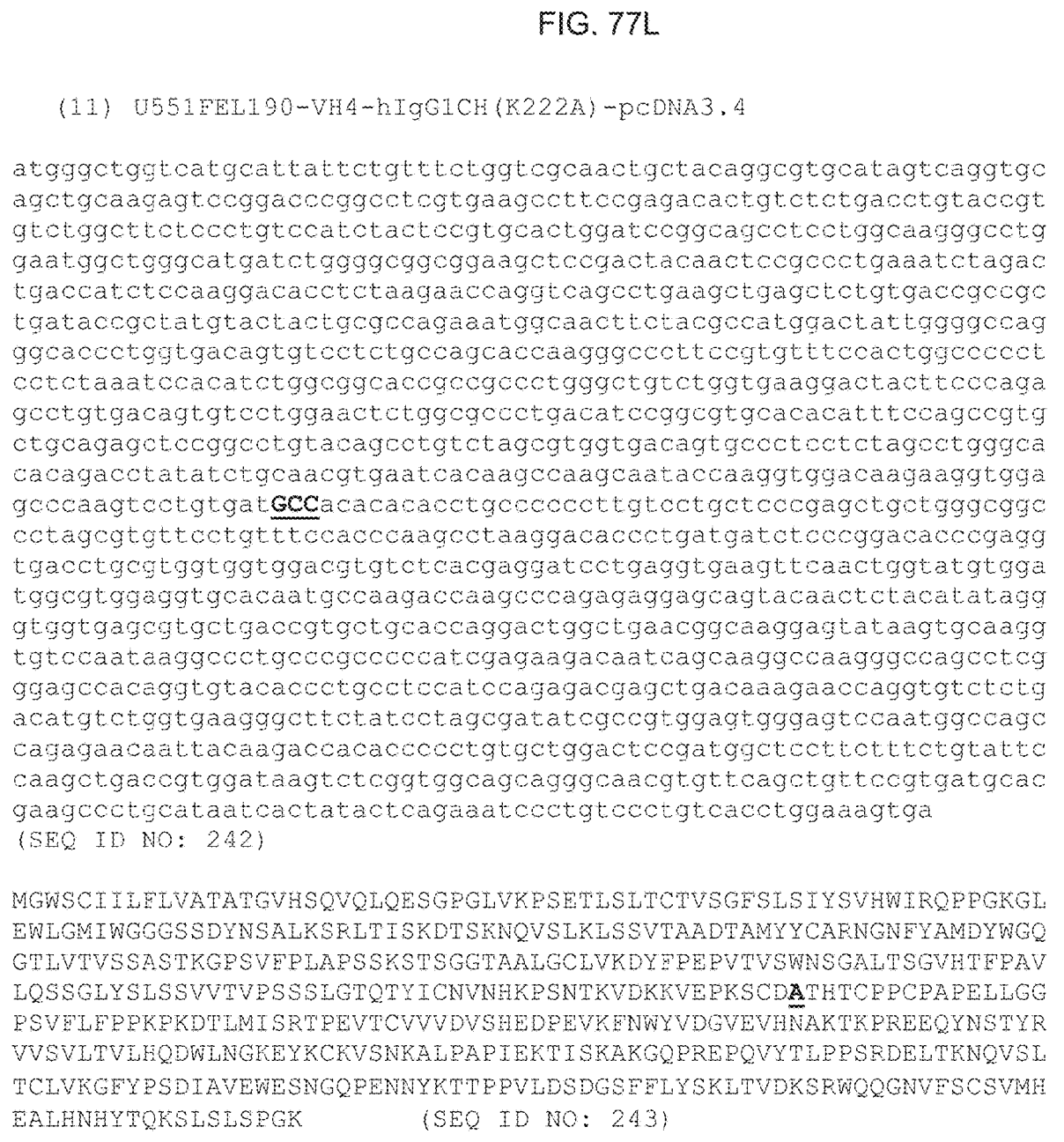

(11) U551FEL190-VH4-hIgG1CH(K222A)-pcDNA3.4 atgggctggtcatgcattattctgtttctggtcgcaactgctacaggcgtgcatagtcaggtgc
agctgcaagagtccggacccggcctcgtgaagccttccgagacactgtctctgacctgtaccgt
gtctggcttctccctgtccatctactccgtgcactggatccggcagcctcctggcaagggcctg
gaatggctgggcatgatctggggcggcggaagctccgactacaactccgccctgaaatctagac
tgaccatctccaaggacacctctaagaaccaggtcagcctgaagctgagctctgtgaccgccgc
tgataccgctatgtactactgcgccagaaatggcaacttctacgccatggactattggggccag
ggcaccctggtgacagtgtcctctgccagcaccaagggcccttccgtgtttccactggcccct
cctctaaatccacatctggcggcaccgcgccctgggctgtctggtgaaggactacttcccaga
gcctgtgacagtgtcctggaactctggcgccctgacatccggcgtgcacacatttccagccgtg
ctgcagagctccggcctgtacagcctgtctagcgtggtgacagtgccctcctctagcctgggca
cacagacctatatctgcaacgtgaatcacaagccaagcaataccaaggtggacaagaaggtgga
gcccaagtcctgtgatGCCacacacacctgccccccttgtcctgctcccgagctgctgggcggc
cctagcgtgttcctgtttccacccaagcctaaggacaccctgatgatctcccggacacccgagg
tgacctgcgtggtggtggacgtgtctcacgaggatcctgaggtgaagttcaactggtatgtgga
tggcgtggaggtgcacaatgccaagaccaagcccagagaggagcagtacaactctacatatagg
gtggtgagcgtgctgaccgtgctgcaccaggactggctgaacggcaaggagtataagtgcaagg
tgtccaataaggccctgcccgcccccatcgagaagacaatcagcaaggccaaggccagcctcg
ggagccacaggtgtacaccctgcctccatccagagacgagctgacaaagaaccaggtgtctctg
acatgtctggtgaagggcttctatcctagcgatatcgccgtggagtgggagtccaatggccagc
cagagaacaattacaagaccacacccctgtgctggactccgatggctccttcttctgtattc
caagctgaccgtggataagtctcggtggcagcagggcaacgtgttcagctgttccgtgatgcac
gaagccctgcataatcactatactcagaaatccctgtccctgtcacctggaaagtga
(SEQ ID NO: 242)

MGWSCIILFLVATATGVHSQVQLQESGPGLVKPSETLSLTCTVSGFSLSIYSVHWIRQPPGKGL
EWLGMIWGGGSSDYNSALKSRLTISKDTSKNQVSLKLSSVTAADTAMYYCARNGNFYAMDYWGQ
GTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDATHTCPPCPAPELLGG
PSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMH
EALHNHYTQKSLSLSPGK          (SEQ ID NO: 243)

Figure 78A:
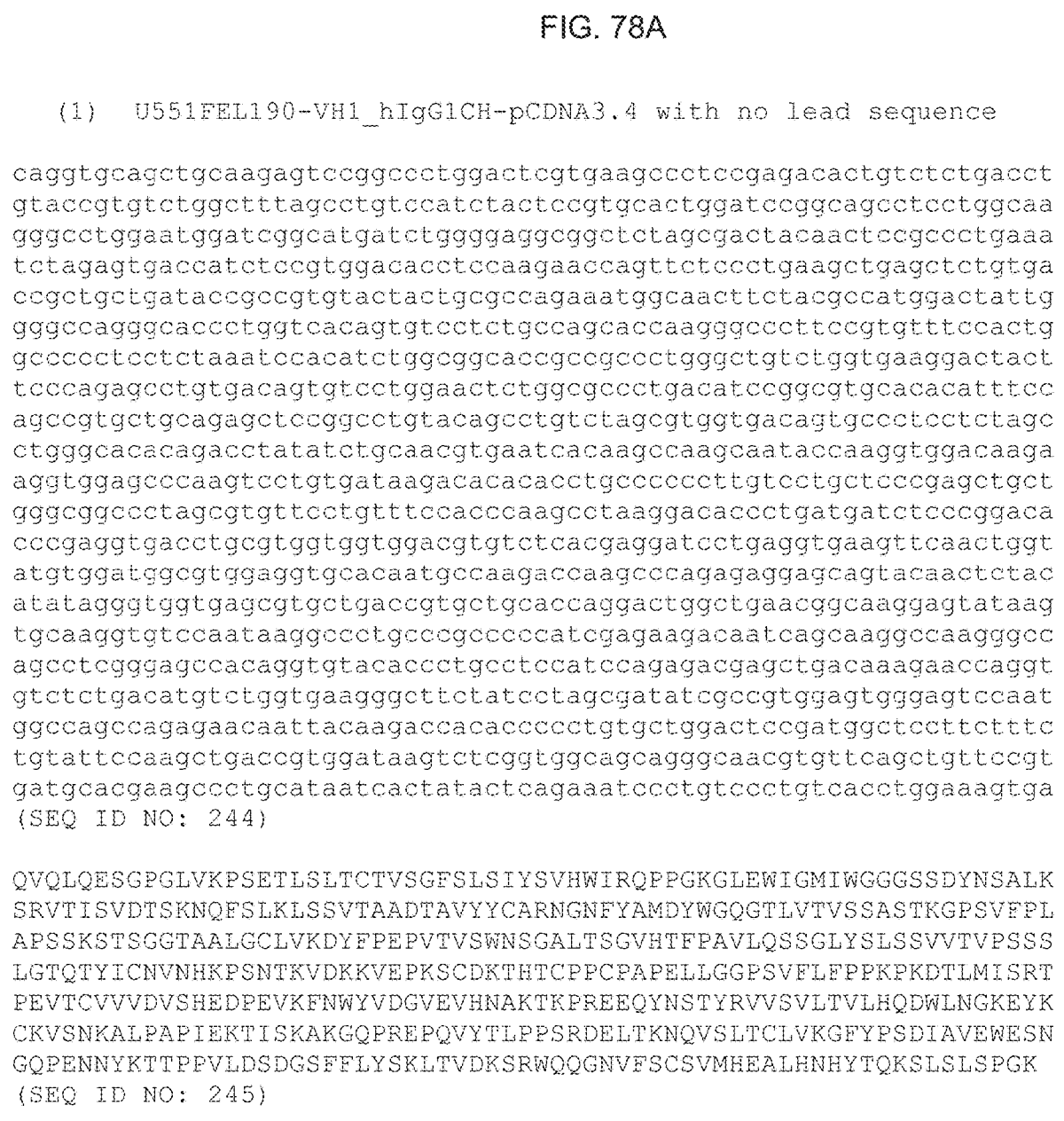

FIG. 78A (1) U551FEL190-VH1_hIgG1CH-pCDNA3.4 with no lead sequence caggtgcagctgcaagagtccggccctggactcgtgaagccctccgagacactgtctctgacct
gtaccgtgtctggctttagcctgtccatctactccgtgcactggatccggcagcctcctggcaa
gggcctggaatggatcggcatgatctggggaggcggctctagcgactacaactccgccctgaaa
tctagagtgaccatctccgtggacacctccaagaaccagttctccctgaagctgagctctgtga
ccgctgctgataccgccgtgtactactgcgccagaaatggcaacttctacgccatggactattg
gggccagggcaccctggtcacagtgtcctctgccagcaccaagggcccttcgtgtttccactg
gccccctcctctaaatccacatctggcggcaccgccgcctgggctgtctggtgaaggactact
tcccagagcctgtgacagtgtcctggaactctggcgccctgacatccggcgtgcacacatttcc
agccgtgctgcagagctccggcctgtacagcctgtctagcgtggtgacagtgccctcctctagc
ctgggcacacagacctatatctgcaacgtgaatcacaagccaagcaataccaaggtggacaaga
aggtggagcccaagtcctgtgataagacacacacctgccccccttgtcctgctcccgagctgct
gggcggccctagcgtgttcctgtttccacccaagcctaaggacaccctgatgatctcccggaca
cccgaggtgacctgcgtggtggtggacgtgtctcacgaggatcctgaggtgaagttcaactggt
atgtggatggcgtggaggtgcacaatgccaagaccaagcccagagaggagcagtacaactctac
atataggtggtgagcgtgctgaccgtgctgcaccaggactggctgaacggcaaggagtataag
tgcaaggtgtccaataaggccctgccgccccccatcgagaagacaatcagcaaggccaagggcc
agcctcgggagccacaggtgtacaccctgcctccatccagagacgagctgacaaagaaccaggt
gtctctgacatgtctggtgaagggcttctatcctagcgatatcgccgtggagtgggagtccaat
ggccagccagagaacaattacaagaccacaccccctgtgctggactccgatggctccttctttc
tgtattccaagctgaccgtggataagtctcggtggcagcagggcaacgtgttcagctgttccgt
gatgcacgaagccctgcataatcactatactcagaaatccctgtccctgtcacctggaaagtga
(SEQ ID NO: 244)

QVQLQESGPGLVKPSETLSLTCTVSGFSLSIYSVHWIRQPPGKGLEWIGMIWGGGSSDYNSALK
SRVTISVDTSKNQFSLKLSSVTAADTAVYYCARNGNFYAMDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
(SEQ ID NO: 245)

FIG. 78B (2)   U551FEL190--VH2_hIgG1CH-pCDNA3.4 with no lead sequence caggtgcagctgcaagagtccggccctggactcgtgaagccctccgagacactgtctctgacat
gtaccgtgtctggcttctccctgtccatctactccgtgcactggatcagacagcctcctggcaa
gggcctggaatggatcggcatgatctggggaggcggctcttccgactacaactccgccctgaaa
tctcggctgaccatctccaaggacacctctaagaaccaggtcagcctgaagctgagctctgtga
ccgctgctgataccgccgtgtactactgcgccagaaatggcaacttctacgccatggactattg
gggccagggcaccctggtgaccgtgtccagcgccagcaccaagggcccttccgtgtttccactg
gcccctcctctaaatccacatctggcggcaccgccgccctgggctgtctggtgaaggactact
tcccagagcctgtgacagtgcctggaactctggcgccctgacatccggcgtgcacacatttcc
agccgtgctgcagagctccggcctgtacagcctgtctagcgtggtgacagtgccctcctctagc
ctgggcacacagacctatatctgcaacgtgaatcacaagcaagcaataccaaggtggacaaga
aggtggagcccagtcctgtgataagacacacacctgcccccttgtcctgctcccgagctgct
gggcggccctagcgtgttcctgtttccacccaagcctaaggacaccctgatgatctcccggaca
cccgaggtgacctgcgtggtggtggacgtgtctcacgaggatcctgaggtgaagttcaactggt
atgtggatggcgtggaggtgcacaatgccaagaccaagcccagagaggagcagtacaactctac
atataggtggtgagcgtgctgaccgtgctgcaccaggactggctgaacggcaaggagtataag
tgcaaggtgtccaataaggccctgccgcccccatcgagaagacaatcagcaaggccaagggcc
agcctcgggagccacaggtgtacaccctgcctccatccagagacgagctgacaaagaaccagt
gtctctgacatgtctggtgaagggcttctatcctagcgatatcgccgtggagtgggagtccaat
ggccagccagagaacaattacaagaccacacccctgtgctggactccgatggctccttctttc
tgtattccaagctgaccgtggataagtctcggtggcagcagggcaacgtgttcagctgttccgt
gatgcacgaagccctgcataatcactatactcagaaatccctgtccctgtcacctggaaagtga
(SEQ ID NO: 246)

QVQLQESGPGLVKPSETLSLTCTVSGFSLSIYSVHWIRQPPGKGLEWIGMIWGGGSSDYNSALK
SRLTISKDTSKNQVSLKLSSVTAADTAVYYCARNGNFYAMDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
(SEQ ID NO: 247)

FIG. 78C (3)    U551FEL190--VH3_hIgG1CH-pCDNA3.4 with no lead sequence

```
caggtgcagctgcaagagtccggccctggactcgtgaagccctccgagacactgtctctgacct
gtaccgtgtctggcttctccctgtccatctactccgtgcactggatccggcagcctcctggcaa
gggcctggaatggctgggcatgatctggggcggaggctctagcgactacaactccgccctgaaa
tctagactgaccatctccgtggacacctccaagaaccaggtcagcctgaagctgagctctgtga
ccgccgctgatacagctatgtactactgcgccagaaatggcaacttctacgccatggactattg
gggccagggcaccctggtgaccgtgtcctctgccagcaccaagggcccttccgtgtttccactg
gcccctcctctaaatccacatctggcggcaccgccgccctgggctgtctggtgaaggactact
tcccagagcctgtgacagtgtcctggaactctggcgccctgacatccggcgtgcacacatttcc
agccgtgctgcagagctccggcctgtacagcctgtctagcgtggtgacagtgccctcctctagc
ctgggcacacagacctatatctgcaacgtgaatcacaagccaagcaataccaaggtggacaaga
aggtggagcccaagtcctgtgataagacacacacctgccccccttgtcctgctcccgagctgct
gggcggccctagcgtgttcctgtttccacccaagcctaaggacaccctgatgatctcccggaca
cccgaggtgacctgcgtggtggtggacgtgtctcacgaggatcctgaggtgaagttcaactggt
atgtggatggcgtggaggtgcacaatgccaagaccaagcccagagaggagcagtacaactctac
atatagggtggtgagcgtgctgaccgtgctgcaccaggactggctgaacggcaaggagtataag
tgcaaggtgtccaataaggccctgccgccccccatcgagaagacaatcagcaaggccaagggcc
agcctcgggagccacaggtgtacaccctgcctccatccagagacgagctgacaaagaaccaggt
gtctctgacatgtctggtgaagggcttctatcctagcgatatcgccgtggagtgggagtccaat
ggccagccagagaacaattacaagaccacacccctgtgctggactccgatggctccttctttc
tgtattccaagctgaccgtggataagtctcggtggcagcagggcaacgtgttcagctgttccgt
gatgcacgaagccctgcataatcactatactcagaaatccctgtccctgtcacctggaaagtga
(SEQ ID NO: 248)
```

```
QVQLQESGPGLVKPSETLSLTCTVSGFSLSIYSVHWIRQPPGKGLEWLGMIWGGGSSDYNSALK
SRLTISVDTSKNQVSLKLSSVTAADTAMYYCARNGNFYAMDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
(SEQ ID NO: 249)
```

FIG. 78D (4)    U551FEL190-VH4_hIgG1CH-pCDNA3.4 with no lead sequence caggtgcagctgcaagagtccggacccggcctcgtgaagccttccgagacactgtctctgacct
gtaccgtgtctggcttctccctgtccatctactccgtgcactggatccggcagcctcctggcaa
gggcctggaatggctgggcatgatctggggcggcggaagctccgactacaactccgccctgaaa
tctagactgaccatctccaaggacacctctaagaaccaggtcagcctgaagctgagctctgtga
ccgccgctgataccgctatgtactactgcgccagaaatggcaacttctacgccatggactattg
gggccagggcaccctggtgacagtgtcctctgccagcaccaagggcccttccgtgtttccactg
gccccctcctctaaatccacatctggcggcaccgccgccctgggctgtctggtgaaggactact
tcccagagcctgtgacagtgtcctggaactctggcgccctgacatccggcgtgcacacatttcc
agccgtgctgcagagctccggcctgtacagcctgtctagcgtggtgacagtgccctcctctagc
ctgggcacacagacctatatctgcaacgtgaatcacaagccaagcaataccaaggtggacaaga
aggtggagcccaagtcctgtgataagacacacacctgcccccttgtcctgctcccgagctgct
gggcggccctagcgtgttcctgtttccacccaagcctaaggacaccctgatgatctcccggaca
cccgaggtgacctgcgtggtggtggacgtgtctcacgaggatcctgaggtgaagttcaactggt
atgtggatggcgtggaggtgcacaatgccaagaccaagcccagagaggagcagtacaactctac
atatagggtggtgagcgtgctgaccgtgctgcaccaggactggctgaacggcaaggagtataag
tgcaaggtgtccaataaggccctgcccgcccccatcgagaagacaatcagcaaggccaagggcc
agcctcgggagccacaggtgtacaccctgcctccatccagagacgagctgacaaagaaccaggt
gtctctgacatgtctggtgaaggcttctatcctagcgatatcgccgtggagtgggagtccaat
ggccagccagagaacaattacaagaccacaccccctgtgctggactccgatggctccttctttc
tgtattccaagctgaccgtggataagtctcggtggcagcagggcaacgtgttcagctgttccgt
gatgcacgaagccctgcataatcactatactcagaaatccctgtccctgtcacctggaaagtga
(SEQ ID NO: 250)

QVQLQESGPGLVKPSETLSLTCTVSGFSLSIYSVHWIRQPPGKGLEWLGMIWGGGSSDYNSALK
SRLTISKDTSKNQVSLKLSSVTAADTAMYYCARNGNFYAMDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
(SEQ ID NO: 251)

FIG. 78E (5) U551FEL190-VL1_hIgkCL-pcDNA3.4 with no lead sequence gagatcgtgctgacccaatctccaggcaccctgtctctcagccctggcgagagagccaccctgt
cctgcaccgcttctagctccgtgtcctccagcttcctgcactggtaccagcagaaacccggcca
ggctcctagactgctgatctattccacctccaacctggcctctggcatccctgaccggttctcc
ggctctggctccggaacagattttacactgaccatctcccggctggaacctgaggacttcgccg
tgtactactgtcaccagtaccaccattctccttacatctacaccttcggcggcggaaccaagct
ggaaatcaagaggacagtggccgcccaagcgtgttcatctttccccttccgacgagcagctg
aagtctggcaccgcagcgtggtgtgcctgctgaacaacttctaccctcgggaggccaaggtcc
agtggaaggtggataacgccctgcagtctggcaatagccaggagtccgtgaccgagcaggactc
taaggatagcacatattccctgtctagcaccctgacactgagcaaggccgattacgagaagcac
aaggtgtatgcctgtgaagtcacccatcaggggctgtcatcacccgtcactaagtcattcaatc
gcggagaatgctga (SEQ ID NO: 252)

EIVLTQSPGTLSLSPGERATLSCTASSSVSSSFLHWYQQKPGQAPRLLIYSTSNLASGIPDRFS
GSGSGTDFTLTISRLEPEDFAVYYCHQYHHSPYIYTFGGGTKLEIKRTVAAPSVFIFPPSDEQL
KSGTASVVCLLNNFYPREAKVQWKVDNALQSGNSQESVTEQDSKDSTYSLSSTLTLSKADYEKH
KVYACEVTHQGLSSPVTKSFNRGEC (SEQ ID NO: 253)

FIG. 78F (6)   U551FEL190-VL2_hIgkCL-pcDNA3.4 with no lead sequence gagatcgtgctgacacaatctcccggcaccctcagcctgtctccaggcgagagagccacactgt
cctgcaccgcttctagctccgtgtcctccagctttctgcactggtaccagcagaaacctggcca
ggctcctcagctgtggatctactccacctccaacctggcctctggcatccctgatcggttctcc
ggctccggctctggcaccgactacaccctgaccatctccagactggaacctgaggacttcgccg
tgtactactgtcaccagtaccaccattctccttacatctataccttcggcggaggaaccaagct
ggaaatcaagaggacagtggccgcccccaagcgtgttcatctttccccttccgacgagcagctg
aagtctggcaccgccagcgtggtgtgcctgctgaacaacttctaccctcgggaggccaaggtcc
agtggaaggtggataacgccctgcagtctggcaatagccaggagtccgtgaccgagcaggactc
taaggatagcacatattccctgtctagcaccctgacactgagcaaggccgattacgagaagcac
aaggtgtatgcctgtgaagtcacccatcaggggctgtcatcacccgtcactaagtcattcaatc
gcggagaatgctga (SEQ ID NO: 254)

EIVLTQSPGTLSLSPGERATLSCTASSSVSSSFLHWYQQKPGQAPQLWIYSTSNLASGIPDRFS
GSGSGTDYTLTISRLEPEDFAVYYCHQYHHSPYIYTFGGGTKLEIKRTVAAPSVFIFPPSDEQL
KSGTASVVCLLNNFYPREAKVQWKVDNALQSGNSQESVTEQDSKDSTYSLSSTLTLSKADYEKH
KVYACEVTHQGLSSPVTKSFNRGEC        (SEQ ID NO: 255)

FIG. 78G (7)  U551FEL190-VL3_hIgkCL-pcDNA3.4 with no lead sequence gagatcgtgctgacccagtctccaggcacactcagcctgtctcctggcgagcgggctaccctgt
cctgcaccgccagcagctccgtgtcctcttcttttctgcactggtaccagcagaaacctggaca
agctcctcagctgtggatctactccacctccaacctggcctctggcatccccgatagattctcc
ggctctggctccggcaccgactacacactgaccatctccagactggaacctgaggacttcgcca
cctactactgtcatcagtaccaccactcccttacatctataccttcggcggaggcaccaagct
ggaaatcaagaggacagtggccgcccaagcgtgttcatctttccccttccgacgagcagctg
aagtctggcaccgccagcgtggtgtgcctgctgaacaacttctaccctcgggaggccaaggtcc
agtggaaggtggataacgccctgcagtctggcaatagccaggagtccgtgaccgagcaggactc
taaggatagcacatattccctgtctagcaccctgacactgagcaaggccgattacgagaagcac
aaggtgtatgcctgtgaagtcacccatcaggggctgtcatcacccgtcactaagtcattcaatc
gcggagaatgctga (SEQ ID NO: 256)

EIVLTQSPGTLSLSPGERATLSCTASSSVSSSFLHWYQQKPGQAPQLWIYSTSNLASGIPDRFS
GSGSGTDYTLTISRLEPEDFATYYCHQYHHSPYIYTFGGGTKLEIKRTVAAPSVFIFPPSDEQL
KSGTASVVCLLNNFYPREAKVQWKVDNALQSGNSQESVTEQDSKDSTYSLSSTLTLSKADYEKH
KVYACEVTHQGLSSPVTKSFNRGEC      (SEQ ID NO: 257)

FIG. 78H (8)   U551FEL190-VL4_hIgkCL-pcDNA3.4 with no lead sequence gagatcgtgctgacccaatctcctggcaccctgtctctgagcccaggcgagagagccacactct
cctgcaccgcttcttcctccgtgtcctctagctttctgcactggtaccagcagaaacccggcca
ggctcctcagctgtggatctactccacctccaacctggcctctggcatccctgccagattctcc
ggatccggctctggcaccgattatacactgaccatctcccggctggaacctgaggacttcgcca
cctactactgtcaccagtaccaccatagccttacatctacaccttcggcggcggaaccaagct
ggaaatcaagaggacagtggccgcccaagcgtgttcatctttccccttccgacgagcagctg
aagtctggcaccgccagcgtggtgtgcctgctgaacaacttctaccctcgggaggccaaggtcc
agtggaaggtggataacgccctgcagtctggcaatagccaggagtccgtgaccgagcaggactc
taaggatagcacatattccctgtctagcaccctgacactgagcaaggccgattacgagaagcac
aaggtgtatgcctgtgaagtcacccatcaggggctgtcatcacccgtcactaagtcattcaatc
gcggagaatgctga (SEQ ID NO: 258)

EIVLTQSPGTLSLSPGERATLSCTASSSVSSSFLHWYQQKPGQAPQLWIYSTSNLASGIPARFS
GSGSGTDYTLTISRLEPEDFATYYCHQYHHSPYIYTFGGGTKLEIKRTVAAPSVFIFPPSDEQL
KSGTASVVCLLNNFYPREAKVQWKVDNALQSGNSQESVTEQDSKDSTYSLSSTLTLSKADYEKH
KVYACEVTHQGLSSPVTKSFNRGEC           (SEQ ID NO: 259)

FIG. 78I (9)   U551FEL190-VH1_hIgG1CH(K222A)-pCDNA3.4 with no lead
      sequence caggtgcagctgcaagagtccggccctggactcgtgaagccctccgagacactgtctctgacct
gtaccgtgtctggctttagcctgtccatctactccgtgcactggatccggcagcctcctggcaa
gggcctggaatggatcggcatgatctggggaggcggctctagcgactacaactccgccctgaaa
tctagagtgaccatctccgtggacacctccaagaaccagttctccctgaagctgagctctgtga
ccgctgctgataccgccgtgtactactgcgccagaaatggcaacttctacgccatggactattg
gggccagggcaccctggtcacagtgtcctctgccagcaccaagggcccttccgtgttccactg
gccccctcctaaatccacatctggcggcaccgccgccctgggctgtctggtgaaggactact
tcccagagcctgtgacagtgtcctggaactctggcgccctgacatccggcgtgcacacatttcc
agccgtgctgcagagctccggcctgtacagcctgtctagcgtggtgacagtgccctcctctagc
ctgggcacacagacctatatctgcaacgtgaatcacaagcaagcaataccaaggtggacaaga
aggtggagcccaagtcctgtgatGCCacacacacctgccccccttgtcctgctcccgagctgct
gggcggccctagcgtgttcctgtttccacccaagcctaggacaccctgatgatctcccggaca
cccgaggtgacctgcgtggtggtggacgtgtctcacgaggatcctgaggtgaagttcaactggt
atgtggatggcgtggaggtgcacaatgccaagaccaagcccagagaggagcagtacaactctac
atatagggtggtgagcgtgctgaccgtgctgcaccaggactggctgaacggcaaggagtataag
tgcaaggtgtccaataaggccctgcccgcccccatcgagaagacaatcagcaaggccaagggcc
agcctcgggagccacaggtgtacaccctgcctccatccagagacgagctgacaaagaaccagt
gtctctgacatgtctggtgaagggcttctatcctagcgatatcgccgtggagtgggagtccaat
ggccagccagagaacaattacaagaccacacccctgtgctggactccgatggctccttcttttc
tgtattccaagctgaccgtggataagtctcggtggcagcagggcaacgtgttcagctgttccgt
gatgcacgaagccctgcataatcactatactcagaaatccctgtccctgtcacctggaaagtga
(SEQ ID NO: 260)

QVQLQESGPGLVKPSETLSLTCTVSGFSLSIYSVHWIRQPPGKGLEWIGMIWGGGSSDYNSALK
SRVTISVDTSKNQFSLKLSSVTAADTAVYYCARNGNFYAMDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSCDATHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
(SEQ ID NO: 261)

FIG. 78J

(10) U551FEL190-VH2-hIgG1CH(K222A)-pcDNA3.4 with no lead
sequence caggtgcagctgcaagagtccggccctggactcgtgaagccctccgagacactgtctctgacat
gtaccgtgtctggcttctccctgtccatctactccgtgcactggatcagacagcctcctggcaa
gggcctggaatggatcggcatgatctggggaggcggctcttccgactacaactccgccctgaaa
tctcggctgaccatctccaaggacacctcaagaaccaggtcagcctgaagctgagctctgtga
ccgctgctgataccgccgtgtactactgcgccagaaatggcaacttctacgccatggactattg
gggccagggcaccctggtgaccgtgtccagcgccagcaccaagggcccttccgtgtttccactg
gcccctcctctaaatccacatctggcggcaccgccgccctgggctgtctggtgaaggactact
tcccagagcctgtgacagtgtcctggaactctggcgccctgacatccggcgtgcacacatttcc
agccgtgctgcagagctccggcctgtacagcctgtctagcgtggtgacagtgccctcctctagc
ctgggcacacagacctatatctgcaacgtgaatcacaagccaagcaataccaaggtggacaaga
aggtggagcccaagtcctgtgatGCCacacacacctgcccccttgtcctgctcccgagctgct
gggcggccctagcgtgttcctgtttccacccaagcctaaggacaccctgatgatctcccggaca
cccgaggtgacctgcgtggtggtggacgtgtctcacgaggatcctgaggtgaagttcaactggt
atgtggatggcgtggaggtgcacaatgccaagaccaagcccagagaggagcagtacaactctac
atataggtggtgagcgtgctgaccgtgctgcaccaggactggctgaacggcaaggagtataag
tgcaaggtgtccaataaggccctgccgccccatcgagaagacaatcagcaaggccaagggcc
agcctcgggagccacaggtgtacaccctgcctccatccagagacgagctgacaagaaccaggt
gtctctgacatgtctggtgaagggcttctatcctagcgatatcgccgtggagtgggagtccaat
ggccagccagagaacaattacaagaccacacccctgtgctggactccgatggctccttctttc
tgtattccaagctgaccgtggataagtctcggtggcagcagggcaacgtgttcagctgttccgt
gatgcacgaagccctgcataatcactatactcagaatccctgtcctgtcacctggaaagtga
(SEQ ID NO: 262)

QVQLQESGPGLVKPSETLSLTCTVSGFSLSIYSVHWIRQPPGKGLEWIGMIWGGGSSDYNSALK
SRLTISKDTSKNQVSLKLSSVTAADTAVYYCARNGNFYAMDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSCDATHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
(SEQ ID NO: 263)

FIG. 78K

(11) U551FEL190-VH3_hIgG1CH(K222A)-pCDNA3.4 with no lead
     sequence caggtgcagctgcaagagtccggccctggactcgtgaagccctccgagacactgtctctgacct
gtaccgtgtctggcttctccctgtccatctactccgtgcactggatccggcagcctcctggcaa
gggcctggaatggctgggcatgatctggggcggaggctctagcgactacaactccgccctgaaa
tctagactgaccatctccgtggacacctccaagaaccaggtcagcctgaagctgagctctgtga
ccgccgctgatacagctatgtactactgcgccagaaatggcaacttctacgccatggactattg
gggccagggcaccctggtgaccgtgtcctctgccagcaccaagggcccttccgtgtttccactg
gcccctcctctaaatccacatctggcggcaccgccgccctgggctgtctggtgaaggactact
tcccagagcctgtgacagtgtcctggaactctggcgccctgacatccggcgtgcacacatttcc
agccgtgctgcagagctccggcctgtacagcctgtctagcgtggtgacagtgccctcctctagc
ctgggcacacagacctatatctgcaacgtgaatcacaagccaagcaataccaaggtggacaaga
aggtggagcccaagtcctgtgatGCCacacacacctgcccccttgtcctgctcccgagctgct
gggcggccctagcgtgttcctgtttccacccaagcctaaggacaccctgatgatctcccggaca
cccgaggtgacctgcgtggtggtggacgtgtctcacgaggatcctgaggtgaagttcaactggt
atgtggatggcgtggaggtgcacaatgccaagaccaagcccagagaggagcagtacaactctac
atatagggtggtgagcgtgctgaccgtgctgcaccaggactggctgaacggcaaggagtataag
tgcaaggtgtccaataaggccctgcccgcccccatcgagaagacaatcagcaaggccaagggcc
agcctcgggagccacaggtgtacaccctgcctccatccagagacgagctgacaaagaaccaggt
gtctctgacatgtctggtgaagggcttctatcctagcgatatcgccgtggagtgggagtccaat
ggccagccagagaacaattacaagaccacaccccctgtgctggactccgatggctccttcttc
tgtattccaagctgaccgtggataagtctcggtggcagcagggcaacgtgttcagctgttccgt
gatgcacgaagccctgcataatcactatactcagaaatccctgtccctgtcacctggaaagtga
(SEQ ID NO: 264)

QVQLQESGPGLVKPSETLSLTCTVSGFSLSIYSVHWIRQPPGKGLEWLGMIWGGGSSDYNSALK
SRLTISVDTSKNQVSLKLSSVTAADTAMYYCARNGNFYAMDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSCDATHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
(SEQ ID NO: 265)

FIG. 78L

(12) U551FEL190-VH4-hIgG1CH(K222A)-pcDNA3.4 with no lead
     sequence caggtgcagctgcaagagtccggacccggcctcgtgaagccttccgagacactgtctctgacct
gtaccgtgtctggcttctccctgtccatctactccgtgcactggatccggcagcctcctggcaa
gggcctggaatggctgggcatgatctggggcggcggaagctccgactacaactccgccctgaaa
tctagactgaccatctccaaggacacctctaagaaccaggtcagcctgaagctgagctctgtga
ccgccgctgataccgctatgtactactgcgccagaaatggcaacttctacgccatggactattg
gggccagggcaccctggtgacagtgtcctctgccagcaccaagggcccttccgtgttccactg
gccccctcctctaaatccacatctggcggcaccgccgccctgggctgtctggtgaaggactact
tcccagagcctgtgacagtgtcctggaactctggcgccctgacatccggcgtgcacaatttcc
agccgtgctgcagagctccggcctgtacagcctgtctagcgtggtgacagtgccctcctctagc
ctgggcacacagacctatatctgcaacgtgaatcacaagccaagcaataccaaggtggacaaga
aggtggagcccaagtcctgtgatGCCacacacacctgcccccttgtcctgctccgagctgct
gggcggccctagcgtgttcctgtttccacccaagcctaggacaccctgatgatctcccggaca
cccgaggtgacctgcgtggtggtggacgtgtctcacgaggatcctgaggtgaagttcaactggt
atgtggatggcgtggaggtgcacaatgccaagaccaagcccagagaggagcagtacaactctac
atataggtggtgagcgtgctgaccgtgctgcaccaggactggctgaacggcaaggagtataag
tgcaaggtgtccaataaggccctgcccgcccccatcgagaagacaatcagcaaggccaagggcc
agcctcgggagccacaggtgtacaccctgcctccatccagagacgagctgacaaagaaccaggt
gtctctgacatgtctggtgaagggcttctatcctagcgatatcgccgtggagtgggagtccaat
ggccagccagagaacaattacaagaccacacccctgtgctggactccgatggctccttctttc
tgtattccaagctgaccgtggataagtctcggtggcagcagggcaacgtgttcagctgttccgt
gatgcacgaagccctgcataatcactatactcagaaatccctgtccctgtcacctggaaagtga
(SEQ ID NO: 266)

QVQLQESGPGLVKPSETLSLTCTVSGFSLSIYSVHWIRQPPGKGLEWLGMIWGGGSSDYNSALK
SRLTISKDTSKNQVSLKLSSVTAADTAMYYCARNGNFYAMDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSCDATHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
     (SEQ ID NO: 267)

FIG. 79

VH region of H5 K222A:
QVQLQESGPGLVKPSETLSLTCTVSGFSLSIYSVHWIRQPPGKGLEWIGMIWGGGSSDYNSALK
SRLTISKDTSKNQVSLKLSSVTAADTAVYYCARNGNFYAMDYWGQGTLVTVSS
(SEQ ID NO: 268)

CH1 region of H5 K222A:
ASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKV        (SEQ ID NO: 269)

Heavy chain Fab of H5 K222A (VH and CH1 regions):
QVQLQESGPGLVKPSETLSLTCTVSGFSLSIYSVHWIRQPPGKGLEWIGMIWGGGSSDYNSALK
SRLTISKDTSKNQVSLKLSSVTAADTAVYYCARNGNFYAMDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKV        (SEQ ID NO: 270)

Hinge region of H5 K222A:
EPKSCDATHTCPPCPAPELLGG        (SEQ ID NO: 271)

CH2 region of H5 K222A:
PSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAK        (SEQ ID NO:272)

CH3 region of H5 K222A:
GQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK    (SEQ ID NO: 273)

Fc region of H5 K222A (Hinge, CH2, and CH3 regions):
ASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDATHTCPPCPAPELLGGPSVFLFPP
KPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHNHYT
QKSLSLSPGK        (SEQ ID NO: 274)

Leader region of H5 K222A:
MGWSCIILFLVATATGVHS (SEQ ID NO: 277)

Leader region + VH region of H5 K222A:
MGWSCIILFLVATATGVHSQVQLQESGPGLVKPSETLSLTCTVSGFSLSIYSVHWIRQPPGKGL
EWIGMIWGGGSSDYNSALKSRLTISKDTSKNQVSLKLSSVTAADTAVYYCARNGNFYAMDYWGQ
GTLVTVSS        (SEQ ID NO: 279)

FIG. 80

VL region of H5 K222A:
EIVLTQSPGTLSLSPGERATLSCTASSSVSSSFLHWYQQKPGQAPRLLIYSTSNLASGIPDRFS
GSGSGTDFTLTISRLEPEDFAVYYCHQYHHSPYIYTFGGGTKLEIK
(SEQ ID NO: 275)

CL region of H5 K222A:
RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC   (SEQ ID NO: 276)

Light chain Fab of H5 K222A (VL and CL regions):
EIVLTQSPGTLSLSPGERATLSCTASSSVSSSFLHWYQQKPGQAPRLLIYSTSNLASGIPDRFS
GSGSGTDFTLTISRLEPEDFAVYYCHQYHHSPYIYTFGGGTKLEIKRTVAAPSVFIFPPSDEQL
KSGTASVVCLLNNFYPREAKVQWKVDNALQSGNSQESVTEQDSKDSTYSLSSTLTLSKADYEKH
KVYACEVTHQGLSSPVTKSFNRGEC       (SEQ ID NO: 253)

Leader region of H5 K222A:
MGWSCIILFLVATATGVHS        (SEQ ID NO: 277)

Leader region + VL region of H5 K222A:
MGWSCIILFLVATATGVHSEIVLTQSPGTLSLSPGERATLSCTASSSVSSSFLHWYQQKPGQAP
RLLIYSTSNLASGIPDRFSGSGSGTDFTLTISRLEPEDFAVYYCHQYHHSPYIYTFGGGTKLEI
K         (SEQ ID NO: 278)

ANTIGEN-BINDING MOLECULES THAT BIND TO *PORPHYROMONAS GINGIVALIS*

CROSS-REFERENCE TO RELATED APPLICATIONS

This application is a continuation in part of PCT App. No. PCT/US2021/057758 filed Nov. 2, 2021 entitled "ANTI-GEN-BINDING MOLECULES THAT BIND TO *PORPHY-ROMONAS GINGIVALIS*," which claims priority to U.S. Prov. App. No. 63/109,286 filed Nov. 3, 2020 entitled "ANTIGEN-BINDING MOLECULES THAT BIND TO *PORPHYROMONAS GINGIVALIS*," to U.S. Prov. App. No. 63/135,878 filed Jan. 11, 2021 entitled "ANTIGEN-BIND-ING MOLECULES THAT BIND TO *PORPHYROMONAS GINGIVALIS*," to U.S. Prov. App. No. 63/208,873 filed Jun. 9, 2021 entitled "ANTIGEN-BINDING MOLECULES THAT BIND TO *PORPHYROMONAS GINGIVALIS*," to U.S. Prov. App. No. 63/221,405 filed Jul. 13, 2021 entitled "ANTIGEN BINDING MOLECULES THAT BIND TO *PORPHYROMONAS GINGIVALIS*," to U.S. Prov. App. No. 63/225,295 filed Jul. 23, 2021 entitled "ANTIGEN-BIND-ING MOLECULES THAT BIND TO *PORPHYROMONAS GINGIVALIS*," to U.S. Prov. App. No. 63/231,964 filed Aug. 11, 2021 entitled "ANTIGEN-BINDING MOLECULES THAT BIND TO *PORPHYROMONAS GINGIVALIS*," which are each incorporated by reference in their entirety. The present application also claims priority to U.S. Prov. App. No. 63/364,182 filed May 4, 2022 entitled "ANTI-GEN-BINDING MOLECULES THAT BIND TO *PORPHY-ROMONAS GINGIVALIS*," and to U.S. Prov. App. No. 63/364,592 filed May 12, 2022 entitled "ANTIGEN-BIND-ING MOLECULES THAT BIND TO *PORPHYROMONAS GINGIVALIS*," which are each incorporated by reference in their entirety.

REFERENCE TO SEQUENCE LISTING

The present application is being filed along with a Sequence Listing in electronic format. The Sequence Listing is provided as a file entitled KEYBI019A.xml created on May 5, 2023 which is 570,983 bytes in size. The information in the electronic format of the Sequence Listing is incorporated herein by reference in its entirety.

FIELD

The present disclosure generally relates to antigen-binding molecules, e.g., biomolecules, such as antibodies, that bind to *Porphyromonas gingivalis*, and the treatment and/or prevention of systemic diseases associated with chronic inflammation, multi-systems inflammation, and/or peri-odontal disease(s) associated with *P. gingivalis* infection and/or the continuous release of exo-toxins therefrom, using such *P. gingivalis* bacteria and exotoxin antigen-binding molecules, e.g., biomolecules.

BACKGROUND

Periodontal disease, including *Porphyromonas gingivalis* infection, has been implicated in various conditions, disorders or diseases including, without limitation, vascular disease (e.g., cardiovascular disease, atherosclerosis, coronary artery disease, myocardial infarction, stroke, and myocardial hypertrophy); systemic disease (e.g., type II diabetes, insulin resistance and metabolic syndrome); rheumatoid arthritis; cancer (e.g., oral, gastrointestinal, or pancreatic cancer);

renal disease, gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity); post event myocardial hypertrophy, wound closure, AMD (age-related macular degeneration), cerebral and abdominal aneurysms, glioma, large vessel stroke C-IMT, microvascular defects and associated dementias (e.g., Parkinson's), Peri-Implantitis and/or periodontal disease and/or associated bone loss, cognitive disorders (e.g., early, middle, and/or late dementia; Alzheimer's disease); and longevity or age-related disorder, regenerative and stem cell dysfunction.

DESCRIPTION OF THE RELATED ART

*Porphyromonas gingivalis* is a gram-negative anaerobic, asaccharolytic, red complex bacteria. *P. gingivalis* can infect and remain permanently in the oral cavity as a polymicrobial biofilm and/or translocate to other body cells/tissues. Upon infection, *P. gingivalis* can produce and excrete outer membrane vesicles (containing gingipains, hemagglutinin, adhesins and LPS) into the gingival sulcus space with its attending fluid, blood and lymphatic circulation. As disclosed herein, the regularly distributed polyclonal bio-film colonies of *P. gingivalis* are deeper in the sulcular tissues and extracellular portions of the oral cavity, while the OMVs produced by *P. gingivalis* are more diffusely spread to surrounding tissues and in the GCF/lymph and micro-vascular systems. *P. gingivalis* infection can lead to a state of oral and systemic dysbiosis (pathological and abnormal change from the normal oral flora/microbiota) and subsequent chronic local and systemic infection/disease(s), further leading to increased vascular and tissue inflammation throughout the entire body. Certain end organs, e.g., heart vessels, carotid arteries, vessels in the brain, liver, joints, lungs, pancreas, reproductive system, etc., are more affected than others. *P. gingivalis*-induced inflammation is implicated in diseases such as cardiovascular disease, heart attacks, atherosclerosis, stroke, various dementias, early and later neuro-cognitive decline, Alzheimer's disease, diabetes, NASH, rheumatoid arthritis, insulin resistance, etc.

SUMMARY

In some embodiments, a human or humanized antigen binding molecule (ABM) that binds to *Porphyromonas gingivalis* is provided. The ABM comprises: a heavy chain comprising an amino acid sequence of SEQ ID NO: 277 and an amino acid sequence of SEQ ID NO: 270, a light chain comprising an amino acid sequence of SEQ ID NO: 277 and an amino acid sequence of SEQ ID NO: 253, and an amino acid sequence of SEQ ID NO: 274.

In some embodiments, a human or humanized antigen binding molecule (ABM) that binds to *Porphyromonas gingivalis* is provided. The ABM comprises: a sequence of SEQ ID NO: 239, and a sequence of SEQ ID NO: 229.

In some embodiments, a human or humanized antigen binding molecule (ABM) that binds to *Porphyromonas gingivalis* is provided. The ABM comprises: an amino acid sequence of SEQ ID NO: 270, an amino acid sequence of SEQ ID NO: 253, and an amino acid sequence of SEQ ID NO: 274.

In some embodiments, a human or humanized antigen binding molecule (ABM) that binds to *Porphyromonas*

*gingivalis* is provided. The ABM comprises: an amino acid sequence of SEQ ID NO: 263, and an amino acid sequence of SEQ ID NO: 253.

In some embodiments, a cell expressing an ABM that binds to *Porphyromonas gingivalis* is provided. The ABM comprises: a VH/CH1 region of SEQ ID NO: 270 and a VL/CL region of SEQ ID NO: 253.

In some embodiments, a nucleic acid comprising the sequence of SEQ ID NO: 228, 238 252, or 262 is provided.

In some embodiments, any of the constructs can comprise one or more of any of the construct components depicted in any one or more of FIGS. 1A, 1B, 26A-37D, 45-47, 55-71, and 74-80. In some embodiments, the construct can have the leader sequence removed from any of the constructs that have a leader sequence in FIGS. 1A, 1B, 26A-37D, 45-47, 55-71, and 74-80. In some embodiments, any of the components in any one or more of FIGS. 1A, 1B, 26A-37D, 45-47, 55-71, and 74-80 can be used in a full length antibody (with each part being used for its designated purpose, for example, a VH and VL region being used in an antibody fragment or full length antibody). In some embodiments, any one or more of the constructs in any one or more of FIGS. 1A, 1B, 26A-37D, 45-47, 55-71, and 74-80 can be used in combination with the 222 mutation disclosed herein (in its corresponding location within that construct, which, depending on the actual construct, may not literally be the 222 amino acid position, but will correspond to that position in the construct, based on its position relative to the rest of the construct (e.g., reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are both referring to the same location in the antibody construct that is being altered. In some embodiments, any one or more of these constructs in any one or more of FIGS. 1A, 1B, 26A-37D, 45-47, 55-71, and 74-80 with the alanine 222 mutation in the hinge region, can have or exclude the leader sequence. In some embodiments, any one or more nucleic acids that encode such amino acid constructs is also provided. Any of the methods provided herein can employ any one or more of these constructs or construct components.

Provided herein is a human or humanized antigen binding molecule (ABM) that binds to *Porphyromonas gingivalis*, wherein the ABM comprises: a heavy chain variable region (HVR) comprising: a complementarity determining region (HCDR) 1 of a HCDR1 of SEQ ID NO: 9 or 37; a HCDR2 of a HCDR2 of SEQ ID NO: 9 or 37; and a HCDR3 of a HCDR2 of SEQ ID NO: 9 or 37; and a light chain variable region (LVR) comprising: a complementarity determining region (LCDR) 1 of a LCDR1 of SEQ ID NO:10 or 38; a LCDR2 of a LCDR2 of SEQ ID NO: 10 or 38; and a LCDR3 of a LCDR2 of SEQ ID NO: 10 or 38, wherein the ABM comprises at least one of: one or more HVR residues selected from L48, L67, K71, V78, and M92, as numbered according to the numbering as provided in SEQ ID NO:37, and one or more LVR residues selected from Q46, W48, A61, Y72, and T86, as numbered according to the numbering as provided in SEQ ID NO:38, wherein the ABM further comprises a variable heavy (VH) and variable light (VL) region, wherein the ABM comprises an amino acid sequence with a point mutation at position 222 in an antibody, as numbered according to the amino acid position 104 in SEQ ID NO: 172 in FIG. 45 to remove the lysine (e.g., in the hinge region). In some embodiments, position 222 is an alanine. In some embodiments, the HVR comprises one or more of a HFR1, HFR2, HFR3, and HFR4 of a HFR1, HFR2, HFR3, and HFR4 of SEQ ID NO:37, respectively. In some embodiments, the LVR comprises one or more of a LFR1, LFR2, LFR3, and LFR4 of a LFR1, LFR2, LFR3, and LFR4 of SEQ ID NO:38, respectively. In some embodiments, the HVR comprises an amino acid sequence at least 80% identical to one of SEQ ID NOS: 29-32. In some embodiments, the LVR comprises an amino acid sequence at least 80% identical to one of SEQ ID NOS: 33-36. In some embodiments, the VH region has at least 80% identity to SEQ ID NO: 29, 30, 31, or 32. In some embodiments, the VL region has at least 80% identity to SEQ ID NO: 33, 34, 35, or 36.

Also provided herein is a human or humanized antigen binding molecule (ABM) that binds to *Porphyromonas gingivalis*, wherein the ABM competes for binding to *Porphyromonas gingivalis* with H5, H7, or H14, wherein the ABM is not KB001, wherein the ABM comprises an amino acid sequence with a point mutation at position 222, as numbered according to the amino acid position 104 in SEQ ID NO: 172 in FIG. 45. In some embodiments, position 222 is an alanine. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the ABM comprises a heavy chain complementarity determining region (HCDR) 1 of SEQ ID NO:3. In some embodiments, the ABM comprises a HCDR2 of SEQ ID NO: 4. In some embodiments, the ABM comprises a HCDR3 of SEQ ID NO:5. In some embodiments, the ABM comprises a LCDR1 of SEQ ID NO:6. In some embodiments, the ABM comprises a LCDR2 of SEQ ID NO:7. In some embodiments, the ABM comprises a LCDR3 of SEQ ID NO:8. In some embodiments, the ABM comprises a HVR of SEQ ID NO: 9. In some embodiments, the ABM comprises a LVR of SEQ ID NO:10. In some embodiments, the ABM comprises a FR sequence of one or more of SEQ ID NOs: 11-18. In some embodiments, the VH region has at least 80% identity to SEQ ID NO: 29, 30, 31, or 32. In some embodiments, the ABM further comprises a variably light (VL) region. In some embodiments, the VL region has at least 80% identity to SEQ ID NO: 33, 34, 35, or 36. In some embodiments, the ABM binds to a same or overlapping epitope as KB001, and wherein the ABM comprises the CDRs of the 6 CDRs in SEQ ID NO: 1 and 2. In some embodiments, the ABM binds to an epitope comprising GVSPKVCKDVTVEGSNEFAPVQNLT (SEQ ID NO: 19) and/or YCVEVKYTAGVSPK (SEQ ID NO:59). In some embodiments, the ABM is resistant to protease cleavage. In some embodiments, the resistance is to cleavage by a bacterial protease. In some embodiments, the resistance is a resistance of 25-75%. In some embodiments, the ABM binds to a gingipain and/or a haemagglutinin. In some embodiments, the gingipain is selected from the group consisting of: lys-gingipain (Kgp), arg-gingipains (Rgp) A and RgpB. In some embodiments, the gingipain comprises a sequence of SEQ ID NO: 19. In some embodiments, the gingipain comprises a sequence of at least one of SEQ ID NOs: 21-28. In some embodiments, the ABM neutralizes the activity of the gingipain. In some embodiments, the activity is at least one of: a peptidase, hemagglutination, haemolysis, adhesin.

In some embodiments, the ABM binds to a propeptide domain, a catalytic domain and/or a C-terminal adhesion domain. In some embodiments, the ABM binds to budding outer membrane vesicles of *P. gingivalis*.

Also provided herein is a human or humanized antigen binding molecule (ABM) that binds to *Porphyromonas gingivalis*, wherein the ABM binds to budding outer membrane vesicles of *P. gingivalis*, wherein the ABM comprises an amino acid sequence with a point mutation at position 222, as numbered according to the amino acid position 104 in SEQ ID NO: 172 in FIG. 45. In some embodiments, position 222 is an alanine. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the ABM is digested at a slower rate than a fully humanized antibody that specifically binds *P. gingivalis*. In some embodiments, the ABM is a Fab, a diabody, Fab', F(ab')2, Fv, single-chain antibody, nanobody, domain antibody, bivalent antibody, bispecific antibody, or peptibody. In some embodiments, the antibody when administered to a subject's mouth reduces a *P. gingivalis* infection in the mouth by at least 80%. In some embodiments, the ABM is of an IgG isotype. In some embodiments, the ABM binds to an epitope within a polypeptide comprising an amino acid sequence of any one of SEQ ID NOs: 77-83.

Also disclosed herein is a nucleic acid encoding the ABM of any one of the present embodiments. Also disclosed herein is a vector comprising the nucleic acid encoding the ABM of any one of the present embodiments. Also disclosed herein is a cell comprising either the nucleic acid, or the vector comprising the nucleic acid encoding the ABM of any one of the present embodiments.

Also disclosed herein is method of administering the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, the method comprising subgingivally administering the ABM to a subject. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the ABM is administered at least two times. In some embodiments, the ABM is administered 10-16 days apart.

Also disclosed herein is a method of treating or preventing a vascular disease or symptoms thereof, the method comprising identifying a subject in need of treating or preventing a vascular disease or symptoms thereof; and administering to the subject a therapeutically effective amount of the ABM of any of the present embodiments, an ABM comprising a VH sequence with at least 80% identity to SEQ ID NO: 29, 30, 31, or, 32, and further comprising a VL sequence with at least 80% identity to SEQ ID NO: 33, 34, 35, or 36, or an ABM having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the vascular disease or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the vascular disease comprises cardiovascular disease, atherosclerosis, coronary artery disease, myocardial infarction, stroke, and myocardial hypertrophy. In some embodiments, the method further comprises administering to the subject at least one other therapeutic agent for treating or preventing the vascular disease, or symptoms thereof. In some embodiments, the other therapeutic agent comprises a serum lipid lowering agent. In some embodiments, the other therapeutic agent is a statin.

Also disclosed herein is a method of treating or preventing a vascular disease or symptoms thereof, the method comprising: administering to a subject in need of treating or preventing a vascular disease, or symptoms thereof, a therapeutically effective amount of at least one therapeutic agent for treating or preventing the vascular disease, or symptoms thereof; and administering an effective amount of the ABM of any one of the present embodiments, an ABM comprising a VH sequence with at least 80% identity to SEQ ID NO: 29, 30, 31, or, 32, and further comprising a VL sequence with at least 80% identity to SEQ ID NO: 33, 34, 35, or 36, or an ABM having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, to thereby enhance the therapeutic effect of the at least one therapeutic agent. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the other therapeutic agent comprises a serum lipid lowering agent. In some embodiments, the other therapeutic agent is a statin.

Also disclosed herein is a method of treating or preventing a systemic disease or symptoms thereof, the method comprising: identifying a subject in need of treating or preventing a systemic disease or symptoms thereof, wherein the systemic disease is one or more of type II diabetes, insulin resistance and metabolic syndrome; and administering to the subject a therapeutically effective amount of the ABM of any of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the systemic disease or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing rheumatoid arthritis or symptoms thereof, the method comprising: identifying a subject in need of treating rheumatoid arthritis or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the rheumatoid arthritis or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing cancer or symptoms thereof, the method comprising: identifying a subject in need of treating cancer or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the cancer or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS.

60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the cancer is oral, gastrointestinal, lung or pancreatic cancer. In some embodiments, the method further comprises administering to the subject at least one other therapeutic agent for treating or preventing the cancer, or symptoms thereof. In some embodiments, the other therapeutic agent comprises a small molecule drug or immunotherapeutic agent.

Also disclosed herein is a method of treating or preventing cancer or symptoms thereof, the method comprising: administering to a subject in need of treating or preventing cancer, or symptoms thereof, a therapeutically effective amount of at least one therapeutic agent for treating or preventing the cancer, or symptoms thereof; and administering an effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, to thereby enhance the therapeutic effect of the at least one therapeutic agent. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the at least one therapeutic agent comprises a small molecule drug or immunotherapeutic agent. In some embodiments, the cancer is oral, gastrointestinal, lung or pancreatic cancer.

Also disclosed herein is a method of treating or preventing a gut microbiome-related disorder or symptoms thereof, the method comprising: identifying a subject in need of treating a gut microbiome-related disorder or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the gut microbiome-related disorder or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the gut microbiome-related disorder comprises inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity.

Also disclosed herein is a method of treating or preventing a cognitive disorder or symptoms thereof, the method comprising: identifying a subject in need of treating a cognitive disorder or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the cognitive disorder or symptoms thereof. In some embodiments, the cognitive disorder is Alzheimer's disease. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the cognitive disorder is early, middle or late dementia.

Also disclosed herein is a method of treating or preventing an age-related or longevity-related disorder, or symptoms thereof, the method comprising: identifying a subject in need of treating an age-related or longevity-related disorder; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the age-related or longevity-related disorder, or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing a post event myocardial hypertrophy or symptoms thereof, comprising: identifying a subject in need of treating or preventing a post event myocardial hypertrophy or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the post event myocardial hypertrophy or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating a wound, comprising: identifying a subject in need of treating a wound; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, whereby closure of the wound is enhanced, thereby treating the wound. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is method of treating or preventing an age-related macular degeneration (AMD) or symptoms thereof, comprising: identifying a subject in need of treating or preventing AMD or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the AMD or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing an aneurysm or symptoms thereof, comprising: identifying a subject in need of treating or preventing an aneurysm or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the aneurysm or symptoms thereof. In some embodiments, the aneurysm is a cerebral or abdominal aneurysm. In some embodiments, the reference to position "222" denotes a hinge residue (but numbered to include amino acids outside of the hinge region). In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. Another way of identifying the same position is shown in FIGS. 66 and 67, as the "A" point mutation (bolded and underlined) within the hinge region (position 7). All three of these descriptors are intended to denote the same amino acid position that is to be altered to avoid degradation of the chimeric antibody construct. Thus, outside of the claims, any one descriptor is also a shorthand for describing the other two options for identifying the particular amino acid that is not to be a "K" and is instead, preferably, an "A".

Also disclosed herein method of treating or preventing a glioma or symptoms thereof, comprising: identifying a subject in need of treating or preventing a glioma or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the glioma or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing a large vessel stroke C-IMT or symptoms thereof, comprising: identifying a subject in need of treating or preventing a large vessel stroke C-IMT or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36 or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the large vessel stroke C-IMT or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing microvascular defects and associated dementias, or symptoms thereof, comprising: identifying a subject in need of treating or preventing microvascular defects and associated dementias, or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the microvascular defects and associated dementias, or symptoms thereof. In some embodiments, the microvascular defects and associated dementias comprises microvascular defects Parkinson's. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing a peri-implantitis or symptoms thereof, comprising: identifying a subject in need of treating or preventing a peri-implantitis or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the peri-implantitis or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing a renal disease or symptoms thereof, comprising: identifying a subject in need of treating or preventing a renal disease or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the renal disease or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing a regenerative and stem cell dysfunction, or symptoms thereof, comprising: identifying a subject in need of treating or preventing a regenerative and stem cell dysfunction, or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36 or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the regenerative and stem cell dysfunction, or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a method of treating or preventing a condition, disorder or disease associated with a *P. gingivalis* infection, or symptoms thereof, comprising: identifying a subject in need of treating or preventing a condition, disorder or disease associated with a *P. gingivalis* infection, or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the condition, disorder or disease associated with a *P. gingivalis* infection, or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the method further comprises administering the therapeutically effective amount of the ABM to treat the condition, disorder or disease associated with a *P. gingivalis* infection, or symptoms thereof. In some embodiments, the method comprises administering the therapeutically effective amount of the ABM to prevent the condition, disorder or disease associated with a *P. gingivalis* infection, or symptoms thereof. In some embodiments, the condition, disorder or disease is associated with a local infection of *P. gingivalis*. In some embodiments, the condition, disorder or disease is associated with a systemic infection of *P. gingivalis*. In some embodiments, the condition, disorder or disease is associated with an oral infection of *P. gingivalis*. In some embodiments, the condition, disorder or disease is one or more of: vascular disease (e.g., cardiovascular disease, atherosclerosis, coronary artery disease, myocardial infarction, stroke, and myocardial hypertrophy); systemic disease (e.g., type II diabetes, insulin resistance and metabolic syndrome); rheumatoid arthritis; cancer (e.g., oral, gastrointestinal, or pancreatic cancer); renal disease, gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity); post event myocardial hypertrophy, wound closure, AMD (age-related macular degeneration), cerebral and abdominal aneurysms, glioma, large vessel stroke C-IMT, microvascular defects and associated dementias (e.g., Parkinson's), Peri-Implantitis and/or periodontal disease and/or associated bone loss, cognitive disorders (e.g., early, middle, and/or late dementia; Alzheimer's disease); regenerative and stem cell dysfunction; and longevity or age-related disorder. In some embodiments, the condition, disorder, or disease is present in multiple systems, organs, or tissues. In some embodiments, the treating or preventing the condition, disorder or disease associated with a *P. gingivalis* infection results in the decrease of CRISPR-Cas gene expression at one or more site of infection. In some embodiments, the treating or preventing the condition, disorder or disease associated with a *P. gingivalis* infection results in a decrease of local inflammation. In some embodiments, the decrease of local inflammation is reduced activity or activation of inflammasomes, reduced cytokine levels, and/or lowered host cell death. In some embodiments, the treating or preventing the condition, disorder or disease associated with a *P. gingivalis* infection results in a decrease of systemic inflammation. In some embodiments, the decrease of systemic inflammation is reduced proinflammatory mediators, and/or reduced chronic distant site inflammatory atherosclerosis.

Also disclosed herein is a method of targeting a *P. gingivalis*, comprising: identifying a subject with a *P. gingivalis* infection, or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36 or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby targeting the *P. gingivalis*, or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the *P. gingivalis* infection is in the mouth. In some embodiments, the *P. gingivalis* infection is in the gums. In some embodiments, the *P. gingivalis* infection is in the brain. In some embodiments, the *P. gingivalis* infection is across the blood brain barrier. In some embodiments, the targeting of the *P. gingivalis* infection further comprises administration of a small molecule, antibiotic, or drug affective against *P. gingivalis*. In some embodiments, the small molecule, antibiotic, or drug targets *P. gingivalis* virulence factors, increases the production of proteases targeting *P. gingivalis*, reduces *P. gingivalis* oxygen and/or iron uptake, alters protein production in *P. gingivalis*, and/or enhances cell death for *P. gingivalis*.

Also disclosed herein is a method of targeting a bacterial infection in a subject, comprising: identifying the subject with a bacterial infection, or symptoms thereof; and administering to the subject a therapeutically effective amount of the ABM of any one the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby targeting the bacterial infection, or symptoms thereof. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the bacterial infection is in the mouth. In some embodiments, the bacterial infection is in the gums. In some embodiments, the bacterial infection is in the brain. In some embodiments, the bacterial infection is in the gut. In some embodiments, the bacterial infection is across the blood brain barrier. In some embodiments, the bacterial infection is systemic, and/or in multiple tissues. In some embodiments, the bacterial infection comprises a *P. gingivalis* infection. In some embodiments, the bacterial infection comprises a *H. pylori* infection. In some embodiments, the bacterial infection comprises more than one bacterial infections. In some embodiments, the targeting of the bacterial infection further comprises administration of a small molecule, antibiotic, or drug. In some embodiments, the small molecule, antibiotic, or drug targets at least one virulence factors, increases the production of proteases, reduces bacterial nutrient uptake, alters bacterial protein production, and/or enhances bacterial cell death. In some embodiments, the administering comprises administering the ABM intravenously, subgingivally, intradermally, subcutaneously, intrathecally, or by nebulization.

Also disclosed herein is a use of an ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, for treatment of a disorder associated with, caused by or complicated by *P. gingivalis*. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. In some embodiments, the disorder associated with, caused by or complicated by *P. gingivalis* is one or more of: vascular disease (e.g., cardiovascular disease, atherosclerosis, coronary artery disease, myocardial infarction, stroke, and myocardial hypertrophy); systemic disease (e.g., type II diabetes, insulin resistance and metabolic syndrome); rheumatoid arthritis; cancer (e.g., oral, gastrointestinal, or pancreatic cancer); renal disease, gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity); post event myocardial hypertrophy, wound closure, AMD (age-related macular degeneration), cerebral and abdominal aneurysms, glioma, large vessel stroke C-IMT, microvascular defects and associated dementias (e.g., Parkinson's), Peri-Implantitis and/or periodontal disease and/or associated bone loss, cognitive disorders (e.g., early, middle, and/or late dementia; Alzheimer's disease); neuroinflammatory diseases; regenerative and stem cell dysfunction; and longevity or age-related disorder.

In some embodiments, wherein the ABM binds to YTYTVYRDGTKIK. In some embodiments, the ABM comprises a point mutation for cleavage resistance from Pg proteases. In some embodiments, the ABM comprises an amino acid sequence at least 80%, 90%, 95, 99%, or 100% identical to SEQ ID NO: 84. In some embodiments, the HVR comprises an amino acid sequence at least 80% identical to one of SEQ ID NOS: 85-86. In some embodiments, the LVR comprises an amino acid sequence at least 80% identical to one of SEQ ID NOS: 87-90. In some embodiments, the ABM comprises an HVR amino acid sequence corresponding to a nucleic acid sequence that is at least 80% identical to one of SEQ ID NOS: 91-92. In some embodiments, the ABM comprises an LVR amino acid sequence corresponding to a nucleic acid sequence that is at least 80% identical to one of SEQ ID NOS: 93-97.

Also disclosed herein is a nucleic acid that is at least 80% identical to one of SEQ ID NOS: 98-101, wherein the nucleic acid confers the expression sequence of an ABM that has a mutation at position 222. In some embodiments, the mutation at position 222 is an alanine. In some embodiments, the reference to position "222" denotes a position in a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45, are the same amino acid position in the hinge region of an ABM, and the dual description is provided herein to clarify the particular position in the ABM hinge that has been or is to be changed.

In some embodiments, the ABM binds to a gingipain and/or a hemagglutinin with a KD that is less than about 2E-9 M, less than about 1E-9 M, less than about 9E-10 M, less than about 8E-10 M, less than about 6E-10 M, less than about 4E-10 M, less than about 2E-10 M, less than about 1E-10 M, less than about 9E-11 M, and/or less than about 7E-11 M. In some embodiments, the ABM further comprises at least one, two, three or all four of: (i) an alanine at position 222; (ii) an amino acid sequence that is at least 80% identical to SEQ ID NO: 84; (iii) an HVR sequence comprising an amino acid sequence at least 80% identical to one of SEQ ID NOS: 85-86; and/or (iv) an LVR sequence comprising an amino acid sequence at least 80% identical to one of SEQ ID NOS: 87-90. In some embodiments, the ABM comprises SEQ ID NO: 1 and SEQ ID NO: 2 as the ABM or instead of the noted ABM in any one of the preceding claims. In some embodiments, the ABM comprises a heavy chain sequence of SEQ ID NO: 30, a light chain sequence of SEQ ID NO: 33, except that the ABM comprises an alanine at position 222. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. In some embodiments, the ABM is H5 K22A.

Also disclosed herein is an ABM that is humanized or human, wherein the ABM comprises an alanine at position 222. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. Also disclosed herein is a method of treating a disorder driven by *P. gingivalis* comprising: providing an antibody that binds to a *P. gingivalis* associated peptide, to a subject, wherein the antibody is known to function to stop a *P. gingivalis* infection, wherein the antibody is a humanized or human antibody, and wherein position 222 of the antibody has been changed to an alanine.

Also disclosed herein is a method of reducing cleavage of an ABM and/or humanized antibody when administered orally to a subject, the method comprising, administering an antibody that has a non-lysine amino acid at position 222 of the antibody, wherein the antibody binds to a *P. gingivalis* associated peptide. In some embodiments, the ABM and/or humanized antibody is anyone of the ABM or humanized antibodies in any one of the preceding claims. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a humanized variant of KB001, wherein 10 μg of the humanized variant of KB001 is not detectably degraded by incubation for 2 h at 37° C. with a gingipain mix, wherein the gingipain mix comprises: Kgp activity of 15.96 mOD/min/μl and Rgp activity of 23.71 mOD/min/μl, at a ratio of Ab:GP (w/w) ratio: 100:1 and/or 500:1 in assay buffer supplemented with 10 mM cysteine. In some embodiments, after incubation: tosyl-L-lysyl-chloromethane hydrochloride (TLCK) is added to a final concentration of 10 mM followed by addition of non-reducing sample buffer, the samples are boiled for 5 min, then the samples are chilled on ice and Dithiothreitol (DTT) is added to the final concentration of 20 mM, the samples are boiled again for 5 min and separated using NuPAGE™ 4 to 12%, Bis-Tris Mini Protein Gels, wherein no separate cleavage bands are identifiable in the variant when the sample is processed as above. In some embodiments, the variant comprises a point mutation at position 222, which removes a lysine at position 222. In some embodiments, the humanized variant comprises SEQ ID NO: 203. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

In some embodiments of any of the humanized variants disclosed herein, the humanized variant comprises at least one of SEQ ID NO: 203, 204, 205, 206, 207, and/or 208. In some embodiments, the humanized variant comprises one of SEQ ID NO: 205, 206, 207, or 208. In some embodiments, the humanized variant comprises one of SEQ ID NO: 203 or 204.

In some embodiments, a method of reducing a biofilm or the development of a biofilm in a subject is provided. The method comprises identifying a subject at risk of developing a biofilm; and administering to the subject a therapeutically effective amount of the ABM: a) of any one of the ABMs provided herein, b) an ABM comprising a VH sequence with at least 80% identity to SEQ ID NO: 29, 30, 31, or 32, and further comprising a VL sequence with at least 80% identity to SEQ ID NO: 33, 34, 35, or 36, or c) an ABM having a LCDR1, a LCDR2, and a LCDR3 within SEQ ID NO: 2 and a HCDR1, a HCDR2, and a HCDR3 within SEQ ID NO: 1. Wherein the ABM further comprises an alanine in its hinge region at a position corresponding to position 105 as numbered in SEQ ID NO: 172 in FIG. 45. This can thereby reduce or prevent the biofilm formation in the subject.

Also disclosed herein is a human or humanized antigen binding molecule (ABM) that binds to *Porphyromonas gingivalis*, wherein the ABM comprises: a heavy chain Fab comprising the leader sequence of SEQ ID NO: 277 and a VH/CH1 region of SEQ ID NO: 270; and a light chain Fab comprising the leader sequence of SEQ ID NO: 277 and a VL/CL region of SEQ ID NO: 253. In some embodiments, the ABM further comprises an Fc region of SEQ ID NO: 274. In some embodiments, the ABM or antibody lacks the leader sequence.

Also disclosed herein is a human or humanized antigen binding molecule (ABM) that binds to *Porphyromonas gingivalis*, wherein the ABM comprises: a VH sequence of SEQ ID NO: 239, and a VL sequence of SEQ ID NO: 229.

Also disclosed herein is a human or humanized antigen binding molecule (ABM) that binds to *Porphyromonas gingivalis*, wherein the ABM comprises: a VH/CH1 region of SEQ ID NO: 270; and a VH/VL region of SEQ ID NO: 253. In some embodiments, the ABM further comprises: an Fc region of SEQ ID NO: 274.

Also disclosed herein is a human or humanized antigen binding molecule (ABM) that binds to *Porphyromonas gingivalis*, wherein the ABM comprises a VH sequence of SEQ ID NO: 263, and a VL sequence of SEQ ID NO: 253.

Also disclosed herein is a cell expressing an ABM that binds to *Porphyromonas gingivalis*, wherein the ABM comprises a VH/CH1 region of SEQ ID NO: 270 and a VL/CL region of SEQ ID NO: 253.

BRIEF DESCRIPTION OF THE DRAWINGS

FIGS. 1A and 1B show the heavy and light chain amino acid sequences, respectively, of KB001 (which includes HC SEQ ID NO: 1 and LC SEQ ID NO: 2). The construct is a mouse construct, which can be used in any of the method embodiments provided herein.

FIG. 2A shows the amino acid sequence of a full length RgpA exotoxin from *Porphyromonas gingivalis*, strain W50.

FIG. 2B shows the amino acid sequence of a full length RgpA exotoxin from *Porphyromonas gingivalis*, strain HG66.

FIG. 3A shows the amino acid sequence of a full length RgpB exotoxin from *P. gingivalis*, strain W50.

FIG. 3B shows the amino acid sequence of a full length RgpB exotoxin from *P. gingivalis*, strain W83.

FIG. 4A shows the amino acid sequence of a full length Kgp exotoxin from *Porphyromonas gingivalis*, strain W83.

FIG. 4B shows the amino acid sequence of a full length Kgp exotoxin from *Porphyromonas gingivalis*, strain ATCC 33277.

FIG. 5A shows the amino acid sequence of a full length HagA from *Porphyromonas gingivalis*, strain W83.

FIG. 5B shows the amino acid sequence of a full length HagA from *Porphyromonas gingivalis*, strain 381.

FIG. 10 is a phylogram of *P. gingivalis* strains, grouped by the presence or absence of accessory genes. The arrows mark the ten strains selected to represent the diversity of P.g. strains.

FIG. 16 is a gel image showing the sensitivity of a PCR-based liquid hybridization assay for detection of *P. gingivalis*.

FIG. 17 is a graph showing dose response titration binding of KB001 monoclonal antibodies from various hybridoma clones to isolated *P. gingivalis* gingipains.

FIG. 18 is a graph showing selection of various KB001 cloned murine monoclonal antibody cell hybridomas selected for the master cell bank.

FIGS. 22A, 22B, 22C, 22D, 22E, 22F, 22G, 22H, 22I, and 22J are mapped protein sequences from the *P. gingivalis* the repeat epitope in hemagglutinin/adhesion and HagA gingipains domain (RE-HagA) protein complex specific to binding of KB-001 and the preliminary linear amino acid sequence of the KB-001 antibody binding epitope, according to some embodiments of the present disclosure, which can be equated to the AP as provided herein.

FIGS. 23A and 23B show expression of human chimeric KB001 monoclonal antibodies, according to some embodiments of the present disclosure.

FIG. 24 is a collection of ELISA graphs showing identification of and down selection of human chimeric KB001 monoclonal antibodies that compete with KB001 and bind gingipains, according to some embodiments of the present disclosure.

FIG. 26A shows non-limiting examples of the amino acid sequences of a CDR grafted ABM variable regions, according to some embodiments of the present disclosure.

FIG. 26B shows non-limiting examples of the amino acid sequences of KB001 variable regions.

FIG. 26C shows an alignment of KB001 heavy chain with structural template 1DVF.

FIG. 26D shows non-limiting examples of the amino acid sequences of KB001 variable regions.

FIG. 26E shows an alignment of the VH and VL amino acid sequences of KB001 with the grafted VH and VL sequences, respectively.

FIGS. 27A, 27B, 27C, and 27D show non-limiting examples of amino acid sequences of heavy chain variable regions of antigen binding molecules, according to some embodiments of the present disclosure.

FIGS. 28A, 28B, 28C, and 28D show non-limiting examples of amino acid sequences of light chain variable regions of antigen binding molecules, according to some embodiments of the present disclosure.

FIG. 29 shows non-limiting examples of amino acid sequences of human heavy chain and light chain constant regions, according to some embodiments of the present disclosure.

FIG. 30 shows non-limiting examples of amino acid sequences of heavy and light chain variable regions of antigen binding molecules, according to some embodiments of the present disclosure.

FIG. 31 shows the amino acid sequence of KB001, according to some embodiments of the present disclosure.

FIG. 32 shows an alignment of some antigen binding molecule heavy chain variable region sequences, according to some embodiments of the present disclosure.

FIGS. 33A, 33B, 33C, and 33D are non-limiting examples of grafted nucleic acid sequences encoding heavy chain variable regions of KB001 antigen binding molecules, according to some embodiments of the present disclosure.

FIGS. 34A, 34B, 34C, and 34D are non-limiting examples of grafted nucleic acid sequences encoding light chain variable regions of KB001 antigen binding molecules, according to some embodiments of the present disclosure.

FIGS. 35A and 35B are non-limiting examples of grafted nucleic acid sequences encoding heavy and light chain variable regions, respectively, of an KB001 antigen binding molecule, according to some embodiments of the present disclosure.

FIGS. 36A and 36B are non-limiting examples of grafted nucleic acid sequences encoding human heavy chain and light chain constant regions of KB001, according to some embodiments of the present disclosure.

FIGS. 37A, 37B, 37C, 37D show nucleotide sequences encoding heavy and light chains of KB001, and their translated amino acid sequences, according to some embodiments of the present disclosure.

FIG. 40A shows an amino acid sequence of hemagglutinin protein HagA from *Porphyromonas gingivalis* strain ATCC 33277. Proteolytic processing sites are marked with bold font.

FIG. 40B shows amino acid sequences of the repeated domains of HagA, RgpA, and Kgp, with sequences encompassing some of the putative epitopes of KB001 underlined, according to some embodiments of the present disclosure. The Hemoglobin Receptor (HbR) domain is boxed in a rectangle. Proteolytic processing sites are marked with bold font. For "Kgp_W83", HA1 is in italic, and proteolytic processing of C-terminal HA part of Kgp W83 is not well defined. For "RgpA_W83", sequence in italics before the boxed sequence shows HA1, sequence in italics at C-terminus shows HA4, and sequence between the boxed sequence and HA4 shows HA3.

FIG. 40C shows a multiple sequence alignment of HA domains of HagA from *Porphyromonas gingivalis* strains W83 and ATCC 33277. Putative epitope of KB001, according to some embodiments, is underlined.

FIG. 40D shows a multiple sequence alignment of RgpA, Kgp and HagA sequences.

FIG. 40E shows a multiple sequence alignment of RgpA, Kgp and HagA sequences.

FIG. 40F shows a multiple sequence alignment of putative sequence motifs in HagA (from W83 and ATCC 33277 strains) and RgpA and Kgp (from W83) encompassing the epitope recognized by KB001, according to some embodiments of the present disclosure.

FIG. 41 displays amino acid and DNA sequences of the GST-TEV-gingipain-His fusion protein used to produce recombinant gingipain fusion proteins in *E. coli*. Linker and TEV protease sequence is bold and underlined. Putative KB001 epitope is shown in bold. The linker between the fusion partners and a TEV protease site is shown bold and underlined. Immediately after this sequence starts the gingipain protein fragment which contains a single KB001 epitope. GST Fusion partner is at the beginning, followed by the linker peptide and the TEV protease site (bold and underlined), and then the gingipain fragment.

FIG. 42A is a sequence of rGP-2

FIG. 42B is a comparison between rGP-1 and rGP-2.

FIG. 43 shows the sequence for Kgp-8HSLA domain N-terminus from the W83 strain of P.g. In some embodiments, this sequence can be used for screening of binding of one or more of the antibody variants thereof provided in the present application.

FIG. 44 shows the sequence for HRgpA-6H domain N-terminus from P.g. In some embodiments, this sequence can be used for screening of binding of one or more of the antibody variants thereof provided in the present disclosure.

FIG. 45 shows the amino acid sequences of alternative heavy chain segments, alternative light chain segments, hIgG1CH, hIgG1CH K22A, and hIgkCL.

FIG. 46 shows the DNA sequences of alternative heavy chain segments, alternative light chain segments, hIgG1CH, hIgG1CH K22A, and hIgkCL.

FIG. 47 is a table of the heavy and light chain segments present in the H5, H6, H7, H8, and H14 sequences.

FIG. 52B shows the Fab VH sequence of the parental mouse (KB001) construct.

FIG. 55 shows a non-limiting example of an experimental plate layout for human sample analysis. In this layout, human plasma samples are tested at 0.1 ul/well, 0.3 ul/well, and 1 ul/well, and up to 6 plasma samples can be tested per ELISA plate with KB001 positive control, PBS only negative control, and a patient 10 standard.

FIG. 55 shows the vector sequences of SEQ ID NOS: 191-196, representing the VH2 nucleotide sequence of K222A, the VH4 nucleotide sequence with K222A, the VL1 nucleotide sequence, the VL2 nucleotide sequence, the VL3 nucleotide sequence, and the nucleotide VL4 sequence, respectively. Also shown are the native (unmutated) VH4 and VH2 nucleotide vector sequences (SEQ ID NOS: 197-198).

FIG. 56A shows the alignment of the VH segments of KB001 (top sequence) and H5 (bottom sequence) ABMs. Highlighted and in boxed are the three CDR regions.

FIG. 56B shows the alignment of the VL segments of KB001 (top sequence) and H5 (bottom sequence) ABMs. Highlighted and in boxed are the three CDR regions.

FIG. 57 shows the alignment between mouse VH, and the humanized grafted sequences VH1, VH2, VH3, and VH4.

FIG. 58 shows the alignment between mouse VL, and the humanized grafted sequences VL1, VL2, VL3, and VL4.

FIG. 59 shows the protein and corresponding nucleotide sequences of the human constant regions SEQ ID NOS: 199-202. The underlined bold section represents the segment of the nucleotide corresponding with a CDR.

FIG. 60 shows the full amino acid sequence of the translated vector U551FEL190-VH2-hIgG1CH(K222A)-pcDNA3.4 (SEQ ID NO: 203), including the VH2 sequence (SEQ ID NO: 30; in brackets), the K222A mutation (bold and highlighted), and the H-CDR1, H-CDR2, and H-CDR3 sequences (SEQ ID NOS: 3-5; underlined). It will be noted that as the K222A mutation is in reference to the "222 position," the subsequence "1 position" is the Glutamine at the start of the VH2 sequence (SEQ ID NO: 30). The "1" position is denoted by a "►" in the figure. In some embodiments, the preferred construct and/or construct for use in the methods provided herein includes any part of the sequence depicted in FIG. 60.

FIG. 61 shows the full amino acid sequence of the translated vector U551FEL190-VH4-hIgG1CH(K222A)-pcDNA3.4 (SEQ ID NO: 204), including the VH4 sequence (SEQ ID NO: 32; in brackets), the K222A mutation (bold and highlighted), and the H-CDR1, H-CDR2, and H-CDR3 sequences (SEQ ID NOS: 3-5; underlined). It will be noted that as the K222A mutation is in reference to the "222 position," the subsequence "1 position" is the Glutamine at the start of the VH4 sequence (SEQ ID NO: 32). The "1" position is denoted by a "►" in the figure. In some embodiments, the preferred construct and/or construct for use in the methods provided herein includes any part of the sequence depicted in FIG. 61.

FIG. 62 shows the full amino acid sequence of the translated vector U551FEL190-VL1-hIgkCLpc-DNA3.4 (SEQ ID NO: 205), including the VL1 sequence (SEQ ID NO: 33; in brackets), and the L-CDR1, L-CDR2, and L-CDR3 sequences (SEQ ID NOS: 6-8; underlined). The "1" position is denoted by a "►" in the figure. In some embodiments, the preferred construct and/or construct for use in the methods provided herein includes any part of the sequence depicted in FIG. 62.

FIG. 63 shows the full amino acid sequence of the translated vector U551FEL190-VL2-hIgkCLpc-DNA3.4 (SEQ ID NO: 206), including the VL2 sequence (SEQ ID NO: 34; in brackets), and the L-CDR1, L-CDR2, and L-CDR3 sequences (SEQ ID NOS: 6-8; underlined). The "1" position is denoted by a "►" in the figure. In some embodiments, the preferred construct and/or construct for use in the methods provided herein includes any part of the sequence depicted in FIG. 63.

FIG. 64 shows the full amino acid sequence of the translated vector U551FEL190-VL3-hIgkCLpc-DNA3.4 (SEQ ID NO: 207), including the VL3 sequence (SEQ ID NO: 35; in brackets), and the L-CDR1, L-CDR2, and L-CDR3 sequences (SEQ ID NOS: 6-8; underlined). The "1" position is denoted by a "▶" in the figure. In some embodiments, the preferred construct and/or construct for use in the methods provided herein includes any part of the sequence depicted in FIG. 64.

FIG. 65 shows the full amino acid sequence of the translated vector U551FEL190-VL4-hIgkCLpc-DNA3.4 (SEQ ID NO: 208), including the VL4 sequence (SEQ ID NO: 36; in brackets), and the L-CDR1, L-CDR2, and L-CDR3 sequences (SEQ ID NOS: 6-8; underlined). The "1" position is denoted by a "▶" in the figure. In some embodiments, the preferred construct and/or construct for use in the methods provided herein includes any part of the sequence depicted in FIG. 65.

FIG. 67 shows the annotated K222A mutant VH4 amino acid sequence (SEQ ID NO: 32) as part of the translated vector U551FEL190-VH4-hIgG1CH(K222A)-pcDNA3.4 (SEQ ID NO: 204). In some embodiments, the preferred construct and/or construct for use in the methods provided herein includes any part of the sequence depicted in FIG. 67.

FIG. 69 shows the annotated VL2 amino acid sequence (SEQ ID NO: 34) as part of the translated vector U551FEL190-VL2-hIgkCLpc-DNA3.4 (SEQ ID NO: 206). In some embodiments, the preferred construct and/or construct for use in the methods provided herein includes any part of the sequence depicted in FIG. 69.

FIG. 74 shows the sequences for human IgG (SEQ ID NOS: 216 and 217), human Ig kappa (SEQ ID NO: 218), and human Ig lambda (SEQ ID NO: 219).

FIG. 75 is a table of constructs H1-H16, and the VH/VL sequences that comprise those constructs.

FIG. 76 is a table of constructs H5, H7, H8, H14, H5 K222A, H7 K222A, H8 K222A, and H14 K222A, and the VH/VL sequences that comprise those constructs.

FIG. 77A is the nucleic acid (top, SEQ ID NO: 220) and amino acid (bottom, SEQ ID NO: 221) sequences for U551FEL190-VH1_hIgG1CH-pCDNA3.4.

FIG. 77B is the nucleic acid (top, SEQ ID NO: 222) and amino acid (bottom, SEQ ID NO: 223) sequences for U551FEL190-VH2_hIgG1CH-pCDNA3.4.

FIG. 77C is the nucleic acid (top, SEQ ID NO: 224) and amino acid (bottom, SEQ ID NO: 225) sequences for U551FEL190-VH3_hIgG1CH-pCDNA3.4.

FIG. 77D is the nucleic acid (top, SEQ ID NO: 226) and amino acid (bottom, SEQ ID NO: 227) sequences for U551FEL190-VH4_hIgG1CH-pCDNA3.4.

FIG. 77E is the nucleic acid (top, SEQ ID NO: 228) and amino acid (bottom, SEQ ID NO: 229) sequences for U551FEL190-VL1_hIgG1CH-pCDNA3.4.

FIG. 77F is the nucleic acid (top, SEQ ID NO: 230) and amino acid (bottom, SEQ ID NO: 231) sequences for U551FEL190-VL2_hIgG1CH-pCDNA3.4.

FIG. 77G is the nucleic acid (top, SEQ ID NO: 232) and amino acid (bottom, SEQ ID NO: 233) sequences for U551FEL190-VL3_hIgG1CH-pCDNA3.4.

FIG. 77H is the nucleic acid (top, SEQ ID NO: 234) and amino acid (bottom, SEQ ID NO: 235) sequences for U551FEL190-VL4_hIgG1CH-pCDNA3.4.

FIG. 77I is the nucleic acid (top, SEQ ID NO: 236) and amino acid (bottom, SEQ ID NO: 237) sequences for the K222A mutant construct U551FEL190-VH1_hIgG1CH (K222A)-pCDNA3.4. The bold/underlined residues mark the K222A substitution.

FIG. 77J is the nucleic acid (top, SEQ ID NO: 238) and amino acid (bottom, SEQ ID NO: 239) sequences for the K222A mutant construct U551FEL190-VH2_hIgG1CH (K222A)-pCDNA3.4. The bold/underlined residues mark the K222A substitution.

FIG. 77K is the nucleic acid (top, SEQ ID NO: 240) and amino acid (bottom, SEQ ID NO: 241) sequences for the K222A mutant construct U551FEL190-VH3_hIgG1CH (K222A)-pCDNA3.4. The bold/underlined residues mark the K222A substitution.

FIG. 77L is the nucleic acid (top, SEQ ID NO: 242) and amino acid (bottom, SEQ ID NO: 243) sequences for the K222A mutant construct U551FEL190-VH4_hIgG1CH (K222A)-pCDNA3.4. The bold/underlined residues mark the K222A substitution.

FIG. 78A is the nucleic acid (top, SEQ ID NO: 244) and amino acid (bottom, SEQ ID NO: 245) sequences for U551FEL190-VH1_hIgG1CH-pCDNA3.4, lacking the leader domain sequence.

FIG. 78B is the nucleic acid (top, SEQ ID NO: 246) and amino acid (bottom, SEQ ID NO: 247) sequences for U551FEL190-VH2_hIgG1CH-pCDNA3.4, lacking the leader domain sequence.

FIG. 78C is the nucleic acid (top, SEQ ID NO: 248) and amino acid (bottom, SEQ ID NO: 249) sequences for U551FEL190-VH3_hIgG1CH-pCDNA3.4, lacking the leader domain sequence.

FIG. 78D is the nucleic acid (top, SEQ ID NO: 250) and amino acid (bottom, SEQ ID NO: 251) sequences for U551FEL190-VH4_hIgG1CH-pCDNA3.4, lacking the leader domain sequence.

FIG. 78E is the nucleic acid (top, SEQ ID NO: 252) and amino acid (bottom, SEQ ID NO: 253) sequences for U551FEL190-VL1_hIgG1CH-pCDNA3.4, lacking the leader domain sequence.

FIG. 78F is the nucleic acid (top, SEQ ID NO: 254) and amino acid (bottom, SEQ ID NO: 255) sequences for U551FEL190-VL2_hIgG1CH-pCDNA3.4, lacking the leader domain sequence.

FIG. 78G is the nucleic acid (top, SEQ ID NO: 256) and amino acid (bottom, SEQ ID NO: 257) sequences for U551FEL190-VL3_hIgG1CH-pCDNA3.4, lacking the leader domain sequence.

FIG. 78H is the nucleic acid (top, SEQ ID NO: 258) and amino acid (bottom, SEQ ID NO: 259) sequences for U551FEL190-VL4_hIgG1CH-pCDNA3.4, lacking the leader domain sequence.

FIG. 78I is the nucleic acid (top, SEQ ID NO: 260) and amino acid (bottom, SEQ ID NO: 261) sequences for the K222A mutant construct U551FEL190-VH1_hIgG1CH (K222A)-pCDNA3.4, lacking the leader domain sequence. The bold/underlined residues mark the K222A substitution.

FIG. 78J is the nucleic acid (top, SEQ ID NO: 262) and amino acid (bottom, SEQ ID NO: 263) sequences for the K222A mutant construct U551FEL190-VH2_hIgG1CH (K222A)-pCDNA3.4, lacking the leader domain sequence. The bold/underlined residues mark the K222A substitution.

FIG. 78K is the nucleic acid (top, SEQ ID NO: 264) and amino acid (bottom, SEQ ID NO: 265) sequences for the K222A mutant construct U551FEL190-VH3_hIgG1CH (K222A)-pCDNA3.4, lacking the leader domain sequence. The bold/underlined residues mark the K222A substitution.

FIG. 78L is the nucleic acid (top, SEQ ID NO: 266) and amino acid (bottom, SEQ ID NO: 267) sequences for the K222A mutant construct U551FEL190-VH4_hIgG1CH (K222A)-pCDNA3.4, lacking the leader domain sequence. The bold/underlined residues mark the K222A substitution.

FIG. 79 shows the VH, CH1, heavy chain Fab, Hinge, CH2, CH3, and Fc, leader sequence, and leader sequence+ VH regions of the H5 K222A protein construct (SEQ ID NOS: 268-274, 277, and 279). The K222A substitution is marked in bold in the hinge region (SEQ ID NO: 271).

FIG. 80 shows the VL, CL, light chain Fab, leader sequence, and leader sequence+VL regions of the K5 K222A protein (SEQ ID NOS: 253 and 275-278).

DETAILED DESCRIPTION

Provided herein are antigen binding molecules (ABMs), e.g., murine, human-chimeric, human or humanized ABMs, that bind to *Porphyromonas gingivalis*. The ABMs, e.g., antibodies, of the present disclosure can specifically bind to an epitope associated with *P. gingivalis*, including certain cell-surface epitopes. The ABMs include one or more mutations that reduce the likelihood that the ABM will be cleaved by enzymatic proteins when used in vivo; preferably through oral administration to a patient. In some embodiments, the ABMs are antibodies that are humanized or are human chimeric antibodies.

The proteinases that cleave the ABMs of the present disclosure are encoded by three genes: rgpA, rgpB and kgp. Arg-specific proteolytic activity is encoded by rgpA/B and the Lys-specific activity by kgp. RgpA and Kgp are polyproteins comprising proteinases with C-terminal adhesin domains that are proteolytically processed. At the cell surface pro-gingipains fold into partially active, single-chain zymogens and undergo autocatalytic, intermolecular processing. Two sequential cleavages within the profragment domain enhance zymogen activity and in the case of RgpA and Kgp are followed by excision of the individual HA domains. These domains are further truncated at the C-terminus by concerted action of Kgp and carboxypeptidase and form a non-covalent multidomain, multifunctional complex anchored into the outer membrane by the glycated, C-terminal HA domain.

Figure 66:
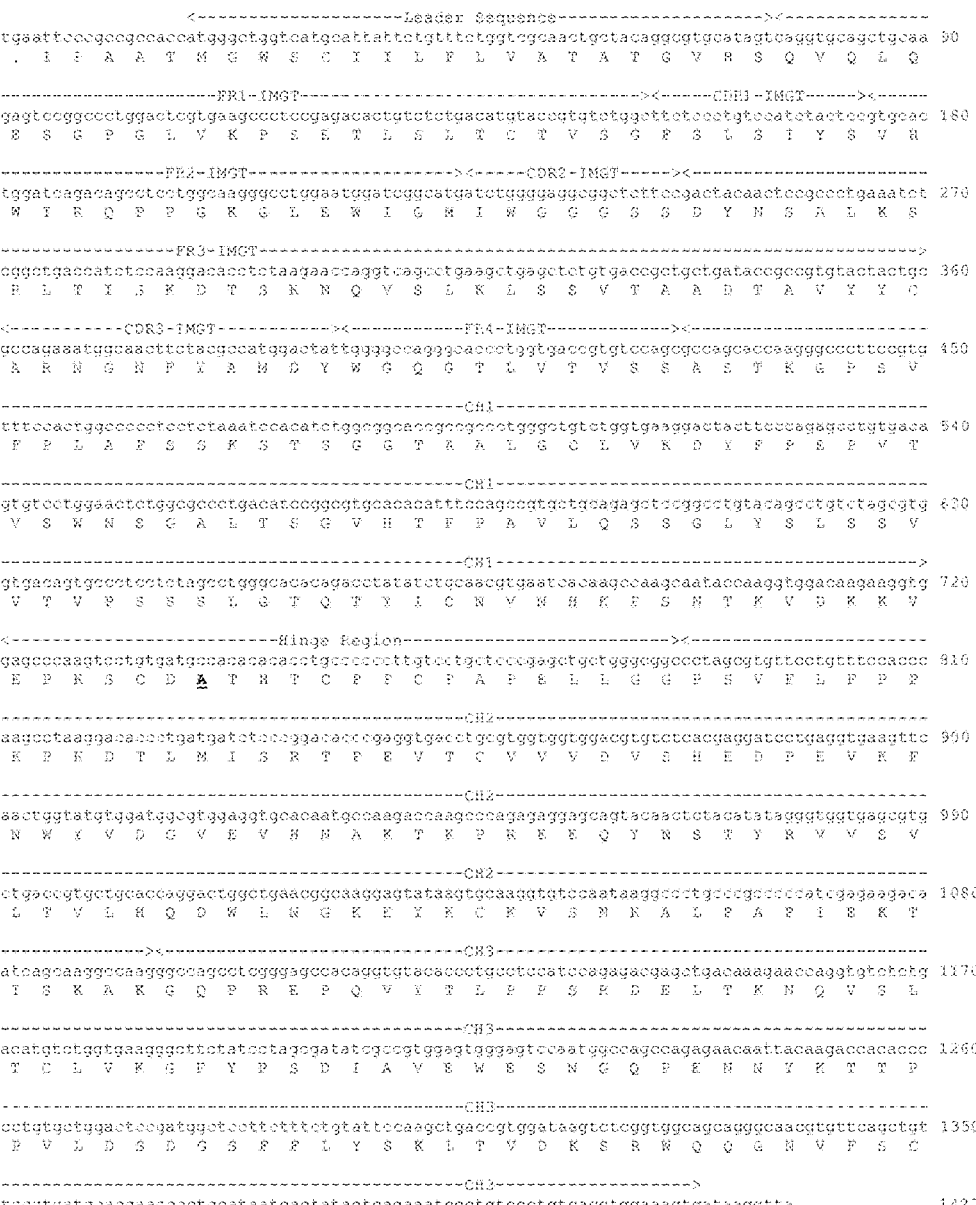
FIG. 66 shows the annotated K222A mutant VH2 amino acid sequence (SEQ ID NO: 30) as part of the translated vector U551FEL190-VH2-hIgG1CH(K222A)-pcDNA3.4 (SEQ ID NO: 203). In some embodiments, the preferred construct and/or construct for use in the methods provided herein includes any part of the sequence depicted in FIG. 66.
Figure 68:
FIG. 68 shows the annotated VL1 amino acid sequence (SEQ ID NO: 33) as part of the translated vector U551FEL190-VL1-hIgkCLpc-DNA3.4 (SEQ ID NO: 205). In some embodiments, the preferred construct and/or construct for use in the methods provided herein includes any part of the sequence depicted in FIG. 68.
Figure 70:
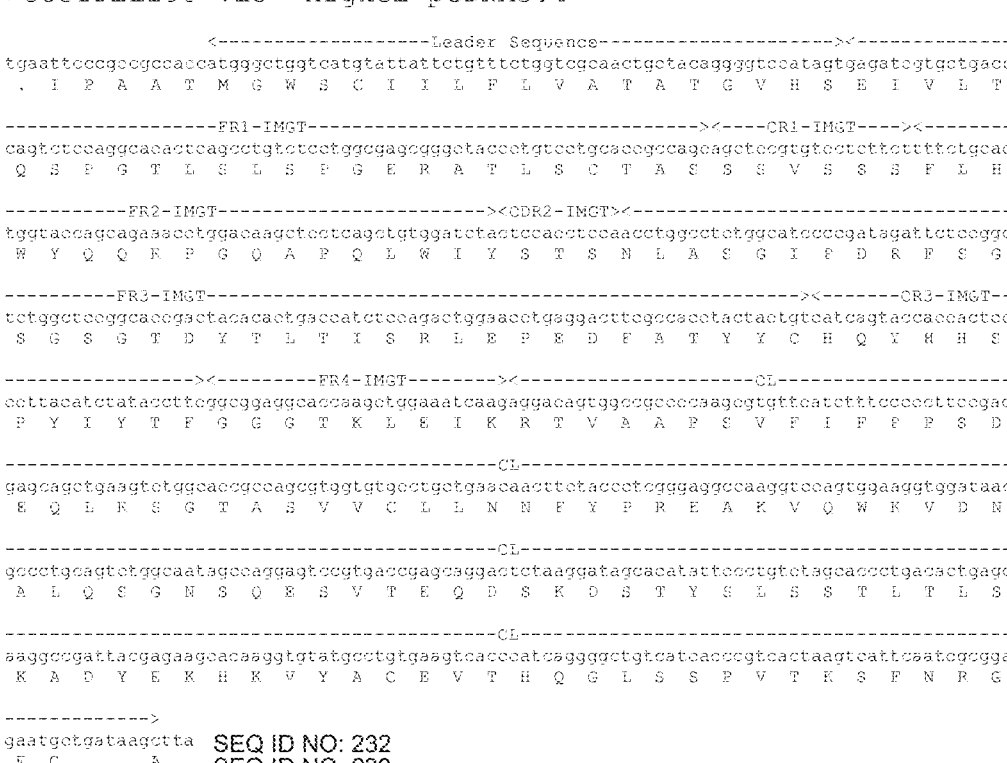
FIG. 70 shows the annotated VL3 amino acid sequence (SEQ ID NO: 35) as part of the translated vector U551FEL190-VL3-hIgkCLpc-DNA3.4 (SEQ ID NO: 207). In some embodiments, the preferred construct and/or construct for use in the methods provided herein includes any part of the sequence depicted in FIG. 70.
Figure 71:
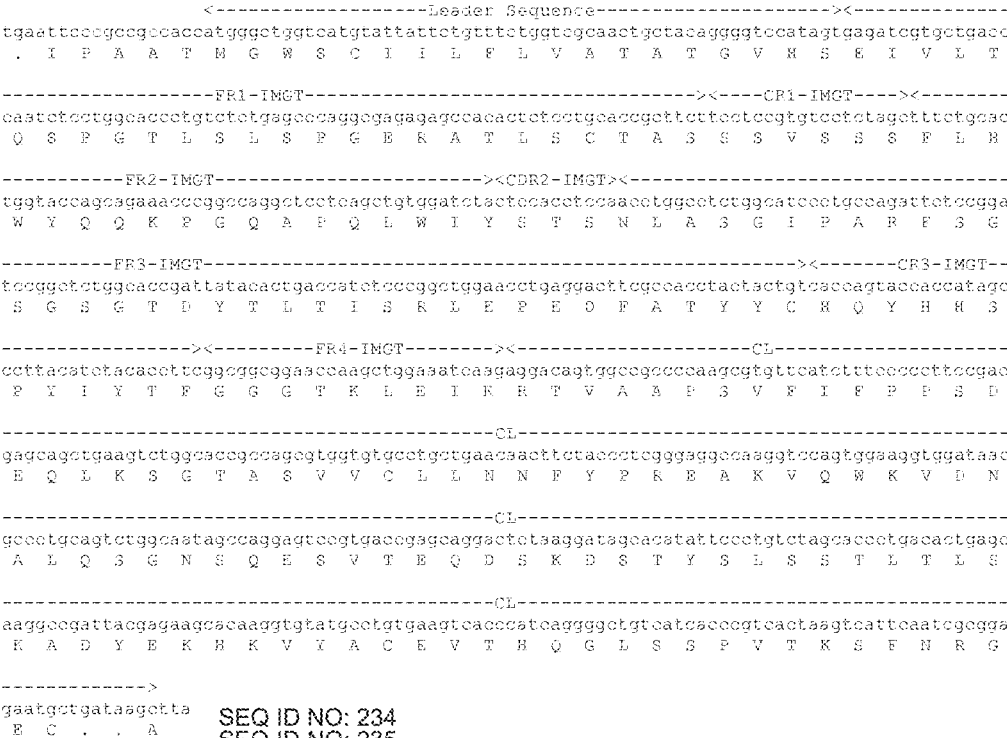
FIG. 71 shows the annotated VL4 amino acid sequence (SEQ ID NO: 36) as part of the translated vector U551FEL190-VL4-hIgkCLpc-DNA3.4 (SEQ ID NO: 208). In some embodiments, the preferred construct and/or construct for use in the methods provided herein includes any part of the sequence depicted in FIG. 71.

Disclosed herein is an ABM with a point mutation at the 222 position. In some embodiments, the 222 position is in the hinge region of the ABM. In some embodiments, the 222 position is downstream of the VH sequence, wherein the first amino acid of the VH sequence is considered to be the "1" position (see FIGS. 60-61, SEQ ID NOS: 30 and 32, and SEQ ID NOS: 203-208). In some embodiments, the 222 point mutation prevents at least 95, 96, 97, 98, 99, and/or 100% of the cleavage of the antibody. In some embodiments, this is as observed on a SDS PAGE protein gel. In some embodiments, this is as determined on a densitometer scan. In some embodiments, this is in vivo. In some embodiments, this is under the parameters in any one or more of the provided examples regarding cleavage (and the lack of cleavage) of the 222 variant. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. Another way of identifying the same position is shown in FIGS. 66 and 67, as the "A" point mutation (bolded and underlined) within the hinge region (position 7). All of these descriptors are intended to denote the same amino acid position that is to be altered to avoid degradation of the chimeric antibody construct. Thus, outside of the claims, any one descriptor is also a shorthand for describing the other options for identifying the particular amino acid that is not to be a "K" and is instead, preferably, an "A".

In some embodiments, the mutation at position 222 (as shown in FIGS. 45-56) can be any amino acid with similar properties to alanine. In some embodiments, the mutation at position 222 (as shown in FIGS. 45-56) can be any amino acid that is not highly related structurally to arginine such that the protease recognized as a cleavage point for proteolytic cleavage. In some embodiments, the mutation at position 222 (as shown in FIGS. 45-56) can be any amino acid that is not a K or an L. In some embodiments, the mutation at position 222 (as shown in FIGS. 45-56) can be any amino acid that is not a K. In some embodiments, the mutation at position 222 (as shown in FIGS. 45-46) can be any amino acid that is not charged. In some embodiments, the mutation at position 222 (as shown in FIGS. 45-46) can be any amino acid that is not charged in a manner similar to lysine. As noted, in some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed. Another way of identifying the same position is shown in FIGS. 66 and 67, as the "A" point mutation (bolded and underlined) within the hinge region (position 7). All of these descriptors are intended to denote the same amino acid position that is to be altered to avoid degradation of the chimeric antibody construct. Thus, outside of the claims, any one descriptor is also a shorthand for describing the other options for identifying the particular amino acid that is not to be a "K" and is instead, preferably, an "A".

In some embodiments, a human or humanized antigen binding molecule (ABM) that binds to *Porphyromonas gingivalis* is provided. The ABM comprises: a heavy chain comprising an amino acid sequence of SEQ ID NO: 277 and an amino acid sequence of SEQ ID NO: 270, a light chain comprising an amino acid sequence of SEQ ID NO: 277 and an amino acid sequence of SEQ ID NO: 253, and an amino acid sequence of SEQ ID NO: 274.

In some embodiments, a human or humanized antigen binding molecule (ABM) that binds to *Porphyromonas gingivalis* is provided. The ABM comprises: a sequence of SEQ ID NO: 239, and a sequence of SEQ ID NO: 229.

In some embodiments, a human or humanized antigen binding molecule (ABM) that binds to *Porphyromonas gingivalis* is provided. The ABM comprises: an amino acid sequence of SEQ ID NO: 270, an amino acid sequence of SEQ ID NO: 253, and an amino acid sequence of SEQ ID NO: 274.

In some embodiments, a human or humanized antigen binding molecule (ABM) that binds to *Porphyromonas gingivalis* is provided. The ABM comprises: an amino acid sequence of SEQ ID NO: 263, and an amino acid sequence of SEQ ID NO: 253.

In some embodiments, a cell expressing an ABM that binds to *Porphyromonas gingivalis* is provided. The ABM comprises: a VH/CH1 region of SEQ ID NO: 270 and a VL/CL region of SEQ ID NO: 253.

In some embodiments, a nucleic acid comprising the sequence of SEQ ID NO: 228, 238 252, or 262 is provided.

As disclosed herein, the ABMs are clinically validated for eliminating *P. gingivalis*. In some embodiments, the anti-genic peptides, proteins, and/or antibodies disrupt the later stages of the major protein surface processing machinery and/or prevent the maturation of the unique subunit toxin "XXX Epitope." This subunit toxin is needed for both *P. gingivalis* survival, and the creation of *P. gingivalis*'s secreted outer membrane vesicles (OMVs) that result in systemic multi-systems pathology. The "XXX Epitope" is a one-of-a-kind virulent subunit protein complex in neuro-anatomic strategic sites of AD brain tissues.

Some of the embodiments disclosed herein relate to a human or humanized antigen binding molecule (ABM) that binds to *Porphyromonas gingivalis*, wherein the ABM com-prises: a heavy chain variable region (HVR) comprising: a complementarity determining region (HCDR) 1 of a HCDR1 of SEQ ID NO: 9 or 37; a HCDR2 of a HCDR2 of SEQ ID NO: 9 or 37; and a HCDR3 of a HCDR2 of SEQ ID NO: 9 or 37; and a light chain variable region (LVR) comprising: a complementarity determining region (LCDR) 1 of a LCDR1 of SEQ ID NO:10 or 38; a LCDR2 of a LCDR2 of SEQ ID NO: 10 or 38; and a LCDR3 of a LCDR2 of SEQ ID NO:10 or 38, wherein the ABM comprises at least one of: one or more HVR residues selected from L48, L67, K71, V78, and M92, as numbered according to the numbering as provided in SEQ ID NO:37, and one or more LVR residues selected from Q46, W48, A61, Y72, and T86, as numbered according to the numbering as provided in SEQ ID NO:38, wherein the ABM further comprises a variable heavy (VH) and variable light (VL) region, wherein the ABM comprises an amino acid sequence with a point mutation at position 222 in an antibody, as numbered according to the amino acid position 104 in SEQ ID NO: 172 in FIG. 45 to remove the lysine (e.g., in the hinge region). Also provided herein is a human or humanized antigen binding molecule (ABM) that binds to *Porphyromonas gingivalis*, wherein the ABM competes for binding to *Porphyromonas gingivalis* with H5, H7, or H14, wherein the ABM is not KB001, wherein the ABM comprises an amino acid sequence with a point mutation at position 222, as numbered according to the amino acid position 104 in SEQ ID NO: 172 in FIG. 45. Also provided herein is a human or humanized antigen binding molecule (ABM) that binds to *Porphyromonas gingivalis*, wherein the ABM binds to bud-ding outer membrane vesicles of *P. gingivalis*, wherein the ABM comprises an amino acid sequence with a point mutation at position 222, as numbered according to the amino acid position 104 in SEQ ID NO: 172 in FIG. 45. Another way of identifying the same position is shown in FIGS. 66 and 67, as the "A" point mutation (bolded and underlined) within the hinge region (position 7). All three of these descriptors are intended to denote the same amino acid position that is to be altered to avoid degradation of the chimeric antibody construct. Thus, outside of the claims, any one descriptor is also a shorthand for describing the other two options for identifying the particular amino acid that is not to be a "K" and is instead, preferably, an "A". Also disclosed herein is a nucleic acid encoding the ABM of any one of the present embodiments. Also disclosed herein is a vector comprising the nucleic acid encoding the ABM of any one of the present embodiments. Also disclosed herein is a cell comprising either the nucleic acid, or the vector com-prising the nucleic acid encoding the ABM of any one of the present embodiments. Also disclosed herein is method of administering the ABM of any one of the present embodi-ments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, the method comprising subgingivally admin-istering the ABM to a subject. Also disclosed herein is a method of treating or preventing a vascular disease or symptoms thereof, the method comprising identifying a subject in need of treating or preventing a vascular disease or symptoms thereof; and administering to the subject a therapeutically effective amount of the ABM of any of the present embodiments, an ABM comprising a VH sequence with at least 80% identity to SEQ ID NO: 29, 30, 31, or, 32, and further comprising a VL sequence with at least 80% identity to SEQ ID NO: 33, 34, 35, or 36, or an ABM having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as num-bered in SEQ ID NO: 172 in FIG. 45, thereby treating or preventing the vascular disease or symptoms thereof. Also disclosed herein is a method of treating or preventing a vascular disease or symptoms thereof, the method comprising: administering to a subject in need of treating or preventing a vascular disease, or symptoms thereof, a therapeutically effective amount of at least one therapeutic agent for treating or preventing the vascular disease, or symptoms thereof; and administering an effective amount of the ABM of any one of the present embodiments, an ABM comprising a VH sequence with at least 80% identity to SEQ ID NO: 29, 30, 31, or, 32, and further comprising a VL sequence with at least 80% identity to SEQ ID NO: 33, 34, 35, or 36, or an ABM having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, to thereby enhance the therapeutic effect of the at least one therapeutic agent. Also disclosed herein is a method of treating or preventing a systemic disease or symptoms thereof, the method comprising: identifying a subject in need of treating or preventing a systemic disease or symptoms thereof, wherein the systemic disease is one or more of type II diabetes, insulin resistance and metabolic syndrome; and administering to the subject a therapeutically effective amount of the ABM of any of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the systemic disease or symptoms thereof. Also disclosed herein is a method of treating or preventing rheumatoid arthritis or symptoms thereof, the method comprising: identifying a subject in need of treating rheumatoid arthritis or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the rheumatoid arthritis or symptoms thereof. Also disclosed herein is a method of treating or preventing cancer or symptoms thereof, the method comprising: identifying a subject in need of treating cancer or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the cancer or symptoms thereof. Also disclosed herein is a method of treating or preventing cancer or symptoms thereof, the method comprising: administering to a subject in need of treating or preventing cancer, or symptoms thereof, a therapeutically effective amount of at least one therapeutic agent for treating or preventing the cancer, or symptoms thereof; and administering an effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, to thereby enhance the therapeutic effect of the at least one therapeutic agent. Also disclosed herein is a method of treating or preventing a gut microbiome-related disorder or symptoms thereof, the method comprising: identifying a subject in need of treating a gut microbiome-related disorder or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the gut microbiome-related disorder or symptoms thereof. Also disclosed herein is a method of treating or preventing a cognitive disorder or symptoms thereof, the method comprising: identifying a subject in need of treating a cognitive disorder or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the cognitive disorder or symptoms thereof. Also disclosed herein is a method of treating or preventing an age-related or longevity-related disorder, or symptoms thereof, the method comprising: identifying a subject in need of treating an age-related or longevity-related disorder; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the age-related or longevity-related disorder, or symptoms thereof. Also disclosed herein is a method of treating or preventing a post event myocardial hypertrophy or symptoms thereof, comprising: identifying a subject in need of treating or preventing a post event myocardial hypertrophy or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the post event myocardial hypertrophy or symptoms thereof. Also disclosed herein is a method of treating a wound, comprising: identifying a subject in need of treating a wound; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, whereby closure of the wound is enhanced, thereby treating the wound. Also disclosed herein is method of treating or preventing an age-related macular degeneration (AMD) or symptoms thereof, comprising: identifying a subject in need of treating or preventing AMD or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the AMD or symptoms thereof. Also disclosed herein is a method of treating or preventing an aneurysm or symptoms thereof, comprising: identifying a subject in need of treating or preventing an aneurysm or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the aneurysm or symptoms thereof. Also disclosed herein method of treating or preventing a glioma or symptoms thereof, comprising: identifying a subject in need of treating or preventing a glioma or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the glioma or symptoms thereof. Also disclosed herein is a method of treating or preventing a large vessel stroke C-IMT or symptoms thereof, comprising: identifying a subject in need of treating or preventing a large vessel stroke C-IMT or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36 or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the large vessel stroke C-IMT or symptoms thereof. Also disclosed herein is a method of treating or preventing microvascular defects and associated dementias, or symptoms thereof, comprising: identifying a subject in need of treating or preventing microvascular defects and associated dementias, or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the microvascular defects and associated dementias, or symptoms thereof. Also disclosed herein is a method of treating or preventing a peri-implantitis or symptoms thereof, comprising: identifying a subject in need of treating or preventing a peri-implantitis or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the peri-implantitis or symptoms thereof. Also disclosed herein is a method of treating or preventing a renal disease or symptoms thereof, comprising: identifying a subject in need of treating or preventing a renal disease or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the renal disease or symptoms thereof. Also disclosed herein is a method of treating or preventing a regenerative and stem cell dysfunction, or symptoms thereof, comprising: identifying a subject in need of treating or preventing a regenerative and stem cell dysfunction, or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36 or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the regenerative and stem cell dysfunction, or symptoms thereof. Also disclosed herein is a method of treating or preventing a condition, disorder or disease associated with a *P. gingivalis* infection, or symptoms thereof, comprising: identifying a subject in need of treating or preventing a condition, disorder or disease associated with a *P. gingivalis* infection, or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the condition, disorder or disease associated with a *P. gingivalis* infection, or symptoms thereof. Also disclosed herein is a method of targeting a *P. gingivalis*, comprising: identifying a subject with a *P. gingivalis* infection, or symptoms thereof; and administering to the subject a therapeutically effective amount of the ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36 or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby targeting the *P. gingivalis*, or symptoms thereof. Also disclosed herein is a method of targeting a bacterial infection in a subject, comprising: identifying the subject with a bacterial infection, or symptoms thereof; and administering to the subject a therapeutically effective amount of the ABM of any one the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby targeting the bacterial infection, or symptoms thereof. Also disclosed herein is a use of an ABM of any one of the present embodiments, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, for treatment of a disorder associated with, caused by or complicated by *P. gingivalis*. Also disclosed herein is a nucleic acid that is at least 80% identical to one of SEQ ID NOS: 98-101, wherein the nucleic acid confers the expression sequence of an ABM that has a mutation at position 222. Also disclosed herein is an ABM that is humanized or human, wherein the ABM comprises an alanine at position 222. Also disclosed herein is a method of reducing cleavage of an ABM and/or humanized antibody when administered orally to a subject. In some embodiments, the method comprises administering an antibody that has a non-lysine amino acid at position 222 of the antibody, wherein the antibody binds to a *P. gingivalis* associated peptide. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

Also disclosed herein is a humanized variant of KB001. In some embodiments, 10 μg of the humanized variant of KB001 is not detectably degraded by incubation for 2 h at 37° C. with a gingipain mix, wherein the gingipain mix comprises: Kgp activity of 15.96 mOD/min/μl and Rgp activity of 23.71 mOD/min/μl, at a ratio of Ab:GP (w/w) ratio: 100:1 and/or 500:1 in assay buffer supplemented with 10 mM cysteine.

Also disclosed herein is a human or humanized antigen binding molecule (ABM) that binds to *Porphyromonas gingivalis*, wherein the ABM comprises any one of the construct combinations as depicted in FIGS. 75 and 76. In some embodiments, the ABM or antibody lacks the leader sequence.

Also disclosed herein is a human or humanized antigen binding molecule (ABM) that binds to *Porphyromonas gingivalis*, wherein the ABM comprises any one or more of the constructs of FIGS. 77A-77L and 78A-78L. In some embodiments, the ABM or antibody lacks the leader sequence.

Also disclosed herein is nucleotide encoding a human or humanized antigen binding molecule (ABM) that binds to *Porphyromonas gingivalis*, wherein the nucleotide comprises any one or more of the nucleotide constructs of FIGS. 77A-77L and 78A-78L. In some embodiments, the ABM or antibody lacks the leader sequence or includes an alternative leader sequence.

Also disclosed herein is a human or humanized antigen binding molecule (ABM) that binds to *Porphyromonas gingivalis*, wherein the ABM comprises any one or more of the constructs of FIGS. 79-80. In some embodiments, the ABM or antibody lacks the leader sequence or includes an alternative leader sequence.

Also disclosed herein is a human or humanized antigen binding molecule (ABM) that binds to *Porphyromonas gingivalis*, wherein the ABM comprises: a heavy chain Fab comprising the leader sequence of SEQ ID NO: 277 and a VH/CH1 region of SEQ ID NO: 270; and a light chain Fab comprising the leader sequence of SEQ ID NO: 277 and a VL/CL region of SEQ ID NO: 253. In some embodiments, the ABM or antibody lacks the leader sequence or includes an alternative leader sequence. In some embodiments, the ABM comprises an at least one leader sequence that is at least about 80%, about 85%, about 90%, about 95%, about 99%, about 100%, or any integer that is between about 80 and about 100%, identical to the sequence of SEQ ID NO: 277. In some embodiments, the ABM comprises a VH/CH1 that is at least about 80%, about 85%, about 90%, about 95%, about 99%, about 100%, or any integer that is between about 80 and about 100%, identical to the sequence of SEQ ID NO: 270. In some embodiments, the ABM comprises a VL/CL that is at least about 80%, about 85%, about 90%, about 95%, about 99%, about 100%, or any integer that is between about 80 and about 100%, identical to the sequence of SEQ ID NO: 253. In some embodiments, the ABM further comprises an Fc region of SEQ ID NO: 274. In some embodiments, the ABM further comprises an Fc region that is at least about 80%, about 85%, about 90%, about 95%, about 99%, about 100%, or any integer that is between about 80 and about 100%, identical to the sequence of SEQ ID NO: 274. In some embodiments, the ABM further comprises a hinge region of SEQ ID NO: 271. In some embodiments, the ABM further comprises a hinge region that is at least about 80%, about 85%, about 90%, about 95%, about 99%, about 100%, or any integer that is between about 80 and about 100%, identical to the sequence of SEQ ID NO: 271. In some embodiments, the ABM further comprises the CH2 region of SEQ ID NO: 272. In some embodiments, the ABM further comprises a CH2 region that is at least about 80%, about 85%, about 90%, about 95%, about 99%, about 100%, or any integer that is between about 80 and about 100%, identical to the sequence of SEQ ID NO: 272. In some embodiments, the ABM further comprises the CH3 region of SEQ ID NO: 273. In some embodiments, the ABM further comprises a CH3 region that is at least about 80%, about 85%, about 90%, about 95%, about 99%, about 100%, or any integer that is between about 80 and about 100%, identical to the sequence of SEQ ID NO: 273.

In any of the embodiments provided herein, with any percent identity recited, in some embodiments, the amino acid position corresponding to amino acid position 222 (as identified herein) can be either an A or a K. As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

In some embodiments, any of the ABM provided herein can be an antibody, e.g., a human or humanized antibody.

Also disclosed herein is a human or humanized antigen binding molecule (ABM) that binds to *Porphyromonas gingivalis*, wherein the ABM comprises: a VH sequence of SEQ ID NO: 239, and a VL sequence of SEQ ID NO: 229. In some embodiments, the ABM comprises a VH sequence that is at least about 80%, about 85%, about 90%, about 95%, about 99%, about 100%, or any integer that is between about 80 and about 100%, identical to the sequence of SEQ ID NO: 239. In some embodiments, the ABM comprises a VL sequence that is at least about 80%, about 85%, about 90%, about 95%, about 99%, about 100%, or any integer that is between about 80 and about 100%, identical to the sequence of SEQ ID NO: 229.

Also disclosed herein is a human or humanized antigen binding molecule (ABM) that binds to *Porphyromonas gingivalis*, wherein the ABM comprises: a VH/CH1 region of SEQ ID NO: 270; and a CL/VL region of SEQ ID NO: 253. In some embodiments, the ABM comprises a VH/CH1 that is at least about 80%, about 85%, about 90%, about 95%, about 99%, about 100%, or any integer that is between about 80 and about 100%, identical to the sequence of SEQ ID NO: 270. In some embodiments, the ABM comprises a VL/CL that is at least about 80%, about 85%, about 90%, about 95%, about 99%, about 100%, or any integer that is between about 80 and about 100%, identical to the sequence of SEQ ID NO: 253. In some embodiments, the ABM further comprises an Fc region of SEQ ID NO: 274. In some embodiments, the ABM further comprises an Fc region that is at least about 80%, about 85%, about 90%, about 95%, about 99%, about 100%, or any integer that is between about 80 and about 100%, identical to the sequence of SEQ ID NO: 274. In some embodiments, the ABM further comprises a hinge region of SEQ ID NO: 271. In some embodiments, the ABM further comprises a hinge region that is at least about 80%, about 85%, about 90%, about 95%, about 99%, about 100%, or any integer that is between about 80 and about 100%, identical to the sequence of SEQ ID NO: 271. In some embodiments, the ABM further comprises the CH2 region of SEQ ID NO: 272. In some embodiments, the ABM further comprises a CH2 region that is at least about 80%, about 85%, about 90%, about 95%, about 99%, about 100%, or any integer that is between about 80 and about 100%, identical to the sequence of SEQ ID NO: 272. In some embodiments, the ABM further comprises the CH3 region of SEQ ID NO: 273. In some embodiments, the ABM further comprises a CH3 region that is at least about 80%, about 85%, about 90%, about 95%, about 99%, about 100%, or any integer that is between about 80 and about 100%, identical to the sequence of SEQ ID NO: 273. In any of the embodiments provided herein, with any percent identity recited, in some embodiments, the amino acid position corresponding to amino acid position 222 (as identified herein) can be either an A or a K. As will be appreciated by one of skill in the art, position 222 of FIGS. 60 and 61 is representative of the amino acid position. In some embodiments, the ABM or antibody lacks the leader sequence or includes an alternative leader sequence.

Also disclosed herein is a human or humanized antigen binding molecule (ABM) that binds to *Porphyromonas gingivalis*, wherein the ABM comprises a VH sequence of SEQ ID NO: 263, and a VL sequence of SEQ ID NO: 253. In some embodiments, the ABM comprises a VH sequence that is at least about 80%, about 85%, about 90%, about 95%, about 99%, about 100%, or any integer that is between about 80 and about 100%, identical to the sequence of SEQ ID NO: 263. In some embodiments, the ABM comprises a VL sequence that is at least about 80%, about 85%, about 90%, about 95%, about 99%, about 100%, or any integer that is between about 80 and about 100%, identical to the sequence of SEQ ID NO: 253. In any of the embodiments provided herein, with any percent identity recited, in some embodiments, the amino acid position corresponding to amino acid position 222 (as identified herein) can be either an A or a K. As will be appreciated by one of skill in the art, position 222 of FIGS. 60 and 61 is representative of the amino acid position.

Also disclosed herein is a cell expressing an ABM that binds to *Porphyromonas gingivalis*, wherein the ABM comprises a VH/CH1 region of SEQ ID NO: 270 and a VL/CL region of SEQ ID NO: 253. In some embodiments, the ABM comprises a VH/CH1 that is at least about 80%, about 85%, about 90%, about 95%, about 99%, about 100%, or any integer that is between about 80 and about 100%, identical to the sequence of SEQ ID NO: 270. In some embodiments, the ABM comprises a VL/CL that is at least about 80%, about 85%, about 90%, about 95%, about 99%, about 100%, or any integer that is between about 80 and about 100%, identical to the sequence of SEQ ID NO: 253. In some embodiments, the ABM further comprises an Fc region of SEQ ID NO: 274. In some embodiments, the ABM further comprises an Fc region that is at least about 80%, about 85%, about 90%, about 95%, about 99%, about 100%, or any integer that is between about 80 and about 100%, identical to the sequence of SEQ ID NO: 274. In some embodiments, the ABM further comprises a hinge region of SEQ ID NO: 271. In some embodiments, the ABM further comprises a hinge region that is at least about 80%, about 85%, about 90%, about 95%, about 99%, about 100%, or any integer that is between about 80 and about 100%, identical to the sequence of SEQ ID NO: 271. In some embodiments, the ABM further comprises the CH2 region of SEQ ID NO: 272. In some embodiments, the ABM further comprises a CH2 region that is at least about 80%, about 85%, about 90%, about 95%, about 99%, about 100%, or any integer that is between about 80 and about 100%, identical to the sequence of SEQ ID NO: 272. In some embodiments, the ABM further comprises the CH3 region of SEQ ID NO: 273. In some embodiments, the ABM further comprises a CH3 region that is at least about 80%, about 85%, about 90%, about 95%, about 99%, about 100%, or any integer that is between about 80 and about 100%, identical to the sequence of SEQ ID NO: 273. In any of the embodiments provided herein, with any percent identity recited, in some embodiments, the amino acid position corresponding to amino acid position 222 (as identified herein) can be either an A or a K. As will be appreciated by one of skill in the art, position 222 of FIGS. 60 and 61 is representative of the amino acid position.

In some embodiments, the ABM is an antibody. For instance, the antibody KB-001 is a monoclonal antibody with unique binding to *P. gingivalis* and its virulence factors. In some embodiments, the ABM binds to an epitope comprising GVSPKVCKDVTVEGSNEFAPVQNLT (SEQ ID NO:19) and/or YCVEVKYTAGVSPK (SEQ ID NO:59) and/or YTYTVYRDGTKIK (SEQ ID NO: 190) found in the HagA repeat epitope hemagglutinin/gingipains/adhesin domain (HXHRE domain).

As demonstrated in the below examples, KB-001 was shown during clinical study to prevent the recolonization of *P. gingivalis*, thereby eliminating all of the virulence factors of *P. gingivalis* contributing to systematic and/or organ-based inflammation at their source. In some embodiments. Kbhu-007 is effective in treating, ameliorating, and/or preventing neurodegenerative disorders, Alzheimer's disease, Parkinson's disease, dementia, systemic wide inflammatory disease and/or cardiometabolic diseases. KBhu-007 and KBhu-0014 are humanized chimeric monoclonal antibody candidates with similar binding to *P. gingivalis* and its "XXX Epitope" as KB-001. In some embodiments, Kbhu-007 is effective in treating, ameliorating, and/or preventing neurodegenerative and/or systemic wide inflammatory disease. In some embodiments, Kbhu-014 is effective in treating, ameliorating, and/or preventing neurodegenerative and/or systemic wide inflammatory disease.

The KB-001 monoclonal antibody recognizes the proteinase/adhesin/hemagglutinating complex. As disclosed herein, the antibody recognized all 22 laboratory and 105 human clinical isolates strains and serotypes by IF. The immunogen used to generate the body was formalinized *Porphyromonas gingivalis*, strain W83 (full length protein). On a gel, KB-001 has multiple bands between 31 and 65 kDa, two bands around 14 kDa, and higher MW bands at around 113 kDa. It has a mouse isotype of IgG1, and is registered with the Entrez Gene ID 2552074 29256891 2551934.

The broader target activity of KB-001 is unusual with possible gene duplication(s) of critical accessory functions. The two arginine-specific gingipains, RgpA and RgpB, possess practically identical caspase-like catalytic domains and specifically cleave Arg-Xaa peptide bonds. RgpA, however, possesses a large C-terminal extension bearing a hemagglutinin-adhesion domain, which is absent from RgpB. The Rgp/Kgp/adhesion/hemagglutinins complex recognized by the antibody KB-001 include RgpA (Gingipain R1; also known as prpR1 or hemagglutinin HagA), Kgp (Lys-gingipain) and HagA (Hemagglutinin A) are responsible for the known major survival virulence factors that include colonization, agglutination, hemagglutination/heme acquisition via RBC lysis, amino acids, adhesion complex, and host defenses against innate complement degradation/inactivation and acquired immunity (antibody cleavage). The activity of RgpA, Kgp. and HagA are mediated through the human IL-1B/NLRP3 pathway, and thus binding of RgpA. Kgp. and/or HagA to KB-001 may also block the advancement and interaction of this cytokine with its receptors and downstream pathways, such as systematic cellular inflammation, host defenses, and pre-oncogenic pathways. Booth et al. showed that subgingical application of an anti-gingipain A1 adhesin monoclonal antibody could prevent recolonization of subgingival plaque by *P. gingivalis*. As disclosed herein, the KB-001 antibody was mapped, and the inventors found that P.g. infected periodontal patients made natural antibody responses directed to non-protective epitope(s) adjacent to the KB-001 monoclonal antibody mapped epitope. Thus, the KB-001 antibody targets a protective epitope(s) that humans do not make under natural infections. Patients who had naturally developed a specific IgG1 and/or response to the gingipains did not exhibit progressive disease, and appeared stable compared with those subjects with predominant IgG2/IgG3 responses.

In some embodiments, the ABM specifically binds a *P. gingivalis* gingipain and/or hemagglutinin/adhesin. In some embodiments, the ABM interferes/blocks/reduces a molecular function(s) of its surface binding, bacterial defense activities and/or metabolic activities, e.g., gingipains and/or a hemagglutinin/adhesin complex. In some embodiments, the ABM, e.g., human-chimeric ABM, competes for binding with an ABM provided herein. Also provided are methods of treating and/or preventing periodontal infection or local and systemic inflammation by targeting *P. gingivalis*, e.g., surface OMV structures of *P. gingivalis*, using an ABM as described herein. In some embodiments, vesicle production, assembly, and OMV structures are regulated in *P. gingivalis*. In some embodiments, normal disease progression from *P. gingivalis* involves the lipopolysaccharide of *P. gingivalis* (LPS-PG) being integrated into and transported via OMVs. These OMVs are then released into tissue. In our own studies of *P. gingivalis* in culture and depending on the strains, hundreds of OMVs can be observed emerging from the cell membrane at the same time and on most if not all cells, suggesting that at any relative time point $1.0 \times 10^{\wedge}9$ CFUs of *P. gingivalis* can produce $1.0 \times 10^{\wedge}11$ or greater OMVs. This contributes to the etiology of distant organ diseases; for example, chronic systemic exposure to the lipopolysaccharide of *P. gingivalis* induces the accumulation of amyloid beta (AB) in the brain of middle-aged mice (a hallmark of Alzheimer's disease). Furthermore, there is evidence that OMVs from periodontal pathogens cause AD via leaky gum. In some embodiments, the targeting of surface OMV structures of *P. gingivalis* by ABM reduces the onset of distant organ disease. In some embodiments, a method of the present disclosure includes identifying a subject in need of treating a condition, disorder or disease associated with *Porphyromonas gingivalis*, and administering to the subject a therapeutically effective amount of an ABM as disclosed herein, to inactivate and reduce/eliminate the bacteria and its toxic OMVs, thus treating the various conditions, disorders or diseases. In some embodiments, the condition, disorder or disease is, without limitation, one or more of vascular disease (e.g., cardiovascular disease, atherosclerosis, coronary artery disease, myocardial infarction, stroke, and cardiac hypertrophy); systemic disease (e.g., type II diabetes, insulin resistance and metabolic syndrome); rheumatoid arthritis; cancer (e.g., oral, gastrointestinal, or pancreatic cancer); renal disease, gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity); post event myocardial hypertrophy, wound closure, AMD age related macro-degeneration, cerebral and abdominal aneurysms, glioma, large vessel stroke C-IMT, microvascular defects and associated dementias (e.g., Parkinson's), Peri-Implantitis and/or periodontal disease and/or associated bone loss, cognitive disorders (e.g., early, middle, or late dementia; Alzheimer's disease); regenerative and stem cell dysfunction; and age-related disorder.

In some embodiments, Pg OMV-mediated sporadic AD and Pg OMV-mediated oral-neurogenic driven diseases are major driving processes for systemic inflammatory diseases. *P. gingivalis* is the most powerful LF-degrading bacterium of several periodontal pathogens tested in vitro. *P. gingivalis* exists initially and possibly ultimately as a small population poly-microbial infection. *P. gingivalis* is a heme auxotroph, and many studies have highlighted the major influence the environmental concentration of heme has on *P. gingivalis* gene and protein expression as well as the growth and virulence capacity of the microorganism. Heme can be derived from host hemoproteins present in the saliva, gingival crevicular fluid, and erythrocytes in the oral cavity. In vivo concentrations of free heme have been found to be too low (10^-24 M) to support bacterial growth without the help of specialized heme acquisition systems produced by the bacteria themselves. Depending on environmental signaling, iron from salivary Lf provide a heme excess environment for so (Phase 1). It is hypothesized that Pg OMVs at this stage have a unique molecular signature that is enriched in various adhesion molecules. These find their way through and around the interstitial spaces (lymphatics) and epithelium/basement membrane to nearby micro-vascular networks. Once there, they circulate to the brain and bind endothelial extravasation signaling molecules, through the BBB/meningeal lining cells, and finally into adjacent neural parenchymal cells. These can explain the early localization to the cholinergic neurons, basal forebrain and anterior hypothalamic regions and regions near ventricles and peripheral neurons, an early pathway to Pg OMV entry to brain (Beginning of Phase 2). Ultimately the brain inflammation in this region leads to a shift in the delicate balance of salivary Lf coming from the decreased production of the salivary glands, shifting the biofilm sensing system to a heme limited environment. It is remarkable that the levels of LF are increased in the brains of AD patients, at least initially, and the also reduced in their whole saliva. The latter scenario could aggravate the BBB and setup the brain for additional less invasive, oro-dontophlic bacteria and other non-specific microbial/viral infections. Phase 3 begins with Pg OMVs enriching their protein cargo for increased iron scavenging. OMVs now entering the brain bring in iron with them and possibly through other unknown endothelial signaling and or now a general breakdown of the BBB these Fe-loaded OMVs target the hippocampus and frontal-temporal lobes and neo-cortex. This is a more pathogenic period for the brain with the loss of the Lf protein protection system of the brain and the more incessant loading of iron a more later advanced stage of AD occurs. Sometime between Phase 2-3 there is a greater chance for the entry of either more Pg bacterial cells other non-specific bacteria, viruses and fungi to locate in the parenchyma. This being due to both the loss of BBB integrity and innate and acquired immune suppression. The early cognitive decline seen in the prodromal period is most likely occurring in Phase 2. The more progressive cognition and memory losses coming in the Phase 3 period when both the Lf protection system is failing and the iron dyshomeostasis is occurring through the iron loaded OMV mediated period.

The extent to which lower amounts of non-iron containing OMVs verses higher containing iron OMVs may be involved in switching the early cognitive-decline form of AD into a more aggressive form of neuropathology and progressing dementia is not known. However it is not unreasonable to think the shift now to a greater deposition of higher iron into the deep gray matter and total neocortex, and regionally in temporal and occipital lobes would not be seen as a poorer prognostic indicator for AD disease progression.

Also provided herein are methods of preventing any one of the conditions, disorders, or diseases, as disclosed herein, by administering to a subject, e.g., a subject at risk of developing the condition, disorder, or disease, an effective amount of an ABM of the present disclosure, to thereby prevent the condition, disorder, or disease or developing. As used herein, "prevent" includes reducing the likelihood of a future event occurring, or delaying the onset of a future event. In some embodiments, the ABM may be used preventatively within the oral subgingival cavity to create a barrier, retardant, and/or non-colonizing effect by *P. gingivalis*, thereby preventing the bacteria from gaining access to the oral cavity, or reducing the likelihood thereof.

In some embodiments, any of the methods provided herein can be used to target Pg and/or its toxins at its source.

In some embodiments, the methods provided in the application can be used for the treatment/prevention of chronic inflammation, including disorders such as: cardiometabolic disease, atherosclerosis, inflammatory cardiovascular disease, stroke, specific cancers (including pancreatic, oral-esophageal, lung), type 2 diabetes mellitus, and neurodegenerative conditions especially Alzheimer's disease.

In some embodiments, the antibodies provided herein can be used to target and/or reduce virulence factor(s) bacterial protein complex produced by Pg in the mouth and transported via the blood to the end organs like the brain and specific neuro-anatomic regions of AD brain tissues. The Pg bacterial toxic protein complex is secreted actively in large amounts by the bacteria, mostly in the mouth, for its own survival and eventually crosses the blood-brain barrier (BBB). Thus, it impacts the brain parenchyma in specific lysine and arginine rich neuro-anatomic locations within the brain explaining AD locations and hence clinical symptoms and associated pathology. This results in a chronic low-grade systemic bacterial toxemia that disrupts our immune system and spreads throughout the body. This discovery explains the large number of inflammatory based diseases mentioned earlier, while at the same time explaining the conundrum of the pathogen driven form of Sporadic Alzheimer's disease. In some embodiments, the Ab or methods provided in the present application can be used to treat the pathogen driven form of Sporadic Alzheimer's disease. In some embodiments, this can employ KB-001 or a variant thereof, which can inactivate and eliminate both the source and the secreted virulence factors. KB-001 disrupts the later stages of the bacteria's required major protein surface processing machinery.

In some embodiments, KB-001, a monoclonal antibody, or any variant thereof or any Ab provided herein, can be used to inactivate and eliminate both the source and the secreted virulence factors. KB-001 disrupts the later stages of the bacteria's required major protein surface processing machinery. In some embodiments, any humanized version can be used in this manner. In some embodiments, any variant of KB-001 provided herein can be used in this manner. In some embodiments KB-001 can be used (e.g. SEQ ID NO: 1 and SEQ ID NO:2).

In some embodiments, KB001 can be used to treat as a combination of aspects including: general dentist and a general and specialty internal medical practice s (e.g., cardiology, primary care). In some embodiments, KB001 can be used as an antibody, or a DNA sequence or RNA (or mRNA) sequence encoding the amino acid (or applicable part thereof) can be used to administer the Ab to the subject. In some embodiments, any nucleic acid encoding any of the Ab provided herein are contemplated a nucleic acid based therapeutics for effectively delivering the Ab. The construct can include a nucleic acid sequence for part or all of the heavy and/or light chains and/or CDRs noted herein, and then be part of or configured for a viral vector delivery system or other system for delivery to humans. In some embodiments, the nucleic acid system includes the mouse sequence (e.g., KB001 or CDRs thereof) and is configured to administration to a human subject directly and either DNA or m-RNA or via any of a number of other nucleic acid delivery systems and viral vector systems.

In some embodiments, KB-001 and/or any of the variants provided in the present application can be used to prevent recolonization for up to 1 year in patients given the antibody.

In some embodiments, therapeutic antibody is a human chimeric monoclonal antibodies, allowing for repeat systemic dosing.

In some embodiments, the therapeutic Ab, including optionally KB-001, or variants thereof, prevents Pg from synthesizing its secreted outer membrane vesicles (OMVs) containing virulence protein complexes, resulting in the bacteria shutting down its metabolic and host defense functions. KB-001 has the capability to treat Pg, eliminating it and all of its virulence factors.

In some embodiments, KB-001 (or a variant thereof) binds directly to a unique hetero-multimer repeat protein epitope involved in the bacterial cargo IX transporter secretion protein complex essential for bacterial survival.

In some embodiments, the antibody can be used to treat an adverse medical condition associated with *Porphyromonas gingivalis* (Pg) infection associated with the long term, oral, biofilm-associated colonization in humans and associated with a state of chronic systemic inflammation and multiple organ system diseases (e.g., atherosclerosis, cardiovascular, stroke, diabetes type 2/metabolic syndrome, cancer, multiple forms of cognitive dementias, Alzheimer, Parkinson etc.

In some embodiments, KB-001 (or a variant thereof) binds directly to a unique hetero-multimer antigen involved in the bacterial cargo IX transporter secretion protein complex through a high affinity bi-valent binding (kD $10^{-8-9}$).

In some embodiments, about 40-60 antibody molecules bind to emerging OMVs per bacterial. Isolated OMVs demonstrate binding to the outer and inner membranes. In some embodiments, the mechanism of action is that the antibody interferes with the proteolytic processing of the larger parent protein required for subsequent endo-peptidase activity and assembly. More specifically, the binding of antibody to this complex prevents the maturation of the gingipains/LPS endo-protease/peptidase system-needed for its absolute survival and the production of its secreted OMVs responsible for the majority of its systemic multi-systems pathology. The paratope binding domain from this murine Mab has been successfully grafted onto a human IgG1 framework thus creating a variant that is a human-chimeric, bio-therapeutic antibody.

In some embodiments, the ABM of the present disclosure has therapeutic properties as a medicament. In some embodiments, the ABM of the present disclosure can be effective for as a medicament for Alzheimer's disease and early, middle and late onset cognitive, frontotemporal Dementias, Parkinson's disease, and Orphan Drug indication for Downs Dementia. In some embodiments, the ABM of the present disclosure can be effective for as a medicament for NASH, Glioma, and myocardium hypertrophy. Furthermore, research disclosed herein indicates the role of Pg in the peripheral model of disease, in which toxic proteins are delivered from Pg into the blood and brain. Consequently, the ABM of the present disclosure can be effective in targeting Pg and its downstream toxins. In some embodiments, the ABM of the present disclosure can be effective against system wide inflammation, neurodegenerative disorders, and other diseases. Non-limiting examples of systemic inflammation that the ABM of the present disclosure can be effective against includes those that are mediated by C-RP, A1c, TNF-alpha, IL1b, NLRP3, Lp-PLA2, and MPO. Non-limiting examples of neurodegenerative disorders that the ABM of the present disclosure can be effective against includes those that are mediated by APP, amyloid beta, TNF-alpha, ApoE fragmentation, tau, iron dysbiosis, and salivary lactoferrin.

In some embodiments, the ABM of the present disclosure can be effective as an anti-inflammatory therapeutic. In some embodiments, the ABM of the present disclosure can be effective as an anti-inflammatory therapeutic for atherosclerosis, cardiovascular disease, type II diabetes, and cardiometabolic diseases.

In some embodiments, the ABM of the present disclosure can be effective in chemotherapy. In some embodiments, the ABM of the present disclosure can be effective as an adjuvant chemotherapy for oncology, including treating such cancers as esophageal, pancreatic, oral, and non-smokers lung cancers.

Also disclosed herein is the mRNA and DNA encoding any one of the ABMs of the present disclosure. In some embodiments, the ABM is formatted for administration to a subject for use as a medicament. In some embodiments, the mRNA and/or DNA encoding the ABM is administered to a subject, tissue, cell, or cell line in order to express or otherwise produce the ABM in vivo. In some embodiments, the mRNA and/or DNA encoding the ABM is administered to a subject, tissue, cell, or cell line for therapeutic use. In some embodiments, the mRNA and/or DNA encoding the ABM is used to generate the ABM, which in turn is used in therapeutics. In some embodiments, the mRNA and/or DNA encoding the ABM is incorporated into a cell line, such that the cell line functions to express the ABM. In some embodiments, a viral construct comprises the mRNA and/or DNA encoding the ABM. In some embodiments, the viral construct is administered to a subject, tissue, cell, or cell line, such that the ABM is expressed in vivo. In some embodiments, the viral construct is administered to a subject, tissue, cell, or cell line as a medicament.

In some embodiments, the ABM of the present disclosure can be effective in preventing the periodontal growth or recolonization by *P. gingivalis* in a subject to which the ABM is administered. Without being bound to theory, the ABM, e.g., antibody, can bind to critical survival surface structures of the bacteria so as to interfere with the bacteria's ability to attach, stay attached to form a protective bio-film, derive metabolites/energy sources, and inactivate anti-bacterial defenses and thus survive. This can cause the bacteria to die and can destroy its biofilm, such destruction of the biofilm changing the nutrient support to other dysbiotic bacteria that may have formed around and have interdependence with *P. gingivalis* colonies. As a result, the bacterial molecules leading to active chronic inflammation and disease e.g. gingipains/LPS are no longer produced, thus reducing and/or eliminating local/systemic inflammation in the human host, leading to repair, healing and re-establishment of a more healthy oral microbiome.

In some embodiments, the ABM provided herein, while human or humanized, can be especially resistant to degradation when used orally. In some embodiments, this can be achieved by retaining primary amino acid sequence structure(s) that confer resistance to bacterial proteases or by engineering the sequences into the AMB constructs.

In some embodiments, the ABM binds to an epitope that includes a "Hag x repeat" section, which is a motif that is present in various proteins/peptides of interest for gingipains. The motif comprises: YTYTVYRDGTKIK (SEQ ID NO: 190) as a component of the epitope for KB001. The motif is present at least once in Pg, but in pre-processed forms of the protein, can be present multiple times (e.g., 2, 3, 4, 5, 6, 7, 8, 9 or 10, 11, 12, 13, 14, 15 times or more for various complexes). By using antibodies that target to this motif, numerous antibodies can bind to the target of interest in an enhanced manner. The motif can comprise longer sequences as well, such as: YTYTVYRDGTKIK (SEQ ID NO: 190). Depending on Pg strain this motif is repeated at least twice on Kgp, 3× on RgpA and up to 6× on HagA. In some embodiments, the epitope occurs at least 10 times on proteins associated with the Pg cell surface, making it superior for therapeutics. The use of such an ABM embodiment is contemplated for all compositions and methods provided herein.

In some embodiments, the methods can involve using one or more of the ABMs presented herein, such as KB001 (or any other variant thereof provided herein, including any one or more of those in Table 13.1), as a therapeutic for a disease and/or a disorder in a subject. In some embodiments, one or more of the ABMs presented herein (including any one or more of those in Table 13.1) is used an indication for an inflammatory disease in a subject. In some embodiments, one or more of the ABMs presented herein (including any one or more of those in Table 13.1) is used to treat an indication for one or more of a neurodegenerative disorder, Alzheimer's Disease, Parkinson's, and/or dementia in a subject. In some embodiments, one or more of the ABMs presented herein (including any one or more of those in Table 13.1) is used to treat an indication involving the presence of *Porphyromonas gingivalis* in a subject. In some embodiments, one or more of the ABMs presented herein (including any one or more of those in Table 13.1) is used to treat an indication for a *Porphyromonas gingivalis*-driven disease in a subject. In some embodiments, one or more of the ABMs presented herein (including any one or more of those in Table 13.1) is used an indication for the presence of toxins as a byproduct of *Porphyromonas gingivalis* in a subject. In some embodiments, one or more of the ABMs presented herein (including any one or more of those in Table 13.1) is used to treat the presence of toxins in blood and/or plasma as a byproduct of *Porphyromonas gingivalis* in a subject. In some embodiments, one or more of the ABMs presented herein (including any one or more of those in Table 13.1) is used to treat a cardiometabolic disease in a subject. In some embodiments, one or more of the ABMs presented herein (including any one or more of those in Table 13.1) is used to treat at least one of a neurodegenerative disease and/or systemic wide inflammatory disease in a subject. In some embodiments, one or more of the ABMs presented herein is used to treat Downs Dementia. In some embodiments, any of the methods provided herein can be applied to the above indications.

In some of the embodiments, the ABM has enhanced resistance against cleavage from P.g. proteases. In some embodiments, the protease is a Lysine or Arginine protease, capable of cleaving proteins at lysine or arginine, respectively. In some embodiments, this enhanced resistance to a protease is conferred through the optimization of the sequence. In some embodiments, the enhanced resistance is at least partially due to a human chimeric sequence. In some embodiments, the enhanced resistance is at least partially due to a point mutation. In some embodiments, the point mutation is to alter at least one native lysine and/or arginine in the ABM. In some embodiments, the point mutation is a change in amino acid to one or more of alanine, valine, leucine, isoleucine, methionine, phenylalanine, tyrosine, tryptophan, glycine, cysteine, selenocysteine, proline, histidine, serine, threonine, asparagine, glutamine, aspartate, and/or glutamate; preferably, the point mutation is a change in amino acid to one or more of alanine, valine, leucine, and/or isoleucine; most preferably, the point mutation is a change in amino acid to alanine. In some embodiments, the point mutation is at position 222 in the amino acid sequence. In some embodiments, the point mutation at position 222 is an alanine. In some embodiments, position 222 can be with reference to SEQ ID NO: 172, in FIGS. 45 and 46. This denotes a confirmation of which residue position is designated 222 for reference to other ABM sequence (thus, the position corresponding in other ABMs to position 222 in SEQ ID NOS: 172 is what is being referred to when the phrase "position 222" or "222" or "K222A" is used herein. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. In some embodiments, the 222 position is adjacent to the VH sequence, wherein the first amino acid of the VH sequence is considered to be the "1" position (see FIGS. 60-61, SEQ ID NOS: 30 and 32, and SEQ ID NOS: 203-208). As will be appreciated by one of skill in the art, position 222 of FIGS. 60 and 61, and position 104 in SEQ ID NO: 172 in FIG. 45 are the same amino acid position in the hinge region of an ABM, and the dual description is provided herein to clarify the particular position in the ABM hinge that has been or is to be changed.

In some embodiments, the preferred construct includes the H5 VH and VL regions, and a K to A mutation at position 222 of FIGS. 60 and 61, or the same position 104 in SEQ ID NO: 172 in FIG. 45. It is noted that this wording denotes the location of the point mutation, and that it can be used within any hinge region for any ABM where the corresponding position is a lysine.

In some embodiments, the ABM comprises an amino acid sequence at least about 70%, at least about 75%, at least about 80%, at least about 85%, at least about 90%, at least about 95%, at least about 99%, and/or at least about 100% identical to SEQ ID NO: 84. In some embodiments, the HVR comprises an amino acid sequence at least about 70%, at least about 75%, at least about 80%, at least about 85%, at least about 90%, at least about 95%, at least about 99%, and/or at least about 100% identical to one of SEQ ID NOS: 85-86. In some embodiments, the LVR comprises an amino acid sequence at least about 70%, at least about 75%, at least about 80%, at least about 85%, at least about 90%, at least about 95%, at least about 99%, and/or at least about 100% identical to one of SEQ ID NOS: 87-90. In some embodiments, the ABM comprises an HVR amino acid sequence corresponding to a nucleic acid sequence that is at least about 70%, at least about 75%, at least about 80%, at least about 85%, at least about 90%, at least about 95%, at least about 99%, and/or at least about 100% identical to one of SEQ ID NOS: 91-92. In some embodiments, the ABM comprises an LVR amino acid sequence corresponding to a nucleic acid sequence that is at least about 70%, at least about 75%, at least about 80%, at least about 85%, at least about 90%, at least about 95%, at least about 99%, and/or at least about 100% identical to one of SEQ ID NOS: 93-97. In some embodiments, the ABM corresponds to a nucleic acid sequence that is at least about 70%, at least about 75%, at least about 80%, at least about 85%, at least about 90%, at least about 95%, at least about 99%, and/or at least about 100% identical to one of SEQ ID NOS: 98-101. In some embodiments, the ABM further comprises at least one of an alanine at position 222, an amino acid sequence that is at least about 70%, at least about 75%, at least about 80%, at least about 85%, at least about 90%, at least about 95%, at least about 99%, and/or at least about 100% identical to SEQ ID NO: 84, an HVR sequence comprising an amino acid sequence at least about 70%, at least about 75%, at least about 80%, at least about 85%, at least about 90%, at least about 95%, at least about 99%, and/or at least about 100% identical to one of SEQ ID NOS: 85-86, and/or an LVR sequence comprising an amino acid sequence at least about 70%, at least about 75%, at least about 80%, at least about 85%, at least about 90%, at least about 95%, at least about 99%, and/or at least about 100% identical to one of SEQ ID NOS: 87-90. In some embodiments, the ABM binds to a gingipain and/or a haemagglutinin with a KD that is less than about 10E-9M, less than about 5E-9M, less than about 2.5E-9M, less than about 2E-9 M, less than about 1E-9 M, less than about 9E-10 M, less than about 8E-10 M, less than about 6E-10 M, less than about 4E-10 M, less than about 2E-10 M, less than about 1E-10 M, less than about 9E-11 M, less than about 7E-11 M, less than about 5E-11 M, less than about 3E-11 M, less than about 1E-11 M, less than about 1E-12 M, less than about 1E-13 M, less than about 1E-14 M, less than about 1E-15 M, and/or less than about 1E-20 M. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. In some embodiments, the 222 position is adjacent to the VH sequence, wherein the first amino acid of the VH sequence is considered to be the "1" position (see FIGS. 60-61, SEQ ID NOS: 30 and 32, and SEQ ID NOS: 203-208).

Also disclosed herein is a nucleic acid that is at least about 70%, at least about 75%, at least about 80%, at least about 85%, at least about 90%, at least about 95%, at least about 99%, and/or at least about 100% identical to one of SEQ ID NOS: 98-101. Also disclosed herein is a human or humanized antigen binding molecule (ABM) that binds to a protein complex, protein, peptide, or amino acid sequence comprising the sequence YTYTVYRDGTKIK (SEQ ID NO: 190). In some embodiments, the human or humanized antigen binding molecule (ABM) that binds to a protein complex, protein, peptide, or amino acid sequence comprises a sequence that is at least about 70%, at least about 75%, at least about 80%, at least about 85%, at least about 90%, at least about 95%, at least about 99%, and/or at least about 100% identical to the sequence YTYTVYRDGTKIK (SEQ ID NO: 190).

In some embodiments, the ABM comprises SEQ ID NO: 1. In some embodiments, the ABM comprises an amino acid sequence that is at least about 70%, at least about 75%, at least about 80%, at least about 85%, at least about 90%, at least about 95%, at least about 99%, and/or at least about 100% identical to SEQ ID NO: 1. In some embodiments, the ABM comprises SEQ ID NO: 2. In some embodiments, the ABM comprises an amino acid sequence that is at least about 70%, at least about 75%, at least about 80%, at least about 85%, at least about 90%, at least about 95%, at least about 99%, and/or at least about 100% identical to SEQ ID NO: 2. In some embodiments, the ABM comprises SEQ ID NO: 1 and SEQ ID NO: 2. In some embodiments, the ABM comprises an amino acid sequence that is at least about 70%, at least about 75%, at least about 80%, at least about 85%, at least about 90%, at least about 95%, at least about 99%, and/or at least about 100% identical to SEQ ID NO: 1, and an amino acid sequence that is at least about 70%, at least about 75%, at least about 80%, at least about 85%, at least about 90%, at least about 95%, at least about 99%, and/or at least about 100% identical to SEQ ID NO: 2. In some embodiments, the ABM is H5 K22A. In some embodiments, the ABM is at least about 70%, at least about 75%, at least about 80%, at least about 85%, at least about 90%, at least about 95%, at least about 99%, and/or at least about 100% identical to H5 K22A. In some embodiments, the ABM is humanized or human. In some embodiments, the ABM is murine. In some embodiments the ABM is chimeric and comprises human and/or mouse sequences. In some embodiments, the ABM comprises an alanine at position 222. In some embodiments, the ABM is human and comprises an alanine at position 222. In some embodiments, the ABM is murine and comprises an alanine at position 222. In some embodiments, the ABM is a human chimera and comprises an alanine at position 222. In some embodiments, the ABM is a murine chimera and comprises an alanine at position 222. In some embodiments, the ABM of the present disclosure comprises a heavy chain sequence of SEQ ID NO: 30, a light chain sequence of SEQ ID NO: 33, except that the ABM comprises an alanine at position 222. In some embodiments, the ABM of the present disclosure comprises a heavy chain sequence of SEQ ID NO: 30 and a light chain sequence of SEQ ID NO: 33. In some embodiments, the ABM of the present disclosure comprises a heavy chain sequence that is at least at least about 70%, at least about 75%, at least about 80%, at least about 85%, at least about 90%, at least about 95%, at least about 99%, and/or at least about 100% identical to SEQ ID NO: 30. In some embodiments, the ABM of the present disclosure comprises a light chain sequence that is at least about 70%, at least about 75%, at least about 80%, at least about 85%, at least about 90%, at least about 95%, at least about 99%, and/or at least about 100% identical to SEQ ID NO: 33. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. In some embodiments, the 222 position is adjacent to the VH sequence, wherein the first amino acid of the VH sequence is considered to be the "1" position (see FIGS. 60-61, SEQ ID NOS: 30 and 32, and SEQ ID NOS: 203-208).

In some embodiments of any of the humanized variants disclosed herein, the humanized variant comprises at least one of SEQ ID NO: 203, 204, 205, 206, 207, and/or 208. In some embodiments, the humanized variant comprises one of SEQ ID NO: 205, 206, 207, or 208. In some embodiments, the humanized variant comprises one of SEQ ID NO: 203 or 204.

Also disclosed herein is a method of treating a disorder driven or associated by *P. gingivalis*. As will be understood by one skilled in the art, the disorder may be any disease or disorder in a subject that has detectable levels of *P. gingivalis* in that subject's cell, cells, blood, plasma, tissue, fat deposits, gums, mouth, brain, brain cavity, organ, and/or organ system. In some embodiments, the method comprises providing an antibody that binds to a *P. gingivalis* associated peptide, to a subject. Optionally, the antibody is known to function to stop a *P. gingivalis* infection. In some embodiments, the antibody is a humanized or human antibody. In some embodiments, position 222 of the antibody has been changed to an alanine. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. In some embodiments, the 222 position is adjacent to the VH sequence, wherein the first amino acid of the VH sequence is considered to be the "1" position (see FIGS. 60-61, SEQ ID NOS: 30 and 32, and SEQ ID NOS: 203-208). As will be appreciated by one skilled in the art, the antibody may be administered alone or in an acceptable pharmaceutical composition, and at any concentration and/or route of administration that provides a therapeutic effect.

Any of the embodiments provided herein can be directed to or substituted with ABM (including antibodies) that bind to the following sequence: YTYTVYRDGTKIK (SEQ ID NO: 190).

In some embodiments, the ABM includes one or more of the sequences in any one or more of FIGS. 55, 59, and/or 60-71 (SEQ ID NOS. 191-208). In some embodiments, any of the methods provided herein can include or use any one or more of the sequences provided in any one or more of FIGS. 55, 59, and/or 60-71 (SEQ ID NOS. 191-208). In some embodiments, any of the arrangements provided herein can employ the H5 construct VH and VL regions, and the hinge region with the K to A mutation (as shown in FIG. 66). In some embodiments, the K to A mutation occurs at position 7 of the hinge region (as shown in FIG. 66.)

*P. gingivalis*

*Porphyromonas gingivalis* is a keystone pathogen that converts the local and distant healthy microbiome of an individual into a disease-forming biofilm of both the mouth and gut. *P. gingivalis* has multiple survival mechanism, which creates a grossly undiagnosed chronic active/inactive infection in the host leading to a "silent" chronic state of systemic and end organ inflammation and ultimate failure.

Pg is unique in that it completely returns one week after regular dental cleaning and re-establishes its life-long biofilm 30 days after non-surgical periodontal treatment. It can even be present in a visually clean and healthy-looking mouth. This leads to a slow, low to high level of local and systematic damage that is mostly clinically silent and often without a person even noticing. In some embodiments, KB-001 prevents Pg from synthesizing its secreted outer membrane vesicles (OMVs) containing virulence protein complexes, resulting in the bacteria shutting down its metabolic and host defense functions. In some embodiments, KB-001 has the capability to treat Pg, eliminating it and all of its virulence factors.

The pathogen hypothesis for Alzheimer's disease has been met with new attention over the last 5 years, but the push back has been the Immune Privilege of the Brain and whether the suspected pathogen source is local or peripheral to the brain tissues. As disclosed herein, the inventors show that the effect of *P. gingivalis* in the brain is mostly if not entirely from an oral peripheral source. Second, the inventors have generated new data from the largest analysis of AD brain tissues to date showing no presence of *P. gingivalis* DNA in the brain. Thirdly, the inventors have identified and discovered a one-of-a-kind virulent subunit of the primary suspected pathogen in the strategic sites of AD brain tissues. It is a unique subunit toxin "XXX Epitope" domain of *P. gingivalis*. This virulent subunit toxin plays a massive role in disrupting the NLRP3 inflammasome and the IL-1b pathways. IL-1b and ubiquinone have been shown to trigger the pathogenesis and progression of Alzheimer's disease. This same virulent subunit toxin plays an equally large role in systemic inflammation, immune disruption, and has disease-causing effects on basic human cellular biology. The delivery of the virulent toxin to the brain appears to be primarily vascular, with possibly additional access through neuronal, all however, occurring from the oral source of *P. gingivalis*. The data described herein strongly suggests for the first time that the "XXX Epitope" and related material are coming to the brain in AD as secreted by outer membrane vesicles from the bacterial surface of oral cavities. Further research is currently being conducted by the inventors into the prevalence of, genotypes of, and relative amounts of the presence of P.g. and its associated secreted exotoxins (OMVs-gingipains and LPS) and anti-P.g./LPS antibodies in patients with increased markers of systemic vascular inflammation and overexpression of inflammasome pathways, as well as the prevalence of increased markers of vascular and gut inflammation in patients with and without P.g. infection.

Definitions

As used herein, the term "antigen binding molecule" (ABM) refers to a polypeptide that includes one or more fragments of an antibody that retain the ability to specifically bind to an antigen, e.g., bacterial antigen (e.g., gingipain, adhesin hemagglutinin complex). ABM encompasses antigen-binding fragments of antibodies (e.g., single chain antibodies, Fab and Fab fragments, F(ab')$_2$, Fd fragments, Fv fragments, scFv, and domain antibodies (dAb) fragments (e.g., nanobodies) (see, e.g. de Wildt et al., Eur J. Immunol. 1996; 26(3):629-39; which is incorporated by reference herein in its entirety)) as well as complete antibodies. An ABM can include an antibody or a polypeptide containing an antigen-binding domain of an antibody. In some embodiments, an ABM can include a monoclonal antibody or a polypeptide containing an antigen-binding domain of a monoclonal antibody. For example, an ABM, e.g., antibody, can include a heavy (H) chain variable region (abbreviated herein as VH), and/or a light (L) chain variable region (abbreviated herein as VL). In another example, an ABM, e.g., antibody, includes two heavy (H) chain variable regions and/or two light (L) chain variable regions. An ABM, e.g., antibody, can have the structural features of IgA, IgG, IgE, IgD, IgM (as well as subtypes and combinations thereof). An ABM, e.g., antibody, can be from any source, including mouse, rabbit, pig, rat, and primate (human and non-human primate) and primatized (e.g., humanized) antibodies. ABM also include mini-bodies, humanized antibodies, chimeric antibodies, and the like, as well as nanobodies (single variable domain with two constant heavy domains) derived from Camelidae (camels and llamas) family. In addition they can be synthesized using protein synthetic chemistries ab initio.

As used herein an "antibody" refers to any immunoglobulin (Ig) molecule comprised of four polypeptide chains, two heavy (H) chains and two light (L) chains, interconnected by disulfide bonds or any functional fragment, mutant, variant, or derivation thereof, which retains the essential epitope binding features of an Ig molecule. The heavy chain constant region can include CH1, hinge, CH2, CH3, and, sometimes, CH4 regions. In some embodiments, for therapeutic purposes, the CH2 domain can be deleted or omitted. "Antibody" also refers to IgG, IgM, IgA, IgD or IgE molecules or antigen-specific antibody fragments thereof (including, but not limited to, a Fab, F(ab')$_2$, Fv, disulfide linked Fv, scFv, single domain antibody, closed conformation multi-specific antibody, disulfide-linked scFv, diabody), whether derived from any species that naturally produces an antibody, or created by recombinant DNA technology; whether isolated from serum, B-cells, hybridomas, transfectomas, yeast or bacteria.

The VH and VL regions can be further subdivided into regions of hypervariability, termed "complementarity determining regions" ("CDR"), interspersed with regions that are more conserved, termed "framework regions" ("FR"). The extent of the framework region and CDRs has been defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4. In some embodiments, an ABM, e.g., antibody, includes 1, 2, 3, 4, 5, and/or 6 CDRs.

The terms "antigen-binding fragment" or "antigen-binding domain," which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, the two domains of the Fv fragment, VL and VH, can be joined, using recombinant methods, by a synthetic linker that enables them to be made as a single protein chain in which the VL and VH regions pair form monovalent molecules known as single chain Fv (scFv). See e.g., U.S. Pat. Nos. 5,260,203, 4,946,778, and 4,881, 175; Bird et al. (1988) Science 242:423-426; and Huston et al. (1988) Proc. Natl. Acad. Sci. USA 85:5879-5883. Antibody fragments can be obtained using any appropriate technique.

The term "Fc region" refers to the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Specifically, in IgG, IgA and IgD types, the Fc region is composed of two identical protein fragments derived from CH2 and CH3 of the heavy chains. Fc regions of IgM and IgE contain three heavy chain constant domains, CH2, CH3, and CH4.

The term "monospecific antibody" refers to an antibody that displays a single binding specificity and affinity for a particular target, e.g., epitope. This term includes a "monoclonal antibody" or "mAb," which as used herein refer to a preparation of antibodies or fragments thereof of single molecular composition, irrespective of how the antibody was generated. The monoclonal antibody can be obtained from a population of substantially homogeneous antibodies, i.e., the individual antibodies comprising the population are identical except for possible naturally occurring mutations that may be present in minor amounts. Monoclonal antibodies can be highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method. In an embodiment, the monoclonal antibody is produced by hybridoma technology.

The term "human antibody" or "human ABM" includes antibodies or ABMs having variable and constant regions corresponding to human germline immunoglobulin sequences as described by Kabat et al. (See Kabat, et al. (1991) Sequences of Proteins of Immunological Interest, Fifth Edition, U.S. Department of Health and Human Services, NIH Publication No. 91-3242) or Chothia, C. et al. (1987) J. Mol. Biol. 196:901-917; which are incorporated by reference herein in their entireties. The human antibodies or ABMs of the present disclosure may include amino acid residues not encoded by human germline immunoglobulin sequences (e.g., mutations introduced by random or site-specific mutagenesis in vitro or by somatic mutation in vivo), for example in the CDRs. Any suitable method for generating human or fully human antibodies or ABMs can be used, including but not limited to, EBV transformation of human B cells, selection of human or fully human antibodies from antibody libraries prepared by phage display, yeast display, mRNA display or other display technologies, and also from mice or other species that are transgenic for all or part of the human Ig locus comprising all or part of the heavy and light chain genomic regions defined further above. Selected human antibodies or ABMs may be affinity matured by art recognized methods including in vitro mutagenesis, preferably of CDR regions or adjacent residues, to enhance affinity for the intended target.

By "humanized antibody" or "humanized ABM" is meant an antibody or ABM that is composed partially or fully of amino acid sequences derived from a human antibody germline by altering the sequence of an antibody having non-human complementarity determining regions (CDR). A humanized antibody or ABM can include an antibody or ABM that comprises heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which non-human CDR sequences are introduced into human VH and VL sequences to replace the corresponding human CDR sequences. Also a "humanized antibody" is an antibody or a variant, derivative, analog or fragment thereof that specifically binds to an antigen of interest and which comprises a framework (FR) region having substantially the amino acid sequence of a human antibody and a CDR having substantially the amino acid sequence of a non-human antibody.

The term "chimeric antibody" refers to an antibody that comprises heavy and light chain variable region sequences from one species (e.g., mouse) and constant region sequences from another species (e.g., human), such as antibodies having murine heavy and light chain variable regions linked to human constant regions.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives to hybridoma-based production systems.

As used herein, an "epitope" can be formed both from contiguous amino acids, or noncontiguous amino acids juxtaposed by folding of a protein. Epitopes formed from contiguous amino acids are typically retained on exposure to denaturing solvents, whereas epitopes formed by folding are typically lost on treatment with denaturing solvents. An epitope includes the unit of structure specifically bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In some embodiments, the epitope may have both linear and conformational sequence determinants and thus be derived from a single monomer, homo-dimer, homo trimer, etc., and/or hetero-dimers, hetero-trimers, etc.

The term "compete" as used herein in the context of antigen binding molecules (e.g., antibodies or antigen-binding fragments thereof) that compete for the same binding target, antigen, or epitope refers to competition between antigen binding molecules as determined by an assay in which the antigen binding molecule (e.g., antibody or immunologically functional fragment thereof) being tested prevents or inhibits (e.g., reduces) specific binding of a reference antigen binding molecule (e.g., a reference antibody) to a common antigen (e.g., *P. gingivalis* gingipain or a fragment thereof). Any suitable competitive binding assay can be used to determine if one antigen binding molecule competes with another, for example: solid phase direct or indirect radioimmunoassay (MA), solid phase direct or indirect enzyme immunoassay (EIA), sandwich competition assay, solid phase direct labeled assay, solid phase direct labeled sandwich assay, solid phase direct label MA using I-125 label, solid phase direct biotin-avidin EIA, and direct labeled MA. Typically, such an assay involves the use of purified antigen bound to a solid surface or cells bearing either of these, an unlabeled test antigen binding protein and a labeled reference antigen binding molecule. Competitive inhibition is measured by determining the amount of label bound to the solid surface or cells in the presence of the test antigen binding molecule. Usually the test antigen binding protein is present in excess. Antigen binding proteins identified by competition assay (competing antigen binding molecules) include antigen binding molecules binding to the same epitope as the reference antigen binding molecules and antigen binding molecules binding to an adjacent epitope sufficiently proximal to the epitope bound by the reference antigen binding molecule for steric hindrance to occur. Usually, when a competing antigen binding molecule is present in excess, it will inhibit (e.g., reduce) specific binding of a reference antigen binding molecule to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologues, paralogs, fragments and other equivalents, variants, fragments, and analogs of the foregoing.

Amino acid substitutions in a native protein sequence may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine).

The terms "polynucleotide" and "nucleic acid." used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this disclosure. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the disclosure.

As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and, therefore, do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Any suitable means for making this adjustment may be used. This may involve scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage can be calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Any suitable methods of alignment of sequences for comparison may be employed. Thus, the determination of percent identity between any two sequences can be accomplished using a mathematical algorithm. Preferred, non-limiting examples of such mathematical algorithms are the algorithm of Myers and Miller, CABIOS, 4:11 (1988), which is hereby incorporated by reference in its entirety; the local homology algorithm of Smith et al, Adv. Appl. Math., 2:482 (1981), which is hereby incorporated by reference in its entirety; the homology alignment algorithm of Needleman and Wunsch, JMB, 48:443 (1970), which is hereby incorporated by reference in its entirety; the search-for-similarity-method of Pearson and Lipman, Proc. Natl. Acad. Sci. USA, 85:2444 (1988), which is hereby incorporated by reference in its entirety; the algorithm of Karlin and Altschul, Proc. Natl. Acad. Sci. USA, 87:2264 (1990), which is hereby incorporated by reference in its entirety; modified as in Karlin and Altschul, Proc. Natl. Acad. Sci. USA, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988), Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994), which are hereby incorporated by reference in their entirety. The ALIGN program is based on the algorithm of Myers and Miller, supra. The BLAST programs of Altschul et al., JMB, 215:403 (1990); Nucl. Acids Res., 25:3389 (1990), which are hereby incorporated by reference in their entirety, are based on the algorithm of Karlin and Altschul supra.

As used herein, the terms "treat," "treatment," "treating." or "amelioration" refer to therapeutic treatments, wherein the object is to reverse, alleviate, ameliorate, inhibit, slow down or stop the progression or severity of a condition, e.g., a chronic inflammatory condition, associated with a disease or disorder, e.g. arteriosclerosis, gingivitis, etc. The term "treating" includes reducing or alleviating at least one adverse effect or symptom of a condition, disease or disorder associated with, e.g., arteriosclerosis, gingivitis, etc. Treatment is generally "effective" if one or more local or systemic conditions, symptoms or clinical biomarkers of disease are reduced. Alternatively, treatment is "effective" if the progression of a disease is reduced or halted. That is, "treatment" includes not just the improvement of symptoms or biomarkers, but also a cessation of, or at least slowing of, progress or worsening of symptoms compared to what would be expected in the absence of treatment. Thus, a treatment is considered effective if one or more of the signs or symptoms of a condition described herein are altered in a beneficial manner, other clinically accepted symptoms are improved, or even ameliorated and/or reversed back to a more normal or normal state, or a desired response is induced e.g., by at least 10% following treatment according to the methods described herein. Beneficial or desired clinical results include, but are not limited to, alleviation of one or more symptom(s), diminishment of extent of disease, e.g., chronic inflammatory disease, stabilized (e.g., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

Efficacy of an agent, e.g., ABM, can be determined by assessing physical indicators of a condition or desired response, e.g. inflammation and/or infection. Efficacy can be assessed in animal models of a condition described herein, for example treatment of systemic chronic inflammatory diseases associated with an oral infection, e.g., periodontal disease. When using an experimental animal model, efficacy of treatment is evidenced when a statistically significant change occurs in one of a number of criteria, including a one or more biomarkers associated with inflammation following infection. In some embodiments, treatment according to the methods described herein can reduce the levels, and/or eliminate and/or prevent the colonization of the disease causing bacteria *Porphyromonas gingivalis*. In some embodiments, treatment according to the methods described herein can reduce the levels of a biomarker(s) or symptom(s) or the tissue pathology of a condition, e.g. infection or recolonization by at least 10%, at least 15%, at least 20%, at least 25%, at least 30%, at least 40%, at least 50%, at least 60%, at least 70%, at least 80%, at least 90% or more, at least 95% or more, at least 98% or more, at least 99% or more, or by about 100%.

The term "effective amount" as used herein refers to the amount of an active agent, e.g., ABM, or composition needed to alleviate at least one or more criteria listed above of the disease or disorder, and relates to a sufficient amount of active agent or pharmacological composition to provide the desired effect. The term "therapeutically effective amount" therefore refers to an amount of active agent or composition that is sufficient to provide a particular anti-bacterial or anti-recolonization effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease.

As used herein, "subject" means a human or animal. The animal can be a vertebrate, including a mammal, such as a primate, dog or rodent. Primates include human, chimpanzees, cynomolgus monkeys, spider monkeys, and macaques, e.g., Rhesus. Rodents include mice, rats, woodchucks, ferrets, rabbits and hamsters. Animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a primate, e.g., a human. The terms, "individual," "patient" and "subject" are used interchangeably herein.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering." refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. Delivery and/or placement options include any suitable medicament delivery systems for intraoral, interproximal, intrasulcular, intra-periodontal pocket, intracanal, and intranasal. In some embodiments, a suitable delivery option includes any suitable mechanical and automated dental and medical syringes, including all calibrated and non-calibrated, all attachments, and all designs of tips including but not limited to blunt ended, and side port; Medicament delivery trays and systems including PerioProtect Trays; Medicament applicator delivery systems; Slow releasing medical preparation for intrasulcular drug delivery; Filler, oral packing, fiber, microparticles, films, gels, injectable gels, vesicular systems, strips compacts, chip, hydrogel, thermal gel, liquid, solid, including Actisite, Arestin, Atridox, Ossix Plus, Periochip, Periostat, Periofil; Injectable systems; Professional irrigation systems including piezoelectric and ultrasonic cavitron units with and without reservoir including Ora-Tec Viajet and Oral irrigation systems including Interplak, Waterpik, Hydrofloss, Viajet, Airfloss and Pro.

The singular terms "a." "an." and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is used herein to indicate a non-limiting example. Thus, "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-91 1910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10:0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Antigen-Binding Molecules

Antigen binding molecules (ABMs) that bind to *Porphyromonas gingivalis* (e.g. via its cell surface-associated and/or fully secreted outer membrane vesicles containing gingipains/hemagglutinin/adhesin/LPS) are provided herein. In certain embodiments, the ABM is a human or humanized ABM. In several embodiments, the ABM is resistant to digestion or cleavage by a protease, e.g., a bacterial protease. In some embodiments, the CDRs are any 1, 2, 3, 4, 5, or 6 CDRs as provided in FIGS. 1A and 1B. In some embodiments, the CDRs are any 1, 2, 3, 4, 5 or 6 CDRs that are within SEQ ID NOS: 1 and 2, per the Kabat or Chothia definitions of CDRs. In some embodiments, the CDRs are any 1, 2, 3, 4, 5 or 6 CDRs that are within SEQ ID NOS: 9 and 10, per the Kabat or Chothia definitions of CDRs. In some embodiments, the CDRs are any 1, 2, 3, 4, 5 or 6 CDRs that are within SEQ ID NOS: 37 and 38, per the Kabat or Chothia definitions of CDRs.

In some embodiments, the ABM, e.g., murine, human or humanized ABM, includes a heavy chain variable region (HVR). In some embodiments, the HVR includes one or more (e.g., 1, 2, or 3) heavy chain CDRs (HCDRs) corresponding to the HCDRs of a heavy chain variable region shown in Table 0.1, per the Kabat or Chothia definitions of CDRs. In some embodiments, the ABM, e.g., murine, human or humanized ABM, includes a light chain variable region (LVR). In some embodiments, the LVR includes one or more (e.g., 1, 2, or 3) light chain CDRs (LCDRs) corresponding to the LCDRs of a light chain variable region shown in Table 0.1, per the Kabat or Chothia definitions of CDRs. In some embodiments, the ABM includes an HVR having an amino acid sequence at least 80%, 85%, 90%, 95%, 97%, or 100% identical to SEQ ID NO:9. In some embodiments, the ABM includes an LVR having an amino acid sequence at least 80%, 85%, 90%, 95%, 97%, or 100% identical to SEQ ID NO:10. In some embodiments, the ABM includes a heavy chain having an amino acid sequence at least 80%, 85%, 90%, 95%, 97%, or 100% identical to SEQ ID NO:74. In some embodiments, the ABM includes a light chain having an amino acid sequence at least 80%, 85%, 90%, 95%, 97%, or 100% identical to SEQ ID NO:76.

TABLE 0.1

| | SEQ ID NO: |
|---|---|
| Heavy chain variable region amino acid sequence | |
| EVQLKQSGPGLVAPSQSLSITCTVSGFSLSIYSVHW VRQPPGKGLEWLGMIWGGGSSDYNSALKSRLSISKD NSKSQVFLKMNSLQTDDTAMYYCARNGNFYAMDYWG QGTSVTVSS | 9 |
| QVQLQESGPGLVKPSETLSLTCTVSGFSLSIYSVHW IRQPPGKGLEWX₁GMIWGGGSSDYNSALKSRX₂TIS X₃DTSKNQX₄SLKLSSVTAADTAX₅YYCARNGNFYAM DYWGQGTLVTVSS, where X₁ is I or L, X₂ is V or L, X₃ is V or K, X₄ is For V, X₅ is V or M. | 37 |
| Light chain variable region amino acid sequence | |
| QIVLTQSPAIMSASLGERVTMTCTASSSVSSSFLHW YQQKPGSSPQLWIYSTSNLASGVPARFSGSGSGTSY SLTISSMEAEDAATYYCHQYHHSPYIYTFGGGTKLE IK | 10 |
| EIVLTQSPGTLSLSPGERATLSCTASSSVSSSFLHW YQQKPGQAPX₁LX₂IYSTSNLASGIPX₃RFSGSGSGT DX₄TLTISRLEPEDFAX₅YYCHQYHHSPYIYTFGGGT KLEIK, where X₁ is Q or R, X₂ is L or W, X₃ is D or A, X₄ is F or Y, X₅ is V or T. | 38 |

In some embodiments, the ABM, e.g., murine, human or humanized ABM, includes a heavy chain CDR1 (HCDR1) of the HCDR1 of SEQ ID NO:9 or 37; a HCDR2 of the HCDR2 of SEQ ID NO:9 or 37; and/or a HCDR3 of the HCDR3 of SEQ ID NO: 9 or 37; and a light chain CDR1 (LCDR1) of the LCDR1 of SEQ ID NO:10 or 38; a LCDR2 of the LCDR2 of SEQ ID NO:10 or 38; and/or a LCDR3 of the LCDR3 of SEQ ID NO: 10 or 38. In some embodiments, the HCDR1 of SEQ ID NO: 9 is FSLSIYS (SEQ ID NO: 3), the HCDR2 of SEQ ID NO: 9 is IWGGGSS (SEQ ID NO:4), and the HCDR3 of SEQ ID NO:9 is ARNGNFYAMDY (SEQ ID NO:5). In some embodiments, the HCDR1 of SEQ ID NO: 37 is GFSLSIYSVH (SEQ ID NO:39), the HCDR2 of SEQ ID NO: 37 is MIWGGGSSDYNSALKS (SEQ ID NO:40), and the HCDR1 of SEQ ID NO: 37 is NGNFYAMDY (SEQ ID NO:41). In some embodiments, the LCDR1 of SEQ ID NO:10 is SSVSSSF (SEQ ID NO:6), the LCDR2 of SEQ ID NO:10 is STS (SEQ ID NO:7), and the LCDR3 of SEQ ID NO: 10 is HQYHHSPYIYT (SEQ ID NO:8). In some embodiments, the LCDR1 of SEQ ID NO:38 is TASSSVSSSFLH (SEQ ID NO:42), the LCDR2 of SEQ ID NO: 38 is STSNLAS (SEQ ID NO:43), and the LCDR3 of SEQ ID NO:38 is HQYHHSPYIYT (SEQ ID NO:8).

In some embodiments, the ABM includes a HCDR1 having the amino acid sequence FSLSIYS (SEQ ID NO:3); a HCDR2 having the amino acid sequence IWGGGSS (SEQ ID NO:4); and/or a HCDR3 having the amino acid sequence ARNGNFYAMDY (SEQ ID NO: 5); and/or a LCDR1 having the amino acid sequence SSVSSSF (SEQ ID NO:6); a LCDR2 having the amino acid sequence STS (SEQ ID NO:7); and/or a LCDR3 having the amino acid sequence HQYHHSPYIYT (SEQ ID NO:8). In some embodiments, the ABM includes 1, 2, 3, 4, 5, or 6 of the CDRs above.

In some embodiments, the ABM includes a HCDR1 having the amino acid sequence GFSLSIYSVH (SEQ ID NO:39); a HCDR2 having the amino acid sequence MIWGGGSSDYNSALKS (SEQ ID NO:40); and/or a HCDR3 having the amino acid sequence NGNFYAMDY (SEQ ID NO:41); and/or a LCDR1 having the amino acid sequence TASSSVSSSFLH (SEQ ID NO:42); a LCDR2 having the amino acid sequence STSNLAS (SEQ ID NO:43); and/or a LCDR3 having the amino acid sequence HQYHHSPYIYT (SEQ ID NO:8). In some embodiments, the ABM includes 1, 2, 3, 4, 5, or 6 of the CDRs above.

In some embodiments, the ABM, e.g., human or humanized ABM, includes at least one human framework region (FR). In some embodiments, the ABM includes at least one framework region having an amino acid sequence at least about 80%, e.g., at least about 85%, at least about 90%, at least about 95%, at least about 97%, at least about 99%, or 100% identical to a corresponding human framework region. In some embodiments, the ABM includes a HVR having at least one human FR. In some embodiments, the HVR includes at least one framework region having an amino acid sequence at least about 80%, e.g., at least about 85%, at least about 90%, at least about 95%, at least about 97%, at least about 99%, or 100% identical to a corresponding human HVR framework region. In some embodiments, the LVR includes at least one framework region having an amino acid sequence at least about 80%, e.g., at least about 85%, at least about 90%, at least about 95%, at least about 97%, at least about 99%, or 100% identical to a corresponding human LVR framework region.

In some embodiments, the ABM, e.g., human or humanized ABM, includes at least one of: the HVR residues selected from L48, L67, K71, V78, and M92, as numbered according to the numbering as provided in SEQ ID NO:37, and the LVR residues selected from Q46, W48, A61, Y72, and T86, as numbered according to the numbering as provided in SEQ ID NO:38. In some embodiments, the ABM includes 1, 2, 3, 4, 5, 6, 7, 8, 9 or all 10 of the HVR residues selected from L48, L67, K71, V78, and M92, as numbered according to the numbering as provided in SEQ ID NO:37, and the LVR residues selected from Q46, W48, A61, Y72, and T86, as numbered according to the numbering as provided in SEQ ID NO:38.

In some embodiments, the ABM, e.g., human or humanized ABM, includes a HVR having one or more residues selected from I48/L48, V67/L67, V71/K71, F78/V78, and V92/M92, as numbered according to the numbering as provided in SEQ ID NO: 37; and a LVR having one or more residues selected from R46/Q46, L48/W48, D61/A61, F72/Y72, and V86/T86, as numbered according to the numbering as provided in SEQ ID NO:38. In some embodiments, the HVR includes I48, V67, V71, F78 and V92. In some embodiments, the HVR includes I48, L67, K71, V78 and V92. In some embodiments, the HVR includes L48, L67, V71, V78, and M92. In some embodiments, the HVR includes L48, L67, K71, V78, and M92. In some embodiments, the LVR includes Q46, W48, D61, F72 and V86. In some embodiments, the LVR includes Q46, W48, D61, Y72 and V86. In some embodiments, the LVR includes Q46, W48, D61, Y72, and T86. In some embodiments, the LVR includes Q46, W48, A61, Y72, and T86.

In some embodiments, the HVR includes 1, 2, or all 3 HCDRs of the HCDRs of SEQ ID NO:9 or 37, and one or more residues selected from I48/L48, V67/L67, V71/K71, F78/V78, and V92/M92, as numbered according to the numbering as provided in SEQ ID NO:37. In some embodiments, the HVR includes a HCDR1 of the HCDR1 of SEQ ID NO: 9 or 37; a HCDR2 of the HCDR2 of SEQ ID NO:9 or 37; and a HCDR3 of the HCDR3 of SEQ ID NO:9 or 37, and one or more residues selected from I48/L48, V67/L67, V71/K71, F78/V78, and V92/M92 as numbered according to the numbering as provided in SEQ ID NO:37. In some embodiments, the HVR includes I48, V67, V71, F78 and V92. In some embodiments, the HVR includes I48, L67, K71, V78 and V92. In some embodiments, the HVR includes L48, L67, V71, V78, and M92. In some embodiments, the HVR includes L48, L67, K71, V78, and M92.

In some embodiments, the LVR includes 1, 2, or all 3 LCDRs of the LCDRs of SEQ ID NO:10 or 38, and one or more residues selected from R46/Q46, L48/W48, D61/A61, F72/Y72, and V86/T86, as numbered according to the numbering as provided in SEQ ID NO:38. In some embodiments, the LVR includes a LCDR 1 of the LCDR1 of SEQ ID NO:10 or 38; a LCDR2 of the LCDR2 of SEQ ID NO:10 or 38; and a LCDR3 of the LCDR3 of SEQ ID NO:10 or 38, and one or more residues selected from R46/Q46, L48/W48, D61/A61, F72/Y72, and V86/T86, as numbered according to the numbering as provided in SEQ ID NO:38. In some embodiments, the LVR includes Q46, W48, D61, F72 and V86. In some embodiments, the LVR includes Q46, W48, D61, Y72 and V86. In some embodiments, the LVR includes Q46, W48, D61, Y72, and T86. In some embodiments, the LVR includes Q46, W48, A61, Y72, and T86.

In some embodiments, the HVR includes an amino acid sequence at least about 80%, e.g., at least about 85%, at least about 90%, at least about 95%, at least about 97%, or about 99%, or 100% identical to SEQ ID NO:37. In some embodiments, the HVR includes: a heavy chain CDR1 (HCDR1) of the HCDR1 of SEQ ID NO:9 or 37; a HCDR2 of the HCDR2 of SEQ ID NO:9 or 37; and/or a HCDR3 of the HCDR3 of SEQ ID NO: 9 or 37; and an amino acid sequence at least about 80%, e.g., at least about 85%, at least about 90%, at least about 95%, at least about 97%, at least about 99%, or 100% identical to SEQ ID NO:37. In some embodiments, the HVR includes: a heavy chain CDR1 (HCDR1) of the HCDR1 of SEQ ID NO:9 or 37; a HCDR2 of the HCDR2 of SEQ ID NO:9 or 37; and a HCDR3 of the HCDR3 of SEQ ID NO:9 or 37; one or more residues selected from I48/L48, V67/L67, V71/K71, F78/V78, and V92/M92, as numbered according to the numbering as provided in SEQ ID NO:37; and an amino acid sequence at least about 80%, e.g., at least about 85%, at least about 90%, at least about 95%, at least about 97%, at least about 99%, or 100% identical to SEQ ID NO:37. In some embodiments, the HVR includes I48, V67, V71, F78 and V92. In some embodiments, the HVR includes I48, L67, K71, V78 and V92. In some embodiments, the HVR includes L48, L67, V71, V78, and M92. In some embodiments, the HVR includes L48, L67, K71, V78, and M92.

In some embodiments, the LVR includes an amino acid sequence at least about 80%, e.g., at least about 85%, at least about 90%, at least about 95%, at least about 97%, about 99%, including 100% identical to SEQ ID NO:38. In some embodiments, the LVR includes: a light chain CDR1 (LCDR1) of the LCDR1 of SEQ ID NO: 10 or 38; a LCDR2 of the LCDR2 of SEQ ID NO:10 or 38; and/or a LCDR3 of the LCDR3 of SEQ ID NO:10 or 38; and an amino acid sequence at least about 80%, e.g., at least about 85%, at least about 90%, at least about 95%, at least about 97%, at least about 99%, including 100% identical to SEQ ID NO:38. In some embodiments, the LVR includes: a light chain CDR1 (LCDR1) of the LCDR1 of SEQ ID NO:10 or 38; a LCDR2 of the LCDR2 of SEQ ID NO:10 or 38; and/or a LCDR3 of the LCDR3 of SEQ ID NO:10 or 38; one or more residues selected from R46/Q46, L48/W48, D61/A61, F72/Y72, and V86/T86, as numbered according to the numbering as provided in SEQ ID NO:38; and an amino acid sequence at least about 80%, e.g., at least about 85%, at least about 90%, at least about 95%, at least about 97%, or at least about 99% identical to SEQ ID NO:38. In some embodiments, the LVR includes Q46, W48, D61, F72 and V86. In some embodiments, the LVR includes Q46, W48, D61, Y72 and V86. In some embodiments, the LVR includes Q46, W48, D61, Y72, and T86. In some embodiments, the LVR includes Q46, W48, A61, Y72, and T86.

In some embodiments, the ABM, e.g., human or humanized ABM, includes a HVR having a heavy chain framework region 1 (HFR1) of the HFR1 in SEQ ID NO: 37; a HFR2 of the HFR2 in SEQ ID NO:37; a HFR3 of the HFR3 in SEQ ID NO:37; and/or a HFR4 of the HFR4 in SEQ ID NO:37. In some embodiments, the ABM, e.g., human or humanized ABM, includes a LVR having a light chain framework region 1 (LFR1) of the LFR1 in SEQ ID NO:38; a LFR2 of the LFR2 in SEQ ID NO:38; a LFR3 of the LFR3 in SEQ ID NO:38; and/or a LFR4 of the LFR4 in SEQ ID NO:38. In some embodiments, the ABM, e.g., human or humanized ABM, includes a HVR having a heavy chain framework region 1 (HFR1) of the HFR1 in SEQ ID NO:37; a HFR2 of the HFR2 in SEQ ID NO:37; a HFR3 of the HFR3 in SEQ ID NO:37; and/or a HFR4 of the HFR4 in SEQ ID NO:37; and a LVR having a light chain framework region 1 (LFR1) of the LFR1 in SEQ ID NO:38; a LFR2 of the LFR2 in SEQ ID NO:38; a LFR3 of the LFR3 in SEQ ID NO:38; and/or a LFR4 of the LFR4 in SEQ ID NO:38.

In some embodiments, the HVR includes a heavy chain framework region 1 (HFR1) of the HFR1 in any one of SEQ ID NOS: 29-32; a HFR2 of the HFR2 in any one of SEQ ID NOS: 29-32; a HFR3 of the HFR3 in any one of SEQ ID NOS: 29-32; and a HFR4 of the HFR4 in any one of SEQ ID NOS: 29-32. In some embodiments, the LVR includes a light chain framework region 1 (LFR1) of the LFR1 in any one of SEQ ID NOS: 33-36; a LFR2 of the LFR2 in any one of SEQ ID NOS: 33-36; a LFR3 of the LFR3 in any one of SEQ ID NOS: 33-36; and a LFR4 of the LFR4 in any one of SEQ ID NOS: 33-36.

In some embodiments, the ABM, e.g., human or humanized ABM, includes a HVR having an amino acid sequence at least about 80%, e.g., at least about 85%, at least about 90%, at least about 95%, at least about 97%, at least about 99%, or 100% identical to any one of SEQ ID NOS: 29-32. In some embodiments, the ABM, e.g., human or humanized ABM, includes a LVR having an amino acid sequence at least about 80%, e.g., at least about 85%, at least about 90%, at least about 95%, at least about 97%, at least about 99%, or 100% identical to any one of SEQ ID NOS: 33-36. In some embodiments, the ABM, e.g., human or humanized ABM, includes a HVR having an amino acid sequence at least about 80%, e.g., at least about 85%, at least about 90%, at least about 95%, at least about 97%, at least about 99%, or 100% identical to any one of SEQ ID NOS: 29-32; and a LVR having an amino acid sequence at least about 80%, e.g., at least about 85%, at least about 90%, at least about 95%, at least about 97%, at least about 99%, or 100% identical to any one of SEQ ID NOS: 33-36. In some embodiments, the ABM, e.g., human or humanized ABM, includes a HVR having a HCDR1 of the HCDR1 of SEQ ID NO:9 or 37; a HCDR2 of the HCDR2 of SEQ ID NO:9 or 37; and a HCDR3 of the HCDR3 of SEQ ID NO:9 or 37; and an amino acid sequence at least about 80%, e.g., at least about 85%, at least about 90%, at least about 95%, at least about 97%, at least about 99%, or 100% identical to any one of SEQ ID NOS: 29-32; and a LVR having a LCDR1 of the LCDR1 of SEQ ID NO:9 or 37; a LCDR2 of the LCDR2 of SEQ ID NO:9 or 37; and a LCDR3 of the LCDR3 of SEQ ID NO:9 or 37; and an amino acid sequence at least about 80%, e.g., at least about 85%, at least about 90%, at least about 95%, at least about 97%, at least about 99%, or 100% identical to any one of SEQ ID NOS: 33-36. In some embodiments, the HVR includes an amino acid sequence at least about 80%, e.g., at least about 85%, at least about 90%, at least about 95%, at least about 97%, at least about 99%, or 100% identical to SEQ ID NO:29; and the LVR includes an amino acid sequence at least about 80%, e.g., at least about 85%, at least about 90%, at least about 95%, at least about 97%, at least about 99%, or 100% identical to any one of SEQ ID NOS: 33-36. In some embodiments, the HVR includes an amino acid sequence at least about 80%, e.g., at least about 85%, at least about 90%, at least about 95%, at least about 97%, at least about 99%, or 100% identical to SEQ ID NO:30; and the LVR includes an amino acid sequence at least about 80%, e.g., at least about 85%, at least about 90%, at least about 95%, at least about 97%, at least about 99%, or 100% identical to any one of SEQ ID NOS: 33-36. In some embodiments, the HVR includes an amino acid sequence at least about 80%, e.g., at least about 85%, at least about 90%, at least about 95%, at least about 97%, at least about 99%, or 100% identical to SEQ ID NO:31 and the LVR includes an amino acid sequence at least about 80%, e.g., at least about 85%, at least about 90%, at least about 95%, at least about 97%, at least about 99%, or 100% identical to any one of SEQ ID NOS: 33-36. In some embodiments, the HVR includes an amino acid sequence at least about 80%, e.g., at least about 85%, at least about 90%, at least about 95%, at least about 97%, at least about 99%, or 100% identical to SEQ ID NO:32; and the LVR includes an amino acid sequence at least about 80%, e.g., at least about 85%, at least about 90%, at least about 95%, at least about 97%, at least about 99%, or 100% identical to any one of SEQ ID NOS: 33-36. In some embodiments, the HVR includes an amino acid sequence at least about 80%, e.g., at least about 85%, at least about 90%, at least about 95%, at least about 97%, at least about 99%, or 100% identical to any one of SEQ ID NOS: 29-32; and the LVR includes an amino acid sequence at least about 80%, e.g., at least about 85%, at least about 90%, at least about 95%, at least about 97%, at least about 99%, or 100% identical to SEQ ID NO:33. In some embodiments, the HVR includes an amino acid sequence at least about 80%, e.g., at least about 85%, at least about 90%, at least about 95%, at least about 97%, at least about 99%, or 100% identical to any one of SEQ ID NOS: 29-32; and the LVR includes an amino acid sequence at least about 80%, e.g., at least about 85%, at least about 90%, at least about 95%, at least about 97%, at least about 99%, or 100% identical to SEQ ID NO:34. In some embodiments, the HVR includes an amino acid sequence at least about 80%, e.g., at least about 85%, at least about 90%, at least about 95%, at least about 97%, at least about 99%, or 100% identical to any one of SEQ ID NOS: 29-32; and the LVR includes an amino acid sequence at least about 80%, e.g., at least about 85%, at least about 90%, at least about 95%, at least about 97%, at least about 99%, or 100% identical to SEQ ID NO:35. In some embodiments, the HVR includes an amino acid sequence at least about 80%, e.g., at least about 85%, at least about 90%, at least about 95%, at least about 97%, at least about 99%, or 100% identical to any one of SEQ ID NOS: 29-32; and the LVR includes an amino acid sequence at least about 80%, e.g., at least about 85%, at least about 90%, at least about 95%, at least about 97%, at least about 99%, or 100% identical to SEQ ID NO:36.

In some embodiments, the ABM, e.g., human or humanized ABM, includes a HVR having an amino acid sequence of any one of SEQ ID NOS: 29-32. In some embodiments, the ABM, e.g., human or humanized ABM, includes a LVR having an amino acid sequence of any one of SEQ ID NOS: 23-36. In some embodiments, the ABM, e.g., human or humanized ABM, includes a HVR having an amino acid sequence of any one of SEQ ID NOS: 29-32; and a LVR having an amino acid sequence of any one of SEQ ID NOS: 33-36. The ABM can have any suitable combination of HVR and LVR, as provided above. In some embodiments, the ABM includes a HVR having an amino acid sequence of SEQ ID NO:29 and a LVR having an amino acid sequence of any one of SEQ ID NOS: 33-36. In some embodiments, the ABM includes a HVR having an amino acid sequence of SEQ ID NO: 30 and a LVR having an amino acid sequence of any one of SEQ ID NOS: 33-36. In some embodiments, the ABM includes a HVR having an amino acid sequence of SEQ ID NO: 31 and a LVR having an amino acid sequence of any one of SEQ ID NOS: 33-36. In some embodiments, the ABM includes a HVR having an amino acid sequence of SEQ ID NO: 32 and a LVR having an amino acid sequence of any one of SEQ ID NOS: 33-36. In some embodiments, the ABM includes a HVR having an amino acid sequence of any one of SEQ ID NOS: 29-32 and a LVR having an amino acid sequence of any one of SEQ ID NOS: 33. In some embodiments, the ABM includes a HVR having an amino acid sequence of any one of SEQ ID NOS: 29-32 and a LVR having an amino acid sequence of any one of SEQ ID NOS: 34. In some embodiments, the ABM includes a HVR having an amino acid sequence of any one of SEQ ID NOS: 29-32 and a LVR having an amino acid sequence of any one of SEQ ID NOS: 35. In some embodiments, the ABM includes a HVR having an amino acid sequence of any one of SEQ ID NOS: 29-32 and a LVR having an amino acid sequence of any one of SEQ ID NOS: 36.

In some embodiments, an ABM of the present disclosure includes a heavy chain variable region having an amino acid sequence at least 80%, 90%, 95%, 97%, 98%, 99%, or 100% identity to SEQ ID NO:32, and a light chain variable region having an amino acid sequence at least 80%, 90%, 95%, 97%, 98%, 99%, or 100% identity to SEQ ID NO:34. In some embodiments, the ABM includes a HVR having a HCDR1 of the HCDR1 of SEQ ID NO: 9 or 37; a HCDR2 of the HCDR2 of SEQ ID NO:9 or 37; and a HCDR3 of the HCDR3 of SEQ ID NO:9 or 37; and an amino acid sequence at least 80%, 90%, 95%, 97%, 98%, 99%, or 100% identity to SEQ ID NO:32; and a LCDR1 of the LCDR1 of SEQ ID NO: 10 or 38; a LCDR2 of the LCDR2 of SEQ ID NO:10 or 38; and/or a LCDR3 of the LCDR3 of SEQ ID NO:10 or 38; and an amino acid sequence at least 80%, 90%, 95%, 97%, 98%, 99%, or 100% identity to SEQ ID NO:34.

In some embodiments, an ABM of the present disclosure includes a heavy chain variable region having an amino acid sequence at least 80%, 90%, 95%, 97%, 98%, 99%, or 100% identity to SEQ ID NO:30, and a light chain variable region having an amino acid sequence at least 80%, 90%, 95%, 97%, 98%, 99%, or 100% identity to SEQ ID NO:33. In some embodiments, the ABM includes a HVR having a HCDR1 of the HCDR1 of SEQ ID NO: 9 or 37; a HCDR2 of the HCDR2 of SEQ ID NO:9 or 37; and a HCDR3 of the HCDR3 of SEQ ID NO:9 or 37; and an amino acid sequence at least 80%, 90%, 95%, 97%, 98%, 99%, or 100% identity to SEQ ID NO:30; and a LCDR1 of the LCDR1 of SEQ ID NO: 10 or 38; a LCDR2 of the LCDR2 of SEQ ID NO:10 or 38; and/or a LCDR3 of the LCDR3 of SEQ ID NO:10 or 38; and an amino acid sequence at least 80%, 90%, 95%, 97%, 98%, 99%, or 100% identity to SEQ ID NO:33.

In some embodiments, an ABM of the present disclosure includes a heavy chain variable region having an amino acid sequence at least 80%, 90%, 95%, 97%, 98%, 99%, or 100% identity to SEQ ID NO:30, and a light chain variable region having an amino acid sequence at least 80%, 90%, 95%, 97%, 98%, 99%, or 100% identity to SEQ ID NO:35. In some embodiments, the ABM includes a HVR having a HCDR1 of the HCDR1 of SEQ ID NO: 9 or 37; a HCDR2 of the HCDR2 of SEQ ID NO:9 or 37; and a HCDR3 of the HCDR3 of SEQ ID NO:9 or 37; and an amino acid sequence at least 80%, 90%, 95%, 97%, 98%, 99%, or 100% identity to SEQ ID NO:30; and a LCDR1 of the LCDR1 of SEQ ID NO: 10 or 38; a LCDR2 of the LCDR2 of SEQ ID NO:10 or 38; and/or a LCDR3 of the LCDR3 of SEQ ID NO:10 or 38; and an amino acid sequence at least 80%, 90%, 95%, 97%, 98%, 99%, or 100% identity to SEQ ID NO:35.

In some embodiments, an ABM of the present disclosure includes a heavy chain variable region having an amino acid sequence at least 80%, 90%, 95%, 97%, 98%, 99%, or 100% identity to SEQ ID NO:30, and a light chain variable region having an amino acid sequence at least 80%, 90%, 95%, 97%, 98%, 99%, or 100% identity to SEQ ID NO:36. In some embodiments, the ABM includes a HVR having a HCDR1 of the HCDR1 of SEQ ID NO: 9 or 37; a HCDR2 of the HCDR2 of SEQ ID NO:9 or 37; and a HCDR3 of the HCDR3 of SEQ ID NO:9 or 37; and an amino acid sequence at least 80%, 90%, 95%, 97%, 98%, 99%, or 100% identity to SEQ ID NO:30; and a LCDR1 of the LCDR1 of SEQ ID NO: 10 or 38; a LCDR2 of the LCDR2 of SEQ ID NO:10 or 38; and/or a LCDR3 of the LCDR3 of SEQ ID NO:10 or 38; and an amino acid sequence at least 80%, 90%, 95%, 97%, 98%, 99%, or 100% identity to SEQ ID NO:36.

In some embodiments, an ABM of the present disclosure includes a heavy chain variable region having an amino acid sequence at least 80%, 90%, 95%, 97%, 98%, 99%, or 100% identity to SEQ ID NO:32, and a light chain variable region having an amino acid sequence at least 80%, 90%, 95%, 97%, 98%, 99%, or 100% identity to SEQ ID NO:35. In some embodiments, the ABM includes a HVR having a HCDR1 of the HCDR1 of SEQ ID NO: 9 or 37; a HCDR2 of the HCDR2 of SEQ ID NO:9 or 37; and a HCDR3 of the HCDR3 of SEQ ID NO:9 or 37; and an amino acid sequence at least 80%, 90%, 95%, 97%, 98%, 99%, or 100% identity to SEQ ID NO:32; and a LCDR1 of the LCDR1 of SEQ ID NO: 10 or 38; a LCDR2 of the LCDR2 of SEQ ID NO:10 or 38; and/or a LCDR3 of the LCDR3 of SEQ ID NO:10 or 38; and an amino acid sequence at least 80%, 90%, 95%, 97%, 98%, 99%, or 100% identity to SEQ ID NO:35.

In some embodiments, the ABM, e.g., human or humanized ABM, is an antibody. In some embodiments, the ABM includes a heavy chain constant region derived from human gamma, mu, alpha, delta, or epsilon heavy chain. In some embodiments, the ABM includes a light chain constant region derived from human lambda or kappa light chain. In some embodiments, the ABM is of a human IgG (e.g. IgG1, IgG2, IgG3 or IgG4), IgM, IgA, IgD, or IgE isotype. In some embodiments, the ABM is of an IgG isotype, e.g., human IgG isotype. In some embodiments, the ABM binds to an epitope within a polypeptide comprising an amino acid sequence of any one of SEQ ID NOs: 77-83.

The ABM, e.g., murine, human or humanized ABM, of the present disclosure generally binds to an antigen associated with, and/or expressed by, *P. gingivalis*. The ABM in certain embodiments binds to one or more strains of *P. gingivalis*. Strains of *P. gingivalis* to which the ABM binds can include, without limitation, strains W83, W12, W50, 381. A7A1-28, HG66 and ATCC33277. In some embodiments, the ABM binds to any one, two, three, four, five or all six of *P. gingivalis* strains W83, W12, W50, 381, A7A1-28, and/or ATCC33277. In some embodiments, the ABM binds to strains W83, W12, W50, 381, A7A1-28, and/or ATCC33277. In some embodiments, the ABM binds to clinically important (e.g., virulent and/or chronic inflammation-causing) strains of *P. gingivalis*. In some embodiments, the ABM binds to clinically isolated strains of *P. gingivalis*.

In some embodiments, the ABM, e.g., murine, human or humanized ABM, of the present disclosure specifically binds to a *P. gingivalis* cell-surface antigen. In some embodiments, the ABM of the present disclosure specifically binds to an antigen associated with outer membrane vesicles (OMVs) of *P. gingivalis*.

In some embodiments, the ABM, e.g., murine, human or humanized ABM, competes with KB001 for binding to *P. gingivalis*. In some embodiments, the ABM binds to the same or overlapping epitope as KB001. In some embodiments, the ABM comprises the CDRs of the 6 CDRs in SEQ ID NO: 1 and 2. In some embodiments, the ABM comprises at least one, two, three, four, five, or all 6 of the CDRs in SEQ ID NO: 1 and 2. In some embodiments, an ABM of the present disclosure, e.g., human or humanized ABM, competes for binding to *P. gingivalis* (e.g., *P. gingivalis* gingipain, hemagglutinin, and/or OMV or budding OMV) with an antibody having a heavy chain variable region containing an amino acid sequence of SEQ ID NO:37, as shown in Table 0.1, and a light chain variable region containing an amino acid sequence of SEQ ID NO:38, as shown in Table 0.1. In some embodiments, an ABM of the present disclosure, e.g., human or humanized ABM, competes for binding to *P. gingivalis* (e.g., *P. gingivalis* gingipain, hemagglutinin, and/or OMV or budding OMV) with an antibody having a heavy chain variable region containing an amino acid sequence of any one of SEQ ID NOS: 29-32, and a light chain variable region containing an amino acid sequence of any one of SEQ ID NOS: 33-36. In some embodiments, an ABM of the present disclosure, e.g., human or humanized ABM, competes for binding to *P. gingivalis* (e.g., *P. gingivalis* gingipain, hemagglutinin, and/or OMV or budding OMV) with an antibody having a heavy chain variable region containing an amino acid sequence of SEQ ID NO: 30 and a light chain variable region containing an amino acid sequence of SEQ ID NO: 33. In some embodiments, an ABM of the present disclosure, e.g., human or humanized ABM, competes for binding to *P. gingivalis* (e.g., *P. gingivalis* gingipain, hemagglutinin, and/or OMV or budding OMV) with an antibody having a heavy chain variable region containing an amino acid sequence of SEQ ID NO:30 and a light chain variable region containing an amino acid sequence of SEQ ID NO:35. In some embodiments, an ABM of the present disclosure, e.g., human or humanized ABM, competes for binding to *P. gingivalis* (e.g., *P. gingivalis* gingipain, hemagglutinin, and/or OMV or budding OMV) with an antibody having a heavy chain variable region containing an amino acid sequence of SEQ ID NO: 32 and a light chain variable region containing an amino acid sequence of SEQ ID NO: 34. In some embodiments, an ABM of the present disclosure, e.g., human or humanized ABM, competes for binding to *P. gingivalis* (e.g., *P. gingivalis* gingipain, hemagglutinin, and/or OMV or budding OMV) with an antibody having heavy chain and light chain variable regions as set forth in Table 13.1. In some embodiments, an ABM of the present disclosure, e.g., human or humanized ABM, competes for binding to *P. gingivalis* (e.g., *P. gingivalis* gingipain, hemagglutinin, and/or OMV or budding OMV) with H5, H7, or H14.

In some embodiments, the ABM specifically binds to an epitope that includes the amino acid sequence GVSPKVCKDVTVEGSNEFAPVQNLT (SEQ ID NO: 19). In certain embodiments, the ABM specifically binds to a polypeptide that includes an amino acid sequence at least about 70%, e.g., at least about 75%, at least about 80%, at least about 85%, at least about 90%, at least about 95%, at least about 97%, at least about 99%, or 100% identical to the sequence: AGTYDFAIAAPQANAKIWIAGQGPTKED-DYVFEAGKKYHFLMKKMGSGDGTELTIS EGGGSDYTYTVYRDGTKIKEGLTATT-FEEDGVAAGNHEYCVEVKYTAGVSPKVCK DVTVEGSNEFAPVQNLT (SEQ ID NO:20). In certain embodiments, the ABM specifically binds to a polypeptide that includes an amino acid sequence at least about 70%, e.g., at least about 75%, at least about 80%, at least about 85%, at least about 90%, at least about 95%, at least about 97%, at least about 99%, or 100% identical to residues 64-129 of the sequence AGTYDFAIAAPQANAKIWI-AGQGPTKED-DYVFEAGKKYHFLMKKMGSGDGTELTIS EGGGSDYTYTVYRDGTKIKEGLTATT-FEEDGVAAGNHEYCVEVKYTAGVSPKVCK DVTVEGSNEFAPVQNLT (SEQ ID NO:20). In some embodiments, the ABM specifically binds to a polypeptide that includes an epitope having the amino acid sequence GVSPKVCKDVTVEGSNEFAPVQNLT (SEQ ID NO:19), and includes an amino acid sequence at least about 70%, e.g., at least about 75%, at least about 80%, at least about 85%, at least about 90%, at least about 95%, at least about 97%, at least about 99%, or 100% identical to the sequence AGTYDFAIAAPQANAKIWIAGQGPTKED-DYVFEAGKKYHFLMKKMGSGDGTELTIS EGGGSDYTYTVYRDGTKIKEGLTATT-FEEDGVAAGNHEYCVEVKYTAGVSPKVCK DVTVEGSNEFAPVQNLT (SEQ ID NO:20). In some embodiments, the ABM specifically binds to a polypeptide that includes an epitope having the amino acid sequence GVSPKVCKDVTVEGSNEFAPVQNLT (SEQ ID NO:19), and includes an amino acid sequence at least about 70%, e.g., at least about 75%, at least about 80%, at least about 85%, at least about 90%, at least about 95%, at least about 97%, at least about 99%, or 100% identical to residues 64-129 of the sequence AGTYDFAIAAPQANAKIWI-AGQGPTKED-DYVFEAGKKYHFLMKKMGSGDGTELTIS EGGGSDYTYTVYRDGTKIKEGLTATT-

FEEDGVAAGNHEYCVEVKYTAGVSPKVCK DVTVEGSNEFAPVQNLT (SEQ ID NO:20).

In some embodiments, the ABM specifically binds to an epitope that includes an amino acid sequence at least about 70%, e.g., at least about 75%, at least about 80%, at least about 85%, at least about 90%, at least about 95%, at least about 97%, at least about 99%, or 100% identical to residues 784 to 1130 of SEQ ID NO:21. In some embodiments, the ABM binds to an epitope within a polypeptide comprising an amino acid sequence that is at least about 70%, e.g., at least about 75%, at least about 80%, at least about 85%, at least about 90%, at least about 95%, at least about 97%, at least about 99%, or 100% identical of any one of SEQ ID NOs: 77-83.

In some embodiments, the ABM specifically binds to an epitope that includes the linear amino acid sequence YCVEVKYTAGVSPK (SEQ ID NO:59). In some embodiments, the ABM competes with an antibody (e.g., KB001) for binding to a polypeptide containing a linear epitope having the amino acid sequence YCVEVKYTAGVSPK (SEQ ID NO:59). In some embodiments, the ABM specifically binds to an epitope that includes the amino acid sequence YCVEVKYX$_1$AGVSPK (SEQ ID NO: 60), where X$_1$ is T or A. In some embodiments, the ABM competes with an antibody (e.g., KB001) for binding to a polypeptide containing a linear epitope having the amino acid sequence YCVEVKYX$_1$AGVSPK (SEQ ID NO:60), where X$_1$ is T or A. In some embodiments, the ABM specifically binds to an epitope that includes the linear amino acid sequence GVSPK (SEQ ID NO:162). In some embodiments, the ABM competes with an antibody (e.g., KB001) for binding to a polypeptide containing a linear epitope having the amino acid sequence GVSPK (SEQ ID NO: 162).

In some embodiments, the ABM binds an epitope in a sequence within a *P. gingivalis* gingipain (e.g., RgpA, Kgp) and/or hemagglutinin (e.g., HagA) from various strains. In some embodiments, the ABM binds an epitope within a sub-sequence of a *P. gingivalis* gingipain (e.g., RgpA, Kgp) and/or hemagglutinin (e.g., HagA) as shown in any one of FIGS. 40A-40F. FIG. 40B, provides non-limiting examples of amino acid sequences of the repeated domains of *P. gingivalis* gingipains and hemagglutinins (e.g., RgpA, Kgp, HagA) with sequences encompassing the putative epitope of an ABM of the present disclosure underlined. In some cases, the *P. gingivalis* gingipains (e.g., RgpA. Kgp) include an amino acid sequence that partially aligns with a sequence encompassing the putative epitope of an ABM of the present disclosure (e.g., broken underlining in C-terminal regions Kgp_W83_C-term, RgpA_W83_C-term, Kgp_W83, and RgpA_W83 in FIG. 40B). In FIG. 40B, the boxed portions indicate the HbR domain. Proteolytic processing sites are marked with bold font. In some embodiments, the ABM binds to an epitope within a repeated domain of a *P. gingivalis* gingipain (e.g., RgpA, Kgp) and/or hemagglutinin (e.g., HagA). In some embodiments, the repeated domain containing the epitope occurs at least 2, 3, 4 or more times within the *P. gingivalis* gingipain (e.g., RgpA, Kgp) and/or hemagglutinin (e.g., HagA). In some embodiments, HagA from W83 and ATCC33277, contains 3 and 4 nearly perfect repeats, respectively, of the sequence containing the putative epitope (FIGS. 40C, 40D, 40E, 40F). In some embodiments, the motif containing the putative epitope occurs twice in a gingipain structure (FIGS. 40D, 40E, 40F). In some embodiments, the third repeat is present in HA4 domain of RgpA but is degenerate in the Kgp (e.g., from W83 strain).

In some embodiments, the ABM binds to an epitope within any one of the amino acid sequences in Table 0.2. In some embodiments, the ABM binds to an epitope within an amino acid sequence at least about 70%, e.g., at least about 75%, at least about 80%, at least about 85%, at least about 90%, at least about 95%, at least about 97%, at least about 99%, or 100% identical to any one of the amino acid sequences in Table 0.2. In some embodiments, the ABM competes with an antibody (e.g., KB001) for binding to a polypeptide containing any one or more of the amino acid sequences shown in Table 0.2. In some embodiments, the ABM competes with an antibody (e.g., KB001) for binding to a polypeptide containing an amino acid sequence at least about 70%, e.g., at least about 75%, at least about 80%, at least about 85%, at least about 90%, at least about 95%, at least about 97%, at least about 99%, or 100% identical to any one of the amino acid sequences shown in Table 0.2.

TABLE 0.2

Putative sequence motifs in HagA, RgpA and Kgp encompassing an epitope recognized by KB001

| Source (see Example 12) | Sequence | SEQ ID NO: |
|---|---|---|
| Kgp_N-term | PASYTYTVYRDGTKIKEGLTATTFEE DGVAAGNHEYCVEVKYTAGVSPKVC | 77 |
| RgpA_N-term | GSDYTYTVYRDGTKIKEGLTATTFEE DGVATGNHEYCVEVKYTAGVSPKVC | 78 |
| RgpA_C-term | PTDYTYTVYRDGTKIKEGLTETTFEE DGVATGNHEYCVEVKYTAGVSPKKC | 79 |
| HagA_W83_R1 | PTDYTYTVYRDGTKIKEGLTETTFEE DGVATGNHEYCVEVKYTAGVSPKEC | 80 |
| HagA_W83_R2 | PTDYTYTVYRDGTKIKEGLTETTFEE DGVATGNHEYCVEVKYTAGVSPKEC | 80 |
| HagA_ATCC_R1 | PTDYTYTVYRDGTKIKEGLTETTFEE DGVATGNHEYCVEVKYTAGVSPKEC | 80 |
| HagA_ATCC_R2 | PTDYTYTVYRDGTKIKEGLTETTFEE DGVATGNHEYCVEVKYTAGVSPKEC | 80 |
| HagA_ATCC_R3 | PTDYTYTVYRDGTKIKEGLTETTFEE DGVATGNHEYCVEVKYTAGVSPKEC | 80 |
| Kgp_C-term | PTDYTYTVYRDGTKIKEGLTETTFEE DGVATGNHEYCVEVKYTAGVSPKKC | 79 |
| HagA_ATCC_R4 | PTDYTYTVYRDGTKIKEGLTETTFEE DGVATGNHEYCVEVKYTAGVSPKVC | 81 |
| HagA_W83_R3 | PTDYTYTVYRDGTKIKEGLTETTFEE DGVATGNHEYCVEVKYTAGVSPKEC | 80 |
| RgpA_C-term2 | PASYTYTVYRDGTKIKEGLTETTYRD AGMSAQSHEYCVEVKYTAGVSPKVC | 82 |
| Kgp_C-term2 | APSYTYTIYRNNTQIASGVTETTYRD PDLATGFYTYGVKVVYPNGESAIET | 83 |

In some embodiments, the ABM specifically binds to one or more P. gingivalis gingipains, where the gingipain is an arg-gingipain (Rgp) or a lys-gingipain (Kgp). In some embodiments, the ABM specifically binds to one or more Rgps selected from RgpA and RgpB. In some embodiments, the ABM specifically binds to RgpA having an amino acid sequence at least about 80%, e.g., at least about 85%, at least about 90%, at least about 95%, at least about 97%, at least about 99%, or 100% identical to SEQ ID NO:21. In some embodiments, the ABM specifically binds to RgpB having an amino acid sequence at least about 80%, e.g., at least about 85%, at least about 90%, at least about 95%, at least about 97%, at least about 99%, or 100% identical to SEQ ID NO:22. In some embodiments, the ABM specifically binds to Kgp having an amino acid sequence at least about 80%, e.g., at least about 85%, at least about 90%, at least about 95%, at least about 97%, at least about 99%, or 100% identical to SEQ ID NO:23. In some embodiments, the ABM specifically binds to a propeptide domain, a catalytic domain and/or a C-terminal adhesion domain of a gingipain. In some embodiments, the ABM specifically binds to a Rgp44 region of an RgpA adhesion domain, as described in, e.g., Li et al., *Eur. J. Microbiol. Immunol.*, 2011, 1:41-58. In some embodiments, the ABM specifically binds to a Kgp39 region of a Kgp adhesion domain, as described in, e.g., Li et al., *Eur. J. Microbiol. Immunol.*, 2011, 1:41-58.

In several embodiments, the ABM specifically binds to a P. gingivalis hemagglutinin/adhesin. In some embodiments, the hemagglutinin is HagA. In some embodiments, HagA has an amino acid sequence at least about 80%, e.g., at least about 85%, at least about 90%, at least about 95%, at least about 97%, at least about 99%, or 100% identical to SEQ ID NO:24. In some embodiments, the ABM specifically binds to an adhesion domain of HagA.

In some embodiments, an ABM of the present disclosure binds to emerging OMVs on P. gingivalis. In some embodiments, an ABM of the present disclosure includes a HVR having an amino acid sequence of SEQ ID NO:30 and a LVR having an amino acid sequence of SEQ ID NO:35. In some embodiments, an ABM of the present disclosure includes a HVR having an amino acid sequence of SEQ ID NO:32 and a LVR having an amino acid sequence of SEQ ID NO:34. In some embodiments, an ABM of the present disclosure includes a HVR having an amino acid sequence of SEQ ID NO:32 and a LVR having an amino acid sequence of SEQ ID NO:35. In some embodiments, an ABM of the present disclosure includes a HVR having an amino acid sequence of SEQ ID NO:30 and a LVR having an amino acid sequence of SEQ ID NO:33. In some embodiments, an ABM of the present disclosure includes a HVR having an amino acid sequence of SEQ ID NO:30 and a LVR having an amino acid sequence of SEQ ID NO:36. In some embodiments, the ABM is at least 80, 85, 90, 95, 96, 97, 98, 99, or 100% identical to one or both of the sequences in Table 0.3.

TABLE 0.3

| Antibody | VH variant | VL variant |
|---|---|---|
| H1 | VH1 (SEQ ID NO: 29) | VL1 (SEQ ID NO: 33) |
| H2 | VH1 (SEQ ID NO: 29) | VL2 (SEQ ID NO: 34) |
| H3 | VH1 (SEQ ID NO: 29) | VL3 (SEQ ID NO: 35) |
| H4 | VH1 (SEQ ID NO: 29) | VL4 (SEQ ID NO: 36) |
| H5 | VH2 (SEQ ID NO: 30) | VL1 (SEQ ID NO: 33) |
| H6 | VH2 (SEQ ID NO: 30) | VL2 (SEQ ID NO: 34) |
| H7 | VH2 (SEQ ID NO: 30) | VL3 (SEQ ID NO: 35) |
| H8 | VH2 (SEQ ID NO: 30) | VL4 (SEQ ID NO: 36) |
| H9 | VH3 (SEQ ID NO: 31) | VL1 (SEQ ID NO: 33) |
| H10 | VH3 (SEQ ID NO: 31) | VL2 (SEQ ID NO: 34) |
| H11 | VH3 (SEQ ID NO: 31) | VL3 (SEQ ID NO: 35) |
| H12 | VH3 (SEQ ID NO: 31) | VL4 (SEQ ID NO: 36) |

TABLE 0.3-continued

| Antibody | VH variant | VL variant |
|---|---|---|
| H13 | VH4 (SEQ ID NO: 32) | VL1 (SEQ ID NO: 33) |
| H14 | VH4 (SEQ ID NO: 32) | VL2 (SEQ ID NO: 34) |
| H15 | VH4 (SEQ ID NO: 32) | VL3 (SEQ ID NO: 35) |
| H16 | VH4 (SEQ ID NO: 32) | VL4 (SEQ ID NO: 36) |

In some embodiments, any of the ABMs from Table 0.3 or the variants noted thereof above, can further include a point mutation at position 222, including the option of an alanine at position 222. In some embodiments, the ABM is H5 having an alanine at position 222, and can be a K222A substitution. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. In some embodiments, the 222 position is adjacent to the VH sequence, wherein the first amino acid of the VH sequence is considered to be the "1" position (see FIGS. 60-61, SEQ ID NOS: 30 and 32, and SEQ ID NOS: 203-208). In some embodiments, the position is in the hinge region with the K to A mutation (as shown in FIG. 66, bolded an underlined). In some embodiments, the K to A mutation occurs at position 7 of the hinge region (as shown in FIG. 66.) This point mutation in the hinge region can be employed in the hinge region of any one of the constructs provided herein, including the H5 arrangement, and any methods provided herein.

Such a substitution will allow the humanized or human chimeric construct to be resistant to degradation.

ABM Functionality/Properties for Some Embodiments

In some embodiments, the binding affinity (Kd) of the ABM to $P.$ $gingivalis$ is about $1\times10^{-7}$ M or less, e.g., about $8\times10^{-8}$ M or less, about $6\times10^{-8}$ M or less, about $4\times10^{-8}$ M or less, about $3\times10^{-8}$ M or less, about $1\times10^{-8}$ M or less, about $8\times10^{-9}$ M or less, about $6\times10^{-9}$ M or less, about $4\times10^{-9}$ M or less, about $2\times10^{-9}$ M or less, about $1\times10^{-9}$ M or less, about $8\times10^{-10}$ M or less, about $6\times10^{-10}$ M or less, about $4\times10^{-10}$ M or less, about $2\times10^{-10}$ M or less, about $1\times10^{-10}$ M or less, about $5\times10^{-11}$ M or less, about $2\times10^{-11}$ M or less, about $1\times10^{-11}$ M or less, about $5\times10^{-12}$ M or less, about $2\times10^{-12}$ M or less, about $1\times10^{-12}$ M or less, or a binding affinity in between any two of the preceding values. In some embodiments, the binding affinity (Kd) of the ABM to $P.$ $gingivalis$ is from about $1\times10^{-7}$ M to about $1\times10^{-12}$ M. e.g., from about $1\times10^{-8}$ M to about $1\times10^{-12}$ M, from about $1\times10^{-8}$ M to about $1\times10^{-11}$ M, from about $1\times10^{-9}$ M to about $1\times10^{-11}$ M, including from about $1\times10^{-9}$ M to about $1\times10^{-10}$ M. In certain embodiments, the ABM has a higher binding affinity (e.g., lower Kd) to $P.$ $gingivalis$ than KB001. In some embodiments, the ABM has a binding affinity to $P.$ $gingivalis$ that is about 1.2, 1.5, 2, 2.2, 2.5, 3, 3.2, 3.5, 4.0, 4.2, 4.5, 5, 6, 7, 8, 9, 10, 15, 20, 25, 30, 35, 40, 45, 50, 60, 70, 80, 90, 100 or more times, or any multiple in between those values listed, stronger than the binding affinity of KB001.

In some embodiments, the ABM prevents adhesion of $P.$ $gingivalis$ at a site of infection (e.g., oral site). In some embodiments, the ABM reduces survivability of $P.$ $gingiva-lis$ at a site of infection (e.g., oral site).

In some embodiments, the ABM binds to one or more virulence factors of $P.$ $gingivalis$. In some embodiments, the one or more virulence factors are small (20-500 nm) proteoliposomal membrane vesicles (OMVs) produced via the Type IX cargo secretion system that organizes and distributes macro and micro molecules through its cell membrane and into specific protein-lipo-protein structures. In some embodiments, the ABM binds to outer membrane vesicles (OMVs) of $P.$ $gingivalis$. In some embodiments, the ABM binds to budding or emerging OMVs of $P.$ $gingivalis$. In some embodiments, the ABM binds to one or more gingipains and/or hemagglutinins associated with OMVs, e.g., budding or emerging OMVs.

In some embodiments, the ABM binds to a $P.$ $gingivalis$ cell at a high density. In some embodiments, the ABM binds to a $P.$ $gingivalis$ cell surface at a density of at least about 1, 2, 3, 4, 5, 7, 10, 15, 20, 25, 30 35, 40, 45, 50, 55, 60, 65, 70, 75, 80, 85, 90, 95, 100, 110, 120, 130, 140, 150 $\mu m^{-2}$, or more, or at a density between any two of the preceding values. In some embodiments, the ABM shows increased binding to a $P.$ $gingivalis$ having a higher density of surface-associated OMVs and/or bleb-like structures than a $P.$ $gin-givalis$ having a lower density. In some embodiments, clinical strains (e.g., clinically relevant strains) of $P.$ $gingivalis$ have a greater ability to secrete OMVs and/or produce a greater number of surface bleb-like structures than a non-clinically relevant strain, and the ABM has a greater affinity to the clinical strains.

In some embodiments, ABMs of the present disclosure find use in detecting $P.$ $gingivalis$ and/or associated exotoxins (e.g., one or more $P.$ $gingivalis$ gingipains) in a sample, e.g., a tissue sample. In some embodiments, an assay for detecting $P.$ $gingivalis$ and/or associated exotoxins in a sample using the ABM provides a sensitive assay. In some embodiments, the ABM provides for an assay for detecting $P.$ $gingivalis$ and/or associated exotoxins in a sample that is more sensitive than an assay based on detection of $P.$ $gingivalis$ nucleic acids, e.g., a PCR-based liquid hybridization assay. In some embodiments, the ABM has sufficient sensitivity to detect $P.$ $gingivalis$ and/or associated exotoxins in a sample where no $P.$ $gingivalis$ nucleic acids is detectably present, e.g., using a PCR-based liquid hybridization assay. In some embodiments, the sample is a brain or gum tissue sample.

In some embodiments, the ABM is resistant to digestion or cleavage, e.g., hydrolytic cleavage, by proteases. In some embodiments, the ABM is resistant to cleavage by a human protease, a bacterial protease and/or a fungal protease. In some embodiments, the ABM is resistant to cleavage by a serine protease, cysteine protease, and/or a metalloprotease. In some embodiments, the ABM is resistant to cleavage by a $P.$ $gingivalis$ protease, e.g., a $P.$ $gingivalis$ extracellular protease. In some embodiments, the ABM is resistant to cleavage by a $P.$ $gingivalis$ gingipain, e.g., RgpA, RgpB, and/or Kgp. In some embodiments, the ABM is resistant to cleavage by a protease as compared to the susceptibility to cleavage by the protease of a fully humanized antibody that specifically binds $P.$ $gingivalis$, e.g., a fully humanized version of KB001. In some embodiments, the ABM is 10-20%, 20-30%, 30-40%, 40-50%, 50-60%, 60-70%, 70-80%, 80-90% or 90-100% or more resistant to proteolysis by the protease compared to the susceptibility to proteolysis by the protease of a fully humanized antibody that specifically binds $P.$ $gingivalis$, e.g., a fully humanized version of KB001.

In some embodiments, the ABM is more resistant to cleavage when administered in vivo.

In some embodiments, the ABM inhibits or neutralizes one or more activities of the target protein to which it specifically binds. In some embodiments, the ABM inhibits or neutralizes an activity of the target protein to which it specifically binds by 10-20%, 20-30%, 30-40%, 40-50%, 50-60%, 60-70%, 70-80%, 80-90% or 90-100%. In some embodiments, the ABM inhibits or neutralizes one or more activities of a P. gingivalis. In some embodiments, the ABM inhibits or neutralizes an activity of P. gingivalis by 10-20%, 20-30%, 30-40%, 40-50%, 50-60%, 60-70%, 70-80%, 80-90% or 90-100%.

In some embodiments, the ABM inhibits or neutralizes one or more activities of P. gingivalis associated with one or more gingipains, e.g., RgpA, RgpB, and/or Kgp. In some embodiments, the ABM inhibits or neutralizes an extracellular protease activity of P. gingivalis. In some embodiments, the extracellular protease activity of P. gingivalis includes a protease activity of one or more gingipains, e.g., RgpA, RgpB, and/or Kgp. In some embodiments, the ABM inhibits or neutralizes full proteolysis of a substrate by one or more P. gingivalis gingipains, e.g., RgpA. RgpB, and/or Kgp. In some embodiments, the ABM inhibits, neutralizes, or reduces processing of a hemagglutinin domain-containing protein by one or more P. gingivalis gingipains, e.g., RgpA, RgpB, and/or Kgp. In some embodiments, the hemagglutinin domain-containing protein is P. gingivalis HagA. In some embodiments, the hemagglutinin domain-containing protein has an amino acid sequence at least 80%, at least 85%, at least 90%, at least 95%, at least 97%, or 100% identical to SEQ ID NO: 24. In some embodiments, the hemagglutinin domain-containing protein has an amino acid sequence at least 80%, at least 85%, at least 90%, at least 95%, at least 97%, or 100% identical to SEQ ID NO: 28. In some embodiments, the ABM inhibits the extracellular protease activity of P. gingivalis by 10-20%, 20-30%, 30-40%, 40-50%, 50-60%, 60-70%, 70-80%, 80-90% or 90-100%. In some embodiments, the ABM reduces processing of a hemagglutinin domain-containing protein by one or more P. gingivalis gingipains, e.g., RgpA, RgpB, and/or Kgp, by 10-20%, 20-30%, 30-40%, 40-50%, 50-60%, 60-70%, 70-80%, 80-90% or 90-100%.

In some embodiments, the ABM inhibits the extracellular protease activity of P. gingivalis with an $IC_{50}$ of about 10 µM or less, e.g., about 5 µM or less, about 2 µM or less, about 1 µM or less, about 0.5 µM or less, about 0.2 µM or less, about 0.1 µM or less, about 0.05 µM or less, about 0.02 µM or less, including about 0.01 µM or less, or an $IC_{50}$ in between any two of the preceding values. Inhibition of extracellular protease activity may be measured using, e.g., a culture plate assay, as described in, e.g., Grenier et al., Effect of Inactivation of the Arg- and/or Lys-Gingipain Gene on Selected Virulence and Physiological Properties of Porphyromonas gingivalis INFECTION AND IMMUNITY, August 2003, p. 4742-4748, which disclosure is incorporated herein by reference.

In some embodiments, the ABM inhibits the hemagglutination activity of P. gingivalis. In some embodiments, the hemagglutination activity of P. gingivalis includes a hemagglutination activity of one or more gingipains, e.g., RgpA, RgpB, and/or Kgp. In some embodiments, the hemagglutination activity of P. gingivalis includes a hemagglutination activity of an agglutinin, e.g., HagA. In some embodiments, the ABM inhibits the hemagglutination activity of P. gingivalis by 10-20%, 20-30%, 30-40%, 40-50%, 50-60%, 60-70%, 70-80%, 80-90% or 90-100%. Inhibition of hemagglutination activity may be measured using a hemagglutination inhibition assay, as described in, e.g., Booth et al., J. Periodont. 1997. 32:45-60, which disclosure is incorporated herein by reference.

In some embodiments, the ABM inhibits the hemolysis activity of P. gingivalis. In some embodiments, the hemolysis activity of P. gingivalis includes a hemolysis activity of one or more gingipains, e.g., RgpA, RgpB, and/or Kgp. In some embodiments, the ABM inhibits the hemolysis activity of P. gingivalis by 10-20%, 20-30%, 30-40%, 40-50%, 50-60%, 60-70%, 70-80%, 80-90% or 90-100%. Inhibition of hemolysis activity may be measured using a hemolysis assay, as described in Chu et al., Infect. Immun. 1991. 59:1932-1940, which disclosure is incorporated herein by reference.

Compositions

Also provided herein is a composition that includes an antigen-binding molecule (ABM) that binds Porphyromonas gingivalis, as described herein. In some embodiments, a property of the ABM, e.g., level or glycosylation, is defined in the context of a population of ABM molecules in a composition. In some embodiments, the composition includes an ABM that includes a heavy chain having an amino acid sequence NST is glycosylated. In some embodiments, 0-10%, 10-20%, 20-30%, 30-40%, 40-50%, 50-60%, 60-70%, 70-80%, 80-90% or 90-100% of the ABM in the composition is glycosylated at the asparagine residue of the amino acid sequence NST in the heavy chain. In some embodiments, the composition includes an ABM that is not glycosylated at a position between MNT and YFVY within the heavy chain. In certain embodiments, at the most about 10%, e.g. at the most about 5%, at the most 4%, at the most 3%, at the most 2%, at the most 1%, at the most 0.5%, at the most 0.3%, at the most 0.2% of the ABM in the composition is glycosylated at a position between MNT and YFVY within the heavy chain.

In certain embodiments, the composition is for the topical, oral, and/or subgingival administration of the ABM, for treating a subject in need of treatment for a P. gingivalis infection, or in need of treatment of a condition, disorder or disease (e.g., vascular disease, systemic disease, rheumatoid arthritis, cancer, gut microbiome-related disorder, cognitive disorder, age-related disorder, etc.), as disclosed herein. Thus, in some embodiments, the composition is a pharmaceutical composition that includes an ABM and a pharmaceutically acceptable carrier or excipient. Pharmaceutically acceptable carriers and excipients include saline, aqueous buffer solutions, solvents and/or dispersion media. Some non-limiting examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, methylcellulose, ethyl cellulose, microcrystalline cellulose and cellulose acetate; powdered tragacanth; malt; gelatin; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol (PEG); esters, such as ethyl oleate and ethyl laurate; agar; buffering agents, such as magnesium hydroxide and aluminum hydroxide; alginic acid; pyrogenfree water; isotonic saline; Ringer's solution; ethyl alcohol; pH buffered solutions; polyesters, polycarbonates and/or polyanhydrides; bulking agents, such as polypeptides and amino acids serum component, such as serum albumin, HDL and LDL; C2-C12 alcohols, such as ethanol; and other non-toxic compatible substances employed in pharmaceutical formulations. The terms such as "excipient," "carrier," "pharmaceutically acceptable carrier" or the like are used interchangeably herein. In some embodiments, the carrier inhibits the degradation of the active agent, e.g. an ABM as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient.

Suitable vehicles that can be used to provide parenteral dosage forms of compounds as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Nucleic Acids, Vectors and Transgenic Cells

Also provided herein are nucleic acids encoding one or more polypeptides of an ABM, as described herein. In some embodiments, the nucleic acid encoding one or more polypeptides of an ABM includes a nucleotide sequence of at least one of SEQ ID NO: 61-70, or a nucleotide sequence having at least about 80%, for example, e.g., at least about 85%, at least about 87%, at least about 90%, at least about 91%, at least about 92%, at least about 93%, at least about 94%, at least about 95%, at least about 96%, at least about 97%, at least about 98%, at least about 99% or greater identity thereto. In some embodiments, the nucleic acid sequence encodes any one or more of the amino acid sequences provided herein.

In some embodiments, a nucleic acid of the present disclosure encoding a variable heavy chain of an ABM as disclosed herein includes a nucleotide sequence at least about 80%, 85%, 90%, 95%, 97%, 98%, 99% or 100% identical to one of SEQ ID NOS: 61-64. In some embodiments, a nucleic acid of the present disclosure encoding a variable heavy chain of an ABM as disclosed herein includes a nucleotide sequence at least about 80%, 85%, 90%, 95%, 97%, 98%, 99% or 100% identical to one of SEQ ID NO:69. In some embodiments, a nucleic acid of the present disclosure encoding a variable light chain of an ABM as disclosed herein includes a nucleotide sequence at least about 80%, 85%, 90%, 95%, 97%, 98%, 99% or 100% identical to one of SEQ ID NOS: 65-68. In some embodiments, a nucleic acid of the present disclosure encoding a variable light chain of an ABM as disclosed herein includes a nucleotide sequence at least about 80%, 85%, 90%, 95%, 97%, 98%, 99% or 100% identical to one of SEQ ID NO:70.

Nucleic acid molecules encoding amino acid sequence of ABMs are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. A nucleic acid sequence encoding at least one ABM, e.g., antibody, antigen-binding portion thereof, or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel, 1987, 1993, and can be used to construct nucleic acid sequences which encode an ABM, e.g., a monoclonal antibody molecule, or antigen binding region thereof. A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. Sec, e.g., Sambrook et al., 1989; Ausubel et al., 1987-1993.

Accordingly, the expression of an ABM, e.g., antibody, or antigen-binding portion thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an ABM, e.g., antibody, or portion thereof as described herein with a specified amino terminus sequence. Moreover, problems associated with retention of initiation codon-derived methionine residues in direct yeast (or bacterial) expression may be avoided. Sabin et al., 7 Bio/Technol. 705 (1989); Miller et al., 7 Bio/Technol. 698 (1989). Any of a series of yeast gene expression systems incorporating promoter and termination elements from the actively expressed genes coding for glycolytic enzymes produced in large quantities when yeast are grown in media rich in glucose can be utilized to obtain recombinant ABMs, e.g., antibodies, or antigen-binding portions thereof. Known glycolytic genes can also provide very efficient transcriptional control signals. For example, the promoter and terminator signals of the phosphoglycerate kinase gene can be utilized.

Production of ABMs, e.g., antibodies, or antigen-binding portions thereof as described herein can be achieved in insects, for example, by infecting the insect host with a baculovirus engineered to express a transmembrane polypeptide by methods known to those of skill in the art. See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those of ordinary skill in the art. See, e.g., Ausubel et al., 1987, 1993. Factors of importance in selecting a particular plasmid or viral vector include: the case with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli*, for example. Other gene expression elements useful for the expression of cDNA encoding ABMs, e.g., antibodies, or antigen-binding portions thereof include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983). Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an ABM (e.g., antibody), antigen-binding portion thereof, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact ABMs, e.g., antibodies, or fragments are recovered from the culture.

In some embodiments, the fused genes encoding the ABM (e.g., antibody) antigen-binding fragment thereof, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human ABMs, e.g., antibodies, described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human ABM (e.g., antibody) construct, antibody, or antigen-binding portion thereof as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 1 1th Intl. Conf. Yeast, Genetics & Molec. Biol. (Montpelier, France, 1982).

Yeast gene expression systems can be routinely evaluated for the levels of production, secretion and the stability of ABMs, e.g., antibodies, and assembled chimeric, humanized, or composite human ABMs (e.g., antibodies), portions and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning 45, (Glover, ed., IRL Press, 1985) and e.g., U.S. Publication No. US 2006/0270045.

Bacterial strains can also be utilized as hosts for the production of the ABM, e.g., antibody, molecules or peptides described herein. *E. coli* K12 strains such as *E. coli* W31 10 (ATCC 27325), *Bacillus* species, enterobacteria such as *Salmonella typhimurium* or *Serratia marcescens*, and various *Pseudomonas* species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized ABMs, e.g., antibodies, and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the ABM, e.g., antibody, molecules, and secretion of functional ABM (e.g., antibody) protein.

In some embodiments, one or more ABMs (e.g., antibodies) as described herein can be produced in vivo in an animal that has been engineered or transfected with one or more nucleic acid molecules encoding the polypeptides, according to any suitable method.

In some embodiments, an ABM, e.g., antibody, as described herein is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of cloned H and L chain genes in mammalian cells (see Glover, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies or antigen-binding portions thereof. The co-expression can occur by using either the same or different plasmids in the same host. Genes for both H and L chains or portions thereof can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antibodies, antigen-binding portions thereof and/or $H_2L_2$ molecules via either route could be transfected with plasmids encoding additional copies of peptides, H. L, or H plus L chains in conjunction with additional selectable markers to generate cell lines with enhanced properties, such as higher production of assembled $H_2L_2$ antibody molecules or enhanced stability of the transfected cell lines.

Additionally, plants have emerged as a convenient, safe and economical alternative mainstream expression systems for recombinant ABM, e.g., antibody, production, which are based on large scale culture of microbes or animal cells. ABMs, e.g., antibodies, can be expressed in plant cell culture, or plants grown conventionally. The expression in plants may be systemic, limited to sub-cellular plastids, or limited to seeds (endosperms). See, e.g., U.S. Patent Pub. No. 2003/0167531; U.S. Pat. No. 6,080,560; No. 6,512, 162; WO 0129242.

Mammalian cells are a preferred host for expressing nucleotide segments encoding immunoglobulins or fragments thereof. See Winnacker, From Genes to Clones, (VCH Publishers, NY, 1987), which is incorporated herein by reference in its entirety. A number of suitable host cell lines capable of secreting intact heterologous proteins have been developed in the art, and include CHO cell lines, various COS cell lines, Hela cells, L cells and multiple myeloma cell lines. Expression vectors for these cells can include expression control sequences, such as an origin of replication, a promoter, an enhancer (Queen et al., "Cell-type Specific Regulation of a Kappa Immunoglobulin Gene by Promoter and Enhancer Elements," Immunol Rev 89:49 (1986), incorporated herein by reference in its entirety), and necessary processing information sites, such as ribosome binding sites, RNA splice sites, polyadenylation sites, and transcriptional terminator sequences. Preferred expression control sequences are promoters substantially similar to a region of the endogenous genes, cytomegalovirus, SV40, adenovirus, bovine papillomavirus, and the like. Sec Co et al., "Chimeric and Humanized Antibodies with Specificity for the CD33 Antigen," J Immunol 148: 1 149 (1992), which is incorporated herein by reference in its entirety.

Alternatively, ABM coding sequences can be incorporated in transgenes for introduction into the genome of a transgenic animal and subsequent expression in the milk of the transgenic animal (e.g., according to methods described in U.S. Pat. Nos. 5,741,957, 5,304,489, 5,849,992, all incorporated by reference herein in their entireties). Suitable transgenes include coding sequences for light and/or heavy chains in operable linkage with a promoter and enhancer from a mammary gland specific gene, such as casein or beta lactoglobulin. The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra, which is herein incorporated by reference in its entirety). For production of transgenic animals, transgenes can be microinjected into fertilized oocytes, or can be incorporated into the genome of embryonic stem cells, and the nuclei of such cells transferred into enucleated oocytes. Once expressed, ABMs, e.g., antibodies, can be purified according to standard procedures of the art, including HPLC purification, column chromatography, gel electrophoresis and the like (see generally, Scopes, Protein Purification (Springer-Verlag, NY, 1982), which is incorporated herein by reference in its entirety).

Once expressed, the whole ABMs (e.g., antibodies), their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, NY, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human ABM, e.g., antibody, can then be used therapeutically or in developing and performing assay procedures, immunofluorescent stainings, and the like. See generally, Vols. I & II Immunol. Meth. (Lefkovits & Pernis, eds., Acad. Press, NY, 1979 and 1981).

Additionally, and as described herein, a recombinant humanized ABM, e.g., antibody, can be further optimized to decrease potential immunogenicity, while maintaining functional activity, for therapy in humans. In this regard, functional activity means a polypeptide capable of displaying one or more known functional activities associated with a recombinant ABM, e.g., antibody, as described herein. Such functional activities include, e.g. the ability to bind to a cancer cell marker.

Chimeric, humanized and human ABMs, e.g., antibodies, are typically produced by recombinant expression. Recombinant polynucleotide constructs typically include an expression control sequence operably linked to the coding sequences of ABM, e.g., antibody, chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting ABMs, e.g., antibodies. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. *E. coli* is one prokaryotic host particularly useful for cloning the DNA sequences. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Methods

Also provided herein are methods of using an antigen-binding molecule (ABM) that binds *Porphyromonas gingivalis*, as described herein, to treat a subject in need of treatment, e.g., for periodontal disease and/or acute/chronic systemic and organ inflammation. In some embodiments, the condition, disorder or disease is, without limitation, one or more of vascular disease (e.g., cardiovascular disease, atherosclerosis, coronary artery disease, myocardial infarction, stroke, and cardiac hypertrophy); systemic disease (e.g., type II diabetes, insulin resistance and metabolic syndrome);

rheumatoid arthritis; cancer (e.g., oral, gastrointestinal, or pancreatic cancer); renal disease, gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity); post event myocardial hypertrophy, wound closure, AMD age related macro-degeneration, cerebral and abdominal aneurysms, glioma, large vessel stroke C-IMT, microvascular defects and associated dementias (e.g., Parkinson's), Peri-Implantitis and/or periodontal disease and/or associated bone loss, cognitive disorders (e.g., early, middle, and/or late dementia; Alzheimer's disease); regenerative and stem cell dysfunction; and age-related disorder.

In general terms, the method includes administering a therapeutically effective amount of an ABM that binds *P. gingivalis*, as described herein, to a subject having an active and/or subclinical infection with or without periodontal disease or inflammation, e.g., gingivitis or periodontitis. In some embodiments, the method includes administering to the subject a therapeutically effective amount of an ABM that binds *P. gingivalis*, as described herein, to a subject having *P. gingivalis* localized in the sub-gingival gum line, either with or without gingivitis, and/or periodontal disease or inflammation. In some embodiments, the ABM for use in the present methods binds to *P. gingivalis* outer membrane forming vesicles and/or secreted outer membrane vesicles containing arg and Lys gingipains/adhesins/hemagglutinins/LPS. In some embodiments, the method includes administering to the subject a therapeutically effective amount of an ABM to a subject having *P. gingivalis* localized in the sub-gingival gum line and leaking or trans-migrating through epithelia cells and into local lymphatic drainage and the blood vascular system. In some embodiments, the method is a method for passive immunization of a subject against a periodontal infection (such as gingivitis or periodontitis) by administering the ABM, as described herein. In some embodiments, the method is a method for passive, topical oral passive administration of a subject against a periodontal infection (such as gingivitis or periodontitis) by administering the ABM, as described herein. In some embodiments, a method for administering an ABM (e.g., a therapeutically and/or preventative effective amount of an ABM) of the present disclosure includes subgingivally placing the ABM into a subject.

The ABM can be administered to subjects having or suffering from one or more of a variety of conditions, disorders or diseases in the present methods. In some embodiments, the subject has a local and/or systemic infection by *P. gingivalis*. In some embodiments, the subject has an oral infection of (e.g., colonization by) *P. gingivalis*. In some embodiments, the subject has an acute or prolonged or chronic *P. gingivalis* infection. In some embodiments, the subject has a subclinical *P. gingivalis* infection. In some embodiments, the subject has a condition, disorder or disease associated with a *P. gingivalis* infection (e.g., oral infection), or symptoms thereof. In some embodiments, the subject has periodontitis, e.g., early or advanced periodontitis. In some embodiments, the condition, disorder or disease is one or more of: vascular disease (e.g., cardiovascular disease, atherosclerosis, coronary artery disease, myocardial infarction, stroke, and myocardial hypertrophy); systemic disease (e.g., type II diabetes, insulin resistance and metabolic syndrome); rheumatoid arthritis; cancer (e.g., oral, gastrointestinal, or pancreatic cancer); renal disease, gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity); post event myocardial hypertrophy, wound closure, AMD (age-related macular degeneration), cerebral and abdominal aneurysms, glioma, large vessel stroke C-IMT, microvascular defects and associated dementias (e.g., Parkinson's), Peri-Implantitis and/or periodontal disease and/or associated bone loss, cognitive disorders (e.g., early, middle, and/or late dementia; Alzheimer's disease); regenerative and stem cell dysfunction; and longevity or age-related disorder.

The ABM can be administered using any suitable route to treat the infection, e.g., periodontal infection. In some embodiments, the ABM is administered orally, subgingivally, subcutaneously, intradermally, or intravenously. In some embodiments, the infection is an infection of the gingiva (e.g. gingivitis or periodontitis), blood vessels, the lungs, heart, liver gastro-intestinal tract, brain, etc., and the method includes subgingivally placing a therapeutically effective amount of the ABM into the subject. The ABM may be placed subgingivally in any suitable manner to treat the periodontal infection. In several embodiments, the ABM is placed subgingivally at 1, 2, 3, 4, 5, or 6 or more sites around each tooth to be treated. In some embodiments, the ABM is placed subgingivally at or around each tooth in a subject's mouth. In some embodiments, the ABM is placed subgingivally at or around each of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 teeth in a subject's mouth. In some embodiments, the ABM is placed subgingivally at or around one or more of the subject's incisor, canine, premolar and/or molar tooth. In some embodiments, the ABM is administered at about 0.001, 0.005, 0.01, 0.02, 0.05, 0.1, 0.2, 0.5, 1, 1.2, 1.5, 2, 2.2, 2.5, 3, 3.2, 3.5, 4, 4.2, 4.5, 5, 5.2, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 70, 80, 90, or 100 μg of the ABM per tooth, or an amount in between any two of the preceding values. In some embodiments, the ABM is administered at about 0.5-10 μg, about 1-8 μg, about 1.5-6 μg, or about 2-5 μg of the ABM per tooth in a treatment. In some embodiments, the ABM is administered at about 3 μg per tooth in a treatment. In some embodiments, the ABM is administered at about 10-400 μg, about 30-300 μg, about 50-200 μg, about 60-160 μg, about 70-140 μg of the ABM per a subject's mouth in a treatment. In some embodiments, the ABM is administered at about 96 μg per subject's mouth in a treatment.

In some embodiments, an ABM of the present disclosure is administered by administering one or more nucleic acids encoding the ABM to a subject in need thereof, as provided herein. Any suitable nucleic acid encoding the ABM can be administered to the subject. In some embodiments, the one or more nucleic acids encoding the ABM is configured to express the ABM when incorporated in a cell of the subject. In some embodiments, the nucleic acid is DNA or RNA. In some embodiments, the one or more nucleic acids is in one or more plasmids or viral vectors (e.g., an adenovirus-associated virus). In some embodiments, the nucleic acid is a mRNA. The nucleic acid encoding the ABM can be delivered to a cell of the subject using any suitable option. In some embodiments, the one or more nucleic acids is delivered to a cell of the subject via viral transduction. In some embodiments, the one or more nucleic acids is delivered to a cell of the subject by electroporation. In some embodiments, the one or more nucleic acids is delivered to a cell of the subject via a lipid nanoparticle. Suitable options for administering an ABM of the present disclosure to a subject is provided in, e.g., Patel et al. "In Vivo Delivery of Nucleic Acid-Encoded Monoclonal Antibodies." BioDrugs (2020) 34:273-293.

In some embodiments, the method includes removing a microbial infection or preventing its re-colonization in a supra- and/or subgingival space of the subject, before administering the ABM. In certain embodiments, the method includes removing plaque from the supra- and/or subgingival space of the subject, before administering the ABM. In some embodiments, the ABM is placed subgingivally after removing plaque from the supra- and/or subgingival space of one or more teeth to be treated. Plaque can be removed using any suitable means. In some embodiments, the plaque is removed by cleaning and/or root planning. In some embodiments, the method includes administering one or more antibiotics to the subject to remove a microbial infection or colonization in a supra- and/or subgingival space of the subject.

In some embodiments, administration of the ABM prevents or prolongs the time before recolonization. "Recolonization" as used herein refers to detectable growth of P. gingivalis in a supra- and/or subgingival plaque after initial removal of P. gingivalis.

In some embodiments, methods of the present disclosure reduces or eliminates a P. gingivalis infection in the subject, e.g., in the subgingival space of the subject. In some embodiments, the P. gingivalis infection is reduced on average about 10% or more, e.g., 20% or more, 30% or more, 40% or more, 50% or more, 60% or more, 70% or more, 80% or more, 90% or more, 95% or more, including about 100%, compared to the pretreatment level of infection.

In some embodiments, methods of the present disclosure prevent recolonization and or initial colonization of the gingiva by P. gingivalis. Recolonization is inhibited when P. gingivalis growth is inhibited after initial removal of P. gingivalis from the gingival and/or subgingival space, e.g., by removal of plaque. Thus, the method in some embodiments includes removing P. gingivalis from a subgingival space of the subject before administering the ABM to the subject. In some embodiments, removing P. gingivalis from a subgingival space includes cleaning and/or root planning to thereby remove plaque from the subgingival space.

In some embodiments, recolonization is inhibited when P. gingivalis remains undetectable, or detectable at 5% or less, 3% or less, 2% or less, or 1% or less, in a subgingival plaque sample, after initial removal of P. gingivalis from the gingival and/or subgingival space. In some embodiments, recolonization is inhibited for about 1, 2, 3, 4, 5, 6, 7, 8, 9, 10, 11, 12, 13, 14, 15, 16, 17, 18, 19, 20, 21, 22, 23, 24 months or more, or for any period of time in between any two of the times listed above, after initial removal of P. gingivalis. P. gingivalis may be detected by, e.g., immunofluorescent staining of a plaque sample using KB001.

Also disclosed herein is a nucleic acid encoding any of the ABMs of the present disclosure. The nucleic acid may be RNA or DNA. The nucleic acid may also be inserted into a cell, tissue, and/or organism for expression of the ABM. As will be appreciated by one skilled in the art, the nucleic acid may be inserted into a host and used to express the ABM using any conventional method, including mutagenesis of the host DNA, viral vector insertion, CRISPR, resistance cassettes, genetic knock-ins, and electroporation with plasmids. Also disclosed herein is a cell expressing any one or more of the ABMs of the present disclosure. In some embodiments, the cell is mammalian. In some embodiments, the cell is human. In some embodiments, the cell is murine.

In some embodiments, the cell is part of cell culture. In some embodiments, the cell is part of a tissue culture. In some embodiments, the cell is incorporated in an organism, such as a human.

In some embodiments, the ABM comprises a heavy chain variable region that is at least 80%, at least 85%, at least 90%, at least 95%, at least 97%, or 100% identical to SEQ ID NO: 1, and a light chain variable region that is at least 80%, at least 85%, at least 90%, at least 95%, at least 97%, or 100% identical to SEQ ID NO: 2. In some embodiments, the ABM comprises a heavy chain variable region that is at least 80%, at least 85%, at least 90%, at least 95%, at least 97%, or 100% identical to SEQ ID NO: 1. In some embodiments, the ABM comprises a light chain variable region that is at least 80%, at least 85%, at least 90%, at least 95%, at least 97%, or 100% identical to SEQ ID NO: 2. In some embodiments, the ABM comprises a heavy chain variable region that is within SEQ ID NO. 1. In some embodiments, the ABM comprises a light chain variable region that is within SEQ ID NO. 2. In some embodiments, the ABM comprises at least one, two, or all three of a LCDR1, a LCDR2, and a LCDR3 within SEQ ID NO: 2 and at least one, two, or all three of a HCDR1, a HCDR2, and a HCDR3 within SEQ ID NO: 1. In some embodiments, the ABM comprises at least one, two, or all three of a LCDR1, a LCDR2, and a LCDR3 within SEQ ID NO: 2. In some embodiments, the ABM comprises at least one, two, or all three of a HCDR1, a HCDR2, and a HCDR3 within SEQ ID NO: 1. In some embodiments, the ABM comprises at least one, two, or all three of a LCDR1, a LCDR2, and a LCDR3 that are at least 80%, at least 85%, at least 90%, at least 95%, at least 97%, or 100% identical to comprises at least one, two, or all three of the LCDR1, the LCDR2, and/or the LCDR3, respectively, of SEQ ID NO: 2. In some embodiments, the ABM comprises at least one, two, or all three of a HCDR1, a HCDR2, and/or a HCDR3 that are at least 80%, at least 85%, at least 90%, at least 95%, at least 97%, or 100% identical to comprises at least one, two, or all three of the HCDR1, the HCDR2, and/or the HCDR3, respectively, of SEQ ID NO: 1.

In some embodiments, the ABM binds to a sequence that is at least 80%, at least 85%, at least 90%, at least 95%, at least 97%, or 100% identical to YTYTVYRDGTKIK (SEQ ID NO: 190).

The ABM can be administered according to any suitable dosing regimen, depending on the embodiment. The dosing regimen may depend on, for example, the severity of periodontal disease (e.g., gingivitis or periodontitis), and/or the strain of *P. gingivalis* involved in the periodontal disease (e.g., the virulence of the strain, the amino acid sequence of the ABM target expressed by the strain, etc.). In some embodiments, an effective dose of the ABM can be administered once to a subject. In some embodiments, an effective dose of the ABM can be administered repeatedly to a subject, e.g., at least 2, 3, 4, 5, 6, 7, 8, 9, 10, 12, 15, 20, 25, 30, 40 or 50 times or more, or any number of times in between any two of the numbers listed above. In some embodiments, the method includes administering the ABM at an interval of about 1, 2, 3, 4, 5, 6, 7, 8, 9, 10, 11, 12, 13, 14, 15, 16, 17, 18, 19, 20, 25, 30, 40, or about 50 days between any two consecutive doses. In some embodiments, the method includes administering the ABM 1-5 days, 6-10 days, 10-16 days, 16-20 days, 20-25 days, 25-30 days, 30-35 days, 35-40 days, including 40-50 days between any two consecutive doses. In some embodiments, after an initial dosing regimen, the ABM can be administered on a less frequent basis. For example, after weekly or biweekly administration for three months, treatment can be repeated once per month, for six months or a year or longer.

For systemic administration, subjects can be administered a therapeutic amount of the ABM, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

The dosage of an ABM as described herein can be determined by a physician and adjusted, as necessary, to suit observed effects of the treatment. With respect to duration and frequency of treatment, depending on the embodiments, a skilled clinicians can monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the ABM. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

The dosage ranges for the administration of the ABMs described herein, according to the methods described herein depend upon, for example, the form of the ABM, its potency, and the desired outcome, e.g., the extent to which symptoms are to be reduced, level of markers, or other indicators of a condition, such as inhibition of recolonization. The dosage should not be so large as to cause adverse side effects. The dosage can vary with the age, condition, and sex of the patient and can be determined by one of skill in the art.

In some embodiments, the method includes administering (e.g., subgingivally) about 2-5 µg, or about 3 µg, per tooth of the ABM in a subject's mouth every 2-4 days for 1-2 weeks (e.g., on days 1, 3, 7, and 10) to prevent recolonization for at least 9 months, e.g., at least 12 months.

Administering the ABM may be done using any suitable option. In some embodiments, the ABM is administered using a syringe, e.g., a Hamilton syringe. In some embodiments, the ABM is administered using a syringe equipped with a suitable gauge needle. In some embodiments, the ABM is administered with a blunt small gauge needle attached to the syringe.

Any suitable delivery system for intraoral, interproximal, intrasulcular, intraperiodontal pocket, intracanal, and intranasal delivery of the ABM can be used to administer the ABM to an oral site. Suitable systems can be, without limitation, mechanical or automated, dental or medical syringes, calibrated or non-calibrated. In some embodiments, a delivery system includes one or more attachments. The delivery system can have any suitable tip, including, but not limited to, blunt ended, and side port. In some embodiments, the delivery system includes a medicament delivery tray and systems, including, without limitation, PerioProtect Trays. In some embodiments, the delivery system includes a medicament applicator delivery system. In some embodiments, the delivery system includes a slow releasing medical preparation, e.g., for intrasulcular drug delivery. In some embodiments, a delivery system includes, without limitation, a filler, oral packing, fiber, microparticles, films, gels, injectable gels, vesicular systems, strips compacts, chip, hydrogel, thermal gel, liquid, solid, including, but not limited to, Actisite, Arestin, Atridox, Ossix Plus, Periochip, Periostat, Periofil. In some embodiments, the delivery system is an injectable system. In some embodiments, the delivery system is an irrigation system including, but not limited to piezoelectric or ultrasonic cavitron units, with or without reservoir, including, without limitation, Ora-Tec Viajet and Oral irrigation systems, including, without limitation, Interplak, Waterpik, Hydrofloss, Viajet, Airfloss and Pro.

In some embodiments, a subject has been diagnosed with a condition or disease, e.g., a *P. gingivalis* infection, chronic inflammation, multi-system inflammation, Alzheimer's disease, etc., that may be treated with a method of the present disclosure. In some embodiments, the subject is diagnosed with a condition or disease using a kit for detecting the presence of *P. gingivalis* on the subject, e.g., at a site of infection. In some embodiments, the kit is configured to detect the presence of *P. gingivalis* in an oral environment of the subject. In some embodiments, the kit is configured to detect the presence of *P. gingivalis* in a gingival environment of the subject. In some embodiments, the kit includes instructions for using the kit and/or provide the subject with recommendations to seek treatment based on the result of the diagnosis.

ADDITIONAL EMBODIMENTS

In some embodiments, an ABM of the present disclosure when topically applied via a solution to the infected gums of patients with *P. gingivalis* binds specifically to the bacterial outer membrane surface, e.g., the molecular complex in the outer- and inner-membranes of the secreted vesicles (exomes) containing complex of toxins (LPS), gingipain proteases, and hemagglutinin. In some embodiments, the ABM binds to a repeating epitope present on multiple localities of the pre- and post-processed hetero-dimer/trimer. In some embodiments, the ABM find use in a prolonged topical oral setting, or intravenous, subcutaneous, intradermal, nebulized or intra-thecal administration. Without being bound to theory, *P. gingivalis* is thought to relocate into various other tissues/organs/end capillary beds throughout the body and cause local inflammation at these sites. In some embodiments, delivering an ABM of the present disclosure to local or primary site of infection (e.g., oral or subgingival infection) addresses the systemic infection or distant infections at one or more secondary sites. In some embodiments, an ABM that is a nanobody allows for deeper tissue penetration, e.g., to treat various *P. gingivalis* related cancers.

A variety of conditions, disorders or diseases may be treated through the use of an ABM of the present disclosure. Without being limited by theory, the use of the ABM of the present disclosure to eliminate and/or prevent re-colonization of *P. gingivalis* in the sub-gingival gum line can in some embodiments interrupt and/or block, or over express the host's inflammatory pathways, such as the inflammasome NLRP3/Interleukin-1β/IL-6 pathways, AIM2, C-reactive protein, the PCSK9 pathway, and the Interleukin-1β innate immunity pathway. In addition, the local and systemic secretion by the bacteria of tissue-damaging outer-membrane vesicles containing a potent mixture of toxins can be curtailed. The ABM of the present disclosure can, in certain embodiments, allow for specifically and locally targeting the *P. gingivalis* oral infection, which can be the root cause of a chronic active inflammation and toxemia throughout the host's body. In some embodiments, use of the ABM to specifically target and eliminate the disease-causing bacterial source, while sparing other existing oral bacterial strains, provides for treatment of the systemic inflammation without interrupting the complex host inflammation pathways. In some embodiments, used of ABM as disclosed herein avoids or reduces local and/or systemic side effects that may result from intervening in the disrupting/reducing/overexpressing inflammatory pathways such as but not limited to inflammasome NLRP3/Interleukin-1β/IL-6 pathways. C-reactive protein, the PCSK9 pathway, and the Interleukin-1β innate immunity pathway for treating a disease.

In some embodiments, *P. gingivalis* infection occurs in the mouth, gum, teeth, oral cavity, brain, across the blood brain barrier, gut, blood, bone, and/or soft tissues. In some embodiments, *P. gingivalis* infection occurs in multiple organs. In some embodiments, *P. gingivalis* infection is local. In some embodiments, *P. gingivalis* infection is systemic. In some embodiments, *P. gingivalis* infection is one of several infections in a subject; non-limiting examples of which include *Helicobacter pylori*, Adenovirus, *Acinetobacter* spp., *Actinomyces* spp., *Aeromonas hydrophila*, *Aggregatibacter actinomycetemcomitans*, *Ascaris lumbricoides*, Astrovirus, *Bacillus* spp., *Bacillus cereus*, *Bifidobacterium* spp., *Campylobacter* spp., *Campylobacter jejuni*, *Campylobacter rectus*, *Candida albicans*, *Chlamydia trachomatis*, *Chlamydophila pneumoniae*, *Clostridium* spp., *Clostridium botulinum*, *Clostridium difficile*, *Clostridium perfringens*, *Clostridium tetanus*, Coronaviridaea, *Corynebacterium diphtheriae*, *Cryptococcus neoformans*, *Cryptosporidium parvum*, *Cyclospora cayetanensis*, *Eikenella corrodens*, *Entamoeba histolytica*, Enterobacteriaceae spp., *Enterobius vermicularis*, Enterovirus, *Escherichia coli*, *Eubacterium nodatum*, *Fusobacterium* spp., *Fusobacterium nucleatum*, *Giardia lamblia*, *Haemophilus influenzae*, *hepatitis*, *Hymenolepis nana*, *influenza*, *Klebsiella* spp., *Klebsiella pneumoniae*, *Lactobacillus casei*, *Listeria monocytogenes*, *Moraxella* spp., *Moraxella catarrhalis*, *Mycobacterium tuberculosis*, *Mycoplasma pneumoniae*, *Necator americanus*, *Neisseria gonorrhoeae*, *Neisseria meningitidis*, Norovirus, *Parvimonas micra*, *Pasteurella multocida*, *Peptostreptococcus*, *Prevotella Prevotella intermedia*, *nigrescens*, *Propionibacterium acne*, *Proteus mirabilis*, *Pseudomonas aeruginosa*, Rotavirus, *Salmonella typhi*, *Salmonella typhimurium*, *Serratia marcescens*, *Shigella dysenteriae*, *Shigella flexneri*, *Shigella sonnei*, *Staphylococcus aureus*, *Staphylococcus epidermidis*, *Streptococcus* spp., *Streptococcus agalactiae*, *Streptococcus enterococci*, *Streptococcus gordonii*, *Streptococcus intermedius*, *Streptococcus mitis*, *Streptococcus mutans*, *Streptococcus oralis*, *Streptococcus pneumoniae*, *Streptococcus pyogenes*, *Streptococcus sanquinis*, *Streptococcus sobrinus*, *Streptococcus viridans*, *Strongyloides stercoralis*, *Taenia saginata*, *Taenia solium*, *Tannerella forsythia*, *Treponema denticola*, *Vibrio cholerae*, and *Yersinia enterocolitica*. In some embodiments, the at least one additional infection is bacterial, viral, and/or parasite. In some embodiments, the multiple infections form a community biofilm. These biofilms may form a combination of virulence factors, any of which may be targeted as part of subsequent treatment. In some embodiments, virulence factors from *P. gingivalis* may be targeted as part of treatment or therapy.

In some embodiments, a *P. gingivalis* infection at an oral site affects end organs, such as, without limitation, large and small vessels of the heart, carotid arteries, vessels in the brain, liver, joints, lungs, pancreas, reproductive system. In some embodiments, the condition, disorder or disease is, without limitation, one or more of vascular disease (e.g., cardiovascular disease, atherosclerosis, coronary artery disease, myocardial infarction, stroke, and cardiac hypertrophy); systemic disease (e.g., type II diabetes, insulin resistance and metabolic syndrome); rheumatoid arthritis; cancer (e.g., oral, gastrointestinal, or pancreatic cancer); renal disease, gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity); post event myocardial hypertrophy, wound closure, AMD age related macro-degeneration, cerebral and abdominal aneurysms, glioma, large vessel stroke C-IMT, microvascular defects and associated dementias (e.g., Parkinson's), Peri-Implantitis, periodontal disease and/or associated bone loss, cognitive disorders (e.g., early middle late dementia Alzheimer's disease); regenerative and stem cell dysfunction; and age-related disorder. In some embodiments, the method involves any one of the above disorders, where the disorder is caused or complicated by *P. gingivalis*.

In some embodiments, the condition, disorder, disease, or complication is present in a single cell, organ, tissue, or organ system. In some embodiments, the condition, disorder, disease, or complication is present in multiple cells, organs, tissues, or organ systems.

As disclosed herein, there are many phenotypes that may occur during *P. gingivalis* infection. Non-limiting examples include an increase in CRISPR-Cas gene expression at the site of infection, an increase in local or systemic inflammation, an increase in the biofilm and/or presence of *P. gingivalis*, an increase in the activity or activation of inflammasomes, the diversion of oxygen, iron, and other nutrients to *P. gingivalis*, an increase in cytokine levels, increased host cell death, an increase in systemic inflammation, change of *P. gingivalis* protein expression, increased proinflammatory mediators, and enhanced chronic distant site inflammatory atherosclerosis. Subsequently, treatment by used of the present ABMs may inhibit, reduce, or eliminate any or multiple of the above phenotypes. In some embodiments, the *P. gingivalis* infection is in the mouth, gums, brain, gut/gastrointestinal system, blood brain barrier, bone, plasma/blood, soft tissue, or any combination thereof. In some embodiments, targeting the *P. gingivalis* infection further comprises administration of a small molecule, antibiotic, or drug affective against *P. gingivalis*. This will be understood to include any effective medicant that acts against *P. gingivalis*, including small molecules, antibiotics, or drugs that target *P. gingivalis* virulence factors, increases the production of proteases targeting *P. gingivalis*, reduces *P. gingivalis* oxygen, iron, and/or other nutrient uptake, alters protein production in *P. gingivalis*, alters bacterial metabolism, and/or enhances cell death for *P. gingivalis*.

Conditions, disorders or diseases treated by administration of an ABM of the present disclosure includes, without limitation, vascular disease (e.g., cardiovascular disease, atherosclerosis, coronary artery disease, myocardial infarction, stroke, and cardiac hypertrophy); systemic disease (e.g., type II diabetes, insulin resistance and metabolic syndrome); rheumatoid arthritis; cancer (e.g., oral squamous carcinomas, gastrointestinal cancer, pancreatic cancer, lung cancer, etc); gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity);

cognitive disorder (e.g., Alzheimer's disease); neuroinflammatory diseases; and longevity and/or age-related disorders. In general terms, the method includes identifying a subject in need of treating a condition, disorder or disease, as disclosed herein, and administering to the subject a therapeutically effective amount of the ABM of the present disclosure, to thereby treat the condition, disorder or disease.

In some embodiments, the condition, disorder or disease is a vascular disease. A variety of vascular diseases can be treated by use of the present ABMs. In some embodiments, the vascular disease is, without limitation, cardiovascular disease, atherosclerosis, coronary artery disease, myocardial infarction, stroke, or cardiac hypertrophy. Without being bound by theory, *P. gingivalis* and its virulence factors (e.g., outer membrane vesicles (OMVs), LPS, peptidylarginine deiminase (PPAD), gingipains, hemagglutinins, and fimbriae) are thought to disrupt the inflammatory pathways of heart and systemic vascular disease (CVD/Stroke), including the NLRP3/Interleukin-1B/IL-6 pathways, C-reactive protein (CRP) elevation, the PCSK9 pathway, and the suppression of adaptive immunity via reduction of regulatory T cells (Tregs). *P. gingivalis* infection can be associated with an increased risk of heart attack, and *P. gingivalis* is involved with forming oxidized LDL taken up by macrophages, leading to foam cell formation. These atherosclerotic lesions can develop a necrotic core, often forming a thrombus, leading to a downstream event (i.e. heart attack, stroke). Periodontal disease and/or *P. gingivalis* can be associated with elevated levels of systemic inflammatory markers, such as CRP, IL-6, and Lp-PLA2, Hb-A1c, IL-1b. *P. gingivalis* can play a major role in Abdominal Aortic Aneurysm development and salivary MPO enzyme activity. Periodontal therapy, as an intervention for improved oral health, can facilitate the management of thrombotic risk, and in the long term can contribute to the prevention of cardiovascular events in patients at risk.

In some cases, the development of atherosclerosis is due to systemic inflammation caused by severe periodontitis. Without being bound by theory, systemic inflammation induced by severe periodontitis, such as those associated with enhanced the secretion of pro-inflammatory cytokines from macrophages and increased the adhesion of monocytes to endothelial cells induce by *P. gingivalis* LPS, can exacerbate atherosclerosis via, in part, causing aberrant functions of vascular endothelial cells and the activation of macrophages. Further, patients with periodontitis can show higher serum pro-inflammatory cytokines such as tumor necrosis factor (TNF)-α, interleukin (IL)-1β, or IL-6. *P. gingivalis* can alter genes responsible for mitochondrial function and downregulate gene expression in the signaling pathway, which can lead to mitochondrial dysfunction and metabolic imbalance that promote the development of atherosclerosis. In some embodiments. *P. gingivalis* can prevent the regression of atherosclerotic plaques by interfering with reverse cholesterol transport. *P. gingivalis* can also promote atherosclerosis through alteration of gut microbiota, increased IL-1β, IL-18, and TNF-α production in peritoneal macrophages and gingival or aortic gene expression of the NOD-like receptor family, NLRP3, IL-1β, pro-IL-18 and pro-caspase-1, activation of the NLRP3 inflammasome, e.g., through CD36/SR-B2 and TLR2.

Chronic periodontitis (CP) can be associated with increased serum levels of HDL, Ox-LDL, hs-CRP, Hb-A1c, Lp-PLA$_2$, MPO, LDH, troponins T & I, NT pro-BNP, and P selectin. Further, infection of type II *P. gingivalis* can cause prolonged cytokine response such as IL-1β, IL-8 and TNFα.

Elevated cardiac markers found in periodontitis patients indicates that they may carry potential risks in developing cardiac lesions.

In some cases, *P. gingivalis* contribute to endothelial dysfunction and/or atherosclerotic cardiovascular disease. Without being limited by theory, *P. gingivalis* may cause vascular damage and increased endothelial permeability by degrading, via gingipain proteases, platelet endothelial cell adhesion molecule-1, and vascular endothelial cadherin, which play a role in endothelial junctional integrity. The vascular damage can increase endothelial permeability and initiate several processes implicated in atherosclerosis, including platelet aggregation, induction of proinflammatory cytokine release, and promotion of leukocyte extravasation to subendothelial regions.

Further, *P. gingivalis* promotes cardiac rupture after myocardial infarction (MI). Without being bound by theory, *P. gingivalis* is thought to invade the ischemic myocardium, promote cardiomyocyte apoptosis through activation of p18 Bax by gingipain, increase oxidative stress and MMP-9 protein level and activity, causing cardiac rupture. *P. gingivalis*-secreted factors can also promote cardiac hypertrophy, through activation of MEK/ERK signal pathways, Toll-like receptor-2 signaling. In some cases, mitogen-activated protein kinase kinase is involved in *P. gingivalis*-induced myocardial cell hypertrophy and apoptosis. In some cases, components of *P. gingivalis* spent culture medium increases total MEK-1 and ERK-1 protein products, but also causes increased cellular size, DNA fragmentation, and nuclear condensation in H9c2 cells. These three parameters, and the phosphorylated ERK-1 protein products of H9c2 cells treated with *P. gingivalis* medium, can be significantly reduced after pre-administration of U0126. The results indicate that *P. gingivalis*-secreted factors may initiate MEK/ERK signal pathways and lead to myocardial cell hypertrophy and apoptosis.

In some cases, *P. gingivalis* induces myocardial hypertrophy through Toll-like receptor-2 signaling in the isoproterenol-induced myocardial hypertrophy model. Regulation of chronic inflammation induced by periodontitis may have a key role in the treatment of myocardial hypertrophy. In some embodiments, *P. gingivalis* enhances myocardial vulnerability, thereby promoting post-infarct cardiac rupture. In some embodiments, Infection with *Porphyromonas gingivalis* (P.g.) promotes cardiac rupture after MI; P.g. invades the ischemic myocardium; Infection with P.g. promotes the accumulation of p18 Bax; Gingipains from P.g. activate Bax and promote cardiomyocyte apoptosis; Infection with P.g. promotes oxidative stress and MMP-9 protein level and activity.

In some embodiments, infection with periodontal pathogens can cause an adverse outcome after myocardial infarction (MI). C57BL/6J mice were inoculated with *Porphyromonas gingivalis* (P.g.), a major periodontal pathogen, or injected with phosphate-buffered saline (PBS) into a subcutaneously-implanted steelcoil chamber before and after coronary artery ligation. A significant increase in mortality, due to cardiac rupture, was observed in the P.g.-inoculated MI mice. Ultrastructural examinations revealed that P.g. invaded the ischemic myocardium of the P.g.-inoculated MI mice. The expression of p18 Bax, an active form of pro-apoptotic Bax protein, markedly increased in the P.g.-inoculated MI hearts. In vitro experiments demonstrated that gingipain, a protease uniquely secreted from P.g., cleaved wild type Bax at Arg34, as evidenced by the observation that the cleavage of Bax by gingipain was completely abolished by the Arg34Ala mutation in Bax. Treatment with immunoglobulin Y against gingipain significantly decreased the mortality of the P.g.-inoculated MI mice caused by cardiac rupture. Furthermore, inoculation of P.g. also resulted in an increase of MMP-9 activity in the post-MI myocardium by enhancing oxidative stress, possibly through impairing the selective autophagy-mediated clearance of damaged mitochondria. Without being bound by theory, infection with P.g. during MI can play a detrimental role in the healing process of the infarcted myocardium by invasion of P.g. into the myocardium, thereby promoting apoptosis and the MMP-9 activity of the myocardium, which, in turn, can cause cardiac rupture.

In some cases, *P. gingivalis* induces cellular hypertrophy and MMP-9 activity via different signaling pathways in H9c2 cardiomyoblast cells. *P. gingivalis* medium can elevate MMP-9 activity and induce cardiomyoblast hypertrophy. *P. gingivalis*-induced H9c2 cell hypertrophy was mediated through p38, ERK, PI3K, calcineurin, and JNK signaling pathways, which are in a totally different regulatory pathway from *P. gingivalis*-elevated MMP-9 activity. *P. gingivalis* infection activated multiple factors via different pathways to induce the development of hypertrophy of H9c2 cardiomyoblast cells.

In some cases, *P. gingivalis* deteriorates Isoproterenol-Induced myocardial remodeling in mice. In some situations, stronger cardiomyocyte hypertrophy can be observed in the ISO(+)/P.g.(+) mice compared with the ISO(+)/P.g.(−) mice. The total square of randomly selected cardiomyocytes was 23% larger in the ISO(+)/P.g.(+) mice than in the ISO(+)/P.g.(−) mice. A higher level of mRNA expression in Toll-like receptor 2 and NADPH oxidase 4 in the ISO(+)/P.g.(−) mice was detected compared with the control group. A periodontal pathogen affected ISO-induced cardiac hypertrophy via oxidative stress.

In some situations, *P. gingivalis*-related cardiac cell apoptosis can be co-activated by p38 and extracellular signal-regulated kinase pathways. In some situations, the development of cardiac cell apoptosis can be directly induced by *P. gingivalis* medium. *Porphyromonas gingivalis*-related H9c2 cell apoptosis was mainly co-activated by p38 and ERK pathways and may be involved in death receptor-dependent (caspase 8) and mitochondria (caspase 9)-dependent apoptotic pathways. *Porphyromonas gingivalis*-related cardiac cell apoptosis was also partially mediated by PI3K or calcineurin signaling pathways, whereas the JNK pathway might play a protective role in *P. gingivalis*-related cardiac cell apoptosis.

In some situations, the miRNA-212/132 family regulates both cardiac hypertrophy and cardiomyocyte autophagy. In some situations, miR-212/132 family has a key role in cardiac hypertrophy and heart failure development. Both miR-212 and miR-132 can target and negatively regulate the expression of the FoxO3 transcription factor, a powerful anti-hypertrophic and pro-autophagic factor in cardiomyocytes. The microRNA (miRNA)-212/132 family can regulate cardiac hypertrophy and autophagy in cardiomyocytes.

In some situations, *Porphyromonas gingivalis*-induced miR-132 regulates TNFα expression in THP-1 derived macrophages Live *P. gingivalis* infection induced miR-132 via TLR signaling and activation of NF-κB. Furthermore, inhibition of miR-132 expression strongly repressed the production of TNFα and increased NFE2L2 and NFAT5. Without being bound by theory, miR-132 modulates TNFα via inhibition of its target genes, which may provide a new window of opportunity to investigate therapeutic intervention for *P. gingivalis*-induced TNFα associated diseases such as periodontitis. Thus, ABMs of the present disclosure targeting *P. gingivalis* can be used to address these disorders, conditions or diseases in some embodiments.

In some embodiments, the condition, disorder or disease treated by the present methods is a wound. In some embodiments, administration of an ABM of the present disclosure promotes wound closure and/or prevents or reduces *P. gingivalis*-induced inhibition of wound closure. In some embodiments, a novel gingipain regulatory gene in *Porphyromonas gingivalis* mediates host cell detachment and inhibition of wound closure. In some situations, the pgn_0361 gene is involved in regulating gingipains. The PGN_0361-defective strain of *P. gingivalis* exhibited reduced virulence in terms of epithelial cell detachment and inhibition of wound closure. The culture supernatant of the mutant strain can highly inhibit wound closure, which may be due to high gingipain activity.

In some situations, the capsular polysaccharide and the Arg- and Lys-gingipains of *P. gingivalis* influences the capacity of *P. gingivalis* to hinder wound healing, while LPS and the major fimbriae may have no effect. In some situations, entry of *Porphyromonas gingivalis* Outer Membrane Vesicles into Epithelial Cells Causes Cellular Functional Impairment. Without being bound to theory, loss of intracellular TfR due to MVs causes serious impairment of cellular migration and proliferation. Fundamental cellular operations, including DNA synthesis and ATP generation, require iron, while transferrin-TfR complexes are internalized and ferric iron is released from transferrin at endosomal pH levels. TfR degradation by *P. gingivalis* can cause impairment of cellular functions, and it is notable that TfR is a target molecule of the bacterium. Thus, ABMs of the present disclosure targeting *P. gingivalis* can be used to address these disorders, conditions or diseases in some embodiments.

In some embodiments a balanced oral pathogenic bacteria and probiotics can promote wound healing via maintaining mesenchymal stem cell homeostasis. In some cases, *P. gingivalis* inhibits the functions of mesenchymal stem cells (MSCs) by activating NLRP3 inflammasome. LPS increase in *P. gingivalis* and thereby inhibits the functions of MSCs by activating NLRP3 inflammasome. Without being bound by theory, homeostasis of oral microbiomes can play a role in maintaining oral heath, provide options for the prevention and treatment of oral diseases, and have referential value for other systemic diseases caused by dysfunction of microbiota and MSCs. It is proposed that *P. gingivalis* lipopolysaccharide-treated human periodontal ligament stem cells (hPDLSCs) could used to study epigenetics modulations associated with periodontitis, which might be helpful to identify novel biomarkers linked to this oral inflammatory disease. Infection of hDFSCs with *P. gingivalis* can prolong the survival of neutrophils and increase their migration. These phenotypic changes can depend on direct cellular contacts and PPAD expression by *P. gingivalis*. Active JNK and ERK pathways in primed human dental follicle stem cells (hDFSCs) can be implicated in the phenotypic changes in neutrophils. In some cases, *P. gingivalis* can modify hDFSCs, thereby causing an immune imbalance and thus stem cell therapies may be improved and enhanced and protected by eliminating P.g. Thus, ABMs of the present disclosure targeting *P. gingivalis* can be used to address these disorders, conditions or diseases in some embodiments.

In some embodiments, the condition, disorder or disease is age-related macular degeneration (AMD). In some situations, *P. gingivalis* invades human retinal pigment epithelial cells, leading to vacuolar/cytosolic localization and autophagy dysfunction. In some situations, Periodontal disease (PD) is linked to age-related macular degeneration (AMD). *Porphyromonas gingivalis* (Pg), a keystone oral-pathobiont, can be causative of PD, and can efficiently invades human gingival epithelial and blood-dendritic cells. Live, but not heat-killed Pg-strains can adhere to and invade ARPEs. This involves early adhesion to ARPE cell membrane, internalization and localization of Pg within single-membrane vacuoles or cytosol, with some nuclear localization apparent. In infected human cells, Pg is found in vacuoles that contain undegraded ribosomes, where Pg ferments amino acids as an energy source. Co-localized ribosomes may provide a particularly digestible source of amino acids because of their enrichment for the positively charged residues that gingipains cleave. Cytosolically free Pg quickly localizes to the rough ER to form autophagosome-like vacuoles. Our model rather suggests that Pg OMVs entering the brain through the BBB are the more likely source of this diffuse toxic insult to the brain and not a direct infection by Pg. No degradation of Pg or localization inside double-membrane autophagosomes was evident, with dividing Pg suggesting a metabolically active state during invasion. Significant downregulation of autophagy-related genes particularly, autophagosome complex, can be observed. Antibiotic protection-based recovery assay further can confirm distinct processes of adhesion, invasion and amplification of Pg within ARPE cells. *P. gingivalis* can invade human-RPEs, begin to characterize intracellular localization and survive within these cells. The dysbiotic periodontal pathogen *P. gingivalis* can efficiently invade retinal epithelial cells in high levels, replicate and are sustained within them. This invasion and autophagy evasion by the keystone species may be one of the contributing elements in the pathogenesis of retinal degenerative diseases.

In some cases, invasion of RPE by Pg and mutants can elevate AMD-related genes involved in angiogenesis; immunosuppression and complement activation which might be the target molecules for both diseases. In some situations, infection of *Porphyromonas gingivalis*, A Keystone Bacterium in Periodontal Microbiota, is associated with a risk for diabetic retinopathy. In some situations, there is a significant association between a specific microbe in periodontal microbiota and DR, and oral microbiota play a role in retinal eye health.

In some situations, retinal blood flow and neurovascular are coupled in patients with Alzheimer's disease and mild cognitive impairment. In patients with MCI and AD, retinal blood flow and arterial vessel diameters can be reduced compared to healthy age- and sex-matched controls. No difference was found in flicker response between groups. This indicates alterations in retinal blood flow in patients with neurodegenerative disease. Thus, ABMs of the present disclosure targeting *P. gingivalis* can be used to address these disorders, conditions or diseases in some embodiments.

In some embodiments, the condition, disorder or disease is autism. In some situations, Autism spectrum disorder (ASD) is associated with several oropharyngeal abnormalities, including dysbiosis in the oral microbiota. Since the oral cavity is the start of the gastrointestinal tract, this strengthens and extends the notion of a microbial gut-brain axis in ASD and even raises the question whether a microbial oral-brain axis exists. It is clear that oral bacteria can find their way to the brain through a number of pathways following routine dental procedures. A connection between the oral microbiota and a number of other brain disorders has been reported.

In some situations, C1q as a regulator of brain development is implicated in autism spectrum disorders. Autism spectrum disorders (ASDs) represents a heterogeneous group of neurodevelopmental disorders with similar core features of social and communication impairments, restricted interests and repetitive behaviors. Early synaptic dysfunction due to neuroinflammatory insults may underpin the pathogenesis of abnormal brain development in some of individuals with ASDs. As a component of the innate immune response, the complement system can comprise both directly acting factors and factors that augment other components of the immune system. Beyond its involvement with innate immune responses in the brain, the complement system also plays important roles in neurodevelopment. Recent studies indicate involvement of complement component C1q in fundamental neurodevelopmental pathways and in maintenance and elimination of dendrites and synapses. The impact of aberrant complement system activity during critical windows of brain development may not only affect the local immune response but lead to atypical brain development. Thus, ABMs of the present disclosure targeting *P. gingivalis* can be used to address these disorders, conditions or diseases in some embodiments.

In some embodiments, the condition, disorder or disease is large vessel stroke, C-IMT (Carotid Intima-media Thickness). In some cases, periodontal treatment can have an effect on carotid intima-media thickness in patients with lifestyle-related diseases. At baseline, LDL-C (low-density lipoprotein cholesterol) levels and percentage (%) of mobile teeth can be positively related to plasma IgG (immunoglobulin) antibody titer against *P. gingivalis*. Corresponding to improvements in periodontal clinical parameters after treatment, right and left max IMT (maximum intima-media thickness) levels cam be decreased significantly after treatment (SPT-S: start of supportive periodontal therapy, SPT-1y: at 1 year under SPT, and SPT-3y: at 3 years under SPT). *P. gingivalis* infection can be positively associated with progression of atherosclerosis. Without being bound by theory, routine screening using plasma IgG antibody titer against *P. gingivalis* and periodontal treatment under collaborative with medical and dental care may prevent cardiovascular accidents caused by atherosclerosis.

*P. gingivalis* infection can be associated with LDL-C level, which facilitates atherosclerosis, and that periodontal treatment, in collaboration with medical care for atherosclerosis, may contribute to improvements in max carotid IMT. Plasma *P. gingivalis* IgG titer may be useful for the early detection of atherosclerosis. Finally, periodontal treatment is considered to be important for preventing the onset of cerebral and myocardial infarctions caused by atherosclerosis.

In some situations, overall periodontal bacterial burden can be related to carotid IMT. In some situations, changes in clinical and microbiological periodontal profiles relate to progression of carotid intima-media thickness. In some situations, improvement in periodontal status—defined both clinically and microbiologically—is associated with less progression in carotid atherosclerosis in a randomly selected population-based sample of men and women. Accelerated atherosclerotic progression can be a mechanistic explanation linking periodontal disease and clinical CVD. Thus, ABMs of the present disclosure targeting *P. gingivalis* can be used to address these disorders, conditions or diseases in some embodiments.

In some embodiments, the condition, disorder or disease is a systemic disease, e.g., a systemic metabolic disorder. A variety of systemic diseases can be treated by use of the present ABMs, as disclosed herein. In some embodiments, the systemic disease is, without limitation, type II diabetes, insulin resistance or metabolic syndrome. Without being bound by theory, *P. gingivalis* virulence factors can allow the pathogen's invasion to the periodontal tissue and subsequent dissemination into the systemic circulation, increasing the risk of systemic chronic diseases such as type 2 diabetes mellitus (T2DM), cardiovascular diseases, nonalcoholic fatty liver disease (NAFLD), rheumatoid arthritis, and Alzheimer disease. As used herein, "insulin resistance" refers to the reduction or loss of the response of the target organs and tissues to the biological effects of insulin, resulting in decreased efficiency of cell uptake and utilization of glucose and the occurrence of abnormal metabolism of glucose and lipids in cells. In some cases, *P. gingivalis* outer membrane vesicles (OMVs) can deliver gingipains to the liver, where gingipains can regulate hepatic glycogen synthesis by attenuating insulin sensitivity through the Akt/GSK-3ß signaling pathway. Thus, *P. gingivalis* in the oral cavity can influence hepatic glucose metabolism by decreasing insulin sensitivity in the liver cells. Further, *P. gingivalis* can induce insulin resistance through branched-chain amino acids (BCAA) biosynthesis. In addition, *P. gingivalis*/gingipain can translocate from the oral cavity to pancreatic islets and become localized primarily in B-cells, and may be epigenetically influencing development of bihormonal cells. Thus, ABMs of the present disclosure targeting *P. gingivalis* can be used to address these disorders, conditions or diseases in some embodiments.

In some embodiments, the condition, disorder or disease is rheumatoid arthritis (RA). Without being bound by theory, antibodies against *P. gingivalis* have been found to be associated with RA and with anti-citrullinated protein antibodies (ACPA). Moreover, the DNA of *P. gingivalis* has been detected in the synovial fluid and plasma samples from patients with RA, and the coexistence of RA and periodontitis increased the probability of finding *P. gingivalis* DNA in these compartments. Clinical signs and symptoms of RA can improve after periodontal treatments and resolution of periodontitis. Thus, ABMs of the present disclosure targeting *P. gingivalis* can be used to address these disorders, conditions or diseases in some embodiments.

In some embodiments, the condition, disorder or disease is cancer. In some embodiments, the cancer is, without limitation, oral, gastrointestinal, or pancreatic cancer. In some embodiments, the cancer is, without limitation, esophageal squamous cell carcinoma, head and neck (larynx, throat, lip, mouth and salivary glands) carcinoma. Without being bound to theory, *P. gingivalis* can promote distant metastasis and chemoresistance to anti-cancer agents and accelerate proliferation of oral tumor cells by affecting gene expression of defensins, by peptidyl-arginine deiminase and noncanonical activation of β-catenin. In some cases, the pathogen can convert ethanol to the carcinogenic intermediate acetaldehyde. In addition, *P. gingivalis* can be implicated in precancerous gastric and colon lesions, esophageal squamous cell carcinoma, head and neck (larynx, throat, lip, mouth and salivary glands) carcinoma, and pancreatic cancer. *P. gingivalis* can have systemic tumorigenic effects in addition to the local effects in its native territory, the oral cavity. Thus, ABMs of the present disclosure targeting *P. gingivalis* can be used to address these disorders, conditions or diseases in some embodiments.

In some embodiments, an ABM of the present disclosure may be administered in conjunction with one or more cancer therapy agents, e.g., chemotherapeutic agent, to enhance the therapeutic effect of the cancer therapy agent. In some embodiments, the cancer therapy agent is a small molecule drug, or an immunotherapeutic agent. In some cases *P. gingivalis*, its OMVs and/or gingipains have been found to cause an overall immunosuppression of the host, suppressing the adaptive immune system and altering the innate immune system. Adjuvant therapy of eliminating P.g. for improved outcomes for current and future chemotherapies. In some cases, *P. gingivalis* can inhibit drug induced apoptosis as well as necrosis (at least the LDH release) in the esophageal squamous cell carcinoma cell line EC0706. When the cancer cells are infected with *P. gingivalis* prior to the treatment with cisplatin, both apoptosis and necrosis is significantly reduced. Tumor xenografts composed of *P. gingivalis*-infected OSCC cells can exhibit a higher resistance to Taxol through Notch1 activation, as compared with uninfected cells. Furthermore, *P. gingivalis*-infected OSCC cells can form more metastatic foci in the lung than uninfected cells. Sustained infection with *P. gingivalis*, can promote distant metastasis of oral cancer, as well as its resistance to anti-cancer agents. Oral cancer cells sustainedly infected with *Porphyromonas gingivalis* can exhibit resistance to Taxol and have higher metastatic potential. Thus, in some embodiments, treating and eliminating P.g. with the ABMs improves multiple primary, secondary and adjuvant related cancer treatments.

In some embodiments, the condition, disorder or disease to be treated by the present methods is a lung disease, such as non-smokers lung cancer and aspiration pneumonia. In some embodiments, targeting inflammation with anti-inflammatory therapy can lead to a significantly lower rate of recurrent cardiovascular events independent of lipid-level lowering. There can be a substantial lowering of non-smokers lung cancer with anti-inflammatory therapy targeting the interleukin-1b innate immunity pathway leading to significantly lower cancer mortality consistent with experimental data relating to interleukin-1b.

In some situations, *Porphyromonas gingivalis* is the primary microbial pathogen as single source driver of inflammation and it's multiple NLRP3/IL-1 β pathway mediated diseases including Atherosclerosis and Cardiovascular disease. In some situations, Infection with *P. gingivalis* can trigger the activation of NLRP3 and AIM2 inflammasomes via TLR2 and TLR4 signaling, leading to IL-1B secretion and pyroptic cell death. In addition, *P. gingivalis*-induced NLRP3 inflammasome activation can be dependent on ATP release, K+ efflux, and cathepsin B. In some embodiments, any of the ABM can be used to alter TLR4 signaling.

Without being bound by theory, the periodontopathogen *Porphyromonas gingivalis* has been shown to have several mechanisms of modulating innate immunity by limiting the activation of the NLRP3 inflammasome. The innate immune system can be the first line of defense against microbial pathogens. *P. gingivalis* can modify innate immunity by affecting inflammasome activity.

Wild type challenge of apolipoprotein E-deficient, spontaneously hyperlipidemic (ApoE) mice with *P. gingivalis* can increase IL-1B, IL-18, and TNF-α production in peritoneal macrophages and gingival or aortic gene expression of the NOD-like receptor family. NLRP3, IL-1β, pro-IL-1β and pro-caspase-1.

In some situations, outer membrane vesicles derived from *Porphyromonas gingivalis* can induce cell death with disruption of tight junctions in human lung epithelial cells. *P.*

*gingivalis* OMVs can cause cell damage with cell membrane destruction in Human lung epithelial cell. *P. gingivalis* OMVs suppressed cell viability of Human lung epithelial cell by causing apoptosis. *P. gingivalis* OMVs translocated through oral cavity may be a trigger for inflammation of airway diseases. Thus, ABMs to this target can be used to address this in some embodiments.

In some situations, *P. gingivalis* OMVs can induce cell death by destroying the barrier system in lung epithelial cells. *P. gingivalis* OMVs may be a factor in the engagement of periodontitis with respiratory system diseases.

In some situations, *Porphyromonas gingivalis* is an aggravating factor for chronic obstructive pulmonary disease patients with periodontitis. The microbial analysis of sputum from COPD patients with CP to detect periodontal pathogen *Porphyromonas gingivalis* (*P. gingivalis*) both before and after nonsurgical periodontal therapy. A decrease in the count of *P. gingivalis* and decreased periodontal indices values can be observed in COPD patients with periodontitis after nonsurgical periodontal therapy. Lung function test (forced expiratory volume in the first/forced vital capacity) can be improved in COPD patients with periodontitis after nonsurgical periodontal therapy. In some embodiments, nonsurgical periodontal therapy can be a part of treatment protocol in COPD patients because it helps in reducing the *P. gingivalis* count and improves the lung function.

In some situations, gingipains are factors in the development of aspiration pneumonia caused by *Porphyromonas gingivalis*. Aspiration pneumonia can be a life-threatening infectious disease often caused by oral anaerobic and periodontal pathogens such as *Porphyromonas gingivalis*. This organism can produce proteolytic enzymes, known as gingipains, which can manipulate innate immune responses and promote chronic inflammation. *P. gingivalis* W83 gingipains can have a role in bronchopneumonia, lung abscess formation, and inflammatory responses. Gingipains can be important for clinical symptoms and infection-related mortality. Pathologies caused by wild-type (WT) *P. gingivalis* W83, including hemorrhage, necrosis, and neutrophil infiltration, can be absent from lungs infected with gingipain-null isogenic strains or WT bacteria preincubated with gingipain-specific inhibitors. Damage to lung tissue can be correlated with systemic inflammatory responses, as manifested by elevated levels of TNF, IL-6, IL-17, and C-reactive protein. These effects can be dependent on gingipain activity. Gingipain activity can also be implicated in the observed increase in IL-17 in lung tissues. Furthermore, gingipains can increase platelet counts in the blood and activated platelets in the lungs. Arginine-specific gingipains can make a greater contribution to *P. gingivalis*-related morbidity and mortality than lysine-specific gingipains. Thus, inhibition of gingipain may be a useful adjunct treatment for *P. gingivalis*-mediated aspiration pneumonia.

One of the pathogenic outcomes of *P. gingivalis*-triggered aspiration pneumonia can be thrombocytosis. Thrombocytosis can be associated with inflammatory disease, and the platelet count can be an acute-phase response to inflammation induced by *P. gingivalis*.

Animals challenged with WT *P. gingivalis* can show a sharp increase in TNF-α. IL-6, and MCP1 levels. The lungs from infected animals can show clear increases in MPO levels, which are indicative of neutrophil infiltration. The highest MPO concentrations can be detected in lung homogenates from animals infected with WT *P. gingivalis*, whereas those from mice infected with the ΔKgp and ΔRgp strains can show significantly lower MPO activity.

Intratracheal inoculation with either WT *P. gingivalis* or ΔKgp can lead to a significant increase in IL-17 expression in lung tissue and peripheral blood. Proteolytically active gingipains can modulate the course of *P. gingivalis*-associated aspiration pneumonia and aggravate the host immune response. *P. gingivalis*-derived enzymes can play an important role not only during chronic disease (e.g. periodontitis) but also during acute, life-threatening pneumonia. In some situations, TLR2 is implicated in Early Innate Immune Response to Acute Pulmonary Infection with *Porphyromonas gingivalis* in Mice. The periodontal pathogen *Porphyromonas gingivalis* is implicated in certain systemic diseases including atherosclerosis and aspiration pneumonia. This organism can induce innate responses predominantly through TLR2, which also mediates its ability to induce experimental periodontitis and accelerate atherosclerosis. TLR2-deficient mice can elicit reduced proinflammatory or antimicrobial responses (KC, MIP-1, TNF-, IL-6, IL-12p70, and NO) in the lung and exhibited impaired clearance of *P. gingivalis* compared with normal controls. However, the influx of polymorphonuclear leukocytes into the lung and the numbers of resident alveolar macrophages (AM) can be comparable between the two groups. TLR2 signaling can be important for in vitro killing of *P. gingivalis* by polymorphonuclear leukocytes or AM and, moreover, the AM bactericidal activity can require NO production. Strikingly, AM can be more potent than peritoneal or splenic macrophages in *P. gingivalis* killing, attributed to diminished AM expression of complement receptor-3 (CR3), which is exploited by *P. gingivalis* to promote its survival. Without being bound by theory, the selective expression of CR3 by tissue macrophages and the requirement of TLR2 inside-out signaling for CR3 exploitation by *P. gingivalis* indicates that the role of TLR2 in host protection may be contextual. In some embodiments, TLR2 may mediate destructive effects, as seen in models of experimental periodontitis and atherosclerosis, and the same receptor can confer protection against *P. gingivalis* in acute lung infection.

In some situations, periodontopathic anaerobes are involved in aspiration pneumonia. *Porphyromonas gingivalis* and *Treponema denticola* can coexist in chronic periodontitis lesions. In some situations, a mixed culture of *P. gingivalis* and *T. denticola* can be inoculated into the mouse trachea; and cause an infection inducing inflammatory cytokine production and pneumonia. In another series of investigations, professional oral health care (POHC), mainly cleansing administered by dental hygienists once a week for 24 months to elderly persons requiring daily care, can result in the reduction of the number of total anaerobes, *Candida albicans*, and *Staphylococcus* species and in the number of cases of fatal aspiration pneumonia. The POHC treatment of elderly persons for 6 months in the winter season can reduce the salivary levels of protease, trypsin-like activity, and neuraminidase and also can decrease the frequency of influenza cases.

In some embodiments, *Porphyromonas gingivalis* can induce inflammatory responses and promote apoptosis in lung epithelial cells infected with H1N1 via the Bcl-2/Bax/Caspase-3 signaling pathway. *P. gingivalis* may induce the production of a large number of inflammatory cytokines in lung epithelial cells. Lung epithelial cells infected with H1N1 and *P. gingivalis* can lead to the promoted production of inflammatory cytokines and the expression of iNOS, which may have also increased the accumulation of NO, resulting in an increased proportion of lung epithelial cells undergoing apoptosis via the Bcl-2/Bax/caspase-3 signaling pathway. Following BEAS-2B cell infection with *P. gingi-*

*valis* and H1N1, the concentrations of TNF-α, IL-1β and IL-6 in the supernatant can be significantly increased at each time point, compared with the H1N1 and *P. gingivalis* alone groups. These results demonstrated that lung epithelial cells infected with H1N1 and *P. gingivalis* can promote the production of inflammatory cytokines.

In some situations, *Porphyromonas gingivalis* modulates *Pseudomonas aeruginosa*-induced apoptosis of respiratory epithelial cells through the STAT3 signaling pathway. *P. gingivalis* invasion can transiently inhibit *P. aeruginosa*-induced apoptosis in respiratory epithelial cells via the signal transducer and activator of transcription 3 (STAT3) signaling pathway. The activated STAT3 can up-regulate the downstream anti-apoptotic moleculars survivin and B-cell leukemia-2 (bcl-2). This process can be accompanied by down-regulation of pro-apoptosis molecular Bcl-2-associated death promoter (bad) and caspase-3 activity inhibition. In addition, the activation of the STAT3 pathway can be affected by *P. gingivalis* in a dose-dependent manner. Finally, co-invasion of *P. aeruginosa* and *P. gingivalis* can lead to greater cell death compared with *P. aeruginosa* challenge alone. These results indicate that regulation of *P. aeruginosa*-induced apoptosis by *P. gingivalis* can contribute to the pathogenesis of respiratory disease. Thus, ABMs of the present disclosure targeting *P. gingivalis* can be used to address these disorders, conditions or diseases in some embodiments.

In some embodiments, oral cancer cells sustainedly infected with *Porphyromonas gingivalis* can exhibit resistance to Taxol and can have higher metastatic potential. Sustained infection with *P. gingivalis*, a major pathogen responsible for chronic periodontitis, can promote distant metastasis of oral cancer, as well as its resistance to anticancer agents. Thus, ABMs of the present disclosure targeting *P. gingivalis* can be used to address these disorders, conditions or diseases in some embodiments.

In some embodiments, the condition, disorder or disease treated by the present methods is Glioma. Without being bound by theory, Cathepsin B plays a critical role in inducing Alzheimer's Disease-like phenotypes following chronic systemic exposure to lipopolysaccharide from *Porphyromonas gingivalis* in mice. In some cases, systemic exposure to LPS from *Porphyromonas gingivalis* can induce AD-like phenotypes; Cathepsin B is implicated in inducing microglia-mediated neuroinflammation; Cathepsin B is implicated in inducing microglia-dependent Aβ accumulation in neurons. In some situations, a strong association can exist between periodontitis and accelerated cognitive decline in Alzheimer's disease (AD). Cathepsin (Cat) B can play a critical role in the initiation of neuroinflammation and neural dysfunction following chronic systemic exposure to lipopolysaccharide from *Porphyromonas gingivalis* (PgLPS). Thus, ABMs of the present disclosure targeting *P. gingivalis* can be used to address these disorders, conditions or diseases in some embodiments.

In some embodiments, the condition, disorder or disease is a gut microbiome-related disorder. A variety of gut microbiome-related disorder can be treated by the ABMs of the present disclosure. In some embodiments, the gut microbiome-related disorder is an intestinal disorder such as, without limitation, inflammatory bowel disease, irritable bowel syndrome (IBS), coeliac disease. In some embodiments, the gut microbiome-related disorder is an extraintestinal disorder such as, without limitation, allergy, asthma, metabolic syndrome, cardiovascular disease, and obesity. Without being limited by theory, endotoxemia that may cause metabolic disorders can be related to changes in the gut microbiota caused by oral bacteria, e.g., *P. gingivalis*. In some cases, periodontal inflammation can affect the mechanical and immune barrier functions of the gut. Orally administered *P. gingivalis* can cause composition shifts in the gut microbiota and increase serum endotoxin and inflammatory markers, and affect the gut immune system. In addition, *P. gingivalis* has been associated with NAFLD and non-alcoholic steatohepatitis (NASH). *P. gingivalis* can be detected in the gut of the NAFLD and NASH patients. Thus, ABMs of the present disclosure targeting *P. gingivalis* can be used to address these disorders, conditions or diseases in some embodiments.

In some embodiments, the condition, disorder or disease is a cognitive disorder. In some embodiments, the condition, disorder or disease is dementia associated with microvasculature defects. In some embodiments, the condition, disorder or disease is microvascular defects Parkinson's.

In some situations, cerebral oxidative stress and microvasculature defects are implicated in TNF-α Expressing Transgenic and *Porphyromonas gingivalis*-Infected ApoE-/- Mice. There can be a major difference in the hippocampi of *P. gingivalis*-infected and sham-infected ApoE-/- mice, in terms of increased protein carbonyl/oxidized protein content in the hippocampal micro-vasculature. Hippocampal microvascular structures and the homeostasis of the brain can be at risk from elevated oxidative stress and oxidative protein damage, following *P. gingivalis* infection. Without being bound by theory, following recurrent episodes of active periodontal disease, there exists a possibility for the development of a defective BBB, post neuroinflammation-mediated cerebral parenchymal tissue injury. The rising levels of intrinsic and extrinsic sources of cytokines, oxidative stress, and developing BBB defects may be implicated as early modifiers of neurodegenerative and disease severity leading to deteriorating memory. Infection with *P. gingivalis* can be interpreted as one of the plausible mechanisms by which a susceptible host can develop dementia.

A variety of cognitive disorders can be treated by the ABMs of the present disclosure. In some embodiments, the cognitive disorder is Alzheimer's disease (AD). Without being bound by theory, periodontitis has been shown to be a risk factor for AD and a more rapid cognitive decline. In some cases, genetic predisposition, *P. gingivalis* infection and microglia could promote neurodegeneration typical of that reported for AD. *P. gingivalis* specific cell free DNA can be detected in the cerebrospinal fluid of AD patients and the pathogen's protease virulence factors, arginine-gingipain (Rgp) and lysine-gingipain (Kgp), can be found in the brains of over 90% of AD patients and can correlate with tau and ubiquitin pathology. Concurrently, there is evidence of Pg OMVs either targeting and/or seeking out tissues higher in arginine and lysine amino acids *P. gingivalis* can invade and persist in mature neurons, which, once infected, can display signs of AD-like neuropathology, including the accumulation of autophagic vacuoles and multivesicular bodies, cytoskeleton disruption, an increase in phosphotau/tau ratio, and synapse loss. Gingipains of *P. gingivalis* can digest tau protein into peptide fragments, some of which include tau residues prone to phosphorylation and some of which include two of the four microtubule binding domains that form paired/straight helical filaments constituting neurofibrillary tangles (NFTs). In some cases, Gingipains have been found to be neurotoxic in vivo and in vitro, having detrimental effects on tau. *P. gingivalis* lipopolysaccharide (LPS) can activate the phosphoinositide 3-kinase/Akt (PI3K/AKT) pathway and increase expression of glycogen synthase kinases-3 beta (GSK-3β), which can phosphorylate tau. *P. gingivalis* can invade and survive in neurons and generate intra-neuronal gingipains that are proteolytically active, leading to neurodegeneration associated with AD. This observation is consistent with studies looking at the neuroanatomical analysis of Pg associated genes (gingipains) which mark cholinergic neurons, basal forebrain and anterior hypothalamic regions; regions near ventricles and peripheral neurons are also enriched, suggesting relevance to Pg brain entry. In addition to amyloid plaques and neurofibrillary tangles, functional studies suggest that hypothalamic dysfunction is a common event in AD, often early in the course of disease. Although there are evidences indicating that certain hypothalamic regions are also affected in Frontal temporal lobe dementia (FTD), specifically those that correlate with abnormal eating behaviors, they are different to those affected in AD. A possible explanation could be that the hypothalamic region, which controls body innate immunity, is affected in the earliest pro-domal stages of AD, but not in FTD. The apparently AD-specific salivary Lf reduction may thus not only be useful in the differential diagnosis but could also provide important insights into selective immune vulnerability in neurodegenerative diseases. As mentioned above the secretion of salivary proteins is controlled by cholinergic parasympathetic nerves that release acetylcholine, evoking the secretion of saliva by acinar cells in the salivary gland. These parasympathetic nerves are connected with the hypothalamus. We propose that early hypothalamic AB accumulation is associated with Pg OMVs gingipains deposition found in postmortem brain tissue with the upregulation of ER translocation genes in the context of Alzheimer's disease. This could be an early switch that begins the loss of control and disrupt hypothalamic function affecting salivary gland regulation that ultimately results in reduced salivary Lf secretion. Pg is known to degrade Lf for its major early iron source in oral cavity. Should neural based impairment of the salivary glands produce a decline in the steady-state level of Lf, a major switch in an otherwise delicate balance between Pg and the oral cavity may ensue. More specifically, the diminishing oral salivary iron source would further signal to Pg the need for new iron source. In some embodiments, a subject with Down's syndrome is at increased risk of developing AD.

In some cases, *P. gingivalis* can induce migration of microglial cells to sites of infection in the brain, through activation of mitogen-activated protein kinase/extracellular signal-regulated kinase (ERK) kinase/ERK pathway. *P. gingivalis* can induce synthesis of matrix metalloproteinases (MMPs), which can have an important role in neuroinflammatory disorders including AD. Oral infection with *P. gingivalis* can result in the pathogen spreading to the brain and activating microglia. *P. gingivalis* can downregulate TREM-2 expression in microglia. Lack of TREM-2 protein may accelerate aging processes, neuronal cell loss and reduce microglial activity leading to neuroinflammation. *P. gingivalis* can contribute to development of AD inflammatory pathology through mechanisms involving acute phase proteins, cytokines and the complement cascade where neurons would be attacked. Inappropriate complement activity can play a significant role in AD pathophysiology.

LPS, a virulence factor of *P. gingivalis*, in the brain can initiate neuroinflammation in the form of microglial cell activation, and the neuroinflammatory response can be stronger with age. Age-associated priming of microglia may have a role in exaggerated inflammation induced by activation of the peripheral immune system. In some cases, *P. gingivalis* can cause an imbalance in M1/M2 activation in macrophages, resulting in a hyperinflammatory environment that promotes the pathogenesis of periodontitis, and leptomeningeal cells can transduce inflammatory signals from peripheral macrophages to brain resident microglia exposed to *P. gingivalis* LPS. In microglia, *P. gingivalis* LPS can increase the production of cathepsin B and pro-forms of caspase-1 and IL-1ß through activation of Toll-Like Receptor (TLR) 2/NF-kB signaling. Cathepsin B is implicated in in *P. gingivalis* LPS-induced AD-like pathology, and may be necessary for the induction of AD-like pathology following chronic systemic exposure to *P. gingivalis* LPS. In some cases, treating periodontitis can lead to improvements in cognition. A chronic infection of the brain with *P. gingivalis* can cause serious consequences for the BBB and subsequent mental health. Thus, ABMs of the present disclosure targeting *P. gingivalis* can be used to address these disorders, conditions or diseases in some embodiments.

In some embodiments, the condition, disorder or disease is an age-related disorder. Without being bound by theory. *P. gingivalis* can impact cellular biochemical pathways that are associated with improved longevity or shortened life spans, e.g., by regulating autophagy and apoptosis, modulating the mTORC1 pathway, or targeting cellular senescence by selectively eliminating senescent cells. Disrupted autophagy has been linked to numerous diseases including Parkinson's disease, and type 2 diabetes. In some cases, *P. gingivalis* minor (Mfa1) fimbriae can manipulate dendritic cell (DC) signaling to perturb both autophagy and apoptosis. Mfa1 can induce Akt nuclear localization and activation, and ultimately can induce mTOR in DCs. *P. gingivalis* can promote DC survival by increasing anti-apoptotic Bcl2 protein expression and decreasing pro-apoptotic proteins Bim, Bax and cleaved caspase-3. In some cases, lipophilic outer membrane vesicles (OMV) shed from *P. gingivalis* can promote monocyte unresponsiveness to live *P. gingivalis*. Full reactivity to *P. gingivalis* can be restored by inhibition of mTOR signaling, which can promote Toll-like receptor 2 and Toll-like receptor 4 (TLR2/4)-mediated tolerance in monocytes. Without being bound by theory, it is thought that *P. gingivalis*, a facultative intracellular microbe, may damage not only cell membranes but also the mitochondrion, triggering a bioenergetic crisis and NLRP3-induced cellular senescence. Moreover, age-related brain LPS elevation may trigger intracellular iron migration, an innate immune response to withhold iron from pathogens.

Without being bound by theory, the major surface glycoproteins of *P. gingivalis*—Pgm6 and Pgm7, also called outer membrane protein A-like proteins (OmpALPs)—mediate resistance to the bactericidal activity of human serum, and specifically protect *P. gingivalis* from the bactericidal activity of LL-37 and from innate immune recognition by TLR4. LL-37 proteolysis by *P. gingivalis* may provide neighboring dental plaque species with resistance to LL-37, which in turn can benefit *P. gingivalis*. Thus, ABMs of the present disclosure targeting *P. gingivalis* can be used to address these disorders, conditions or diseases in some embodiments.

In some embodiments, the condition, disorder or disease is an aneurysm, e.g., cerebral or abdominal aneurysm. In some cases, pro-inflammatory response elicited by *Porphyromonas gingivalis* lipopolysaccharide exacerbates the rupture of experimental cerebral aneurysms. *Porphyromonas gingivalis* LPS can exacerbate vascular inflammation and can enhance the rupture of intracranial aneurysms.

In some situations, CPI can be significantly higher in patients with IAs than the controls (2.7 vs 1.9, p<0.05) and their DNA level of subgingival plaques and their plasma IgG titers of Pg can also be higher. Periodontal disease can be more severe and the plasma IgG titers of Pg can be higher in patients with ruptured—than unruptured IAs, suggesting that Pg is associated not only with the formation but also the rupture of IAs. Severe periodontal disease and Pg infection may be involved in the pathophysiology of IAs.

In some situations, the condition, disorder or disease is depression. Without being bound by theory, it is thought *Porphyromonas gingivalis* can induce depression via downregulating p75NTR-mediated BDNF maturation in astrocytes. In some embodiments, Pg-LPS decreases the level of astrocytic p75NTR and then downregulates BDNF maturation, leading to depression-like behavior in mice. Pg can be a modifiable risk factor for depression. In some embodiments, *Porphyromonas gingivalis* (Pg) can induce depression-like behaviors; Astrocytic p75NTR can be decreased in Pg-colonized mice; Overexpression of p75NTR in astrocytes can rescue depressive behaviors; Antibiotic therapy can ameliorate Pg-induced depressive behavior in mice. Thus, ABMs of the present disclosure targeting *P. gingivalis* can be used to address these disorders, conditions or diseases in some embodiments.

In some embodiments, the condition, disorder or disease is peri-implantitis. In some situations, oral infection with *Porphyromonas gingivalis* can induce peri-implantitis, and can be implicated in bone loss and the local inflammatory response. *Porphyromonas gingivalis* infection can induce greater bone loss around implants than around teeth. In non-infected animals, the presence of the implant can correlate with elevated expression of Il-10, Foxp3 and Rankl/Opg ratio, while Tnf-α levels can be decreased relative to tissue around teeth. Six weeks following infection. Tnf-α can be increased significantly while the expression of Foxp3 can be decreased in the tissue around the implants. Oral infection with *P. gingivalis* of mice with implants can induce bone loss and a shift in gingival cytokine expression. In some situations, the fimA type Ib genotype of *P. gingivalis* can play a role in the destruction of peri-implant tissue, indicating that it may be a distinct risk factor for peri-implantitis.

In some situations, biocorrosion of pure and SLA titanium surfaces is observed in the presence of *Porphyromonas gingivalis* and can have effects on osteoblast behavior. *P. gingivalis* can colonize on the pure and SLA titanium surfaces and weaken their surface properties, especially a decrease in the protective TiO2 film, which can induce the biocorrosion and further negatively affected the osteoblast behavior.

In some situations, titanium can have an influence on in vitro fibroblast-*Porphyromonas gingivalis* interaction in peri-implantitis. Higher doses of $TiO_2$ can be toxic to PIGFs and in sub-toxic doses, $TiO_2$ can cause an increase in gene expression of tumour necrosis factor (TNF)-A and increase protein production of TNF-α, interleukin (IL)-6 and IL-8. A challenge with *P. gingivalis* alone can induce gene expression of TNF-A, IL-1β, IL-6 and IL-8. A combined challenge with $TiO_2$ and *P. gingivalis* can cause a stronger increase in gene expression of TNF-A and protein production of TNF-α and MCP-1 than *P. gingivalis* alone. $TiO_2$ particles and *P. gingivalis*, individually, can induce pro-inflammatory responses in PIGFs. Furthermore, $TiO_2$ particles and viable *P. gingivalis* can further enhance gene expression and production of TNF-α by PIGFs. Without being bound by theory. Ti wear particles in the peri-implant tissues in combination with *P. gingivalis* infection may contribute to the pathogenesis of peri-implantitis by enhancing the inflammation in peri-implant tissues.

In some situations, cytokine and matrix metalloproteinase expression in fibroblasts from peri-implantitis lesions can be observed response to viable *Porphyromonas gingivalis*. Fibroblasts from peri-implantitis and periodontitis lesions can exhibit a more pronounced inflammatory response to the *P. gingivalis* challenge than fibroblasts from healthy donors. Without being bound by theory, they may therefore be involved in the development of inflammation in peri-implantitis and periodontitis. Moreover, the sustained upregulation of inflammatory mediators and MMP-1 in peri-implantitis fibroblasts may play a role in the pathogenesis of peri-implantitis.

In some embodiments, the condition, disorder or disease is bone loss or osteoporosis. In some cases periodontal disease and associated bone loss by *Porphyromonas gingivalis* Stimulates bone resorption by enhancing RANKL (Receptor Activator of NF-κB Ligand) through Activation of Toll-like Receptor 2 in Osteoblasts. LPS *P. gingivalis* and Pam2 can enhance osteoclast formation in periosteal/endosteal cell cultures by increasing RANKL. LPS *P. gingivalis* and Pam2 can also up-regulate RANKL and osteoclastic genes in vivo, resulting in an increased number of periosteal osteoclasts and immense bone loss in wild type mice but not in Tlr2-deficient mice. In some cases, LPS *P. gingivalis* can stimulate periosteal osteoclast formation and bone resorption by stimulating RANKL in osteoblasts via TLR2. Without being bound by theory, this effect might be important for periodontal bone loss and for the enhanced bone loss seen in rheumatoid arthritis patients with concomitant periodontal disease. In some situations, activation of TLR2 in osteoblasts by *P. gingivalis* increases RANKL production, osteoclast formation, and bone loss both ex vivo and in vivo. *P. gingivalis* can stimulate alveolar bone loss can cause a more severe loss of juxta-articular bone in RA. In some situations, TLR2, which is highly expressed in RA synovium, is not only activated by pathogen-associated molecular patterns such as *P. gingivalis* but also by endogenous ligands present in RA synovium such as gp96 and Snapin. There may be a role of endogenous ligands in the pathogenesis of RA bone erosions. Moreover, genetic or antibody-mediated inactivation of TLR2 can reduce cytokine production in *P. gingivalis*-stimulated neutrophils or macrophages, suggesting that TLR2 plays a non-redundant role in the host response to *P. gingivalis*. In the absence of MyD88, inflammatory TLR2 signaling in *P. gingivalis*-stimulated neutrophils or macrophages can depend upon PI3K. TLR2-PI3K signaling may be implicated in *P. gingivalis* evasion of killing by macrophages, since their ability to phagocytose this pathogen can be reduced in a TLR2 and PI3K-dependent manner. Moreover, within those cells that did phagocytose bacteria, TLR2-PI3K signaling can block phago-lysosomal maturation, thereby revealing a novel mechanism whereby *P. gingivalis* can enhance its intracellular survival. In some cases, *P. gingivalis* can uncouple inflammation from bactericidal activity by substituting TLR2-PI3K in place of TLR2-MyD88 signaling. *P. gingivalis* can be a keystone pathogen, which can manipulate the host inflammatory response in a way that promotes bone loss but not bacterial clearance. Without being bound by theory, modulation of these host response factors may be a therapeutic approach to improve outcomes in disease conditions associated with *P. gingivalis*.

In some cases, periodontal pathogenic bacteria as well as intestinal dysbiosis are involved in the determinism of bone mineral density BMD loss, and contribute to the onset and worsening of osteoporosis OP. Thus, ABMs of the present disclosure targeting *P. gingivalis* can be used to address these disorders, conditions or diseases in some embodiments.

In some situations, early host-microbe interaction is implicated in a peri-implant oral mucosa-biofilm model. In some situations, various factors (*V. dispar, P. gingivalis*, immune cells) could be involved in the disruption or maintenance of homeostasis. Thus, ABMs of the present disclosure targeting *P. gingivalis* can be used to address these disorders, conditions or diseases in some embodiments.

In some embodiments, a subject has been found to have detectable levels of gingipains associated with *P. gingivalis* such as Rgp and Kgp in the blood that may be eliminated with a method of the present disclosure in order to maintain wellness. In some embodiments, the wellness can be maintained through the optimization of the gut biome, prevention, initiation or progression of conditions such as vascular inflammation or other disease states to the point of clinical symptoms. In some embodiments, the method includes retreatment of the subject with the ABM. In some embodiments, the method includes obtaining one or more measures of blood borne gingipains associated with *P. gingivalis* to determine whether the subject requires retreatment with the ABM. Thus, ABMs of the present disclosure targeting *P. gingivalis* can be used to address these disorders, conditions or diseases in some embodiments.

In some embodiments methods of the resent disclosure include administering to the subject an ABM of the present disclosure in conjunction with one or more treatments of telomer length and/or prevention with various drugs and or natural supplements. Without being bound by theory, it has been shown that shorter telomere lengths are associated with a diagnosis of periodontitis and their measures correlate with the oxidative stress and severity of disease. Thus, ABMs of the present disclosure targeting *P. gingivalis* can be used to address these disorders, conditions or diseases in some embodiments.

Also provided herein are methods of preventing one or more conditions, disorders, or diseases, as disclosed herein, by administering to a subject, e.g., a subject at risk of developing the condition, disorder, or disease, an effective amount of an ABM of the present disclosure, to thereby prevent the condition, disorder, or disease or developing. In some embodiments, the subject is predisposed to developing the condition, disorder, or disease. In some embodiments, the subject has a past history of an *P. gingivalis* infection and/or condition or disease associated with a *P. gingivalis* infection, as disclosed herein. In some embodiments, the subject is genetically predisposed to develop the condition, disorder, or disease. In some embodiments, the method includes identifying a subject predisposed to developing any one or more of the conditions, disorders, or diseases, as disclosed herein, and administering to the subject an effective amount of an ABM of the present disclosure to thereby prevent, reduce the likelihood and/or delay the onset of the conditions, disorders, or diseases.

In any of the above methods, the ABM can be administered in conjunction with one or more additional therapeutic agents for treating or preventing the condition, disease or disorder. In some embodiments, a therapeutic agent for treating or preventing the condition, disease or disorder, as disclosed herein, can be administered to a subject in need thereof in at a therapeutically effective amount, and an effective amount of the ABM of the present disclosure can be administered to the subject. Administration of the ABM can in some embodiments improve or enhance the therapeutic effect of the other therapeutic agent. As used herein, a first agent administered in conjunction with administering a second agent can include administering the first agent before, after, or simultaneously as the second agent. In some embodiments, the first agent and second agent are administered within an interval such that the therapeutic effect of the first agent is present in the subject when the second agent is administered to the subject.

By way of non-limiting examples, the ABM can in some embodiments be administered in conjunction with one or more additional therapeutic agents for treating or preventing a vascular disease, as disclosed herein. In some embodiments, the other therapeutic agent includes a serum lipid lowering agent. Any suitable serum lipid lowering agent can be used. In some embodiments, the serum lipid lowering agent includes, without limitation, statins (e.g., atorvastatin, cerivastatin, fluvastatin, lovastatin, mevastatin, pitavastatin, pravastatin, rosuvastatin, simvastatin), Nicotinic acid (Niacin) (e.g., NIACOR, NIASPAN (slow release niacin), SLO-NIACIN (slow release niacin), CORDAPTIVE (laropiprant)), Fibric acid (e.g., LOPID (Gemfibrozil), TRICOR (fenofibrate), Bile acid sequestrants (e.g., QUESTRAN (cholestyramine), colesevelam (WELCHOL), colestipol (COLESTID)), Cholesterol absorption inhibitors (e.g., ZETIA (ezetimibe)), PPAR gamma agonists, PPAR alpha/gamma agonists, squalene synthase inhibitors, CETP inhibitors, anti-hypertensives, anti-diabetic agents (such as sulphonyl ureas, insulin, GLP-1 analogs, DDPIV inhibitors, e.g., metformin), ApoB modulators, such as mipomersen, MTP inhibitor is and/or arteriosclerosis obliterans treatments.

The ABM can in some embodiments be administered in conjunction with one or more additional therapeutic agents for treating or preventing cancer, as disclosed herein. In some embodiments, the other therapeutic agent includes an anti-cancer therapeutic that is a small molecule drug or immunotherapeutic agent. Any suitable small molecule drug or immunotherapeutic agent can be used.

In some embodiments, a dosing strategy for therapeutics can optimize the therapeutic outcome by minimizing adverse effects and maximizing efficacy across the target patient population. Multiple factors including pharmacokinetics, pharmacodynamics, exposure-response (efficacy/safety) relationships, disease burden, patient characteristics, compliance and pharmaco-economics can affect the decision on the clinical dose and dose regimen. In some embodiments, a consideration here is whether patients should be dosed based on body size, or whether body size-independent (fixed) dosing offers a viable alternative. The dosing strategy can vary. In some embodiments, body size based dosing (i.e. a dose proportional to the body size) can be used for mAbs. In some embodiments, this dosing approach can reduce inter-subject variability in drug exposure, and controlling for this pharmacokinetic variability in turn can significantly reduce variability in the response to drug treatment across the population. In some embodiments, mAbs are dosed based on body size. In some embodiments, body size-based dosing is used when there is a statistically significant body size effect on pharmacokinetic parameter(s) in the population pharmacokinetic analysis.

For systemic administration, subjects can be administered a therapeutic amount of the ABM, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more, or an amount in a range defined by any two of the preceding values.

Kits

Also provided herein are kits that include an antigen-binding molecule (ABM) of the present disclosure. In several embodiments, the kit includes a pharmaceutically acceptable excipient or a buffer. In some embodiments, the kits of the present disclosure may be suitable for performing the methods of administering the ABM to a subject, as described herein. In some embodiments, components of the kit is packaged individually in vials or bottles or in combination in containers or multi-container units. In some embodiments, kits include instructions, in words, diagrams, or combinations thereof, for administering the ABMs, as described herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

As used herein, table numbering is assigned so as to provide a shorthand reference to the example, if any, that the table is discussed. Tables that are only discussed in the detailed description can be denoted by a sub 1 value (e.g., 0.1). This is not meant to limit the relevance or discussion or implications of the tables, but to serve as a quick reference guide.

The technology described herein is further illustrated by the following examples which in no way should be construed as being further limiting.

In some embodiments, an ABM of the present disclosure includes a heavy chain variable region having an amino acid sequence at least 80%, 90%, 95%, 97%, 98%, 99%, or 100% identity to SEQ ID NO:32, and a light chain variable region having an amino acid sequence at least 80%, 90%, 95%, 97%, 98%, 99%, or 100% identity to SEQ ID NO:34. In some embodiments, an ABM of the present disclosure includes a heavy chain variable region having an amino acid sequence at least 80%, 90%, 95%, 97%, 98%, 99%, or 100% identity to SEQ ID NO:30, and a light chain variable region having an amino acid sequence at least 80%, 90%, 95%, 97%, 98%, 99%, or 100% identity to SEQ ID NO:33. In some embodiments, an ABM of the present disclosure includes a heavy chain variable region having an amino acid sequence at least 80%, 90%, 95%, 97%, 98%, 99%, or 100% identity to SEQ ID NO:30, and a light chain variable region having an amino acid sequence at least 80%, 90%, 95%, 97%, 98%, 99%, or 100% identity to SEQ ID NO:35. In some embodiments, an ABM of the present disclosure includes a heavy chain variable region having an amino acid sequence at least 80%, 90%, 95%, 97%, 98%, 99%, or 100% identity to SEQ ID NO:30, and a light chain variable region having an amino acid sequence at least 80%, 90%, 95%, 97%, 98%, 99%, or 100% identity to SEQ ID NO:36. In some embodiments, an ABM of the present disclosure includes a heavy chain variable region having an amino acid sequence at least 80%, 90%, 95%, 97%, 98%, 99%, or 100% identity to SEQ ID NO:32, and a light chain variable region having an amino acid sequence at least 80%, 90%, 95%, 97%, 98%, 99%, or 100% identity to SEQ ID NO:35. In some embodiments, an ABM of the present disclosure competes with KB001 for binding to a *P. gingivalis* gingipain, e.g., RgpA. In some embodiments, any one of these sequences can further include a point mutation at position 222, such as to an alanine. In some embodiments, the reference to position "222" denotes a hinge residue. In some embodiments, the reference to 222 denotes a position in the hinge corresponding to the alanine shown at position 105 as numbered in SEQ ID NO: 172 in FIG. 45. In some embodiments, the 222 position is adjacent to the VH sequence, wherein the first amino acid of the VH sequence is considered to be the "1" position (see FIGS. 60-61, SEQ ID NOS: 30 and 32, and SEQ ID NOS: 203-208). In some embodiments, the corresponding "position 222" is as shown in FIGS. 66 and/or 67, and is the 7th amino acid in the noted hinge region. Any disclosure provided herein relating to position "222" can also denote/be applied to position 7 of the hinge region as shown in FIGS. 66 and/or 67, as being present in the construct (just the hinge region or the entire construct), having the alanine mutation present at position 7. In some embodiments, any of the % ID or variants provided herein can also apply to any one or more of the constructs in FIGS. 66-71, as long as there is an alanine at position 7 of the hinge (as numbered by the start of the hinge region in FIG. 66).

In some embodiments, an ABM of the present disclosure detects *P. gingivalis* gingipain/hemagglutinin in a biological sample which does not include detectable *P. gingivalis* genomic DNA. In some embodiments, an ABM of the present disclosure detects *P. gingivalis* gingipain/hemagglutinin in a brain tissue sample which does not include detectable *P. gingivalis* genomic DNA.

In some embodiments, a method of reducing a biofilm or the development of a biofilm in a subject is provided. The method comprises identifying a subject at risk of developing a biofilm; and administering to the subject a therapeutically effective amount of the ABM: a) of any one of the ABMs provided herein, b) an ABM comprising a VH sequence with at least 80% identity to SEQ ID NO: 29, 30, 31, or 32, and further comprising a VL sequence with at least 80% identity to SEQ ID NO: 33, 34, 35, or 36, or c) an ABM having a LCDR1, a LCDR2, and a LCDR3 within SEQ ID NO: 2 and a HCDR1, a HCDR2, and a HCDR3 within SEQ ID NO: 1. Wherein the ABM further comprises an alanine in its hinge region at a position corresponding to position 105 as numbered in SEQ ID NO: 172 in FIG. 45. This can thereby reduce or prevent the biofilm formation in the subject. In some embodiments, the antibody or ABM need not have the cleavage resistant point mutation provided herein (e.g., at position 222). In some embodiments, the biofilm is caused by *P. gingivalis*. In some embodiments, the biofilm formation is reduced by at least 75% aftering administering a therapeutically effective amount of the ABM. In some embodiments, the biofilm formation is reduced in a subject within 24-48 hours following the administration of a therapeutically effective amount of the ABM. In some embodiments, the ABM is administered to the subject at a dose of 0.1, 1.0, or 10 μg/mL, or any concentration that is between 0.1-10 ug/mL. In some embodiments, the ABM is administered orally to the subject. By reduce, it is meant that some degree of reduction is observable. By prevent, it is noted that this encompasses delaying the onset of an indication or symptom.

In some embodiments, the technology described herein is further illustrated by the following arrangements which in no way should be construed as being further limiting.

1. A human or humanized antigen binding molecule (ABM) that binds to *Porphyromonas gingivalis*, wherein the ABM comprises:
   a heavy chain variable region (HVR) comprising:
   a complementarity determining region (HCDR) 1 of a HCDR1 of SEQ ID NO: 9 or 37;
   a HCDR2 of a HCDR2 of SEQ ID NO:9 or 37; and
   a HCDR3 of a HCDR2 of SEQ ID NO:9 or 37; and
   a light chain variable region (LVR) comprising:
   a complementarity determining region (LCDR) 1 of a LCDR1 of SEQ ID NO: 10 or 38;
   a LCDR2 of a LCDR2 of SEQ ID NO:10 or 38; and
   a LCDR3 of a LCDR2 of SEQ ID NO:10 or 38,
   wherein the ABM comprises at least one of:
   one or more HVR residues selected from L48, L67, K71, V78, and M92, as numbered according to the numbering as provided in SEQ ID NO:37, and
   one or more LVR residues selected from Q46, W48, A61, Y72, and T86, as numbered according to the numbering as provided in SEQ ID NO:38,
   wherein the ABM further comprises a variable heavy (VH) and variable light (VL) region,
   wherein the ABM comprises an amino acid sequence with a point mutation at position 222 in an antibody as numbered in FIG. 60-61 or as numbered according to the amino acid position 104 in SEQ ID NO: 172 in FIG. 45 to remove the lysine.

2. The ABM of arrangement 1, wherein position 222 is an alanine.

3. The ABM of arrangement 1 or 2, wherein the HVR comprises one or more of a HFR1, HFR2, HFR3, and HFR4 of a HFR1, HFR2, HFR3, and HFR4 of SEQ ID NO:37, respectively.

4. The ABM of any one of the preceding arrangements, wherein the LVR comprises one or more of a LFR1, LFR2, LFR3, and LFR4 of a LFR1, LFR2, LFR3, and LFR4 of SEQ ID NO:38, respectively.

5. The ABM of any one of the preceding arrangements, wherein the HVR comprises an amino acid sequence at least 80% identical to one of SEQ ID NOS: 29-32.

6. The ABM of any one of the preceding arrangements, wherein the LVR comprises an amino acid sequence at least 80% identical to one of SEQ ID NOS: 33-36.

7. The ABM of any one of the proceeding arrangements, wherein the VH region has at least 80% identity to SEQ ID NO: 29, 30, 31, or 32.

8. The ABM of any one of the proceeding arrangements, wherein the VL region has at least 80% identity to SEQ ID NO: 33, 34, 35, or 36.

9. A human or humanized antigen binding molecule (ABM) that binds to *Porphyromonas gingivalis*, wherein the ABM competes for binding to *Porphyromonas gingivalis* with H5, H7, or H14, wherein the ABM is not KB001, wherein the ABM comprises a variable heavy region (VH), wherein the ABM comprises an amino acid sequence with a point mutation at position 222 as numbered in FIG. 60-61 or as numbered according to the amino acid position 104 in SEQ ID NO: 172 in FIG. 45.

10. The ABM of arrangement 9, wherein position 222 is an alanine.

11. The ABM of arrangements 9 or 10, comprising a heavy chain complementarity determining region (HCDR) 1 of SEQ ID NO:3.

12. The ABM of arrangement 9-11, comprising a HCDR2 of SEQ ID NO:4.

13. The ABM of any one of arrangements 9-12, comprising a HCDR3 of SEQ ID NO: 5.

14. The ABM of any one of arrangements 9-13, comprising a LCDR1 of SEQ ID NO: 6.

15. The ABM of any one of arrangements 9-14, comprising a LCDR2 of SEQ ID NO: 7.

16. The ABM of any one of arrangements 9-15, comprising a LCDR3 of SEQ ID NO: 8.

17. The ABM of any one of arrangements 9-16, comprising a HVR of SEQ ID NO: 9.

18. The ABM of any one of arrangements 9-17, comprising a LVR of SEQ ID NO: 10.

19. The ABM of any one of arrangements 9-18, comprising a FR sequence of one or more of SEQ ID NOs: 11-18.

20. The ABM of any one of arrangements 9-19, wherein the VH region has at least 80% identity to SEQ ID NO: 29, 30, 31, or 32.

21. The ABM of any one of arrangements 9-20, wherein the ABM further comprises a variably light (VL) region.

22. The ABM of arrangement 21, wherein the VL region has at least 80% identity to SEQ ID NO: 33, 34, 35, or 36.

23. The ABM of any one of the preceding arrangements, wherein the ABM binds to a same or overlapping epitope as KB001, and wherein the ABM comprises the CDRs of the 6 CDRs in SEQ ID NO: 1 and 2.

24. The ABM of any one of the preceding arrangements, wherein the ABM binds to an epitope comprising GVSPKVCKDVTVEGSNEFAPVQNLT (SEQ ID NO:19) and/or YCVEVKYTAGVSPK (SEQ ID NO:59).

25. The ABM of any one of the preceding arrangements, wherein the ABM is resistant to protease cleavage.

26. The ABM of arrangement 25, wherein the resistance is to cleavage by a bacterial protease.

27. The ABM of arrangement 26, wherein the resistance is a resistance of 25-75%.

28. The ABM of any one of the preceding arrangements, wherein the ABM binds to a gingipain and/or a haemagglutinin.

29. The ABM of arrangement 28, wherein the gingipain is selected from the group consisting of: lys-gingipain (Kgp), arg-gingipains (Rgp) A and RgpB.

30. The ABM of arrangement 29, wherein the gingipain comprises a sequence of SEQ ID NO:19.

31. The ABM of arrangement 29, wherein the gingipain comprises a sequence of at least one of SEQ ID NOs: 21-28.

32. The ABM of any one of arrangements 29-31, wherein the ABM neutralizes the activity of the gingipain.

33. The ABM of arrangement 32, wherein the activity is at least one of: a peptidase, hemagglutination, haemolysis, adhesin.

34. The ABM of any one of arrangements 29-33, wherein the ABM binds to a propeptide domain, a catalytic domain and/or a C-terminal adhesion domain.

35. The ABM of any one of the preceding arrangements, wherein the ABM binds to budding outer membrane vesicles of *P. gingivalis*.

36. A human or humanized antigen binding molecule (ABM) that binds to *Porphyromonas gingivalis*, wherein the ABM binds to budding outer membrane vesicles of *P. gingivalis*, wherein the ABM comprises a variable heavy region (VH), wherein the ABM comprises an amino acid sequence with a point mutation at position 222 as numbered in FIG. 60-61 or as numbered according to the amino acid position 104 in SEQ ID NO: 172 in FIG. 45.

37. The ABM of arrangement 36, wherein position 222 is an alanine.

38. The ABM of any one of the preceding arrangements, wherein the ABM is digested at a slower rate than a fully humanized antibody that specifically binds *P. gingivalis*.

39. The ABM of any one of the preceding arrangements, wherein the ABM is a Fab, a diabody, Fab', F(ab')$_2$, Fv, single-chain antibody, nanobody, domain antibody, bivalent antibody, bispecific antibody, or peptibody.

40. The ABM of any one of the preceding arrangements, wherein the antibody when administered to a subject's mouth reduces a *P. gingivalis* infection in the mouth by at least 80%.

41. The ABM of any one of the preceding arrangements, wherein the ABM is of an IgG isotype.

42. The ABM of any one of the preceding arrangements, wherein the ABM binds to an epitope within a polypeptide comprising an amino acid sequence of any one of SEQ ID NOs: 77-83.

43. A nucleic acid encoding the ABM of any one of the preceding arrangements.

44. A vector comprising the nucleic acid of arrangement 43.

45. A cell comprising the nucleic acid of arrangement 43 or the vector of arrangement 44.

46. The cell of arrangement 45, wherein the cell is a HEK 293 cell or a derivative of HEK 293.

47. The cell of arrangement 45 or 56, wherein the cell is Expi293F.

48. A method of administering the ABM of any one of arrangements 1-42, the method comprising subgingivally administering the ABM to a subject.

49. A method of administering the ABM:
of any one of arrangements 1-42,
comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, the method comprising subgingivally administering the ABM to a subject.

50. The method of arrangement 49, wherein the ABM is administered at least two times.

51. The method of any one of arrangements 49-50, wherein the ABM is administered 10-16 days apart.

52. A method of treating or preventing a disease, disorder, or symptom in a subject in need thereof, the method comprising:

administering to the subject a therapeutically effective amount of the ABM of any one of arrangements 1-42, thereby treating or preventing the disease, disorder, or symptom thereof.

53. The method of arrangement 52, wherein the disease, disorder, or symptom is one or more of a vascular disease or symptoms thereof, a systemic disease or symptoms thereof, rheumatoid arthritis or symptoms thereof, cancer or symptoms thereof, Alzheimer's or symptoms thereof, a gut-microbiome related disorder or symptoms thereof, a cognitive disorder or symptoms thereof, an age-related disorder or symptoms thereof, a longevity-related disorder or symptoms thereof, a post event myocardial hypertrophy or symptoms thereof, a wound, inflammation, an injury, an age-related macular degeneration (AMD) or symptoms thereof, an aneurysm or symptoms thereof, a glioma or symptoms thereof, a large vessel stroke C-IMT or symptoms thereof, microvascular defects and associated dementias, or symptoms thereof, a peri-implantitis or symptoms thereof, a renal disease or symptoms thereof, a renal disease or symptoms thereof, a regenerative dysfunction, and/or a stem cell dysfunction, or symptoms thereof.

54. The method of any one of arrangements 52 or 53, wherein the disease, disorder, or symptom is one or more of a cardiovascular disease, atherosclerosis, coronary artery disease, myocardial infarction, stroke, myocardial hypertrophy, type II diabetes, insulin resistance, metabolic syndrome, oral cancer, gastrointestinal cancer, lung cancer, pancreatic cancer, inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, obesity, early dementia, middle dementia, late dementia, cerebral aneurysm, abdominal aneurysm, and/or Parkinson's disease.

55. The method of any one of arrangements 52-54, further comprising administering to the subject at least one other therapeutic agent for treating or preventing the disease, disorder, or symptom thereof.

56. The method of arrangement 55, wherein the other therapeutic agent comprises a serum lipid lowering agent.

57. The method of arrangement 56, wherein the other therapeutic agent is a statin.

58. A method of treating or preventing a vascular disease or symptoms thereof, comprising:

identifying a subject in need of treating or preventing a vascular disease or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the vascular disease or symptoms thereof.

59. The method of arrangement 58, wherein the vascular disease comprises cardiovascular disease, atherosclerosis, coronary artery disease, myocardial infarction, stroke, and myocardial hypertrophy.

60. The method of arrangement 58 or 59, further comprising administering to the subject at least one other therapeutic agent for treating or preventing the vascular disease, or symptoms thereof.

61. The method of arrangement 60, wherein the other therapeutic agent comprises a serum lipid lowering agent.

62. The method of arrangement 61, wherein the other therapeutic agent is a statin.

63. A method of treating or preventing a vascular disease or symptoms thereof, comprising:

administering to a subject in need of treating or preventing a vascular disease, or symptoms thereof, a therapeutically effective amount of at least one therapeutic agent for treating or preventing the vascular disease, or symptoms thereof; and administering an effective amount of the ABM of any one of:

arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, to thereby enhance the therapeutic effect of the at least one therapeutic agent.

64. The method of arrangement 63, wherein the other therapeutic agent comprises a serum lipid lowering agent.

65. The method of arrangement 64, wherein the other therapeutic agent is a statin.

66. A method of treating or preventing a systemic disease or symptoms thereof, comprising:

identifying a subject in need of treating or preventing a systemic disease or symptoms thereof, wherein the systemic disease is one or more of type II diabetes, insulin resistance and metabolic syndrome; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the systemic disease or symptoms thereof.

67. A method of treating or preventing rheumatoid arthritis or symptoms thereof, comprising:

identifying a subject in need of treating rheumatoid arthritis or symptoms thereof; and administering to the subject a therapeutically effective amount of the ABM: of any one of arrangements 1-42 comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the rheumatoid arthritis or symptoms thereof.

68. A method of treating or preventing cancer or symptoms thereof, comprising: identifying a subject in need of treating cancer or symptoms thereof; and administering to the subject a therapeutically effective amount of the ABM: of any one of arrangements 1-42 comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the cancer or symptoms thereof.

69. The method of arrangement 68, wherein the cancer is oral, gastrointestinal, lung or pancreatic cancer.

70. The method of arrangement 68 or 69, further comprising administering to the subject at least one other therapeutic agent for treating or preventing the cancer, or symptoms thereof.

71. The method of arrangement 70, wherein the other therapeutic agent comprises a small molecule drug or immunotherapeutic agent.

72. A method of treating or preventing cancer or symptoms thereof, comprising:

administering to a subject in need of treating or preventing cancer, or symptoms thereof, a therapeutically effective amount of at least one therapeutic agent for treating or preventing the cancer, or symptoms thereof; and administering an effective amount of the ABM:

of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, to thereby enhance the therapeutic effect of the at least one therapeutic agent.

73. The method of arrangement 72, wherein the at least one therapeutic agent comprises a small molecule drug or immunotherapeutic agent.

74. The method of arrangement 72 or 73, wherein the cancer is oral, gastrointestinal, lung or pancreatic cancer.

75. A method of treating or preventing a gut microbiome-related disorder or symptoms thereof, comprising:

identifying a subject in need of treating a gut microbiome-related disorder or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the gut microbiome-related disorder or symptoms thereof.

76. The method of arrangement 75, wherein the gut microbiome-related disorder comprises inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity.

77. A method of treating or preventing a cognitive disorder or symptoms thereof, comprising:

identifying a subject in need of treating a cognitive disorder or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the cognitive disorder or symptoms thereof.

78. The method of arrangement 77, wherein the cognitive disorder is Alzheimer's disease.

79. The method of arrangement 77 or 78, wherein the cognitive disorder is early, middle or late dementia.

80. The method of any one of arrangements 77-79, wherein gingipain is present in the hippocampus, and/or the temporal brain region of the subject.

81. The method of any one of arrangements 77-80, wherein the ABM binds directly to an at least one exo-toxin in the subject.

82. The method of arrangement 81, wherein the at least one exo-toxin is located in the brain of the subject.

83. A method of treating or preventing an age-related or longevity-related disorder, or symptoms thereof, comprising:

identifying a subject in need of treating an age-related or longevity-related disorder; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the age-related or longevity-related disorder, or symptoms thereof.

84. A method of treating or preventing a post event myocardial hypertrophy or symptoms thereof, comprising:

identifying a subject in need of treating or preventing a post event myocardial hypertrophy or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the post event myocardial hypertrophy or symptoms thereof.

85. A method of treating a wound, comprising:

identifying a subject in need of treating a wound; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, whereby closure of the wound is enhanced, thereby treating the wound.

86. A method of treating or preventing an age-related macular degeneration (AMD) or symptoms thereof, comprising:

identifying a subject in need of treating or preventing AMD or symptoms thereof; and administering to the subject a therapeutically effective amount of the ABM: of any one of arrangements 1-42 comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the AMD or symptoms thereof.

87. A method of treating or preventing an aneurysm or symptoms thereof, comprising:

identifying a subject in need of treating or preventing an aneurysm or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the aneurysm or symptoms thereof.

88. The method of arrangement 87, wherein the aneurysm is a cerebral or abdominal aneurysm.

89. A method of treating or preventing a glioma or symptoms thereof, comprising:

identifying a subject in need of treating or preventing a glioma or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the glioma or symptoms thereof.

90. A method of treating or preventing a large vessel stroke C-IMT or symptoms thereof, comprising:

identifying a subject in need of treating or preventing a large vessel stroke C-IMT or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the large vessel stroke C-IMT or symptoms thereof.

91. A method of treating or preventing microvascular defects and associated dementias, or symptoms thereof, comprising:

identifying a subject in need of treating or preventing microvascular defects and associated dementias, or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the microvascular defects and associated dementias, or symptoms thereof.

92. The method of arrangement 91, wherein the microvascular defects and associated dementias comprises microvascular defects Parkinson's.

93. A method of treating or preventing a peri-implantitis or symptoms thereof, comprising:

identifying a subject in need of treating or preventing a peri-implantitis or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the peri-implantitis or symptoms thereof.

94. A method of treating or preventing a renal disease or symptoms thereof, comprising:

identifying a subject in need of treating or preventing a renal disease or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the renal disease or symptoms thereof.

95. A method of treating or preventing a regenerative and stem cell dysfunction, or symptoms thereof, comprising:

identifying a subject in need of treating or preventing a regenerative and stem cell dysfunction, or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, thereby treating or preventing the regenerative and stem cell dysfunction, or symptoms thereof.

96. A method of treating or preventing a condition, disorder or disease associated with a *P. gingivalis* infection, or symptoms thereof, comprising:

identifying a subject in need of treating or preventing a condition, disorder or disease associated with a *P. gingivalis* infection, or symptoms thereof; and administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1, wherein the ABM further comprises an alanine in its hinge region at a position corresponding to position 105 as numbered in SEQ ID NO: 172 in FIG. 45, thereby treating or preventing the condition, disorder or disease associated with a *P. gingivalis* infection, or symptoms thereof.

97. The method of arrangement 96, comprising administering the therapeutically effective amount of the ABM to treat the condition, disorder or disease associated with a *P. gingivalis* infection, or symptoms thereof.

98. The method of arrangement 96, comprising administering the therapeutically effective amount of the ABM to prevent the condition, disorder or disease associated with a *P. gingivalis* infection, or symptoms thereof.

99. The method of any one of arrangements 96-98, wherein the condition, disorder or disease is associated with a local infection of *P. gingivalis*.

100. The method of any one of arrangements 96-98, wherein the condition, disorder or disease is associated with a systemic infection of *P. gingivalis*.

101. The method of arrangement 99, wherein the condition, disorder or disease is associated with an oral infection of *P. gingivalis*.

102. The method of any one of arrangements 96-101, wherein the condition, disorder or disease is one or more of: vascular disease (e.g., cardiovascular disease, atherosclerosis, coronary artery disease, myocardial infarction, stroke, and myocardial hypertrophy); systemic disease (e.g., type II diabetes, insulin resistance and metabolic syndrome); rheumatoid arthritis; cancer (e.g., oral, gastrointestinal, or pancreatic cancer); renal disease, gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity); post event myocardial hypertrophy, wound closure, AMD (age-related macular degeneration), cerebral and abdominal aneurysms, glioma, large vessel stroke C-IMT, microvascular defects and associated dementias (e.g., Parkinson's), Peri-Implantitis and/or periodontal disease and/or associated bone loss, cognitive disorders (e.g., early, middle, and/or late dementia; Alzheimer's disease); regenerative and stem cell dysfunction; and longevity or age-related disorder.

103. The method of any one of arrangements 96-102, wherein the ABM binds directly to an at least one exo-toxin in the subject.

104. The method of arrangement 103, wherein the at least one exo-toxin is located in the brain of the subject.

105. The method of any one of arrangements 96-104, wherein the condition, disorder, or disease is present in multiple systems, organs, or tissues.

106. The method of any one of arrangements 96-105, wherein the gingipain is present in the hippocampus, and/or the temporal brain region of the subject.

107. The method of any one of arrangements 96-106, wherein treating or preventing the condition, disorder or disease associated with a *P. gingivalis* infection results in the decrease of CRISPR-Cas gene expression at one or more site of infection.

108. The method of any one of arrangements 96-107, wherein treating or preventing the condition, disorder or disease associated with a *P. gingivalis* infection results in a decrease of local inflammation.

109. The method of arrangement 108, wherein the decrease of local inflammation is reduced activity or activation of inflammasomes, reduced cytokine levels, and/or lowered host cell death.

110. The method of any one of arrangements 96-109, wherein treating or preventing the condition, disorder or disease associated with a *P. gingivalis* infection results in a decrease of systemic inflammation.

111. The method of arrangement 110, wherein the decrease of systemic inflammation is reduced proinflammatory mediators, and/or reduced chronic distant site inflammatory atherosclerosis.

112. A method of targeting a *P. gingivalis*, comprising:
identifying a subject with a *P. gingivalis* infection, or symptoms thereof; and
administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or
having a LCDR1, a LCDR2, and a LCDR3 within SEQ ID NO: 2 and a HCDR1, a HCDR2, and a HCDR3 within SEQ ID NO: 1,
wherein the ABM further comprises an alanine in its hinge region at a position corresponding to position 105 as numbered in SEQ ID NO: 172 in FIG. 45, thereby targeting the *P. gingivalis*, or symptoms thereof.

113. The method of arrangement 112, wherein the *P. gingivalis* infection is in the mouth.

114. The method of arrangement 112, wherein the *P. gingivalis* infection is in the gums.

115. The method of arrangement 112, wherein the *P. gingivalis* infection is in the brain.

116. The method of arrangement 112, wherein the *P. gingivalis* infection is in the hippocampus and/or the temporal region of the brain.

117. The method of arrangement 112, wherein the *P. gingivalis* infection is across the blood brain barrier.

118. The method of any one of arrangements 112-117, wherein the targeting of the *P. gingivalis* infection further comprises administration of a small molecule, antibiotic, or drug affective against *P. gingivalis*.

119. The method of arrangement 118, wherein the small molecule, antibiotic, or drug targets *P. gingivalis* virulence factors, increases the production of proteases targeting *P. gingivalis*, reduces *P. gingivalis* oxygen and/or iron uptake, alters protein production in *P. gingivalis*, and/or enhances cell death for *P. gingivalis*.

120. A method of targeting a bacterial infection in a subject, comprising:
identifying the subject with a bacterial infection, or symptoms thereof; and
administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or having a LCDR1, a LCDR2, and a LCDR3 within SEQ ID NO: 2 and a HCDR1, a HCDR2, and a HCDR3 within SEQ ID NO: 1,
wherein the ABM further comprises an alanine in its hinge region at a position corresponding to position 105 as numbered in SEQ ID NO: 172 in FIG. 45, thereby targeting the bacterial infection, or symptoms thereof.

121. The method of arrangement 120, wherein the bacterial infection is in the mouth.

122. The method of arrangement 120, wherein the bacterial infection is in the gums.

123. The method of arrangement 120, wherein the bacterial infection is in the brain.

124. The method of arrangement 120, wherein the *P. gingivalis* infection is in the hippocampus and/or the temporal region of the brain.

125. The method of arrangement 120, wherein the bacterial infection is in the gut.

126. The method of arrangement 120, wherein the bacterial infection is across the blood brain barrier.

127. The method of any one of arrangements 120-126, wherein the bacterial infection is systemic, and/or in multiple tissues.

128. The method of any one of arrangements 120-127, wherein the bacterial infection comprises a *P. gingivalis* infection.

129. The method of any one of arrangements 120-128, wherein the bacterial infection comprises a *H. pylori* infection.

130. The method of any one of arrangements 120-129, wherein the bacterial infection comprises more than one bacterial infections.

131. The method of any one of arrangements 120-130, wherein the targeting of the bacterial infection further comprises administration of a small molecule, antibiotic, or drug.

132. The method of arrangement 131, wherein the small molecule, antibiotic, or drug targets at least one virulence factors, increases the production of proteases, reduces bacterial nutrient uptake, alters bacterial protein production, and/or enhances bacterial cell death.

133. The method of any one of arrangements 120-132, wherein the administering comprises administering the ABM intravenously, subgingivally, intradermally, subcutaneously, intrathecally, or by nebulization.

134. Use of an ABM:
of any one of arrangements 1-42,
comprising a VH sequence with at least 80% identity to SEQ ID NO: 29, 30, 31, or, 32, and further comprising a VL sequence with at least 80% identity to SEQ ID NO: 33, 34, 35, or 36, or
having a LCDR1, a LCDR2, and a LCDR3 within SEQ ID NO: 2 and a HCDR1, a HCDR2, and a HCDR3 within SEQ ID NO: 1,
wherein the ABM further comprises an alanine in its hinge region at a position corresponding to position 105 as numbered in SEQ ID NO: 172 in FIG. 45, for treatment of a disorder associated with, caused by or complicated by *P. gingivalis*.

135. The use of arrangement 134, wherein the disorder associated with, caused by or complicated by *P. gingivalis* is one or more of: vascular disease (e.g., cardiovascular disease, atherosclerosis, coronary artery disease, myocardial infarction, stroke, and myocardial hypertrophy); systemic disease (e.g., type II diabetes, insulin resistance and metabolic syndrome); rheumatoid arthritis; cancer (e.g., oral, gastrointestinal, or pancreatic cancer); renal disease, gut microbiome-related disorder (e.g., inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, and obesity); post event myocardial hypertrophy, wound closure, AMD (age-related macular degeneration), cerebral and abdominal aneurysms, glioma, large vessel stroke C-IMT, microvascular defects and associated dementias (e.g., Parkinson's), Peri-Implantitis and/or periodontal disease and/or associated bone loss, cognitive disorders (e.g., early, middle, and/or late dementia; Alzheimer's disease); neuroinflammatory diseases; regenerative and stem cell dysfunction; and longevity or age-related disorder.

136. The use of arrangements 134-135, wherein the ABM binds directly to an at least one exo-toxin in the subject.

137. The use of arrangement 136, wherein the at least one exo-toxin is located in the brain of the subject.

138. The method, use, of ABM of any one of the preceding arrangements, wherein the ABM binds to YTYTVYRDGTKIK.

139. The ABM, method, or use of ABM of any one of the preceding arrangements, wherein the ABM comprises a point mutation for cleavage resistance from Pg proteases.

140. The ABM, method, or use of ABM of any one of the preceding arrangements, wherein the ABM comprises an amino acid sequence at least 80%, 90%, 95, 99%, or 100% identical to SEQ ID NO: 84.

141. The ABM, method, or use of ABM of any one of the preceding arrangements, wherein the HVR comprises an amino acid sequence at least 80% identical to one of SEQ ID NOS: 85-86.

142. The ABM, method, or use of ABM of any one of the preceding arrangements, wherein the LVR comprises an amino acid sequence at least 80% identical to one of SEQ ID NOS: 87-90.

143. The ABM, method, or use of ABM of any one of the preceding arrangements, wherein the ABM comprises an HVR amino acid sequence corresponding to a nucleic acid sequence that is at least 80% identical to one of SEQ ID NOS: 91-92.

144. The ABM, method, or use of ABM of any one of the preceding arrangements, wherein the ABM comprises an LVR amino acid sequence corresponding to a nucleic acid sequence that is at least 80% identical to one of SEQ ID NOS: 93-97.

145. A nucleic acid that is at least 80% identical to one of SEQ ID NOS: 98-101, wherein the nucleic acid confers the expression sequence of an ABM that has a mutation at position 222, as numbered according to the amino acid position 104 in SEQ ID NO: 172 in FIG. 45.

146. The nucleic acid of arrangement 145, wherein the mutation at position 222 is an alanine.

147. The ABM, method, or use of ABM of any one of the preceding arrangements, wherein the ABM binds to a gingipain and/or a haemagglutinin with a KD that is less than about 2E-9 M, less than about 1E-9 M, less than about 9E-10 M, less than about 8E-10 M, less than about 6E-10 M, less than about 4E-10 M, less than about 2E-10 M, less than about 1E-10 M, less than about 9E-11 M, and/or less than about 7E-11 M.

148. The ABM, method, or use of ABM of any one of the preceding arrangements, wherein the ABM prevents the processing of HagA by P. gingivalis gingipains.

149. The ABM, method, or use of ABM of any one of the preceding arrangements, wherein the ABM binds to a gingipain and/or a haemagglutinin with a KD that is less than about $10^{-7}$ M, less than about $5 \times 10^{-8}$ M, less than about $2 \times 10^{-8}$ M, and/or less than about $1 \times 10^{-8}$ M.

150. The ABM, method, or use of ABM of any one of the preceding arrangements or Arrangements 1-42, wherein the ABM further comprises at least one, two, three or all four of:
  an alanine at position 222, as numbered according to the amino acid position 104 in SEQ ID NO: 172 in FIG. 45;
  an amino acid sequence that is at least 80% identical to SEQ ID NO: 84;
  an HVR sequence comprising an amino acid sequence at least 80% identical to one of SEQ ID NOS: 85-86; and/or
  an LVR sequence comprising an amino acid sequence at least 80% identical to one of SEQ ID NOS: 87-90.

151. The method or use of ABM of any one of the preceding arrangements, wherein the ABM comprises SEQ ID NO: 1 and SEQ ID NO: 2 as the ABM or instead of the noted ABM in any one of the preceding arrangements.

152. The ABM or method or use of ABM of any one of the preceding arrangements, wherein the ABM comprises a heavy chain sequence of SEQ ID NO: 30, a light chain sequence of SEQ ID NO: 33, except that the ABM comprises an alanine at position 222, as numbered according to the amino acid position 104 in SEQ ID NO: 172 in FIG. 45.

153. The ABM or method or use of ABM of any one of the preceding arrangements, wherein the ABM is H5 K22A.

154. An ABM that is humanized or human, wherein the ABM comprises an alanine at position 222, as numbered according to the amino acid position 104 in SEQ ID NO: 172 in FIG. 45.

155. A method of treating a disorder driven by P. gingivalis comprising:
  providing an antibody that binds to a P. gingivalis associated peptide, to a subject,
  wherein the antibody is known to function to stop a P. gingivalis infection,
  wherein the antibody is a humanized or human antibody, and
  wherein the amino acid at position 222, as numbered according to the amino acid position 104 in SEQ ID NO: 172 in FIG. 45 of the antibody has been changed to an alanine.

156. A method of reducing cleavage of an ABM and/or humanized antibody when administered orally to a subject, the method comprising, administering an antibody that has a non-lysine amino acid at position 222, as numbered according to the amino acid position 104 in SEQ ID NO: 172 in FIG. 45 of the antibody, wherein the antibody binds to a P. gingivalis associated peptide.

157. The method of arrangement 156, wherein the ABM and/or humanized antibody is anyone of the ABM or humanized antibodies in any one of the preceding arrangements.

158. A humanized variant of KB001, wherein 10 μg of the humanized variant of KB001 is not detectably degraded by incubation for 2 h at 37° C. with a gingipain mix, wherein the gingipain mix comprises: Kgp activity of 15.96 mOD/min/μl and Rgp activity of 23.71 mOD/min/μl,
  at a ratio of Ab:GP (w/w) ratio: 100:1 and/or 500:1 in assay buffer supplemented with 10 mM cysteine.

159. The humanized variant of arrangement 158, wherein after incubation:
  tosyl-L-lysyl-chloromethane hydrochloride (TLCK) is added to a final concentration of 10 mM followed by addition of non-reducing sample buffer, the samples are boiled for 5 min,
  then the samples are chilled on ice and Dithiothreitol (DTT) is added to the final concentration of 20 mM, the samples are boiled again for 5 min and separated using NuPAGE™ 4 to 12%, Bis-Tris Mini Protein Gels,
wherein no separate cleavage bands are identifiable in the variant when the sample is processed as above.

160. The humanized variant of arrangement 158 or 159, wherein the variant comprises a point mutation at position 222, as numbered according to the amino acid position 104 in SEQ ID NO: 172 in FIG. 45, which removes a lysine at position 222.

161. The humanized variant of any one of arrangements 158-160, wherein the humanized variant comprises at least one of SEQ ID NO: 203, 204, 205, 206, 207, and/or 208.

162. The humanized variant of arrangement 161, wherein the humanized variant comprises one of SEQ ID NO: 205, 206, 207, or 208.

163. The humanized variant of any one of arrangements 161, wherein the humanized variant comprises one of SEQ ID NO: 203 or 204.

164. A human chimeric antibody comprising:
a variable heavy chain comprising the sequence of SEQ ID NO: 30;
a variable light chain comprising the sequence of SEQ ID NO: 33; and
a hinge region that is lacking a lysine.

165. The human chimeric antibody of arrangement 164, wherein the lysine is the lysine as numbered according to the amino acid position 104 in SEQ ID NO: 172 in FIG. 45.

166. The human chimeric antibody of arrangement 164, wherein the hinge region is the hinge region in FIG. 66, and the mutation is position 7, which is an alanine.

167. The human chimeric antibody of any one of the preceding arrangements, wherein the antibody comprises a hinge region, and wherein the 7th position of the hinge region (as numbered in FIG. 66) is an alanine.

168. The human chimeric antibody of arrangement 167, wherein the hinge region is the hinge region of FIG. 66.

169. Any one of the preceding methods, wherein the ABM or antibody used is that in arrangement 164-168.

170. A method of reducing a biofilm or the development of a biofilm in a subject, comprising:
identifying a subject at risk of developing a biofilm; and
administering to the subject a therapeutically effective amount of the ABM: of any one of arrangements 1-42, comprising a VH sequence with at least 80% identity to SEQ ID NO: 29, 30, 31, or, 32, and further comprising a VL sequence with at least 80% identity to SEQ ID NO: 33, 34, 35, or 36, or
having a LCDR1, a LCDR2, and a LCDR3 within SEQ ID NO: 2 and a HCDR1, a HCDR2, and a HCDR3 within SEQ ID NO: 1,
wherein the ABM further comprises an alanine in its hinge region at a position corresponding to position 105 as numbered in SEQ ID NO: 172 in FIG. 45, thereby reducing or preventing the biofilm formation in the subject.

171. The method of arrangement 170, wherein the biofilm is caused by *P. gingivalis*.

172. The method of any one of arrangements 170 or 171, wherein the biofilm formation is reduced by at least 75% aftering administering a therapeutically effective amount of the ABM.

173. The method of any one of arrangements 170-172, wherein the biofilm formation is reduced in a subject within 24-48 hours following the administration of a therapeutically effective amount of the ABM.

174. The method of any one of arrangements 170-173, wherein the ABM is administered to the subject at a dose of 0.1, 1.0, or 10 ug/mL, or any concentration that is between 0.1-10 ug/mL.

175. The method of any one of arrangements 170-174, wherein the ABM is administered orally to the subject.

176. A human or humanized antigen binding molecule (ABM) that binds to *Porphyromonas gingivalis*, wherein the ABM comprises:
a variable heavy (VH) region of SEQ ID NO: 29, 30, 31, or 32;
a variable light (VL) region of SEQ ID NO: 33, 34, 35, or 36;
wherein the ABM comprises an amino acid sequence with a point mutation at position 222 in an antibody as numbered in FIG. 60-61 or as numbered according to the amino acid position 104 in SEQ ID NO: 172 in FIG. 45 to remove the lysine.

177. The ABM of arrangement 176, wherein the ABM has a VH region of SEQ ID NO: 30.

178. The ABM of arrangements 176 or 177, wherein the ABM has a VL region of SEQ ID NO: 33.

179. The ABM of any one of arrangements 176-178, wherein the point mutation is an alanine.

180. The ABM of any one of arrangements 176-179, wherein the ABM further comprises:
a heavy chain complementarity determining region (HCDR) 1 of a HCDR1 of SEQ ID NO:9 or 37;
a HCDR2 of a HCDR2 of SEQ ID NO:9 or 37; and
a HCDR3 of a HCDR2 of SEQ ID NO:9 or 37; and
a light chain variable region (LVR) comprising:
a light chain complementarity determining region (LCDR) 1 of a LCDR1 of SEQ ID NO:10 or 38;
a LCDR2 of a LCDR2 of SEQ ID NO:10 or 38; and
a LCDR3 of a LCDR2 of SEQ ID NO:10 or 38.

181. The ABM of any one of arrangements 176-180, wherein the ABM further comprises:
a HCDR1 of SEQ ID NO: 3 or 39;
a HCDR2 of SEQ ID NO:4 or 40;
a HCDR3 of SEQ ID NO:5 or 41;
a LCDR1 of SEQ ID NO:6 or 42;
a LCDR2 of SEQ ID NO:7 or 43; and
a LCDR3 of SEQ ID NO:8 or 44.

182. A human or humanized antigen binding molecule (ABM) that binds to *Porphyromonas gingivalis*, wherein the ABM comprises:
a variable heavy (VH) region of SEQ ID NO: 29, 30, 31, or 32; and
a variable light (VL) region of SEQ ID NO: 33, 34, 35, or 36;
(ii) a HCDR1 of SEQ ID NO: 3 or 39;
a HCDR2 of SEQ ID NO:4 or 40;
a HCDR3 of SEQ ID NO:5 or 41;
a LCDR1 of SEQ ID NO:6 or 42;
a LCDR2 of SEQ ID NO:7 or 43; and
a LCDR3 of SEQ ID NO:8 or 44;
(iii) an Ig lambda region of SEQ ID NO: 219;
(iv) an Ig kappa region of SEQ ID NO: 218; and
(v) a IgG region of sequences SEQ ID NO: 216 and SEQ ID NO: 217;
wherein the ABM comprises an amino acid sequence with a point mutation at position 222 in an antibody as numbered in FIG. 60-61 or as numbered according to the amino acid position 104 in SEQ ID NO: 172 in FIG. 45 to remove a lysine and replace the lysine with an alanine.

183. A method of administering the ABM of arrangement 182, the method comprising subgingivally administering the ABM to a subject.

184. A method of treating or preventing a disease, disorder, or symptom in a subject in need thereof, the method comprising:

administering to the subject a therapeutically effective amount of the ABM, wherein the ABM comprises:

a variable heavy (VH) region of SEQ ID NO: 29, 30, 31, or 32; and a variable light (VL) region of SEQ ID NO: 33, 34, 35, or 36;

(ii) a HCDR1 of SEQ ID NO: 3 or 39;

a HCDR2 of SEQ ID NO:4 or 40;

a HCDR3 of SEQ ID NO:5 or 41;

a LCDR1 of SEQ ID NO:6 or 42;

a LCDR2 of SEQ ID NO:7 or 43; and a LCDR3 of SEQ ID NO:8 or 44;

(iii) an Ig lambda region of SEQ ID NO: 219;

(iv) an Ig kappa region of SEQ ID NO: 218; and (v) a IgG region of sequences SEQ ID NO: 216 and SEQ ID NO: 217;

wherein the ABM comprises an amino acid sequence with a point mutation at position 222 in an antibody as numbered in FIG. 60-61 or as numbered according to the amino acid position 104 in SEQ ID NO: 172 in FIG. 45 to remove a lysine and replace the lysine with an alanine, thereby treating or preventing the disease, disorder, or symptom thereof.

185. The method of arrangement 184, wherein the disease, disorder, or symptom is one or more of a vascular disease or symptoms thereof, a systemic disease or symptoms thereof, rheumatoid arthritis or symptoms thereof, cancer or symptoms thereof, Alzheimer's or symptoms thereof, a gut-microbiome related disorder or symptoms thereof, a cognitive disorder or symptoms thereof, an age-related disorder or symptoms thereof, a longevity-related disorder or symptoms thereof, a post event myocardial hypertrophy or symptoms thereof, a wound, inflammation, an injury, an age-related macular degeneration (AMD) or symptoms thereof, an aneurysm or symptoms thereof, a glioma or symptoms thereof, a large vessel stroke C-IMT or symptoms thereof, microvascular defects and associated dementias, or symptoms thereof, a peri-implantitis or symptoms thereof, a renal disease or symptoms thereof, a renal disease or symptoms thereof, a regenerative dysfunction, and/or a stem cell dysfunction, or symptoms thereof.

186. The method of any one of arrangements 184 or 185, wherein the disease, disorder, or symptom is one or more of a cardiovascular disease, atherosclerosis, coronary artery disease, myocardial infarction, stroke, myocardial hypertrophy, type II diabetes, insulin resistance, metabolic syndrome, oral cancer, gastrointestinal cancer, lung cancer, pancreatic cancer, inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, obesity, early dementia, middle dementia, late dementia, cerebral aneurysm, abdominal aneurysm, and/or Parkinson's disease.

187. The method of any one of arrangements 184-186, further comprising administering to the subject at least one other therapeutic agent for treating or preventing the disease, disorder, or symptom thereof.

188. The method of arrangement 187, wherein the other therapeutic agent comprises a serum lipid lowering agent.

189. The method of arrangement 188, wherein the other therapeutic agent is a statin.

190. The method of any one of arrangements 184-189, wherein the ABM is administered in a solution of saline or histidine.

191. The method of any one of arrangements 184-190, wherein the ABM is administered topically.

192. The method of any one of arrangements 184-191, wherein the ABM is administered orally.

193. A human or humanized antigen binding molecule (ABM) that binds to *Porphyromonas gingivalis*, wherein the ABM comprises:

a VH sequence comprising SEQ ID NO: 221, 223, 225, 227, 237, 239, 241, 243, 245, 247, 249, 251, 261, 263, 265, or 267; and a VL sequence comprising SEQ ID NO: 229, 231, 233, 235, 253, 255, 257, or 259.

194. The ABM of arrangement 193, wherein the ABM comprises a VH sequence of SEQ ID NO: 223, and a VL sequence of SEQ ID NO: 229.

195. The ABM of arrangements 193, wherein the ABM comprises a VH sequence of SEQ ID NO: 239, and a VL sequence of SEQ ID NO: 229.

196. The ABM of arrangement 193, wherein the ABM comprises a VH sequence of SEQ ID NO: 247, and a VL sequence of SEQ ID NO: 253.

197. The ABM of arrangements 193, wherein the ABM comprises a VH sequence of SEQ ID NO: 263, and a VL sequence of SEQ ID NO: 253.

198. A composition comprising the ABM of any one of arrangements 193-197 and a pharmaceutically acceptable carrier or excipient.

199. A nucleic acid sequence of SEQ ID NO: 220, 222, 224, 226, 236, 238, 240, 242, 244, 246, 248, 250, 260, 262, 264, 266, 228, 230, 232, 234, 252, 254, 256, or 258.

200. A method of expressing the ABM of arrangement 193 in a cell, the method comprising:

transfecting the cell with a first nucleic acid sequence of SEQ ID NO: 220, 222, 224, 226, 236, 238, 240, 242, 244, 246, 248, 250, 260, 262, 264, or 266; and transfecting the cell with a second nucleic acid sequence of SEQ ID NO: 228, 230, 232, 234, 252, 254, 256, or 258.

201. A method of treating or preventing a disease, disorder, or symptom in a subject in need thereof, the method comprising:

administering to the subject a therapeutically effective amount of the ABM of arrangement 193 or the composition of arrangement 194.

202. The method of arrangement 201, wherein the disease, disorder, or symptom is one or more of a vascular disease or symptoms thereof, a systemic disease or symptoms thereof, rheumatoid arthritis or symptoms thereof, cancer or symptoms thereof, Alzheimer's or symptoms thereof, a gut-microbiome related disorder or symptoms thereof, a cognitive disorder or symptoms thereof, an age-related disorder or symptoms thereof, a longevity-related disorder or symptoms thereof, a post event myocardial hypertrophy or symptoms thereof, a wound, inflammation, an injury, an age-related macular degeneration (AMD) or symptoms thereof, an aneurysm or symptoms thereof, a glioma or symptoms thereof, a large vessel stroke C-IMT or symptoms thereof, microvascular defects and associated dementias, or symptoms thereof, a peri-implantitis or symptoms thereof, a renal disease or symptoms thereof, a renal disease or symptoms thereof, a regenerative dysfunction, and/or a stem cell dysfunction, or symptoms thereof.

203. The method of any one of arrangements 201 or 202, wherein the disease, disorder, or symptom is one or more of a cardiovascular disease, atherosclerosis, coronary artery disease, myocardial infarction, stroke, myocardial hypertrophy, type II diabetes, insulin resistance, metabolic syndrome, oral cancer, gastrointestinal cancer, lung cancer, pancreatic cancer, inflammatory bowel disease, irritable bowel syndrome (IBS), coeliac disease, non-alcoholic fatty liver disease (NAFLD), non-alcoholic steatohepatitis (NASH), allergy, asthma, metabolic syndrome, cardiovascular disease, obesity, early dementia, middle dementia, late dementia, cerebral aneurysm, abdominal aneurysm, and/or Parkinson's disease.

204. The method of any one of arrangements 201-203, further comprising administering to the subject at least one other therapeutic agent for treating or preventing the disease, disorder, or symptom thereof.

205. The method of arrangement 204, wherein the other therapeutic agent comprises a serum lipid lowering agent.

206. The method of arrangement 204, wherein the other therapeutic agent is a statin.

207. The method of any one of arrangements 201-206, wherein the ABM is administered in a solution of saline or histidine.

208. The method of any one of arrangements 201-207, wherein the ABM is administered topically.

209. The method of any one of arrangements 201-208, wherein the ABM is administered orally.

EXAMPLES

Example 1: Amino Acid Sequence of the Heavy and Light Chains of KB001 Antibody Generation of purified mouse IgG1 monoclonal antibody: Hybridoma mAb03 was obtained and propagated in HyClone ADCF-MAb media supplemented with penicillin and streptomycin. The doubling time of the cells was approximately 36 hours.

Purification of monoclonal antibody: IgG from approximately 100 mL of conditioned media was purified using a standard Protein A column to confirm that the cell line produced antibody. Approximately 100 micrograms of antibody was purified. IgG from approximately 750 mL of conditioned media was processed to generate approximately 4 milligrams of IgG. It was estimated the hybridoma produced approximately 8 mg of antibody per Liter.

Sequencing the antibody: RNA from cultured cells was prepared using the RNAzol method. cDNA was synthesized using both random hexamer and oligo (dT) primers. Degenerative primers were designed to amplify conserved, constant regions of the Heavy and Light chains. Due to uncertainties of the sequence, approximately 24 primers were used. PCR fragments were synthesized and sent for sequence analysis. Initial efforts yielded the sequences of the hypervariable regions. Additional efforts were required to derive the sequences of the remaining regions. Preliminary plans called for grafting the hypervariable regions onto constant domains in silico. However, the IgG eluted from Protein A resin at a higher pH than normal (4.7 vs. 3.7) and suggested the constant regions may have some variation from conserved sequences. The presence of variant sequences was confirmed by the unusually rigorous efforts that were required to amplify and sequence the cDNA fragments. The nucleotide sequence data were used to create contiguous sequences and then translated to putative amino acid sequences for analysis. The nucleotide sequences encoding the heavy and light chains, including the signal peptide, are depicted in FIGS. 37A and 37C, respectively. The nucleotide sequences encoding the heavy and light chain variable regions are depicted in FIGS. 35A and 35B, respectively.

The amino acid sequences of the heavy and light chains, of KB001 is shown in FIGS. 1A and 1B, respectively.

The translated amino acid sequences were analyzed by BLAST to align with the nearest neighbor for the purpose of identifying antibody domains. The heavy chain aligned most closely with IgG1 heavy chains. The light chain aligned most closely with Lambda light chains.

Example 2: Epitope Mapping of KB-001 Antibody

This non-limiting example shows a procedure for tryptic digest and mass spectrometry (MS) analysis of gingipains for epitope mapping of KB-001. Such epitopes can be used to define various APs.

Figure 21A:
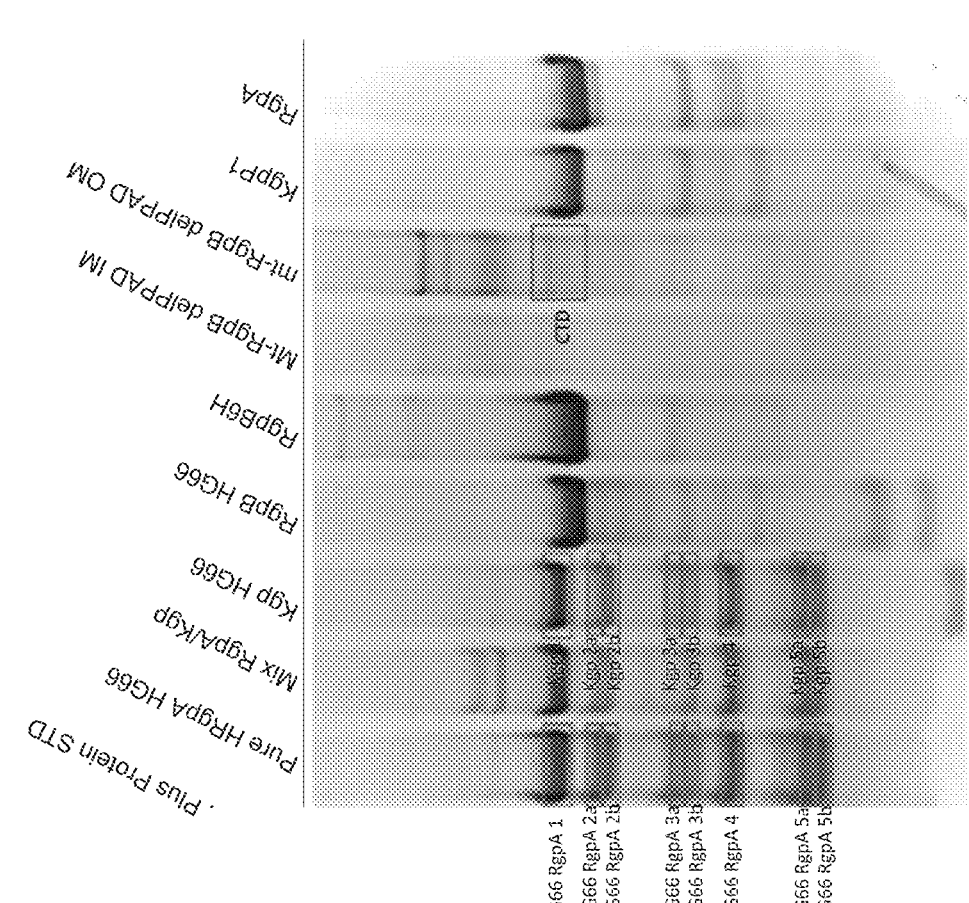
FIGS. 21A and 21B are images showing mapping of KB001 mouse monoclonal antibody target binding by N-term sequencing and mass spectrometry, which can be equated to the relevant AP sections, as disclosed herein.
Figure 21B:
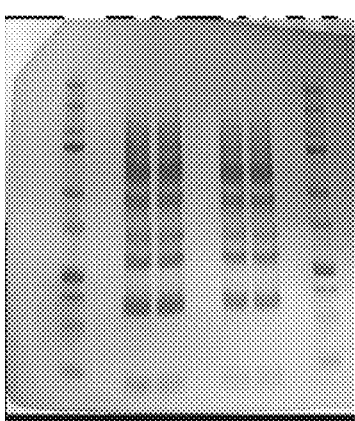

To determine viable APs, one can first identify the epitope on *P. gingivalis* target proteins of KB-001, gingipains (RgpA, Kgp) and hemagglutinin from various *P. gingivalis* strains were digested with trypsin and the tryptic digests were probed for KB-001 binding (FIGS. 21A and 21B). Peptides fragments binding to KB-001 were analyzed by MS and N-terminal sequencing.

The deduced sequences of linear portion KB-001-binding fragments and the position of these sequences in the full protein are listed in FIGS. 22A-22J. Linear analysis indicated that the binding epitope to include: YCVEVKYTAGVSPK. Thus, a viable AP would include, in some embodiments, this sequence.

Sequences within gingipains (RgpA, Kgp) and hemagglutinin (HagA) from various *P. gingivalis* strains that encompass the putative linear portion of the epitope sequence recognized by KB-001 are indicated in FIGS. 40A-40F. HagA from W83 and ATCC33277 contain 3 and 4 nearly perfect repeats, respectively, of the sequence containing the putative epitope (FIGS. 40C, 40D, 40E, 40F). As a nearly perfect repeat the motif occurs twice in gingipain structure (FIGS. 40D, 40E, 40F). The third repeat is present in HA4 domain of RgpA but is degenerate in the Kgp (from W83 strain). The presence of the epitope within the sequences shown in FIG. 40F was verified by WB analysis of mAbs reactivity with different domains of RgpA and Kgp.

Based on the above example, in some embodiments, an AP of the present disclosure includes any one or more of the following sequences:

```
                                    (SEQ ID NO: 209)
PASYTYTVYRDGTKIKEGLTATTFEEDGVAAGNHEYCVEVKYTA
GVSPKVC;
                                    (SEQ ID NO: 210)
GSDYTYTVYRDGTKIKEGLTATTFEEDGVATGNHEYCVEVKYTA
GVSPKVC;
                                    (SEQ ID NO: 211)
PTDYTYTVYRDGTKIKEGLTETTFEEDGVATGNHEYCVEVKYTAG
VSPKKC;
                                    (SEQ ID NO: 212)
PTDYTYTVYRDGTKIKEGLTETTFEEDGVATGNHEYCVEVKYTAG
VSPKEC;
                                    (SEQ ID NO: 213)
PTDYTYTVYRDGTKIKEGLTETTFEEDGVATGNHEYCVEVKYTAG
VSPKVC;
```

-continued (SEQ ID NO: 214)
PASYTYTVYRDGTKIKEGLTETTYRDAGMSAQSHEYCVEVKYTA
GVSPKVC; and/or (SEQ ID NO: 215)
APSYTYTIYRNNTQIASGVTETTYRDPDLATGFYTYGVKVVYPNG
ESAIET.

Example 3: Binding Analysis of the KB001 Antibody to *Porphyromonas gingivalis*

As disclosed herein, a GST-TEV-gingipain-His fusion protein was used to produce recombinant gingipain fusion proteins in *E. coli* (FIG. 41).

Figure 6A:
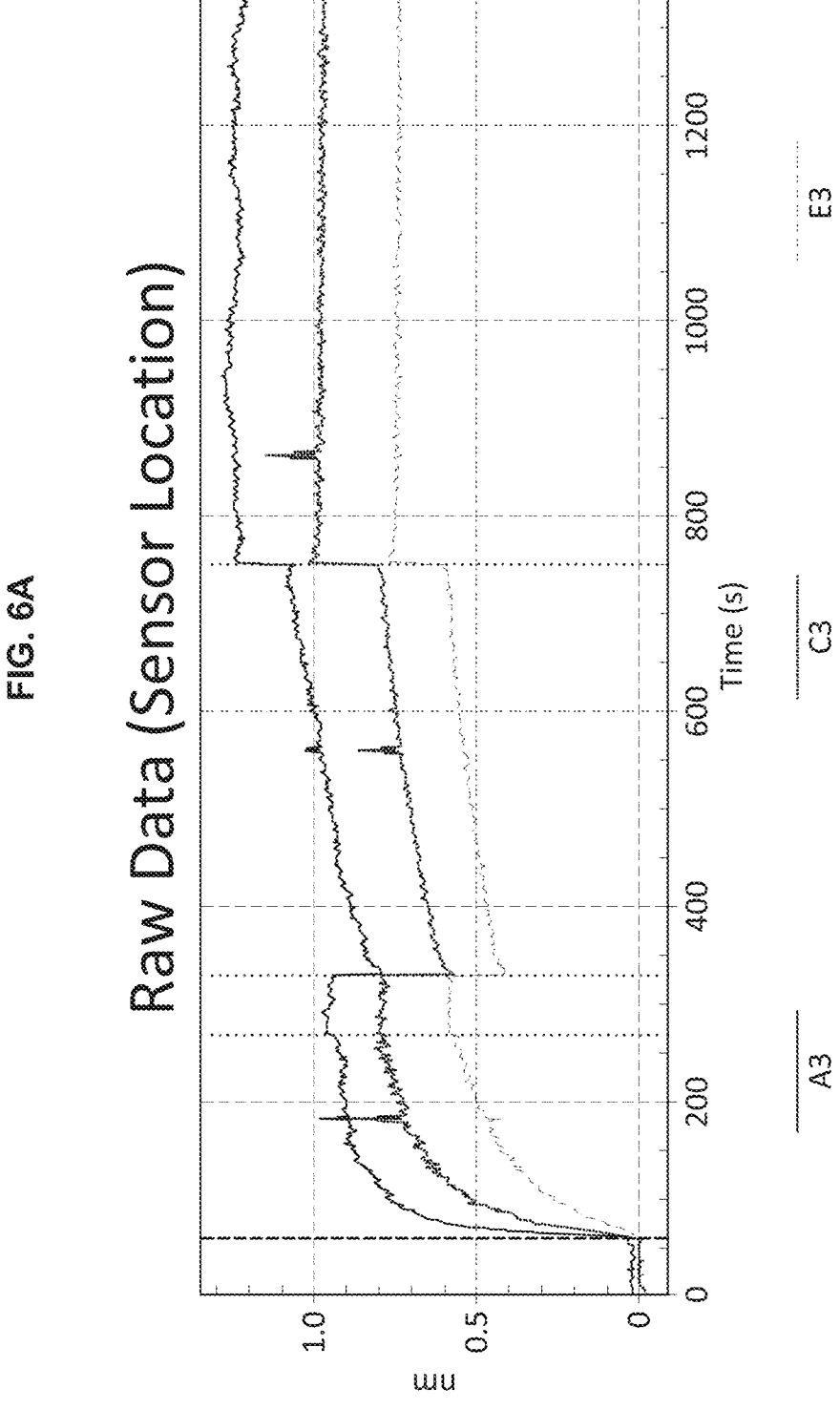
FIG. 6A shows the response curves at antibody concentrations of 33.3 nM (E3), 100 nM (C3) and 200 nM (A3).
Figure 6B:
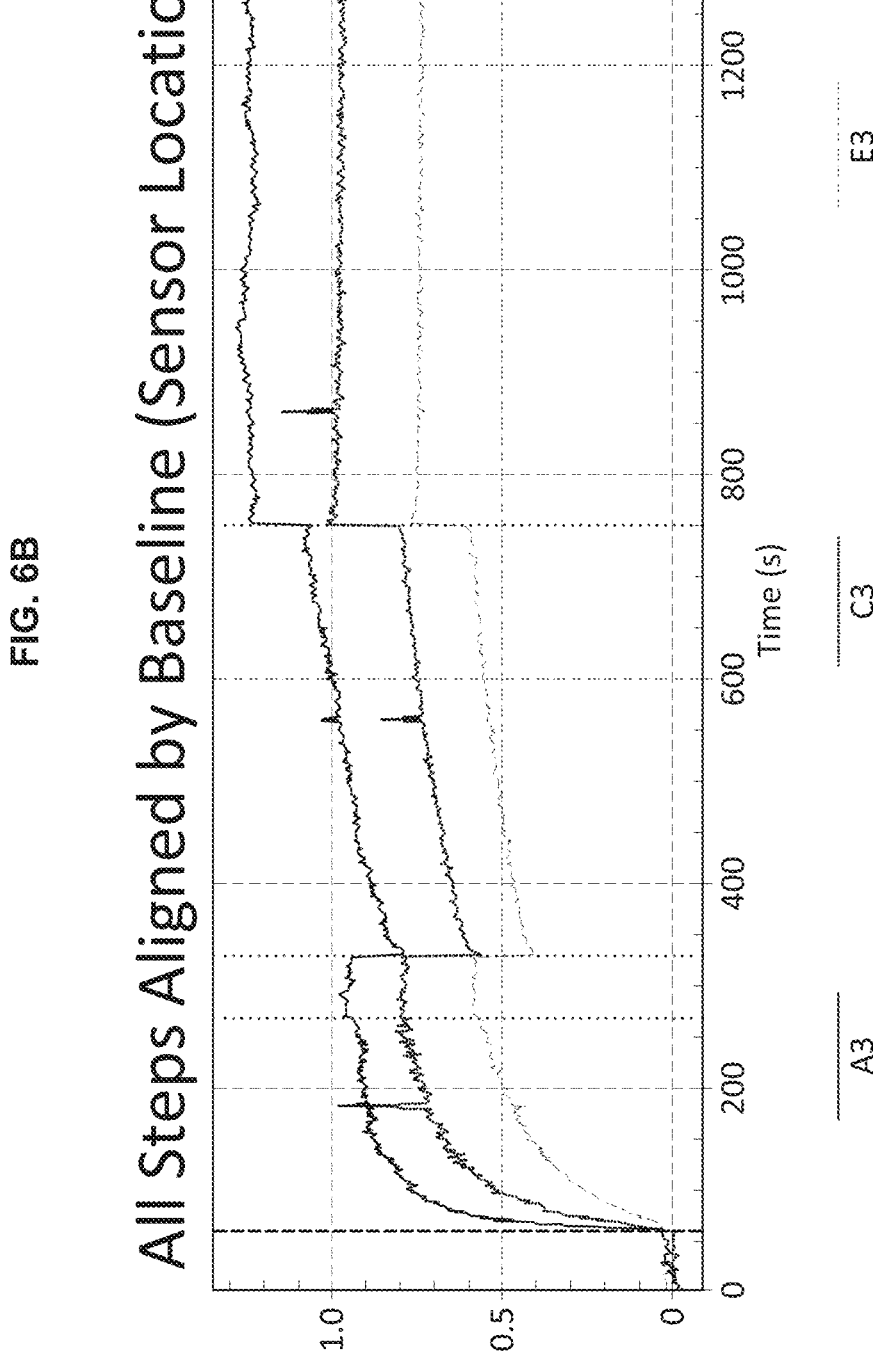
FIG. 6B shows the data aligned by the step baseline. The data was further fitted, as shown in FIGS. 6C and 6D. These graphs show the response curves for KB001 binding to whole *P. gingivalis* cells, at different concentrations of antibody, measured using surface plasmon resonance. Table 2.1 summarizes the results.
Figure 6C:
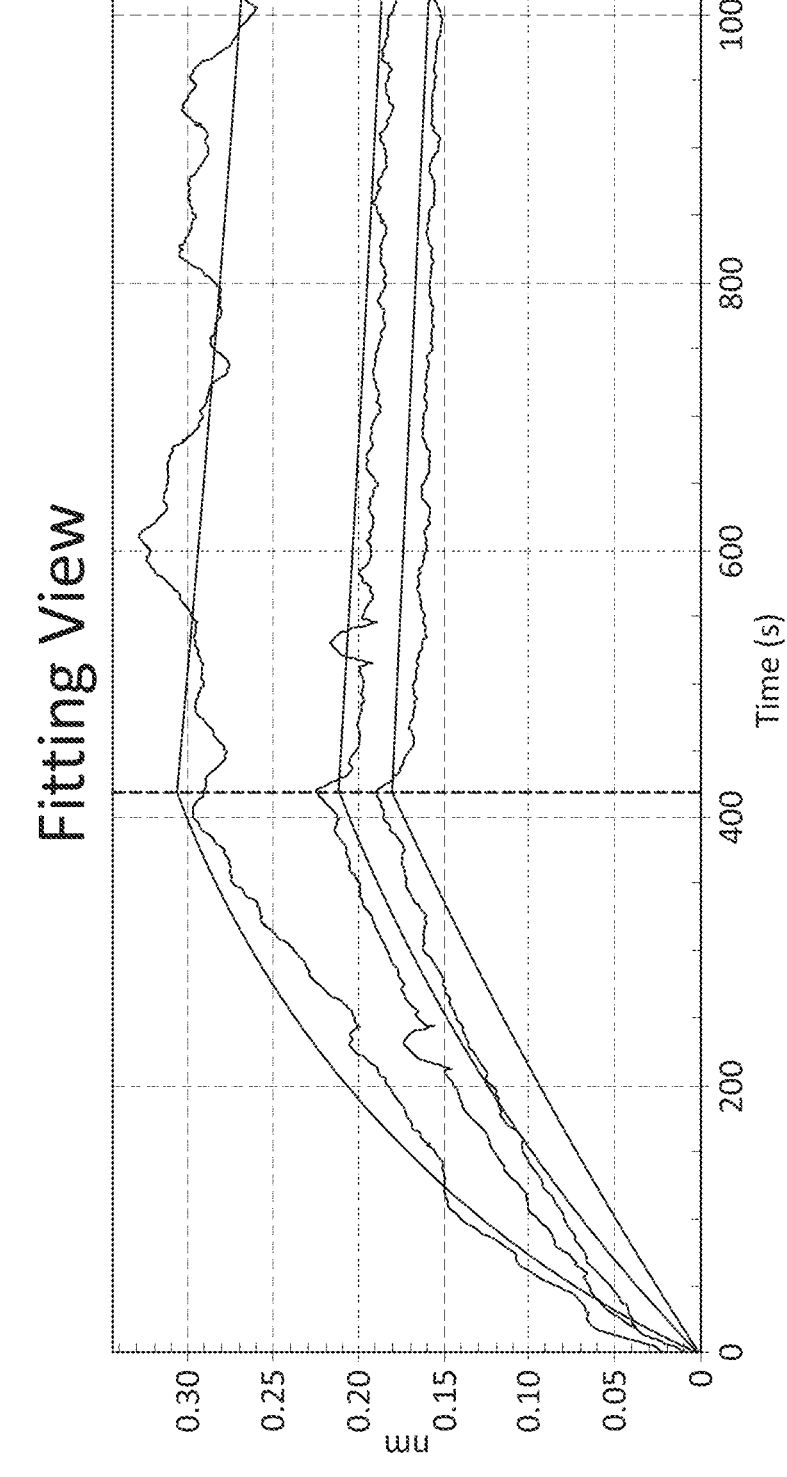
Figure 6D:
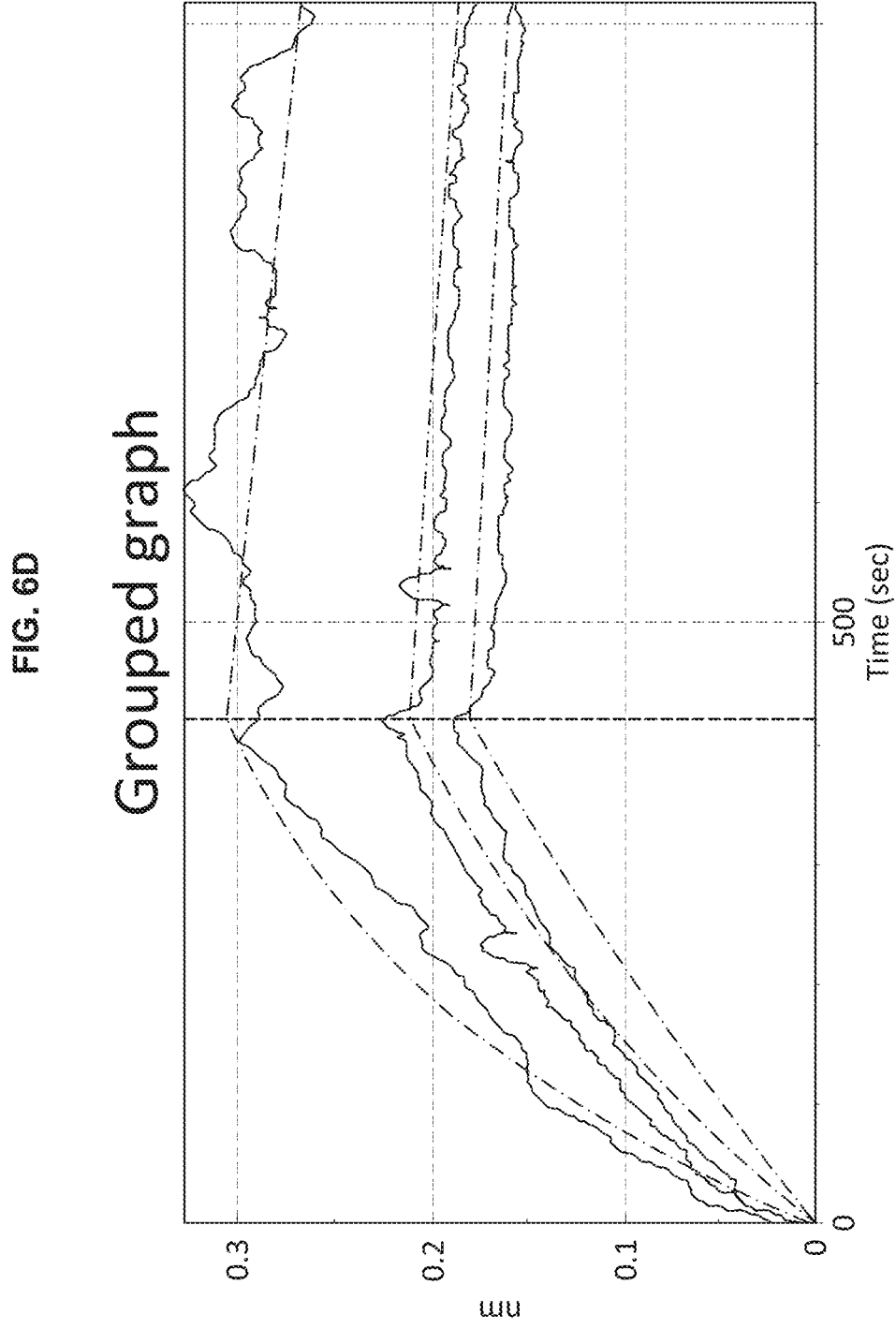

The binding affinity of KB001 for whole *P. gingivalis* cells (strain W83) was measured using surface plasmon resonance. The response curves at antibody concentrations of 33.3 nM (E3), 100 nM (C3) and 200 nM (A3) are show in FIG. 6A. FIG. 6B shows the data aligned by the step baseline. The data was further fitted, as shown in FIGS. 6C and 6D. Analysis of the rate of association, dissociation and the binding affinity are shown in Table 2.1. The data showed KB001 binds to whole *P. gingivalis* cells with an apparent Kd in the nanomolar range. In further analysis, KB-001 recognized all 22 laboratory strains and serotypes of P.g. tested as well as 105 human clinical isolates (data not shown).

132

These blebs are critical for the bacterial survival system as they serve to both feed and/or maintain its energetics, adhesion and biofilm maintenance for the bacteria, and protect it from host defense molecules. In addition, these blebs are considered outer-membrane vesicles, or "microbullets" containing exo-toxins (such as gingipains or LPS) that can flood the systemic circulation, reach the arteries of the heart and large carotid arteries of the neck, thereby increasing the risk of stroke. The outer-membrane vesicles and/or contents thereof can also end up in the brain (see Example 4).

Figure 9:
FIG. 9 is a Western blot of *P. gingivalis* Outer Membrane Vesicles (OMV) probed with KB001.

FIG. 9 shows KB001 staining OMV from *P. gingivalis* strain 33277 and a Peptidylarginine deiminase PPAD C351A 33277 strain in a Western blot demonstrating broad binding activity against different pathogenic strains. PPAD is a virulence factor unique to pathogenic *Porphyromonas* species, especially *P. gingivalis*. 100 ul Base samples (conc 500 ug/ml) and 100 µl of NuPAGE loading buffer (novex NP007) with 10% BME (Sigma M-7522) was mixed and heated at 100° C. for 10 min. 5× serial dilutions were made with cold loading buffer. Samples were electrophoresed by using 4-12% Bis-Tris SDS-PAGE (Invitrogen) at 160 v for 60 min.

Subsequently proteins were transferred onto nitrocellulose membrane (Biorad) at 100 v for 60 min, then blocked in 5% milk overnight at R.T. After washing 3×5 min with

TABLE 2.1

| Conc. (nM) | Response | KD (M) | KD Error | kon(1/Ms) | kon Error | kdis(1/s) | kdis Error |
|---|---|---|---|---|---|---|---|
| 200 | 0.2969 | 1.14E−08 | 1.51E−09 | 1.92E+04 | 1.35E+03 | 2.19E−04 | 2.45E−05 |
| 100 | 0.2157 | 1.14E−08 | 1.51E−09 | 1.92E+04 | 1.35E+03 | 2.19E−04 | 2.45E−05 |
| 33.3 | 0.1858 | 1.14E−08 | 1.51E−09 | 1.92E+04 | 1.35E+03 | 2.19E−04 | 2.45E−05 |

In some embodiments, an antigen binding molecule (ABM) of the present disclosure binds to *P. gingivalis* with a Kd of $10^{-7}$ M or less, $5×10^{-8}$ M or less, $2×10^{-8}$ M or less, or about $1×10^{-8}$ M.

Figure 7:
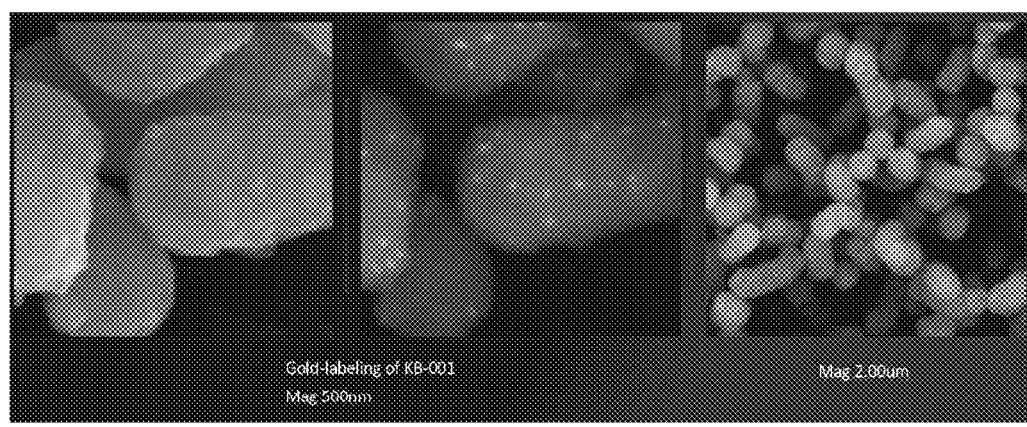
FIG. 7 is SEM imaging of KB-001 binding to the *P. gingivalis*. strain W83. The left panel shows the cell surface at 500 nm magnification, using gold labeling. The middle panel shows KB-001 localization at 500 nm magnification. The right panel shows KB-001 localization at 2 μm magnification.

Binding of KB001 to *P. gingivalis* (W83) was also observed using scanning electron microscopy. The bacteria were labeled with KB001 attached to a gold particles. FIG. 7 shows scanning electron micrographs showing representative images of *P. gingivalis* without (top panel) and with (bottom panel) filtering to visualize the gold particles. The scanning electron micrographs show approximately 6 individual bacterial cells, and the same view is shown in the top and bottom panels. Direct binding of individual IgG molecules is seen attaching to the cell surface in specific locations on developing/emerging outer membrane blebs/vesicles (OMV). Around 60-80 molecules of the IgG molecules appears bound per bacteria.

Morphological differences in *P. gingivalis* strains in terms of OMV production and extracellular polymeric substance (EPS) were observed. Clinical isolates were able to produce more OMV and EPS than laboratory strains. KB001 was observed to be binding more to OMV than whole surface. Thus, there exists critical differences among the *P. gingivalis* strains in terms of OMV and EPS production. The specificity of KB001 may be further defined by testing clinical strains.

Figure 8:
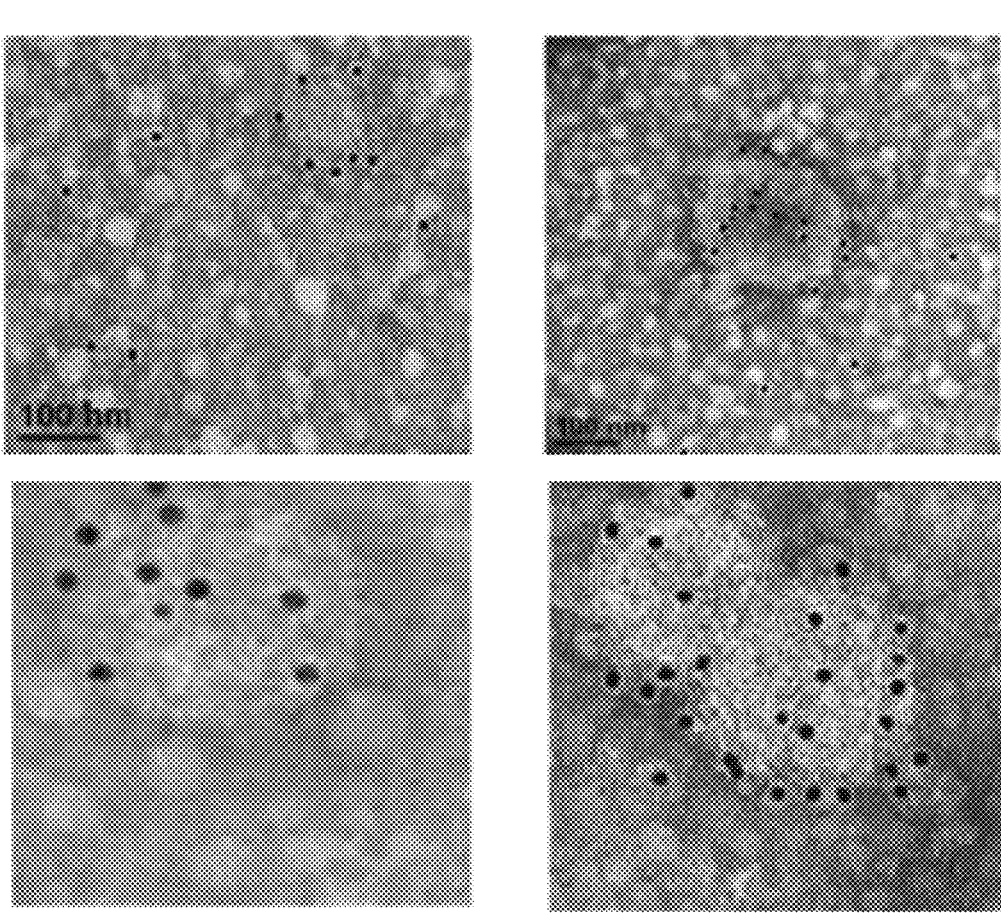
FIG. 8 is a collection of images showing binding of KB001 to outer membrane vesicles (OMV) and OMV blebs of *P. gingivalis*, W 83, visualized using secondary gold-labeled anti-mouse antibody.

FIG. 8 shows additional electron microscopy images showing binding of KB001 to outer membrane vesicles (OMV) of *P. gingivalis*, W83. The antibody appears to exhibit strong binding to the OMVs. The size distribution of the OMV ranged from 80-150 nm. KB001 bound to the inner as well outer surface of the OMV bleb.

TTBS (20 mM Tris, 500 mM NaCl, 0.1% Tween-20 pH 8.0), the membrane was incubated with KB001 (1 ug/ml in 10 ml 1% milk) for 2 hrs at R.T. The membrane was then washed 3×5 min in TTBS before probing with secondary antibody anti-mouse (Sigma A4312-1 mL whole molecule alkaline phosphatase 1:10000 in 1% milk) for 2 hr. at room temperature. Membrane was washed 4×5 min with TTBS before developing. Membrane was developed over 5 min using AP-conjugated Substrate kit (Biorad, ref 170643). Molecular mass (Precision Plus Protein Standards, Biorad) is indicated to the left of the membrane.

Without being bound by theory, mechanistically, PPAD activity, in conjunction with Arg-specific gingipains, generates protein fragments with citrullinated C-termini. Such polypeptides are potential de novo epitopes that are key drivers of rheumatoid arthritis. This process could underlie the observed clinical association between rheumatoid arthritis and periodontitis.

In some embodiments, an ABM of the present disclosure binds to outer membrane vesicles (OMV) of *P. gingivalis*. In some embodiments, the ABM binds to budding or emerging OMV of *P. gingivalis*.

Example 4: Specificity of KB-001 Across P.g. Strains

This non-limiting example shows binding of KB001 to phylogenetically diverse strains of *P. gingivalis*.

Clinical isolates as well as pathologically significant strains of *P. gingivalis* were genetically characterized to identify the phylogenetic diversity, using PACBIO sequencing. A distinct phyolgram was generated from the genetic relatedness observations. As show in FIG. 10, a phylogenetic tree of *P. gingivalis* strains was constructed using binary presence/absence of accessory genes. Using the phyolgram, genetically diverse *P. gingivalis* strains were identified.

Immuno-electron microscopy of genetically diverse strains of *P. gingivalis* was done by immunogold labelling to detect specificity of KB001 against *P. gingivalis*. Ten strains that represent the diversity of strains as determined by comparison of genome sequences (dendrogram, see FIG. 10) were chosen for analysis. The reaction of gold-labeled KB monoclonal antibody with each strain was determined by SEM analysis. The KB-001 antibody was found to bind all genetically diverse strains representing the entire P.g. family.

FIG. 41 shows KB001 binds to *P. gingivalis* strains W83 and A7436, as well as a clinical isolate. KB001 specifically bound to surface-associated blebs as well as secreted OMVs with the same affinity. The average labeled density of the strains was 50 $\mu m^{-2}$. The smallest distance between gold particles (labels) was 0.063 $\mu m$, and the largest distance was 0.14 $\mu m$. Clinical strains produced a greater number of bleb-like structures on their surface and increased binding by KB001. Without being bound by theory, this may be due to a greater ability of the clinical strains to secrete OMVs. A number of the clinical strains were observed to produce an increase of OMVs and greater binding on the exterior in comparison to surface of the cells.

KB001 recognized 22 laboratory and 105 human clinical isolates and serotypes by immunofluorescence.

Example 5: Comparison of KB001 Binding Vs 1A1 Binding

This non-limiting example shows the difference in binding characteristics between KB001 and another gingipain monoclonal antibody, 1A1.

Figure 11:
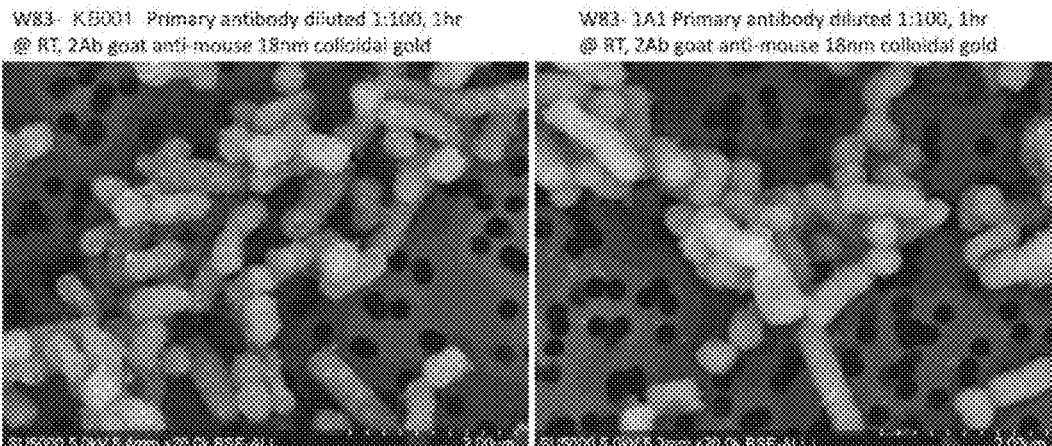
FIG. 11 is a collection of SEM images showing W83 immunogold labeling against KB001 (left panel) and 1A1 (right panel) primary antibody, single label.

When *P. gingivalis* W83 was immunogold labeled with the respective antibodies, a difference in binding specificity of 1A1 and KB001 was observed (FIG. 11). KB001 was found to binding more to bleb specific regions on the surface of *P. gingivalis*. In contrast, 1A1 was binding to the general surface. Further, KB001 binding to the W83 was unchanged in dilutions of 1:10, 1:100, 1:1000 tested. Therefore, overall, KB001 has more binding affinity than 1A1.

Example 6: Loss of KB001 Binding in Pg Knockout Strains

This non-limiting example shows KB001 has reduced or no binding to gingipain knock out strains of *P. gingivalis*.

Figure 12:
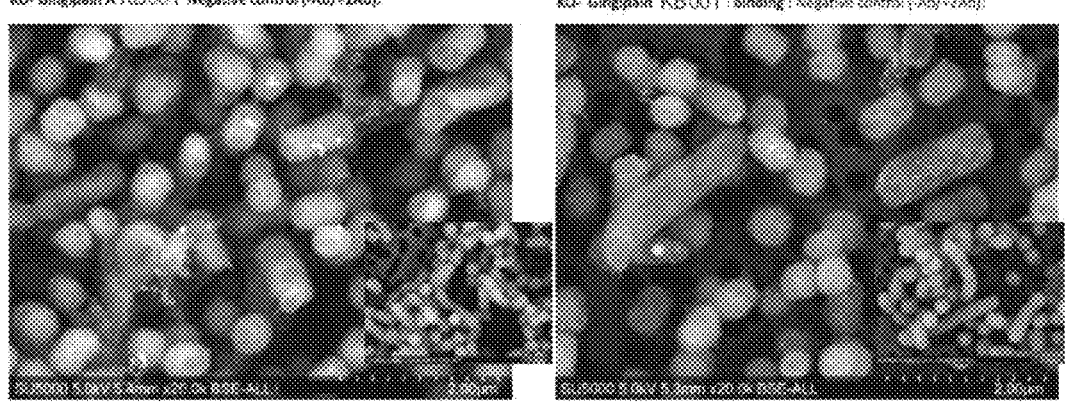
FIG. 12 is a collection of SEM images showing the lack of KB001 binding to gingipain mutants of *P. gingivalis*. Left panel is a RgpA−/KgP− gingipain knockout strain, and right panel is a RgpB−/KgP− gingipain knockout strain.

Immunogold staining of gingipain knock out strains (A & B) of *P. gingivalis* were carried out using KB001. The binding of KB-001 was monitored for two strains: RgpA−/KgP−, and RgpB−/KgP−. It was possible to significantly decrease or result in no binding of the KB-001 antibody to the surface of both gingipain knock out strains in comparison to the W83 strain (FIG. 12). There was decreased or no binding of the antibody to the surface of the gingipain knock out strains in comparison to the W83 strain (a known gingipain rich strain). The minimal binding observed was restricted to the bleb/OMV surface area signifying the potential specificity of KB001 to OMV.

Example 7: Binding of KB001 to Purified Gingipain

Figure 13:
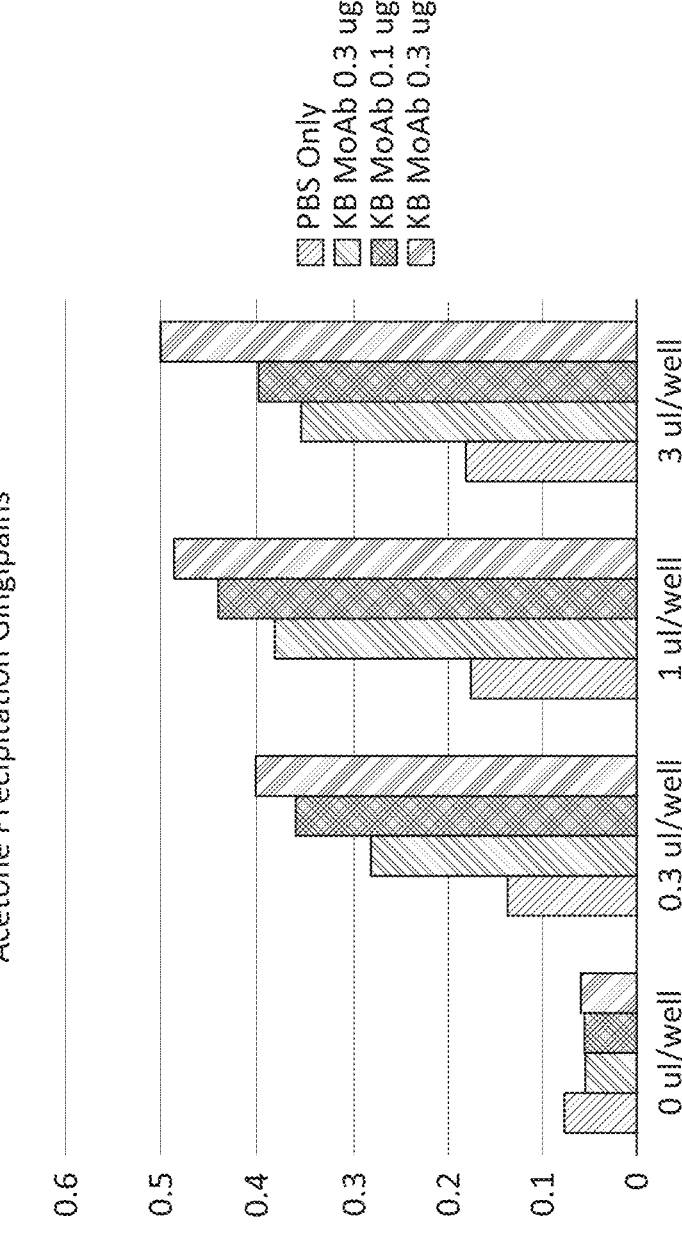
FIG. 13 is a graph showing binding of KB001 to acetone precipitated gingipain.

This non-limiting example shows an assay to measure binding of a *P. gingivalis* gingipain antibody (e.g., KB001)

to acetone precipitated gingipain. Plates were coated with 0, 0.3, 1, or 3 $\mu l$/well of acetone precipitated gingipain sample and probed with 0, 0.3, 1, and 3 $\mu l$/well concentrations of KB001. Crude gingipain was used to coat the wells. Binding was measured by ELISA (FIG. 13) and confirmed the specificity of binding to fully secreted and extruded OMVs from *P. gingivalis*.

Figure 14A:
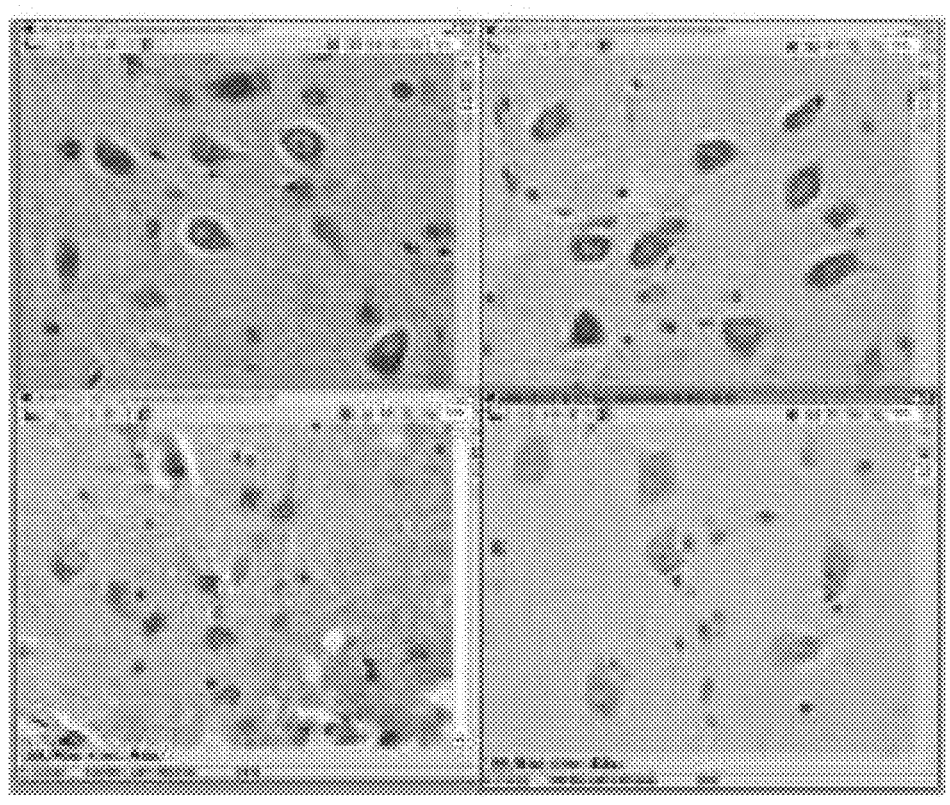
FIG. 14A is a collection of images showing immunohistochemistry staining (IHC) of hippocampal tissue slices from the brain of a deceased Alzheimer's disease patient using KB001.
Figure 14B:
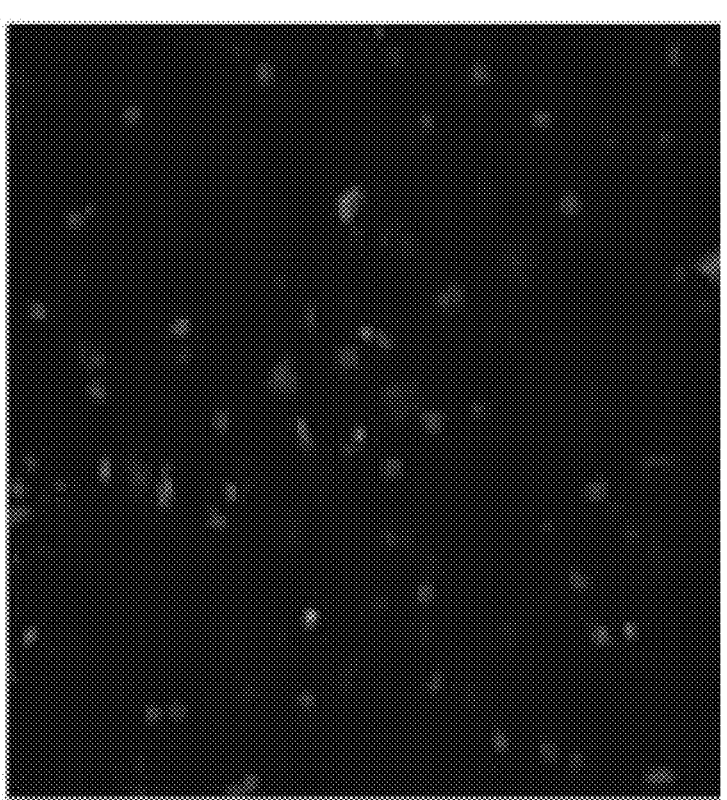
FIG. 14B shows imaging of AD brain tissue. The brain tissue is labeled for gingipain using binding by KB-001.
Figure 14C:
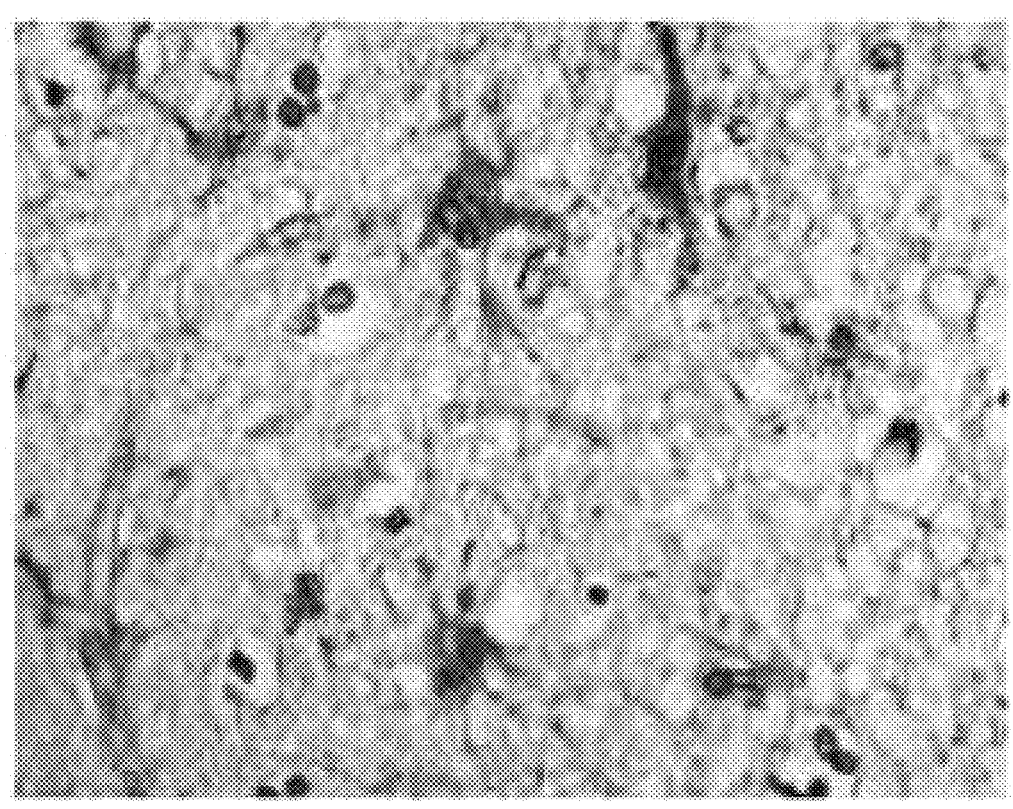
FIG. 14C shows immunohistochemistry staining of *P. gingivalis* using KB001 binding to intra-cellular accumulated gingipains located in a hippocampal tissue from the brain of a deceased Alzheimer's disease patient.
Figure 14D:
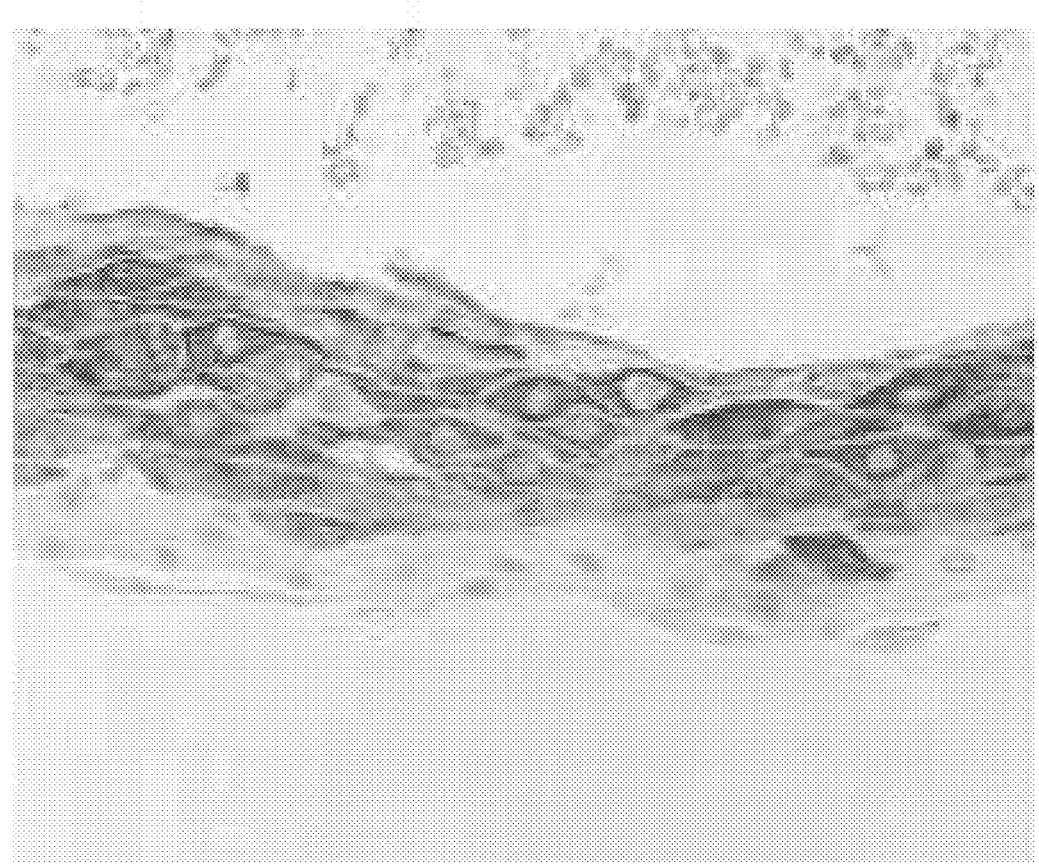
FIG. 14D is an image showing a *P. gingivalis* positive control human gum tissue used in brain IHC analysis.
Figure 14E:
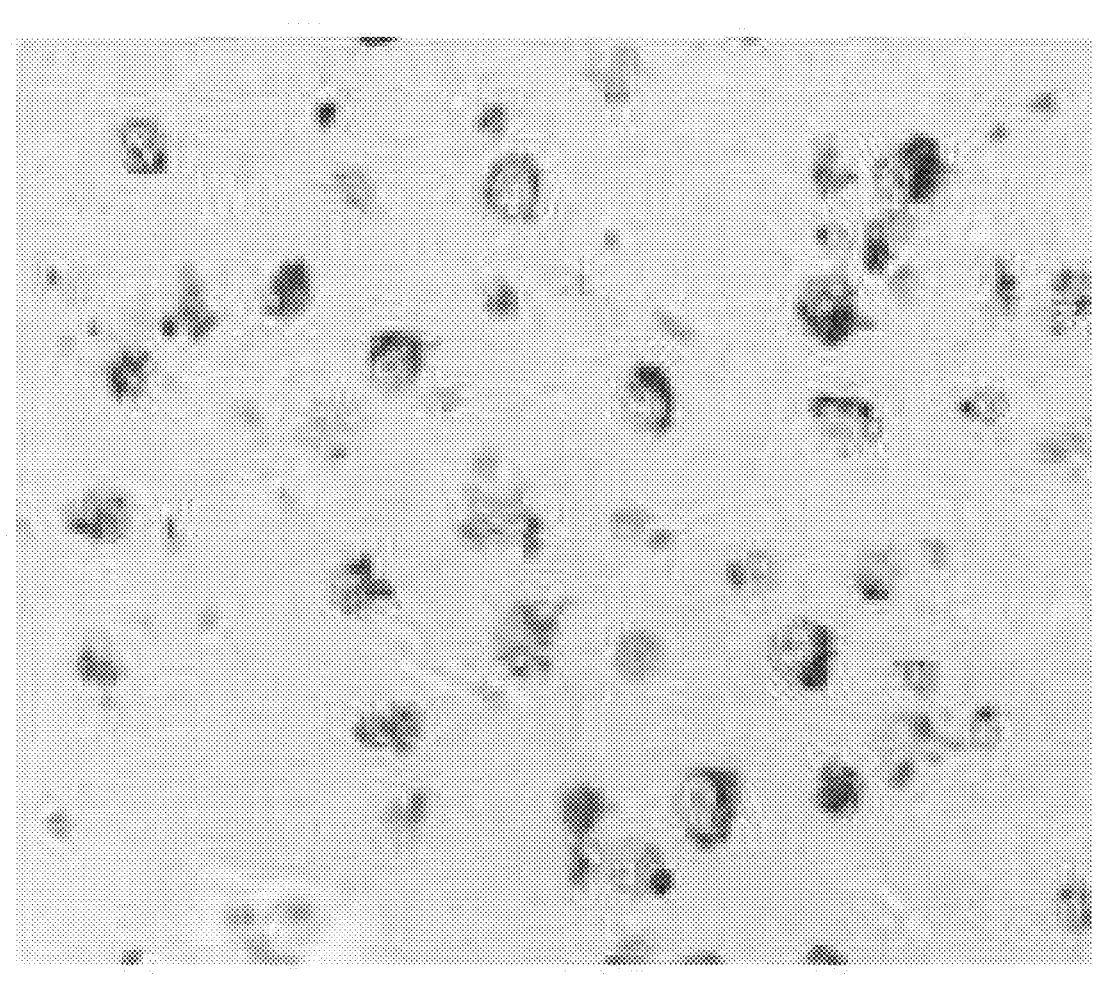
FIG. 14E shows frontal lobe using immunohistochemistry staining with KB001.

Example 8: Binding of KB001 Antibody to Targets in Brain Tissue of a Deceased Alzheimer's Disease Patient Periodontal disease has been implicated as a risk factor for Alzheimer's disease (AD). Neuropathological characteristics of AD includes accumulation of amyloid-beta (Aβ), which may be related to an innate immune response to infection. To test the hypothesis that periodontal *P. gingivalis* infection can induce immune responses in the brain, a brain tissue section from a deceased AD patient was immunohistochemically assayed using KB001. FIG. 14C shows a representative image of staining of the tissue section by KB001. The brown granular staining was observed in hippocampal neurons, microglia and astrocytes, as the antibody bound to gingipain or other *P. gingivalis*-derived targets in the cells. Thus, KB001 appeared to bind directly to the accumulated exo-toxins in the brain of the AD patient. The antibody labeled neurons, astrocytes and micro-glial cells. FIG. 14A shows further staining of brain tissue sections from an AD patient, using KB001. The staining indicates binding of KB001 to intra-cellular accumulated gingipains located in the brain. FIG. 14E shows IHC staining of the frontal lobe using KB001. These results indicate accumulation of *P. gingivalis* exo-toxins can occur in an AD patient's brain.

This non-limiting example shows higher sensitivity of KB001 detection of *P. gingivalis* in tissue samples compared to a PCR-based assay.

Figures 15A, 15B:
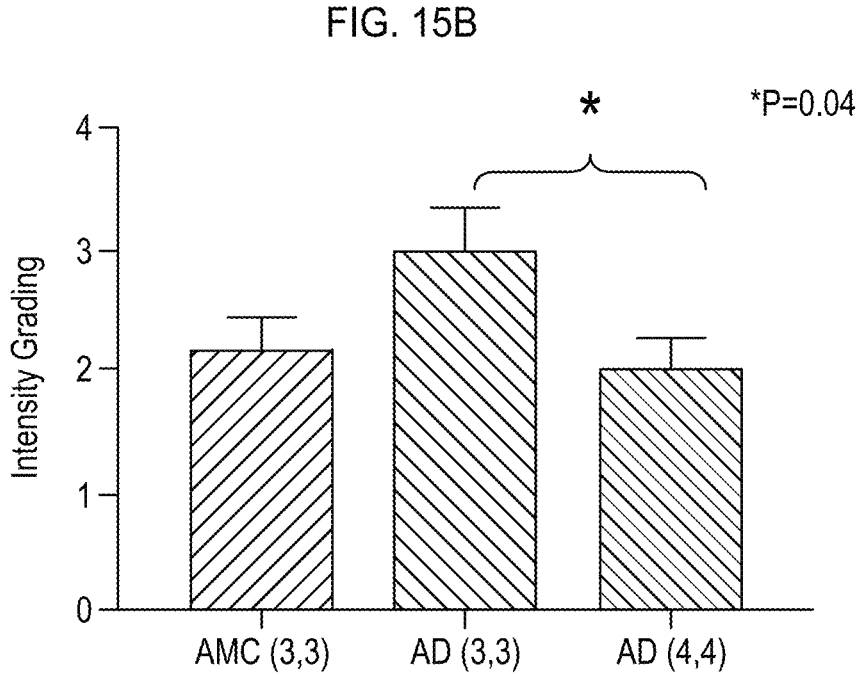
FIG. 15A shows the gingipain antibody signal intensity from frontal lobe immunostaining of subjects AMC3,3, AD3,3, and AD4,4.
FIG. 15B shows the gingipain antibody signal intensity from occipital lobe immunostaining of subjects AMC3,3, AD3,3, and AD4,4.
Figure 15C:
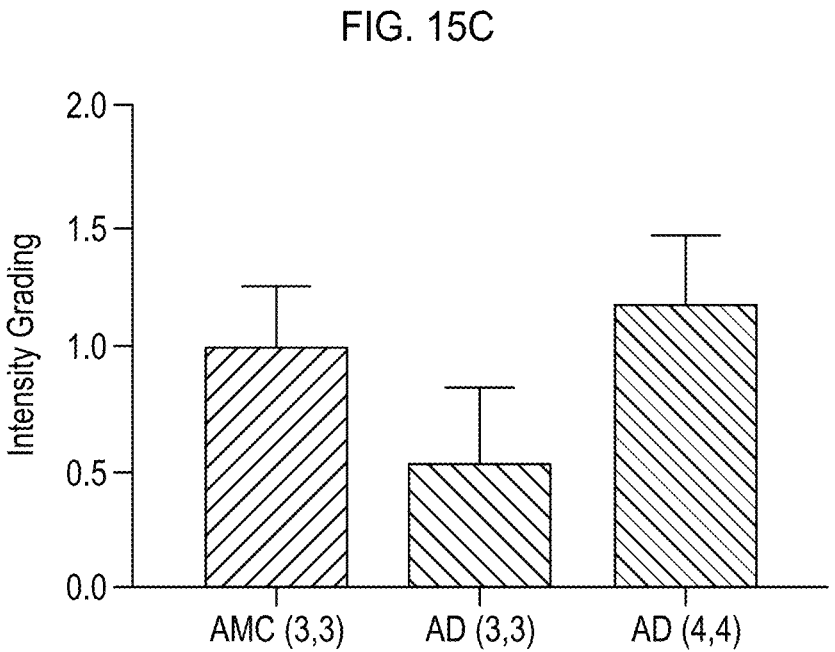
FIG. 15C shows the gingipain antibody signal intensity from cerebellum immunostaining of subjects AMC3,3, AD3, 3, and AD4,4.
Figure 15D:
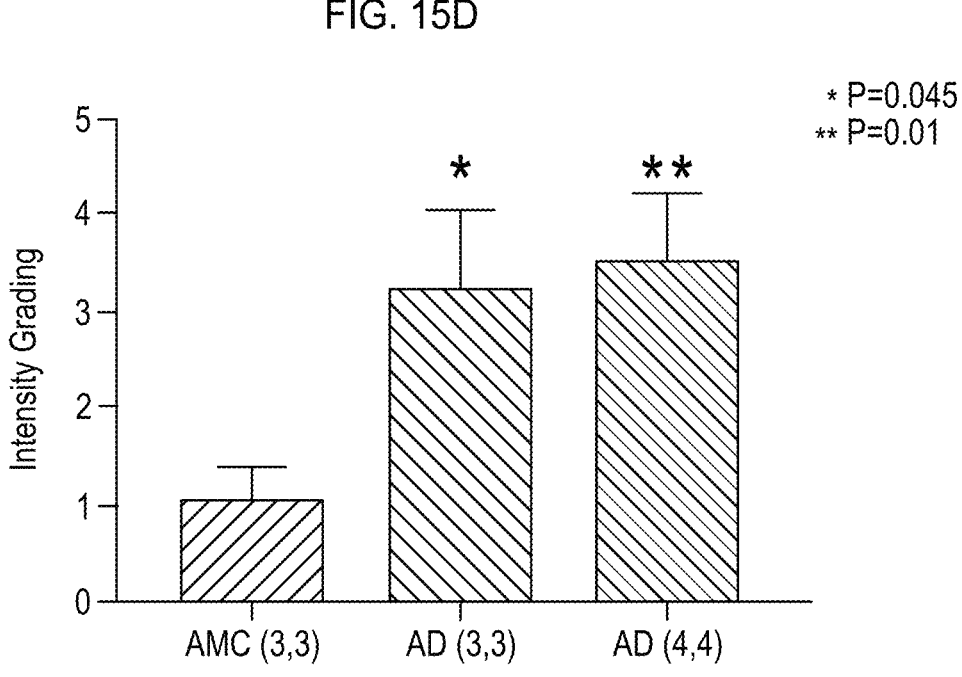
FIG. 15D shows the gingipain antibody signal intensity from hippocampus immunostaining of subjects AMC3,3, AD3,3, and AD4,4.

*P. gingivalis* was carried out using PCR-based liquid hybridization assay of human AD brains and comparative IHC. Forty-six brain tissue samples (frontal and temporal biopsies) from 23 brain specimens (7 AD and 16 AMC) were subjected to PCR-based liquid hybridization assay (PCR-LH) to detect *P. gingivalis* DNA. Each PCR analysis for Pg DNA used ~1 microgram of total human DNA extracted from the fresh frozen brain tissue. Since a human genome is approximately three picograms, this represented approximately ~300,000 human cells worth of DNA/assay. Semi-quantitative analyses based on the intensity of the autoradiographic signal following PCR-LH to obtain the approximate number of Pg genomic equivalents (copy numbers) for each specimen studied. All samples were negative for *P. gingivalis* DNA (Table 9.1). FIG. 15D (bottom right panel) shows increased gingipain staining in hippocampus.

To determine Pg genomics equivalents (copy number) per assayed specimen, a series of diluted positive control Pg DNA was isolated and analyzed from pure culture consisting of: 1 pg, 0.5 pg, 100 fg. 20 fg, and 2 fg. These amounts of Pg genomic DNA translate into approximately 500, 250, 50, 10 and 1 genomic equivalents, respectively. 500 genomic equivalents of Pg from an input of one microgram of human DNA corresponds to ~1 Pg genome/600 human brain cells-similarly if only 10 Pg genomic equivalents from 1 microgram of input DNA that would correspond to 1 Pg genome 30,000 human brain cells.

The densities of immunohistochemical intensity of P. gingipains were assessed relative to none (0) on a scale of 1 to 5 in 7u sections of temporal lobe/hippocampal area from brains of the age matched control ("AMC") who were clinically and neuropathologically evaluated by Braak and Braak, and by antibody staging of appropriate region analysis (see Table 8.1 below). Similar assessments were made of analogous areas from brains of patients that were evaluated and determined to be neuropathologically as having met the criteria for a diagnosis of Alzheimer's disease.

TABLE 8.1

Table densitometric comparisons of *P. gingipains* in Alzheimer and control brains, segregated by APOE genotypes 3,3 or 4,4

| AMC 3,3- | | AD 3,3- | | Diagnosis | |
|---|---|---|---|---|---|
| G03-26 | 1 | C03-54 | 1 | C00-29 | 5 |
| G04-05 | 2 | C05-51 | 4 | C01-80 | 5 |
| G04-21 | 2 | C05-64 | 0 | C07-71 | 5 |
| G05-17 | 0 | C06-35 | 5 | C99-76 | 1 |
| G97-86 | 1 | G04-15 | 5 | G01-78 | 3 |
| G98-114 | 0 | G90-122 | 4 | G03-16 | 2 |

Surprisingly, no significant difference was detected from gingipain antibody staining in the frontal lobe region between control and AD patients. In contrast, AD patient had significantly higher gingipain antibody signal intensity in the hippocampus region.

Staining intensity in the temporal lobe/hippocampal area was measured semi-quantitatively, as shown in FIG. 17B, and results from multiple stained samples are shown in Table 8.2.

TABLE 8.2

| sample_id | specimen_id | diagnosis | location | *P. gingivalis* detection | IHC result* |
|---|---|---|---|---|---|
| uams_S21-1 | uams_S21 | AD | frontal | Negative | |
| uams_S21-2 | uams_S21 | AD | temporal | Negative | |
| uams_S7-3 | uams_S7 | AD | frontal | Negative | |
| uams_S7-4 | uams_S7 | AD | temporal | Negative | |
| uams_S6-5 | uams_S6 | AD | frontal | Negative | |
| uams_S6-6 | uams_S6 | AD | temporal | Negative | |
| uams_S9-7 | uams_S9 | AD | frontal | Negative | |
| uams_S9-8 | uams_S9 | AD | temporal | Negative | |
| uams_S3-9 | uams_S3 | AD | frontal | Negative | |
| uams_S3-10 | uams_S3 | AD | temporal | Negative | |
| uams_S32-11 | uams_S32 | AD | frontal | Negative | |
| uams_S32-12 | uams_S32 | AD | temporal | Negative | |
| uams_S29-13 | uams_S29 | AD | frontal | Negative | |
| uams_S29-14 | uams_S29 | AD | temporal | Negative | |
| uams_S26-49 | uams_S26 | AMC | frontal | Negative | Positive |
| uams_S26-50 | uams_S26 | AMC | temporal | Negative | Positive |
| uams_S23-51 | uams_S23 | AMC | frontal | Negative | |
| uams_S23-52 | uams_S23 | AMC | temporal | Negative | |
| uams_S12-53 | uams_S12 | AMC | frontal | Negative | |

TABLE 8.2-continued

| sample_id | specimen_id | diagnosis | location | *P. gingivalis* detection | IHC result* |
|---|---|---|---|---|---|
| uams_S12-54 | uams_S12 | AMC | temporal | Negative | |
| uams_S1-55 | uams_S1 | AMC | frontal | Negative | |
| uams_S1-56 | uams_S1 | AMC | temporal | Negative | |
| uams_S22-57 | uams_S22 | AMC | frontal | Negative | |
| uams_S22-58 | uams_S22 | AMC | temporal | Negative | |
| uams_S14-59 | uams_S14 | AMC | frontal | Negative | Positive |
| uams_S14-60 | uams_S14 | AMC | temporal | Negative | Positive |
| uams_S28-61 | uams_S28 | AMC | frontal | Negative | |
| uams_S28-62 | uams_S28 | AMC | temporal | Negative | |
| uams_S30-63 | uams_S30 | AMC | frontal | Negative | |
| uams_S30-64 | uams_S30 | AMC | temporal | Negative | |
| uams_S13-33 | uams_S13 | AMC | frontal | Negative | |
| uams_S13-34 | uams_S13 | AMC | temporal | Negative | |
| uams_S5-35 | uams_S5 | AMC | frontal | Negative | |
| uams_S5-36 | uams_S5 | AMC | temporal | Negative | |
| uams_S10-37 | uams_S10 | AMC | frontal | Negative | Positive |
| uams_S10-38 | uams_S10 | AMC | temporal | Negative | Positive |
| uams_S11-39 | uams_S11 | AMC | frontal | Negative | |
| uams_S11-40 | uams_S11 | AMC | temporal | Negative | |
| uams_S18-41 | uams_S18 | AMC | frontal | Negative | |
| uams_S18-42 | uams_S18 | AMC | temporal | Negative | |
| uams_S16-43 | uams_S16 | AMC | frontal | Negative | |
| uams_S16-44 | uams_S16 | AMC | temporal | Negative | |
| uams_S19-45 | uams_S19 | AMC | frontal | Negative | |
| uams_S19-46 | uams_S19 | AMC | temporal | Negative | |
| uams_S20-47 | uams_S20 | AMC | frontal | Negative | |
| uams_S20-48 | uams_S20 | AMC | temporal | Negative | |

Sensitivity of PCR-based liquid hybridization assay for detection of *P. gingivalis* was tested. Autoradiography of gel electrophoresis (FIG. 16) shows the PCR-based assay was able to detect 2 fg to 0.5 pg of input purified *P. gingivalis* genomic DNA. (N: PCR negative control.) Using the PCR-based liquid hybridization assay, all samples were negative for *P. gingivalis* genomic DNA (Table 9.1). Six samples were positive for KB001 IHC staining.

Figure 14F:
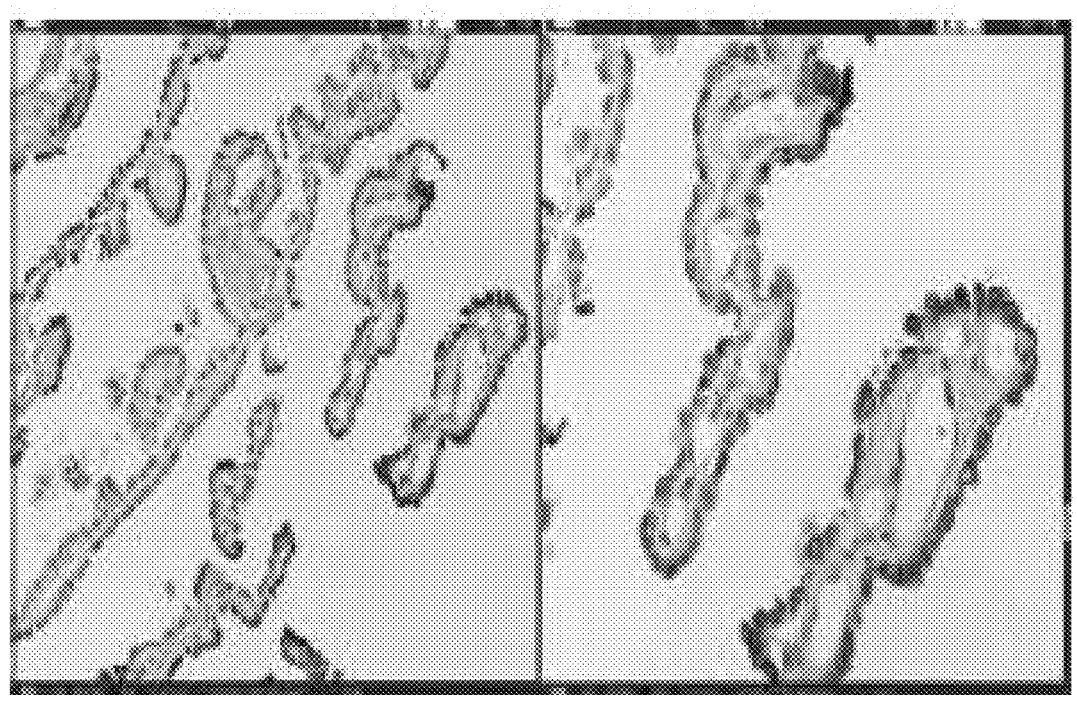
FIG. 14F is an image showing human choroid plexus IHC stained section of AD brains using KB001 (20×-left panel and 40×-right panel).

IHC of 18 hippocampal sections were evaluated and 10 of these were found to be positive (FIG. 14F). As a positive control, KB001 was used to stain gum tissue from a biopsy of a *P. gingivalis* colonized patient. Brown colored granules are the intra-cellular cytoplasmic localized gingipains as detected with KB001 (FIG. 14D).

Example 9: Safety/Toxicity Study of KB-001 in Dogs

As disclosed herein, the safety/toxicity profile of KB-001 was assessed in beagle dogs. The test comprised 5 groups, each with 3 males/3 females. Each dog was given a repeat dose sub-gingival or IV application of KB-001 between 0 to 0.33 mg/mL. At day 22 and 43, a necropsy was performed (see Table 3 below).

TABLE 3

Safety/Toxicity study of KB-001 in beagles
Study Design

| | | | | | | Number of Animals per Necropsy Interval | |
|---|---|---|---|---|---|---|---|
| Group | Treatment | Dose Route | Dose | Dose Volume | Conc (mg/mL) | Day 22 | Day 43 |
| 1 | Vehicle Control (sterile saline) | Gingival | 0 µg | 960 µg | 0 | 3M/3F | 3M/3F |
| 2 | PrevEvent | Gingival | 96 µg | 960 µg | 0.10 | 3M/3F | 3M/3F |
| 3 | PrevEvent | Gingival | 160 µg | 960 µg | 0.17 | 3M/3F | 3M/3F |

TABLE 3-continued

| | | | | | | Number of Animals per Necropsy Interval | |
| Group | Treatment | Dose Route | Dose | Dose Volume | Conc (mg/mL) | Day 22 | Day 43 |
|---|---|---|---|---|---|---|---|
| 4 | PrevEvent | Gingival | 320 μg | 960 μg | 0.33 | 3M/3F | 3M/3F |
| 5 | PrevEvent | IV | 320 μg | 1 mL | 0.32 | — | 3M/3F |

Safety/Toxicity study of KB-001 in beagles
Study Design

Example 10: KB-001 Activity

This non-limiting example shows KB001 prevents processing of HagA by *P. gingivalis* gingipains.

Figure 19A:
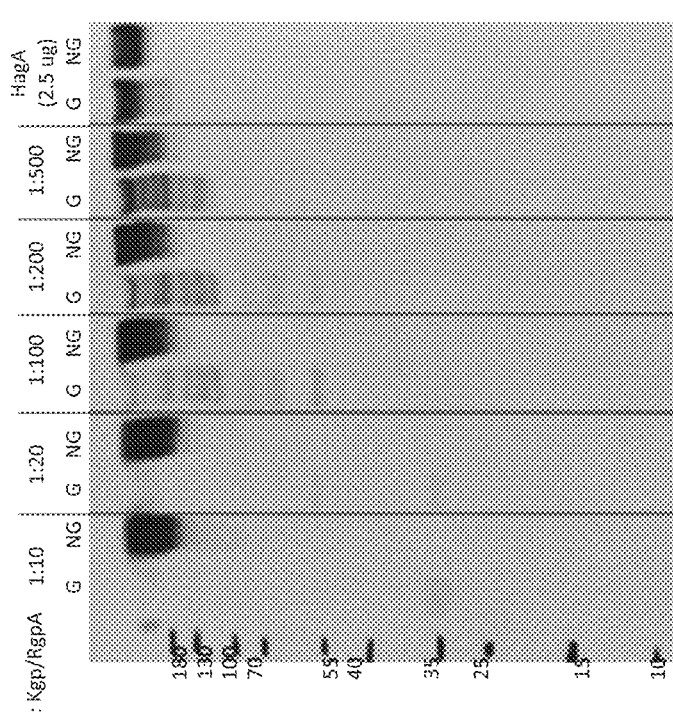
FIG. 19A is an image of a Western blot showing HagA processing by gingipains Kgp/RgpA mix, with KB001 interfering/blocking its normal bacterial proteolytic processing, according to embodiments of the present disclosure.
Figure 19B:
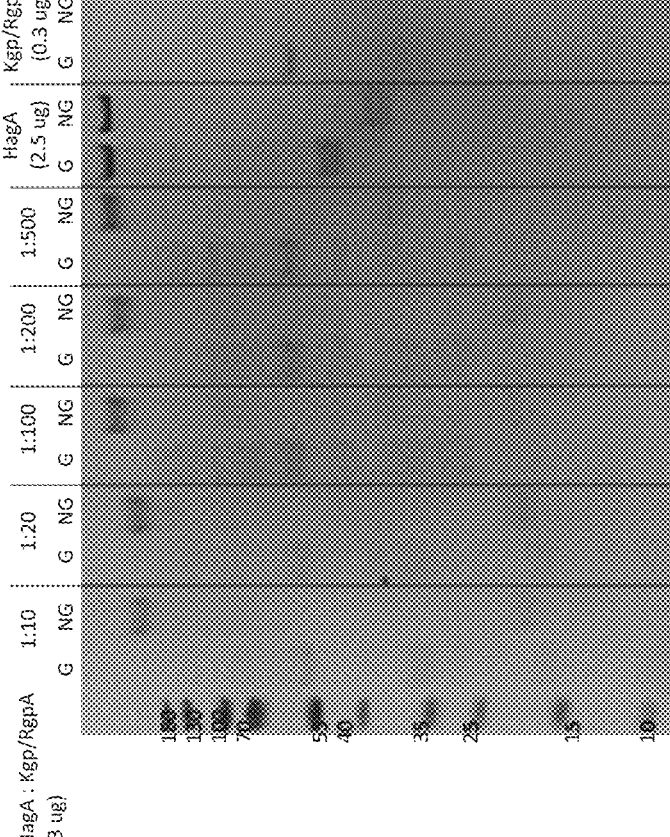
FIG. 19B is an image of an SDS-PAGE showing uninhibited processing of HagA by gingipains Kgp/RgpA mixture.
Figure 20:
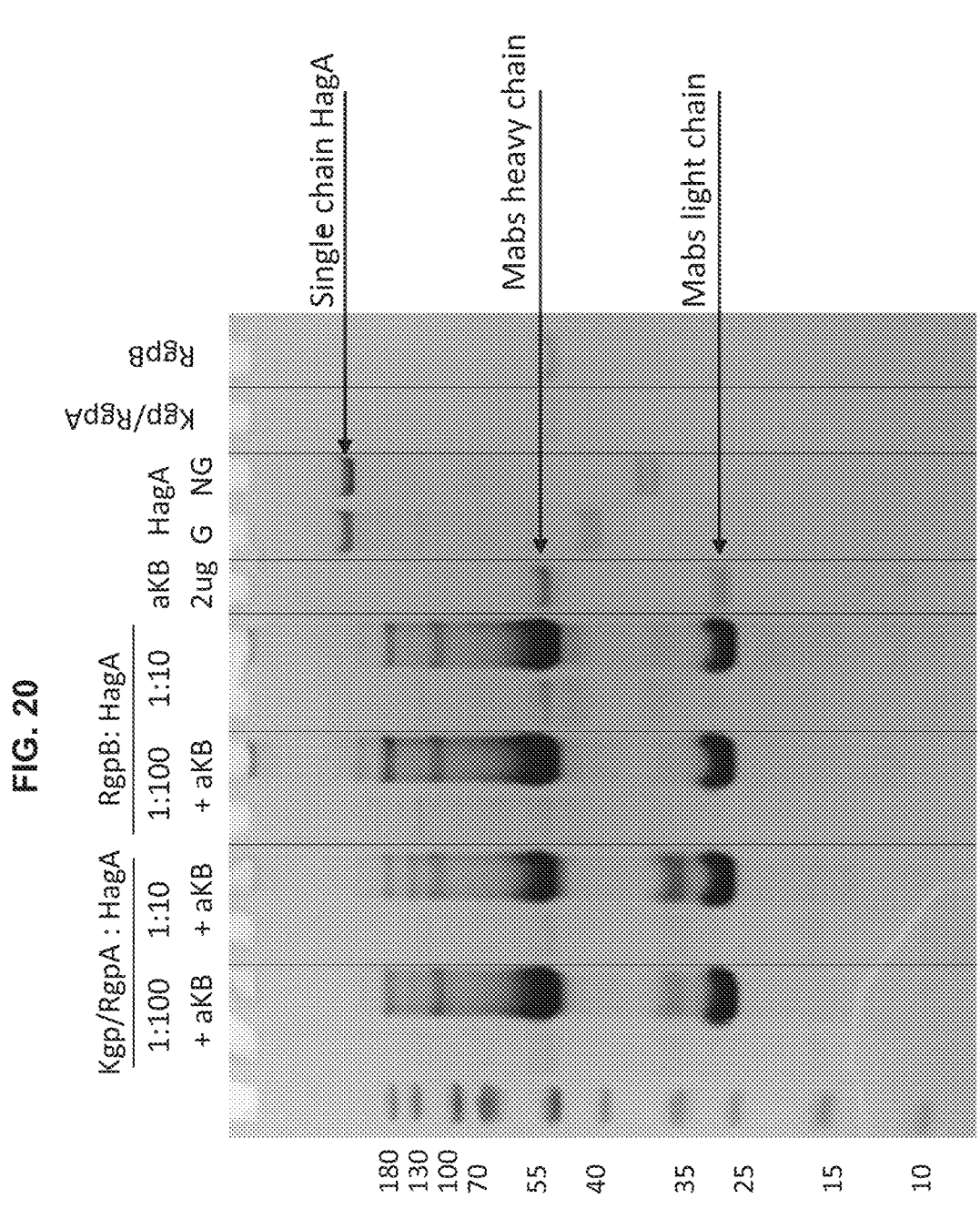
FIG. 20 shows a Western Blot for KB-001 binding to Kgp/RgpA:HagA and RgpB:HagA complexes.

Single chain HagA is processed by gingipains to hemagglutinin/adhesion (HA) domains, which are held together through non-covalent interactions. Mature HagA may assemble on *P. gingivalis* surface through this process. In FIGS. 19A and 19B, single chain HagA was incubated at the indicated (w:w) ratios with a Kgp/RgpA mixture for 2 hours, and after incubation, boiled or non-boiled samples were resolved by SDS-PAGE. Incubation of single chain HagA with Kgp/RgpA or RgpB generated a complex of the HA domains (FIG. 19B). Without boiling ("NG"), the HA domain complexes were stable in SDS-PAGE (FIG. 20). The individual HA domains were resolved by boiling ("G"). KB001 interfered/blocked full proteolysis of HagA by the gingpain mixture (FIG. 19A).

10× excess of KB001 prevented full proteolysis of HagA by the gingpains (Kgp/RgpA mix or RgpB). Similar results were observed with 100× excess of KB001.

In some embodiments, an ABM of the present disclosure prevents or reduces processing of HagA by *P. gingivalis* gingipains, e.g., RgpA, RgpB, and/or Kgp. In some embodiments, an ABM of the present disclosure prevents or reduces full proteolysis of HagA by *P. gingivalis* gingipains, e.g., RgpA, RgpB, and/or Kgp.

Example 11: Human-Chimeric Antibodies

This non-limiting example shows antigen binding of human-chimeric antibodies derived from KB001, screened and down selected for the best binding as described herein. The antibodies were diluted to 3, 1, 0.3 or 0.1 μg/mL, and binding to gingipain (RgpA) at each dilution of antibody was quantitated by ELISA (FIG. 17). FIG. 17 shows that the antibody binding signal depended on the dilution.

Figure 18:
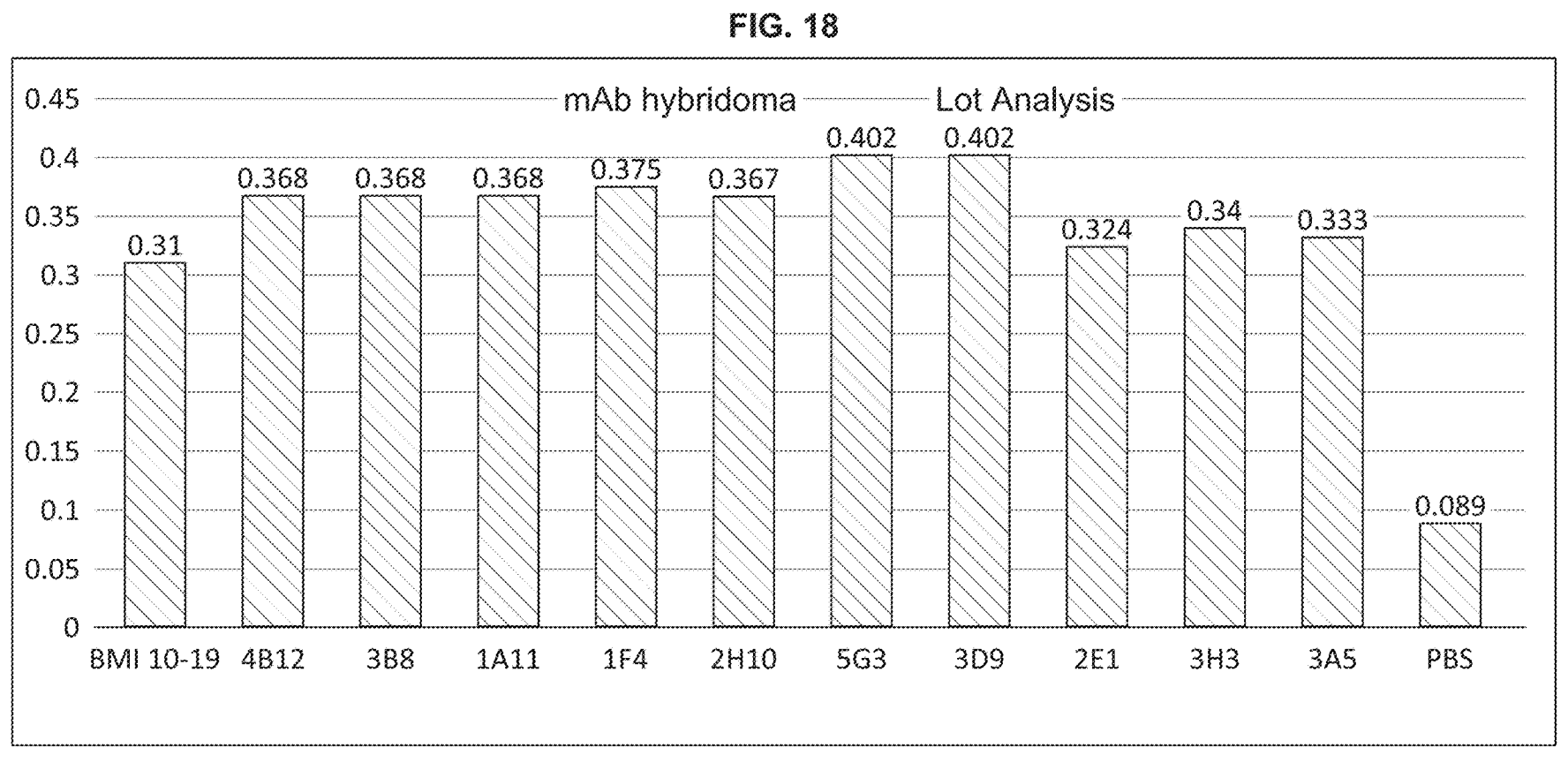

ELISA assay was performed at 0.3 μg/mL of antibody with 6 replicates each. FIG. 18 shows range determination ELISA assay of the 10 antibodies, as described above, against a control standard lot (BMI lot 10-19) at a concentration of 0.3 μg/mL. The best binders were 5G3 and 3D9.

Example 13: Human-Chimeric Antibodies

This non-limiting example shows the design, generation and production of human-chimeric antibodies to *P. gingivalis* based on KB001.

Figure 38:
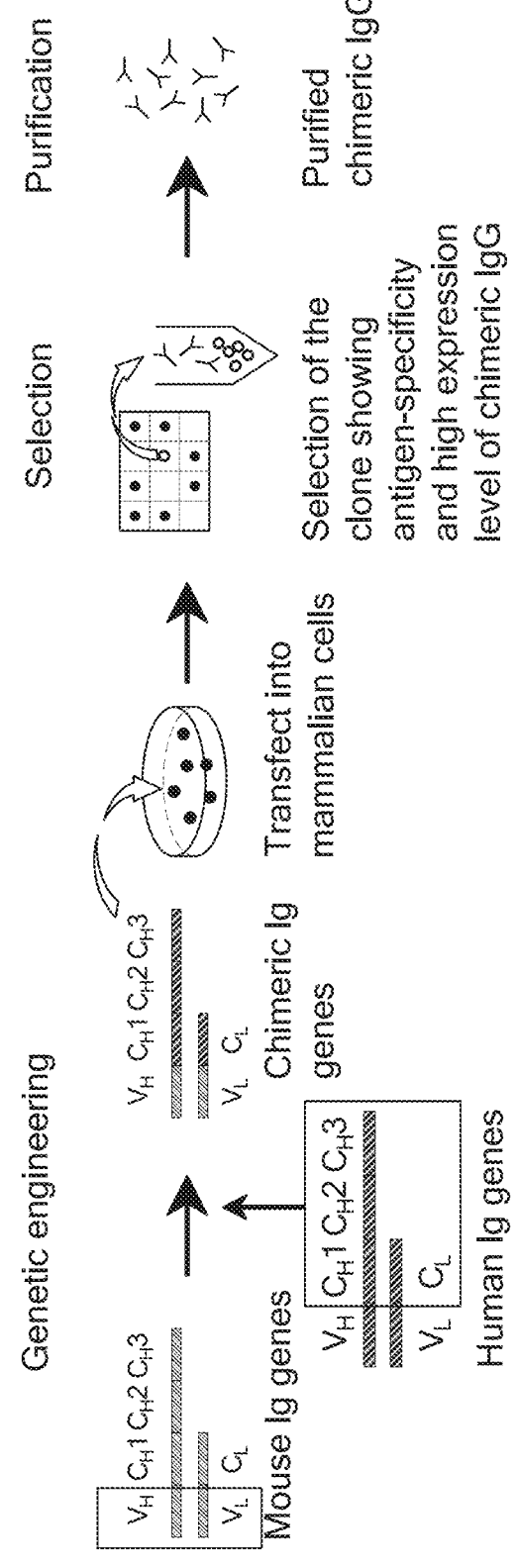
FIG. 38 shows a schematic design of constructing Hu-chimeric antibodies from a mouse parent IgG1 (KB001), according to some embodiments of the present disclosure.

The VH and VL amino acid and corresponding nucleic acid sequences of KB001 are as shown in FIGS. 31, 35A-35B, and 37A-D. The CDRs of the VH and VL of KB001 was grafted onto a human VH and VL framework (FIG. 26A). A schematic design for constructing the humanized chimeric (Hu-Chimeric) antibody is shown in FIG. 38.

Non-limiting examples of grafted VH and VL sequences and their alignments to KB001 are given in FIGS. 32-34D. Non-limiting examples of grafted nucleic acid sequences encoding human heavy chain and light chain constant regions of KB001 are given in FIGS. 36A-36B. Back mutations were designed and introduced as follows. The sequences of KB001 antibody were analyzed. Framework region (FR) residues that are believed to be important for the binding activity, e.g., canonical FR residues (underlined) and VH-VL interface residues (bold and italic), of antibody-VH/VL were identified and are shown in FIG. 26B.

Homology modeling of KB001 antibody Fv fragments was carried out. KB001 sequences were BLAST searched against PDB Antibody database for identifying the best templates for Fv fragments and especially for building the domain interface. Structural template1DVF was selected, identity=66%. Amino acid sequence alignment between KB001 antibody and 1DVF template is shown in FIG. 26C, where '|' is the chain break and * indicates identical amino acid residues in both sequences.

Homology models were built using customized Build Homology Models protocol. Disulfide bridges were specified and linked. Loops were optimized using DOPE method. Based on the homology model of KB001 all framework residues in inner core were highlighted (FIG. 26D). To mutate such residues back to KB001 antibody counterparts can retain inner hydrophobic interaction and reduce potential immunogenicity resulted from back mutation. Residues for back mutating were identified by aligning the VH and VL amino acid sequences of KB001 with the grafted VH and VL sequences, respectively, as shown in FIG. 26E.

FR residues of the grafted antibody were selected for replacement with KB001 antibody Fv equivalent according to the following guideline:

1. FR canonical residues, which do not conform to the canonical structure set, should be selected for priority back mutation;
2. FR residues in the inner core should be selected for priority back mutation;
3. VH-VL interface residues should be selected for priority back mutation;
4. Of all the potential back mutations except the residues in the grafted antibody belonging in all 3 categories aforementioned, the residues that are similar or with same R group in the grafted antibody should be selected for less priority back mutation.

Residues in the grafted antibody that fall in all categories above are different from those of KB001 antibody should be selected for replacement with KB001 antibody counterparts (shown in boxes in FIG. 26E).

The grafted and back-mutated heavy and light chain variable regions are shown in FIGS. 27A-27D and 28A-28D, respectively, as well as in FIG. 30.

All antibodies included heavy chain and light chain constant regions as shown in FIG. 29 (human IgG1 and human Ig kappa). The following combinations were designed, as shown in Table 13.1, and generated, as shown in FIGS. 23A, 23B, and 47. FIGS. 23A and 23B are images of reduced SDS PAGE gels of individual antibody clones showing heavy and light chains.

TABLE 13.1

| Antibody | VH variant | VL variant |
|---|---|---|
| H1 | VH1 (SEQ ID NO: 29) | VL1 (SEQ ID NO: 33) |
| H2 | VH1 (SEQ ID NO: 29) | VL2 (SEQ ID NO: 34) |
| H3 | VH1 (SEQ ID NO: 29) | VL3 (SEQ ID NO: 35) |
| H4 | VH1 (SEQ ID NO: 29) | VL4 (SEQ ID NO: 36) |
| H5 | VH2 (SEQ ID NO: 30) | VL1 (SEQ ID NO: 33) |
| H6 | VH2 (SEQ ID NO: 30) | VL2 (SEQ ID NO: 34) |
| H7 | VH2 (SEQ ID NO: 30) | VL3 (SEQ ID NO: 35) |
| H8 | VH2 (SEQ ID NO: 30) | VL4 (SEQ ID NO: 36) |
| H9 | VH3 (SEQ ID NO: 31) | VL1 (SEQ ID NO: 33) |
| H10 | VH3 (SEQ ID NO: 31) | VL2 (SEQ ID NO: 34) |
| H11 | VH3 (SEQ ID NO: 31) | VL3 (SEQ ID NO: 35) |
| H12 | VH3 (SEQ ID NO: 31) | VL4 (SEQ ID NO: 36) |
| H13 | VH4 (SEQ ID NO: 32) | VL1 (SEQ ID NO: 33) |
| H14 | VH4 (SEQ ID NO: 32) | VL2 (SEQ ID NO: 34) |
| H15 | VH4 (SEQ ID NO: 32) | VL3 (SEQ ID NO: 35) |
| H16 | VH4 (SEQ ID NO: 32) | VL4 (SEQ ID NO: 36) |

In some embodiments, an ABM of the present disclosure includes a humanized heavy chain variable region (HVR) with one or more back mutations as indicated by rectangular boxes in the VH alignment in FIG. 26E. In some embodiments, an ABM of the present disclosure includes a humanized light chain variable region (LVR) with one or more back mutations as indicated by rectangular boxes in the VL alignment in FIG. 26E. In some embodiments, an ABM of the present disclosure includes a HVR having an amino acid sequences of one of SEQ ID NOS: 29-32. In some embodiments, an ABM of the present disclosure includes a LVR having an amino acid sequences of one of SEQ ID NOS: 33-36.

Example 14: Variant Humanized Antibodies

This non-limiting example shows variant humanized antibodies derived from KB001 binding to gingipain, and quantitating binding using ELISA.

Binding of variant antibodies to gingipain (RgpA) was quantitated by ELISA (FIG. 24). FIG. 24, top panel, shows the signal from HuAb probed with anti-human secondary (bar labeled "B" for each variant) and the signal from the HuAb probed with anti-mouse secondary (bar labeled "A" for each variant). H14, H5, H7 showed the greatest binding, and H11, H1, H2, H3, and H4 showed weaker binding. The low signal for anti-mouse secondary demonstrates that the mouse antibody is specific for mouse IgG and does not react well with human IgG, as expected. FIG. 24, bottom panel, shows the signal from the HuAb+KB001 complex probed with anti-human secondary (bar labeled "B" for each variant) and the signal from the KB001 probed with anti-mouse (bar labeled "A" for each variant), which provides the competitive ELISA data (the lower the bar, the better the competition from HuAb). Here, H14 and H7 demonstrated the most robust binding, while H8 and H14 showed the greatest competition in a 1-hour binding assay. H5, H7, and H15 also exhibited very good competition. The majority of HuAb bind the gingipain antigen well and compete with KB001.

Figure 25A:
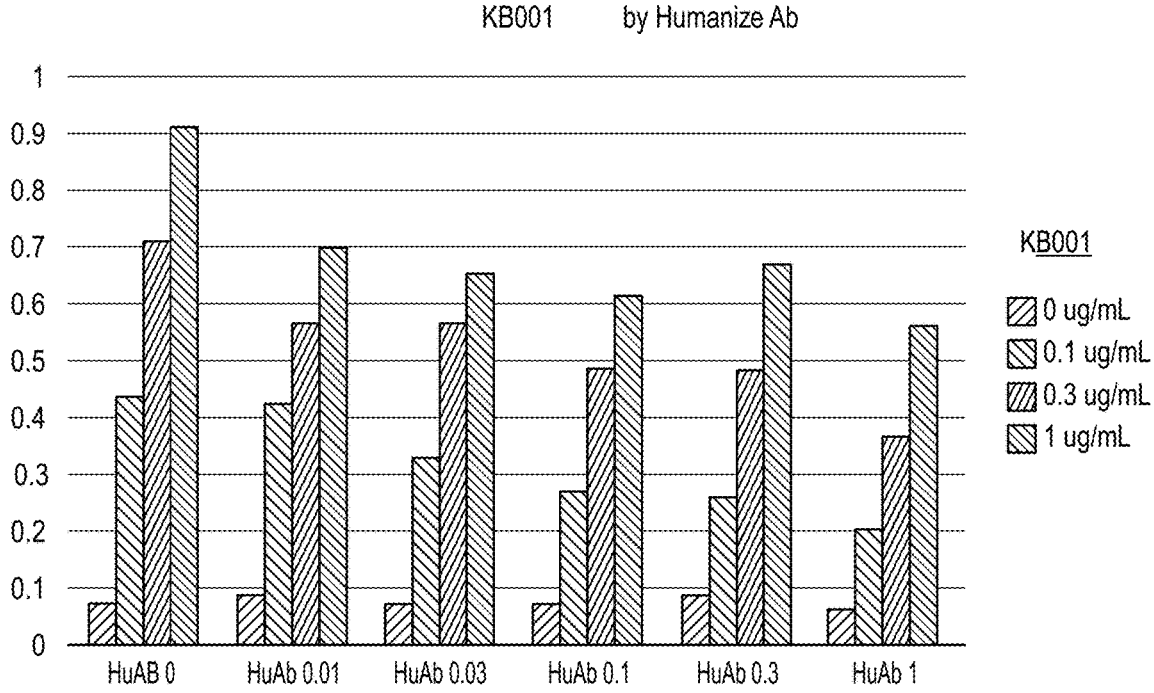
FIGS. 25A and 25B are graphs showing ELISA results from competition binding assay of varying concentrations of the KB001 and a humanized variant, according to some embodiments of the present disclosure.
Figure 25B:
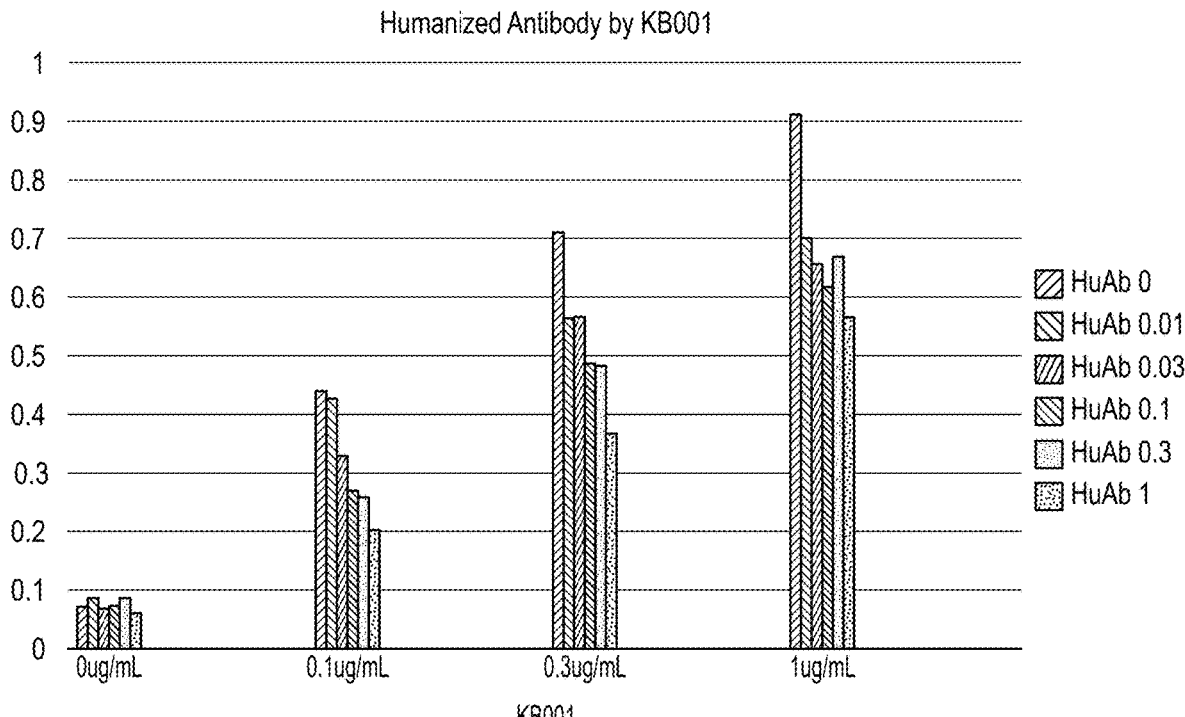

FIGS. 25A and 25B show two presentations of HuAb competition binding assay with KB001 using ELISA. FIG. 25A shows KB001 antibody is increased in competition with six concentrations of HuAb (in μg/mL). FIG. 25B shows the Humanized Ab is increased in competition with four KB001 MoAb concentrations.

These results show antibodies having improved binding affinity compared to KB001 were generated.

Example 15: Binding Properties of Human-Chimeric Antibodies Using SEM

This non-limiting example shows binding of Hu-Chimeric antibodies using whole *P. gingivalis* bacteria binding assay.

Methodology: Scanning electron Microscopy (SEM)
SEM detection: 1) SE detection
2) BSE detection Five out of 16 total Hu-chimeric MAbs were down selected via a ELISA screening binding and competition assays. The selected Hu-chimeric MAbs were H5: VH2+VL1; H7: VH2+VL3; H8: VH2+VL4; H14: VH4+VL2; H15: VH4+VL3.

Specimens bound to select Hu-chimeric MAbs were examined with secondary electrons (SE) and backscatter electrons (BSE), and digital micrographs were acquired with a field-emission SEM (SU-5000, Hitachi High Technologies America, Schaumburg, IL, USA) operated at 5 kV.

Methodology: SEM Fragment Immunolabelling
Fragment Immunolabeling:
*P. gingivalis* cells were resuspended into primary fixative containing 4% paraformaldehyde in PBS. Cells were deposited onto poly-L-lysine treated 0.2 μm membrane filters. Filters were incubated onto primary fixative for 30 minutes at room temperature. After fixation, immunogold labeling was performed by exposure of the filters at room temperature as follows: filters were treated with NH4Cl in PBS, rinsed with PBS, incubated in a blocking solution (1% non-fat dry milk, 0.5% cold water fish skin gelatin, 0.01% Tween-20 in PBS) and exposed to the primary antibody fragments that the researcher provide data 1:4000 dilution. Negative control was established by replacing primary antibody with PBS. Filters were washed in PBS and incubated with a 4 nm Colloidal Gold AffiniPure Goat Anti-Human IgG, Fcγ fragment specific (1:200 dilution; Jackson ImmunoResearch Laboratories, West Grove, PA), washed in PBS, fixed in Trump's fixative (Electron Microscopy Sciences, Hatfield, PA), and water washed. Filters were then enhanced using an HQ Silver Enhancer for 4 minutes (Nanoprobes, Inc., Yaphank, NY) followed by a water wash. After immunogold labeling, the filters were processed for SEM with the aid of a Pelco BioWave laboratory microwave (Ted, Pella, Redding CA, USA). Filters were dehydrated in a graded ethanol series 25%, 50%, 75%, 95%, 100% and critical point dried (Autosamdri-815, Tousimis, Rockville, MD, USA). Filters were mounted on carbon adhesive tabs on aluminum specimen mounts, and carbon coated (Cressington 328/308R, Ted Pella, Redding, CA, USA). Samples were kept under house vacuum until ready to image.

SEM Imaging

Specimens were examined with secondary electrons (SE) and backscatter electrons (BSE), and digital micrographs were acquired with a field-emission SEM (SU-5000, Hitachi High Technologies America, Schaumburg, IL, USA) operated at 5 kV.

Results

Figure 39A:
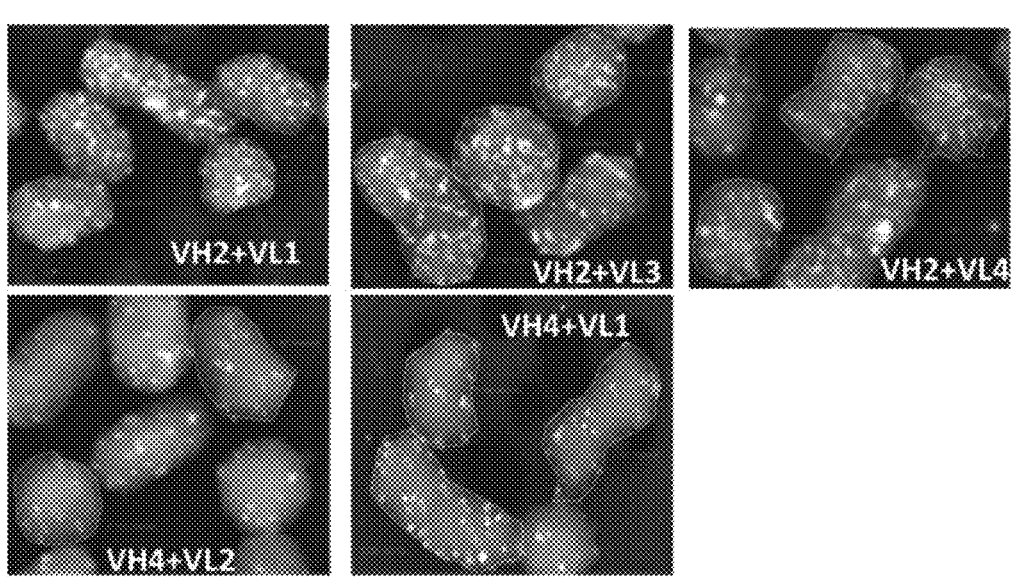
FIGS. 39A and 39B show SEM images from whole *P. gingivalis* bacterial cell gold-label binding assay of antigen binding molecules, according to some embodiments of the present disclosure.
Figure 39B:
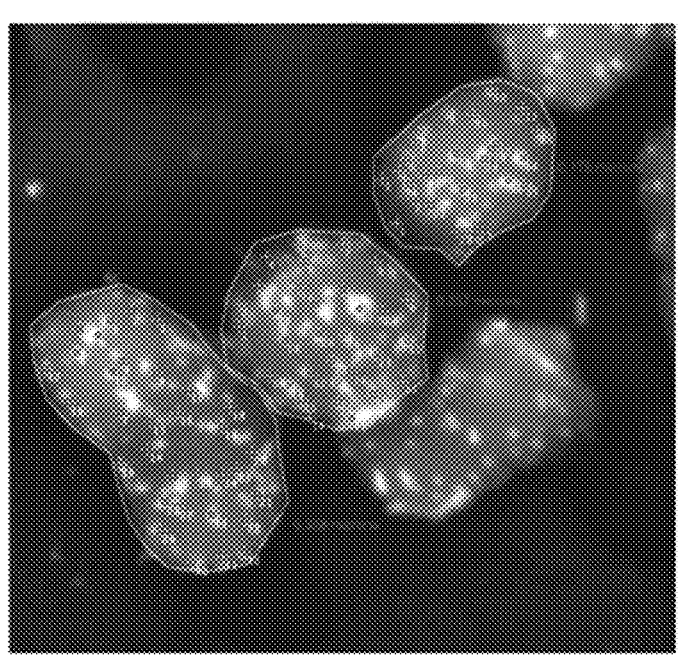
Figure 42C:
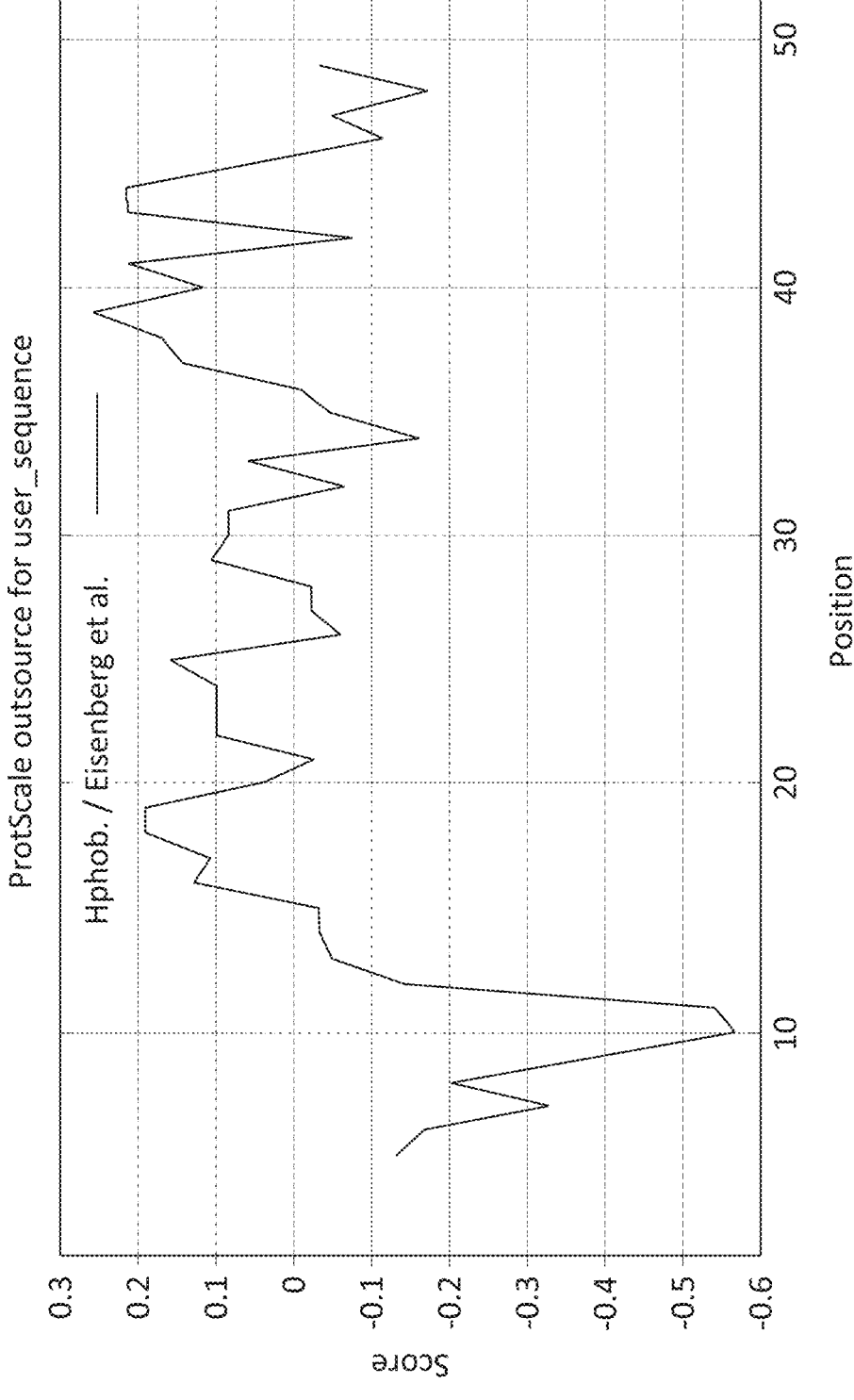
FIG. 42C is a hydrophobicity plot of rGP-2.
Figure 48A:
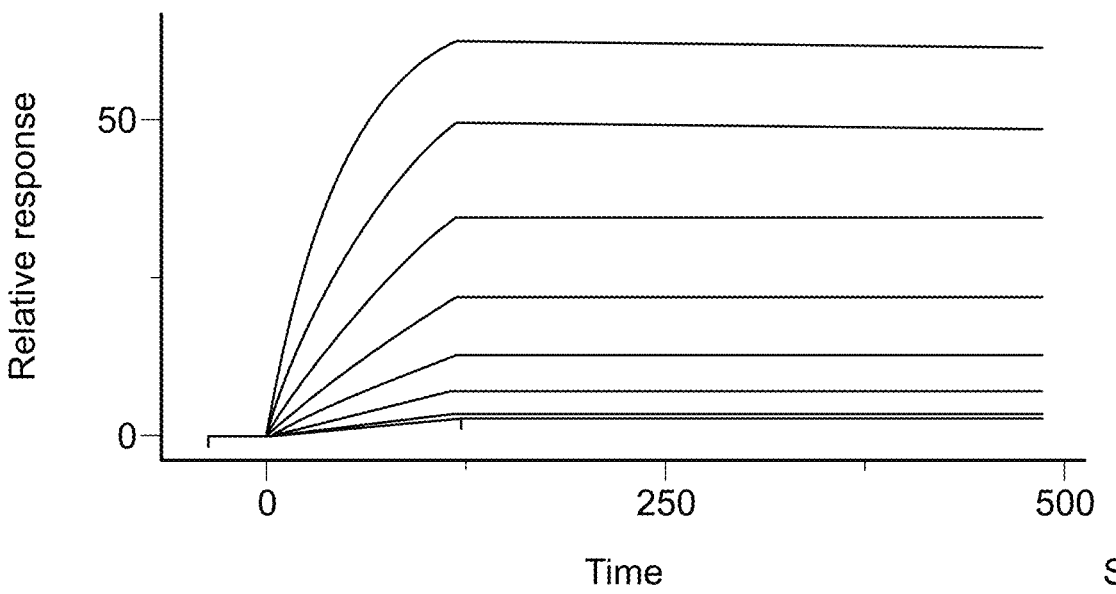
FIG. 48A shows the binding kinetics (or "sensor-grams") of H8 to HRgpA-6H.
Figure 48B:
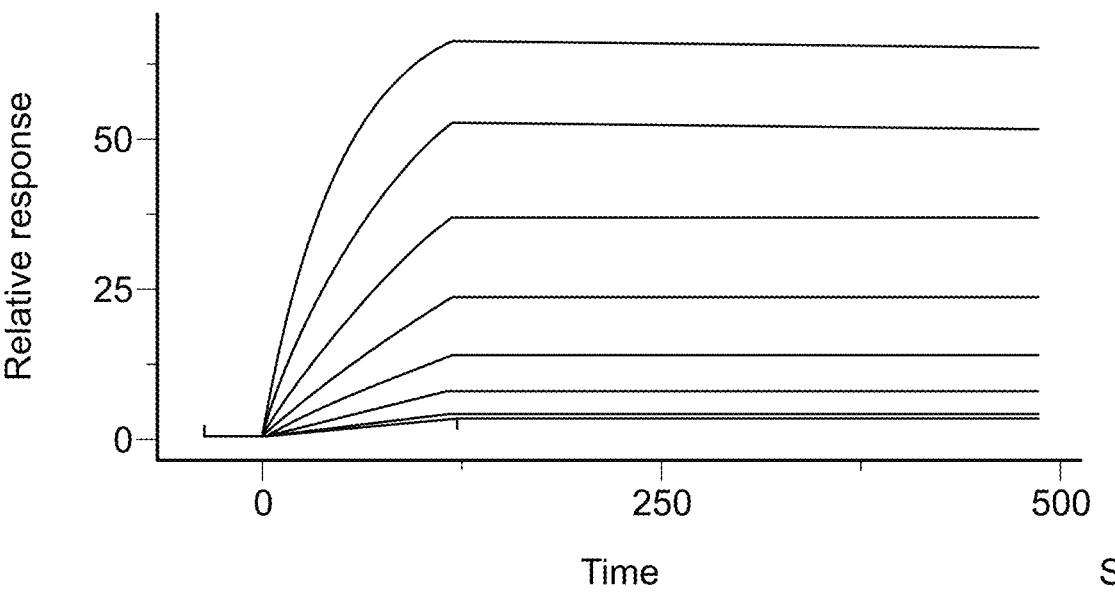
FIG. 48B shows the binding kinetics of H14 to HRgpA-6H.
Figure 48C:
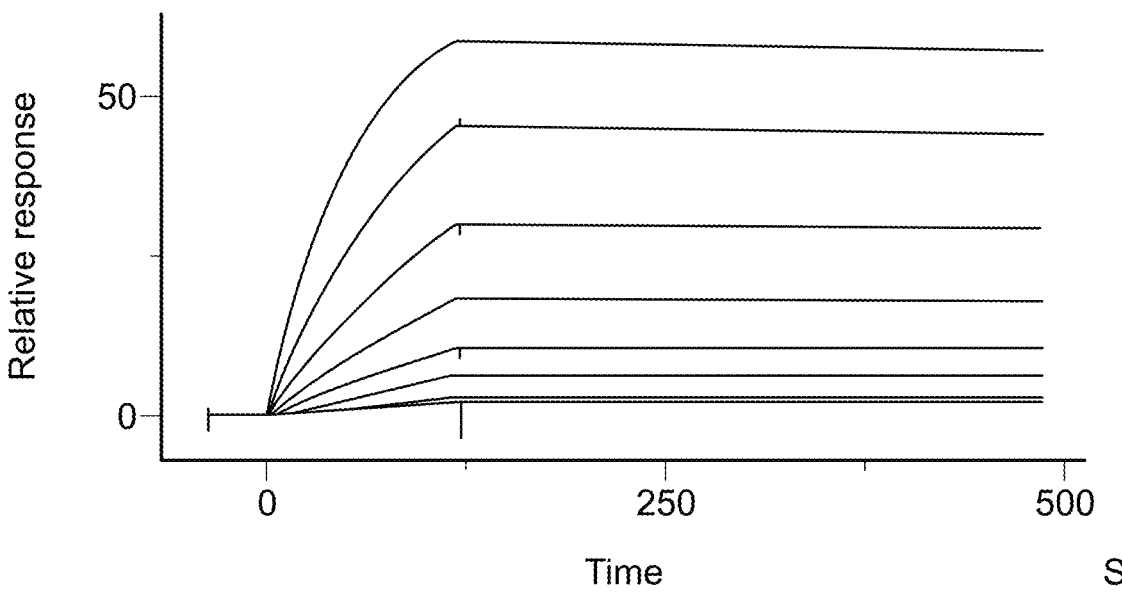
FIG. 48C shows the binding kinetics of KB001 to HRgpA-6H.
Figure 48D:
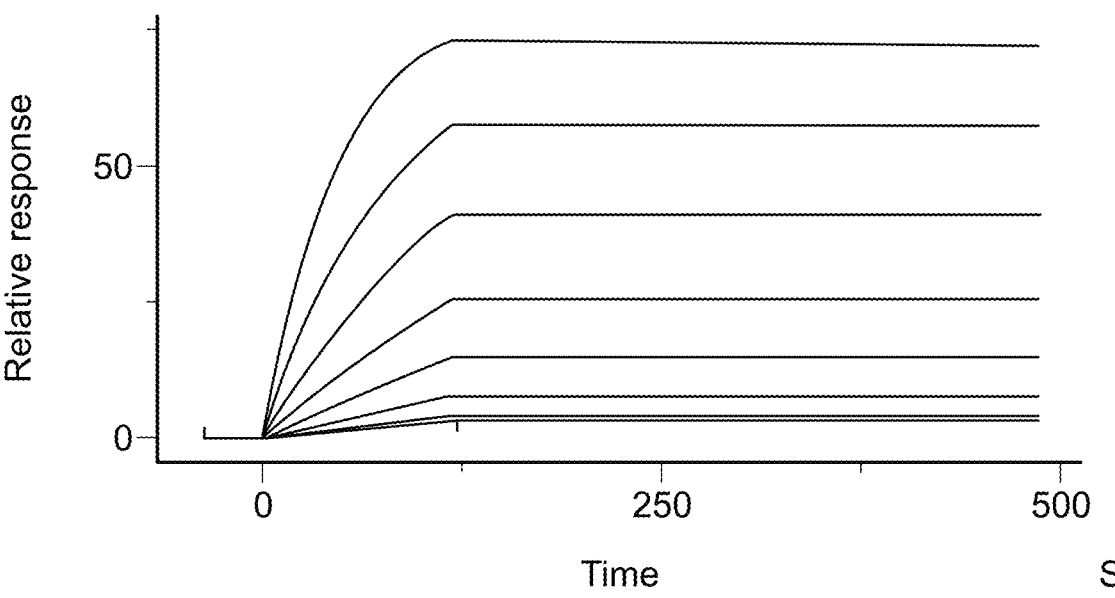
FIG. 48D shows the binding kinetics of H5 to HRgpA-6H.
Figure 48E:
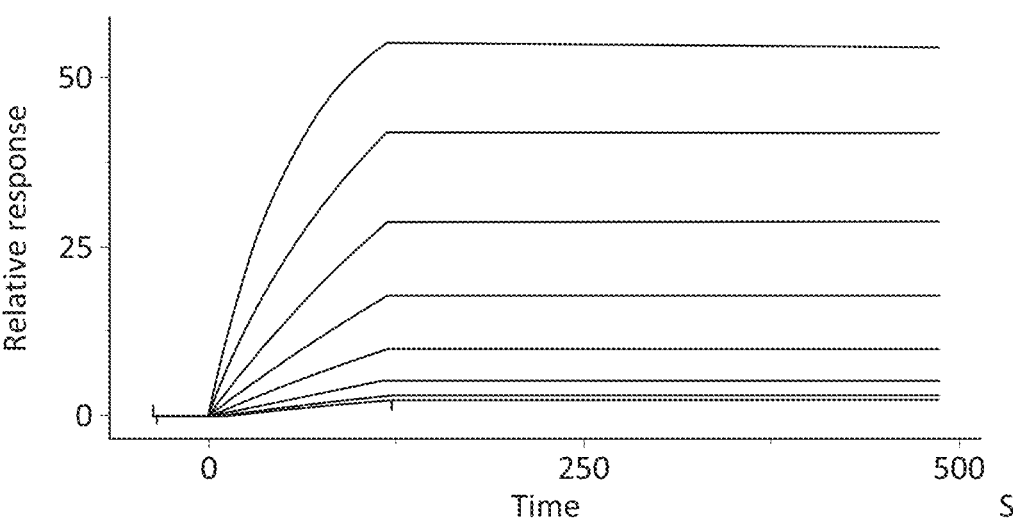
FIG. 48E shows the binding kinetics of H7 to HRgpA-6H.
Figure 49:
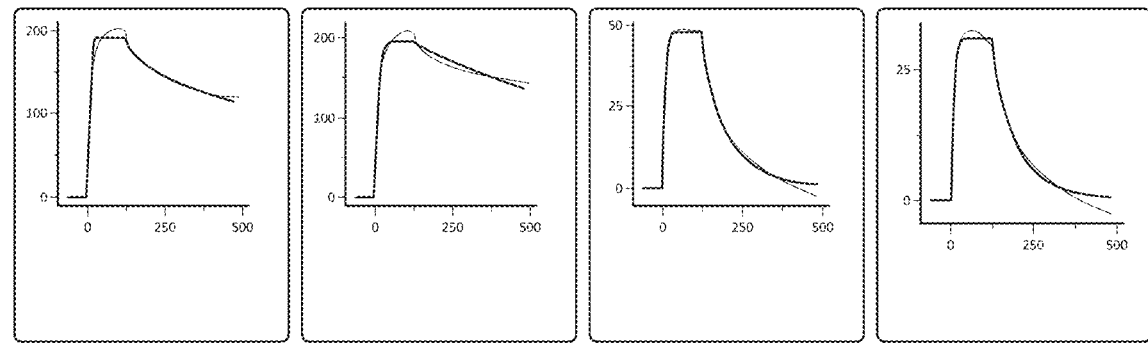
FIG. 49 shows the sensor-grams of the parental mouse (KB001) Fab FASEBA supernatant to antigen in a low salt buffer.
Figures 50, 51A:
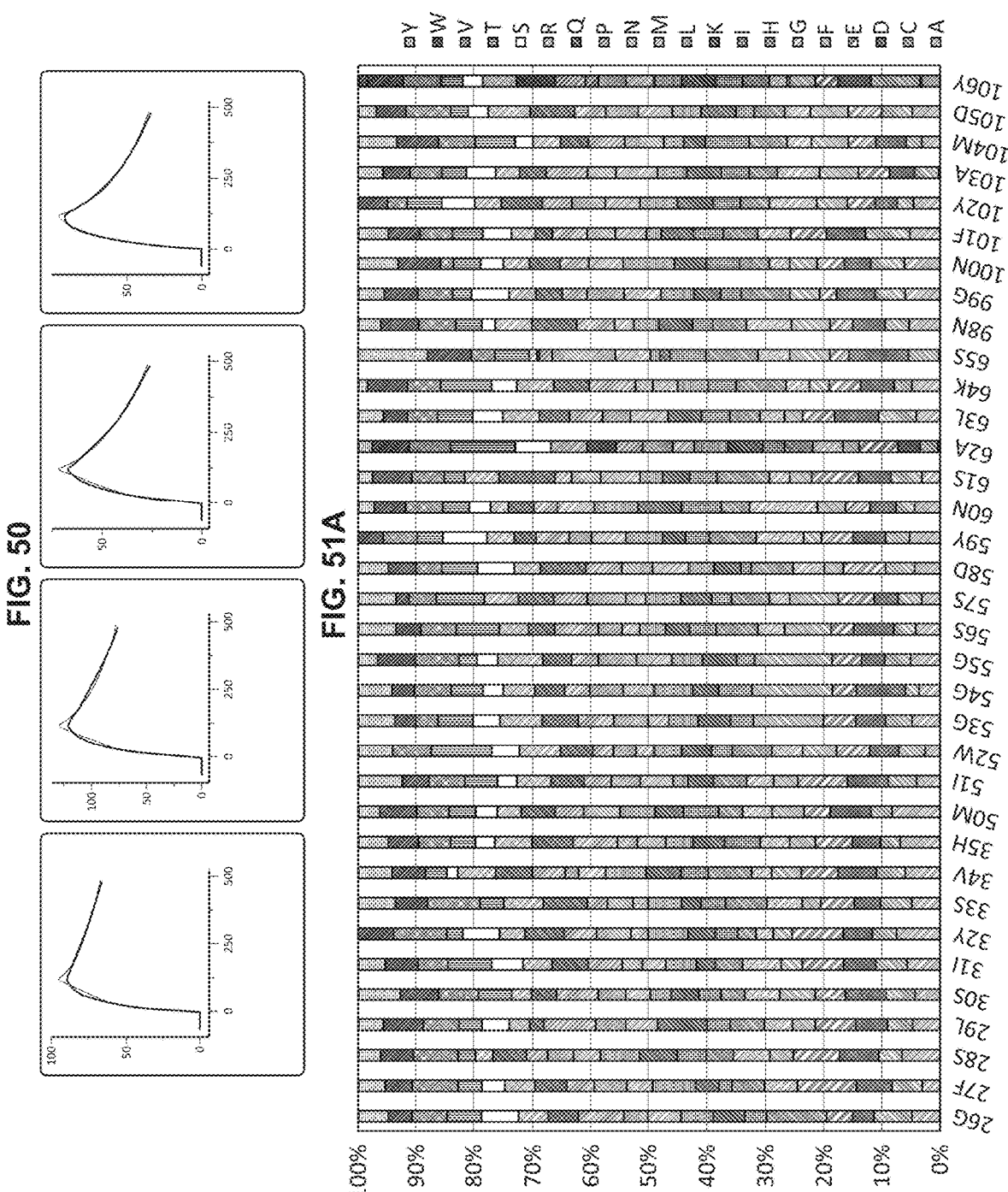
FIG. 50 shows the sensor-grams of the parental mouse (KB001) Fab FASEBA supernatant to antigen in a high salt buffer.
FIG. 51A shows the read coverage and distribution of VH-CDRs across chimeric variants.
Figures 51B, 52A:
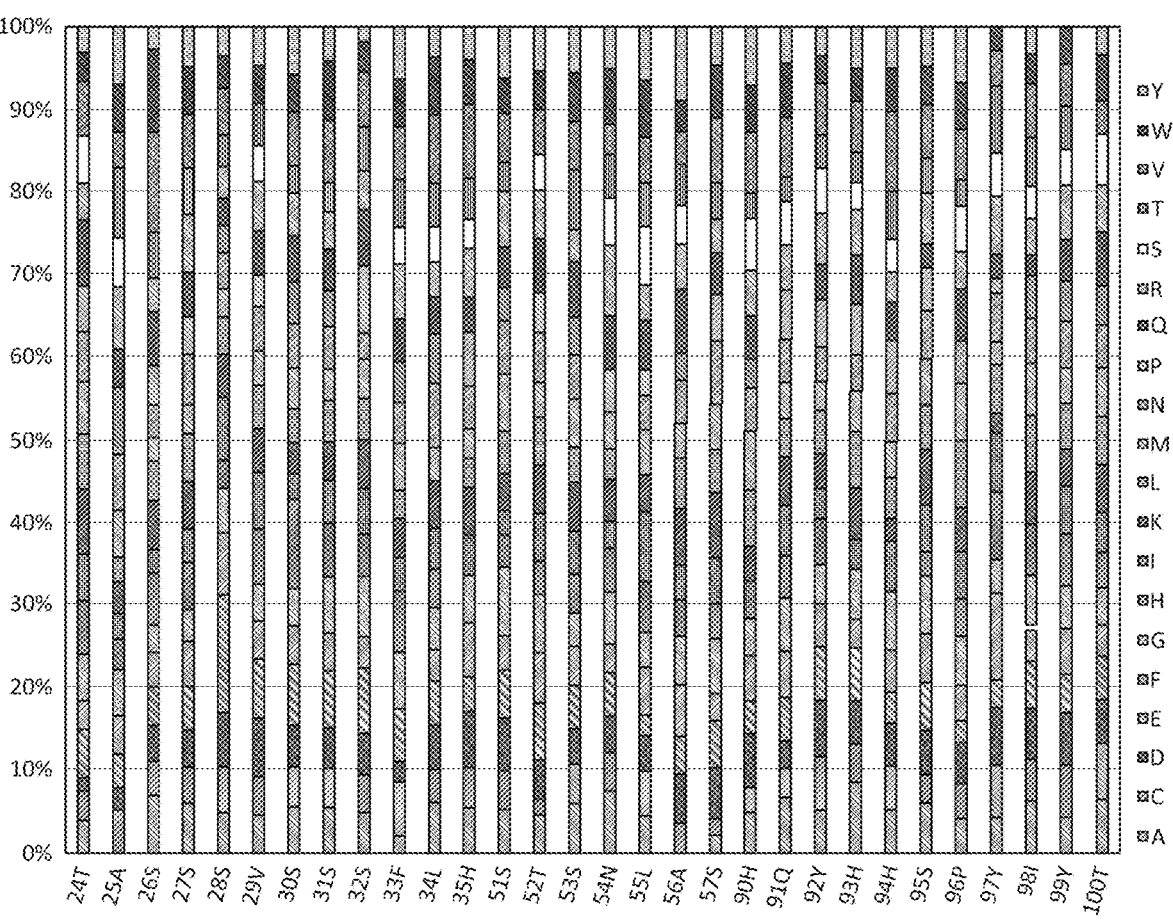
FIG. 51B shows the read coverage and distribution of VL-CDRs across chimeric variants.
FIG. 52A shows the Fab VH sequence of the parental mouse (KB001) construct.
Figure 53A:
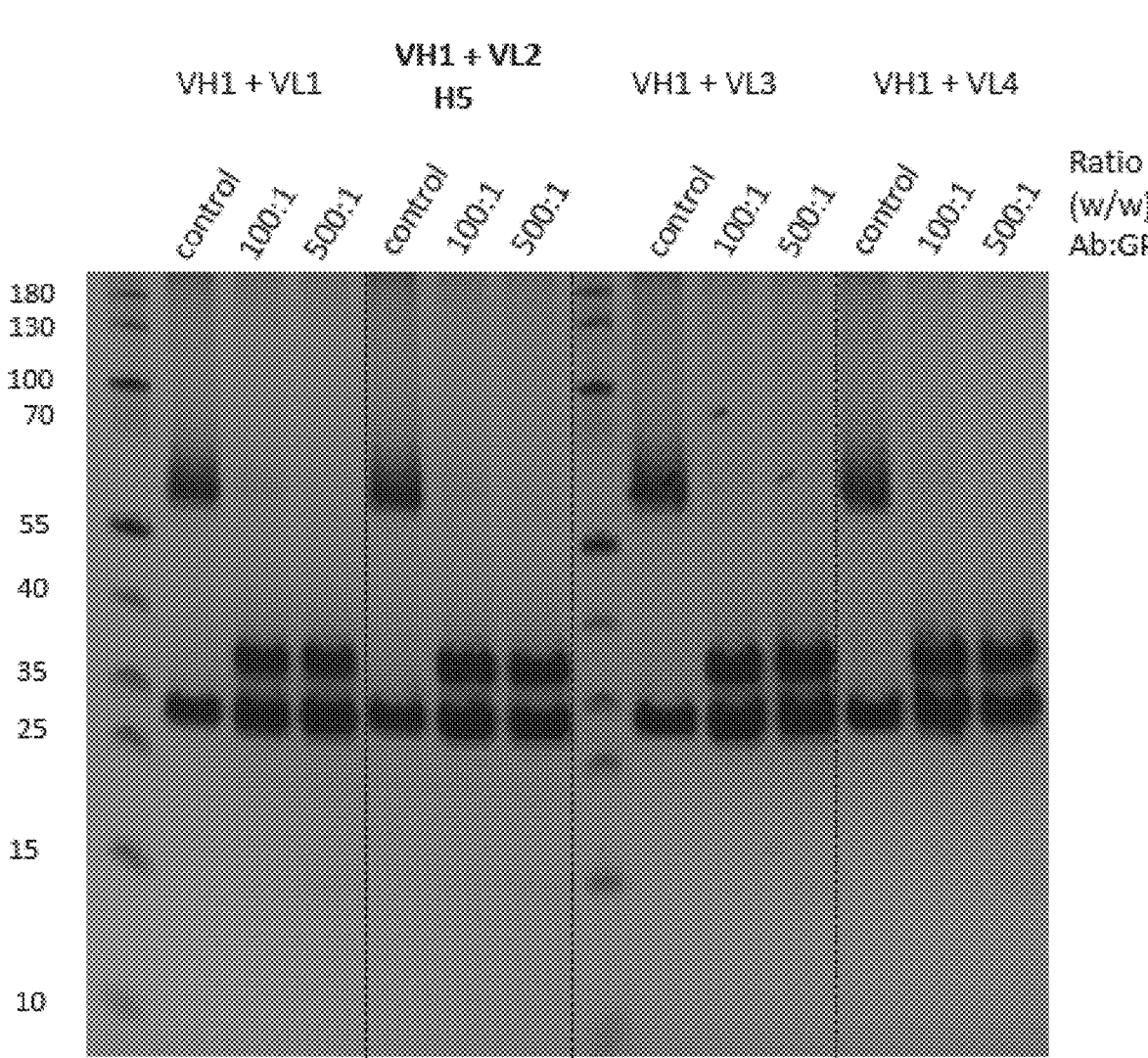
FIGS. 53A-53D show SDS-PAGE gels of the original human-chimeric mAbs bound to gingipain at an antibody: gingipain ratio of 1:0 ("control"), 100:1, and 500:1 by weight. The gels show the binding of human-chimeric mAbs with the sequences of (FIG. 53A) VH1+VL1, VH1+VL2, VH1+VL3, and VH1+VL4, (FIG. 53B) VH2+VL1, VH2+VL2, VH2+VL3, and VH2+VL4, (FIG. 53C) VH3+VL1, VH3+VL2, VH3+VL3, and VH3+VL4, and (FIG. 53D) VH4+VL1, VH4+VL2, VH4+VL3, and VH4+VL4.
Figure 53B:
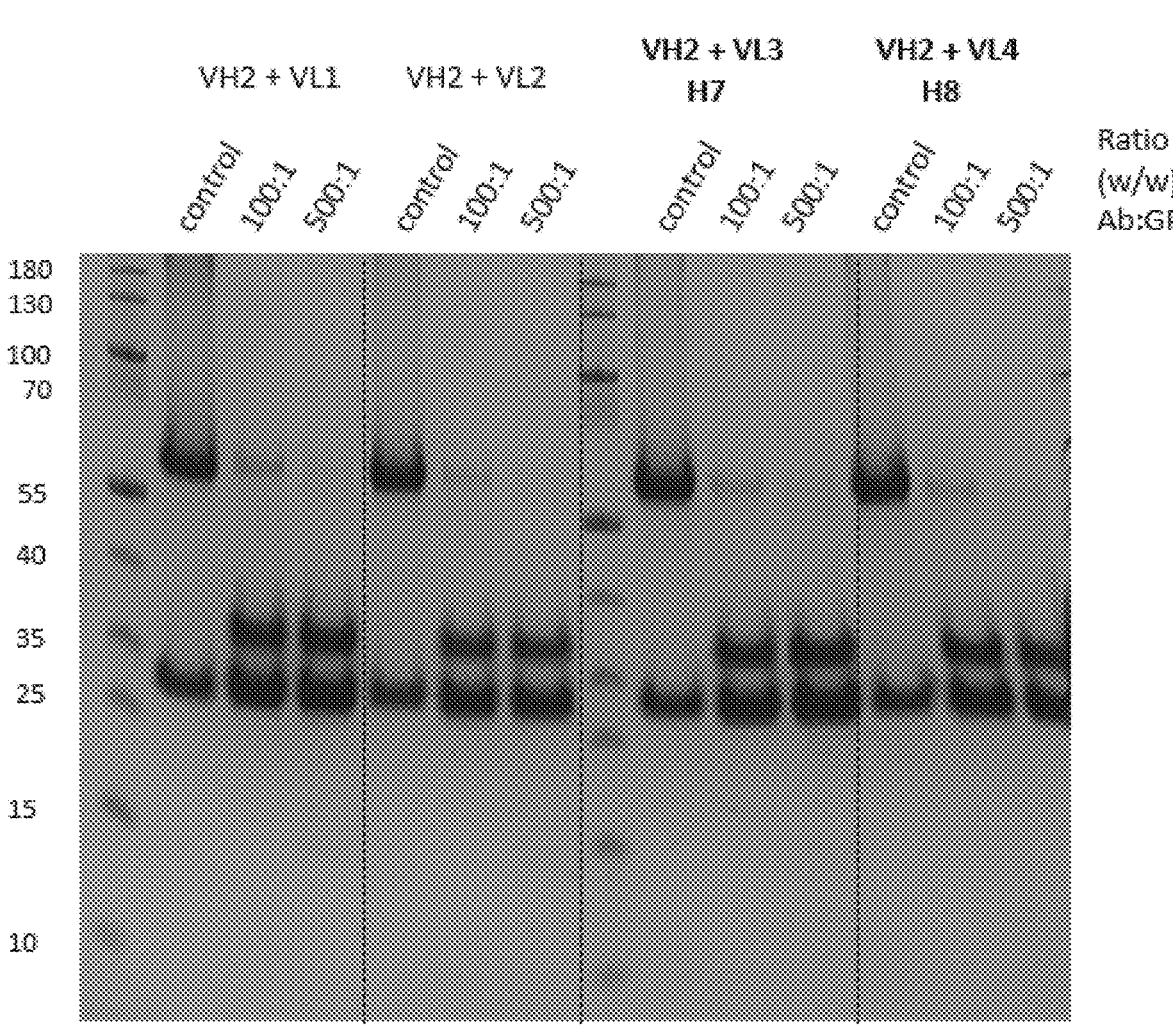
Figure 53C:
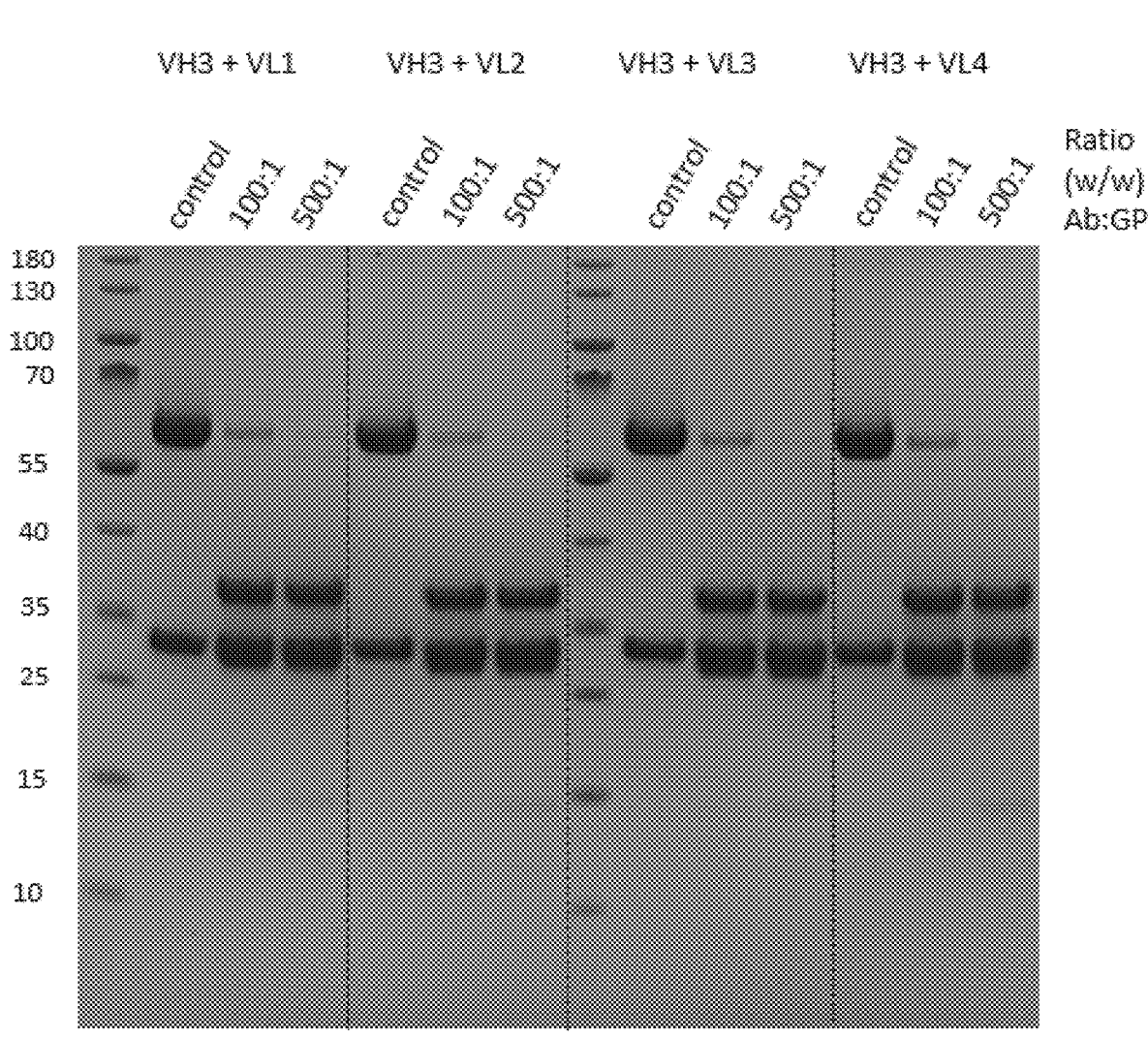
Figure 53D:
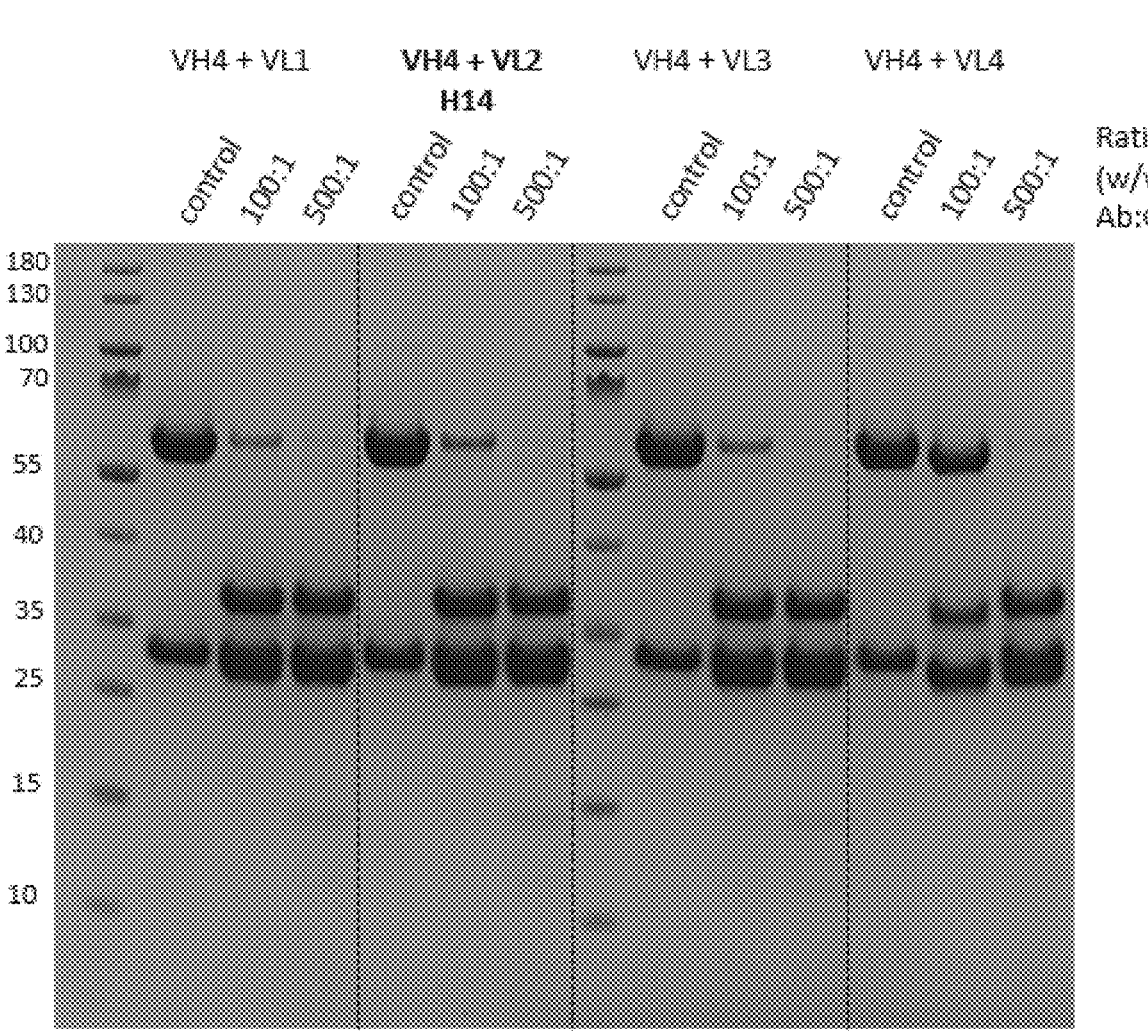

All 5 Hu-chimeric gold labeled Mab fragments demonstrated direct binding to the bacterial surface being located on and associated with emerging/forming outer membrane vesicles (OMVs) (FIG. 39A). The best Hu-chimeric MAbs were H7 And H14. Detailed densitometric measurements were made quantitating the distance and number of bound antibody fragments. FIG. 39B shows magnified, quantitated binding events of H7 (VH2+VL3).

There existed a difference in the binding ability of the human chimeric-antibodies against *P. gingivalis* (W83). VH4-containing antibodies had a lower binding affinity compared to the VH2-containing antibodies. Among the 5 chimeric antibodies that were compared, VH2+VL3 had the greatest binding in comparison to the other chimeric-antibody combinations.

Example 16: Binding Properties of Human-Chimeric Antibodies Using SPR

This study was performed to measure the binding affinity of antibodies to HRGPA-6H using Biacore 8K.

TABLE 16.1

| Sample Materials | | |
|---|---|---|
| Samples | MW (KDa) | Concentration (mg/ml) |
| HRGPA-6H | 70.5 | 0.85 |
| H14 | 150 | 0.503 |
| H5 | 150 | 0.647 |
| H7 | 150 | 0.515 |
| H8 | 150 | 0.593 |
| KB001 | 150 | 4 |

TABLE 16.2

| Instrument and Reagent | | | |
|---|---|---|---|
| Names | Cat. No. | Lot. No. | Vendor |
| Biacore T200: GR18010468 | N/A | N/A | GE Healthcare |
| HBS-EP+ buffer | BR-1006-69 | 31644 | GE Healthcare |
| Series S Sensor Chip CM5 | BR-1005-30 | 10299106 | GE Healthcare |
| 10 mM sodium acetate, pH 4.5 | BR-1003-50 | 30789 | GE Healthcare |
| Amine coupling kit | BR-1000-50 | 31165 | GE Healthcare |
| Regeneration buffer: 10 mM Glycine-HCl pH1.7 | Jan. 5, 2021 | Jan. 5, 2021 | Genscript |

Methodology: Immobilization of HRGPA-6H onto CM5 Sensor Chip

The immobilization of HRGPA-6H was performed under 25 degrees Celsius while HBS-EP was used as the running buffer. The sensor chip surface of flow cells 1, 2 were activated by freshly mixed 50 mmol/L N-Hydroxysuccinimide (NHS) and 200 mmol/L 1-ethyl-3-(3-dimethylaminopropyl) carbodiimide hydrochloride (EDC) for 120s (10 µL/min). Afterwards, HRGPA-6H diluted in 10 mmol/L NaAC (pH 4.5) to 4 ug/ml were injected into the flow cell 1.2 to achieve conjugation of appropriate Response Unit respectively. After the amine coupling reaction, the remaining active coupling sites on chip surface were blocked with 120s injection of 1 mol/L ethanolamine hydrochloride.

Methodology: Affinity Measurement of Antibodies to HRGPA-6H

The assay was performed at 25° C. and the running buffer was HBS-EP+. Diluted antibodies were captured on the sensor chip through Fc capture method. HRGPA-6H was used as the analyte, followed by injecting running buffer as dissociation phase. The running configuration was as listed in TABLE 16.3.

TABLE 16.3

| Running configuration | |
|---|---|
| Capture | |
| Ligand | antibodies |
| Immobilization level(RU) | ~80 |
| Association & Dissociation | |
| Association contact time(s) | 120 |
| Dissociation contact time(s) | 360 |
| Flow rate(µl/min) | 30 |
| Sample concentrations(nM) | 400, 200, 100, 50, 25, 12.5, 6.25 |
| Surface regeneration | |
| Regeneration buffer | 10 mM Glycine-HCl |
| Contact time(s) | 30 |
| Flow rate(µl/min) | 30 |

All the data were processed using the Biacore 8K Evaluation software version 1.1. Flow cell 1 and blank injection of buffer in each cycle were used as double reference for Response Units subtraction. The binding kinetic data is given in TABLE 16.4, and the binding sensor-grams are shown in FIGS. 48A-48E. According to the results, the affinity of H7 to HRgpA-6H was stronger than other tested antibodies to HRgpA-6H.

TABLE 16.4

| Binding kinetics | | | | | | |
|---|---|---|---|---|---|---|
| Ligand | Analyte | ka (1/Ms) | kd (1/s) | KD (M) | Rmax (RU) | Chi$^2$ (RU$^2$) |
| HRgpA-6H | H8 | 5.03E+04 | 6.70E−05 | 1.33E−09 | 63.7 | 1.40E−01 |
| HRgpA-6H | H14 | 5.21E+04 | 4.89E−05 | 9.39E−10 | 68.5 | 1.75E−01 |

TABLE 16.4-continued

| Binding kinetics | | | | | | |
| --- | --- | --- | --- | --- | --- | --- |
| Ligand | Analyte | ka (1/Ms) | kd (1/s) | KD (M) | Rmax (RU) | Chi$^2$ (RU$^2$) |
| HRgpA-6H | KB001 | 4.26E+04 | 8.62E−05 | 2.02E−09 | 62.5 | 1.22E−01 |
| HRgpA-6H | H5 | 5.45E+04 | 4.50E−05 | 8.25E−10 | 74.7 | 1.61E−01 |
| HRgpA-6H | H7 | 4.14E+04 | 1.07E−05 | 2.58E−10 | 57.9 | 5.20E−02 |

Similar binding was assessed with the K222A mutant antibodies against the recombinant Pg protein target/ligand HRgpA-6H (Table 16.5). All four of the K222A mutants were found to have as good or better affinity than their parents. H5 K222A had the overall greatest affinity for HRgpA-6H.

Then the FASEBA vector was transferred into TG1 competent, and after selecting positive clones for culture, IPTG induced parental Fab expression. The mouse Fab and chimeric Fab were expressed for further validation.
Methodology: Affinity Measurement of Parental Antibody and Parental Mouse Fab FASEBA Sample

TABLE 16.4

| Binding kinetics of K222A antibody variants | | | | | | | |
| --- | --- | --- | --- | --- | --- | --- | --- |
| Affinity | Ligand | Analyte | Chi$^2$ (RU$^2$) | ka (1/Ms) | kd (1/s) | KD (M) | Rmax (RU) |
| excellent | HRgpA-6H | H5 K222A | 1.22E−01 | 5.02E+04 | 3.42E−06 | 6.80E−11 | 68 |
| good | HRgpA-6H | H7 K222A | 7.21E−02 | 5.48E+04 | 4.36E−05 | 7.95E−10 | 77.1 |
| good | HRgpA-6H | H8 K222A | 9.25E−02 | 5.80E+04 | 3.30E−05 | 5.70E−10 | 80 |
| moderate | HRgpA-6H | H14 K222A | 7.99E−02 | 5.01E+04 | 6.53E−05 | 1.30E−09 | 68.6 |

Example 17: Binding Affinity Maturation Through Antibody Mutagenesis

This non-limiting example shows binding of the parental mouse antibody, as well as human chimeric cleavage resistant constructs, to HRGPA-6H. The constructs were made through affinity maturation to enhance the affinity of antibody to HRgpA-6H according to the strategy of PML saturation mutagenesis and FASEBA screening.
Materials
   Amino acid sequences of parental antibody (provided by the client)
   Antigen: HRgpA-6H (provided by the client)
   Parental antibody: KB001 (provided by the client)
   *E. coli* TG1
   Ampicillin stock, 100 mg/ml
   2×YT: 1.6% Tryptone, 1.0% Yeast Extract, 0.5% NaCl
   IPTG 0.1 mM
   Microtiter ELISA plates
   Coating buffer: CBS (1.588 g/L Na$_2$CO$_3$, 2.928 g/L NaHCO$_3$)
   Blocking buffer: 3% MPBS
   Washing buffer: 0.05% PBST
   BSA, 10 μg/ml
   Tetramethylbenzidine (TMB)
   1M HCl
   Goat Anti-MOUSE IgG (Fab specific) [HRP]
   Goat Anti-Human IgG, F(ab')$_2$ [HRP]
   Mouse Anti-Human IgG, F(ab')$_2$ [HRP]
   Goat Anti-Human IgG (H+L) [HRP]
   Anti-BSA [HRP]
   Biacore 8K (GE Healthcare)
   Series S Sensor Chip CM5 (GE Healthcare, Cat. No.: BR-1005-30)
Methodology: Construction and Production of Parental Fab FASEBA Sample
   The DNA sequences encoding the antibody heavy and light chains were synthesized and inserted into FASEBA vector to construct expression plasmids of parental Fab.

The affinity of parental antibody to antigen protein was determined using a Surface Plasmon Resonance (SPR) biosensor, Biacore 8K (GE Healthcare). The measurements were performed at 25° C. HRGPA-6H was immobilized on the Series S Sensor Chip CM5. KB001-WT-Ab was used as the analyte with association time of 120s and buffer flow was maintained for 360 s for dissociation. The data of dissociation (kd) and association (ka) rate constants were obtained using Biacore 8K evaluation software. The equilibrium dissociation constants (KD) were calculated from the ratio of kd over ka. The affinity of parental mouse Fab FASEBA supernatant to antigen protein was determined using Biacore 8K (GE Healthcare). FASEBA supernatant was captured on the sensor chip. Antigen was used as the analyte with association time of 120s and buffer flow was maintained for 360 s for dissociation. The data of dissociation (kd) and association (ka) rate constants were obtained using Biacore 8K evaluation software.
Methodology: ELISA Assay of Parental Fab FASEBA Sample
   The affinity of parental mouse Fab and chimeric Fab binding to HRGPA-6H was individually determined using ELISA. Microtiter ELISA plates were coated with 10 μg/ml BSA (expression detection) and 2, 1, 0.5, 0.25, 0.125, 0.0625, 0.03125, 0.015625, 0.0078125, 0.0039063 μg/ml antigen protein (binding evaluation) in 100 μl CBS at 4° C. overnight, and subsequently incubated with blocking buffer at 37° C. for 1 hour. Then the plates were washed with washing buffer and incubated with diluted 50 μl FASEBA supernatant in 50 μl 0.1% PBST at RT for 2 hours. Next the plates were washed with washing buffer and incubated with 100 μl secondary antibody for 45 minutes. The secondary antibody used Goat Anti-MOUSE IgG (Fab specific) [HRP] for parental mouse Fab and four secondary antibodies (Goat Anti-Human IgG, F(ab')$_2$ [HRP]; Mouse Anti-Human IgG, F(ab')$_2$ [HRP]; Goat Anti-Human IgG (H+L) [HRP]; Anti-BSA [HRP]) were used for parental chimeric Fab. After washing, the reaction was developed with 100 μl TMB substrate for 10 minutes at room temperature and stopped by adding 50 μl of 1 M HCl. The absorbance values were measured at 450 nm using a spectrometer. The HRGPA-6H concentration that OD450 range from 0.5 to 0.8 were selected for subsequent PML library ELISA screening.

Methodology: Construction of PML Library

According to the parental mouse Fab FASEBA template, a total of 65 residues in CDR region were mutated into other 19 desired amino acids using optimal codons for *E. coli*. DNA oligonucleotide library synthesis was performed on a programmable microarray. The library quality was ensured through NGS and guarantee a minimal coverage of 90%. 44-48 clones were randomly selected from each PML library for expression in *E. coli*.

Methodology: FASEBA Screening 44-48 clones were selected from each PML library for expression in 96-deep-well plates. The crude protein secreted in medium was analyzed by ELISA against BSA and HRGPA-6H for the assessment of expression and binding specificity, respectively. Totally 65 PML libraries were tested for binding evaluation and 12 PML libraries were randomly selected for expression detection. Microtiter ELISA plates were coated with 0.0625 μg/ml HRGPA-6H (binding evaluation) and 10 μg/ml BSA (expression detection). The secondary antibody used Goat Anti-MOUSE IgG (Fab specific) [HRP]. The binding ratio was calculated from the mutants OD450 over parental OD450. The mutants with a ratio of >0.8 were selected for DNA sequencing.

Results: Affinity Measurement of Parental Antibody and Parental Mouse Fab FASEBA Sample The affinity of parental antibody with target antigen was measured by Biacore 8K. The result was as shown in Table 17.1. The affinity of parental mouse Fab FASEBA supernatant with target antigen was measured by Biacore 8K. The result were as shown is FIGS. 49-50. Real-time responses were shown, as are the fitting of Biacore experimental data to 1:1 interaction model. According to the curves of non-related FASEBA supernatant (NC) and 2YT medium (Blank), there was non-specific binding for the antigen to chip in low salt buffer and high salt buffer.

TABLE 17.1

| | | Binding kinetics of parental antibody to antigen | | | | |
| | | | | | Rma | $Chi^2$ |
| Ligand | Analyte | ka (1/Ms) | kd (1/s) | KD (M) | (RU) | $(RU^2)$ |
| HRGPA-6H | KB001-WT-Ab | 4.26E+04 | 8.62E−05 | 2.02E−09 | 62.5 | 1.22E−01 |

Results: ELISA Assay of Parental Fab FASEBA Sample

The ELISA assay of parental mouse Fab FASEBA was shown in Table 17.2. The concentration of 0.0625 μg/ml HRgpA-6H was selected for further PML library screening. The ELISA assay of parental chimeric Fab FASEBA was shown in Table 17.3. Four secondary antibodies used for parental chimeric Fab FASEBA showed non-specific binding to antigen. The expression validation of parental Fab FASEBA was shown in Table 17.4. The expression level of parental chimeric Fab FASEBA was higher than parental mouse Fab FASEBA.

TABLE 17.2

The ELISA assay between serial diluted antigen with parental mouse Fab FASEBA sample

| Coating Ag concentration (μg/ml) | 2 | 1 | 0.5 | 0.25 | 0.125 | 6.25E−02 | Parental-Fab FASEBA Sample |
|---|---|---|---|---|---|---|---|
| A | 2.035 | 1.941 | 1.757 | 1.584 | 1.169 | 0.755 | Sample #1 |
| B | 1.975 | 2.024 | 1.82 | 1.509 | 1.132 | 0.687 | Sample #2 |

| Coating Ag concentration (μg/ml) | 3.13E−02 | 1.56E−02 | 7.81E−03 | NC 1 | NC 2 | Blank | Parental-Fab FASEBA Sample |
|---|---|---|---|---|---|---|---|
| A | 0.429 | 0.245 | 0.167 | 0.065 | 0.078 | 0.071 | Sample #1 |
| B | 0.441 | 0.241 | 0.201 | 0.088 | 0.073 | 0.073 | Sample #2 |

TABLE 17.3

| The ELISA assay between serial diluted antigen with parental chemiric Fab FASEBA sample | | | | | | | |
|---|---|---|---|---|---|---|---|
| Coating Ag concentration (μg/ml) | 2 | 1 | 0.5 | 0.25 | 0.125 | 6.25E−02 | Secondary Ab |
| A | 2.792 | 3.009 | 2.865 | 2.668 | 2.511 | 2.062 | Goat Anti-Human IgG, F(ab')₂ |
| B | 3.076 | 2.886 | 2.687 | 2.213 | 1.78 | 1.3 | Anti-BSA (HRP) |
| A | 2.22 | 2.244 | 2.167 | 1.844 | 1.468 | 1.006 | Mouse Anti-Human IgG, F(ab')₂ |
| B | 2.274 | 2.328 | 2.315 | 2.066 | 1.891 | 1.414 | Goat Anti-Human IgG (H + L) |

| Coating Ag concentration (μg/ml) | 3.13E−02 | 1.56E−02 | 7.81E−03 | 3.91E−04 | NC | Blank | Secondary Ab |
|---|---|---|---|---|---|---|---|
| A | 1.814 | 1.361 | 0.948 | 0.627 | 0.672 | 1.048 | Goat Anti-Human IgG, F(ab')₂ |
| B | 0.776 | 0.522 | 0.3 | 0.165 | 1.088 | 1.853 | Anti-BSA (HRP) |

| Coating Ag concentration (μg/ml) | 3.13E−02 | 1.56E−02 | NC 1 | NC 2 | Blank 1 | Blank 2 | Secondary Ab |
|---|---|---|---|---|---|---|---|
| A | 0.59 | 0.36 | 0.552 | 0.288 | 1.13 | 0.992 | Mouse Anti-Human IgG, F(ab')₂ |
| B | 1.012 | 0.664 | 1.151 | 0.736 | 1.728 | 1.752 | Goat Anti-Human IgG (H + L) |

TABLE 17.4

| The expression validation of parental Fab FASEBA sample | | | | | | |
|---|---|---|---|---|---|---|
| | Sample 1 | Sample 2 | NC 1 | NC 2 | Blank 1 | Blank 2 | Parental-Fab FASEBA Sample |
| A | 1.862 | 1.894 | 3.408 | 3.259 | 0.042 | 0.044 | mouse Fab FASEBA |
| B | 3.028 | 3.015 | 2.941 | 3.029 | 0.054 | 0.054 | chimeric Fab FASEBA |

Results: PML Library Construction

The Precise Mutagenesis Library was synthesized through GenScript advanced oligonucleotide techniques, cloned into U8085FJ210-mouse-Fab-pFASEBA vector as a sub-pool. Each individual PML was generated per residue based on the FASEBA platform with a theoretical diversity at 20. 65 residues in CDR region were selected to mutate (Table 17.5). The library QC was ensured through NGS and results was shown in FIGS. 51A-51B. The parental mouse Fab sequence was as listed in FIGS. 52A-52B.

In this non-limiting example, two formats (parental mouse Fab FASEBA and parental chimeric Fab FASEBA) were tested to binding and expression validation. The expression level of parental chimeric Fab FASEBA was higher than parental mouse Fab FASEBA. Due to non-specific binding of HRgpA-6H antigen to chips and four secondary antibodies. From 65 PML libraries, over 2990 individual clones were tested by ELISA. Finally, 802 mutants that binding ratio >0.8 were selected for DNA sequencing.

TABLE 17.5

| Residues selected for PML construction | | | | | | |
|---|---|---|---|---|---|---|
| CDRs | VH-CDR1 | VH-CDR2 | VH-CDR3 | VL-CDR1 | VL-CDR2 | VL-CDR3 |
| Residue No. | 26-35 | 50-65 | 98-106 | 24-35 | 51-57 | 90-100 |

Results: FASEBA Screening

From each PML library, more than 44 clones grown and tested for binding activity by ELISA, compared with parental FASEBA supernatant, NC (non-related FASEBA supernatant), blank (2YT medium). The parental was marked in blue and NC was marked in gray. The results were as shown in Tables 17.6-17.7. The ratio was calculated from the mutants OD450 over parental OD450. The mutants that had a ratio of >0.8 were selected for DNA sequencing.

TABLE 17.6

| Fold-change in VH variant binding affinity | | | |
|---|---|---|---|
| Sample | Sequence Variation from WT | OD450 nm | Ratio* |
| AHF14445 | S30D | 0.579 | 1.148 |
| AHF14446 | S30D | 0.563 | 1.116 |

TABLE 17.6-continued

Fold-change in VH variant binding affinity

| Sample | Sequence Variation from WT | OD450 nm | Ratio* |
|---|---|---|---|
| AHF14447 | S30E | 0.567 | 1.124 |
| AHF14448 | S30D | 0.617 | 1.223 |
| AHF14449 | S30N | 0.565 | 1.120 |
| AHF14450 | S61E | 0.603 | 1.222 |
| AHF14451 | S61Q | 0.634 | 1.285 |
| AHF14452 | S61E | 0.567 | 1.149 |
| AHF14453 | S61E | 0.588 | 1.191 |
| AHF14454 | IS61D | 0.562 | 1.139 |
| AHF14594 | WT | 0.538 | 1.059 |
| AHF14595 | S28P | 0.545 | 1.009 |
| AHF14596 | WT | 0.568 | 1.052 |
| AHF14597 | S28E | 0.561 | 1.039 |
| AHF14598 | S28E | 0.551 | 1.020 |
| AHF14599 | S30D | 0.528 | 1.047 |
| AHF14600 | S30D | 0.540 | 1.070 |
| AHF14601 | S30D | 0.552 | 1.094 |
| AHF14602 | WT | 0.550 | 1.090 |
| AHF14603 | S30G | 0.533 | 1.056 |
| AHF14604 | S30N | 0.560 | 1.110 |
| AHF14605 | S30Y | 0.530 | 1.051 |
| AHF14606 | S30G | 0.515 | 1.021 |
| AHF14607 | S30A | 0.534 | 1.058 |
| AHF14608 | S30D | 0.547 | 1.084 |
| AHF14609 | WT | 0.531 | 1.053 |
| AHF14610 | I31T | 0.560 | 1.110 |
| AHF14611 | I31V | 0.537 | 1.064 |
| AHF14612 | I31M | 0.522 | 1.035 |
| AHF14613 | I31T | 0.534 | 1.058 |
| AHF14614 | No Sequence | 0.515 | 1.021 |
| AHF14615 | I31V | 0.521 | 1.033 |
| AHF14616 | V34I | 0.891 | 1.081 |
| AHF14617 | WT | 0.924 | 1.121 |
| AHF14618 | V34I | 0.868 | 1.053 |
| AHF14619 | V34I | 0.866 | 1.050 |
| AHF14620 | WT | 0.945 | 1.146 |
| AHF14621 | WT | 0.955 | 1.158 |
| AHF14622 | WT | 0.891 | 1.013 |
| AHF14623 | S56A | 0.891 | 1.013 |
| AHF14624 | WT | 0.898 | 1.021 |
| AHF14625 | S57A | 0.922 | 1.048 |
| AHF14626 | S57V | 0.911 | 1.036 |
| AHF14627 | S57Q | 0.915 | 1.040 |
| AHF14628 | Y59V | 0.830 | 1.049 |
| AHF14629 | S61D | 0.547 | 1.108 |
| AHF14630 | S61T | 0.543 | 1.100 |
| AHF14631 | S61N | 0.537 | 1.088 |
| AHF14632 | S61D | 0.549 | 1.112 |
| AHF14633 | S61E | 0.547 | 1.108 |
| AHF14634 | K64A | 0.890 | 1.076 |
| AHF14635 | K64R | 0.870 | 1.052 |
| AHF14636 | IS65T | 0.883 | 1.068 |
| AHF14637 | S65D | 0.866 | 1.047 |
| AHF14638 | S65V | 0.867 | 1.048 |
| AHF14639 | S65D | 0.897 | 1.085 |
| AHF14640 | G99Y | 0.835 | 1.048 |
| AHF14641 | G99S | 0.809 | 1.015 |
| AHF14642 | N100E | 0.886 | 1.046 |
| AHF14643 | A103S | 0.909 | 1.055 |
| AHF14644 | Y106L | 0.791 | 1.029 |
| AHF14645 | Y106T | 0.827 | 1.075 |
| AHF14646 | Y106A | 0.821 | 1.068 |
| AHF14647 | Y106V | 0.795 | 1.034 |
| AHF14648 | Y106R | 0.793 | 1.031 |
| AHF14649 | Y106I | 0.803 | 1.044 |
| AHF14650 | Y106M | 0.794 | 1.033 |
| AHF14651 | Y106M | 0.840 | 1.092 |
| AHF14652 | Y106A | 0.835 | 1.086 |
| AHF14653 | Y106F | 0.815 | 1.060 |
| AHF14654 | Y106V | 0.840 | 1.092 |
| AHF14655 | Y106Q | 0.792 | 1.030 |
| AHF14656 | Y106K | 0.807 | 1.049 |
| AHF14657 | Y106F | 0.856 | 1.113 |
| AHF14658 | Y106S | 0.852 | 1.108 |
| AHF14659 | Y106S | 0.849 | 1.104 |

TABLE 17.6-continued

Fold-change in VH variant binding affinity

| Sample | Sequence Variation from WT | OD450 nm | Ratio* |
|---|---|---|---|
| AHF14660 | Y106N | 0.792 | 1.030 |
| AHF14661 | Y106W | 0.791 | 1.029 |
| AHF14662 | Y106V | 0.802 | 1.043 |
| AHF14663 | Y106W | 0.809 | 1.052 |
| AHF14664 | Y106W | 0.820 | 1.066 |
| AHF15280 | G26D | 0.470 | 0.925 |
| AHF15281 | G26N | 0.445 | 0.876 |
| AHF15282 | G26D | 0.481 | 0.947 |
| AHF15283 | S28H | 0.511 | 0.946 |
| AHF15284 | S28L | 0.435 | 0.806 |
| AHF15285 | S28G | 0.468 | 0.867 |
| AHF15286 | S28H | 0.526 | 0.974 |
| AHF15287 | S28A | 0.488 | 0.904 |
| AHF15288 | S28P | 0.452 | 0.837 |
| AHF15289 | S28R | 0.458 | 0.848 |
| AHF15290 | S28N | 0.530 | 0.981 |
| AHF15291 | S28L | 0.468 | 0.867 |
| AHF15292 | S28Y | 0.437 | 0.809 |
| AHF15293 | S28G | 0.486 | 0.900 |
| AHF15294 | S28E | 0.494 | 0.915 |
| AHF15295 | S28P | 0.514 | 0.952 |
| AHF15296 | L29P | 0.468 | 0.867 |
| AHF15297 | L29T | 0.502 | 0.930 |
| AHF15298 | L29T | 0.512 | 0.948 |
| AHF15299 | L29V | 0.446 | 0.826 |
| AHF15300 | L29T | 0.501 | 0.928 |
| AHF15301 | S30Q | 0.470 | 0.932 |
| AHF15302 | S30R | 0.481 | 0.953 |
| AHF15303 | S30Y | 0.488 | 0.967 |
| AHF15304 | S30A | 0.499 | 0.989 |
| AHF15305 | S30T | 0.457 | 0.906 |
| AHF15306 | S30K | 0.460 | 0.912 |
| AHF15307 | S30L | 0.468 | 0.928 |
| AHF15308 | S30F | 0.438 | 0.868 |
| AHF15309 | S30K | 0.467 | 0.926 |
| AHF15310 | S30Q | 0.483 | 0.957 |
| AHF15311 | S30K | 0.493 | 0.977 |
| AHF15312 | S30M | 0.437 | 0.866 |
| AHF15313 | S30W | 0.469 | 0.930 |
| AHF15314 | S30H | 0.482 | 0.955 |
| AHF15315 | S30D | 0.448 | 0.888 |
| AHF15316 | S30A | 0.494 | 0.979 |
| AHF15317 | I31Y | 0.449 | 0.890 |
| AHF15318 | I31E | 0.420 | 0.833 |
| AHF15319 | I31F | 0.450 | 0.892 |
| AHF15320 | I31Q | 0.440 | 0.872 |
| AHF15321 | I31Q | 0.439 | 0.870 |
| AHF15322 | I31Y | 0.436 | 0.864 |
| AHF15323 | I31E | 0.458 | 0.908 |
| AHF15324 | I31P | 0.471 | 0.934 |
| AHF15325 | I31L | 0.442 | 0.876 |
| AHF15326 | I31N | 0.429 | 0.850 |
| AHF15327 | I31Y | 0.462 | 0.916 |
| AHF15328 | I31Y | 0.454 | 0.900 |
| AHF15329 | I31E | 0.428 | 0.848 |
| AHF15330 | I31P | 0.428 | 0.848 |
| AHF15331 | I31Y | 0.466 | 0.924 |
| AHF15332 | I31W | 0.459 | 0.910 |
| AHF15333 | I31L | 0.431 | 0.854 |
| AHF15334 | WT | 0.843 | 0.996 |
| AHF15335 | Y32S | 0.717 | 0.847 |
| AHF15336 | Y32S | 0.783 | 0.925 |
| AHF15337 | Y32W | 0.731 | 0.864 |
| AHF15338 | Y32W | 0.718 | 0.848 |
| AHF15339 | Y32S | 0.718 | 0.848 |
| AHF15340 | Y32N | 0.826 | 0.976 |
| AHF15341 | Y32N | 0.775 | 0.916 |
| AHF15342 | Y32W | 0.747 | 0.882 |
| AHF15343 | Y32F | 0.814 | 0.962 |
| AHF15344 | Y32F | 0.807 | 0.953 |
| AHF15345 | V34M | 0.793 | 0.962 |
| AHF15346 | V34M | 0.791 | 0.959 |
| AHF15347 | H35V | 0.706 | 0.856 |
| AHF15348 | WT | 0.733 | 0.830 |

151 | 152

TABLE 17.6-continued | TABLE 17.6-continued

| Sample | Sequence Variation from WT | OD450 nm | Ratio* | Sample | Sequence Variation from WT | OD450 nm | Ratio* |
|---|---|---|---|---|---|---|---|
| AHF15349 | I51Q/M92I | 0.722 | 0.817 | AHF15423 | N60Q | 0.447 | 0.906 |
| AHF15350 | I51V | 0.798 | 0.903 | AHF15424 | N60Q | 0.402 | 0.815 |
| AHF15351 | G53A | 0.664 | 0.834 | AHF15425 | S61W | 0.435 | 0.881 |
| AHF15352 | G53P | 0.754 | 0.947 | AHF15426 | S61Y | 0.423 | 0.857 |
| AHF15353 | G53P | 0.716 | 0.899 | AHF15427 | S61R | 0.438 | 0.888 |
| AHF15354 | WT | 0.795 | 0.998 | AHF15428 | S61G | 0.460 | 0.932 |
| AHF15355 | G53S | 0.686 | 0.861 | AHF15429 | S61F | 0.432 | 0.875 |
| AHF15356 | G53A | 0.741 | 0.930 | AHF15430 | S61W | 0.429 | 0.869 |
| AHF15357 | G53A | 0.670 | 0.841 | AHF15431 | S61M | 0.493 | 0.999 |
| AHF15358 | G53A | 0.699 | 0.878 | AHF15432 | S61G | 0.476 | 0.965 |
| AHF15359 | G55D | 0.697 | 0.866 | AHF15433 | S61C | 0.431 | 0.873 |
| AHF15360 | G55N | 0.652 | 0.810 | AHF15434 | S61M | 0.479 | 0.971 |
| AHF15361 | S56G | 0.794 | 0.903 | AHF15435 | S61K | 0.490 | 0.993 |
| AHF15362 | IS56V | 0.761 | 0.865 | AHF15436 | S61H | 0.469 | 0.950 |
| AHF15363 | S56P | 0.855 | 0.972 | AHF15437 | S61F | 0.473 | 0.958 |
| AHF15364 | S56T | 0.838 | 0.953 | AHF15438 | S61L | 0.448 | 0.908 |
| AHF15365 | S56E | 0.772 | 0.878 | AHF15439 | S61D | 0.472 | 0.956 |
| AHF15366 | S56N | 0.759 | 0.863 | AHF15440 | S61T | 0.447 | 0.906 |
| AHF15367 | S56L | 0.710 | 0.807 | AHF15441 | A62N | 0.721 | 0.825 |
| AHF15368 | S56Q | 0.718 | 0.816 | AHF15442 | A62N | 0.799 | 0.914 |
| AHF15369 | S56P | 0.788 | 0.896 | AHF15443 | A62M | 0.770 | 0.881 |
| AHF15370 | S56Q | 0.764 | 0.869 | AHF15444 | A62G | 0.813 | 0.930 |
| AHF15371 | S56G | 0.823 | 0.936 | AHF15445 | A62Q | 0.737 | 0.843 |
| AHF15372 | S56M | 0.809 | 0.920 | AHF15446 | A62H | 0.819 | 0.937 |
| AHF15373 | S56G | 0.861 | 0.979 | AHF15447 | A62V | 0.742 | 0.849 |
| AHF15374 | S56A | 0.860 | 0.978 | AHF15448 | Bad Sequence | 0.824 | 0.943 |
| AHF15375 | S56T | 0.844 | 0.960 | AHF15449 | A62V | 0.757 | 0.866 |
| AHF15376 | Bad Sequence | 0.738 | 0.839 | AHF15450 | A62D | 0.853 | 0.976 |
| AHF15377 | S56T | 0.853 | 0.970 | AHF15451 | A62L | 0.812 | 0.929 |
| AHF15378 | S56N | 0.743 | 0.845 | AHF15452 | A62D | 0.851 | 0.974 |
| AHF15379 | S56P | 0.824 | 0.937 | AHF15453 | A62T | 0.839 | 0.960 |
| AHF15380 | S56V | 0.775 | 0.881 | AHF15454 | A62T | 0.812 | 0.929 |
| AHF15381 | S56E | 0.713 | 0.811 | AHF15455 | A62F | 0.843 | 0.965 |
| AHF15382 | S56G | 0.819 | 0.931 | AHF15456 | JA62I | 0.702 | 0.803 |
| AHF15383 | S56V | 0.777 | 0.883 | AHF15457 | Bad Sequence | 0.759 | 0.868 |
| AHF15384 | S56Q | 0.728 | 0.828 | AHF15458 | Bad Sequence | 0.786 | 0.899 |
| AHF15385 | S56A | 0.820 | 0.932 | AHF15459 | A62R | 0.733 | 0.839 |
| AHF15386 | S56Q | 0.775 | 0.881 | AHF15460 | A62R | 0.847 | 0.969 |
| AHF15387 | S56V | 0.760 | 0.864 | AHF15461 | JA62Q | 0.869 | 0.994 |
| AHF15388 | S57E | 0.777 | 0.883 | AHF15462 | A62T | 0.782 | 0.895 |
| AHF15389 | S57R | 0.796 | 0.905 | AHF15463 | A62E | 0.854 | 0.977 |
| AHF15390 | S57H | 0.800 | 0.910 | AHF15464 | A62F | 0.733 | 0.839 |
| AHF15391 | S57M | 0.748 | 0.850 | AHF15465 | A62I | 0.808 | 0.924 |
| AHF15392 | S57P | 0.789 | 0.897 | AHF15466 | A62M | 0.735 | 0.841 |
| AHF15393 | S57Q | 0.863 | 0.981 | AHF15467 | A62R | 0.809 | 0.926 |
| AHF15394 | S57P | 0.801 | 0.911 | AHF15468 | A62T | 0.827 | 0.946 |
| AHF15395 | S57E | 0.781 | 0.888 | AHF15469 | A62T | 0.856 | 0.979 |
| AHF15396 | IS57P | 0.747 | 0.849 | AHF15470 | WT | 0.867 | 0.992 |
| AHF15397 | S57E | 0.723 | 0.822 | AHF15471 | A62H | 0.834 | 0.954 |
| AHF15398 | S57T | 0.843 | 0.958 | AHF15472 | A62H | 0.844 | 0.966 |
| AHF15399 | S57T | 0.849 | 0.965 | AHF15473 | A62T | 0.839 | 0.960 |
| AHF15400 | S57E | 0.769 | 0.874 | AHF15474 | A62G | 0.785 | 0.898 |
| AHF15401 | S57V | 0.869 | 0.988 | AHF15475 | L63V | 0.784 | 0.897 |
| AHF15402 | IS57Q | 0.836 | 0.951 | AHF15476 | L63V | 0.770 | 0.881 |
| AHF15403 | S57P | 0.724 | 0.823 | AHF15477 | L63Y | 0.836 | 0.957 |
| AHF15404 | WT | 0.785 | 0.992 | AHF15478 | L63Y | 0.846 | 0.968 |
| AHF15405 | D58S | 0.646 | 0.817 | AHF15479 | L63Y | 0.801 | 0.916 |
| AHF15406 | D58G | 0.778 | 0.984 | AHF15480 | L63H | 0.818 | 0.936 |
| AHF15407 | Y59K | 0.648 | 0.819 | AHF15481 | L63V | 0.778 | 0.890 |
| AHF15408 | Y59T | 0.744 | 0.941 | AHF15482 | L63H | 0.843 | 0.965 |
| AHF15409 | Y59L | 0.758 | 0.958 | AHF15483 | L63H | 0.822 | 0.941 |
| AHF15410 | Y59R | 0.633 | 0.800 | AHF15484 | L63M | 0.800 | 0.915 |
| AHF15411 | Y59V | 0.790 | 0.999 | AHF15485 | L63F | 0.743 | 0.850 |
| AHF15412 | Y59M/S57I | 0.701 | 0.886 | AHF15486 | K64I | 0.743 | 0.898 |
| AHF15413 | Y59L | 0.775 | 0.980 | AHF15487 | K64V | 0.715 | 0.865 |
| AHF15414 | Y59L | 0.752 | 0.951 | AHF15488 | K64M | 0.799 | 0.966 |
| AHF15415 | Y59F | 0.668 | 0.845 | AHF15489 | K64G | 0.806 | 0.975 |
| AHF15416 | Y59L | 0.691 | 0.874 | AHF15490 | K64H | 0.752 | 0.909 |
| AHF15417 | WT | 0.698 | 0.882 | AHF15491 | K64S | 0.808 | 0.977 |
| AHF15418 | N60S | 0.452 | 0.916 | AHF15492 | K64V | 0.714 | 0.863 |
| AHF15419 | N60P | 0.440 | 0.892 | AHF15493 | WT | 0.803 | 0.971 |
| AHF15420 | N60T | 0.406 | 0.823 | AHF15494 | K64I | 0.756 | 0.914 |
| AHF15421 | N60P | 0.428 | 0.867 | AHF15495 | K64M | 0.757 | 0.915 |
| AHF15422 | WT | 0.476 | 0.965 | AHF15496 | K64M | 0.780 | 0.943 |

TABLE 17.6-continued

| | Fold-change in VH variant binding affinity | | |
|---|---|---|---|
| Sample | Sequence Variation from WT | OD450 nm | Ratio* |
| AHF15497 | K64I | 0.715 | 0.865 |
| AHF15498 | K64Y | 0.763 | 0.923 |
| AHF15499 | K64H | 0.788 | 0.953 |
| AHF15500 | K64H | 0.806 | 0.975 |
| AHF15501 | K64H | 0.730 | 0.883 |
| AHF15502 | K64G | 0.811 | 0.981 |
| AHF15503 | K64Q | 0.789 | 0.954 |
| AHF15504 | K64D | 0.781 | 0.944 |
| AHF15505 | K64L | 0.664 | 0.803 |
| AHF15506 | K64M | 0.784 | 0.948 |
| AHF15507 | K64E | 0.789 | 0.954 |
| AHF15508 | S65H | 0.823 | 0.995 |
| AHF15509 | S65Y | 0.724 | 0.875 |
| AHF15510 | S65P | 0.814 | 0.984 |
| AHF15511 | S65R | 0.794 | 0.960 |
| AHF15512 | IS65F | 0.740 | 0.895 |
| AHF15513 | S65L | 0.728 | 0.880 |
| AHF15514 | S65G | 0.825 | 0.998 |
| AHF15515 | S65H | 0.767 | 0.927 |
| AHF15516 | IS65T | 0.759 | 0.918 |
| AHF15517 | G99F | 0.771 | 0.967 |
| AHF15518 | G99S | 0.769 | 0.965 |
| AHF15519 | G99S | 0.739 | 0.927 |
| AHF15520 | G99N | 0.639 | 0.802 |
| AHF15521 | G99N | 0.698 | 0.876 |
| AHF15522 | G99A | 0.740 | 0.928 |
| AHF15523 | G99S | 0.770 | 0.966 |
| AHF15524 | G99Y | 0.769 | 0.965 |
| AHF15525 | G99C | 0.776 | 0.974 |
| AHF15526 | N100D | 0.820 | 0.968 |
| AHF15527 | N100P | 0.757 | 0.894 |
| AHF15528 | N100I | 0.796 | 0.940 |
| AHF15529 | N100S | 0.799 | 0.943 |
| AHF15530 | N100L | 0.817 | 0.965 |
| AHF15531 | N100A | 0.809 | 0.955 |
| AHF15532 | Bad Sequence | 0.683 | 0.806 |
| AHF15533 | N100D | 0.784 | 0.926 |
| AHF15534 | N100F | 0.779 | 0.920 |
| AHF15535 | N100C | 0.688 | 0.812 |
| AHF15536 | N100G | 0.769 | 0.908 |
| AHF15537 | N100E | 0.823 | 0.972 |
| AHF15538 | N100T | 0.756 | 0.893 |
| AHF15539 | N100L | 0.736 | 0.869 |
| AHF15540 | N100K | 0.801 | 0.946 |
| AHF15541 | N100I | 0.833 | 0.983 |
| AHF15542 | N100L | 0.789 | 0.932 |
| AHF15543 | IN100D | 0.841 | 0.993 |
| AHF15544 | N100S | 0.844 | 0.996 |
| AHF15545 | N100R | 0.788 | 0.930 |
| AHF15546 | N100S | 0.805 | 0.950 |
| AHF15547 | N100Q | 0.846 | 0.999 |
| AHF15548 | N100D | 0.842 | 0.994 |
| AHF15549 | N100Y | 0.757 | 0.894 |
| AHF15550 | N100Y | 0.784 | 0.926 |
| AHF15551 | N100G | 0.814 | 0.961 |
| AHF15552 | N100Y | 0.699 | 0.825 |
| AHF15553 | N100K | 0.791 | 0.934 |
| AHF15554 | N100T | 0.783 | 0.924 |
| AHF15555 | F101S | 0.678 | 0.800 |
| AHF15556 | F101Y | 0.690 | 0.815 |
| AHF15557 | F101S | 0.725 | 0.856 |
| AHF15558 | F101W | 0.825 | 0.974 |
| AHF15559 | F101M | 0.755 | 0.891 |
| AHF15560 | F101W | 0.828 | 0.978 |
| AHF15561 | F101Y | 0.718 | 0.848 |
| AHF15562 | F101Y | 0.738 | 0.871 |
| AHF15563 | F101L | 0.681 | 0.804 |
| AHF15564 | F101Y | 0.713 | 0.842 |
| AHF15565 | F101Y | 0.732 | 0.864 |
| AHF15566 | F101W | 0.802 | 0.947 |
| AHF15567 | A103G | 0.815 | 0.945 |
| AHF15568 | Bad Sequence | 0.850 | 0.986 |
| AHF15569 | A103V | 0.849 | 0.985 |
| AHF15570 | A103V | 0.807 | 0.936 |

TABLE 17.6-continued

| | Fold-change in VH variant binding affinity | | |
|---|---|---|---|
| Sample | Sequence Variation from WT | OD450 nm | Ratio* |
| AHF15571 | A103G | 0.804 | 0.933 |
| AHF15572 | A103L | 0.783 | 0.908 |
| AHF15573 | A103 | 0.850 | 0.986 |
| AHF15574 | A103M | 0.811 | 0.941 |
| AHF15575 | A103K | 0.723 | 0.839 |
| AHF15576 | A103I | 0.695 | 0.806 |
| AHF15577 | A103G | 0.755 | 0.876 |
| AHF15578 | A103C | 0.770 | 0.893 |
| AHF15579 | A103I | 0.693 | 0.804 |
| AHF15580 | M104L | 0.786 | 0.904 |
| AHF15581 | WT | 0.831 | 0.956 |
| AHF15582 | Y106Q | 0.768 | 0.999 |
| AHF15583 | Y106E | 0.687 | 0.893 |
| AHF15584 | Y106I | 0.730 | 0.949 |
| AHF15585 | Y106E | 0.705 | 0.917 |
| AHF15586 | Y106H | 0.722 | 0.939 |
| AHF15587 | Y106W | 0.733 | 0.953 |
| AHF15588 | Y106D | 0.675 | 0.878 |
| AHF15589 | Y106E | 0.721 | 0.938 |
| AHF15590 | Y106I | 0.728 | 0.947 |
| AHF15591 | Bad Sequence | 0.761 | 0.990 |
| AHF15592 | Y106E | 0.686 | 0.892 |
| AHF15593 | Y106W | 0.748 | 0.973 |
| AHF15594 | Y106I | 0.764 | 0.993 |
| AHF15595 | Y106K | 0.767 | 0.997 |
| AHF15596 | M104V | 0.654 | 0.850 |

*Ratio = OD(Variant)/OD(WT) = fold-change in affinity, as characterized by ELISA

TABLE 17.7

| | Fold-change in VL variant binding affinity | | |
|---|---|---|---|
| Sample | Sequence Variation from WT | OD450 nm | Ratio* |
| AHF14455 | T100E | 0.674 | 1.287 |
| AHF14456 | T100A | 0.630 | 1.203 |
| =AHF14457 | T100A | 0.636 | 1.215 |
| AHF14458 | T100S | 0.664 | 1.268 |
| AHF14459 | T100K | 0.625 | 1.194 |
| AHF14460 | T100D | 0.645 | 1.232 |
| AHF14461 | T100A | 0.625 | 1.194 |
| AHF14462 | T100H | 0.631 | 1.205 |
| AHF14463 | T100A | 0.631 | 1.205 |
| AHF14464 | T100S | 0.625 | 1.194 |
| AHF14665 | T24N | 0.800 | 1.040 |
| AHF14666 | T24S | 0.822 | 1.069 |
| AHF14667 | T24E | 0.810 | 1.053 |
| AHF14668 | WT | 0.806 | 1.048 |
| AHF14669 | T24S | 0.798 | 1.038 |
| AHF14670 | T24M | 0.797 | 1.036 |
| AHF14671 | T24S | 0.812 | 1.056 |
| AHF14672 | T24K | 0.797 | 1.036 |
| AHF14673 | WT | 0.809 | 1.052 |
| AHF14674 | T24E | 0.852 | 1.108 |
| AHF14675 | T24H | 0.795 | 1.034 |
| AHF14676 | WT | 0.796 | 1.035 |
| AHF14677 | WT | 0.831 | 1.061 |
| AHF14678 | A25F | 0.818 | 1.045 |
| AHF14679 | A25T | 0.823 | 1.051 |
| AHF14680 | WT | 0.835 | 1.066 |
| AHF14681 | A25T | 0.801 | 1.023 |
| AHF14682 | A25F | 0.827 | 1.056 |
| AHF14683 | No Sequence | 0.889 | 1.135 |
| AHF14684 | S26N | 0.823 | 1.051 |
| AHF14685 | WT | 0.809 | 1.033 |
| AHF14686 | S26D | 0.821 | 1.049 |
| AHF14687 | WT | 0.829 | 1.059 |
| AHF14688 | WT | 0.823 | 1.051 |
| AHF14689 | S27K | 0.783 | 1.043 |
| AHF14690 | S27T | 0.783 | 1.043 |

TABLE 17.7-continued

Fold-change in VL variant binding affinity

| Sample | Sequence Variation from WT | OD450 nm | Ratio* |
|--------|----------------------------|----------|--------|
| AHF14691 | S27A | 0.816 | 1.087 |
| AHF14692 | S27A | 0.808 | 1.077 |
| AHF14693 | S28P | 0.808 | 1.077 |
| AHF14694 | S28W | 0.817 | 1.089 |
| AHF14695 | S28K | 0.801 | 1.067 |
| AHF14696 | S28G | 0.818 | 1.090 |
| AHF14697 | S28V | 0.786 | 1.047 |
| AHF14698 | S30F | 0.911 | 1.057 |
| AHF14699 | S30G | 0.916 | 1.063 |
| AHF14700 | S31P | 0.870 | 1.030 |
| AHF14701 | S31E | 0.903 | 1.069 |
| AHF14702 | S31Y | 0.849 | 1.005 |
| AHF14703 | S31G | 0.864 | 1.022 |
| AHF14704 | S31G | 0.899 | 1.064 |
| AHF14705 | S31F | 0.854 | 1.011 |
| AHF14706 | S31P | 0.875 | 1.036 |
| AHF14707 | S31T | 0.859 | 1.017 |
| AHF14708 | S31P | 0.856 | 1.013 |
| AHF14709 | S31N | 0.869 | 1.028 |
| AHF14710 | WT | 0.916 | 1.084 |
| AHF14711 | WT | 0.872 | 1.032 |
| AHF14712 | WT | 0.852 | 1.008 |
| AHF14713 | S51G | 0.915 | 1.046 |
| AHF14714 | T52A | 0.923 | 1.172 |
| AHF14715 | T52A | 0.848 | 1.077 |
| AHF14716 | T52S | 0.833 | 1.058 |
| AHF14717 | T52A | 0.851 | 1.081 |
| AHF14718 | S53N | 0.838 | 1.064 |
| AHF14719 | S53H | 0.827 | 1.050 |
| AHF14720 | S53Q | 0.835 | 1.060 |
| AHF14721 | S53K | 0.841 | 1.068 |
| AHF14722 | N54Q | 0.868 | 1.108 |
| AHF14723 | WT | 0.825 | 1.053 |
| AHF14724 | N54R | 0.876 | 1.118 |
| AHF14725 | WT | 0.828 | 1.057 |
| AHF14726 | N54S | 0.835 | 1.066 |
| AHF14727 | L55N | 0.816 | 1.041 |
| AHF14728 | L55N | 0.815 | 1.040 |
| AHF14729 | L55P | 0.827 | 1.056 |
| AHF14730 | WT | 0.842 | 1.032 |
| AHF14731 | S57N | 0.857 | 1.051 |
| AHF14732 | S57R | 0.845 | 1.036 |
| AHF14733 | S57T | 0.843 | 1.034 |
| AHF14734 | S57K | 0.841 | 1.031 |
| AHF14735 | S57E | 0.843 | 1.034 |
| AHF14736 | S57K | 0.841 | 1.031 |
| AHF14737 | S57P | 0.858 | 1.052 |
| AHF14738 | S57Q | 0.858 | 1.052 |
| AHF14739 | S57G | 0.873 | 1.071 |
| AHF14740 | No Sequence | 0.880 | 1.079 |
| AHF14741 | S57G | 0.825 | 1.012 |
| AHF14742 | S57Q | 0.838 | 1.028 |
| AHF14743 | S57K | 0.840 | 1.030 |
| AHF14744 | S57K | 0.864 | 1.059 |
| AHF14745 | S57R | 0.849 | 1.041 |
| AHF14746 | S57K | 0.846 | 1.037 |
| AHF14747 | S57K | 0.879 | 1.078 |
| AHF14748 | WT | 0.868 | 1.008 |
| AHF14749 | H90W | 0.913 | 1.060 |
| AHF14750 | S95Q | 0.931 | 1.014 |
| AHF14751 | S95Q | 0.936 | 1.019 |
| AHF14752 | S95Q | 0.927 | 1.009 |
| AHF14753 | Y97E | 0.793 | 1.005 |
| AHF14754 | T100Q | 0.586 | 1.119 |
| AHF14755 | T100G | 0.603 | 1.152 |
| AHF14756 | T100Y | 0.546 | 1.043 |
| AHF14757 | T100F | 0.552 | 1.054 |
| AHF14758 | T100R | 0.616 | 1.177 |
| AHF14759 | T100H | 0.597 | 1.140 |
| AHF14760 | T100Q | 0.596 | 1.138 |
| AHF14761 | T100W | 0.585 | 1.117 |
| AHF14762 | T100Q | 0.604 | 1.154 |
| AHF14763 | T100G | 0.597 | 1.140 |
| AHF14764 | T100E | 0.613 | 1.171 |
| AHF14765 | T100M | 0.589 | 1.125 |

TABLE 17.7-continued

Fold-change in VL variant binding affinity

| Sample | Sequence Variation from WT | OD450 nm | Ratio* |
|--------|----------------------------|----------|--------|
| AHF14766 | T100E | 0.621 | 1.186 |
| AHF14767 | T100L | 0.587 | 1.121 |
| AHF14768 | T100A | 0.616 | 1.177 |
| AHF14769 | T100S | 0.602 | 1.150 |
| AHF14770 | T100L | 0.566 | 1.081 |
| AHF15597 | T24I | 0.741 | 0.964 |
| AHF15598 | T24K/R18S | 0.761 | 0.990 |
| AHF15599 | T24L | 0.753 | 0.979 |
| AHF15600 | T24A | 0.757 | 0.984 |
| AHF15601 | T24L | 0.752 | 0.978 |
| AHF15602 | T24Q | 0.765 | 0.995 |
| AHF15603 | T24N/G67D | 0.755 | 0.982 |
| AHF15604 | T24G | 0.686 | 0.892 |
| AHF15605 | T24M | 0.750 | 0.975 |
| AHF15606 | T24K | 0.734 | 0.954 |
| AHF15607 | Bad Sequence | 0.752 | 0.978 |
| AHF15608 | T24N | 0.715 | 0.930 |
| AHF15609 | T24G | 0.735 | 0.956 |
| AHF15610 | T24L | 0.667 | 0.867 |
| AHF15611 | T24S | 0.704 | 0.915 |
| AHF15612 | A25Y | 0.755 | 0.964 |
| AHF15613 | A25F | 0.775 | 0.990 |
| AHF15614 | A25G | 0.668 | 0.853 |
| AHF15615 | A25P | 0.742 | 0.948 |
| AHF15616 | A25Y | 0.757 | 0.967 |
| AHF15617 | A25V | 0.768 | 0.981 |
| AHF15618 | A25E | 0.655 | 0.837 |
| AHF15619 | A25G | 0.699 | 0.893 |
| AHF15620 | A25P | 0.766 | 0.978 |
| AHF15621 | A25G | 0.673 | 0.860 |
| AHF15622 | A25P | 0.749 | 0.957 |
| AHF15623 | S26G | 0.730 | 0.932 |
| AHF15624 | S26N | 0.749 | 0.957 |
| AHF15625 | S26P | 0.644 | 0.822 |
| AHF15626 | S26T | 0.761 | 0.972 |
| AHF15627 | S26P | 0.677 | 0.865 |
| AHF15628 | S27H | 0.664 | 0.885 |
| AHF15629 | S27T | 0.702 | 0.935 |
| AHF15630 | S27N | 0.675 | 0.899 |
| AHF15631 | S27N | 0.724 | 0.965 |
| AHF15632 | S27A | 0.714 | 0.951 |
| AHF15633 | S27K | 0.745 | 0.993 |
| AHF15634 | S27Y | 0.617 | 0.822 |
| AHF15635 | S27T | 0.743 | 0.990 |
| AHF15636 | S27K | 0.697 | 0.929 |
| AHF15637 | S27H | 0.630 | 0.839 |
| AHF15638 | S27L | 0.649 | 0.865 |
| AHF15639 | S27H | 0.726 | 0.967 |
| AHF15640 | S27A | 0.722 | 0.962 |
| AHF15641 | S27V | 0.645 | 0.859 |
| AHF15642 | S27V | 0.646 | 0.861 |
| AHF15643 | Bad Sequence | 0.640 | 0.853 |
| AHF15644 | S27N | 0.640 | 0.853 |
| AHF15645 | S27T | 0.737 | 0.982 |
| AHF15646 | S27W | 0.601 | 0.801 |
| AHF15647 | S27K/S68Y | 0.736 | 0.981 |
| AHF15648 | S27M | 0.709 | 0.945 |
| AHF15649 | S27T | 0.710 | 0.946 |
| AHF15650 | S28F | 0.674 | 0.898 |
| AHF15651 | S28F | 0.721 | 0.961 |
| AHF15652 | S28M | 0.706 | 0.941 |
| AHF15653 | S28T/S12R | 0.747 | 0.995 |
| AHF15654 | S28V | 0.731 | 0.974 |
| AHF15655 | Bad Sequence | 0.716 | 0.954 |
| AHF15656 | S28P | 0.726 | 0.967 |
| AHF15657 | S28W | 0.745 | 0.993 |
| AHF15658 | S28H | 0.719 | 0.958 |
| AHF15659 | S28N | 0.743 | 0.990 |
| AHF15660 | S28F | 0.740 | 0.986 |
| AHF15661 | S28V | 0.717 | 0.955 |
| AHF15662 | S28D | 0.745 | 0.993 |
| AHF15663 | Bad Sequence | 0.690 | 0.919 |
| AHF15664 | Bad Sequence | 0.714 | 0.951 |
| AHF15665 | S28M | 0.675 | 0.899 |
| AHF15666 | S28F | 0.678 | 0.903 |

TABLE 17.7-continued

Fold-change in VL variant binding affinity

| Sample | Sequence Variation from WT | OD450 nm | Ratio* |
|---|---|---|---|
| AHF15667 | S28D | 0.722 | 0.962 |
| AHF15668 | V29I | 0.853 | 0.990 |
| AHF15669 | V29L | 0.751 | 0.871 |
| AHF15670 | S30H | 0.808 | 0.937 |
| AHF15671 | Bad Sequence | 0.841 | 0.976 |
| AHF15672 | S30G | 0.858 | 0.995 |
| AHF15673 | S30R | 0.778 | 0.903 |
| AHF15674 | S30T | 0.838 | 0.972 |
| AHF15675 | S30E | 0.813 | 0.943 |
| AHF15676 | S30D | 0.702 | 0.814 |
| AHF15677 | S30R | 0.793 | 0.920 |
| AHF15678 | S30W | 0.823 | 0.955 |
| AHF15679 | S30T | 0.817 | 0.948 |
| AHF15680 | S30L | 0.813 | 0.943 |
| AHF15681 | S30D | 0.723 | 0.839 |
| AHF15682 | S30I | 0.860 | 0.998 |
| AHF15683 | S30R | 0.802 | 0.930 |
| AHF15684 | S30M | 0.818 | 0.949 |
| AHF15685 | S30H | 0.747 | 0.867 |
| AHF15686 | S30K | 0.770 | 0.893 |
| AHF15687 | S31F | 0.688 | 0.814 |
| AHF15688 | S31N | 0.791 | 0.936 |
| AHF15689 | S31T | 0.740 | 0.876 |
| AHF15690 | S31Q | 0.830 | 0.982 |
| AHF15691 | Bad Sequence | 0.774 | 0.916 |
| AHF15692 | S31E | 0.798 | 0.944 |
| AHF15693 | S31N | 0.749 | 0.886 |
| AHF15694 | S31F | 0.693 | 0.820 |
| AHF15695 | S31N | 0.789 | 0.934 |
| AHF15696 | S31W | 0.808 | 0.956 |
| AHF15697 | WT | 0.697 | 0.825 |
| AHF15698 | S31D | 0.762 | 0.902 |
| AHF15699 | S31L | 0.742 | 0.878 |
| AHF15700 | S31Q | 0.745 | 0.882 |
| AHF15701 | S31G | 0.824 | 0.975 |
| AHF15702 | S31L | 0.739 | 0.875 |
| AHF15703 | S31N | 0.769 | 0.910 |
| AHF15704 | S31L | 0.745 | 0.882 |
| AHF15705 | S31G | 0.776 | 0.918 |
| AHF15706 | S31T | 0.782 | 0.925 |
| AHF15707 | S31Q | 0.782 | 0.925 |
| AHF15708 | S31L | 0.691 | 0.818 |
| AHF15709 | S32A | 0.748 | 0.885 |
| AHF15710 | S32G | 0.759 | 0.898 |
| AHF15711 | S32A | 0.805 | 0.953 |
| AHF15712 | S32Y | 0.753 | 0.891 |
| AHF15713 | S32P | 0.744 | 0.880 |
| AHF15714 | S32Q | 0.716 | 0.847 |
| AHF15715 | S32W | 0.649 | 0.856 |
| AHF15716 | WT | 0.729 | 0.962 |
| AHF15717 | F33N | 0.640 | 0.844 |
| AHF15718 | F33H | 0.736 | 0.971 |
| AHF15719 | L34V | 0.641 | 0.846 |
| AHF15720 | L34M | 0.736 | 0.971 |
| AHF15721 | L34M | 0.741 | 0.978 |
| AHF15722 | L34V | 0.634 | 0.836 |
| AHF15723 | L34I | 0.670 | 0.884 |
| AHF15724 | WT | 0.710 | 0.811 |
| AHF15725 | S51G | 0.777 | 0.888 |
| AHF15726 | S51G | 0.851 | 0.973 |
| AHF15727 | T52K | 0.681 | 0.865 |
| AHF15728 | T52A | 0.782 | 0.993 |
| AHF15729 | T52R | 0.724 | 0.919 |
| AHF15730 | T52L | 0.769 | 0.977 |
| AHF15731 | T52R | 0.681 | 0.865 |
| AHF15732 | WT | 0.767 | 0.974 |
| AHF15733 | T52R | 0.685 | 0.870 |
| AHF15734 | WT | 0.705 | 0.895 |
| AHF15735 | T52M | 0.662 | 0.841 |
| AHF15736 | S53D | 0.775 | 0.984 |
| AHF15737 | S53C | 0.697 | 0.885 |
| AHF15738 | S53H | 0.777 | 0.987 |
| AHF15739 | S53A | 0.784 | 0.996 |
| AHF15740 | S53R | 0.637 | 0.809 |
| AHF15741 | S53W | 0.727 | 0.923 |

TABLE 17.7-continued

Fold-change in VL variant binding affinity

| Sample | Sequence Variation from WT | OD450 nm | Ratio* |
|---|---|---|---|
| AHF15742 | S53L | 0.639 | 0.811 |
| AHF15743 | S53Y | 0.776 | 0.985 |
| AHF15744 | S53Y | 0.781 | 0.992 |
| AHF15745 | S53Q | 0.751 | 0.954 |
| AHF15746 | S53E | 0.766 | 0.973 |
| AHF15747 | S53L | 0.636 | 0.808 |
| AHF15748 | S53Q | 0.726 | 0.922 |
| AHF15749 | S53N | 0.707 | 0.898 |
| AHF15750 | S53V | 0.702 | 0.891 |
| AHF15751 | Bad Sequence | 0.668 | 0.853 |
| AHF15752 | N54S | 0.732 | 0.934 |
| AHF15753 | N54I | 0.755 | 0.964 |
| AHF15754 | Bad Sequence | 0.684 | 0.873 |
| AHF15755 | Bad Sequence | 0.746 | 0.952 |
| AHF15756 | N54K | 0.727 | 0.928 |
| AHF15757 | N54W | 0.646 | 0.825 |
| AHF15758 | N54E | 0.744 | 0.950 |
| AHF15759 | N54D | 0.725 | 0.925 |
| AHF15760 | N54I | 0.772 | 0.985 |
| AHF15761 | L34M | 0.714 | 0.911 |
| AHF15762 | N54F | 0.765 | 0.976 |
| AHF15763 | N54I | 0.754 | 0.962 |
| AHF15764 | N54E | 0.740 | 0.944 |
| AHF15765 | N54L | 0.774 | 0.988 |
| AHF15766 | Bad Sequence | 0.766 | 0.978 |
| AHF15767 | N54S | 0.776 | 0.990 |
| AHF15768 | N54A | 0.776 | 0.990 |
| AHF15769 | L55Q | 0.711 | 0.907 |
| AHF15770 | L55S | 0.672 | 0.858 |
| AHF15771 | L55P | 0.764 | 0.975 |
| AHF15772 | L55N | 0.777 | 0.992 |
| AHF15773 | L55T | 0.727 | 0.928 |
| AHF15774 | L55H | 0.695 | 0.887 |
| AHF15775 | L55H | 0.731 | 0.933 |
| AHF15776 | L55Q | 0.692 | 0.883 |
| AHF15777 | L55Q | 0.684 | 0.873 |
| AHF15778 | L55K | 0.769 | 0.981 |
| AHF15779 | L55V | 0.706 | 0.901 |
| AHF15780 | L55P | 0.724 | 0.924 |
| AHF15781 | L55R/S51G | 0.748 | 0.955 |
| AHF15782 | L55Q | 0.662 | 0.845 |
| AHF15783 | L55H | 0.640 | 0.817 |
| AHF15784 | L55S | 0.655 | 0.836 |
| AHF15785 | A56T | 0.731 | 0.896 |
| AHF15786 | A56N | 0.712 | 0.873 |
| AHF15787 | A56Q | 0.705 | 0.865 |
| AHF15788 | A56H | 0.704 | 0.863 |
| AHF15789 | A56R | 0.728 | 0.893 |
| AHF15790 | A56Y | 0.673 | 0.825 |
| AHF15791 | Bad Sequence | 0.733 | 0.899 |
| AHF15792 | A56Y | 0.712 | 0.873 |
| AHF15793 | A56H | 0.699 | 0.857 |
| AHF15794 | A56V | 0.794 | 0.974 |
| AHF15795 | A56Y | 0.726 | 0.890 |
| AHF15796 | A56S | 0.772 | 0.947 |
| AHF15797 | A56H | 0.759 | 0.931 |
| AHF15798 | A56S | 0.751 | 0.921 |
| AHF15799 | A56R | 0.734 | 0.900 |
| AHF15800 | A56H | 0.739 | 0.906 |
| AHF15801 | A56S | 0.774 | 0.949 |
| AHF15802 | A56N | 0.775 | 0.950 |
| AHF15803 | A56P | 0.748 | 0.917 |
| AHF15804 | A56V | 0.795 | 0.975 |
| AHF15805 | A56Y | 0.696 | 0.853 |
| AHF15806 | A56M | 0.802 | 0.983 |
| AHF15807 | A56Y | 0.698 | 0.856 |
| AHF15808 | A56R | 0.751 | 0.921 |
| AHF15809 | A56M | 0.701 | 0.860 |
| AHF15810 | S57A | 0.806 | 0.988 |
| AHF15811 | S57L | 0.781 | 0.958 |
| AHF15812 | S57F | 0.785 | 0.963 |
| AHF15813 | S57F | 0.787 | 0.965 |
| AHF15814 | S57I | 0.791 | 0.970 |
| AHF15815 | S57Q | 0.658 | 0.807 |
| AHF15816 | S57N | 0.813 | 0.997 |

TABLE 17.7-continued

| | Fold-change in VL variant binding affinity | | |
| Sample | Sequence Variation from WT | OD450 nm | Ratio* |
| --- | --- | --- | --- |
| AHF15817 | S57K | 0.712 | 0.873 |
| AHF15818 | S57W | 0.784 | 0.961 |
| AHF15819 | S57F | 0.797 | 0.977 |
| AHF15820 | S57E | 0.751 | 0.921 |
| AHF15821 | S57R | 0.746 | 0.915 |
| AHF15822 | S57M | 0.745 | 0.914 |
| AHF15823 | H90L | 0.785 | 0.911 |
| AHF15824 | H90W | 0.763 | 0.886 |
| AHF15825 | H90L | 0.694 | 0.806 |
| AHF15826 | Q91M | 0.757 | 0.879 |
| AHF15827 | Q91E | 0.709 | 0.823 |
| AHF15828 | Q91E | 0.694 | 0.806 |
| AHF15829 | Q91E | 0.701 | 0.814 |
| AHF15830 | Y92D | 0.758 | 0.805 |
| AHF15831 | Y92N | 0.773 | 0.821 |
| AHF15832 | H93N | 0.857 | 0.910 |
| AHF15833 | H94Y | 0.865 | 0.942 |
| AHF15834 | H94F | 0.770 | 0.838 |
| AHF15835 | S95F | 0.837 | 0.911 |
| AHF15836 | S95E | 0.855 | 0.931 |
| AHF15837 | S95Q | 0.893 | 0.972 |
| AHF15838 | S95W | 0.804 | 0.875 |
| AHF15839 | S95N | 0.863 | 0.940 |
| AHF15840 | S95W | 0.790 | 0.860 |
| AHF15841 | S95N | 0.884 | 0.962 |
| AHF15842 | S95K | 0.841 | 0.916 |
| AHF15843 | S95A | 0.830 | 0.904 |
| AHF15844 | S95T | 0.871 | 0.948 |
| AHF15845 | S95E | 0.820 | 0.893 |
| AHF15846 | WT | 0.900 | 0.980 |
| AHF15847 | S95I | 0.846 | 0.921 |
| AHF15848 | S95A | 0.872 | 0.949 |
| AHF15849 | S95I | 0.817 | 0.889 |
| AHF15850 | S95K | 0.824 | 0.897 |
| AHF15851 | S95K | 0.813 | 0.885 |
| AHF15852 | S95K | 0.790 | 0.860 |
| AHF15853 | S95H | 0.800 | 0.871 |
| AHF15854 | WT | 0.889 | 0.968 |
| AHF15855 | S95Y | 0.827 | 0.900 |
| AHF15856 | Bad Sequence | 0.884 | 0.962 |
| AHF15857 | S95C | 0.849 | 0.924 |
| AHF15858 | S95I | 0.791 | 0.861 |
| AHF15859 | Y97H | 0.775 | 0.982 |
| AHF15860 | Y97Q | 0.687 | 0.871 |
| AHF15861 | Y97S | 0.633 | 0.802 |
| AHF15862 | Y97R | 0.769 | 0.975 |
| AHF15863 | Y97I | 0.667 | 0.845 |
| AHF15864 | Y97K | 0.654 | 0.829 |
| AHF15865 | Y97F | 0.750 | 0.951 |
| AHF15866 | Y97F | 0.756 | 0.958 |
| AHF15867 | Y97V | 0.662 | 0.839 |
| AHF15868 | Y97L | 0.739 | 0.937 |
| AHF15869 | Bad Sequence | 0.743 | 0.849 |
| AHF15870 | I98L | 0.836 | 0.955 |
| AHF15871 | I98V | 0.832 | 0.951 |
| AHF15872 | I98R | 0.726 | 0.830 |
| AHF15873 | I98R | 0.722 | 0.825 |
| AHF15874 | I98M | 0.729 | 0.833 |
| AHF15875 | I98V | 0.838 | 0.958 |
| AHF15876 | I98V | 0.787 | 0.899 |
| AHF15877 | T100F | 0.494 | 0.944 |
| AHF15878 | T100I | 0.493 | 0.942 |
| AHF15879 | T100P | 0.460 | 0.879 |
| AHF15880 | T100V | 0.461 | 0.881 |
| AHF15881 | T100F | 0.492 | 0.940 |
| AHF15882 | T100F | 0.480 | 0.917 |
| AHF15883 | T100F | 0.517 | 0.988 |
| AHF15884 | T100V | 0.428 | 0.818 |

*Ratio = OD(Variant)/OD(WT) = fold-change in affinity, as characterized by ELISA

Example 18: Recombinant Antibody Expression

Methodology: Cell Preparation

Actively growing Expi293F cells were inoculated and grown in serum-free Expression Medium for 24 hour before transfection, at 37° C. with 8% $CO_2$ in a shaker. The cells were carefully examined for contamination and counted for cell density.

Methodology: Transfection

Pre-heated Opti-PRO medium was added into two centrifuge tubes.

Plasmids conferring expression of heavy or light chain of the ABM were used (see FIG. 55, SEQ ID NOS: 191-198). To the first tube, a heavy chain expression plasmid and light chain expression plasmid were added and mixed. To the second tube, a transfection reagent was added and mixed. The plasmids and reagent medium were mixed together immediately, followed by incubation for 2 minutes at room temperature. The mixture was then added into Expi293F cells and incubated for 16-18 hours at 37° C., 8% CO2.

Enhancer and Feed was added into the cells at 18-22 hours after transfection, and then the cells were put back into the shaker and incubated at 32° C., 5% CO2.

Methodology: Harvest

The cells were carefully examined for possible contamination. The cells were then centrifuged at 3000 rpm for 10 min, and the supernatant was collected for downstream experiments.

Methodology: Purification and Sample Treatment

The solution containing plasmids was transferred into a centrifuge bottle, and the supernatant was filtered using a 0.22 um microfiltration membrane. NaCl and 2M Tris were added into the supernatant at a ratio of 1 g NaCl and 0.5 ml 2M Tris for 10 ml supernatant. The supernatant sample was then loaded into the purification column. The antibody eluate was transferred to a dialysis bag and dialyzed against 1*PBS at room temperature for 2 hours. The buffer was then replaced, and the antibody eluate was dialyzed at 4° C. overnight. At the end of dialysis, the concentration of the antibody eluate was measured by Nanodrop 2000 and recorded. The sample was then aliquoted for analysis by SDS-Page (FIGS. 53A-53D) and ELISA.

Example 19: Proteolytic Cleavage of Human-Chimeric mAbs

The VH1+VL1 sequence antibody was tested for cleavage, along with K222A mutant proteins for H5, H7, H8, and H14 sequences. 10 µg of humanized antibody was incubated for 2 hours at 37° C. with gingipain mix. The Gingiapin mix contained Kgp1 W83 at 670 µg/ml. The Kgp activity in the mix was measured to be 15.96 mOD/min/µl, and the Rgp activity was measured to be at 23.71 mOD/min/µl. The mix was added to the antibody at a 2:1 Ab:GP (w/w) ratio, then at 100:1 and 500:1 in assay buffer supplemented with 10 mM cysteine.

After incubation, Tosyl-L-lysyl-chloromethane hydrochloride (TLCK) was added to a final concentration of 10 mM, followed by the addition of non-reducing sample buffer. The samples were then boiled for 5 min. Afterwards, the samples were chilled on ice and Dithiothreitol (DTT) was added to the final concentration of 20 mM. The samples were boiled again for 5 min and separated using NuPAGE™ 4 to 12%, Bis-Tris Mini Protein Gels (FIGS. 54A-54B).

Figure 54A:
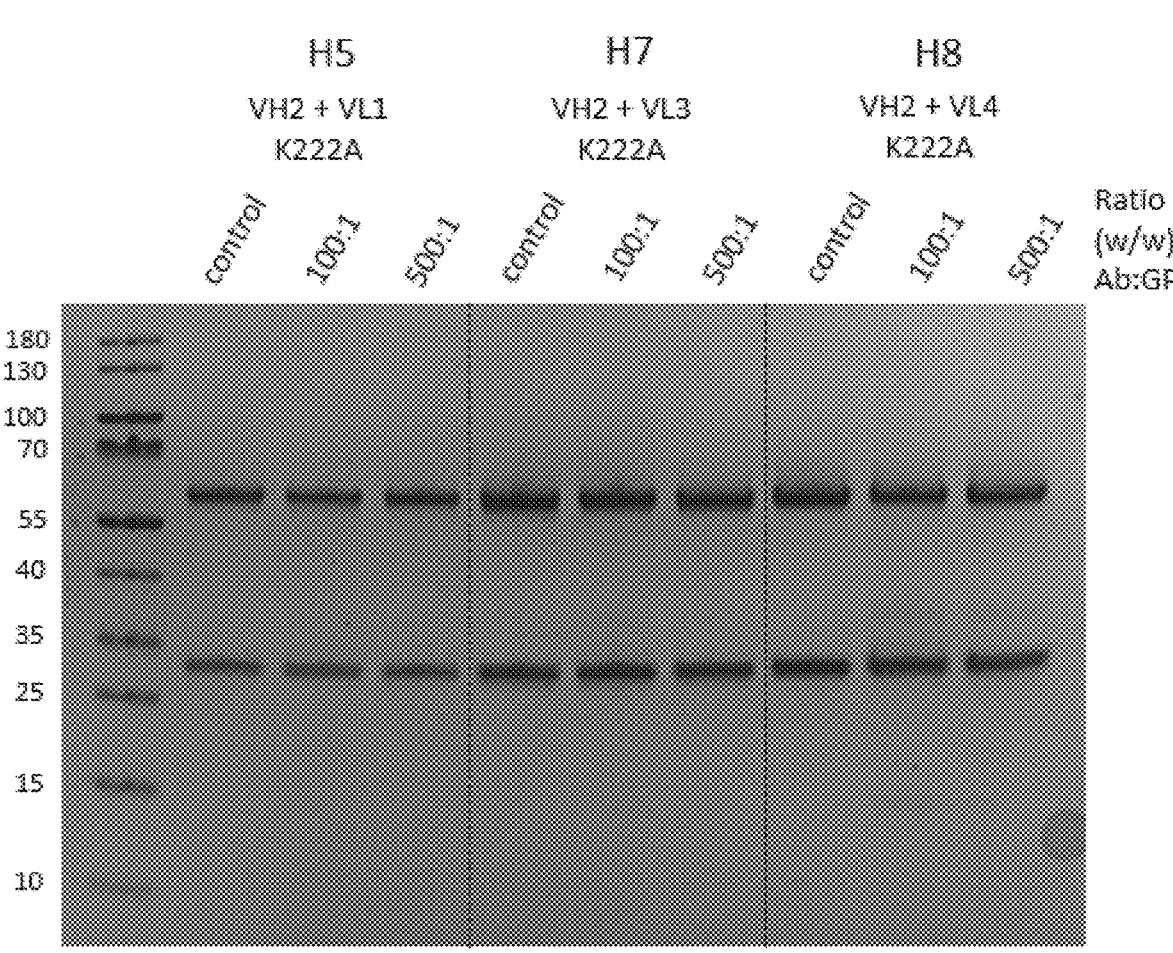
FIGS. 54A-54B show Nu-PAGE gels of the proteolytic cleavage of original human-chimeric mAbs bound to gingipain at an antibody:gingipain ratio of 1:0 ("control"), 100:1, and 500:1 by weight. The gels show the total proteolytic cleavage of human-chimeric mAbs with the sequences of (FIG. 54A) H5 K222A, H7 K222A, and H8 K222A, and (FIG. 54B) H14 K222A and VH1+VL1.
Figure 54B:
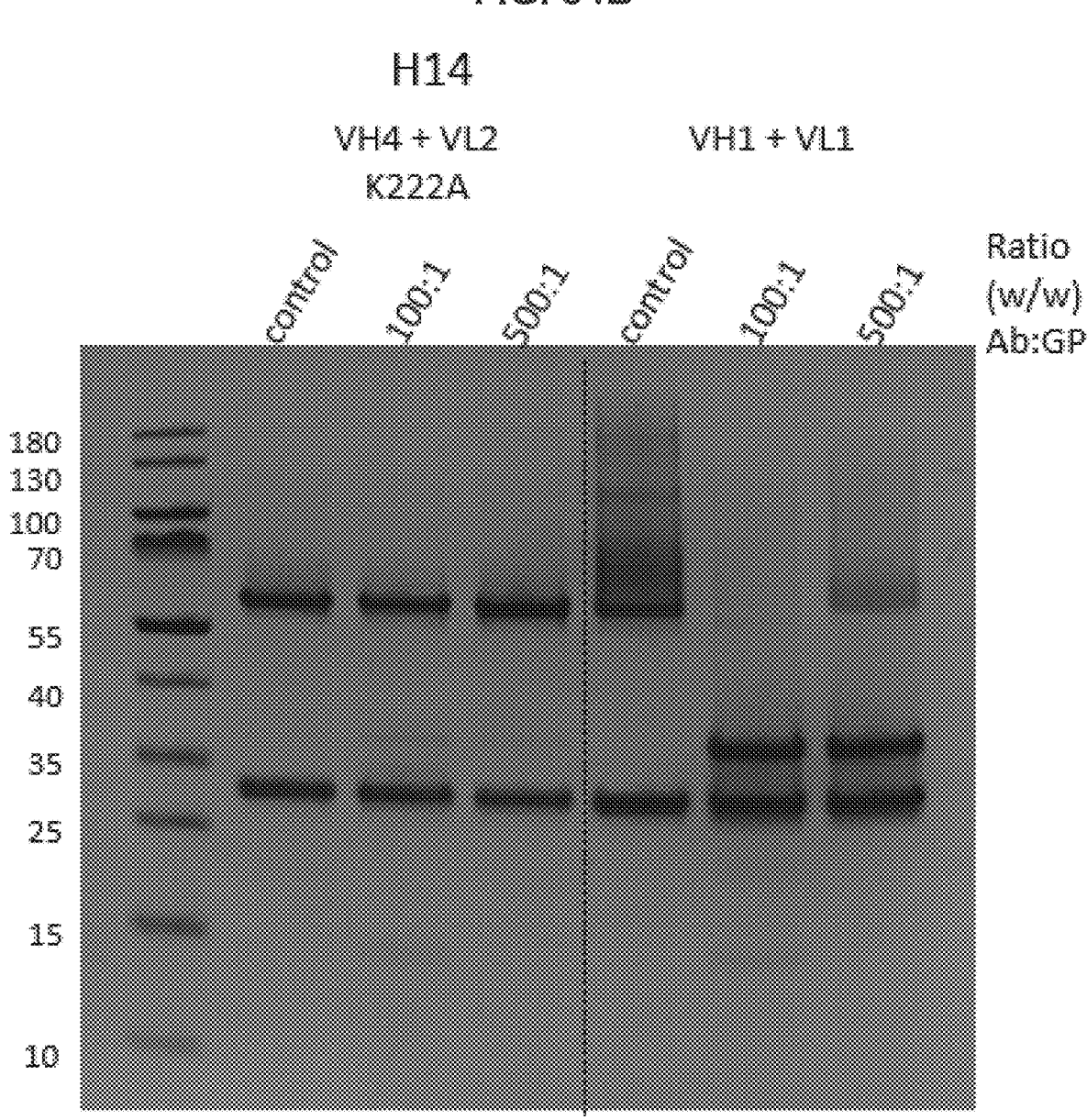

As shown in FIGS. 54A-54B, all K222A mutant antibodies showed significant resistance to proteolytic cleavage compared to the unmodified antibody. It was also confirmed that K222A mutant antibodies still bind to the same peptide/epitope that the parent antibody binds to.

Example 20: Ability of ABMs to Inhibit *P. gingivalis* Biofilm Formation

Biofilm formation was tested for disruption in the presence of antibody. *P. gingivalis* strain PGW83 at a titer of 6.0E+07 was exposed to KB001 at an increasing dosage over 48 hours. Briefly, an overnight culture was diluted 1:50 into fresh LB media. Four tubes were adjusted to the various Ab concentrations and then these were distributed to the growth tubes. At the indicated times, the OD600 was measured as a surrogate for cell growth. 25 mL of each culture were placed into 100 mm Petri dishes and titanium coupons added (these are roughly 0.3 mm thick by 2 cm×6 cm). The dishes were placed at 37 C. The next morning the coupons and plates were washed to remove non-adhered cells. One set was scraped and titered. The other was continued for another day in culture and then processed on Day 2.

Figure 72:
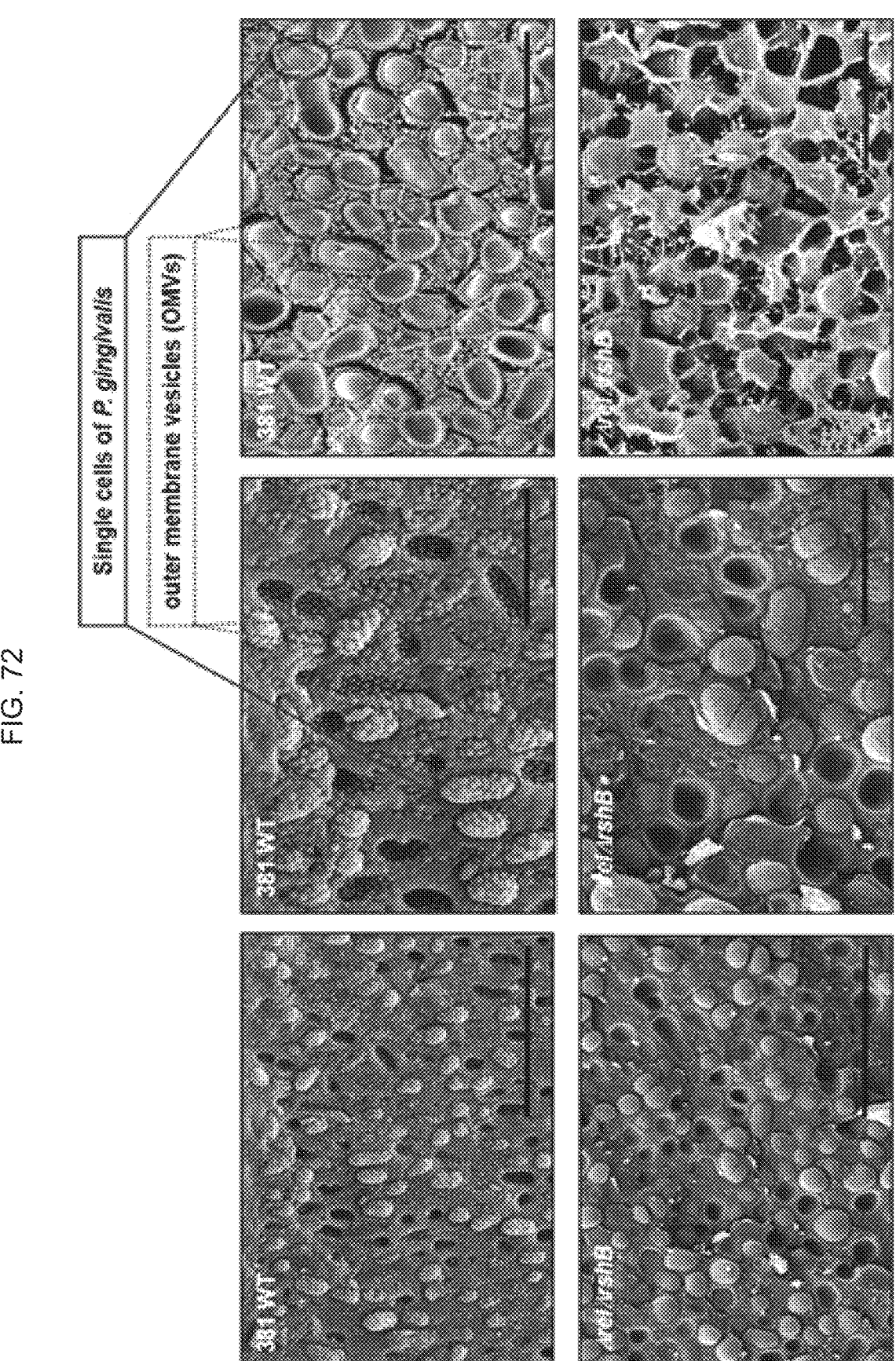
FIG. 72 shows the biofilm formation of wild type (WT; top panel row) and delta vshB (bottom panel row) *P. gingivalis* cells at three different magnifications. These cells have been exposed to KB001 at 0.01 ug/mL (left panel column), 1.0 ug/mL (middle panel column), and 10.0 ug/mL (right panel column).
Figure 73:
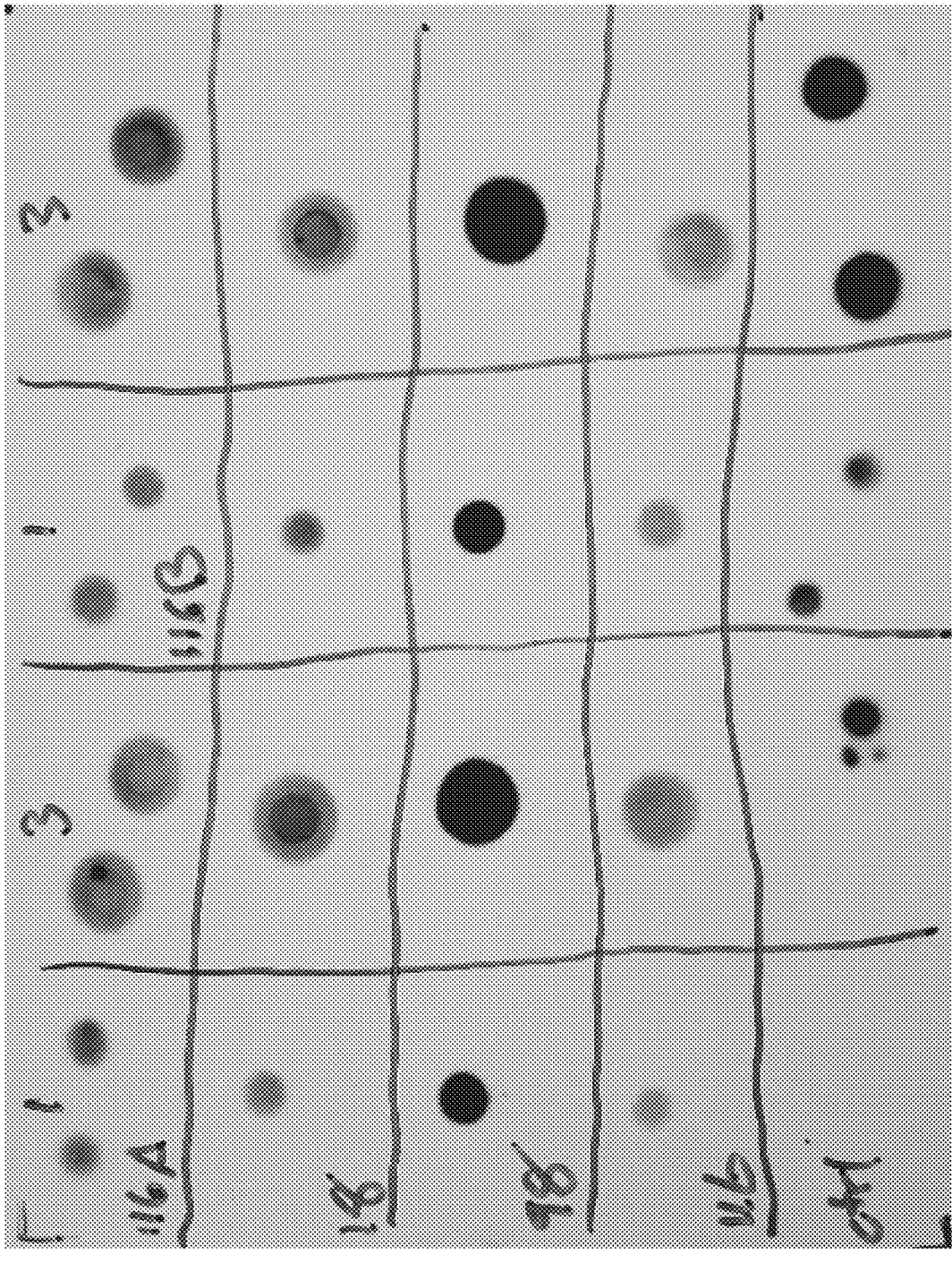
FIG. 73 shows a Dot Blot of human plasma samples in which the gingipain is dissociated from IgG with low pH before development using KB001-HRP for detection. Samples 116A (top row, left two panels) and 116B (top row, right two panels) represent a slit sample from patient 116, which were spiked with the recombinant gingipain toxin to represent a pre-dissociated sera sample control. The other samples from patient 18 (second row), patient 98 (third row), patient 116 (fourth row) and control (bottom row) show a positive response of KB001 binding to gingipain following acid dissociation. Samples from the first and third column are blotted at 1 uL per sample, and samples from the second and fourth column are blotted at 3 uL per sample.

At 24 hours and 48 hours, KB001 was shown to significantly reduce biofilm formation (Table 20.1). This further demonstrated that KB001 is capable of binding to and disarming the bacteria's adherence and colonization system. Further scans of the biofilm under exposure to KB001 also demonstrated that KB001 targets *P. gingivalis*'s toxic outer membrane vesicles, disarms its capabilities for acquiring food, and reduces its overall lifespan (FIG. 72).

TABLE 20.1

Inhibition of PGW83 biofilm growth during ABM exposure

| | Day 1 | | Day 2 | |
|---|---|---|---|---|
| Ab conc. | Titer | % reduction | Titer | % reduction |
| 0 ug/mL | 6.0E+07 | 0.00 | 4.4E+05 | 0.00 |
| 0.1 ug/mL | 6.0E+06 | 90.00 | 8.0E+04 | 81.82 |
| 1.0 ug/mL | 2.0E+06 | 96.67 | 6.0E+04 | 86.36 |
| 10 ug/mL | 6.0E+05 | 99.00 | 5.0E+04 | 88.64 |

What is claimed is:

1. An antigen-binding molecule that binds to *Porphyromonas gingivalis*, wherein the antigen-binding molecule comprises:

a heavy chain comprising a heavy chain variable region (HVR) comprising an HVR complementarity determining region (HCDR) 1, an HCDR2, and an HCDR3 from the sequence of SEQ ID NO:9 or 37 per the Kabat or Chothia definition of CDRs; and a light chain comprising a light chain variable region (LVR) comprising an LVR complementarity determining region (LCDR) 1, an LCDR2, and an LCDR3 from the sequence of SEQ ID NO:10 or 38 per the Kabat or Chothia definition of CDRs;

wherein the heavy chain comprises an amino acid other than lysine at position 105 as numbered according to the numbering as provided in the sequence of SEQ ID NO: 172; and wherein the heavy chain comprises an amino sequence at least 80% identical to the sequence of SEQ ID NO:263 and the light chain comprises an amino sequence at least 80% identical to the sequence of SEQ ID NO:253.

2. The antigen-binding molecule of claim 1, wherein the HCDR1 comprises the sequence of SEQ ID NO:3, the HCDR2 comprises the sequence of SEQ ID NO: 4, the HCDR3 comprises the sequence of SEQ ID NO:5, the LCDR1 comprises the sequence of SEQ ID NO:6, the LCDR2 comprises the sequence of SEQ ID NO:7, and the LCDR3 comprises the sequence of SEQ ID NO:8.

3. The antigen-binding molecule of claim 1, wherein the HVR comprises the sequence of SEQ ID NO:37 and the LVR comprises the amino acid sequence of SEQ ID NO:38.

4. The antigen-binding molecule of claim 1, wherein the antigen-binding molecule comprises at least one of:

one or more HVR residues selected from L48, L67, K71, V78, and M92, as numbered according to the numbering as provided in the sequence of SEQ ID NO:37, and one or more LVR residues selected from Q46, W48, A61, Y72, and T86, as numbered according to the numbering as provided in the sequence of SEQ ID NO:38.

5. The antigen-binding molecule of claim 1, wherein the HVR comprises an amino acid sequence at least 80% identical to the sequence of any one of SEQ ID NOs: 29-32 and the LVR comprises an amino acid sequence at least 80% identical to the sequence of any one of SEQ ID NOs: 33-36.

6. The antigen-binding molecule of claim 1, wherein the HVR comprises the sequence of any one of SEQ ID NOs: 29-32 and the LVR comprises the sequence of any one of SEQ ID NOs: 33-36.

7. The antigen-binding molecule of claim 1, wherein the HVR comprises the sequence of SEQ ID NO:30 and the LVR comprises the sequence of SEQ ID NOs: 33.

8. The antigen-binding molecule of claim 1, wherein the HVR comprises the sequence of SEQ ID NO:30 and the LVR comprises the sequence of SEQ ID NO: 35.

9. The antigen-binding molecule of claim 1, wherein the antigen-binding molecule is humanized.

10. The antigen-binding molecule of claim 1, wherein the amino acid other than lysine at position 105 as numbered in the sequence of SEQ ID NO:172 is an alanine.

11. An antigen-binding molecule that binds to *Porphyromonas gingivalis*, wherein the antigen-binding molecule comprises a heavy chain and a light chain, wherein the heavy chain comprises the sequence of any one of SEQ ID NOs: 245, 247, 249, 251, 261, 263, 265, and 267 and the light chain comprises the sequence of any one of SEQ ID NOs: 253, 255, 257, and 259.

12. An antigen-binding molecule that binds to *Porphyromonas gingivalis*, wherein the antigen-binding molecule comprises a heavy chain and a light chain, wherein the heavy chain comprises the sequence of SEQ ID NO:263 and the light chain comprises the sequence of SEQ ID NO:253.

13. The antigen-binding molecule of claim 12, wherein the heavy chain comprises the sequence of SEQ ID NO:239 and the light chain comprises the sequence of SEQ ID NO:229.

14. An antigen-binding molecule that binds to *Porphyromonas gingivalis*, wherein the antigen-binding molecule comprises a heavy chain and a light chain, wherein the heavy chain comprises the sequence of SEQ ID NO:263 and the light chain comprises the sequence of SEQ ID NO:357.

15. The antigen-binding molecule of claim 14, wherein the heavy chain comprises the sequence of SEQ ID NO:239 and the light chain comprises the sequence of SEQ ID NO:233.

16. A pharmaceutical composition comprising the antigen-binding molecule of claim 1, and a pharmaceutically acceptable carrier.

17. A pharmaceutical composition comprising the antigen-binding molecule of claim 11, and a pharmaceutically acceptable carrier.

18. A nucleic acid encoding the antigen-binding molecule of claim 1.

19. A nucleic acid encoding the antigen-binding molecule of claim 11.

20. A vector comprising the nucleic acid of claim 18.

21. A vector comprising the nucleic acid of claim 19.

22. A cell comprising a nucleic acid encoding the antigen-binding molecule of claim 1, or a vector comprising the nucleic acid.

23. A cell comprising a nucleic acid encoding the antigen-binding molecule of claim 11, or a vector comprising the nucleic acid.

24. A method of treating a condition, disorder, or disease associated with a *P. gingivalis* infection in a subject in need thereof, the method comprising administering to the subject a therapeutically effective amount of the antigen-binding molecule of claim 1.

25. A method of treating a condition, disorder, or disease associated with a *P. gingivalis* infection in a subject in need thereof, the method comprising administering to the subject a therapeutically effective amount of the antigen-binding molecule of claim 11.

26. The method of claim 24, wherein the condition, disorder, or disease associated with a *P. gingivalis* infection is an age-related cognitive disorder.

27. The method of claim 26, wherein the age-related cognitive disorder is dementia or Alzheimer's disease.

28. The method of claim 24, wherein the condition, disorder, or disease associated with a *P. gingivalis* infection is a vascular disease.

29. The method of claim 28, wherein the vascular disease is cardiovascular disease, atherosclerosis, coronary artery disease, myocardial infarction, stroke, or cardiac hypertrophy.

30. The method of claim 24, further comprising administering to the subject at least one other therapeutic agent for treating the condition, disorder, or disease associated with a *P. gingivalis* infection.

31. The method of claim 25, wherein the condition, disorder, or disease associated with a *P. gingivalis* infection is an age-related cognitive disorder.

32. The method of claim 31, wherein the age-related cognitive disorder is dementia or Alzheimer's disease.

33. The method of claim 25, wherein the condition, disorder, or disease associated with a *P. gingivalis* infection is a vascular disease.

34. The method of claim 33, wherein the vascular disease is cardiovascular disease, atherosclerosis, coronary artery disease, myocardial infarction, stroke, or cardiac hypertrophy.

35. The method of claim 25, further comprising administering to the subject at least one other therapeutic agent for treating the condition, disorder, or disease associated with a *P. gingivalis* infection.

* * * * *

SEQUENCE LISTING

```
Sequence total quantity: 300
SEQ ID NO: 1               moltype = AA  length = 441
FEATURE                    Location/Qualifiers
source                     1..441
                           mol_type = protein
                           organism = Mus musculus
SEQUENCE: 1
EVQLKQSGPG LVAPSQSLSI TCTVSGFSLS IYSVHWVRQP PGKGLEWLGM IWGGGSSDYN   60
SALKSRLSIS KDNSKSQVFL KMNSLQTDDT AMYYCARNGN FYAMDYWGQG TSVTVSSAKT  120
TPPSVYPLAP GSAAQTNSMV TLGCLVKGYF PEPVTVTWNS GSLSSGVHTF PAVLQSDLYT  180
LSSSVTVPSS TWPSETVTCN VAHPASSTKV DKKIVPRDCG CKPCICTVPE VSSVFIFPPK  240
PKDVLTITLT PKVTCVVVDI SKDDPEVQFS WFVDDVEVHT AQTQPREEQF NSTFRSVSEL  300
PIMHQDWLNG KEFKCRVNSA AFPAPIEKTI SKTKGRPKAP QVYTIPPPKE QMAKDKVSLT  360
CMITDFFPED ITVEWQWNGQ PAENYKNTQP IMNTNGSYFV YSKLNVQKSN WEAGNTFTCS  420
VLHEGLHNHH TEKSLSHSPG K                                            441

SEQ ID NO: 2               moltype = AA  length = 239
FEATURE                    Location/Qualifiers
source                     1..239
                           mol_type = protein
                           organism = Mus musculus
SEQUENCE: 2
MDFQVQIFSF LLISASVIMS RGQIVLTQSP AIMSASLGER VTMTCTASSS VSSSFLHWYQ   60
QKPGSSPQLW IYSTSNLASG VPARFSGSGS GTSYSLTISS MEAEDAATYY CHQYHHSPYI  120
YTFGGGTKLE IKRADAAPTV SIFPPSSEQL TSGGASVVCF LNNFYPKDIN VKWKIDGSER  180
QNGVLNSWTD QDSKDSTYSM SSTLTLTKDE YERHNSYTCE ATHKTSTSPI VKSFNRNEC   239

SEQ ID NO: 3               moltype = AA  length = 7
FEATURE                    Location/Qualifiers
REGION                     1..7
                           note = Synthetic polypeptide
source                     1..7
                           mol_type = protein
                           organism = synthetic construct
SEQUENCE: 3
FSLSIYS                                                              7

SEQ ID NO: 4               moltype = AA  length = 7
FEATURE                    Location/Qualifiers
REGION                     1..7
                           note = Synthetic polypeptide
source                     1..7
                           mol_type = protein
                           organism = synthetic construct
SEQUENCE: 4
IWGGGSS                                                              7

SEQ ID NO: 5               moltype = AA  length = 11
FEATURE                    Location/Qualifiers
REGION                     1..11
                           note = Synthetic polypeptide
```

-continued

```
source                   1..11
                         mol_type = protein
                         organism = synthetic construct
SEQUENCE: 5
ARNGNFYAMD Y                                                              11

SEQ ID NO: 6             moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 6
SSVSSSF                                                                   7

SEQ ID NO: 7             moltype =    length =
SEQUENCE: 7
000

SEQ ID NO: 8             moltype = AA  length = 11
FEATURE                  Location/Qualifiers
REGION                   1..11
                         note = Synthetic polypeptide
source                   1..11
                         mol_type = protein
                         organism = synthetic construct
SEQUENCE: 8
HQYHHSPYIY T                                                             11

SEQ ID NO: 9             moltype = AA  length = 117
FEATURE                  Location/Qualifiers
REGION                   1..117
                         note = Synthetic polypeptide
source                   1..117
                         mol_type = protein
                         organism = synthetic construct
SEQUENCE: 9
EVQLKQSGPG LVAPSQSLSI TCTVSGFSLS IYSVHWVRQP PGKGLEWLGM IWGGGSSDYN  60
SALKSRLSIS KDNSKSQVFL KMNSLQTDDT AMYYCARNGN FYAMDYWGQG TSVTVSS      117

SEQ ID NO: 10            moltype = AA  length = 110
FEATURE                  Location/Qualifiers
REGION                   1..110
                         note = Synthetic polypeptide
source                   1..110
                         mol_type = protein
                         organism = synthetic construct
SEQUENCE: 10
QIVLTQSPAI MSASLGERVT MTCTASSSVS SSFLHWYQQK PGSSPQLWIY STSNLASGVP  60
ARFSGSGSGT SYSLTISSME AEDAATYYCH QYHHSPYIYT FGGGTKLEIK             110

SEQ ID NO: 11            moltype = AA  length = 26
FEATURE                  Location/Qualifiers
REGION                   1..26
                         note = Synthetic polypeptide
source                   1..26
                         mol_type = protein
                         organism = synthetic construct
SEQUENCE: 11
EVQLKQSGPG LVAPSQSLSI TCTVSG                                              26

SEQ ID NO: 12            moltype = AA  length = 17
FEATURE                  Location/Qualifiers
REGION                   1..17
                         note = Synthetic polypeptide
source                   1..17
                         mol_type = protein
                         organism = synthetic construct
SEQUENCE: 12
VHWVRQPPGK GLEWLGM                                                       17

SEQ ID NO: 13            moltype = AA  length = 38
FEATURE                  Location/Qualifiers
REGION                   1..38
                         note = Synthetic polypeptide
source                   1..38
                         mol_type = protein
                         organism = synthetic construct
```

```
SEQUENCE: 13
DYNSALKSRL SISKDNSKSQ VFLKMNSLQT DDTAMYYC                                    38

SEQ ID NO: 14              moltype = AA  length = 11
FEATURE                    Location/Qualifiers
REGION                     1..11
                           note = Synthetic polypeptide
source                     1..11
                           mol_type = protein
                           organism = synthetic construct
SEQUENCE: 14
WGQGTSVTVS S                                                                 11

SEQ ID NO: 15              moltype = AA  length = 26
FEATURE                    Location/Qualifiers
REGION                     1..26
                           note = Synthetic polypeptide
source                     1..26
                           mol_type = protein
                           organism = synthetic construct
SEQUENCE: 15
QIVLTQSPAI MSASLGERVT MTCTAS                                                 26

SEQ ID NO: 16              moltype = AA  length = 17
FEATURE                    Location/Qualifiers
REGION                     1..17
                           note = Synthetic polypeptide
source                     1..17
                           mol_type = protein
                           organism = synthetic construct
SEQUENCE: 16
LHWYQQKPGS SPQLWIY                                                           17

SEQ ID NO: 17              moltype = AA  length = 36
FEATURE                    Location/Qualifiers
REGION                     1..36
                           note = Synthetic polypeptide
source                     1..36
                           mol_type = protein
                           organism = synthetic construct
SEQUENCE: 17
NLASGVPARF SGSGSGTSYS LTISSMEAED AATYYC                                      36

SEQ ID NO: 18              moltype = AA  length = 10
FEATURE                    Location/Qualifiers
REGION                     1..10
                           note = Synthetic polypeptide
source                     1..10
                           mol_type = protein
                           organism = synthetic construct
SEQUENCE: 18
FGGGTKLEIK                                                                   10

SEQ ID NO: 19              moltype = AA  length = 25
FEATURE                    Location/Qualifiers
REGION                     1..25
                           note = Synthetic polypeptide
source                     1..25
                           mol_type = protein
                           organism = synthetic construct
SEQUENCE: 19
GVSPKVCKDV TVEGSNEFAP VQNLT                                                  25

SEQ ID NO: 20              moltype = AA  length = 128
FEATURE                    Location/Qualifiers
REGION                     1..128
                           note = Synthetic polypeptide
source                     1..128
                           mol_type = protein
                           organism = synthetic construct
SEQUENCE: 20
AGTYDFAIAA PQANAKIWIA GQGPTKEDDY VFEAGKKYHF LMKKMGSGDG TELTISEGGG  60
SDYTYTVYRD GTKIKEGLTA TTFEEDGVAA GNHEYCVEVK YTAGVSPKVC KDVTVEGSNE  120
FAPVQNLT                                                          128

SEQ ID NO: 21              moltype = AA  length = 1706
FEATURE                    Location/Qualifiers
source                     1..1706
                           mol_type = protein
```

```
                             organism = Porphyromonas gingivalis
SEQUENCE: 21
MKNLNKFVSI ALCSSLLGGM AFAQQTELGR NPNVRLLEST QQSVTKVQFR MDNLKFTEVQ    60
TPKGMAQVPT YTEGVNLSEK GMPTLPILSR SLAVSDTREM KVEVVSSKFI EKKNVLIAPS   120
KGMIMRNEDP KKIPYVGKS YSQNKFFPGE IATLDDPFIL RDVRGQVVNF APLQYNPVTK   180
TLRIYTEITV AVSETSEQGK NILNKKGTFA GFEDTYKRMF MNYEPGRYTP VEEKQNGRMI   240
VIVAKKYEGD IKDFVDWKNQ RGLRTEVKVA EDIASPVTAN AIQQFVKQEY EKEGNDLTYV   300
LLIGDHKDIP AKITPGIKSD QVYGQIVGND HYNEVFIGRF SCESKEDLKT QIDRTIHYER   360
NITTEDKWLG QALCIASAEG GPSADNGESD IQHENVIANL LTQYGYTKII KCYDPGVTPK   420
NIIDAFNGGI SLANYTGHGS ETAWGTSHFG TTHVKQLTNS NQLPFIFDVA CVNGDFLFSM   480
PCFAEALMRA QKDGKPTGTV AIIASTINQS WASPMRGQDE MNEILCEKHP NNIKRTFGGV   540
TMNGMFAMVE KYKKDGEKML DTWTVFGDPS LLVRTLVPTK MQVTAPAQIN LTDASVNVSC   600
DYNGAIATIS ANGKMFGSAV VENGTATINL TGLTNESTLT LTVVGYNKET VIKTINTNGE   660
PNPYQPVSNL TATTQGQKVT LKWDAPSTKT NATTNTARSV DGIRELVLLS VSDAPELLRS   720
GQAEIVLEAH DVWNDGSGYQ ILLDADHDQY GQVIPSDTHT LWPNCSVPAN LFAPFEYTVP   780
ENADPSCSPT NMIMDGTASV NIPAGTYDFA IAAPQANAKI WIAGQGPTKE DDYVFEAGKK   840
YHFLMKKMGS GDGTELTISE GGGSDYTYTV YRDGTKIKEG LTATTFEEDG VAAGNHEYCV   900
EVKYTAGVSP KVCKDVTVEG SNEFAVQNL TGSAVGQKVT LKWDAPNGTP NPNPNPNPNP   960
NPGTTTLSES FENGIPASWK TIDADGDGHG WKPGNAPGIA GYNSNGCVYS ESFGLGGIGV  1020
LTPDNYLITP ALDLPNGGKL TFWVCAQDAN YASEHYAVYA SSTGNDASNF TNALLEETIT  1080
AKGVRSPEAI RGRIQSTWRQ KTVDLPAGTK YVAFRHFQST DMFYIDLDEV EIKANGKRAD  1140
FTETFESSTH GEATAEWTTI DADGDGQGWL CLSSGQLDWL TAHGGTNVVS SFSWNGMALN  1200
PDNYLISKDV TGATKVKYYY AVNDGFPGDH YAVMISKTGT NAGDFTVVFE ETPNGINKGG  1260
ARFGLSTEAD GAKPQSVWIE RTVDLPAGTK YVAFRHYNCS DLNYILLDDI QFTMGGSPTP  1320
TDYTYTVYRD GTKIKEGLTE TTFEEDGVAT GNHEYCVEVK YTAGVSPKKC VNVTVNSTQF  1380
NPVKNLKAQP DGGDVVLKWE APSAKKTEGS REVKRIGDGL FVTIEPANDV RANEAKVVLA  1440
ADNVWGDNTG YQFLLDADHN TFGSVIPATG PLFTGTASSD LYSANFEYLI PANADPVVTT  1500
QNIIVTQGGE VVIPGGVYDY CITNPEPASG KMWIAGDGGN QPARYDDFTF EAGKKYTFTM  1560
RRAGMGDGTD MEVEDDSPAS YTYTVYRDGT KIKEGLTETT YRDAGMSAQS HEYCVEVKYT  1620
AGVSPKVCVD YIPDGVADVT AQKPYTLTVV GKTITVTCQG EAMIYDMNGR RLAAGRNTVV  1680
YTAQGGYYAV MVVVDGKSYV KKLAIK                                       1706

SEQ ID NO: 22       moltype = AA  length = 736
FEATURE             Location/Qualifiers
source              1..736
                    mol_type = protein
                    organism = Porphyromonas gingivalis
SEQUENCE: 22
MKKNFSRIVS IVAFSSLLGG MAFAQPAERG RNPQVRLLSA EQSMSKVQFR MDNLQFTDVQ    60
TSKGVAQVPT FTEGVNISEK GTPILPILSR SLAVSETRAM KVEVVSSKFI EKKDVLIAPS   120
KGVISRAENP DQIPYVYGQS YNEDKFFPGE IATLSDPFIL RDVRGQVVNF APLQYNPVTK   180
TLRIYTEIVV AVSETAEAGQ NTISLVKNST FTGFEDIYKS VFMNYEATRY TPVEEKENGR   240
MIVIVPKKYE EDIEDFVDWK NQRGLRTEVK VAEDIASPVT ANAIQQFVKQ EYEKEGNDLT   300
YVLLVGDHKD IPAKITPGIK SDQVYGQIVG NDHYNEVFIG RFSCESKEDL KTQIDRTIHY   360
ERNITTEDKW LGQALCIASA EGGPSADNGE SDIQHENVIA DLLTQYGYTK IIKCYDPGVT   420
PKNIIDAFNG GISLVNYTGH GSETAWGTSH FGTTHVKQLT NSNQLPFIFD VACVNGDFLY   480
NVPCFAEALM RAQKDGKPTG TVAIIASTIN QYWAPPMRGQ DEMNEILCEK HPNNIKRTFG   540
GVTMNGMFAM VEKYKKDGEN MLDTWTVFGD PSLLVRTLVP TEMQVTAPAN ISASAQTFEV   600
ACDYNGAIAT LSDDGDMVGT AIVKDGKAII KLNESIADET NLTLTVVGYN KVTVIKDVKV   660
EGTSIADVAN DKPYTVAVSG KTITVESPAA GLTIFDMNGR RVATAKNRMV FEAQNGVYAV   720
RIATEGKTYT EKVIVK                                                   736

SEQ ID NO: 23       moltype = AA  length = 1732
FEATURE             Location/Qualifiers
source              1..1732
                    mol_type = protein
                    organism = Porphyromonas gingivalis
SEQUENCE: 23
MRKLLLLIAA SLLGVGLYAQ SAKIKLDAPT TRTTCTNNSF KQFDASFSFN EVELTKVETK    60
GGTFASVSIP GAFPTGEVGS PEVPAVRKLI AVPVGATPVV RVKSFTEQVY SLNQYGSEKL   120
MPHQPSMSKS DDPEKVPFVY NAAAYARKGF VGQELTQVEM LGTMRGVRIA ALTINPVQYD   180
VVANQLKVRN NIEIEVSFQG ADEVATQRLY DASFSPYFET AYKQLFNRDV YTDHGDLYNT   240
PVRMLVVAGA KFKEALKPWL TWKAQKGFYL DVHYTDEAEV GTTNASIKAF IHKKYNDGLA   300
ASAAPVFLAL VGDTDVISGE KGKKTKKVTD LYYSAVDGDY FPEMYTFRMS ASSPEELTNI   360
IDKVLMYEKA TMPDKSYLEK VLLIAGADYS WNSQVGQPTI KYGMQYYYNQ EHGYTDVYNY   420
LKAPYTGCYS HLNTGVSFAN YTAHGSETAW ADPLLTTSQL KALTNKDKYF LAIGNCCITA   480
QFDYVQPCFG EVITRVKEKG AYAYIGSSPN SYWGEDYYWS VGANAVFGVQ PTFEGTSMGS   540
YDATFLEDSY NTVNSIMWAG NLAATHAGNI GNITHIGAHY YWEAYHVLGD GSVMPYRAMP   600
KTNTYTLPAS LPQNQASYSI QASAGSYVAI SKDGVLYGTG VANASGVATV SMTKQITENG   660
NYDVVITRSN YLPVIKQIQV GEPSPYQPVS NLTATTQGQK VTLKWEAPSA KKAEGSREVK   720
RIGDGLFVTI EPANDVRANE AKVVLAADNV WGDNTGYQFL LDADHNTFGS VIPATGPLFT   780
GTASSNLYSA NFEYLVPANA DPVVTTQNII VTGQGEVVIP GGVYDYCITN PEPASGKMWI   840
AGDGGNQPAR YDDFTFEAGK KYTFTMRRAG MGDGTDMEVE DDSPASYTYT VYRDGTKIKE   900
GLTATTFEED GVAAGNHEYC VEVKYTAGVS PKVCKDVTVE GSNEFAPVQN LTGSSVGQKV   960
TLKWDAPNGT PNPNPNPNPN PGTTLSESFE NGIPASWKTI DADGDGHGWK PGNAPGIAGY  1020
NSNGCVYSES FGLGGIGVLT PDNYLITPAL DLPNGGKLTF WVCAQDANYA SEHYAVYASS  1080
TGNDASNFTN ALLEETITAK GVRSPKAIRG RIQGTWRQKT VDLPAGTKYV AFRHFQSTDM  1140
FYIDLDEVEI KANGKRADFT ETFESSTHGE APAEWTTIDA DGDGQGWLCL SSGQLDWLTA  1200
HGGSNVVSSF SWNGMALNPD NYLISKDVTG ATKVKYYYAV NDGFPGDHYA VMISKTGTNA  1260
```

-continued

```
GDFTVVFEET PNGINKGGAR FGLSTEANGA KPQSVWIERT VDLPAGTKYV AFRHYNCSDL   1320
NYILLDDIQF TMGGSPTPTD YTYTVYRDGT KIKEGLTETT FEEDGVATGN HEYCVEVKYT   1380
AGVSPKKCVD VTVNSTQFNP VQNLTAEQAP NSMDAILKWN APASKRAEVL NEDFENGIPA   1440
SWKTIDADGD GNNWTTTPPP GGSSFAGHNS AICVSSASHI NFEGPQNPDN YLVTPELSLP   1500
GGGTLTFWVC AQDANYASEH YAVYASSTGN DASNFANALL EEVLTAKTVV TAPEAIRGTR   1560
AQGTWYQKTV QLPAGTKYVA FRHFGCTDFF WINLDDVVIT SGNAPSYTYT IYRNNTQIAS   1620
GVTETTYRDP DLATGFYTYG VKVVYPNGES AIETATLNIT SLADVTAQKP YTLTVVGKTI   1680
TVTCQGEAMI YDMNGRRLAA GRNTVVYTAQ GGHYAVMVVV DGKSYEVKLA VK           1732

SEQ ID NO: 24           moltype = AA  length = 2105
FEATURE                 Location/Qualifiers
source                  1..2105
                        mol_type = protein
                        organism = Porphyromonas gingivalis
SEQUENCE: 24
MARIILEAHD VWEDGTGYQM LWDADHNQYG ASIPEESFWF ANGTIPAGLY DPFEYKVPVN   60
ADASFSPTNF VLDGTASADI PAGTYDYVII NPNPGIIYIV GEGVSKGNDY VVEAGKTYHF   120
TVQRQGPGDA ASVVVTGEGG NEFAPVQNLQ WSVSGQTVTL TWQAPASDKR TYVLNESFDT   180
QTLPNGWTMI DADGDGHNWL STINVYNTAT HTGDGAMFSK SWTASSGAKI DLSPDNYLVT   240
PKFTVPENGK LSYWVSSQEP WTNEHYGVFL STTGNEAANF TIKLLEETLG SGKPAPMNLV   300
KSEGVKAPAP YQERTIDLSA YAGQQVYLAF RHFGCTGIFR LYLDDVAVSG EGSSNDYTYT   360
VYRDNVVIAQ NLTATTFNQE NVAPGQYNYC VEVKYTAGVS PKVCKDVTVE GSNEFAPVQN   420
LTGSAVGQKV TLKWDAPNGT PNPNPGTTTL SESFENGIPA SWKTIDADGD GNNWTTTPPP   480
GGSSFAGHNS AICVSSASYI NFEGPQNPDN YLVTPELSLP NGGTLTFWVC AQDANYASEH   540
YAVYASSTGN DASNFANALL EEVLTAKTVV TAPEAIRGTR VQGTWYQKTV QLPAGTKYVA   600
FRHFGCTDFF WINLDDVEIK ANGKRADFTE TFESSTHGEA PAEWTTIDAD GDGQGWLCLS   660
SGQLGWLTAH GGTNVVASFS WNGMALNPDN YLISKDVTGA TKVKYYYAVN DGFPGDHYAV   720
MISKTGTNAG DFTVVFEETP NGINKGGARF GLSTEANGAK PQSVWIERTV DLPAGTKYVA   780
FRHYNCSDLN YILLDDIQFT MGGSPTPTDY TYTVYRDGTK IKEGLTETTF EEDGVATGNH   840
EYCVEVKYTA GVSPKECVNV TVDPVQFNPV QNLTGSAVGQ KVTLKWDAPN GTPNPNPGTT   900
TLSESFENGI PASWKTIDAD GDGNNWTTTP PPGGTSFAGH NSAICVSSAS YINFEGPQNP   960
DNYLVTPELS LPNGGTLTFW VCAQDANYAS EHYAVYASST GNDASNFANA LLEEVLTAKT   1020
VVTAPEAIRG TRVQGTWYQK TVQLPAGTKY VAFRHFGCTD FFWINLDDVE IKANGKRADF   1080
TETFESSTHG EAPAEWTTID ADGDGQGWLC LSSGQLDWLT AHGGTNVVAS FSWNGMALNP   1140
DNYLISKDVT GATKVKYYYA VNDGFPGDHY AVMISKTGTN AGDFTVVFEE TPNGINKGGA   1200
RFGLSTEANG AKPQSVWIER TVDLPAGTKY VAFRHYNCSD LNYILLDDIQ FTMGGSPTPT   1260
DYTYTVYRDG TKIKEGLTET TFEEDGVATG NHEYCVEVKY TAGVSPKECV NVTVDPVQFN   1320
PVQNLTGSAV GQKVTLKWDA PNGTPNPNPG TTTLSESFEN GIPASWKTID ADGDGNNWTT   1380
TPPPGGTSFA GHNSAICVSS ASYINFEGPQ NPDNYLVTPE LSLPNGGTLT FWVCAQDANY   1440
ASEHYAVYAS STGNDASNFA NALLEEVLTA KTVVTAPEAI RGTRVQGTWY QKTVQLPAGT   1500
KYVAFRHFGC TDFFWINLDD VEIKANGKRA DFTETFESST HGEAPAEWTT IDADGDGQGW   1560
LCLSSGQLGW LTAHGGTNVV ASFSWNGMAL NPDNYLISKD VTGATKVKYY YAVNDGFPGD   1620
HYAVMISKTG TNAGDFTVVF EETPNGINKG GARFGLSTEA KPQSVWI ERTVDLPAGT   1680
KYVAFRHYNC SDLNYILLDD IQFTMGGSPT PTDYTYTVYR DGTKIKEGLT ETTFEEDGVA   1740
TGNHEYCVEV KYTAGVSPKE CVNVTINPTQ FNPVQNLTAE QAPNSMDAIL KWNAPASKRA   1800
EVLNEDFENG IPASWKTIDA DGDGNNWTTT PPPGGSSFAG HNSAICVSSA SYINFEGPQN   1860
PDNYLVTPEL SLPGGGTLTF WVCAQDANYA SEHYAVYASS TGNDASNFAN ALLEEVLTAK   1920
TVVTAPEAIR GTRVQGTWYQ KTVQLPAGTK YVAFRHFGCT DFFWINLDDV VITSGNAPSY   1980
TYTIYRNNTQ IASGVTETTY RDPDLATGFY TYGVKVVYPN GESAIETATL NITSLADVTA   2040
QKPYTLTVVG KTITVTCQGE AMIYDMNGRR LAAGRNTVVY TAQGGHYAVM VVVDGKSYVE   2100
KLAVK                                                              2105

SEQ ID NO: 25           moltype = AA  length = 991
FEATURE                 Location/Qualifiers
source                  1..991
                        mol_type = protein
                        organism = Porphyromonas gingivalis
SEQUENCE: 25
MKNLNKFVSI ALCSSLLGGM AFAQQTELGR NPNVRLLEST QQSVTKVQFR MDNLKFTEVQ   60
TPKGMAQVPT YTEGVNLSEK GMPTLPILSR SLAVSDTREM KVEVVSSKFI EKKNVLIAPS   120
KGMIMRNEDP KKIPYVYGKS YSQNKFFPGE IATLDDDPFIL RDVRGQVVNF APLQYNPVTK   180
TLRIYTEITV AVSETSEQGK NILNKKGTFA GFEDTYKRMF MNYEPGRYTP VEEKQNGRMI   240
VIVAKKYEGD IKDFVDWKNQ RGLRTEVKVA EDIASPVTAN AIQQFVKQEY EKEGNDLTYV   300
LLVGDHKDIP AKITPGIKSD QVYGQIVGND HYNEVFIGRF SCESKEDLKT QIDRTIHYER   360
NITTEDKWLG QALCIASAEG GPSADNGESD IQHENVIANL LTQYGYTKII KCYDPGVTPK   420
NIIDAFNGGI SLVNYTGHGS ETAWGTSHFG TTHVKQLTNS NQLPFIFDVA CVNGDFLFSM   480
PCFAEALMRA QKDGKPTGTV AIIASTINQS WASPMRGQDE MNEILCEKHP NNIKRTFGGV   540
TMNGMFAMVE KYKKDGEKML DTWTVFGDPS LLVRTLVPTK MQVTAPAQIN LTDASVNVSC   600
DYNGAIATIS ANGKMFGSAV VENGTATINL TGLTNESTLT LTVVGYNKET VIKTINTNGE   660
PNPYQPVSNL TATTGQKVT LKWDAPSTKT NATTNTARSV DGIRELVLLS VSDAPELLRS   720
GQAEIVLEAH DVWNDGSGYQ ILLDADHDQY GQVIPSDTHT LWPNCSVPAN LFAPFEYTVP   780
ENADPSCSPT NMIMDGTASV NIPAGTYDFA IAAPQANAKI WIAGQGPTKE DDYVFEAGKK   840
YHFLMKKMGS GDGTELTISE GGGSDYTYTV YRDGTKIKEG LTETTYRDAG MSAQSHEYCV   900
EVKYAAGVSP KVCVDYIPDG VADVTAQKPY TLTVVGKTIT VTCQGEAMIY DMNGRRLAAG   960
RNTVVYTAQG GYYAVMVVVD GKSYEVKLAV K                                  991

SEQ ID NO: 26           moltype = AA  length = 736
FEATURE                 Location/Qualifiers
source                  1..736
```

```
                        mol_type = protein
                        organism = Porphyromonas gingivalis
SEQUENCE: 26
MKKNFSRIVS IVAFSSLLGG MAFAQPAERG RNPQVRLLSA EQSMSKVQFR MDNLQFTGVQ      60
TSKGVAQVPT FTEGVNISEK GTPILPILSR SLAVSETRAM KVEVVSSKFI EKKDVLIAPS     120
KGVISRAENP DQIPYVYGQS YNEDKFFPGE IATLSDPFIL RDVRGQVVNF APLQYNPVTK     180
TLRIYTEIVV AVSETAEAGQ NTISLVKNST FTGFEDIYKS VFMNYEATRY TPVEEEKENGR    240
MIVIVPKKYE EDIEDFVDWK NQRGLRTEVK VAEDIASPVT ANAIQQFVKQ EYEKEGNDLT     300
YVLLVGDHKD IPAKITPGIK SDQVYGQIVG NDHYNEVFIG RFSCESKEDL KTQIDRTIHY     360
ERNITTEDKW LGQALCIASA EGGPSADNGE SDIQHENIIA NLLTQYGYTK IIKCYDPGVT     420
PKNIIDAFNG GISLANYTGH GSETAWGTSH FGTTHVKQLT NSNQLPFIFD VACVNGDFLY     480
NVPCFAEALM RAQKDGKPTG TVAIIASTIN QSWASPMRGQ DEMNEILCEK HPNNIKRTFG     540
GVTMNGMFAM VEKYKKDGEK MLDTWTVFGD PSLLVRTLVP TKMQVTAPAN ISASAQTFEV     600
ACDYNGAIAT LSDDGDMVGT AIVKDGKAII KLNESIADET NLTLTVVGYN KVTVIKDVKV     660
EGTSIADVAN DKPYTVAVSG KTITVESPAA GLTIFDMNGR RVATAKNRMV FEAQNGVYAV     720
RIATEGKTYT EKVIVK                                                     736

SEQ ID NO: 27        moltype = AA  length = 1723
FEATURE              Location/Qualifiers
source               1..1723
                     mol_type = protein
                     organism = Porphyromonas gingivalis
SEQUENCE: 27
MRKLLLLIAA SLLGVGLYAQ SAKIKLDAPT TRTTCTNNSF KQFDASFSFN EVELTKVETK      60
GGTFASVSIP GAFPTGEVGS PEVPAVRKLI AVPVGATPVV RVKSFTEQVY SLNQYGSEKL     120
MPHQPSMSKS DDPEKVPFVY NAAAYARKGF VGQELTQVEM LGTMRGVRIA ALTINPVQYD     180
VVANQLKVRN NIEIEVSFQG ADEVATQRLY DASFSPYFET AYKQLFNRDV YTDHGDLYNT     240
PVRMLVVAGA KFKEALKPWL TWKAQKGFYL DVHYTDEAEV GTTNASIKAF IHKKYNDGLA     300
ASAAPVFLAL VGDTDVISGE KGKKTKKVTD LYYSAVDGDY FPEMYTFRMS ASSPEELTNI     360
IDKVLMYEKA TMPDKSYLEK ALLIAGADSY WNPKIGQQTI KYAVQYYYNQ DHGYTDVYSY     420
PKAPYTGCYS HLNTGVGFAN YTAHGSETSW ADPSLTATQV KALTNKDKYF LAIGNCCVTA     480
QFDYPQPCFG EVMTRVKEKG AYAYIGSSPN SYWGEDYYWS VGANAVFGVQ PTFEGTSMGS     540
YDATFLEDSY NTVNSIMWAG NLAATHAGNI GNITHIGAHY YWEAYHVLGD GSVMPYRAMP     600
KTNTYTLPAS LPQNQASYSI QASAGSYVAI SKDGVLYGTG VANASGVATV NMTKQITENG     660
NYDVVITRSN YLPVIKQIQA GEPSPYQPVS NLTATTQGQK VTLKWDAPSA KKAEASREVK     720
RIGDGLFVTI EPANDVRANE AKVVLAADNV WGDNTGYQFL LDADHNTFGS VIPATGPLFT     780
GTASSNLYSA NFEYLIPANA DPVVTTQNII VTGQGEVVIP GGVYDYCITN PEPASGKMWI     840
AGDGGNQPAR YDDFTFEAGK KYTFTMRRAG MGDGTDMEVE DDSPASYTYT VYRDGTKIQE     900
GLTATTFEED GVAAGNHEYC VEVKYTAGVS PKVCKDVTVE GSNEFAPVQN LTGSAVGQKV     960
TLKWDAPNGT PNPNPNPNPG TTTLSESFEN GIPASWKTID ADGDGHGWKP GNAPGIAGYN    1020
SNGCVYSESF GLGGIGVLTP DNYLITPALD LPNGGKLTFW VCAQDANYAS EHYAVYASST    1080
GNDASNFTNA LLEETITAKG VRSPEAIRGR IQGTWRQKTV DLPAGTKYVA FRHFQSTDMP    1140
YIDLDEVEIK ANGKRADFTE TFESSTHGEA PAEWTTIDAD GDGQDWLCLS SGQLDWLTAH    1200
GGTNVVASFS WNGMALNPDN YLISKDVTGA TKVKYYYAVN DGFPGDHYAV MISKTGTNAG    1260
DFTVVFEETP NGINKGGARF GLSTEANGAK PQSVWIERTV DLPAGTKYVA FRHYNCSDLN    1320
YILLDDDIQFT MGGSPTPTDY TYTVYRDGTK IKEGLTETTF EEDGVATGNH EYCVEVKYTA    1380
GVSPKVCVNV TINPTQFNPV KNLKAQPDGG DVVLKWEAPS GKRGELLNED FEGDAIPTGW    1440
TALDADGDGN NWDITLNEFT RGERHVLSPL RASNVAISYS SLLQGQEYLP LTPNNFLITP    1500
KVEGAKKITY KVGSPGLPQW SHDHYALCIS KSGTAAADFE VIFEETMTYT QGGANLTREK    1560
DLPAGTKYVA FRHYNCTDVL GIMIDDVVIT GEGEGPSYTY TVYRDGTKIQ EGLTETTYRD    1620
AGMSAQSHEY CVEVKYAAGV SPKVCVDYIP DGVADVTAQK PYTLTVVGKT ITVTCQGEAM    1680
IYDMNGRRLA AGRNTVVYTA QGGYYAVMVV VDGKSYVEKL AIK                      1723

SEQ ID NO: 28        moltype = AA  length = 2628
FEATURE              Location/Qualifiers
source               1..2628
                     mol_type = protein
                     organism = Porphyromonas gingivalis
SEQUENCE: 28
MRKLNSLFSL AVLLSLLCWG QTAAAQGGPK TAPSVTHQAV QKGIRTSKVK DLRDPIPAGM      60
ARIILEAHDV WEDGTGYQML WDADHNQYGA SIPEESFWFA NGTIPAGLYD PFEYKVPVNA     120
DASFSPTNFV LDGTASADIP AGTYDYVIIN PNPGIIYIVG EGVSKGNDYV VEAGKTYHFT     180
VQRQGPGDAA SVVVTGEGGN EFAPVQNLQW SVSGQTVTLT WQAPASDKRT YVLNESFDTQ     240
TLPNGWTMID ADGDGHNWLS TINVYNTATH TGDGAMFSKS WTASGGAKID LSPDNYLVTP     300
KVTVPENGKL SYWVSSQVPW TNEHYGVFLS TTGNEAANFT IKLLEETLGS DKPAPMNLVK     360
SEGVKLPAPY QERTIDLSAY AGQQVYLAFR HFNSTGIFRL YLDDVAVSGE GSSNDYTYTV     420
YRDNVVIAQN LAATTFNQEN VAPGQYNYCV EVKYTAGVSP KVCKDVTVEG SNEFAHVQNL     480
TGSAVGQKVT LKWDAPNGTP NPNPGTTTLS ESFENGIPAS WKTIDADGDG NNWTTTPPPG     540
GTSFAGHNSA ICASSASYIN FEGPQNPDNY LVTPELSLPN GGTLTFWVCA QDANYASEHY     600
AVYASSTGND ASNFANALLE EVLTAKTVVT APEAIRGTRV QGTWYQKTVQ LPAGTKYVAF     660
RHFGCTDFFW INLDDVEIKA NGKRADFTET FESSTHGEAP AEWTTIDADG DGQGWLCLSS     720
GQLDWLTAHG GTNVVASFSW NGMALNPDNY LISKDVTGAT KVKYYYAVND GFPGDHYAVM     780
ISKTGTNAGD FTVVFEETPN GINKGGARFG LSTEADGAKP QSVWIERTVD LPAGTKYVAF     840
RHYNCSDLNY ILLDDDIQFTM GGSPTPTDYT YTVYRDGTKI KEGLTETTFE EDGVATGNHE     900
YCVEVKYTAG VSPKECVNVT VDPVQFNPVQ NLTGSAVGQK VTLKWDAPNG TPNPNPNPNP     960
GTTTLSESFE NGIPASWKTI DADGDGNNWT TTPPPGGTSF AGHNSAICAS SASYINFEGP    1020
QNPDNYLVTP ELSLPNGGTL TFWVCAQDAN YASEHYAVYA SSTGNDASNF ANALLEEVLT    1080
AKTVVTAPEA IRGTRVQGTW YQKTVQLPAG TKYVAFRHFG CTDFFWINLD DVEIKANGKR    1140
ADFTETFESS THGEAPAEWT TIDADGDGQG WLCLSSGQLG WLTAHGGTNV VASFSWNGMA    1200
```

-continued

```
LNPDNYLISK DVTGATKVKY YYAVNDGFPG DHYAVMISKT GTNAGDFTVV FEETPNGINK   1260
GGARFGLSTE ADGAKPQSVW IERTVDLPAG TKYVAFRHYN CSDLNYILLD DIQFTMGGSP   1320
TPTDYTYTVY RDGTKIKEGL TETTFEEDGV ATGNHEYCVE VKYTAGVSPK ECVNVTVDPV   1380
QFNPVQNLTG SAVGQKVTLK WDAPNGTPNP NPNPNPGTTT LSESFENGIP ASWKTIDADG   1440
DGNNWTTTPP PGGTSFAGHN SAICASSASY INFEGPQNPD NYLVTPELSL PNGGTLTFWV   1500
CAQDANYASE HYAVYASSTG NDASNFANAL LEEVLTAKTV VTAPEAIRGT RVQGTWYQKT   1560
VQLPAGTKYV AFRHFGCTDF FWINLDDVEI KANGKRADFT ETFESSTHGE APAEWTTIDA   1620
DGDGQGWLCL SSGQLGWLTA HGGTNVVASF SWNGMALNPD NYLISKDVTG ATKVKYYYAV   1680
NDGFPGDHYA VMISKTGTNA GDFTVVFEET PNGINKGGAR FGLSTEADGA KPQSVWIERT   1740
VDLPAGTKYV AFRHYNCSDL NYILLDDIQF TMGGSPTPTD YTYTVYRDGT KIKEGLTETT   1800
FEEDGVATGN HEYCVEVKYT AGVSPKECVN VTVDPVQFNP VQNLTGSAVG QKVTLKWDAP   1860
NGTPNPNPNP NPGTTTLSES FENGIPASWK TIDADGDGNN WTTTPPPGGT SFAGHNSAIC   1920
VSSASYINFE GPQNPDNYLV TPELSLPGGG TLTFWVCAQD ANYASEHYAV YASSTGNDAS   1980
NFANALLEEV LTAKTVVTAP EAIRGTRVQG TWYQKTVQLP AGTKYVAFRH FGCTDFFWIN   2040
LDEVEIKANG KRADFTETFE SSTHGEAPAE WTTIDADGDG QGWLCLSSGQ LDWLTAHGGT   2100
NVVASFSWNG MALNPDNYLI SKDVTGATKV KYYYAVNDGF PGDHYAVMIS KTGTNAGDFT   2160
VVFEETPNGI NKGGARFGLS TEADGAKPQS VWIERTVDLP AGTKYVAFRH YNCSDLNYIL   2220
LDDIQFTMGG SPTPTDYTYT VYRDGTKIKE GLTETTFEED GVATGNHEYC VEVKYTAGVS   2280
PKVCVNVTIN PTQFNPVQNL TAEQAPNSMD AILKWNAPAS KRAEVLNEDF ENGIPSSWKT   2340
IDADGDGNNW TTTPPPGGSS FAGHNSAICV SSASYINFEG PQNPDNYLVT PELSLPGGGT   2400
LTFWVCAQDA NYASEHYAVY ASSTGNDASN FANALLEEVL TAKTVVTAPE AIRGTRVQGT   2460
WYQKTVQLPA GTKYVAFRHF GCTDFFWINL DDVVITSGNA PSYTYTIYRN NTQIASGVTE   2520
TTYRDPDLAT GFYTYGVKVV YPNGESAIET ATLNITSLAD VTAQKPYTLT VVGKTITVTC   2580
QGEAMIYDMN GRRLAAGRNT VVYTAQGGHY AVMVVVDGKS YVEKLAVK            2628
```

```
SEQ ID NO: 29            moltype = AA  length = 117
FEATURE                  Location/Qualifiers
REGION                   1..117
                         note = Synthetic polypeptide
source                   1..117
                         mol_type = protein
                         organism = synthetic construct
SEQUENCE: 29
QVQLQESGPG LVKPSETLSL TCTVSGFSLS IYSVHWIRQP PGKGLEWIGM IWGGGSSDYN   60
SALKSRVTIS VDTSKNQFSL KLSSVTAADT AVYYCARNGN FYAMDYWGQG TLVTVSS     117
```

```
SEQ ID NO: 30            moltype = AA  length = 117
FEATURE                  Location/Qualifiers
REGION                   1..117
                         note = Synthetic polypeptide
source                   1..117
                         mol_type = protein
                         organism = synthetic construct
SEQUENCE: 30
QVQLQESGPG LVKPSETLSL TCTVSGFSLS IYSVHWIRQP PGKGLEWIGM IWGGGSSDYN   60
SALKSRLTIS KDTSKNQVSL KLSSVTAADT AVYYCARNGN FYAMDYWGQG TLVTVSS     117
```

```
SEQ ID NO: 31            moltype = AA  length = 117
FEATURE                  Location/Qualifiers
REGION                   1..117
                         note = Synthetic polypeptide
source                   1..117
                         mol_type = protein
                         organism = synthetic construct
SEQUENCE: 31
QVQLQESGPG LVKPSETLSL TCTVSGFSLS IYSVHWIRQP PGKGLEWLGM IWGGGSSDYN   60
SALKSRLTIS VDTSKNQVSL KLSSVTAADT AMYYCARNGN FYAMDYWGQG TLVTVSS     117
```

```
SEQ ID NO: 32            moltype = AA  length = 117
FEATURE                  Location/Qualifiers
REGION                   1..117
                         note = Synthetic polypeptide
source                   1..117
                         mol_type = protein
                         organism = synthetic construct
SEQUENCE: 32
QVQLQESGPG LVKPSETLSL TCTVSGFSLS IYSVHWIRQP PGKGLEWLGM IWGGGSSDYN   60
SALKSRLTIS KDTSKNQVSL KLSSVTAADT AMYYCARNGN FYAMDYWGQG TLVTVSS     117
```

```
SEQ ID NO: 33            moltype = AA  length = 110
FEATURE                  Location/Qualifiers
REGION                   1..110
                         note = Synthetic polypeptide
source                   1..110
                         mol_type = protein
                         organism = synthetic construct
SEQUENCE: 33
EIVLTQSPGT LSLSPGERAT LSCTASSSVS SSFLHWYQQK PGQAPRLLIY STSNLASGIP   60
DRFSGSGSGT DFTLTISRLE PEDFAVYYCH QYHHSPYIYT FGGGTKLEIK            110
```

-continued

```
SEQ ID NO: 34              moltype = AA  length = 110
FEATURE                    Location/Qualifiers
REGION                     1..110
                           note = Synthetic polypeptide
source                     1..110
                           mol_type = protein
                           organism = synthetic construct
SEQUENCE: 34
EIVLTQSPGT LSLSPGERAT LSCTASSSVS SSFLHWYQQK PGQAPQLWIY STSNLASGIP  60
DRFSGSGSGT DYTLTISRLE PEDFAVYYCH QYHHSPYIYT FGGGTKLEIK            110

SEQ ID NO: 35              moltype = AA  length = 110
FEATURE                    Location/Qualifiers
REGION                     1..110
                           note = Synthetic polypeptide
source                     1..110
                           mol_type = protein
                           organism = synthetic construct
SEQUENCE: 35
EIVLTQSPGT LSLSPGERAT LSCTASSSVS SSFLHWYQQK PGQAPQLWIY STSNLASGIP  60
DRFSGSGSGT DYTLTISRLE PEDFATYYCH QYHHSPYIYT FGGGTKLEIK            110

SEQ ID NO: 36              moltype = AA  length = 110
FEATURE                    Location/Qualifiers
REGION                     1..110
                           note = Synthetic polypeptide
source                     1..110
                           mol_type = protein
                           organism = synthetic construct
SEQUENCE: 36
EIVLTQSPGT LSLSPGERAT LSCTASSSVS SSFLHWYQQK PGQAPQLWIY STSNLASGIP  60
ARFSGSGSGT DYTLTISRLE PEDFATYYCH QYHHSPYIYT FGGGTKLEIK            110

SEQ ID NO: 37              moltype = AA  length = 117
FEATURE                    Location/Qualifiers
REGION                     1..117
                           note = Synthetic polypeptide
VARIANT                    48
                           note = Xaa is I or L
VARIANT                    67
                           note = Xaa can be any naturally occurring amino acid
VARIANT                    71
                           note = Xaa can be any naturally occurring amino acid
VARIANT                    78
                           note = Xaa can be any naturally occurring amino acid
VARIANT                    92
                           note = Xaa can be any naturally occurring amino acid
source                     1..117
                           mol_type = protein
                           organism = synthetic construct
SEQUENCE: 37
QVQLQESGPG LVKPSETLSL TCTVSGFSLS IYSVHWIRQP PGKGLEWXGM IWGGGSSDYN  60
SALKSRXTIS XDTSKNQXSL KLSSVTAADT AXYYCARNGN FYAMDYWGQG TLVTVSS    117

SEQ ID NO: 38              moltype = AA  length = 110
FEATURE                    Location/Qualifiers
REGION                     1..110
                           note = Synthetic polypeptide
VARIANT                    46
                           note = Xaa can be any naturally occurring amino acid
VARIANT                    48
                           note = Xaa can be any naturally occurring amino acid
VARIANT                    61
                           note = Xaa can be any naturally occurring amino acid
VARIANT                    72
                           note = Xaa can be any naturally occurring amino acid
VARIANT                    86
                           note = Xaa can be any naturally occurring amino acid
source                     1..110
                           mol_type = protein
                           organism = synthetic construct
SEQUENCE: 38
EIVLTQSPGT LSLSPGERAT LSCTASSSVS SSFLHWYQQK PGQAPXLXIY STSNLASGIP  60
XRFSGSGSGT DXTLTISRLE PEDFAXYYCH QYHHSPYIYT FGGGTKLEIK            110

SEQ ID NO: 39              moltype = AA  length = 10
FEATURE                    Location/Qualifiers
REGION                     1..10
```

-continued

```
                              note = Synthetic polypeptide
source                        1..10
                              mol_type = protein
                              organism = synthetic construct
SEQUENCE: 39
GFSLSIYSVH                                                              10

SEQ ID NO: 40                 moltype = AA  length = 16
FEATURE                       Location/Qualifiers
REGION                        1..16
                              note = Synthetic polypeptide
source                        1..16
                              mol_type = protein
                              organism = synthetic construct
SEQUENCE: 40
MIWGGGSSDY NSALKS                                                       16

SEQ ID NO: 41                 moltype = AA  length = 9
FEATURE                       Location/Qualifiers
REGION                        1..9
                              note = Synthetic polypeptide
source                        1..9
                              mol_type = protein
                              organism = synthetic construct
SEQUENCE: 41
NGNFYAMDY                                                               9

SEQ ID NO: 42                 moltype = AA  length = 12
FEATURE                       Location/Qualifiers
REGION                        1..12
                              note = Synthetic polypeptide
source                        1..12
                              mol_type = protein
                              organism = synthetic construct
SEQUENCE: 42
TASSSVSSSF LH                                                           12

SEQ ID NO: 43                 moltype = AA  length = 7
FEATURE                       Location/Qualifiers
REGION                        1..7
                              note = Synthetic polypeptide
source                        1..7
                              mol_type = protein
                              organism = synthetic construct
SEQUENCE: 43
STSNLAS                                                                 7

SEQ ID NO: 44                 moltype = AA  length = 25
FEATURE                       Location/Qualifiers
REGION                        1..25
                              note = Synthetic polypeptide
source                        1..25
                              mol_type = protein
                              organism = synthetic construct
SEQUENCE: 44
QVQLQESGPG LVKPSETLSL TCTVS                                             25

SEQ ID NO: 45                 moltype = AA  length = 14
FEATURE                       Location/Qualifiers
REGION                        1..14
                              note = Synthetic polypeptide
source                        1..14
                              mol_type = protein
                              organism = synthetic construct
SEQUENCE: 45
WIRQPPGKGL EWIG                                                         14

SEQ ID NO: 46                 moltype = AA  length = 14
FEATURE                       Location/Qualifiers
REGION                        1..14
                              note = Synthetic polypeptide
source                        1..14
                              mol_type = protein
                              organism = synthetic construct
SEQUENCE: 46
WIRQPPGKGL EWLG                                                         14

SEQ ID NO: 47                 moltype = AA  length = 32
FEATURE                       Location/Qualifiers
```

-continued

```
REGION                  1..32
                        note = Synthetic polypeptide
source                  1..32
                        mol_type = protein
                        organism = synthetic construct
SEQUENCE: 47
RLTISKDTSK NQVSLKLSSV TAADTAVYYC AR                                  32

SEQ ID NO: 48           moltype = AA  length = 32
FEATURE                 Location/Qualifiers
REGION                  1..32
                        note = Synthetic polypeptide
source                  1..32
                        mol_type = protein
                        organism = synthetic construct
SEQUENCE: 48
RLTISVDTSK NQVSLKLSSV TAADTAMYYC AR                                  32

SEQ ID NO: 49           moltype = AA  length = 32
FEATURE                 Location/Qualifiers
REGION                  1..32
                        note = Synthetic polypeptide
source                  1..32
                        mol_type = protein
                        organism = synthetic construct
SEQUENCE: 49
RLTISKDTSK NQVSLKLSSV TAADTAMYYC AR                                  32

SEQ ID NO: 50           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 50
WGQGTLVTVS S                                                         11

SEQ ID NO: 51           moltype = AA  length = 23
FEATURE                 Location/Qualifiers
REGION                  1..23
                        note = Synthetic polypeptide
source                  1..23
                        mol_type = protein
                        organism = synthetic construct
SEQUENCE: 51
EIVLTQSPGT LSLSPGERAT LSC                                            23

SEQ ID NO: 52           moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 52
WYQQKPGQAP RLLIY                                                     15

SEQ ID NO: 53           moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 53
WYQQKPGQAP QLWIY                                                     15

SEQ ID NO: 54           moltype = AA  length = 32
FEATURE                 Location/Qualifiers
REGION                  1..32
                        note = Synthetic polypeptide
source                  1..32
                        mol_type = protein
                        organism = synthetic construct
SEQUENCE: 54
GIPDRFSGSG SGTDFTLTIS RLEPEDFAVY YC                                  32

SEQ ID NO: 55           moltype = AA  length = 32
```

181                                                                                             182

```
FEATURE                 Location/Qualifiers
REGION                  1..32
                        note = Synthetic polypeptide
source                  1..32
                        mol_type = protein
                        organism = synthetic construct
SEQUENCE: 55
GIPDRFSGSG SGTDYTLTIS RLEPEDFAVY YC                                    32

SEQ ID NO: 56           moltype = AA  length = 32
FEATURE                 Location/Qualifiers
REGION                  1..32
                        note = Synthetic polypeptide
source                  1..32
                        mol_type = protein
                        organism = synthetic construct
SEQUENCE: 56
GIPDRFSGSG SGTDYTLTIS RLEPEDFATY YC                                    32

SEQ ID NO: 57           moltype = AA  length = 32
FEATURE                 Location/Qualifiers
REGION                  1..32
                        note = Synthetic polypeptide
source                  1..32
                        mol_type = protein
                        organism = synthetic construct
SEQUENCE: 57
GIPARFSGSG SGTDYTLTIS RLEPEDFATY YC                                    32

SEQ ID NO: 58           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 58
FGGGTKLEIK                                                             10

SEQ ID NO: 59           moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 59
YCVEVKYTAG VSPK                                                        14

SEQ ID NO: 60           moltype = AA  length = 14
FEATURE                 Location/Qualifiers
REGION                  1..14
                        note = Synthetic polypeptide
VARIANT                 8
                        note = Xaa can be any naturally occurring amino acid
source                  1..14
                        mol_type = protein
                        organism = synthetic construct
SEQUENCE: 60
YCVEVKYXAG VSPK                                                        14

SEQ ID NO: 61           moltype = DNA  length = 351
FEATURE                 Location/Qualifiers
misc_feature            1..351
                        note = Synthetic polynucleotide
source                  1..351
                        mol_type = other DNA
                        organism = synthetic construct
SEQUENCE: 61
caggtgcagc tgcaagagtc cggccctgga ctcgtgaagc cctccgagac actgtctctg    60
acctgtaccg tgtctggctt tagcctgtcc atctactccg tgcactggat ccggcagcct   120
cctggcaagg gcctggaatg gatcggcatg atctggggag gcggctctag cgactacaac   180
tccgccctga aatctagagt gaccatctcc gtggacacct ccaagaacca gttctccctg   240
aagctgagct ctgtgaccgc tgctgatacc gccgtgtact actgcgccag aaatggcaac   300
ttctacgcca tggactattg gggccagggc accctggtca cagtgtcctc t             351

SEQ ID NO: 62           moltype = DNA  length = 351
FEATURE                 Location/Qualifiers
misc_feature            1..351
```

-continued

```
                      note = Synthetic polynucleotide
source                1..351
                      mol_type = other DNA
                      organism = synthetic construct
SEQUENCE: 62
caggtgcagc tgcaagagtc cggccctgga ctcgtgaagc cctccgagac actgtctctg   60
acatgtaccg tgtctggctt ctccctgtcc atctactccg tgcactggat cagcagcct   120
cctggcaagg gcctggaatg gatcggcatg atctggggag gcggctcttc cgactacaac   180
tccgccctga aatctcggct gaccatctcc aaggacacct ctaagaacca ggtcagcctg   240
aagctgagct ctgtgaccgc tgctgatacc gccgtgtact actgcgccag aaatggcaac   300
ttctacgcca tggactattg gggccagggc accctggtga ccgtgtccag c             351

SEQ ID NO: 63          moltype = DNA  length = 351
FEATURE                Location/Qualifiers
misc_feature           1..351
                       note = Synthetic polynucleotide
source                 1..351
                       mol_type = other DNA
                       organism = synthetic construct
SEQUENCE: 63
caggtgcagc tgcaagagtc cggccctgga ctcgtgaagc cctccgagac actgtctctg   60
acctgtaccg tgtctggctt ctccctgtcc atctactccg tgcactggat ccggcagcct   120
cctggcaagg gcctggaatg gctgggcatg atctggggcg gaggctctag cgactacaac   180
tccgccctga aatctagact gaccatctcc gtggacacct ccaagaacca ggtcagcctg   240
aagctgagct ctgtgaccgc cgctgataca gctatgtact actgcgccag aaatggcaac   300
ttctacgcca tggactattg gggccagggc accctggtga ccgtgtcctc t             351

SEQ ID NO: 64          moltype = DNA  length = 351
FEATURE                Location/Qualifiers
misc_feature           1..351
                       note = Synthetic polynucleotide
source                 1..351
                       mol_type = other DNA
                       organism = synthetic construct
SEQUENCE: 64
caggtgcagc tgcaagagtc cggacccggc ctcgtgaagc cttccgagac actgtctctg   60
acctgtaccg tgtctggctt ctccctgtcc atctactccg tgcactggat ccggcagcct   120
cctggcaagg gcctggaatg gctgggcatg atctggggcg gcggaagctc cgactacaac   180
tccgccctga aatctagact gaccatctcc aaggacacct ctaagaacca ggtcagcctg   240
aagctgagct ctgtgaccgc cgctgatacc gctatgtact actgcgccag aaatggcaac   300
ttctacgcca tggactattg gggccagggc accctggtga cagtgtcctc t             351

SEQ ID NO: 65          moltype = DNA  length = 330
FEATURE                Location/Qualifiers
misc_feature           1..330
                       note = Synthetic polynucleotide
source                 1..330
                       mol_type = other DNA
                       organism = synthetic construct
SEQUENCE: 65
gagatcgtgc tgacccaatc tccaggcacc ctgtctctca gccctggcga gagagccacc   60
ctgtcctgca ccgcttctag ctccgtgtcc tccagcttcc tgcactggta ccagcagaaa   120
cccggccagg ctcctagact gctgatctat tccacctcca acctggcctc tggcatccct   180
gaccggttct ccggctctgg ctccggaaca gattttacac tgaccatctc ccggctggaa   240
cctgaggact tcgccgtgta ctactgtcac cagtaccacc attctcctta catctacacc   300
ttcggcggcg gaaccaagct ggaaatcaag                                     330

SEQ ID NO: 66          moltype = DNA  length = 330
FEATURE                Location/Qualifiers
misc_feature           1..330
                       note = Synthetic polynucleotide
source                 1..330
                       mol_type = other DNA
                       organism = synthetic construct
SEQUENCE: 66
gagatcgtgc tgacacaatc tcccggcacc ctcagcctgt ctccaggcga gagagccaca   60
ctgtcctgca ccgcttctag ctccgtgtcc tccagctttc tgcactggta ccagcagaaa   120
cctggccagg ctcctcagct gtggatctac tccacctcca acctggcctc tggcatccct   180
gatcggttct ccggctccgg ctctggcacc gactacacct gaccatctc cagactggaa   240
cctgaggact tcgccgtgta ctactgtcac cagtaccacc attctcctta catctatacc   300
ttcggcggag gaaccaagct ggaaatcaag                                     330

SEQ ID NO: 67          moltype = DNA  length = 330
FEATURE                Location/Qualifiers
misc_feature           1..330
                       note = Synthetic polynucleotide
source                 1..330
                       mol_type = other DNA
                       organism = synthetic construct
```

```
SEQUENCE: 67
gagatcgtgc tgacccagtc tccaggcaca ctcagcctgt ctcctggcga gcgggctacc   60
ctgtcctgca ccgccagcag ctccgtgtcc tcttcttttc tgcactggta ccagcagaaa  120
cctggacaag ctcctcagct gtggatctac tccacctcca acctggcctc tggcatcccc  180
gatagattct ccggctctgg ctccggcacc gactacacac tgaccatctc cagactggaa  240
cctgaggact tcgccaccta ctactgtcat cagtaccacc actcccctta catctatacc  300
ttcggcggag gcaccaagct ggaaatcaag                                   330

SEQ ID NO: 68           moltype = DNA   length = 330
FEATURE                 Location/Qualifiers
misc_feature            1..330
                        note = Synthetic polynucleotide
source                  1..330
                        mol_type = other DNA
                        organism = synthetic construct
SEQUENCE: 68
gagatcgtgc tgacccaatc tcctggcacc ctgtctctga gcccaggcga gagagccaca   60
ctctcctgca ccgcttcttc ctccgtgtcc tctagctttc tgcactggta ccagcagaaa  120
cccggccagg ctcctcagct gtggatctac tccacctcca acctggcctc tggcatccct  180
gccagattct ccggatccgg ctctggcacc gattatacac tgaccatctc ccggctggaa  240
cctgaggact tcgccaccta ctactgtcac cagtaccacc atagcccttac catctacacc  300
ttcggcggcg gaaccaagct ggaaatcaag                                   330

SEQ ID NO: 69           moltype = DNA   length = 351
FEATURE                 Location/Qualifiers
misc_feature            1..351
                        note = Synthetic polynucleotide
source                  1..351
                        mol_type = other DNA
                        organism = synthetic construct
SEQUENCE: 69
gaggtgcagc tgaagcaaag cggtccgggt ctggttgcgc cgagccaaag cctgagcatc   60
acctgcaccg tgagcggctt cagcctgagc atctacagcg tgcactgggt tcgtcagccg  120
ccgggcaagg gtctggaatg gctgggtatg atctggggtg gcggtagcag cgactataac  180
agcgcgctga gagccgtct gagcattagc aaggataaca gcaaaagcca ggtttttcctg  240
aaaatgaaca gcctgcaaac cgacgatacc gcgatgtact attgcgcgcg taacggcaac  300
ttttacgcga tggactattg gggccaaggt accagcgtga ccgttagcag c           351

SEQ ID NO: 70           moltype = DNA   length = 300
FEATURE                 Location/Qualifiers
misc_feature            1..300
                        note = Synthetic polynucleotide
source                  1..300
                        mol_type = other DNA
                        organism = synthetic construct
SEQUENCE: 70
cagatcgtgc tgacccaaag cccggttacc atgacctgca ccgcgagcag cagcgtgagc   60
agcagcttcc tgcactggta ccagcaaaag ccgggtagca gcccgcagct gtggatctat  120
agcaccagca acctgcgag cggtgttccg gcgcgtttta gcggtagcgg tagcggcacc  180
agctacagcc tgaccattag cagcatggag gcggaagacg cggcgaccta ctattgccac  240
caatatcacc acagcccgta catctatacc ttcggtggcg gtaccaagct ggagatcaag  300

SEQ ID NO: 71           moltype = DNA   length = 996
FEATURE                 Location/Qualifiers
misc_feature            1..996
                        note = Synthetic polynucleotide
source                  1..996
                        mol_type = other DNA
                        organism = synthetic construct
SEQUENCE: 71
gccagcacca agggcccttc cgtgttccca ctggcccct cctctaaatc cacatctggc   60
ggcaccgccg ccctgggctg tctggtgaag gactacttcc cagagcctgt gacagtgtcc  120
tggaactctg gcgccctgac atccggcgtg cacacatttc cagccgtgct gcagagctcc  180
ggcctgtaca gcctgtctag cgtggtgaca gtgccctcct ctagcctggg cacacagacc  240
tatatctgca acgtgaatca caagccaagc aataccaagg tggacaagaa ggtggagccc  300
aagtcctgtg ataagacaca cacctgcccc ccttgtcctg ctcccgagct gctgggcggc  360
cctagcgtgt tcctgtttcc acccaagcct aaggacaccc tgatgatctc ccggacaccc  420
gaggtgacct gcgtggtggt ggacgtgtct cacgaggatc ctgaggtgaa gttcaactgg  480
tatgtggatg gcgtggaggt gcacaatgcc aagaccaagc cagagagga gcagtacaac  540
tctacatata gggtggtgag cgtgctgacc gtgctgcacc aggactggct gaacggcaag  600
gagtataagt gcaaggtgtc caataaggcc ctgcccgccc ccatcgagaa gacaatcagc  660
aaggccaagg gccagcctcg ggagccacag gtgtacaccc tgcctccatc cagagacgag  720
ctgacaaaga accaggtgtc tctgacatgt ctggtgaagg gcttctatcc tagcgatatc  780
gccgtggagt gggagtccaa tggccagcca gagaacaatt acaagaccac acccccctg  840
ctggactccg atggctcctt ctttctgtat tccaagctga ccgtggataa gtctcggtgg  900
cagcagggca acgtgttcag ctgttccgtg atgcacgaag ccctgcataa tcactatact  960
cagaaatccc tgtccctgtc acctggaaag tgataa                            996

SEQ ID NO: 72           moltype = DNA   length = 327
```

```
FEATURE            Location/Qualifiers
misc_feature       1..327
                   note = Synthetic polynucleotide
source             1..327
                   mol_type = other DNA
                   organism = synthetic construct
SEQUENCE: 72
aggacagtgg ccgccccaag cgtgttcatc tttccccctt ccgacgagca gctgaagtct    60
ggcaccgcca gcgtggtgtg cctgctgaac aacttctacc ctcgggaggc caaggtccag   120
tggaaggtgg ataacgccct gcagtctggc aatagccagg agtccgtgac cgagcaggac   180
tctaaggata gcacatattc cctgtctagc accctgacac tgagcaaggc cgattacgag   240
aagcacaagg tgtatgcctg tgaagtcacc catcaggggc tgtcatcacc cgtcactaag   300
tcattcaatc gcggagaatg ctgataa                                       327

SEQ ID NO: 73     moltype = DNA   length = 1383
FEATURE            Location/Qualifiers
misc_feature       1..1383
                   note = Synthetic polynucleotide
source             1..1383
                   mol_type = other DNA
                   organism = synthetic construct
SEQUENCE: 73
atgggatgga gctggatctt tctctttctc ctgtcaggaa ctgcaggtgt cctctctgag    60
gtccagctgc aacaatcagg acctggcctg gtggcaccct cacagagcct gtccatcaca   120
tgcactgtct ctgggttctc attatccata tatagtgtac actgggttcg ccagcctcca   180
ggaaagggtc tggagtggct gggaatgata tggggtggtg gaagctcaga ctataattca   240
gctctcaaat ccagactgag catcagcaag gacaactcca agagccaagt tttcttaaaa   300
atgaacagtc tgcaaactga tgacacagcc atgtactact gtgccagaaa cggtaacttc   360
tatgctatgg actactgggg tcaaggaacc tcagtcaccg tctcctcagc caaaacgaca   420
cccccatctg tctatccact ggcccctgga tctgctgccc aaactaactc catggtgacc   480
ctgggatgcc tggtcaaggg ctatttccct gagccagtga cagtgacctg gaactctgga   540
tccctgtcca gcggtgtgca caccttccca gctgtcctgc agtctgacct ctacactctg   600
agcagctcag tgactgtccc ctccagcacc tggcccagcg agaccgtcac ctgcaacgtt   660
gcccacccgg ccagcagcac caaggtggac aagaaaattg tgcccaggga ttgtggttgt   720
aagccttgca tatgtacagt cccagaagta tcatctgtct tcatcttccc cccaaagccc   780
aaggatgtgc tcaccattac tctgactcct aaggtcacgt gtgttgtggt agacatcagc   840
aaggatgatc ccgaggtcca gttcagctgg tttgtagatg atgtggaggt gcacacagct   900
cagacgcaac ccgggagga gcagttcaac agcactttcc gctcagtcag tgaacttccc   960
atcatgcacc aggactggct caatggcaag gagttcaaat gcagggtcaa cagtgcagct  1020
ttccctgccc ccatcgagaa aaccatctcc aaaaccaaag gcagaccgaa ggctccacag  1080
gtgtacacca ttccacctcc caaggagcag atggccaagg ataaagtcag tctgacctgc  1140
atgataacag acttcttccc tgaagacatt actgtggagt ggcagtggaa tgggcagcca  1200
gcggagaact acaagaacac tcagcccatc atgaacacga atggctctta cttcgtctac  1260
agcaagctca atgtgcagaa gagcaactgg gaggcaggaa atactttcac ctgctctgtg  1320
ttacatgagg gcctgcacaa ccaccatact gagaagagcc tctcccactc tcctggtaaa  1380
tga                                                                1383

SEQ ID NO: 74     moltype = AA   length = 460
FEATURE            Location/Qualifiers
REGION             1..460
                   note = Synthetic polypeptide
source             1..460
                   mol_type = protein
                   organism = synthetic construct
SEQUENCE: 74
MGWSWIFLFL LSGTAGVLSE VQLQQSGPGL VAPSQSLSIT CTVSGFSLSI YSVHWVRQPP    60
GKGLEWLGMI WGGGSSDYNS ALKSRLSISK DNSKSQVFLK MNSLQTDDTA MYYCARNGNF   120
YAMDYWGQGT SVTVSSAKTT PPSVYPLAPG SAAQTNSMVT LGCLVKGYFP EPVTVTWNSG   180
SLSSGVHTFP AVLQSDLYTL SSSVTVPSST WPSETVTCNV AHPASSTKVD KKIVPRDCGC   240
KPCICTVPEV SSVFIFPPKP KDVLTITLTP KVTCVVVDIS KDDPEVQFSW FVDDVEVHTA   300
QTQPREEQFN STFRSVSELP IMHQDWLNGK EFKCRVNSAA FPAPIEKTIS KTKGRPKAPQ   360
VYTIPPPKEQ MAKDKVSLTC MITDFFPEDI TVEWQWNGQP AENYKNTQPI MNTNGSYFVY   420
SKLNVQKSNW EAGNTFTCSV LHEGLHNHHT EKSLSHSPGK                         460

SEQ ID NO: 75     moltype = DNA   length = 714
FEATURE            Location/Qualifiers
misc_feature       1..714
                   note = Synthetic polynucleotide
source             1..714
                   mol_type = other DNA
                   organism = synthetic construct
SEQUENCE: 75
atggattttc aggtgcagat tttcagcttc ctgctaatca gtgcctcagt cataatgtcc    60
agaggacaaa ttgttctcac ccagtctcca gcaatcatgt ctgcatctct aggggaacgg   120
gtcaccatga cctgcactgc cagctcaagt gtaagttcca gttacttgca ctggtaccag   180
cagaagccag atcctcccc caaactctgg atttatagca catccaacct ggcttctgga   240
gtcccagctc gcttcagtgg cagtgggtct gggacctctt actctctcac aatcagcagc   300
atggaggctg aagatgctgc cacttattac tgccaccagt atcatcgttt cccacacacg   360
ttcggagggg ggaccaagct ggaaataaaa cgggctgatg ctgcaccaac tgtatccatc   420
```

-continued

```
ttcccaccat ccagtgagca gttaacatct ggaggtgcct cagtcgtgtg cttcttgaac   480
aacttctacc ccaaagacat caatgtcaag tggaagattg atggcagtga acgacaaaat   540
ggcgtcctga acagttggac tgatcaggac agcaaagaca gcacctacag catgagcagc   600
accctcacgt tgaccaagga cgagtatgaa cgacataaca gctatacctg tgaggccact   660
cacaagacat caacttcacc cattgtcaag agcttcaaca ggaatgagtg ttag         714
```

```
SEQ ID NO: 76            moltype = AA  length = 237
FEATURE                  Location/Qualifiers
REGION                   1..237
                         note = Synthetic polypeptide
source                   1..237
                         mol_type = protein
                         organism = synthetic construct
SEQUENCE: 76
MDFQVQIFSF LLISASVIMS RGQIVLTQSP AIMSASLGER VTMTCTASSS VSSSYLHWYQ   60
QKPGSSPKLW IYSTSNLASG VPARFSGSGS GTSYSLTISS MEAEDAATYY CHQYHRFPHT  120
FGGGTKLEIK RADAAPTVSI FPPSSEQLTS GGASVVCFLN NFYPKDINVK WKIDGSERQN  180
GVLNSWTDQD SKDSTYSMSS TLTLTKDEYE RHNSYTCEAT HKTSTSPIVK SFNRNEC     237
```

```
SEQ ID NO: 77            moltype = AA  length = 51
FEATURE                  Location/Qualifiers
REGION                   1..51
                         note = Synthetic polypeptide
source                   1..51
                         mol_type = protein
                         organism = synthetic construct
SEQUENCE: 77
PASYTYTVYR DGTKIKEGLT ATTFEEDGVA AGNHEYCVEV KYTAGVSPKV C            51
```

```
SEQ ID NO: 78            moltype = AA  length = 51
FEATURE                  Location/Qualifiers
REGION                   1..51
                         note = Synthetic polypeptide
source                   1..51
                         mol_type = protein
                         organism = synthetic construct
SEQUENCE: 78
GSDYTYTVYR DGTKIKEGLT ATTFEEDGVA TGNHEYCVEV KYTAGVSPKV C            51
```

```
SEQ ID NO: 79            moltype = AA  length = 51
FEATURE                  Location/Qualifiers
REGION                   1..51
                         note = Synthetic polypeptide
source                   1..51
                         mol_type = protein
                         organism = synthetic construct
SEQUENCE: 79
PTDYTYTVYR DGTKIKEGLT ETTFEEDGVA TGNHEYCVEV KYTAGVSPKK C            51
```

```
SEQ ID NO: 80            moltype = AA  length = 51
FEATURE                  Location/Qualifiers
REGION                   1..51
                         note = Synthetic polypeptide
source                   1..51
                         mol_type = protein
                         organism = synthetic construct
SEQUENCE: 80
PTDYTYTVYR DGTKIKEGLT ETTFEEDGVA TGNHEYCVEV KYTAGVSPKE C            51
```

```
SEQ ID NO: 81            moltype = AA  length = 51
FEATURE                  Location/Qualifiers
REGION                   1..51
                         note = Synthetic polypeptide
source                   1..51
                         mol_type = protein
                         organism = synthetic construct
SEQUENCE: 81
PTDYTYTVYR DGTKIKEGLT ETTFEEDGVA TGNHEYCVEV KYTAGVSPKV C            51
```

```
SEQ ID NO: 82            moltype = AA  length = 51
FEATURE                  Location/Qualifiers
REGION                   1..51
                         note = Synthetic polypeptide
source                   1..51
                         mol_type = protein
                         organism = synthetic construct
SEQUENCE: 82
PTDYTYTVYR DGTKIKEGLT ETTFEEDGVA TGNHEYCVEV KYTAGVSPKV C            51
```

```
SEQ ID NO: 83            moltype = AA   length = 51
FEATURE                  Location/Qualifiers
REGION                   1..51
                         note = Synthetic polypeptide
source                   1..51
                         mol_type = protein
                         organism = synthetic construct
SEQUENCE: 83
APSYTYTIYR NNTQIASGVT ETTYRDPDLA TGFYTYGVKV VYPNGESAIE T          51

SEQ ID NO: 84            moltype = AA   length = 11
FEATURE                  Location/Qualifiers
REGION                   1..11
                         note = Synthetic polypeptide
VARIANT                  6
                         note = Xaa can be any naturally occurring amino acid
source                   1..11
                         mol_type = protein
                         organism = synthetic construct
SEQUENCE: 84
DVYTDXGDLY N                                                       11

SEQ ID NO: 85            moltype = AA   length = 11
FEATURE                  Location/Qualifiers
REGION                   1..11
                         note = Synthetic polypeptide
VARIANT                  5
                         note = Xaa can be any naturally occurring amino acid
VARIANT                  8
                         note = Xaa can be any naturally occurring amino acid
source                   1..11
                         mol_type = protein
                         organism = synthetic construct
SEQUENCE: 85
PQSVXIEXTV D                                                       11

SEQ ID NO: 86            moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 86
ANEAKVVLAA D                                                       11

SEQ ID NO: 87            moltype = AA   length = 711
FEATURE                  Location/Qualifiers
REGION                   1..711
                         note = Synthetic polypeptide
source                   1..711
                         mol_type = protein
                         organism = synthetic construct
SEQUENCE: 87
ANEAKVVLAA DNVWGDNTGY QFLLDADHNT FGSVIPATGP LFTGTASSNL YSANFEYLIP  60
ANADPVVTTQ NIIVTGQGEV VIPGGVYDYC ITNPEPASGK MWIAGDGGNQ PARYDDFTFE  120
AGKKYTFTMR RAGMGDGTDM EVEDDSPASY TYTVYRDGTK IKEGLTATTF EEDGVAAGNH  180
EYCVEVKYTA GVSPKVCKDV TVEGSNFEAP VQNLTGSAVG QKVTLKWDAP NGTPNPNPNP  240
NPGTTTLSES FENGIPASWK TIDADGDGHG WKPGNAPGIA GYNSNGCVYS ESFGLGGIGV  300
LTPDNYLITP ALDLPNGGKL TFWVCAQDAN YASEHYAVYA SSTGNDASFN TNALLEETIT  360
AKGVRSPEAI RGRIQGTWRQ KTVDLPAGTK YVAFRHFQST DMFYIDLDEV EIKANGKRAD  420
FTETFESSTH GEAPAEWTTI DADGDGQGWL CLSSGQLDWL TAHGGTNVVA SFSWNGMALN  480
PDNYLISKDV TGATKVKYYY AVNDGFPGDH YAVMISKTGT NAGDFTVVFE ETPNGINKGG  540
ARFGLSTEAD GAKPQSVWIE RTVDLPAGTK YVAFRHYNCS DLNYILLDDI QFTMGGSPTP  600
TDYTYTVYRD GTKIKEGLTE TTFEEDGVAT GNHEYCVEVK YTAGVSPKKC VNVTINPTQF  660
NPVKNLKAQP DGGDVVLKWE APSAKKAEGS REVKRIGDGL FVTIEPANDV R           711

SEQ ID NO: 88            moltype = AA   length = 11
FEATURE                  Location/Qualifiers
REGION                   1..11
                         note = Synthetic polypeptide
VARIANT                  6
                         note = Xaa can be any naturally occurring amino acid
source                   1..11
                         mol_type = protein
                         organism = synthetic construct
SEQUENCE: 88
DVYTDXGDLY N                                                       11
```

```
SEQ ID NO: 89          moltype = AA   length = 11
FEATURE                Location/Qualifiers
REGION                 1..11
                       note = Synthetic polypeptide
VARIANT                11
                       note = Xaa can be any naturally occurring amino acid
source                 1..11
                       mol_type = protein
                       organism = synthetic construct
SEQUENCE: 89
YTPVEEKQNG X                                                               11

SEQ ID NO: 90          moltype = AA   length = 553
FEATURE                Location/Qualifiers
REGION                 1..553
                       note = Synthetic polypeptide
source                 1..553
                       mol_type = protein
                       organism = synthetic construct
SEQUENCE: 90
ANEAKVVLAA DNVWGDNTGY QFLLDADHNT FGSVIPATGP LFTGTASSNL YSANFEYLIP  60
ANADPVVTTQ NIIVTGQGEV VIPGGVYDYC ITNPEPASGK MWIAGDGGNQ PARYDDFTFE  120
AGKKYTFTMR RAGMGDGTDM EVEDDSPASY TYTVYRDGTK IKEGLTATTF EEDGVAAGNH  180
EYCVEVKYTA GVSPKVCKDV TVEGSNEFAP VQNLTGSAVG QKVTLKWDAP NGTPNPNPNP  240
NPGTTTLSES FENGIPASWK TIDADGDGHG WKPGNAPGIA GYNSNGCVYS ESFGLGGIGV  300
LTPDNYLITP ALDLPNGGKL TFWVCAQDAN YASEHYAVYA SSTGNDASFN TNALLEETIT  360
AKGVRSPEAI RGRIQGTWRQ KTVDLPAGTK YVAFRHFQST DMFYIDLDEV EIKANGKRAD  420
FTETFESSTH GEAPAEWTTI DADGDGQGWL CLSSGQLDWL TAHGGTNVVA SFSWNGMALN  480
PDNYLISKDV TGATKVKYYY AVNDGFPGDH YAVMISKTGT NAGDFTVVFE ETPNGINKGG  540
ARFGLSTEAD GAK                                                     553

SEQ ID NO: 91          moltype = AA   length = 11
FEATURE                Location/Qualifiers
REGION                 1..11
                       note = Synthetic polypeptide
VARIANT                11
                       note = Xaa can be any naturally occurring amino acid
source                 1..11
                       mol_type = protein
                       organism = synthetic construct
SEQUENCE: 91
SGQAEIVLEA X                                                               11

SEQ ID NO: 92          moltype = AA   length = 417
FEATURE                Location/Qualifiers
REGION                 1..417
                       note = Synthetic polypeptide
source                 1..417
                       mol_type = protein
                       organism = synthetic construct
SEQUENCE: 92
SGQAEIVLEA HDVWNDGSGY QILLDADHDQ YGQVIPSDTH TLWPNCSVPA NLFAPFEYTV  60
PENADPSCSP TNMIMDGTAS VNIPAGTYDF AIAAPQANAK IWIAGQGPTK EDDYVFEAGK  120
KYHFLMKKMG SGDGTELTIS EGGGSDYTYT VYRDGTKIKE GLTATTFEED GVATGNHEYC  180
VEVKYTAGVS PKVCKDVTVE GSNFEAPVQN LTGSAVGQKV TLKWDAPNGT PNPNPNPNPN  240
PGTTTLSESF ENGIPASWKT IDADGDGHGW KPGNAPGIAG YNSNGCVYSE SFGLGGIGVL  300
TPDNYLITPA LDLPNGGKLT FWVCAQDANY ASEHYAVYAS STGNDASFNT NALLEETITA  360
KGVRSPEAIR GRIQGTWRQK TVDLPAGTKY VAFRHFQSTD MFYIDLDEVE IKANGKR     417

SEQ ID NO: 93          moltype = AA   length = 418
FEATURE                Location/Qualifiers
REGION                 1..418
                       note = Synthetic polypeptide
source                 1..418
                       mol_type = protein
                       organism = synthetic construct
SEQUENCE: 93
ANEAKVVLAA DNVWGDNTGY QFLLDADHNT FGSVIPATGP LFTGTASSNL YSANFEYLIP  60
ANADPVVTTQ NIIVTGQGEV VIPGGVYDYC ITNPEPASGK MWIAGDGGNQ PARYDDFTFE  120
AGKKYTFTMR RAGMGDGTDM EVEDDSPASY TYTVYRDGTK IKEGLTATTF EEDGVAAGNH  180
EYCVEVKYTA GVSPKVCKDV TVEGSNEFAP VQNLTGSAVG QKVTLKWDAP NGTPNPNPNP  240
NPGTTTLSES FENGIPASWK TIDADGDGHG WKPGNAPGIA GYNSNGCVYS ESFGLGGIGV  300
LTPDNYLITP ALDLPNGGKL TFWVCAQDAN YASEHYAVYA SSTGNDASFN TNALLEETIT  360
AKGVRSPEAI RGRIQGTWRQ KTVDLPAGTK YVAFRHFQST DMFYIDLDEV EIKANGKR    418

SEQ ID NO: 94          moltype = AA   length = 373
FEATURE                Location/Qualifiers
REGION                 1..373
                       note = Synthetic polypeptide
```

```
source                  1..373
                        mol_type = protein
                        organism = synthetic construct
SEQUENCE: 94
ANEAKVVLAA DNVWGDNTGY QFLLDADHNT FGSVIPATGP LFTGTASSNL YSANFEYLIP   60
ANADPVVTTQ NIIVTGQGEV VIPGGVYDYC ITNPEPASGK MWIAGDGGNQ PARYDDFTFE  120
AGKKYTFTMR RAGMGDGTDM EVEDDSPASY TYTVYRDGTK IKEGLTATTF EEDGVAAGNH  180
EYCVEVKYTA GVSPKVCKDV TVEGSNEFAP VQNLTGSAVG QKVTLKWDAP NGTPNPNPNP  240
NPGTTTLSES FENGIPASWK TIDADGDGHG WKPGNAPGIA GYNSNGCVYS ESFGLGGIGV  300
LTPDNYLITP ALDLPNGGKL TFWVCAQDAN YASEHYAVYA SSTGNDASFN TNALLEETIT  360
AKGVRSPEAI RGR                                                     373

SEQ ID NO: 95          moltype = AA  length = 373
FEATURE                Location/Qualifiers
REGION                 1..373
                       note = Synthetic polypeptide
source                 1..373
                       mol_type = protein
                       organism = synthetic construct
SEQUENCE: 95
ANEAKVVLAA DNVWGDNTGY QFLLDADHNT FGSVIPATGP LFTGTASSNL YSANFEYLIP   60
ANADPVVTTQ NIIVTGQGEV VIPGGVYDYC ITNPEPASGK MWIAGDGGNQ PARYDDFTFE  120
AGKKYTFTMR RAGMGDGTDM EVEDDSPASY TYTVYRDGTK IKEGLTATTF EEDGVAAGNH  180
EYCVEVKYTA GVSPKVCKDV TVEGSNEFAP VQNLTGSAVG QKVTLKWDAP NGTPNPNPNP  240
NPGTTTLSES FENGIPASWK TIDADGDGHG WKPGNAPGIA GYNSNGCVYS ESFGLGGIGV  300
LTPDNYLITP ALDLPNGGKL TFWVCAQDAN YASEHYAVYA SSTGNDASFN TNALLEETIT  360
AKGVRSPEAI RGR                                                     373

SEQ ID NO: 96          moltype = AA  length = 361
FEATURE                Location/Qualifiers
REGION                 1..361
                       note = Synthetic polypeptide
source                 1..361
                       mol_type = protein
                       organism = synthetic construct
SEQUENCE: 96
PQSVWIERTV DLPAGTKYVA FRHYNCSDLN YILLDDIQFT MGGSPTPTDY TYTVYRDGTK   60
IKEGLTETTF EEDGVATGNH EYCVEVKYTA GVSPKECVNV TINPTQFNPV KNLKAQPDGG  120
DVVLKWEAPS AKKTEGSREV KRIGDGLFVT IEPANDVRAN EAKVVLAADN VWGDNTGYQF  180
LLDADHNTFG SVIPATGPLF TGTASSNLYS ANFEYLIPAN ADPVVTTQNI IVTGQGEVVI  240
PGGVYDYCIT NPEPASGKMW IAGDGGNQPA RYDDFTFEAG KKYTFTMRRA GMGDGTDMEV  300
EDDSPASYTY TVYRDGTKIK EGLTETTYRD AGMSAQSHEY CVEVKYAAGV SPKVCVDYIP  360
D                                                                  361

SEQ ID NO: 97          moltype = AA  length = 361
FEATURE                Location/Qualifiers
REGION                 1..361
                       note = Synthetic polypeptide
source                 1..361
                       mol_type = protein
                       organism = synthetic construct
SEQUENCE: 97
PQSVWIERTV DLPAGTKYVA FRHYNCSDLN YILLDDIQFT MGGSPTPTDY TYTVYRDGTK   60
IKEGLTETTF EEDGVATGNH EYCVEVKYTA GVSPKKCVNV TINPTQFNPV KNLKAQPDGG  120
DVVLKWEAPS AKKAEGSREV KRIGDGLFVT IEPANDVRAN EAKVVLAADN VWGDNTGYQF  180
LLDADHNTFG SVIPATGPLF TGTASSNLYS ANFEYLIPAN ADPVVTTQNI IVTGQGEVVI  240
PGGVYDYCIT NPEPASGKMW IAGDGGNQPA RYDDFTFEAG KKYTFTMRRA GMGDGTDMEV  300
EDDSPASYTY TVYRDGTKIK EGLTETTYRD AGMSAQSHEY CVEVKYAAGV SPKVCVDYIP  360
D                                                                  361

SEQ ID NO: 98          moltype = AA  length = 11
FEATURE                Location/Qualifiers
REGION                 1..11
                       note = Synthetic polypeptide
VARIANT                7
                       note = Xaa can be any naturally occurring amino acid
VARIANT                11
                       note = Xaa can be any naturally occurring amino acid
source                 1..11
                       mol_type = protein
                       organism = synthetic construct
SEQUENCE: 98
LPAPYQXNDI X                                                        11

SEQ ID NO: 99          moltype = AA  length = 203
FEATURE                Location/Qualifiers
REGION                 1..203
                       note = Synthetic polypeptide
source                 1..203
```

```
                        mol_type = protein
                        organism = synthetic construct
SEQUENCE: 99
ANEAKVVLAA DNVWGDNTGY QFLLDADHNT FGSVIPATGP LFTGTASSNL YSANFEYLIP      60
ANADPVVTTQ NIIVTGQGEV VIPGGVYDYC ITNPEPASGK MWIAGDGGNQ PARYDDFTFE     120
AGKKYTFTMR RAGMGDGTDM EVEDDSPASY TYTVYRDGTK IKEGLTETTY RDAGMSAQSH     180
EYCVEVKYAA GVSPKVCVDY IPD                                            203

SEQ ID NO: 100         moltype = AA   length = 203
FEATURE                Location/Qualifiers
REGION                 1..203
                        note = Synthetic polypeptide
source                 1..203
                        mol_type = protein
                        organism = synthetic construct
SEQUENCE: 100
ANEAKVVLAA DNVWGDNTGY QFLLDADHNT FGSVIPATGP LFTGTASSNL YSANFEYLIP      60
ANADPVVTTQ NIIVTGQGEV VIPGGVYDYC ITNPEPASGK MWIAGDGGNQ PARYDDFTFE     120
AGKKYTFTMR RAGMGDGTDM EVEDDSPASY TYTVYRDGTK IKEGLTETTY RDAGMSAQSH     180
EYCVEVKYAA GVSPKVCVDY IPD                                            203

SEQ ID NO: 101         moltype = AA   length = 373
FEATURE                Location/Qualifiers
REGION                 1..373
                        note = Synthetic polypeptide
source                 1..373
                        mol_type = protein
                        organism = synthetic construct
SEQUENCE: 101
ANEAKVVLAA DNVWGDNTGY QFLLDADHNT FGSVIPATGP LFTGTASSNL YSANFEYLIP      60
ANADPVVTTQ NIIVTGQGEV VIPGGVYDYC ITNPEPASGK MWIAGDGGNQ PARYDDFTFE     120
AGKKYTFTMR RAGMGDGTDM EVEDDSPASY TYTVYRDGTK IKEGLTATTF EEDGVAAGNH     180
EYCVEVKYTA GVSPKVCKDV TVEGSNFEAP VQNLTGSAVG QKVTLKWDAP NGTPNPNPNP     240
NPGTTTLSES FENGIPASWK TIDADGDGHG WKPGNAPGIA GYNSNGCVYS ESFGLGGIGV     300
LTPDNYLITP ALDLPNGGKL TFWVCAQDAN YASEHYAVYA SSTGNDASFN TNALLEETIT     360
AKGVRSPEAI RGR                                                      373

SEQ ID NO: 102         moltype = AA   length = 10
FEATURE                Location/Qualifiers
REGION                 1..10
                        note = Synthetic polypeptide
source                 1..10
                        mol_type = protein
                        organism = synthetic construct
SEQUENCE: 102
ADFTETFESS                                                           10

SEQ ID NO: 103         moltype = AA   length = 135
FEATURE                Location/Qualifiers
REGION                 1..135
                        note = Synthetic polypeptide
source                 1..135
                        mol_type = protein
                        organism = synthetic construct
SEQUENCE: 103
ADFTETFESS THGEAPAEWT TIDADGDGQG WLCLSSGQLD WLTAHGGTNV VAFSSWNGMA      60
LNPDNYLISK DVTGATKVKY YYAVNDGFPG DHYAVMISKT GTNAGDFTVV FEETPNGINK     120
GGARFGLSTE ANGAK                                                     135

SEQ ID NO: 104         moltype = AA   length = 13
FEATURE                Location/Qualifiers
REGION                 1..13
                        note = Synthetic polypeptide
source                 1..13
                        mol_type = protein
                        organism = synthetic construct
SEQUENCE: 104
IQGTWYQKTV DLP                                                       13

SEQ ID NO: 105         moltype = AA   length = 45
FEATURE                Location/Qualifiers
REGION                 1..45
                        note = Synthetic polypeptide
source                 1..45
                        mol_type = protein
                        organism = synthetic construct
SEQUENCE: 105
IQGTWRQKTV DLPAGTKYVA FRHFQSTDMF YIDLDEVEIK ANGKR                    45
```

-continued

```
SEQ ID NO: 106          moltype = AA   length = 1586
FEATURE                 Location/Qualifiers
REGION                  1..1586
                        note = Synthetic polypeptide
source                  1..1586
                        mol_type = protein
                        organism = synthetic construct
SEQUENCE: 106
MRKLLLLIAA SLLGVGLYAQ NAKIKLDAPT TRTTCTNNSF KQFDASFSFN EVELTKVETK    60
GGTFASVSIP GAFPTGEVGS PEVPAVRKLI AVPVGATPVV RVKSFTEQVY SLNQYGSEKL   120
MPHQPSMSKS DDPEKVPFAY NAAAYARKGF VGQELTQVEM LGTMRGVRIA ALTINPVQYD   180
VVANQLKVRN NIEIEVSFQG ADEVATQRLY DASFSPYFET AYKQLFNRDV YTDHGDLYNT   240
PVRMLVVAGA KFKEALKPWL TWKAQKGFYL DVHYTDEAEV GTTNASIKAF IHKKYNDGLA   300
ASAAPVFLAL VGDTDVISGE KGKKTKKVTD LYYSAVDGDY FPEMYTRFMS ASSPEELTNI   360
IDKVLMYEKA TMPDKSYLEK ALLIAGADSY WNPKIGQQTI KYAVQYYYNQ DHGYTDVYSY   420
PKAPYTGCYS HLNTGVGFAN YTAHGSETSW ADPSVTATQV KALTNKNKYF LAIGNCCVTA   480
QFDYPQPCFG EVMTRVKEKG AYAYIGSSPN SYWGEDYYWS VGANAVFGVQ PTFEGTSMGS   540
YDATFLEDSY NTVNSIMWAG NLAATHAENI GNVTHIGAHY YWEAYHVLGD GSVMPYRAMP   600
KTNTYTLPAS LPQNQASYSI QASAGSYVAI SKDGVLYGTG VANASGVATV NMTKQITENG   660
NYDVVITRSN YLPVIKQIQA GEPSPYQPVS NLTATTQGQK VTLKWDAPSA KKAEGRSEVK   720
RIGDGLFVTI EPANDVRANE AKVVLAADNV WGDNTGYQFL LDADHNTFGS VIPATGPLFT   780
GTASSNLYSA NFEYLIPANA DPVVTTQNII VTGQGEVVIP GGVYDYCITN PEPASGKMWI   840
AGDGGNQPAR YDDFTFEAGK KYTFTMRRAG MGDGTDMEVE DDSPASYTYT VYRDGTKIKE   900
GLTATTFEED GVAAGNHEYC VEVKYTAGVS PKVCKDVTVE GSNEFAPVQN LTGSAVGQKV   960
TLKWDAPNGT PNPNPNPNPG TTTLSESFEN GIPASWKTID ADGDGHGWKP GNAPGIAGYN  1020
SNGCVYSESF GLGGIGLVTP DNYLITPALD LPNGGKLTFW VCAQDANYAS EHYAVYASST  1080
GNDASNFTNA LLEETITAKG RVSPEAIRGR IQGTWRQKTV DLPAGTKYVA FRHFQSTDMF  1140
YIDLDEVEIK ANGKRPQSVW IERTVDPAGT KYVAFRHYNC SDLNYILLDD IQFTMGGSPT  1200
PTDYTYTVYR DGTKIKEQLT ETTFEEDGVA TGNHEYCVEV KYTAGVSPKK CVNVTINPTQ  1260
FNPVKNLKAQ PDGGDVVLKW EAPSAKKAEG SREVKRIGDG LFVTIEPAND VRANEAKVVL  1320
AADNVWGDNT GYQFLLDADH NTFGSVIPAT GPLFTGTASS NLYSANFEYL IPANADPVVT  1380
TQNIIVTGQG EVVIPGGVYD YCITNPEPAS GKMWIAGDGG NQPARYDDFT FEAGKKYTFT  1440
MRRAGMGDGT DMEVEDDSPA STYTVYRDGT KIKEQLTETT YRDAGMSAGS HEYCVEVKYA  1500
AQVSPKVCVD YIPDGVADVT AQKPYTLTVV GKTITVTCQG EAMIYDMNGR RLAAGRNTVV  1560
YTAQGGYYAV MVVVDGKSYV EKLAVK                                       1586

SEQ ID NO: 107          moltype = AA   length = 1704
FEATURE                 Location/Qualifiers
REGION                  1..1704
                        note = Synthetic polypeptide
source                  1..1704
                        mol_type = protein
                        organism = synthetic construct
SEQUENCE: 107
MKNLNKFVSI ALCSSLLGGM AFAQQTELGR NPNVRLLEST QQSVTKVQFR MDNLKFTEVQ    60
TPKGIGQVPT YTEGVNLSEK GMPTLPILSR SLAVSDTREM KVEVVSSKFI EKKNVLIAPS   120
KGMIMRNEDP KKIPYVGKS YSQNKFFPGE IATLDDPFIL RDVRGQVVNF APLQYNPVTK   180
TLRIYTEITV AVSETSEQGK NILNKKGTFA GFEDTYKRMF MNYEPGRYTP VEEKQNGRMI   240
VIVAKKYEGD IKDFVDWKNQ RGLRTEVKVA EDIASPVTAN AIQQFVKQEY EKEGNDLTYV   300
LLVGDHKDIP AKITPGIKSD QVYGQIVGND HYNEVFIGRF SCESKEDLKT QIDRTIHYER   360
NITTEDKWLG QALCIASAEG GPSADNGESD IQHENVIANL LTQYGYTKII KCYDPGYTVK   420
NIIDAFNGGI SLVNYTGHGS ETAWGTSHFG TTHVKQLTNS NQLPFIFDVA CVNGDFLFSM   480
PCFAEALMRA QKDGKPTGTV AIIASTINQS WASPRMGQDE MNEILCEKHP NNIKRTFGGV   540
TMNGMFAMVE KYKKDGEKML DTWTVFGDPS LLVRTLVPTK MQVTAPAQIN LTDASVNVSC   600
DYNGAIATIS ANGKMFGSAV VENGTATINL TGLTNESTLT LTVVGYNKET VIKTINTNGE   660
PNPYQPVSNL TATTQGQKVT LKWDAPSTKT NATTNTARSV DGIRELVLLS VSDAPELLRS   720
GGAEIVLEAH DVWNDGSGYQ ILLDADHDQY QGVIPSDTHT LWPNCSVPAN LFAPFEYTVP   780
ENADPSCSPT NMIMDGTASV NIPAGTYDFA IAAPQANAKI WIAGQGPTKE DDYVFEAGKK   840
YHFLMKKMGS GDGTELTISE GGGSDYTYTV YRDGTKIKEQ LTATTFEEDG VATGNHEYCV   900
EVKYTAQVSP KVCKDVTVEG SNEFAPVQNL TGSAVGQKVT LKWDAPNGTP NPNPNPNPNP   960
GTTTLSESFE NGIPASWKTI DADGDGHGWK PGNAPGIAGY NSNGCVYSES FGLGGIGVLT  1020
PDNYLITPAL DLPNGGKLTF WVCAQDANYA SEHYAVYASS TGNDASNFTN ALLEETITAK  1080
GVRSPEAIRG RIQGTWRQKT VDLPAGTKYV AFRHFQSTDM FYIDLDEVEI KANGKRADFT  1140
ETFESSTHGE APAEWTTIDA DGDGQGWLCL SSGQLDWLTA HGGTNVVASF SWNGMALNPD  1200
NYLISKDVTG ATKVKYYYAV NDGFPGDHYA VMISKTGTNA GDFTVVFEET PNGINKGGAR  1260
FGLSTEANGA KPQSVWIERT VDLPAGTKYV AFRHYNCSDL NYILLDDIQF TMGGSPTPTD  1320
YTYTVYRDGT KIKEQLTETT FEEDGVATGN HEYCVEVKYT AQVSPKECVN VTINPTGFNP  1380
VKNLKAGPDG GDVVLKWEAP SAKKTEGSRE VKRIGDGLFV TIEPANDVRA NEAKVVLAAD  1440
NVWGDNTGYQ FLLDADHNTF GSVIPATGPL FTGTASSNLY SANFEYLIPA NADPVVTTQN  1500
IIVTGQGEVV IPGGVYDYCI TNPEPASGKM WIAGDGGNQP ARYDDFTFEA GKKYTFTMRR  1560
AGMGDGTDME VEDDSPASYT YTVYRDGTKI KEQLTETTYR DAGMSAGSHE YCVEVKYAAQ  1620
VSPKVCVDYI PDGVADVTAQ KPYTLTVVGK TITVTCQGEA MIYDMNGRRL AAGRNTVVYT  1680
AQGGYYAVMV VVDGKSYVEK LAVK                                        1704

SEQ ID NO: 108          moltype = AA   length = 78
FEATURE                 Location/Qualifiers
REGION                  1..78
                        note = Synthetic polypeptide
source                  1..78
```

-continued

```
                        mol_type = protein
                        organism = synthetic construct
SEQUENCE: 108
YTYTVYRDGT KIKEGLTATT FEEDGVAAGN HEYCVEVKYT AGVSPKVCKD VTVEGSNEFA   60
PVQNLTGSAV GQKVTLKW                                                 78

SEQ ID NO: 109         moltype = AA  length = 77
FEATURE                Location/Qualifiers
REGION                 1..77
                       note = Synthetic polypeptide
source                 1..77
                       mol_type = protein
                       organism = synthetic construct
SEQUENCE: 109
YTYTVYRDGT KIKEGLTETT FEEDGVATGN HEYCVEVKYT AGVSPKKCVN VTINPTQFNP   60
VKNLKAQPDG GDVVLKW                                                  77

SEQ ID NO: 110         moltype = AA  length = 54
FEATURE                Location/Qualifiers
REGION                 1..54
                       note = Synthetic polypeptide
source                 1..54
                       mol_type = protein
                       organism = synthetic construct
SEQUENCE: 110
YTYTVYRDGT KIKEGLTETT YRDAGMSAQS HEYCVEVKYA AGVSPKVCVD YIPD         54

SEQ ID NO: 111         moltype = AA  length = 78
FEATURE                Location/Qualifiers
REGION                 1..78
                       note = Synthetic polypeptide
source                 1..78
                       mol_type = protein
                       organism = synthetic construct
SEQUENCE: 111
YTYTVYRDGT KIKEGLTATT FEEDGVATGN HEYCVEVKYT AGVSPKVCKD VTVEGSNEFA   60
PVQNLTGSAV GQKVTLKW                                                 78

SEQ ID NO: 112         moltype = AA  length = 77
FEATURE                Location/Qualifiers
REGION                 1..77
                       note = Synthetic polypeptide
source                 1..77
                       mol_type = protein
                       organism = synthetic construct
SEQUENCE: 112
YTYTVYRDGT KIKEGLTETT FEEDGVATGN HEYCVEVKYT AGVSPKECVN VTINPTQFNP   60
VKNLKAQPDG GDVVLKW                                                  77

SEQ ID NO: 113         moltype = AA  length = 78
FEATURE                Location/Qualifiers
REGION                 1..78
                       note = Synthetic polypeptide
source                 1..78
                       mol_type = protein
                       organism = synthetic construct
SEQUENCE: 113
YTYTVYRDGT KIQEGLTATT FEEDGVAAGN HEYCVEVKYT AGVSPKVCKD VTVEGSNEFA   60
PVQNLTGSAV GQKVTLKW                                                 78

SEQ ID NO: 114         moltype = AA  length = 77
FEATURE                Location/Qualifiers
REGION                 1..77
                       note = Synthetic polypeptide
source                 1..77
                       mol_type = protein
                       organism = synthetic construct
SEQUENCE: 114
YTYTVYRDGT KIKEGLTETT FEEDGVATGN HEYCVEVKYT AGVSPKVCVN VTINPTQFNP   60
VKNLKAQPDG GDVVLKW                                                  77

SEQ ID NO: 115         moltype = AA  length = 55
FEATURE                Location/Qualifiers
REGION                 1..55
                       note = Synthetic polypeptide
source                 1..55
                       mol_type = protein
                       organism = synthetic construct
SEQUENCE: 115
```

-continued

```
YTYTVYRDGT KIQEGLTETT YRDAGMSAQS HEYCVEVKYA AGVSPKVCVD YIPDG          55

SEQ ID NO: 116            moltype = AA   length = 53
FEATURE                   Location/Qualifiers
REGION                    1..53
                          note = Synthetic polypeptide
source                    1..53
                          mol_type = protein
                          organism = synthetic construct
SEQUENCE: 116
YTYTIYRNNT QIASGVTETT YRDPDLATGF YTYGVKVVYP NGESAIETAT LNI            53

SEQ ID NO: 117            moltype = AA   length = 55
FEATURE                   Location/Qualifiers
REGION                    1..55
                          note = Synthetic polypeptide
source                    1..55
                          mol_type = protein
                          organism = synthetic construct
SEQUENCE: 117
YTYTVYRDGT KIKEGLTETT YRDAGMSAQS HEYCVEVKYA AGVSPKVCVD YIPDG          55

SEQ ID NO: 118            moltype = AA   length = 77
FEATURE                   Location/Qualifiers
REGION                    1..77
                          note = Synthetic polypeptide
source                    1..77
                          mol_type = protein
                          organism = synthetic construct
SEQUENCE: 118
YTYTVYRDGT KIKEGLTETT FEEDGVATGN HEYCVEVKYT AGVSPKKCVN VTVNSTQFNP    60
VKNLKAQPDG GDVVLKW                                                   77

SEQ ID NO: 119            moltype = AA   length = 54
FEATURE                   Location/Qualifiers
REGION                    1..54
                          note = Synthetic polypeptide
source                    1..54
                          mol_type = protein
                          organism = synthetic construct
SEQUENCE: 119
YTYTVYRDGT KIKEGLTETT YRDAGMSAQS HEYCVEVKYT AGVSPKVCVD YIPD          54

SEQ ID NO: 120            moltype = AA   length = 54
FEATURE                   Location/Qualifiers
REGION                    1..54
                          note = Synthetic polypeptide
source                    1..54
                          mol_type = protein
                          organism = synthetic construct
SEQUENCE: 120
YTYTVYRDGT KIKEGLTETT YRDAGMSAQS HEYCVEVKYA AGVSPKVCVD YIPD          54

SEQ ID NO: 121            moltype = AA   length = 54
FEATURE                   Location/Qualifiers
REGION                    1..54
                          note = Synthetic polypeptide
source                    1..54
                          mol_type = protein
                          organism = synthetic construct
SEQUENCE: 121
YTYTVYRDNV VIAQNLTATT FNQENVAPGQ YNYCVEVKYT AGVSPKVCKD VTVE          54

SEQ ID NO: 122            moltype = AA   length = 54
FEATURE                   Location/Qualifiers
REGION                    1..54
                          note = Synthetic polypeptide
source                    1..54
                          mol_type = protein
                          organism = synthetic construct
SEQUENCE: 122
YTYTVYRDGT KIKEGLTETT FEEDGVATGN HEYCVEVKYT AGVSPKECVN VTVD          54

SEQ ID NO: 123            moltype = AA   length = 54
FEATURE                   Location/Qualifiers
REGION                    1..54
                          note = Synthetic polypeptide
source                    1..54
                          mol_type = protein
```

```
                              organism = synthetic construct
SEQUENCE: 123
YTYTVYRDGT KIKEGLTETT FEEDGVATGN HEYCVEVKYT AGVSPKECVN VTIN          54

SEQ ID NO: 124              moltype = AA  length = 54
FEATURE                    Location/Qualifiers
REGION                     1..54
                           note = Synthetic polypeptide
source                     1..54
                           mol_type = protein
                           organism = synthetic construct
SEQUENCE: 124
YTYTIYRNNT QIASGVTETT YRDPDLATGF YTYGVKVVYP NGESAIETAT LNIT          54

SEQ ID NO: 125              moltype = AA  length = 2618
FEATURE                    Location/Qualifiers
REGION                     1..2618
                           note = Synthetic polypeptide
source                     1..2618
                           mol_type = protein
                           organism = synthetic construct
SEQUENCE: 125
MRKLNSLFSL AVLLSLLCWG QTAAAQGGPK TAPSVTHQAV QKGIRTSKVK DLRDPIPAGM    60
ARIILEAHDV WEDGTGYQML WDADHNQYGA SIPEESFWFA NGTIPAGLYD PFEYKVPVNA    120
DASFSPTNFV LDGTASADIP AGTYDYVIIN PNPGIIYIVG EGVSKGNDYV VEAGKTYHFT    180
VQRQGPGDAA SWVTGEGGNE FAPVQNLQWS VSGQTVTLTW QAPASDKRTY VLNESFDTQT    240
LPNGWTMIDA DGDGHNWLST INVYNTATHT GDGAFMSKSW TASGGAKIDL SPDNYLVTPK    300
VTVPENGKLS YWVSSQVPWT NEHYGVFLST TGNEAANFTI KLLEETLGSD KPAPMNLVKS    360
EGVKLPAPYQ ERTIDLSAYA GQQVYLAFRH FNSTGIFRLY LDDVAVSGEG SSNDYTYTVY    420
RDNWIAQNLA ATTFNQENVA PGQYNYCVEV KYTAGVSPKV CKDVTVEGSN EFAPVQNLTG    480
SAVGQKVTLK WDAPNGTPNP NPGTTTLSEF SENGIPASWK TIDADGDGNN WTTTPPPGGT    540
SFAGHNSAIC ASSASYINFE GPQNPDNYLV TPELSLPNGG TLTFWVCAQD ANYASEHYAV    600
YASSTGNDAS NFANALLEEV LTAKTVVTAP EAIRGTRVQG TWYQKTVQLP AGTKYVFARH    660
FGCTDFFWIN LDDVEIKANG KRADFTETFE SSTHGEAPAE WTTIDADGDG QGWLCLSSGQ    720
LGWLTAHGGT NVVASFSWNG MALNPDNYLI SKDVTGATKV KYYYAVNDGF PGDHYAVMIS    780
KTGTNAGDFT VVFEETPNGI NKGGARFGLS TEADGAKPQS VWIERTVDLP AGTKYVAFRH    840
YNCSDLNYIL LDDIQFTMGG SPTPTDYTYT VYRDGTKIKE GLTETFTEED GVATGNHEYC    900
VEVKYTAGVS PKECVNVTVD PVQFNPVQNL TGSAVGQKVT LKWDAPNGTP NPNPNPNPGT    960
TTLSESFENG IPASWKTIDA DGDGNNWTTT PPPGGTSFAG HNSAICASSA SYINFEGPQN    1020
PDNYLVTPEL SLPNGGTLTF WVCAQDANYA SEHYAVYASS TGNDASNFAN ALLEEVLTAK    1080
TVVTAPEAIR GTRVQGTWYQ KTVQLPAGTK YVFARHFGCT DFFWINLDDV EIKANGKRAD    1140
FTETFESSTH GEAPAEWTTI DADGDGQGWL CLSSGQLGWL TAHGGTNVVA FSSWNGMALN    1200
PDNYLISKDV TGATKVKYYY AVNDGFPGDH YAVMISKTGT NAGDFTWEET PNGINKGGAR    1260
FGLSTEADGA KPQSVWIERT VDLPAGTKYV AFRHYNCSDL NYILLDDIQF TMGGSPTPTD    1320
YTYTVYRDGT KIKEGLTETF TEEDGVATGN HEYCVEVKYT AGVSPKECVN VTVDPVFQNP    1380
VQNLTGSAVG QKVTLKWDAP NGTPNPNPNP NPGTTTLSES FENGIPASWK TIDADGDGNN    1440
WTTTPPPGGT SFAGHNSAIC VSSASYINFE GPQNPDNYLV TPELSLPNGG TLTFWVCAQD    1500
ANYASEHYAV YASSTGNDAS NFANALLEEV LTAKTVVTAP EAIRGTRVQG TWYQKTVQLP    1560
AGTKYVAFRH FGCTDFFWIN LDDVEIKANG KRADFTETFE SSTHGEAPAE WTTIDADGDG    1620
QGWLCLSSGQ LGWLTAHGGT NVVASFSWNG MALNPDNYLI SKDVTGATKV KYYYAVNDGF    1680
PGDHYAVMIS KTGTNAGDFT WFEETPNGIN KGGARFGLST EADGAKPQSV WIERTVDLPA    1740
GTKYVAFRHY NCSDLNYILL DDIQFTMGGS PTPTDYTYTV YRDGTKIKEG LTETTFEEDG    1800
VATGNHEYCV EVKYTAGVSP KECVNVTVDP VFQNPVQNLT GSAVGQKVTL KWDAPNGTPN    1860
PNPNPNPGTT TLSESFENGI PASWKTIDAD GDGNNWTTTP PPGGTSFAGH NSAICVSSAS    1920
YINFEGPQNP DNYLVTPELS LPGGGTLTFW VCAQDANYAS EHYAVYASST GNDASNFANA    1980
LLEEVLTAKT WTAPEAIRGT RVQGTWYQKT VQLPAGTKYV AFRHFGCTDF FWINLDEVEI    2040
KANGKRADFT ETFESSTHGE APAEWTTIDA DGDGQGWLCL SSGQLDWLTA HGGTNVVASF    2100
SWNGMALNPD NYLISKDVTG ATKVKYYYAV NDGFPGDHYA VMISKTGTNA GDFTWFEETP    2160
NGINKGGARF GLSTEADGAK PQSVWIERTV DLPAGTKYVA FRHYNCSDLN YILLDDIQFT    2220
MGGSPTPTDY TYTVYRDGTK IKEGLTETTF EEDGVATGNH EYCVEVKYTA GVSPKVCNVV    2280
ITNPTQFNPV QNLTAEQAPN SMDAILKWNA PASKRAEVLN EDFENGIPSS WKTIDADGDG    2340
NNWTTTPPPG GSSFAGHNSA ICVSSASYIN FEGPQNPDNY LVTPELSLPG GGTLTFWVCA    2400
QDANYASEHY AVYASSTGND ASNFANALLE EVLTAKTVVT APEAIRGTRV QGTWYQKTVQ    2460
LPAGTKYVAF RHFGCTDFFW INLDDVVITS GNAPSYTYTI YRNNTQIASG VTETTYRDPD    2520
LATGFYTYGV KWPNGESAIE TATLNITSLA DVTAQKPYTL TWGKTITVTC QGEAMIYDMN    2580
GRRLAAGRNT VVYTAQGGHY AVMVVVDGKS YVEKLAVK                           2618

SEQ ID NO: 126              moltype = AA  length = 54
FEATURE                    Location/Qualifiers
REGION                     1..54
                           note = Synthetic polypeptide
source                     1..54
                           mol_type = protein
                           organism = synthetic construct
SEQUENCE: 126
YTYTVYRDNV VIAQNLAATT FNQENVAPGQ YNYCVEVKYT AGVSPKVCKD VTVE          54

SEQ ID NO: 127              moltype = AA  length = 54
FEATURE                    Location/Qualifiers
```

-continued

```
REGION                  1..54
                        note = Synthetic polypeptide
source                  1..54
                        mol_type = protein
                        organism = synthetic construct
SEQUENCE: 127
YTYTVYRDGT KIKEGLTETT FEEDGVATGN HEYCVEVKYT AGVSPKVCVN VTIN          54

SEQ ID NO: 128          moltype = AA  length = 55
FEATURE                 Location/Qualifiers
REGION                  1..55
                        note = Synthetic polypeptide
source                  1..55
                        mol_type = protein
                        organism = synthetic construct
SEQUENCE: 128
YTYTVYRDGT KIQEGLTATT FEEDGVAAGN HEYCVEVKYT AGVSPKVCKD VTVEG         55

SEQ ID NO: 129          moltype = AA  length = 55
FEATURE                 Location/Qualifiers
REGION                  1..55
                        note = Synthetic polypeptide
source                  1..55
                        mol_type = protein
                        organism = synthetic construct
SEQUENCE: 129
YTYTVYRDGT KIKEGLTETT FEEDGVATGN HEYCVEVKYT AGVSPKVCVN VTINP        55

SEQ ID NO: 130          moltype = AA  length = 55
FEATURE                 Location/Qualifiers
REGION                  1..55
                        note = Synthetic polypeptide
source                  1..55
                        mol_type = protein
                        organism = synthetic construct
SEQUENCE: 130
YTYTVYRDGT KIKEGLTATT FEEDGVAAGN HEYCVEVKYT AGVSPKVCKD VTVEG         55

SEQ ID NO: 131          moltype = AA  length = 55
FEATURE                 Location/Qualifiers
REGION                  1..55
                        note = Synthetic polypeptide
source                  1..55
                        mol_type = protein
                        organism = synthetic construct
SEQUENCE: 131
YTYTVYRDGT KIKEGLTETT FEEDGVATGN HEYCVEVKYT AGVSPKKCVN VTINP        55

SEQ ID NO: 132          moltype = AA  length = 55
FEATURE                 Location/Qualifiers
REGION                  1..55
                        note = Synthetic polypeptide
source                  1..55
                        mol_type = protein
                        organism = synthetic construct
SEQUENCE: 132
YTYTVYRDGT KIKEGLTATT FEEDGVATGN HEYCVEVKYT AGVSPKVCKD VTVEG         55

SEQ ID NO: 133          moltype = AA  length = 55
FEATURE                 Location/Qualifiers
REGION                  1..55
                        note = Synthetic polypeptide
source                  1..55
                        mol_type = protein
                        organism = synthetic construct
SEQUENCE: 133
YTYTVYRDGT KIKEGLTETT FEEDGVATGN HEYCVEVKYT AGVSPKECVN VTINP        55

SEQ ID NO: 134          moltype = AA  length = 55
FEATURE                 Location/Qualifiers
REGION                  1..55
                        note = Synthetic polypeptide
source                  1..55
                        mol_type = protein
                        organism = synthetic construct
SEQUENCE: 134
YTYTVYRDGT KIKEGLTETT FEEDGVATGN HEYCVEVKYT AGVSPKKCVN VTVNS        55

SEQ ID NO: 135          moltype = AA  length = 223
```

-continued

```
FEATURE              Location/Qualifiers
REGION               1..223
                     note = Synthetic polypeptide
source               1..223
                     mol_type = protein
                     organism = synthetic construct
SEQUENCE: 135
QVQLQESGPG LVAPSQSLSI TCTVSGFSLT GYGVNWVRQP PGKGLEWLGM IWGDGNTDYN    60
SALKSRLSIS KDNSKSQVFL KMNSLHTDDT ARYYCARERD YRLDYWGQGT TLTVSSDIQL   120
TQSPSSLSAS LGDRVTISCR ASQDISNYLN WYQQKPDGTV KLLIYYTSRL HSGVPSRFSG   180
SGSGTDYSLT ISNLEQEDIA TYFCQQGNTL PWTFGGGTKL EIK                     223

SEQ ID NO: 136       moltype = AA  length = 330
FEATURE              Location/Qualifiers
REGION               1..330
                     note = Synthetic polypeptide
source               1..330
                     mol_type = protein
                     organism = synthetic construct
SEQUENCE: 136
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 137       moltype = AA  length = 107
FEATURE              Location/Qualifiers
REGION               1..107
                     note = Synthetic polypeptide
source               1..107
                     mol_type = protein
                     organism = synthetic construct
SEQUENCE: 137
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 138       moltype = AA  length = 458
FEATURE              Location/Qualifiers
REGION               1..458
                     note = Synthetic polypeptide
source               1..458
                     mol_type = protein
                     organism = synthetic construct
SEQUENCE: 138
RADFTETFES STHGEAPAEW TTIDADGDGQ GWLCLSSGQL GWLTAHGGTN VVASFSWNGM    60
ALNPDNYLIS KDVTGATKVK YYYAVNDGFP FDHYAVMISM TGTNAGDFTV VFEETPNGIN   120
KGGARFGLST EADGAKPQSV WIERTVFLPA GTKYVAFRHY NCSDLNYILL DDIWFTMGGS   180
PTPTDYTYTV YRDGTKIKEG LTETTFEEDG VATGNHEYCV EVKYTAGVSP KECVNVTVDP   240
VQFNPWQNLT GSAVGQKVTL KWDAPNGTPN PNPNPNPGTT TLSESFENGI PASWKTIDAD   300
GDGNNWTTTP PPGGTSFAGH NSAICASSAS YINFEGPQNP DNYLVTPELS LPNGGTLTFW   360
VCAQDANYAS EHYAVYASST GNDASNFANA LLEEVLTAKT VVTAPEAIRG TRVQGTWYQK   420
TVQLPAGTKY VAFRHFGCTD FFWINLDDVE IKANGKRA                           458

SEQ ID NO: 139       moltype = AA  length = 458
FEATURE              Location/Qualifiers
REGION               1..458
                     note = Synthetic polypeptide
source               1..458
                     mol_type = protein
                     organism = synthetic construct
SEQUENCE: 139
RADFTETFES STHGEAPAEW TTIDADGDGQ GWLCLSSGQL GWLTAHGGTN VVASFSWNGM    60
ALNPDNYLIS KDVTGATKVK YYYAVNDGFP FDHYAVMISM TGTNAGDFTV VFEETPNGIN   120
KGGARFGLST EADGAKPQSV WIERTVFLPA GTKYVAFRHY NCSDLNYILL DDIWFTMGGS   180
PTPTDYTYTV YRDGTKIKEG LTETTFEEDG VATGNHEYCV EVKYTAGVSP KECVNVTVDP   240
VQFNPWQNLT GSAVGQKVTL KWDAPNGTPN PNPNPNPGTT TLSESFENGI PASWKTIDAD   300
GDGNNWTTTP PPGGTSFAGH NSAICASSAS YINFEGPQNP DNYLVTPELS LPNGGTLTFW   360
VCAQDANYAS EHYAVYASST GNDASNFANA LLEEVLTAKT VVTAPEAIRG TRVQGTWYQK   420
TVQLPAGTKY VAFRHFGCTD FFWINLDDVE IKANGKRA                           458

SEQ ID NO: 140       moltype = AA  length = 456
FEATURE              Location/Qualifiers
REGION               1..456
                     note = Synthetic polypeptide
source               1..456
                     mol_type = protein
                     organism = synthetic construct
```

```
SEQUENCE: 140
RADFTETFES STHGEAPAEW TTIDADGDGQ GWLCLSSGQL GWLTAHGGTN VVASFSWNGM   60
ALNPDNYLIS KDVTGATKVK YYYAVNDGFP GDHYAVMISK TGTNAGDFTV VFEETPNGIN  120
KGGARFGLST EADGAKPQSV WIERTVDLPA GTKYVAFRHY NCSDLNYILL DDIQFTMGGS  180
PTPTDYTYTV YRDGTKKIKE GLTETTFEED GVATGNHEYC VEVKYTAGVS PKECVNVTVD  240
PVQFNPWQNL TGSAVGQKKV TLKWDAPNGT PNPNPNPNPG TTTLSASFEN GIPASWKTID  300
ADGDGNNQTT TPPPGGTSFA GHNSAICSSA SYINFEGPQN PDNYLCTPEL SPGGGTLTFW  360
VCAQDANYAS EHYAVYASST GNDASNFANA LEEVLTAKTV VTAPEAIRGT RVQGTWYQKT  420
VQLPAGTKYV AFRHFGCTDF FWINLDEVEI KANKRA                           456

SEQ ID NO: 141        moltype = AA  length = 508
FEATURE               Location/Qualifiers
REGION                1..508
                      note = Synthetic polypeptide
source                1..508
                      mol_type = protein
                      organism = synthetic construct
SEQUENCE: 141
RADFTETFES STHGEAPAEW TTIDADGDGD QGWLCLSSGQ LDWLTAHGGT NVVASFSWNG   60
MALNPADNYL ISKDVTGATK VKYYYAVNDG PFGDHYAVMI SKTGTNAGDF TVVFEETPNG  120
INKGGARFGL STEADGAKPQ SVWIERTVDL PAGTKYVAFR HYNCSDLNYI LLDDIQFTMG  180
GSPTPTDYTY TVYRDGTKIK EGLTETTFEE DGVATGNHEY GVEVKYTAGV SPKVCVNVTI  240
NPTQFNPWQN LTAEQAPNSM DAILKWNAPA SKRAEVLNED FENGIPSSWK TIDADGDGNN  300
WTTTPPPGGS SFAGHNSAIC VSSASYINFE GPQNPDNYLV TPELSLPGGG TLTFWVCAQD  360
ANYASEHYAV YASSTGNDAS NFANALLEEV LTAKTVVTAP EAIRGTRVQG TWYQKTVQLP  420
AGTKYVAFRH FGCTDFFWIN LDDVVITSGN APSYTYTIYR NNTQIASGVT ETTYRDPDLA  480
TGFYTYGVKV VYPNGESAIE TATLNITS                                    508

SEQ ID NO: 142        moltype = AA  length = 452
FEATURE               Location/Qualifiers
REGION                1..452
                      note = Synthetic polypeptide
source                1..452
                      mol_type = protein
                      organism = synthetic construct
SEQUENCE: 142
ADFTETFESS THGEAPAEWT TIDADGDGQG WLCLSSGQLG WLTAHGGTNV VASFSWNGMA   60
LNPDNYLISK DVTGATKVKY YYAVNDGFPG DHYAVMISKT GTNAGDFTVV FEETPNGINK  120
GGARFGLSTE ANGAKPQSVW IERTVDLPAG TKYVAFRHYN CSDLNYILLD DIQFTMGGSP  180
TPTDYTYTVY RDGTKIKEGL TETTFEEDGV ATGNHEYCVE VKYTAGVSPK ECVNVTVDPV  240
QFNPVQNLTG SAVGQKVTLK WDAPNGTPNP NPGTTTLSES FENGIPASWK TIDADGDGNN  300
WTTTPPPGGT SFAGHNSAIC VSSASYINFE GPQNPDNYLV TPELSLPNGG TLTFWVCAQD  360
ANYASEHYAV YASSTGNDAS NFANALLEEV LTAKTVVTAP EAIRGTRVQG TWYQKTVQLP  420
AGTKYVAFRH FGCTDFFWIN LDDVEIKANG KR                               452

SEQ ID NO: 143        moltype = AA  length = 452
FEATURE               Location/Qualifiers
REGION                1..452
                      note = Synthetic polypeptide
source                1..452
                      mol_type = protein
                      organism = synthetic construct
SEQUENCE: 143
ADFTETFESS THGEAPAEWT TIDADGDGQG WLCLSSGQLD WLTAHGGTNV VASFSWNGMA   60
LNPDNYLISK DVTGATKVKY YYAVNDGFPG DHYAVMISKT GTNAGDFTVV FEETPNGINK  120
GGARFGLSTE ANGAKPQSVW IERTVDLPAG TKYVAFRHYN CSDLNYILLD DIQFTMGGSP  180
TPTDYTYTVY RDGTKIKEGL TETTFEEDGV ATGNHEYCVE VKYTAGVSPK ECVNVTVDPV  240
QFNPVQNLTG SAVGQKVTLK WDAPNGTPNP NPGTTTLSES FENGIPASWK TIDADGDGNN  300
WTTTPPPGGT SFAGHNSAIC VSSASYINFE GPQNPDNYLV TPELSLPNGG TLTFWVCAQD  360
ANYASEHYAV YASSTGNDAS NFANALLEEV LTAKTVVTAP EAIRGTRVQG TWYQKTVQLP  420
AGTKYVAFRH FGCTDFFWIN LDDVEIKANG KR                               452

SEQ ID NO: 144        moltype = AA  length = 504
FEATURE               Location/Qualifiers
REGION                1..504
                      note = Synthetic polypeptide
source                1..504
                      mol_type = protein
                      organism = synthetic construct
SEQUENCE: 144
ADFTETFESS THGEAPAEWT TIDADGDGQG WLCLSSGQLG WLTAHGGTNV VASFSWNGMA   60
LNPDNYLISK DVTGATKVKY YYAVNDGFPG DHYAVMISKT GTNAGDFTVV FEETPNGINK  120
GGARFGLSTE ANGAKPQSVW IERTVDLPAG TKYVAFRHYN CSDLNYILLD DIQFTMGGSP  180
TPTDYTYTVY RDGTKIKEGL TETTFEEDGV ATGNHEYCVE VKYTAGVSPK ECVNVTINPT  240
QFNPVQNLTA EQAPNSMDAI LKWNAPASKR AEVLNEDFEN GIPASWKTID ADGDGNNWTT  300
TPPPGGSSFA GHNSAICVSS ASYINFEGPQ NPDNYLVTPE LSLPGGGTLT FWVCAQDANY  360
ASEHYAVYAS STGNDASNFA NALLEEVLTA KTVVTAPEAI RGTRVQGTWY QKTVQLPAGT  420
KYVAFRHFGC TDFFWINLDD VVITSGNAPS YTYTIYRNNT QIASGVTETT YRDPDLATGF  480
YTYGVKVVYP NGESAIETAT LNIT                                        504
```

-continued

```
SEQ ID NO: 145              moltype = AA  length = 421
FEATURE                     Location/Qualifiers
REGION                      1..421
                            note = Synthetic polypeptide
source                      1..421
                            mol_type = protein
                            organism = synthetic construct
SEQUENCE: 145
RANEAKVVLA AADNVWGDNT GYQFLLDADH NTFGSVIPAT GPLFTGTASS NLYSANFEYL    60
VPANADPVVT TQNIIVTGQG EVVIPGGVYD YCITNPEPAS GKMWIAGDGG NQPARYDDFT   120
FEAGKKYTFT MRRAGMGDGT DMEVEDDSPA SYTYTVYRDG TKIKEGLTAT TFEEDGVAAG   180
NHEYCVECKY TAGVSPKVCK DVTVEGSNEF APVQNLTGSS VGQKVTLKWD APNGTPNPNP   240
NPNPNPGTTL SESFENGIPA SWKTIDADGD GHGWKPGNAP GIAGYNSNGC VYSESFGLGG   300
IGVLTPDNYL ITPALDLPNG GKLTFWVCAQ DANYASEHYA VYASSTGNDA SNFTNALLEE   360
TITAKGVRSP KAIRGRIQGT WRQKTVDLPA GTKYVAFRHF QSTDMFYIDL DEVEIKANGK   420
R                                                                  421

SEQ ID NO: 146              moltype = AA  length = 505
FEATURE                     Location/Qualifiers
REGION                      1..505
                            note = Synthetic polypeptide
source                      1..505
                            mol_type = protein
                            organism = synthetic construct
SEQUENCE: 146
ADFTETFESS THGEAPAEWT TIDADGDGQG WLCLSSGQLD WLTAHGGSNV VSSFSWNGMA    60
LNPDNYLISK DVTGATKVKY YYAVNDGFPG DHYAVMISKT GTNAGDFTVV FEETPNGINK   120
GGARFGLSTE ANGAKPQSVW IERTVDLPAG TKYVAFRHYN CSDLNYILLD DIQFTMGGSP   180
TPTDYTYTVY RDGTKIKEGL TETTFEEDGV ATGNHEYCVE VKYTAGVSPK KCVDVTVNST   240
QFNPVQNLTA EQAPNSMDAI LKWNAPASKR AEVLNEDFEN GIPASWKTID ADGDGNNWTT   300
TPPPGGSSFA GHNSAICVSS ASHINFEGPQ NPDNYLVTPE LSLPGGGTLT FWVCAQDANY   360
ASEHYAVYAS STGNDASNFA NALLEEVLTA KTVVTAPEAI RGTRAQGTWY QKTVQLPAGT   420
KYVAFRHFGC TDFFWINLDD VVITSGNAPS YTYTIYRNNT QIASGVTETT YRDPDLATGF   480
YTYGVKVVYP NGESAIETAT LNITS                                        505

SEQ ID NO: 147              moltype = AA  length = 421
FEATURE                     Location/Qualifiers
REGION                      1..421
                            note = Synthetic polypeptide
source                      1..421
                            mol_type = protein
                            organism = synthetic construct
SEQUENCE: 147
RSGQAEIVLE AHDVWNDGSG YQILLDADHD QYGQVIPSDT HTLWPNCSVP ANLFAPFEYT    60
VPENADPSCS PTNMIMDGTA SVNIPAGTYD FAIAAPQANA KIWIAGQGPT KEDDYWFEAG   120
KKYHFLMKKM GSGDGTELTI SEGGGSDYTY TVYRDGTKIK EGLTATTFEE DGVATGNHEY   180
CVEVKYTAGV SPKVCKDVTV EGSNEFAPVQ NLTGSAVGQK VTLKWDAPNG TPNPNPNPNP   240
NPNPGTTTLS ESFENGIPAS WKTIDADGDG HGWKPGNAPG IAGYNSNGCV YSESFGLLGG   300
IGVLTPDNYL ITPALDLPNG GKLTFWVCAQ DANYASEHYA VYASSTGNDA SNFTNALLEE   360
TITAKGVRSP EAMRGRIQGT WRQKTVDLPA GTKYVAFRHF QSTDMFYIDL DEVEIKANGK   420
R                                                                  421

SEQ ID NO: 148              moltype = AA  length = 496
FEATURE                     Location/Qualifiers
REGION                      1..496
                            note = Synthetic polypeptide
source                      1..496
                            mol_type = protein
                            organism = synthetic construct
SEQUENCE: 148
ADFTETFESS THGEAPAEWT TIDADGDGQG WLCLSSGQLD WLTAHGGTNV VSSFSWNGMA    60
LNPDNYLISK DVTGATKVKY YYAVNDGFPG DHYAVMISKT GTNAGDFTVV FEETPNGINK   120
GGARFGLSTE ADGAKPQSVW IERTVDLPAG TKYVAFRHYN CSDLNYILLD DIQFTMGGSP   180
TPTDYTYTVY RDGTKIKEGL TETTFEEDGV ATGNHEYCVE VKYTAGVSPK KCVNVTVNST   240
QFNPVKNLKA QPDGGDVVLK WEAPSAKKTE GSREVKRIGD GLFVTIEPAN DVRANEAKVV   300
LAADNVWGDN TGYQFLLDAD HNTFGSVIPA TGPLFTGTAS SDLYSANFES LIPANADPVV   360
TTQNIIVTGQ GEVVIPGGVY DYCITNPEPA SGKMWIAGDG GNQPARYDDF TFEAGKKYTF   420
TMRRAGMGDG TDMEVEDDSP ASYTYTVYRD GTKIKEGLTE TTYRDAGMSA QAHEYCVEWK   480
YTAGVSPKVC VDYIPD                                                  496

SEQ ID NO: 149              moltype = AA  length = 925
FEATURE                     Location/Qualifiers
REGION                      1..925
                            note = Synthetic polypeptide
source                      1..925
                            mol_type = protein
                            organism = synthetic construct
SEQUENCE: 149
```

-continued

```
RANEAKVVLA ADNVWGDNTG YQFLLDADHN TFGSVIPATG PLFTGTASSN LYSANFEYLV    60
PANADPVVTT QNIIVGQGEV VIPGGVYDYC ITNPEPASGK MWIAGDGGNQ PARYDDFTFE   120
AGKKYTFTMR RAGMGDGTDM EVEDDSPASY TYTVYRDGTK IKEGLTATTF EEDGVAAGNH   180
EYCVEVKYTA GVSPKVCKDV TVEGSNEFAP VQNLTGSSVG QKVTLKWDAP NGTPNPNPNP   240
NPNPGTTLSE SFENGIPASW KTIDADGDGH GWKPPGNAPG IAGYNSNGCV YSESFGLGGI   300
GVLTPDNYLI TPALDLPNGG KLTFWVCAQD ANYASEHYAV YASSTGNDAS NFTNALLEET   360
ITAKGVRSPK AIRGRIGGTW RQKTVDLPAG TKYVAFRHFQ STDMFYIDLD EVEIKANGKR   420
ADFTETFESS THGEAPAEWT TIDADGDGQG WLCLSSGQLD WLTAHGGSNV VSSFSWNGMA   480
LNPDNYLISK DVTGATKVKY YYAVNDGFPG DHYAVMISKT GTNAGDFTVV FEETPNGINK   540
GGARFGLSTE ANGAKPQSVW IERTVDLPAG TKYVAFRHYN CSDLNYILLD DIQFTMGGSP   600
TPTDYTYTVY RDGTKIKEGL TETTFEEDGV ATGNHEYCVE VKYTAGVSPK KCVDVTVNST   660
QFNPVQNLTA EQAPNSMDAI LKWNAPASKR AEVLNEDFEN GIPASWKTID ADGDGNNWTT   720
TPPPGGSSFA GHNSAICVSS ASHINFEGPQ NPDNYLVTPE LSLPGGGTLT FWVCAQDANY   780
ASEHYAVYAS STGNDASNFA NALLEEVLTA KTVVTAPEAI RGTRAQGTWY QKTVQLPAGT   840
KYWAFRHFGC TDFFWINLDD VVITSGNAPS YTYTIYRNNT QIASGVTETT YRDPDLATGF   900
YTYGVKVVYP NGESAIETAT LNITS                                         925

SEQ ID NO: 150        moltype = AA   length = 916
FEATURE               Location/Qualifiers
REGION                1..916
                      note = Synthetic polypeptide
source                1..916
                      mol_type = protein
                      organism = synthetic construct
SEQUENCE: 150
RSGQAEIVLL EAHDVQNDGS GYQILLDADH DQYGQVIPSD THTLWPNCSV PANLFAPFEY    60
TVPENADPSC SPTNMIMDGT ASVNIPAGTY DFAIAAPQAN AKIWIAGQGP TKEDDYVFEA   120
GKKYHFIMKK MGSDGTELTI SEGGSDYTYT VYRDGTKIKE GLTATTFEED GVATGNHEYC   180
VEVKYTAGVS PKVCKDVTVE GNSNEFAPVQ NLTGSAVGQK VTLKWDAPNG TPNPNPNPNP   240
NPNPGTTTLS ESFENGIPAS WKTIDADGDG HGWKPGNAPG IAGYNSNGCV YSESPGLGGI   300
GVLTPDNYLI TPALDLPNGG KLTFWVCAQD ANYASEHYAV YASSTGNDAS NFTNALLEET   360
ITAKGVRSPE AMRGRIQGTW RQKTVDLPAG TKYVAFRHFQ STDMFYIDLD EVEIKANGKR   420
ADFTETFESS THGEAPAEWT TIDADGDGQG WLCLSSGQLD WLTAHGGTNV VSSFSWNGMA   480
LNPDNYLISK DVTGATKVKY YYAVNDGFPG DHYAVMISKT GTNAGDFTVV FEETPNGINK   540
GGARFGLSTE ADGAKPQSVW IERTVDLPAG TKYVAFRHYN CSDLNYILLD DIQFTMGGSP   600
TPTDYTYTVY RDGTKIKEGL TETTFEEDGV ATGNHEYCVE VKYTAGVSPK KCVNVTVNST   660
QFNPVKNLKA QPDGGDVVLK WEAPSAKKTE GSREVKRIGD GLFVTIEPAN DVRANEAKVV   720
LAADNVWGDN TGYQFLLDAD HNTFGSVIPA TGPLFTGTAS SDLYSANFES LIPANADPVV   780
TTQNIIVTGQ GEVVIPGGVY DYCITNPEPA SGKMWIAGDG GNQPARYDDF TFEAGKKYTF   840
TMRRAGMGDG TDMEVEDDSP ASYTYTVYRD GTKIKEGLTE TTYRDAGMSA QSHEYCVEVK   900
YTAGVSPKVC VDYIPD                                                   916

SEQ ID NO: 151        moltype = AA   length = 502
FEATURE               Location/Qualifiers
REGION                1..502
                      note = Synthetic polypeptide
source                1..502
                      mol_type = protein
                      organism = synthetic construct
SEQUENCE: 151
ADFTETFESS THGEAPAEWT TIDADGDGQG WLCLSSGQLD WLTAHGGTNV VASFSWNGMA    60
LNPDNYLISK DVTGATKVKY YYAVNDGFPG DHYAVMISKT GTNAGDFTVV FEETPNGINK   120
GGARFGLSTE ADGAKPQSVW IERTVDLPAG TKYVAFRHYN CSDLNYILLD DIQFTMGGSP   180
TPTDYTYTVY RDGTKIKEGL TETTFEEDGV ATGNHEYCVE VKYTAGVSPK VCVNVTINPT   240
QFNPVQNLTA EQAPNSMDAI LKWNAPASKR AEVLNEDFEN GIPASWKTID ADGDGNNWTT   300
TPPPGGSSFA GHNSAICVSS ASYINFEGPQ NPDNYLVTPE LSLPGGGTLT FWVCAQDANY   360
ASEHYAVYAS STGNDASNFA NALLEEVLTA KTVVTAPEAI RGTRVQGTWY QKTVQLPAGT   420
KYVAFRHFGC TDFFWINLDD WITSGNAPSY TYTIYRNNTQ IASGVTETTY RDPDLATGFY   480
TYGVKWYPNG ESAIETATLN IT                                            502

SEQ ID NO: 152        moltype = AA   length = 456
FEATURE               Location/Qualifiers
REGION                1..456
                      note = Synthetic polypeptide
source                1..456
                      mol_type = protein
                      organism = synthetic construct
SEQUENCE: 152
ADFTETFESS THGEAPAEWT TIDADGDGQG WLCLSSGQLG WLTAHGGTNV VASFSWNGMA    60
LNPDNYLISK DVTGATKVKY YYAVNDGFPG DHYAVMISKT GTNAGDFTVV FEETPNGINK   120
GGARFGLSTE ADGAKPQSVW IERTVDLPAG TKYVAFRHYN CSDLNYILLD DIQFTMGGSP   180
TPTDYTYTVY RDGTKIKEGL TETTFEEDGV ATGNHEYCVE VKYTAGVSPK ECVNVTVDPV   240
QFNPVQNLTG SAVGQKVTLK WDAPNGTPNP NPNPNPGTTT LSESEFENGIP ASWKTIDADG   300
DGNNWTTTPP PGGTSFAGHN SAICASSASY INFEGPQNPD NYLVTPELSL PNGGTLTFWV   360
CAQDANYASE HYAVYASSTG NDASNFANAL LEEVLTAKTV VTAPEAIRGT RVQGTWYQKT   420
VQLPAGTKYV AFRHFGCTDF FWINLDDVEI KANGKR                             456

SEQ ID NO: 153        moltype = AA   length = 456
FEATURE               Location/Qualifiers
```

```
REGION                    1..456
                          note = Synthetic polypeptide
source                    1..456
                          mol_type = protein
                          organism = synthetic construct
SEQUENCE: 153
ADFTETFESS THGEAPAEWT TIDADGDGQG WLCLSSGQLG WLTAHGGTNV VASFSWNGMA   60
LNPDNYLISK DVTGATKVKY YYAVNDGFPG DHYAVMISKT GTNAGDFTVV FEETPNGINK  120
GGARFGLSTE ADGAKPQSVW IERTVDLPAG TKYVAFRHYN CSDLNYILLD DIQFTMGGSP  180
TPTDYTYTVY RDGTKIKEGL TETTFEEDGV ATGNHEYCVE VKYTAGVSPK ECVNVTVDPV  240
QFNPVQNLTG SAVGQKVTLK WDAPNGTPNP NPNPNPGTTT LSESFENGIP ASWKTIDADG  300
DGNNWTTTPP PGGTSFAGHN SAICVSSASY INFEGPQNPD NYLVTPELSL PGGGTLTFWV  360
CAQDANYASE HYAVYASSTG NDASNFANAL LEEVLTAKTV VTAPEAIRGT RVQGTWYQKT  420
VQLPAGTKYV AFRHFGCTDF FWINLDDVEI KANGKR                           456

SEQ ID NO: 154           moltype = AA   length = 456
FEATURE                  Location/Qualifiers
REGION                    1..456
                          note = Synthetic polypeptide
source                    1..456
                          mol_type = protein
                          organism = synthetic construct
SEQUENCE: 154
ADFTETFESS THGEAPAEWT TIDADGDGQG WLCLSSGQLG WLTAHGGTNV VASFSWNGMA   60
LNPDNYLISK DVTGATKVKY YYAVNDGFPG DHYAVMISKT GTNAGDFTVV FEETPNGINK  120
GGARFGLSTE ADGAKPQSVW IERTVDLPAG TKYVAFRHYN CSDLNYILLD DIQFTMGGSP  180
TPTDYTYTVY RDGTKIKEGL TETTFEEDGV ATGNHEYCVE VKYTAGVSPK ECVNVTVDPV  240
QFNPVQNLTG SAVGQKVTLK WDAPNGTPNP NPNPNPGTTT LSESFENGIP ASWKTIDADG  300
DGNNWTTTPP PGGTSFAGHN SAICVSSASY INFEGPQNPD NYLVTPELSL PGGGTLTFWV  360
CAQDANYASE HYAVYASSTG NDASNFANAL LEEVLTAKTV VTAPEAIRGT RVQGTWYQKT  420
VQLPAGTKYV AFRHFGCTDF FWINLDEVEI KANGKR                           456

SEQ ID NO: 155           moltype = AA   length = 503
FEATURE                  Location/Qualifiers
REGION                    1..503
                          note = Synthetic polypeptide
source                    1..503
                          mol_type = protein
                          organism = synthetic construct
SEQUENCE: 155
ADFTETFESS THGEAPAEWT TIDADGDGQG WLCLSSGQLD WLTAHGGTNV VASFSWNGMA   60
LNPDNYLISK DVTGATKVKY YYAVNDGFPG DHYAVMISKT GTNAGDFTWF EETPNGINKG  120
GARFGLSTEA DGAKPQSVWI ERTVDLPAGT KYVAFRHYNC SDLNYILLDD IQFTMGGSPT  180
PTDYTYTVYR DGTKIKEGLT ETTFEEDGVA TGNHEYCVEV KYTAGVSPKV CVNVTINPTQ  240
FNPVQNLTAE QAPNSMDAIL KWNAPASKRA EVLNEDFENG IPSSWKTIDA DGDGNNWTTT  300
PPPGGSSFAG HNSAICVSSA SYINFEGPQN PDNYLVTPEL SLPGGGTLTF WVCAQDANYA  360
SEHYAVYASS TGNDASNFAN ALLEEVLTAK TVVTAPEAIR GTRVQGTWYQ KTVQLPAGTK  420
YVAFRHFGCT DFFWINLDDV VITSGNAPSY TYTIYRNNTQ IASGVTETTY RDPDLATGFY  480
TYGVKVVYPN GESAIETATL NIT                                         503

SEQ ID NO: 156           moltype = AA   length = 450
FEATURE                  Location/Qualifiers
REGION                    1..450
                          note = Synthetic polypeptide
source                    1..450
                          mol_type = protein
                          organism = synthetic construct
SEQUENCE: 156
ANEAKWLAAD NVWGDNTGYQ FLLDADHNTF GSVIPATGPL FTGTASSNLY SANFEYLVPA   60
NADPVVTTQN IIVTGQGEWI PGGVYDYCIT NPEPASGKMW IAGDGGNQPA RYDDFTFEAG  120
KKYTFTMRRA GMGDGTDMEV EDDSPASYTY TVYRDGTKIK EGLTATTFEE DGVAAGNHEY  180
CVEVKYTAGV SPKVCKDVTV EGSNEFAPVQ NLTGSSVGQK VTLKWDAPNG TPNPNPNPNP  240
NPGTTLSESF ENGIPASWKT IDADGDGHGW KPGNAPGIAG YNSNGCVYSE SFGLGGIGVL  300
TPDNYLITPA LDLPNGGKLT FWVCAQDANY ASEHYAVYAS STGNDASNFT NALLEETITA  360
KGVRSPKAIR GRIQGTWRQK TDVLYTYTVY RDGTKIKEGL TETTFEEDGV ATGNHEYPAG  420
TKYVAFRHFQ STDMFYIDLD EVEIKANGKR                                  450

SEQ ID NO: 157           moltype = AA   length = 419
FEATURE                  Location/Qualifiers
REGION                    1..419
                          note = Synthetic polypeptide
source                    1..419
                          mol_type = protein
                          organism = synthetic construct
SEQUENCE: 157
SGQAEIVLEA HDVWNDGSGY QILLDADHDQ YGQVIPSDTH TLWPNCSVPA NLFAPFEYTV   60
PENADPSCSP TNMIMDGTAS VNIPAGTYDF AIAAPQANAK IWIAGQGPTK EDDYVFEAGK  120
KYHFLMKKMG SGDGTELTIS EGGGSDYTYT VYRDGTKIKE GLTATTFEED GVATGNHEYC  180
VEVKYTAGVS PKVCKDVTVE GSNEFAPVQN LTGSAVGQKV TLKWDAPNGT PNPNPNPNPN  240
```

-continued

```
PNPGTTTLSE SFENGIPASW KTIDADGDGH GWKPGNAPGI AGYNSNGCVY SESFGLGGIG    300
VLTPDNYLIT PALDLPNGGK LTFWVCAQAD NYASEHYAVY ASSTGNDASN FTNALLEETI    360
TAKGVRSPEA MRGRIQGTWR QKTVDLPAGT KYVAFRHFQS TDMFYIDLDE VEIKANGKR     419

SEQ ID NO: 158            moltype = AA  length = 439
FEATURE                   Location/Qualifiers
REGION                    1..439
                          note = Synthetic polypeptide
source                    1..439
                          mol_type = protein
                          organism = synthetic construct
SEQUENCE: 158
ADFTETFESS THGEAPAEWT TIDADGDGQG WLCLSSGQLG WLTAHGGTNW ASFSWNGMAL    60
NPDNYLISKD VTGATKVKYY YAVNDGFPGD HYAVMISKTG TNAGDFTVVF EETPNGINKP    120
QSVWIERTVD LPAGTKYVAF RHYNCSDLNY ILLDDIQFTM GGSPTPTDYT YTVYRDGTKI    180
KELGTETTFE EDGVATGNHE YCVEVKYTAG VSPKECVNVT VDPVQFNPVQ NLTGSAVGQK    240
VTLKWDAPNG TPNPNPNPNP GTTTLSESFE NGIPASWKTI DADGDGNNWT TTPPPGGTSF    300
AGHNSAICAS SASYINFEGP QNPDNYLVTP ELSLPNGGTL TFWVCAQDAN YASEHYAVYA    360
SSTGNDASNF ANALLEEVLT AKTWTAPEAI RGTRVQGTWY QKTVQLPAGT KYVAFRHFGC    420
TDFFWINLDD VEIKANGKR                                                439

SEQ ID NO: 159            moltype = AA  length = 439
FEATURE                   Location/Qualifiers
REGION                    1..439
                          note = Synthetic polypeptide
source                    1..439
                          mol_type = protein
                          organism = synthetic construct
SEQUENCE: 159
ADFTETFESS THGEAPAEWT TIDADGDGQG WLCLSSGQLG WLTAHGGTNW ASFSWNGMAL    60
NPDNYLISKD VTGATKVKYY YAVNDGFPGD HYAVMISKTG TNAGDFTVVF EETPNGINKP    120
QSVWIERTVD LPAGTKYVAF RHYNCSDLNY ILLDDIQFTM GGSPTPTDYT YTVYRDGTKI    180
KELGTETTFE EDGVATGNHE YCVEVKYTAG VSPKECVNVT VDPVQFNPVQ NLTGSAVGQK    240
VTLKWDAPNG TPNPNPNPNP GTTTLSESFE NGIPASWKTI DADGDGNNWT TTPPPGGTSF    300
AGHNSAICVS SASYINFEGP QNPDNYLVTP ELSLPGGGTL TFWVCAQDAN YASEHYAVYA    360
SSTGNDASNF ANALLEEVLT AKTWTAPEAI RGTRVQGTWY QKTVQLPAGT KYVAFRHFGC    420
TDFFWINLDD VEIKANGKR                                                439

SEQ ID NO: 160            moltype = AA  length = 439
FEATURE                   Location/Qualifiers
REGION                    1..439
                          note = Synthetic polypeptide
source                    1..439
                          mol_type = protein
                          organism = synthetic construct
SEQUENCE: 160
ADFTETFESS THGEAPAEWT TIDADGDGQG WLCLSSGQLG WLTAHGGTNW ASFSWNGMAL    60
NPDNYLISKD VTGATKVKYY YAVNDGFPGD HYAVMISKTG TNAGDFTVVF EETPNGINKP    120
QSVWIERTVD LPAGTKYVAF RHYNCSDLNY ILLDDIQFTM GGSPTPTDYT YTVYRDGTKI    180
KELGTETTFE EDGVATGNHE YCVEVKYTAG VSPKECVNVT VDPVQFNPVQ NLTGSAVGQK    240
VTLKWDAPNG TPNPNPNPNP GTTTLSESFE NGIPASWKTI DADGDGNNWT TTPPPGGTSF    300
AGHNSAICVS SASYINFEGP QNPDNYLVTP ELSLPGGGTL TFWVCAQDAN YASEHYAVYA    360
SSTGNDASNF ANALLEEVLT AKTWTAPEAI RGTRVQGTWY QKTVQLPAGT KYVAFRHFGC    420
TDFFWINLDE VEIKANGKR                                                439

SEQ ID NO: 161            moltype = AA  length = 447
FEATURE                   Location/Qualifiers
REGION                    1..447
                          note = Synthetic polypeptide
source                    1..447
                          mol_type = protein
                          organism = synthetic construct
SEQUENCE: 161
ADFTETFESS THGEAPAEWT TIDADGDGQG WLCLSSGQLD WLTAHGGTNW ASFSWNGMAL    60
NPDNYLISKD VTGATKVKYY YAVNDGFPGD HYAVMISKTG TNAGDFTVVF EETPNGINKP    120
QSVWIERTVD LPAGTKYVAF RHYNCSDLNY ILLDDIQFTM GGSPTPTDYT YTVYRDGTKI    180
KELGTETTFE EDGVATGNHE YCVEVKYTAG VSPKVCVNVT INPTQFNPVQ NLTAEQAPNS    240
MDAILKWNAP ASKFAGHNSA ICVSSASYIN FEGPQNPDNY LVTPELSLPG GGTLTFWVCA    300
QDANYASEHY AVYASSTGND ASNFANALLE EVLTAKTWTA PEAIRGTRVQ GTWYQKTVQL    360
PAGTKYVAFR HFGCTDFFWI NLDDWITSGN APSYTYTIYR NNTQIASGVT ETTYRDPDLA    420
TGFYTYGVKV VYPNGESAIE TATLNIT                                       447

SEQ ID NO: 162            moltype = AA  length = 413
FEATURE                   Location/Qualifiers
REGION                    1..413
                          note = Synthetic polypeptide
source                    1..413
                          mol_type = protein
                          organism = synthetic construct
```

```
SEQUENCE: 162
MSPILGYWKI KGLVQPTRLL LEYLEEKYEE HLYERDEGDK WRNKKFELGL EFPNLPYYID  60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD RARYLANASR CGSAENLYFQ  240
GADPSCSPTN MIMDGTASVN IPAGTYDFAI AAPQANAKIW IAGQGPTKED DYVFEAGKKY  300
HPLMKKMGSG DGTELTISEG GGSDYTYTVY RDGTKIKEGL TATTFEEDGV AAGNHEYCVE  360
VKYTAGVSPK VCKDVTVEGS NEFAPVQNLT GSAVGQKVTL KWDAPNGHHH HHH         413

SEQ ID NO: 163          moltype = DNA  length = 720
FEATURE                 Location/Qualifiers
misc_feature            1..720
                        note = Synthetic polynucleotide
source                  1..720
                        mol_type = other DNA
                        organism = synthetic construct
SEQUENCE: 163
atgtccccta tactaggtta ttggaaaatt aagggccttg tgcaacccac tcgacttctt  60
ttggaatatc ttgaagaaaa atatgaagag catttgtatg agcgcgatga aggtgataaa  120
tggcgaaaca aaaagtttga attgggtttg gagtttccca atcttcctta ttatattgat  180
ggtgatgtta aattaacaca gtctatggcc atcatacgtt atatagctga caagcacaac  240
atgttgggtg gttgtccaaa agagcgtgca gagatttcaa tgcttgaagg agcggttttg  300
gatattagat acggtgtttc gagaattgca tatagtaaag actttgaaac tctcaaagtt  360
gattttctta gcaagctacc tgaaatgctg aaaatgttcg aagatcgttt atgtcataaa  420
acatatttaa atggtgatca tgtaacccat cctgacttca tgttgtatga cgctcttgat  480
gttgttttat acatggaccc aaatgtgcctg gatgcgttcc caaaattagt ttgttttaaa  540
aaacgtattg aagctatccc acaaattgat aagtacttga aatccagcaa gtatatagca  600
tggcctttgc agggctggca agccacgttt ggtggtggcg accatcctcc aaaatcggat  660
ctggttccgc gtggatcccc ggaattcccg ggtcgactcg agcggccgca tcgtgactga  720

SEQ ID NO: 164          moltype = DNA  length = 585
FEATURE                 Location/Qualifiers
misc_feature            1..585
                        note = Synthetic polynucleotide
source                  1..585
                        mol_type = other DNA
                        organism = synthetic construct
SEQUENCE: 164
cgagctcggt acctcgcgaa tgcatctaga tgcggatccg cagagaatct gtactttcaa  60
ggagcagatc cgagctgtag tccaacgaat atgattatgg atggcaccgc atctgtcaac  120
attccagccg gaacctacga ttttgctatt gccgcaccac aagcaaatgc aaaaatttgg  180
atcgcaggac aaggaccaac caaagaagat gattatgtgt ttgaagcggg gaagaaatat  240
cactttctga tgaaaaaaat gggcagtggg gatggaaccg aattgacgat tagcgaaggg  300
ggaggctcag attatacata caccgtatac cgggatggta ctaaaattaa agaaggttta  360
acagcaacaa cgtttgaaga ggatggcgta gcagcgggta atcacgaata ttgtgtagaa  420
gtaaagtata ctgccggagt gtcacctaaa gtgtgtaaag atgtaacagt tgaaggtagt  480
aacgaatttg cgccggtaca aaatttaacg ggtagtgcag tgggccagaa agtaactttg  540
aaatgggatg cgccaaatgg tcaccaccat catcatcatt aatag               585

SEQ ID NO: 165          moltype = AA  length = 117
FEATURE                 Location/Qualifiers
REGION                  1..117
                        note = Synthetic polypeptide
source                  1..117
                        mol_type = protein
                        organism = synthetic construct
SEQUENCE: 165
QVQLQESGPG LVKPSETLSL TCTVSGFSLS IYSVHWIRQP PGKGLEWIGM IWGGGSSDYN  60
SALKSRLTIS KDTSKNQVSL KLSSVTAADT AVYYCARNGN FYAMDYWGQG TLVTVSS     117

SEQ ID NO: 166          moltype = AA  length = 117
FEATURE                 Location/Qualifiers
REGION                  1..117
                        note = Synthetic polypeptide
source                  1..117
                        mol_type = protein
                        organism = synthetic construct
SEQUENCE: 166
QVQLQESGPG LVKPSETLSL TCTVSGFSLS IYSVHWIRQP PGKGLEWLGM IWGGGSSDYN  60
SALKSRLTIS KDTSKNQVSL KLSSVTAADT AMYYCARNGN FYAMDYWGQG TLVTVSS     117

SEQ ID NO: 167          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 167
```

-continued

```
EIVLTQSPGT LSLSPGERAT LSCTASSSVS SSFLHWYQQK PGQAPRLLIY STSNLASGIP   60
DRFSGSGSGT DFTLTISRLE PEDFAVYYCH QYHHSPYIYT FGGGTKLEIK              110

SEQ ID NO: 168            moltype = AA  length = 110
FEATURE                   Location/Qualifiers
REGION                    1..110
                          note = Synthetic polypeptide
source                    1..110
                          mol_type = protein
                          organism = synthetic construct
SEQUENCE: 168
EIVLTQSPGT LSLSPGERAT LSCTASSSVS SSFLHWYQQK PGQAPQLWIY STSNLASGIP   60
DRFSGSGSGT DYTLTISRLE PEDFAVYYCH QYHHSPYIYT FGGGTKLEIK              110

SEQ ID NO: 169            moltype = AA  length = 110
FEATURE                   Location/Qualifiers
REGION                    1..110
                          note = Synthetic polypeptide
source                    1..110
                          mol_type = protein
                          organism = synthetic construct
SEQUENCE: 169
EIVLTQSPGT LSLSPGERAT LSCTASSSVS SSFLHWYQQK PGQAPQLWIY STSNLASGIP   60
DRFSGSGSGT DYTLTISRLE PEDFATYYCH QYHHSPYIYT FGGGTKLEIK              110

SEQ ID NO: 170            moltype = AA  length = 110
FEATURE                   Location/Qualifiers
REGION                    1..110
                          note = Synthetic polypeptide
source                    1..110
                          mol_type = protein
                          organism = synthetic construct
SEQUENCE: 170
EIVLTQSPGT LSLSPGERAT LSCTASSSVS SSFLHWYQQK PGQAPQLWIY STSNLASGIP   60
ARFSGSGSGT DYTLTISRLE PEDFATYYCH QYHHSPYIYT FGGGTKLEIK              110

SEQ ID NO: 171            moltype = AA  length = 330
FEATURE                   Location/Qualifiers
REGION                    1..330
                          note = Synthetic polypeptide
source                    1..330
                          mol_type = protein
                          organism = synthetic construct
SEQUENCE: 171
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 172            moltype = AA  length = 330
FEATURE                   Location/Qualifiers
REGION                    1..330
                          note = Synthetic polypeptide
source                    1..330
                          mol_type = protein
                          organism = synthetic construct
SEQUENCE: 172
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDATHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 173            moltype = AA  length = 107
FEATURE                   Location/Qualifiers
REGION                    1..107
                          note = Synthetic polypeptide
source                    1..107
                          mol_type = protein
                          organism = synthetic construct
SEQUENCE: 173
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 174            moltype = DNA  length = 351
FEATURE                   Location/Qualifiers
```

```
misc_feature              1..351
                          note = Synthetic polynucleotide
source                    1..351
                          mol_type = other DNA
                          organism = synthetic construct
SEQUENCE: 174
caggtgcagc tgcaagagtc cggccctgga ctcgtgaagc cctccgagac actgtctctg   60
acatgtaccg tgtctggctt ctccctgtcc atctactccg tgcactggat cagacagcct  120
cctggcaagg gcctggaatg gatcggcatg atctgggggag gcggctcttc cgactacaac  180
tccgccctga aatctcggct gaccatctcc aaggacacct ctaagaacca ggtcagcctg  240
aagctgagct ctgtgaccgc tgctgatacc gccgtgtact actgcgccag aaatggcaac  300
ttctacgcca tggactattg gggccagggc accctggtga ccgtgtccag c           351

SEQ ID NO: 175           moltype = DNA   length = 351
FEATURE                  Location/Qualifiers
misc_feature             1..351
                         note = Synthetic polynucleotide
source                   1..351
                         mol_type = other DNA
                         organism = synthetic construct
SEQUENCE: 175
caggtgcagc tgcaagagtc cggacccggc ctcgtgaagc cttccgagac actgtctctg   60
acctgtaccg tgtctggctt ctccctgtcc atctactccg tgcactggat ccggcagcct  120
cctggcaagg gcctggaatg gctgggcatg atctggggcg gcggaagctc cgactacaac  180
tccgccctga aatctagact gaccatctcc aaggacacct ctaagaacca ggtcagcctg  240
aagctgagct ctgtgaccgc cgctgatacc gctatgtact actgcgccag aaatggcaac  300
ttctacgcca tggactattg gggccagggc accctggtga cagtgtcctc t           351

SEQ ID NO: 176           moltype = DNA   length = 330
FEATURE                  Location/Qualifiers
misc_feature             1..330
                         note = Synthetic polynucleotide
source                   1..330
                         mol_type = other DNA
                         organism = synthetic construct
SEQUENCE: 176
gagatcgtgc tgacccaatc tccaggcacc ctgtctctca gccctggcga gagagccacc   60
ctgtcctgca ccgcttctag ctccgtgtcc tccagcttcc tgcactggta ccagcagaaa  120
cccggccagg ctcctagact gctgatctat tccacctcca acctggcctc tggcatccct  180
gaccggttct ccggctctgg ctccggaaca gattttacac tgaccatctc ccggctggaa  240
cctgaggact tcgccgtgta ctactgtcac cagtaccacc attctcctta catctacacc  300
ttcggcggcg gaaccaagct ggaaatcaag                                    330

SEQ ID NO: 177           moltype = DNA   length = 330
FEATURE                  Location/Qualifiers
misc_feature             1..330
                         note = Synthetic polynucleotide
source                   1..330
                         mol_type = other DNA
                         organism = synthetic construct
SEQUENCE: 177
gagatcgtgc tgacacaatc tcccggcacc ctcagcctgt ctccaggcga gagagccaca   60
ctgtcctgca ccgcttctag ctccgtgtcc tccagctttc tgcactggta ccagcagaaa  120
cctggccagg ctcctcagct gtggatctac tccacctcca acctggcctc tggcatccct  180
gatcggttct ccggctccgg ctctggcacc gactacaccc tgaccatctc cagactggaa  240
cctgaggact tcgccgtgta ctactgtcac cagtaccacc attctcctta catctatacc  300
ttcggcggag gaaccaagct ggaaatcaag                                    330

SEQ ID NO: 178           moltype = DNA   length = 330
FEATURE                  Location/Qualifiers
misc_feature             1..330
                         note = Synthetic polynucleotide
source                   1..330
                         mol_type = other DNA
                         organism = synthetic construct
SEQUENCE: 178
gagatcgtgc tgacccagtc tccaggcaca ctcagcctgt ctcctggcga gcgggctacc   60
ctgtcctgca ccgccagcag ctccgtgtcc tcttcttttc tgcactggta ccagcagaaa  120
cctggacaag ctcctcagct gtggatctac tccacctcca acctggcctc tggcatccct  180
gatagattct ccggctctgg ctccggcacc gactacacac tgaccatctc cagactggaa  240
cctgaggact tcgccaccta ctactgtcat cagtaccacc actcccctta catctatacc  300
ttcggcggag gcaccaagct ggaaatcaag                                    330

SEQ ID NO: 179           moltype = DNA   length = 330
FEATURE                  Location/Qualifiers
misc_feature             1..330
                         note = Synthetic polynucleotide
source                   1..330
                         mol_type = other DNA
```

-continued

```
                          organism = synthetic construct
SEQUENCE: 179
gagatcgtgc tgacccaatc tcctggcacc ctgtctctga gcccaggcga gagagccaca   60
ctctcctgca ccgcttcttc ctccgtgtcc tctagctttc tgcactggta ccagcagaaa  120
cccggccagg ctcctcagct gtggatctac tccacctcca acctggcctc tggcatccct  180
gccagattct ccggatccgg ctctggcacc gattatacac tgaccatctc ccggctggaa  240
cctgaggact tcgccaccta ctactgtcac cagtaccacc atagcccta catctacacc  300
ttcggcggcg gaaccaagct ggaaatcaag                                    330

SEQ ID NO: 180            moltype = DNA   length = 996
FEATURE                   Location/Qualifiers
misc_feature              1..996
                          note = Synthetic polynucleotide
source                    1..996
                          mol_type = other DNA
                          organism = synthetic construct
SEQUENCE: 180
gccagcacca agggcccttc cgtgtttcca ctggcccct cctctaaatc cacatctggc    60
ggcaccgccg ccctgggctg tctggtgaag gactacttcc cagagcctgt gacagtgtcc  120
tggaactctg gcgccctgac atccggcgtg cacacatttc cagccgtgct gcagagctcc  180
ggcctgtaca gcctgtctag cgtggtgaca gtgccctcct ctagcctggg cacacagacc  240
tatatctgca acgtgaatca caagccaagc aataccaagc tggacaagaa ggtggagccc  300
aagtcctgtg ataagacaca cacctgcccc ccttgtcctg ctcccgagct gctgggcggc  360
cctagcgtgt tcctgtttcc acccaagcct aaggacaccc tgatgatctc ccggacaccc  420
gaggtgacct gcgtggtggt ggacgtgtct cacgaggatc ctgaggtgaa gttcaactgg  480
tatgtggatg gcgtggaggt gcacaatgcc aagaccaagc cagagagga gcagtacaac  540
tctacatata gggtggtgag cgtgctgacc gtgctgcacc aggactggct gaacggcaag  600
gagtataagt gcaaggtgtc caataaggcc ctgcccgccc ccatcgagaa gacaatcagc  660
aaggccaagg gccagcctcg ggagccacag gtgtacaccc tgcctccatc cagagacgag  720
ctgacaaaga accaggtgtc tctgacatgt ctggtgaagg gcttctatcc tagcgatatc  780
gccgtggagt gggagtccaa tggccagcca gagaacaatt acaagaccac accccctgtg  840
ctggactccg atggctcctt ctttctgtat tccaagctga ccgtggataa gtctcggtgg  900
cagcagggca acgtgttcag ctgttccgtg atgcacgaag ccctgcataa tcactatact  960
cagaaatccc tgtccctgtc acctggaaag tgataa                             996

SEQ ID NO: 181            moltype = DNA   length = 327
FEATURE                   Location/Qualifiers
misc_feature              1..327
                          note = Synthetic polynucleotide
source                    1..327
                          mol_type = other DNA
                          organism = synthetic construct
SEQUENCE: 181
aggacagtgg ccgccccaag cgtgttcatc tttccccctt ccgacgagca gctgaagtct    60
ggcaccgcca gcgtggtgtg cctgctgaac aacttctacc ctcgggaggc caaggtccag  120
tggaaggtgg ataacgccct gcagtctggc aatagccagg agtccgtgac cgagcaggac  180
tctaaggata gcacatattc cctgtctagc accctgacac tgagcaaggc cgattacgag  240
aagcacaagg tgtatgcctg tgaagtcacc catcaggggc tgtcatcacc cgtcactaag  300
tcattcaatc gcggagaatg ctgataa                                       327

SEQ ID NO: 182            moltype = DNA   length = 7436
FEATURE                   Location/Qualifiers
misc_feature              1..7436
                          note = Synthetic polynucleotide
source                    1..7436
                          mol_type = other DNA
                          organism = synthetic construct
SEQUENCE: 182
gttaggcgtt ttgcgctgct tcgcgatgta cgggccagat atacgcgttg acattgatta    60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgc caataatgac gtatgttccc atagtaacgc caatagggac tttccattga  240
cgtcaatggg tggagtattt acggtaaact gcccacttgg cagtacatca agtgtatcat  300
atgccaagta cgcccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatacg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct tgaattcccg ccgccaccat gggctggtca tgcattattc  780
tgtttctggt cgcaactgct acaggcgtgc atagtcaggt gcagctgcaa gagtccggc  840
ctggactcgt gaagccctcc gagacactgt ctctgacatg taccgtgtct ggcttctccc  900
tgtccatcta ctccgtgcac tggatcagac agcctcctgg caagggcctg gaatggatcc  960
gcatgatctc gggaggcggc tcttccgact acaactccgc cctgaaatct cggctgacca  1020
tctccaagga cacctctaag aaccaggtca gcctgaagct gagctctgtg accgctgctg  1080
ataccgccgt gtactactgc gccagaaatg gcaacttcta cgccatggac tattgggggcc  1140
agggcaccct ggtgaccgtg tccagcgcca gcaccaaggg cccttccgtg tttccactgg  1200
ccccctcctc taaatccaca tctggcggca ccgccgccct gggctgtctg gtgaaggact  1260
```

-continued

```
acttcccaga gcctgtgaca gtgtcctgga actctggcgc cctgacatcc ggcgtgcaca   1320
catttccagc cgtgctgcag agctccggcc tgtacagcct gtctagcgtg gtgacagtgc   1380
cctcctctag cctgggcaca cagacctata tctgcaacgt gaatcacaag ccaagcaata   1440
ccaaggtgga caagaaggtg gagcccaagt cctgtgataa gacacacacc tgcccccctt   1500
gtcctgctcc cgagctgctg ggcggcccta gcgtgttcct gtttccaccc aagcctaagg   1560
acaccctgat gatctcccgg acacccgagg tgacctgcgt ggtggtggac gtgtctcacg   1620
aggatcctga ggtgaagttc aactggtatg tggatggcgt ggaggtgcac aatgccaaga   1680
ccaagcccag agaggagcag tacaactcta catatagggt ggtgagcgtg ctgaccgtgc   1740
tgcaccagga ctggctgaac ggcaaggagt ataagtgcaa ggtgtccaat aaggccctgc   1800
ccgcccccat cgagaagaca atcagcaagg ccaaggggca gcctcgggag ccacaggtgt   1860
acaccctgcc tccatccaga gacgagctga caaagaacca ggtgtctctg acatgtctgg   1920
tgaagggctt ctatcctagc gatatcgccg tggagtggga gtccaatggc cagccagaga   1980
acaattacaa gaccacaccc cctgtgctgg actccgatgg ctccttcttt ctgtattcca   2040
agctgaccgt ggataagtct cggtggcagc agggcaacgt gttcagctgt tccgtgatgc   2100
acgaagccct gcataatcac tatactcaga aatccctgtc cctgtcacct ggaaagtgat   2160
aagcttaagg gttcgatccc taccggttag taatgagttt gatatctcga caatcaacct   2220
ctggattaca aaatttgtga agattgact  ggtattctta actatgttgc tccttttacg   2280
ctatgtggat acgctgcttt aatgcctttg tatcatgcta ttgcttcccg tatggctttc   2340
attttctcct ccttgtataa atcctggttg ctgtctcttt atgaggagtt gtggcccgtt   2400
gtcaggcaac gtggcgtggt gtgcactgtg tttgctgacg caacccccac tggttggggc   2460
attgccacca cctgtcagct cctttccggg actttcgctt tccccctccc tattgccacg   2520
gcggaactca tcgccgcctg ccttgcccgc tgctggacag ggctctgcc gttgggcact   2580
gacaattccg tggtgttgtc ggggaagctg acgtcctttc catggctgct cgcctgtgtt   2640
gccacctgga ttctgcgcgg gacgtccttc tgctacgtcc cttcggccct caatccagcg   2700
gaccttcctt cccgcggcct gctgccggct ctgcggcctc ttccgcgtct tcgccttcgc   2760
cctcagacga gtcggatctc cctttggcc gcctcccgc ctggaaacgg gggaggctaa   2820
ctgaaacacg gaaggagaca ataccggaag gaacccgcgc tatgacggca ataaaaagac   2880
agaataaaac gcacgggtgt tgggtcgttt gttcataaac gcggggttcg gtcccagggc   2940
tggcactctg tcgataccc  accgagaccc cattgggggc aatacgcccg cgtttcttcc   3000
ttttccccac cccacccccc aagttcgggt gaaggcccag ggctcgcagc caacgtcggg   3060
gcggcaggcc ctgccatagc agatctgcgc agctggggct ctaggggta tccccacgcg   3120
ccctgtagcg gcgcattaag cgcggcgggt gtggtggtta cgcgcagcgt gaccgctaca   3180
cttgccagcg ccctagcgcc cgctcctttc gctttcttcc cttcctttct cgccacgttc   3240
gccggctttc cccgtcaagc tctaaatcgg ggcatccctt tagggttccg atttagtgct   3300
ttacggcacc tcgaccccaa aaaacttgat tagggtgatg gttcacgtag tgggccatcg   3360
ccctgataga cggtttttcg cccttttgacg ttggagtcca cgttctttaa tagtggactc   3420
ttgttccaaa ctggaacaac actcaaccct atctcggtct attctttga  tttataaggg   3480
attttgggga tttcggccta ttggttaaaa aatgagctga tttaacaaaa atttaacgcg   3540
aattaattct gtggaatgtg tgtcagttag ggtgtggaaa gtccccaggc tccccagcag   3600
gcagaagtat gcaaagcatg catctcaatt agtcagcaac caggtgtgga aagtccccag   3660
gctccccagc aggcagaagt atgcaaagca tgcatctcaa ttagtcagca accatagtcc   3720
cgcccctaac tccgcccatc ccgcccctaa ctccgcccag ttccgcccat tctccgcccc   3780
atggctgact aattttttt  atttatgcag aggccgaggc cgcctctgcc tctgagctat   3840
tccagaagta gtgaggaggc ttttttggag gcctaggctt ttgcaaaaag ctccccggag   3900
cttgtatatc cattttcgga tctgatcaag agacaggatg aggatcgttt cgcatgattg   3960
aacaagatgg attgcacgca ggttctccgg ccgcttgggt ggagaggcta ttcggctatg   4020
actgggcaca acagacaatc ggctgctctg atgccgccgt gttccggctg tcagcgcagg   4080
ggcgcccggt tctttttgtc aagaccgacc tgtccggtgc cctgaatgaa ctgcaggacg   4140
aggcagcgcg gctatcgtgg ctggccacga cgggcgttcc ttgcgcagct gtgctcgacg   4200
ttgtcactga agcgggaagg gactggctgc tattgggcga agtgccgggg caggatctcc   4260
tgtcatctca ccttgctcct gccgagaaag tatccatcat ggctgatgca atgcggcgga   4320
tgcatacgct tgatccggct acctgcccat tcgaccacca agcgaaacat cgcatcgagc   4380
gagcacgtac tcggatggaa gccggtcttg tcgatcagga tgatctggac gaagagcatc   4440
aggggctcgc gccagccgaa ctgttcgcca ggctcaaggc gcgcatgccc gacggcgagg   4500
atctcgtcgt gacccatggc gatgcctgct tgccgaatat catggtggaa aatggccgct   4560
tttctggatt catcgactgt ggccggctgg gtgtggcgga ccgctatcag gacatagcgt   4620
tggctacccg tgatattgct gaagagcttg gcggcgaatg ggctgaccgc ttcctcgtgc   4680
tttacggtat cgccgctccc gattcgcagc gcatcgcctt ctatcgcctt cttgacgagt   4740
tcttctgagc gggactctgg ggttcgcgaa atgaccgacc aagcgacgcc caacctgcca   4800
tcacgagatt tcgattccac cgccgccttc tatgaaaggt tgggcttcgg aatcgttttc   4860
cgggacgccg ctggatgat  cctccagcgc ggggatctca tgctggagtt cttcgcccac   4920
cccaacttgt ttattgcagc ttataatggt tacaaataaa gcaatagcat cacaaatttc   4980
acaaataaag catttttttc actgcattct agttgtggtt tgtccaaact catcaatgta   5040
tcttatcatg tctgtatacc gtcgacctct agctaggact tggcgtaatc atggtcatag   5100
ctgtttcctg tgtgaaattg ttatccgctc acaattccac acaacatacg agccggaagc   5160
ataaagtgta aagcctgggg tgcctaatga gtgagctaac tcacattaat tgcgttgcgc   5220
tcactgcccg ctttccagtc gggaaacctg tcgtgccagc tgcattaatg aatcggccaa   5280
cgcgcggga  gaggcggttt gcgtattggg cgctcttccg cttcctcgct cactgactcg   5340
ctgcgctcgg tcgttcggct gcggcgagcg gtatcagctc actcaaaggc ggtaatacgg   5400
ttatccacag aatcagggga taacgcagga agaacatgt  gagcaaaagg ccagcaaaag   5460
gccaggaacc gtaaaaaggc cgcgttgctg gcgtttttcc ataggctccg cccccctgac   5520
gagcatcaca aaaatcgacg ctcaagtcag aggtggcgaa acccgacagg actataaaga   5580
taccaggcgt ttccccctgg aagctccctc gtgcgctctc ctgttccgac cctgccgctt   5640
accggatacc tgtccgcctt tctcccttcg ggaagcgtgg cgctttctca atgctcacgc   5700
tgtaggtatc tcagttcggt gtaggtcgtt cgctccaagc tgggctgtgt gcacgaaccc   5760
cccgttcagc ccgaccgctg cgccttatcc ggtaactatc gtcttgagtc caacccggta   5820
agacacgact tatcgccact ggcagcagcc actggtaaca ggattagcag agcgaggtat   5880
gtaggcggtg ctacagagtt cttgaagtgg tggcctaact acggctacac tagaaggaca   5940
gtatttggta tctgcgctct gctgaagcca gttaccttcg gaaaaagagt tggtagctct   6000
```

-continued

```
tgatccggca aacaaaccac cgctggtagc ggtggttttt ttgtttgcaa gcagcagatt   6060
acgcgcagaa aaaaggatc  tcaagaagat cctttgatct tttctacggg gtctgacgct   6120
cagtggaacg aaaactcacg ttaagggatt ttggtcatga gattatcaaa aaggatcttc   6180
acctagatcc ttttaaatta aaaatgaagt tttaaatcaa tctaaagtat atatgagtaa   6240
acttggtctg acagttacca atgcttaatc agtgaggcac ctatctcagc gatctgtcta   6300
tttcgttcat ccatagttgc ctgactcccc gtcgtgtaga taactacgat acgggagggc   6360
ttaccatctg gccccagtgc tgcaatgata ccgcgagacc cacgctcacc ggctccagat   6420
ttatcagcaa taaaccagcc agccggaagg gccgagcgca gaagtggtcc tgcaacttta   6480
tccgcctcca tccagtctat taattgttgc cgggaagcta gagtaagtag ttcgccagtt   6540
aatagtttgc gcaacgttgt tgccattgct acaggcatcg tggtgtcacg ctcgtcgttt   6600
ggtatggctt cattcagctc cggttccaa  cgatcaaggc gagttacatg atcccccatg   6660
ttgtgcaaaa aagcggttag ctccttcggt cctccgatcg ttgtcagaag taagttggcc   6720
gcagtgttat cactcatggt tatggcagca ctgcataatt ctcttactgt catgccatcc   6780
gtaagatgct tttctgtgac tggtgagtac tcaaccaagt cattctgaga atagtgtatg   6840
cggcgaccga gttgctcttg cccggcgtca atacgggata ataccgcgcc acatagcaga   6900
actttaaaag tgctcatcat tggaaaacgt tcttcggggc gaaaactctc aaggatctta   6960
ccgctgttga tccagttc   gatgtaaccc actcgtgcac ccaactgatc ttcagcatct   7020
tttactttca ccagcgtttc tgggtgagca aaaacaggaa ggcaaaatgc cgcaaaaaag   7080
ggaataaggg cgacacggaa atgttgaata ctcatactct tcctttttca atattattga   7140
agcatttatc agggttattg tctcatgagc ggatacatat ttgaatgtat ttagaaaaat   7200
aaacaaatag gggttccgcg cacatttccc cgaaaagtgc cacctgacgt cgacggatcg   7260
ggagatctcc cgatccccta tggtcgactc tcagtacaat ctgctctgat gccgcatagt   7320
taagccagta tctgctccct gcttgtgtgt tggaggtcgc tgagtagtgc gcgagcaaaa   7380
tttaagctac aacaaggcaa ggcttgaccg acaattgcat gaagaatctg cttagg        7436
```

```
SEQ ID NO: 183       moltype = DNA   length = 7436
FEATURE              Location/Qualifiers
misc_feature         1..7436
                     note = Synthetic polynucleotide
source               1..7436
                     mol_type = other DNA
                     organism = synthetic construct
SEQUENCE: 183
gttaggcgtt ttgcgctgct tcgcgatgta cgggccagat atacgcgttg acattgatta   60
ttgactagtt attaatagta atcaattacg gggtcattag ttcatagccc atatatggag   120
ttccgcgtta cataacttac ggtaaatggc ccgcctggct gaccgcccaa cgacccccgc   180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgccccctat tgacgtcaat gacggtaaat ggcccgcctg gcattatgcc   360
cagtacatga ccttatggga ctttcctact tggcagtaca tctacgtatt agtcatcgct   420
attaccatgg tgatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc cagcctccgg   720
actctagagg atcgaaccct tgaattcccg ccgccaccat gggctggtca tgcattattc   780
tgtttctggt cgcaactgct acaggcgtgc atagtcaggt cagctgcaa  gagtccggac   840
ccggcctcgt gaagccttcc gagacactgt ctctgacctg taccgtgtct ggcttctccc   900
tgtccatcta ctccgtgcac tggatccggc agcctcctgg caagggcctg gaatggctgg   960
gcatgatctg gggcggcgga agctccgact acaactccgc cctgaaatct agactgacca   1020
tctccaagga cacctctaag aaccaggtca gcctgaagct gagctctgtg accgccgctg   1080
ataccgctat gtactactgc gccagaaatg gcaacttcta cgccatggac tattgggggc   1140
agggcaccct ggtgacagtg tcctctgcca gcaccaaggg cccttccgtg tttccactgg   1200
cccctctc   taaatccaca tctggcggca ccgccgccct gggctgtctg gtgaaggact   1260
acttcccaga gcctgtgaca gtgtcctgga actctggcgc cctgacatct ggcgtgcaca   1320
catttccagc cgtgctgcag agctccggcc tgtacagcct gtctagcgtg gtgacagtgc   1380
cctcctctag cctgggcaca cagacctata tctgcaacgt gaatcacaag ccaagcaata   1440
ccaaggtgga caagaaggtg gagcccagt  cctgtgataa gacacacacc tgcccccctt   1500
gtcctgctcc cgagctgctg ggcggcccta gcgtgttcct gtttccaccc aagcctaagg   1560
acaccctgat gatctcccgg acacccgagg tgacctgcgt ggtggtggac gtgtctcacg   1620
aggatcctga ggtgaagttc aactggtatg tggatggcgt ggaggtgcac aatgccaaga   1680
ccaagccag  agaggagcag tacaactcta catatagggt ggtgagcgtg ctgaccgtgc   1740
tgcaccagga ctggctgaac ggcaaggagt ataagtgcaa ggtgtccaat aaggccctgc   1800
cgcccccat  cgagaagaca atcagcaagg ccaagggcca gccacaggtg   1860
acaccctgcc tccatccaga gacgagctga caaagaacca ggtgtctctg acatgtctgg   1920
tgaagggctt ctatcctagc gatatcgccg tggagtggga gtccaatggc cagccagaga   1980
acaattacaa gaccacaccc cctgtgctgg actccgatgg ctccttcttt ctgtattcca   2040
agctgaccgt ggataagtct cggtggcagc agggcaacgt gttcagctgt tccgtgatgc   2100
acgaagccct gcataatcac tatactcaga atccctccac ggaaagtgat   2160
aagcttaagg gttcgatccc taccggttag taatgagttt gatatctcga caatcaacct   2220
ctggattaca aaatttgtga agattgact  ggtattctta actatgttgc tccttttacg   2280
ctatgtggat acgctgcttt aatgcctttg tatcatgcta ttgcttcccg tatggctttc   2340
attttctcct ccttgtataa atcctggttg ctgtctcttt atgaggagtt gtggcccgtt   2400
gtcaggcaac gtggcgtggt gtgcactgtg tttgctgacg caacccccac tggttggggc   2460
attgccacca cctgtcagct cctttccggg actttcgctt tccccctccc tattgccacg   2520
gcggaactca tcgccgcctg ccttgcccgc tgctggacag gggctcggct gttgggcact   2580
gacaattccg tggtgttgtc ggggaagctg acgtcctttc catggctgct cgcctgtgtt   2640
gccacctgga ttctgcgcgg gacgtccttc tgctacgtcc cttcggccct caatccagcg   2700
gaccttcctt cccgcggcct gctgccggct ctgcggcctc ttccgcgtct tcgccttcgc   2760
```

-continued

```
cctcagacga gtcggatctc cctttgggcc gcctccccgc ctggaaacgg gggaggctaa    2820
ctgaaacacg gaaggagaca ataccggaag gaacccgcgc tatgacggca ataaaaagac    2880
agaataaaac gcacgggtgt tgggtcgttt gttcataaac gcggggttcg gtcccagggc    2940
tggcactctg tcgataccccc accgagaccc cattgggggcc aatacgcccg cgtttcttcc    3000
ttttccccac cccacccccc aagttcgggt gaaggcccag ggctcgcagc caacgtcggg    3060
gcggcaggcc ctgccatagc agatctgcgc agctgggggct ctaggggggta tccccacgcg    3120
ccctgtagcg gcgcattaag cgcggcgggt gtggtggtta cgcgcagcgt gaccgctaca    3180
cttgccagcg ccctagcgcc cgctcctttc gctttcttcc cttcctttct cgccacgttc    3240
gccggctttc cccgtcaagc tctaaatcgg ggcatcccctt tagggttccg atttagtgct    3300
ttacggcacc tcgaccccaa aaaacttgat tagggtgatg gttcacgtag tgggccatcg    3360
ccctgataga cggtttttcg cccctttgacg ttggagtcca cgttctttaa tagtggactc    3420
ttgttccaaa ctggaacaac actcaaccct atctcggtct attcttttga tttataaggg    3480
attttgggga tttcggccta ttggttaaaa aatgagctga tttaacaaaa atttaacgcg    3540
aattaattct gtggaatgtg tgtcagttag ggtgtgaaa gtccccaggc tccccagcag    3600
gcagaagtat gcaaagcatg catctcaatt agtcagcaac caggtgtgga aagtccccag    3660
gctccccagc aggcagaagt atgcaaagca tgcatctcaa ttagtcagca accatagtcc    3720
cgcccctaac tccgcccatc ccgcccctaa ctccgcccag ttccgcccat tctccgcccc    3780
atggctgact aatttttttt atttatgcag aggccgaggc cgcctctgcc tctgagctat    3840
tccagaagta gtgaggaggc ttttttttggag gcctaggctt ttgcaaaaag ctcccgggag    3900
cttgtatatc cattttcgga tctgatcaag agacaggatg aggatcgttt cgcatgattg    3960
aacaagatgg attgcacgca ggttctccgg ccgcttgggt ggagaggcta ttcggctatg    4020
actgggcaca acagacaatc ggctgctctg atgccgccgt gttccggctg tcagcgcagg    4080
ggcgcccggt tctttttgtc aagaccgacc tgtccggtgc cctgaatgaa ctgcaggacg    4140
aggcagcgcg gctatcgtgg ctggccacga cgggcgttcc ttgcgcagct gtgctcgacg    4200
ttgtcactga agcgggaagg gactggctgc tattgggcga agtgccgggg caggatctcc    4260
tgtcatctca ccttgctcct gccgagaaag tatccatcat ggctgatgca atgcggcggc    4320
tgcatacgct tgatccggct acctgcccat tcgaccacca agcgaaacat cgcatcgagc    4380
gagcacgtac tcggatggaa gccggtcttg tcgatcagga tgatctggac gaagagcatc    4440
aggggctcgc gccagccgaa ctgttcgcca ggctcaaggc gcgcatgccc gacggcgagg    4500
atctcgtcgt gacccatggc gatgcctgct tgccgaatat catggtggaa aatggccgct    4560
tttctggatt catcgactgt ggccggctgg gtgtggcgga ccgctatcag gacatagcgt    4620
tggctacccg tgatattgct gaagagcttg gcggcgaatg ggctgaccgc ttcctcgtgc    4680
tttacggtat cgccgctccc gattcgcagc gcatcgcctt ctatcgcctt cttgacgagt    4740
tcttctgagc gggactctgg ggttcgcgaa atgaccgacc aagcgacgcc caacctgcca    4800
tcacgagatt tcgattccac cgccgccttc tatgaaaggt tgggcttcgg aatcgttttc    4860
cgggacgccg gctggatgat cctccagcgc ggggatctca tgctggagtt cttcgcccac    4920
cccaacttgt ttattgcagc ttataatggt tacaaataaa gcaatagcat cacaaatttc    4980
acaaataaag cattttttttc actgcattct agttgtggtt tgtccaaact catcaatgta    5040
tcttatcatg tctgtatacc gtcgacctct agctagagct tggctaatc atggtcatag    5100
ctgtttcctg tgtgaaattg ttatccgctc acaattccac acaacatacg agccggaagc    5160
ataaagtgta aagcctgggg tgcctaatga gtgagctaac tcacattaat tgcgttgcgc    5220
tcactgcccg ctttccagtc gggaaacctg tcgtgccagc tgcattaatg aatcggccaa    5280
cgcgcgggga gaggcggttt gcgtattggg cgctcttccg cttcctcgct cactgactcg    5340
ctgcgctcgg tcgttcggct gcggcgagcg gtatcagctc actcaaaggc ggtaatacgg    5400
ttatccacag aatcagggga taacgcagga agaacatgt gagcaaaagg ccagcaaaag    5460
gccaggaacc gtaaaaaggc cgcgttgctg gcgtttttcc ataggctccg cccccctgac    5520
gagcatcaca aaaatcgacg ctcaagtcag aggtggcgaa acccgacagg actataaaga    5580
taccaggcgt ttccccctgg aagctccctc gtgcgctctc ctgttccgac cctgccgctt    5640
accggatacc tgtccgcctt tctcccttcg ggaagcgtgg cgctttctca atgctcacgc    5700
tgtaggtatc tcagttcggt gtaggtcgtt cgctccaagc tgggctgtgt gcacgaaccc    5760
cccgttcagc ccgaccgctg cgccttatcc ggtaactatc gtcttgagtc caacccggta    5820
agacacgact tatcgccact ggcagcagcc actggtaaca ggattagcag agcgaggtat    5880
gtaggcggtg ctacagagtt cttgaagtgg tggcctaact acggctacac tagaaggaca    5940
gtatttggta tctgcgctct gctgaagcca gttaccttcg gaaaaagagt tggtagctct    6000
tgatccggca aacaaaccac cgctggtagc ggtggttttt ttgtttgcaa gcagcagatt    6060
acgcgcagaa aaaaaggatc tcaagaagat cctttgatct tttctacggg gtctgacgct    6120
cagtggaacg aaaactcacg ttaagggatt ttggtcatga gattatcaaa aaggatcttc    6180
acctagatcc ttttaaatta aaaatgaagt tttaaatcaa tctaaagtat atatgagtaa    6240
acttggtctg acagttacca atgcttaatc agtgaggcac ctatctcagc gatctgtcta    6300
tttcgttcat ccatagttgc ctgactcccc gtcgtgtaga taactacgat acgggagggc    6360
ttaccatctg gccccagtgc tgcaatgata ccgcgagacc cacgctcacc ggctccagat    6420
ttatcagcaa taaaccagcc agccggaagg gccgagcgca gaagtggtcc tgcaacttta    6480
tccgcctcca tccagtctat taattgttgc cgggaagcta gagtaagtag ttcgccagtt    6540
aatagtttgc gcaacgttgt tgccattgct acaggcatcg tggtgtcacg ctcgtcgttt    6600
ggtatggctt cattcagctc cggttcccaa cgatcaaggc gagttacatg atcccccatg    6660
ttgtgcaaaa aagcggttag ctccttcggt cctccgatcg ttgtcagaag taagttggcc    6720
gcagtgttat cactcatggt tatggcagca ctgcataatt ctcttactgt catgccatcc    6780
gtaagatgct tttctgtgac tggtgagtac tcaaccaagt cattctgaga atagtgtatg    6840
cggcgaccga gttgctcttg cccggcgtca atacgggata ataccgcgcc acatagcaga    6900
actttaaaag tgctcatcat tggaaaacgt tcttcggggc gaaaactctc aaggatctta    6960
ccgctgttga tccagttcga tgtaacccca ctcgtgcac ccaactgatc ttcagcatct    7020
tttactttca ccagcgtttc tgggtgagca aaaacaggaa ggcaaaatgc cgcaaaaaag    7080
ggaataaggg cgacacggaa atgttgaata ctcatactct tcctttttca atattattga    7140
agcatttatc agggttattg tctcatgagc ggatacatat ttgaatgtat ttagaaaaat    7200
aaacaaatag gggttccgcg cacatttccc cgaaaagtgc cacctgacgt cgacggatcg    7260
ggagatctcc cgatccccta tggtcgactc tcagtacaat ctgctctgat gccgcatagt    7320
taagccagta tctgctccct gcttgtgtgt tggaggtcgc tgagtagtgc gcgagcaaaa    7380
tttaagctac aacaaggcaa ggcttgaccg acaattgcat gaagaatctg cttagg       7436
```

-continued

```
SEQ ID NO: 184      moltype = DNA   length = 6746
FEATURE             Location/Qualifiers
misc_feature        1..6746
                    note = Synthetic polynucleotide
source              1..6746
                    mol_type = other DNA
                    organism = synthetic construct SEQUENCE: 184
gttaggcgtt ttgcgctgct tcgcgatgta cgggccagat atacgcgttg acattgatta   60
ttgactagtt attaatagta atcaattacg gggtcattag ttcatagccc atatatggag   120
ttccgcgtta cataacttac ggtaaatggc ccgcctggct gaccgcccaa cgaccccgc   180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgcccccctat tgacgtcaat gacggtaaat ggcccgcctg gcattatgcc   360
cagtacatga ccttatggga ctttcctact tggcagtaca tctacgtatt agtcatcgct   420
attaccatgg tgatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc cagcctccgg   720
actctagagg atcgaaccct tgaattcccg ccgccaccat gggctggtca tgtattattc   780
tgtttctggt cgcaactgct acagggggtcc atagtgagat cgtgctgacc caatctccag   840
gcaccctgtc tctcagccct ggcgagagag ccaccctgtc ctgcaccgct tctagctccg   900
tgtcctccag cttcctgcac tggtaccagc agaaacccgg ccaggctcct agactgctga   960
tctattccac ctccaacctg gcctctggca tccctgaccg gttctccggc tctggctccg   1020
gaacagattt tacactgacc atctcccggc tggaacctga gagttacatc aagttgtact   1080
gtcaccagta ccaccattct ccttacatct acaccttcgg cggcggaacc aagctggaaa   1140
tcaagaggac agtggccgcc caagcgtgt tcatctttcc cccttccgac gagcagctga   1200
agtctggcac cgccagcgtg gtgtgcctgc tgaacaactt ctaccctcgg gaggccaagg   1260
tccagtggaa ggtggataac gccctgcagt ctggcaatag ccaggagtcc gtgaccgagc   1320
aggactctaa ggatagcaca tattccctgt ctagcaccct gacactgagc aaggccgatt   1380
acgagaagca caaggtgtat gcctgtgaag tcacccatca ggggctgtca tcacccgtca   1440
ctaagtcatt caatcgcgga gaatgctgat aagcttaagg gttcgatccc taccggttag   1500
taatgagttt gatatctcga caatcaacct ctggattaca aaatttgtga aagattgact   1560
ggtattctta actatgttgc tccttttacg ctatgtggat acgctgcttt aatgcctttg   1620
tatcatgcta ttgcttccg tatggctttc attttctcct ccttgtataa atcctggttg   1680
ctgtctcttt atgaggagtt gtggcccgtt gtcaggcaac gtggcgtggt gtgcactgtg   1740
tttgctgacg caaccccac tggttggggc attgccacca cctgtcagct cctttccggg   1800
actttcgctt tccccctccc tattgccacg cggaactca tcgccgcctg ccttgcccgc   1860
tgctggacag gggctcggct gttgggcact gacaattccg tggtgttgtc ggggaagctg   1920
acgtcctttc catggctgct cgcctgtgtt gccacctgga ttctgcgcgg gacgtccttc   1980
tgctacgtcc cttcggccct caatccagcg gaccttcctt cccgcggcct gctgccggct   2040
ctgcggcctc ttccgcgtct tcgccttcgc cctcagacga gtcggatctc cctttgggag   2100
gcctcccgc ctggaaacgg gggaggctaa ctgaaacacg gaaggagaca ataccggaag   2160
gaacccgcgc tatgacggca ataaaaagac agaataaaac gcacgggtgt tgggtcgttt   2220
gttcataaac gcggggttcg gtcccagggc tggcactctg tcgataccc accgagaccc   2280
cattggggcc aatacgcccg cgtttcttcc ttttccccac cccacccccc aagttcgggt   2340
gaaggcccag ggctcgcagc caacgtcggg gcggcaggcc ctgccatagc agatctgcgc   2400
agctggggct ctagggggta tccccacgcg ccctgtagcg gcgcattaag cgcggcgggt   2460
gtggtggtta cgcgcagcgt gaccgctaca cttgccagcg ccctagcgcc cgctcctttc   2520
gctttcttcc cttcctttct cgccacgttc gccggctttc cccgtcaagc tctaaatcgg   2580
ggcatccctt tagggttccg atttagtgct ttacggcacc tcgaccccaa aaaacttgat   2640
tagggtgatg gttcacgtag tgggccatcg ccctgataga cggttttttcg ccctttgacg   2700
ttggagtcca cgttctttaa tagtggactc ttgttccaaa ctggaacaac actcaaccct   2760
atctcggtct attcttttga tttataaggg attttgggga tttcggcctta ttggttaaaa   2820
aatgagctga tttaacaaaa atttaacgcg aattaattct gtggaatgtg tgtcagttag   2880
ggtgtggaaa gtccccaggc tccccagcag cagaagtat gcaaagcatg catctcaatt   2940
agtcagcaac caggtgtgga aagtccccag gctccccagc aggcagaagt atgcaaagca   3000
tgcatctcaa ttagtcagca accatagtcc cgccccctaac tccgcccatc ccgcccctaa   3060
ctccgcccag ttccgcccat tctccgcccc atggctgact aatttttttt atttatgcag   3120
aggccgaggc cgcctctgcc tctgagctat tccagaagta gtgaggaggc ttttttggag   3180
gcctaggctt ttgcaaaaag ctcccgggag cttgtatatc cattttcgga tctgatcaag   3240
agacaggatg aggatcgttt cgcatgattg aacaagatgg attgcacgca ggttctccgg   3300
ccgcttgggt ggagaggcta ttcggctatg actgggcaca acagacaatc ggctgctctg   3360
atgccgccgt gttccggctg tcagcgcagg ggcgcccggt tctttttgtc aagaccgacc   3420
tgtccggtgc cctgaatgaa ctgcaggacg aggcagcgcg gctatcgtgg ctggccacga   3480
cgggcgttcc ttgcgcagct gtgctcgacg ttgtcactga agcgggaagg gactggctgc   3540
tattgggcga agtgccgggg caggatctcc tgtcatctca ccttgctcct gccgagaaag   3600
tatccatcat ggctgatgca atgcggcggc tgcatacgct tgatccggct acctgcccat   3660
tcgaccacca agcgaaacat cgcatcgagc gagcacgtac tcggatggaa gccggtcttg   3720
tcgatcagga tgatctggac gaagagcatc aggggctcgc gccagccgaa ctgttcgcca   3780
ggctcaaggc gcgcatgccc gacggcgagg atctcgtcgt gacccatggc gatgcctgct   3840
tgccgaatat catggtggaa aatggccgct tttctggatt catcgactgt ggccggctgg   3900
gtgtggcgga ccgctatcag gacatagcgt tggctacccg tgatattgct gaagagcttg   3960
gcggcgaatg ggctgaccgc ttcctcgtgc tttacggtat cgccgctccc gattcgcagc   4020
gcatcgcctt ctatcgcctt cttgacgagt tcttctgagc gggactctgg ggttcgcgaa   4080
atgaccgacc aagcgacgcc caacctgcca tcacgagatt cgattccac cgccgccttc   4140
tatgaaaggt tgggcttcgg aatcgttttc cgggacgccg gctggatgat cctccagcgc   4200
ggggatctca tgctggagtt cttcgcccac cccaacttgt ttattgcagc ttataatggt   4260
```

```
tacaaataaa gcaatagcat cacaaatttc acaaataaag cattttttttc actgcattct  4320
agttgtggtt tgtccaaact catcaatgta tcttatcatg tctgtatacc gtcgacctct  4380
agctagagct tggcgtaatc atggtcatag ctgtttcctg tgtgaaattg ttatccgctc  4440
acaattccac acaacatacg agccggaagc ataaagtgta aagcctgggg tgcctaatga  4500
gtgagctaac tcacattaat tgcgttgcgc tcactgcccg ctttccagtc gggaaacctg  4560
tcgtgccagc tgcattaatg aatcggccaa cgcgcgggga gaggcggttt gcgtattggg  4620
cgctcttccg cttcctcgct cactgactcg ctgcgctcgg tcgttcggct gcggcgagcg  4680
gtatcagctc actcaaaggc ggtaatacgg ttatccacag aatcagggga taacgcagga  4740
aagaacatgt gagcaaaagg ccagcaaaag gccaggaacc gtaaaaaggc cgcgttgctg  4800
gcgtttttcc ataggctccg cccccctgac gagcatcaca aaaatcgacg ctcaagtcag  4860
aggtggcgaa acccgacagg actataaaga taccaggcgt ttcccccctgg aagctccctc  4920
gtgcgctctc ctgttccgac cctgccgctt accggatacc tgtccgcctt tctcccttcg  4980
ggaagcgtgg cgctttctca atgctcacgc tgtaggtatc tcagttcggt gtaggtcgtt  5040
cgctccaagc tgggctgtgt gcacgaaccc cccgttcagc ccgaccgctg cgccttatcc  5100
ggtaactatc gtcttgagtc caacccggta agacacgact tatcgccact ggcagcagcc  5160
actggtaaca ggattagcag agcgaggtat gtaggcggtg ctacagagtt cttgaagtgg  5220
tggcctaact acggctacac tagaaggaca gtatttggta tctgcgctct gctgaagcca  5280
gttaccttcg gaaaaagagt tggtagctct tgatccggca aacaaaccac cgctggtagc  5340
ggtggttttt ttgtttgcaa gcagcagatt acgcgcagaa aaaaaggatc tcaagaagat  5400
cctttgatct tttctacggg gtctgacgct cagtggaacg aaaactcacg ttaagggatt  5460
ttggtcatga gattatcaaa aaggatcttc acctagatcc ttttaaatta aaaatgaagt  5520
tttaaatcaa tctaaagtat atatgagtaa acttggtctg acagttacca atgcttaatc  5580
agtgaggcac ctatctcagc gatctgtcta tttcgttcat ccatagttgc ctgactcccc  5640
gtcgtgtaga taactacgat acgggagggc ttaccatctg gccccagtgc tgcaatgata  5700
ccgcgagacc cacgctcacc ggctccagat ttatcagcaa taaaccagcc agccggaagg  5760
gccgagcgca gaagtggtcc tgcaacttta tccgcctcca tccagtctat taattgttgc  5820
cgggaagcta gagtaagtag ttcgccagtt aatagtttgc gcaacgttgt tgccattgct  5880
acaggcatcg tggtgtcacg ctcgtcgttt ggtatggctt cattcagctc cggttcccaa  5940
cgatcaaggc gagttacatg atcccccatg ttgtgcaaaa aagcggttag ctccttcggt  6000
cctccgatcg ttgtcagaag taagttggcc gcagtgttat cactcatggt tatggcagca  6060
ctgcataatt ctcttactgt catgccatcc gtaagatgct tttctgtgac tggtgagtac  6120
tcaaccaagt cattctgaga atagtgtatg cggcgaccga gttgctcttg cccggcgtca  6180
atacgggata ataccgcgcc acatagcaga actttaaaag tgctcatcat tggaaaacgt  6240
tcttcggggc gaaaactctc aaggatctta ccgctgttga gatccagttc gatgtaaccc  6300
actcgtgcac ccaactgatc ttcagcatct tttactttca ccagcgtttc tgggtgagca  6360
aaaacaggaa ggcaaaatgc cgcaaaaaag ggaataaggg cgacacggaa atgttgaata  6420
ctcatactct tcctttttca atattattga agcatttatc agggttattg tctcatgagc  6480
ggatacatat ttgaatgtat ttagaaaaat aaacaaatag gggttccgcg cacatttccc  6540
cgaaaagtgc cacctgacgt cgacggatcg gggagatccc cgatccccta tggtcgactc  6600
tcagtacaat ctgctctgat gccgcatagt taagccagta tctgctccct gcttgtgtgt  6660
tggaggtcgc tgagtagtgc gcgagcaaaa tttaagctac aacaaggcaa ggcttgaccg  6720
acaattgcat gaagaatctg cttagg                                       6746
```

SEQ ID NO: 185          moltype = DNA   length = 6746
FEATURE                 Location/Qualifiers
misc_feature            1..6746
                        note = Synthetic polynucleotide
source                  1..6746
                        mol_type = other DNA
                        organism = synthetic construct
SEQUENCE: 185

```
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgcccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatgggg agtttgtttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct tgaattcccg ccgccacta gggcggtgtca tgtattattc  780
tgtttctggt cgcaactgct acaggggtcc atagtgagat cgtgctgaca caatctcccc  840
gcaccctcag cctgtctcca ggcgagagag ccacactgtc ctgcaccgct tctagctccg  900
tgtcctccac ctttctgcac tggtaccagc agaaacctgg ccaggctcct cagctgtgga  960
tctactccac ctccaacctg gcctctggca tccctgatcg gttctccggc tccggctctg  1020
gcaccgacta caccctgacc atctccagac tggaacctga gacttcgcc gtgtactact  1080
gtcaccagta ccaccattct ccttacatct ataccttcgg cggaggaacc aagctggaaa  1140
tcaagaggac agtggccgcc ccaagcgtgt tcatctttcc ccttccgac gagcagctga  1200
agtctggcac cgccagcgtg gtgtgcctgc tgaacaactt ctaccctcgg gaggccaag  1260
tccagtggaa ggtggataac gccctgcagt ctggcaatag ccaggagtcc gtgaccgagc  1320
aggactctaa ggatagcaca tattccctgt ctagcaccct gacactgagc aaggccgatt  1380
acgagaagca caaggtgtat gcctgtgaag tcacccatca ggggctgtca tcacccgtca  1440
ctaagtcatt caatcgcgga gaatgctgat aagcttaagg gttcgatccc taccggttag  1500
taatgagttt gatatctcga caatcaacct ctggattaca aaatttgtga agattgact  1560
ggtattctta actatgttgc tccttttacg ctatgtggat acgctgcttt aatgcctttg  1620
tatcatgcta ttgcttcccg tatggctttc attttctcct ccttgtataa atcctggttg  1680
```

-continued

```
ctgtctcttt atgaggagtt gtggcccgtt gtcaggcaac gtggcgtggt gtgcactgtg   1740
tttgctgacg caaccccac tggttggggc attgccacca cctgtcagct cctttccggg     1800
actttcgctt tccccctccc tattgccacg gcggaactca tcgccgcctg ccttgcccgc    1860
tgctggacag gggctcggct gttgggcact gacaattccg tggtgttgtc ggggaagctg    1920
acgtcctttc catggctgct cgcctgtgtt gccacctgga ttctgcgcgg gacgtccttc    1980
tgctacgtcc cttcggccct caatccagcg gaccttcctt cccgcggcct gctgccggct    2040
ctgcggcctc ttccgcgtct tcgccttcgc cctcagacga gtcggatctc cctttggggcc   2100
gcctccccgc ctggaaacgg gggaggctaa ctgaaacacg gaaggagaca ataccggaag    2160
gaacccgcgc tatgacggca ataaaaagac agaataaaac gcacgggtgt tgggtcgttt     2220
gttcataaac gcggggttcg gtcccagggc tggcactctg tcgatacccc accgagaccc     2280
cattgggggcc aatacgcccg cgtttcttcc ttttccccac cccacccccc aagttcgggt    2340
gaaggcccag ggctcgcagc caacgtcggg gcggcaggcc ctgccatagc agatctgcgc     2400
agctggggct ctaggggggta tccccacgcg ccctgtagcg gcgcattaag cgcggcgggt    2460
gtggtggtta cgcgcagcgt gaccgctaca cttgccaggg ccctagcgcc cgctccttc     2520
gctttcttcc cttcctttct cgccacgttc gccggctttc cccgtcaagc tctaaatcgg     2580
ggcatccctt tagggttccg atttagtgct ttacggcacc tcgaccccaa aaaacttgat     2640
tagggtgatg gttcacgtag tgggccatcg ccctgataga cggttttttcg ccctttgacg    2700
ttggagtcca cgttctttaa tagtggactc ttgttccaaa ctggaacaac actcaaccct     2760
atctcggtct attcttttga tttataaggg attttggggga tttcggccta ttggttaaaa     2820
aatgagctga tttaacaaaa atttaacgcg aattaattct gtggaatgtg tgtcagttag     2880
ggtgtggaaa gtccccaggc tccccagcag gcagaagtat gcaaagcatg catctcaatt     2940
agtcagcaac caggtgtgga aagtccccag gctccccagc aggcagaagt atgcaaagca     3000
tgcatctcaa ttagtcagca accatagtcc cgcccctaac tccgcccatc ccgcccctaa    3060
ctccgcccag ttccgcccat tctccgcccc atggctgact aatttttttt atttatgcag     3120
aggccgaggc cgcctctgcc tctgagctat tccagaagta gtgaggaggc ttttttggag    3180
gcctaggctt ttgcaaaaag ctcccgggag cttgtatatc cattttcgga tctgatcaag    3240
agacaggatg aggatcgttt cgcatgattg aacaagatgg attgcacgca ggttctccgg    3300
ccgcttgggt ggagaggcta ttcggctatg actgggcaca acagacaatc ggctgctctg    3360
atgccgccgt gttccggctg tcagcgcagg ggcgcccggt tctttttgtc aagaccgacc    3420
tgtccggtgc cctgaatgaa ctgcaggacg aggcagcgcg gctatcgtgg ctggccacga    3480
cgggcgttcc ttgcgcagct gtgctcgacg ttgtcactga agcgggaagg gactggctgc    3540
tattgggcga gtgccggggg caggatctcc tgtcatctca ccttgctcct gccgagaaag    3600
tatccatcat ggctgatgca atgcggcggc tgcatacgct tgatccggct acctgcccat    3660
tcgaccacca agcgaaacat cgcatcgagc gagcacgtac tcggatggaa gccggtcttg    3720
tcgatcagga tgatctggac gaagagcatc aggggctcgc gccagccgaa ctgttcgcca    3780
ggctcaaggc gcgcatgccc gacggcgagg atctcgtcgt gacccatggc gatgcctgct    3840
tgccgaatat catggtggaa aatggccgct tttctggatt catcgactgt ggccggctgg    3900
gtgtggcgga ccgctatcag gacatagcgt tggctacccg tgatattgct gaagagcttg    3960
gcggcgaatg ggctgaccgc ttcctcgtgc tttacggtat cgccgctccc gattcgcagc    4020
gcatcgcctt ctatcgcctt cttgacgagt tcttctgagc gggactctgg ggttcgcgaa    4080
atgaccgacc aagcgacgcc caacctgcca tcacgagatt tcgattccac cgccgccttc    4140
tatgaaaggt tgggcttcgg aatcgttttc cgggacgccg gctggatgat cctccagcgc     4200
ggggatctca tgctggagtt cttcgcccac cccaacttgt ttattgcagc ttataatggt    4260
tacaaataaa gcaatagcat cacaaatttc acaaataaag catttttttc actgcattct     4320
agttgtggtt tgtccaaact catcaatgta tcttatcatg tctgtatacc gtcgacctct     4380
agctagagct tggcgtaatc atggtcatag ctgtttcctg tgtgaaattg ttatccgctc     4440
acaattccac acaacatacg agccggaagc ataaagtgta aagcctgggg tgcctaatga    4500
gtgagctaac tcacattaat tgcgttgcgc tcactgcccg ctttccagtc gggaaacctg    4560
tcgtgccagc tgcattaatg aatcggccaa cgcgcgggga gaggcggttt gcgtattggg    4620
cgctcttccg cttcctcgct cactgactcg ctgcgctcgg tcgttcggct gcggcgagcg    4680
gtatcagctc actcaaaggc ggtaatacgg ttatccacag aatcagggga taacgcagga   4740
aagaacatgt gagcaaaagg ccagcaaaag gccaggaacc gtaaaaaggc cgcgttgctg    4800
gcgtttttcc ataggctccg cccccctgac gagcatcaca aaaatcgacg ctcaagtcag    4860
aggtggcgaa acccgacagg actataaaga taccaggcgt ttccccctgg aagctccctc     4920
gtgcgctctc ctgttccgac cctgccgctt accggatacc tgtccgcctt tctccccttcg    4980
ggaagcgtgg cgctttctca atgctcacgc tgtaggtatc tcagttcggt gtaggtcgtt    5040
cgctccaagc tgggctgtgt gcacgaaccc cccgttcagc ccgaccgctg cgccttatcc    5100
ggtaactatc gtcttgagtc caacccggta agacacgact tatcgccact ggcagcagcc    5160
actggtaaca ggattagcag agcgaggtat gtaggcggtg ctacagagtt cttgaagtgg    5220
tggcctaact acggctacac tagaaggaca gtatttggta tctgcgctct gctgaagcca    5280
gttaccttcg gaaaaagagt tggtagctct tgatccggca aacaaaccac cgctggtagc    5340
ggtggttttt ttgtttgcaa gcagcagatt acgcgcagaa aaaaaggatc tcaagaagat   5400
cctttgatct tttctacggg gtctgacgct cagtggaacg aaaactcacg ttaagggatt    5460
ttggtcatga gattatcaaa aaggatcttc acctagatcc ttttaaatta aaaatgaagt    5520
tttaaatcaa tctaaagtat atatgagtaa acttggtctg acagttacca atgcttaatc    5580
agtgaggcac ctatctcagc gatctgtcta tttcgttcat ccatagttgc ctgactcccc    5640
gtcgtgtaga taactacgat acgggagggc ttaccatctg gccccagtgc tgcaatgata    5700
ccgcgagacc cacgctcacc ggctccagat ttatcagcaa taaaccagcc agccggaagg    5760
gccgagcgca gaagtggtcc tgcaacttta tccgcctcca tccagtctat taattgttgc    5820
cgggaagcta gagtaagtag ttcgccagtt aatagtttgc gcaacgttgt tgccattgct    5880
acaggcatcg tggtgtcacg ctcgtcgttt ggtatggctt cattcagctc cggttcccaa    5940
cgatcaaggc gagttacatg atcccccatg ttgtgcaaaa aagcggttag ctccttcggt     6000
cctccgatcg ttgtcagaag taagttggcc gcagtgttat cactcatggt tatggcagca    6060
ctgcataatt ctcttactgt catgccatcc gtaagatgct tttctgtgac tggtgagtac    6120
tcaaccaagt cattctgaga atagtgtatg cggcgaccga gttgctcttg cccggcgtca   6180
atacgggata ataccgcgcc acatagcaga actttaaaag tgctcatcat tggaaaacgt    6240
tcttcgggggc gaaaactctc aaggatctta ccgctgttga tccagttc gatgtaaccc    6300
actcgtgcac ccaactgatc ttcagcatct tttactttca ccagcgtttc tgggtgagca    6360
aaaacaggaa ggcaaaatgc cgcaaaaaag ggaataaggg cgacacggaa atgttgaata    6420
```

```
ctcatactct tccttttca atattattga agcatttatc aggggttattg tctcatgagc   6480
ggatacatat ttgaatgtat ttagaaaaat aaacaaatag gggttccgcg cacatttccc   6540
cgaaaagtgc cacctgacgt cgacggatcg ggagatctcc cgatccccta tggtcgactc   6600
tcagtacaat ctgctctgat gccgcatagt taagccagta tctgctccct gcttgtgtgt   6660
tggaggtcgc tgagtagtgc gcgagcaaaa tttaagctac aacaaggcaa ggcttgaccg   6720
acaattgcat gaagaatctg cttagg                                       6746

SEQ ID NO: 186          moltype = DNA   length = 6746
FEATURE                 Location/Qualifiers
misc_feature            1..6746
                        note = Synthetic polynucleotide
source                  1..6746
                        mol_type = other DNA
                        organism = synthetic construct
SEQUENCE: 186
gttaggcgtt ttgcgctgct tcgcgatgta cgggccagat atacgcgttg acattgatta    60
ttgactagtt attaatagta atcaattacg gggtcattag ttcatagccc atatatggag   120
ttccgcgtta cataacttac ggtaaatggc ccgcctggct gaccgcccaa cgacccccgc   180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgcccctat tgacgtcaat gacggtaaat ggcccgcctg gcattatgcc   360
cagtacatga cctatatggga ctttcctact tggcagtaca tctacgtatt agtcatcgct   420
attaccatgg tgatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgtt tgacctccat agaagacacc gggaccgatc cagcctccgg   720
actctagagg atcgaaccct tgaattcccg ccgccaccat gggctggtca tgtattattc   780
tgtttctggt cgcaactgct acaggggtcc atagtgagat cgtgctgacc cagtctccag   840
gcacactcag cctgtctcct ggcgagcggg ctaccctggc ctgcaccgcc agcagctccg   900
tgtcctcttc ttttctgcac tggtaccagc agaaacctgg acaagctcct cagctgtgga   960
tctactccac ctccaacctg gcctctggca tccccgatag attctccggc tctggctccg  1020
gcaccgacta cacactgacc atctccagac tggaacctga ggacttcgcc acctactact  1080
gtcatcagta ccaccactcc ccttacatct ataccttcgg cggaggcacc aagctggaaa  1140
tcaagaggac agtggccgcc ccaagcgtgt tcatcttcc ccttccgac gagcagctga  1200
agtctggcac cgccagcgtg gtgtgcctgc tgaacaactt ctaccctcgg gaggccaagg  1260
tccagtggaa ggtggataac gccctgcagt ctggcaatag ccaggagtcc gtgaccgagc  1320
aggactctaa ggatagcaca tattccctgt ctagcaccct gacactgagc aaggccgatt  1380
acgagaagca caaggtgtat gcctgtgaag tcacccatca ggggctgtca tcacccgtca  1440
ctaagtcatt caatcgcgga gaatgctgat aagcttaagg gttcgatccc taccggttag  1500
taatgagttt gatatctcga caatcaacct ctggattaca aaatttgtga agagattgact  1560
ggtattctta actatgttgc tccttttacg ctatgtggat acgctgcttt aatgcctttg  1620
tatcatgcta ttgcttcccg tatggctttc attttctcct ccttgtataa atcctggttg  1680
ctgtctcttt atgaggagtt gtggcccgtt gtcaggcaac gtggcgtggt gtgcactgtg  1740
tttgctgacg caacccccac tggttggggc attgccacca cctgtcagct cctttccggg  1800
actttcgctt tccccctccc tattgccacg gcggaactca tcgccgcctg ccttgcccgc  1860
tgctggacag gggctcggct gttgggcact gacaattccg tggtgttgtc ggggaagctg  1920
acgtcctttc catggctgct cgcctgtgtt gccacctgga ttctgcgcgg gacgtccttc  1980
tgctacgtcc cttcggccct caatccagcg gaccttcctt cccgcggcct gctgccggct  2040
ctgcggcctc ttccgcgtct tcgccttcgc cctcagacga gtcggatctc cctttgggcc  2100
gcctccccgc ctggaaacgg gggaggctaa ctgaaacacg gaaggagaca ataccggaag  2160
gaacccgcgc tatgacggca ataaaaagac agaataaaac gcacgggtgt tgggtcgttt  2220
gttcataaac gcggggttcg gtcccagggc tggcactctg tcgataccc accgagaccc  2280
cattggggcc aatacgcccg cgtttcttcc ttttccccac cccaccccc aagttcgggt  2340
gaaggcccag ggctcgcagc caacgtcggg gcggcaggcc ctgccatagc agatctgcgc  2400
agctggggct ctaggggggta tccccacgcg ccctgtagcg gcgcattaag cgcggcgggt  2460
gtggtggtta cgcgcagcgt gaccgctaca cttgccagcg ccctagcgcc cgctcctttc  2520
gctttcttcc cttcctttct cgccacgttc gccggctttc cccgtcaagc tctaaatcgg  2580
ggcatccctt tagggttccg atttagtgct ttacggcacc tcgaccccaa aaaacttgat  2640
tagggtgatg gttcacgtag tgggccatcg ccctgataga cggtttttcg ccctttgacg  2700
ttggagtcca cgttctttaa tagtggactc ttgttccaaa ctggaacaac actcaaccct  2760
atctcggtct attcttttga tttataaggg attttgggga tttcggccta ttggttaaaa  2820
aatgagctga tttaacaaaa atttaacgcg aattaattct gtggaatgtg tgtcagttag  2880
ggtgtgaaa gtccccaggc tccccagcag gcagaagtat gcaaagcatg catctcaatt  2940
agtcagcaac caggtgtgga aagtccccag gctccccagc aggcagaagt atgcaaagca  3000
tgcatctcaa ttagtcagca accatagtcc cgcccctaac tccgcccatc ccgcccctaa  3060
ctccgcccag ttccgcccat tctccgcccc atggctgact aattttttt atttatgcag  3120
aggccgaggc cgcctctgcc tctgagctat tccagaagta gtgaggaggc ttttttggag  3180
gcctaggctt ttgcaaaaag ctcccgggag cttgtatatc cattttcgga tctgatcaag  3240
agacaggatg aggatcgttt cgcatgattg aacaagatgg attgcacgca ggttctccgg  3300
ccgcttgggt ggagaggcta ttcggctatg actgggcaca acagacaatc ggctgctctg  3360
atgccgcccg ttccggctg tcagcgcagg ggcgcccggg tcttttgtc aagaccgacc  3420
tgtccggtgc cctgaatgaa ctgcaggacg aggcagcgcg gctatcgtgg ctggccacga  3480
cgggcgttcc ttgcgcagct gtgctcgacg ttgtcactga agcgggaagg gactggctgc  3540
tattgggcga agtgccgggg caggatctcc tgtcatctca ccttgctcct gccgagaaag  3600
tatccatcat ggctgatgca atgcggcggc tgcatacgct tgatccggct acctgcccat  3660
tcgaccacca agcgaaacat cgcatcgagc gagcacgtac tcggatggaa gccggtcttg  3720
tcgatcagga tgatctggac gaagagcatc aggggctcgc gccagccgaa ctgttcgcca  3780
ggctcaaggc gcgcatgccc gacggcgagg atctcgtcgt gacccatggc gatgcctgct  3840
```

-continued

```
tgccgaatat catggtggaa aatggccgct tttctggatt catcgactgt ggccggctgg   3900
gtgtggcgga ccgctatcag gacatagcgt tggctacccg tgatattgct gaagagcttg   3960
gcggcgaatg ggctgaccgc ttcctcgtgc tttacggtat cgccgctccc gattcgcagc   4020
gcatcgcctt ctatcgcctt cttgacgagt tcttctgagc gggactctgg ggttcgcgaa   4080
atgaccgacc aagcgacgcc caacctgcca tcacgagatt tcgattccac cgccgccttc   4140
tatgaaaggt tgggcttcgg aatcgttttc cgggacgccg gctggatgat cctccagcgc   4200
ggggatctca tgctggagtt cttcgcccac cccaacttgt ttattgcagc ttataatggt   4260
tacaaataaa gcaatagcat cacaaatttc acaaataaag catttttttc actgcattct   4320
agttgtggtt tgtccaaact catcaatgta tcttatcatg tctgtatacc gtcgacctct   4380
agctagagct tggcgtaatc atggtcatag ctgtttcctg tgtgaaattg ttatccgctc   4440
acaattccac acaacatacg agccggaagc ataaagtgta aagcctgggg tgcctaatga   4500
gtgagctaac tcacattaat tgcgttgcgc tcactgcccg ctttccagtc gggaaacctg   4560
tcgtgccagc tgcattaatg aatcggccaa cgcgcgggga gaggcggttt gcgtattggg   4620
cgctcttccg cttcctcgct cactgactcg ctgcgctcgg tcgttcggct gcggcgagcg   4680
gtatcagctc actcaaaggc ggtaatacgg ttatccacag aatcagggga taacgcagga   4740
aagaacatgt gagcaaaagg ccagcaaaag gccaggaacc gtaaaaaggc cgcgttgctg   4800
gcgtttttcc ataggctccg cccccctgac gagcatcaca aaaatcgacg ctcaagtcag   4860
aggtggcgaa acccgacagg actataaaga taccaggcgt ttccccctgg aagctccctc   4920
gtgcgctctc ctgttccgac cctgccgctt accggatacc tgtccgcctt tctcccttcg   4980
ggaagcgtgg cgctttctca atgctcacgc tgtaggtatc tcagttcggt gtaggtcgtt   5040
cgctccaagc tgggctgtgt gcacgaaccc ccgttcagc ccgaccgctg cgccttatcc   5100
ggtaactatc gtcttgagtc caacccggta agacacgact tatcgccact ggcagcagcc   5160
actggtaaca ggattagcag agcgaggtat gtaggcggtg ctacagagtt cttgaagtgg   5220
tggcctaact acggctacac tagaaggaca gtatttggta tctgcgctct gctgaagcca   5280
gttaccttcg gaaaaagagt tggtagctct tgatccggca aacaaaccac cgctggtagc   5340
ggtggttttt ttgtttgcaa gcagcagatt acgcgcagaa aaaaaggatc tcaagaagat   5400
cctttgatct tttctacggg gtctgacgct cagtggaacg aaaactcacg ttaagggatt   5460
ttggtcatga gattatcaaa aaggatcttc acctagatcc ttttaaatta aaaatgaagt   5520
tttaaatcaa tctaaagtat atatgagtaa acttggtctg acagttacca atgcttaatc   5580
agtgaggcac ctatctcagc gatctgtcta tttcgttcat ccatagttgc ctgactcccc   5640
gtcgtgtaga taactacgat acgggagggc ttaccatctg gccccagtgc tgcaatgata   5700
ccgcgagacc cacgctcacc ggctccagat ttatcagcaa taaaccagcc agccggaagg   5760
gccgagcgca gaagtggtcc tgcaacttta tccgcctcca tccagtctat taattgttgc   5820
cgggaagcta gagtaagtag ttcgccagtt aatagtttgc gcaacgttgt tgccattgct   5880
acaggcatcg tggtgtcacg ctcgtcgttt ggtatggctt cattcagctc cggttcccaa   5940
cgatcaaggc gagttacatg atcccccatg ttgtgcaaaa aagcggttag ctccttcggt   6000
cctccgatcg ttgtcagaag taagttggcc gcagtgttat cactcatggt tatggcagca   6060
ctgcataatt ctcttactgt catgccatcc gtaagatgct tttctgtgac tggtgagtac   6120
tcaaccaagt cattctgaga atagtgtatg cggcgaccga gttgctcttg cccggcgtca   6180
atacgggata ataccgcgcc acatagcaga actttaaaag tgctcatcat tggaaaacgt   6240
tcttcggggc gaaaactctc aaggatctta ccgctgttga tccagttc gatgtaaccc   6300
actcgtgcac ccaactgatc ttcagcatct tttactttca ccagcgtttc tgggtgagca   6360
aaaacaggaa ggcaaaatgc cgcaaaaaag ggaataagg gacacggaa atgttgaata   6420
ctcatactct tccttttca atattattga agcatttatc agggttattg tctcatgagc   6480
ggatacatat ttgaatgtat ttagaaaaat aaacaaatag gggttccgcg cacatttccc   6540
cgaaaagtgc cacctgacgt cgacggatcg ggagatctcc cgatccccta tggtcgactc   6600
tcagtacaat ctgctctgat gccgcatagt taagccagta tctgctccct gcttgtgtgt   6660
tggaggtcgc tgagtagtgc gcgagcaaaa tttaagctac aacaaggcaa ggcttgaccg   6720
acaattgcat gaagaatctg cttagg                                       6746
```

```
SEQ ID NO: 187        moltype = DNA   length = 6746
FEATURE               Location/Qualifiers
misc_feature          1..6746
                      note = Synthetic polynucleotide
source                1..6746
                      mol_type = other DNA
                      organism = synthetic construct
SEQUENCE: 187
gttaggcgtt ttgcgctgct tcgcgatgta cgggccagat atacgcgttg acattgatta   60
ttgactagtt attaatagta atcaattacg gggtcattag ttcatagccc atatatggag   120
ttccgcgtta cataacttac ggtaaatggc ccgcctggct gaccgcccaa cgacccccgc   180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgccccctat tgacgtcaat gacggtaaat ggcccgcctg gcattatgcc   360
cagtacatga ccttatggga ctttcctact tggcagtaca tctacgtatt agtcatcgct   420
attaccatgg tgatgcggtt ttggcagtac atcaatgggc gtggatacgc gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc agcctccgg   720
actctagagg atcgaaccct tgaattcccg ccgccaccat gggctggtca tgtattattc   780
tgtttctggt cgcaactgct acaggggtcc atagtgagat cgtgctgacc caatctcctg   840
gcaccctgtc tctgagccca ggcgagagag ccacactctc ctgcaccgct tcttcctccg   900
tgtcctctag ctttctctgc ac tggtaccagc agaaacccgg gcaggctgtg tgtga      960
tctactccac ctccaacctg gcctctggca tccctgccag attctccgga tccggctctg   1020
gcaccgatta tacactgacc atctcccggc tggaacctga ggacttcgcc acctactact   1080
gtcaccagta ccaccatagc ccttacatct acacttcgg cggcggaacc aagctggaaa   1140
tcaagaggac agtggccgcc ccaagcgtgt tcatctttcc cccttccgac gagcagctga   1200
agtctggcac cgccagcgtg gtgtgcctgc tgaacaactt ctaccctcgg gaggccaagg   1260
```

-continued

```
tccagtggaa ggtggataac gccctgcagt ctggcaatag ccaggagtcc gtgaccgagc   1320
aggactctaa ggatagcaca tattccctgt ctagcaccct gacactgagc aaggccgatt   1380
acgagaagca caaggtgtat gcctgtgaag tcacccatca ggggctgtca tcacccgtca   1440
ctaagtcatt caatcgcgga gaatgctgat aagcttaagg gttcgatccc taccggttag   1500
taatgagttt gatatctcga caatcaacct ctggattaca aaatttgtga aagattgact   1560
ggtattctta actatgttgc tccttttacg ctatgtggat acgctgcttt aatgcctttg   1620
tatcatgcta ttgcttccg tatggctttc attttctcct ccttgtataa atcctggttg   1680
ctgtctcttt atgaggagtt gtggcccgtt gtcaggcaac gtggcgtggt gtgcactgtg   1740
tttgctgacg caaccccac tggttggggc attgccacca cctgtcagct cctttccggg   1800
actttcgctt tccccctccc tattgccacg gcggaactca tcgccgcctg ccttgcccgc   1860
tgctggacag gggctcggct gttgggcact gacaattccg tggtgttgtc ggggaagctg   1920
acgtcctttc catggctgct cgcctgtgtt gccacctgga ttctgcgcgg gacgtccttc   1980
tgctacgtcc cttcggccct caatccagcg gaccttcctt cccgcggcct gctgccggct   2040
ctgcggcctc ttccgcgtct tcgccttcgc cctcagacga gtcggatctc cctttgggcc   2100
gcctccccgc ctggaaacgg gggaggctaa ctgaaacacg gaaggagaca ataccggaag   2160
gaacccgcgc tatgacggca ataaaaagac agaataaaac gcacgggtgt tgggtcgttt   2220
gttcataaac gcggggttcg gtcccagggc tggcactctg tcgataccc accgagaccc   2280
cattggggcc aatacgcccg cgtttcttcc ttttccccac cccacccccc aagttcgggt   2340
gaaggcccag ggctcgcagc caacgtcggg cgggcaggcc ctgccatagc agatctgcgc   2400
agctgggggct ctaggggta tccccacgcg ccctgtagcg gcgcattaag cgcggcgggt   2460
gtggtggtta cgcgcagcgt gaccgctaca cttgccagcg ccctagcgcc cgctcctttc   2520
gctttcttcc cttcctttct cgccacgttc gccggctttc cccgtcaagc tctaaatcgg   2580
ggcatccctt tagggttccg atttagtgct ttacggcacc tcgaccccaa aaaacttgat   2640
tagggtgatg gttcacgtag tgggccatcg ccctgataga cggttttttcg ccctttgacg   2700
ttggagtcca cgttctttaa tagtggactc ttgttccaaa ctggaacaac actcaaccct   2760
atctcggtct attctttga tttataaggg attttgggga tttcggccta ttggttaaaa   2820
aatgagctga tttaacaaaa atttaacgcg aattaattct gtggaatgtg tgtcagttag   2880
ggtgtggaaa gtcccaggc tccccagcag gcagaagtat gcaaagcatg catctcaatt   2940
agtcagcaac caggtgtgga aagtccccag gctccccagc aggcagaagt atgcaaagca   3000
tgcatctcaa ttagtcagca accatagtcc cgcccctaac tccgcccatc ccgcccctaa   3060
ctccgcccag ttccgcccat tctccgcccc atggctgact aattttttt atttatgcag   3120
aggccgaggc cgcctctgcc tctgagctat tccagaagta gtgaggaggc tttttttggag   3180
gcctaggctt ttgcaaaaag ctcccgggag cttgtatatc cattttcgga tctgatcaag   3240
agacaggatg aggatcgttt cgcatgattg aacaagatgg attgcacgca ggttctccgg   3300
ccgcttgggt ggagaggcta ttcggctatg actgggcaca acagacaatc ggctgctctg   3360
atgccgccgt gttccggctg tcagcgcagg ggcgcccggt tctttttgtc aagaccgacc   3420
tgtccggtgc cctgaatgaa ctgcaggacg aggcagcgcg gctatcgtgg ctggccacga   3480
cgggcgttcc ttgcgcagct gtgctcgacg ttgtcactga agcgggaagg gactggctgc   3540
tattggccga agtgccgggg caggatctcc tgtcatctca ccttgctcct gccgagaaag   3600
tatccatcat ggctgatgca atgcggcggc tgcatacgct tgatccggct acctgcccat   3660
tcgaccacca agcgaaacat cgcatcgagc gagcacgtac tcggatggaa gccggtcttg   3720
tcgatcagga tgatctggac gaagagcatc aggggctcgc gccagccgaa ctgttcgcca   3780
ggctcaaggc gcgcatgccc gacggcgagg atctcgtcgt gacccatggc gatgcctgct   3840
tgccgaatat catggtggaa aatggccgct tttctggatt catcgactgt ggccggctgg   3900
gtgtggcgga ccgctatcag gacatagcgt tggctacccg tgatattgct gaagagcttg   3960
gcggcgaatg ggctgaccgc ttcctcgtgc tttacggtat cgccgctccc gattcgcagc   4020
gcatcgcctt ctatcgcctt cttgacgagt tcttctgagc gggactctgg ggttcgcgaa   4080
atgaccgacc aagcgacgcc caacctgcca tcacgagatt tcgattccac cgccgccttc   4140
tatgaaaggt tgggcttcgg aatcgttttc cgggacgccg gctggatgat cctccagcgc   4200
ggggatctca tgctggagtt cttcgcccac cccaacttgt ttattgcagc ttataatggt   4260
tacaaataaa gcaatagcat cacaaatttc acaaataaag catttttttc actgcattct   4320
agttgtggtt tgtccaaact catcaatgta tcttatcatg tctgtatacc gtcgacctct   4380
agctagagct tggcgtaatc atggtcatag ctgtttcctg tgtgaaattg ttatccgctc   4440
acaattccac acaacatacg agccggaagc ataaagtgta aagcctgggg tgcctaatga   4500
gtgagctaac tcacattaat tgcgttgcgc tcactgcccg ctttccagtc gggaaacctg   4560
tcgtgccagc tgcattaatg aatcggccaa cgcgcgggga gaggcggttt gcgtattggg   4620
cgctcttccg cttcctcgct cactgactcg ctgcgctcgg tcgttcggct gcggcgagcg   4680
gtatcagctc actcaaaggc ggtaatacgg ttatccacag aatcaggggga taacgcagga   4740
aagaacatgt gagcaaaagg ccagcaaaag gccaggaacc gtaaaaaggc cgcgttgctg   4800
gcgtttttcc ataggctccg cccccctgac gagcatcaca aaaatcgacg ctcaagtcag   4860
aggtggcgaa acccgacagg actataaaga taccaggcgt ttcccctgg aagctccctc   4920
gtgcgctctc ctgttccgac cctgccgctt accggatacc tgtccgcctt tctcccttcg   4980
ggaagcgtgg cgctttctca atgctcacgc tgtaggtatc tcagttcggt gtaggtcgtt   5040
cgctccaagc tgggctgtgt gcacgaaccc cccgttcagc ccgaccgctg cgccttatcc   5100
ggtaactatc gtcttgagtc caacccggta agacacgact tatcgccact ggcagcagcc   5160
actggtaaca ggattagcag agcgaggtat gtaggcggtg ctacagagtt cttgaagtgg   5220
tggcctaact acggctacac tagaaggaca gtatttggta tctgcgctct gctgaagcca   5280
gttaccttcg gaaaaagagt tggtagctct tgatccggca aacaaaccac cgctggtagc   5340
ggtggttttt ttgtttgcaa gcagcagatt acgcgcagaa aaaaaggatc tcaagaagat   5400
cctttgatct tttctacggg gtctgacgct cagtggaacg aaaactcacg ttaagggatt   5460
ttggtcatga gattatcaaa aaggatcttc acctagatcc ttttaaatta aaaatgaagt   5520
tttaaatcaa tctaaagtat atatgagtaa acttggtctg acagttacca atgcttaatc   5580
agtgaggcac ctatctcagc gatctgtcta tttcgttcat ccatagttgc ctgactcccc   5640
gtcgtgtaga taactacgat acgggagggc ttaccatctg gccccagtgc tgcaatgata   5700
ccgcgagacc cacgctcacc ggctccagat ttatcagcaa taaaccagcc agccggaagg   5760
gccgagcgca gaagtggtcc tgcaacttta tccgcctcca tccagtctat taattgttgc   5820
cgggaagcta gagtaagtag ttcgccagtt aatagtttgc gcaacgttgt tgccattgct   5880
acaggcatcg tggtgtcacg ctcgtcgttt ggtatggctt cattcagctc cggttcccaa   5940
cgatcaaggc gagttacatg atcccccatg ttgtgcaaaa aagcggttag ctccttcggt   6000
```

-continued

```
cctccgatcg ttgtcagaag taagttggcc gcagtgttat cactcatggt tatggcagca  6060
ctgcataatt ctcttactgt catgccatcc gtaagatgct tttctgtgac tggtgagtac  6120
tcaaccaagt cattctgaga atagtgtatg cggcgaccga gttgctcttg cccggcgtca  6180
atacgggata ataccgcgcc acatagcaga actttaaaag tgctcatcat tggaaaacgt  6240
tcttcggggc gaaaactctc aaggatctta ccgctgttga gatccagttc gatgtaaccc  6300
actcgtgcac ccaactgatc ttcagcatct tttactttca ccagcgtttc tgggtgagca  6360
aaaacaggaa ggcaaaatgc cgcaaaaaag ggaataaggg cgacacggaa atgttgaata  6420
ctcatactct tcctttttca atattattga agcatttatc agggttattg tctcatgagc  6480
ggatacatat ttgaatgtat ttagaaaaat aaacaaatag gggttccgcg cacatttccc  6540
cgaaaagtgc cacctgacgt cgacggatcg ggagatctcc cgatcccta tggtcgactc  6600
tcagtacaat ctgctctgat gccgcatagt taagccagta tctgctccct gcttgtgtgt  6660
tggaggtcgc tgagtagtgc gcgagcaaaa tttaagctac aacaaggcaa ggcttgaccg  6720
acaattgcat gaagaatctg cttagg                                        6746
```

```
SEQ ID NO: 188          moltype = DNA   length = 7436
FEATURE                 Location/Qualifiers
misc_feature            1..7436
                        note = Synthetic polynucleotide
source                  1..7436
                        mol_type = other DNA
                        organism = synthetic construct
SEQUENCE: 188
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caataagggac tttccattga  240
cgtcaatggg tggagtattt acggtaaact gcccacttgg cagtacatca agtgtatcat  300
atgccaagta cgcccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct tgaattcccg ccgccaccat gggctggtca tgcattattc  780
tgtttctggt cgcaactgct acaggcgtgc atagtcaggt gcagctgcaa gagtccggcc  840
ctggactcgt gaagccctcc gagacactgt ctctgacatg taccgtgtct ggcttctccc  900
tgtccatcta ctccgtgcac tggatcagac agcctcctgg caagggcctg gaatggatcg  960
gcatgatctg gggaggcggc tcttccgact acaactccgc cctgaaatct cggctgacca  1020
tctccaagga cacctctaag aaccaggtca gcctgaagct gagctctgtg accgctgctg  1080
ataccgccgt gtactactgc gccagaaatg gcaacttcta cgccatggac tattggggcc  1140
agggcaccct ggtgaccgtg tccagcgcca gcaccaaggg cccttccgtg tttccactgg  1200
ccccctcctc taaatccaca tctggcggca ccgccgccct gggctgtctg gtgaaggact  1260
acttcccaga gcctgtgaca gtgtcctgga actctggcgc cctgacatcc ggcgtgcaca  1320
catttccagc cgtgctgcag agctccggcc tgtacagcct gtctagcgtg gtgacagtgc  1380
cctcctctag cctgggcaca cagacctata tctgcaacgt gaatcacaag ccaagcaata  1440
ccaaggtgga caagaaggtg gagcccaagt cctgtgatga cacacacacc tgccccccctt  1500
gtccctgctcc cgagctgctg ggcggcccta gcgtgttcct gtttcccacc aagcctaagg  1560
acaccctgat gatctcccgg acacccgagg tgacctgcgt ggtggtggac gtgtctcacg  1620
aggatcctga ggtgaagttc aactggtatg tggatggcgt ggaggtgcac aatgccaaga  1680
ccaagccag agaggagcag tacaactcta catatagggt ggtgagcgtg ctgaccgtgc  1740
tgcaccagga ctggctgaac ggcaaggagt ataagtgcaa ggtgtccaat aaggccctgc  1800
ccgcccccat cgagaagaca atcagcaagg ccaaggggcca gcctcgggag ccacaggtgt  1860
acaccctgcc tccatccaga gacgagctga caaagaacca ggtgtctctg acatgtctgg  1920
tgaagggctt ctatcctagc gatatcgccg tggagtggga gtccaatggc cagccagaga  1980
acaattacaa gaccacaccc cctgtgctgg actccgatgg ctccttcttt ctgtattcca  2040
agctgaccgt ggataagtct cggtggcagc agggcaacgt gttcagctgt tccgtgatgc  2100
acgaagccct gcataatcac tatactcaga atccctgtc cctgtcacct ggaaagtgat  2160
aagcttaagg gttcgatccc taccggttag taatgagttt gatatctcga caatcaacct  2220
ctggattaca aaatttgtga aagattgact ggtattctta actatgttgc tccttttacg  2280
ctatgtggat acgctgcttt aatgcctttg tatcatgcta ttgcttcccg tatggctttc  2340
attttctcct ccttgtataa atcctggttg ctgtctcttt atgaggagtt gtggcccgtt  2400
gtcaggcaac gtggcgtggt gtgcactgtg tttgctgacg caaccccac tggttggggc  2460
attgccacca cctgtcagct cctttccggg actttcgctt tccccctctc cccctcg  2520
gcggaactca tcgccgcctg ccttgcccgc tgctggacag gggctcggct gttgggcact  2580
gacaattccg tggtgttgtc ggggaagctg acgtccttc catggctgct cgcctgtgtt  2640
gccacctgga ttctgcgcgg gacgtccttc tgctacgtcc cttcggccct caatccagcg  2700
gaccttcctt cccgcggcct gctgccggct ctgcggcctc ttccgcgtct tcgccttcgc  2760
cctcagacga gtcggatctc cctttgggcc gcctccccgc ctggaacg ggggaggctaa  2820
ctgaaacacg gaaggagaca ataccggaag aacccgcgc tatgacggca ataaaaagac  2880
agaataaaac gcacgggtgt tgggtcgttt gttcataaac gcggggttcg tcccagggc  2940
tggcactctg tcgataccc accgagacc cattggggcc aatacgcccg cgtttcttcc  3000
ttttcccac cccaccccccc aagttcgggt gaaggcccag ggctcgcagc caacgtcggg  3060
gcggcaggcc ctgccatagc agatctgcgc agctggggta ctagggggta tcccacgcg  3120
ccctgtagcg gcgcattaag cgcggcgggt gtggtggtta cgcgcagcgt gaccgctaca  3180
cttgccagcg ccctagcgcc cgctcctttt gctttcttcc cttcctttct cgccacgttc  3240
gccggctttc cccgtcaagc tctaaatcgg ggcatccctt tagggttccg atttagtgct  3300
ttacggcacc tcgaccccaa aaaacttgat tagggtgatg gttcacgtag tgggccatcg  3360
ccctgataga cggtttttcg ccctttgacg ttggagtcca cgttctttaa tagtggactc  3420
```

```
ttgttccaaa ctggaacaac actcaaccct atctcggtct attcttttga ttttataaggg   3480
attttgggga tttcggccta ttggttaaaa aatgagctga tttaacaaaa atttaacgcg   3540
aattaattct gtggaatgtg tgtcagttag ggtgtggaaa gtccccaggc tccccagcag   3600
gcagaagtat gcaaagcatg catctcaatt agtcagcaac caggtgtgga aagtccccag   3660
gctccccagc aggcagaagt atgcaaagca tgcatctcaa ttagtcagca accatagtcc   3720
cgccctaac tccgcccatc ccgcccctaa ctccgcccag ttccgcccat tctccgcccc   3780
atggctgact aattttttt atttatgcag aggccgaggc cgcctctgcc tctgagctat   3840
tccagaagta gtgaggaggc tttttttggag gcctaggctt ttgcaaaaag ctcccgggag   3900
cttgtatatc cattttcgga tctgatcaag agacaggatg aggatcgttt cgcatgattg   3960
aacaagatgg attgcacgca ggttctccgg ccgcttgggt ggagaggcta ttcggctatg   4020
actgggcaca acagacaatc ggctgctctg atgccgccgt gttccggctg tcagcgcagg   4080
ggcgcccggt tctttttgtc aagaccgacc tgtccggtgc cctgaatgaa ctgcaggacg   4140
aggcagcgcg gctatcgtgg ctggccacga cgggcgttcc ttgcgcagct gtgctcgacg   4200
ttgtcactga agcgggaagg gactggctgc tattgggcga agtgccgggg caggatctcc   4260
tgtcatctca ccttgctcct gccgagaaag tatccatcat ggctgatgca atgcggcggc   4320
tgcatacgct tgatccggct acctgcccat tcgaccacca agcgaaacat cgcatcgagc   4380
gagcacgtac tcggatggaa gccggtcttg tcgatcagga tgatctggac gaagagcatc   4440
aggggctcgc gccagccgaa ctgttcgcca ggctcaagtc ggctcaagtc gacggcgagg   4500
atctcgtcgt gacccatggc gatgcctgct tgccgaatat catggtggaa aatggccgct   4560
tttctggatt catcgactgt ggccggctgg gtgtggcgga ccgctatcag gacatagcgt   4620
tggctaccctg tgatattgct gaagagcttg gcggcgaatg ggctgaccgc ttcctcgtgc   4680
tttacggtat cgccgctccc gattcgcagc gcatcgcctt ctatcgcctt cttgacgagt   4740
tcttctgagc gggactctgg ggttcgcgaa atgaccgacc aagcgacgcc caacctgcca   4800
tcacgagatt tcgattccac cgccgccttc tatgaaaggt tgggcttcgg aatcgttttc   4860
cgggacgccg gctggatgat cctccagcgc ggggatctca tgctggagtt cttcgcccac   4920
cccaacttgt ttattgcagc ttataatggt tacaaataaa gcaatagcat cacaaatttc   4980
acaaataaag cattttttc actgcattct agttgtggtt tgtccaaact catcaatgta   5040
tcttatcatg tctgtatacc gtcgacctct agctagagct tggcgtaatc atggtcatag   5100
ctgtttcctg tgtgaaattg ttatccgctc acaattccac acaacatacg agccggaagc   5160
ataaagtgta aagcctgggg tgcctaatga gtgagctaac tcacattaat tgcgttgcgc   5220
tcactgcccg ctttccagtc gggaaacctg tcgtgccagc tgcattaatg aatcggccaa   5280
cgcgcgggga gaggcggttt gcgtattggg cgctcttccg cttcctcgct cactgactcg   5340
ctgcgctcgg tcgttcggct gcggcgagcg gtatcagctc actcaaaggc ggtaatacgg   5400
ttatccacag aatcagggga taacgcagga aagaacatgt gagcaaaagg ccagcaaaag   5460
gccaggaacc gtaaaaaggc cgcgttgctg gcgtttttcc ataggctccg cccccctgac   5520
gagcatcaca aaaatcgacg ctcaagtcag aggtggcgaa acccgacagg actataaaga   5580
taccaggcgt ttccccctgg aagctccctc gtgcgctctc ctgttccgac cctgccgctt   5640
accggatacc tgtccgcctt tctcccttcg ggaagcgtgg cgctttctca atgctcacgc   5700
tgtaggtatc tcagttcggt gtaggtcgtt cgctccaagc tgggctgtgt gcacgaaccc   5760
cccgttcagc ccgaccgctg cgccttatcc ggtaactatc gtcttgagtc caacccggta   5820
agacacgact tatcgccact ggcagcagcc actggtaaca ggattagcag agcgaggtat   5880
gtaggcggtg ctacagagtt cttgaagtgg tggcctaact acggctacac tagaaggaca   5940
gtatttggta tctgcgctct gctgaagcca gttaccttcg gaaaaagagt tggtagctct   6000
tgatccggca aacaaaccac cgctggtagc ggtggttttt ttgtttgcaa gcagcagatt   6060
acgcgcagaa aaaaaggatc tcaagaagat cctttgatct tttctacggg gtctgacgct   6120
cagtggaacg aaaactcacg ttaagggatt ttggtcatga gattatcaaa aaggatcttc   6180
acctagatcc tttttaaatta aaaatgaagt tttaaatcaa tctaaagtat atatgagtaa   6240
acttggtctg acagttacca atgcttaatc agtgaggcac ctatctcagc gatctgtcta   6300
tttcgttcat ccatagttgc ctgactcccc gtcgtgtaga taactacgat acgggagggc   6360
ttaccatctg gccccagtgc tgcaatgata ccgcgagacc cacgctcacc ggctccagat   6420
ttatcagcaa taaaccagcc agccggaagg gccgagcgca gaagtggtcc tgcaacttta   6480
tccgcctcca tccagtctat taattgttgc cgggaagcta gagtaagtag ttcgccagtt   6540
aatagtttgc gcaacgttgt tgccattgct acaggcatcg tggtgtcacg ctcgtcgttt   6600
ggtatggctt cattcagctc cggttcccaa cgatcaaggc gagttacatg atcccccatg   6660
ttgtgcaaaa aagcggttag ctccttcggt cctccgatcg ttgtcagaag taagttggcc   6720
gcagtgttat cactcatggt tatggcagca ctgcataatt ctcttactgt catgccatcc   6780
gtaagatgct tttctgtgac tggtgagtac tcaaccaagt cattctgaga atagtgtatg   6840
cggcgaccga gttgctcttg cccggcgtca atacgggata ataccgcgcc acatagcaga   6900
actttaaaag tgctcatcat tggaaaacgt tcttcggggc gaaaactctc aaggatctta   6960
ccgctgttga gatccagttc gatgtaaccc actcgtgcac ccaactgatc ttcagcatct   7020
tttactttca ccagcgtttc tgggtgagca aaaacaggaa ggcaaaatgc cgcaaaaaag   7080
ggaataaggc cgcacggaa atgttgaata ctcatactct tcctttttca atattattga   7140
agcatttatc agggttattg tctcatgagc ggatacatat ttgaatgtat ttagaaaaat   7200
aaacaaatag gggttccgcg cacatttccc cgaaaagtgc cacctgacgt cgacggatcg   7260
ggagatctcc cgatccccta tggtcgactc tcagtacaat ctgctctgat gccgcatagt   7320
taagccagta tctgctccct gcttgtgtgt tggaggtcgc tgagtagtgc gcgagcaaaa   7380
tttaagctac aacaaggcaa ggcttgaccg acaattgcat gaagaatctg cttagg   7436
```

SEQ ID NO: 189        moltype = DNA  length = 7436
FEATURE               Location/Qualifiers
misc_feature         1..7436
                      note = Synthetic polynucleotide
source               1..7436
                      mol_type = other DNA
                      organism = synthetic construct
SEQUENCE: 189
```
gttaggcgtt ttgcgctgct tcgcgatgta cgggccagat atacgcgttg acattgatta   60
ttgactagtt attaatagta atcaattacg gggtcattag ttcatagccc atatatggag   120
ttccgcgtta cataacttac ggtaaatggc ccgcctggct gaccgcccaa cgacccccgc   180
```

-continued

```
ccattgacgt caataatgac gtatgttccc atagtaacgc caataggggac tttccattga  240
cgtcaatggg tggagtattt acggtaaact gcccacttgg cagtacatca agtgtatcat  300
atgccaagta cgcccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgcccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct tgaattcccg ccgccaccat gggctggtca tgcattattc  780
tgtttctggt cgcaactgct acaggcgtgc atagtcaggt gcagctgcaa gagtccggac  840
ccggcctcgt gaagccttcc gagacactgt ctctgacctg taccgtgtct ggcttctccc  900
tgtccatcta ctccgtgcac tggatccggc agcctcctgg caagggcctg gaatggctgg  960
gcatgatctg gggcggcgga agctccgact acaactccgc cctgaaatct agactgacca  1020
tctccaagga cacctctaag aaccaggtca gcctgaagct gagctctgtg accgccgctg  1080
ataccgctat gtactactgc gccagaaatg gcaacttcta cgccatggac tattggggcc  1140
agggcaccct ggtgacagtg tcctctgcca gcaccaaggg cccttccgtg tttccactgg  1200
ccccctcctc taaatccaca tctggcggca ccgccgccct gggctgtctg gtgaaggact  1260
acttcccaga gcctgtgaca gtgtcctgga actctggcgc cctgacatcc ggcgtgcaca  1320
catttccagc cgtgctgcag agctccggcc tgtacagcct gtctagcgtg gtgacagtgc  1380
cctcctctag cctgggcaca cagacctata tctgcaacgt gaatcacaag ccaagcaata  1440
ccaaggtgga caagaaggtg gagcccaagt cctgtgatgc cacacacacc tgccccccctt  1500
gtcctgctcc cgagctgctg ggcggcccta gcgtgttcct gtttccaccc aagcctaagg  1560
acaccctgat gatctcccgg acacccgagg tgacctgcgt ggtggtggac gtgtctcacg  1620
aggatcctga ggtgaagttc aactggtatg tggatggcgt ggaggtgcac aatgccaaga  1680
ccaagccag agaggagcag tacaactcta catataggt ggtgagcgtg ctgaccgtgc  1740
tgcaccagga ctggctgaac ggcaaggagt ataagtgcaa ggtgtccaat aaggccctgc  1800
ccgcccccat cgagaagaca atcagcaagg ccaagggcca gcctcgggag ccacaggtgt  1860
acaccctgcc tccatccaga gacgagctga caaagaacca ggtgtctctg acatgtctgg  1920
tgaagggctt ctatcctagc gatatcgccg tggagtggga gtccaatggc cagccagaga  1980
acaattacaa gaccacaccc cctgtgctgg actccgatgg ctccttcttt ctgtattcca  2040
agctgaccgt ggataagtct cggtggcagc agggcaacgt gttcagctgt tccgtgatgc  2100
acgaagccct gcataatcac tatactcaga aatccctgtc cctgtcacct ggaaagtgat  2160
aagcttaagg gttcgatccc taccggttag taatgagttt gatatctcga caatcaacct  2220
ctggattaca aaatttgtga aagattgact ggtattctta actatgttgc tccttttacg  2280
ctatgtggat acgctgcttt aatgcctttg tatcatgcta ttgcttcccg tatggctttc  2340
attttctcct ccttgtataa atcctggttg ctgtctcttt atgaggagtt gtggcccgtt  2400
gtcaggcaac gtggcgtggt gtgcactgtg tttgctgacg caacccccac tggttggggc  2460
attgccacca cctgtcagct cctttccggg actttcgctt tcccccctccc tattgccacg  2520
gcggaactca tcgccgcctg ccttgcccgc tgctggacag gggctcggct gttgggcact  2580
gacaattccg tggtgttgtc ggggaagctg acgtcctttc catggctgct cgcctgtgtt  2640
gccacctgga ttctgcgcgg gacgtccttc tgctacgtcc cttcggccct caatccagcg  2700
gaccttcctt cccgcggcct gctgccggct ctgcggcctc ttccgcgtct tcgccttcgc  2760
cctcagacga gtcggatctc cctttgggcc gcctccccgc ctggaaacgg gggaggctaa  2820
ctgaaacacg gaaggagaca ataccggaag gaacccgcgc tatgacggca ataaaaagac  2880
agaataaaac gcacgggtgt tgggtcgttt gttcataaac gcggggttcg tcccagggc  2940
tggcactctg tcgatacccc accgagaccc cattggggcc aatacgcccg cgtttcttcc  3000
ttttccccac cccaccccc aagttcgggg gaaggcccag ggctcgcagc caacgtcggg  3060
gcggcaggcc ctgccatagc agatctgcgc agctgggggct ctaggggta tccccacgcg  3120
ccctgtagcg gcgcattaag cgcggcgggt gtggtggtta cgcgcagcgt gaccgctaca  3180
cttgccacgt ccctagcgcc cgctccttc gctttcttcc cttcctttct cgccacgttc  3240
gccggcttc cccgtcaagc tctaaatcgg ggcatccctt tagggttccg atttagtgct  3300
ttacggcacc tcgacccaa aaaacttgat tagggtgatg gttcacgtag tgggccatcg  3360
ccctgataga cggtttttcg ccctttgacg ttggagtcca cgttctttaa tagtggactc  3420
ttgttccaaa ctggaacaac actcaaccct atctcggtct attctttttg atttataaggg  3480
attttgggga tttcggccta ttggttaaaa aatgagctga tttaacaaaa atttaacgcg  3540
aattaattct gtggaatgtg tgtcagttag ggtgtggaaa gtccccaggc tccccagcag  3600
gcagaagtat gcaaagcatg catctcaatt agtcagcaac caggtgtgga aagtccccag  3660
gctccccagc aggcagaagt atgcaaagca tgcatctcaa ttagtcagca accatagtcc  3720
cgcccctaac tccgcccatc ccgcccctaa ctccgcccag ttccgcccat tctccgcccc  3780
atggctgact aatttttttt atttatgcag aggccgaggc cgcctctgcc tctgagctat  3840
tccagaagta gtgaggaggc ttttttggag gcctaggct tttgcaaaaag ctcccgggag  3900
cttgtatatc cattttcgga tctgatcaag agacaggatg aggatcgttt cgcatgattg  3960
aacaagatgg attgcacgca ggttctccgg ccgcttgggt ggagaggcta ttcggctacg  4020
actgggcaca acagacaatc ggctgctctg atgccgccgt gttccggctg tcagcgcagg  4080
ggcgcccggt tctttttgtc aagaccgacc tgtccggtgc cctgaatgaa ctgcaggacg  4140
aggcagcgcg gctatcgtgg ctggccacga cgggcgttcc ttgcgcagct gtgctcgacg  4200
ttgtcactga agcgggaagg gactggctgc tattgggcga agtgccgggg caggatctcc  4260
tgtcatctca ccttgctcct gccgagaaag tatccatcat ggctgatgca atgcggcggc  4320
tgcatacgct tgatccggct acctgcccat tcgaccacca agcgaaacat cgcatcgagc  4380
gagcacgtac tcggatggaa gccggtcttg tcgatcagga tgatctggac gaagagcatc  4440
aggggctcgc gccagccgaa ctgttcgcca ggctcaaggc gcgcatgccc gacggcgagg  4500
atctcgtcgt gacccatggc gatgcctgct tgccgaatat catggtggaa aatggccgct  4560
tttctggatt catcgactgt ggccggctgg gtgtggcgga ccgctatcag gacatagcgt  4620
tggctacccg tgatattgct gaagagcttg gcggcgaatg ggctgaccgc ttcctcgtgc  4680
tttacggtat cgccgctccc gattcgcagc gcatcgcctt ctatcgcctt cttgacgagt  4740
tcttctgagc gggactctgg ggttcgcgaa atgaccgacc aagcgacgcc caacctgcca  4800
tcacgagatt tcgattccac cgccgccttc tatgaaaggt tgggcttcgg aatcgttttc  4860
cgggacgccg gctggatgat cctccagcgc ggggatctca tgctggagtt cttcgcccac  4920
```

```
cccaacttgt ttattgcagc ttataatggt tacaaataaa gcaatagcat cacaaatttc   4980
acaaataaag cattttttc actgcattct agttgtggtt tgtccaaact catcaatgta   5040
tcttatcatg tctgtatacc gtcgacctct agctagagct tggcgtaatc atggtcatag   5100
ctgtttcctg tgtgaaattg ttatccgctc acaattccac acaacatacg agccggaagc   5160
ataaagtgta aagcctgggg tgcctaatga gtgagctaac tcacattaat tgcgttgcgc   5220
tcactgcccg ctttccagtc gggaaacctg tcgtgccagc tgcattaatg aatcggccaa   5280
cgcgcgggga gaggcggttt gcgtattggg cgctcttccg cttcctcgct cactgactcg   5340
ctgcgctcgg tcgttcggct gcggcgagcg gtatcagctc actcaaaggc ggtaatacgg   5400
ttatccacag aatcagggga taacgcagga agaacatgt gagcaaaagg ccagcaaaag   5460
gccaggaacc gtaaaaaggc cgcgttgctg gcgtttttcc ataggctccg cccccctgac   5520
gagcatcaca aaaatcgacg ctcaagtcag aggtggcgaa acccgacagg actataaaga   5580
taccaggcgt ttcccctgg aagctccctc gtgcgctctc ctgttccgac cctgccgctt   5640
accggatacc tgtccgcctt tctcccttcg ggaagcgtgg cgctttctca atgctcacgc   5700
tgtaggtatc tcagttcggt gtaggtcgtt cgctccaagc tgggctgtgt gcacgaaccc   5760
cccgttcagc ccgaccgctg cgccttatcc ggtaactatc gtcttgagtc caacccggta   5820
agacacgact tatcgccact ggcagcagcc actggtaaca ggattagcag agcgaggtat   5880
gtaggcggtg ctacagagtt cttgaagtgg tggcctaact acggctacac tagaaggaca   5940
gtatttggta tctgcgctct gctgaagcca gttaccttcg gaaaaagagt tggtagctct   6000
tgatccggca aacaaaccac cgctggtagc ggtggttttt ttgtttgcaa gcagcagatt   6060
acgcgcagaa aaaaaggatc tcaagaagat cctttgatct tttctacggg gtctgacgct   6120
cagtggaacg aaaactcacg ttaagggatt ttggtcatga gattatcaaa aaggatcttc   6180
acctagatcc ttttaaatta aaaatgaagt tttaaatcaa tctaaagtat atatgagtaa   6240
acttggtctg acagttacca atgcttaatc agtgaggcac ctatctcagc gatctgtcta   6300
tttcgttcat ccatagttgc ctgactcccc gtcgtgtaga taactacgat acgggagggc   6360
ttaccatctg gccccagtgc tgcaatgata ccgcgagacc cacgctcacc ggctccagat   6420
ttatcagcaa taaaccagcc agccggaagg gccgagcgca gaagtggtcc tgcaacttta   6480
tccgcctcca tccagtctat taattgttgc cgggaagcta gagtaagtag ttcgccagtt   6540
aatagtttgc gcaacgttgt tgccattgct acaggcatcg tggtgtcacg ctcgtcgttt   6600
ggtatggctt cattcagctc cggttcccaa cgatcaaggc gagttacatg atcccccatg   6660
ttgtgcaaaa aagcggttag ctccttcggt cctccgatcg ttgtcagaag taagttggcc   6720
gcagtgttat cactcatggt tatggcagca ctgcataatt ctcttactgt catgccatcc   6780
gtaagatgct tttctgtgac tggtgagtac tcaaccaagt cattctgaga atagtgtatg   6840
cggcgaccga gttgctcttg cccggcgtca atacgggata ataccgcgcc acatagcaga   6900
actttaaaag tgctcatcat tggaaaacgt tcttcggggc gaaaactctc aaggatctta   6960
ccgctgttga gatccagttc gatgtaaccc actcgtgcac ccaactgatc ttcagcatct   7020
tttactttca ccagcgtttc tgggtgagca aaaacaggaa ggcaaaatgc cgcaaaaaag   7080
ggaataaggg cgacacggaa atgttgaata ctcatactct tcctttttca atattattga   7140
agcatttatc agggttattg tctcatgagc ggatacatat ttgaatgtat ttagaaaaat   7200
aaacaaatag gggttccgcg cacatttccc cgaaaagtgc cacctgacgt cgacggatcg   7260
ggagatctcc cgatccccta tggtcgactc tcagtacaat ctgctctgat gccgcatagt   7320
taagccagta tctgctccct gcttgtgtgt tggaggtcgc tgagtagtgc gcgagcaaaa   7380
tttaagctac aacaaggcaa ggcttgaccg acaattgcat gaagaatctg cttagg        7436
```

```
SEQ ID NO: 190          moltype = AA  length = 13
FEATURE                 Location/Qualifiers
source                  1..13
                        mol_type = protein
                        organism = Porphyromonas gingivalis
SEQUENCE: 190
YTYTVYRDGT KIK                                                        13

SEQ ID NO: 191          moltype = DNA  length = 7436
FEATURE                 Location/Qualifiers
misc_feature            1..7436
                        note = Synthetic Polynucleotide
source                  1..7436
                        mol_type = other DNA
                        organism = synthetic construct
SEQUENCE: 191
gttaggcgtt ttgcgctgct tcgcgatgta cgggccagat atacgcgttg acattgatta   60
ttgactagtt attaatagta atcaattacg gggtcattag ttcatagccc atatatggag   120
ttccgcgtta cataacttac ggtaaatggc ccgcctggct gaccgcccaa cgaccccgc    180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgcccctat tgacgtcaat gacggtaaat ggcccgcctg gcattatgcc   360
cagtacatga ccttatggga ctttcctact tggcagtaca tctacgtatt agtcatcgct   420
attaccatgt gatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc cagcctccgg   720
actctagagg atcgaaccct tgaattcccg ccgccaccat gggctggtca tgcattattc   780
tgtttctggt cgcaactgct acaggcgtgc atagtcaggt gcagctgcaa gagtccggcc   840
ctggactcgt gaagccctcc gagacactgt ctctgacatg tactgtgtct ggcttctctca   900
tgtccatcta ctccgtgcac tggatccagca gcctcctgg caagggcctg gaatggatca   960
gcatgatctg gggaggcggc tcttccgact acaactccgc cctgaaatct cggctgacca   1020
tctccaagga cacctctaag aaccaggtca gcctgaagct gagctctgtg accgctgctg   1080
ataccgccgt gtactactgc gccagaaatg gcaacttcta cgccatggac tattggggcc   1140
agggcaccct ggtgaccgtg tccagcgcca gcaccaaggg cccttccgtg tttccactgg   1200
```

```
ccccctcctc taaatccaca tctggcggca ccgccgccct gggctgtctg gtgaaggact   1260
acttccagaa gcctgtgaca gtgtcctgga actctggcgc cctgacatcc ggcgtgcaca   1320
catttccagc cgtgctgcag agctccggcc tgtacagcct gtctagcgtg gtgacagtgc   1380
cctcctctag cctgggcaca cagacctata tctgcaacgt gaatcacaag ccaagcaata   1440
ccaaggtgga caagaaggtg gagcccaagt cctgtgatgc cacacacacc tgcccccctt   1500
gtcctgctcc cgagctgctg ggcggcccta gcgtgttcct gtttccaccc aagcctaagg   1560
acaccctgat gatctcccgg acacccgagg tgacctgcgt ggtggtggac gtgtctcacg   1620
aggatcctga ggtgaagttc aactggtatg tggatggcgt ggaggtgcac aatgccaaga   1680
ccaagcccag agaggagcag tacaactcta catatagggt ggtgagcgtg ctgaccgtgc   1740
tgcaccagga ctggctgaac ggcaaggagt ataagtgcaa ggtgtccaat aaggccctgc   1800
ccgcccccat cgagaagaca atcagcaagg ccaagggcca gcctcgggag ccacaggtgt   1860
acaccctgcc tccatccaga gacgagctga caaagaacca ggtgtctctg acatgtctgg   1920
tgaagggctt ctatcctagc gatatcgccg tggagtggga gtccaatggc cagccagaga   1980
acaattacaa gaccacaccc cctgtgctgg actccgatgg ctccttcttt ctgtattcca   2040
agctgaccgt ggataagtct cggtggcagc agggcaacgt gttcagctgt tccgtgatgc   2100
acgaagccct gcataatcac tatactcaga aatccctgtc cctgtcacct ggaaagtgat   2160
aagcttaagg gttcgatccc taccggttag taatgagttt gatatctcga caatcaacct   2220
ctggattaca aaatttgtga aagattgact ggtattctta actatgttgc tccttttacg   2280
ctatgtggat acgctgcttt aatgcctttg tatcatgcta ttgcttcccg tatggctttc   2340
attttctcct ccttgtataa atcctggttg ctgtctcttt atgaggagtt gtggcccgtt   2400
gtcaggcaac gtggcgtggt gtgcactgtg tttgctgacg caacccccac tggttggggc   2460
attgccacca cctgtcagct cctttccggg actttgcctt tccccctccc tattgccacg   2520
gcggaactca tcgccgcctg ccttgcccgc tgctggacag gggctcggct gttgggcact   2580
gacaattccg tggtgttgtc ggggaagctg acgtcctttc catggctgct cgcctgtgtt   2640
gccacctgga ttctgcgcgg gacgtccttc tgctacgtcc cttcggccct caatccagcg   2700
gaccttcctt cccgcggcct gctgccggct ctgcggcctc ttccgcgtct tcgccttcgc   2760
cctcagacga gtcggatctc cctttggccc gcctccccgc ctggaaacgg gggaggctaa   2820
ctgaaacacg gaaggagaca ataccggaag gaacccgcgc tatgacggca ataaaaagac   2880
agaataaaac gcacgggtgt tgggtcgttt gttcataaac gcggggttcg gtcccagggc   2940
tggcactctg tcgataccccc accgagaccc cattggggcc aatacgcccg cgtttcttcc   3000
ttttccccac cccaccccccc aagttcgggg gaaggcccag ggctcgcagc caacgtcggg   3060
gcggcaggcc ctgccatagc agatctgcgc agctggggct ctaggggta tccccacgcg   3120
ccctgtagcg gcgcattaag cgcggcgggt gtggtggtta cgcgcagcgt gaccgctaca   3180
cttgccagcg ccctagcgcc cgctcctttc gctttcttcc cttcctttct cgccacgttc   3240
gccggctttc cccgtcaagc tctaaatcgg ggcatccctt tagggttccg atttagtgct   3300
ttacggcacc tcgaccccaa aaaacttgat tagggtgatg gttcacgtag tgggccatcg   3360
ccctgataga cggtttttcg cccttttacg ttggagtcca cgttctttaa tagtggactc   3420
ttgttccaaa ctggaacaac actcaaccct atctcggtct attcttttga tttataaggg   3480
attttgggcta tttcggccta ttggttaaaa aatgagctga tttaacaaaa atttaacgcg   3540
aattaattct gtggaatgtg tgtcagttag ggtgtggaaa gtcccaggc tccccagcag   3600
gcagaagtat gcaaagcatg catctcaatt agtcagcaac caggtgtgga aagtccccag   3660
gctccccagc aggcagaagt atgcaaagca tgcatctcaa ttagtcagca accatagtcc   3720
cgcccctaac tccgcccatc ccgcccctaa ctccgcccca tctccgccca tctccgcccc   3780
atggctgact aattttttttt atttatgcag aggccgaggc cgcctctgcc tctgagctat   3840
tccagaagta gtgaggaggc ttttttggag gcctaggctt ttgcaaaaag ctcccgggag   3900
cttgtatatc cattttcgga tctgatcaag agacaggatg aggatcgttt cgcatgattg   3960
aacaagatgg attgcacgca ggttctccgg ccgcttggtg ggagaggcta ttcggctatg   4020
actgggcaca acagacaatc ggctgctctg atgccgccgt gttccggctg tcagcgcagg   4080
ggcgcccggt tctttttgtc aagaccgacc tgtccggtgc cctgaatgaa ctgcaggacg   4140
aggcagcgcg gctatcgtgg ctggccacga cgggcgttcc ttgcgcagct gtgctcgacg   4200
ttgtcactga gcgggaagg gactggctgc tattgggcga agtgccgggg caggatctcc   4260
tgtcatctca ccttgctcct gccgagaaag tatccatcat ggctgatgca atgcggcggc   4320
tgcatacgct tgatccggct acctgcccat tcgaccacca agcgaaacat cgcatcgagc   4380
gagcacgtac tcggatggaa gccggtcttg tcgatcagga tgatctggac gaagagcatc   4440
aggggctcgc gccagccgaa ctgttcgcca ggctcaaggc gcgcatgccc gacggcgagg   4500
atctcgtcgt gacccatggc gatgcctgct tgccgaatat catggtggaa aatggccgct   4560
tttctggatt catcgactgt ggccggctgg gtgtggcgga ccgctatcag gacatagcgt   4620
tggctacccg tgatattgct gaagagcttg gcggcgaatg ggctgaccgc ttcctcgtgc   4680
tttacggtat cgccgctccc gattcgcagc gcatcgcctt ctatcgcctt cttgacgagt   4740
tcttctgagc gggactctgg ggttcgcgaa atgaccgacc aagcgacgcc caacctgcca   4800
tcacgagatt cgattccacc gccgccttct atgaaaggt tgggcttcgg aatcgttttc   4860
cgggacgccg gctggatgat cctccagcgc ggggatctca tgctggagtt cttcgcccac   4920
cccaacttgt ttattgcagc ttataatggt tacaaataaa gcaatagcat cacaaatttc   4980
acaataaag catttttttc actgcattct agttgtggtt tgtccaaact catcaatgta   5040
tcttatcatg tctgtatacc gtcgacctct agctagagct tggcgtaatc atggtcatag   5100
ctgtttcctg tgtgaaattg ttatccgctc acaattccac acaacatacg agccggaagc   5160
ataaagtgta aagcctgggg tgcctaatga gtgagctaac tcacattaat tgcgttgcgc   5220
tcactgcccg ctttccagtc gggaaacctg tcgtgccagc tgcattaatg aatcggccaa   5280
cgcgcgggga gaggcggttt gcgtattggg cgctcttccg cttcctcgct cactgactcg   5340
ctgcgctcgg tcgttcggct gcggcgagcg gtatcagctc actcaaaggc ggtaatacgg   5400
ttatccacag aatcagggga taacgcagga agaacatgt gagcaaaagg ccagcaaaag   5460
gccaggaacc gtaaaaaggc cgcgttgctg gcgtttttcc ataggctccg cccccctgac   5520
gagcatcaca aaaatcgacg ctcaagtcag aggtggcgaa acccgacagg actataaaga   5580
taccaggcgt ttccccctgg aagctccctc gtgcgctctc ctgttccgac cctgccgctt   5640
accggatacc tgtccgcctt tctcccttcg ggaagcgtgg cgctttctca atgctcacgc   5700
tgtaggtatc tcagttcggt gtaggtcgtt cgctccaagc tgggctgtgt gcacgaaccc   5760
cccgttcagc ccgaccgctg cgccttatcc ggtaactatc gtcttgagtc caacccggta   5820
agacacgact tatcgccact ggcagcagcc actggtaaca ggattagcag agcgaggtat   5880
gtaggcggtg ctacagagtt cttgaagtgg tggcctaact acggctacac tagaaggaca   5940
```

```
gtatttggta tctgcgctct gctgaagcca gttaccttcg gaaaaagagt tggtagctct  6000
tgatccggca aacaaaccac cgctggtagc ggtggttttt ttgtttgcaa gcagcagatt  6060
acgcgcagaa aaaaggatc tcaagaagat cctttgatct tttctacggg gtctgacgct  6120
cagtggaacg aaaactcacg ttaagggatt ttggtcatga gattatcaaa aaggatcttc  6180
acctagatcc ttttaaatta aaaatgaagt tttaaatcaa tctaaagtat atatgagtaa  6240
acttggtctg acagttacca atgcttaatc agtgaggcac ctatctcagc gatctgtcta  6300
tttcgttcat ccatagttgc ctgactcccc gtcgtgtaga taactacgat acgggagggc  6360
ttaccatctg gccccagtgc tgcaatgata ccgcgagacc cacgctcacc ggctccagat  6420
ttatcagcaa taaaccagcc agccggaagg gccgagcgca gaagtggtcc tgcaacttta  6480
tccgcctcca tccagtctat taattgttgc cgggaagcta gagtaagtag ttcgccagtt  6540
aatagtttgc gcaacgttgt tgccattgct acaggcatcg tggtgtcacg ctcgtcgttt  6600
ggtatggctt cattcagctc cggttcccaa cgatcaaggc gagttacatg atcccccatg  6660
ttgtgcaaaa aagcggttag ctccttcggt cctccgatcg ttgtcagaag taagttggcc  6720
gcagtgttat cactcatggt tatggcagca ctgcataatt ctcttactgt catgccatcc  6780
gtaagatgct tttctgtgac tggtgagtac tcaaccaagt cattctgaga atagtgtatg  6840
cggcgaccga gttgctcttg cccggcgtca atacgggata ataccgcgcc acatagcaga  6900
actttaaaag tgctcatcat tggaaaacgt tcttcggggc gaaaactctc aaggatctta  6960
ccgctgttga gatccagttc gatgtaaccc actcgtgcac ccaactgatc ttcagcatct  7020
tttactttca ccagcgtttc tgggtgagca aaaacaggaa ggcaaaatgc cgcaaaaaag  7080
ggaataaggg cgacacggaa atgttgaata ctcatactct tcctttttca atattattga  7140
agcatttatc agggttattg tctcatgagc ggatacatat ttgaatgtat ttagaaaaat  7200
aaacaaatag gggttccgcg cacatttccc cgaaaagtgc cacctgacgt cgacggatcg  7260
ggagatctcc cgatccccta tggtcgactc tcagtacaat ctgctctgat gccgcatagt  7320
taagccagta tctgctccct gcttgtgtgt tggaggtcgc tgagtagtgc gcgagcaaaa  7380
tttaagctac aacaaggcaa ggcttgaccg acaattgcat gaagaatctg cttagg       7436
```

SEQ ID NO: 192            moltype = DNA   length = 7436
FEATURE                   Location/Qualifiers
misc_feature              1..7436
                          note = Synthetic Polynucleotide
source                    1..7436
                          mol_type = other DNA
                          organism = synthetic construct SEQUENCE: 192
```
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatgggt agttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct tgaattcccg ccgccaccat gggctggtca tgcattattc  780
tgtttctggt cgcaactgct acaggcgtgc atagtcaggt gcagctgcaa gagtccggac  840
ccggcctcgt gaagccttcc gagacactgt ctctgacctg taccgtgtct ggcttctccc  900
tgtccatcta ctccgtgcac tggatccggc agcctcctgg caagggcctg gaatggctgg  960
gcatgatcgg gggcggcgga agctccgact acaactccgc cctgaaatct agactgacca  1020
tctccaagga cacctctaag aaccaggtca gcctgaagct gagctctgtg accgccgctg  1080
ataccgctat gtactactgc gccagaaatg gcaacttcta cgccatggac tattggggcc  1140
agggcacccT ggtgacagtg tcctctgcca gcaccaaggg cccttccgtg tttccactgg  1200
cccctcctc taaatccaca tctggcggca ccgccgccct gggctgtctg gtgaaggact  1260
acttcccaga gcctgtgaca gtgtcctgga actctggcgc cctgacatcc ggcgtgcaca  1320
catttccagc cgtgctgcag agctccggcc tgtacagcct gtctagcgtg gtgacagtgc  1380
cctcctctag cctgggcaca cagacctata tctgcaacgt gaatcacaag ccaagcaata  1440
ccaaggtgga caagaaggtg gagcccaagt cctgtgatgc cacacacacc tgccccccctt  1500
gtcctgctcc cgagctgctg ggcggcccta gcgtgttcct gtttccaccc aagcctaagg  1560
acaccctgat gatctcccgg acacccgagg tgacctgcgt ggtggtggac gtgtctcacg  1620
aggatcctga ggtgaagttc aactggtatg tggatggcgt ggaggtgcac aatgccaaga  1680
ccaagcccag agaggagcag tacaactcta catatagggt ggtgagcgtg ctgaccgtgc  1740
tgcaccagga ctggctgaac ggcaaggagt ataagtgcaa ggtgtccaat aaggccctgc  1800
ccgcccccat cgagaagaca atcagcaagg ccaaggggca gcctcgggag ccacaggtgt  1860
acaccctgcc tccatccaga gacgagctga aaagaacca ggtgtctctg acatgtctgg  1920
tgaagggctt ctatcctagc gatatcgccg tggagtggga gtccaatggc cagccagaga  1980
acaattacaa gaccacaccc cctgtgctgg actccgatgg ctccttcttt ctgtattcca  2040
agctgaccgt ggataagtct cggtggcagc agggcaacgt gttcagctgt tccgtgatgc  2100
acgaagccct gcataatcac tatactcaga atccctgtc cctgtcacct ggaaagtgat  2160
aagcttaagg gttcgatccc taccggttag taatgagttt gatatctcga caatcaacct  2220
ctggattaca aaatttgtga agattgact ggtattctta actatgttgc tccttttacg  2280
ctatgtggat acgctgcttt aatgcctttg tatcatgcta ttgcttcccg tatggctttc  2340
attttctcct ccttgtataa atcctggttg ctgtctcttt atgaggagtt gtggcccgtt  2400
gtcaggcaac gtggcgtggt gtgcactgtg tttgctgacg caacccccac tggttggggc  2460
attgccacca cctgtcagct cctttccggg actttcgctt tccccctccc tattgccacg  2520
gcggaactca tcgccgcctg ccttgcccgc tgctggacag gggctcggct gttgggcact  2580
gacaattccg tggtgttgtc ggggaagctg acgtcctttc catggctgct cgcctgtgtt  2640
gccacctgga ttctgcgcgg gacgtccttc tgctacgtcc cttcggccct caatccagcg  2700
```

-continued

```
gaccttcctt cccgcggcct gctgccggct ctgcggcctc ttccgcgtct tcgccttcgc  2760
cctcagacga gtcggatctc cctttgggcc gcctccccgc ctggaaacgg gggaggctaa  2820
ctgaaacacg gaaggagaca ataccggaag gaacccgcgc tatgacggca ataaaaagac  2880
agaataaaac gcacgggtgt tgggtcgttt gttcataaac gcggggttcg gtcccagggc  2940
tggcactctg tcgatacccc accgagaccc cattggggcg aatacgcccg cgtttcttcc  3000
ttttccccac cccacccccc aagttcgggt gaaggcccag ggctcgcagc caacgtcggg  3060
gcggcaggcc ctgccatagc agatctgcgc agctggggct ctaggggta tccccacgcg  3120
ccctgtagcg gcgcattaag cgcggcgggt gtggtggtta cgcgcagcgt gaccgctaca  3180
cttgccagcg ccctagcgcc cgctcctttc gctttcttcc cttcctttct cgccacgttc  3240
gccggctttc cccgtcaagc tctaaatcgg ggcatccctt tagggttccg atttagtgct  3300
ttacggcacc tcgaccccaa aaaacttgat tagggtgatg gttcacgtag tgggccatcg  3360
ccctgataga cggttttttcg ccctttgacg ttggagtcca cgttctttaa tagtggactc  3420
ttgttccaaa ctggaacaac actcaaccct atctcggtct attctttttga tttataaggg  3480
attttgggga tttcggccta ttggttaaaa aatgagctga tttaacaaaa atttaacgcg  3540
aattaattct gtgaatgtg tgtcagttag ggtgtggaaa gtcccaggc tcccagcag  3600
gcagaagtat gcaaagcatg catctcaatt agtcagcaac caggtgtgga aagtccccag  3660
gctccccagc aggcagaagt atgcaaagca tgcatctcaa ttagtcagca accatagtcc  3720
cgccctaac tccgcccatc ccgcccctaa ctccgcccag ttccgcccat tctccgcccc  3780
atggctgact aatttttttt atttatgcag aggccgaggc cgcctctgcc tctgagctat  3840
tccagaagta gtgaggaggc ttttttggag gcctaggctt ttgcaaaag ctcccgggag  3900
cttgtatatc cattttcgga tctgatcaag agacaggatg aggatcgttt cgcatgattg  3960
aacaagatgg attgcacgca ggttctccgg ccgcttgggt ggagaggcta ttcggctatg  4020
actgggcaca acagacaatc ggctgctctg atgccgccgt gttccggctg tcagcgcagg  4080
ggcgcccggt tctttttgtc aagaccgacc tgtccggtgc cctgaatgaa ctgcaggacg  4140
aggcagcgcg gctatcgtgg ctggccacga cgggcgttcc ttgcgcagct gtgctcgacg  4200
ttgtcactga agcgggaagg gactggctgc tattgggcga agtgccgggg caggatctcc  4260
tgtcatctca ccttgctcct gccgagaaag tatccatcat ggctgatgca atgcggcggc  4320
tgcatacgct tgatccggct acctgcccat tcgaccacca agcgaaacat cgcatcgagc  4380
gagcacgtac tcggatggaa gccggtcttg tcgatcagga tgatctggac gaagagcatc  4440
aggggctcgc gccagccgaa ctgttcgcca ggctcaaggc gcgcatgccc gacggcgagg  4500
atctcgtcgt gacccatggc gatgcctgct tgccgaatat catggtggaa aatggccgct  4560
tttctggatt catcgactgt ggccggctgg gtgtggcgga ccgctatcag gacatagcgt  4620
tggctacccg tgatattgct gaagagcttg gcggcgaatg ggctgaccgc ttcctcgtgc  4680
tttacggtat cgccgctccc gattcgcagc gcatcgcctt ctatcgcctt cttgacgagt  4740
tcttctgagc gggactctgg ggttcgcgaa atgaccgacc aagcgacgcc caacctgcca  4800
tcacgagatt tcgattccac cgccgccttc tatgaaaggt tgggcttcgg aatcgttttc  4860
cgggacgccg gctggatgat cctccagcgc ggggatctca tgctggagtt cttcgcccac  4920
cccaacttgt ttattgcagc ttataatggt tacaaataaa gcaatagcat cacaaatttc  4980
acaaataaag catttttttc actgcattct agttgtggtt tgtccaaact catcaatgta  5040
tcttatcatg tctgtatacc gtcgacctct agctagagct tggcgtaatc atggtcatag  5100
ctgtttcctg tgtgaaattg ttatccgctc acaattccac acaacatacg agccggaagc  5160
ataaagtgta aagcctgggg tgcctaatga gtgagctaac tcacattaat tgcgttgcgc  5220
tcactgcccg ctttccagtc gggaaacctg tcgtgccagc tgcattaatg aatcggccaa  5280
cgcgcgggga gaggcggttt gcgtattggg cgctcttccg cttcctcgct cactgactcg  5340
ctgcgctcgg tcgttcggct gcggcgagcg gtatcagctc actcaaaggc ggtaatacgg  5400
ttatccacag aatcagggga taacgcagga agaacatgt gagcaaaagg ccagcaaaag  5460
gccaggaacc gtaaaaaggc cgcgttgctg gcgtttttcc ataggctccg cccccctgac  5520
gagcatcaca aaaatcgacg ctcaagtcag aggtggcgaa acccgacagg actataaaga  5580
taccaggcgt ttccccctgg aagctccctc gtgcgctctc ctgttccgac cctgccgctt  5640
accggatacc tgtccgcctt tctcccttcg ggaagcgtgg cgctttctca atgctcacgc  5700
tgtaggtatc tcagttcggt gtaggtcgtt cgctccaagc tgggctgtgt gcacgaaccc  5760
cccgttcagc ccgaccgctg cgccttatcc ggtaactatc gtcttgagtc caacccggta  5820
agacacgact tatcgccact ggcagcagcc actggtaaca ggattagcag agcgaggtat  5880
gtaggcggtg ctacagagtt cttgaagtgg tggcctaact acggctacac tagaaggaca  5940
gtatttggta tctgcgctct gctgaagcca gttaccttcg gaaaaagagt tggtagctct  6000
tgatccggca aacaaaccac cgctggtagc ggtggttttt ttgtttgcaa gcagcagatt  6060
acgcgcagaa aaaaaggatc tcaagaagat cctttgatct tttctacggg gtctgacgct  6120
cagtggaacg aaaactcacg ttaagggatt ttggtcatga gattatcaaa aaggatcttc  6180
acctagatcc ttttaaatta aaaatgaagt tttaaatcaa tctaaagtat atatgagtaa  6240
acttggtctg acagttacca atgcttaatc agtgaggcac ctatctcagc gatctgtcta  6300
tttcgttcat ccatagttgc ctgactcccc gtcgtgtaga taactacgat acgggagggc  6360
ttaccatctg gccccagtgc tgcaatgata ccgcgagacc cacgctcacc ggctccagat  6420
ttatcagcaa taaaccagcc agccggaagg gccgagcgca gaagtggtcc tgcaacttta  6480
tccgcctcca tccagtctat taattgttgc cgggaagcta gagtaagtag ttcgccagtt  6540
aatagtttgc gcaacgttgt tgccattgct acaggcatcg tggtgtcacg ctcgtcgttt  6600
ggtatggctt cattcagctc cggttcccaa cgatcaaggc gagttacatg atcccccatg  6660
ttgtgcaaaa aagcggttag ctccttcggt cctccgatcg ttgtcagaag taagttggcc  6720
gcagtgttat cactcatggt tatggcagca ctgcataatt ctcttactgt catgccatcc  6780
gtaagatgct tttctgtgac tggtgagtac tcaaccaagt cattctgaga atagtgtatg  6840
cggcgaccga gttgctcttg cccggcgtca atacggata taccgcgcc acatagcaga  6900
actttaaaag tgctcatcat tggaaaacgt tcttcggggc gaaaactctc aaggatctta  6960
ccgctgttga tccagttcga tgtaacccca ctcgtgcac ccaactgatc ttcagcatct  7020
tttactttca ccagcgtttc tgggtgagca aaaacaggaa ggcaaaatgc cgcaaaaaag  7080
ggaataaggg cgacacggaa atgttgaata ctcatactct tcctttttca atattattga  7140
agcatttatc agggttattg tctcatgagc ggatacatat ttgaatgtat ttagaaaaat  7200
aaacaaatag gggttccgcg cacatttccc cgaaaagtgc cacctgacgt cgacggatcg  7260
ggagatctcc cgatccccta tggtcgactc tcagtacaat ctgctctgat gccgcatagt  7320
taagccagta tctgctccct gcttgtgtgt tggaggtcgc tgagtagtgc gcgagcaaaa  7380
tttaagctac aacaaggcaa ggcttgaccg acaattgcat gaagaatctg cttagg      7436
```

```
SEQ ID NO: 193          moltype = DNA  length = 6746
FEATURE                 Location/Qualifiers
misc_feature            1..6746
                        note = Synthetic Polynucleotide
source                  1..6746
                        mol_type = other DNA
                        organism = synthetic construct
SEQUENCE: 193
gttaggcgtt ttgcgctgct tcgcgatgta cgggccagat atacgcgttg acattgatta    60
ttgactagtt attaatagta atcaattacg gggtcattag ttcatagccc atatatggag   120
ttccgcgtta cataacttac ggtaaatggc ccgcctggct gaccgcccaa cgaccccgc    180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgccccctat tgacgtcaat gacggtaaat ggcccgcctg gcattatgcc   360
cagtacatga ccttatggga ctttcctact tggcagtaca tctacgtatt agtcatcgct   420
attaccatgg tgatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc cagcctccgg   720
actctagagg atcgaaccct tgaattcccg ccgccaccat gggctggtca tgtattattc   780
tgtttctggt cgcaactgct acaggggtcc atagtgagat cgtgctgacc caatctccag   840
gcaccctgtc tctcagccct ggcgagagag ccaccctgtc ctgcaccgct tctagctccg   900
tgtcctccag cttcctgcac tggtaccagc agaaacccgg ccaggctcct agactgctga   960
tctattccac ctccaacctg gcctctggca tccctgaccg gttctccggc tctggctccg  1020
gaacagattt tacactgacc atctcccggc tggaacctga ggacttcgcc gtgtactact  1080
gtcaccagta ccaccattct ccttacatct acaccttcgg cggcggaacc aagctggaaa  1140
tcaagaggac agtggccgcc ccaagcgtgt tcatcttttc cccttccgac gagcagctga  1200
agtctggcac cgccagcgtg gtgtgcctgc tgaacaactt ctaccctcgg gaggccaagg  1260
tccagtggaa ggtggataac gccctgcagt ctggcaatag ccaggagtcc gtgaccgagc  1320
aggactctaa ggatagcaca tattccctgt ctagcaccct gacactgagc aaggccgatt  1380
acgagaagca caaggtgtat gcctgtgaag tcacccatca ggggctgtca tcacccgtca  1440
ctaagtcatt caatcgcgga gaatgctgat aagcttaagg gttcgatccc taccggttag  1500
taatgagttt gatatctcga caatcaacct ctggattaca aaatttgtga aagattgact  1560
ggtattctta actatgttgc tccttttacg ctatgtggat acgctgcttt aatgcctttg  1620
tatcatgcta ttgcttcccg tatggctttc attttctcct ccttgtataa atcctggttg  1680
ctgtctcttt atgaggagtt gtggcccgtt gtcaggcaac gtggcgtggt gtgcactgtg  1740
tttgctgacg caaccccac tggttggggc attgccacca cctgtcagct cctttccggg  1800
actttcgctt tccccctccc tattgccacg gcggaactca tcgccgcctg ccttgcccgc  1860
tgctggacag gggctcggct gttgggcact gacaattccg tggtgttgtc ggggaagctg  1920
acgtcctttc catggctgct cgcctgtgtt gccacctgga ttctgcgcgg gacgtccttc  1980
tgctacgtcc cttcggccct caatccagcg gaccttcctt ccgcggcct gctgccggct  2040
ctgcggcctc ttccgcgtct tcgccttcgc cctcagacga gtcggatctc cctttgggcc  2100
gcctccccgc ctggaaacgg gggaggctaa ctgaaacacg gaaggagaca ataccggaag  2160
gaacccgcgc tatgacggca ataaaaagac agaataaaac gcacgggtgt tgggtcgttt  2220
gttcataaac gcggggttcg gtcccagggc tggcactcg tcgataccc accgagaccc  2280
cattggggcc aatacgcccg cgtttcttcc ttttccccac cccacccccc aagttcgggt  2340
gaaggcccag ggctcgcagc caacgtcggg gcggcaggcc ctgccatagc agatctgcgc  2400
agctggggct ctagggggta tccccacgcg ccctgtagcg gcgcattaag cgcggcgggt  2460
gtggtggtta cgcgcagcgt gaccgctaca cttgccagcg ccctagcgcc cgctccttcg  2520
gctttcttcc cttcctttct cgccacgttc gccggctttc cccgtcaagc tctaaatcgg  2580
ggcatccctt tagggttccg atttagtgct ttacggcacc tcgaccccaa aaaacttgat  2640
tagggtgatg gttcacgtag tgggccatcg ccctgataga cggtttttcg ccctttgacg  2700
ttggagtcca cgttctttaa tagtggactc ttgttccaaa ctggaacaac actcaaccct  2760
atctcggtct attcttttga tttataaggg attttgggga tttcggccta ttggttaaaa  2820
aatgagctga tttaacaaaa atttaacgcg aattaattct gtggaatgtg tgtcagttag  2880
ggtgtggaaa gtcccaggc tccccagcag gcagaagtat gcaaagcatg catctcaatt  2940
agtcagcaac caggtgtgga aagtcccag gctccccage aggcagaagt atgcaaagca  3000
tgcatctcaa ttagtcagca accatagtcc cgccctaac ccgcccatc ccgcccctaa  3060
ctccgcccag ttccgcccat tctccgcccc atggctgact aatttttttt atttatgcag  3120
aggccgaggc cgcctctgcc tctgagctat tccagaagta gtgaggaggc ttttttggag  3180
gcctaggctt ttgcaaaaag ctcccgggag cttgtatatc cattttcgga tctgatcaag  3240
agacaggatg aggatcgttt cgcatgattg aacaagatgg attgcacgca ggttctccgg  3300
ccgcttgggt ggagaggcta ttcggctatg actgggcaca acagacaatc ggctgctctg  3360
atgccgccgt gttccggctg tcagcgcagg ggcgcccgt tctttttgtc aagaccgacc  3420
tgtccggtgc cctgaatgaa ctgcaggacg aggcagcgcg gctatcgtgg ctggccacga  3480
cgggcgttcc ttgcgcagct gtgctcgacg ttgtcactga agcgggaagg gactggctgc  3540
tattgggcga agtgccgggg caggatctcc tgtcatctca ccttgctcct gccgagaaag  3600
tatccatcat ggctgatgca atgcggcggc tgcatacgct tgatccggct acctgcccat  3660
tcgaccacca agcgaaacat cgcatcgagc gagcacgtac tcggatggaa gccggtcttg  3720
tcgatcagga tgatctggac gaagagcatc aggggctcgc gccagccgaa ctgttcgcca  3780
ggctcaaggc gcgcatgccc gacggcgagg atctcgtcgt gacccatggc gatgcctgct  3840
tgccgaatat catggtggaa aatggccgct tttctggatt catcgactgt ggccggctgg  3900
gtgtggcgga ccgctatcag gacatagcgt tggctaccg tgatattgct gaagagcttg  3960
gcggcgaatg ggctgaccgc ttcctcgtgc tttacggtat cgccgctccc gattcgcagc  4020
gcatcgcctt ctatcgcctt cttgacgagt cttctgagc gggactctgg ggttcgcgaa  4080
atgaccgacc aagcgacgcc caacctgcca tcacgagatt cgattccac cgccgccttc  4140
tatgaaaggt tgggcttcgg aatcgttttc cgggacgccg gctggatgat cctccagcgc  4200
```

```
ggggatctca tgctggagtt cttcgcccac cccaacttgt ttattgcagc ttataatggt  4260
tacaaataaa gcaatagcat cacaaatttc acaaataaag catttttttc actgcattct  4320
agttgtggtt tgtccaaact catcaatgta tcttatcatg tctgtatacc gtcgacctct  4380
agctagagct tggcgtaatc atggtcatag ctgtttcctg tgtgaaattg ttatccgctc  4440
acaattccac acaacatacg agccggaagc ataaagtgta aagcctgggg tgcctaatga  4500
gtgagctaac tcacattaat tgcgttgcgc tcactgcccg ctttccagtc gggaaacctg  4560
tcgtgccagc tgcattaatg aatcggccaa cgcgcgggga gaggcggttt gcgtattggg  4620
cgctcttccg cttcctcgct cactgactcg ctgcgctcgg tcgttcggct gcggcgagcg  4680
gtatcagctc actcaaaggc ggtaatacgg ttatccacag aatcagggga taacgcagga  4740
aagaacatgt gagcaaaagg ccagcaaaag gccaggaacc gtaaaaaggc cgcgttgctg  4800
gcgtttttcc ataggctccg cccccctgac gagcatcaca aaaatcgacg ctcaagtcag  4860
aggtggcgaa acccgacagg actataaaga taccaggcgt ttcccctgg aagctccctc  4920
gtgcgctctc ctgttccgac cctgccgctt accggatacc tgtccgcctt tctcccttcg  4980
ggaagcgtgg cgctttctca atgctcacgc tgtaggtatc tcagttcggt gtaggtcgtt  5040
cgctccaagc tgggctgtgt gcacgaaccc cccgttcagc ccgaccgctg cgccttatcc  5100
ggtaactatc gtcttgagtc caacccggta agacacgact tatcgccact ggcagcagcc  5160
actggtaaca ggattagcag agcgaggtat gtaggcggtg ctacagagtt cttgaagtgg  5220
tggcctaact acggctacac tagaaggaca gtatttggta tctgcgctct gctgaagcca  5280
gttaccttcg gaaaaagagt tggtagctct tgatccggca aacaaaccac cgctggtagc  5340
ggtggttttt ttgtttgcaa gcagcagatt acgcgcagaa aaaaaggatc tcaagaagat  5400
cctttgatct tttctacggg gtctgacgct cagtggaacg aaaactcacg ttaagggatt  5460
ttggtcatga gattatcaaa aaggatcttc acctagatcc ttttaaatta aaaatgaagt  5520
tttaaatcaa tctaaagtat atatgagtaa acttggtctg acagttacca atgcttaatc  5580
agtgaggcac ctatctcagc gatctgtcta tttcgttcat ccatagttgc ctgactcccc  5640
gtcgtgtaga taactacgat acgggagggc ttaccatctg gccccagtgc tgcaatgata  5700
ccgcgagacc cacgctcacc ggctccagat ttatcagcaa taaaccagcc agccggaagg  5760
gccgagcgca gaagtggtcc tgcaacttta tccgcctcca tccagtctat taattgttgc  5820
cgggaagcta gagtaagtag ttcgccagtt aatagtttgc gcaacgttgt tgccattgct  5880
acaggcatcg tggtgtcacg ctcgtcgttt ggtatggctt cattcagctc cggttcccaa  5940
cgatcaaggc gagttacatg atcccccatg ttgtgcaaaa aagcggttag ctccttcggt  6000
cctccgatcg ttgtcagaag taagttggcc gcagtgttat cactcatggt tatggcagca  6060
ctgcataatt ctcttactgt catgccatcc gtaagatgct tttctgtgac tggtgagtac  6120
tcaaccaagt cattctgaga atagtgtatg cggcgaccga gttgctcttg cccggcgtca  6180
atacgggata ataccgcgcc acatagcaga actttaaaag tgctcatcat tggaaaacgt  6240
tcttcggggc gaaaactctc aaggatctta ccgctgttga tccagttc gatgtaaccc  6300
actcgtgcac ccaactgatc ttcagcatct tttactttca ccagcgtttc tgggtgagca  6360
aaaacaggaa ggcaaaatgc cgcaaaaaag ggaataaggg cgacacggaa atgttgaata  6420
ctcatactct tcctttttca atattattga agcatttatc agggttattg tctcatgagc  6480
ggatacatat ttgaatgtat ttagaaaaat aaacaaatag gggttccgcg cacatttccc  6540
cgaaaagtgc cacctgacgt cgacggatcg gagatctcc cgatccccta tggtcgactc  6600
tcagtacaat ctgctctgat gccgcatagt taagccagta tctgctccct gcttgtgtgt  6660
tggaggtcgc tgagtagtgc gcgagcaaaa tttaagctac aacaaggcaa ggcttgaccg  6720
acaattgcat gaagaatctg cttagg                                       6746
```

SEQ ID NO: 194      moltype = DNA  length = 6746
FEATURE             Location/Qualifiers
misc_feature       1..6746
                    note = Synthetic Polynucleotide
source             1..6746
                    mol_type = other DNA
                    organism = synthetic construct
SEQUENCE: 194

```
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggc gaccgcccaa cgacccccgt  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgcccctat tgacgtcaat gacggtaaat ggcccgcctg gcattatgcc  360
cagtacatga cctatgggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct tgaattcccc ccgccaccat gggctggtca tgtattattc  780
tgtttctggt cgcaactgct acaggggtcc atagtgagat cgtgctgaca caatctcccg  840
gcaccctcag cctgtctcca ggcgagagag ccacactgtc ctgcaccgct tctagctccg  900
tgtcctccag ctttctgcac tggtaccagc agaaacctgg ccaggctcct cagtcgtgga  960
tctactccac ctccaacctg gcctctggca tccctgatcg gttctccggc tccggctctg  1020
gcaccgacta caccctgacc atctccagac tggaaccgga ggacttcgcc gtgtactact  1080
gtcaccagta ccaccattct ccttacatct ataccttcgg cggaggaacc aagctggaaa  1140
tcaagaggac agtggccgcc ccaagcgtgt tcatctttcc cccttccgac gagcagctga  1200
agtctggcac cgccagcgtg gtgtgcctgc tgaacaactt ctaccctcgg gaggccaagg  1260
tccagtggaa ggtggataac gccctgcagt ctggcaatag ccaggagtcc gtgaccgagc  1320
aggactctaa ggatagcaca tattccctgt ctagcaccct gacactgagc aaggccgatt  1380
acgagaagca caaggtgtat gcctgtgaag tcacccatca ggggctgtca tcaccgtca  1440
ctaagtcatt caatcgcgga gaatgctgat aagcttaagg gttcgatccc taccggttag  1500
taatgagttt gatatctcga caatcaacct ctggattaca aaatttgtga agattgact  1560
ggtattctta actatgttgc tcctttacg ctatgtggat acgctgcttt aatgcctttg  1620
```

-continued

```
tatcatgcta ttgcttcccg tatggctttc attttctcct ccttgtataa atcctggttg    1680
ctgtctcttt atgaggagtt gtggcccgtt gtcaggcaac gtggcgtggt gtgcactgtg    1740
tttgctgacg caaccccac tggttggggc attgccacca cctgtcagct cctttccggg     1800
actttcgctt tccccctccc tattgccacg gcggaactca tcgccgcctg ccttgccgc     1860
tgctggacag gggctcggct gttgggcact gacaattccg tggtgttgtc ggggaagctg     1920
acgtcctttc catggctgct cgcctgtgtt gccacctgga ttctgcgcgg gacgtccttc     1980
tgctacgtcc cttcggccct caatccagcg gaccttcctt cccgcggcct gctgccggct     2040
ctgcggcctc ttccgcgtct tcgccttcgc cctcagacga gtcggatctc cctttgggcc     2100
gcctccccgc ctggaaacgg gggaggctaa ctgaaacacg gaaggagaca ataccggaag     2160
gaacccgcgc tatgacggca ataaaaagac agaataaaac gcacgggtgt tgggtcgttt     2220
gttcataaac gcggggttcg gtcccaggac tggcactctg tcgatacccc accgagaccc     2280
cattgggggc aatacgcccg cgtttcttcc ttttccccac cccaccccc aagttcgggt      2340
gaaggcccag ggctcgcagc caacgtcggg gcggcaggcc ctgccatagc agatctgcgc     2400
agctggggct ctaggggta tccccacgcg ccctgtagcg gcgcattaag cgcggcgggt      2460
gtggtggtta cgcgcagcgt gaccgctaca cttgccagcg ccctagcgcc cgctcctttc     2520
gctttcttcc cttcctttct cgccacgttc gccggctttc cccgtcaagc tctaaatcgg     2580
ggcatccctt tagggttccg atttagtgct ttacggcacc tcgaccccaa aaaacttgat     2640
tagggtgatg gttcacgtag tgggccatcg ccctgataga cggttttcg ccctttgacg      2700
ttggagtcca cgttctttaa tagtggactc ttgttccaaa ctggaacaac actcaaccct     2760
atctcggtct attcttttga tttataaggg attttgggga tttcggccta ttggttaaaa     2820
aatgagctga tttaacaaaa atttaacgcg aattaattct gtggaatgtg tgtcagttag     2880
ggtgtggaaa gtccccaggc tccccagcag gcagaagtat gcaaagcatg catctcaatt     2940
agtcagcaac caggtgtgga aagtccccag gctccccagc aggcagaagt atgcaaagca     3000
tgcatctcaa ttagtcagca accatagtcc cgcccctaac tccgcccatc ccgcccctaa     3060
ctccgcccag ttccgcccat tctccgcccc atggctgact aatttttttt atttatgcag     3120
aggccgaggc cgcctctgcc tctgagctat tccagaagta gtgaggaggc tttttttggag     3180
gcctaggctt ttgcaaaaag ctccggggag cttgtatatc cattttcgga tctgatcaag     3240
agacaggatg aggatcgttt cgcatgattg aacaagatgg attgcacgca ggttctccgg     3300
ccgcttgggt ggagaggcta ttcggctatg actgggcaca acagacaatc ggctgctctg     3360
atgccgccgt gttccggctg tcagcgcagg ggcgcccggt tctttttgtc aagaccgacc     3420
tgtccggtgc cctgaatgaa ctgcaggacg aggcagcgcg gctatcgtgg ctggccacga     3480
cgggcgttcc ttgcgcagct gtgctcgacg ttgtcactga agcgggaagg gactggctgc     3540
tattgggcga agtgccgggg caggatctcc tgtcatctca ccttgctcct gccgagaaag     3600
tatccatcat ggctgatgca atgcggcggc tgcatacgct tgatccggct acctgcccat     3660
tcgaccacca agcgaaacat cgcatcgagc gagcacgtac tcggatggaa gccggtcttg     3720
tcgatcagga tgatctggac gaagagcatc aggggctcgc gccagccgaa ctgttcgcca     3780
ggctcaaggc gcgcatgccc gacggcgagg atctcgtcgt gacccatggc gatgcctgct     3840
tgccgaatat catggtggaa aatggccgct tttctggatt catcgactgt ggccggctgg     3900
gtgtggcgga ccgctatcag gacatagcgt tggctacccg tgatattgct gaagagcttg     3960
gcggcgaatg ggctgaccgc ttcctcgtgc tttacggtat cgccgctccc gattcgcagc     4020
gcatcgcctt ctatcgcctt cttgacgagt tcttctgagc gggactctgg ggttcgcgaa     4080
atgaccgacc aagcgacgcc caacctgcca tcacagatt tcgattccac cgccgccttc      4140
tatgaaaggt tgggcttcgg aatcgttttc cgggacgccg gctggatgat cctccagcgc     4200
ggggatctca tgctggagtt cttcgcccac cccaacttgt ttattgcagc ttataatggt     4260
tacaaataaa gcaatagcat cacaaatttc acaaataaag catttttttc actgcattct     4320
agttgtggtt tgtccaaact catcaatgta tcttatcatg tctgtatacc gtcgacctct     4380
agctagagct tggcgtaatc atggtcatag ctgtttcctg tgtgaaattg ttatccgctc     4440
acaattccac acaacatacg agccggaagc ataaagtgta aagcctgggg tgcctaatga     4500
gtgagctaac tcacattaat tgcgttgcgc tcactgcccg ctttccagtc gggaaacctg     4560
tcgtgccagc tgcattaatg aatcggccaa cgcgcgggga gaggcggttt gcgtattggg     4620
cgctcttccg cttcctcgct cactgactcg ctgcgctcgg tcgttcggct gcggcgagcg     4680
gtatcagctc actcaaaggc ggtaatacgg ttatccacag aatcagggga taacgcagga     4740
aagaacatgt gagcaaaagg ccagcaaaag gccaggaacc gtaaaaaggc cgcgttgctg     4800
gcgtttttcc ataggctccg cccccctgac gagcatcaca aaaatcgacg ctcaagtcag     4860
aggtggcgaa acccgacagg actataaaga taccaggcgt ttccccctgg aagctccctc     4920
gtgcgctctc ctgttccgac cctgccgctt accggatacc tgtccgcctt tctcccttcg     4980
ggaagcgtgg cgctttctca atgctcacgc tgtaggtatc tcagttcggt gtaggtcgtt     5040
cgctccaagc tgggctgtgt gcacgaaccc ccgttcagc ccgaccgctg cgccttatcc      5100
ggtaactatc gtcttgagtc caacccggta agacacgact tatcgccact ggcagcagcc     5160
actggtaaca ggattagcag agcgaggtat gtaggcggtg ctacagagtt cttgaagtgg     5220
tggcctaact acggctacac tagaaggaca gtatttggta tctgcgctct gctgaagcca     5280
gttaccttcg gaaaaagagt tggtagctct tgatccggca aacaaaccac cgctggtagc     5340
ggtggttttt ttgtttgcaa gcagcagatt acgcgcagaa aaaaaggatc tcaagaagat     5400
cctttgatct tttctacggg gtctgacgct cagtggaacg aaaactcacg ttaagggatt     5460
ttggtcatga gattatcaaa aaggatcttc acctagatcc ttttaaatta aaaatgaagt     5520
tttaaatcaa tctaaagtat atatgagtaa acttggtctg acagttacca atgcttaatc     5580
agtgaggcac ctatctcagc gatctgtcta tttcgttcat ccatagttgc ctgactcccc     5640
gtcgtgtaga taactacgat acgggagggc ttaccatctg gccccagtgc tgcaatgata     5700
ccgcgagacc cacgctcacc ggctccagat ttatcagcaa taaaccagcc agccggaagg     5760
gccgagcgca gaagtggtcc tgcaacttta tccgcctcca tccagtctat taattgttgc     5820
cgggaagcta gagtaagtag ttcgccagtt aatagtttgc gcaacgttgt tgccattgct     5880
acaggcatcg tggtgtcacg ctcgtcgttt ggtatggctt cattcagctc cggttcccaa     5940
cgatcaaggc gagttacatg atcccccatg ttgtgcaaaa aagcggttag ctccttcggt     6000
cctccgatcg ttgtcagaag taagttggcc gcagtgttat cactcatggt tatggcagca     6060
ctgcataatt ctcttactgt catgccatcc gtaagatgct tttctgtgac tggtgagtac     6120
tcaaccaagt cattctgaga atagtgtatg cggcgaccga gttgctcttg cccggcgtca     6180
atacgggata ataccgcgcc acatagcaga actttaaaag tgctcatcat ggaaaacgt      6240
tcttcggggc gaaaactctc aaggatctta ccgctgttga gatccagttc gatgtaaccc     6300
actcgtgcac ccaactgatc ttcagcatct tttactttca ccagcgtttc tgggtgagca     6360
```

-continued

```
aaaacaggaa ggcaaaatgc cgcaaaaaag ggaataaggg cgacacggaa atgttgaata   6420
ctcatactct tccttttttca atattattga agcatttatc agggttattg tctcatgagc   6480
ggatacatat ttgaatgtat ttagaaaaat aaacaaatag gggttccgcg cacatttccc   6540
cgaaaagtgc cacctgacgt cgacggatcg ggagatctcc cgatccccta tggtcgactc   6600
tcagtacaat ctgctctgat gccgcatagt taagccagta tctgctccct gcttgtgtgt   6660
tggaggtcgc tgagtagtgc gcgagcaaaa tttaagctac aacaaggcaa ggcttgaccg   6720
acaattgcat gaagaatctg cttagg                                        6746

SEQ ID NO: 195          moltype = DNA  length = 6746
FEATURE                 Location/Qualifiers
misc_feature            1..6746
                        note = Synthetic Polynucleotide
source                  1..6746
                        mol_type = other DNA
                        organism = synthetic construct
SEQUENCE: 195
gttaggcgtt ttgcgctgct tcgcgatgta cgggccagat atacgcgttg acattgatta   60
ttgactagtt attaatagta atcaattacg gggtcattag ttcatagccc atatatggag   120
ttccgcgtta cataacttac ggtaaatggc ccgcctggct gaccgcccaa cgacccccgc   180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgcccectat tgacgtcaat gacggtaaat ggcccgcctg gcattatgcc   360
cagtacatga ccttatggga ctttcctact tggcagtaca tctacgtatt agtcatcgct   420
attaccatgg tgatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc cagcctccgg   720
actctagagg atcgaaccct tgaattcccg ccgccaccat gggctggtca tgtattattc   780
tgtttctggt cgcaactgct acaggggtcc atagtgagat cgtgctgacc cagtctccag   840
gcacactcag cctgtctcct ggcgagcggg ctaccctgtc ctgcaccgcc agcagctccg   900
tgtcctcttc ttttctgcac tggtaccagc agaaacctgg acaagctcct cagctgtgga   960
tctactccac ctccaacctg gcctctggca tccccgatag attctccggc tctggctccg   1020
gcaccgacta cacactgacc atctccagac tggaacctga ggacttcgcc acctactact   1080
gtcatcagta ccaccactcc cttacatatc ataccttcgg cggaggcacc aagctggaaa   1140
tcaagaggac agtggccgcc ccaagcgtgt tcatctttcc cccttccgac gagcagctga   1200
agtctggcac cgccagcgtg gtgtgcctgc tgaacaactt ctaccctcgg gaggccaagg   1260
tccagtggaa ggtggataac gccctgcagt ctggcaatag ccaggagtcc gtgaccgagc   1320
aggactctaa ggatagcaca tattccctgt ctagcaccct gacactgagc aaggccgatt   1380
acgagaagca caaggtgtat gcctgtgaag tcacccatca ggggctgtca tcacccgtca   1440
ctaagtcatt caatcgcgga gaatgctgat aagcttaagg gttcgatccc taccggttag   1500
taatgagttt gatatctcga caatcaacct ctggattaca aaatttgtga agattgact    1560
ggtattctta actatgttgc tccttttacg ctatgtggat acgctgcttt aatgcctttg   1620
tatcatgcta ttgcttcccg tatggctttc attttctcct ccttgtataa atcctggttg   1680
ctgtctcttt atgaggagtt gtggcccgtt gtcaggcaac gtggcgtggt gtgcactgtg   1740
tttgctgacg caacccccac tggttggggc attgccacca cctgtcagct cctttccggg   1800
actttcgctt tccccctccc tattgccacg gcggaactca tcgccgcctg ccttgcccgc   1860
tgctggacag gggctcggct gttgggcact gacaattccg tggtgttgtc ggggaagctg   1920
acgtcctttc catggctgct cgcctgtgtt gccacctgga ttctgcgcgg gacgtccttc   1980
tgctacgtcc cttcggccct caatccagcg gaccttcctt cccgcggcct gctgccggct   2040
ctgcggcctc ttccgcgtct tcgccttcgc cctcagacga gtcggatctc ccttgggcc    2100
gcctccccgc ctggaaacgg gggaggctaa ctgaaacacg aaggagaca ataccggaag    2160
gaacccgcgc tatgacggca ataaaaagac agaataaaac gcacgggtgt tgggtcgttt   2220
gttcataaac gcggggttcg gtcccagggc tggcactctg tcgataccac accgagaccc   2280
cattggggcca aatacgcccg cgtttcttcc ttttccccac cccaccccc aagttcgggt   2340
gaaggcccag ggctcgcagc caacgtcggg gcggcaggcc ctgccatagc agatctgcgc   2400
agctggggct ctaggggta tccccacgcg ccctgtagcg gcgcattaag cgcggcgggt   2460
gtggtggtta cgcgcagcgt gaccgctaca cttgccagcg ccctagcgcc cgctcctttc   2520
gctttcttcc cttcctttct cgccacgttc gccggctttc cccgtcaagc tctaaatcgg   2580
ggcatccctt tagggttccg atttagtgct ttacggcacc tcgaccccaa aaaacttgat   2640
tagggtgatg gttcacgtag tgggccatcg ccctgataga cggttttcg cccttttgacg   2700
ttggagtcca cgttctttaa tagtggactc ttgttccaaa ctggaacaac actcaaccct   2760
atctcggtct attcttttga tttataaggg attttgggga tttcggccta ttggttaaaa   2820
aatgagctga tttaacaaaa atttaacgcg aattaattct gtggaatgtg tgtcagttag   2880
ggtgtggaaa gtccccaggc tccccagcag gcagaagtat gcaaagcatg catctcaatt   2940
agtcagcaac caggtgtgga aagtccccag gctccccagc aggcagaagt atgcaaagca   3000
tgcatctcaa ttagtcagca accatagtcc cgcccctaac tccgcccatc ccgccctaa    3060
ctccgcccag ttccgcccat tctccgcccc atggctgact aatttttttt atttatgcag   3120
aggccgagge cgcctctgcc tctgagctat tccagaagta gtgaggaggc tttttggagg   3180
cctaggcctt ttgcaaaaag ctcccgggag cttgtatatc cattttcgga tctgatcaag   3240
agacaggatg aggatcgttt cgcatgattg aacaagatgg attgcacgca ggttctccgg   3300
ccgcttgggt ggagaggcta ttcggctatg actgggcaca acagacaatc ggctgctctg   3360
atgccgccgt gttccggctg tcagcgcagg ggcgcccggt tctttttgtc aagaccgacc   3420
tgtccggtga ccctgaatga actgcaggac gaggcagcgc ggctatcgtg gctggccacg   3480
cgggcgttcc ttgcgcagct gtgctcgacg ttgtcactga agcgggaagg gactggctgc   3540
tattgggcga agtgccgggg caggatctcc tgtcatctca ccttgctcct gccgagaaag   3600
tatccatcat ggctgatgca atgcggcggc tgcatacgct tgatccggct acctgcccat   3660
tcgaccacca agcgaaacat cgcatcgagc gagcacgtac tcggatggaa gccggtcttg   3720
tcgatcagga tgatctggac gaagagcatc aggggctcgc gccagccgaa ctgttcgcca   3780
```

-continued

```
ggctcaaggc gcgcatgccc gacggcgagg atctcgtcgt gacccatggc gatgcctgct  3840
tgccgaatat catggtggaa aatggccgct tttctggatt catcgactgt ggccggctgg  3900
gtgtggcgga ccgctatcag gacatagcgt tggctacccg tgatattgct gaagagcttg  3960
gcggcgaatg ggctgaccgc ttcctcgtgc tttacggtat cgccgctccc gattcgcagc  4020
gcatcgcctt ctatcgcctt cttgacgagt tcttctgagc gggactctgg ggttcgcgaa  4080
atgaccgacc aagcgacgcc caacctgcca tcacgagatt tcgattccac cgccgccttc  4140
tatgaaaggt tgggcttcgg aatcgttttc cgggacgccg gctggatgat cctccagcgc  4200
ggggatctca tgctggagtt cttcgcccac cccaacttgt ttattgcagc ttataatggt  4260
tacaaataaa gcaatagcat cacaaatttc acaaataaag cattttttc actgcattct  4320
agttgtggtt tgtccaaact catcaatgta tcttatcatg tctgtatacc gtcgacctct  4380
agctagagct tggcgtaatc atggtcatag ctgtttcctg tgtgaaattg ttatccgctc  4440
acaattccac acaacatacg agccggaagc ataaagtgta aagcctgggg tgcctaatga  4500
gtgagctaac tcacattaat tgcgttgcgc tcactgcccg ctttccagtc gggaaacctg  4560
tcgtgccagc tgcattaatg aatcggccaa cgcgcgggga gaggcggttt gcgtattggg  4620
cgctcttccg cttcctcgct cactgactcg ctgcgctcgg tcgttcggct gcggcgagcg  4680
gtatcagctc actcaaaggc ggtaatacgg ttatccacag aatcagggga taacgcagga  4740
aagaacatgt gagcaaaagg ccagcaaaag gccaggaacc gtaaaaaggc cgcgttgctg  4800
gcgttttccc ataggctccg cccccctgac gagcatcaca aaaatcgacg ctcaagtcag  4860
aggtggcgaa acccgacagg actataaaga taccaggcgt ttcccctgg aagctccctc  4920
gtgcgctctc ctgttccgac cctgccgctt accggatacc tgtccgcctt tctcccttcg  4980
ggaagcgtgg cgctttctca atgctcacgc tgtaggtatc tcagttcggt gtaggtcgtt  5040
cgctccaagc tgggctgtgt gcacgaaccc cccgttcagc ccgaccgctg cgccttatcc  5100
ggtaactatc gtcttgagtc caacccggta agacacgact tatcgccact ggcagcagcc  5160
actggtaaca ggattagcag agcgaggtat gtaggcggtg ctacagagtt cttgaagtgg  5220
tggcctaact acggctacac tagaaggaca gtatttggta tctgcgctct gctgaagcca  5280
gttaccttcg gaaaaagagt tggtagctct tgatccggca aacaaaccac cgctggtagc  5340
ggtggttttt ttgtttgcaa gcagcagatt acgcgcagaa aaaaaggatc tcaagaagat  5400
cctttgatct tttctacggg gtctgacgct cagtggaacg aaaactcacg ttaagggatt  5460
ttggtcatga gattatcaaa aaggatcttc acctagatcc ttttaaatta aaaatgaagt  5520
tttaaatcaa tctaaagtat atatgagtaa acttggtctg acagttacca atgcttaatc  5580
agtgaggcac ctatctcagc gatctgtcta tttcgttcat ccatagttgc ctgactcccc  5640
gtcgtgtaga taactacgat acgggagggc ttaccatctg gccccagtgc tgcaatgata  5700
ccgcgagacc cacgctcacc ggctccagat ttatcagcaa taaaccagcc agccggaagg  5760
gccgagcgca gaagtggtcc tgcaacttta tccgcctcca tccagtctat taattgttgc  5820
cgggaagcta gagtaagtag ttcgccagtt aatagtttgc gcaacgttgt tgccattgct  5880
acaggcatcg tggtgtcacg ctcgtcgttt ggtatggctt cattcagctc cggttcccaa  5940
cgatcaaggc gagttacatg atcccccatg ttgtgcaaaa aagcggttag ctccttcggt  6000
cctccgatcg ttgtcagaag taagttggcc gcagtgttat cactcatggt tatggcagca  6060
ctgcataatt ctcttactgt catgccatcc gtaagatgct tttctgtgac tggtgagtac  6120
tcaaccaagt cattctgaga atagtgtatg cggcgaccga gttgctcttg cccggcgtca  6180
atacgggata ataccgcgcc acatagcaga actttaaaag tgctcatcat tggaaaacgt  6240
tcttcggggc gaaaactctc aaggatctta ccgctgttga tccagttc gatgtaaccc  6300
actcgtgcac ccaactgatc ttcagcatct tttactttca ccagcgtttc tgggtgagca  6360
aaaacaggaa ggcaaaatgc cgcaaaaaag ggaataaggg cgacacggaa atgttgaata  6420
ctcatactct tcctttttca atattattga agcatttatc agggttattg tctcatgagc  6480
ggatacatat ttgaatgtat ttagaaaaat aaacaaatag gggttccgcg cacatttccc  6540
cgaaaagtgc cacctgacgt cgacggatcg ggagatctcc cgatccccta tggtcgactc  6600
tcagtacaat ctgctctgat gccgcatagt taagccagta tctgctccct gcttgtgtgt  6660
tggaggtcgc tgagtagtgc gcgagcaaaa tttaagctac aacaaggcaa ggcttgaccg  6720
acaattgcat gaagaatctg cttagg                                       6746
```

```
SEQ ID NO: 196        moltype = DNA  length = 6746
FEATURE               Location/Qualifiers
misc_feature          1..6746
                      note = Synthetic Polynucleotide
source                1..6746
                      mol_type = other DNA
                      organism = synthetic construct
SEQUENCE: 196
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct tgaattcccg ccgccaccat gggctggtca tgtattattc  780
tgtttctggt cgcaactgct acaggggtcc atagtgagat cgtgctgacc caatctcctg  840
gcaccctgtc tctgagccca ggcgagagag ccacactctc ctgccgctct tcttccagtg  900
tgtcctctag ctttctgcac tggtaccagc agaaacccgg ccaggctcct cagctgtgga  960
tctactccac ctccaacctg gcctctggca tccctgccag attctccgga tccggctctg  1020
gcaccgatta tactgacc atctcccggc tggaacctga ggacttcgcc acctactact  1080
gtcaccagta ccaccatagc ccttacatct acaccttcgg cggcggaacc aagctggaaa  1140
tcaagaggac agtggccgcc ccaagcgtgt tcatctttcc cccttccgac gagcagctga  1200
```

-continued

```
agtctggcac cgccagcgtg gtgtgcctgc tgaacaactt ctaccctcgg gaggccaagg   1260
tccagtggaa ggtggataac gccctgcagt ctggcaatag ccaggagtcc gtgaccgagc   1320
aggactctaa ggatagcaca tattccctgt ctagcaccct gacactgagc aaggccgatt   1380
acgagaagca caaggtgtat gcctgtgaag tcacccatca ggggctgtca tcacccgtca   1440
ctaagtcatt caatcgcgga gaatgctgat aagcttaagg gttcgatccc taccggttag   1500
taatgagttt gatatctcga caatcaacct ctggattaca aaatttgtga aagattgact   1560
ggtattctta actatgttgc tccttttacg ctatgtggat acgctgcttt aatgcctttg   1620
tatcatgcta ttgcttcccg tatggctttc attttctcct ccttgtataa atcctggttg   1680
ctgtctcttt atgaggagtt gtggcccgtt gtcaggcaac gtggcgtggt gtgcactgtg   1740
tttgctgacg caaccccac tggttggggc attgccacca cctgtcagct cctttccggg   1800
actttcgctt tccccctccc tattgccacg cgcgaactca tcgccgcctg ccttgcccgc   1860
tgctggacag gggctcggct gttgggcact gacaattccg tggtgttgtc ggggaagctg   1920
acgtcctttc catggctgct cgcctgtgtt gccacctgga ttctgcgcgg gacgtccttc   1980
tgctacgtcc cttcggccct caatccagcg gaccttcctt cccgcggcct gctgccggct   2040
ctgcggcctc ttccgcgtct tcgccttcgc cctcagacga gtcggatctc cctttgggcc   2100
gcctccccgc ctggaaacgg gggaggctaa ctgaaacacg gaaggagaca ataccggaag   2160
gaacccgcgc tatgacggca ataaaaagac agaataaaac gcacgggtgt tgggtcgttt   2220
gttcataaac gcggggttcg gtcccagggc tggcactctg tcgataccc accgagaccc    2280
cattgggggcc aatacgcccg cgtttcttcc tttttcccccac cccaccccc aagttcgggt   2340
gaaggcccag ggctcgcagc caacgtcggg gcggcaggcc ctgccatagc agatctgcgc   2400
agctggggct ctaggggggta tccccacgcg ccctgtagcg gcgcattaag cgcggcgggt   2460
gtggtggtta cgcgcagcgt gaccgctaca cttgccagcg ccctagcgcc cgctcctttc   2520
gctttcttcc cttcctttct cgccacgttc gccggctttc cccgtcaagc tctaaatcgg   2580
ggcatccctt tagggttccg atttagtgct ttacggcacc tcgaccccaa aaaacttgat   2640
tagggtgatg gttcacgtag tgggccatcg ccctgataga cggtttttcg ccctttgacg   2700
ttggagtcca cgttctttaa tagtggactc ttgttccaaa ctggaacaac actcaaccct   2760
atctcggtct attcttttga tttataaggg attttgggga tttcggccta ttggttaaaa   2820
aatgagctga tttaacaaaa atttaacgcg aattaattct gtggaatgtg tgtcagttag   2880
ggtgtggaaa gtccccaggc tccccagcag gcagaagtat gcaaagcatg catctcaatt   2940
agtcagcaac caggtgtgga aagtccccag gctccccagc aggcagaagt atgcaaagca   3000
tgcatctcaa ttagtcagca accatagtcc cgcccctaac tccgcccatc ccgcccctaa   3060
ctccgcccag ttccgcccat tctccgcccc atggctgact aatttttttt atttatgcag   3120
aggccgaggc cgcctctgcc tctgagctat tccagaagta gtgaggaggc ttttttggag   3180
gcctaggctt ttgcaaaaag ctcccgggag cttgtatatc cattttcgga tctgatcaag   3240
agacaggatg aggatcgttt cgcatgattg aacaagatgg attgcacgca ggttctccgg   3300
ccgcttgggt ggagaggcta ttcggctatg actgggcaca acagacaatc ggctgctctg   3360
atgccgccgcg gttccggctg tcagcgcagg ggcgcccggt tcttttttgtc aagaccgacc   3420
tgtccggtgc cctgaatgaa ctgcaggacg aggcagcgcg gctatcgtgg ctggccacga   3480
cgggcgttcc ttgcgcagct gtgctcgacg ttgtcactga agcgggaagg gactggctgc   3540
tattgggcga agtgccgggg caggatctcc tgtcatctca ccttgctcct gccgagaaag   3600
tatccatcat ggctgatgca atgcggcggc tgcatacgct tgatccggct acctgcccat   3660
tcgaccacca agcgaaacat cgcatcgagc gagcacgtac tcggatggaa gccggtcttg   3720
tcgatcagga tgatctggac gaagagcatc aggggctcgc gccagccgaa ctgttcgcca   3780
ggctcaaggc gcgcatgccc gacggcgagg atctcgtcgt gacccatggc gatgcctgct   3840
tgccgaatat catggtggaa aatggccgct tttctggatt catcgactgt ggccggctgg   3900
gtgtggcgga ccgctatcag gacatagcgt tggctacccg tgatattgct gaagagcttg   3960
gcggcgaatg ggctgaccgc ttcctcgtgc tttacggtat cgccgctccc gattcgcagc   4020
gcatcgcctt ctatcgcctt cttgacgagt tcttctgagc gggactctgg ggttcgcgaa   4080
atgaccgacc aagcgacgcc caacctgcca tcacgagatt tcgattccac cgccgccttc   4140
tatgaaaggt tgggcttcgg aatcgttttc cgggacgccg gctggatgat cctccagcgc   4200
ggggatctca tgctggagtt cttcgcccac cccaacttgt ttattgcagc ttataatggt   4260
tacaaataaa gcaatagcat cacaaatttc acaaataaag catttttttc actgcattct   4320
agttgtggtt tgtccaaact catcaatgta tcttatcatg tctgtatacc gtcgacctct   4380
agctagagct tggcgtaatc atggtcatag ctgtttcctg tgtgaaattg ttatccgctc   4440
acaattccac acaacatacg agccggaagc ataaagtgta aagcctgggg tgcctaatga   4500
gtgagctaac tcacattaat tgcgttgcgc tcactgcccg ctttccagtc gggaaacctg   4560
tcgtgccagc tgcattaatg aatcggccaa cgcgcgggga gaggcggttt gcgtattggg   4620
cgctcttccg cttcctcgct cactgactcg ctgcgctcgg tcgttcggct gcggcgagcg   4680
gtatcagctc actcaaaggc ggtaatacgg ttatccacag aatcagggga taacgcagga   4740
aagaacatgt gagcaaaagg ccagcaaaag gccaggaacc gtaaaaaggc cgcgttgctg   4800
gcgtttttcc ataggctccg cccccctgac gagcatcaca aaaatcgacg ctcaagtcag   4860
aggtggcgaa acccgacagg actataaaga taccaggcgt ttccccctgg aagctccctc   4920
gtgcgctctc ctgttccgac cctgccgctt accggatacc tgtccgcctt tctcccttcg   4980
ggaagcgtgg cgctttctca atgctcacgc tgtaggtatc tcagttcggt gtaggtcgtt   5040
cgctccaagc tgggctgtgt gcacgaaccc cccgttcagc ccgaccgctg cgccttatcc   5100
ggtaactatc gtcttgagtc caacccggta agacacgact tatcgccact ggcagcagcc   5160
actggtaaca ggattagcag agcgaggtat gtaggcggtg ctacagagtt cttgaagtgg   5220
tggcctaact acggctacac tagaaggaca gtatttggta tctgcgctct gctgaagcca   5280
gttaccttcg gaaaaagagt tggtagctct tgatccggca aacaaaccac cgctggtagc   5340
ggtggttttt ttgtttgcaa gcagcagatt acgcgcagaa aaaaaggatc tcaagaagat   5400
cctttgatct tttctacggg gtctgacgct cagtggaacg aaaactcacg ttaagggatt   5460
ttggtcatga gattatcaaa aaggatcttc acctagatcc ttttaaatta aaaatgaagt   5520
tttaaatcaa tctaaagtat atatgagtaa acttggtctg acagttacca atgcttaatc   5580
agtgaggcac ctatctcagc gatctgtcta tttcgttcat ccatagttgc ctgactcccc   5640
gtcgtgtaga taactacgat acgggagggc ttaccatctg gccccagtgc tgcaatgata   5700
ccgcgagacc cacgctcacc ggctccagat ttatcagcaa taaaccagcc agccggaagg   5760
gccgagcgca gaagtggtcc tgcaacttta tccgcctcca tccagtctat taattgttgc   5820
cgggaagcta gagtaagtag ttcgccagtt aatagtttgc gcaacgttgt tgccattgct   5880
acaggcatcg tggtgtcacg ctcgtcgttt ggtatggctt cattcagctc cggttcccaa   5940
```

-continued

```
cgatcaaggc gagttacatg atcccccatg ttgtgcaaaa aagcggttag ctccttcggt    6000
cctccgatcg ttgtcagaag taagttggcc gcagtgttat cactcatggt tatggcagca    6060
ctgcataatt ctcttactgt catgccatcc gtaagatgct tttctgtgac tggtgagtac    6120
tcaaccaagt cattctgaga atagtgtatg cggcgaccga gttgctcttg cccggcgtca    6180
atacgggata ataccgcgcc acatagcaga actttaaaag tgctcatcat tggaaaacgt    6240
tcttcggggc gaaaactctc aaggatctta ccgctgttga gatccagttc gatgtaaccc    6300
actcgtgcac ccaactgatc ttcagcatct tttactttca ccagcgtttc tgggtgagca    6360
aaaacaggaa ggcaaaatgc cgcaaaaaag ggaataaggg cgacacgaaa atgttgaata    6420
ctcatactct tcctttttca atattattga agcatttatc agggttattg tctcatgagc    6480
ggatacatat ttgaatgtat ttagaaaaat aaacaaatag gggttccgcg cacatttccc    6540
cgaaaagtgc cacctgacgt cgacggatcg ggagatctcc cgatccccta tggtcgactc    6600
tcagtacaat ctgctctgat gccgcatagt taagccagta tctgctccct gcttgtgtgt    6660
tggaggtcgc tgagtagtgc gcgagcaaaa tttaagctac aacaaggcaa ggcttgaccg    6720
acaattgcat gaagaatctg cttagg                                        6746
```

SEQ ID NO: 197         moltype = DNA   length = 7436
FEATURE                Location/Qualifiers
misc_feature           1..7436
                       note = Synthetic Polynucleotide
source                 1..7436
                       mol_type = other DNA
                       organism = synthetic construct
SEQUENCE: 197

```
gttaggcgtt ttgcgctgct tcgcgatgta cgggccagat atacgcgttg acattgatta     60
ttgactagtt attaatagta atcaattacg gggtcattag ttcatagccc atatatggag    120
ttccgcgtta cataacttac ggtaaatggc ccgcctggct gaccgcccaa cgacccccgc    180
ccattgacgt caataatgac gtatgttccc atagtaacgc caatagggac tttccattga    240
cgtcaatggg tggagtattt acggtaaact gcccacttgg cagtacatca agtgtatcat    300
atgccaagta cgccccctat tgacgtcaat gacggtaaat ggcccgcctg gcattatgcc    360
cagtacatga ccttatggga ctttcctact tggcagtaca tctacgtatt agtcatcgct    420
attaccatgg tgatgcggtt ttggcagtac atcaatgggc gtggatagcg gtttgactca    480
cggggatttc caagtctcca ccccattgac gtcaatggga gtttgttttg gcaccaaaat    540
caacgggact ttccaaaatg tcgtaacaac tccgccccat tgacgcaaat gggcggtagg    600
cgtgtacggt gggaggtcta tataagcaga gctcgtttag tgaaccgtca gatcgcctgg    660
agacgccatc cacgctgttt tgacctccat agaagacacc gggaccgatc cagcctccgg    720
actctagagg atcgaaccct tgaattcccc ccgccaccat gggctggtca tgcattattc    780
tgtttctggt cgcaactgct acaggcgtgc atagtcaggt gcagctgcaa gagtccggcc    840
ctggactcgt gaagccctcc gagacactgt ctctgacatg taccgtgtct ggcttctccc    900
tgtccatcta ctccgtgcac tggatcagac agcctcctgg caagggcctg gaatggatcg    960
gcatgatctg ggggaggcggc tcttccgact acaactccgc cctgaaatct cggctgacca   1020
tctccaagga cacctctaag aaccaggtca gcctgaagct gagctctgtg accgctgctg   1080
ataccgccgt gtactactgc gccagaaatg gcaacttcta cgccatggac tattggggcc   1140
agggcaccct ggtgaccgtg tccagcgcca gcaccaaggg tcccagcgtgt ttcccactgg   1200
ccccctcctc taaatccaca tctggcggca ccgccgccct gggctgtctg gtgaaggact   1260
acttccagga gcctgtgaca gtgtcctgga actctggcgc cctgacatcc ggcgtgcaca   1320
catttccagc cgtgctgcag agctccggcc tgtacagcct gtctagcgtg gtgacagtgc   1380
cctcctctag cctgggcaca cagacctata tctgcaacgt gaatcacaag ccaagcaata   1440
ccaaggtgga caagaaggtg gagcccaagt cctgtgataa gacacacacc tgcccccctt   1500
gtcctgctcc cgagctgctg ggcggcccta gcgtgttcct gtttccaccc aagcctaagg   1560
acaccctgat gatctcccgg acacccgagg tgacctgcgt ggtggtggac gtgtctcacg   1620
aggatcctga ggtgaagttc aactggtatg tggatggcgt ggaggtgcac aatgccaaga   1680
ccaagcccag agaggagcag tacaactcta catataggg ggtgagcgtg ctgaccgtgc   1740
tgcaccagga ctggctgaac ggcaaggagt ataagtgcaa ggtgtccaat aaggccctgc   1800
ccgcccccat cgagaagaca atcagcaagg ccaagggcca gcctcgggag ccacaggtgt   1860
acaccctgcc tccatccaga gacgagctga caaagaacca ggtgtctctg acatgtctgg   1920
tgaagggctt ctatcctagc gatatcgccg tggagtggga gtccaatggc cagccagaga   1980
acaattacaa gaccacaccc cctgtgctgg actccgatgg ctccttcttt ctgtattcca   2040
agctgaccgt ggataagtct cggtggcagc agggcaacgt gttcagctgt tccgtgatgc   2100
acgaagccct gcataatcac tatactcaga atccctgtc cctgtcacct ggaaagtgat   2160
aagcttaagg gttcgatccc taccggttag taatgagttt gatatctcga caatcaacct   2220
ctggattaca aaatttgtga agattgact ggtattctta actatgttgc tccttttacg   2280
ctatgtggat acgctgcttt aatgcctttg tatcatgcta ttgcttcccg tatggctttc   2340
attttctcct ccttgtataa atcctggttg ctgtctcttt atgaggagtt gtggcccgtt   2400
gtcaggcaac gtggcgtggt gtgcactgtg tttgctgacg caacccccac tggttgggg   2460
attgccacca cctgtcagct cctttccggg actttcgctt tccccctccc tattgccacg   2520
gcggaactca tcgccgcctg ccttgcccgc tgctggacag gggctcggct gttgggcact   2580
gacaattccg tggtgttgtc ggggaagctg acgtcctttc catggctgct cgcctgtgtt   2640
gccacctgga ttctgcgcgg gacgtccttc tgctacgtcc cttcggccct caatccagcg   2700
gaccttcctt cccgcggcct gctgccggct ctgcggcctc ttccgcgtct tcgccttcgc   2760
cctcagacga gtcggatctc cctttgggcc gcctccccgc ctggaaacgg gggaggctaa   2820
ctgaaacacg gaaggagaca ataccggaag gaacccgcgc tatgacggca ataaaaagac   2880
agaataaaac gcacgggtgt tgggtcgttt gttcataaac gcggggttcg tcccagggc    2940
tggcactctg tcgataccc accgagaccc cattggggcc aatacgcccg cgtttcttcc   3000
ttttccccac cccacccccc aagttcgggt gaaggcccag ggctcgcagc caacgtcggg   3060
gcggcaggcc ctgccatagc agatctgcgc agctggggct ctaggggta tccccacgcg   3120
ccctgtagcg gcgcattaag cgcggcgggt gtggtggtta cgcgcagcgt gaccgctaca   3180
cttgccagcg ccctagcgcc cgctcctttc gctttcttcc cttcctttct cgccacgttc   3240
gccggctttc cccgtcaagc tctaaatcgg ggcatccctt tagggttccg atttagtgct   3300
ttacggcacc tcgaccccaa aaaacttgat tagggtgatg gttcacgtag tgggccatcg   3360
```

```
ccctgataga cggttttttcg ccctttgacg ttggagtcca cgttctttaa tagtggactc   3420
ttgttccaaa ctggaacaac actcaaccct atctcggtct attcttttga tttataaggg   3480
attttgggga tttcggccta ttggttaaaa aatgagctga tttaacaaaa atttaacgcg   3540
aattaattct gtgtgaatgtg tgtcagttag ggtgtggaaa gtccccaggc tccccagcag   3600
gcagaagtat gcaaagcatg catctcaatt agtcagcaac caggtgtgga aagtcccaag   3660
gctccccagc aggcagaagt atgcaaagca tgcatctcaa ttagtcagca accatagtcc   3720
cgcccctaac tccgcccatc ccgcccctaa ctccgcccag ttccgcccat tctccgcccc   3780
atggctgact aatttttttt atttatgcag aggccgaggc cgcctctgcc tctgagctat   3840
tccagaagta gtgaggaggc ttttttggag gcctaggctt ttgcaaaaag ctcccgggag   3900
cttgtatatc cattttcgga tctgatcaag agacaggatg aggatcgttt cgcatgattg   3960
aacaagatgg attgcacgca ggttctccgg ccgcttgggt ggagaggcta ttcggctatg   4020
actgggcaca acagacaatc ggctgctctg atgccgccgt gttccggctg tcagcgcagg   4080
ggcgcccggt tctttttgtc aagaccgacc tgtccggtgc cctgaatgaa ctgcaggacg   4140
aggcagcgcg gctatcgtgg ctggccacga cgggcgttcc ttgcgcagct gtgctcgacg   4200
ttgtcactga agcggggaagg gactggctgc tattgggcga agtgccgggg caggatctcc   4260
tgtcatctca ccttgctcct gccgagaaag tatccatcat ggctgatgca atgcggcggc   4320
tgcatacgct tgatccggct acctgcccat tcgaccacca agcgaaacat cgcatcgagc   4380
gagcacgtac tcggatggaa gccggtcttg tcgatcagga tgatctggac gaagagcatc   4440
aggggctcgc gccagccgaa ctgttcgcca ggctcaaggc gcgcatgccc gacggcgagg   4500
atctcgtcgt gacccatggc gatgcctgct tgccgaatat catggtggaa aatggccgct   4560
tttctggatt catcgactgt ggccggctgg gtgtggcgga ccgctatcag gacatagcgt   4620
tggctacccg tgatattgct gaagagcttg gcggcgaatg ggctgaccgc ttcctcgtgc   4680
tttacggtat cgccgctccc gattcgcagc gcatcgcctt ctatcgcctt cttgacgagt   4740
tcttctgagc gggactctgg ggttcgcgaa atgaccgacc aagcgacgcc caacctgcca   4800
tcacgagatt tcgattccac cgccgccttc tatgaaaggt tgggcttcgg aatcgttttc   4860
cgggacgccg gctggatgat cctccagcgc ggggatctca tgctggagtt cttcgcccac   4920
cccaacttgt ttattgcagc ttataatggt tacaaataaa gcaatagcat cacaaatttc   4980
acaaataaag cattttttttc actgcattct agttgtggtt tgtccaaact catcaatgta   5040
tcttatcatg tctgtatacc gtcgacctct agctagagct tggcgtaatc atggtcatag   5100
ctgtttcctg tgtgaaattg ttatccgctc acaattccac acaacatacg agccggaagc   5160
ataaagtgta aagcctgggg tgcctaatga gtgagctaac tcacattaat tgcgttgcgc   5220
tcactgcccg ctttccagtc gggaaacctg tcgtgccagc tgcattaatg aatcggccaa   5280
cgcgcgggga gaggcggttt gcgtattggg cgctcttccg cttcctcgct cactgactcg   5340
ctgcgctcgg tcgttcggct gcggcgagcg gtatcagctc actcaaaggc ggtaatacgg   5400
ttatccacag aatcaggggga taacgcagga aagaacatgt gagcaaaagg ccagcaaaag   5460
gccaggaacc gtaaaaaggc cgcgttgctg gcgtttttcc ataggctccg cccccctgac   5520
gagcatcaca aaaatcgacg ctcaagtcag aggtggcgaa acccgacagg actataaaga   5580
taccaggcgt ttccccctgg aagctccctc gtgcgctctc ctgttccgac cctgccgctt   5640
accggatacc tgtccgcctt tctcccttcg ggaagcgtgg cgctttctca atgctcaccg   5700
tgtaggtatc tcagttcggt gtaggtcgtt cgctccaagc tgggctgtgt gcacgaaccc   5760
cccgttcagc ccgaccgctg cgccttatcc ggtaactatc gtcttgagtc caacccggta   5820
agacacgact tatcgccact ggcagcagcc actggtaaca ggattagcag agcgaggtat   5880
gtaggcggtg ctacagagtt cttgaagtgg tggcctaact acggctacac tagaaggaca   5940
gtatttggta tctgcgctct gctgaagcca gttaccttcg gaaaaagagt ggtagctct   6000
tgatccggca aacaaaccac cgctggtagc ggtggttttt ttgtttgcaa gcagcagatt   6060
acgcgcagaa aaaaaggatc tcaagaagat cctttgatct tttctacggg gtctgacgct   6120
cagtgaacg aaaactcacg ttaagggatt ttggtcatga gattatcaaa aaggatcttc   6180
acctagatcc ttttaaatta aaaatgaagt tttaaatcaa tctaaagtat atatgagtaa   6240
acttggtctg acagttacca atgcttaatc agtgaggcac ctatctcagc gatctgtcta   6300
tttcgttcat ccatagttgc ctgactcccc gtcgtgtaga taactacgat acgggagggc   6360
ttaccatctg gccccagtgc tgcaatgata ccgcgagacc cacgctcacc ggctccagat   6420
ttatcagcaa taaaccagcc agccggaagg gccgagcgca gaagtggtcc tgcaactttta   6480
tccgcctcca tccagtctat taattgttgc cgggaagcta gagtaagtag ttcgccagtt   6540
aatagtttgc gcaacgttgt tgccattgct acaggcatcg tggtgtcacg ctcgtcgttt   6600
ggtatggctt cattcagctc cggttcccaa cgatcaaggc gagttacatg atcccccatg   6660
ttgtgcaaaa aagcggttag ctccttcggt cctccgatcg ttgtcagaag taagttggcc   6720
gcagtgttat cactcatggt tatggcagca ctgcataatt ctcttactgt catgccatcc   6780
gtaagatgct tttctgtgac tggtgagtac tcaaccaagt cattctgaga atagtgtatg   6840
cggcgaccga gttgctcttg cccggcgtca atacgggata ataccgcgcc acatagcaga   6900
actttaaaag tgctcatcat tggaaaacgt tcttcggggc gaaaactctc aaggatctta   6960
ccgctgttga tccagttc gatgtaaccc actcgtgcac ccaactgatc ttcagcatct   7020
tttactttca ccagcgtttc tgggtgagca aaaacaggaa ggcaaaatgc cgcaaaaaag   7080
ggaataaggg cgacacggaa atgttgaata ctcatactct tcctttttca atattattga   7140
agcatttatc agggttattg tctcatgagc ggatacatat ttgaatgtat ttagaaaaat   7200
aaacaaatag gggttccgcg cacatttccc cgaaaagtgc cacctgacgt cgacggatcg   7260
ggagatctcc cgatccccta tggtcgactc tcagtacaat ctgctctgat gccgcatagt   7320
taagccagta tctgctccct gcttgtgtgt tggaggtcgc tgagtagtgc gcgagcaaaa   7380
tttaagctac aacaaggcaa ggcttgaccg acaattgcat gaagaatctg cttagg        7436
```

```
SEQ ID NO: 198          moltype = DNA   length = 7436
FEATURE                 Location/Qualifiers
misc_feature            1..7436
                        note = Synthetic Polynucleotide
source                  1..7436
                        mol_type = other DNA
                        organism = synthetic construct
SEQUENCE: 198
gttaggcgtt ttgcgctgct tcgcgatgta cgggccagat atacgcgttg acattgatta   60
ttgactagtt attaatagta atcaattacg gggtcattag ttcatagccc atatatggag   120
```

```
ttccgcgtta cataacttac ggtaaatggc ccgcctggct gaccgcccaa cgacccccgc   180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgcccctat tgacgtcaat gacggtaaat ggcccgcctg gcattatgcc   360
cagtacatga ccttatggga ctttcctact tggcagtaca tctacgtatt agtcatcgct   420
attaccatgg tgatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc cagcctccgg   720
actctagagg atcgaaccct tgaattcccg ccgccaccat gggctggtca tgcattattc   780
tgtttctggt cgcaactgct acaggcgtgc atagtcaggt gcagctgcaa gagtccggac   840
ccggcctcgt gaagccttcc gagacactgt ctctgacctg taccgtgtct ggcttctccc   900
tgtccatcta ctccgtgcac tggatccggc agcctcctgg caagggcctg gaatggctgg   960
gcatgatctg gggcggcgga agctccgact acaactccgc cctgaaatct agactgacca   1020
tctccaagga cacctctaag aaccaggtca gcctgaagct gagctctgtg accgccgctg   1080
ataccgctat gtactactgc gccagaaatg gcaacttcta cgccatggac tattggggcc   1140
aagggcaccct ggtgacagtg tcctctgcca gcaccaaggg cccttccgtg tttccactgg   1200
ccccctcctc taaatccaca tctggcggca ccgccgccct gggctgtctg gtgaaggact   1260
acttccagga gcctgtgaca gtgtcctgga actctggcgc cctgacatcc ggcgtgcaca   1320
catttccagc cgtgctgcag agctccggcc tgtacagcct gtctagcgtg gtgacagtgc   1380
cctcctctag cctgggcaca cagacctata tctgcaacgt gaatcacaag ccaagcaata   1440
ccaaggtgga caagaaggtg gagcccaagt cctgtgataa gacacacacc tgcccccctt   1500
gtcctgctcc cgagctgctg ggcggcccta gcgtgttcct gtttccaccc aagcctaagg   1560
acaccctgat gatctcccgg acacccgagg tgacctgcgt ggtggtggac gtgtctcacg   1620
aggatcctga ggtgaagttc aactggtatg tggatggcgt ggaggtgcac aatgccaaga   1680
ccaagcccag agaggagcag tacaactcta catataggg ggtgagcgtg ctgaccgtgc   1740
tgcaccagga ctggctgaac ggcaaggagt ataagtgcaa ggtgtccaat aaggccctgc   1800
ccgcccccat cgagaagaca atcagcaagg ccaagggcca gcctcgggag ccacaggtgt   1860
acaccctgcc tccatccaga gacgagctga caaagaacca ggtgtctctg acatgtctgg   1920
tgaagggctt ctatcctagc gatatcgccg tggagtggga gtccaatggc cagccagaga   1980
acaattacaa gaccacaccc cctgtgctgg actccgatgg ctccttcttt ctgtattcca   2040
agctgaccgt ggataagtct cggtggcagc agggcaacgt gttcagctgt tccgtgatgc   2100
acgaagccct gcataatcac tatactcaga aatccctgtc cctgtcacct ggaaagtgat   2160
aagcttaagg gttcgatccc taccggttag taatgagttt gatatctcga caatcaacct   2220
ctggattaca aaatttgtga agattgact ggtattctta actatgttgc tccttttacg   2280
ctatgtggat acgctgcttt aatgcctttg tatcatgcta ttgcttcccg tatggctttc   2340
attttctcct ccttgtataa atcctggttg ctgtctcttt atgaggagtt gtggcccgtt   2400
gtcaggcaac gtggcgtggt gtgcactgtg tttgctgacg caaccccac tggttggggc   2460
attgccacca cctgtcagct cctttccggg actttcgctt tcccctccc tattgccacg   2520
gcggaactca tcgccgcctg ccttgcccgc tgctggacag gggctcggct gttgggcact   2580
gacaattccg tggtgttgtc ggggaagctg acgtcctttc catggctgct cgcctgtgtt   2640
gccacctgga ttctgcgcgg gacgtccttc tgctacgtcc cttcggccct caatccagcg   2700
gaccttcctt cccgcggcct gctgccggct ctgcggcctc ttccgcgtct tcgccttcgc   2760
cctcagacga gtcggatctc cctttgggcc gcctccccgc ctggaaacgg gggaggctaa   2820
ctgaaacacg gaaggagaca ataccggaag gaacccgcgc tatgacggca ataaaaagac   2880
agaataaaac gcacgggtgt tgggtcgttt gttcataaac gcggggttcg gtcccaggac   2940
tggcactctg tcgataccc accgagaccc cattggggcc aatacgcccg cgtttcttcc   3000
ttttccccac cccacccccc aagttcgggt gaaggcccag ggctcgcagc caacgtcggg   3060
gcggcaggcc ctgccatagc agatctgcgc agctggggct ctaggggta tccccacgcg   3120
ccctgtagcg gcgcattaag cgcggcgggt gtggtggtta cgcgcagcgt gaccgctaca   3180
cttgccagcg ccctagcgcc cgctcctttc gctttcttcc cttccttct cgccacgttc   3240
gccggctttc cccgtcaagc tctaaatcgg ggcatccctt tagggttccg atttagtgct   3300
ttacggcacc tcgaccccaa aaaacttgat tagggtgatg gttcacgtag tgggccatcg   3360
ccctgataga cggttttcg cccttttgacg ttggagtcca cgttctttaa tagtggactc   3420
ttgttccaaa ctggaacaac actcaaccct atctcggtct attctttga tttataaggg   3480
attttgggga tttcggccta ttggttaaaa aatgagctga tttaacaaaa atttaacgcg   3540
aattaattct gtggaatgtg tgtcagttag ggtgtggaaa gtccccaggc tccccagcag   3600
gcagaagtat gcaaagcatg catctcaatt agtcagcaac caggtgtgga aagtccccag   3660
gctccccagc aggcagaagt atgcaaagca tgcatctcaa ttagtcagca accatagtcc   3720
cgcccctaac tccgcccatc ccgcccctaa ctccgcccag ttccgcccat tctccgcccc   3780
atggctgact aatttttttt atttatgcag aggccgaggc cgcctctgcc tctgagctat   3840
tccagaagta gtgaggaggc ttttttggag gcctaggctt ttgcaaaaag ctcccgggag   3900
cttgtatatc catttcgga tctgatcaag agacaggatg aggatcgttt cgcatgattg   3960
aacaagatgg attgcacgca ggttctccgg ccgcttgggt ggagaggcta ttcggctatg   4020
actgggcaca acagacaatc ggctgctctg atgccgccgt gttccggctg tcagcgcagg   4080
ggcgcccggt tctttttgtc aagaccgacc tgtccggtgc cctgaatgaa ctgcaggacg   4140
aggcagcgcg gctatcgtgg ctggccacga cgggcgttcc ttgcgcagct gtgctcgacg   4200
ttgtcactga agcgggaagg gactggctgc tattgggcga agtgccgggg caggatctcc   4260
tgtcatctca ccttgctcct gccgagaaag tatccatcat ggctgatgca atgcggcggc   4320
tgcatacgct tgatccggct acctgcccat tcgaccacca agcgaaacat cgcatcgagc   4380
gagcacgtac tcggatggaa gccggtcttg tcgatcagga tgatctggac gaagagcatc   4440
aggggctcgc gccagccgaa ctgttcgcca ggctcaaggc gcgcatgccc gacggcgagg   4500
atctcgtcgt gacccatggc gatgcctgct tgccgaatat catggtggaa aatggccgct   4560
tttctggatt catcgactgt ggccggctgg gtgtggcgga ccgctatcag gacatagcgt   4620
tggctacccg tgatattgct gaagagcttg gcggcgaatg ggctgaccgc ttcctcgtgc   4680
tttacggtat cgccgctccc gattcgcagc gcatcgcctt ctatcgcctt cttgacgagt   4740
tcttctgagc gggactctgg ggttcgcgaa atgaccgacc aagcgacgcc caacctgcca   4800
tcacgagatt tcgattccac cgccgccttc tatgaaaggt tgggcttcgg aatcgttttc   4860
```

```
cgggacgccg gctggatgat cctccagcgc ggggatctca tgctggagtt cttcgcccac  4920
cccaacttgt ttattgcagc ttataatggt tacaaataaa gcaatagcat cacaaatttc  4980
acaaataaag cattttttc actgcattct agttgtggtt tgtccaaact catcaatgta  5040
tcttatcatg tctgtatacc gtcgacctct agctagagct tggcgtaatc atggtcatag  5100
ctgtttcctg tgtgaaattg ttatccgctc acaattccac acaacatacg agccggaagc  5160
ataaagtgta aagcctgggg tgcctaatga gtgagctaac tcacattaat tgcgttgcgc  5220
tcactgcccg ctttccagtc gggaaacctg tcgtgccagc tgcattaatg aatcggccaa  5280
cgcgcgggga gaggcggttt gcgtattggg cgctcttccg cttcctcgct cactgactcg  5340
ctgcgctcgg tcgttcggct gcggcgagcg gtatcagctc actcaaaggc ggtaatacgg  5400
ttatccacag aatcagggga taacgcagga agaacatgt gagcaaaagg ccagcaaaag  5460
gccaggaacc gtaaaaaggc cgcgttgctg gcgtttttcc ataggctccg cccccctgac  5520
gagcatcaca aaaatcgacg ctcaagtcag aggtggcgaa acccgacagg actataaaga  5580
taccaggcgt ttccccctgg aagctccctc gtgcgctctc ctgttccgac cctgccgctt  5640
accggatacc tgtccgcctt tctcccttcg ggaagcgtgg cgctttctca atgctcacgc  5700
tgtaggtatc tcagttcggt gtaggtcgtt cgctccaagc tgggctgtgt gcacgaaccc  5760
cccgttcagc ccgaccgctg cgccttatcc ggtaactatc gtcttgagtc caacccggta  5820
agacacgact tatcgccact ggcagcagcc actggtaaca ggattagcag agcgaggtat  5880
gtaggcggtg ctacagagtt cttgaagtgg tggcctaact acggctacac tagaaggaca  5940
gtatttggta tctgcgctct gctgaagcca gttaccttcg gaaaaagagt tggtagctct  6000
tgatccggca aacaaaccac cgctggtagc ggtggttttt ttgtttgcaa gcagcagatt  6060
acgcgcagaa aaaaaggatc tcaagaagat cctttgatct tttctacggg gtctgacgct  6120
cagtggaacg aaaactcacg ttaagggatt ttggtcatga gattatcaaa aaggatcttc  6180
acctagatcc ttttaaatta aaaatgaagt tttaaatcaa tctaaagtat atatgagtaa  6240
acttggtctg acagttacca atgcttaatc agtgaggcac ctatctcagc gatctgtcta  6300
tttcgttcat ccatagttgc ctgactcccc gtcgtgtaga taactacgat acgggagggc  6360
ttaccatctg gccccagtgc tgcaatgata ccgcgagacc cacgctcacc ggctccagat  6420
ttatcagcaa taaaccagcc agccggaagg gccgagcgca gaagtggtcc tgcaacttta  6480
tccgcctcca tccagtctat taattgttgc cgggaagcta gagtaagtag ttcgccagtt  6540
aatagtttgc gcaacgttgt tgccattgct acaggcatcg tggtgtcacg ctcgtcgttt  6600
ggtatggctt cattcagctc cggttcccaa cgatcaaggc gagttacatg atccccatg  6660
ttgtgcaaaa aagcggttag ctccttcggt cctccgatcg ttgtcagaag taagttggcc  6720
gcagtgttat cactcatggt tatggcagca ctgcataatt ctcttactgt catgccatcc  6780
gtaagatgct tttctgtgac tggtgagtac tcaaccaagt cattctgaga atagtgtatg  6840
cggcgaccga gttgctcttg cccggcgtca atacgggata ataccgcgcc acatagcaga  6900
actttaaaag tgctcatcat tggaaaacgt tcttcggggc gaaaactctc aaggatctta  6960
ccgctgttga tccagttc gatgtaaccc actcgtgcac ccaactgatc ttcagcatct  7020
tttactttca ccagcgtttc tgggtgagca aaaacaggaa ggcaaaatgc cgcaaaaaag  7080
ggaataaggc gacacggaa atgttgaata ctcatactct tcctttttca atattattga  7140
agcatttatc agggttattg tctcatgagc ggatacatat ttgaatgtat ttagaaaaat  7200
aaacaaatag gggttccgcg cacatttccc cgaaaagtgc cacctgacgt cgacggatcg  7260
ggagatctcc cgatcccta tggtcgactc tcagtacaat ctgctctgat gccgcatagt  7320
taagccagta tctgctccct gcttgtgtgt tggaggtcgc tgagtagtgc gcgagcaaaa  7380
tttaagctac aacaaggcaa ggcttgaccg acaattgcat gaagaatctg cttagg       7436
```

```
SEQ ID NO: 199           moltype = AA  length = 330
FEATURE                  Location/Qualifiers
source                   1..330
                         mol_type = protein
                         organism = Homo sapiens
SEQUENCE: 199
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330
```

```
SEQ ID NO: 200           moltype = DNA  length = 996
FEATURE                  Location/Qualifiers
source                   1..996
                         mol_type = genomic DNA
                         organism = Homo sapiens
SEQUENCE: 200
gccagcacca agggcccttc cgtgtttcca ctggccccct cctctaaatc cacatctggc   60
ggcaccgccg ccctgggctg tctggtgaag gactacttcc cagagcctgt gacagtgtcc  120
tggaactctg gcgccctgac atccggcgtg cacacatttc cagccgtgct gcagagctcc  180
ggcctgtaca gcctgtctag cgtggtgaca gtgccctcct ctagcctggg cacacagacc  240
tatatctgca acgtgaatca caagccaagc aataccaagg tggacaagaa ggtggagccc  300
aagtcctgca ataagacaca cacctgccc cccttgtcctg ctcccgagct gctgggcgga  360
cctagcgtgt tcctgtttcc acccaagcct aaggacaccc tgatgatctc ccggacaccc  420
gaggtgacct gcgtggtggt ggacgtgtct cacgaggatc ctgaggtgaa gttcaactgg  480
tatgtggatg gcgtggaggt gcacaatgcc aagaccaagc cagagagga gcagtacaac  540
tctacatata gggtggtgag cgtgctgacc gtgctgcacc aggactggct gaacggcaag  600
gagtataagt gcaaggtgtc caataaggcc ctgcccgccc ccatcgagaa gacaatcagt  660
aaggccaagg gccagcctcg ggagccacac gtgtacaccc tgcctccatc cagagacgag  720
ctgacaaaga accaggtgtc tctgacatgt ctggtgaagg gcttctatcc tagcgatatc  780
gccgtggagt gggagtccaa tggccagcca gagaacaatt acaagaccac accccctgtg  840
ctggactccg atggctcctt cttctctgtat tccaagctga ccgtggataa gtctcggtgg  900
cagcagggca cgtgttcag ctgttccgtg atgcacgaag ccctgcataa tcactatact  960
```

-continued

```
cagaaatccc tgtccctgtc acctggaaag tgataa                          996

SEQ ID NO: 201            moltype = AA  length = 107
FEATURE                   Location/Qualifiers
source                    1..107
                          mol_type = protein
                          organism = Homo sapiens
SEQUENCE: 201
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 202            moltype = DNA  length = 327
FEATURE                   Location/Qualifiers
source                    1..327
                          mol_type = genomic DNA
                          organism = Homo sapiens
SEQUENCE: 202
aggacagtgg ccgccccaag cgtgttcatc tttccccctt ccgacgagca gctgaagtct  60
ggcaccgcca gcgtggtgtg cctgctgaac aacttctacc ctcgggaggc caaggtccag 120
tggaaggtgg ataacgccct gcagtctggc aatagccagg agtccgtgac cgagcaggac 180
tctaaggata gcacatattc cctgtctagc accctgacac tgagcaaggc cgattacgag 240
aagcacaagg tgtatgcctg tgaagtcacc catcaggggc tgtcatcacc cgtcactaag 300
tcattcaatc gcggagaatg ctgataa                                     327

SEQ ID NO: 203            moltype = AA  length = 2393
FEATURE                   Location/Qualifiers
REGION                    1..2393
                          note = Synthetic Polypeptide
source                    1..2393
                          mol_type = protein
                          organism = synthetic construct
SEQUENCE: 203
AFCAASRCTG QIYALTLIID LLIVINYGVI SSPIYGVPRY ITYGKWPAWL TAQRPPPIDV  60
NNDVCSHSNA NRDFPLTSMG GVFTVNCPLG STSSVSYAKY APYRQRMARL ALCPVHDLMG 120
LSYLAVHLRI SHRYYHGDAV LAVHQWAWIA VLTGISKSPP HRQWEFVLAP KSTGLSKMSQ 180
LRPIDANGRA CTVGGLYKQS SFSEPSDRLE TPSTLFPPKT PGPIQPPDSR GSNPIPAATM 240
GWSCIILFLV ATATGVHSQV QLQESGPGLV KPSETLSLTC TVSGFSLSIY SVHWIRQPPG 300
KGLEWIGMIW GGGSSDYNSA LKSRLTISKD TSKNQVSLKL SSVTAADTAV YYCARNGNFY 360
AMDYWGQGTL VTVSSASTKG PSVFPLAPSS KSTSGGTAAL GCLVKDYFPE PVTVSWNSGA 420
LTSGVHTFPA VLQSSGLYSL SSVVTVPSSS LGTQTYICNV NHKPSNTKVD KKVEPKSCDA 480
THTCPPCPAP ELLGGPSVFL FPPKPKDTLM ISRTPEVTCV VVDVSHEDPE VKFNWYVDGV 540
EVHNAKTKPR EEQYNSTYRV VSVLTVLHQD WLNGKEYKCK VSNKALPAPI EKTISKAKGQ 600
PREPQVYTLP PSRDELTKNQ VSLTCLVKGF YPSDIAVEWE SNGQPENNYK TTPPVLDSDG 660
SFFLYSKLTV DKSRWQQGNV FSCSVMHEAL HNHYTQKSLS LSPGKAGFDP YRLVMSLISR 720
QSTSGLQNLK IDWYSLCCSF YAMWIRCFNA FVSCYCFPYG FHFLLLVILV AVSLGVVARC 780
QATWRGVHCV CRNPHWLGHC HHLSAPFRDF RFPPPYCHGG THRRLPCPLL DRGSAVGHQF 840
RGVVGEADVL SMAARLCCHL DSARDVLLLR PFGPQSSGRS FPRPAAGSAA SSASSPSPSD 900
ESDLPLGRLP AWKRGRLTET RKETIPEGTR AMTAIKRQNK THGCWVVCST RGSVPGLALC 960
RYPTETPLGP IRPRFFLFPT PPPKFGRPRA RSQRRGGRPC HSRSAQLGLG VSPRALRRIK 1020
RGGCGGYAQR DRYTCQRPSA RSFRFLPFLS RHVRRLSPSS SKSGHPFRVP ICFTAPRPQK 1080
TLGWFTWAIA LIDGFSPFDV GVHVLWTLVP NWNNTQPYLG LFFFIRDFGD FGLLVKKADL 1140
TKIRELILWN VCQLGCGKSP GSPAGRSMQS MHLNSATRCG KSPGSPAGRS MQSMHLNSAT 1200
IVPPLTPPIP PLTPPSSAHS PPHGLIFFIY AEAEAASASE LFQKGGFFGG LGFCKKLPGA 1260
CISIFGSDQE TGGSFRMIEQ DGLHAGSPAA WVERLFGYDW AQQTIGCSDA AVFRLSAQGR 1320
PVLFVKTDLS GALNELQDEA ARLSWLATTG VPCAAVLDVV TEAGRDWLLL GEVPGQDLLS 1380
SHLAPAEKVS IMADAMRRLH TLDPATCPFD HQAKHRIERA RTRMEAGLVD QDDLDEEHQG 1440
LAPAELFARL KARMPDGEDL VVTHGDACLP NIMVENGRFS GFIDCGRLGV ADRYQDIALA 1500
TRDIAEELGG EWADRFLVLY GIAAPDSQRI AFYRLLDEFF AGLWGSRNDR PSDAQPAITR 1560
FRFHRRLLKV GLRNRFPGRR LDDPPARGSH AGVLRPPQLV YCSLWLQIKQ HHKFHKSIFF 1620
TAFLWFVQTH QCILSCLYTV DLLELGVIMV IAVSCVKLLS AHNSTQHTSR KHKVSLGCLM 1680
SELTHINCVA LTARPPVGKP VVPAALMNRP TRGERRFAYW ALFRFLAHLA ALGRSAAASG 1740
ISSLKGGNTV IHRIRGRRKE HVSKRPAKGQ EPKGRVAGVF PAPPPRASQK STLKSEVAKP 1800
DRTIKIPGVS PWKLPRALSC SDPAAYRIPV RLSPFGKRGA FSMLTLVSQF GVGRSLQAGL 1860
CARTPRSARP LRLIRLSSVQ PGKTRLIATG SSHWQDQSEV CRRCYRVLEV VALRLHKDSI 1920
WYLRSAEASY LRKKSWLLIR QTNHRWRWFF CLQAADYAQK KRISRRSFDL FYGVRSVERK 1980
LTLRDFGHEI IKKDLHLDPF KLKMKFINLK YIVNLVQLPM LNQGTYLSDL SISFIHSCLT 2040
PRRVDNYDTG GLTIWPQCCN DTARPTLTGS RFISNKPASR KGRAQKWSCN FIRLHPVYLL 2100
PGSSKPASFA QRCCHCYRHR GVTLVVWYGF IQLRFPTIKA SYMIPHVVQK SGLLRSSDRC 2160
QKVGRSVITH GYGSTAFSYC HAIRKMLFCD WVLNQVILRI VYAATELLLP GVNTGYRATQ 2220
NFKSAHHWKT FFGAKTLKDL TAVEIQFDVT HSCTQLIFSI FYFHQRFWVS KNRKAKCRKK 2280
GNKGDTEMLN THTLPFSILL KHLSGLLSHE RIHIMYLEKT NRGSAHISPK SATRRRIGRS 2340
PDPLWSTLST ICSDAALSQY LLPACVLEVA ECASKIATTR QGLTDNCMKN LLR       2393

SEQ ID NO: 204            moltype = AA  length = 2393
FEATURE                   Location/Qualifiers
REGION                    1..2393
                          note = Synthetic Polypeptide
source                    1..2393
                          mol_type = protein
```

```
                    organism = synthetic construct
SEQUENCE: 204
AFCAASRCTG QIYALTLIID LLIVINYGVI SSPIYGVPRY ITYGKWPAWL TAQRPPPIDV    60
NNDVCSHSNA NRDFPLTSMG GVFTVNCPLG STSSVSYAKY APYRQRMARL ALCPVHDLMG   120
LSYLAVHLRI SHRYYHGDAV LAVHQWAWIA VLTGISKSPP HRQWEFVLAP KSTGLSKMSQ   180
LRPIDANGRA CTVGGLYKQS SFSEPSDRLE TPSTLFPPKT PGPIQPPDSR GSNPIPAATM   240
GWSCIILFLV ATATGVHSQV QLQESGPGLV KPSETLSLTC TVSGFSLSIY SVHWIRQPPG   300
KGLEWLGMIW GGGSSDYNSA LKSRLTISKD TSKNQVSLKL SSVTAADTAM YYCARNGNFY   360
AMDYWGQGTL VTVSSASTKG PSVFPLAPSS KSTSGGTAAL GCLVKDYFPE PVTVSWNSGA   420
LTSGVHTFPA VLQSSGLYSL SSVVTVPSSS LGTQTYICNV NHKPSNTKVD KKVEPKSCDA   480
THTCPPCPAP ELLGGPSVFL FPPKPKDTLM ISRTPEVTCV VVDVSHEDPE VKFNWYVDGV   540
EVHNAKTKPR EEQYNSTYRV VSVLTVLHQD WLNGKEYKCK VSNKALPAPI EKTISKAKGQ   600
PREPQVYTLP PSRDELTKNQ VSLTCLVKGF YPSDIAVEWE SNGQPENNYK TTPPVLDSDG   660
SFFLYSKLTV DKSRWQQGNV FSCSVMHEAL HNHYTQKSLS LSPGKAGFDP YRLVMSLISR   720
QSTSGLQNLK IDWYSLCCSF YAMWIRCFNA FVSCYCFPYG FHFLLLVILV AVSLGVVARC   780
QATWRGVHCV CRNPHWLGHC HHLSAPFRDF RFPPPYCHGG THRRLPCPLL DRGSAVGHQF   840
RGVVGEADVL SMAARLCCHL DSARDVLLLR PFGPQSSGPS FPRPAAGSAA SSASSPSPSD   900
ESDLPLGRLP AWKRGRLTET RKETIPEGTR AMTAIKRQNK THGCWVVCST RGSVPGLALC   960
RYPTETPLGP IRPRFFLFPT PPPKFGRPRA RSQRRGGRPC HSRSAQLGLG VSPRALRRIK  1020
RGGCGGYAQR DRYTCQRPSA RSFRFLPFLS RHVRRLSPSS SKSGHPFRVP ICFTAPRPQK  1080
TLGWFTWAIA LIDGFSPFDV GVHVLWTLVP NWNNTQPYLG LFFFIRDFGD FGLLVKKADL  1140
TKIRELILWN VCQLGCGKSP GSPAGRSMQS MHLNSATRCG KSPGSPAGRS MQSMHLNSAT  1200
IVPPLTPPIP PLTPPSSAHS PPHGLIFFIY AEAEAASASE LFQKGGFFGG LGFCKKLPGA  1260
CISIFGSDQE TGGSFRMIEQ DGLHAGSPAA WVERLFGYDW AQQTIGCSDA AVFRLSAQGR  1320
PVLFVKTDLS GALNELQDEA ARLSWLATTG VPCAAVLDVV TEAGRDWLLL GEVPGQDLLS  1380
SHLAPAEKVS IMADAMRRLH TLDPATCPFD HQAKHRIERA RTRMEAGLVD QDDLDEEHQG  1440
LAPAELFARL KARMPDGEDL VVTHGDACLP NIMVENGRFS GFIDCGRLGV ADRYQDIALA  1500
TRDIAEELGG EWADRFLVLY GIAAPDSQRI AFYRLLDEFF AGLWGSRNDR PSDAQPAITR  1560
FRFHRRLLKV GLRNRFPGRR LDDPPARGSH AGVLRPPQLV YCSLWLQIKQ HHKFHKSIFF  1620
TAFLWFVQTH QCILSCLYTV DLLELGVIMV IAVSCVKLLS AHNSTQHTSR KHKVSLGCLM  1680
SELTHINCVA LTARFPVGKP VVPAALMNRP TRGERRFAYW ALFRFLAHLA ALGRSAAASG  1740
ISSLKGGNTV IHRIRGRRKE HVSKRPAKGQ EPKGRVAGVF PAPPPRASQK STLKSEVAKP  1800
DRTIKIPGVS PWKLPRALSC SDPAAYRIPV RLSPFGKRGA FSMLTLVSQF GVGRSLQAGL  1860
CARTPRSARP LRLIRLSSVQ PGKTRLIATG SSHWQDQSEV CRRCYRVLEV VALRLHKDSI  1920
WYLRSAEASY LRKKSWLLIR QTNHRWRWFF CLQAADYAQK KRISRRSFDL FYGVRSVERK  1980
LTLRDFGHEI IKKDLHLDPF KLKMKFINLK YIVNLVQLPM LNQGTYLSDL SISFIHSCLT  2040
PRRVDNYDTG GLTIWPQCCN DTARPTLTGS RFISNKPASR KGRAQKWSCN FIRLHPVYLL  2100
PGSSKFASFA QRCCHCYRHR GVTLVVWYGF IQLRFPTIKA SYMIPHVVQK SGLLRSSDRC  2160
QKVGRSVITH GYGSTAFSYC HAIRKMLFCD WVLNQVILRI VYAATELLLP GVNTGYRATQ  2220
NFKSAHHWKT FFGAKTLKDL TAVEIQFDVT HSCTQLIFSI FYFHQRFWVS KNRKAKCRKK  2280
GNKGDTEMLN THTLPFSILL KHLSGLLSHE RIHIMYLEKT NRGSAHISPK SATRRRIGRS  2340
PDPLWSTLST ICSDAALSQY LLPACVLEVA ECASKIATTR QGLTDNCMKN LLR          2393

SEQ ID NO: 205        moltype = AA  length = 2163
FEATURE               Location/Qualifiers
REGION                1..2163
                      note = Synthetic Polypeptide
source                1..2163
                      mol_type = protein
                      organism = synthetic construct
SEQUENCE: 205
AFCAASRCTG QIYALTLIID LLIVINYGVI SSPIYGVPRY ITYGKWPAWL TAQRPPPIDV    60
NNDVCSHSNA NRDFPLTSMG GVFTVNCPLG STSSVSYAKY APYRQRMARL ALCPVHDLMG   120
LSYLAVHLRI SHRYYHGDAV LAVHQWAWIA VLTGISKSPP HRQWEFVLAP KSTGLSKMSQ   180
LRPIDANGRA CTVGGLYKQS SFSEPSDRLE TPSTLFPPKT PGPIQPPDSR GSNPIPAATM   240
GWSCIILFLV ATATGVHSEI VLTQSPGTLS LSPGERATLS CTASSSVSSS FLHWYQQKPG   300
QAPRLLIYST SNLASGIPDR FSGSGSGTDF TLTISRLEPE DFAVYYCHQY HHSPYIYTFG   360
GGTKLEIKRT VAAPSVFIFP PSDEQLKSGT ASVVCLLNNF YPREAKVQWK VDNALQSGNS   420
QESVTEQDSK DSTYSLSSTL TLSKADYEKH KVYACEVTHQ GLSSPVTKSF NRGECAGFDP   480
YRLVMSLISR QSTSGLQNLK IDWYSLCCSF YAMWIRCFNA FVSCYCFPYG FHFLLLVILV   540
AVSLGVVARC QATWRGVHCV CRNPHWLGHC HHLSAPFRDF RFPPPYCHGG THRRLPCPLL   600
DRGSAVGHQF RGVVGEADVL SMAARLCCHL DSARDVLLLR PFGPQSSGPS FPRPAAGSAA   660
SSASSPSPSD ESDLPLGRLP AWKRGRLTET RKETIPEGTR AMTAIKRQNK THGCWVVCST   720
RGSVPGLALC RYPTETPLGP IRPRFFLFPT PPPKFGRPRA RSQRRGGRPC HSRSAQLGLG   780
VSPRALRRIK RGGCGGYAQR DRYTCQRPSA RSFRFLPFLS RHVRRLSPSS SKSGHPFRVP   840
ICFTAPRPQK TLGWFTWAIA LIDGFSPFDV GVHVLWTLVP NWNNTQPYLG LFFFIRDFGD   900
FGLLVKKADL TKIRELILWN VCQLGCGKSP GSPAGRSMQS MHLNSATRCG KSPGSPAGRS   960
MQSMHLNSAT IVPPLTPPIP PLTPPSSAHS PPHGLIFFIY AEAEAASASE LFQKGGFFGG  1020
LGFCKKLPGA CISIFGSDQE TGGSFRMIEQ DGLHAGSPAA WVERLFGYDW AQQTIGCSDA  1080
AVFRLSAQGR PVLFVKTDLS GALNELQDEA ARLSWLATTG VPCAAVLDVV TEAGRDWLLL  1140
GEVPGQDLLS SHLAPAEKVS IMADAMRRLH TLDPATCPFD HQAKHRIERA RTRMEAGLVD  1200
QDDLDEEHQG LAPAELFARL KARMPDGEDL VVTHGDACLP NIMVENGRFS GFIDCGRLGV  1260
ADRYQDIALA TRDIAEELGG EWADRFLVLY GIAAPDSQRI AFYRLLDEFF AGLWGSRNDR  1320
PSDAQPAITR FRFHRRLLKV GLRNRFPGRR LDDPPARGSH AGVLRPPQLV YCSLWLQIKQ  1380
HHKFHKSIFF TAFLWFVQTH QCILSCLYTV DLLELGVIMV IAVSCVKLLS AHNSTQHTSR  1440
KHKVSLGCLM SELTHINCVA LTARFPVGKP VVPAALMNRP TRGERRFAYW ALFRFLAHLA  1500
ALGRSAAASG ISSLKGGNTV IHRIRGRRKE HVSKRPAKGQ EPKGRVAGVF PAPPPRASQK  1560
STLKSEVAKP DRTIKIPGVS PWKLPRALSC SDPAAYRIPV RLSPFGKRGA FSMLTLVSQF  1620
GVGRSLQAGL CARTPRSARP LRLIRLSSVQ PGKTRLIATG SSHWQDQSEV CRRCYRVLEV  1680
```

```
VALRLHKDSI WYLRSAEASY LRKKSWLLIR QTNHRWRWFF CLQAADYAQK KRISRRSFDL     1740
FYGVRSVERK LTLRDFGHEI IKKDLHLDPF KLKMKFINLK YIVNLVQLPM LNQGTYLSDL     1800
SISFIHSCLT PRRVDNYDTG GLTIWPQCCN DTARPTLTGS RFISNKPASR KGRAQKWSCN     1860
FIRLHPVYLL PGSSKFASFA QRCCHCYRHR GVTLVVWYGF IQLRFPTIKA SYMIPHVVQK     1920
SGLLRSSDRC QKVGRSVITH GYGSTAFSYC HAIRKMLFCD WVLNQVILRI VYAATELLLP     1980
GVNTGYRATQ NFKSAHHWKT FFGAKTLKDL TAVEIQFDVT HSCTQLIFSI FYFHQRFWVS     2040
KNRKAKCRKK GNKGDTEMLN THTLPFSILL KHLSGLLSHE RIHIMYLEKT NRGSAHISPK     2100
SATRRRIGRS PDPLWSTLST ICSDAALSQY LLPACVLEVA ECASKIATTR QGLTDNCMKN     2160
LLR                                                                  2163

SEQ ID NO: 206          moltype = AA  length = 2163
FEATURE                 Location/Qualifiers
REGION                  1..2163
                        note = Synthetic Polypeptide
source                  1..2163
                        mol_type = protein
                        organism = synthetic construct
SEQUENCE: 206
AFCAASRCTG QIYALTLIID LLIVINYGVI SSPIYGVPRY ITYGKWPAWL TAQRPPPIDV     60
NNDVCSHSNA NRDFPLTSMG GVFTVNCPLG STSSVSYAKY APYRQRMARL ALCPVHDLMG     120
LSYLAVHLRI SHRYYHGDAV LAVHQWAWIA VLTGISKSPP HRQWEFVLAP KSTGLSKMSQ     180
LRPIDANGRA CTVGGLYKQS SFSEPSDRLE TPSTLFPPKT PGPIQPPDSR GSNPIPAATM     240
GWSCIILFLV ATATGVHSEI VLTQSPGTLS LSPGERATLS CTASSSVSSS FLHWYQQKPG     300
QAPQLWIYST SNLASGIPDR FSGSGSGTDY TLTISRLEPE DFAVYYCHQY HHSPYIYTFG     360
GGTKLEIKRT VAAPSVFIFP PSDEQLKSGT ASVVCLLNNF YPREAKVQWK VDNALQSGNS     420
QESVTEQDSK DSTYSLSSTL TLSKADYEKH KVYACEVTHQ GLSSPVTKSF NRGECAGFDP     480
YRLVMSLISR QSTSGLQNLK IDWYSLCCSF YAMWIRCFNA FVSCYCFPYG FHFLLLVILV     540
AVSLGVVARC QATWRGVHCV CRNPHWLGHC HHLSAPFRDF RFPPPYCHGG THRRLPCPLL     600
DRGSAVGHQF RGVVGEADVL SMAARLCCHL DSARDVLLLR PFGPQSSGPS FPRPAAGSAA     660
SSASSPSPSD ESDLPLGRLP AWKRGRLTET RKETIPEGTR AMTAIKRQNK THGCWVVCST     720
RGSVPGLALC RYPTETPLGP IRPRFFLFPT PPPKFGRPRA RSQRRGGRPC HSRSAQLGLG     780
VSPRALRRIK RGGCGGYAQR DRYTCQRPSA RSFRFLPFLS RHVRRLSPSS SKSGHPFRVP     840
ICFTAPRPQK TLGWFTWAIA LIDGFSPFDV GVHVLWTLVP NWNNTQPYLG LFFFIRDFGD     900
FGLLVKKADL TKIRELILWN VCQLGCGKSP GSPAGRSMQS MHLNSATRCG KSPGSPAGRS     960
MQSMHLNSAT IVPPLTPPIP PLTPPSSAHS PPHGLIFFIY AEAEAASASE LFQKGGFFGG     1020
LGFCKKLPGA CISIFGSDQE TGGSFRMIEQ DGLHAGSPAA WVERLFGYDW AQQTIGCSDA     1080
AVFRLSAQGR PVLFVKTDLS GALNELQDEA ARLSWLATTG VPCAAVLDVV TEAGRDWLLL     1140
GEVPGQDLLS SHLAPAEKVS IMADAMRRLH TLDPATCPFD HQAKHRIERA RTRMEAGLVD     1200
QDDLDEEHQG LAPAELFARL KARMPDGEDL VVTHGDACLP NIMVENGRFS GFIDCGRLGV     1260
ADRYQDIALA TRDIAEELGG EWADRFLVLY GIAAPDSQRI AFYRLLDEFF AGLWGSRNDR     1320
PSDAQPAITR FRFHRRLLKV GLRNRFPGRR LDDPPARGSH AGVLRPPQLV YCSLWLQIKQ     1380
HHKFHKSIFF TAFLWFVQTH QCILSCLYTV DLLELGVIMV IAVSCVKLLS AHNSTQHTSR     1440
KHKVSLGCLM SELTHINCVA LTARFPVGKP VVPAALMNRP TRGERRFAYW ALFRFLAHLA     1500
ALGRSAAASG ISSLKGGNTV IHRIRGRRKE HVSKRPAKGQ EPKGRVAGVF PAPPPRASQK     1560
STLKSEVAKP DRTIKIPGVS PWKLPRALSC SDPAAYRIPV RLSPFGKRGA FSMLTLVSQF     1620
GVGRSLQAGL CARTPRSARP LRLIRLSSVQ PGKTRLIATG SSHWQDQSEV CRRCYRVLEV     1680
VALRLHKDSI WYLRSAEASY LRKKSWLLIR QTNHRWRWFF CLQAADYAQK KRISRRSFDL     1740
FYGVRSVERK LTLRDFGHEI IKKDLHLDPF KLKMKFINLK YIVNLVQLPM LNQGTYLSDL     1800
SISFIHSCLT PRRVDNYDTG GLTIWPQCCN DTARPTLTGS RFISNKPASR KGRAQKWSCN     1860
FIRLHPVYLL PGSSKFASFA QRCCHCYRHR GVTLVVWYGF IQLRFPTIKA SYMIPHVVQK     1920
SGLLRSSDRC QKVGRSVITH GYGSTAFSYC HAIRKMLFCD WVLNQVILRI VYAATELLLP     1980
GVNTGYRATQ NFKSAHHWKT FFGAKTLKDL TAVEIQFDVT HSCTQLIFSI FYFHQRFWVS     2040
KNRKAKCRKK GNKGDTEMLN THTLPFSILL KHLSGLLSHE RIHIMYLEKT NRGSAHISPK     2100
SATRRRIGRS PDPLWSTLST ICSDAALSQY LLPACVLEVA ECASKIATTR QGLTDNCMKN     2160
LLR                                                                  2163

SEQ ID NO: 207          moltype = AA  length = 2163
FEATURE                 Location/Qualifiers
REGION                  1..2163
                        note = Synthetic Polypeptide
source                  1..2163
                        mol_type = protein
                        organism = synthetic construct
SEQUENCE: 207
AFCAASRCTG QIYALTLIID LLIVINYGVI SSPIYGVPRY ITYGKWPAWL TAQRPPPIDV     60
NNDVCSHSNA NRDFPLTSMG GVFTVNCPLG STSSVSYAKY APYRQRMARL ALCPVHDLMG     120
LSYLAVHLRI SHRYYHGDAV LAVHQWAWIA VLTGISKSPP HRQWEFVLAP KSTGLSKMSQ     180
LRPIDANGRA CTVGGLYKQS SFSEPSDRLE TPSTLFPPKT PGPIQPPDSR GSNPIPAATM     240
GWSCIILFLV ATATGVHSEI VLTQSPGTLS LSPGERATLS CTASSSVSSS FLHWYQQKPG     300
QAPQLWIYST SNLASGIPDR FSGSGSGTDY TLTISRLEPE DFATYYCHQY HHSPYIYTFG     360
GGTKLEIKRT VAAPSVFIFP PSDEQLKSGT ASVVCLLNNF YPREAKVQWK VDNALQSGNS     420
QESVTEQDSK DSTYSLSSTL TLSKADYEKH KVYACEVTHQ GLSSPVTKSF NRGECAGFDP     480
YRLVMSLISR QSTSGLQNLK IDWYSLCCSF YAMWIRCFNA FVSCYCFPYG FHFLLLVILV     540
AVSLGVVARC QATWRGVHCV CRNPHWLGHC HHLSAPFRDF RFPPPYCHGG THRRLPCPLL     600
DRGSAVGHQF RGVVGEADVL SMAARLCCHL DSARDVLLLR PFGPQSSGPS FPRPAAGSAA     660
SSASSPSPSD ESDLPLGRLP AWKRGRLTET RKETIPEGTR AMTAIKRQNK THGCWVVCST     720
RGSVPGLALC RYPTETPLGP IRPRFFLFPT PPPKFGRPRA RSQRRGGRPC HSRSAQLGLG     780
VSPRALRRIK RGGCGGYAQR DRYTCQRPSA RSFRFLPFLS RHVRRLSPSS SKSGHPFRVP     840
ICFTAPRPQK TLGWFTWAIA LIDGFSPFDV GVHVLWTLVP NWNNTQPYLG LFFFIRDFGD     900
```

```
FGLLVKKADL TKIRELILWN VCQLGCGKSP GSPAGRSMQS MHLNSATRCG KSPGSPAGRS   960
MQSMHLNSAT IVPPLTPPIP PLTPPSSAHS PPHGLIFFIY AEAEAASASE LFQKGGFFGG  1020
LGFCKKLPGA CISIFGSDQE TGGSFRMIEQ DGLHAGSPAA WVERLFGYDW AQQTIGCSDA  1080
AVFRLSAQGR PVLFVKTDLS GALNELQDEA ARLSWLATTG VPCAAVLDVV TEAGRDWLLL  1140
GEVPGGQDLLS SHLAPAEKVS IMADAMRRLH TLDPATCPFD HQAKHRIERA RTRMEAGLVD  1200
QDDLDEEHQG LAPAELFARL KARMPDGEDL VVTHGDACLP NIMVENGRFS GFIDCGRLGV  1260
ADRYQDIALA TRDIAEELGG EWADRFLVLY GIAAPDSQRI AFYRLLDEFF AGLWGSRNDR  1320
PSDAQPAITR FRFHRRLLKV GLRNRFPGRR LDDPPARGSH AGVLRPPQLV YCSLWLQIKQ  1380
HHKFHKSIFF TAFLWFVQTH QCILSCLYTV DLLELGVIMV IAVSCVKLLS AHNSTQHTSR  1440
KHKVSLGCLM SELTHINCVA LTARFPVGKP VVPAALMNRP TRGERRFAYW ALFRFLAHLA  1500
ALGRSAAASG ISSLKGGNTV IHRIRGRRKE HVSKRPAKGQ EPKGRVAGVF PAPPPRASQK  1560
STLKSEVAKP DRTIKIPGVS PWKLPRALSC SDPAAYRIPV RLSPFGKRGA FSMLTLVSQF  1620
GVGRSLQAGL CARTPRSARP LRLIRLSSVQ PGKTRLIATG SSHWQDQSEV CRRCYRVLEV  1680
VALRLHKDSI WYLRSAEASY LRKKSWLLIR QTNHRWRWFF CLQAADYAQK KRISRRSFDL  1740
FYGVRSVERK LTLRDFGHEI IKKDLHLDPF KLKMKFINLK YIVNLVQLPM LNQGTYLSDL  1800
SISFIHSCLT PRRVDNYDTG GLTIWPQCCN DTARPTLTGS RFISNKPASR KGRAQKWSCN  1860
FIRLHPVYLL PGSSKFASFA QRCCHCYRHR GVTLVVWYGF IQLRFPTIKA SYMIPHVVQK  1920
SGLLRSSDRC QKVGRSVITH GYGSTAFSYC HAIRKMLFCD WVLNQVILRI VYAATELLLP  1980
GVNTGYRATQ NFKSAHHWKT FFGAKTLKDL TAVEIQFDVT HSCTQLIFSI FYFHQRFWVS  2040
KNRKAKCRKK GNKGDTEMLN THTLPFSILL KHLSGLLSHE RIHIMYLEKT NRGSAHISPK  2100
SATRRRIGRS PDPLWSTLST ICSDAALSQY LLPACVLEVA ECASKIATTR QGLTDNCMKN  2160
LLR                                                                2163
```

SEQ ID NO: 208          moltype = AA  length = 2163
FEATURE                 Location/Qualifiers
REGION                  1..2163
                        note = Synthetic Polypeptide
source                  1..2163
                        mol_type = protein
                        organism = synthetic construct
SEQUENCE: 208

```
AFCAASRCTG QIYALTLIID LLIVINYGVI SSPIYGVPRY ITYGKWPAWL TAQRPPPIDV   60
NNDVCSHSNA NRDFPLTSMG GVFTVNCPLG STSSVSYAKY APYRQRMARL ALCPVHDLMG  120
LSYLAVHLRI SHRYYHGDAV LAVHQWAWIA VLTGISKSQP HRQWEFVLAP KSTGLSKMSQ  180
LRPIDANGRA CTVGGLYKQS SFSEPSDRLE TPSTLFPPKT PGPIQPPDSR GSNPIPAATM  240
GWSCIILFLV ATATGVHSEI VLTQSPGTLS LSPGERATLS CTASSSVSSS FLHWYQQKPG  300
QAPQLWIYST SNLASGIPAR FSGSGSGTDY TLTISRLEPE DFATYYCHQY HHSPYIYTFG  360
GGTKLEIKRT VAAPSVFIFP PSDEQLKSGT ASVVCLLNNF YPREAKVQWK VDNALQSGNS  420
QESVTEQDSK DSTYSLSSTL TLSKADYEKH KVYACEVTHQ GLSSPVTKSF NRGECAGFDP  480
YRLVMSLISR QSTSGLQNLK IDWYSLCCSF YAMWIRCFNA FVSCYCFPYG FHFLLLVILV  540
AVSLGVVARC QATWRGVHCV CRNPHWLGHC HHLSAPFRDF RFPPPYCHGG THRRLPCPLL  600
DRGSAVGHQF RGVVGEADVL SMAARLCCHL DSARDVLLLR PFGPQSSGPS FPRPAAGSAA  660
SSASSPSPSD ESDLPLGRLP AWKRGRLTET RKETIPEGTR AMTAIKRQNK THGCWVVCST  720
RGSVPGLALC RYPTETPLGP IRPRFFLFPT PPPKFGRPRA RSQRRGGRPC HSRSAQLGLG  780
VSPRALRRIK RGGCGGYAQR DRYTCQRPSA RSFRFLPFLS RHVRRLSPSS SKSGHPFRVP  840
ICFTAPRPQK TLGWFTWAIA LIDGFSPFDV GVHVLWTLVP NWNNTQPYLG LFFFIRDFGD  900
FGLLVKKADL TKIRELILWN VCQLGCGKSP GSPAGRSMQS MHLNSATRCG KSPGSPAGRS  960
MQSMHLNSAT IVPPLTPPIP PLTPPSSAHS PPHGLIFFIY AEAEAASASE LFQKGGFFGG  1020
LGFCKKLPGA CISIFGSDQE TGGSFRMIEQ DGLHAGSPAA WVERLFGYDW AQQTIGCSDA  1080
AVFRLSAQGR PVLFVKTDLS GALNELQDEA ARLSWLATTG VPCAAVLDVV TEAGRDWLLL  1140
GEVPGGQDLLS SHLAPAEKVS IMADAMRRLH TLDPATCPFD HQAKHRIERA RTRMEAGLVD  1200
QDDLDEEHQG LAPAELFARL KARMPDGEDL VVTHGDACLP NIMVENGRFS GFIDCGRLGV  1260
ADRYQDIALA TRDIAEELGG EWADRFLVLY GIAAPDSQRI AFYRLLDEFF AGLWGSRNDR  1320
PSDAQPAITR FRFHRRLLKV GLRNRFPGRR LDDPPARGSH AGVLRPPQLV YCSLWLQIKQ  1380
HHKFHKSIFF TAFLWFVQTH QCILSCLYTV DLLELGVIMV IAVSCVKLLS AHNSTQHTSR  1440
KHKVSLGCLM SELTHINCVA LTARFPVGKP VVPAALMNRP TRGERRFAYW ALFRFLAHLA  1500
ALGRSAAASG ISSLKGGNTV IHRIRGRRKE HVSKRPAKGQ EPKGRVAGVF PAPPPRASQK  1560
STLKSEVAKP DRTIKIPGVS PWKLPRALSC SDPAAYRIPV RLSPFGKRGA FSMLTLVSQF  1620
GVGRSLQAGL CARTPRSARP LRLIRLSSVQ PGKTRLIATG SSHWQDQSEV CRRCYRVLEV  1680
VALRLHKDSI WYLRSAEASY LRKKSWLLIR QTNHRWRWFF CLQAADYAQK KRISRRSFDL  1740
FYGVRSVERK LTLRDFGHEI IKKDLHLDPF KLKMKFINLK YIVNLVQLPM LNQGTYLSDL  1800
SISFIHSCLT PRRVDNYDTG GLTIWPQCCN DTARPTLTGS RFISNKPASR KGRAQKWSCN  1860
FIRLHPVYLL PGSSKFASFA QRCCHCYRHR GVTLVVWYGF IQLRFPTIKA SYMIPHVVQK  1920
SGLLRSSDRC QKVGRSVITH GYGSTAFSYC HAIRKMLFCD WVLNQVILRI VYAATELLLP  1980
GVNTGYRATQ NFKSAHHWKT FFGAKTLKDL TAVEIQFDVT HSCTQLIFSI FYFHQRFWVS  2040
KNRKAKCRKK GNKGDTEMLN THTLPFSILL KHLSGLLSHE RIHIMYLEKT NRGSAHISPK  2100
SATRRRIGRS PDPLWSTLST ICSDAALSQY LLPACVLEVA ECASKIATTR QGLTDNCMKN  2160
LLR                                                                2163
```

SEQ ID NO: 209          moltype = AA  length = 51
FEATURE                 Location/Qualifiers
source                  1..51
                        mol_type = protein
                        organism = synthetic construct
SEQUENCE: 209

```
PASYTYTVYR DGTKIKEGLT ATTFEEDGVA AGNHEYCVEV KYTAGVSPKV C            51
```

SEQ ID NO: 210          moltype = AA  length = 51
FEATURE                 Location/Qualifiers

```
source                      1..51
                            mol_type = protein
                            organism = synthetic construct
SEQUENCE: 210
GSDYTYTVYR DGTKIKEGLT ATTFEEDGVA TGNHEYCVEV KYTAGVSPKV C            51

SEQ ID NO: 211             moltype = AA  length = 50
FEATURE                    Location/Qualifiers
source                      1..50
                            mol_type = protein
                            organism = synthetic construct
SEQUENCE: 211
PTDYTYTVYR DGTKIKEGLT ETTFEEDGVA TGNHEYCVEV KYTAGVSPKK              50

SEQ ID NO: 212             moltype = AA  length = 51
FEATURE                    Location/Qualifiers
source                      1..51
                            mol_type = protein
                            organism = synthetic construct
SEQUENCE: 212
PTDYTYTVYR DGTKIKEGLT ETTFEEDGVA TGNHEYCVEV KYTAGVSPKE C            51

SEQ ID NO: 213             moltype = AA  length = 51
FEATURE                    Location/Qualifiers
source                      1..51
                            mol_type = protein
                            organism = synthetic construct
SEQUENCE: 213
PTDYTYTVYR DGTKIKEGLT ETTFEEDGVA TGNHEYCVEV KYTAGVSPKV C            51

SEQ ID NO: 214             moltype = AA  length = 51
FEATURE                    Location/Qualifiers
source                      1..51
                            mol_type = protein
                            organism = synthetic construct
SEQUENCE: 214
PASYTYTVYR DGTKIKEGLT ETTYRDAGMS AQSHEYCVEV KYTAGVSPKV C            51

SEQ ID NO: 215             moltype = AA  length = 51
FEATURE                    Location/Qualifiers
source                      1..51
                            mol_type = protein
                            organism = synthetic construct
SEQUENCE: 215
APSYTYTIYR NNTQIASGVT ETTYRDPDLA TGFYTYGVKV VYPNGESAIE T            51

SEQ ID NO: 216             moltype = AA  length = 103
FEATURE                    Location/Qualifiers
source                      1..103
                            mol_type = protein
                            organism = synthetic construct
SEQUENCE: 216
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSC                    103

SEQ ID NO: 217             moltype = AA  length = 227
FEATURE                    Location/Qualifiers
source                      1..227
                            mol_type = protein
                            organism = synthetic construct
SEQUENCE: 217
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                227

SEQ ID NO: 218             moltype = AA  length = 107
FEATURE                    Location/Qualifiers
source                      1..107
                            mol_type = protein
                            organism = synthetic construct
SEQUENCE: 218
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 219             moltype = AA  length = 106
FEATURE                    Location/Qualifiers
source                      1..106
                            mol_type = protein
```

-continued

```
                         organism = synthetic construct
SEQUENCE: 219
GQPKAAPSVT LFPPSSEELQ ANKATLVCLI SDFYPGAVTV AWKADSSPVK AGVETTTPSK   60
QSNNKYAASS YLSLTPEQWK SHRSYSCQVT HEGSTVEKTV APTECS                  106

SEQ ID NO: 220          moltype = DNA  length = 1401
FEATURE                 Location/Qualifiers
source                  1..1401
                        mol_type = other DNA
                        organism = synthetic construct
SEQUENCE: 220
atgggctggt catgcattat tctgtttctg gtcgcaactg ctacaggcgt gcatagtcag   60
gtgcagctgc aagagtccgg ccctggactc gtgaagccct ccgagacact gtctctgacc  120
tgtaccgtgt ctggctttag cctgtccatc tactccgtgc actggatccg gcagcctcct  180
ggcaagggcc tggaatggat cggcatgatc tggggaggcg gctctagcga ctacaactcc  240
gccctgaaat ctagagtgac catctccgtg gacacctcca agaaccagtt ctccctgaag  300
ctgagctctg tgaccgctgc tgataccgcc gtgtactact gcgccagaaa tggcaacttc  360
tacgccatgg actattgggg ccagggcacc ctggtcacag tgtcctctgc cagcaccaag  420
ggcccttccg tgtttccact ggccccctcc tctaaatcca catctggcgg caccgccgcc  480
ctgggctgtc tggtgaagga ctacttccca gagcctgtga cagtgtcctg gaactctggc  540
gccctgacat ccggcgtgca cacatttcca gccgtgctgc agagctccgg cctgtacagc  600
ctgtctagcg tggtgacagt gccctcctct agcctgggca cagaccta tatctgcaac   660
gtgaatcaca agccaagcaa taccaaggtg gacaagaagg tggagcccaa gtcctgtgat  720
aagacacaca cctgccccc ttgtcctgct cccgagctgc tgggcggccc tagcgtgttc   780
ctgtttccac ccaagcctaa ggacaccctg atgatctccc ggacacccga ggtgacctgc  840
gtggtggtgg acgtgtctca cgaggatcct gaggtgaagt tcaactggta tgtggatggc  900
gtggaggtgc acaatgccaa gaccaagccc agagaggagc agtacaactc tacatatagg  960
gtggtgagcg tgctgaccgt gctgcaccag gactggctga acggcaagga gtataagtgc 1020
aaggtgtcca ataaggccct gcccgccccc atcgagaaga caatcagcaa ggccaagggc 1080
cagcctcggg agccacaggt gtacaccctg cctccatcca gagacgagct gacaaagaac 1140
caggtgtctc tgacatgtct ggtgaagggc ttctatccta gcgatatcgc cgtggagtgg 1200
gagtccaatg gccagccaga gaacaattac aagaccacac ccctgtgct ggactccgat  1260
ggctccttct ttctgtattc caagctgacc gtggataagt ctcggtggca gcagggcaac 1320
gtgttcagct gttccgtgat gcacgaagcc ctgcataatc actatactca gaaatccctg 1380
tccctgtcac ctggaaagtg a                                           1401

SEQ ID NO: 221          moltype = AA  length = 466
FEATURE                 Location/Qualifiers
source                  1..466
                        mol_type = protein
                        organism = synthetic construct
SEQUENCE: 221
MGWSCIILFL VATATGVHSQ VQLQESGPGL VKPSETLSLT CTVSGFSLSI YSVHWIRQPP   60
GKGLEWIGMI WGGGSSDYNS ALKSRVTISV DTSKNQFSLK LSSVTAADTA VYYCARNGNF  120
YAMDYWGQGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSCD  240
KTHTCPPCPA PELLGGPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPSRDELTKN QVSLTCLVKG FYPSDIAVEW ESNGQPENNY KTTPPVLDSD  420
GSFFLYSKLT VDKSRWQQGN VFSCSVMHEA LHNHYTQKSL SLSPGK                 466

SEQ ID NO: 222          moltype = DNA  length = 1401
FEATURE                 Location/Qualifiers
source                  1..1401
                        mol_type = other DNA
                        organism = synthetic construct
SEQUENCE: 222
atgggctggt catgcattat tctgtttctg gtcgcaactg ctacaggcgt gcatagtcag   60
gtgcagctgc aagagtccgg ccctggactc gtgaagccct ccgagacact gtctctgaca  120
tgtaccgtgt ctggcttctc cctgtccatc tactccgtgc actggatcag acagcctcct  180
ggcaagggcc tggaatggat cggcatgatc tggggaggcg gctcttccga ctacaactcc  240
gccctgaaat ctcggctgac catctccaag gacacctcta agaaccaggt cagcctgaag  300
ctgagctctg tgaccgctgc tgataccgcc gtgtactact gcgccagaaa tggcaacttc  360
tacgccatgg actattgggg ccagggcacc ctggtgaccg tgtccagcgc cagcaccaag  420
ggcccttccg tgtttccact ggccccctcc tctaaatcca catctggcgg caccgccgcc  480
ctgggctgtc tggtgaagga ctacttccca gagcctgtga cagtgtcctg gaactctggc  540
gccctgacat ccggcgtgca cacatttcca gccgtgctgc agagctccgg cctgtacagc  600
ctgtctagcg tggtgacagt gccctcctct agcctgggca cagaccta tatctgcaac   660
gtgaatcaca agccaagcaa taccaaggtg gacaagaagg tggagcccaa gtcctgtgat  720
aagacacaca cctgccccc ttgtcctgct cccgagctgc tgggcggccc tagcgtgttc   780
ctgtttccac ccaagcctaa ggacaccctg atgatctccc ggacacccga ggtgacctgc  840
gtggtggtgg acgtgtctca cgaggatcct gaggtgaagt tcaactggta tgtggatggc  900
gtggaggtgc acaatgccaa gaccaagccc agagaggagc agtacaactc tacatatagg  960
gtggtgagcg tgctgaccgt gctgcaccag gactggctga acggcaagga gtataagtgc 1020
aaggtgtcca ataaggccct gcccgccccc atcgagaaga caatcagcaa ggccaagggc 1080
cagcctcggg agccacaggt gtacaccctg cctccatcca gagacgagct gacaaagaac 1140
caggtgtctc tgacatgtct ggtgaagggc ttctatccta gcgatatcgc cgtggagtgg 1200
gagtccaatg gccagccaga gaacaattac aagaccacac ccctgtgct ggactccgat  1260
ggctccttct ttctgtattc caagctgacc gtggataagt ctcggtggca gcagggcaac 1320
```

-continued

```
gtgttcagct gttccgtgat gcacgaagcc ctgcataatc actatactca gaaatccctg   1380
tccctgtcac ctggaaagtg a                                             1401

SEQ ID NO: 223          moltype = AA  length = 466
FEATURE                 Location/Qualifiers
source                  1..466
                        mol_type = protein
                        organism = synthetic construct
SEQUENCE: 223
MGWSCIILFL VATATGVHSQ VQLQESGPGL VKPSETLSLT CTVSGFSLSI YSVHWIRQPP    60
GKGLEWIGMI WGGGSSDYNS ALKSRLTISK DTSKNQVSLK LSSVTAADTA VYYCARNGNF    120
YAMDYWGQGT LVTVSSASTK GPSVFPLAPS SKSTSGGTAA LGCLVKDYFP EPVTVSWNSG    180
ALTSGVHTFP AVLQSSGLYS LSSVVTVPSS SLGTQTYICN VNHKPSNTKV DKKVEPKSCD    240
KTHTCPPCPA PELLGGPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPSRDELTKN QVSLTCLVKG FYPSDIAVEW ESNGQPENNY KTTPPVLDSD    420
GSFFLYSKLT VDKSRWQQGN VFSCSVMHEA LHNHYTQKSL SLSPGK                  466

SEQ ID NO: 224          moltype = DNA  length = 1401
FEATURE                 Location/Qualifiers
source                  1..1401
                        mol_type = other DNA
                        organism = synthetic construct
SEQUENCE: 224
atgggctggt catgcattat tctgtttctg gtcgcaactg ctacaggcgt gcatagtcag    60
gtgcagctgc aagagtccgg ccctggactc gtgaagcct ccgagacact gtctctgacc    120
tgtaccgtgt ctggcttctc cctgtccatc tactccgtgc actggatccg gcagcctcct    180
ggcaagggcc tggaatggct gggcatgatc tggggcggag gctctagcga ctacaactcc    240
gccctgaaat ctagactgac catctccgtg gacacctcca gaaaccaggt cagcctgaag    300
ctgagctctg tgaccgccgc tgatacagct atgtactact gcgccagaaa tggcaacttc    360
tacgccatgg actattgggg ccagggcacc ctggtgaccg tgtcctctgc cagcaccaag    420
ggcccttccg tgtttccact ggcccctcc tctaaatcca catctggcgg caccgccgcc    480
ctgggctgtc tggtgaagga ctacttccca gagcctgtga cagtgtcctg gaactctggc    540
gccctgacat ccggcgtgca cacatttcca gccgtgctgc agagctccgg cctgtacagc    600
ctgtctagcg tggtgacagt gccctcctct agcctgggca cacagaccta tatctgcaac    660
gtgaatcaca gccaagcaa taccaaggtg gacaagaagg tggagcccaa gtcctgtgat    720
aagacacaca cctgccccc ttgtcctgct cccgagctgc tgggcggcc tagcgtgttc    780
ctgtttccac ccaagcctaa ggacaccctg atgatctccc ggacacccga ggtgacctgc    840
gtggtggtgg acgtgtctca cgaggatcct gaggtgaagt tcaactggta tgtggatggc    900
gtggaggtgc acaatgccaa gaccaagccc agagaggagc agtacaactc tacatatagg    960
gtggtgagcg tgctgaccgt gctgcaccag gactggctga acggcaagga gtataagtgc    1020
aaggtgtcca ataaggccct gcccgcccc atcgagaaga caatcagcaa ggccaagggc    1080
cagcctcggg agccacaggt gtacacctg cctccatcca gagacgagct gacaaagaac    1140
caggtgtctc tgacatgtct ggtgaagggc ttctatccta gcgatatcgc cgtggagtgg    1200
gagtccaatg gccagccaga gaacaattac aagaccacac cccctgtgct ggactccgat    1260
ggctccttct ttctgtattc caagctgacc gtggataagt ctcggtggca gcagggcaac    1320
gtgttcagct gttccgtgat gcacgaagcc ctgcataatc actatactca gaaatccctg    1380
tccctgtcac ctggaaagtg a                                             1401

SEQ ID NO: 225          moltype = AA  length = 466
FEATURE                 Location/Qualifiers
source                  1..466
                        mol_type = protein
                        organism = synthetic construct
SEQUENCE: 225
MGWSCIILFL VATATGVHSQ VQLQESGPGL VKPSETLSLT CTVSGFSLSI YSVHWIRQPP    60
GKGLEWLGMI WGGGSSDYNS ALKSRLTISV DTSKNQVSLK LSSVTAADTA MYYCARNGNF    120
YAMDYWGQGT LVTVSSASTK GPSVFPLAPS SKSTSGGTAA LGCLVKDYFP EPVTVSWNSG    180
ALTSGVHTFP AVLQSSGLYS LSSVVTVPSS SLGTQTYICN VNHKPSNTKV DKKVEPKSCD    240
KTHTCPPCPA PELLGGPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPSRDELTKN QVSLTCLVKG FYPSDIAVEW ESNGQPENNY KTTPPVLDSD    420
GSFFLYSKLT VDKSRWQQGN VFSCSVMHEA LHNHYTQKSL SLSPGK                  466

SEQ ID NO: 226          moltype = DNA  length = 1401
FEATURE                 Location/Qualifiers
source                  1..1401
                        mol_type = other DNA
                        organism = synthetic construct
SEQUENCE: 226
atgggctggt catgcattat tctgtttctg gtcgcaactg ctacaggcgt gcatagtcag    60
gtgcagctgc aagagtccgg acccggcctc gtgaagcctt ccgagacact gtctctgacc    120
tgtaccgtgt ctggcttctc cctgtccatc tactccgtgc actggatccg gcagcctcct    180
ggcaagggcc tggaatggct gggcatgatc tggggcggcg gaagctccga ctacaactcc    240
gccctgaaat ctagactgac catctccaag gacacctcta gaaaccaggt cagcctgaag    300
ctgagctctg tgaccgccgc tgataccgct atgtactact gcgccagaaa tggcaacttc    360
tacgccatgg actattgggg ccagggcacc ctggtgacag tgtcctctgc cagcaccaag    420
ggcccttccg tgtttccact ggcccctcc tctaaatcca catctggcgg caccgccgcc    480
ctgggctgtc tggtgaagga ctacttccca gagcctgtga cagtgtcctg gaactctggc    540
```

```
gccctgacat ccggcgtgca cacatttcca gccgtgctgc agagctccgg cctgtacagc      600
ctgtctagcg tggtgacagt gccctcctct agcctgggca cacagaccta tatctgcaac      660
gtgaatcaca agccaagcaa taccaaggtg gacaagaagg tggagcccaa gtcctgtgat      720
aagacacaca cctgccccc ttgtcctgct cccgagctgc tgggcggccc tagcgtgttc      780
ctgtttccac ccaagcctaa ggacaccctg atgatctccc ggacacccga ggtgacctgc      840
gtggtggtgg acgtgtctca cgaggatcct gaggtgaagt tcaactggta tgtggatggc      900
gtggaggtgc acaatgccaa gaccaagccc agagaggagc agtacaactc tacatatagg      960
gtggtgagcg tgctgaccgt gctgcaccag gactggctga acggcaagga gtataagtgc     1020
aaggtgtcca ataaggccct gcccgccccc atcgagaaga caatcagcaa ggccaagggc     1080
cagcctcggg agccacaggt gtacaccctg cctccatcca gagacgagct gacaaagaac     1140
caggtgtctc tgacatgtct ggtgaagggc ttctatccta gcgatatcgc cgtggagtgg     1200
gagtccaatg gccagccaga gaacaattac aagaccacac ccctgtgct ggactccgat     1260
ggctccttct ttctgtattc caagctgacc gtggataagt ctcggtggca gcagggcaac     1320
gtgttcagct gttccgtgat gcacgaagcc ctgcataatc actatactca gaaatccctg     1380
tccctgtcac ctggaaagtg a                                               1401

SEQ ID NO: 227        moltype = AA   length = 466
FEATURE               Location/Qualifiers
source                1..466
                      mol_type = protein
                      organism = synthetic construct
SEQUENCE: 227
MGWSCIILFL VATATGVHSQ VQLQESGPGL VKPSETLSLT CTVSGFSLSI YSVHWIRQPP      60
GKGLEWLGMI WGGGSSDYNS ALKSRLTISK DTSKNQVSLK LSSVTAADTA MYYCARNGNF     120
YAMDYWGQGT LVTVSSASTK GPSVFPLAPS SKSTSGGTAA LGCLVKDYFP EPVTVSWNSG     180
ALTSGVHTFP AVLQSSGLYS LSSVVTVPSS SLGTQTYICN VNHKPSNTKV DKKVEPKSCD     240
KTHTCPPCPA PELLGGPSVF LFPPKPKDTL MISRTPEVTC VVVDVSHEDP EVKFNWYVDG     300
VEVHNAKTKP REEQYNSTYR VVSVLTVLHQ DWLNGKEYKC KVSNKALPAP IEKTISKAKG     360
QPREPQVYTL PPSRDELTKN QVSLTCLVKG FYPSDIAVEW ESNGQPENNY KTTPPVLDSD     420
GSFFLYSKLT VDKSRWQQGN VFSCSVMHEA LHNHYTQKSL SLSPGK                    466

SEQ ID NO: 228        moltype = DNA   length = 711
FEATURE               Location/Qualifiers
source                1..711
                      mol_type = other DNA
                      organism = synthetic construct
SEQUENCE: 228
atgggctggt catgtattat tctgtttctg gtcgcaactg ctacaggggt ccatagtgag      60
atcgtgctga cccaatctcc aggcaccctg tctctcagcc ctggcagagg agccaccctg     120
tcctgcaccg cttctagctc cgtgtcctcc agcttcctgc actggtacca gcagaaaccc     180
ggccaggctc ctagactgct gatctattcc acctccaacc tggcctctgg catccctgac     240
cggttctccg gctctggctc cggaacagat tttacactga ccatctcccg gctggaacct     300
gaggacttcg ccgtgtacta ctgtcaccag taccaccatt ctccttacat ctataccttc     360
ggcggcggaa ccaagctgga aatcaagagg acagtggccg ccccaagcgt gttcatcttt     420
cccccttccg acgagcagct gaagtctggc accgccagcg tggtgtgcct gctgaacaac     480
ttctaccctc gggaggccaa ggtccagtgg aaggtggata cgccctgca gtctggcaat     540
agccaggagt ccgtgaccga gcaggactct aaggatagca catattccct gtctagcacc     600
ctgacactga gcaaggccga ttacgagaag cacaaggtgt atgcctgtga agtcacccat     660
caggggctgt catcacccgt cactaagtca ttcaatcgcg agaatgctg a               711

SEQ ID NO: 229        moltype = AA   length = 236
FEATURE               Location/Qualifiers
source                1..236
                      mol_type = protein
                      organism = synthetic construct
SEQUENCE: 229
MGWSCIILFL VATATGVHSE IVLTQSPGTL SLSPGERATL SCTASSSVSS SFLHWYQQKP      60
GQAPRLLIYS TSNLASGIPD RFSGSGSGTD FTLTISRLEP EDFAVYYCHQ YHHSPYIYTF     120
GGGTKLEIKR TVAAPSVFIF PPSDEQLKSG TASVVCLLNN FYPREAKVQW KVDNALQSGN     180
SQESVTEQDS KDSTYSLSST LTLSKADYEK HKVYACEVTH QGLSSPVTKS FNRGEC          236

SEQ ID NO: 230        moltype = DNA   length = 711
FEATURE               Location/Qualifiers
source                1..711
                      mol_type = other DNA
                      organism = synthetic construct
SEQUENCE: 230
atgggctggt catgtattat tctgtttctg gtcgcaactg ctacaggggt ccatagtgag      60
atcgtgctga cacaatctcc cggcaccctc agcctgtctc aggcgagag agccacactg     120
tcctgcaccg cttctagctc cgtgtcctcc agctttctgc actggtacca gcagaaacct     180
ggccaggctc ctcagctgtg gatctactcc acctccaacc tggcctctgg catccctgat     240
cggttctccg gctccggctc tggcaccgac tacaccctga ccatctccag actggaacct     300
gaggacttcg ccgtgtacta ctgtcaccag taccaccatt ctccttacat ctataccttc     360
ggcggaggaa ccaagctgga aatcaagagg acagtggccg ccccaagcgt gttcatcttt     420
cccccttccg acgagcagct gaagtctggc accgccagcg tggtgtgcct gctgaacaac     480
ttctaccctc gggaggccaa ggtccagtgg aaggtggata cgccctgca gtctggcaat     540
agccaggagt ccgtgaccga gcaggactct aaggatagca catattccct gtctagcacc     600
ctgacactga gcaaggccga ttacgagaag cacaaggtgt atgcctgtga agtcacccat     660
caggggctgt catcacccgt cactaagtca ttcaatcgcg agaatgctg a               711
```

```
SEQ ID NO: 231              moltype = AA   length = 236
FEATURE                    Location/Qualifiers
source                     1..236
                           mol_type = protein
                           organism = synthetic construct
SEQUENCE: 231
MGWSCIILFL VATATGVHSE IVLTQSPGTL SLSPGERATL SCTASSSVSS SFLHWYQQKP   60
GQAPQLWIYS TSNLASGIPD RFSGSGSGTD YTLTISRLEP EDFAVYYCHQ YHHSPYIYTF   120
GGGTKLEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236

SEQ ID NO: 232              moltype = DNA   length = 711
FEATURE                    Location/Qualifiers
source                     1..711
                           mol_type = other DNA
                           organism = synthetic construct
SEQUENCE: 232
atgggctggt catgtattat tctgtttctg gtcgcaactg ctacaggggt ccatagtgag   60
atcgtgctga cccagtctcc aggcacactc agcctgtctc ctggcgagcg ggctaccctg   120
tcctgcaccg ccagcagctc cgtgtcctct tcttttctgc actggtacca gcagaaacct   180
ggacaagctc ctcagctgtg gatctactcc acctccaacc tggcctctgg catccccgat   240
agattctccg gctctggctc cggcaccgac tacacactga ccatctccag actggaacct   300
gaggacttcg ccacctacta ctgtcatcag taccaccact cccccttacat ctataccttc   360
ggcggaggca ccaagctgga aatcaagagg acagtggccg ccccaagcgt gttcatcttt   420
cccccttccg acgagcagct gaagtctggc accgccagcg tggtgtgcct gctgaacaac   480
ttctaccctc gggaggccaa ggtccagtgg aaggtggata cgccctgca gtctggcaat   540
agccaggagt ccgtgaccga gcaggactct aaggatagca catattccct gtctagcacc   600
ctgacactga gcaggccga ttacgagaag cacaaggtgt atgcctgtga agtcacccat   660
cagggggctgt catcacccgt cactaagtca ttcaatcgcg gagaatgctg a           711

SEQ ID NO: 233              moltype = AA   length = 236
FEATURE                    Location/Qualifiers
source                     1..236
                           mol_type = protein
                           organism = synthetic construct
SEQUENCE: 233
MGWSCIILFL VATATGVHSE IVLTQSPGTL SLSPGERATL SCTASSSVSS SFLHWYQQKP   60
GQAPQLWIYS TSNLASGIPD RFSGSGSGTD YTLTISRLEP EDFATYYCHQ YHHSPYIYTF   120
GGGTKLEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236

SEQ ID NO: 234              moltype = DNA   length = 711
FEATURE                    Location/Qualifiers
source                     1..711
                           mol_type = other DNA
                           organism = synthetic construct
SEQUENCE: 234
atgggctggt catgtattat tctgtttctg gtcgcaactg ctacaggggt ccatagtgag   60
atcgtgctga cccaatctcc tggcaccctg tctctgagcc caggcgagag agccacactc   120
tcctgcaccg cttcttcctc cgtgtcctct agctttctgc actggtacca gcagaaacct   180
ggccaggctc ctcagctgtg gatctactcc acctccaacc tggcctctgg catccctgcc   240
agattctccg gatccggctc tggcaccgat tatacactga ccatctcccg gctggaacct   300
gaggacttcg ccacctacta ctgtcaccag taccaccata gcccttacat ctacaccttc   360
ggcggcggaa ccaagctgga aatcaagagg acagtggccg ccccaagcgt gttcatcttt   420
cccccttccg acgagcagct gaagtctggc accgccagcg tggtgtgcct gctgaacaac   480
ttctaccctc gggaggccaa ggtccagtgg aaggtggata cgccctgca gtctggcaat   540
agccaggagt ccgtgaccga gcaggactct aaggatagca catattccct gtctagcacc   600
ctgacactga gcaggccga ttacgagaag cacaaggtgt atgcctgtga agtcacccat   660
cagggggctgt catcacccgt cactaagtca ttcaatcgcg gagaatgctg a           711

SEQ ID NO: 235              moltype = AA   length = 236
FEATURE                    Location/Qualifiers
source                     1..236
                           mol_type = protein
                           organism = synthetic construct
SEQUENCE: 235
MGWSCIILFL VATATGVHSE IVLTQSPGTL SLSPGERATL SCTASSSVSS SFLHWYQQKP   60
GQAPQLWIYS TSNLASGIPA RFSGSGSGTD YTLTISRLEP EDFATYYCHQ YHHSPYIYTF   120
GGGTKLEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236

SEQ ID NO: 236              moltype = DNA   length = 1401
FEATURE                    Location/Qualifiers
source                     1..1401
                           mol_type = other DNA
                           organism = synthetic construct
SEQUENCE: 236
atgggctggt catgcattat tctgtttctg gtcgcaactg ctacaggcgt gcatagtcag   60
```

-continued

```
gtgcagctgc aagagtccgg ccctggactc gtgaagccct ccgagacact gtctctgacc    120
tgtaccgtgt ctggctttag cctgtccatc tactccgtgc actggatccg gcagcctcct    180
ggcaagggcc tggaatggat cggcatgatc tggggaggcg gctctagcga ctacaactcc    240
gccctgaaat ctagagtgac catctccgtg gacacctcca agaaccagtt ctccctgaag    300
ctgagctctg tgaccgctgc tgataccgcc gtgtactact gcgccagaaa tggcaacttc    360
tacgccatgg actattgggg ccagggcacc ctggtcacag tgtcctctgc cagcaccaag    420
ggcccttccg tgtttccact ggccccctcc tctaaatcca catctggcgg caccgccgcc    480
ctgggctgtc tggtgaagga ctacttccca gagcctgtga cagtgtcctg gaactctggc    540
gccctgacat ccggcgtgca cacatttcca gccgtgctgc agagctccgg cctgtacagg    600
ctgtctagcg tggtgacagt gccctcctct agcctgggca cacagaccta tatctgcaac    660
gtgaatcaca agccaagcaa taccaaggtg gacaagaagg tggagcccaa gtcctgtgat    720
gccacacaca cctgcccccc ttgtcctgct cccgagctgc tgggcggccc tagcgtgttc    780
ctgtttccac ccaagcctaa ggacaccctg atgatctccc ggacacccga ggtgacctgc    840
gtggtggtgg acgtgtctca cgaggatcct gaggtgaagt tcaactggta tgtggatggc    900
gtggaggtgc acaatgccaa gaccaagccc agagaggagc agtacaactc tacatatagg    960
gtggtgagcg tgctgaccgt gctgcaccag gactggctga acggcaagga gtataagtgc   1020
aaggtgtcca ataaggccct gcccgccccc atcgagaaga caatcagcaa ggccaagggc   1080
cagcctcggg agccacaggt gtacaccctg cctccatcca gagacgagct gacaaagaac   1140
caggtgtctc tgacatgtct ggtgaagggc ttctatccta gcgatatcgc cgtggagtgg   1200
gagtccaatg gccagccaga gaacaattac aagaccacac ccctgtgct ggactccgat    1260
ggctccttct ttctgtattc caagctgacc gtggataagt ctcggtggca gcagggcaac   1320
gtgttcagct gttccgtgat gcacgaagcc ctgcataatc actatactca gaaatccctg   1380
tccctgtcac ctggaaagtg a                                             1401
```

```
SEQ ID NO: 237          moltype = AA  length = 466
FEATURE                 Location/Qualifiers
source                  1..466
                        mol_type = protein
                        organism = synthetic construct
SEQUENCE: 237
MGWSCIILFL VATATGVHSQ VQLQESGPGL VKPSETLSLT CTVSGFSLSI YSVHWIRQPP    60
GKGLEWIGMI WGGGSSDYNS ALKSRVTISV DTSKNQFSLK LSSVTAADTA VYYCARNGNF   120
YAMDYWGQGT LVTVSSASTK GPSVFPLAPS SKSTSGGTAA LGCLVKDYFP EPVTVSWNSG   180
ALTSGVHTFP AVLQSSGLYS LSSVVTVPSS SLGTQTYICN VNHKPSNTKV DKKVEPKSCD   240
ATHTCPPCPA PELLGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSRDELTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGK                  466
```

```
SEQ ID NO: 238          moltype = DNA  length = 1401
FEATURE                 Location/Qualifiers
source                  1..1401
                        mol_type = other DNA
                        organism = synthetic construct
SEQUENCE: 238
atgggctggt catgcattat tctgtttctg gtcgcaactg ctacaggcgt gcatagtcag    60
gtgcagctgc aagagtccgg ccctggactc gtgaagccct ccgagacact gtctctgaca   120
tgtaccgtgt ctggcttctc cctgtccatc tactccgtgc actggatcag acagcctcct   180
ggcaagggcc tggaatggat cggcatgatc tggggaggcg gctcttccga ctacaactcc   240
gccctgaaat ctcggctgac catctccaag gacacctcta agaaccaggt cagcctgaag   300
ctgagctctg tgaccgctgc tgataccgcc gtgtactact gcgccagaaa tggcaacttc   360
tacgccatgg actattgggg ccagggcacc ctggtgaccg tgtccagcgc cagcaccaag   420
ggcccttccg tgtttccact ggccccctcc tctaaatcca catctggcgg caccgccgcc   480
ctgggctgtc tggtgaagga ctacttccca gagcctgtga cagtgtcctg gaactctggc   540
gccctgacat ccggcgtgca cacatttcca gccgtgctgc agagctccgg cctgtacagg   600
ctgtctagcg tggtgacagt gccctcctct agcctgggca cacagaccta tatctgcaac   660
gtgaatcaca agccaagcaa taccaaggtg gacaagaagg tggagcccaa gtcctgtgat   720
gccacacaca cctgcccccc ttgtcctgct cccgagctgc tgggcggccc tagcgtgttc   780
ctgtttccac ccaagcctaa ggacaccctg atgatctccc ggacacccga ggtgacctgc   840
gtggtggtgg acgtgtctca cgaggatcct gaggtgaagt tcaactggta tgtggatggc   900
gtggaggtgc acaatgccaa gaccaagccc agagaggagc agtacaactc tacatatagg   960
gtggtgagcg tgctgaccgt gctgcaccag gactggctga acggcaagga gtataagtgc   1020
aaggtgtcca ataaggccct gcccgccccc atcgagaaga caatcagcaa ggccaagggc   1080
cagcctcggg agccacaggt gtacaccctg cctccatcca gagacgagct gacaaagaac   1140
caggtgtctc tgacatgtct ggtgaagggc ttctatccta gcgatatcgc cgtggagtgg   1200
gagtccaatg gccagccaga gaacaattac aagaccacac ccctgtgct ggactccgat    1260
ggctccttct ttctgtattc caagctgacc gtggataagt ctcggtggca gcagggcaac   1320
gtgttcagct gttccgtgat gcacgaagcc ctgcataatc actatactca gaaatccctg   1380
tccctgtcac ctggaaagtg a                                             1401
```

```
SEQ ID NO: 239          moltype = AA  length = 466
FEATURE                 Location/Qualifiers
source                  1..466
                        mol_type = protein
                        organism = synthetic construct
SEQUENCE: 239
MGWSCIILFL VATATGVHSQ VQLQESGPGL VKPSETLSLT CTVSGFSLSI YSVHWIRQPP    60
GKGLEWIGMI WGGGSSDYNS ALKSRLTISK DTSKNQVSLK LSSVTAADTA VYYCARNGNF   120
YAMDYWGQGT LVTVSSASTK GPSVFPLAPS SKSTSGGTAA LGCLVKDYFP EPVTVSWNSG   180
```

```
ALTSGVHTFP AVLQSSGLYS LSSVVTVPSS SLGTQTYICN VNHKPSNTKV DKKVEPKSCD  240
ATHTCPPCPA PELLGGPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPSRDELTKN QVSLTCLVKG FYPSDIAVEW ESNGQPENNY KTTPPVLDSD  420
GSFFLYSKLT VDKSRWQQGN VFSCSVMHEA LHNHYTQKSL SLSPGK              466

SEQ ID NO: 240            moltype = DNA   length = 1401
FEATURE                   Location/Qualifiers
source                    1..1401
                          mol_type = other DNA
                          organism = synthetic construct
SEQUENCE: 240
atgggctggt catgcattat tctgtttctg gtcgcaactg ctacaggcgt gcatagtcag  60
gtgcagctgc aagagtccgg ccctggactc gtgaagccct ccgagacact gtctctgacc  120
tgtaccgtgt ctggcttctc cctgtccatc tactccgtgc actggatccg gcagcctcct  180
ggcaagggcc tggaatggct gggcatgatc tggggcggag gctctagcga ctacaactcc  240
gccctgaaat ctagactgac catctccgtg gacacctcca agaaccaggt cagcctgaag  300
ctgagctctg tgaccgccgc tgatacagct atgtactact gcgccagaaa tggcaacttc  360
tacgccatgg actattgggg ccagggcacc ctggtgaccg tgtcctctgc cagcaccaag  420
ggcccttccg tgtttccact ggccccctcc tctaaatcca catctggcgg caccgccgcc  480
ctgggctgtc tggtgaagga ctacttccca gagcctgtga cagtgtcctg gaactctggc  540
gccctgacat ccggcgtgca cacatttcca gccgtgctgc agagctccgg cctgtacagc  600
ctgtctagcg tggtgacagt gccctcctct agcctgggca cacagaccta tatctgcaac  660
gtgaatcaca agccaagcaa taccaaggtg gacaagaagg tggagcccaa gtcctgtgat  720
gccacacaca cctgcccccc ttgtcctgct cccgagctgc tggggcggccc tagcgtgttc  780
ctgtttccac ccaagcctaa ggacaccctg atgatctccc ggacacccga ggtgacctgc  840
gtggtggtgg acgtgtctca cgaggatcct gaggtgaagt tcaactggta tgtggatggc  900
gtggaggtgc acaatgccaa gaccaagccc agagaggagc agtacaactc tacatatagg  960
gtggtgagcg tgctgaccgt gctgcaccag gactggctga acggcaagga gtataagtgc  1020
aaggtgtcca ataaggccct gcccgccccc atcgagaaa caatcagcaa ggccaagggc  1080
cagcctcggg agccacaggt gtacaccctg cctccatcca gagacgagct gacaaagaac  1140
caggtgtctc tgacatgtct ggtgaagggc ttctatccta gcgatatcgc cgtggagtgg  1200
gagtccaatg gccagccaga gaacaattac aagaccacac cccctgtgct ggactccgat  1260
ggctccttct ttctgtattc caagctgacc gtggataagt ctcggtggca gcagggcaac  1320
gtgttcagct gttccgtgat gcacgaagcc ctgcataatc actatactca gaaatccctg  1380
tccctgtcac ctggaaagtg a                                      1401

SEQ ID NO: 241            moltype = AA   length = 466
FEATURE                   Location/Qualifiers
source                    1..466
                          mol_type = protein
                          organism = synthetic construct
SEQUENCE: 241
MGWSCIILFL VATATGVHSQ VQLQESGPGL VKPSETLSLT CTVSGFSLSI YSVHWIRQPP  60
GKGLEWLGMI WGGGSSDYNS ALKSRLTISV DTSKNQVSLK LSSVTAADTA MYYCARNGNF  120
YAMDYWGQGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSCD  240
ATHTCPPCPA PELLGGPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPSRDELTKN QVSLTCLVKG FYPSDIAVEW ESNGQPENNY KTTPPVLDSD  420
GSFFLYSKLT VDKSRWQQGN VFSCSVMHEA LHNHYTQKSL SLSPGK              466

SEQ ID NO: 242            moltype = DNA   length = 1401
FEATURE                   Location/Qualifiers
source                    1..1401
                          mol_type = other DNA
                          organism = synthetic construct
SEQUENCE: 242
atgggctggt catgcattat tctgtttctg gtcgcaactg ctacaggcgt gcatagtcag  60
gtgcagctgc aagagtccgg acccggcctc gtgaagcctt ccgagacact gtctctgacc  120
tgtaccgtgt ctggcttctc cctgtccatc tactccgtgc actggatccg gcagcctcct  180
ggcaagggcc tggaatggct gggcatgatc tggggcggcg gaagctccga ctacaactcc  240
gccctgaaat ctagactgac catctccaag gacacctcta agaaccaggt cagcctgaag  300
ctgagctctg tgaccgccgc tgataccgct atgtactact gcgccagaaa tggcaacttc  360
tacgccatgg actattgggg ccagggcacc ctggtgacag tgtcctctgc cagcaccaag  420
ggcccttccg tgtttccact ggccccctcc tctaaatcca catctggcgg caccgccgcc  480
ctgggctgtc tggtgaagga ctacttccca gagcctgtga cagtgtcctg gaactctggc  540
gccctgacat ccggcgtgca cacatttcca gccgtgctgc agagctccgg cctgtacagc  600
ctgtctagcg tggtgacagt gccctcctct agcctgggca cacagaccta tatctgcaac  660
gtgaatcaca agccaagcaa taccaaggtg gacaagaagg tggagcccaa gtcctgtgat  720
gccacacaca cctgcccccc ttgtcctgct cccgagctgc tggggcggccc tagcgtgttc  780
ctgtttccac ccaagcctaa ggacaccctg atgatctccc ggacacccga ggtgacctgc  840
gtggtggtgg acgtgtctca cgaggatcct gaggtgaagt tcaactggta tgtggatggc  900
gtggaggtgc acaatgccaa gaccaagccc agagaggagc agtacaactc tacatatagg  960
gtggtgagcg tgctgaccgt gctgcaccag gactggctga acggcaagga gtataagtgc  1020
aaggtgtcca ataaggccct gcccgccccc atcgagaaga caatcagcaa ggccaagggc  1080
cagcctcggg agccacaggt gtacaccctg cctccatcca gagacgagct gacaaagaac  1140
caggtgtctc tgacatgtct ggtgaagggc ttctatccta gcgatatcgc cgtggagtgg  1200
gagtccaatg gccagccaga gaacaattac aagaccacac cccctgtgct ggactccgat  1260
```

```
ggctccttct ttctgtattc caagctgacc gtggataagt ctcggtggca gcagggcaac    1320
gtgttcagct gttccgtgat gcacgaagcc ctgcataatc actatactca gaaatccctg    1380
tccctgtcac ctggaaagtg a                                              1401

SEQ ID NO: 243           moltype = AA  length = 466
FEATURE                  Location/Qualifiers
source                   1..466
                         mol_type = protein
                         organism = synthetic construct
SEQUENCE: 243
MGWSCIILFL VATATGVHSQ VQLQESGPGL VKPSETLSLT CTVSGFSLSI YSVHWIRQPP    60
GKGLEWLGMI WGGGSSDYNS ALKSRLTISK DTSKNQVSLK LSSVTAADTA MYYCARNGNF    120
YAMDYWGQGT LVTVSSASTK GPSVFPLAPS SKSTSGGTAA LGCLVKDYFP EPVTVSWNSG    180
ALTSGVHTFP AVLQSSGLYS LSSVVTVPSS SLGTQTYICN VNHKPSNTKV DKKVEPKSCD    240
ATHTCPPCPA PELLGGPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPSRDELTKN QVSLTCLVKG FYPSDIAVEW ESNGQPENNY KTTPPVLDSD    420
GSFFLYSKLT VDKSRWQQGN VFSCSVMHEA LHNHYTQKSL SLSPGK                   466

SEQ ID NO: 244           moltype = DNA  length = 1344
FEATURE                  Location/Qualifiers
source                   1..1344
                         mol_type = other DNA
                         organism = synthetic construct
SEQUENCE: 244
caggtgcagc tgcaagagtc cggccctgga ctcgtgaagc cctccgagac actgtctctg    60
acctgtaccg tgtctggctt tagcctgtcc atctactccg tgcactggat ccggcagcct    120
cctggcaagg gcctggaatg gatcggcatg atctggggag cggctctag cgactacaac     180
tccgccctga atctagagt gaccatctcc gtggacacct ccaagaacca gttctccctg     240
aagctgagct ctgtgaccgc tgctgatacc gccgtgtact actgcgccag aaatggcaac    300
ttctacgcca tggactattg gggccagggc accctggtca cagtgtcctc tgccagcacc    360
aagggccctt ccgtgtttcc actggccccc tcctctaaat ccacatctgg cggcaccgcc    420
gccctgggct gtctggtgaa ggactacttc ccagagcctg tgacagtgtc ctggaactct    480
ggcgccctga catccggcgt gcacacattt ccagccgtgc tgcagagctc cggcctgtac    540
agcctgtcta gcgtggtgac agtgccctcc tctagcctgg gcacacagac ctatatctgt    600
aacgtgaatc acaagccaag caataccaag gtggacaaga aggtggagcc caagtcctgt    660
gataagacac acacctgccc cccttgtcct gctcccgagc tgctgggcgg ccctagcgtg    720
ttcctgtttc cacccaagcc taaggacacc ctgatgatct cccggacacc cgaggtgacc    780
tgcgtggtgg tggacgtgtc tcacgaggat cctgaggtga agttcaactg gtatgtggat    840
ggcgtggag tgcacaatgc caagaccaag cccagagag agcagtacaa ctctacatat     900
agggtggtga gcgtgctgac cgtgctgcac caggactggc tgaacggcaa ggagtataag    960
tgcaaggtgt ccaataaggc cctgcccgcc cccatcgaga gacaatcag caaggccaag     1020
ggccagccctc gggagccaca ggtgtacacc ctgcctccat ccagagagag gctgacaaag   1080
aaccaggtgt ctctgacatg tctggtgaag ggcttctatc ctagcgatat cgccgtggag    1140
tgggagtcca atggccagcc agagaacaat tacaagacca caccccctgt gctggactcc    1200
gatggctcct tctttctgta ttccaagctg accgtggata agtctcggtg gcagcagggc    1260
aacgtgttca gctgttccgt gatgcacgaa gccctgcata atcactatac tcagaaatcc    1320
ctgtccctgt cacctggaaa gtga                                          1344

SEQ ID NO: 245           moltype = AA  length = 447
FEATURE                  Location/Qualifiers
source                   1..447
                         mol_type = protein
                         organism = synthetic construct
SEQUENCE: 245
QVQLQESGPG LVKPSETLSL TCTVSGFSLS IYSVHWIRQP PGKGLEWIGM IWGGGSSDYN    60
SALKSRVTIS VDTSKNQFSL KLSSVTAADT AVYYCARNGN FYAMDYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                       447

SEQ ID NO: 246           moltype = DNA  length = 1344
FEATURE                  Location/Qualifiers
source                   1..1344
                         mol_type = other DNA
                         organism = synthetic construct
SEQUENCE: 246
caggtgcagc tgcaagagtc cggccctgga ctcgtgaagc cctccgagac actgtctctg    60
acatgtaccg tgtctggctt ctccctgtcc atctactccg tgcactggat cagacagcct    120
cctggcaagg gcctggaatg gatcggcatg atctggggag cggctcttc cgactacaac     180
tccgccctga atctcggct gaccatctcc aaggacacct ctaagaacca ggtcagcctg     240
aagctgagct ctgtgaccgc tgctgatacc gccgtgtact actgcgccag aaatggcaac    300
ttctacgcca tggactattg gggccagggc accctggtga ccgtgtccag cgccagcacc    360
aagggccctt ccgtgtttcc actggccccc tcctctaaat ccacatctgg cggcaccgcc    420
gccctgggct gtctggtgaa ggactacttc ccagagcctg tgacagtgtc ctggaactct    480
ggcgccctga catccggcgt gcacacattt ccagccgtgc tgcagagctc cggcctgtac    540
```

```
agcctgtcta gcgtggtgac agtgccctcc tctagcctgg gcacacagac ctatatctgc    600
aacgtgaatc acaagccaag caataccaag gtggacaaga aggtggagcc caagtcctgt    660
gataagacac acacctgccc cccttgtcct gctcccgagc tgctgggcgg ccctagcgtg    720
ttcctgtttc cacccaagcc taaggacacc ctgatgatct cccggacacc cgaggtgacc    780
tgcgtggtgg tggacgtgtc tcacgaggat cctgaggtga agttcaactg gtatgtggat    840
ggcgtggagg tgcacaatgc caagaccaag cccagagagg agcagtacaa ctctacatat    900
agggtggtga gcgtgctgac cgtgctgcac caggactggc tgaacggcaa ggagtataag    960
tgcaaggtgt ccaataaggc cctgcccgcc cccatcgaga agacaatcag caaggccaag   1020
ggccagcctc gggagccaca ggtgtacacc ctgcctccat ccagagacga gctgacaaag   1080
aaccaggtgt ctctgacatg tctggtgaag ggcttctatc ctagcgatat cgccgtggag   1140
tgggagtcca atggccagcc agagaacaat tacaagacca cacccctgt gctggactcc    1200
gatggctcct tctttctgta ttccaagctg accgtggata gtctcggtg gcagcagggc    1260
aacgtgttca gctgttccgt gatgcacgaa gccctgcata atcactatac tcagaaatcc   1320
ctgtccctgt cacctggaaa gtga                                          1344
```

SEQ ID NO: 247          moltype = AA   length = 447
FEATURE                 Location/Qualifiers
source                  1..447
                        mol_type = protein
                        organism = synthetic construct
SEQUENCE: 247
```
QVQLQESGPG LVKPSETLSL TCTVSGFSLS IYSVHWIRQP PGKGLEWIGM IWGGGSSDYN    60
SALKSRLTIS KDTSKNQVSL KLSSVTAADT AVYYCARNGN FYAMDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447
```

SEQ ID NO: 248          moltype = DNA   length = 1344
FEATURE                 Location/Qualifiers
source                  1..1344
                        mol_type = other DNA
                        organism = synthetic construct
SEQUENCE: 248
```
caggtgcagc tgcaagagtc cggccctgga ctcgtgaagc cctccgagac actgtctctg    60
acctgtaccg tgtctggctt ctccctgtcc atctactccg tgcactggat ccggcagcct   120
cctgggcaag gcctggaatg gctgggcatg atctggggcg gaggctctag cgactacaac   180
tccgccctga atctagact gaccatctcc gtggacacct ccaagaacca ggtcagcctg    240
aagctgagct ctgtgaccgc cgctgataca gctatgtact actgcgccag aaatggcaac   300
ttctacgcca tggactattg gggccagggc accctggtga ccgtgtcctc tgccagcacc   360
aagggccctt ccgtgtttcc actggccccc tcctctaagt ccacatctgg cggcaccgcc   420
gccctgggct gtctggtgaa ggactacttc ccagagcctg tgacagtgtc ctggaactct   480
ggcgccctga tccggcgt gcacacattt ccagccgtgc tgcagagctc cggcctgtac    540
agcctgtcta gcgtggtgac agtgccctcc tctagcctgg gcacacagac ctatatctgc   600
aacgtgaatc acaagccaag caataccaag gtggacaaga aggtggagcc caagtcctgt    660
gataagacac acacctgccc cccttgtcct gctcccgagc tgctgggcgg ccctagcgtg    720
ttcctgtttc cacccaagcc taaggacacc ctgatgatct cccggacacc cgaggtgacc    780
tgcgtggtgg tggacgtgtc tcacgaggat cctgaggtga agttcaactg gtatgtggat    840
ggcgtggagg tgcacaatgc caagaccaag cccagagagg agcagtacaa ctctacatat    900
agggtggtga gcgtgctgac cgtgctgcac caggactggc tgaacggcaa ggagtataag    960
tgcaaggtgt ccaataaggc cctgcccgcc cccatcgaga agacaatcag caaggccaag   1020
ggccagcctc gggagccaca ggtgtacacc ctgcctccat ccagagacga gctgacaaag   1080
aaccaggtgt ctctgacatg tctggtgaag ggcttctatc ctagcgatat cgccgtggag   1140
tgggagtcca atggccagcc agagaacaat tacaagacca cacccctgt gctggactcc    1200
gatggctcct tctttctgta ttccaagctg accgtggata gtctcggtg gcagcagggc    1260
aacgtgttca gctgttccgt gatgcacgaa gccctgcata atcactatac tcagaaatcc   1320
ctgtccctgt cacctggaaa gtga                                          1344
```

SEQ ID NO: 249          moltype = AA   length = 447
FEATURE                 Location/Qualifiers
source                  1..447
                        mol_type = protein
                        organism = synthetic construct
SEQUENCE: 249
```
QVQLQESGPG LVKPSETLSL TCTVSGFSLS IYSVHWIRQP PGKGLEWLGM IWGGGSSDYN    60
SALKSRLTIS VDTSKNQVSL KLSSVTAADT AMYYCARNGN FYAMDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447
```

SEQ ID NO: 250          moltype = DNA   length = 1344
FEATURE                 Location/Qualifiers
source                  1..1344
                        mol_type = other DNA

```
                        organism = synthetic construct
SEQUENCE: 250
caggtgcagc tgcaagagtc cggacccggc ctcgtgaagc cttccgagac actgtctctg     60
acctgtaccg tgtctggctt ctccctgtcc atctactccg tgcactggat ccggcagcct    120
cctggcaagg gcctggaatg gctgggcatg atctggggcg gcggaagctc cgactacaac    180
tccgccctga aatctagact gaccatctcc aaggacacct ctaagaacca ggtcagcctg    240
aagctgagct ctgtgaccgc cgctgatacc gctatgtact actgcgccag aaatggcaac    300
ttctacgcca tggactattg gggccagggc accctggtga cagtgtcctc tgccagcacc    360
aagggccctt ccgtgtttcc actggccccc tcctctaaat ccacatctgg cggcaccgcc    420
gccctgggct gtctggtgaa ggactacttc ccagagcctg tgacagtgtc ctggaactct    480
ggcgccctga tccggcgt gcacacattt ccagccgtgc tgcagagctc cggcctgtac    540
agcctgtcta gcgtggtgac agtgccctcc tctagcctgg gcacacagac ctatatctgc    600
aacgtgaatc acaagccaag caataccaag gtggacaaga aggtggagcc caagtcctgt    660
gataagacac acacctgccc cccttgtcct gctcccgagc tgctgggcgg ccctagcgtg    720
ttcctgtttc cacccaagcc taaggacacc ctgatgatct cccggacacc cgaggtgacc    780
tgcgtggtgg tggacgtgtc tcacgaggat cctgaggtga agttcaactg gtatgtggat    840
ggcgtggagg tgcacaatgc caagaccaag cccagagagg agcagtacaa ctctacatat    900
agggtggtga gcgtgctgac cgtgctgcac caggactggc tgaacggcaa ggagtataag    960
tgcaaggtgt ccaataaggc cctgcccgcc cccatcgaga gacaatcag caaggccaag   1020
ggccagcctc gggagccaca ggtgtacacc ctgcctccat ccagagcga gctgacaaag   1080
aaccaggtgt ctctgacatg tctggtgaag ggcttctatc ctagcgatat cgccgtggag   1140
tgggagtcca atggccagcc agagaacaat tacaagacca cacccctgt gctggactcc   1200
gatggctcct tctttctgta ttccaagctg accgtggaca agtctcggtg gcagcagggc   1260
aacgtgttca gctgttccgt gatgcacgaa gccctgcata tcactatac tcagaaatcc   1320
ctgtccctgt cacctggaaa gtga                                         1344

SEQ ID NO: 251        moltype = AA  length = 447
FEATURE               Location/Qualifiers
source                1..447
                      mol_type = protein
                      organism = synthetic construct
SEQUENCE: 251
QVQLQESGPG LVKPSETLSL TCTVSGFSLS IYSVHWIRQP PGKGLEWLGM IWGGGSSDYN     60
SALKSRLTIS KDTSKNQVSL KLSSVTAADT AMYYCARNGN FYAMDYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                       447

SEQ ID NO: 252        moltype = DNA  length = 654
FEATURE               Location/Qualifiers
source                1..654
                      mol_type = other DNA
                      organism = synthetic construct
SEQUENCE: 252
gagatcgtgc tgacccaatc tccaggcacc ctgtctctca gccctggcga gagagccacc     60
ctgtcctgca ccgcttctag ctccgtgtcc tccagcttcc tgcactggta ccagcagaaa    120
cccgccagg ctcctagact gctgatctat tccacctcca acctggcctc tggcatccct    180
gaccggttct ccggctctgg ctccggaaca gattttacac tgaccatctc ccggctggaa    240
cctgaggact cgccgtgta ctactgtcac cagtaccacc attctcctta catctacacc    300
ttcggcggcg gaaccaagct ggaaatcaag aggacagtgg ccgccccaag cgtgttcatc    360
tttccccctt ccgacgagca gctgaagtct ggcaccgcca gcgtggtgtg cctgctgaac    420
aacttctacc ctcgggaggc caaggtccaa tggaaggtga ataacgccct gcagtctggc    480
aatagccagg agtccgtgac cgagcaggac tctaaggata gcacatattc cctgtctagc    540
accctgacac tgagcaaggc cgattacgag aagcacaagg tgtatgcctg tgaagtcacc    600
catcaggggc tgtcatcacc cgtcactaag tcattcaatc gcggagaatg ctga          654

SEQ ID NO: 253        moltype = AA  length = 217
FEATURE               Location/Qualifiers
source                1..217
                      mol_type = protein
                      organism = synthetic construct
SEQUENCE: 253
EIVLTQSPGT LSLSPGERAT LSCTASSSVS SSFLHWYQQK PGQAPRLLIY STSNLASGIP     60
DRFSGSGSGT DFTLTISRLE PEDFAVYYCH QYHHSPYIYT FGGGTKLEIK RTVAAPSVFI    120
FPPSDEQLKS GTASVVCLLN NFYPREAKVQ WKVDNALQSG NSQESVTEQD SKDSTYSLSS    180
TLTLSKADYE KHKVYACEVT HQGLSSPVTK SFNRGEC                            217

SEQ ID NO: 254        moltype = DNA  length = 654
FEATURE               Location/Qualifiers
source                1..654
                      mol_type = other DNA
                      organism = synthetic construct
SEQUENCE: 254
gagatcgtgc tgacacaatc tcccggcacc ctcagcctgt ctccaggcga gagagccaca     60
ctgtcctgca ccgcttctag ctccgtgtcc tccagctttc tgcactggta ccagcagaaa    120
cctgccagg ctcctcagct gtggatctac tccacctcca acctggcctc tggcatccct    180
```

```
gatcggttct ccggctccgg ctctggcacc gactacaccc tgaccatctc cagactggaa   240
cctgaggact tcgccgtgta ctactgtcac cagtaccacc attctcctta catctatacc   300
ttcggcggag gaaccaagct ggaaatcaag aggacagtgg ccgccccaag cgtgttcatc   360
tttcccctt  ccgacgagca gctgaagtct ggcaccgcca gcgtggtgtg cctgctgaac   420
aacttctacc ctcgggaggc caaggtccag tggaaggtgg ataacgccct gcagtctggc   480
aatagccagg agtccgtgac cgagcaggac tctaaggata gcacatattc cctgtctagc   540
accctgacac tgagcaaggc cgattacgag aagcacaagg tgtatgcctg tgaagtcacc   600
catcagggc  tgtcatcacc cgtcactaag tcattcaatc gcggagaatg ctga          654
```

```
SEQ ID NO: 255               moltype = AA  length = 217
FEATURE                      Location/Qualifiers
source                       1..217
                             mol_type = protein
                             organism = synthetic construct
SEQUENCE: 255
EIVLTQSPGT LSLSPGERAT LSCTASSSVS SSFLHWYQQK PGQAPQLWIY STSNLASGIP   60
DRFSGSGSGT DYTLTISRLE PEDFAVYYCH QYHHSPYIYT FGGGTKLEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                           217
```

```
SEQ ID NO: 256               moltype = DNA  length = 654
FEATURE                      Location/Qualifiers
source                       1..654
                             mol_type = other DNA
                             organism = synthetic construct
SEQUENCE: 256
gagatcgtgc tgacccagtc tccaggcaca ctcagcctgt ctcctggcga gcgggctacc   60
ctgtcctgca ccgccagcag ctccgtgtcc tcttcttttc tgcactggta ccagcagaaa   120
cctggacaag ctcctcagct gtggatctac tccacctcca acctggcctc tggcatcccc   180
gatagattct ccggctctgg ctccggcacc gactacaccc tgaccatctc cagactggaa   240
cctgaggact tcgccaccta ctactgtcat cagtaccacc actcccctta catctatacc   300
ttcggcggag gcaccaagct ggaaatcaag aggacagtgg ccgccccaag cgtgttcatc   360
tttcccctt  ccgacgagca gctgaagtct ggcaccgcca gcgtggtgtg cctgctgaac   420
aacttctacc ctcgggaggc caaggtccag tggaaggtgg ataacgccct gcagtctggc   480
aatagccagg agtccgtgac cgagcaggac tctaaggata gcacatattc cctgtctagc   540
accctgacac tgagcaaggc cgattacgag aagcacaagg tgtatgcctg tgaagtcacc   600
catcagggc  tgtcatcacc cgtcactaag tcattcaatc gcggagaatg ctga          654
```

```
SEQ ID NO: 257               moltype = AA  length = 217
FEATURE                      Location/Qualifiers
source                       1..217
                             mol_type = protein
                             organism = synthetic construct
SEQUENCE: 257
EIVLTQSPGT LSLSPGERAT LSCTASSSVS SSFLHWYQQK PGQAPQLWIY STSNLASGIP   60
DRFSGSGSGT DYTLTISRLE PEDFATYYCH QYHHSPYIYT FGGGTKLEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                           217
```

```
SEQ ID NO: 258               moltype = DNA  length = 654
FEATURE                      Location/Qualifiers
source                       1..654
                             mol_type = other DNA
                             organism = synthetic construct
SEQUENCE: 258
gagatcgtgc tgacccaatc tcctggcacc ctgtctctga gcccaggcga gagagccaca   60
ctctcctgca ccgcttcttc ctccgtgtcc tctagctttc tgcactggta ccagcagaaa   120
cccggccagg ctcctcagct gtggatctac tccacctcca acctggcctc tggcatccct   180
gccagattct ccggatccgg ctctggcacc gattatacac tgaccatctc ccggctggaa   240
cctgaggact tcgccaccta ctactgtcac cagtaccacc atagccctta catctacacc   300
ttcggcggcg gaaccaagct ggaaatcaag aggacagtgg ccgccccaag cgtgttcatc   360
tttcccctt  ccgacgagca gctgaagtct ggcaccgcca gcgtggtgtg cctgctgaac   420
aacttctacc ctcgggaggc caaggtccag tggaaggtgg ataacgccct gcagtctggc   480
aatagccagg agtccgtgac cgagcaggac tctaaggata gcacatattc cctgtctagc   540
accctgacac tgagcaaggc cgattacgag aagcacaagg tgtatgcctg tgaagtcacc   600
catcagggc  tgtcatcacc cgtcactaag tcattcaatc gcggagaatg ctga          654
```

```
SEQ ID NO: 259               moltype = AA  length = 217
FEATURE                      Location/Qualifiers
source                       1..217
                             mol_type = protein
                             organism = synthetic construct
SEQUENCE: 259
EIVLTQSPGT LSLSPGERAT LSCTASSSVS SSFLHWYQQK PGQAPQLWIY STSNLASGIP   60
ARFSGSGSGT DYTLTISRLE PEDFATYYCH QYHHSPYIYT FGGGTKLEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                           217
```

```
SEQ ID NO: 260               moltype = DNA  length = 1344
```

-continued

```
FEATURE          Location/Qualifiers
source           1..1344
                 mol_type = other DNA
                 organism = synthetic construct SEQUENCE: 260
caggtgcagc tgcaagagtc cggccctgga ctcgtgaagc cctccgagac actgtctctg    60
acctgtaccg tgtctggctt tagcctgtcc atctactccg tgcactggat ccggcagcct   120
cctggcaagg gcctggaatg gatcggcatg atctggggga gcggctctag cgactacaac   180
tccgccctga aatctagagt gaccatctcc gtggacaact ccaagaacca gttctccctg   240
aagctgagct ctgtgaccgc tgctgatacc gccgtgtact actgcgccag aaatggcaac   300
ttctacgcca tggactattg gggccagggc accctggtca cagtgtcctc tgccagcacc   360
aagggccctt ccgtgtttcc actggccccc tcctctaaat ccacatctgg cggcaccgcc   420
gccctgggct gtctggtgaa ggactacttc ccagagcctg tgacagtgtc ctggaactct   480
ggcgccctga catccggcgt gcacacattt ccagccgtgc tgcagagctc cggcctgtac   540
agcctgtcta gcgtggtgac agtgccctcc tctagcctgg gcacacagac ctatatctgc   600
aacgtgaatc acaagccaag caataccaag gtggacaaga aggtggagcc caagtcctgt   660
gatgccacac acacctgccc cccttgtcct gctcccgagc tgctgggcgg ccctagcgtg   720
ttcctgtttc cacccaagcc taaggacacc ctgatgatct cccggacacc cgaggtgacc   780
tgcgtggtgg tggacgtgtc tcacgaggat cctgaggtga agttcaactg gtatgtggat   840
ggcgtggagg tgcacaatgc caagaccaag cccagagagg agcagtacaa ctctacatat   900
agggtggtga gcgtgctgac cgtgctgcac caggactggc tgaacggcaa ggagtataag   960
tgcaaggtgt ccaataaggc cctgcccgcc cccatcgaga agacaatcag caaggccaag   1020
ggccagcctc gggagccaca ggtgtacacc ctgcctccat ccagagacga gctgacaaag  1080
aaccaggtgt ctctgacatg tctggtgaag ggcttctatc ctagcgatat cgccgtggag  1140
tgggagtcca atggccagcc agagaacaat tacaagacca caccccctgt gctggactcc  1200
gatggctcct tctttctgta ttccaagctg accgtggata agtctcggtg gcagcagggc  1260
aacgtgttca gctgttccgt gatgcacgaa gccctgcata tcactatac tcagaaatcc  1320
ctgtccctgt cacctggaaa gtga                                        1344
```

```
SEQ ID NO: 261       moltype = AA  length = 447
FEATURE              Location/Qualifiers
source               1..447
                     mol_type = protein
                     organism = synthetic construct SEQUENCE: 261
QVQLQESGPG LVKPSETLSL TCTVSGFSLS IYSVHWIRQP PGKGLEWIGM IWGGGSSDYN    60
SALKSRVTIS VDTSKNQFSL KLSSVTAADT AVYYCARNGN FYAMDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DATHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447
```

```
SEQ ID NO: 262       moltype = DNA  length = 1344
FEATURE              Location/Qualifiers
source               1..1344
                     mol_type = other DNA
                     organism = synthetic construct SEQUENCE: 262
caggtgcagc tgcaagagtc cggccctgga ctcgtgaagc cctccgagac actgtctctg    60
acatgtaccg tgtctggctt ctccctgtcc atctactccg tgcactggat cagacagcct   120
cctggcaagg gcctggaatg gatcggcatg atctggggga gcggctcttc cgactacaac   180
tccgccctga aatctcggct gaccatctcc aaggacacct ctaagaacca ggtcagcctg   240
aagctgagct ctgtgaccgc tgctgatacc gccgtgtact actgcgccag aaatggcaac   300
ttctacgcca tggactattg gggccagggc accctggtga ccgtgtccag cgccagcacc   360
aagggccctt ccgtgtttcc actggccccc tcctctaaat ccacatctgg cggcaccgcc   420
gccctgggct gtctggtgaa ggactacttc ccagagcctg tgacagtgtc ctggaactct   480
ggcgccctga catccggcgt gcacacattt ccagccgtgc tgcagagctc cggcctgtac   540
agcctgtcta gcgtggtgac agtgccctcc tctagcctgg gcacacagac ctatatctgc   600
aacgtgaatc acaagccaag caataccaag gtggacaaga aggtggagcc caagtcctgt   660
gatgccacac acacctgccc cccttgtcct gctcccgagc tgctgggcgg ccctagcgtg   720
ttcctgtttc cacccaagcc taaggacacc ctgatgatct cccggacacc cgaggtgacc   780
tgcgtggtgg tggacgtgtc tcacgaggat cctgaggtga agttcaactg gtatgtggat   840
ggcgtggagg tgcacaatgc caagaccaag cccagagagg agcagtacaa ctctacatat   900
agggtggtga gcgtgctgac cgtgctgcac caggactggc tgaacggcaa ggagtataag   960
tgcaaggtgt ccaataaggc cctgcccgcc cccatcgaga agacaatcag caaggccaag   1020
ggccagcctc gggagccaca ggtgtacacc ctgcctccat ccagagacga gctgacaaag  1080
aaccaggtgt ctctgacatg tctggtgaag ggcttctatc ctagcgatat cgccgtggag  1140
tgggagtcca atggccagcc agagaacaat tacaagacca caccccctgt gctggactcc  1200
gatggctcct tctttctgta ttccaagctg accgtggata agtctcggtg gcagcagggc  1260
aacgtgttca gctgttccgt gatgcacgaa gccctgcata tcactatac tcagaaatcc  1320
ctgtccctgt cacctggaaa gtga                                        1344
```

```
SEQ ID NO: 263       moltype = AA  length = 447
FEATURE              Location/Qualifiers
source               1..447
                     mol_type = protein
                     organism = synthetic construct
```

```
SEQUENCE: 263
QVQLQESGPG LVKPSETLSL TCTVSGFSLS IYSVHWIRQP PGKGLEWIGM IWGGGSSDYN      60
SALKSRLTIS KDTSKNQVSL KLSSVTAADT AVYYCARNGN FYAMDYWGQG TLVTVSSAST     120
KGPSVFPLAP SSKSTSGGTA ALGCLVKDYF PEPVTVSWNS GALTSGVHTF PAVLQSSGLY     180
SLSSVVTVPS SSLGTQTYIC NVNHKPSNTK VDKKVEPKSC DATHTCPPCP APELLGGPSV     240
FLFPPKPKDT LMISRTPEVT CVVVDVSHED PEVKFNWYVD GVEVHNAKTK PREEQYNSTY     300
RVVSVLTVLH QDWLNGKEYK CKVSNKALPA PIEKTISKAK GQPREPQVYT LPPSRDELTK     360
NQVSLTCLVK GFYPSDIAVE WESNGQPENN YKTTPPVLDS DGSFFLYSKL TVDKSRWQQG     420
NVFSCSVMHE ALHNHYTQKS LSLSPGK                                        447

SEQ ID NO: 264          moltype = DNA  length = 1344
FEATURE                 Location/Qualifiers
source                  1..1344
                        mol_type = other DNA
                        organism = synthetic construct SEQUENCE: 264
caggtgcagc tgcaagagtc cggccctgga ctcgtgaagc cctccgagac actgtctctg      60
acctgtaccg tgtctggctt ctccctgtcc atctactccg tgcactggat ccggcagcct     120
cctggcaagg gcctggaatg gctgggcatg atctggggcg gaggctctag cgactacaac     180
tccgccctga atctagact gaccatctcc gtggacacct ccaagaacca ggtcagcctg     240
aagctgagct ctgtgaccgc cgctgataca gctatgtact actgcgccag aaatggcaac     300
ttctacgcca tggactattg gggccagggc accctggtga cagtgtcctc tgccagcacc     360
aagggccctt ccgtgtttcc actggcccc tcctctaaat ccacatctgg cggcaccgcc     420
gccctgggct gtctggtgaa ggactactc ccagagcctg tgacagtgtc ctggaactct     480
ggcgccctga catccggcgt gcacacattt ccagccgtgc tgcagagctc cggcctgtac     540
agcctgtcta cgtggtgac agtgccctcc tctagcctgg gcacacagac ctatatctgc     600
aacgtgaatc acaagccaag caataccaag gtggacaaga aggtggagcc caagtcctgt     660
gatgccacac acacctgccc cccttgtcct gctcccgagc tgctgggcgg ccctagcgtg     720
ttcctgtttc cacccaagcc taaggacacc ctgatgatct cccggacacc cgaggtgacc     780
tgcgtggtgg tggacgtgtc tcacgaggat cctgaggtga agttcaactg gtatgtggat     840
ggcgtggagg tgcacaatgc caagaccaag cccagagagg agcagtacaa ctctacatat     900
agggtggtga gcgtgctgac cgtgctgcac caggactggc tgaacggcaa ggagtataag     960
tgcaaggtgt ccaataaggc cctgcccgcc cccatcgaga gacaatcag caaggccaag    1020
ggccagcctc gggagccaca ggtgtacacc ctgcctccat ccagagacga gctgacaaag    1080
aaccaggtgt ctctgacatg tctggtgaag ggcttctatc ctagcgatat cgccgtggag    1140
tgggagtcca atggccagcc agagaacaat tacaagacca ccccccctgt gctggactcc    1200
gatggctcct ctttctgta ttccaagctg accgtggata gtctcggtg gcagcagggc    1260
aacgtgttca gctgttccgt gatgcacgaa gccctgcata tcactatac tcagaaatcc    1320
ctgtccctgt cacctggaaa gtga                                          1344

SEQ ID NO: 265          moltype = AA  length = 447
FEATURE                 Location/Qualifiers
source                  1..447
                        mol_type = protein
                        organism = synthetic construct SEQUENCE: 265
QVQLQESGPG LVKPSETLSL TCTVSGFSLS IYSVHWIRQP PGKGLEWLGM IWGGGSSDYN      60
SALKSRLTIS VDTSKNQVSL KLSSVTAADT AMYYCARNGN FYAMDYWGQG TLVTVSSAST     120
KGPSVFPLAP SSKSTSGGTA ALGCLVKDYF PEPVTVSWNS GALTSGVHTF PAVLQSSGLY     180
SLSSVVTVPS SSLGTQTYIC NVNHKPSNTK VDKKVEPKSC DATHTCPPCP APELLGGPSV     240
FLFPPKPKDT LMISRTPEVT CVVVDVSHED PEVKFNWYVD GVEVHNAKTK PREEQYNSTY     300
RVVSVLTVLH QDWLNGKEYK CKVSNKALPA PIEKTISKAK GQPREPQVYT LPPSRDELTK     360
NQVSLTCLVK GFYPSDIAVE WESNGQPENN YKTTPPVLDS DGSFFLYSKL TVDKSRWQQG     420
NVFSCSVMHE ALHNHYTQKS LSLSPGK                                        447

SEQ ID NO: 266          moltype = DNA  length = 1344
FEATURE                 Location/Qualifiers
source                  1..1344
                        mol_type = other DNA
                        organism = synthetic construct SEQUENCE: 266
caggtgcagc tgcaagagtc cggacccggc ctcgtgaagc cttccgagac actgtctctg      60
acctgtaccg tgtctggctt ctccctgtcc atctactccg tgcactggat ccggcagcct     120
cctggcaagg gcctggaatg gctgggcatg atctggggcg gcggaagctc cgactacaac     180
tccgccctga atctagact gaccatctcc aaggacacct ctaagaacca ggtcagcctg     240
aagctgagct ctgtgaccgc cgctgatacc gctatgtact actgcgccag aaatggcaac     300
ttctacgcca tggactattg gggccagggc accctggtga cagtgtcctc tgccagcacc     360
aagggccctt ccgtgtttcc actggcccc tcctctaaat ccacatctgg cggcaccgcc     420
gccctgggct gtctggtgaa ggactactc ccagagcctg tgacagtgtc ctggaactct     480
ggcgccctga catccggcgt gcacacattt ccagccgtgc tgcagagctc cggcctgtac     540
agcctgtcta cgtggtgac agtgccctcc tctagcctgg gcacacagac ctatatctgc     600
aacgtgaatc acaagccaag caataccaag gtggacaaga aggtggagcc caagtcctgt     660
gatgccacac acacctgccc cccttgtcct gctcccgagc tgctgggcgg ccctagcgtg     720
ttcctgtttc cacccaagcc taaggacacc ctgatgatct cccggacacc cgaggtgacc     780
tgcgtggtgg tggacgtgtc tcacgaggat cctgaggtga agttcaactg gtatgtggat     840
ggcgtggagg tgcacaatgc caagaccaag cccagagagg agcagtacaa ctctacatat     900
agggtggtga gcgtgctgac cgtgctgcac caggactggc tgaacggcaa ggagtataag     960
tgcaaggtgt ccaataaggc cctgcccgcc cccatcgaga gacaatcag caaggccaag    1020
ggccagcctc gggagccaca ggtgtacacc ctgcctccat ccagagacga gctgacaaag    1080
```

-continued

```
aaccaggtgt ctctgacatg tctggtgaag ggcttctatc ctagcgatat cgccgtggag   1140
tgggagtcca atggccagcc agagaacaat tacaagacca cacccccctgt gctggactcc   1200
gatggctcct ctttctgta ttccaagctg accgtggata agtctcggtg gcagcagggc    1260
aacgtgttca gctgttccgt gatgcacgaa gccctgcata atcactatac tcagaaatcc   1320
ctgtccctgt cacctggaaa gtga                                          1344

SEQ ID NO: 267            moltype = AA   length = 447
FEATURE                   Location/Qualifiers
source                    1..447
                          mol_type = protein
                          organism = synthetic construct
SEQUENCE: 267
QVQLQESGPG LVKPSETLSL TCTVSGFSLS IYSVHWIRQP PGKGLEWLGM IWGGGSSDYN    60
SALKSRLTIS KDTSKNQVSL KLSSVTAADT AMYYCARNGN FYAMDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DATHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 268            moltype = AA   length = 117
FEATURE                   Location/Qualifiers
source                    1..117
                          mol_type = protein
                          organism = synthetic construct
SEQUENCE: 268
QVQLQESGPG LVKPSETLSL TCTVSGFSLS IYSVHWIRQP PGKGLEWIGM IWGGGSSDYN    60
SALKSRLTIS KDTSKNQVSL KLSSVTAADT AVYYCARNGN FYAMDYWGQG TLVTVSS      117

SEQ ID NO: 269            moltype = AA   length = 98
FEATURE                   Location/Qualifiers
source                    1..98
                          mol_type = protein
                          organism = synthetic construct
SEQUENCE: 269
ASTKGPSVFP LAPSSKSTSG GTAALGCLVK DYFPEPVTVS WNSGALTSGV HTFPAVLQSS    60
GLYSLSSVVT VPSSLGTQT YICNVNHKPS NTKVDKKV                            98

SEQ ID NO: 270            moltype = AA   length = 215
FEATURE                   Location/Qualifiers
source                    1..215
                          mol_type = protein
                          organism = synthetic construct
SEQUENCE: 270
QVQLQESGPG LVKPSETLSL TCTVSGFSLS IYSVHWIRQP PGKGLEWIGM IWGGGSSDYN    60
SALKSRLTIS KDTSKNQVSL KLSSVTAADT AVYYCARNGN FYAMDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKV                              215

SEQ ID NO: 271            moltype = AA   length = 22
FEATURE                   Location/Qualifiers
source                    1..22
                          mol_type = protein
                          organism = synthetic construct
SEQUENCE: 271
EPKSCDATHT CPPCPAPELL GG                                            22

SEQ ID NO: 272            moltype = AA   length = 103
FEATURE                   Location/Qualifiers
source                    1..103
                          mol_type = protein
                          organism = synthetic construct
SEQUENCE: 272
PSVFLFPPKP KDTLMISRTP EVTCVVVDVS HEDPEVKFNW YVDGVEVHNA KTKPREEQYN    60
STYRVVSVLT VLHQDWLNGK EYKCKVSNKA LPAPIEKTIS KAK                     103

SEQ ID NO: 273            moltype = AA   length = 107
FEATURE                   Location/Qualifiers
source                    1..107
                          mol_type = protein
                          organism = synthetic construct
SEQUENCE: 273
GQPREPQVYT LPPSRDELTK NQVSLTCLVK GFYPSDIAVE WESNGQPENN YKTTPPVLDS    60
DGSFFLYSKL TVDKSRWQQG NVFSCSVMHE ALHNHYTQKS LSLSPGK                 107

SEQ ID NO: 274            moltype = AA   length = 330
FEATURE                   Location/Qualifiers
source                    1..330
```

-continued

```
                            mol_type = protein
                            organism = synthetic construct
SEQUENCE: 274
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDATHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                     330

SEQ ID NO: 275            moltype = AA  length = 110
FEATURE                   Location/Qualifiers
source                    1..110
                          mol_type = protein
                          organism = synthetic construct
SEQUENCE: 275
EIVLTQSPGT LSLSPGERAT LSCTASSSVS SSFLHWYQQK PGQAPRLLIY STSNLASGIP    60
DRFSGSGSGT DFTLTISRLE PEDFAVYYCH QYHHSPYIYT FGGGTKLEIK              110

SEQ ID NO: 276            moltype = AA  length = 107
FEATURE                   Location/Qualifiers
source                    1..107
                          mol_type = protein
                          organism = synthetic construct
SEQUENCE: 276
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 277            moltype = AA  length = 19
FEATURE                   Location/Qualifiers
source                    1..19
                          mol_type = protein
                          organism = synthetic construct
SEQUENCE: 277
MGWSCIILFL VATATGVHS                                                 19

SEQ ID NO: 278            moltype = AA  length = 129
FEATURE                   Location/Qualifiers
source                    1..129
                          mol_type = protein
                          organism = synthetic construct
SEQUENCE: 278
MGWSCIILFL VATATGVHSE IVLTQSPGTL SLSPGERATL SCTASSSVSS SFLHWYQQKP    60
GQAPRLLIYS TSNLASGIPD RFSGSGSGTD FTLTISRLEP EDFAVYYCHQ YHHSPYIYTF   120
GGGTKLEIK                                                           129

SEQ ID NO: 279            moltype = AA  length = 136
FEATURE                   Location/Qualifiers
source                    1..136
                          mol_type = protein
                          organism = synthetic construct
SEQUENCE: 279
MGWSCIILFL VATATGVHSQ VQLQESGPGL VKPSETLSLT CTVSGFSLSI YSVHWIRQPP    60
GKGLEWIGMI WGGGSSDYNS ALKSRLTISK DTSKNQVSLK LSSVTAADTA VYYCARNGNF   120
YAMDYWGQGT LVTVSS                                                   136

SEQ ID NO: 280            moltype = AA  length = 1412
FEATURE                   Location/Qualifiers
source                    1..1412
                          mol_type = protein
                          organism = Porphyromonas gingivalis
SEQUENCE: 280
YTPVEEKQNG RMIVIVAKKY EGDIKDFVDW KNQRGLRTEV KVAEDIASPV TANAIQQFVK    60
QEYEKEGNDL TYVLLIGDHK DIPAKITPGI KSDQVYGQIV GNDHYNEVFI GRFSCESKED   120
LKTQIDRTIH YERNITTEDK WLGQALCIAS AEGGPSADNG ESDIQHENVI ANLLTQYGYT   180
KIIKCYDPGV TPKNIIDAFN GGISLANYTG HGSETAWGTS HFGTTHVKQL TNSNQLPFIF   240
DVACVNGDFL FSMPCFAEAL MRAQKDGKPT GTVAIIASTI NQSWASPMRG QDEMNEILCE   300
KHPNNIKRTF GGVTMNGMFA MVEKYKKDGE KMLDTWTVPG DPSLLVRTLV PTKMQVTAPA   360
QINLTDASVN VSCDYNGAIA TISANGKMFG SAVVENGTAT INLTGLTNES TLTLTVVGYN   420
KETVIKTINT NGEPNPYQPV SNLTATTQGQ KVTLKWDAPS TKTNATTNTA RSVDGIRELV   480
LLSVSDAPEL LRSGQAEIVL EAHDVWNDGS GYQILLDADH DQYGQVIPSD THTLWPNCSV   540
PANLFAPFEY TVPENADPSC SPTNMIMDGT ASVNIPAGTY DFAIAAPQAN AKIWIAGQGP   600
TKEDDYVFEA GKKYHFLMKK MGSGDGTELT ISEGGGSDYT YTVYRDGTKI KEGLTATTFE   660
EDGVATGNHE YCVEVKYTAG VSPKVCKDVT VEGSNEFAPV QNLTGSAVGQ KVTLKWDAPN   720
GTPNPNPNPN PNPNPGTTTL SESFENGIPA SWKTIDADGD GHGWKPGNAP GIAGYNSNGC   780
VYSESFGLGG IGVLTPDNYL ITPALDLPNG GKLTFWVCAQ DANYASEHYA VYASSTGNDA   840
SNFTNALLEE TITAKGVRSP EAMRGRIQGT WRQKTVDLPA GTKYVAFRHF QSTDMFYIDL   900
DEVEIKANGK RADFTETFES STHGEAPAEW TTIDADGDGQ GWLCLSSGQL DWLTAHGGTN   960
VVSSFSWNGM ALNPDNYLIS KDVTGATKVK YYYAVNDGFP GDHYAVMISK TGTNAGDFTV  1020
```

-continued

```
VFEETPNGIN KGGARFGLST EADGAKPQSV WIERTVDLPA GTKYVAFRHY NCSDLNYILL   1080
DDIQFTMGGS PTPTDYTYTV YRDGTKIKEG LTETTFEEDG VATGNHEYCV EVKYTAGVSP   1140
KKCVNVTVNS TQFNPVKNLK AQPDGGDVVL KWEAPSAKKT EGSREVKRIG DGLFVTIEPA   1200
NDVRANEAKV VLAADNVWGD NTGYQFLLDA DHNTFGSVIP ATGPLFTGTA SSDLYSANFE   1260
SLIPANADPV VTTQNIIVTG QGEVVIPGGV YDYCITNPEP ASGKMWIAGD GGNQPARYDD   1320
FTFEAGKKYT FTMRRAGMGD GTDMEVEDDS PASYTYTVYR DGTKIKEGLT ETTYRDAGMS   1380
AQSHEYCVEV KYTAGVSPKV CVDYIPHHHH HH                                 1412

SEQ ID NO: 281            moltype = AA  length = 227
FEATURE                  Location/Qualifiers
source                   1..227
                         mol_type = protein
                         organism = Porphyromonas gingivalis
SEQUENCE: 281
LWPNCSVPAN LFAPFEYTVP ENADPSCSPT NMIMDGTASV NIPAGTYDFA IAAPQANAKI   60
WIAGQGPTKE DDYVFEAGKK YHFLMKKMGS GDGTELTISE GGGSDYTYTV YRDGTKIKEG   120
LTATTFEEDG VATGNHEYCV EVKYTAGVSP KVCKDVTVEG SNEFAPVQNL TGSAVGQKVT   180
LKWDAPNGTP NPNPNPNPNP NPGTTTLSES FENGIPASWK TIDADGD                227

SEQ ID NO: 282            moltype = AA  length = 171
FEATURE                  Location/Qualifiers
source                   1..171
                         mol_type = protein
                         organism = Porphyromonas gingivalis
SEQUENCE: 282
DPSCSPTNMI MDGTASVNIP AGTYDFAIAA PQANAKIWIA GQGPTKEDDY VFEAGKKYHF   60
LMKKMGSGDG TELTISEGGG SDYTYTVYRD GTKIKEGLTA TTFEEDGVAA GNHEYCVEVK   120
YTAGVSPKVC KDVTVEGSNE FAPVQNLTGS AVGQKVTLKW DAPNGHHHHH H          171

SEQ ID NO: 283            moltype = AA  length = 53
FEATURE                  Location/Qualifiers
source                   1..53
                         mol_type = protein
                         organism = Porphyromonas gingivalis
SEQUENCE: 283
YTYTVYRDGT KIKEGLTATT FEEDGVATGN HEYCVEVKYT AGVSPKVCKD VTV          53

SEQ ID NO: 284            moltype = AA  length = 1736
FEATURE                  Location/Qualifiers
source                   1..1736
                         mol_type = protein
                         organism = Porphyromonas gingivalis
SEQUENCE: 284
MRKLLLLIAA SLLGVGLYAQ SAKIKLDAPT TRTTCTNNSF KQFDASFSFN EVELTKVETK   60
GGTFASVSIP GAFPTGEVGS PEVPAVRKLI AVPVGATPVV RVKSFTEQVY SLNQYGSEKL   120
MPHQPSMSKS DDPEKVPFVY NAAAYARKGF VGQELTQVEM LGTMRGVRIA ALTINPVQYD   180
VVANQLKVRN NIEIEVSFQG ADEVATQRLY DASFSPYFET AYKQLFNFDV YTDHGDLYNT   240
PVRMLVVAGA KFKEALKPWL TWKAQKGFYL DVHYTDEAEV GTTNASIKAF IHKKYNDGLA   300
ASAAPVFLAL VGDTDVISGE KGKKTKKVTD LYYSAVDGDY FPEMYTFRMS ASSPEELTNI   360
IDKVLMYEKA TMPDKSYLEK VLLIAGADYS WNSQVGQPTI KYGMQYYYNQ EHGYTDVYNY   420
LKAPYTGCYS HLNTGVSFAN YTAHGSETAW ADPLLTTSQL KALTNKDKYF LAIGNCCITA   480
QFDYVQPCFG EVITRVKEKG AYAYIGSSPN SYWGEDYYWS VGANAVFGVQ PTFEGTSMGS   540
YDATFLEDSY NTVNSIMWAG NLAATHAGNI GNITHIGAHY YWEAYHVLGD GSVMPYRAMP   600
KTNTYTLPAS LPQNQASYSI QASAGSYVAI SKDGVLYGTG VANASGVATV SMTKQITENG   660
NYDVVITRSN YLPVIKQIQV GEPSPYQPVS NLTATTQGQK VTLKWEAPSA KKAEGSREVK   720
RIGDGLFVTI EPANDVRANE AKVVLAADNV WGDNTGYQFL LDADHNTFGS VIPATGPLFT   780
GTASSNLYSA NFEYLIPANA DPVVTTQNII VTGQGEVVIP GGVYDYCITN PEPASGKMWI   840
AGDGGNQPAR YDDFTFEAGK KYTFTMRRAG MGDGTDMEVE DDSPASYTYT VYRDGTKIKE   900
GLTATTFEED GVAAGNHEYC VEVKYTAGVS PKVCKDVTVE GSNEFAPVQN LTGSSVGQKV   960
TLKWDAPNGT PNPNPNPNPN PGTTLSESFE NGIPASWKTI DADGDGHGWK PGNAPGIAGY   1020
NSNGCVYSES FGLGGIGVLT PDNYLITPAL DLPNGGKLTF WVCAQDANYA SEHYAVYASS   1080
TGNDASNFTN ALLEETITAK GVRSPKAIRG RIQGTWKTVD LPAGTKYVAF RHFQSTDMFY   1140
IDLDEVEIKA NGKRADFTET FESSTHGEAP AEWTTIDADG DGQGWLCLSS GQLDWLTAHG   1200
GSNVVSSFSW NGMALNPDNY LISKDVTGAT KVKYYYAVND GFPGDHYAVM ISKTGTNAGD   1260
FTVVFEETPN GINKGGARFG LSTEANGAKQ SVWIERTVDL PAGTKYVAFR HYNCSDLNYI   1320
LLDDIQFTMG GSPTPTDYTY TVYRDGTKIK EGLTETTFEE DGVATGNHEY CVEVKYTAGV   1380
SPKKCVNVTV NSTQFNPVQN LTAEQAPNSM DAILKWNAPA SKRAEVLNED FENGIPASWK   1440
TIDADGDGNN WTTTPPPGGS SFAGHNSAIC VSSASYINFE GPQNDNYLVT PELSLPGGGT   1500
LTFWVCAQDA NYASEHYAVY ASSTGNDASN FANALLEEVL TAKTVVTAPE AIRGTRAQGT   1560
WYQKTVQLPA GTKYVAFRHF GCTDFFWINL DDVVITSGNA PSYTYTIYRN NTQIASGVTE   1620
TTYRDPDLAT GFYTYGVKVV YPNGESAIET ATLNITHHHH HHHHSLADVT AQKPYTLTVV   1680
GKTITVTCQG EAMIYDMNGR RLAAGRNTVV YTAQGGHYAV MVVVDGKSYV EKLAVK       1736

SEQ ID NO: 285            moltype = AA  length = 14
FEATURE                  Location/Qualifiers
source                   1..14
                         mol_type = protein
                         organism = Porphyromonas gingivalis
SEQUENCE: 285
```

-continued

```
DVYTDHGDLY NTPV                                                        14

SEQ ID NO: 286          moltype = AA   length = 11
FEATURE                 Location/Qualifiers
source                  1..11
                        mol_type = protein
                        organism = Porphyromonas gingivalis
SEQUENCE: 286
ANEAKVVLAA D                                                           11

SEQ ID NO: 287          moltype = AA   length = 9
FEATURE                 Location/Qualifiers
source                  1..9
                        mol_type = protein
                        organism = Porphyromonas gingivalis
SEQUENCE: 287
MAVVINXFF                                                              9

SEQ ID NO: 288          moltype = AA   length = 9
FEATURE                 Location/Qualifiers
source                  1..9
                        mol_type = protein
                        organism = Porphyromonas gingivalis
SEQUENCE: 288
AEVLNEDFE                                                              9

SEQ ID NO: 289          moltype = AA   length = 9
FEATURE                 Location/Qualifiers
source                  1..9
                        mol_type = protein
                        organism = Porphyromonas gingivalis
SEQUENCE: 289
GGSPTPTDY                                                              9

SEQ ID NO: 290          moltype = AA   length = 9
FEATURE                 Location/Qualifiers
source                  1..9
                        mol_type = protein
                        organism = Porphyromonas gingivalis
SEQUENCE: 290
AQGTWYQKT                                                              9

SEQ ID NO: 291          moltype = AA   length = 11
FEATURE                 Location/Qualifiers
source                  1..11
                        mol_type = protein
                        organism = Porphyromonas gingivalis
SEQUENCE: 291
SGNAPSYTYT I                                                          11

SEQ ID NO: 292          moltype = AA   length = 1711
FEATURE                 Location/Qualifiers
source                  1..1711
                        mol_type = protein
                        organism = Porphyromonas gingivalis
SEQUENCE: 292
MKNLNKFVSI ALCSSLLGGM AFAQQTELGR NPNVRLLEST QQSVTKVQFR MDNLKFTEVQ    60
TPKGIGQVPT YTEGVNLSEK GMPTLPILSR SLAVSDTREM KVEVVSSKFI EKKNVLIAPS   120
KGMIMRNEDP KKIPYVYGKT YSQNKFFPGE IATLDDPFIL RDVRGQVVNF APLQYNPVTK   180
TLRIYTEITV AVSETSEQGK NILNKKGTFA GFEDTYKRMF MNYEPGRYTP VEEKQNGRMI   240
VIVAKKYEGD IKDFVDWKNQ RGLRTEVKVA EDIASPVTAN AIQQFVKQEY EKEGNDLTYV   300
LLIGDHKDIP AKITPGIKSD QVYGQIVGND HYNEVFIGRF SCESKEDLKT QIDRTIHYER   360
NITTEDKWLG QALCIASAEG GPSADNGESD IQHENVIANL LTQYGYTKII KCYDPGVTPK   420
NIIDAFNGGI SLANYTGHGS ETAWGTSHFG TTHVKQLTNS NQLPFIFDVA CVNGDFLFSM   480
PCFAEALMRA QKDGKPTGTV AIIASTINQS WASPMRGQDE MNEILCEKHP NNIKRTFGGV   540
TMNGMFAMVE KYKKDGEKML DTWTVFGDPS LLVRTLVPTK MQVTAPAQIN LTDASVNVSC   600
DYNGAIATIS ANGKMFGSAV VENGTATINL TGLTNESTLT LTVVGYNKET VIKTINTNGE   660
PNPYQPVSNL TATTQGQKVT LKWDAPSTKT NATTNTARSV DGIRELVLLS VSDAPELLRS   720
GQAEIVLEAH DVWNDGSGYQ ILLDADHDQY GQVIPSDTHT LWPNCSVPAN LFAPFEYTVP   780
ENADPSCSPT NMIMDGTASV NIPAGTYDFA IAAPQANAKI WIAGQGPTKE DDYVFEAGKK   840
YHFLMKKMGS GDGTELTISE GGGSDYTYTV YRDGTKIKEG LTATTFEEDG VATGNHEYCV   900
EVKYTAGVSP KVCKDVTVEG SNEFAPVQNL TGSAVGQKVT LKWDAPNGTP NPNPNPNPNP   960
NPGTTTLSES FENGIPASWK TIDADGDGHG WKPGNAPGIA GYNSNGCVYS ESFGLGGIGV  1020
LTPDNYLITP ALDLPNGGKL TFWVCAQDAN YASEHYAVYA SSTGNDASNF TNALLEETIT  1080
AKGVRSPEAM RGRIQGIWRQ KLVDLPAGTK YVAFRHFQST DMFYIDLDEV EIKANGKRAD  1140
FTETFESSTH GEAPAEWTTI DADGDGQGWL CLSSGQLDWL TAHGGTNVVS SFSWNGMALN  1200
PDNYLISKDV TGATKVKYYY AVNDGFPGDH YAVMISKTGT NAGDFTVVFE ETPNGINKGG  1260
ARFGLSTEAD GAKPQSVWIE RTVDLPAGTK YVAFRHYNCS DLNYILLDDI QFTMGGSPTP  1320
TDTYTVYRDG TKIKEGLTET TFEEDGVATG NHEYCVEVKY TAGVSPKKCV NVTVNSTQFN  1380
```

-continued

```
PVKNLKAQPD GGDVVLKWEA PSAKKTEGSR EVKRIGDGLF VTIEPANDVR ANEAKVVLAA    1440
DNVWGDNTGY QFLLDADHNT FGSVIPATGP LFTGTASSDL YSANFESLIP ANADPVVTTQ    1500
NIIVTGQGEV VIPGGVYDYC ITNPEPASGK MWIAGDGGNQ PARYDDFTFE AGKKYTFTMR    1560
RAGMGDGTDM EVEDDSPASY TYTVYRDGTK IKEGLTETTY RDAGMSAQSH EYCVEVKYTA    1620
GVSPKVCVDY IPDHHHHHHG VADVTAQKPY TLTVVGKTIT VTCQGEAMIY DMNGRRLAAG    1680
RNTVVYTAQG GYYAVMVVVD GKSYVEKLAI K                                  1711

SEQ ID NO: 293           moltype = AA  length = 14
FEATURE                  Location/Qualifiers
source                   1..14
                         mol_type = protein
                         organism = Porphyromonas gingivalis
SEQUENCE: 293
YTPVEEKQNG RMIV                                                            14

SEQ ID NO: 294           moltype = AA  length = 11
FEATURE                  Location/Qualifiers
source                   1..11
                         mol_type = protein
                         organism = Porphyromonas gingivalis
SEQUENCE: 294
SGQAEIVLEA H                                                               11

SEQ ID NO: 295           moltype = AA  length = 11
FEATURE                  Location/Qualifiers
source                   1..11
                         mol_type = protein
                         organism = Porphyromonas gingivalis
SEQUENCE: 295
ANEAKVVLAA D                                                               11

SEQ ID NO: 296           moltype = AA  length = 9
FEATURE                  Location/Qualifiers
source                   1..9
                         mol_type = protein
                         organism = Porphyromonas gingivalis
SEQUENCE: 296
DFTETFESS                                                                   9

SEQ ID NO: 297           moltype = AA  length = 11
FEATURE                  Location/Qualifiers
source                   1..11
                         mol_type = protein
                         organism = Porphyromonas gingivalis
SEQUENCE: 297
PQSVWIERTV D                                                               11

SEQ ID NO: 298           moltype = AA  length = 11
FEATURE                  Location/Qualifiers
source                   1..11
                         mol_type = protein
                         organism = Porphyromonas gingivalis
SEQUENCE: 298
YVAFRHYNCS D                                                               11

SEQ ID NO: 299           moltype = AA  length = 11
FEATURE                  Location/Qualifiers
source                   1..11
                         mol_type = protein
                         organism = Porphyromonas gingivalis
VARIANT                  2
                         note = X can also be aspartate
VARIANT                  3..4
                         note = X can also be proline
VARIANT                  5
                         note = X can also be tyrosine or glutamate
VARIANT                  6
                         note = X can also be tyrosine
VARIANT                  7..8
                         note = X can also be aspartate
VARIANT                  9
                         note = X can also be valine or glycine
VARIANT                  10
                         note = X can also be isoleucine
VARIANT                  11
                         note = X can also be valine or glycine
VARIANT                  1
                         note = X can be alanineor any amino acid
VARIANT                  1
```

-continued

```
                    note = X can also be any amino acid
SEQUENCE: 299
AQSTTDQKYT Q                                                    11

SEQ ID NO: 300      moltype = AA  length = 11
FEATURE             Location/Qualifiers
source              1..11
                    mol_type = protein
                    organism = synthetic construct
SEQUENCE: 300
IQGTWRQKTV D                                                    11
```